(12) United States Patent
Toda et al.

(10) Patent No.: US 12,350,344 B2
(45) Date of Patent: *Jul. 8, 2025

(54) METHODS OF TREATING A TUMOR BY ADMINISTERING A CLAUDIN-6 (CLDN6) OR CLDN9 ANTIBODY-PYRROLOBENZODIAZEPINE DERIVATIVE CONJUGATE

(71) Applicant: DAIICHI SANKYO COMPANY, LIMITED, Tokyo (JP)

(72) Inventors: Narihiro Toda, Tokyo (JP); Yusuke Ota, Tokyo (JP); Fuminao Doi, Tokyo (JP); Masaki Meguro, Tokyo (JP); Ichiro Hayakawa, Tokyo (JP); Shinji Ashida, Tokyo (JP); Takeshi Masuda, Tokyo (JP); Takashi Nakada, Tokyo (JP); Mitsuhiro Iwamoto, Tokyo (JP); Naoya Harada, Tokyo (JP); Tomoko Terauchi, Tokyo (JP); Daisuke Okajima, Tokyo (JP); Kensuke Nakamura, Tokyo (JP); Hiroaki Uchida, Tokyo (JP); Hirofumi Hamada, Tokyo (JP)

(73) Assignee: DAIICHI SANKYO COMPANY, LIMITED, Tokyo (JP)

(*) Notice: Subject to any disclaimer, the term of this patent is extended or adjusted under 35 U.S.C. 154(b) by 192 days.

This patent is subject to a terminal disclaimer.

(21) Appl. No.: 17/714,032

(22) Filed: Apr. 5, 2022

(65) Prior Publication Data

US 2023/0084707 A1 Mar. 16, 2023

Related U.S. Application Data

(60) Division of application No. 17/543,697, filed on Dec. 6, 2021, now Pat. No. 11,583,590, which is a continuation of application No. 16/651,501, filed as application No. PCT/JP2018/036252 on Sep. 28, 2018, now Pat. No. 11,628,223.

(30) Foreign Application Priority Data

Sep. 29, 2017 (JP) .................................. 2017-190713

(51) Int. Cl.
| A61K 47/68 | (2017.01) |
|---|---|
| A61K 35/00 | (2006.01) |
| A61P 35/00 | (2006.01) |
| C07D 487/04 | (2006.01) |
| C07K 16/30 | (2006.01) |

(52) U.S. Cl.
CPC .......... *A61K 35/00* (2013.01); *A61K 47/6803* (2017.08); *A61K 47/68035* (2023.08); *C07D 487/04* (2013.01); *C07K 16/30* (2013.01)

(58) Field of Classification Search
CPC ... A61K 47/6803; A61P 35/00; C07D 487/04; C07K 16/30

See application file for complete search history.

(56) References Cited

U.S. PATENT DOCUMENTS

| 4,427,588 | A | 1/1984 | Kaneko et al. |
|---|---|---|---|
| 9,381,256 | B2 | 7/2016 | Chari et al. |
| 10,238,748 | B2 | 3/2019 | Bialucha et al. |
| 2003/0120069 | A1 | 6/2003 | Thurston et al. |
| 2003/0195196 | A1 | 10/2003 | Thurston et al. |
| 2004/0092736 | A1 | 5/2004 | Thurston et al. |
| 2004/0192679 | A1 | 9/2004 | Kamal et al. |
| 2004/0198722 | A1 | 10/2004 | Thurston et al. |
| 2006/0128693 | A1 | 6/2006 | Thurston et al. |
| 2006/0264622 | A1 | 11/2006 | Howard et al. |
| 2006/0270661 | A1 | 11/2006 | Liu et al. |
| 2007/0072846 | A1 | 3/2007 | Vishnuvajjala et al. |
| 2007/0173497 | A1 | 7/2007 | Howard et al. |
| 2007/0185073 | A1 | 8/2007 | Howard et al. |
| 2007/0191309 | A1 | 8/2007 | Howard et al. |
| 2007/0249591 | A1 | 10/2007 | Howard et al. |
| 2008/0039448 | A1 | 2/2008 | Liu et al. |
| 2008/0090812 | A1 | 4/2008 | Pepper et al. |
| 2008/0138855 | A1 | 6/2008 | Wang |
| 2008/0167293 | A1 | 7/2008 | Howard et al. |
| 2009/0149449 | A1 | 6/2009 | Liu et al. |
| 2010/0113425 | A1 | 5/2010 | Howard et al. |
| 2011/0059469 | A1 | 3/2011 | Aburatani et al. |
| 2011/0070607 | A1 | 3/2011 | Wang |
| 2011/0160192 | A1 | 6/2011 | Howard et al. |
| 2011/0162227 | A1 | 7/2011 | Howard et al. |
| 2011/0196148 | A1 | 8/2011 | Howard et al. |
| 2011/0201803 | A1 | 8/2011 | Howard et al. |
| 2011/0236507 | A1 | 9/2011 | Lloyd et al. |
| 2011/0262454 | A1 | 10/2011 | Park et al. |
| 2011/0300144 | A1 | 12/2011 | Sahin et al. |

(Continued)

FOREIGN PATENT DOCUMENTS

| CN | 105142674 A | 12/2015 |
|---|---|---|
| CN | 105813650 A | 7/2016 |

(Continued)

OTHER PUBLICATIONS

Office Action issued in corresponding Indonesian Patent Application No. P00202001967 dated Jun. 14, 2022.
B.Tran, et al., "Survival comparison between glioblastoma multiforme and other incurable cancers," Journal of Clinical Neuroscience, 2010, vol. 17, pp. 417-421.

(Continued)

*Primary Examiner* — Robert S Landsman
(74) *Attorney, Agent, or Firm* — Foley & Lardner LLP

(57) ABSTRACT

The present invention provides a novel antibody-pyrrolodiazepine derivative and a novel antibody-pyrrolodiazepine derivative conjugate using the same, and a novel CLDN6 and/or CLDN9 antibody.

36 Claims, 48 Drawing Sheets

Specification includes a Sequence Listing.

(56) References Cited

U.S. PATENT DOCUMENTS

| | | |
|---|---|---|
| 2012/0226024 A1 | 9/2012 | Wang et al. |
| 2013/0028919 A1 | 1/2013 | Howard et al. |
| 2013/0035484 A1 | 2/2013 | Howard et al. |
| 2013/0059800 A1 | 3/2013 | Howard et al. |
| 2013/0131325 A1 | 5/2013 | Wang |
| 2013/0137857 A1 | 5/2013 | Wang |
| 2013/0183305 A1 | 7/2013 | Sahin et al. |
| 2013/0266595 A1 | 10/2013 | Flygare et al. |
| 2013/0309223 A1 | 11/2013 | Sutherland et al. |
| 2013/0337506 A1 | 12/2013 | Sonderegger et al. |
| 2014/0030279 A1 | 1/2014 | Polakis et al. |
| 2014/0030280 A1 | 1/2014 | Polakis et al. |
| 2014/0066435 A1 | 3/2014 | Howard et al. |
| 2014/0234346 A1 | 8/2014 | Howard |
| 2014/0274907 A1 | 9/2014 | Howard et al. |
| 2014/0275522 A1 | 9/2014 | Howard et al. |
| 2014/0286970 A1 | 9/2014 | Jeffrey et al. |
| 2014/0294868 A1 | 10/2014 | Howard et al. |
| 2014/0302066 A1 | 10/2014 | Jeffrey et al. |
| 2015/0087811 A1 | 3/2015 | Wang |
| 2015/0087814 A1 | 3/2015 | Wang et al. |
| 2015/0126495 A1 | 5/2015 | Howard et al. |
| 2015/0133435 A1 | 5/2015 | Howard et al. |
| 2015/0147316 A1 | 5/2015 | Sutherland et al. |
| 2015/0158869 A1 | 6/2015 | Howard |
| 2015/0209444 A1 | 7/2015 | Chari et al. |
| 2015/0274737 A1 | 10/2015 | Howard |
| 2015/0291609 A1 | 10/2015 | Wang et al. |
| 2015/0315193 A1 | 11/2015 | Li et al. |
| 2015/0315196 A1 | 11/2015 | Howard |
| 2015/0320882 A1 | 11/2015 | Van Delft et al. |
| 2015/0344482 A1 | 12/2015 | Howard |
| 2016/0031887 A1 | 2/2016 | Howard |
| 2016/0039870 A1 | 2/2016 | Meyer et al. |
| 2016/0045615 A1 | 2/2016 | Li et al. |
| 2016/0095938 A1 | 4/2016 | Fishkin et al. |
| 2016/0106861 A1 | 4/2016 | Beau-Larvor et al. |
| 2016/0106863 A1 | 4/2016 | Chari et al. |
| 2016/0129013 A1 | 5/2016 | Howard et al. |
| 2016/0137995 A1 | 5/2016 | Wang |
| 2016/0144052 A1 | 5/2016 | Howard et al. |
| 2016/0159901 A1 | 6/2016 | Sahin et al. |
| 2016/0207949 A1 | 7/2016 | Zhao |
| 2016/0235861 A1 | 8/2016 | Van Delft et al. |
| 2016/0237075 A1 | 8/2016 | Chen et al. |
| 2016/0250344 A1 | 9/2016 | Howard et al. |
| 2016/0250345 A1 | 9/2016 | Howard et al. |
| 2016/0250346 A1 | 9/2016 | Howard et al. |
| 2016/0250347 A1 | 9/2016 | Van Delft et al. |
| 2016/0256561 A1 | 9/2016 | Howard et al. |
| 2016/0257764 A1 | 9/2016 | Van Delft et al. |
| 2016/0263239 A1 | 9/2016 | Howard et al. |
| 2016/0263242 A1 | 9/2016 | Howard et al. |
| 2016/0272711 A1 | 9/2016 | Sahin et al. |
| 2016/0280797 A1 | 9/2016 | Van Delft et al. |
| 2016/0287721 A1 | 10/2016 | Jeffrey et al. |
| 2016/0289239 A1 | 10/2016 | Jeffrey et al. |
| 2016/0289332 A1 | 10/2016 | Santaguida et al. |
| 2016/0297890 A1 | 10/2016 | Agatsuma et al. |
| 2016/0303254 A1 | 10/2016 | Kolakowski et al. |
| 2016/0310611 A1 | 10/2016 | Flygare et al. |
| 2016/0310612 A1 | 10/2016 | Lyon et al. |
| 2016/0355604 A1 | 12/2016 | Sahin et al. |
| 2016/0361436 A1 | 12/2016 | Davis et al. |
| 2016/0367698 A1 | 12/2016 | Chari et al. |
| 2017/0014522 A1 | 1/2017 | Yoder et al. |
| 2017/0015720 A1 | 1/2017 | Sahin et al. |
| 2017/0029514 A1 | 2/2017 | Kovtun et al. |
| 2017/0037007 A1 | 2/2017 | Ruebsam et al. |
| 2017/0058040 A1 | 3/2017 | Wang et al. |
| 2017/0095570 A1 | 4/2017 | Dragovich et al. |
| 2017/0143846 A1 | 5/2017 | Howard et al. |
| 2017/0204180 A1 | 7/2017 | Sutherland et al. |
| 2017/0232112 A1 | 8/2017 | Li et al. |
| 2017/0274091 A1 | 9/2017 | Chari et al. |
| 2017/0290920 A1 | 10/2017 | Polakis et al. |
| 2017/0290924 A1 | 10/2017 | Jeffrey et al. |
| 2017/0298137 A1 | 10/2017 | Jeffrey et al. |
| 2017/0333442 A1 | 11/2017 | Yin et al. |
| 2017/0334991 A1 | 11/2017 | Escarpe et al. |
| 2017/0340749 A1 | 11/2017 | Chari et al. |
| 2018/0079819 A1 | 3/2018 | Kovtun et al. |
| 2018/0119146 A1 | 5/2018 | Sahin et al. |
| 2018/0125997 A1 | 5/2018 | Howard et al. |
| 2018/0140634 A1 | 5/2018 | Sahin et al. |
| 2018/0142033 A1 | 5/2018 | Sahin et al. |
| 2018/0169257 A1 | 6/2018 | Lewis et al. |
| 2018/0169259 A1 | 6/2018 | Polakis et al. |
| 2018/0185486 A1 | 7/2018 | Dragovich et al. |
| 2018/0186847 A1 | 7/2018 | Wang et al. |
| 2018/0208915 A1 | 7/2018 | Kawaguchi et al. |
| 2018/0228916 A1 | 8/2018 | Howard et al. |
| 2018/0326062 A1 | 11/2018 | Dragovich et al. |
| 2018/0355047 A1 | 12/2018 | Kovtun et al. |
| 2018/0369408 A1 | 12/2018 | Li et al. |
| 2019/0015524 A1 | 1/2019 | Feingold et al. |
| 2019/0055311 A1 | 2/2019 | Sahin et al. |
| 2019/0070194 A1 | 3/2019 | Yin et al. |
| 2019/0070305 A1 | 3/2019 | Chari et al. |
| 2019/0077876 A1 | 3/2019 | Santaguida et al. |
| 2019/0083645 A1 | 3/2019 | Fong et al. |
| 2019/0169293 A1 | 6/2019 | Iwamoto et al. |
| 2019/0169614 A1 | 6/2019 | Sahin et al. |
| 2019/0225706 A1 | 7/2019 | Van Delft et al. |
| 2019/0309067 A1 | 10/2019 | Sahin et al. |
| 2019/0367570 A1 | 12/2019 | Wang et al. |
| 2019/0389920 A1 | 12/2019 | Sahin et al. |
| 2020/0199221 A1 | 6/2020 | Mitnacht-Kraus et al. |

FOREIGN PATENT DOCUMENTS

| | | |
|---|---|---|
| JP | S57131791 | 8/1982 |
| JP | S5841884 | 3/1983 |
| JP | S63107992 A | 5/1988 |
| JP | H01121296 | 5/1989 |
| JP | 2015-534996 | 12/2015 |
| JP | 2016-531893 | 10/2016 |
| JP | 2016-536020 | 11/2016 |
| JP | 2017-513942 | 6/2017 |
| JP | 2017-524364 A | 8/2017 |
| JP | 2017-526614 | 9/2017 |
| JP | 2018-532695 A | 11/2018 |
| RU | 2314309 C2 | 1/2008 |
| TW | 201726175 A | 8/2017 |
| WO | WO-93/18045 | 9/1993 |
| WO | WO-00/12506 | 3/2000 |
| WO | WO-00/12507 | 3/2000 |
| WO | WO-00/12508 | 3/2000 |
| WO | WO-00/12509 | 3/2000 |
| WO | WO-2004/043963 | 5/2004 |
| WO | WO-2004/087711 | 10/2004 |
| WO | WO-2004/087717 | 10/2004 |
| WO | WO-2005/023814 | 3/2005 |
| WO | WO-2005/042535 | 5/2005 |
| WO | WO-2005/063758 | 7/2005 |
| WO | WO-2005/063760 | 7/2005 |
| WO | WO-2005/085177 | 9/2005 |
| WO | WO-2005/085251 | 9/2005 |
| WO | WO-2005/085259 | 9/2005 |
| WO | WO-2005/085260 | 9/2005 |
| WO | WO-2005/110423 | 11/2005 |
| WO | WO-2006/111759 | 10/2006 |
| WO | WO-2007/085930 | 8/2007 |
| WO | WO-2007/133855 | 11/2007 |
| WO | WO-2008/010101 | 1/2008 |
| WO | WO-2008/047242 | 4/2008 |
| WO | WO-2009/016516 | 2/2009 |
| WO | WO-2009/087978 | 7/2009 |
| WO | WO-2010/010347 | 1/2010 |
| WO | WO-2010/043877 | 4/2010 |
| WO | WO-2010/043880 | 4/2010 |
| WO | WO-2010/065159 | 6/2010 |
| WO | WO-2010/091150 | 8/2010 |
| WO | WO-2010/094499 | 8/2010 |

(56) References Cited

FOREIGN PATENT DOCUMENTS

| | | |
|---|---|---|
| WO | WO-2011/023883 | 3/2011 |
| WO | WO-2011/057788 | 5/2011 |
| WO | WO-2011/128650 | 10/2011 |
| WO | WO-2011/130598 | 10/2011 |
| WO | WO-2011/130613 | 10/2011 |
| WO | WO-2011/130616 | 10/2011 |
| WO | WO-2012/003956 | 1/2012 |
| WO | WO-2012/014147 | 2/2012 |
| WO | WO-2012/112687 | 8/2012 |
| WO | WO-2012/112708 | 8/2012 |
| WO | WO-2012/128868 | 9/2012 |
| WO | WO-2012/156018 | 11/2012 |
| WO | WO-2013/041606 | 3/2013 |
| WO | WO-2013/053871 | 4/2013 |
| WO | WO-2013/053872 | 4/2013 |
| WO | WO-2013/053873 | 4/2013 |
| WO | WO-2013/055987 | 4/2013 |
| WO | WO-2013/055990 | 4/2013 |
| WO | WO-2013/055993 | 4/2013 |
| WO | WO-2013/120066 | 8/2013 |
| WO | WO-2013/164592 | 11/2013 |
| WO | WO-2013/164593 | 11/2013 |
| WO | WO-2013/173496 | 11/2013 |
| WO | WO-2013/177481 | 11/2013 |
| WO | WO-2014/011518 | 1/2014 |
| WO | WO-2014/011519 | 1/2014 |
| WO | WO-2014/031566 | 2/2014 |
| WO | WO-2014/057072 | 4/2014 |
| WO | WO-2014/057073 | 4/2014 |
| WO | WO-2014/057074 | 4/2014 |
| WO | WO-2014/057113 | 4/2014 |
| WO | WO-2014/057114 | 4/2014 |
| WO | WO-2014/057115 | 4/2014 |
| WO | WO-2014/057117 | 4/2014 |
| WO | WO-2014/057118 | 4/2014 |
| WO | WO-2014/057119 | 4/2014 |
| WO | WO-2014/057120 | 4/2014 |
| WO | WO-2014/057122 | 4/2014 |
| WO | WO-2014/057687 A1 | 4/2014 |
| WO | WO-2014/075697 | 5/2014 |
| WO | WO-2014/075788 | 5/2014 |
| WO | WO-2014/096365 | 6/2014 |
| WO | WO-2014/096368 | 6/2014 |
| WO | WO-2014/130879 | 8/2014 |
| WO | WO-2014/140174 | 9/2014 |
| WO | WO-2014/140862 | 9/2014 |
| WO | WO-2014/143622 | 9/2014 |
| WO | WO-2014/159981 | 10/2014 |
| WO | WO-2014/165119 | 10/2014 |
| WO | WO-2014/174111 | 10/2014 |
| WO | WO-2015/014376 | 2/2015 |
| WO | WO-2015/014870 | 2/2015 |
| WO | WO-2015/028850 | 3/2015 |
| WO | WO-2015/031693 | 3/2015 |
| WO | WO-2015/052321 | 4/2015 |
| WO | WO-2015/052322 | 4/2015 |
| WO | WO-2015/052532 | 4/2015 |
| WO | WO-2015/052533 | 4/2015 |
| WO | WO-2015/052534 | 4/2015 |
| WO | WO-2015/052535 | 4/2015 |
| WO | WO-2015/057063 | 4/2015 |
| WO | WO-2015/057064 | 4/2015 |
| WO | WO-2015/057065 | 4/2015 |
| WO | WO-2015/057066 | 4/2015 |
| WO | WO-2015/057699 | 4/2015 |
| WO | WO-2015/069794 | 5/2015 |
| WO | WO-2015/095124 | 6/2015 |
| WO | WO-2015/095755 | 6/2015 |
| WO | WO-2015/150327 | 10/2015 |
| WO | WO-2015/155753 A2 | 10/2015 |
| WO | WO-2016/024195 A1 | 2/2016 |
| WO | WO-2016/036794 | 3/2016 |
| WO | WO-2016/036804 | 3/2016 |
| WO | WO-2016/073649 | 5/2016 |
| WO | WO-2016/115191 | 7/2016 |
| WO | WO-2016/150400 | 9/2016 |
| WO | WO-2016/180467 | 11/2016 |
| WO | WO-2017/004025 | 1/2017 |
| WO | WO-2017/004026 | 1/2017 |
| WO | WO-2017/004330 | 1/2017 |
| WO | WO-2017/020972 | 2/2017 |
| WO | WO-2017/059289 | 4/2017 |
| WO | WO-2017/096163 | 6/2017 |
| WO | WO-2017/137556 | 8/2017 |
| WO | WO-2017/201132 | 11/2017 |
| WO | WO-2018/003983 | 1/2018 |
| WO | WO-2018/054973 | 3/2018 |
| WO | WO-2017/010559 | 4/2018 |
| WO | WO-2018/107116 | 6/2018 |
| WO | WO-2018/212136 A1 | 11/2018 |
| WO | WO-2019/048040 | 3/2019 |
| WO | WO-2019/048489 | 3/2019 |
| WO | WO-2019/056023 | 3/2019 |
| WO | WO-2019/065964 A1 | 4/2019 |
| WO | WO-2020/196474 A1 | 10/2020 |
| WO | WO-2020/196475 A1 | 10/2020 |
| WO | WO-2020/196712 A1 | 10/2020 |

OTHER PUBLICATIONS

M. López-Lázaro, "The migration ability of stem cells can explain the existence of cancer of unknown primary site. Rethinking metastasis." Oncoscience, 2015, vol. 2, No. 5, p. 467. doi:10.18632/oncoscience.159.

Office Action issued in corresponding Russian Patent Application No. 2020109412/10(015472), dated May 11, 2023.

P. Derksen, et al., "Illegitimate WNT signaling promotes proliferation of multiple myeloma cells," Proceedings of the National Academy of Sciences, 2004, vol. 101, No. 16, pp. 6122-6127.

P. Dirks, "Brain Tumor Stem Cells: Bringing Order to the Chaos of Brain Cancer." Journal of Clinical Oncology, 2008, vol. 26, No. 17, pp. 2916-2924. DOI:10.1200/jco.2008.17.679 (abstract).

Antonow et al., "Synthesis of DNA-Interactive Pyrrolo[2,1-c][1,4]benzodiazepines (PBDs)," Chemical Reviews, vol. 111, Issue 4, 2010, pp. 2815-2864.

Bialucha et al., "Discovery and Optimization of HKT288, a Cadherin-6-Targeting ADC for the Treatment of Ovarian and Renal Cancers," Cancer Discovery, vol. 7, 2017, pp. 1030-1045.

Bose et al., "Rational design of a highly efficient irreversible DNA interstrand cross-linking agent based on the pyrrolobenzodiazepine ring system," Journal of the American Chemical Society, vol. 114, Issue 12, 1992, pp. 4939-4941.

Cho et al., "Differential expression and function of cadherin-6 during renal epithelium development," Development, vol. 125, Issue 5, Mar. 1998, pp. 803-812.

Colman, PM (1994) Research in Immunology, Elsevier, NY, 145(1):33-36.

Decision of Rejection issued in corresponding Japanese Patent Application No. 2021-180848 dated Apr. 26, 2022.

Goeppert B, et al., "Cadherin-6 is a putative tumor suppressor and target of epigenetically dysregulated miR-429 in cholangiocarcinoma," Epigenetics, vol. 11, Issue 11, Nov. 2016, pp. 780-790.

Gugnoni et al., "Cadherin-6 promotes EMT and cancer metastasis by restraining autophagy," Oncogene, vol. 36, Issue 5, Feb. 2, 2017, pp. 667-677.

Hurley et al., "Covalent binding of antitumor antibiotics in the minor groove of DNA. Mechanism of action of CC-1065 and the pyrrolo(1,4)benzodiazepines," Accounts of Chemical Research, vol. 19, 1986, pp. 230-237.

Inoue et al., "Cadherin-6 Expression Transiently Delineates Specific Rhombomeres, Other Neural TubeSubdivisions, and Neural Crest Subpopulations in Mouse Embryos," Developmental Biology, vol. 183, 1197, pp. 183-194, (Mar. 15, 1997).

International Searching Authority, "International Search Report," issued in connection with International Patent Application No. PCT/JP2019/044588, dated Dec. 24, 2019.

International Searching Authority, "Written Opinion," issued in connection with International Patent Application No. PCT/JP2019/044588, dated Dec. 24, 2019.

(56) References Cited

OTHER PUBLICATIONS

Köbel et al., "Ovarian Carcinoma Subtypes Are Different Diseases: Implications for Biomarker Studies," PLoS Medicine, vol. 5, Issue 12, e232, Dec. 2008, pp. 1749-1760.
Kohn, Kurt W., "Anthramycin," In Antibiotics III. Springer Verlag, New York, 1975, pp. 3-11.
Lombana TN, et al. (Dec. 3, 2015) Sci Rep. 5:17488. (doi:10.1038/srep17488).
Mah et al., "Kidney Development in Cadherin-6 Mutants: Delayed Mesenchyme-to-Epithelial Conversion and Loss of Nephrons," Developmental Biology, vol. 223, Issue 1, Aug. 2000, pp. 38-53.
Mantaj et al., "From Anthramycin to Pyrrolobenzodiazepine (PBD)-Containing Antibody—Drug Conjugates (ADCs)," Angewandte Chemie International Edition, vol. 55, 2016, pp. 2-29.
Office Action issued in corresponding Russian Patent Application No. 2020109412 dated May 13, 2022.
Osterhout et al., "Cadherin-6 mediates axon-target matching in a non-image-forming visual circuit," Neuron, vol. 71, Issue 4, Aug. 25, 2011, pp. 632-639.
Ovchinnikov V, et al. (2018) elife. 7:33038. 24 pages. (https://doi.org/10.7554/elife.33038.001).
Paul et al., "Cadherin-6, a Cell Adhesion Molecule Specifically Expressed in the Proximal Renal Tubule and Renal Cell Carcinoma," Cancer Research, vol. 57, Issue 13, Jul. 1997, pp. 2741-2748.
Paul, WE (1993) Fundamental Immunology, 3rd ed. Raven Press, NY, Chap. 9, pp. 292-295.
Peters et al., "Antibody-drug conjugates as novel anti-cancer chemotherapeutics," Bioscience Reports, vol. 35, Issue 4, e00225, Jun. 12, 2015, pp. 1-20.
Polakis, Paul, "Antibody Drug Conjugates for Cancer Therapy," Pharmacological Reviews, vol. 68, Issue 1, Jan. 2016, pp. 3-19.
Rudikoff, S et al. (1982) Proc. Natl. Acad. Sci. USA, 79:1979-1983.
Shimazui et al., "The level of cadherin-6 mRNA in peripheral blood is associated with the site of metastasis and with the subsequent occurrence of metastases in renal cell carcinoma," Cancer, vol. 101, Issue 5, Sep. 1, 2004, pp. 963-968.
Shimoyama et al., "Isolation and Sequence Analysis of Human Cadherin-6 Complementary DNA for the Full Coding Sequence and Its Expression in Human Carcinoma Cells," Cancer Research, vol. 55, May 15, 1995, pp. 2206-2211.
Thurston et al., "Synthesis of Sequence-Selective C8-Linked Pyrrolo[2,1-c][1,4]benzodiazepine DNA Interstrand Cross-Linking Agents," Journal of Organic Chemistry, vol. 61. Issue 23, 1996, 8141-8147.
Yokoi et al., "A Novel Target Gene, SKP2, within the 5p13 Amplicon That Is Frequently Detected in Small Cell Lung Cancers," American Journal of Pathology, vol. 161, No. 1, Jul. 2002, pp. 207-216.
Office Action issued in corresponding Malaysian Patent Application No. PI2020000936 dated Nov. 22, 2023 (4 pages).
Office Action dated Jan. 18, 2022 in the corresponding Japanese Patent Application No. 2021-180848 (6 pages).
Supplementary Partial European Search Report issued in corresponding European Patent Application No. 19884507.5, dated Oct. 12, 2022.
ACS Chem. Biol. 2012, 7, 973-977.
Am J Surg Pathol. Jan. 2012 ; 36(1): 73-80.
Angew.Chem.Int.Ed. 2016,55,2361-2367.
Bioconjugate Chem. 2013, 24(7), 1256-1263.
Bioconjugate Chemistry 2015, 26, 2233-2242.
Bioorganic & Medicinal Chemistry Letters 10 (2000) 1845-1847.
Bioorganic & Medicinal Chemistry Letters 19 (2009) 6463-6466.
Biotechnol. J. 2018, 13, 1700345.
Blood. Aug. 22, 2013;122(8):1455-63.
Brain Pathology 20 (2010) 140-150.
C.M. Van Itallie, et al., "The Cytoplasmic . . . Stability", The Journal of Membrane Biology, vol. 199, pp. 29-38, 2004.
Cancer Chemother Pharmacol (2011) 68: 777-786.
Cancer Res 2010; 70:6849-6858.
Chem. Commun. , 2002, 1764-1765.
Chem. Res. Toxicol. 1988,1, 258-268.
Clin Cancer Res. Jun. 1, 2011; 17(11): 3794-3802.
Current Medicinal Chemistry, 2012, 19, 364-385.
D. Subhas Bose, et al., "Rational Design . . . Ring System", Journal of the American Chemical Society, vol. 114, pp. 4939-4941, 1992.
David E. Thurston, et al., "Synthesis of . . . Cross-Linking Agents", Journal of Organic Chemistry, vol. 61, pp. 8141-8147, 1996.
Diagnostic Pathology 2013, 8:190.
Diagnostic Pathology; vol. 7, Article No. 33 (2012).
Dyeison Antonow et al., "Synthesis of . . . (PBDs)", Chemical Reviews, vol. 111, pp. 2815-2864, 2011.
Expert Opin. Investig. Drugs (2011) 20(6):733-744.
IBL Data Sheet, Code No. 18865, Anti-Mouse Claudin-6 (C) Rabbit IgG Affinity Purify.
Int. J. Mol. Sci. 2017, 18, 1863.
International Searching Authority, "International Preliminary Report on Patentability with Written Opinion," issued in connection with International Patent Application No. PCT/JP2018/036252, dated Mar. 31, 2020.
International Searching Authority, "International Search Report," issued in connection with International Patent Application No. PCT/JP2018/036252, dated Nov. 6, 2018.
J Antimicrob Chemother 2012; 67: 1683-1696.
J Exp Clin Cancer Res. 2016; 35: 120.
J. Am. Chem. Soc. 2012, 134, 12308-12318.
J. Am. Chem. Soc. 2012, 134, 8030-8033.
J. Med. Chem. 1994,37, 4529-4537.
J. Med. Chem. 2004, 47, 1161-1174.
J. Med. Chem. 2006, 49, 5442-5461.
J. Med. Chem. 2010, 53, 2927-2941.
Julia Mantaj, et al., "From Anthramycin . . . (ADCs)", Angewandte Chemie Internationl Edtion, vol. 55, pp. 2-29, 2016.
Kaliszczak, Maciej, "The rational design of pyrrolobenzodiazepine derivatives," Thesis presented for degree of Doctor of Philosophy, the University of Edinburgh, Apr. 2009, 253 pages.
Kurt W. Kohn, "Anthramycin", In Antibiotics III. Springer Verlag, New York, pp. 3-11, 1975.
Kyle J Hewitt, et al., "The claudin gene family: expression in normal and neoplastic tissues", BMC Cancer, vol. 6, 186, 2006.
Laurence H. Hurley, et al., "Covalent Binding . . . benzodiazepines", Accounts of Chemical Research, vol. 19, pp. 230-237, 1986.
Lena M. Kranz, et al., 14th Annu Meet Cancer Immunother (CIMT) (May 10-12, Mainz) Abst 185, 2016.
Medicinal Research Reviews, 32, No. 2, 254-293, 2012.
Mol Cell Biochem; https://doi.org/10.1007/s11010-017-3221-8, (2018).
Nat Commun 2013;4:1992.
Nucleic Acids Res. Jul. 2011; 39(13): 5800-5812.
ONCOIMMUNOL 2016, vol. 5, No. 3, e1091555.
OncoTargets and Therapy 2018:11 6351-6360.
Origene, "Rabbit polyclonal anti-CLDN6 antibody," Product Data Sheet—Antibody, Catalog TA311706, 2015.
Patrick Micke, et al., "Aberrantly activated claudin 6 and 18.2 as potential therapy targets in non-small-cell lung cancer", International Journal of Cancer, vol. 135, pp. 2206-2214, 2014.
Pharm. Pharmacol. Commun. 1999, 5: 555-560.
R&D Systems Tools for Cell Biology Research, "Human Claudin-6 Antibody, Monoclonal Mouse LgG2B Clone #342927," Catalog No. MAB3656, Revised on Feb. 17, 2011.
Sci Transl Med 7, 302ra136 (2015).
Tetrahedron Letters 56 (2015) 4512-4515.
Ushiku et al., "Distinct expression pattern of claudin-6, a primitive phenotypic tight junction molecule, in germ cell tumours and visceral carcinomas", Histopathology, vol. 61, 2012, pp. 1043-1056.
Tsugaya et al. "The treatment of bladder cancer by neothramycin," Hinyokika Kiyo, 1986, vol. 32, Issue 10, pp. 1443-1448.
Extended European Search Report dated Apr. 19, 2021 for corresponding European Patent Application No. 18862011.6.
Office Action issued in corresponding Korean Patent Application No. 10-2020-7011831 dated Jan. 31, 2024 (22 pages).
Office Action issued in corresponding Israeli Patent Application No. 301636 dated Oct. 19, 2023 (9 pages).
Abcam, Product Datasheet, Anti-Claudin 6 antibody ab107059, Retrieved Sep. 2020, 4 pages.

(56) References Cited

OTHER PUBLICATIONS

Office Action issued in corresponding Australian Patent Application No. 2018342527 dated Apr. 11, 2024 (3 pages).
Office Action issued in corresponding Japanese Patent Application No. 2023-023178 dated Apr. 2, 2024 (8 pages).
Office Action issued in corresponding Japanese Patent Application No. 2023-023179 dated Apr. 2, 2024 (5 pages).
Office Action issued in corresponding Brazilian Patent Application No. 112020004126-2 dated Sep. 10, 2024 (7 pages).
Office Action issued in corresponding Taiwanese Patent Application No. 112140159 dated Sep. 10, 2024 (9 pages).
Office Action issued in corresponding Taiwanese Patent Application No. 112140158 dated Sep. 12, 2024 (9 pages).
Office Action issued in corresponding Mexican Patent Application No. MX/a/2020/003125 dated Mar. 10, 2025.
Office Action issued in corresponding Philippines Patent Application No. Jan. 2020/500398 dated Mar. 4, 2025.

Figure 10

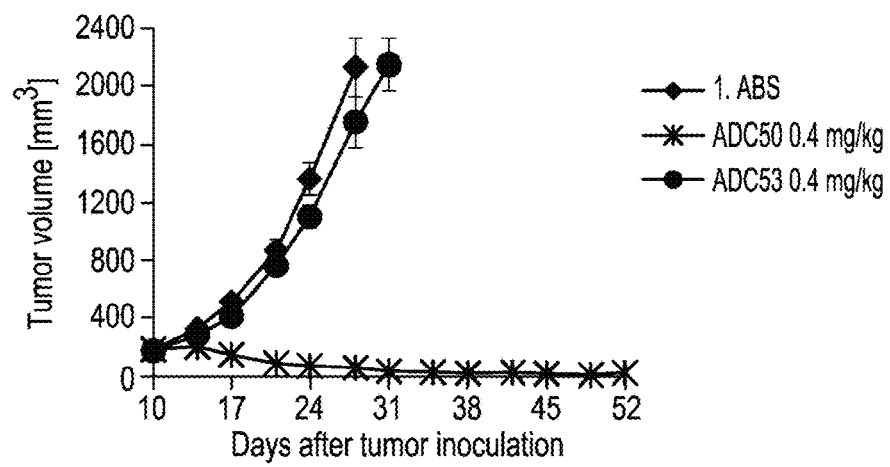

Figure 11

Full-length amino acid sequence of human CLDN6 (SEQ ID NO: 1)
MASAGMQILGVVLTLLGWVNGLVSCALPMWKVTAFIGNSIVVAQVVWEGLWMSCVVQSTGQMQCKVYDSL
LALPQDLQAARALCVIALLVALFGLLVYLAGAKCTTCVEEKDSKARLVLTSGIVFVISGVLTLIPVCWTA
HAIIRDFYNPLVAEAQKRELGASLYLGWAASGLLLLGGGLLCCTCPSGGSQGPSHYMARYSTSAPAISRG
PSEYPTKNYV Nucleotide sequence of full-length cDNA for human CLDN6 (SEQ ID NO: 2)

atggcctctgccggaatgcagatcctgggagtcgtcctgacactgctgggctgggtgaatggcctggtct
cctgtgccctgcccatgtggaaggtgaccgctttcatcggcaacagcatcgtggtggcccaggtggtgtg
ggagggcctgtggatgtcctgcgtggtgcagagcaccggccagatgcagtgcaaggtgtacgactcactg
ctggcgctgccacaggacctgcaggctgcacgtgccctctgtgtcatcgccctccttgtggccctgttcg
gcttgctggtctaccttgctggggccaagtgtaccacctgtgtggaggagaaggattccaaggcccgcct
ggtgctcacctctgggattgtctttgtcatctcaggggtcctgacgctaatccccgtgtgctggacggcg
catgccatcatccgggacttctataaccccctggtggctgaggcccaaaagcgggagctgggggcctccc
tctacttgggctgggcggcctcaggccttttgttgctgggtgggggttgctgtgctgcacttgcccctc
gggggggtcccagggccccagccattacatggcccgctactcaacatctgccctgccatctctcggggg
ccctctgagtaccctaccaagaattacgtctga

Figure 12

Full-length amino acid sequence of human CLDN9 (SEQ ID NO: 3)

MASTGLELLGMTLAVLGWLGTLVSCALPLWKVTAFIGNSIVVAQVVWEGLWMSCVVQSTGQMQCKVY
DSLLALPQDLQAARALCVIALLLALLGLLVAITGAQCTTCVEDEGAKARIVLTAGVILLLAGILVLI
PVCWTAHAIIQDFYNPLVAEALKRELGASLYLGWAAAALLMLGGGLLCCTCPPPQVERPRGPRLGYS
IPSRSGASGLDKRDYV

Nucleotide sequence of full-length cDNA for human CLDN9 (SEQ ID NO: 4)

```
atggcttcgaccggcttagaactgctgggcatgaccctggctgtgctgggctggctggggaccctgg
tgtcctgcgccctgccctgtggaaggtgaccgccttcatcggcaacagcatcgtggtggcccaggt
ggtgtgggagggcctgtggatgtcctgcgtggtgcagagcacgggccagatgcagtgcaaggtgtac
gactcactgctggctctgccgcaggacctgcaggccgcacgtgccctctgtgtcattgccctcctgc
tggccctgcttggcctcctggtggccatcacaggtgcccagtgtaccacgtgtgtggaggacgaagg
tgccaaggcccgtatcgtgctcaccgcggggtcatcctcctcctcgccggcatcctggtgctcatc
cctgtgctggacggcgcacgccatcatccaggacttctacaaccccctggtggctgaggccctca
gcggggagctgggggcctccctctacctgggctgggcggcggctgcactgcttatgctgggcgggg
gctcctctgctgcacgtgcccccgcccaggtcgagcggcccgcggacctcggctgggctactcc
atcccctcccgctcgggtgcatctggactggacaagagggactacgtgtga
```

Figure 13

Amino acid sequence of CDRL1 of B1 antibody light chain (SEQ ID NO: 5)

RASQDINNYLN

Amino acid sequence of CDRL2 of B1 antibody light chain (SEQ ID NO: 6)

FTSRLHS

Amino acid sequence of CDRL3 of B1 antibody light chain (SEQ ID NO: 7)

QQGYPLPWT

Figure 14

Amino acid sequence of CDRL3 of humanized B1 antibody light chain L4 (SEQ ID NO: 8)

QQGNTLPWT

Figure 15

Amino acid sequence of CDRH1 of B1 antibody heavy chain (SEQ ID NO: 9)

GYTFTEYTMH

Amino acid sequence of CDRH2 of B1 antibody heavy chain (SEQ ID NO: 10)

GVNPNSGDTS

Amino acid sequence of CDRH3 of B1 antibody heavy chain (SEQ ID NO: 11)

PGGYDVGYYAMDY

Figure 16

Amino acid sequence of CDRL1 of C7 antibody light chain (SEQ ID NO: 12)

RASQDINNYLN

Amino acid sequence of CDRL2 of C7 antibody light chain (SEQ ID NO: 13)

STSRLHS

Amino acid sequence of CDRL3 of C7 antibody light chain (SEQ ID NO: 14)

QQGYPLPWT

Figure 17

Amino acid sequence of CDRH1 of C7 antibody heavy chain (SEQ ID NO: 15)

GYTFTEYTMH

Amino acid sequence of CDRH2 of C7 antibody heavy chain (SEQ ID NO: 16)

GVNPNSGDTS

Amino acid sequence of CDRH3 of C7 antibody heavy chain (SEQ ID NO: 17)

PGGYDVGYYAMDY

Figure 18

Nucleotide sequence of cDNA encoding variable region of B1 antibody light chain (SEQ ID NO: 18)

GATATCCAGATGACACAGACTGCATCCTCCCTGTCTGCCTCTCTTGGAGACAGAGTCACCATCAGTT
GCAGGGCAAGTCAGGACATTAACAATTATTTAAACTGGTATCAGCAGAAACCAGATGGAACTGTTAA
ACTCCTGATCTACTTCACATCAAGATTACACTCAGGAGTCCCATCAAGGTTCAGTGGCAGTGGGTCT
GGAACACATTATTCTCTCACCATTACTAACCTGGAACAAGAAGATATTGCCACTTACTTTTGCCAAC
AGGGTTATCCGCTTCCGTGGACGTTCGGTGGAGGCACCAAACTGGAAATCAAA

Amino acid sequence of variable region of B1 antibody light chain (SEQ ID NO: 19)

DIQMTQTASSLSASLGDRVTISC<u>RASQDINNYLN</u>WYQQKPDGTVKLLIY<u>FTSRLHS</u>GVPSRFSGSGS
GTHYSLTITNLEQEDIATYFC<u>QQGYPLPWT</u>FGGGTKLEIK

Figure 19

Nucleotide sequence of cDNA encoding variable region of B1 antibody heavy chain (SEQ ID NO: 20)

GAGGTCCAGCTTCAACAGTCTGGACCTGAACTGGTGAAGCCTGGGGCTTCAGTGAAGATATCCTGCA
AGACTTCTGGATACACATTCACTGAATACACCATGCACTGGGTGCAGCAGAGCCATGGAAAGAGCCT
TGAGTGGATTGGAGGTGTTAATCCTAATAGTGGTGATACTAGCTACAACCAGAAGTTCAAGGGCAAG
GCCACATTGACTGTTGACAAGTCCTCCAGCACAGCCTACATGGAGCTCCGCAGCCTGACATCTGAGG
ATTCTGCAGTCTATTACTGTGCAAGACCCGGGGGGTACGACGTGGGTTACTATGCTATGGACTACTG
GGGTCAAGGAACCTCAGTCACCGTCTCCTCA

Amino acid sequence of variable region of B1 antibody heavy chain (SEQ ID NO: 21)

EVQLQQSGPELVKPGASVKISCKTS<u>GYTFTEYTMH</u>WVQQSHGKSLEWIG<u>GVNPNSGDTS</u>YNQKFKGK
ATLTVDKSSTAYMELRSLTSEDSAVYYCAR<u>PGGYDVGYYAMDY</u>WGQGTSVTVSS

Figure 20

Nucleotide sequence of cDNA encoding variable region of C7 antibody light chain (SEQ ID NO: 22)

GATATCCAGATGACACAGACTGCATCCTCCCTGTCTGCCTCTCTTGGAGACAGAGTCACCATCAGTT
GCAGGGCAAGTCAGGACATTAACAATTATTTAAACTGGTATCAGCAGAAACCAGATGGAACTGTTAA
ACTCCTGATCTACTCCACATCAAGATTACACTCAGGAGTCCCATCAAGGTTCAGTGGCAGTGGGTCT
GGAACACATTATTCTCTCACCATTACTCACCTGGAACAAGAAGATATTGCCACTTACTTTTGCCAAC
AGGGTTATCCGCTTCCGTGGACGTTCGGTGGAGGCACCAAACTGGAAATCAAA

Amino acid sequence of variable region of C7 antibody light chain (SEQ ID NO: 23)

DIQMTQTASSLSASLGDRVTISC<u>RASQDINNYLN</u>WYQQKPDGTVKLLIY<u>STSRLHS</u>GVPSRFSGSGS
GTHYSLTITHLEQEDIATYFC<u>QQGYPLPWT</u>FGGGTKLEIK

Figure 21

Nucleotide sequence of cDNA encoding variable region of C7 antibody heavy chain (SEQ ID NO: 24)

GAGGTCCAGCTTCAACAGTCTGGACCTGAACTGGTGAAGCCTGGGGCTTCAGTGAAGATATCCTGCA
AGACTTCTGGATACACATTCACTGAATACACCATGCACTGGGTGCAGCAGAGCCATGGAAAGAGCCT
TGAGTGGATTGGAGGTGTTAATCCTAATAGTGGTGATACTAGCTACAACCAGAAGTTCAAGGGCAAG
GCCACATTGACTGTTGACAAGTCCTCCAGCACAGCCTACATGGAGCTCCGCAGCCTGACATCTGAGG
ATTCTGCAGTCTATTACTGTGCAAGACCCGGGGGGTACGACGTGGGTTACTATGCTATGGACTACTG
GGGTCAAGGAACCTCAGTCACCGTCTCCTCA

Amino acid sequence of variable region of C7 antibody heavy chain (SEQ ID NO: 25)

EVQLQQSGPELVKPGASVKISCKTSGYTFTEYTMH<u>WVQQSHGKSLEWIGGVNPNSGDTSYNQKFKGK</u>
ATLTVDKSSSTAYMELRSLTSEDSAVYYCA<u>RPGGYDVGYYAMDY</u>WGQGTSVTVSS

Figure 22

Amino acid sequence of chB1 light chain (SEQ ID NO: 28)

MVLQTQVFISLLLWISGAYGDIQMTQTASSLSASLGDRVTISCRASQDINNYLNWYQQKPDGTVKLL
IYFTSRLHSGVPSRFSGSGSGTHYSLTITNLEQEDIATYFCQQGYPLPWTFGGGTKLEIKRAVAAPS
VFIFPPSDEQLKSGTASVVCLLNNFYPREAKVQWKVDNALQSGNSQESVTEQDSKDSTYSLSSTLTL
SKADYEKHKVYACEVTHQGLSSPVTKSFNRGEC

Signal sequence (1 - 20), Light chain variable region (21 - 127), Light chain constant region (128 - 234)

DNA fragment including DNA sequence encoding amino acid sequence of chB1 light chain (SEQ ID NO: 29)

ccagcctccggactctagagccaccATGGTGCTGCAGACCCAGGTGTTCATCAGCCTGCTGCTGTGG
ATCAGCGGCGCCTACGGCGACATCCAGATGACCCAGACAGCCAGCAGCCTGAGCGCCAGCCTGGGCG
ATAGAGTGACCATCAGCTGCAGAGCCAGCCAGGACATCAACAACTACCTGAACTGGTATCAGCAGAA
ACCCGACGGCACCGTGAAGCTGCTGATCTACTTCACCAGCAGACTGCACAGCGGCGTGCCCAGCAGA
TTTTCTGGCAGCGGCTCTGGCACCCACTACAGCCTGACCATCACCAACCTGGAACAGGAAGATATCG
CTACCTACTTCTGTCAGCAAGGCTACCCCCTGCCCTGGACCTTTGGCGGCGGAACAAAGCTGGAAAT
CAAGCGGGCCGTGGCCGCTCCCTCCGTGTTCATCTTTCCACCCAGCGACGAGCAGCTGAAGTCCGGC
ACAGCTAGCGTCGTGTGCCTGCTGAACAACTTCTACCCCGCGAGGCCAAGGTGCAGTGGAAGGTGG
ACAATGCCCTGCAGAGCGGCAACAGCCAGGAAAGCGTGACCGAGCAGGACAGCAAGGACTCCACCTA
CTCCCTGAGCAGCACCCTGACCCTGAGCAAGGCCGACTACGAGAAGCACAAGGTGTACGCCTGCGAA
GTGACCCACCAGGGCCTGTCTAGCCCCGTGACCAAGAGCTTCAACCGGGGCGAGTGTtgagtttaaa
cgggggaggctaact Signal sequence (26 - 85), Light chain variable region (86 - 406), Light chain constant region (407 - 727)

Figure 23

Amino acid sequence of variable region of chB1 light chain (SEQ ID NO: 30)

DIQMTQTASSLSASLGDRVTISCRASQDINNYLNWYQQKPDGTVKLLIYFTSRLHSGVPSRFSGSGS
GTHYSLTITNLEQEDIATYFCQQGYPLPWTFGGGTKLEIK

Nucleotide sequence encoding chB1 light chain variable region (SEQ ID NO: 31)

GACATCCAGATGACCCAGACAGCCAGCAGCCTGAGCGCCAGCCTGGGCGATAGAGTGACCATCAGCT
GCAGAGCCAGCCAGGACATCAACAACTACCTGAACTGGTATCAGCAGAAACCCGACGGCACCGTGAA
GCTGCTGATCTACTTCACCAGCAGACTGCACAGCGGCGTGCCCAGCAGATTTTCTGGCAGCGGCTCT
GGCACCCACTACAGCCTGACCATCACCAACCTGGAACAGGAAGATATCGCTACCTACTTCTGTCAGC
AAGGCTACCCCCTGCCCTGGACCTTTGGCGGCGGAACAAAGCTGGAAATCAAG

Figure 24

Amino acid sequence of chB1 heavy chain (SEQ ID NO: 32)

MKHLWFFLLLVAAPRWVLSEVQLQQSGPELVKPGASVKISCKTSGYTFTEYTMHWVQQSHGKSLEWI
GGVNPNSGDTSYNQKFKGKATLTVDKSSSTAYMELRSLTSEDSAVYYCARPGGYDVGYYAMDYWGQG
TSVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPEAAGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK

Signal sequence (1 - 19), Heavy chain variable region (20 - 141), Heavy chain constant region (142 - 471)

Nucleotide sequence encoding chB1 heavy chain (SEQ ID NO: 33)

ATGAAACACCTGTGGTTCTTCCTCCTGCTGGTGGCAGCTCCCAGATGGGTGCTGAGCGAAGTGCAGC
TGCAGCAGTCTGGCCCCGAGCTCGTGAAACCTGGCGCCTCCGTGAAGATCAGCTGCAAGACCAGCGG
CTACACCTTCACCGAGTACACCATGCACTGGGTGCAGCAGAGCCACGGCAAGAGCCTGGAATGGATC
GGCGGCGTGAACCCCAACAGCGGCGACACCAGCTACAACCAGAAGTTCAAGGGCAAGGCCACCCTGA
CCGTGGACAAGAGCAGCAGCACCGCCTACATGGAACTGCGGAGCCTGACCAGCGAGGACAGCGCCGT
GTACTACTGTGCCAGACCTGGCGGCTACGACGTGGGCTACTACGCCATGGATTACTGGGGCCAGGGC
ACCAGCGTGACCGTCAGCTCAGCCTCCACCAAGGGCCCAAGCGTCTTCCCCCTGGCACCCTCCTCCA
AGAGCACCTCTGGCGGCACAGCCGCCCTGGGCTGCCTGGTCAAGGACTACTTCCCCGAACCCGTGAC
CGTGAGCTGGAACTCAGGCGCCCTGACCAGCGGCGTGCACACCTTCCCCGCTGTCCTGCAGTCCTCA
GGACTCTACTCCCTCAGCAGCGTGGTGACCGTGCCCTCCAGCAGCTTGGGCACCCAGACCTACATCT
GCAACGTGAATCACAAGCCCAGCAACACCAAGGTGGACAAGAGAGTTGAGCCCAAATCTTGTGACAA
AACTCACACATGCCCACCCTGCCCAGCACCTGAAGCCGCGGGGGGACCCTCAGTCTTCCTCTTCCCC
CCAAAACCCAAGGACACCCTCATGATCTCCCGGACCCCTGAGGTCACATGCGTGGTGGTGGACGTGA
GCCACGAAGACCCTGAGGTCAAGTTCAACTGGTACGTGGACGGCGTGGAGGTGCATAATGCCAAGAC
AAAGCCCCGGGAGGAGCAGTACAACAGCACGTACCGGGTGGTCAGCGTCCTCACCGTCCTGCACCAG
GACTGGCTGAATGGCAAGGAGTACAAGTGCAAGGTCTCCAACAAAGCCCTCCCAGCCCCCATCGAGA
AAACCATCTCCAAAGCCAAAGGCCAGCCCCGGGAACCACAGGTGTACACCCTGCCCCCATCCCGGGA
GGAGATGACCAAGAACCAGGTCAGCCTGACCTGCCTGGTCAAAGGCTTCTATCCCAGCGACATCGCC
GTGGAGTGGGAGAGCAATGGCCAGCCGGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTT
CTCATGCTCCGTGATGCATGAGGCTCTGCACAACCACTACACCCAGAAGAGCCTCTCCCTGTCTCCC
GGCAAA

Signal sequence (1 - 57), Heavy chain variable region (58 - 423), Heavy chain constant region (424 - 1413)

Figure 25

Amino acid sequence of variable region of chB1 heavy chain (SEQ ID NO: 34)

EVQLQQSGPELVKPGASVKISCKTSGYTFTEYTMHWVQQSHGKSLEWIGGVNPNSGDTSYNQKFKGK
ATLTVDKSSSTAYMELRSLTSEDSAVYYCARPGGYDVGYYAMDYWGQGTSVTVSS

Nucleotide sequence encoding variable region of chB1 heavy chain (SEQ ID NO: 35)
GAAGTGCAGCTGCAGCAGTCTGGCCCCGAGCTCGTGAAACCTGGCGCCTCCGTGAAGATCAGCTGCA
AGACCAGCGGCTACACCTTCACCGAGTACACCATGCACTGGGTGCAGCAGAGCCACGGCAAGAGCCT
GGAATGGATCGGCGGCGTGAACCCCAACAGCGGCGACACCAGCTACAACCAGAAGTTCAAGGGCAAG
GCCACCCTGACCGTGGACAAGAGCAGCAGCACCGCCTACATGGAACTGCGGAGCCTGACCAGCGAGG
ACAGCGCCGTGTACTACTGTGCCAGACCTGGCGGCTACGACGTGGGCTACTACGCCATGGATTACTG
GGGCCAGGGCACCAGCGTGACCGTCAGCTCA

Figure 26

Amino acid sequence of humanized antibody light chain hL1 (SEQ ID NO: 36)

MVLQTQVFISLLLWISGAYGDIQMTQSPSSLSASVGDRVTITCRASQDINNYLNWYQQKPGKAPKLL
IYFTSRLHSGVPSRFSGSGSGTDYTLTISSLQPEDFATYYCQQGYPLPWTFGQGTKVEIKRTVAAPS
VFIFPPSDEQLKSGTASVVCLLNNFYPREAKVQWKVDNALQSGNSQESVTEQDSKDSTYSLSSTLTL
SKADYEKHKVYACEVTHQGLSSPVTKSFNRGEC

Signal sequence (1 - 20), Light chain variable region (21 - 127), Light chain constant region (128 - 234)

Nucleotide sequence encoding humanized antibody light chain hL1 (SEQ ID NO: 37)
ATGGTGCTGCAGACCCAGGTGTTCATCTCCCTGCTGCTGTGGATCTCCGGCGCGTACGGCGACATCC
AGATGACCCAGAGCCCTAGCAGCCTGAGCGCCAGCGTGGGCGACAGAGTGACCATCACCTGTAGAGC
CAGCCAGGACATCAACAACTACCTGAACTGGTATCAGCAGAAGCCCGGCAAGGCCCCCAAGCTGCTG
ATCTACTTCACCAGCAGACTGCACAGCGGCGTGCCCAGCAGATTTTCTGGCAGCGGCTCCGGCACCG
ACTACACCCTGACAATCAGCAGCCTGCAGCCCGAGGACTTCGCCACCTACTACTGCCAGCAGGGCTA
CCCCCTGCCTTGGACATTTGGCCAGGGCACCAAGGTGGAAATCAAGCGTACGGTGGCCGCCCCCTCC
GTGTTCATCTTCCCCCCCTCCGACGAGCAGCTGAAGTCCGGCACCGCCTCCGTGGTGTGCCTGCTGA
ATAACTTCTACCCCAGAGAGGCCAAGGTGCAGTGGAAGGTGGACAACGCCCTGCAGTCCGGGAACTC
CCAGGAGAGCGTGACCGAGCAGGACAGCAAGGACAGCACCTACAGCCTGAGCAGCACCCTGACCCTG
AGCAAAGCCGACTACGAGAAGCACAAGGTGTACGCCTGCGAGGTGACCCACCAGGGCCTGAGCTCCC
CCGTCACCAAGAGCTTCAACAGGGGGGAGTGT Signal sequence (1 - 60), Light chain variable region (61 - 381), Light chain constant region (382 - 702)

Figure 27

Amino acid sequence of variable region of humanized antibody light chain hL1 (SEQ ID NO: 38)

```
DIQMTQSPSSLSASVGDRVTITCRASQDINNYLNWYQQKPGKAPKLLIYFTSRLHSGVPSRFSGSGS
GTDYTLTISSLQPEDFATYYCQQGYPLPWTFGQGTKVEIK
```

Nucleotide sequence encoding variable region of humanized antibody light chain hL1 (SEQ ID NO: 39)

```
GACATCCAGATGACCCAGAGCCCTAGCAGCCTGAGCGCCAGCGTGGGCGACAGAGTGACCATCACCT
GTAGAGCCAGCCAGGACATCAACAACTACCTGAACTGGTATCAGCAGAAGCCCGGCAAGGCCCCCAA
GCTGCTGATCTACTTCACCAGCAGACTGCACAGCGGCGTGCCCAGCAGATTTTCTGGCAGCGGCTCC
GGCACCGACTACACCCTGACAATCAGCAGCCTGCAGCCCGAGGACTTCGCCACCTACTACTGCCAGC
AGGGCTACCCCCTGCCTTGGACATTTGGCCAGGGCACCAAGGTGGAAATCAAG
```

Figure 28

Amino acid sequence of humanized antibody light chain hL2 (SEQ ID NO: 40)

```
MVLQTQVFISLLLWISGAYGDIQMTQSPSSLSASVGDRVTITCRASQDINNYLNWYQQKPGKAVKLL
IYFTSRLHSGVPSRFSGSGSGTHYTLTISSLQPEDFATYYCQQGYPLPWTFGQGTKVEIKRTVAAPS
VFIFPPSDEQLKSGTASVVCLLNNFYPREAKVQWKVDNALQSGNSQESVTEQDSKDSTYSLSSTLTL
SKADYEKHKVYACEVTHQGLSSPVTKSFNRGEC
```

Signal sequence (1 - 20), Light chain variable region (21 - 127), Light chain constant region (128 - 234)

Nucleotide sequence encoding humanized antibody light chain hL2 (SEQ ID NO: 41)

```
ATGGTGCTGCAGACCCAGGTGTTCATCTCCCTGCTGCTGTGGATCTCCGGCGCGTACGGCGACATCC
AGATGACCCAGAGCCCTAGCAGCCTGAGCGCCAGCGTGGGCGACAGAGTGACCATCACCTGTAGAGC
CAGCCAGGACATCAACAACTACCTGAACTGGTATCAGCAGAAACCCGGCAAGGCCGTGAAGCTGCTG
ATCTACTTCACCAGCAGACTGCACAGCGGCGTGCCCAGCAGATTTTCTGGCAGCGGCTCTGGCACCC
ACTACACCCTGACAATCAGCAGCCTGCAGCCCGAGGACTTCGCCACCTACTACTGCCAGCAGGGCTA
CCCCCTGCCTTGGACATTTGGCCAGGGCACCAAGGTGGAAATCAAGCGTACGGTGGCCGCCCCCTCC
GTGTTCATCTTCCCCCCCTCCGACGAGCAGCTGAAGTCCGGCACCGCCTCCGTGGTGTGCCTGCTGA
ATAACTTCTACCCCAGAGAGGCCAAGGTGCAGTGGAAGGTGGACAACGCCCTGCAGTCCGGGAACTC
CCAGGAGAGCGTGACCGAGCAGGACAGCAAGGACAGCACCTACAGCCTGAGCAGCACCCTGACCCTG
AGCAAAGCCGACTACGAGAAGCACAAGGTGTACGCCTGCGAGGTGACCCACCAGGGCCTGAGCTCCC
CCGTCACCAAGAGCTTCAACAGGGGGGAGTGT
```

Signal sequence (1 - 60), Light chain variable region (61 - 381), Light chain constant region (382 - 702)

Figure 29

Amino acid sequence of variable region of humanized antibody light chain hL2 (SEQ ID NO: 42)

DIQMTQSPSSLSASVGDRVTITC<u>RASQDINNYLN</u>WYQQKPGKAVKLLIY<u>FTSRLHS</u>GVPSRFSGSGS
GTHYTLTISSLQPEDFATYYC<u>QQGYPLPWT</u>FGQGTKVEIK

Nucleotide sequence encoding variable region of humanized antibody light chain hL2 (SEQ ID NO: 43)

GACATCCAGATGACCCAGAGCCCTAGCAGCCTGAGCGCCAGCGTGGGCGACAGAGTGACCATCACCT
GTAGAGCCAGCCAGGACATCAACAACTACCTGAACTGGTATCAGCAGAAACCCGGCAAGGCCGTGAA
GCTGCTGATCTACTTCACCAGCAGACTGCACAGCGGCGTGCCCAGCAGATTTTCTGGCAGCGGCTCT
GGCACCCACTACACCCTGACAATCAGCAGCCTGCAGCCCGAGGACTTCGCCACCTACTACTGCCAGC
AGGGCTACCCCCTGCCTTGGACATTTGGCCAGGGCACCAAGGTGGAAATCAAG

Figure 30

Amino acid sequence of humanized antibody light chain hL3 (SEQ ID NO: 44)

MVLQTQVFISLLLWISGAYGDIQMTQSPSSLSASVGDRVTITC<u>RASQDINNYLN</u>WYQQKPGGAVKLL
IY<u>FTSRLHS</u>GVPSRFSGSGSGTDYTLTISSLQPEDFATYYC<u>QQGYPLPWT</u>FGGGTKVEIKRTVAAPS
VFIFPPSDEQLKSGTASVVCLLNNFYPREAKVQWKVDNALQSGNSQESVTEQDSKDSTYSLSSTLTL
SKADYEKHKVYACEVTHQGLSSPVTKSFNRGEC

Signal sequence (1 - 20), Light chain variable region (21 - 127), Light chain constant region (128 - 234)

Nucleotide sequence encoding humanized antibody light chain hL3 (SEQ ID NO: 45)

ATGGTGCTGCAGACCCAGGTGTTCATCTCCCTGCTGCTGTGGATCTCCGGCGCGTACGGCGACATCC
AGATGACCCAGAGCCCTAGCAGCCTGAGCGCCAGCGTGGGCGACAGAGTGACCATCACCTGTAGAGC
CAGCCAGGACATCAACAACTACCTGAACTGGTATCAGCAGAAACCCGGCGGAGCCGTGAAGCTGCTG
ATCTACTTCACCAGCAGACTGCACAGCGGCGTGCCCAGCAGATTTTCTGGCAGCGGCTCCGGCACCG
ACTACACCCTGACAATCAGCAGCCTGCAGCCCGAGGACTTCGCCACCTACTACTGCCAGCAGGGCTA
CCCCCTGCCCTGGACATTTGGCGGCGGAACAAAGGTGGAAATCAAGCGTACGGTGGCCGCCCCCTCC
GTGTTCATCTTCCCCCCCTCCGACGAGCAGCTGAAGTCCGGCACCGCCTCCGTGGTGTGCCTGCTGA
ATAACTTCTACCCCAGAGAGGCCAAGGTGCAGTGGAAGGTGGACAACGCCCTGCAGTCCGGGAACTC
CCAGGAGAGCGTGACCGAGCAGGACAGCAAGGACAGCACCTACAGCCTGAGCAGCACCCTGACCCTG
AGCAAAGCCGACTACGAGAAGCACAAGGTGTACGCCTGCGAGGTGACCCACCAGGGCCTGAGCTCCC
CCGTCACCAAGAGCTTCAACAGGGGGGAGTGT

Signal sequence (1 - 60), Light chain variable region (61 - 381), Light chain constant region (382 - 702)

Figure 31

Amino acid sequence of variable region of humanized antibody light chain hL3 (SEQ ID NO: 46)

DIQMTQSPSSLSASVGDRVTITC<u>RASQDINNYLN</u>WYQQKPGGAVKLLIY<u>FTSRLHS</u>GVPSRFSGSGS
GTDYTLTISSLQPEDFATYYC<u>QQGYPLPWT</u>FGGGTKVEIK

Nucleotide sequence encoding variable region of humanized antibody light chain hL3 (SEQ ID NO: 47)

GACATCCAGATGACCCAGAGCCCTAGCAGCCTGAGCGCCAGCGTGGGCGACAGAGTGACCATCACCT
GTAGAGCCAGCCAGGACATCAACAACTACCTGAACTGGTATCAGCAGAAACCCGGCGGAGCCGTGAA
GCTGCTGATCTACTTCACCAGCAGACTGCACAGCGGCGTGCCCAGCAGATTTCTGGCAGCGGCTCC
GGCACCGACTACACCCTGACAATCAGCAGCCTGCAGCCCGAGGACTTCGCCACCTACTACTGCCAGC
AGGGCTACCCCCTGCCCTGGACATTTGGCGGCGGAACAAAGGTGGAAATCAAG

Figure 32

Amino acid sequence of humanized antibody light chain hL4 (SEQ ID NO: 48)

MVLQTQVFISLLLWISGAYGDIQMTQSPSSLSASVGDRVTITC<u>RASQDINNYLN</u>WYQQKPGGAVKLL
IY<u>FTSRLHS</u>GVPSRFSGSGSGTDYTLTISSLQPEDFATYYC<u>QQGNTLPWT</u>FGGGTKVEIKRTVAAPS
VFIFPPSDEQLKSGTASVVCLLNNFYPREAKVQWKVDNALQSGNSQESVTEQDSKDSTYSLSSTLTL
SKADYEKHKVYACEVTHQGLSSPVTKSFNRGEC

Signal sequence (1 - 20), Light chain variable region (21 - 127), Light chain constant region (128 - 234)

Nucleotide sequence encoding humanized antibody light chain hL4 (SEQ ID NO: 49)

ATGGTGCTGCAGACCCAGGTGTTCATCTCCCTGCTGCTGTGGATCTCCGGCGCGTACGGCGACATCC
AGATGACCCAGAGCCCTAGCAGCCTGAGCGCCAGCGTGGGCGACAGAGTGACCATCACCTGTAGAGC
CAGCCAGGACATCAACAACTACCTGAACTGGTATCAGCAGAAACCCGGCGGAGCCGTGAAGCTGCTG
ATCTACTTCACCAGCAGACTGCACAGCGGCGTGCCCAGCAGATTTCTGGCAGCGGCTCCGGCACCG
ACTACACCCTGACAATCAGCAGCCTGCAGCCCGAGGACTTCGCCACCTACTACTGCCAGCAGGGCAA
CACCCTGCCCTGGACATTTGGCGGAGGCACCAAGGTGGAAATCAAGCGTACGGTGGCCGCCCCCTCC
GTGTTCATCTTCCCCCCTCCGACGAGCAGCTGAAGTCCGGCACCGCCTCCGTGGTGTGCCTGCTGA
ATAACTTCTACCCCAGAGAGGCCAAGGTGCAGTGGAAGGTGGACAACGCCCTGCAGTCCGGGAACTC
CCAGGAGAGCGTGACCGAGCAGGACAGCAAGGACAGCACCTACAGCCTGAGCAGCACCCTGACCCTG
AGCAAAGCCGACTACGAGAAGCACAAGGTGTACGCCTGCGAGGTGACCCACCAGGGCCTGAGCTCCC
CCGTCACCAAGAGCTTCAACAGGGGGGAGTGT

Signal sequence (1 - 60), Light chain variable region (61 - 381), Light chain constant region (382 - 702)

Figure 33

Amino acid sequence of variable region of humanized antibody light chain hL4 (SEQ ID NO: 50)

DIQMTQSPSSLSASVGDRVTITCRASQDINNYLNWYQQKPGGAVKLLIYETSRLHSGVPSRFSGSGS
GTDYTLTISSLQPEDFATYCQQGNTLPWTFGGGTKVEIK

Nucleotide sequence encoding variable region of humanized antibody light chain hL4 (SEQ ID NO: 51)

GACATCCAGATGACCCAGAGCCCTAGCAGCCTGAGCGCCAGCGTGGGCGACAGAGTGACCATCACCT
GTAGAGCCAGCCAGGACATCAACAACTACCTGAACTGGTATCAGCAGAAACCCGGGAGCCGTGAA
GCTGCTGATCTACTTCACCAGCACTGCACAGACTGCCCAGCGGCGTGCCCAGCAGCCTGGAGGCTCC
GGCACCGACTACACCCTGACAATCAGCAGCCTGCAGCCCGAGGACTTCGCCACCTACTACTGCCAGC
AGGGCAACACCCTGCCCTGGACATTTGGCGGAGGCACCAAGGTGGAAATCAAG

Figure 34

Amino acid sequence of humanized antibody heavy chain hH1 (SEQ ID NO: 52)
MKHLWFFLLLVAAPRWVLSQVQLVQSGAEVKKPGASVKVSCKASGYTFTEYTMHWVRQAPGQGLEWM
GGVNPNSGDTSYAQKFQGRVTITADTSTSTAYMELSSLRSEDTAVYYCARPGGYDVGYYAMDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPEAAGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK Signal sequence (1 - 19), Heavy chain variable region (20 - 141), Heavy chain constant region (142 - 471)

Nucleotide sequence encoding humanized antibody heavy chain hH1 (SEQ ID NO: 53)
ATGAAACACCTGTGGTTCTTCCTCCTGCTGGTGGCAGCTCCCAGATGGGTGCTGAGCCAGGTGCAGC
TGGTGCAGTCTGGCGCCGAAGTGAAGAAACCAGGCGCCAGCGTGAAGGTGTCCTGCAAGGCCAGCGG
CTACACCTTTACCGAGTACACCATGCACTGGGTGCGCCAGGCTCCAGGCCAGGGACTGGAATGGATG
GGCGGCGTGAACCCCAACAGCGGCGATACAAGCTACGCCCAGAAATTCCAGGGCAGAGTGACCATCA
CCGCCGACACCAGCACCTCCACCGCCTACATGGAACTGAGCAGCCTGCGGAGCGAGGACACCGCCGT
GTACTACTGTGCTAGACCTGGCGGCTACGACGTGGGCTACTACGCCATGGATTACTGGGGCCAGGGC
ACCCTCGTGACCGTCAGCTCAGCCTCCACCAAGGGCCCAAGCGTCTTCCCCCTGGCACCCTCCTCCA
AGAGCACCTCTGGCGGCACAGCCGCCCTGGGCTGCCTGGTCAAGGACTACTTCCCCGAACCCGTGAC
CGTGAGCTGGAACTCAGGCGCCCTGACCAGCGGCGTGCACACCTTCCCCGCTGTCCTGCAGTCCTCA
GGACTCTACTCCCTCAGCAGCGTGGTGACCGTGCCCTCCAGCAGCTTGGGCACCCAGACCTACATCT
GCAACGTGAATCACAAGCCCAGCAACACCAAGGTGGACAAGAGAGTTGAGCCCAAATCTTGTGACAA
AACTCACACATGCCCACCCTGCCCAGCACCTGAAGCCGCGGGGGGACCCTCAGTCTTCCTCTTCCCC
CCAAAACCCAAGGACACCCTCATGATCTCCCGGACCCCTGAGGTCACATGCGTGGTGGTGGACGTGA
GCCACGAAGACCCTGAGGTCAAGTTCAACTGGTACGTGGACGGCGTGGAGGTGCATAATGCCAAGAC
AAAGCCCCGGGAGGAGCAGTACAACAGCACGTACCGGGTGGTCAGCGTCCTCACCGTCCTGCACCAG
GACTGGCTGAATGGCAAGGAGTACAAGTGCAAGGTCTCCAACAAAGCCCTCCCAGCCCCCATCGAGA
AAACCATCTCCAAAGCCAAAGGCCAGCCCCGGGAACCACAGGTGTACACCCTGCCCCCATCCCGGGA
GGAGATGACCAAGAACCAGGTCAGCCTGACCTGCCTGGTCAAAGGCTTCTATCCCAGCGACATCGCC
GTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTT
CTCATGCTCCGTGATGCATGAGGCTCTGCACAACCACTACACCCAGAAGAGCCTCTCCCTGTCTCCC
GGCAAA Signal sequence (1 - 57), Heavy chain variable region (58 - 423), Heavy chain constant region (424 - 1413)

Figure 35

Amino acid sequence of variable region of humanized antibody heavy chain hH1 (SEQ ID NO: 54)

QVQLVQSGAEVKKPGASVKVSCKASGYTFTEYTMHWVRQAPGQGLEWMGGVNPNSGDTSYAQKFQGR
VTITADTSTSTAYMELSSLRSEDTAVYYCARPGGYDVGYYAMDYWGQGTLVTVSS

Nucleotide sequence encoding variable region of humanized antibody heavy chain hH1 (SEQ ID NO: 55)

CAGGTGCAGCTGGTGCAGTCTGGGGCGCCAGAAGTGAAGAAACCAGGGCCCAGCGTGAAGGTGTCCTGCA
AGGCCAGCGGCTACACCTTTACCGAGTACACCATGCACTGGGTGCGCCAGGCTCCAGGCCAGGGACT
GGAATGGGCGGGCGTGAACCCCAACAGCGGCGATACAAGCTACGCCCAGAAATTCCAGGGCAGA
GTGACCATCACCGCCGACACCAGCACCTCCACCGCCTACATGGAACTGAGCAGCCTGCGGAGCGAGG
ACACCGCCGTGTACTACTGTGCTAGACCTGGCGGCTACGACGTGGGCTACTACGCCATGGATTACTG
GGGCCAGGGCACCCTCGTGACCGTCAGCTCA

Figure 36

Amino acid sequence of humanized antibody heavy chain hH2 (SEQ ID NO: 56)
MKHLWFFLLLVAAPRWVLSEVQLVQSGAEVKKPGASVKVSCKTSGYTFTEYTMHWVRQAPGKSLEWM
GGVNPNSGDTSYAQKFQGRVTITADTSTSTAYMELSSLRSEDTAVYYCARPGGYDVGYYAMDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPEAAGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK Signal sequence (1 - 19), Heavy chain variable region (20 - 141), Heavy chain constant region (142 - 471)

Nucleotide sequence encoding humanized antibody heavy chain hH2 (SEQ ID NO: 57)
ATGAAACACCTGTGGTTCTTCCTCCTGCTGGTGGCAGCTCCCAGATGGGTGCTGAGCGAAGTGCAGC
TGGTGCAGTCTGGCGCCGAAGTGAAGAAACCAGGCGCCAGCGTGAAGGTGTCCTGCAAGACCAGCGG
CTACACCTTTACCGAGTACACCATGCACTGGGTGCGCCAGGCCCCTGGCAAGAGCCTGGAATGGATG
GGCGGCGTGAACCCCAACAGCGGCGATACAAGCTACGCCCAGAAATTCCAGGGCAGAGTGACCATCA
CCGCCGACACCAGCACCTCCACCGCCTACATGGAACTGAGCAGCCTGCGGAGCGAGGACACCGCCGT
GTACTACTGTGCTAGACCTGGCGGCTACGACGTGGGCTACTACGCCATGGATTACTGGGGCCAGGGC
ACCCTCGTGACCGTCAGCTCAGCCTCCACCAAGGGCCCAAGCGTCTTCCCCCTGGCACCCTCCTCCA
AGAGCACCTCTGGCGGCACAGCCGCCCTGGGCTGCCTGGTCAAGGACTACTTCCCCGAACCCGTGAC
CGTGAGCTGGAACTCAGGCGCCCTGACCAGCGGCGTGCACACCTTCCCCGCTGTCCTGCAGTCCTCA
GGACTCTACTCCCTCAGCAGCGTGGTGACCGTGCCCTCCAGCAGCTTGGGCACCCAGACCTACATCT
GCAACGTGAATCACAAGCCCAGCAACACCAAGGTGGACAAGAGAGTTGAGCCCAAATCTTGTGACAA
AACTCACACATGCCCACCCTGCCCAGCACCTGAAGCCGCGGGGGGACCCTCAGTCTTCCTCTTCCCC
CCAAAACCCAAGGACACCCTCATGATCTCCCGGACCCCTGAGGTCACATGCGTGGTGGTGGACGTGA
GCCACGAAGACCCTGAGGTCAAGTTCAACTGGTACGTGGACGGCGTGGAGGTGCATAATGCCAAGAC
AAAGCCCCGGGAGGAGCAGTACAACAGCACGTACCGGGTGGTCAGCGTCCTCACCGTCCTGCACCAG
GACTGGCTGAATGGCAAGGAGTACAAGTGCAAGGTCTCCAACAAAGCCCTCCCAGCCCCCATCGAGA
AAACCATCTCCAAAGCCAAAGGCCAGCCCCGGGAACCACAGGTGTACACCCTGCCCCCATCCCGGGA
GGAGATGACCAAGAACCAGGTCAGCCTGACCTGCCTGGTCAAAGGCTTCTATCCCAGCGACATCGCC
GTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTT
CTCATGCTCCGTGATGCATGAGGCTCTGCACAACCACTACACCCAGAAGAGCCTCTCCCTGTCTCCC
GGCAAA Signal sequence (1 - 57), Heavy chain variable region (58 - 423), Heavy chain constant region (424 - 1413)

Figure 37

Amino acid sequence of variable region of humanized antibody heavy chain hH2 (SEQ ID NO: 58)

EVQLVQSGAEVKKPGASVKVSCKTSGYTFTEYTMHWVRQAPGKSLEWMGGVNPNSGDTSYAQKFQGR
VTITADTSTSTAYMELSSLRSEDTAVYYCARPGGYDVGYYAMDYWGQGTLVTVSS

Nucleotide sequence encoding variable region of humanized antibody heavy chain hH2 (SEQ ID NO: 59)

GAAGTGCAGCTGGTGCAGTCTGGCGCCGAAGTGAAGAAACCAGGCGCCAGCGTGAAGGTGTCCTGCA
AGACCAGCGGCTACACCTTTACCGAGTACACCATGCACTGGGTGCGCCAGGCCCCTGGCAAGAGCCT
GGAATGGATGGGCGGCGTGAACCCCAACAGCGGCGATACAAGCTACGCCCAGAAATTCCAGGGCAGA
GTGACCATCACCGCCGACACCAGCACCTCCACCGCCTACATGGAACTGAGCAGCCTGCGCGAGCGAGG
ACACCGCCGTGTACTACTGTGCTAGACCTGGCGGCTACGACGTGGGCTACTACGCCATGGATTACTG
GGGCCAGGGCACCCTCGTGACCGTCAGCTCA

Figure 38

Amino acid sequence of humanized antibody heavy chain hH3 (SEQ ID NO: 60)
MKHLWFFLLLVAAPRWVLSEVQLVQSGAEVKKPGASVKVSCKTSGYTFTEYTMHWVRQAPGQGLEWM
GGVNPNSGDTSYAQKFQGRVTLTVDKSTSTAYMELSSLRSEDTAVYYCARPGGYDVGYYAMDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPEAAGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK Signal sequence (1 - 19), Heavy chain variable region (20 - 141), Heavy chain constant region (142 - 471)

Nucleotide sequence encoding humanized antibody heavy chain hH3 (SEQ ID NO: 61)
ATGAAACACCTGTGGTTCTTCCTCCTGCTGGTGGCAGCTCCCAGATGGGTGCTGAGCGAAGTGCAGC
TGGTGCAGTCTGGCGCCGAAGTGAAGAAACCAGGCGCCAGCGTGAAGGTGTCCTGCAAGACCAGCGG
CTACACCTTTACCGAGTACACCATGCACTGGGTGCGCCAGGCTCCAGGCCAGGGACTGGAATGGATG
GGCGGCGTGAACCCCAACAGCGGCGATACAAGCTACGCCCAGAAATTCCAGGGCAGAGTGACCCTGA
CCGTGGACAAGAGCACCAGCACCGCCTACATGGAACTGAGCAGCCTGCGGAGCGAGGACACCGCCGT
GTACTACTGTGCTAGACCTGGCGGCTACGACGTGGGCTACTACGCCATGGATTACTGGGGCCAGGGC
ACCCTCGTGACCGTCAGCTCAGCCTCCACCAAGGGCCCAAGCGTCTTCCCCCTGGCACCCTCCTCCA
AGAGCACCTCTGGCGGCACAGCCGCCCTGGGCTGCCTGGTCAAGGACTACTTCCCCGAACCCGTGAC
CGTGAGCTGGAACTCAGGCGCCCTGACCAGCGGCGTGCACACCTTCCCCGCTGTCCTGCAGTCCTCA
GGACTCTACTCCCTCAGCAGCGTGGTGACCGTGCCCTCCAGCAGCTTGGGCACCCAGACCTACATCT
GCAACGTGAATCACAAGCCCAGCAACACCAAGGTGGACAAGAGAGTTGAGCCCAAATCTTGTGACAA
AACTCACACATGCCCACCCTGCCCAGCACCTGAAGCCGCGGGGGGACCCTCAGTCTTCCTCTTCCCC
CCAAAACCCAAGGACACCCTCATGATCTCCCGGACCCCTGAGGTCACATGCGTGGTGGTGGACGTGA
GCCACGAAGACCCTGAGGTCAAGTTCAACTGGTACGTGGACGGCGTGGAGGTGCATAATGCCAAGAC
AAAGCCCCGGGAGGAGCAGTACAACAGCACGTACCGGGTGGTCAGCGTCCTCACCGTCCTGCACCAG
GACTGGCTGAATGGCAAGGAGTACAAGTGCAAGGTCTCCAACAAAGCCCTCCCAGCCCCCATCGAGA
AAACCATCTCCAAAGCCAAAGGCCAGCCCCGGGAACCACAGGTGTACACCCTGCCCCCATCCCGGGA
GGAGATGACCAAGAACCAGGTCAGCCTGACCTGCCTGGTCAAAGGCTTCTATCCCAGCGACATCGCC
GTGGAGTGGGAGAGCAATGGCCAGCCGGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTT
CTCATGCTCCGTGATGCATGAGGCTCTGCACAACCACTACACCCAGAAGAGCCTCTCCCTGTCTCCC
GGCAAA Signal sequence (1 - 57), Heavy chain variable region (58 - 423), Heavy chain constant region (424 - 1413)

Figure 39

Amino acid sequence of variable region of humanized antibody heavy chain hH3 (SEQ ID NO: 62)

EVQLVQSGAEVKKPGASVKVSCKTSGYTFTEYTMHWVRQAPGQGLEWMGGVNPNSGDTSYAQKFQGR VTLTVDKSTSTAYMELSSLRSEDTAVYYCARPGGYDVGYYAMDYWGQGTLVTVSS

Nucleotide sequence encoding variable region of humanized antibody heavy chain hH3 (SEQ ID NO: 63)

GAAGTGCAGCTGGTGCAGTCTGGGGCCGAAGTGAAGAAACCAGGCGCCAGCGTGAAGGTGTCCTGCA
AGACCAGCGGCTACACCTTTACCGAGTACACCATGCACTGGGTGCGCCAGGCTCCAGGCCAGGGACT
GGAATGGATGGGCGGCGTGAACCCCAACAGCGGCGATACAAGCTACGCCCAGAAATTCCAGGGCAGA
GTGACCCTGACCGTGGACAAGAGCACCAGCACCGCCTACATGGAACTGAGCAGCCTGCGGAGCGAGG
ACACCGCCGTGTACTACTGTGCTAGACCTGGCGGCTACGACGTGGGCTACTACGCCATGGATTACTG
GGGCCAGGGCACCCTCGTGACCGTCAGCTCA

Figure 43

Amino acid sequence of trastuzumab light chain (SEQ ID NO: 64)

DIQMTQSPSSLSASVGDRVTITCRASQDVNTAVAWYQQKPGKAPKLLIYSASFLYSGVPSRFSGSRS
GTDFTLTISSLQPEDFATYYCQQHYTTPPTFGQGTKVEIKRTVAAPSVFIFPPSDEQLKSGTASVVC
LLNNFYPREAKVQWKVDNALQSGNSQESVTEQDSKDSTYSLSSTLTLSKADYEKHKVYACEVTHQGL
SSPVTKSFNRGEC

Amino acid sequence of trastuzumab heavy chain (SEQ ID NO: 65)

EVQLVESGGGLVQPGGSLRLSCAASGFNIKDTYIHWVRQAPGKGLEWVARIYPTNGYTRYADSVKGR
FTISADTSKNTAYLQMNSLRAEDTAVYYCSRWGGDGFYAMDYWGQGTLVTVSSASTKGPSVFPLAPS
SKSTSGGTAALGCLVKDYFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPI
EKTISKAKGQPREPQVYTLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGK

Figure 44

Amino acid sequence of trastuzumab variant light chain (SEQ ID NO: 73)

MVLQTQVFISLLLWISGAYGDIQMTQSPSSLSASVGDRVTITCRASQDVNTAVAWYQQKPGKAPKLLIYSAS
FLYSGVPSRFSGSRSGTDFTLTISSLQPEDFATYYCQQHYTTPPTFGQGTKVEIKRTVAAPSVFIFPPSDEQ
LKSGTASVVCLLNNFYPREAKVQWKVDNALQSGNSQESVTEQDSKDSTYSLSSTLTLSKADYEKHKVYACEV
THQGLSSPVTKSFNRGEC

Signal sequence (1 - 20), Light chain variable region (21 - 127), Light chain constant region (128 - 234)

Amino acid sequence of trastuzumab variant heavy chain (SEQ ID NO: 75)

MKHLWFFLLLVAAPRWVLSEVQLVESGGGLVQPGGSLRLSCAASGFNIKDTYIHWVRQAPGKGLEWVARIYP
TNGYTRYADSVKGRFTISADTSKNTAYLQMNSLRAEDTAVYYCSRWGGDGFYAMDYWGQGTLVTVSSASTKG
PSVFPLAPSSKSTSGGTAALGCLVKDYFPEPVTVSWNSGALTSGVHTFPAVLQSSGLYSLSSVVTVPSSSLG
TQTYICNVNHKPSNTKVDKRVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLDSDGSFFLYSKL
TVDKSRWQQGNVFSCSVMHEALHNHYTQKSLSLSPGK

Signal sequence (1 - 19), Heavy chain variable region (20 - 139), Heavy chain constant region (140 - 469)

Figure 45

```
chB1_H  1 EVQLQQSGPELVKPGASVKISCKTSGYTFTEYTMHWVQQSHGKSLEWIGGVNPNSGDTSYNQKFKGKATL  70
hH1     1 .Q.....A.VK.......V...A..........R.AP.QG...M..................A...Q.RV.I  70
hH2     1 .......V.A.VK......V...A..........R.AP.....M..................A...Q.RV.I  70
hH3     1 .......V.A.VK......V..............R.AP.QG...M..................A...Q.RV..  70 chB1_H 71 TVDKSSSTAYMELRSLTSEDSAVYYCARPGGYDVGYYAMDYWGQGTSVTVSS           SEQ ID NO:34  122
hH1    71 .A.T..T........S..R....T.............................L.....  SEQ ID NO:54  122
hH2    71 .A.T..T........S..R....T.............................L.....  SEQ ID NO:58  122
hH3    71 ......T........S..R....T.............................L.....  SEQ ID NO:62  122
```

Figure 46

```
chB1_L   1 DIQMTQTASSLSASLGDRVTISCRASQDINNYLNWYQQKPDGTVKLLIYFTSRLHSGVPS  60
hL1      1 ..........SP.......V...T................................... 60
hL2      1 ..........SP.......V...T..........................GKAP..... 60
hL3      1 ..........SP.......V...T..........................GKA...... 60
hL4      1 ..........SP.......V...T..........................G.A...... 60 chB1_L  61 RFSGSGSGTHYSLTITNLEQEDIATYFCQQGYPLPWTFGGGTKLEIK SEQ ID NO:30 107
hL1     61 .........D.T...SS.QP...F...Y...........Q...V.. SEQ ID NO:38 107
hL2     61 .........D.T...SS.QP...F...Y...........Q...V.. SEQ ID NO:42 107
hL3     61 .........D.T...SS.QP...F...Y...............V.. SEQ ID NO:46 107
hL4     61 .........D.T...SS.QP...F...Y....NT..........V.. SEQ ID NO:50 107
```

[Formula 122]

(r1, r2) = any of (1, 0), (0, 1), and (1, 1)

[Formula 179]

[Formula 180]

[Formula 181]

[Formula 182]

[Formula 183]

[Formula 184]

[Formula 185]

[Formula 186]

[Formula 187]

[Formula 188]

[Formula 189]

[Formula 190]

[Formula 191]

[Formula 192]

[Formula 193]

Figure 66
[Formula 194]
R =
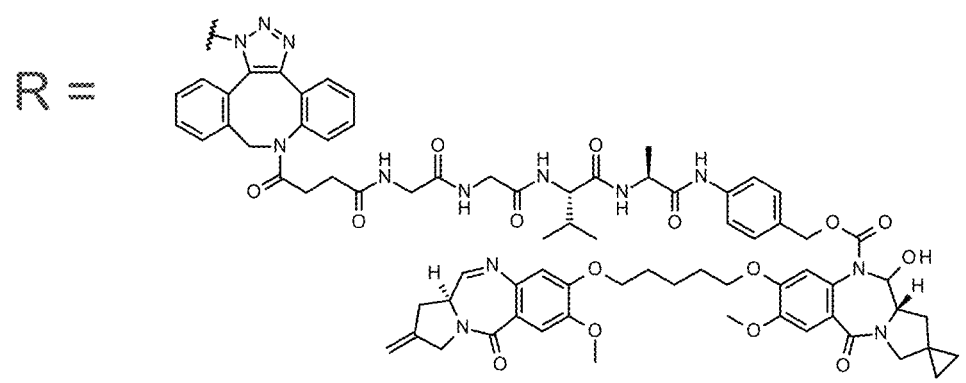
or
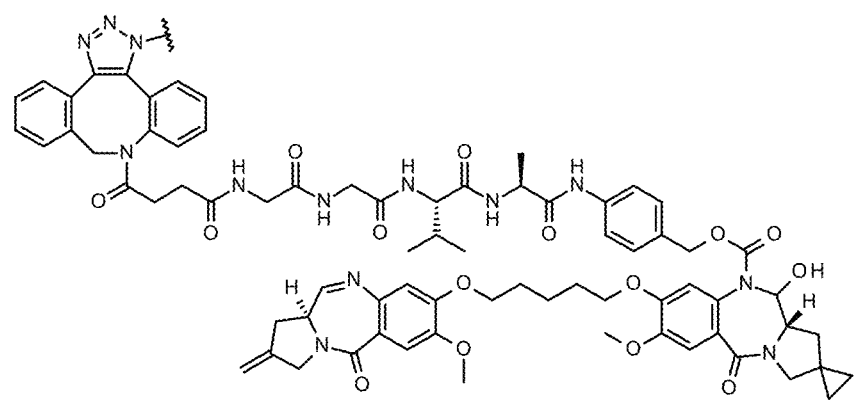

[Formula 233]

Figure 68
[Formula 234]
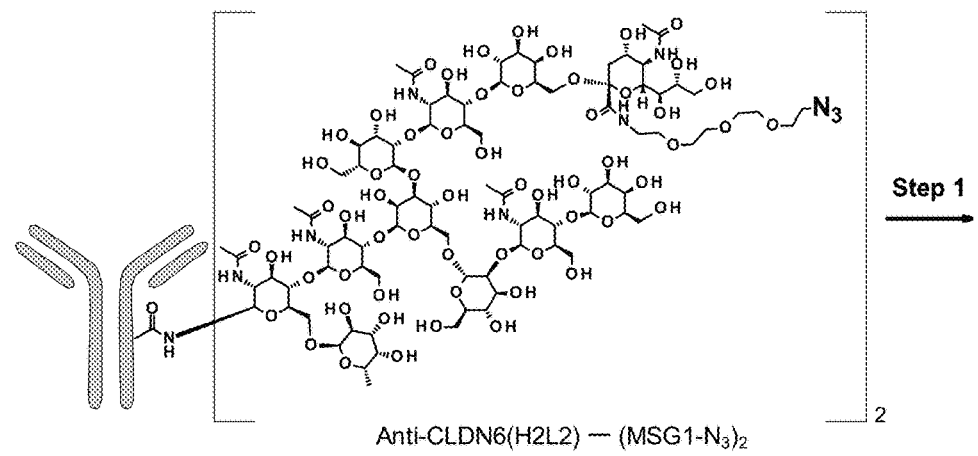
Anti-CLDN6(H2L2) — (MSG1-N₃)₂
Step 1
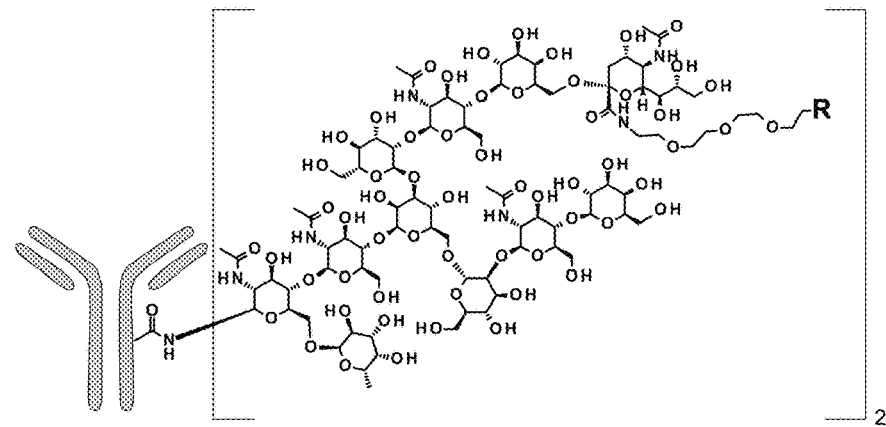
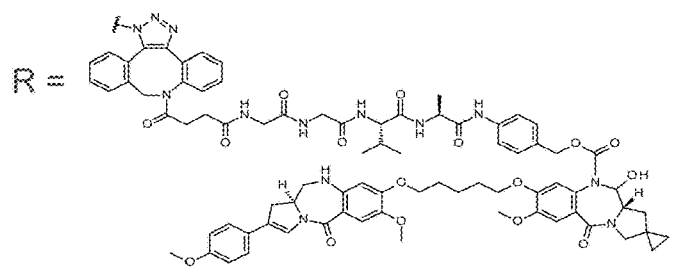
or

Figure 69
[Formula 235]
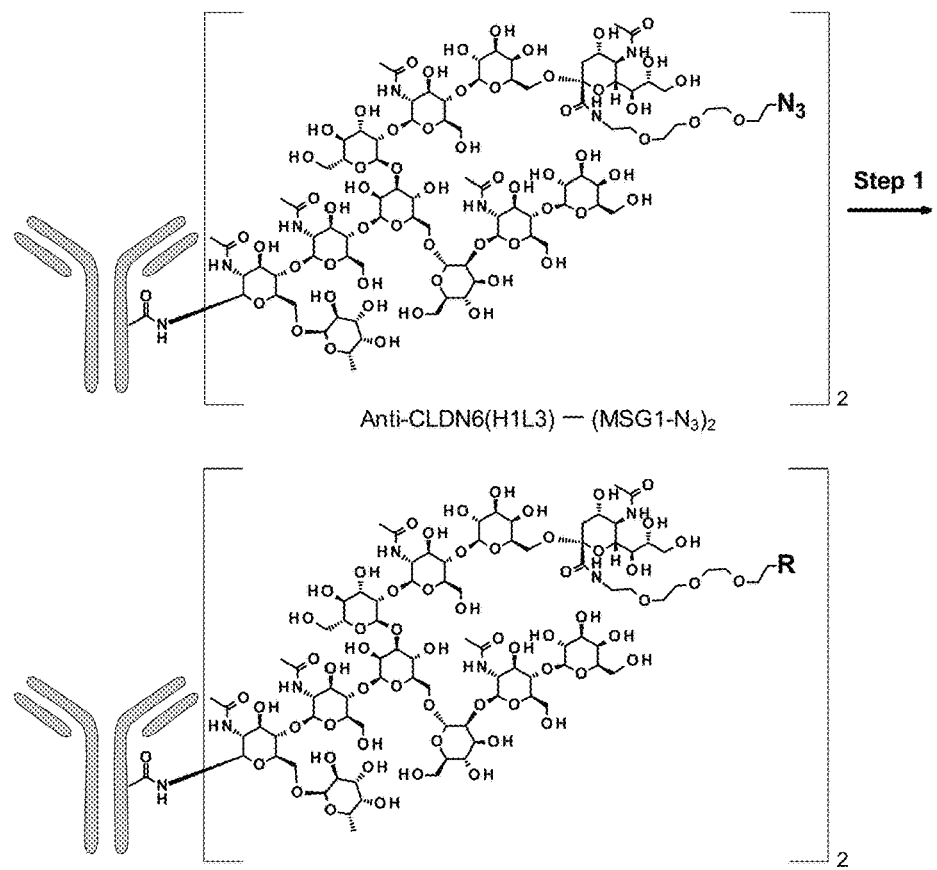
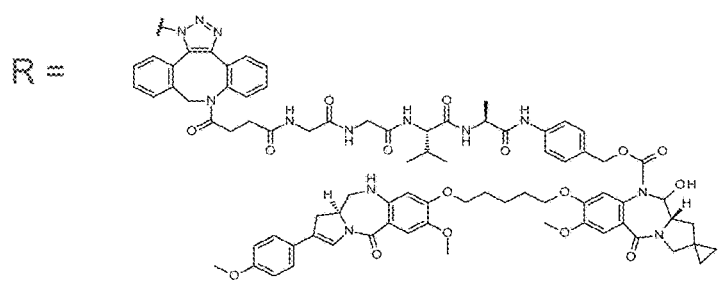
R =
or
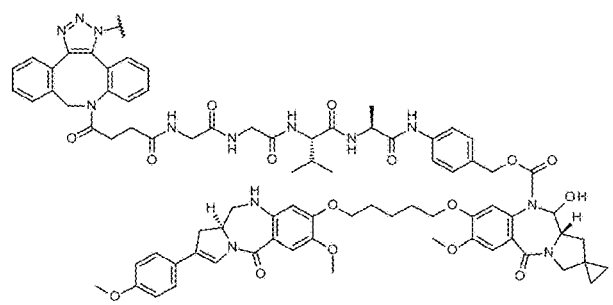

Figure 70
[Formula 243]
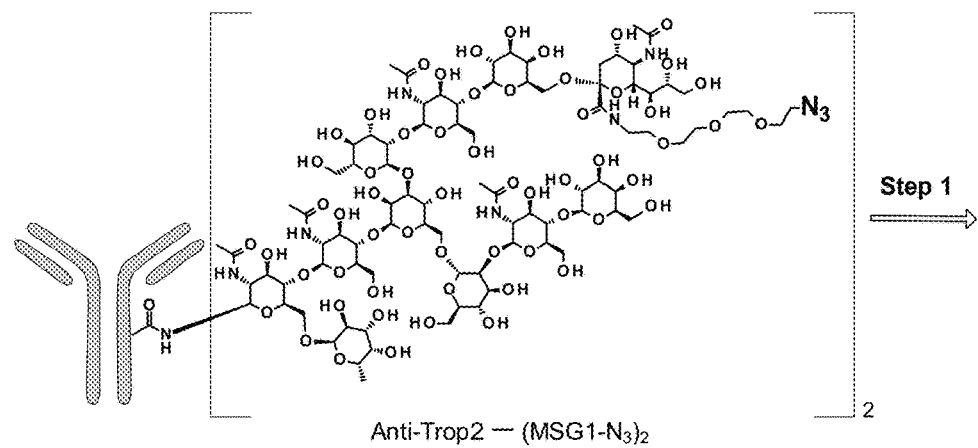
Anti-Trop2 — (MSG1-N₃)₂
Step 1
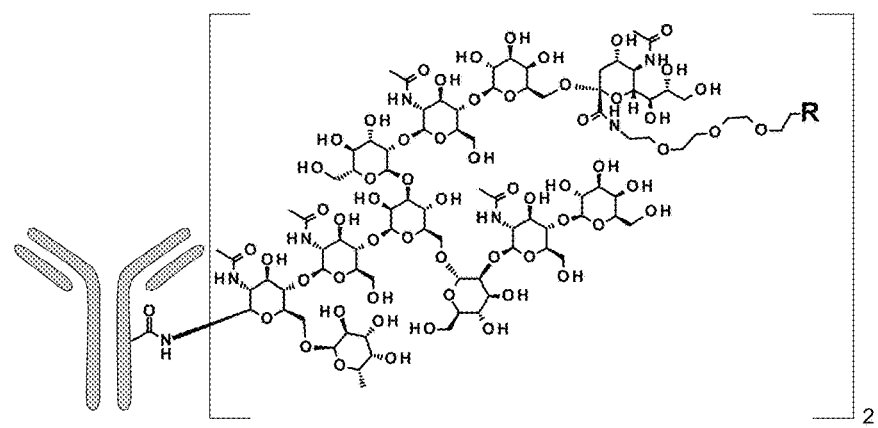
R =
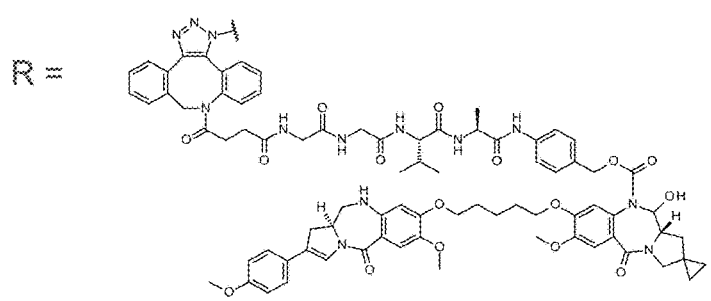
or
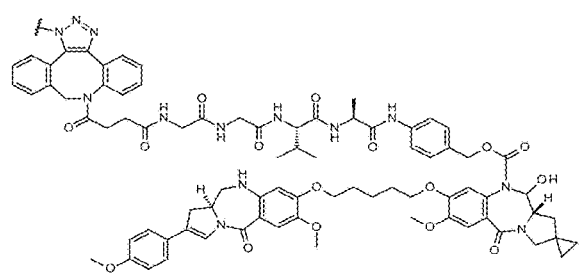

Figure 71
[Formula 244]
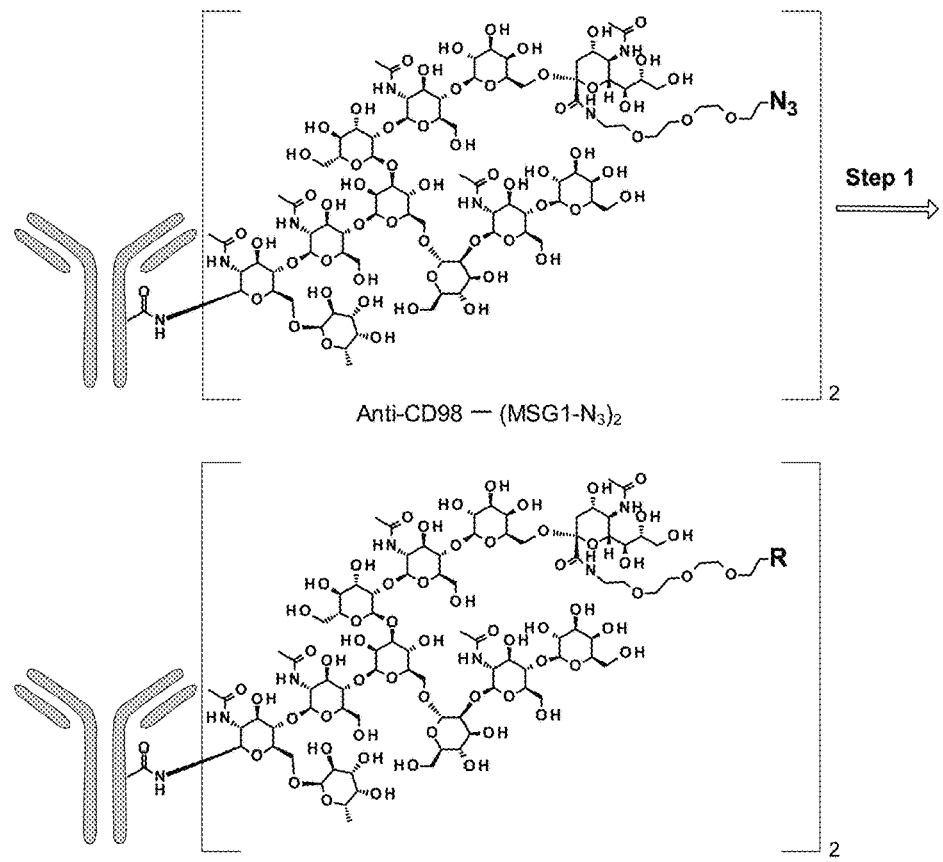
Anti-CD98 — (MSG1-N₃)₂
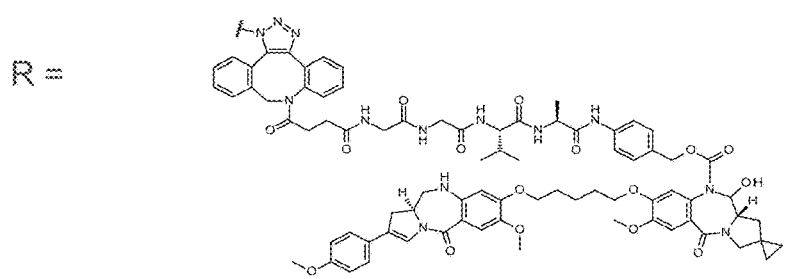
or
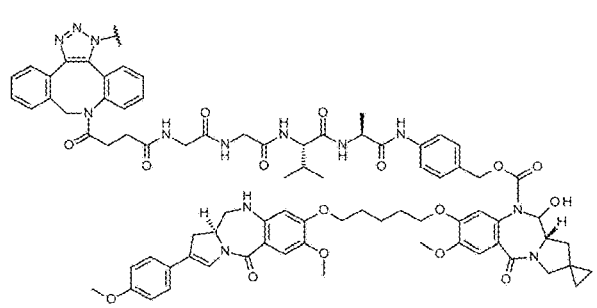

Figure 72
[Formula 246]
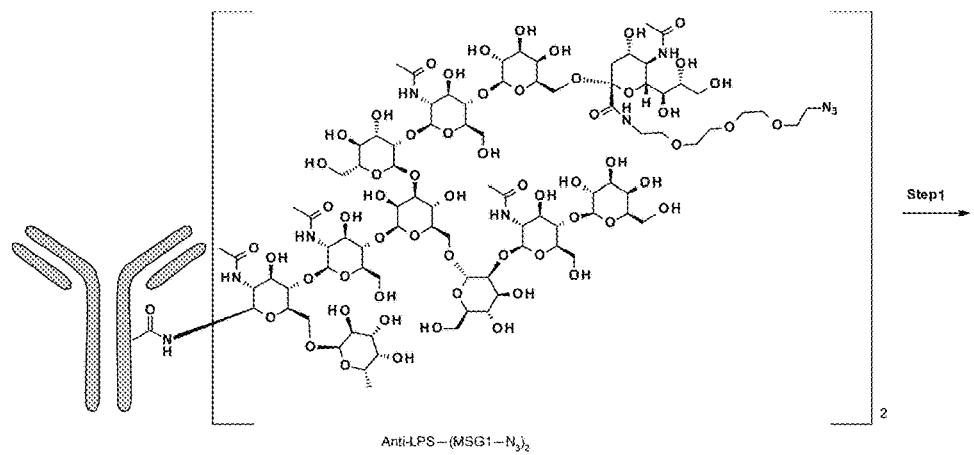
Anti-LPS—(MSG1—N₃)₂
Step1 →
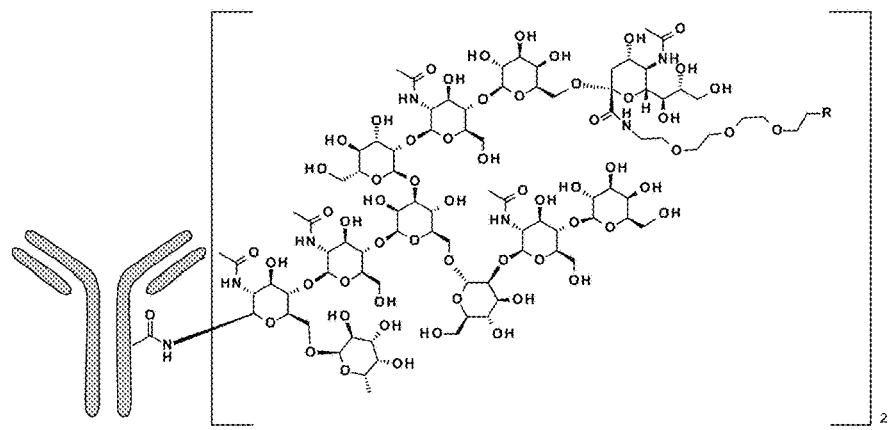
R =
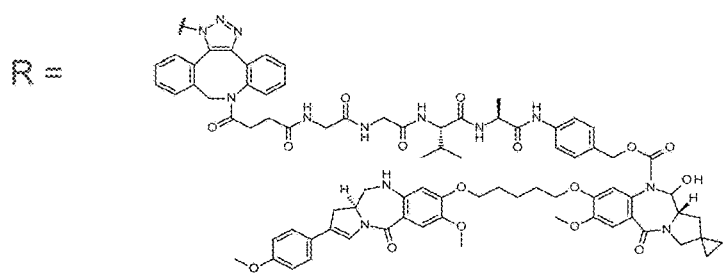
or
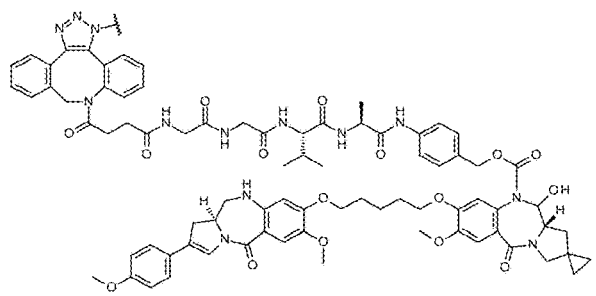

SEQUENCE LISTING

```
<160> NUMBER OF SEQ ID NOS: 94

<210> SEQ ID NO 1
<211> LENGTH: 220
<212> TYPE: PRT
<213> ORGANISM: Homo sapiens
<220> FEATURE:
<223> OTHER INFORMATION: amino acid sequence of human CLDN6

<400> SEQUENCE: 1

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
```

```
            100             105             110
Ser Lys Ala Arg Leu Val Leu Thr Ser Gly Ile Val Phe Val Ile Ser
            115             120             125

Gly Val Leu Thr Leu Ile Pro Val Cys Trp Thr Ala His Ala Ile Ile
            130             135             140

Arg Asp Phe Tyr Asn Pro Leu Val Ala Glu Ala Gln Lys Arg Glu Leu
145             150             155             160

Gly Ala Ser Leu Tyr Leu Gly Trp Ala Ala Ser Gly Leu Leu Leu Leu
                165             170             175

Gly Gly Gly Leu Leu Cys Cys Thr Cys Pro Ser Gly Gly Ser Gln Gly
                180             185             190

Pro Ser His Tyr Met Ala Arg Tyr Ser Thr Ser Ala Pro Ala Ile Ser
            195             200             205

Arg Gly Pro Ser Glu Tyr Pro Thr Lys Asn Tyr Val
210             215             220

<210> SEQ ID NO 2
<211> LENGTH: 663
<212> TYPE: DNA
<213> ORGANISM: Homo sapiens
<220> FEATURE:
<223> OTHER INFORMATION: nucleotide sequence of cDNA encoding amino acid
      sequence of human CLDN6

<400> SEQUENCE: 2
atggcctctg ccggaatgca gatcctggga gtcgtcctga cactgctggg ctgggtgaat      60
ggcctggtct cctgtgccct gcccatgtgg aaggtgaccg cttttatcgg caacagcatc     120
gtggtggccc aggtggtgtg ggagggcctg tggatgtcct gcgtggtgca gagcaccggc     180
cagatgcagt gcaaggtgta cgactcactg ctggcgctgc acaggacct gcaggctgca     240 cgtgccctct gtgtcatcgc cctccttgtg ccctgttcg gcttgctggt ctaccttgct     300
ggggccaagt gtaccacctg tgtggaggag aaggattcca aggcccgcct ggtgctcacc     360
tctgggattg tctttgtcat ctcaggggtc ctgacgctaa tccccgtgtg ctggacggcg     420
catgccatca tccgggactt ctataacccc ctggtggctg aggcccaaaa gcgggagctg     480
ggggcctccc tctacttggg ctgggcggcc tcaggccttt tgttgctggg tgggggttg     540 ctgtgctgca cttgccccctc gggggggtcc cagggcccca gccattacat ggcccgctac     600
tcaacatctg cccctgccat ctctcggggg ccctctgagt accctaccaa gaattacgtc     660
tga                                                                   663

<210> SEQ ID NO 3
<211> LENGTH: 217
<212> TYPE: PRT
<213> ORGANISM: Homo sapiens
<220> FEATURE:
<223> OTHER INFORMATION: amino acid sequence of human CLDN9

<400> SEQUENCE: 3

Met Ala Ser Thr Gly Leu Glu Leu Leu Gly Met Thr Leu Ala Val Leu
1               5               10              15

Gly Trp Leu Gly Thr Leu Val Ser Cys Ala Leu Pro Leu Trp Lys Val
                20              25              30

Thr Ala Phe Ile Gly Asn Ser Ile Val Val Ala Gln Val Val Trp Glu
            35              40              45

Gly Leu Trp Met Ser Cys Val Val Gln Ser Thr Gly Gln Met Gln Cys
        50              55              60
```

```
Lys Val Tyr Asp Ser Leu Leu Ala Leu Pro Gln Asp Leu Gln Ala Ala
 65                  70                  75                  80

Arg Ala Leu Cys Val Ile Ala Leu Leu Ala Leu Leu Gly Leu Leu
                 85                  90                  95

Val Ala Ile Thr Gly Ala Gln Cys Thr Thr Cys Val Glu Asp Glu Gly
            100                 105                 110

Ala Lys Ala Arg Ile Val Leu Thr Ala Gly Val Ile Leu Leu Leu Ala
                115                 120                 125

Gly Ile Leu Val Leu Ile Pro Val Cys Trp Thr Ala His Ala Ile Ile
130                 135                 140

Gln Asp Phe Tyr Asn Pro Leu Val Ala Glu Ala Leu Lys Arg Glu Leu
145                 150                 155                 160

Gly Ala Ser Leu Tyr Leu Gly Trp Ala Ala Ala Leu Leu Met Leu
                165                 170                 175

Gly Gly Gly Leu Leu Cys Cys Thr Cys Pro Pro Gln Val Glu Arg
                180                 185                 190

Pro Arg Gly Pro Arg Leu Gly Tyr Ser Ile Pro Ser Arg Ser Gly Ala
                195                 200                 205

Ser Gly Leu Asp Lys Arg Asp Tyr Val
    210                 215
```

<210> SEQ ID NO 4
<211> LENGTH: 654
<212> TYPE: DNA
<213> ORGANISM: Homo sapiens
<220> FEATURE:
<223> OTHER INFORMATION: nucleotide sequence of cDNA encoding amino acid
      sequence of human CLDN9

<400> SEQUENCE: 4

```
atggcttcga ccggcttaga actgctgggc atgaccctgg ctgtgctggg ctggctgggg    60
accctggtgt cctgcgccct gccctgtgg aaggtgaccg ccttcatcgg caacagcatc   120
gtggtggccc aggtggtgtg ggagggcctg tggatgtcct gcgtggtgca gagcacgggc   180
cagatgcagt gcaaggtgta cgactcactg ctggctctgc cgcaggacct gcaggccgca   240
cgtgccctct gtgtcattgc cctcctgctg gccctgcttg gcctcctggt ggccatcaca   300
ggtgcccagt gtaccacgtg tgtggaggac aaggtgccca aggcccgtat cgtgctcacc   360
gcgggggtca tcctcctcct cgccggcatc ctggtgctca tccctgtgtg ctggacggcg   420
cacgccatca tccaggactt ctacaacccc ctggtggctg aggccctcaa gcgggagctg   480
ggggcctccc tctacctggg ctgggcggcg gctgcactgc ttatgctggg cggggggctc   540
ctctgctgca cgtgcccccc gccccaggtc gagcggcccc gcggacctcg gctgggctac   600
tccatcccct cccgctcggg tgcatctgga ctggacaaga gggactacgt gtga          654
```

<210> SEQ ID NO 5
<211> LENGTH: 11
<212> TYPE: PRT
<213> ORGANISM: Mus musculus
<220> FEATURE:
<223> OTHER INFORMATION: amino acid sequence of CDRL1 of B1 antibody
      light chain

<400> SEQUENCE: 5

```
Arg Ala Ser Gln Asp Ile Asn Asn Tyr Leu Asn
1               5                   10
```

```
<210> SEQ ID NO 6
<211> LENGTH: 7
<212> TYPE: PRT
<213> ORGANISM: Mus musculus
<220> FEATURE:
<223> OTHER INFORMATION: amino acid sequence of CDRL2 of B1 antibody
      light chain

<400> SEQUENCE: 6

Phe Thr Ser Arg Leu His Ser
1               5

<210> SEQ ID NO 7
<211> LENGTH: 9
<212> TYPE: PRT
<213> ORGANISM: Mus musculus
<220> FEATURE:
<223> OTHER INFORMATION: amino acid sequence of CDRL3 of B1 antibody
      light chain

<400> SEQUENCE: 7

Gln Gln Gly Tyr Pro Leu Pro Trp Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of CDRL3 of humanized B1
      antibody light chain L4

<400> SEQUENCE: 8

Gln Gln Gly Asn Thr Leu Pro Trp Thr
1               5

<210> SEQ ID NO 9
<211> LENGTH: 10
<212> TYPE: PRT
<213> ORGANISM: Mus musculus
<220> FEATURE:
<223> OTHER INFORMATION: amino acid sequence of CDRH1 of B1 antibody
      heavy chain

<400> SEQUENCE: 9

Gly Tyr Thr Phe Thr Glu Tyr Thr Met His
1               5                   10

<210> SEQ ID NO 10
<211> LENGTH: 10
<212> TYPE: PRT
<213> ORGANISM: Mus musculus
<220> FEATURE:
<223> OTHER INFORMATION: amino acid sequence of CDRH2 of B1 antibody
      heavy chain

<400> SEQUENCE: 10

Gly Val Asn Pro Asn Ser Gly Asp Thr Ser
1               5                   10

<210> SEQ ID NO 11
<211> LENGTH: 13
<212> TYPE: PRT
<213> ORGANISM: Mus musculus
<220> FEATURE:
<223> OTHER INFORMATION: amino acid sequence of CDRH3 of B1 antibody
``` heavy chain

<400> SEQUENCE: 11

Pro Gly Gly Tyr Asp Val Gly Tyr Tyr Ala Met Asp Tyr
1               5                   10

<210> SEQ ID NO 12
<211> LENGTH: 11
<212> TYPE: PRT
<213> ORGANISM: Mus musculus
<220> FEATURE:
<223> OTHER INFORMATION: amino acid sequence of CDRL1 of C7 antibody
      light chain

<400> SEQUENCE: 12

Arg Ala Ser Gln Asp Ile Asn Asn Tyr Leu Asn
1               5                   10

<210> SEQ ID NO 13
<211> LENGTH: 7
<212> TYPE: PRT
<213> ORGANISM: Mus musculus
<220> FEATURE:
<223> OTHER INFORMATION: amino acid sequence of CDRL2 of C7 antibody
      light chain

<400> SEQUENCE: 13

Ser Thr Ser Arg Leu His Ser
1               5

<210> SEQ ID NO 14
<211> LENGTH: 9
<212> TYPE: PRT
<213> ORGANISM: Mus musculus
<220> FEATURE:
<223> OTHER INFORMATION: amino acid sequence of CDRL3 of C7 antibody
      light chain

<400> SEQUENCE: 14

Gln Gln Gly Tyr Pro Leu Pro Trp Thr
1               5

<210> SEQ ID NO 15
<211> LENGTH: 10
<212> TYPE: PRT
<213> ORGANISM: Mus musculus
<220> FEATURE:
<223> OTHER INFORMATION: amino acid sequence of CDRH1 of C7 antibody
      heavy chain

<400> SEQUENCE: 15

Gly Tyr Thr Phe Thr Glu Tyr Thr Met His
1               5                   10

<210> SEQ ID NO 16
<211> LENGTH: 10
<212> TYPE: PRT
<213> ORGANISM: Mus musculus
<220> FEATURE:
<223> OTHER INFORMATION: amino acid sequence of CDRH2 of C7 antibody
      heavy chain

<400> SEQUENCE: 16

Gly Val Asn Pro Asn Ser Gly Asp Thr Ser
1               5                   10

<210> SEQ ID NO 17

```
<211> LENGTH: 13
<212> TYPE: PRT
<213> ORGANISM: Mus musculus
<220> FEATURE:
<223> OTHER INFORMATION: amino acid sequence of CDRH3 of C7 antibody
      heavy chain

<400> SEQUENCE: 17

Pro Gly Gly Tyr Asp Val Gly Tyr Tyr Ala Met Asp Tyr
1               5                   10

<210> SEQ ID NO 18
<211> LENGTH: 321
<212> TYPE: DNA
<213> ORGANISM: Mus musculus
<220> FEATURE:
<223> OTHER INFORMATION: nucleotide sequence of cDNA encoding variable
      region of B1 antibody light chain

<400> SEQUENCE: 18
gatatccaga tgacacagac tgcatcctcc ctgtctgcct ctcttggaga cagagtcacc      60
atcagttgca gggcaagtca ggacattaac aattatttaa actggtatca gcagaaacca     120
gatggaactg ttaaactcct gatctacttc acatcaagat acactcagg agtcccatca      180 aggttcagtg gcagtgggtc tggaacacat tattctctca ccattactaa cctggaacaa     240
gaagatattg ccacttactt tgccaacag ggttatccgc ttccgtggac gttcggtgga      300
ggcaccaaac tggaaatcaa a                                                321

<210> SEQ ID NO 19
<211> LENGTH: 107
<212> TYPE: PRT
<213> ORGANISM: Mus musculus
<220> FEATURE:
<223> OTHER INFORMATION: amino acid sequence of variable region of B1
      antibody light chain

<400> SEQUENCE: 19

Asp Ile Gln Met Thr Gln Thr Ala Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr His Tyr Ser Leu Thr Ile Thr Asn Leu Glu Gln
65                  70                  75                  80

Glu Asp Ile Ala Thr Tyr Phe Cys Gln Gln Gly Tyr Pro Leu Pro Trp
                85                  90                  95

Thr Phe Gly Gly Gly Thr Lys Leu Glu Ile Lys
            100                 105

<210> SEQ ID NO 20
<211> LENGTH: 366
<212> TYPE: DNA
<213> ORGANISM: Mus musculus
<220> FEATURE:
<223> OTHER INFORMATION: nucleotide sequence of cDNA encoding variable
      region of B1 antibody heavy chain

<400> SEQUENCE: 20
gaggtccagc ttcaacagtc tggacctgaa ctggtgaagc ctggggcttc agtgaagata      60
```

```
tcctgcaaga cttctggata cacattcact gaatacacca tgcactgggt gcagcagagc    120
catggaaaga gccttgagtg gattggaggt gttaatccta atagtggtga tactagctac    180
aaccagaagt tcaagggcaa ggccacattg actgttgaca gtcctccag cacagcctac     240 atggagctcc gcagcctgac atctgaggat tctgcagtct attactgtgc aagacccggg    300
gggtacgacg tgggttacta tgctatggac tactggggtc aaggaacctc agtcaccgtc    360
tcctca                                                               366
```

<210> SEQ ID NO 21
<211> LENGTH: 122
<212> TYPE: PRT
<213> ORGANISM: Mus musculus
<220> FEATURE:
<223> OTHER INFORMATION: amino acid sequence of variable region of B1
      antibody heavy chain

<400> SEQUENCE: 21

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Gln Gln Ser His Gly Lys Ser Leu Glu Trp Ile
        35                  40                  45

Gly Gly Val Asn Pro Asn Ser Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Pro Gly Gly Tyr Asp Val Gly Tyr Tyr Ala Met Asp Tyr Trp
            100                 105                 110

Gly Gln Gly Thr Ser Val Thr Val Ser Ser
        115                 120

<210> SEQ ID NO 22
<211> LENGTH: 321
<212> TYPE: DNA
<213> ORGANISM: Mus musculus
<220> FEATURE:
<223> OTHER INFORMATION: nucleotide sequence of cDNA encoding variable
      region of C7 antibody light chain

<400> SEQUENCE: 22

```
gatatccaga tgacacagac tgcatcctcc ctgtctgcct ctcttggaga cagagtcacc    60
atcagttgca gggcaagtca ggacattaac aattatttaa actggtatca gcagaaacca    120
gatggaactg ttaaactcct gatctactcc acatcaagat acactcagg agtcccatca    180 aggttcagtg gcagtgggtc tggaacacat tattctctca ccattactca cctgaacaa    240 gaagatattg ccacttactt ttgccaacag ggttatccgc ttccgtggac gttcggtgga   300
ggcaccaaac tggaaatcaa a                                              321
```

<210> SEQ ID NO 23
<211> LENGTH: 107
<212> TYPE: PRT
<213> ORGANISM: Mus musculus
<220> FEATURE:
<223> OTHER INFORMATION: amino acid sequence of variable region of C7
      antibody light chain

<400> SEQUENCE: 23

Asp Ile Gln Met Thr Gln Thr Ala Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Ser Thr Ser Arg Leu His Ser Gly Val Pro Ser Arg Phe Ser Gly
    50                  55                  60

Ser Gly Ser Gly Thr His Tyr Ser Leu Thr Ile Thr His Leu Glu Gln
65                  70                  75                  80

Glu Asp Ile Ala Thr Tyr Phe Cys Gln Gln Gly Tyr Pro Leu Pro Trp
                85                  90                  95

Thr Phe Gly Gly Gly Thr Lys Leu Glu Ile Lys
            100                 105

<210> SEQ ID NO 24
<211> LENGTH: 366
<212> TYPE: DNA
<213> ORGANISM: Mus musculus
<220> FEATURE:
<223> OTHER INFORMATION: nucleotide sequence of cDNA encoding variable
      region of C7 antibody heavy chain

<400> SEQUENCE: 24
gaggtccagc ttcaacagtc tggacctgaa ctggtgaagc ctggggcttc agtgaagata      60
tcctgcaaga cttctggata cacattcact gaatacacca tgcactgggt gcagcagagc     120
catggaaaga gccttgagtg gattggaggt gttaatccta atagtggtga tactagctac     180
aaccagaagt tcaagggcaa ggccacattg actgttgaca gtcctccag cacagcctac      240 atggagctcc gcagcctgac atctgaggat tctgcagtct attactgtgc aagacccggg     300
gggtacgacg tgggttacta tgctatggac tactggggtc aaggaacctc agtcaccgtc     360
tcctca                                                                 366

<210> SEQ ID NO 25
<211> LENGTH: 122
<212> TYPE: PRT
<213> ORGANISM: Mus musculus
<220> FEATURE:
<223> OTHER INFORMATION: amino acid sequence of variable region of C7
      antibody heavy chain

<400> SEQUENCE: 25

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Gln Gln Ser His Gly Lys Ser Leu Glu Trp Ile
        35                  40                  45

Gly Gly Val Asn Pro Asn Ser Gly Asp Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Pro Gly Gly Tyr Asp Val Gly Tyr Tyr Ala Met Asp Tyr Trp

```
              100                 105                 110
Gly Gln Gly Thr Ser Val Thr Val Ser Ser
        115                 120
```

<210> SEQ ID NO 26
<211> LENGTH: 449
<212> TYPE: DNA
<213> ORGANISM: Homo sapiens
<220> FEATURE:
<223> OTHER INFORMATION: DNA fragment comprising DNA sequence encoding
      human light chain signal sequence and human ?? chain constant
      region

<400> SEQUENCE: 26

```
gcctccggac tctagagcca ccatggtgct gcagacccag gtgttcatct ccctgctgct    60
gtggatctcc ggcgcgtacg gcgatatcgt gatgattaaa cgtacggtgg ccgcccctc    120 cgtgttcatc ttcccccct  ccgacgagca gctgaagtcc ggcaccgcct ccgtggtgtg   180
cctgctgaat aacttctacc ccagagaggc caaggtgcag tggaaggtgg acaacgccct   240
gcagtccggg aactcccagg agagcgtgac cgagcaggac agcaaggaca gcacctacag   300
cctgagcagc accctgaccc tgagcaaagc cgactacgag aagcacaagg tgtacgcctg   360
cgaggtgacc caccagggcc tgagctcccc cgtcaccaag agcttcaaca ggggggagtg   420
ttagggcccc gtttaaacgg gggaggcta                                     449
```

<210> SEQ ID NO 27
<211> LENGTH: 1137
<212> TYPE: DNA
<213> ORGANISM: Homo sapiens
<220> FEATURE:
<223> OTHER INFORMATION: DNA fragment comprising DNA sequence encoding
      human heavy chain signal sequence and human IgG1 LALA constant
      region

<400> SEQUENCE: 27

```
ccagcctccg gactctagag ccaccatgaa acacctgtgg ttcttcctcc tgctggtggc    60
agctcccaga tgggtgctga gccaggtgca attgtgcagg cggttagctc agcctccacc   120
aagggcccaa gcgtcttccc cctggcaccc tcctccaaga gcacctctgg cggcacagcc   180
gccctgggct gcctggtcaa ggactacttc cccgaacccg tgaccgtgag ctggaactca   240
ggcgccctga ccagcggcgt gcacaccttc cccgctgtcc tgcagtcctc aggactctac   300
tccctcagca gcgtggtgac cgtgccctcc agcagcttgg gcacccagac ctacatctgc   360
aacgtgaatc acaagcccag caacaccaag gtggacaaga gagttgagcc caaatcttgt   420
gacaaaactc acacatgccc accctgccca gcacctgaag ccgcgggggg accctcagtc   480
ttcctcttcc cccaaaaacc caaggacacc ctcatgatct cccggacccc tgaggtcaca   540
tgcgtggtgg tggacgtgag ccacgaagac cctgaggtca agttcaactg gtacgtggac   600
ggcgtggagg tgcataatgc caagacaaag ccccggagg  agcagtacaa cagcacgtac   660
cgggtggtca gcgtcctcac cgtcctgcac caggactggc tgaatggcaa ggagtacaag   720
tgcaaggtct ccaacaaagc cctcccagcc cccatcgaga aaaccatctc caaagccaaa   780
ggccagcccc gggaaccaca ggtgtacacc ctgcccccat cccgggagga gatgaccaag   840
aaccaggtca gcctgacctg cctggtcaaa ggcttctatc ccagcgacat cgccgtggag   900
tgggagagca atggccagcc cgagaacaac tacaagacca cccctcccgt gctggactcc   960
gacggctcct tcttcctcta cagcaagctc accgtggaca agagcaggtg gcagcagggc  1020
```

```
aacgtcttct catgctccgt gatgcatgag gctctgcaca accactacac ccagaagagc    1080
ctctccctgt ctcccggcaa atgagatatc gggcccgttt aaacggggga ggctaac      1137
```

<210> SEQ ID NO 28
<211> LENGTH: 234
<212> TYPE: PRT
<213> ORGANISM: Artificial Sequence
<220> FEATURE:
<223> OTHER INFORMATION: Description of Artificial Sequence: Synthetic
      chimeric antibody
<220> FEATURE:
<223> OTHER INFORMATION: amino acid sequence of chB1 light chain

<400> SEQUENCE: 28

```
Met Val Leu Gln Thr Gln Val Phe Ile Ser Leu Leu Trp Ile Ser
1               5                   10                  15

Gly Ala Tyr Gly Asp Ile Gln Met Thr Gln Thr Ala Ser Ser Leu Ser
            20                  25                  30

Ala Ser Leu Gly Asp Arg Val Thr Ile Ser Cys Arg Ala Ser Gln Asp
        35                  40                  45

Ile Asn Asn Tyr Leu Asn Trp Tyr Gln Gln Lys Pro Asp Gly Thr Val
50                  55                  60

Lys Leu Leu Ile Tyr Phe Thr Ser Arg Leu His Ser Gly Val Pro Ser
65                  70                  75                  80

Arg Phe Ser Gly Ser Gly Ser Gly Thr His Tyr Ser Leu Thr Ile Thr
                85                  90                  95

Asn Leu Glu Gln Glu Asp Ile Ala Thr Tyr Phe Cys Gln Gln Gly Tyr
            100                 105                 110

Pro Leu Pro Trp Thr Phe Gly Gly Gly Thr Lys Leu Glu Ile Lys Arg
        115                 120                 125

Ala Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 29
<211> LENGTH: 752
<212> TYPE: DNA
<213> ORGANISM: Artificial Sequence
<220> FEATURE:
<223> OTHER INFORMATION: Description of Artificial Sequence: Synthetic
      chimeric antibody
<220> FEATURE:
<223> OTHER INFORMATION: DNA fragment comprising DNA sequence encoding
      amino acid sequence of chB1 light chain

<400> SEQUENCE: 29

```
ccagcctccg gactctagag ccaccatggt gctgcagacc caggtgttca tcagcctgct    60
gctgtggatc agcggcgcct acggcgacat ccagatgacc cagacagcca gcagcctgag   120
```

```
cgccagcctg ggcgatagag tgaccatcag ctgcagagcc agccaggaca tcaacaacta    180
cctgaactgg tatcagcaga aacccgacgg caccgtgaag ctgctgatct acttcaccag    240
cagactgcac agcggcgtgc ccagcagatt ttctggcagc ggctctggca cccactacag    300
cctgaccatc accaacctgg aacaggaaga tatcgctacc tacttctgtc agcaaggcta    360
ccccctgccc tggacctttg gcggcggaac aaagctggaa atcaagcggg ccgtggccgc    420 tcccteegtg ttcatctttc cacccagcga cgagcagctg aagtccggca cagctagegt    480 cgtgtgcctg ctgaacaact ctacccccg cgaggccaag gtgcagtgga aggtggacaa    540
tgccctgcag agcggcaaca gccaggaaag cgtgaccgag caggacagca aggactccac    600
ctactccctg agcagcaccc tgaccctgag caaggccgac tacgagaagc acaaggtgta    660
cgcctgcgaa gtgacccacc agggcctgtc tagccccgtg accaagagct caaccgggg    720 cgagtgttga gtttaaacgg gggaggctaa ct    752

<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      chimeric antibody
<220> FEATURE:
<223> OTHER INFORMATION: amino acid sequence of variable region of chB1
      light chain

<400> SEQUENCE: 30

Asp Ile Gln Met Thr Gln Thr Ala Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr His Tyr Ser Leu Thr Ile Thr Asn Leu Glu Gln
65                  70                  75                  80

Glu Asp Ile Ala Thr Tyr Phe Cys Gln Gln Gly Tyr Pro Leu Pro Trp
                85                  90                  95

Thr Phe Gly Gly Gly Thr Lys Leu Glu Ile Lys
            100                 105

<210> SEQ ID NO 31
<211> LENGTH: 321
<212> TYPE: DNA
<213> ORGANISM: Artificial Sequence
<220> FEATURE:
<223> OTHER INFORMATION: Description of Artificial Sequence: Synthetic
      chimeric antibody
<220> FEATURE:
<223> OTHER INFORMATION: nucleotide sequence encoding amino acid
      sequence of variable region of chB1 light chain

<400> SEQUENCE: 31
gacatccaga tgacccagac agccagcagc ctgagcgcca gcctgggcga tagagtgacc    60
atcagctgca gagccagcca ggacatcaac aactacctga ctggtatca gcagaaaccc    120 gacggcaccg tgaagctgct gatctacttc accagcagac tgcacagcgg cgtgcccagc    180
agattttctg gcagcggctc tggcacccac tacagcctga ccatcaccaa cctggaacag    240
```

```
gaagatatcg ctacctactt ctgtcagcaa ggctaccccc tgccctggac ctttggcggc    300
ggaacaaagc tggaaatcaa g                                              321
```

<210> SEQ ID NO 32
<211> LENGTH: 471
<212> TYPE: PRT
<213> ORGANISM: Artificial Sequence
<220> FEATURE:
<223> OTHER INFORMATION: Description of Artificial Sequence: Synthetic
      chimeric antibody
<220> FEATURE:
<223> OTHER INFORMATION: amino acid sequence of chB1 heavy chain

<400> SEQUENCE: 32

```
Met Lys His Leu Trp Phe Phe Leu Leu Leu Val Ala Ala Pro Arg Trp
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Thr Ser Gly Tyr Thr Phe
        35                  40                  45

Thr Glu Tyr Thr Met His Trp Val Gln Gln Ser His Gly Lys Ser Leu
    50                  55                  60

Glu Trp Ile Gly Gly Val Asn Pro Asn Ser Gly Asp Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Arg Pro Gly Gly Tyr Asp Val Gly Tyr Tyr Ala Met
        115                 120                 125

Asp Tyr Trp Gly Gln Gly Thr Ser Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Ala Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
```

```
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
            355                 360                 365
Glu Pro Gln Val Tyr Thr Leu Pro Pro Ser Arg Glu Glu Met Thr Lys
        370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
            435                 440                 445
Cys Ser Val Met His Glu Ala Leu His Asn His Tyr Thr Gln Lys Ser
        450                 455                 460
Leu Ser Leu Ser Pro Gly Lys
465                 470

<210> SEQ ID NO 33
<211> LENGTH: 1413
<212> TYPE: DNA
<213> ORGANISM: Artificial Sequence
<220> FEATURE:
<223> OTHER INFORMATION: Description of Artificial Sequence: Synthetic
      chimeric antibody
<220> FEATURE:
<223> OTHER INFORMATION: nucleotide sequence encoding chB1 heavy chain

<400> SEQUENCE: 33
atgaaacacc tgtggttctt cctcctgctg gtggcagctc ccagatgggt gctgagcgaa      60
gtgcagctgc agcagtctgg ccccgagctc gtgaaacctg cgcctccgt gaagatcagc     120 tgcaagacca gcggctacac cttcaccgag tacaccatgc actgggtgca gcagagccac     180
ggcaagagcc tggaatggat cggcggcgtg aaccccaaca gcggcgacac cagctacaac     240
cagaagttca agggcaaggc caccctgacc gtggacaaga gcagcagcac cgcctacatg     300
gaactgcgga gcctgaccag cgaggacagc gccgtgtact actgtgccag acctggcggc     360
tacgacgtgg gctactacgc catggattac tggggccagg gcaccagcgt gaccgtcagc     420
tcagcctcca ccaagggccc aagcgtcttc cccctggcac cctcctccaa gagcacctct     480
ggcggcacag ccgccctggg ctgcctggtc aaggactact ccccgaaacc cgtgaccgtg     540
agctggaact caggcgccct gaccagcggc gtgcacacct tcccggctgt cctgcagtcc     600
tcaggactct actccctcag cagcgtggtg accgtgccct ccagcagctt gggcacccag     660
acctacatct gcaacgtgaa tcacaagccc agcaacacca aggtggacaa gagagttgag     720
cccaaatctt gtgacaaaac tcacacatgc ccaccctgcc cagcacctga gccgcgggg     780 ggaccctcag tcttcctctt ccccccaaaa cccaaggaca cctcatgat ctcccggacc     840 cctgaggtca catgcgtggt ggtggacgtg agccacgaag accctgaggt caagttcaac     900
tggtacgtgg acggcgtgga ggtgcataat gccaagacaa agcccgggga ggagcagtac     960
aacagcacgt accgggtggt cagcgtcctc accgtcctgc accaggactg gctgaatggc    1020
aaggagtaca agtgcaaggt ctccaacaaa gccctcccag cccccatcga gaaaaccatc    1080
tccaaagcca aggccagcc ccgggaacca caggtgtaca ccctgccccc atcccgggag    1140
```

```
gagatgacca agaaccaggt cagcctgacc tgcctggtca aaggcttcta tcccagcgac    1200
atcgccgtgg agtgggagag caatggccag cccgagaaca actacaagac cacccctccc    1260
gtgctggact ccgacggctc cttcttcctc tacagcaagc tcaccgtgga caagagcagg    1320
tggcagcagg gcaacgtctt ctcatgctcc gtgatgcatg aggctctgca caaccactac    1380
acccagaaga gcctctccct gtctcccggc aaa                                  1413
```

<210> SEQ ID NO 34
<211> LENGTH: 122
<212> TYPE: PRT
<213> ORGANISM: Artificial Sequence
<220> FEATURE:
<223> OTHER INFORMATION: Description of Artificial Sequence: Synthetic chimeric antibody
<220> FEATURE:
<223> OTHER INFORMATION: amino acid sequence of variable region of chB1 heavy chain

<400> SEQUENCE: 34

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Gln Gln Ser His Gly Lys Ser Leu Glu Trp Ile
        35                  40                  45

Gly Gly Val Asn Pro Asn Ser Gly Asp Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Pro Gly Gly Tyr Asp Val Gly Tyr Tyr Ala Met Asp Tyr Trp
            100                 105                 110

Gly Gln Gly Thr Ser Val Thr Val Ser Ser
        115                 120
```

<210> SEQ ID NO 35
<211> LENGTH: 366
<212> TYPE: DNA
<213> ORGANISM: Artificial Sequence
<220> FEATURE:
<223> OTHER INFORMATION: Description of Artificial Sequence: Synthetic chimeric antibody
<220> FEATURE:
<223> OTHER INFORMATION: nucleotide sequence encoding variable region of chB1 heavy chain

<400> SEQUENCE: 35

```
gaagtgcagc tgcagcagtc tggccccgag ctcgtgaaac ctggcgcctc cgtgaagatc    60
agctgcaaga ccagcggcta caccttcacc gagtacacca tgcactgggt gcagcagagc    120
cacggcaaga gcctggaatg gatcggcggc gtgaacccca acagcggcga caccagctac    180
aaccagaagt tcaagggcaa ggccacccto accgtggaca gagcagcag caccgcctac    240 atggaactgc ggagcctgac cagcgaggac agcgccgtgt actactgtgc cagacctggc    300
ggctacgacg tgggctacta cgccatggat tactggggcc agggcaccag cgtgaccgtc    360
agctca                                                                366
```

<210> SEQ ID NO 36

```
<211> LENGTH: 234
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of humanized antibody light
      chain hL1

<400> SEQUENCE: 36

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Asn Asn Tyr Leu Asn Trp Tyr Gln Gln Lys Pro Gly Lys Ala Pro
    50                  55                  60

Lys Leu Leu Ile Tyr Phe Thr Ser Arg Leu His Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln Gln Gly Tyr
            100                 105                 110

Pro Leu Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 37
<211> LENGTH: 702
<212> TYPE: DNA
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: nucleotide sequence encoding humanized antibody
      light chain hL1

<400> SEQUENCE: 37
atggtgctgc agacccaggt gttcatctcc ctgctgctgt ggatctccgg cgcgtacggc       60
gacatccaga tgacccagag ccctagcagc ctgagcgcca gcgtgggcga cagagtgacc      120
atcacctgta gagccagcca ggacatcaac aactacctga actggtatca gcagaagccc      180
ggcaaggccc ccaagctgct gatctacttc accagcagac tgcacagcgg cgtgcccagc      240
```

```
agattttctg gcagcggctc cggcaccgac tacaccctga caatcagcag cctgcagccc      300
gaggacttcg ccacctacta ctgccagcag ggctaccccc tgccttggac atttggccag      360
ggcaccaagg tggaaatcaa gcgtacggtg gccgccccct ccgtgttcat cttccccccc      420
tccgacgagc agctgaagtc cggcaccgcc tccgtggtgt gcctgctgaa taacttctac      480
cccagagagg ccaaggtgca gtggaaggtg gacaacgccc tgcagtccgg gaactcccag      540
gagagcgtga ccgagcagga cagcaaggac agcacctaca gcctgagcag cacccctgacc     600 ctgagcaaag ccgactacga aagcacaag gtgtacgcct gcgaggtgac ccaccagggc      660
ctgagctccc ccgtcaccaa gagcttcaac agggggagt gt                         702
```

```
<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of variable region of
      humanized antibody light chain hL1

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Tyr Pro Leu Pro Trp
                85                  90                  95

Thr Phe Gly Gln Gly Thr Lys Val Glu Ile Lys
            100                 105
```

```
<210> SEQ ID NO 39
<211> LENGTH: 321
<212> TYPE: DNA
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: nucleotide sequence encoding variable region of
      humanized antibody light chain hL1

<400> SEQUENCE: 39
gacatccaga tgacccagag ccctagcagc ctgagcgcca gcgtgggcga cagagtgacc       60
atcacctgta gagccagcca ggacatcaac aactacctga ctggtatca gcagaagccc      120 ggcaaggccc ccaagctgct gatctacttc accagcagac tgcacagcgg cgtgcccagc     180
agattttctg gcagcggctc cggcaccgac tacaccctga caatcagcag cctgcagccc     240
gaggacttcg ccacctacta ctgccagcag ggctaccccc tgccttggac atttggccag     300
ggcaccaagg tggaaatcaa g                                                321
```

```
<210> SEQ ID NO 40
```

<211> LENGTH: 234
<212> TYPE: PRT
<213> ORGANISM: Artificial Sequence
<220> FEATURE:
<223> OTHER INFORMATION: Description of Artificial Sequence: Synthetic humanized antibody
<220> FEATURE:
<223> OTHER INFORMATION: amino acid sequence of humanized antibody light chain hL2

<400> SEQUENCE: 40

| | | | | | | | | | | | | | | | |
|---|---|---|---|---|---|---|---|---|---|---|---|---|---|---|---|
| Met | Val | Leu | Gln | Thr | Gln | Val | Phe | Ile | Ser | Leu | Leu | Trp | Ile | Ser | |
| 1 | | | | 5 | | | | | 10 | | | | | 15 | |
| Gly | Ala | Tyr | Gly | Asp | Ile | Gln | Met | Thr | Gln | Ser | Pro | Ser | Ser | Leu | Ser |
| | | | 20 | | | | | 25 | | | | | 30 | | |
| Ala | Ser | Val | Gly | Asp | Arg | Val | Thr | Ile | Thr | Cys | Arg | Ala | Ser | Gln | Asp |
| | | 35 | | | | | 40 | | | | | 45 | | | |
| Ile | Asn | Asn | Tyr | Leu | Asn | Trp | Tyr | Gln | Gln | Lys | Pro | Gly | Lys | Ala | Val |
| | 50 | | | | | 55 | | | | | 60 | | | | |
| Lys | Leu | Leu | Ile | Tyr | Phe | Thr | Ser | Arg | Leu | His | Ser | Gly | Val | Pro | Ser |
| 65 | | | | | 70 | | | | | 75 | | | | | 80 |
| Arg | Phe | Ser | Gly | Ser | Gly | Ser | Gly | Thr | His | Tyr | Thr | Leu | Thr | Ile | Ser |
| | | | | 85 | | | | | 90 | | | | | 95 | |
| Ser | Leu | Gln | Pro | Glu | Asp | Phe | Ala | Thr | Tyr | Tyr | Cys | Gln | Gln | Gly | Tyr |
| | | | 100 | | | | | 105 | | | | | 110 | | |
| Pro | Leu | Pro | Trp | Thr | Phe | Gly | Gln | Gly | Thr | Lys | Val | Glu | Ile | Lys | Arg |
| | | 115 | | | | | 120 | | | | | 125 | | | |
| Thr | Val | Ala | Ala | Pro | Ser | Val | Phe | Ile | Phe | Pro | Pro | Ser | Asp | Glu | Gln |
| | 130 | | | | | 135 | | | | | 140 | | | | |
| Leu | Lys | Ser | Gly | Thr | Ala | Ser | Val | Val | Cys | Leu | Leu | Asn | Asn | Phe | Tyr |
| 145 | | | | | 150 | | | | | 155 | | | | | 160 |
| Pro | Arg | Glu | Ala | Lys | Val | Gln | Trp | Lys | Val | Asp | Asn | Ala | Leu | Gln | Ser |
| | | | | 165 | | | | | 170 | | | | | 175 | |
| Gly | Asn | Ser | Gln | Glu | Ser | Val | Thr | Glu | Gln | Asp | Ser | Lys | Asp | Ser | Thr |
| | | | 180 | | | | | 185 | | | | | 190 | | |
| Tyr | Ser | Leu | Ser | Ser | Thr | Leu | Thr | Leu | Ser | Lys | Ala | Asp | Tyr | Glu | Lys |
| | | 195 | | | | | 200 | | | | | 205 | | | |
| His | Lys | Val | Tyr | Ala | Cys | Glu | Val | Thr | His | Gln | Gly | Leu | Ser | Ser | Pro |
| | 210 | | | | | 215 | | | | | 220 | | | | |
| Val | Thr | Lys | Ser | Phe | Asn | Arg | Gly | Glu | Cys | | | | | | |
| 225 | | | | | 230 | | | | | | | | | | |

<210> SEQ ID NO 41
<211> LENGTH: 702
<212> TYPE: DNA
<213> ORGANISM: Artificial Sequence
<220> FEATURE:
<223> OTHER INFORMATION: Description of Artificial Sequence: Synthetic humanized antibody
<220> FEATURE:
<223> OTHER INFORMATION: nucleotide sequence encoding humanized antibody light chain hL2

<400> SEQUENCE: 41
atggtgctgc agacccaggt gttcatctcc ctgctgctgt ggatctccgg cgcgtacggc    60
gacatccaga tgacccagag ccctagcagc ctgagcgcca gcgtgggcga cagagtgacc   120
atcacctgta gagccagcca ggacatcaac aactacctga actggtatca gcagaaaccc   180
ggcaaggccg tgaagctgct gatctacttc accagcagac tgcacagcgg cgtgcccagc   240

```
agattttctg gcagcggctc tggcacccac tacaccctga caatcagcag cctgcagccc    300
gaggacttcg ccacctacta ctgccagcag ggctaccccc tgccttggac atttggccag    360
ggcaccaagg tggaaatcaa gcgtacggtg gccgccccct ccgtgttcat cttcccccc     420 tccgacgagc agctgaagtc cggcaccgcc tccgtggtgt gcctgctgaa taacttctac    480
cccagagagg ccaaggtgca gtggaaggtg gacaacgccc tgcagtccgg gaactcccag    540
gagagcgtga ccgagcagga cagcaaggac agcacctaca gcctgagcag caccctgacc    600
ctgagcaaag ccgactacga aagcacaag gtgtacgcct gcgaggtgac ccaccagggc     660
ctgagctccc ccgtcaccaa gagcttcaac aggggggagt gt                      702
```

```
<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of variable region of
      humanized antibody light chain hL2

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Ala Val Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr His Tyr Thr Leu Thr Ile Ser Ser Leu Gln Pro
65                  70                  75                  80

Glu Asp Phe Ala Thr Tyr Tyr Cys Gln Gln Gly Tyr Pro Leu Pro Trp
                85                  90                  95

Thr Phe Gly Gln Gly Thr Lys Val Glu Ile Lys
            100                 105
```

```
<210> SEQ ID NO 43
<211> LENGTH: 321
<212> TYPE: DNA
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: nucleotide sequence encoding variable region of
      humanized antibody light chain hL2

<400> SEQUENCE: 43
gacatccaga tgacccagag ccctagcagc ctgagcgcca gcgtgggcga cagagtgacc     60
atcacctgta gagccagcca ggacatcaac aactacctga actggtatca gcagaaaccc    120
ggcaaggccg tgaagctgct gatctacttc accagcagac tgcacagcgg cgtgcccagc    180
agattttctg gcagcggctc tggcacccac tacaccctga caatcagcag cctgcagccc    240
gaggacttcg ccacctacta ctgccagcag ggctaccccc tgccttggac atttggccag    300
ggcaccaagg tggaaatcaa g                                              321
```

```
<210> SEQ ID NO 44
```

<211> LENGTH: 234
<212> TYPE: PRT
<213> ORGANISM: Artificial Sequence
<220> FEATURE:
<223> OTHER INFORMATION: Description of Artificial Sequence: Synthetic humanized antibody
<220> FEATURE:
<223> OTHER INFORMATION: amino acid sequence of humanized antibody light chain hL3

<400> SEQUENCE: 44

```
Met Val Leu Gln Thr Gln Val Phe Ile Ser Leu Leu Trp Ile Ser
1               5                   10                  15
Gly Ala Tyr Gly Asp Ile Gln Met Thr Gln Ser Pro Ser Ser Leu Ser
            20                  25                  30
Ala Ser Val Gly Asp Arg Val Thr Ile Thr Cys Arg Ala Ser Gln Asp
        35                  40                  45
Ile Asn Asn Tyr Leu Asn Trp Tyr Gln Gln Lys Pro Gly Gly Ala Val
    50                  55                  60
Lys Leu Leu Ile Tyr Phe Thr Ser Arg Leu His Ser Gly Val Pro Ser
65                  70                  75                  80
Arg Phe Ser Gly Ser Gly Ser Gly Thr Asp Tyr Thr Leu Thr Ile Ser
                85                  90                  95
Ser Leu Gln Pro Glu Asp Phe Ala Thr Tyr Tyr Cys Gln Gln Gly Tyr
            100                 105                 110
Pro Leu Pro Trp Thr Phe Gly Gly Gly Thr Lys Val Glu Ile Lys Arg
        115                 120                 125
Thr Val Ala Ala Pro Ser Val Phe Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
    210                 215                 220
Val Thr Lys Ser Phe Asn Arg Gly Glu Cys
225                 230
```

<210> SEQ ID NO 45
<211> LENGTH: 702
<212> TYPE: DNA
<213> ORGANISM: Artificial Sequence
<220> FEATURE:
<223> OTHER INFORMATION: Description of Artificial Sequence: Synthetic humanized antibody
<220> FEATURE:
<223> OTHER INFORMATION: nucleotide sequence encoding humanized antibody light chain hL3

<400> SEQUENCE: 45

```
atggtgctgc agacccaggt gttcatctcc ctgctgctgt ggatctccgg cgcgtacggc      60
gacatccaga tgacccagag ccctagcagc ctgagcgcca gcgtgggcga cagagtgacc     120
atcacctgta gagccagcca ggacatcaac aactacctga actggtatca gcagaaaccc     180
ggcggagccg tgaagctgct gatctacttc accagcagac tgcacagcgg cgtgcccagc     240
```

```
agatttctg gcagcggctc cggcaccgac tacaccctga caatcagcag cctgcagccc      300
gaggacttcg ccacctacta ctgccagcag ggctaccccc tgccctggac atttggcggc      360
ggaacaaagg tggaaatcaa gcgtacggtg gccgccccct ccgtgttcat cttccccccc      420
tccgacgagc agctgaagtc cggcaccgcc tccgtggtgt gcctgctgaa taacttctac      480
cccagagagg ccaaggtgca gtggaaggtg gacaacgccc tgcagtccgg gaactcccag      540
gagagcgtga ccgagcagga cagcaaggac agcacctaca gcctgagcag caccctgacc      600
ctgagcaaag ccgactacga gaagcacaag gtgtacgcct gcgaggtgac ccaccagggc      660
ctgagctccc ccgtcaccaa gagcttcaac agggggggagt gt                        702
```

```
<210> SEQ ID NO 46
<211> LENGTH: 107
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of variable region of
      humanized antibody light chain hL3

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Gly Ala Val Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Tyr Pro Leu Pro Trp
                85                  90                  95

Thr Phe Gly Gly Gly Thr Lys Val Glu Ile Lys
            100                 105
```

```
<210> SEQ ID NO 47
<211> LENGTH: 321
<212> TYPE: DNA
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: nucleotide sequence encoding variable region of
      humanized antibody light chain hL3

<400> SEQUENCE: 47
gacatccaga tgacccagag ccctagcagc ctgagcgcca gcgtgggcga cagagtgacc       60
atcacctgta gagccagcca ggacatcaac aactacctga actggtatca gcagaaaccc      120
ggcggagccg tgaagctgct gatctacttc accagcagac tgcacagcgg cgtgcccagc      180 agatttctg gcagcggctc cggcaccgac tacaccctga caatcagcag cctgcagccc      240
gaggacttcg ccacctacta ctgccagcag ggctaccccc tgccctggac atttggcggc      300
ggaacaaagg tggaaatcaa g                                                 321
```

```
<210> SEQ ID NO 48
```

<211> LENGTH: 234
<212> TYPE: PRT
<213> ORGANISM: Artificial Sequence
<220> FEATURE:
<223> OTHER INFORMATION: Description of Artificial Sequence: Synthetic humanized antibody
<220> FEATURE:
<223> OTHER INFORMATION: amino acid sequence of humanized antibody light chain hL4

<400> SEQUENCE: 48

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Asn Asn Tyr Leu Asn Trp Tyr Gln Gln Lys Pro Gly Gly Ala Val
    50                  55                  60

Lys Leu Leu Ile Tyr Phe Thr Ser Arg Leu His Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln Gln Gly Asn
            100                 105                 110

Thr Leu Pro Trp Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 49
<211> LENGTH: 702
<212> TYPE: DNA
<213> ORGANISM: Artificial Sequence
<220> FEATURE:
<223> OTHER INFORMATION: Description of Artificial Sequence: Synthetic humanized antibody
<220> FEATURE:
<223> OTHER INFORMATION: nucleotide sequence encoding humanized antibody light chain hL4

<400> SEQUENCE: 49

```
atggtgctgc agacccaggt gttcatctcc ctgctgctgt ggatctccgg cgcgtacggc      60
gacatccaga tgacccagag ccctagcagc ctgagcgcca gcgtgggcga cagagtgacc     120
atcacctgta gagccagcca ggacatcaac aactacctga actggtatca gcagaaaccc     180
ggcggagccg tgaagctgct gatctacttc accagcagac tgcacagcgg cgtgcccagc     240
```

```
agattttctg gcagcggctc cggcaccgac tacaccctga caatcagcag cctgcagccc    300
gaggacttcg ccacctacta ctgccagcag ggcaacaccc tgccctggac atttggcgga    360
ggcaccaagg tggaaatcaa gcgtacggtg gccgccccct ccgtgttcat cttcccccc     420 tccgacgagc agctgaagtc cggcaccgcc tccgtggtgt gcctgctgaa taacttctac    480
cccagagagg ccaaggtgca gtggaaggtg gacaacgccc tgcagtccgg gaactcccag    540
gagagcgtga ccgagcagga cagcaaggac agcacctaca gcctgagcag caccctgacc    600
ctgagcaaag ccgactacga aagcacaag gtgtacgcct gcgaggtgac ccaccagggc    660
ctgagctccc ccgtcaccaa gagcttcaac agggggagt gt                       702
```

```
<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of variable region of
      humanized antibody light chain hL4

<400> SEQUENCE: 50

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Gly Ala Val Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys
            100                 105
```

```
<210> SEQ ID NO 51
<211> LENGTH: 321
<212> TYPE: DNA
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: nucleotide sequence encoding variable region of
      humanized antibody light chain hL4

<400> SEQUENCE: 51
gacatccaga tgacccagag ccctagcagc ctgagcgcca gcgtgggcga cagagtgacc    60
atcacctgta gagccagcca ggacatcaac aactacctga actggtatca gcagaaaccc    120
ggcggagccg tgaagctgct gatctacttc accagcagac tgcacagcgg cgtgcccagc    180
agattttctg gcagcggctc cggcaccgac tacaccctga caatcagcag cctgcagccc    240
gaggacttcg ccacctacta ctgccagcag ggcaacaccc tgccctggac atttggcgga    300
ggcaccaagg tggaaatcaa g                                              321
```

```
<210> SEQ ID NO 52
```

```
<211> LENGTH: 471
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of humanized antibody heavy
      chain hH1

<400> SEQUENCE: 52

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Glu Tyr Thr Met His Trp Val Arg Gln Ala Pro Gly Gln Gly Leu
    50                  55                  60

Glu Trp Met Gly Gly Val Asn Pro Asn Ser Gly Asp Thr Ser Tyr Ala
65                  70                  75                  80

Gln Lys Phe Gln Gly Arg Val Thr Ile Thr Ala Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Pro Gly Gly Tyr Asp Val Gly Tyr Tyr Ala Met
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Ala Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
```

```
                355                 360                 365
Glu Pro Gln Val Tyr Thr Leu Pro Pro Ser Arg Glu Glu Met Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 53
<211> LENGTH: 1413
<212> TYPE: DNA
<213> ORGANISM: Artificial Sequence
<220> FEATURE:
<223> OTHER INFORMATION: Description of Artificial Sequence: Synthetic humanized antibody
<220> FEATURE:
<223> OTHER INFORMATION: nucleotide sequence encoding humanized antibody heavy chain hH1

<400> SEQUENCE: 53

```
atgaaacacc tgtggttctt cctcctgctg gtggcagctc ccagatgggt gctgagccag      60
gtgcagctgg tgcagtctgg cgccgaagtg aagaaaccag cgccagcgt gaaggtgtcc     120
tgcaaggcca gcggctacac ctttaccgag tacaccatgc actgggtgcg ccaggctcca     180
ggccagggac tggaatggat gggcggcgtg aaccccaaca gcggcgatac aagctacgcc     240
cagaaattcc agggcagagt gaccatcacc gccgacacca gcacctccac cgcctacatg     300
gaactgagca gcctgcggag cgaggacacc gccgtgtact actgtgctag acctggcggc     360
tacgacgtgg gctactacgc catggattac tggggccagg gcaccctcgt gaccgtcagc     420
tcagcctcca ccaagggccc aagcgtcttc cccctggcac cctcctccaa gagcacctct     480
ggcggcacag ccgccctggg ctgcctggtc aaggactact ccccgaacc cgtgaccgtg     540
agctggaact caggcgccct gaccagcggc gtgcacacct tcccgctgt cctgcagtcc     600
tcaggactct actccctcag cagcgtggtg accgtgccct ccagcagctt gggcacccag     660
acctacatct gcaacgtgaa tcacaagccc agcaacacca aggtggacaa gagagttgag     720
cccaaatctt gtgacaaaac tcacacatgc ccaccctgcc cagcacctga gccgcgggg     780
ggaccctcag tcttcctctt cccccaaaa cccaaggaca ccctcatgat ctcccggacc     840
cctgaggtca catgcgtggt ggtggacgtg agccacgaag accctgaggt caagttcaac     900
tggtacgtgg acggcgtgga ggtgcataat gccaagacaa agccccggga ggagcagtac     960
aacagcacgt accgggtggt cagcgtcctc accgtcctgc accaggactg gctgaatggc    1020
aaggagtaca agtgcaaggt ctccaacaaa gcccctccag cccccatcga gaaaaccatc    1080
tccaaagcca aggcccagcc ccgggaacca caggtgtaca ccctgccccc atcccgggag    1140
gagatgacca agaaccaggt cagcctgacc tgcctggtca aaggcttcta tcccagcgac    1200
atcgccgtgg agtgggagag caatggccag cccgagaaca actacaagac cacccctccc    1260
```

```
gtgctggact ccgacggctc cttcttcctc tacagcaagc tcaccgtgga caagagcagg    1320
tggcagcagg gcaacgtctt ctcatgctcc gtgatgcatg aggctctgca caaccactac    1380
acccagaaga gcctctccct gtctcccggc aaa                                 1413
```

<210> SEQ ID NO 54
<211> LENGTH: 122
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of variable region of
      humanized antibody heavy chain hH1

<400> SEQUENCE: 54

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Gly Val Asn Pro Asn Ser Gly Asp Thr Ser Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Gly Tyr Asp Val Gly Tyr Tyr Ala Met Asp Tyr Trp
            100                 105                 110

Gly Gln Gly Thr Leu Val Thr Val Ser Ser
        115                 120
```

<210> SEQ ID NO 55
<211> LENGTH: 366
<212> TYPE: DNA
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: nucleotide sequence encoding variable region of
      humanized antibody heavy chain hH1

<400> SEQUENCE: 55

```
caggtgcagc tggtgcagtc tggcgccgaa gtgaagaaac caggcgccag cgtgaaggtg     60
tcctgcaagg ccagcggcta cacctttacc gagtacacca tgcactgggt gcgccaggct    120
ccaggccagg gactggaatg gatgggcggc gtgaacccca acagcggcga taagctac      180 gcccagaaat tccagggcag agtgaccatc accgccgaca ccagcacctc caccgcctac    240
atggaactga gcagcctgcg gagcgaggac accgccgtgt actactgtgc tagacctggc    300
ggctacgacg tgggctacta cgccatggat tactggggcc agggcaccct cgtgaccgtc    360
agctca                                                              366
```

<210> SEQ ID NO 56
<211> LENGTH: 471
<212> TYPE: PRT
<213> ORGANISM: Artificial Sequence
<220> FEATURE:
<223> OTHER INFORMATION: Description of Artificial Sequence: Synthetic humanized antibody
<220> FEATURE:
<223> OTHER INFORMATION: amino acid sequence of humanized antibody heavy
      chain hH2

<400> SEQUENCE: 56

Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ala Ser Val Lys Val Ser Cys Lys Thr Ser Gly Tyr Thr Phe
        35                  40                  45

Thr Glu Tyr Thr Met His Trp Val Arg Gln Ala Pro Gly Lys Ser Leu
    50                  55                  60

Glu Trp Met Gly Gly Val Asn Pro Asn Ser Gly Asp Thr Ser Tyr Ala
65                  70                  75                  80

Gln Lys Phe Gln Gly Arg Val Thr Ile Thr Ala Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Pro Gly Gly Tyr Asp Val Gly Tyr Tyr Ala Met
        115                 120                 125

Asp Tyr Trp Gly Gln Gly Thr Leu Val Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Ala Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

```
Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 57
<211> LENGTH: 1413
<212> TYPE: DNA
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: nucleotide sequence encoding humanized antibody
      heavy chain hH2

<400> SEQUENCE: 57
atgaaacacc tgtggttctt cctcctgctg gtggcagctc ccagatgggt gctgagcgaa      60
gtgcagctgg tgcagtctgg cgccgaagtg aagaaaccag cgccagcgt gaaggtgtcc      120 tgcaagacca gcggctacac ctttaccgag tacaccatgc actgggtgcg ccaggcccct     180
ggcaagagcc tggaatggat gggcggcgtg aaccccaaca gcggcgatac aagctacgcc     240
cagaaattcc agggcagagt gaccatcacc gccgacacca gcacctccac cgcctacatg     300
gaactgagca gcctgcggag cgaggacacc gccgtgtact actgtgctag acctggcggc     360
tacgacgtgg gctactacgc catggattac tggggccagg gcaccctcgt gaccgtcagc     420
tcagcctcca ccaagggccc aagcgtcttc ccctggcac cctcctccaa gagcacctct     480
ggcggcacag ccgccctggg ctgcctggtc aaggactact ccccgaacc cgtgaccgtg      540 agctggaact caggcgccct gaccagcggc gtgcacacct tcccgctgt cctgcagtcc      600 tcaggactct actccctcag cagcgtggtg accgtgccct ccagcagctt gggcacccag     660
acctacatct gcaacgtgaa tcacaagccc agcaacacca aggtggacaa gagagttgag     720
cccaaatctt gtgacaaaac tcacacatgc ccaccctgcc cagcacctga gccgcgggg     780 ggaccctcag tcttcctctt ccccccaaaa cccaaggaca ccctcatgat ctcccggacc     840
cctgaggtca catgcgtggt ggtggacgtg agccacgaag accctgaggt caagttcaac     900
tggtacgtgg acggcgtgga ggtgcataat gccaagacaa agccccggga ggagcagtac     960
aacagcacgt accgggtggt cagcgtcctc accgtcctgc accaggactg gctgaatggc    1020
aaggagtaca agtgcaaggt ctccaacaaa gccctcccag ccccatcga gaaaaccatc    1080 tccaaagcca aggccagccc ccgggaacca caggtgtaca ccctgccccc atcccgggag    1140
gagatgacca agaaccaggt cagcctgacc tgcctggtca aaggcttcta tcccagcgac    1200
atcgccgtgg agtgggagag caatggccag ccggagaaca actacaagac caccctcccc    1260
gtgctggact ccgacggctc cttcttcctc tacagcaagc tcaccgtgga caagagcagg    1320
tggcagcagg gcaacgtctt ctcatgctcc gtgatgcatg aggctctgca caaccactac    1380
acccagaaga gcctctccct gtctccgggc aaa                                 1413
```

<210> SEQ ID NO 58
<211> LENGTH: 122
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of variable region of
      humanized antibody heavy chain hH2

<400> SEQUENCE: 58

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Met His Trp Val Arg Gln Ala Pro Gly Lys Ser Leu Glu Trp Met
        35                  40                  45

Gly Gly Val Asn Pro Asn Ser Gly Asp Thr Ser Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Gly Tyr Asp Val Gly Tyr Tyr Ala Met Asp Tyr Trp
            100                 105                 110

Gly Gln Gly Thr Leu Val Thr Val Ser Ser
        115                 120

<210> SEQ ID NO 59
<211> LENGTH: 366
<212> TYPE: DNA
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: nucleotide sequence encoding variable region of
      humanized antibody heavy chain hH2

<400> SEQUENCE: 59
gaagtgcagc tggtgcagtc tggcgccgaa gtgaagaaac caggcgccag cgtgaaggtg      60
tcctgcaaga ccagcggcta cacctttacc gagtacacca tgcactgggt gcgccaggcc     120
cctggcaaga gcctggaatg gatgggcggc gtgaaccccaa cagcggcga tacaagctac     180 gcccagaaat tccagggcag agtgaccatc accgccgaca ccagcacctc caccgcctac     240
atggaactga gcagcctgcg gagcgaggac accgccgtgt actactgtgc tagacctggc     300
ggctacgacg tgggctacta cgccatggat tactggggcc agggcaccct cgtgaccgtc     360
agctca                                                                366

<210> SEQ ID NO 60
<211> LENGTH: 471
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of humanized antibody heavy
      chain hH3

```
<400> SEQUENCE: 60

Met Lys His Leu Trp Phe Phe Leu Leu Leu Val Ala Ala Pro Arg Trp
 1               5                  10                  15

Val Leu Ser Glu Val Gln Leu Val Gln Ser Gly Ala Glu Val Lys Lys
             20                  25                  30

Pro Gly Ala Ser Val Lys Val Ser Cys Lys Thr Ser Gly Tyr Thr Phe
         35                  40                  45

Thr Glu Tyr Thr Met His Trp Val Arg Gln Ala Pro Gly Gln Gly Leu
     50                  55                  60

Glu Trp Met Gly Gly Val Asn Pro Asn Ser Gly Asp Thr Ser Tyr Ala
 65                  70                  75                  80

Gln Lys Phe Gln Gly Arg Val Thr Leu Thr Val Asp Lys Ser Thr Ser
                 85                  90                  95

Thr Ala Tyr Met Glu Leu Ser Ser Leu Arg Ser Glu Asp Thr Ala Val
            100                 105                 110

Tyr Tyr Cys Ala Arg Pro Gly Gly Tyr Asp Val Gly Tyr Tyr Ala Met
        115                 120                 125

Asp Tyr Trp Gly Gln Gly Thr Leu Val Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Ala Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415
```

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 61
<211> LENGTH: 1413
<212> TYPE: DNA
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: nucleotide sequence encoding humanized antibody
      heavy chain hH3

<400> SEQUENCE: 61
atgaaacacc tgtggttctt cctcctgctg gtggcagctc ccagatgggt gctgagcgaa    60
gtgcagctgg tgcagtctgg cgccgaagtg aagaaaccag gcgccagcgt gaaggtgtcc   120
tgcaagacca gcggctacac ctttaccgag tacaccatgc actgggtgcg ccaggctcca   180
ggccagggac tggaatggat gggcggcgtg aaccccaaca cggcgatac aagctacgcc    240 cagaaattcc agggcagagt gaccctgacc gtggacaaga gcaccagcac cgcctacatg   300
gaactgagca gcctgcggag cgaggacacc gccgtgtact actgtgctag acctggcggc   360
tacgacgtgg gctactacgc catggattac tggggccagg gcaccctcgt gaccgtcagc   420
tcagcctcca ccaagggccc aagcgtcttc cccctggcac cctcctccaa gagcacctct   480
ggcggcacag ccgccctggg ctgcctggtc aaggactact ccccgaacc cgtgaccgtg    540 agctggaact caggcgccct gaccagcggc gtgcacacct tccccgctgt cctgcagtcc   600
tcaggactct actccctcag cagcgtggtg accgtgccct ccagcagctt gggcacccag   660
acctacatct gcaacgtgaa tcacaagccc agcaacacca aggtggacaa gagagttgag   720
cccaaatctt gtgacaaaac tcacacatgc ccaccctgcc cagcacctga gccgcgggg    780 ggaccctcag tcttcctctt ccccccaaaa cccaaggaca cctcatgat ctcccggacc    840 cctgaggtca catgcgtggt ggtggacgtg agccacgaag accctgaggt caagttcaac   900
tggtacgtgg acggcgtgga ggtgcataat gccaagacaa agcccggaa ggagcagtac   960 aacagcacgt accgggtggt cagcgtcctc accgtcctgc accaggactg gctgaatggc  1020
aaggagtaca agtgcaaggt ctccaacaaa gccctcccag cccccatcga gaaaaccatc  1080
tccaaagcca aggccagccc cgggaaccca ggtgtaca ccctgccccc atcccgggag    1140
gagatgacca gaaccaggt cagcctgacc tgcctggtca aaggcttcta tcccagcgac   1200
atcgccgtgg agtgggagag caatggccag ccgagaaca actacaagac cacccctccc    1260
gtgctggact ccgacggctc cttcttcctc tacagcaagc tcaccgtgga caagagcagg   1320
tggcagcagg gcaacgtctt ctcatgctcc gtgatgcatg aggctctgca caaccactac  1380
acccagaaga gcctctccct gtctccggc aaa                                 1413

<210> SEQ ID NO 62
<211> LENGTH: 122
<212> TYPE: PRT

<213> ORGANISM: Artificial Sequence
<220> FEATURE:
<223> OTHER INFORMATION: Description of Artificial Sequence: Synthetic humanized antibody
<220> FEATURE:
<223> OTHER INFORMATION: amino acid sequence of variable region of humanized antibody heavy chain hH3

<400> SEQUENCE: 62

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Gly Val Asn Pro Asn Ser Gly Asp Thr Ser Tyr Ala Gln Lys Phe
    50                  55                  60

Gln Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Gly Tyr Asp Val Gly Tyr Tyr Ala Met Asp Tyr Trp
            100                 105                 110

Gly Gln Gly Thr Leu Val Thr Val Ser Ser
        115                 120
```

<210> SEQ ID NO 63
<211> LENGTH: 366
<212> TYPE: DNA
<213> ORGANISM: Artificial Sequence
<220> FEATURE:
<223> OTHER INFORMATION: Description of Artificial Sequence: Synthetic humanized antibody
<220> FEATURE:
<223> OTHER INFORMATION: nucleotide sequence encoding variable region of humanized antibody heavy chain hH3

<400> SEQUENCE: 63

```
gaagtgcagc tggtgcagtc tggcgccgaa gtgaagaaac caggcgccag cgtgaaggtg      60
tcctgcaaga ccagcggcta cacctttacc gagtacacca tgcactgggt gcgccaggct     120
ccaggccagg gactggaatg gatgggcggc gtgaacccca acagcggcga taagctac       180 gcccagaaat tccagggcag agtgaccctg accgtggaca gagcaccag caccgcctac      240 atggaactga gcagcctgcg gagcgaggac accgccgtgt actactgtgc tagacctggc     300
ggctacgacg tgggctacta cgccatggat tactggggcc agggcaccct cgtgaccgtc     360
agctca                                                                366
```

<210> SEQ ID NO 64
<211> LENGTH: 214
<212> TYPE: PRT
<213> ORGANISM: Artificial Sequence
<220> FEATURE:
<223> OTHER INFORMATION: Description of Artificial Sequence: Synthetic humanized antibody
<220> FEATURE:
<223> OTHER INFORMATION: amino acid sequence of Trastuzumab light chain

<400> SEQUENCE: 64

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
```

```
                20                  25                  30
Val Ala Trp Tyr Gln Gln Lys Pro Gly Lys Ala Pro Lys Leu Leu Ile
            35                  40                  45
Tyr Ser Ala Ser Phe Leu Tyr Ser Gly Val Pro Ser Arg Phe Ser Gly
        50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 65
<211> LENGTH: 450
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of Trastuzumab heavy chain

<400> SEQUENCE: 65

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
```

```
                145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
                210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
450

<210> SEQ ID NO 66
<211> LENGTH: 234
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of anti-LPS antibody
      (h#1G5-H1L1) light chain

<400> SEQUENCE: 66

Met Val Leu Gln Thr Gln Val Phe Ile Ser Leu Leu Leu Trp Ile Ser
1               5                   10                  15
Gly Ala Tyr Gly Asp Ile Val Met Thr Gln Ser Pro Asp Ser Leu Ala
                20                  25                  30
```

```
Val Ser Leu Gly Glu Arg Ala Thr Ile Asn Cys Lys Ala Ser Glu Asn
            35                  40                  45

Val Gly Asn Ser Val Ser Trp Tyr Gln Gln Lys Pro Gly Gln Pro Pro
 50                  55                  60

Lys Leu Leu Ile Tyr Gly Ala Ser Asn Arg Tyr Thr Gly Val Pro Asp
 65                  70                  75                  80

Arg Phe Ser Gly Ser Gly Ser Gly Thr Asp Phe Thr Leu Thr Ile Ser
                 85                  90                  95

Ser Leu Gln Ala Glu Asp Val Ala Val Tyr Tyr Cys Gln Gln Ser Tyr
                100                 105                 110

Ser Tyr Pro Tyr Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230
```

<210> SEQ ID NO 67
<211> LENGTH: 474
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of anti-LPS antibody
      (h#1G5-H1L1) heavy chain

<400> SEQUENCE: 67

```
Met Lys His Leu Trp Phe Phe Leu Leu Leu Val Ala Ala Pro Arg Trp
 1               5                  10                  15

Val Leu Ser Gln Val Gln Leu Val Gln Ser Gly Ala Glu Val Lys Lys
                 20                  25                  30

Pro Gly Ala Ser Val Lys Val Ser Cys Lys Ala Ser Gly Tyr Thr Phe
             35                  40                  45

Thr Ser Tyr Trp Ile Asn Trp Val Arg Gln Ala Pro Gly Gln Gly Leu
 50                  55                  60

Glu Trp Met Gly Asn Ile Tyr Pro Gly Ser Ser Ile Asn Tyr Asn
 65                  70                  75                  80

Glu Lys Phe Lys Ser Arg Val Thr Ile Thr Ala Asp Thr Ser Thr Ser
                 85                  90                  95

Thr Ala Tyr Met Glu Leu Ser Ser Leu Arg Ser Glu Asp Thr Ala Val
                100                 105                 110

Tyr Tyr Cys Ala Arg Thr Ile Tyr Asn Tyr Gly Ser Ser Gly Tyr Asn
            115                 120                 125

Tyr Ala Met Asp Tyr Trp Gly Gln Gly Thr Leu Val Thr Val Ser Ser
130                 135                 140
```

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
            165                 170                 175

Phe Pro Glu Pro Val Thr Val Ser Trp Asn Ser Gly Ala Leu Thr Ser
        180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
        290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 68
<211> LENGTH: 234
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of anti-TROP2 antibody
      (hRS7) light chain

<400> SEQUENCE: 68

Met Val Leu Gln Thr Gln Val Phe Ile Ser Leu Leu Leu Trp Ile Ser

-continued

```
                1               5                      10                      15
     Gly Ala Tyr Gly Asp Ile Gln Leu Thr Gln Ser Pro Ser Ser Leu Ser
                        20                      25                      30

Ala Ser Val Gly Asp Arg Val Ser Ile Thr Cys Lys Ala Ser Gln Asp
                        35                      40                      45

Val Ser Ile Ala Val Ala Trp Tyr Gln Gln Lys Pro Gly Lys Ala Pro
              50                      55                      60

Lys Leu Leu Ile Tyr Ser Ala Ser Tyr Arg Tyr Thr Gly Val Pro Asp
     65                      70                      75                      80

Arg Phe Ser Gly Ser Gly Ser Gly Thr Asp Phe Thr Leu Thr Ile Ser
                             85                      90                      95

Ser Leu Gln Pro Glu Asp Phe Ala Val Tyr Tyr Cys Gln Gln His Tyr
                        100                     105                     110

Ile Thr Pro Leu Thr Phe Gly Ala Gly Thr Lys Val Glu Ile Lys Arg
                        115                     120                     125

Thr Val Ala Ala Pro Ser Val Phe Ile Phe Pro Pro Ser Asp Glu Gln
                   130                     135                     140

Leu Lys Ser Gly Thr Ala Ser Val Val Cys Leu Leu Asn Asn Phe Tyr
     145                     150                     155                     160

Pro Arg Glu Ala Lys Val Gln Trp Lys Val Asp Asn Ala Leu Gln Ser
                        165                     170                     175

Gly Asn Ser Gln Glu Ser Val Thr Glu Gln Asp Ser Lys Asp Ser Thr
                        180                     185                     190

Tyr Ser Leu Ser Ser Thr Leu Thr Leu Ser Lys Ala Asp Tyr Glu Lys
                        195                     200                     205

His Lys Val Tyr Ala Cys Glu Val Thr His Gln Gly Leu Ser Ser Pro
                   210                     215                     220

Val Thr Lys Ser Phe Asn Arg Gly Glu Cys
     225                     230

<210> SEQ ID NO 69
<211> LENGTH: 470
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of anti-TROP2 antibody
      (hRS7) heavy chain

<400> SEQUENCE: 69

Met Lys His Leu Trp Phe Phe Leu Leu Leu Val Ala Ala Pro Arg Trp
     1               5                      10                      15

Val Leu Ser Gln Val Gln Leu Gln Gln Ser Gly Ser Glu Leu Lys Lys
                        20                      25                      30

Pro Gly Ala Ser Val Lys Val Ser Cys Lys Ala Ser Gly Tyr Thr Phe
                        35                      40                      45

Thr Asn Tyr Gly Met Asn Trp Val Lys Gln Ala Pro Gly Gln Gly Leu
              50                      55                      60

Lys Trp Met Gly Trp Ile Asn Thr Tyr Thr Gly Glu Pro Thr Tyr Thr
     65                      70                      75                      80

Asp Asp Phe Lys Gly Arg Phe Ala Phe Ser Leu Asp Thr Ser Val Ser
                             85                      90                      95

Thr Ala Tyr Leu Gln Ile Ser Ser Leu Lys Ala Asp Asp Thr Ala Val
                        100                     105                     110
```

Tyr Phe Cys Ala Arg Gly Gly Phe Gly Ser Ser Tyr Trp Tyr Phe Asp
            115                 120                 125

Val Trp Gly Gln Gly Ser Leu Val Thr Val Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
            210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 70
<211> LENGTH: 240
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of anti-CD98 antibody (hM23-H1L1) light chain

<400> SEQUENCE: 70

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Arg Tyr Tyr Gly Tyr Pro Trp Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 465
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: amino acid sequence of anti-CD98 antibody
      (hM23-H1L1) heavy chain

<400> SEQUENCE: 71

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ala Phe
        35                  40                  45

Ser Asn Tyr Leu Ile Glu Trp Val Arg Gln Ala Pro Gly Gln Gly Leu
    50                  55                  60

Glu Trp Met Gly Val Ile Asn Pro Gly Ser Gly Val Thr Asn Tyr Asn
65                  70                  75                  80

Glu Lys Phe Lys Gly Arg Val Thr Ile Thr Ala Asp Thr Ser Thr Ser

```
                85                  90                  95
Thr Ala Tyr Met Glu Leu Ser Ser Leu Arg Ser Glu Asp Thr Ala Val
            100                 105                 110
Tyr Tyr Cys Ala Arg Ala Glu Ala Trp Phe Ala Tyr Trp Gly Gln Gly
            115                 120                 125
Thr Leu Val Thr Val Ser Ser Ala Ser Thr Lys Gly Pro Ser Val Phe
        130                 135                 140
Pro Leu Ala Pro Ser Ser Lys Ser Thr Ser Gly Gly Thr Ala Ala Leu
145                 150                 155                 160
Gly Cys Leu Val Lys Asp Tyr Phe Pro Glu Pro Val Thr Val Ser Trp
                165                 170                 175
Asn Ser Gly Ala Leu Thr Ser Gly Val His Thr Phe Pro Ala Val Leu
            180                 185                 190
Gln Ser Ser Gly Leu Tyr Ser Leu Ser Ser Val Val Thr Val Pro Ser
            195                 200                 205
Ser Ser Leu Gly Thr Gln Thr Tyr Ile Cys Asn Val Asn His Lys Pro
        210                 215                 220
Ser Asn Thr Lys Val Asp Lys Arg Val Glu Pro Lys Ser Cys Asp Lys
225                 230                 235                 240
Thr His Thr Cys Pro Pro Cys Pro Ala Pro Glu Leu Leu Gly Gly Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser His Glu Asp
            275                 280                 285
Pro Glu Val Lys Phe Asn Trp Tyr Val Asp Gly Val Glu Val His Asn
        290                 295                 300
Ala Lys Thr Lys Pro Arg Glu Glu Gln Tyr Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Ala Leu Pro Ala Pro Ile Glu Lys
            340                 345                 350
Thr Ile Ser Lys Ala Lys Gly Gln Pro Arg Glu Pro Gln Val Tyr Thr
            355                 360                 365
Leu Pro Pro Ser Arg Glu Glu Met Thr Lys Asn Gln Val Ser Leu Thr
        370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Lys Leu Thr Val Asp Lys
            420                 425                 430
Ser Arg Trp Gln Gln Gly Asn Val Phe Ser Cys Ser Val Met His Glu
            435                 440                 445
Ala Leu His Asn His Tyr Thr Gln Lys Ser Leu Ser Leu Ser Pro Gly
        450                 455                 460
Lys
465

<210> SEQ ID NO 72
<211> LENGTH: 702
<212> TYPE: DNA
<213> ORGANISM: Artificial Sequence
```

<220> FEATURE:
<223> OTHER INFORMATION: Description of Artificial Sequence: Synthetic humanized antibody
<220> FEATURE:
<223> OTHER INFORMATION: nucleotide sequence encoding Trastuzumab mutant light chain

<400> SEQUENCE: 72

```
atggtgctgc agacccaggt gttcatctcc ctgctgctgt ggatctccgg cgcgtacggc      60
gacatccaga tgacacagag ccctagcagc ctgtctgcca gcgtgggaga cagagtgacc     120
atcacctgta gagccagcca ggacgtgaac acagccgtgg cttggtatca gcagaagcct     180
ggcaaggccc ctaagctgct gatctacagc gccagctttc tgtacagcgg cgtgcccagc     240
agattcagcg gctctagaag cggcaccgac ttcaccctga ccataagcag tctgcagccc     300
gaggacttcg ccacctacta ctgtcagcag cactacacca cctccaac ctttggccag       360
ggcaccaagg tggaaatcaa gcgtacggtg gccgccccct ccgtgttcat cttcccccc      420
tccgacgagc agctgaagtc cggcaccgcc tccgtggtgt gcctgctgaa taacttctac     480
cccagagagg ccaaggtgca gtggaaggtg gacaacgccc tgcagtccgg aactcccag      540
gagagcgtga ccgagcagga cagcaaggac agcacctaca gcctgagcag caccctgacc     600
ctgagcaaag ccgactacga aagcacaag gtgtacgcct gcgaggtgac ccaccagggc      660
ctgagctccc ccgtcaccaa gagcttcaac agggggagt gt                         702
```

<210> SEQ ID NO 73
<211> LENGTH: 234
<212> TYPE: PRT
<213> ORGANISM: Artificial Sequence
<220> FEATURE:
<223> OTHER INFORMATION: Description of Artificial Sequence: Synthetic humanized antibody
<220> FEATURE:
<223> OTHER INFORMATION: amino acid sequence of Trastuzumab mutant light chain

<400> SEQUENCE: 73

```
Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175
```

```
Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 74
<211> LENGTH: 1407
<212> TYPE: DNA
<213> ORGANISM: Artificial Sequence
<220> FEATURE:
<223> OTHER INFORMATION: Description of Artificial Sequence: Synthetic
      humanized antibody
<220> FEATURE:
<223> OTHER INFORMATION: nucleotide sequence encoding Trastuzumab mutant
      heavy chain

<400> SEQUENCE: 74
atgaaacacc tgtggttctt cctcctgctg gtggcagctc ccagatgggt gctgagcgag    60
gtgcagctgg ttgaatctgg cggaggactg gttcagcctg gcggatctct gagactgtct   120
tgtgccgcca gcggcttcaa catcaaggac acctacatcc actgggtccg acaggccct    180 ggcaaaggac ttgaatgggt cgccagaatc taccccacca acggctacac cagatacgcc   240
gactctgtga aggcagatt caccatcagc gccgacacca gcaagaacac cgcctacctg   300
cagatgaaca gcctgagagc cgaggacacc gccgtgtact actgttctag atggggaggc   360
gacggcttct acgccatgga ttattgggc cagggcaccc tggttaccgt tagctcagcc   420
tccaccaagg gcccaagcgt cttccccctg gcaccctcct ccaagagcac ctctgcggc   480 acagccgccc tgggctgcct ggtcaaggac tacttcccg aacccgtgac cgtgagctgg   540
aactcaggcg ccctgaccag cggcgtgcac accttccccg ctgtcctgca gtcctcagga   600
ctctactccc tcagcagcgt ggtgaccgtg ccctccagca gcttgggcac ccagacctac   660
atctgcaacg tgaatcacaa gcccagcaac accaaggtgg acaagagagt tgagcccaaa   720
tcttgtgaca aaactcacac atgcccaccc tgcccagcac ctgaagccgc ggggggaccc   780
tcagtcttcc tcttcccccc aaaacccaag gacaccctca tgatctcccg gacccctgag   840
gtcacatgcg tggtggtgga cgtgagccac gaagaccctg aggtcaagtt caactggtac   900
gtggacggcg tggaggtgca taatgccaag acaaagcccc gggaggagca gtacaacagc   960
acgtaccggg tggtcagcgt cctcaccgtc ctgcaccagg actggctgaa tggcaaggag  1020
tacaagtgca aggtctccaa caaagccctc ccagccccca tcgagaaaac catctccaaa  1080
gccaaaggcc agccccggga accacaggtg tacaccctgc ccccatcccg ggaggagatg  1140
accaagaacc aggtcagcct gacctgcctg gtcaaaggct tctatcccag cgacatcgcc  1200
gtggagtggg agagcaatgg ccagcccgag aacaactaca agaccacccc tcccgtgctg  1260
gactccgacg gctccttctt cctctacagc aagctcaccg tggacaagag caggtggcag  1320
cagggcaacg tcttctcatg ctccgtgatg catgaggctc tgcacaacca ctacacccag  1380
aagagcctct ccctgtctcc cggcaaa                                     1407

<210> SEQ ID NO 75
<211> LENGTH: 469
<212> TYPE: PRT
```

<213> ORGANISM: Artificial Sequence
<220> FEATURE:
<223> OTHER INFORMATION: Description of Artificial Sequence: Synthetic humanized antibody
<220> FEATURE:
<223> OTHER INFORMATION: amino acid sequence of Trastuzumab mutant heavy chain

<400> SEQUENCE: 75

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Ala
                245                 250                 255

Ala Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365
```

```
Gln Val Tyr Thr Leu Pro Pro Ser Arg Glu Glu Met Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys
465

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Gly Val Ala
1

<210> SEQ ID NO 77
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Gly Phe Gly
1

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Gly Pro Ile
1

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Citrulline

<400> SEQUENCE: 79

Gly Gly Val Xaa
```

```
<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Gly Val Lys
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Gly Pro Leu
1

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu Gly Gly Val Ala
1               5

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Gly Gly Phe
1

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Gly Gly Phe
1

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
                            peptide

<400> SEQUENCE: 85

Ser Gly Gly Phe
1

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Lys Gly Gly Phe
1

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Gly Gly Phe Gly
1               5

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Gly Phe Gly Gly
1               5

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asp Asp Gly Gly Phe Gly
1               5
```

```
<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Lys Asp Gly Gly Phe Gly
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Gly Phe Gly Gly Gly Phe
1               5

<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asp Asp Gly Gly
1

<210> SEQ ID NO 93
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Asp Gly Gly
1

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ornithine

<400> SEQUENCE: 94

Gly Gly Val Xaa
1
```

METHODS OF TREATING A TUMOR BY ADMINISTERING A CLAUDIN-6 (CLDN6) OR CLDN9 ANTIBODY-PYRROLOBENZODIAZEPINE DERIVATIVE CONJUGATE

CROSS-REFERENCE TO RELATED APPLICATIONS

The present application is a Divisional of U.S. patent application Ser. No. 17/543,697, now U.S. Pat. No. 11,583,590, filed on Dec. 6, 2021, which is a Continuation of U.S. patent application Ser. No. 16/651,501, now U.S. Pat. No. 11,628,223, filed on Mar. 27, 2020, which claims priority under 35 U.S.C. § 371 to International Patent Application No. PCT/JP2018/036252, filed Sep. 28, 2018, which claims priority to and the benefit of Japanese Patent Application No. 2017-190713, filed on Sep. 29, 2017. The contents of these applications are hereby incorporated by reference in their entireties.

SEQUENCE LISTING

The instant application contains a Sequence Listing which has been submitted via USPTO Patent Center and is hereby incorporated by reference in its entirety. Said Sequence Listing, is named 122763-0109_Updated_SL.xml and is 162,920 bytes in size.

TECHNICAL FIELD

The present invention relates to an antibody-drug conjugate useful as an antitumor drug, the antibody-drug conjugate having an antibody capable of targeting tumor cells and a pyrrolobenzodiazepine derivative that are conjugated to each other via a linker structure moiety.

BACKGROUND ART

Antibody-drug conjugates (ADCs) have a drug with cytotoxic activity conjugated to an antibody that binds to an antigen expressed on the surface of cancer cells and is capable of cellular internalization of the antigen through the binding. ADCs can effectively deliver the drug to cancer cells, and are thus expected to cause accumulation of the drug within the cancer cells and to kill the cancer cells.

For example, the ADC Adcetris (TM) (brentuximab vedotin), which has monomethyl auristatin E conjugated to an anti-CD30 monoclonal antibody, has been approved as a therapeutic drug for Hodgkin's lymphoma and anaplastic large-cell lymphoma. Kadcyla (TM) (trastuzumab emtansine), which has emtansine conjugated to an anti-HER2 monoclonal antibody, is used for treatment of HER2-positive advanced and recurrent breast cancers.

A useful example of drugs to be conjugated for ADCs is pyrrolobenzodiazepine (PBD). PBD exhibits cytotoxicity, for example, by binding to the PuGPu sequence in the DNA minor groove. Anthramycin, a naturally-occurring PBD, was first discovered in 1965, and since this discovery various naturally-occurring PBDs and analog PBDs thereof have been discovered (Non Patent Literatures 1 to 4).

The general structural formula of PBDs is represented by the following formula:

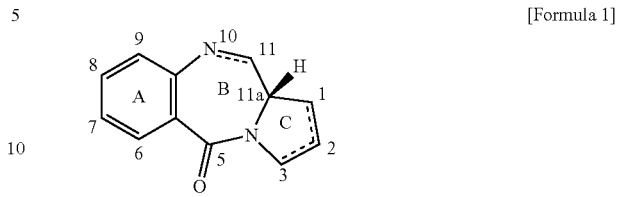

[Formula 1]

Known are PBDs different in the number of, types of, and sites of substituents in the A and C ring parts, and those different in degree of unsaturation in the B and C ring parts.

PBDs are known to come to have dramatically enhanced cytotoxicity through formation of a dimer structure (Non Patent Literatures 5, 6), and various ADCs with a dimer PBD have been reported (Patent Literatures 1 to 13). However, a PBD having a spiro ring at its C2-position and an ADC form thereof have not known.

Human CLDN6 (claudin-6, hereinafter expressed as hCLDN6), a member of claudin (CLDN) family proteins, is a four-transmembrane protein consisting of 220 amino acid residues. Previous studies have suggested that hCLDN6 is overexpressed in some cancers, and is an attractive cancer therapeutic target (Non Patent Literatures 7 to 9). CLDN family proteins are incorporated into cells by endocytosis, and some of the family proteins have been reported to have short turnover time (Non Patent Literature 10), and hence CLDN family proteins are considered to be suitable as the target of antibody-drug conjugates (ADCs).

From such information suggesting the relation to cancer, monoclonal antibodies capable of specifically recognizing hCLDN6 have been discovered (Patent Literatures 14, 15), and ADCs having monomethyl auristatin E (MMAE) or maytansinoid (DM1), which are tubulin polymerization inhibitors, conjugated to a CLDN6-specific monoclonal antibody have been reported (Non Patent Literature 11).

On the other hand, antibodies capable of recognizing multiple members of the CLDN family are considered to allow a wider range of application of treatment, and in view of this an ADC having a pyrrolobenzodiazepine (PBD) with potent cytocidal effect conjugated to an antibody capable of recognizing CLDN6 and CLDN9 (Patent Literature 16) has been disclosed (Patent Literature 17).

However, the intensities of activity of the ADCs are still insufficient, and there exist unmet medical needs for use of hCLDN6 as a therapeutic target.

CITATION LIST

Patent Literature

Patent Literature 1: WO 2013/173496
Patent Literature 2: WO 2014/130879
Patent Literature 3: WO 2017/004330
Patent Literature 4: WO 2017/004025
Patent Literature 5: WO 2017/020972
Patent Literature 6: WO 2016/036804
Patent Literature 7: WO 2015/095124
Patent Literature 8: WO 2015/052322
Patent Literature 9: WO 2015/052534
Patent Literature 10: WO 2016/115191
Patent Literature 11: WO 2015/052321
Patent Literature 12: WO 2015/031693

Patent Literature 13: WO 2011/130613
Patent Literature 14: WO 2009/087978
Patent Literature 15: WO 2011/057788
Patent Literature 16: WO 2015/069794
Patent Literature 17: WO 2017/096163

Non Patent Literature

Non Patent Literature 1: Julia Mantaj, et al., Angewandte Chemie Internationl Edition 2016, 55, 2-29
Non Patent Literature 2: Dyeison Antonow. et al., Chemical Reviews 2010, 111, 2815-2864
Non Patent Literature 3: In Antibiotics III. Springer Verlag, New York, pp. 3-11
Non Patent Literature 4: Accounts of Chemical Research 1986, 19, 230
Non Patent Literature 5: Journal of the American Chemical Society 1992, 114, 4939
Non Patent Literature 6: Journal of Organic Chemistry 1996, 61, 8141
Non Patent Literature 7: BMC Cancer, 2006, 6, 186.
Non Patent Literature 8: Histopathology, 2012, 61, 1043-1056.
Non Patent Literature 9: Int J Cancer, 2014, 135, 2206-2214.
Non Patent Literature 10: J Membrane Biol, 2004, 199, 29-38.
Non Patent Literature 11: 14th Annu Meet Cancer Immunother (CIMT) (May 10-12, Mainz) 2016, Abst 185

SUMMARY OF INVENTION

Problems to be resolved by the Invention

The present invention provides a novel antibody-pyrrolobenzodiazepine (PBD) derivative conjugate and a novel pyrrolobenzodiazepine (PBD) derivative.

The present invention provides a novel anti-CLDN6 antibody.

In addition, the present invention provides a pharmaceutical composition containing the antibody-PBD derivative conjugate, PBD derivative, or anti-CLDN6 antibody with antitumor activity.

Further, the present invention provides a method for treating cancer by using the antibody-PBD derivative conjugate, PBD derivative, or anti-CLDN6 antibody.

Means of Solving the Problems

The present inventors diligently examined to find that a novel antibody-pyrrolobenzodiazepine (PBD) derivative conjugate has strong antitumor activity, thereby completing the present invention.

Specifically, the present invention relates to the following.

[1] An antibody-drug conjugate represented by the following formula:

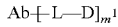 [Formula 2]

wherein
m¹ represents an integer of 1 to 10, preferably an integer of 2 to 8;
Ab represents an antibody or a functional fragment of the antibody, where the antibody optionally has a remodeled glycan;
L represents a linker linking Ab and D;
Ab may bond directly via its amino acid residue to L, or may bond via a glycan or a remodeled glycan of Ab to L; and
D represents a drug represented by the following formula:

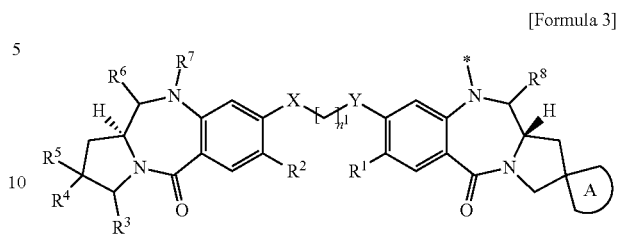

[Formula 3]

wherein
the asterisk represents bonding to L;
$n^1$ represents an integer of 2 to 8;
A represents a spiro-bonded three- to five-membered saturated hydrocarbon ring or three- to five-membered saturated heterocycle optionally substituted with one to four halogen atoms;
$R^1$ and $R^2$ each independently represent a C1 to C6 alkoxy group, a C1 to C6 alkyl group, a hydrogen atom, a hydroxy group, a thiol group, a C1 to C6 alkylthio group, a halogen atom, or —NR'R", wherein R' and R" each independently represent a hydrogen atom or a C1 to C6 alkyl group;
$R^3$, $R^4$, and $R^5$ are selected from (i) to (iii):
(i) $R^3$ and $R^4$ are combined, together with the carbon atoms to which $R^3$ and $R^4$ are bound, to form a double bond, and $R^5$ represents an aryl group or heteroaryl group optionally having one or more substituents selected from group 1 or a C1 to C6 alkyl group optionally having one or more substituents selected from group 2,
(ii) $R^3$ represents a hydrogen atom, and $R^4$ and $R^5$ are combined, together with the carbon atom to which $R^4$ and $R^5$ are bound, to form a three- to five-membered saturated hydrocarbon ring or a three- to five-membered saturated heterocycle, or $CH_2$=, and
(iii) $R^3$, $R^4$, and $R^5$ are combined, together with the carbon atom to which $R^3$ is bound and the carbon atom to which $R^4$ and $R^5$ are bound, to form a benzene ring or six-membered heterocycle optionally having one or more substituents selected from group 3;
$R^6$ and $R^7$ each represent a hydrogen atom, or $R^6$ and $R^7$ are combined to represent an imine bond (C=N);
$R^8$ represents a hydroxy group or a C1 to C3 alkoxy group;
X and Y each independently represent an oxygen atom, a nitrogen atom, or a sulfur atom;
group 1 represents:
a) a C1 to C6 alkoxy group optionally substituted with one to three halogen atoms,
b) a C1 to C6 alkyl group optionally substituted with any one selected from one to three halogen atoms, a hydroxy group, —OCOR', —NR'R", —C(NR')—NR"R''', and —NHC(=NR')—NR"R''',
c) a halogen atom,
d) a C3 to C5 cycloalkoxy group,
e) a C1 to C6 alkylthio group,
f) —NR'R",
g) —C(=NR')—NR"R''',
h) —NHC(=NR')—NR"R''',
i) —NHCOR', or
j) a hydroxy group, wherein R' and R" are as defined above, and R'" each independently represents a hydrogen atom or a C1 to C6 alkyl group;

group 2 represents a halogen atom, a hydroxy group, or a C1 to C6 alkoxy group; and group 3 represents a halogen atom, or a C1 to C6 alkyl group or C1 to C6 alkoxy group optionally substituted with one to three halogen atoms.

[2] The antibody-drug conjugate according to [1], wherein

A represents a spiro-bonded three- to five-membered saturated hydrocarbon ring optionally substituted with one or two halogen atoms;

$R^1$ and $R^2$ each independently represent a C1 to C3 alkoxy group;

$R^3$ and $R^4$ are combined together with the carbon atoms to which $R^3$ and $R^4$ are bound to form a double bond;

$R^5$ represents an aryl group or heteroaryl group optionally having one or more substituents selected from group 4, or a C1 to C3 alkyl group optionally having one or more substituents selected from group 5;

X and Y are each an oxygen atom;

group 4 represents:
a) a C1 to C3 alkoxy group optionally substituted with one to three halogen atoms,
b) a C1 to C3 alkyl group optionally substituted with any one selected from one to three halogen atoms, a hydroxy group, —OCOR", —C(=NR')—NR"R'", and —NHC(=NR')—NR"R'",
c) a C3 to C5 cycloalkoxy group,
d) —C(=NR')—NR"R'",
e) —NHC(=NR')—NR"R'", or
f) a hydroxy group, wherein R', R", and R'" each independently represent a hydrogen atom or a C1 to C3 alkyl group; and group 5 represents a halogen atom, a hydroxy group, or a C1 to C3 alkoxy group.

[3] The antibody-drug conjugate according to [1], wherein

A represents a spiro-bonded three- to five-membered saturated hydrocarbon ring optionally substituted with one or two halogen atoms;

$R^1$ and $R^2$ each independently represent a C1 to C3 alkoxy group;

$R^3$ represents a hydrogen atom;

$R^4$ and $R^5$ are combined, together with the carbon atom to which $R^4$ and $R^5$ are bound, to form a three- to five-membered saturated hydrocarbon ring, or =CH$_2$; and X and Y are each an oxygen atom.

[4] The antibody-drug conjugate according to [1], wherein

A represents a spiro-bonded three- to five-membered saturated hydrocarbon ring optionally substituted with one or two halogen atoms;

$R^1$ and $R^2$ each independently represent a C1 to C3 alkoxy group;

$R^3$, $R^4$, and $R^5$ are combined, together with the carbon atom to which $R^3$ is bound and the carbon atom to which $R^4$ and $R^5$ are bound, to form a benzene ring optionally having one or more substituents selected from group 6;

X and Y are each an oxygen atom; and group 6 represents a halogen atom, or a C1 to C3 alkyl group or C1 to C3 alkoxy group optionally substituted with one to three halogen atoms.

[5] The antibody-drug conjugate according to [1] or [2], wherein D is represented by any one of the following two formulas:

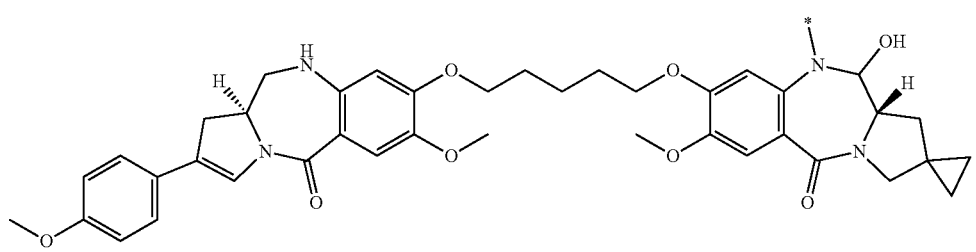

[Formula 4]

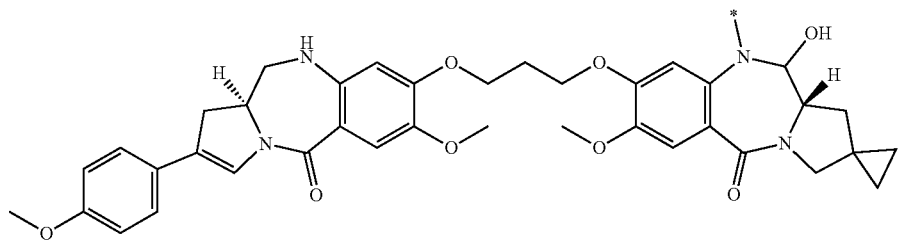

wherein each asterisk represents bonding to L.

[6] The antibody-drug conjugate according to [1] or [3], wherein D is represented by any one of the following two formulas:

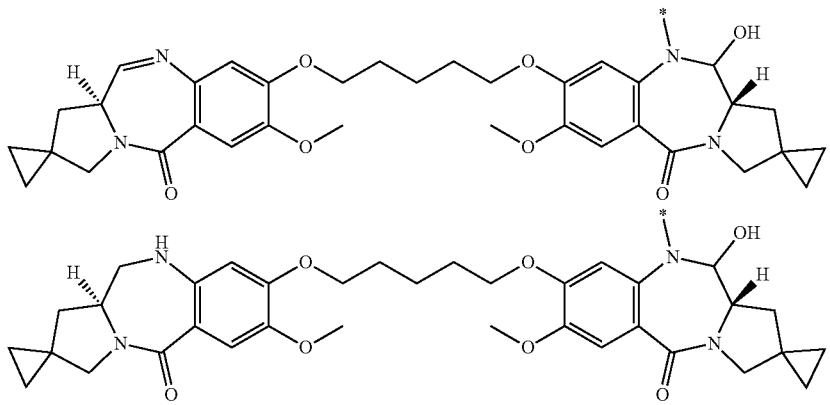
[Formula 5]

wherein each asterisk represents bonding to L.

[7] The antibody-drug conjugate according to any one of [1] to [6], wherein
L is represented by -Lb-La-Lp-NH—B—CH$_2$—O(C=O)—*, the asterisk representing bonding to D;
B represents a phenyl group or a heteroaryl group;
Lp represents a linker consisting of an amino acid sequence cleavable in a target cell;
La represents any one selected from the group:
—C(=O)—(CH$_2$CH$_2$)n$^2$-C(=O)—, —C(=O)—(CH$_2$CH$_2$)n$^2$-C(=O)—NH—(CH$_2$CH$_2$)n$^3$-C(=O)—, —C(=O)—(CH$_2$CH$_2$)n$^2$-C(=O)—NH—(CH$_2$CH$_2$O)n$^3$-CH$_2$—C(=O)—, —C(=O)—(CH$_2$CH$_2$)n$^2$-NH—C(=O)—(CH$_2$CH$_2$O)n$^3$-CH$_2$CH$_2$—C(=O)—, and —(CH$_2$)n$^4$-O—C(=O)—;
n$^2$ represents an integer of 1 to 3, n$^3$ represents an integer of 1 to 5, and n$^4$ represents an integer of 0 to 2; and
Lb represents a spacer bonding La and a glycan or remodeled glycan of Ab.

[8] The antibody-drug conjugate according to [7], wherein B is any one selected from a 1,4-phenyl group, a 2,5-pyridyl group, a 3,6-pyridyl group, a 2,5-pyrimidyl group, and a 2,5-thienyl group.

[9] The antibody-drug conjugate according to [8], wherein B is a 1,4-phenyl group.

[10] The antibody-drug conjugate according to any one of [7] to [9], wherein Lp is amino acid residues composed of two to seven amino acids.

[11] The antibody-drug conjugate according to any one of [7] to [10], wherein Lp is amino acid residues consisting of amino acids selected from glycine, valine, alanine, phenylalanine, glutamic acid, isoleucine, proline, citrulline, leucine, serine, lysine, and aspartic acid.

[12] The antibody-drug conjugate according to any one of [7] to [11], wherein Lp is selected from the following group:
-GGVA- (SEQ ID NO: 76), -GG-(D-)VA- (SEQ ID NO: 95), —VA-, -GGFG- (SEQ ID NO: 77), -GGPI— (SEQ ID NO: 78), -GGVCit- (SEQ ID NO: 79), -GGVK— (SEQ ID NO: 80), -GG(D-)PI— (SEQ ID NO: 96), and -GGPL- (SEQ ID NO: 81).

[13] The antibody-drug conjugate according to any one of [7] to [12], wherein La is selected from the following group:
—C(=O)—CH$_2$CH$_2$—C(=O)—, —C(=O)—(CH$_2$CH$_2$)$_2$—C(=O)—, —C(=O)—CH$_2$CH$_2$—C(=O)—NH—(CH$_2$CH$_2$)$_2$—C(=O)—, —C(=O)—CH$_2$CH$_2$—C(=O)—NH—(CH$_2$CH$_2$O)$_2$—CH$_2$—C(=O)—, —C(=O)—CH$_2$CH$_2$—NH—C(=O)—(CH$_2$CH$_2$O)$_4$—CH$_2$CH$_2$—C(=O)—, —CH$_2$—OC(=O)—, and —OC(=O)—.

[14] The antibody-drug conjugate according to any one of [7] to [13], wherein Lb is represented by the following formula:

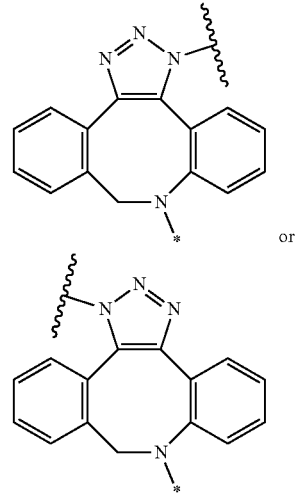
[Formula 6]

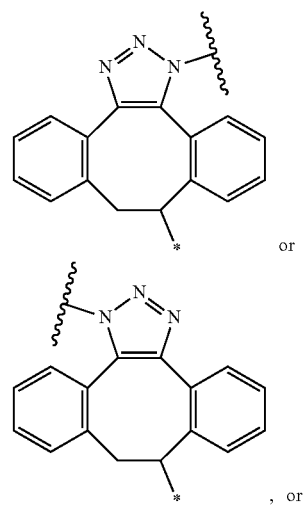
[Formula 7]

-continued

[Formula 8]

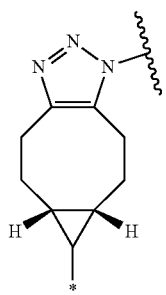

or

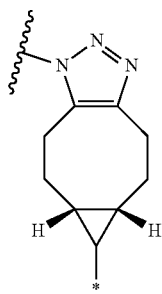

wherein, in each structural formula for Lb shown above,
each asterisk represents bonding to La, and each wavy line represents bonding to a glycan or remodeled glycan of Ab.

[15] The antibody-drug conjugate according to any one of [7] to [14], wherein

L is represented by -Lb-La-Lp-NH—B—CH$_2$—O(C=O)—*, wherein

B is a 1,4-phenyl group;

Lp represents any one selected from the following group:
-GGVA- (SEQ ID NO: 76), -GG-(D-)VA- (SEQ ID NO: 95), —VA-, -GGFG- (SEQ ID NO: 77), -GGPI— (SEQ ID NO: 78), -GGVCit- (SEQ ID NO: 79), -GGVK— (SEQ ID NO: 80), and -GGPL- (SEQ ID NO: 81);

La represents any one selected from the following group:
—C(=O)—CH$_2$CH$_2$—C(=O)—, —C(=O)—(CH$_2$CH$_2$)$_2$—C(=O)—, —C(=O)—CH$_2$CH$_2$—C(=O)—NH—(CH$_2$CH$_2$)$_2$—C(=O)—, —C(=O)—CH$_2$CH$_2$—C(=O)—NH—(CH$_2$CH$_2$O)$_2$—CH$_2$—C(=O)—, —C(=O)—CH$_2$CH$_2$—NH—C(=O)—(CH$_2$CH$_2$O)$_4$—CH$_2$CH$_2$—C(=O)—, —CH$_2$—OC(=O)—, and —OC(=O)—; and Lb is represented by the following formula:

[Formula 9]

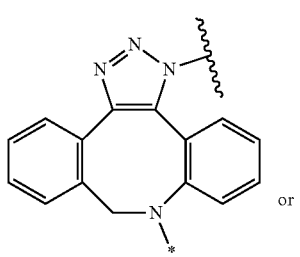

or

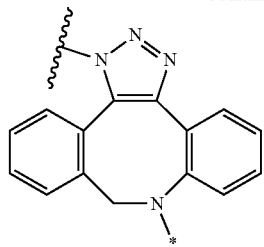

or

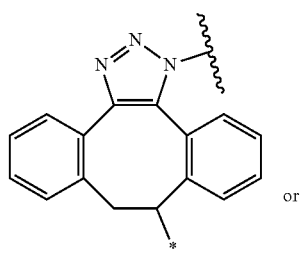

[Formula 10]

or

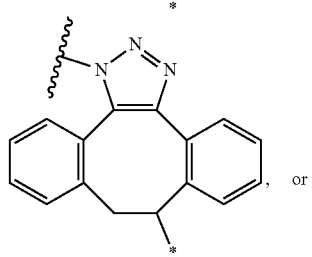

[Formula 11]

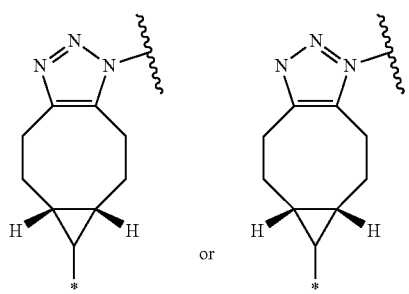

or wherein, in each structural formula for Lb shown above,
each asterisk represents bonding to La, and each wavy line represents bonding to a glycan or remodeled glycan of Ab.

[16] The antibody-drug conjugate according to any one of [7] to [15], wherein

L is selected from the following group:
—Z$^1$—C(=O)—CH$_2$CH$_2$—C(=O)-GGVA-NH—B—CH$_2$—OC(=O)—("GGVA" disclosed as SEQ ID NO: 76),
—Z$^1$—C(=O)—CH$_2$CH$_2$—C(=O)-GG-(D-)VA (SEQ ID NO: 95) —NH—B—CH$_2$—OC(=O)—, —Z$^1$—C(=O)—CH$_2$CH$_2$—C(=O)—VA-NH—B—CH$_2$—OC(=O)—, —Z$^1$—C(=O)—(CH$_2$CH$_2$)$_2$—C(=O)—VA-NH—B—CH$_2$—OC(=O)—, —Z$^1$—C(=O)—CH$_2$CH$_2$—C(=O)-GGPI—NH—B—CH$_2$—OC(=O)—("GGPI" disclosed as SEQ ID NO: 78),
—Z$^1$—C(=O)—CH$_2$CH$_2$—C(=O)-GGFG-NH—B—CH$_2$—OC(=O)—("GGFG" disclosed as SEQ ID NO: 77),
—Z$^1$—C(=O)—CH$_2$CH$_2$—C(=O)-GGVCit-NH—B—CH$_2$—OC(=O)—("GGVCit" disclosed as SEQ ID NO: 79), —Z¹—C(=O)—CH₂CH₂—C(=O)-GGVK—NH—B—CH₂—OC(=O)—("GGVK" disclosed as SEQ ID NO: 80), —Z¹—C(=O)—CH₂CH₂—C(=O)-GGPL-NH—B—CH₂—OC(=O)—("GGPL" disclosed as SEQ ID NO: 81), —Z¹—C(=O)—CH₂CH₂—C(=O)—NH—(CH₂CH₂)₂—C(=O)—VA-NH—B—CH₂—OC(=O)—, —Z¹—C(=O)—CH₂CH₂—C(=O)—NH—(CH₂CH₂O)₂—CH₂—C(=O)—VA-NH—B—CH₂—OC(=O)—, —Z¹—C(=O)—CH₂CH₂—NH—C(=O)—(CH₂CH₂O)₄—CH₂CH₂—C(=O)—VA-NH—B—CH₂—OC(=O)—, —Z²—OC(=O)-GGVA-NH—B—CH₂—OC(=O)— ("GGVA" disclosed as SEQ ID NO: 76), and —Z³—CH₂—OC(=O)-GGVA-NH—B—CH₂—OC(=O)— ("GGVA" disclosed as SEQ ID NO: 76), wherein Z¹ represents the following structural formula:

[Formula 12]

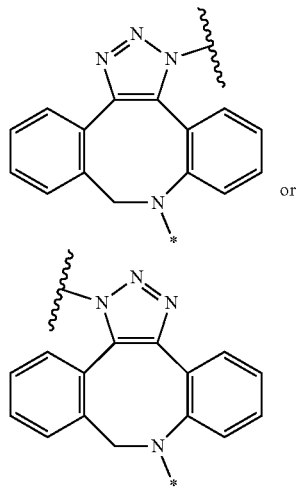

Z² represents the following structural formula:

[Formula 13]

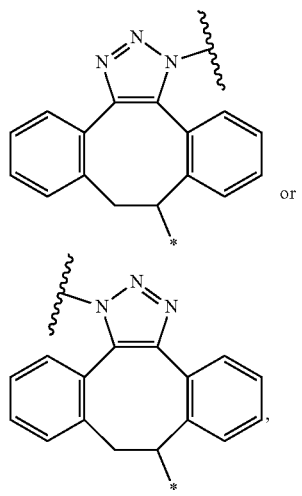

and
Z³ represents the following structural formula:

[Formula 14]

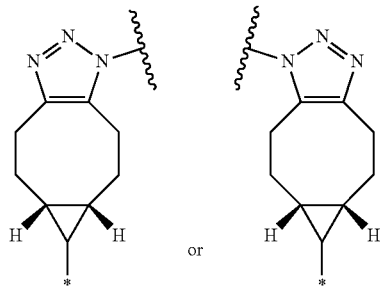

wherein, in each structural formula for Z¹, Z², and Z³,
each asterisk represents bonding to La, each wavy line represents bonding to a glycan or remodeled glycan of Ab; and B represents a 1,4-phenyl group.

[17] The antibody-drug conjugate according to [16], wherein

L is selected from the following group:
—Z¹—C(=O)—CH₂CH₂—C(=O)-GGVA-NH—B—CH₂—OC(=O)— ("GGVA" disclosed as SEQ ID NO: 76), —Z¹—C(=O)—CH₂CH₂—C(=O)—VA-NH—B—CH₂—OC(=O)—, —Z¹—C(=O)—(CH₂CH₂)₂—C(=O)—VA-NH—B—CH₂—OC(=O)—, —Z¹—C(=O)—CH₂CH₂—C(=O)-GGVCit-NH—B—CH₂—OC(=O)— ("GGVCit" disclosed as SEQ ID NO: 79), —Z¹—C(=O)—CH₂CH₂—C(=O)—NH—(CH₂CH₂)₂—C(=O)—VA-NH—B—CH₂—OC(=O)—, —Z¹—C(=O)—CH₂CH₂—C(=O)—NH—(CH₂CH₂O)₂—CH₂—C(=O)—VA-NH—B—CH₂—OC(=O)—, and —Z¹—C(=O)—CH₂CH₂—NH—C(=O)—(CH₂CH₂O)₄—CH₂CH₂—C(=O)—VA-NH—B—CH₂—OC(=O)—, wherein B is a 1,4-phenyl group, and Z¹ represents the following structural formula:

[Formula 15]

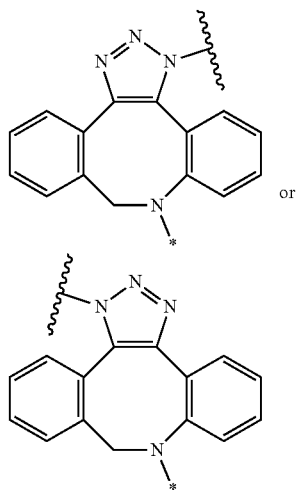

wherein, in the structural formula for $Z^1$,
each asterisk represents bonding to C(=O) neighboring to $Z^1$, and each wavy line represents bonding to a glycan or remodeled glycan of Ab.

[18] The antibody-drug conjugate according to any one of [1] to [6], wherein
L is represented by -Lb-La-Lp-NH—B—CH$_2$—O(C=O)—*, wherein the asterisk represents bonding to D;
B represents a 1,4-phenyl group;
Lp represents -GGVA- (SEQ ID NO: 76) or -VA;
La represents —(CH$_2$)n$^9$-C(=O)— or —(CH$_2$CH$_2$)n$^{10}$-C(=O)—NH—(CH$_2$CH$_2$O)$_n{}^9$—CH$_2$CH$_2$—C(=O)—, wherein n$^9$ represents an integer of 2 to 7, n$^{10}$ represents an integer of 1 to 3, and n$^{11}$ represents an integer of 6 to 10; and
Lb is -(succinimid-3-yl-N)—.

[19] The antibody-drug conjugate according to [18], wherein
L represents any one selected from the following group:
-(succinimid-3-yl-N)—(CH$_2$)$_5$—C(=O)—VA-NH—B—CH$_2$—OC(=O)—,
-(succinimid-3-yl-N)—(CH$_2$)$_5$—C(=O)-GGVA-NH—B—CH$_2$—OC(=O)— ("GGVA" disclosed as SEQ ID NO: 76), and
-(succinimid-3-yl-N)—CH$_2$CH$_2$—C(=O)—NH—(CH$_2$CH$_2$O)$_8$—CH$_2$CH$_2$—C(=O)—VA-NH—B—CH$_2$—OC(=O)—, wherein B is a 1,4-phenyl group.

[20] The antibody-drug conjugate according to any one of [1] to [19], wherein the antibody is IgG.

[21] The antibody-drug conjugate according to [20], wherein the antibody is IgG1, IgG2, or IgG4.

[22] The antibody-drug conjugate according to any one of [1] to [21], wherein the antibody binds to a tumor cell, and is incorporated and internalizes in the tumor cell.

[23] The antibody-drug conjugate according to [22], wherein the antibody further has antitumor effect.

[24] The antibody-drug conjugate according to any one of [1] to [17] and [20] to [23],
wherein the antibody bonds via a glycan bonding to Asn297 of the antibody (N297 glycan) to L.

[25] The antibody-drug conjugate according to [24], wherein the N297 glycan is a remodeled glycan.

[26] The antibody-drug conjugate according to [24] or [25], wherein the N297 glycan is N297-(Fuc)MSG1, N297-(Fuc)MSG2, or a mixture thereof, or N297-(Fuc)SG, with N297-(Fuc)MSG1, N297-(Fuc)MSG2, and N297-(Fuc)SG having structures represented by the following formulas:

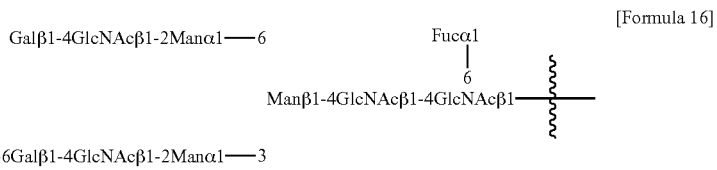

[N297-(Fuc)MSG1]

wherein
the wavy line represents bonding to Asn297 of the antibody;
L(PEG) represents —(CH$_2$CH$_2$—O)n$^5$-CH$_2$CH$_2$—NH—, wherein the amino group at the right end is bound via an amide bond to carboxylic acid at the 2-position of a sialic acid at the non-reducing terminal in the 1-3 branched chain of 3-Man in the N297 glycan;
the asterisk represents bonding to linker L; and
n$^5$ represents an integer of 2 to 10,

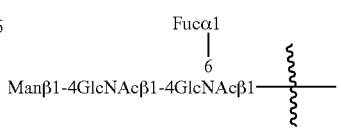

[N297-(Fuc)MSG2]

wherein
the wavy line represents bonding to Asn297 of the antibody;
L(PEG) represents —(CH$_2$CH$_2$—O)n$^5$-CH$_2$CH$_2$—NH—, wherein the amino group at the right end is bound via an amide bond to carboxylic acid at the 2-position of a sialic acid at the non-reducing terminal in the 1-6 branched chain of 3-Man in the N297 glycan;
the asterisk represents bonding to linker L; and
n$^5$ represents an integer of 2 to 10, and

[Formula 18]

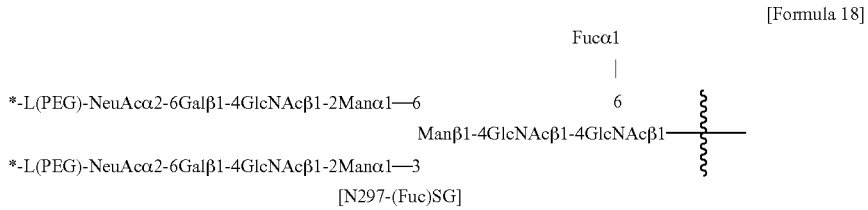

[N297-(Fuc)SG]

wherein
the wavy line represents bonding to Asn297 of the antibody;
L(PEG) represents —(CH$_2$CH$_2$—O)n$^5$-CH$_2$CH$_2$—NH—, wherein the amino group at the right end is bound via an amide bond to carboxylic acid at the 2-position of a sialic acid at the non-reducing terminal in each of the 1-3 and 1-6 branched chains of j-Man in the N297 glycan;
the asterisk represents bonding to linker L; and
n$^5$ represents an integer of 2 to 10.
[27] The antibody-drug conjugate according to [26], wherein n$^5$ is an integer of 2 to 5.
[28] The antibody-drug conjugate according to any one of [24] to [27], represented by the following formula:

[Formula 19]

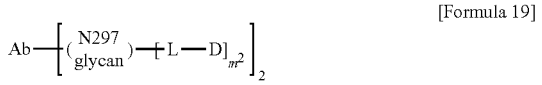

wherein
m$^2$ represents an integer of 1 or 2;
L is a linker linking the N297 glycan of Ab and D, and being any one selected from the following group:
Z$^1$—C(=O)—CH$_2$CH$_2$—C(=O)-GGVA-NH—B—CH$_2$—OC(=O)— ("GGVA" disclosed as SEQ ID NO: 76),
—Z$^1$—C(=O)—CH$_2$CH$_2$—C(=O)—VA-NH—B—CH$_2$—OC(=O)—, —Z$^1$—C(=O)—(CH$_2$CH$_2$)$_2$—C(=O)—VA-NH—B—CH$_2$—OC(=O)—, —Z$^1$—C(=O)—CH$_2$CH$_2$—C(=O)-GGVCit-NH—B—CH$_2$—OC(=O)— ("GGVCit" disclosed as SEQ ID NO: 79),
—Z$^1$—C(=O)—CH$_2$CH$_2$—C(=O)—NH—(CH$_2$CH$_2$)$_2$—C(=O)—VA-NH—B—CH$_2$—OC(=O)—, —Z$^1$—C(=O)—CH$_2$CH$_2$—C(=O)—NH—(CH$_2$CH$_2$O)$_2$—CH$_2$—C(=O)—VA-NH—B—CH$_2$—OC(=O)—, and —Z$^1$—C(=O)—CH$_2$CH$_2$—NH—C(=O)—(CH$_2$CH$_2$O)$_4$—CH$_2$CH$_2$—C(=O)—VA-NH—B—CH$_2$—OC(=O)—, wherein
B is a 1,4-phenyl group, and Z$^1$ represents the following structural formula:

[Formula 20]

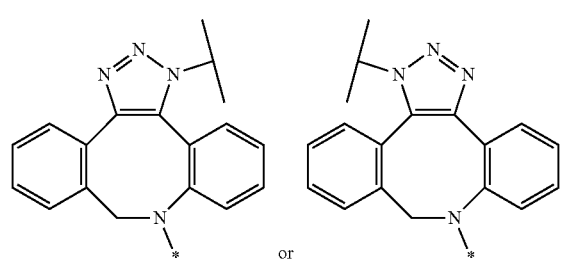

wherein, in the structural formulas for Z$^1$,
each asterisk represents bonding to C(=O) neighboring to Z$^1$, and each wavy line represents bonding to the N297 glycan of Ab;
Ab represents an IgG antibody or a functional fragment of the antibody;
the N297 glycan of Ab represents any one of N297-(Fuc)MSG1, N297-(Fuc)MSG2, and a mixture thereof, and N297-(Fuc)SG, with N297-(Fuc)MSG1, N297-(Fuc)MSG2, and N297-(Fuc)SG having structures represented by the following formulas:

[Formula 21]

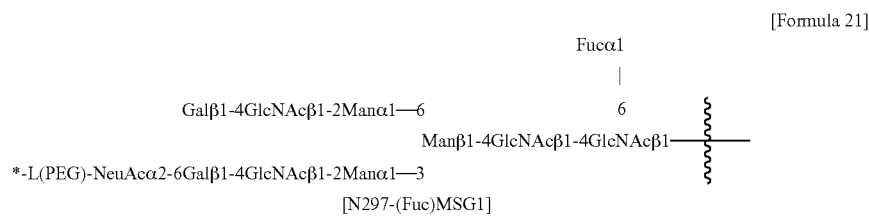

[N297-(Fuc)MSG1]

-continued

[Formula 22]

```
                                    Fucα1
                                      |
*-L(PEG)-NeuAcα2-6Galβ1-4GlcNAcβ1-2Manα1—6
                                          Manβ1-4GlcNAcβ1-4GlcNAcβ1——⌇
                Galβ1-4GlcNAcβ1-2Manα1—3
                  [N297-(Fuc)MSG2]
```

[Formula 23]

```
                                    Fucα1
                                      |
*-L(PEG)-NeuAcα2-6Galβ1-4GlcNAcβ1-2Manα1—6
                                          Manβ1-4GlcNAcβ1-4GlcNAcβ1——⌇
*-L(PEG)-NeuAcα2-6Galβ1-4GlcNAcβ1-2Manα1—3
                  [N297-(Fuc)SG]
``` wherein
  each wavy line represents bonding to Asn297 of the antibody,
  L(PEG) in the N297 glycan represents —NH—CH$_2$CH$_2$—(O—CH$_2$CH$_2$)n$^5$-*, wherein n$^5$ represents an integer of 2 to 5, the amino group at the left end is bound via an amide bond to carboxylic acid at the 2-position of a sialic acid at the non-reducing terminal in each or either one of the 1-3 and 1-6 branched chains of 3-Man in the N297 glycan, and each asterisk represents bonding to a nitrogen atom at the 1- or 3-position of the triazole ring of Z$^1$ in linker L; and
  D is any one selected from the following group:

[Formula 24]

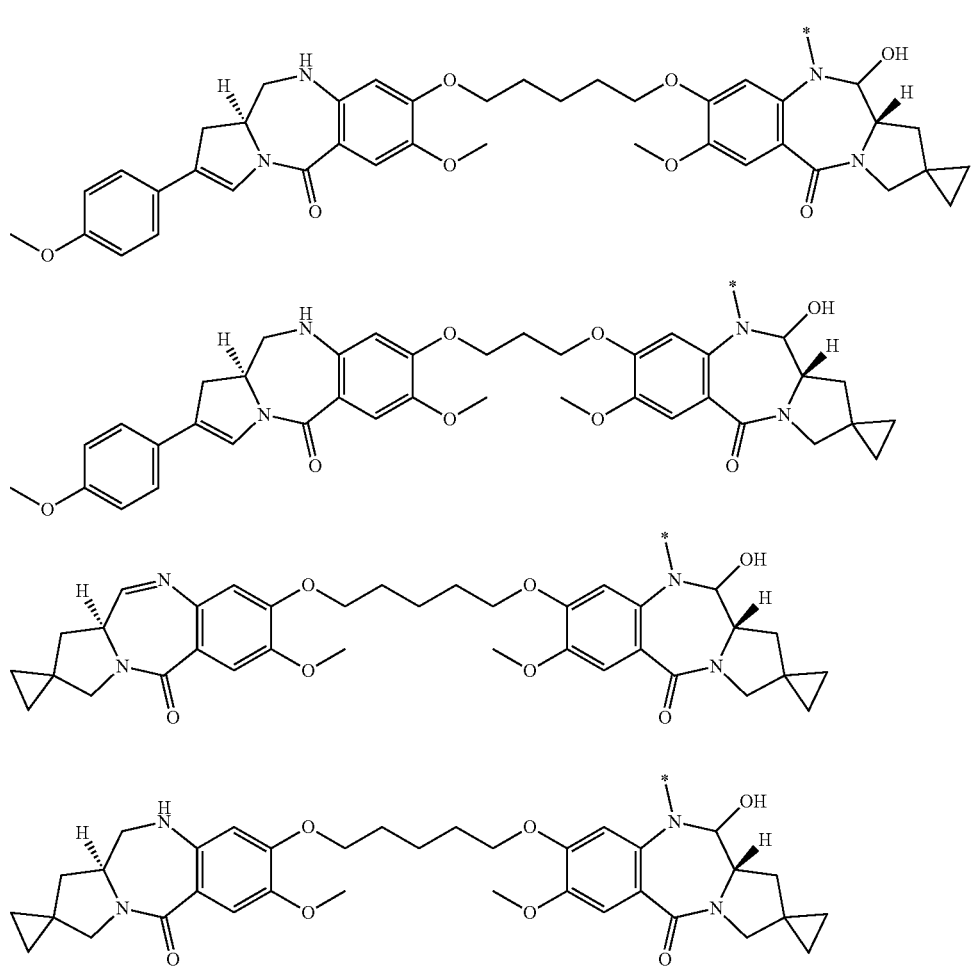

wherein
each asterisk represents bonding to L.
[29] An antibody-drug conjugate selected from the following group:
[Formula 25]
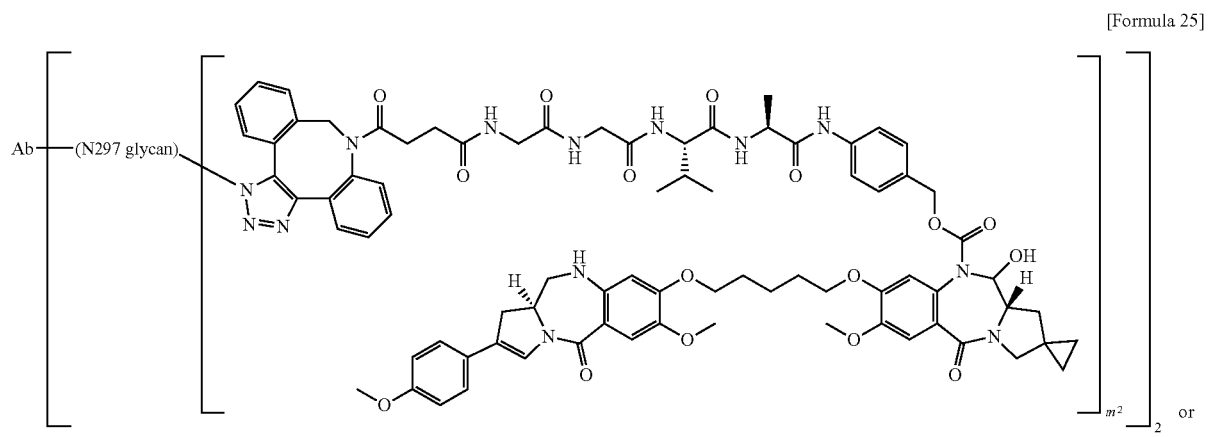
or
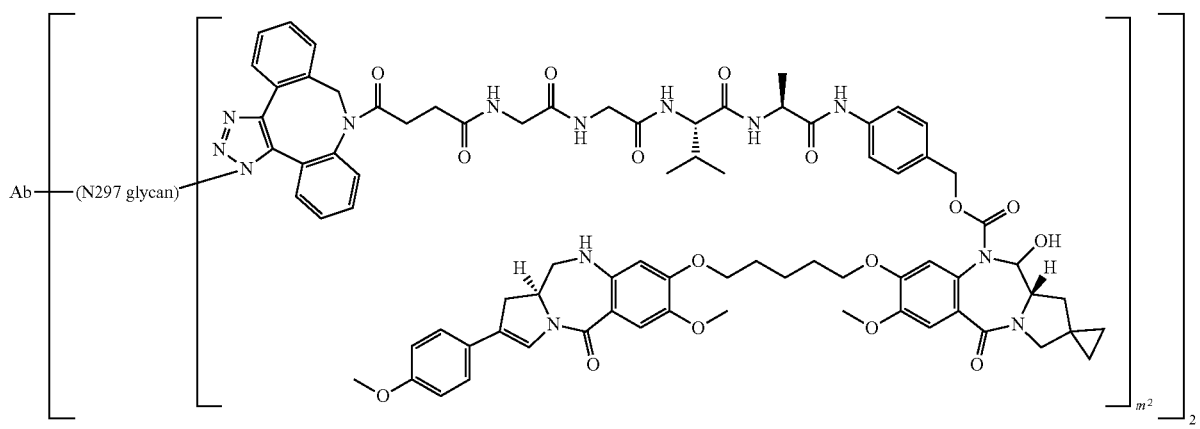
[Formula 26]
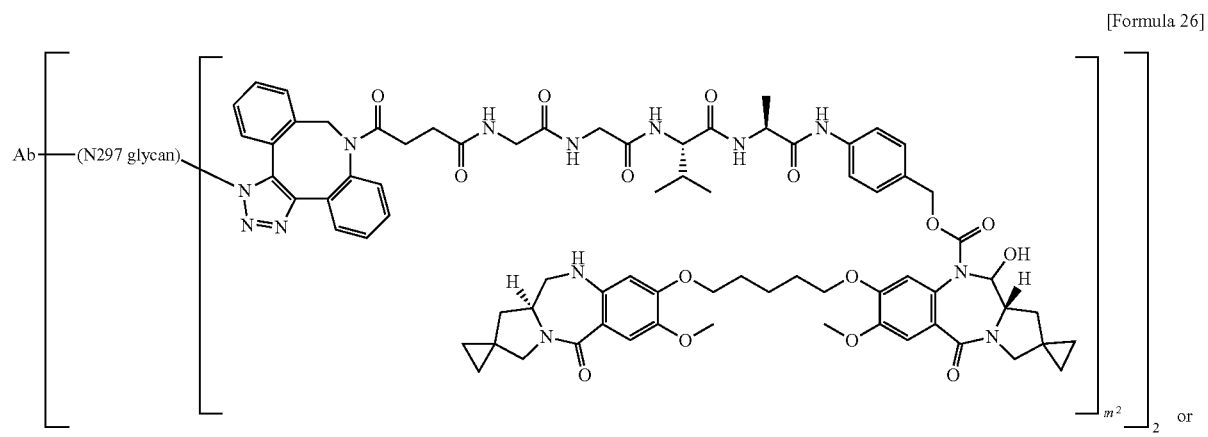
or -continued
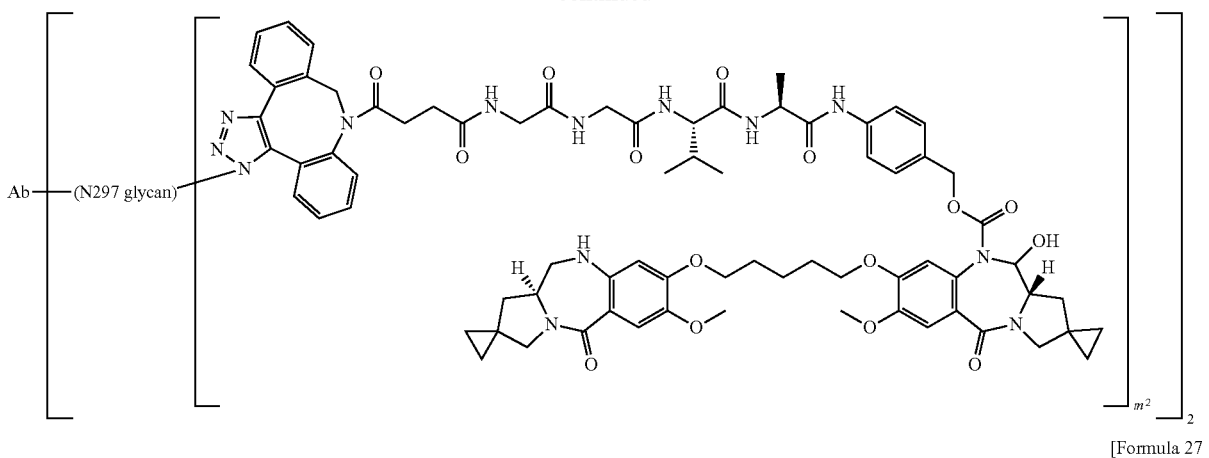
[Formula 27]
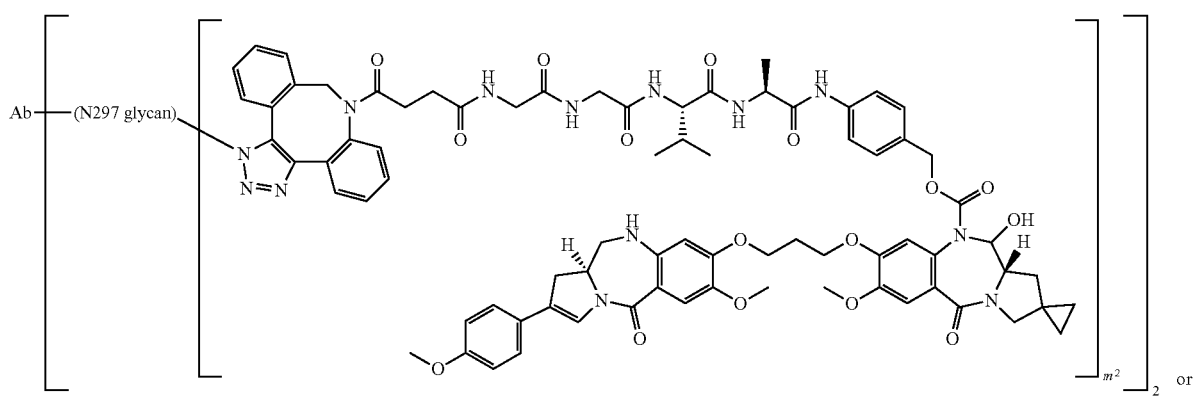
or
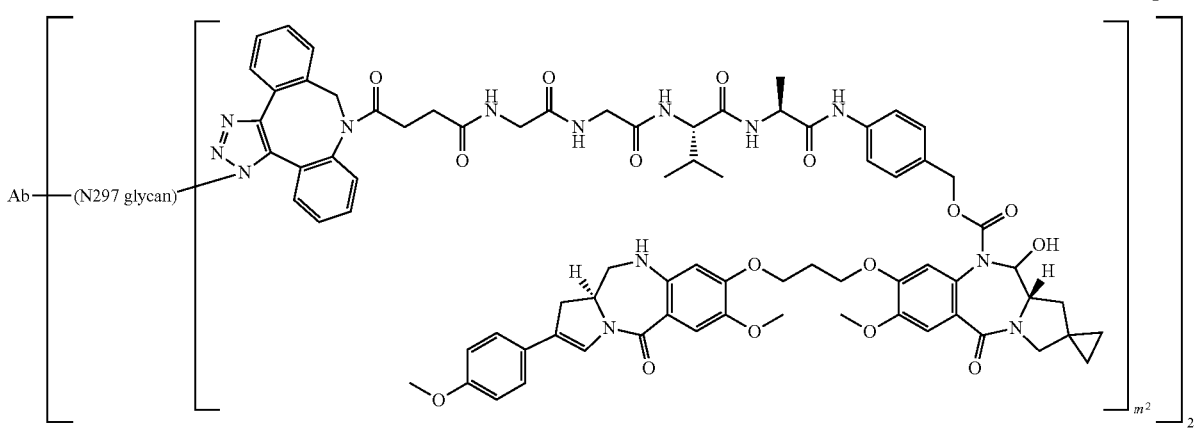
[Formula 28]
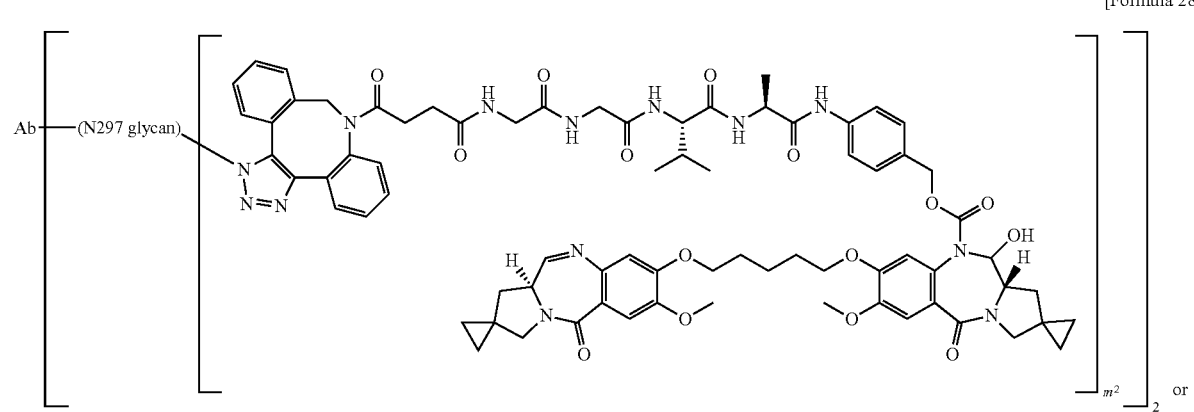
or

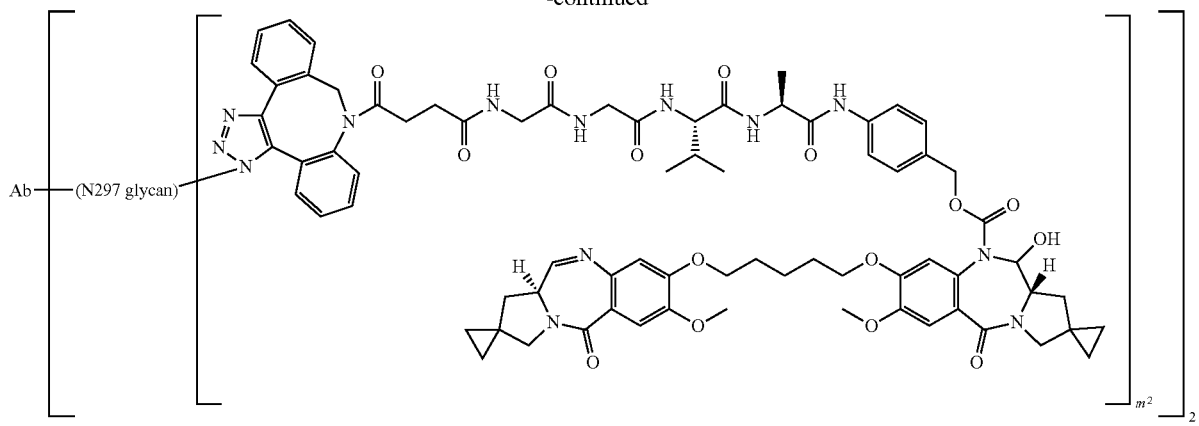

wherein, in each structural formula shown above,
$m^2$ represents an integer of 1 or 2;
Ab represents an IgG antibody or a functional fragment of the antibody;
the N297 glycan of Ab represents any one of N297-(Fuc)MSG1, N297-(Fuc)MSG2, and a mixture thereof, and N297-(Fuc)SG, with N297-(Fuc)MSG1, N297-(Fuc)MSG2, and N297-(Fuc)SG having structures represented by the following formulas:

[31] The antibody according to [30] or a functional fragment of the antibody, wherein CLDN6 is a molecule consisting of an amino acid sequence represented by SEQ ID NO: 1, and CLDN9 is a molecule consisting of an amino acid sequence represented by SEQ ID NO: 3.

[32] The antibody according to [30] or [31] or a functional fragment of the antibody, the antibody comprising a heavy chain comprising CDRH1, CDRH2, and CDRH3 and a light

[Formula 29]

```
                    Galβ1——4GlcNAcβ1——2Manα1——6
                                                    Fucα1
                                                      |
                                                      6
                                         Manβ1——4GlcNAcβ1——4GlcNAcβ1—⌇—
*——L(PEG)—NeuAcα2——6Galβ1——4GlcNAcβ1——2Manα1——3
```

[N297——(Fuc)MSG1]

[Formula 30]

```
*——L(PEG)—NeuAcα2——6Galβ1——4GlcNAcβ1——2Manα1——6
                                                    Fucα1
                                                      |
                                                      6
                                         Manβ1——4GlcNAcβ1——4GlcNAcβ1—⌇—
                    Galβ1——4GlcNAcβ1——2Manα1——3
```

[N297——(Fuc)MSG2]

[Formula 31]

```
*——L(PEG)—NeuAcα2——6Galβ1——4GlcNAcβ1——2Manα1——6
                                                    Fucα1
                                                      |
                                                      6
                                         Manβ1——4GlcNAcβ1——4GlcNAcβ1—⌇—
*——L(PEG)—NeuAcα2——6Galβ1——4GlcNAcβ1——2Manα1——3
```

[N297——(Fuc)SG]

wherein
each wavy line represents bonding to Asn297 of the antibody,
L(PEG) in the N297 glycan represents —NH—CH$_2$CH$_2$—(O—CH$_2$CH$_2$)$_3$—*, wherein
the amino group at the left end is bound via an amide bond to carboxylic acid at the 2-position of a sialic acid at the non-reducing terminal in each or either one of the 1-3 and 1-6 branched chains of β-Man in the N297 glycan, and each asterisk represents bonding to a nitrogen atom at the 1- or 3-position of the triazole ring in the corresponding structural formula.

[30] An antibody which binds to CLDN6 and/or CLDN9, or a functional fragment of the antibody.

chain comprising CDRL1, CDRL2, and CDRL3 as described in any one of the following (a) and (b):
(a) CDRH1 consisting of an amino acid sequence represented by SEQ ID NO: 9, CDRH2 consisting of an amino acid sequence represented by SEQ ID NO: 10, and CDRH3 consisting of an amino acid sequence represented by SEQ ID NO: 11, and CDRL1 consisting of an amino acid sequence represented by SEQ ID NO: 5, CDRL2 consisting of an amino acid sequence represented by SEQ ID NO: 6, and CDRL3 consisting of an amino acid sequence represented by SEQ ID NO: 7 or an amino acid sequence having one or two amino acid substitutions in the amino acid sequence represented by SEQ ID NO: 7; and (b) CDRH1 consisting of an amino acid sequence represented by SEQ ID NO: 15, CDRH2 consisting of an amino acid sequence represented by SEQ ID NO: 16, and CDRH3 consisting of an amino acid sequence represented by SEQ ID NO: 17, and CDRL1 consisting of an amino acid sequence represented by SEQ ID NO: 12, CDRL2 consisting of an amino acid sequence represented by SEQ ID NO: 13, and CDRL3 consisting of an amino acid sequence represented by SEQ ID NO: 14.

[33] The antibody according to [32] or a functional fragment of the antibody, the antibody comprising a heavy chain comprising CDRH1, CDRH2, and CDRH3 and a light chain comprising CDRL1, CDRL2, and CDRL3 as described in any one of the following (a) and (b):

(a) CDRH1 consisting of an amino acid sequence represented by SEQ ID NO: 9, CDRH2 consisting of an amino acid sequence represented by SEQ ID NO: 10, and CDRH3 consisting of an amino acid sequence represented by SEQ ID NO: 11, and CDRL1 consisting of an amino acid sequence represented by SEQ ID NO: 5, CDRL2 consisting of an amino acid sequence represented by SEQ ID NO: 6, and CDRL3 consisting of an amino acid sequence represented by SEQ ID NO: 7 or an amino acid sequence represented by SEQ ID NO: 8; and (b) CDRH1 consisting of an amino acid sequence represented by SEQ ID NO: 15, CDRH2 consisting of an amino acid sequence represented by SEQ ID NO: 16, and CDRH3 consisting of an amino acid sequence represented by SEQ ID NO: 17, and CDRL1 consisting of an amino acid sequence represented by SEQ ID NO: 12, CDRL2 consisting of an amino acid sequence represented by SEQ ID NO: 13, and CDRL3 consisting of an amino acid sequence represented by SEQ ID NO: 14.

[34] The antibody according to any one of [30] to [33] or a functional fragment of the antibody, the antibody comprising a heavy chain variable region and a light chain variable region as described in any one of the following (a) and (b):

(a) a heavy chain variable region consisting of an amino acid sequence represented by SEQ ID NO: 21 and a light chain variable region consisting of an amino acid sequence represented by SEQ ID NO: 19; and (b) a heavy chain variable region consisting of an amino acid sequence represented by SEQ ID NO: 25 and a light chain variable region consisting of an amino acid sequence represented by SEQ ID NO: 23.

[35] The antibody according to any one of [30] to [34] or a functional fragment of the antibody, the antibody comprising a heavy chain variable region consisting of an amino acid sequence selected from the group consisting of the following (a) to (e) and a light chain variable region consisting of an amino acid sequence selected from the group consisting of the following (f) to (k):

(a) an amino acid sequence represented by SEQ ID NO: 54;

(b) an amino acid sequence represented by SEQ ID NO: 58;

(c) an amino acid sequence represented by SEQ ID NO: 62;

(d) an amino acid sequence with a homology of at least 95% or higher to a sequence of a framework region excluding CDR sequences in any of the sequences (a) to (c);

(e) an amino acid sequence having one to several amino acid deletions, substitutions, or additions in a sequence of a framework region excluding CDR sequences in any of the sequences (a) to (c);

(f) an amino acid sequence represented by SEQ ID NO: 38;

(g) an amino acid sequence represented by SEQ ID NO: 42;

(h) an amino acid sequence represented by SEQ ID NO: 46;

(i) an amino acid sequence represented by SEQ ID NO: 50;

(j) an amino acid sequence with a homology of at least 95% or higher to a sequence of a framework region excluding CDR sequences in any of the sequences (f) to (i); and (k) an amino acid sequence having one to several amino acid deletions, substitutions, or additions in a sequence of a framework region excluding CDR sequences in any of the sequences (f) to (i).

[36] The antibody according to [35] or a functional fragment of the antibody, the antibody comprising a heavy chain variable region and a light chain variable region selected from the group consisting of the following (a) to (e):

(a) a heavy chain variable region consisting of an amino acid sequence represented by SEQ ID NO: 54 and a light chain variable region consisting of an amino acid sequence represented by SEQ ID NO: 38;

(b) a heavy chain variable region consisting of an amino acid sequence represented by SEQ ID NO: 58 and a light chain variable region consisting of an amino acid sequence represented by SEQ ID NO: 42;

(c) a heavy chain variable region consisting of an amino acid sequence represented by SEQ ID NO: 54 and a light chain variable region consisting of an amino acid sequence represented by SEQ ID NO: 46;

(d) a heavy chain variable region consisting of an amino acid sequence represented by SEQ ID NO: 58 and a light chain variable region consisting of an amino acid sequence represented by SEQ ID NO: 50; and (e) a heavy chain variable region consisting of an amino acid sequence represented by SEQ ID NO: 62 and a light chain variable region consisting of an amino acid sequence represented by SEQ ID NO: 46.

[37] The antibody according to any one of [30] to [36] or a functional fragment of the antibody, wherein the antibody is a chimeric antibody.

[38] The antibody according to any one of [30] to [36] or a functional fragment of the antibody, wherein the antibody is a humanized antibody.

[39] The antibody according to any one of [30] to [38] or a functional fragment of the antibody, the antibody comprising a heavy chain constant region of human IgG1, human IgG2, or human IgG4.

[40] The antibody according to [38] or [39] or a functional fragment of the antibody, the antibody comprising a heavy chain and a light chain selected from the group consisting of the following (a) to (e):

(a) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 36 (H1L1);

(b) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 40 (H2L2);

(c) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 44 (H1L3);

(d) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 48 (H2L4); and (e) a heavy chain consisting of an amino acid sequence consisting of amino acid residues 20 to 471 of SEQ ID NO: 60 and a light chain consisting of an amino acid sequence consisting of amino acid residues 21 to 234 of SEQ ID NO: 44 (H3L3).

[41] The antibody according to [30] or [31] or a functional fragment of the antibody,
wherein the antibody binds to a site of an antigen recognizable to the antibody according to any one of [32] to [36] and [40].

[42] The antibody according to [30] or [31] or a functional fragment of the antibody, wherein the antibody competes with the antibody according to any one of [32] to [36] and [40] for binding to CLDN6 and/or CLDN9.

[43] A polynucleotide encoding the antibody according to any one of [30] to [42].

[44] The polynucleotide according to [43], comprising a polynucleotide selected from the group consisting of the following (a) to (j):

(a) a polynucleotide encoding a heavy chain variable region consisting of an amino acid sequence represented by SEQ ID NO: 54 and a polynucleotide encoding a light chain variable region consisting of an amino acid sequence represented by SEQ ID NO: 38;

(b) a polynucleotide encoding a heavy chain variable region consisting of an amino acid sequence represented by SEQ ID NO: 58 and a polynucleotide encoding a light chain variable region consisting of an amino acid sequence represented by SEQ ID NO: 42;

(c) a polynucleotide encoding a heavy chain variable region consisting of an amino acid sequence represented by SEQ ID NO: 54 and a polynucleotide encoding a light chain variable region consisting of an amino acid sequence represented by SEQ ID NO: 46;

(d) a polynucleotide encoding a heavy chain variable region consisting of an amino acid sequence represented by SEQ ID NO: 58 and a polynucleotide encoding a light chain variable region consisting of an amino acid sequence represented by SEQ ID NO: 50;

(e) a polynucleotide encoding a heavy chain variable region consisting of an amino acid sequence represented by SEQ ID NO: 62 and a polynucleotide encoding a light chain variable region consisting of an amino acid sequence represented by SEQ ID NO: 46;

(f) a polynucleotide encoding a heavy chain consisting of an amino acid sequence consisting of amino acid residues 20 to 471 of SEQ ID NO: 52 and a polynucleotide encoding a light chain consisting of an amino acid sequence consisting of amino acid residues 21 to 234 of SEQ ID NO: 36;

(g) a polynucleotide encoding a heavy chain consisting of an amino acid sequence consisting of amino acid residues 20 to 471 of SEQ ID NO: 56 and a polynucleotide encoding a light chain consisting of an amino acid sequence consisting of amino acid residues 21 to 234 of SEQ ID NO: 40;

(h) a polynucleotide encoding a heavy chain consisting of an amino acid sequence consisting of amino acid residues 20 to 471 of SEQ ID NO: 52 and a polynucleotide encoding a light chain consisting of an amino acid sequence consisting of amino acid residues 21 to 234 of SEQ ID NO: 44;

(i) a polynucleotide encoding a heavy chain consisting of an amino acid sequence consisting of amino acid residues 20 to 471 of SEQ ID NO: 56 and a polynucleotide encoding a light chain consisting of an amino acid sequence consisting of amino acid residues 21 to 234 of SEQ ID NO: 48; and (j) a polynucleotide encoding a heavy chain consisting of an amino acid sequence consisting of amino acid residues 20 to 471 of SEQ ID NO: 60 and a polynucleotide encoding a light chain consisting of an amino acid sequence consisting of amino acid residues 21 to 234 of SEQ ID NO: 44.

[45] An expression vector comprising the polynucleotide according to [43] or [44].

[46] A host cell transformed with the expression vector according to [45].

[47] The host cell according to [46], wherein the host cell is a eukaryotic cell.

[48] The host cell according to [47], wherein the host cell is an animal cell.

[49] A method for producing the antibody according to any one of [30] to [42] or a functional fragment of the antibody, the method comprising the steps of: culturing the host cell according to any one of [46] to [48]; and collecting a targeted antibody from the culture obtained in the step of culturing.

[50] An antibody obtained by using the method according to [49], or a functional fragment of the antibody.

[51] The antibody according to any one of [30] to [42] and [50] or a functional fragment of the antibody, the antibody comprising one or two or more modifications selected from the group consisting of N-linked glycosylation, O-linked glycosylation, N-terminal processing, C-terminal processing, deamidation, isomerization of aspartic acid, oxidation of methionine, addition of a methionine residue at an N terminus, amidation of a proline residue, and deletion of one or two amino acid residues at the carboxyl terminus of a heavy chain.

[52] The antibody according to [51] or a functional fragment of the antibody, wherein one or several amino acid residues are deleted at the carboxyl terminus of a heavy chain.

[53] The antibody according to [52] or a functional fragment of the antibody, wherein one amino acid residue is deleted at the carboxyl terminus of each of the two heavy chains.

[54] The antibody according to any one of [50] to [53] or a functional fragment of the antibody, wherein a proline residue at the carboxyl terminus of a heavy chain is further amidated.

[55] A method for producing a glycan-remodeled antibody, the method comprising the steps of:
i) culturing the host cell according to any one of [46] to [48] and collecting a targeted antibody from the culture obtained;
ii) treating the antibody obtained in step i) with hydrolase to produce a (Fucα1,6)GlcNAc-antibody; and iii) −1 reacting the (Fucα1,6)GlcNAc-antibody and a glycan donner molecule in the presence of transglycosidase, the glycan donner molecule obtained by introducing a PEG linker having an azide group to the carbonyl group of carboxylic acid at the 2-position of a sialic acid in MSG (9) or SG (10) and oxazolinating the reducing terminal, or iii)-2 reacting the (Fucα1,6)GlcNAc-antibody and a glycan donner molecule in the presence of transglycosidase, the glycan donner molecule obtained by introducing a PEG linker having an azide group to the carbonyl group of carboxylic acid at the 2-position of a sialic acid in (MSG-)Asn or (SG-)Asn with an α-amino group optionally protected and to the carbonyl group of carboxylic acid in the Asn, causing action of hydrolase, and then oxazolinating the reducing terminal.

[56] The method according to [55], further comprising the step of purifying the (Fucα1,6)GlcNAc-antibody through purification of a reaction solution in step ii) with a hydroxyapatite column.

[57] A method for producing the antibody-drug conjugate according to any one of [1] to [29], the method comprising the steps of:
  i) producing a glycan-remodeled antibody by using the method according to [55] or [56]; and
  ii) reacting a drug-linker having DBCO (a production intermediate) and an azide group in a glycan of the glycan-remodeled antibody made in step i).

[58] A glycan-remodeled antibody obtained by using the method according to [55] or [56].

[59] An antibody-drug conjugate obtained by using the method according to [57].

[60] An antibody-drug conjugate selected from the following group:

[Formula 32]

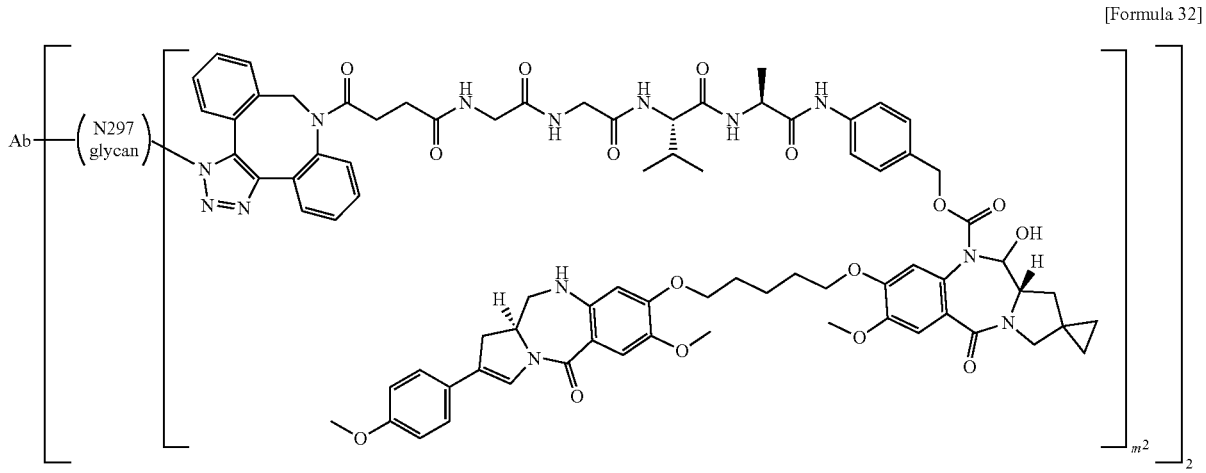

or

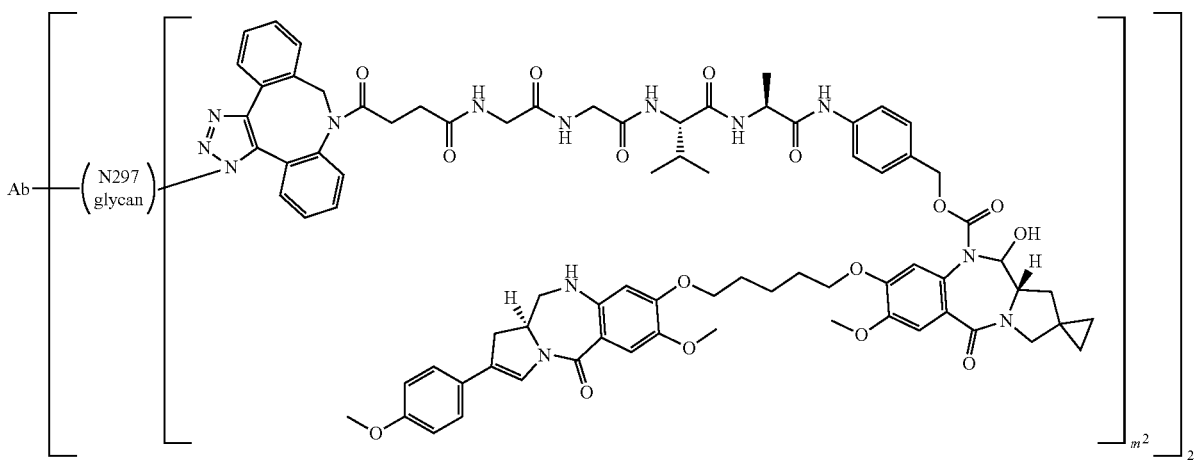

[Formula 33]
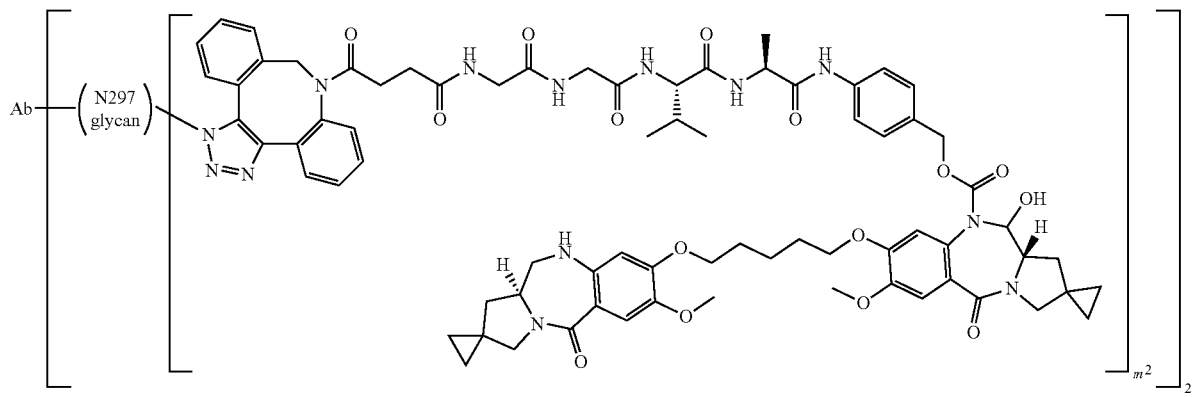
or
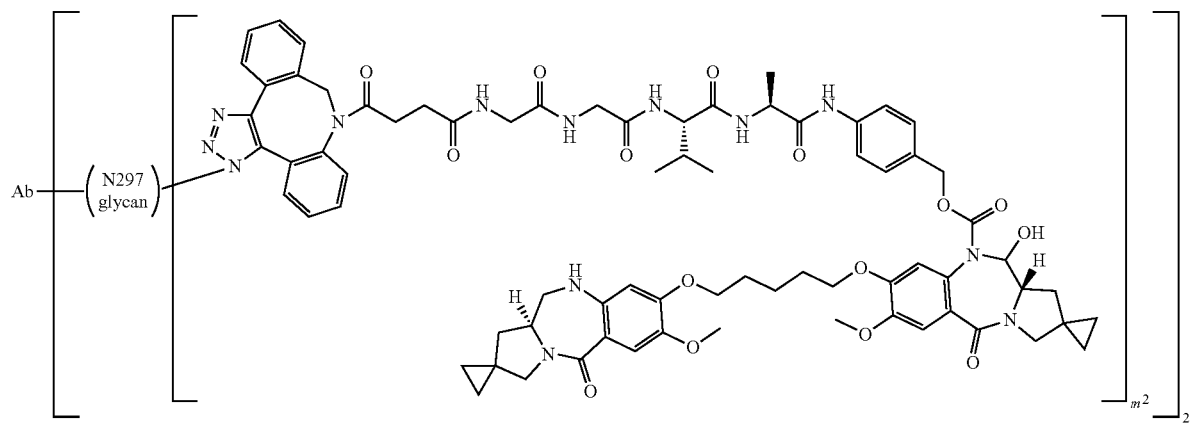
[Formula 34]
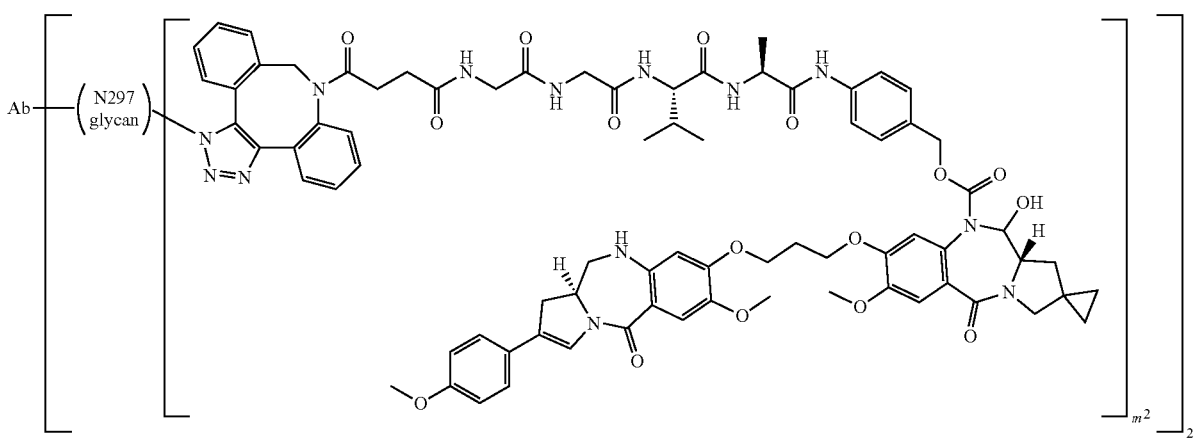

or

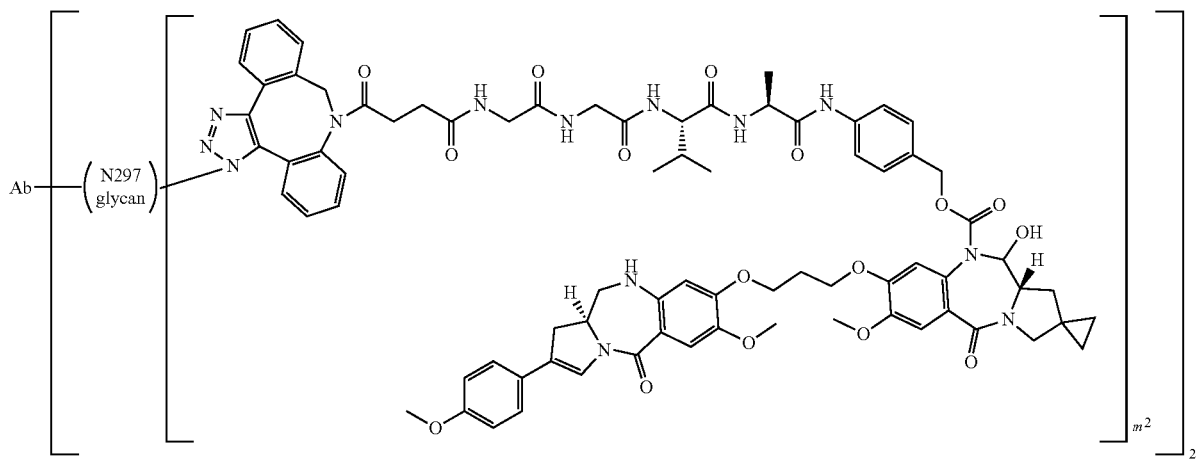

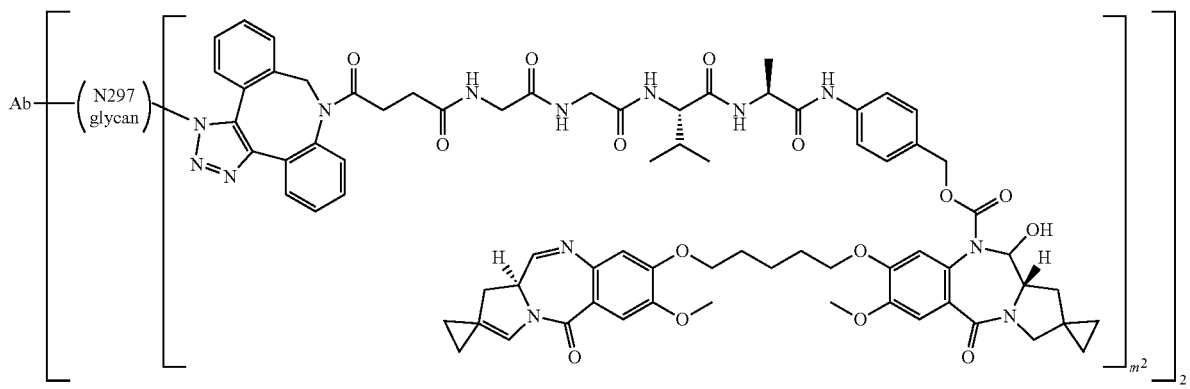

or

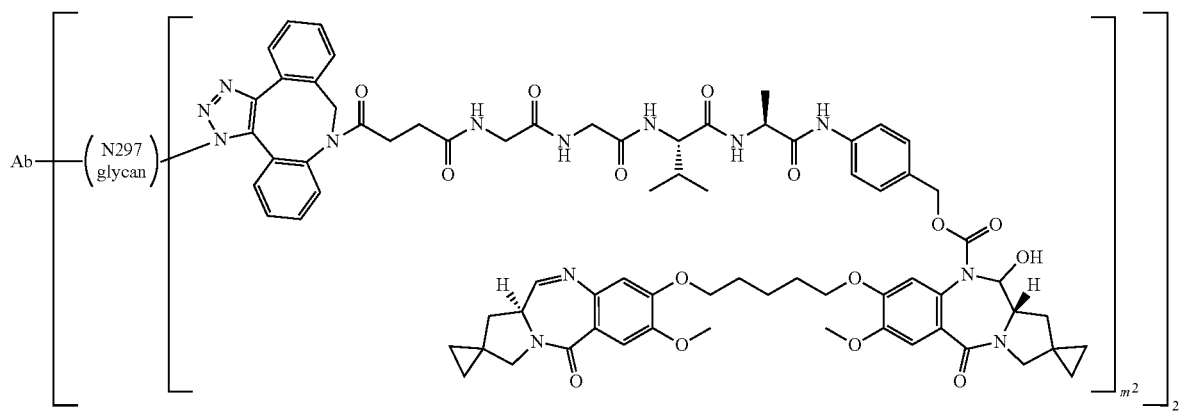

wherein, in each structural formula shown above, m² represents an integer of 1 or 2;

Ab represents the antibody according to any one of [30] to [42], [50] to [54], and [58] or a functional fragment of the antibody, or an anti-HER2 antibody; and the N297 glycan of Ab represents any one of N297-(Fuc)MSG1, N297-(Fuc)MSG2, and a mixture thereof, and N297-(Fuc)SG, with N297-(Fuc)MSG1, N297-(Fuc)MSG2, and N297-(Fuc)SG having structures represented by the following formulas:

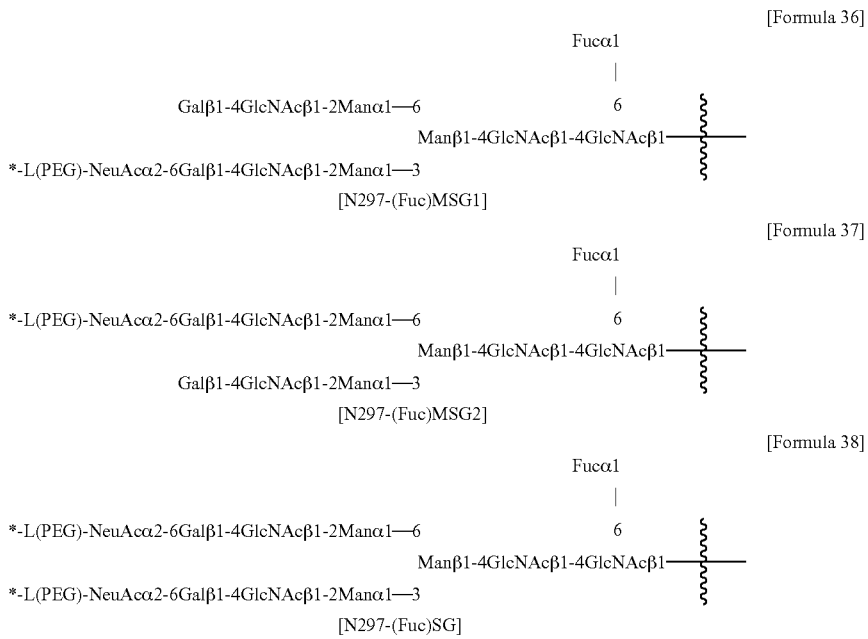

wherein
each wavy line represents bonding to Asn297 of the antibody,
L(PEG) represents —NH—CH$_2$CH$_2$—(O—CH$_2$CH$_2$)$_3$—*, wherein the amino group at the left end is bound via an amide bond to carboxylic acid at the 2-position of a sialic acid at the non-reducing terminal in each or either one of the 1-3 and 1-6 branched chains of β-Man in the N297 glycan, and each asterisk represents bonding to a nitrogen atom at the 1- or 3-position of the triazole ring in the corresponding structural formula.

[61] The antibody-drug conjugate according to any one of [1] to [29], [59], and [60], wherein the average number of conjugated drug molecules per antibody molecule in the antibody-drug conjugate is 1 to 3 or 3 to 5.

[62] A compound, a salt of the compound, or a hydrate of the compound or the salt, the compound represented by the following formula:

[Formula 39]

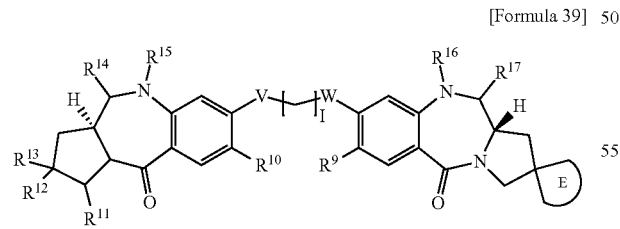

wherein
l represents an integer of 2 to 8;
E represents a spiro-bonded three- to five-membered saturated hydrocarbon ring or three- to five-membered saturated heterocycle optionally substituted with one to four halogen atoms;
$R^9$ and $R^{10}$ each independently represent a C1 to C6 alkoxy group, a C1 to C6 alkyl group, a hydrogen atom, a hydroxy group, a thiol group, a C1 to C6 alkylthio group, a halogen atom, or —NR'R", wherein
R' and R" each independently represent a hydrogen atom or a C1 to C6 alkyl group;
$R^{11}$, $R^{12}$ and $R^{13}$ are selected from the following (i) to (iii):
(i) $R^{11}$ and $R^{12}$ are combined, together with the carbon atoms to which $R^{11}$ and $R^{12}$ are bound, to form a double bond, and $R^{13}$ represents an aryl group or heteroaryl group optionally having one or more substituents selected from group 7 or a C1 to C6 alkyl group optionally having one or more substituents selected from group 8,
(ii) $R^{11}$ represents a hydrogen atom, and $R^{12}$ and $R^{13}$ are combined together to form a three- to five-membered saturated hydrocarbon ring or a three- to five-membered saturated heterocycle, or CH$_2$=, and
(iii) $R^{11}$ and $R^{12}$ are combined together to form a benzene ring or six-membered heterocycle optionally having one or more substituents selected from group 9, and $R^{13}$ represents a single bond;
$R^{14}$ and $R^{15}$ each represent a hydrogen atom, or $R^{14}$ and $R^{15}$ are combined to represent an imine bond (C=N);
$R^{16}$ and $R^{17}$ represent any one of the following (a) and (b):
(a) $R^{16}$ and $R^{17}$ are combined to form an imine bond (N=C), and
(b) $R^{16}$ represents J-La'-Lp'—NH—B'—CH$_2$—O(C=O)—*,
wherein
the asterisk represents bonding to the nitrogen atom neighboring to $R^{16}$,
B' represents a phenyl group or a heteroaryl group,
Lp' represents a linker consisting of an amino acid sequence cleavable in a target cell, La' represents any one of the following group:
—C(=O)—(CH$_2$CH$_2$)n$^6$-C(=O)—, —C(=O)—(CH$_2$CH$_2$)n$^6$-C(=O)—NH—(CH$_2$CH$_2$)n$^7$-C(=O)—, —C(=O)—(CH$_2$CH$_2$)n$^6$-C(=O)—NH—(CH$_2$CH$_2$O)n$^7$-CH$_2$—C(=O)—, —C(=O)—(CH$_2$CH$_2$)n$^6$-NH—C(=O)—(CH$_2$CH$_2$O)n$^7$-CH$_2$CH$_2$—C(=O)—, —(CH$_2$)n$^8$-O—C(=O)—, (CH$_2$)n$^{12}$-C(=O)—, and —(CH$_2$CH$_2$)n$^{13}$-C(=O)—NH—(CH$_2$CH$_2$O)n$^{14}$-CH$_2$CH$_2$—C(=O)—, wherein n$^6$ represents an integer of 1 to 3, n$^7$ represents an integer of 1 to 5, n$^8$ represents an integer of 0 to 2, n$^{12}$ represents an integer of 2 to 7, n$^{13}$ represents an integer of 1 to 3, and n$^{14}$ represents an integer of 6 to 10, J represents any one of the following:

[Formula 40]

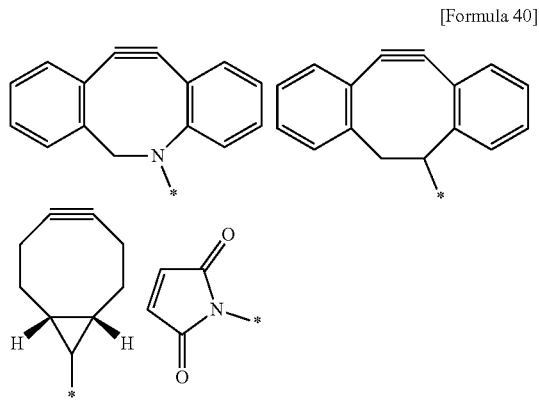

wherein, in the structural formulas for J shown above, each asterisk represents bonding to La';

R$^{17}$ represents a hydroxy group or a C1 to C3 alkoxy group;

V and W are each independently an oxygen atom, a nitrogen atom, or a sulfur atom; group 7 represents:
a) a C1 to C6 alkoxy group optionally substituted with one to three halogen atoms,
b) a C1 to C6 alkyl group optionally substituted with any one selected from one to three halogen atoms, a hydroxy group, —OCOR', —NR'R'', —C(NR')—NR''R''', and —NHC(=NR')—NR''R''',
c) a halogen atom,
d) a C3 to C5 cycloalkoxy group,
e) a C1 to C6 alkylthio group,
f) —NR'R'',
g) —C(=NR')—NR''R''',
h) —NHC(=NR')—NR''R''',
i) —NHCOR', or
j) a hydroxy group,
wherein
R' and R'' are as defined above, and R''' each independently represents a hydrogen atom or a C1 to C6 alkyl group;
group 8 represents a halogen atom, a hydroxy group, or a C1 to C6 alkoxy group; and
group 9 represents a halogen atom or a C1 to C6 alkyl group or a C1 to C6 alkoxy group optionally substituted with one to three halogen atoms.

[63] The compound according to [62], a salt of the compound, or a hydrate of the compound or the salt, wherein E represents a spiro-bonded three- to five-membered saturated hydrocarbon ring optionally substituted with one or two halogen atoms;

R$^9$ and R$^{10}$ each independently represent a C1 to C3 alkoxy group;

R$^{11}$ and R$^{12}$ are combined together with the carbon atoms to which R$^{11}$ and R$^{12}$ are bound to form a double bond;

R$^{13}$ represents an aryl group or heteroaryl group optionally having one or more substituents selected from group 10, or a C1 to C3 alkyl group optionally having one or more substituents selected from group 11;

V and W are each an oxygen atom;

group 10 represents:
a) a C1 to C3 alkoxy group optionally substituted with one to three halogen atoms,
b) a C1 to C3 alkyl group optionally substituted with any one selected from one to three halogen atoms, a hydroxy group, —OCOR'', —C(=NR')—NR''R''', and —NHC(=NR')—NR''R''',
c) a C3 to C5 cycloalkoxy group,
d) —C(=NR')—NR''R''',
e) —NHC(=NR')—NR''R''', or
f) a hydroxy group,
wherein
R', R'', and R''' each independently represent a hydrogen atom or a C1 to C3 alkyl group; and
group 11 represents a halogen atom, a hydroxy group, or a C1 to C3 alkoxy group.

[64] The compound according to [62], a salt of the compound, or a hydrate of the compound or the salt, wherein E represents a spiro-bonded three- to five-membered saturated hydrocarbon ring optionally substituted with one or two halogen atoms;

R$^9$ and R$^{10}$ each independently represent a C1 to C3 alkoxy group;

R$^{11}$ represents a hydrogen atom;

R$^{12}$ and R$^{13}$ are combined, together with the carbon atom to which R$^{12}$ and R$^{13}$ are bound, to form a three- to five-membered saturated hydrocarbon ring, or =CH$_2$; and V and W are each an oxygen atom.

[65] The compound according to [62], a salt of the compound, or a hydrate of the compound or the salt, wherein E represents a spiro-bonded three- to five-membered saturated hydrocarbon ring optionally substituted with one or two halogen atoms;

R$^9$ and R$^{10}$ each independently represent a C1 to C3 alkoxy group;

R$^1$, R$^{12}$, and R$^{13}$ are combined, together with the carbon atom to which R'' is bound and the carbon atom to which R$^{12}$ and R$^{13}$ are bound, to form a benzene ring optionally having one or more substituents selected from group 12;

V and W are each an oxygen atom; and group 12 represents a halogen atom or a C1 to C3 alkyl group or a C1 to C3 alkoxy group optionally substituted with one to three halogen atoms.

[66] The compound according to any one of [62] to [65], a salt of the compound, or a hydrate of the compound or the salt, wherein B' is any one selected from a 1,4-phenyl group, a 2,5-pyridyl group, a 3,6-pyridyl group, a 2,5-pyrimidyl group, and a 2,5-thienyl group.

[67] The compound according to [66], a salt of the compound, or a hydrate of the compound or the salt, wherein B' is a 1,4-phenyl group.

[68] The compound according to any one of [62] to [67], a salt of the compound, or a hydrate of the compound or the salt, wherein Lp' is amino acid residues selected from the following group:

-GGVA-, (SEQ ID NO: 76)

-GG-(D-)VA-,

-VA-,

-GGFG-, (SEQ ID NO: 77)

-GGPI-, (SEQ ID NO: 78)

-GGVCit-, (SEQ ID NO: 79)

-GGVK-, (SEQ ID NO: 80)

-GG(D-)P-I-, and

-GGPL-. (SEQ ID NO: 81)

[69] The compound according to any one of [62] to [68], a salt of the compound, or a hydrate of the compound or the salt, wherein La' is selected from the following group:
—C(=O)—CH$_2$CH$_2$—C(=O)—, —C(=O)—(CH$_2$CH$_2$)$_2$—C(=O)—, —C(=O)—CH$_2$CH$_2$—C(=O)—NH—(CH$_2$CH$_2$)$_2$—C(=O)—, —C(=O)—CH$_2$CH$_2$—C(=O)—NH—(CH$_2$CH$_2$O)$_2$—CH$_2$—C(=O)—, —C(=O)—CH$_2$CH$_2$—NH—C(=O)—(CH$_2$CH$_2$O)$_4$—CH$_2$CH$_2$—C(=O)—, —CH$_2$—OC(=O)—, —OC(=O)—, (CH$_2$)$_5$—C(=O)—, and —CH$_2$CH$_2$—C(=O)—NH—(CH$_2$CH$_2$O)$_8$—CH$_2$CH$_2$—C(=O)—.

[70] The compound according to any one of [62] to [69], a salt of the compound, or a hydrate of the compound or the salt, wherein
R$^{16}$ is represented by J-La'-Lp'—NH—B'—CH$_2$—O(C=O)—*, wherein
B' is a 1,4-phenyl group;
Lp' represents any one selected from the following group:

-GGVA-, (SEQ ID NO: 76)

-GG-(D-)VA-,

-VA-,

-GGFG-, (SEQ ID NO: 77)

-GGPI-, (SEQ ID NO: 78)

-GGVCit-, (SEQ ID NO: 79)

-GGVK-, (SEQ ID NO: 80)

-GG(D-)P-I-, and

-GGPL-. (SEQ ID NO: 81)

La' represents any one selected from the following group:
—C(=O)—CH$_2$CH$_2$—C(=O)—, —C(=O)—(CH$_2$CH$_2$)$_2$—C(=O)—, —C(=O)—CH$_2$CH$_2$—C(=O)—NH—(CH$_2$CH$_2$)$_2$—C(=O)—, —C(=O)—CH$_2$CH$_2$—C(=O)—NH—(CH$_2$CH$_2$O)$_2$—CH$_2$—C(=O)—, —C(=O)—CH$_2$CH$_2$—NH—C(=O)—(CH$_2$CH$_2$O)$_4$—CH$_2$CH$_2$—C(=O)—, —CH$_2$—OC(=O)—, —OC(=O)—, (CH$_2$)$_5$—C(=O)—, and —CH$_2$CH$_2$—C(=O)—NH—(CH$_2$CH$_2$O)$_8$—CH$_2$CH$_2$—C(=O)—; and
J represents any one of the following:

[Formula 41]

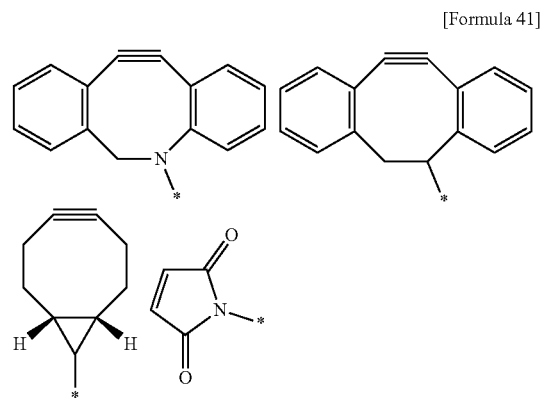

wherein, in the structural formulas for J,
each asterisk represents bonding to La'.

[71] The compound according to any one of [62] to [70], a salt of the compound, or a hydrate of the compound or the salt, wherein
R$^{16}$ is selected from the following group:
J$^1$-C(=O)—CH$_2$CH$_2$—C(=O)-GGVA-NH—B'—CH$_2$—OC(=O)— ("GGVA" disclosed as SEQ ID NO: 76),
J$^1$-C(=O)—CH$_2$CH$_2$—C(=O)-GG-(D-)VA (SEQ ID NO: 95)—NH—B'—CH$_2$—OC(=O)—, J$^1$-C(=O)—CH$_2$CH$_2$—C(=O)—VA-NH—B'—CH$_2$—OC(=O)—, J$^1$-C(=O)—(CH$_2$CH$_2$)$_2$—C(=O)—VA-NH—B'—CH$_2$—OC(=O)—, J$^1$-C(=O)—CH$_2$CH$_2$—C(=O)-GGPI—NH—B'—CH$_2$—OC(=O)— ("GGPI" disclosed as SEQ ID NO: 78),
J$^1$-C(=O)—CH$_2$CH$_2$—C(=O)-GGFG-NH—B'—CH$_2$—OC(=O)— ("GGFG" disclosed as SEQ ID NO: 77),
J$^1$-C(=O)—CH$_2$CH$_2$—C(=O)-GGVCit-NH—B'—CH$_2$—OC(=O)— ("GGVCit" disclosed as SEQ ID NO: 79),
J$^1$-C(=O)—CH$_2$CH$_2$—C(=O)-GGVK—NH—B'—CH$_2$—OC(=O)— ("GGVK" disclosed as SEQ ID NO: 80),
J$^1$-C(=O)—CH$_2$CH$_2$—C(=O)-GGPL-NH—B'—CH$_2$—OC(=O)— ("GGPL" disclosed as SEQ ID NO: 81),
J$^1$-C(=O)—CH$_2$CH$_2$—C(=O)—NH—(CH$_2$CH$_2$)$_2$—C(=O)—VA-NH—B'—CH$_2$—OC(=O)—, J$^1$-C(=O)—CH$_2$CH$_2$—C(=O)—NH—(CH$_2$CH$_2$O)$_2$—CH$_2$—C(=O)—VA-NH—B'—CH$_2$—OC(=O)—,
J$^1$-C(=O)—CH$_2$CH$_2$—NH—C(=O)—(CH$_2$CH$_2$O)$_4$—CH$_2$CH$_2$—C(=O)—VA-NH—B'—CH$_2$—OC(=O)—, J$_2$-OC(=O)-GGVA-NH—B'—CH$_2$—OC(=O)— ("GGVA" disclosed as SEQ ID NO: 76),
J$^1$-CH$_2$—OC(=O)-GGVA-NH—B'—CH$_2$—OC(=O)— ("GGVA" disclosed as SEQ ID NO: 76),
J$^4$-(CH$_2$)$_5$—C(=O)-GGVA-NH—B'—CH$_2$—OC(=O)— ("GGVA" disclosed as SEQ ID NO: 76),
J$^4$-(CH$_2$)$_5$—C(=O)—VA-NH—B'—CH$_2$—OC(=O)—, and J$^4$-CH$_2$CH$_2$—C(=O)—NH—(CH$_2$CH$_2$O)$_8$—CH$_2$CH$_2$—C(=O)—VA-NH—B'—CH$_2$—OC(=O)—, wherein $J^1$, $J^2$, $J^3$, and $J^4$ represent the following structural formulas:

[Formula 42]

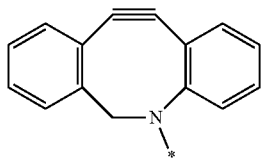
J1

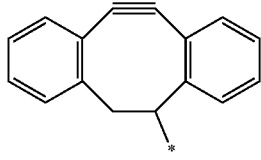
J2

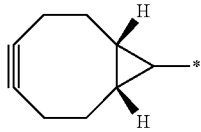
J3

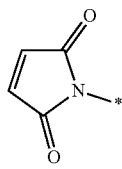
J4 wherein, in the structural formulas for $J^1$, $J^2$, $J^3$, and $J^4$, each asterisk represents bonding to a neighboring group, and
B' is a 1,4-phenyl group.

[72] The compound according to any one of [62] to [71], a salt of the compound, or a hydrate of the compound or the salt, wherein
$R^{16}$ is selected from the following group:
$J^1$-C(=O)—CH$_2$CH$_2$—C(=O)-GGVA-NH—B'—CH$_2$—OC(=O)— ("GGVA" disclosed as SEQ ID NO: 76),
$J^1$-C(=O)—CH$_2$CH$_2$—C(=O)—VA-NH—B'—CH$_2$—OC(=O)—, $J^1$-C(=O)—(CH$_2$CH$_2$)$_2$—C(=O)—VA-NH—B'—CH$_2$—OC(=O)—, $J^1$-C(=O)—CH$_2$CH$_2$—C(=O)-GGVCit-NH—B'—CH$_2$—OC(=O)— ("GGVCit" disclosed as SEQ ID NO: 79),
$J^1$-C(=O)—CH$_2$CH$_2$—C(=O)—NH—(CH$_2$CH$_2$)$_2$—C(=O)—VA-NH—B'—CH$_2$—OC(=O)—, $J^1$-C(=O)—CH$_2$CH$_2$—C(=O)—NH—(CH$_2$CH$_2$O)$_2$—CH$_2$—C(=O)—VA-NH—B'—CH$_2$—OC(=O)—, $J^1$-C(=O)—CH$_2$CH$_2$—NH—C(=O)—(CH$_2$CH$_2$O)$_4$—CH$_2$CH$_2$—C(=O)—VA-NH—B'—CH$_2$—OC(=O)—, $J^4$-(CH$_2$)$_5$—C(=O)-GGVA-NH—B'—CH$_2$—OC(=O)— ("GGVA" disclosed as SEQ ID NO: 76), and
$J^4$-(CH$_2$)$_5$—C(=O)—VA-NH—B'—CH$_2$—OC(=O)—,
wherein
B' is a 1,4-phenyl group, and
$J^1$ and $J^4$ represent the following structural formulas:

[Formula 43]

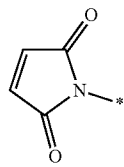
J1

J4 wherein, in the structural formulas for $J^P$ and $J^4$,
each asterisk represents bonding to a neighboring group.

[73] A compound, a salt of the compound, or a hydrate of the compound or the salt, wherein the compound is any one compound selected from the following formulas:

[Formula 44]

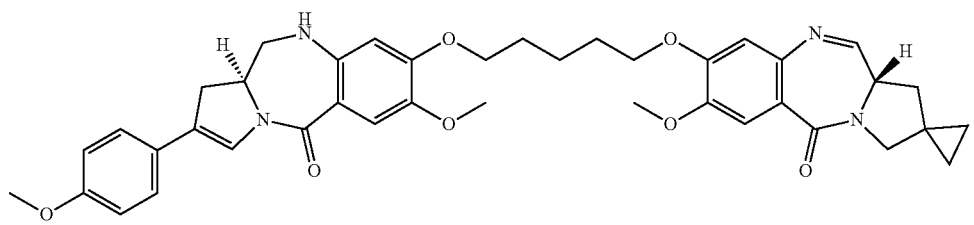

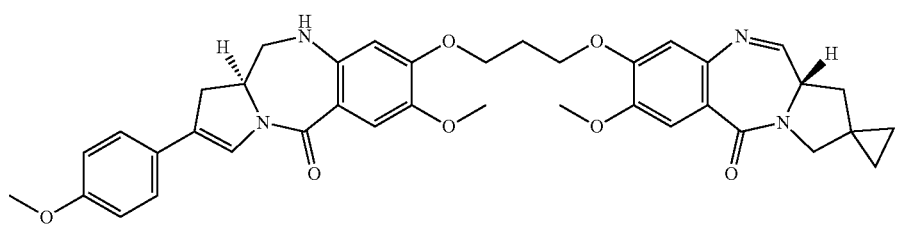

-continued
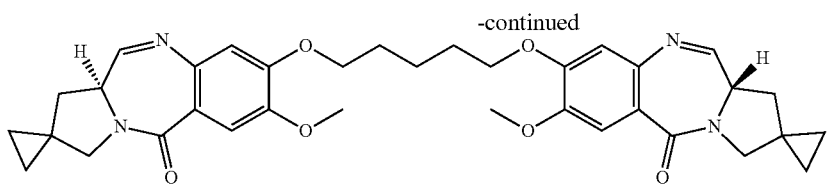
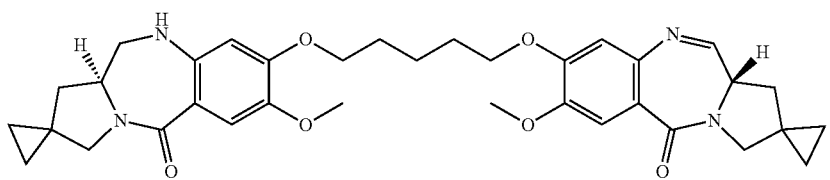
20
[74] A compound, a salt of the compound, or a hydrate of the compound or the salt, wherein the compound is any one compound selected from the following formulas:
[Formula 45]
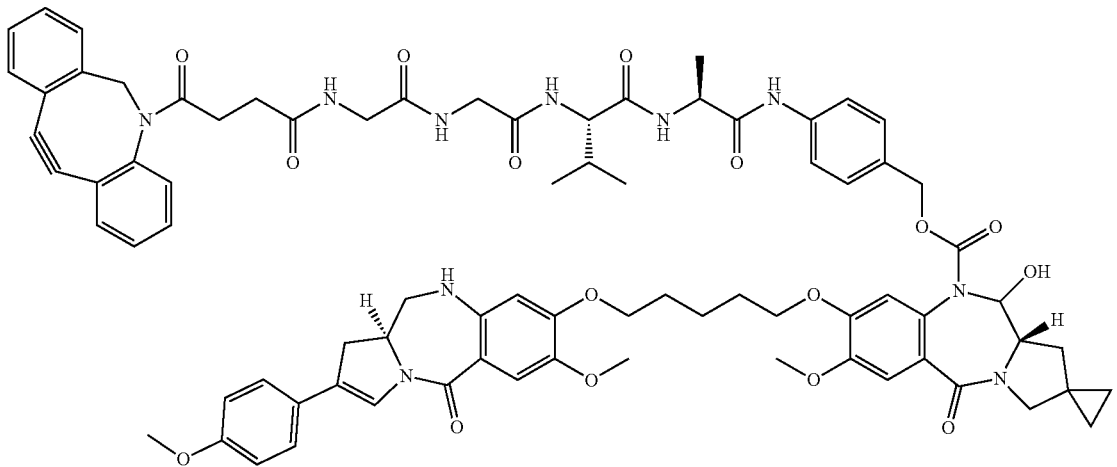
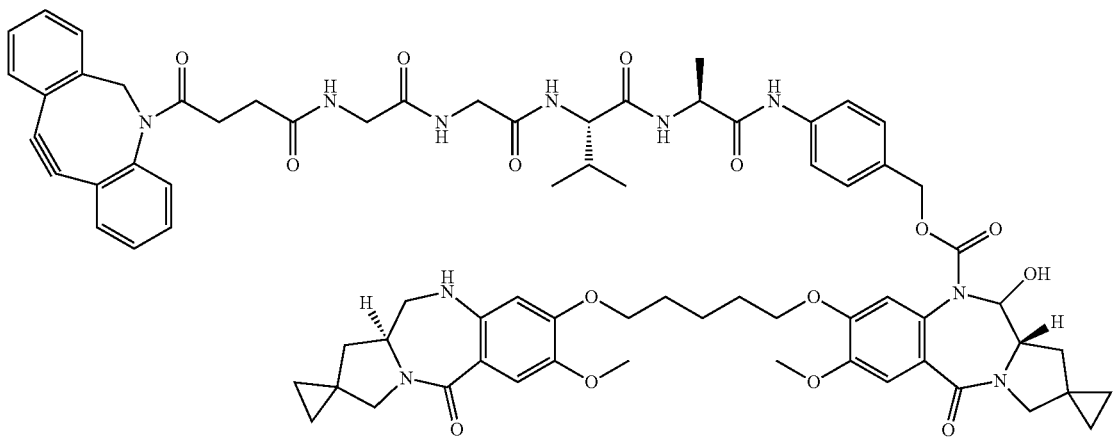

-continued

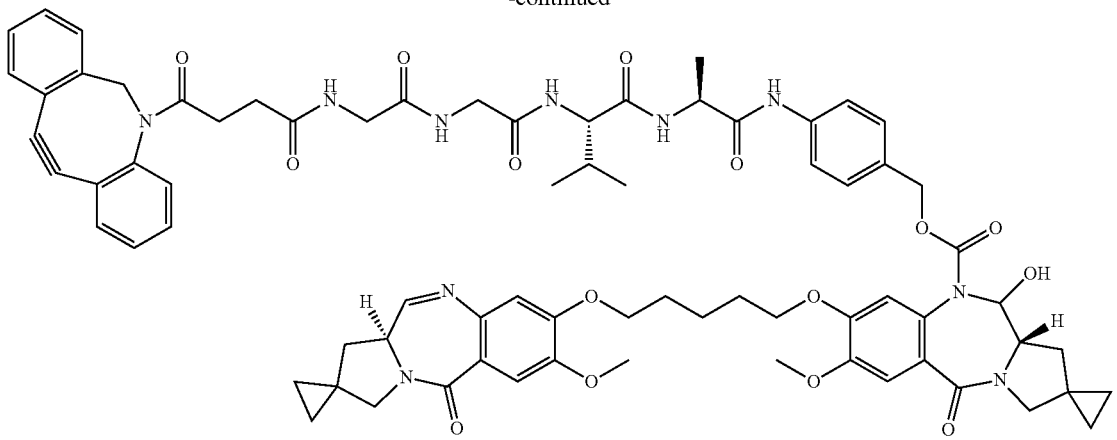

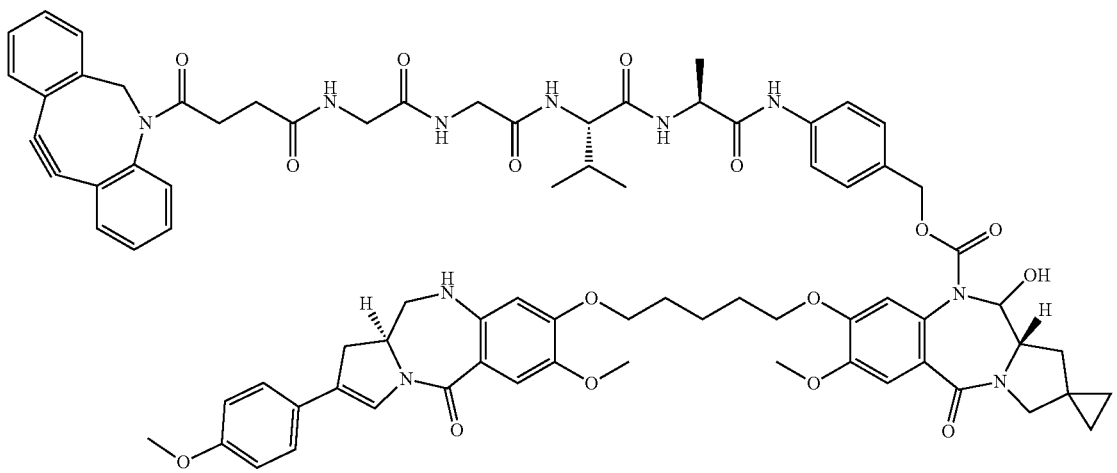

[75] The antibody-drug conjugate according to any one of [1] to [29] and [59] to [61], wherein D is represented by the following formula:

[Formula 46]

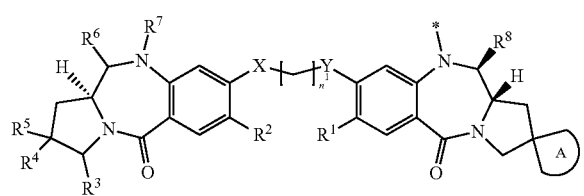

[76] The compound according to any one of [62] to [72] and [74], a salt of the compound, or a hydrate of the compound or the salt, the compound represented by the following formula:

[Formula 47]

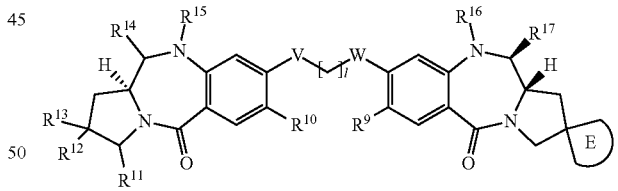

[77] The antibody-drug conjugate according to any one of [1] to [29] and [59] to [61], wherein D is represented by the following formula:

[Formula 48]

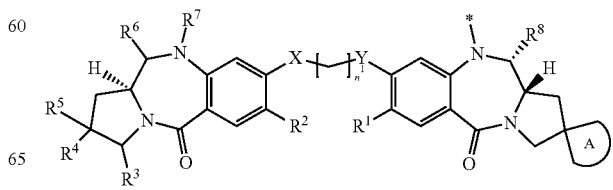

The compound according to any one of [62] to [72] and [74], a salt of the compound, or a hydrate of the compound or the salt, the compound represented by the following formula:

[Formula 49]

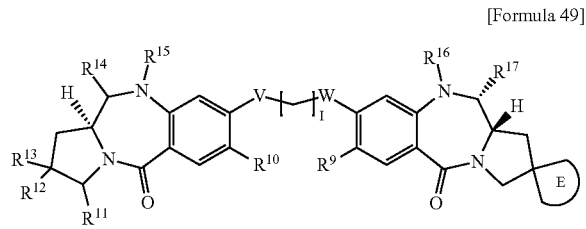

[79] A pharmaceutical composition comprising any of the antibody-drug conjugate according to any one of [1] to [29] and [59] to [61], [75] and [77], a salt of the antibody-drug conjugate, or a hydrate of the antibody-drug conjugate or the salt; the antibody according to any one of [30] to [42], [50] to [54], and [58] or a functional fragment of the antibody; and the compound according to any one of [62] to [74], [76] and [78], a salt of the compound, or a hydrate of the compound or the salt.

[80] The pharmaceutical composition according to [79], being an antitumor drug.

[81] The pharmaceutical composition according to [80], wherein the tumor is a tumor expressing CLDN6 and/or CLDN9.

[82] The pharmaceutical composition according to [80] or [81], wherein the tumor is ovarian cancer (surface epithelial tumor, stromal tumor, or germ cell tumor), lung cancer (non-small cell lung cancer or small cell lung cancer), gastric cancer, endometrial cancer, testicular cancer (seminoma, or non-seminoma), uterine cervix cancer, placental choriocarcinoma, kidney cancer, urothelial cancer, colorectal cancer, prostate cancer, glioblastoma multiforme, brain tumor, pancreatic cancer, breast cancer, melanoma, liver cancer, bladder cancer, or esophageal cancer.

[83] A method for treating a tumor, wherein any of the antibody-drug conjugate according to any one of [1] to [29] and [59] to [61], [75] and [77], a salt of the antibody-drug conjugate, or a hydrate of the antibody-drug conjugate or the salt; the antibody according to any one of [30] to [42], [50] to [54], and [58] or a functional fragment of the antibody; and the compound according to any one of [62] to [74], [76] and [78], a salt of the compound, or a hydrate of the compound or the salt is administered to an individual.

[84] The method according to [83], wherein the tumor is a tumor expressing CLDN6 and/or CLDN9.

[85] The method according to [83] or [84], wherein the tumor is ovarian cancer (surface epithelial tumor, stromal tumor, or germ cell tumor), lung cancer (non-small cell lung cancer or small cell lung cancer), gastric cancer, endometrial cancer, testicular cancer (seminoma or non-seminoma), uterine cervix cancer, placental choriocarcinoma, kidney cancer, urothelial cancer, colorectal cancer, prostate cancer, glioblastoma multiforme, brain tumor, pancreatic cancer, breast cancer, melanoma, liver cancer, bladder cancer, or esophageal cancer.

[86] A method for treating a tumor, wherein a pharmaceutical composition comprising at least one selected from the antibody-drug conjugate according to any one of [1] to [29] and [59] to [61], [75] and [77], a salt of the antibody-drug conjugate, or a hydrate of the antibody-drug conjugate or the salt; the antibody according to any one of [30] to [42], [50] to [54], and [58] or a functional fragment of the antibody; and the compound according to any one of [62] to [74], [76] and [78], a salt of the compound, or a hydrate of the compound or the salt, and at least one antitumor drug are administered to an individual simultaneously, separately, or consecutively.

[87] A compound exhibiting proton NMR having peak positions substantially similar to peak positions listed in Table 1 or Table 2.

Advantageous Effects of Invention

The novel antibody-pyrrolobenzodiazepine (PBD) derivative conjugate provided by the present invention is superior in antitumor activity and safety, and hence useful as an antitumor agent. The PBD derivative of the present invention has antitumor activity, and thus is useful as a drug for the conjugate. In addition, the antibody of the present invention recognizes tumor cells or binds to tumor cells, and hence is useful as an antibody for the conjugate.

BRIEF DESCRIPTION OF DRAWINGS

In FIG. 2A, (e) indicates N297 glycan consisting only of GlcNAc at the 6-position connected to 1-positions of Fuc via an α glycosidic bond. In FIG. 2B, (d) indicates the same N297 glycan as in FIG. 1, and (f) indicates a structure of a PEG linker portion having an azide group, specifically, an azide group to be bonded to liker L at the end. The bonding mode of the PEG linker having an azide group is as described for FIG. 1.

FIG. 3A illustrates the step of producing homogeneous (Fucα1,6)GlcNAc-antibody (II) by treating heterogeneous N297 glycan moieties of (IV) with hydrolase such as EndoS. FIG. 3B illustrates the step of producing the MSG-type glycan-remodeled antibody of (III) by subjecting GlcNAc of N297 glycan in antibody (II) to transglycosidase such as an EndoS D233Q/Q303L variant to transglycosylate the glycan of an MSG-type glycan donor molecule. The MSG-type glycan donor molecule used here has a sialic acid at the non-reducing terminal of MSG modified with a PEG linker having an azide group. Thus, resulting MSG-type N297 glycan-remodeled antibody also has a sialic acid at the non-reducing terminal modified in the same manner as described for FIG. 2B. For convenience, FIG. 3B shows MSG as a donor molecule. However, a glycan-remodeled antibody in which a linker molecule having an azide group bonds to each non-reducing terminal of N297 glycan also can be synthesized as the remodeled antibody of (III) by using SG (10) as a glycan donor.

FIG. 10 shows the effects of the anti-TROP2 antibody-drug conjugate ADC50 and the anti-LPS antibody-drug conjugate ADC53 on subcutaneously transplanted FaDu cells, a human head-and-neck cancer cell line.

FIG. 11 shows the full-length amino acid sequence of human CLDN6 (SEQ ID NO: 1) and the nucleotide sequence of full-length cDNA for human CLDN6 (SEQ ID NO: 2).

FIG. 12 shows the full-length amino acid sequence of human CLDN9 (SEQ ID NO: 3) and the nucleotide sequence of full-length cDNA for human CLDN9 (SEQ ID NO: 4).

FIG. 13 shows the amino acid sequences of CDRL1 to 3 of a B1 antibody light chain (SEQ ID NOs: 5 to 7).

FIG. 14 shows the amino acid sequence of CDRL3 of the humanized B1 antibody light chain L4 (SEQ ID NO: 8).

FIG. 15 shows the amino acid sequences of CDRH1 to 3 of a B1 antibody heavy chain (SEQ ID NOs: 9 to 11).

FIG. 16 shows the amino acid sequences of CDRL1 to 3 of a C7 antibody light chain (SEQ ID NOs: 12 to 14).

FIG. 17 shows the amino acid sequences of CDRH1 to 3 of a C7 antibody heavy chain (SEQ ID NOs: 15 to 17).

FIG. 18 shows the nucleotide sequence of cDNA encoding the variable region of a B1 antibody light chain (SEQ ID NO: 18) and the amino acid sequence of the variable region of a B1 antibody light chain (SEQ ID NO: 19). Each underline in the amino acid sequence indicates a CDR sequence.

FIG. 19 shows the nucleotide sequence of cDNA encoding the variable region of a B1 antibody heavy chain (SEQ ID NO: 20) and the amino acid sequence of the variable region of a B1 antibody heavy chain (SEQ ID NO: 21). Each underline in the amino acid sequence indicates a CDR sequence.

FIG. 20 shows the nucleotide sequence of cDNA encoding the variable region of a C7 antibody light chain (SEQ ID NO: 22) and the amino acid sequence of the variable region of a C7 antibody light chain (SEQ ID NO: 23). Each underline in the amino acid sequence indicates a CDR sequence.

FIG. 21 shows the nucleotide sequence of cDNA encoding the variable region of a C7 antibody heavy chain (SEQ ID NO: 24) and the amino acid sequence of the variable region of a C7 antibody heavy chain (SEQ ID NO: 25). Each underline in the amino acid sequence indicates a CDR sequence.

FIG. 22 shows the amino acid sequence of a chB1 light chain (SEQ ID NO: 28) and a DNA fragment including a DNA sequence encoding the amino acid sequence of a chB1 light chain (SEQ ID NO: 29). Each underline in the amino acid sequence indicates a CDR sequence.

FIG. 23 shows the amino acid sequence of the variable region of a chB1 light chain (SEQ ID NO: 30) and the nucleotide sequence encoding a chB1 light chain variable region (SEQ ID NO: 31). Each underline in the amino acid sequence indicates a CDR sequence.

FIG. 24 shows the amino acid sequence of a chB1 heavy chain (SEQ ID NO: 32) and the nucleotide sequence encoding a chB1 heavy chain (SEQ ID NO: 33). Each underline in the amino acid sequence indicates a CDR sequence.

FIG. 25 shows the amino acid sequence of the variable region of a chB1 heavy chain (SEQ ID NO: 34) and the nucleotide sequence encoding a variable region of a chB1 heavy chain (SEQ ID NO: 35). Each underline in the amino acid sequence indicates a CDR sequence.

FIG. 26 shows the amino acid sequence of the humanized antibody light chain hL1 (SEQ ID NO: 36) and the nucleotide sequence encoding the humanized antibody light chain hL1 (SEQ ID NO: 37). Each underline in the amino acid sequence indicates a CDR sequence.

FIG. 27 shows the amino acid sequence of the variable region of the humanized antibody light chain hL1 (SEQ ID NO: 38) and the nucleotide sequence encoding the variable region of the humanized antibody light chain hL1 (SEQ ID NO: 39). Each underline in the amino acid sequence indicates a CDR sequence.

FIG. 28 shows the amino acid sequence of the humanized antibody light chain hL2 (SEQ ID NO: 40) and the nucleotide sequence encoding the humanized antibody light chain hL2 (SEQ ID NO: 41). Each underline in the amino acid sequence indicates a CDR sequence.

FIG. 29 shows the amino acid sequence of the variable region of the humanized antibody light chain hL2 (SEQ ID NO: 42) and the nucleotide sequence encoding the variable region of the humanized antibody light chain hL2 (SEQ ID NO: 43).

FIG. 30 shows the amino acid sequence of the humanized antibody light chain hL3 (SEQ ID NO: 44) and the nucleotide sequence encoding the humanized antibody light chain hL3 (SEQ ID NO: 45). Each underline in the amino acid sequence indicates a CDR sequence.

FIG. 31 shows the amino acid sequence of the variable region of the humanized antibody light chain hL3 (SEQ ID NO: 46) and the nucleotide sequence encoding the variable region of the humanized antibody light chain hL3 (SEQ ID NO: 47). Each underline in the amino acid sequence indicates a CDR sequence.

FIG. 32 shows the amino acid sequence of the humanized antibody light chain hL4 (SEQ ID NO: 48) and the nucleotide sequence encoding the humanized antibody light chain hL4 (SEQ ID NO: 49). Each underline in the amino acid sequence indicates a CDR sequence.

FIG. 33 shows the amino acid sequence of the variable region of the humanized antibody light chain hL4 (SEQ ID NO: 50) and the nucleotide sequence encoding the variable region of the humanized antibody light chain hL4 (SEQ ID NO: 51). Each underline in the amino acid sequence indicates a CDR sequence.

FIG. 34 shows the amino acid sequence of the humanized antibody heavy chain hH1 (SEQ ID NO: 52) and the nucleotide sequence encoding the humanized antibody heavy chain hH1 (SEQ ID NO: 53). Each underline in the amino acid sequence indicates a CDR sequence.

FIG. 35 shows the amino acid sequence of the variable region of the humanized antibody heavy chain hH1 (SEQ ID NO: 54) and the nucleotide sequence encoding the variable region of the humanized antibody heavy chain hH1 (SEQ ID NO: 55). Each underline in the amino acid sequence indicates a CDR sequence.

FIG. 36 shows the amino acid sequence of the humanized antibody heavy chain hH2 (SEQ ID NO: 56) and the nucleotide sequence encoding the humanized antibody heavy chain hH2 (SEQ ID NO: 57). Each underline in the amino acid sequence indicates a CDR sequence.

FIG. 37 shows the amino acid sequence of the variable region of the humanized antibody heavy chain hH2 (SEQ ID NO: 58) and the nucleotide sequence encoding the variable region of the humanized antibody heavy chain hH2 (SEQ ID NO: 59).

FIG. 38 shows the amino acid sequence of the humanized antibody heavy chain hH3 (SEQ ID NO: 60) and the nucleotide sequence encoding the humanized antibody heavy chain hH3 (SEQ ID NO: 61). Each underline in the amino acid sequence indicates a CDR sequence.

FIG. 39 shows the amino acid sequence of the variable region of the humanized antibody heavy chain hH3 (SEQ ID NO: 62) and the nucleotide sequence encoding the variable region of the humanized antibody heavy chain hH3 (SEQ ID NO: 63). Each underline in the amino acid sequence indicates a CDR sequence.

FIG. 43 shows the amino acid sequence of the trastuzumab light chain (SEQ ID NO: 64) and the amino acid sequence of the trastuzumab heavy chain (SEQ ID NO: 65).

FIG. 44 shows the amino acid sequence of a light chain of a trastuzumab variant (SEQ ID NO: 73) and the amino acid sequence of a heavy chain of a trastuzumab variant (SEQ ID NO: 75).

FIG. 45 shows comparison of the amino acid sequences of chB1_H(SEQ ID NO: 34), which is a heavy chain of the chimerized human anti-CLDN6 antibody chB1, and the humanized antibody heavy chains hH1 (SEQ ID NO: 54), hH2 (SEQ ID NO: 58), and hH3 (SEQ ID NO: 62). The symbol "." indicates an amino acid residue identical to the corresponding amino acid residue of chB1_H, and each position with a symbol of an amino acid residue indicates a substituted amino acid residue. Figure discloses SEQ ID NOS 34, 54, 58, and 62, respectively, in order of appearance.

FIG. 46 shows comparison of the amino acid sequences of chB1_L (SEQ ID NO: 30), which is a light chain of the chimerized human anti-CLDN6 antibody chB1, and the humanized antibody light chains hL1 (SEQ ID NO: 38), hL2 (SEQ ID NO: 42), hL3 (SEQ ID NO: 46), and hL4 (SEQ ID NO: 50). The symbol "." indicates an amino acid residue identical to the corresponding amino acid residue of chB1_L, and each position with symbol of an amino acid residue indicates a substituted amino acid residue. Figure discloses SEQ ID NOS 30, 38, 42, 46, and 50, respectively, in order of appearance.

FIG. 66 shows Formula 194, wherein the triazole ring to be formed in step 1 has geometric isomers, and the compound obtained in step 1 of Example 67 has a linker as a mixture of the two structures shown as R.

FIG. 68 shows Formula 234, wherein the triazole ring to be formed in step 1 has geometric isomers, and the compound obtained in step 1 of Example 107 has a linker as a mixture of the two structures shown as R.

FIG. 69 shows Formula 235, wherein the triazole ring to be formed in step 1 has geometric isomers, and the compound obtained in step 1 of Example 108 has a linker as a mixture of the two structures shown as R.

FIG. 70 shows Formula 243, wherein the triazole ring to be formed in step 1 has geometric isomers, and the compound obtained in step 1 of Example 116 has a linker as a mixture of the two structures shown as R.

FIG. 71 shows Formula 244, wherein the triazole ring to be formed in step 1 has geometric isomers, and the compound obtained in step 1 of Example 117 has a linker as a mixture of the two structures shown as R.

FIG. 72 shows Formula 246, wherein the triazole ring to be formed in step 1 has geometric isomers, and the compound obtained in step 1 of Example 119 has a linker as a mixture of the two structures shown as R.

DESCRIPTION OF EMBODIMENTS

Figure 1:
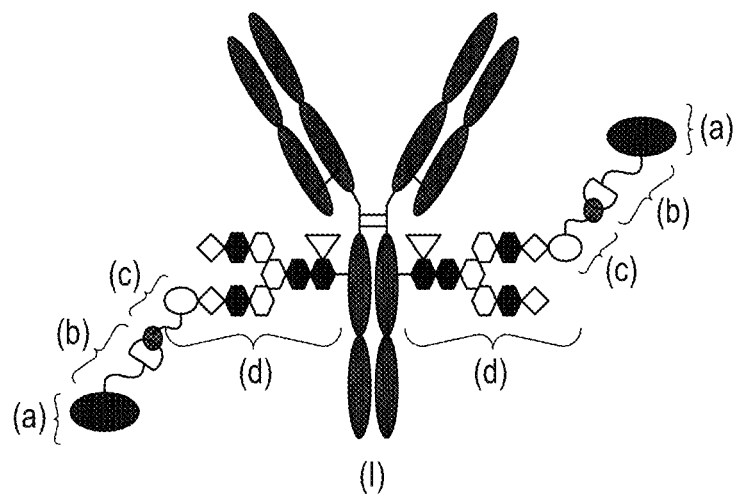
FIG. 1 is a schematic diagram of the drug-conjugate of the present invention (the molecule of (I)). (a) indicates drug D, (b) indicates linker L, (c) indicates $N_3$-L(PEG)-, and (d) indicates N297 glycan (open ellipse: NeuAc(Sia), open hexagon: Man, filled hexagon: GlcNAc, open diamond: Gal, open inverted triangle: Fuc). (b) and (c) are combined together to form a triazole ring by reaction between the azide group (filled teardrop shape) of (c) and the spacer (open semicircle) of (b). The Y-shaped diagram represents antibody Ab. For convenience, in this schematic diagram, N297 glycan is indicated as N297-(Fuc)MSG and the diagram shows an embodiment wherein any one of two branches in each of N297 glycans has a sialic acid to which a PEG linker having an azide group ($N_3$-L(PEG)-) bonds while other branch has no sialic acid at the non-reducing terminal (i.e. N297-(Fuc)MSG); however, another embodiment wherein each of two branches of N297 glycan has a sialic acid to which a PEG linker having an azide group bonds at the non-reducing terminal (i.e. N297-(Fuc)SG) is also acceptable. Unless otherwise stated, such a manner of illustration is applied throughout the present specification.

The antibody-drug conjugate of the present invention is an antitumor drug having an antitumor compound conjugated via a linker structure moiety to an antibody capable of recognizing or binding to tumor cells.

In the present invention, examples of "halogen atom" may include, but are not limited to, a fluorine atom, a chlorine atom, a bromine atom, and an iodine atom.

In the present invention, "C1 to C6 alkyl group" refers to a linear or branched alkyl group having one to six carbon atoms. Examples of "C1 to C6 alkyl group" may include, but are not limited to, a methyl group, an ethyl group, a n-propyl group, an i-propyl group, a n-butyl group, an i-butyl group, a s-butyl group, a t-butyl, a n-pentyl group, and a n-hexyl.

In the present invention, "C1 to C6 alkoxy group" refers to an alkoxy group having a linear or branched alkyl group having one to six carbon atoms. Examples of "C1 to C6 alkoxy group" may include, but are not limited to, a methoxy group, an ethoxy group, a n-propoxy group, an i-propoxy group, a n-butoxy group, an i-butoxy, a s-butoxy group, a n-pentyloxy group, and a n-hexyloxy.

In the present invention, "C1 to C6 alkylthio group" refers to an alkylthio group having a linear or branched alkyl group having one to six carbon atoms. Examples of "C1 to C6 alkylthio group" may include, but are not limited to, a methylthio group, an ethylthio group, a n-propylthio group, an i-propylthio group, a n-butylthio group, an i-butylthio group, a s-butylthio group, a t-butylthio group, a n-pentylthio group, and a n-hexylthio group.

In the present invention, "three- to five-membered saturated hydrocarbon ring" refers to a saturated cyclic hydrocarbon group having three to five carbon atoms. Examples of "three- to five-membered saturated hydrocarbon ring" may include, but are not limited to, a cyclopropyl group, a cyclobutyl group, and a cyclopentyl group.

In the present invention, "C3 to C5 cycloalkoxy group" refers to a cycloalkoxy group having a saturated cyclic hydrocarbon group having three to five carbon atoms. Examples of "C3 to C5 cycloalkoxy group" may include, but are not limited to, a cyclopropoxy group, a cyclobutoxy group, and a cyclopentyloxy group.

In the present invention, examples of "three- to five-membered saturated heterocycle" may include, but are not limited to, 1,3-propylene oxide, azacyclobutane, trimethylene sulfide, tetrahydrofuran, and pyrrolidine.

In the present invention, examples of "aryl group" may include, but are not limited to, a phenyl group, a benzyl group, an indenyl group, a naphthyl group, a fluorenyl group, an anthranyl group, and a phenanthrenyl group.

In the present invention, examples of "heteroaryl group" may include, but are not limited to, a thienyl group, a pyrrolyl group, a pyrazolyl group, a triazolyl group, an oxazolyl group, an oxadiazolyl group, a thiazolyl group, a pyridyl group, a pyrimidyl group, a pyridazyl group, a pyrazinyl group, a quinolyl group, a quinoxalyl group, a benzothiophenyl group, a benzimidazolyl group, a benzotriazolyl group, and a benzofuranyl group.

In the present invention, examples of "six-membered heterocycle" may include, but are not limited to, a pyridine ring, a pyrimidine ring, and a pyridazine ring.

In the present invention, "spiro-bonded" refers to the situation in which, as exemplified in Examples, A and a pyrrolidine ring to which A bonds, or E and a pyrrolidine ring to which E bonds form a spiro ring.

[Antibody-Drug Conjugate]

The antibody-drug conjugate of the present invention is represented by the following formula:

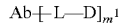   [Formula 50]

$m_1$ represents the number of conjugated drug molecules per antibody molecule in the antibody-drug conjugate, Ab represents an antibody or a functional fragment of the antibody, L represents a linker linking Ab and D, and D represents a drug.

<Drug>

Drug D conjugated in the antibody-drug conjugate of the present invention will be described. Drug D of the present invention is preferably an antitumor compound. The antitumor compound develops antitumor effect, when a part or the entire of the linker is cleaved in a tumor cell and the antitumor compound moiety is released. When the linker and the drug are cleaved apart at the bonding part, the antitumor compound in the original structure is released and the original antitumor effect is exerted.

The antitumor compound in the antibody-drug conjugate of the present invention is a pyrrolobenzodiazepine derivative (PBD derivative) represented by general formula (V):

[Formula 51]

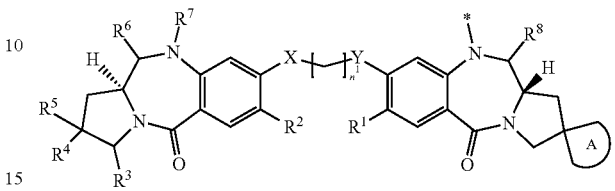

(V)

$n^1$ represents an integer of 2 to 8, and is preferably an integer of 2 to 6, and more preferably an integer of 3 to 5.

The alkyl chain with the subscript $n^1$ being an integer of 2 to 8, preferably an integer of 2 to 6, and more preferably an integer of 3 to 5, may include a double bond.

A represents a spiro-bonded three- to five-membered saturated hydrocarbon ring or a three- to five-membered saturated heterocycle, and is preferably a three- to five-membered saturated hydrocarbon ring (cyclopropane, cyclobutane, or cyclopentane), more preferably cyclopropane or cyclobutane, and most preferably cyclopropane.

The spiro-bonded three- to five-membered saturated hydrocarbon ring may be substituted with one to four halogen atoms, and may be preferably substituted with one or two fluorine atoms (e.g., 2,2-difluorocyclopropane).

$R^1$ and $R^2$ each independently represent a C1 to C6 alkoxy group, a C1 to C6 alkyl group, a hydrogen atom, a hydroxy group, a thiol group, a C1 to C6 alkylthio group, a halogen atom, or —NR'R", and are each preferably a C1 to C6 alkoxy group, a C1 to C6 alkyl group, or a hydroxy group, more preferably a C1 to C3 alkoxy group, and most preferably a methoxy group.

$R^3$, $R^4$, and $R^5$ are as described in any of the following (i) to (iii).

(i) If $R^3$ and $R^4$ are combined together with the carbon atoms to which $R^3$ and $R^4$ are bound to form a double bond as shown in the following:

[Formula 52]

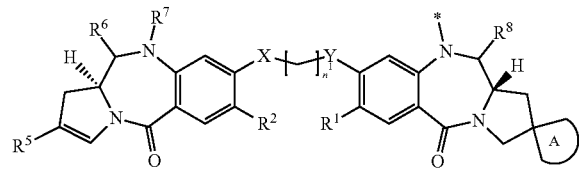

$R^5$ represents an aryl group or heteroaryl group optionally having one or more substituents selected from group 1 or a C1 to C6 alkyl group optionally having one or more substituents selected from group 2, and is preferably an aryl group optionally having one or more substituents selected from group 1.

"Aryl group" in "aryl group or heteroaryl group optionally having one or more substituents selected from group 1" for $R^5$ is preferably a phenyl group or a naphthyl group, and more preferably a phenyl group.

"Heteroaryl group" in "aryl group or heteroaryl group optionally having one or more substituents selected from group 1" for $R^5$ is preferably a thienyl group, a pyridyl group, a pyrimidyl group, a quinolyl group, a quinoxalyl group, or a benzothiophenyl group, more preferably a 2-thienyl group, a 3-thienyl group, a 2-pyridyl group, a 3-pyridyl group, or a 4-pyridyl group, and even more preferably a 3-pyridyl group or a 3-thienyl group.

Examples of substituents of the aryl group or heteroaryl group for $R^5$ may include, but are not limited to, the following a) to j):

a) a C1 to C6 alkoxy group optionally substituted with one to three halogen atoms,
b) a C1 to C6 alkyl group optionally substituted with any one selected from one to three halogen atoms, a hydroxy group, —OCOR', —NR"R", —C(NR')—NR"R''', and —NHC(=NR')—NR"R''',
c) a halogen atom,
d) a C3 to C5 cycloalkoxy group,
e) a C1 to C6 alkylthio group,
f) —NR'R",
g) —C(=NR')—NR"R''',
h) —NHC(=NR')—NR"R''',
i) —NHCOR', and
j) a hydroxy group, Here, R', R", and R''' in b) and f) to i) each independently represent a hydrogen atom or a C1 to C6 alkyl group, and are preferably each independently a hydrogen atom or a C1 to C3 alkyl group.

a) to j) are preferably as follows:

a) a C1 to C3 alkoxy group optionally substituted with one to three halogen atoms, more preferably a methoxy group, an ethoxy group, an n-propoxy group, an i-propoxy group, or a trifluoromethoxy, even more preferably a methoxy group, an ethoxy group, or a trifluoromethoxy group, and most preferably a methoxy group;
b) a C1 to C3 alkyl group optionally substituted with one to three halogen atoms, a hydroxy group, —OCOR', —C(=NR')—NR"R''', or —NHC(=NR')—NR"R''', wherein R', R", and R''' are each independently a hydrogen atom or a C1 to C3 alkyl group, more preferably a C1 to C3 alkyl group optionally substituted with any selected from one to three halogen atoms, a hydroxy group, —OCOR', —C(=NR')—NR"R''', and —NHC(=NR')—NR"R''', wherein R', R", and R''' are each independently a hydrogen atom or a methyl group, even more preferably a methyl group, an ethyl group, a n-propyl group, an i-propyl group, a fluoromethyl group, a difluoromethyl group, a trifluoromethyl group, a hydroxymethyl group, —CH$_2$OCOMe, —CH$_2$—NHC(=NH)—NH$_2$, or —CH$_2$—NHC(=NMe)-NH$_2$;
c) a halogen atom, preferably a fluorine atom or a chlorine atom;
d) a C3 to C5 cycloalkoxy group, more preferably a cyclopropoxy group;
e) a C1 to C3 alkylthio group, more preferably a methylthio group or an ethylthio group;
f) —NR'R", wherein R' and R" are each independently a hydrogen atom or a C1 to C3 alkyl group, more preferably —NH$_2$, —NHMe, —NMe$_2$, —NHEt, or —NEt$_2$;
g) —C(=NR')—NR"R''', wherein R', R", and R''' are each independently a hydrogen atom or a C1 to C3 alkyl group, more preferably —C(=NH)—NH$_2$ or —C(=NMe)-NH$_2$;
h) —NHC(=NR')—NR"R''', wherein R', R", and R''' are each independently a hydrogen atom or a C1 to C3 alkyl group, more preferably —NHC(=NH)—NH$_2$ or —NHC(=NMe)-NH$_2$;
i) —NHCOR', wherein R' is a hydrogen atom or a C1 to C3 alkyl group, more preferably —NHCOMe or —NHCOEt; and
j) a hydroxy group.

The aryl group (preferably, a phenyl group) or heteroaryl group (preferably, a pyridyl group) for $R^5$ may have at least one substituent at any position. If a plurality of substituents is present, the substituents may be the same or different.

If $R^5$ is an aryl group, each substituent is preferably a), b), d), g), h), or j), and more preferably a), b), d), or j).

If $R^5$ is a phenyl group, $R^5$ may have a substituent at any position and may have a plurality of substituents, and preferably one or two substituents are present at the 3-position and/or the 4-position, and more preferably one substituent is present at the 4-position.

If $R^5$ is a naphthyl group, $R^5$ may have a substituent at any position and may have a plurality of substituents, and preferably one substituent is present at the 6-position.

If $R^5$ is a phenyl group, $R^5$ is more preferably a phenyl group, a 4-methoxyphenyl group, a 3-methoxyphenyl group, a 4-ethoxyphenyl group, a 4-(n-propoxy)-phenyl group, a 4-(i-propoxy)-phenyl group, a 4-cyclopropoxy-phenyl group, a 4-trifluoromethylphenyl group, a 4-hydroxymethyl-phenyl group, a 4-acetoxymethyl-phenyl group, or a 4-carbamimidamidomethyl-phenyl group, and even more preferably a phenyl group, a 4-methoxyphenyl group, a 3-methoxyphenyl group, a 4-cyclopropoxy-phenyl group, a 4-hydroxymethyl-phenyl group, a 4-acetoxymethyl-phenyl group, a 4-carbamimidamidomethyl-phenyl group, or a 4-trifluoromethylphenyl group.

If $R^5$ is a naphthyl group, $R^5$ is more preferably a naphthyl group or a 6-methoxy-2-naphthyl group.

The most preferred is a 4-methoxyphenyl group.

If $R^5$ is a heteroaryl group, each substituent is preferably a), b), d), g), h), or j), and more preferably a) or b).

If $R^5$ is a heteroaryl group, $R^5$ may have at least one substituent at any position. If $R^5$ is a 3-pyridyl group, its substituent(s) is preferably present at the 6-position and/or the 5-position. If $R^5$ is 2-pyridyl, its substituent(s) is preferably present at the 5-position and/or the 4-position, or at the 5-position and/or the 6-position. If $R^5$ is 4-pyridyl, its substituent(s) is preferably present at the 2-position and/or the 6-position.

If $R^5$ is a heteroaryl group, $R^5$ may have a plurality of substituents, and preferably has one or two substituents, and preferably has one substituent.

If $R^5$ is a pyridyl group, $R^5$ is preferably a 6-methoxy-3-pyridyl group or a 6-methyl-3-pyridyl group.

If $R^5$ is a 3-thienyl group or a 6-quinoxalyl group, $R^5$ is preferably unsubstituted.

"C1 to C6 alkyl group" in "C1 to C6 alkyl group optionally having one or more substituents selected from group 2" for $R^5$ is preferably a C1 to C3 alkyl group, and more preferably a methyl group or an ethyl group.

The substituents in "C1 to C6 alkyl group optionally having one or more substituents selected from group 2" for $R^5$ are each a halogen atom, a hydroxy group, or a C1 to C6 alkoxy group (preferably, a C1 to C3 alkoxy group), preferably a hydroxy group, a methoxy group, or an ethoxy group, and more preferably a hydroxy group.

(ii) If $R^3$ represents a hydrogen atom, $R^4$ and $R^5$ are combined, together with the carbon atom to which $R^4$ and $R^5$ are bound, to form a three- to five-membered saturated hydrocarbon ring or three- to five-membered saturated heterocycle, or CH$_2$= as shown in the following:

[Formula 53]

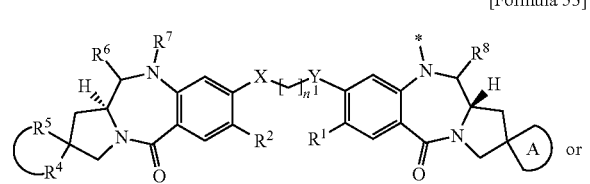

[Formula 54]

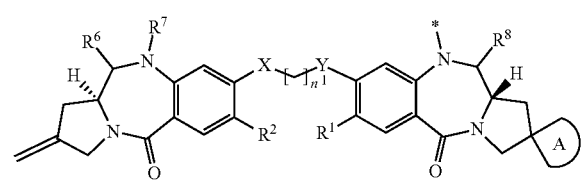

The three- to five-membered saturated hydrocarbon ring may be substituted with one to four halogen atoms, and may be preferably substituted with one or two fluorine atoms.

R$^4$ and R$^5$ are preferably combined to form a three- to five-membered saturated hydrocarbon ring or CH$_2$=, more preferably to form cyclopropane, cyclobutane, or CH$_2$- (exomethylene group), and even more preferably to form cyclopropane.

If R$^4$ and R$^5$ are combined to form a three- to five-membered saturated hydrocarbon ring or three- to five-membered saturated heterocycle, the three- to five-membered saturated hydrocarbon ring or three- to five-membered saturated heterocycle is preferably the same as A. More preferably, A is a three- to five-membered saturated hydrocarbon ring and R$^4$ and R$^5$ are combined to form a three- to five-membered saturated hydrocarbon ring, and even more preferably A is a cyclopropane ring and R$^4$ and R$^5$ are combined to form a cyclopropane ring.

(iii) R$^3$, R$^4$, and R$^5$ are combined, together with the carbon atom to which R$^3$ is bound and the carbon atom to which R$^4$ and R$^5$ are bound, to form a benzene ring or six-membered heterocycle optionally having one or more substituents selected from group 3.

The following formula shows the case in which R$^3$ and R$^4$ are combined to form a benzene ring optionally having one or more substituents:

[Formula 55]

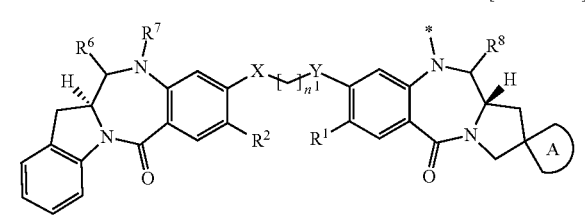

The benzene ring or heterocycle may have at least one substituent at any position. If a plurality of substituents is present, the substituents may be the same or different.

Each substituent of the benzene ring or the heterocycle is a halogen atom, a C1 to C6 alkyl group optionally substituted with one to three halogen atoms, or a C1 to C6 alkoxy group, preferably a halogen atom, a C1 to C3 alkyl group optionally substituted with one to three halogen atoms, or a C1 to C3 alkoxy, and more preferably a halogen atom, a methyl group, or a methoxy group.

"Benzene ring or six-membered heterocycle optionally having one or more substituents" is preferably an unsubstituted benzene ring.

R$^3$, R$^4$ and R$^5$ most preferably satisfy the above (i).

R$^6$ and R$^7$ each represent a hydrogen atom, or R$^6$ and R$^7$ are combined to represent an imine bond (C=N).

R' is a hydroxy group or a C1 to C3 alkoxy group, preferably a hydroxy group or a methoxy group, and more preferably a hydroxy group. R$^1$ may be a hydrogensulfite adduct (OSO$_3$M, wherein M is a metal cation).

Since R' bonds to an asymmetric carbon atom, a steric configuration represented by partial structure (Va) or (Vb) below is provided. Each wavy line represents bonding to Y in general formula (V), and each asterisk represents bonding to L.

[Formula 56]

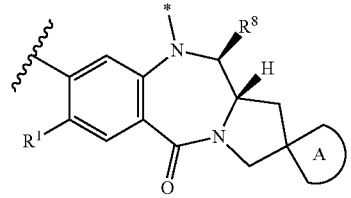

V (a)

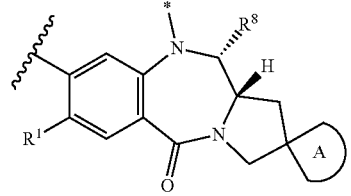

V (b)

X and Y are each independently an oxygen atom, a nitrogen atom, or a sulfur atom, and preferably an oxygen atom.

Drug D of the present invention is preferably any one compound selected from the following group:
[Formula 57]
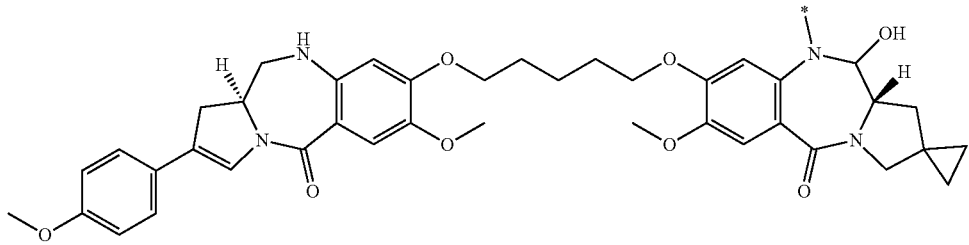
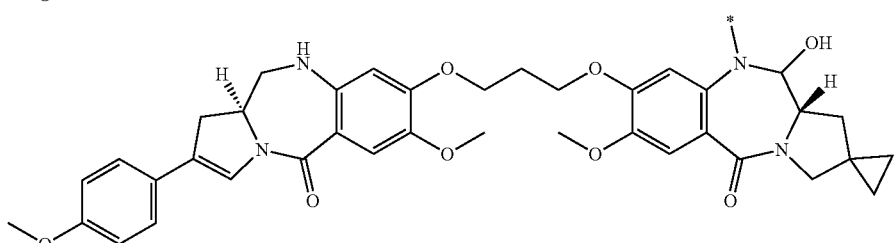
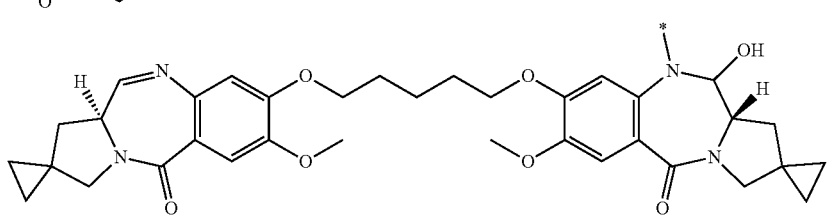
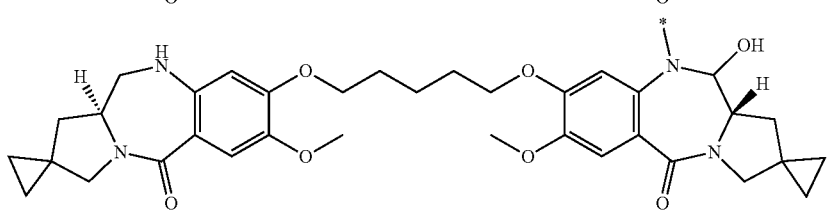
[Formula 58]
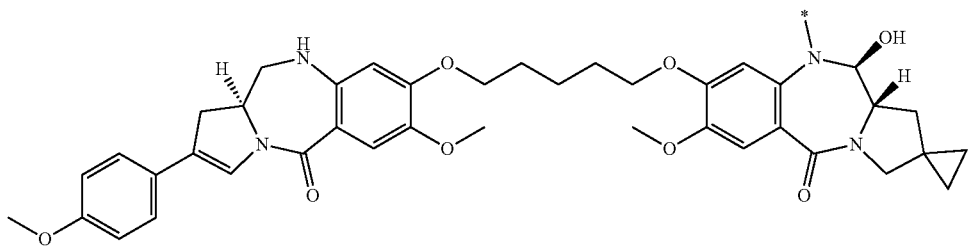
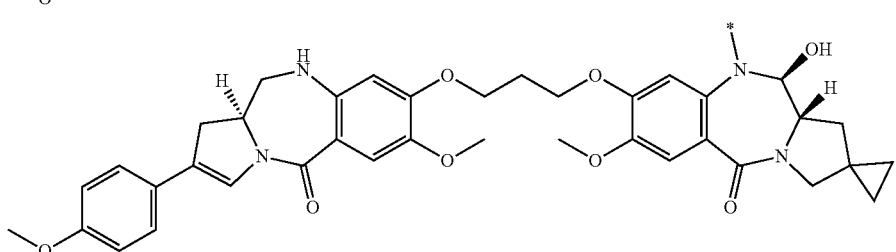
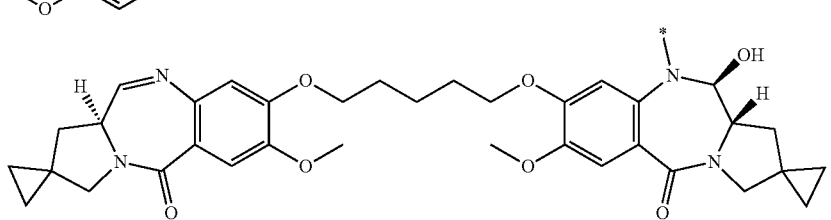

-continued

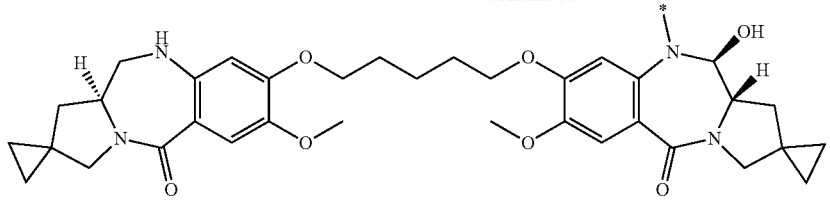

[Formula 59]

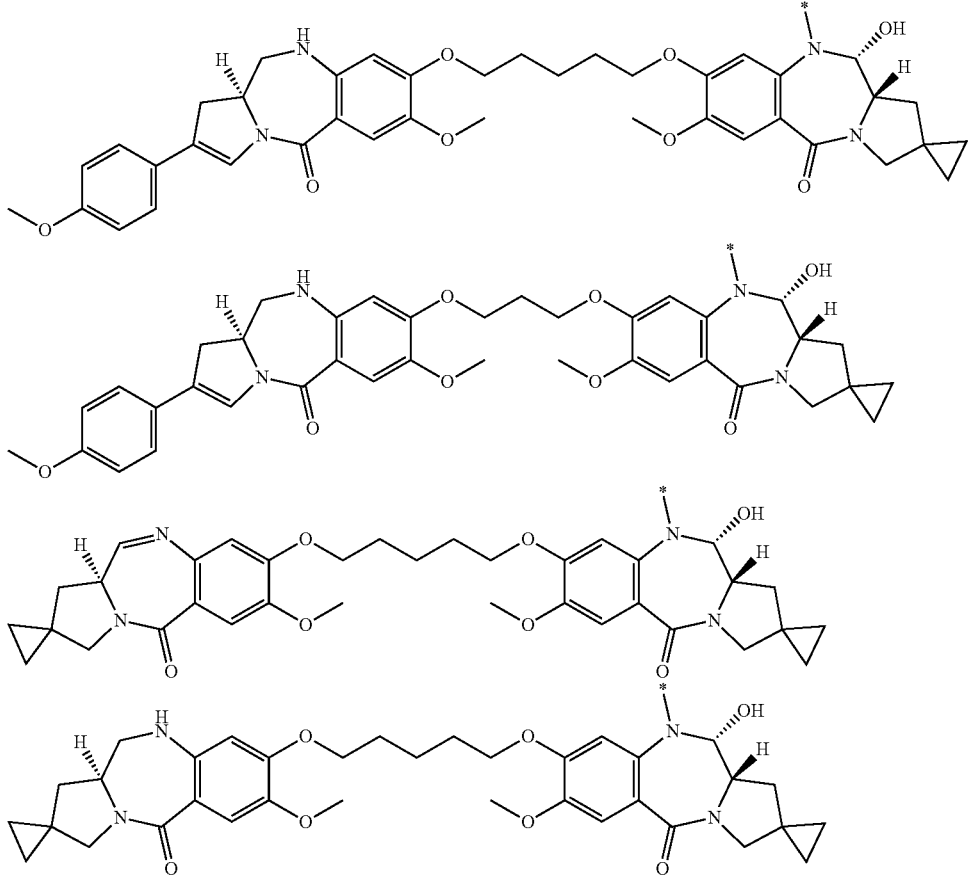

<Linker Structure>

The linker structure to bond the antitumor drug to the antibody in the antibody-drug conjugate of the present invention will be described.

Linker L is represented by the following formula:

-Lb-La-Lp-NH—B—CH₂—O(C=O)—*

The asterisk represents bonding to the nitrogen atom at the N10'-position of drug D, Lb represents a spacer which connects La to a glycan or remodeled glycan of Ab, or a spacer which connects La to a side chain of an amino acid residue (e.g., cysteine, or lysine) of antibody Ab.

B represents a phenyl group or a heteroaryl group, and is preferably a 1,4-phenyl group, a 2,5-pyridyl group, a 3,6-pyridyl group, a 2,5-pyrimidyl group, or a 2,5-thienyl group, and more preferably a 1,4-phenyl group.

Lp represents a linker consisting of an amino acid sequence cleavable in vivo or in a target cell. Lp is, for example, cleaved by the action of an enzyme such as esterase and peptidase.

Lp is a peptide residue composed of two to seven (preferably, two to four) amino acids. That is, Lp is composed of an oligopeptide residue in which two to seven amino acids are connected via peptide bonding.

Lp is bound at the N terminal to a carbonyl group of La in Lb-La—, and forms at the C terminal an amide bond with the amino group (—NH—) of the part —NH—B—CH₂—O(C=O)— of the linker. The bond between the C terminal of Lp and —NH— is cleaved by the enzyme such as esterase.

The amino acids constituting Lp are not limited to particular amino acids, and, for example are L- or D-amino acids, and preferably L-amino acids. The amino acids may be not only α-amino acids, but may include an amino acid with structure, for example, of β-alanine, ε-aminocaproic acid, or γ-aminobutyric acid, and may further include a non-natural amino acid such as an N-methylated amino acid.

The amino acid sequence of Lp is not limited to a particular amino acid sequence, and examples of amino acids that constitute Lp may include, but are not limited to, glycine (Gly; G), valine (Val; V), alanine (Ala; A), phenylalanine (Phe; F), glutamic acid (Glu; E), isoleucine (Ile; I), proline (Pro; P), citrulline (Cit), leucine (Leu; L), serine (Ser; S), lysine (Lys; K), and aspartic acid (Asp; D). Preferred among them are glycine (Gly; G), valine (Val; V), alanine (Ala; A), and citrulline (Cit).

Any of these amino acids may appear multiple times, and Lp has an amino acid sequence including arbitrarily selected amino acids. Drug release pattern may be controlled via amino acid type.

Specific examples of linker Lp may include, but are not limited to, -GGVA- (SEQ ID NO: 76), -GG-(D-)VA- (SEQ ID NO: 95), —VA-, -GGFG- (SEQ ID NO: 77), -GGPI— (SEQ ID NO: 78), -GGVCit- (SEQ ID NO: 79), -GGVK— (SEQ ID NO: 80), -GG(D-)PI— (SEQ ID NO: 96), -GGPL- (SEQ ID NO: 81), -EGGVA (SEQ ID NO: 82), —PI—, -GGF—, DGGF— (SEQ ID NO: 83), (D-)D-GGF(SEQ ID NO: 97)-, -EGGF— (SEQ ID NO: 84), —SGGF— (SEQ ID NO: 85), —KGGF— (SEQ ID NO: 86), -DGGFG- (SEQ ID NO: 87), -GGFGG- (SEQ ID NO: 88), -DDGGFG- (SEQ ID NO: 89), —KDGGFG— (SEQ ID NO: 90), and -GGFGGGF— (SEQ ID NO: 91).

Here, "(D-)V" indicates D-valine, "(D)-P" indicates D-proline, and "(D-)D" indicates D-aspartic acid.

Linker Lp is preferably any of the following:

-GGVA-, (SEQ ID NO: 76)

-GG-(D-)VA-,

-VA-,

-GGFG-, (SEQ ID NO: 77)

-GGPI-, (SEQ ID NO: 78)

-GGVCit-, (SEQ ID NO: 79)

-GGVK-, (SEQ ID NO: 80)

-GG(D-)P-I-, and

-GGPL-. (SEQ ID NO: 81)

Linker Lp is more preferably any of the following:

-GGVA-, (SEQ ID NO: 76)

-GGVCit-, (SEQ ID NO: 79) and

-VA-.

Lb represents: i) a spacer which connects La to a glycan or remodeled glycan of Ab; or ii) a spacer which connects La to a side chain of an amino acid residue (e.g., cysteine, or lysine) of antibody Ab.

If Lb is i), Lb represents any one selected from the following group:
—C(=O)—(CH$_2$CH$_2$)n$^2$-C(=O)—,    —C(=O)—(CH$_2$CH$_2$)n$^2$-C(=O)—NH—(CH$_2$CH$_2$)n$^3$-C(=O)—, —C(=O)—(CH$_2$CH$_2$)n$^2$-C(=O)—NH—(CH$_2$CH$_2$O)n$^3$-CH$_2$—C(=O)—,    —C(=O)—(CH$_2$CH$_2$)n$^2$-NH—C(=O)—(CH$_2$CH$_2$O)n$^3$-CH$_2$CH$_2$—C(=O)—, —(CH$_2$)n$^4$-O—C(=O)— wherein,
n$^2$ represents an integer of 1 to 3 (preferably, 1 or 2), n$^3$ represents an integer of 1 to 5 (preferably, an integer of 2 to 4, more preferably, 2 or 4), and n$^4$ represents an integer of 0 to 2 (preferably, 0 or 1).

If Lb is i), La preferably represents any one selected from the following group:
—C(=O)—CH$_2$CH$_2$—C(=O)—,    —C(=O)—(CH$_2$CH$_2$)$_2$—C(=O)—,    —C(=O)—CH$_2$CH$_2$—C(=O)—NH—(CH$_2$CH$_2$)$_2$—C(=O)—,    —C(=O)—CH$_2$CH$_2$—C(=O)—NH—(CH$_2$CH$_2$O)$_2$—CH$_2$—C(=O)—,    —C(=O)—CH$_2$CH$_2$—NH—C(=O)—(CH$_2$CH$_2$O)$_4$—CH$_2$CH$_2$—C(=O)—,    —CH$_2$—OC(=O)—, and    —OC(=O)—, and
La is more preferably —C(=O)—CH$_2$CH$_2$—C(=O)— or —C(=O)—(CH$_2$CH$_2$)$_2$—C(=O)—.

Spacer Lb is not limited to a particular spacer, and examples thereof may include, but are not limited to, a spacer represented by the following formulas.

[Formula 60]

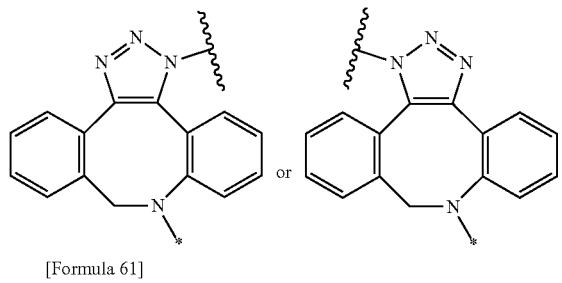

(Lb-1)

[Formula 61]

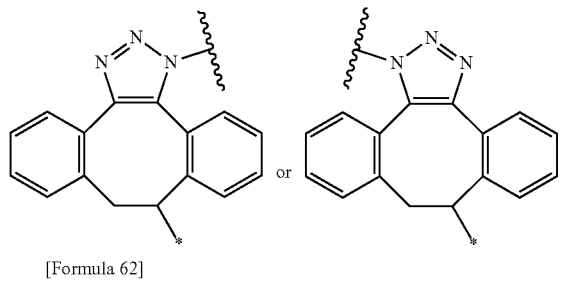

(Lb-2)

[Formula 62]

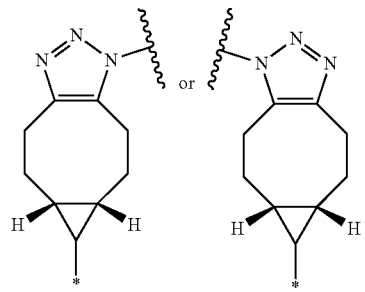

(Lb-3)

In the structural formulas for Lb shown above, each asterisk represents bonding to —(C=O) or —(CH$_2$)n$^4$ at the left end of La, and each wavy line represents bonding to a glycan or remodeled glycan of Ab.

In each structural formula for Lb (Lb-1, Lb-2, or Lb-3) shown above, the triazole ring site formed through click reaction of an azide group and DBCO provides structures of geometric isomers, and molecules of Lb exist as any one of the two structures or as a mixture of both of them. There exist $m^1$ "-L-D" moieties per molecule of the antibody-drug conjugate of the present invention, and either one of the two structures exist or both of them coexist as Lb (Lb-1, Lb-2, or Lb-3) in L of each of the $m^{1}$"-L-D" moieties.

If Lb is i), L is preferably represented by -Lb-La-Lp-NH—B—CH$_2$—O(C=O)—*, wherein B is a 1,4-phenyl group, Lp represents any one selected from the following group:
GGVA- (SEQ ID NO: 76), -GG-(D-)VA- (SEQ ID NO: 95), —VA-, -GGFG- (SEQ ID NO: 77), -GGPI— (SEQ ID NO: 78), -GGVCit- (SEQ ID NO: 79), -GGVK— (SEQ ID NO: 80), -GG(D-)PI— (SEQ ID NO: 96), and -GGPL- (SEQ ID NO: 81), La represents any one selected from the following group:
—C(=O)—CH$_2$CH$_2$—C(=O)—, —C(=O)—(CH$_2$CH$_2$)$_2$—C(=O)—, —C(=O)—CH$_2$CH$_2$—C(=O)—NH—(CH$_2$CH$_2$)$_2$—C(=O)—, —C(=O)—CH$_2$CH$_2$—C(=O)—NH—(CH$_2$CH$_2$O)$_2$—CH$_2$—C(=O)—, —C(=O)—CH$_2$CH$_2$—NH—C(=O)—(CH$_2$CH$_2$O)$_4$—CH$_2$CH$_2$—C(=O)—, —CH$_2$—OC(=O)—, —OC(=O)—, and Lb represents any of the structural formulas above for Lb.

If Lb is i), L is more preferably any one selected from the following group:

—$Z^1$—C(=O)—CH$_2$CH$_2$—C(=O)-GGVA-NH—B—CH$_2$—OC(=O)— ("GGVA" disclosed as SEQ ID NO: 76), —$Z^1$—C(=O)—CH$_2$CH$_2$—C(=O)-GG-(D-)VA (SEQ ID NO: 95) —NH—B—CH$_2$—OC(=O)—, —$Z^1$—C(=O)—CH$_2$CH$_2$—C(=O)—VA-NH—B—CH$_2$—OC(=O)—, —$Z^1$—C(=O)—(CH$_2$CH$_2$)$_2$—C(=O)—VA-NH—B—CH$_2$—OC(=O)—, —$Z^1$—C(=O)—CH$_2$CH$_2$—C(=O)-GGPI—NH—B—CH$_2$—OC(=O)— ("GGPI" disclosed as SEQ ID NO: 78), —$Z^1$—C(=O)—CH$_2$CH$_2$—C(=O)-GGFG-NH—B—CH$_2$—OC(=O)— ("GGFG" disclosed as SEQ ID NO: 77), —$Z^1$—C(=O)—CH$_2$CH$_2$—C(=O)-GGVCit-NH—B—CH$_2$—OC(=O)— ("GGVCit" disclosed as SEQ ID NO: 79), —$Z^1$—C(=O)—CH$_2$CH$_2$—C(=O)-GGVK—NH—B—CH$_2$—OC(=O)— ("GGVK" disclosed as SEQ ID NO: 80), —$Z^1$—C(=O)—CH$_2$CH$_2$—C(=O)-GGPL-NH—B—CH$_2$—OC(=O)— ("GGPL" disclosed as SEQ ID NO: 81), —$Z^1$—C(=O)—CH$_2$CH$_2$—C(=O)—NH—(CH$_2$CH$_2$)$_2$—C(=O)—VA-NH—B—CH$_2$—OC(=O)—, —$Z^1$—C(=O)—CH$_2$CH$_2$—C(=O)—NH—(CH$_2$CH$_2$O)$_2$—CH$_2$—C(=O)—VA-NH—B—CH$_2$—OC(=O)—, —$Z^1$—C(=O)—CH$_2$CH$_2$—NH—C(=O)—(CH$_2$CH$_2$O)$_4$—CH$_2$CH$_2$—C(=O)—VA-NH—B—CH$_2$—OC(=O)—, —$Z^2$—OC(=O)-GGVA-NH—B—CH$_2$—OC(=O)— ("GGVA" disclosed as SEQ ID NO: 76), —$Z^3$—CH$_2$—OC(=O)-GGVA-NH—B—CH$_2$—OC(=O)— ("GGVA" disclosed as SEQ ID NO: 76) wherein $Z^1$ represents the following structural formula as described for Lb:

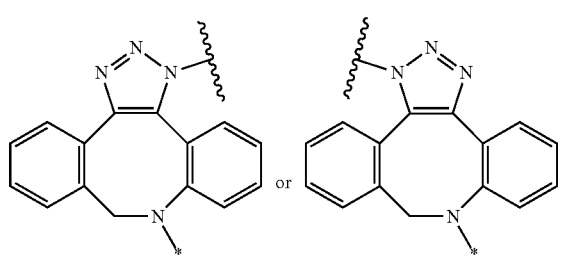

[Formula 63]

$Z^2$ represents the following structural formula as described for Lb:

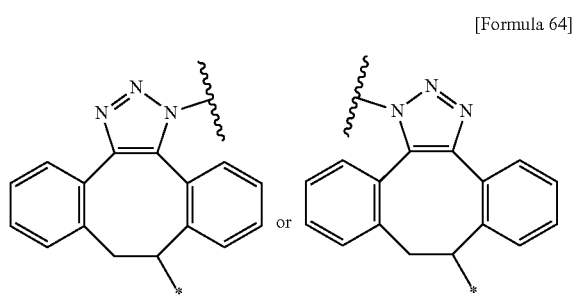

[Formula 64]

$Z^3$ represents the following structural formula as described for Lb:

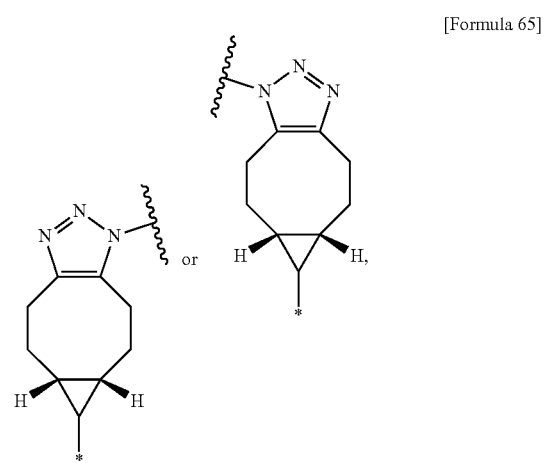

[Formula 65]

and B is a 1,4-phenyl group.

L is most preferably any of the following:
—$Z^1$—C(=O)—CH$_2$CH$_2$—C(=O)-GGVA-NH—B—CH$_2$—OC(=O)— ("GGVA" disclosed as SEQ ID NO: 76),
—$Z^1$—C(=O)—CH$_2$CH$_2$—C(=O)—VA-NH—B—CH$_2$—OC(=O)—, —$Z^1$—C(=O)—(CH$_2$CH$_2$)$_2$—C(=O)—VA-NH—B—CH$_2$—OC(=O)—, —$Z^1$—C(=O)—CH$_2$CH$_2$—C(=O)-GGVCit-NH—B—CH$_2$—OC(=O)— ("GGVCit" disclosed as SEQ ID NO: 79),
—$Z^1$—C(=O)—CH$_2$CH$_2$—C(=O)—NH—(CH$_2$CH$_2$)$_2$—C(=O)—VA-NH—B—CH$_2$—OC (=O)—, —Z¹—C(=O)—CH₂CH₂—C(=O)—NH—(CH₂CH₂O)₂—CH₂—C(=O)—VA-NH—B—CH₂—OC(=O)—, and —Z¹—C(=O)—CH₂CH₂—NH—C(=O)—(CH₂CH₂O)₄—CH₂CH₂—C(=O)—VA-NH—B—CH₂—OC(=O)—, wherein B is a 1,4-phenyl group, and $Z^1$ represents the following structural formula as described for Lb:

[Formula 66]

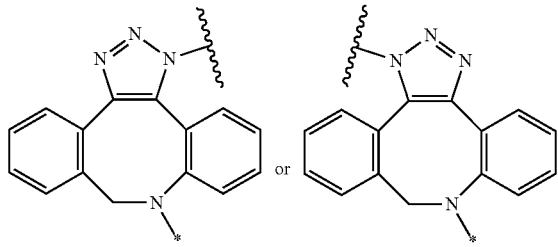

or

If Lb is ii) and the amino acid residue is a cysteine residue, the spacer Lb is not limited to a particular spacer, and examples thereof may include, but are not limited to, -(succinimid-3-yl-N)—.

"-(succinimid-3-yl-N)—" has a structure represented by the following structure:

[Formula 67]

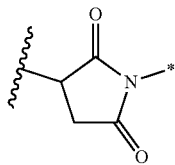

In the structural formula shown above, the asterisk represents bonding to La. The wavy line represents bonding to the thiol group of a cysteine residue of the antibody via a thiol bond, and the bonding may be site-specific cysteine conjugation (RSC Adv., 2017, 7, 24828-24832, etc.).

If Lb is ii), L is represented by -Lb-La-Lp-NH—B—CH₂—O(C=O)—*, wherein

B is a 1,4-phenyl group;
Lp represents any one of -GGVA- (SEQ ID NO: 76), -GG-(D-)VA- (SEQ ID NO: 95), —VA-, and -GGFG- (SEQ ID NO: 77);
La represents —(CH₂)$n^9$-C(=O)— or —(CH₂CH₂)$n^{10}$-C(=O)—NH—(CH₂CH₂O)$n^{11}$—CH₂CH₂—C(=O)—, wherein
$n^9$ represents an integer of 2 to 7 (preferably, an integer of 2 to 5, more preferably 2, or 5), $n^{10}$ represents an integer of 1 to 3 (preferably, 1), and $n^{11}$ represents an integer of 6 to 10 (preferably, 8); and
Lb represents -(succinimid-3-yl-N)—.

If Lb is ii), L is preferably any of the following:
-(Succinimid-3-yl-N)—(CH₂)₅—C(=O)—VA-NH—B—CH₂—OC(=O)—,
-(Succinimid-3-yl-N)—(CH₂)—C(=O)-GGVA-NH—B—CH₂—OC(=O)— ("GGVA" disclosed as SEQ ID NO: 76), or,
-(Succinimid-3-yl-N)—CH₂CH₂—C(=O)—NH—(CH₂CH₂O)₈—CH₂CH₂—C(=O)—VA-NH—B—CH₂—OC(=O)—
wherein B is a 1,4-phenyl group.

The antibody-drug conjugate of the present invention is inferred to exhibit antitumor activity through a process in which most molecules of the antibody-drug conjugate migrate into tumor cells, and a linker portion (e.g., Lp) is then cleaved by an enzyme or the like to activate the antibody-drug conjugate, which releases the portion of drug D (hereinafter, referred to as a free drug (described later)).

Therefore, it is preferable that the antibody-drug conjugate of the present invention is stable outside of tumor cells.

<Free Drug and Production Intermediate>

The intermediate and free drug of the antibody-drug conjugate of the present invention is represented by the following formula:

[Formula 68]

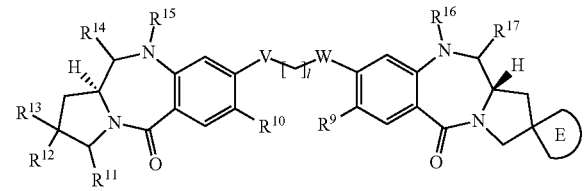

(VI)

This will be described in the following.

The free drug of the present invention is generated through a process in which the antibody-drug conjugate migrates into tumor cells and the portion of linker L in the antibody-drug conjugate is then cleaved. Examples of the free drug may include, but are not limited to, drugs 1 to 16 in Examples 45 to 54 and 150 to 152.

The antibody-drug conjugate of the present invention is produced by using the production intermediate.

The free drug for the antibody-drug conjugate of the present invention corresponds to the case in which (a) $R^{16}$ and $R^{17}$ are combined to form an imine bond (N=C).

The production intermediate for the antibody-drug conjugate of the present invention corresponds to the case in which (b) $R^{16}$ is represented by J-La'-Lp'—NH—B'—CH₂—O (C=O)—*.

Accordingly, 1 and $n^1$, E and A, $R^9$ and $R^1$, $R^{10}$ and $R^2$, $R^{11}$ and $R^3$, $R^{12}$ and $R^4$, $R^{13}$ and $R^5$, $R^{14}$ and $R^6$, $R^{15}$ and $R^7$, V and X, W and Y, group 7 and group 1, group 8 and group 2, group 9 and group 3, group 10 and group 4, group 11 and group 5, and group 12 and group 6 in the formulas are respectively synonymous.

1 represents an integer of 2 to 8, and is preferably an integer of 2 to 6, and more preferably an integer of 3 to 5.

The alkyl chain with 1 being an integer of 2 to 8, preferably an integer of 2 to 6, and more preferably an integer of 3 to 5, may include a double bond.

E represents a spiro-bonded three- to five-membered saturated hydrocarbon ring or a three- to five-membered saturated heterocycle, and is preferably a three- to five-membered saturated hydrocarbon ring (cyclopropane, cyclobutane, or cyclopentane), more preferably cyclopropane or cyclobutane, and most preferably cyclopropane.

The spiro-bonded three- to five-membered saturated hydrocarbon ring may be substituted with one to four halogen atoms, and may be preferably substituted with one or two fluorine atoms (e.g., 2,2-difluorocyclopropane).

$R^9$ and $R^{10}$ each independently represent a C1 to C6 alkoxy group, a C1 to C6 alkyl group, a hydrogen atom, a hydroxy group, a thiol group, a C1 to C6 alkylthio group, a halogen atom, or —NR'R", and are each preferably a C1 to C6 alkoxy group, a C1 to C6 alkyl group, or a hydroxy group, more preferably a C1 to C3 alkoxy group, and most preferably a methoxy group.

$R^{11}$, $R^{12}$, and $R^{13}$ are as described in any of the following (i) to (iii).

(i) If $R^{11}$ and $R^{12}$ are combined together with the carbon atoms to which $R^3$ and $R^4$ are bound to form a double bond, $R^{13}$ represents an aryl group or heteroaryl group optionally having one or more substituents selected from group 7 or a C1 to C6 alkyl group optionally having one or more substituents selected from group 8, and is preferably an aryl group optionally having one or more substituents selected from group 7.

"Aryl group" in "aryl group or heteroaryl group optionally having one or more substituents selected from group 7" for $R^{13}$ is preferably a phenyl group or a naphthyl group, and more preferably a phenyl group.

"Heteroaryl group" in "aryl group or heteroaryl group optionally having one or more substituents selected from group 7" for $R^{13}$ is preferably a thienyl group, a pyridyl group, a pyrimidyl group, a quinolyl group, a quinoxalyl group, or a benzothiophenyl group, more preferably a 2-thienyl group, a 3-thienyl group, a 2-pyridyl group, a 3-pyridyl group, or a 4-pyridyl group, and even more preferably a 3-pyridyl group or a 3-thienyl group.

Examples of substituents of the aryl group or heteroaryl group for $R^{13}$ may include, but are not limited to, the following a) to j):

a) a C1 to C6 alkoxy group optionally substituted with one to three halogen atoms,
b) a C1 to C6 alkyl group optionally substituted with any one selected from one to three halogen atoms, a hydroxy group, —OCOR', —NR'R", —C(NR')—NR"R''', and —NHC(=NR')—NR"R''',
c) a halogen atom,
d) a C3 to C5 cycloalkoxy group,
e) a C1 to C6 alkylthio group,
f) —NR'R",
g) —C(=NR')—NR"R''',
h) —NHC(=NR')—NR"R''',
i) —NHCOR', and
j) a hydroxy group, Here, R', R", and R''' in b) and f) to i) each independently represent a hydrogen atom or a C1 to C6 alkyl group, and are preferably each independently a hydrogen atom or a C1 to C3 alkyl group.

a) to j) are preferably as follows:

a) a C1 to C3 alkoxy group optionally substituted with one to three halogen atoms, more preferably a methoxy group, an ethoxy group, a n-propoxy group, an i-propoxy group, or a trifluoromethoxy group, even more preferably a methoxy group, an ethoxy group, or a trifluoromethoxy group, most preferably a methoxy group;
b) a C1 to C3 alkyl group optionally substituted with any selected from one to three halogen atoms, a hydroxy group, —OCOR', —C(=NR')—NR"R''', and —NHC(=NR')—NR"R''', wherein R', R", and R''' are each independently a hydrogen atom or a C1 to C3 alkyl group, more preferably a C1 to C3 alkyl group optionally substituted with any selected from one to three halogen atoms, a hydroxy group, —OCOR', —C(=NR')—NR"R''', and —NHC(=NR')—NR"R''', wherein R', R", and R''' are each independently a hydrogen atom or a methyl group, even more preferably a methyl group, an ethyl group, a n-propyl group, an i-propyl group, a fluoromethyl group, a difluoromethyl group, a trifluoromethyl group, a hydroxymethyl group, —CH₂OCOMe, —CH₂—NHC(=NH)—NH₂, or —CH₂—NHC(=NMe)-NH₂;
c) a halogen atom, preferably a fluorine atom or a chlorine atom;
d) a C3 to C5 cycloalkoxy group, more preferably a cyclopropoxy group;
e) a C1 to C3 alkylthio group, more preferably a methylthio group or an ethylthio group;
f) —NR'R", wherein R' and R" are each independently a hydrogen atom or a C1 to C3 alkyl group, more preferably —NH₂, —NHMe, —NMe₂, —NHEt, or —NEt₂;
g) —C(=NR')—NR"R''', wherein R', R", and R''' are each independently a hydrogen atom or a C1 to C3 alkyl group, more preferably —C(=NH)—NH₂ or —C(=NMe)-NH₂;
h) —NHC(=NR')—NR"R''', wherein R', R", and R''' are each independently a hydrogen atom or a C1 to C3 alkyl group, more preferably —NHC(=NH)—NH₂ or —NHC(=NMe)-NH₂;
i) —NHCOR', wherein R' is a hydrogen atom or a C1 to C3 alkyl group, more preferably —NHCOMe or —NHCOEt; and
j) a hydroxy group.

The aryl group (preferably, a phenyl group) or heteroaryl group (preferably, a pyridyl group) for $R^{13}$ may have at least one substituent at any position. If a plurality of substituents is present, the substituents may be the same or different.

If $R^{13}$ is an aryl group, each substituent is preferably a), b), d), g), h), or j), and more preferably a), b), d), or j).

If $R^{13}$ is a phenyl group, $R^{13}$ may have a substituent at any position and may have a plurality of substituents, and preferably one or two substituents are present at the 3-position and/or the 4-position, and more preferably one substituent is present at the 4-position.

If $R^5$ is a naphthyl group, $R^5$ may have a substituent at any position and may have a plurality of substituents, and preferably one substituent is present at the 6-position.

If $R^{13}$ is a phenyl group, $R^{13}$ is more preferably a phenyl group, a 4-methoxyphenyl group, a 3-methoxyphenyl group, a 4-ethoxyphenyl group, a 4-(n-propoxy)-phenyl group, a 4-(i-propoxy)-phenyl group, a 4-cyclopropoxy-phenyl group, a 4-trifluoromethylphenyl group, a 4-hydroxymethyl-phenyl group, a 4-acetoxymethyl-phenyl group, or a 4-carbamimidamidomethyl-phenyl group, and even more preferably a phenyl group, a 4-methoxyphenyl group, a 3-methoxyphenyl group, a 4-cyclopropoxy-phenyl group, a 4-hydroxymethyl-phenyl group, a 4-acetoxymethyl-phenyl group, a 4-carbamimidamidomethyl-phenyl group, or a 4-trifluoromethylphenyl group.

If $R^{13}$ is a naphthyl group, $R^{13}$ is more preferably a naphthyl group or a 6-methoxy-2-naphthyl group.

The most preferred is a 4-methoxyphenyl group.

If $R^{13}$ is a heteroaryl group, each substituent is preferably a), b), d), g), h), or j), and more preferably a) or b).

If $R^{13}$ is a heteroaryl group, $R^{13}$ may have at least one substituent at any position. If $R^{13}$ is a 3-pyridyl group, its substituent(s) is preferably present at the 6-position and/or the 5-position. If $R^{13}$ is 2-pyridyl, its substituent(s) is preferably present at the 5-position and/or the 4-position or at the 5-position and/or the 6-position. If $R^{13}$ is 4-pyridyl, its substituent is preferably present at the 2-position and/or the 6-position.

If $R^{13}$ is a heteroaryl group, $R^{13}$ may have a plurality of substituents, and preferably has one or two substituents, and preferably has one substituent.

If $R^{13}$ is a pyridyl group, $R^{13}$ is preferably a 6-methoxy-3-pyridyl group or a 6-methyl-3-pyridyl group.

If $R^{13}$ is a 3-thienyl group or a 6-quinoxalyl group, $R^{13}$ is preferably unsubstituted.

"C1 to C6 alkyl group" in "C1 to C6 alkyl group optionally having one or more substituents selected from group 8" for $R^{13}$ is preferably a C1 to C3 alkyl group, and more preferably a methyl group or an ethyl group.

The substituents in "C1 to C6 alkyl group optionally having one or more substituents selected from group 8" for $R^{13}$ are each a halogen atom, a hydroxy group, or a C1 to C6 alkoxy group (preferably, a C1 to C3 alkoxy group), preferably a hydroxy group, a methoxy group, or an ethoxy group, and more preferably a hydroxy group.

(ii) If $R^{11}$ represents a hydrogen atom, $R^{12}$ and $R^{13}$ are combined, together with the carbon atom to which $R^{12}$ and $R^{13}$ are bound, to form a three- to five-membered saturated hydrocarbon ring or a three- to five-membered saturated heterocycle, or $CH_2$—.

The three- to five-membered saturated hydrocarbon ring may be substituted with one to four halogen atoms, and may be preferably substituted with one or two fluorine atoms.

$R^{12}$ and $R^{13}$ are preferably combined to form a three- to five-membered saturated hydrocarbon ring or $CH_2$=, more preferably to form cyclopropane, cyclobutane, or $CH_2$- (exomethylene group), and even more preferably to form cyclopropane.

If $R^{12}$ and $R^{13}$ are combined to form a three- to five-membered saturated hydrocarbon ring or a three- to five-membered saturated heterocycle, the three- to five-membered saturated hydrocarbon ring or a three- to five-membered saturated heterocycle is preferably the same as E. More preferably, E is a three- to five-membered saturated hydrocarbon ring and $R^{12}$ and $R^{13}$ are combined to form a three- to five-membered saturated hydrocarbon ring, and even more preferably E is a cyclopropane ring and $R^{12}$ and $R^{13}$ are combined to form a cyclopropane ring.

(iii) $R^{11}$, $R^{12}$, and $R^{13}$ are combined, together with the carbon atom to which $R^{11}$ is bound and the carbon atom to which $R^{12}$ and $R^{13}$ are bound, to form a benzene ring or six-membered heterocycle optionally having one or more substituents selected from group 9.

The benzene ring or heterocycle may have at least one substituent at any position. If a plurality of substituents is present, the substituents may be the same or different.

Each substituent of the benzene ring or heterocycle is a halogen atom, a C1 to C6 alkyl group optionally substituted with one to three halogen atoms, or a C1 to C6 alkoxy group, preferably a halogen atom, a C1 to C3 alkyl group optionally substituted with one to three halogen atoms, or a C1 to C3 alkoxy, and more preferably a halogen atom, a methyl group, or a methoxy group.

"Benzene ring or six-membered heterocycle optionally having one or more substituents" is preferably an unsubstituted benzene ring.

$R^{11}$, $R^{12}$ and $R^{13}$ most preferably satisfy the above (i).

$R^{14}$ and $R^{15}$ each represent a hydrogen atom, or $R^{14}$ and $R^{15}$ are combined to represent an imine bond (C=N).

V and W are each independently an oxygen atom, a nitrogen atom, or a sulfur atom, and preferably an oxygen atom.

$R^{16}$ and $R^{17}$ are such that:
(a) $R^{16}$ and $R^{17}$ are combined to form an imine bond (N=C); or (b) $R^{16}$ represents J-La'-Lp'—NH—B'—$CH_2$—O (C=O)—* and $R^{17}$ represents a hydroxy group or a C1 to C3 alkoxy group.

In the case of (b) $R^{16}$ is J-La'-Lp'—NH—B'—$CH_2$—O(C=O)—*, the asterisk in the formula represents bonding to the N10'-position of the pyrrolobenzodiazepine ring represented by the above formula.

B' represents a phenyl group or a heteroaryl group, and is preferably a 1,4-phenyl group, a 2,5-pyridyl group, a 3,6-pyridyl group, a 2,5-pyrimidyl group, or a 2,5-thienyl group, and more preferably a 1,4-phenyl group.

Lp' represents a linker consisting of an amino acid sequence cleavable in vivo or in a target cell. Lp is, for example, cleaved by the action of an enzyme such as esterase and peptidase.

Specific examples of linker Lp' may include, but are not limited to, -GGVA- (SEQ ID NO: 76), -GG-(D-)VA- (SEQ ID NO: 95), —VA-, -GGFG- (SEQ ID NO: 77), -GGPI— (SEQ ID NO: 78), -GGVCit- (SEQ ID NO: 79), -GGVK— (SEQ ID NO: 80), -GG(D-)PI— (SEQ ID NO: 96), -GGPL- (SEQ ID NO: 81), -EGGVA (SEQ ID NO: 82), —PI—, -GGF—, DGGF— (SEQ ID NO: 83), (D-)D-GGF(SEQ ID NO: 97)-, -EGGF— (SEQ ID NO: 84), —SGGF— (SEQ ID NO: 85), —KGGF— (SEQ ID NO: 86), -DGGFG- (SEQ ID NO: 87), -GGFGG- (SEQ ID NO: 88), -DDGGFG- (SEQ ID NO: 89), —KDGGFG- (SEQ ID NO: 90), and -GGFGGGF— (SEQ ID NO: 91).

Here, "(D-)V" indicates D-valine, "(D)-P" indicates D-proline, and "(D-)D" indicates D-aspartic acid.

Linker Lp' is preferably as follows:

```
                                  (SEQ ID NO: 76)
-GGVA-,

-GG-(D-)VA-,

-VA-,
                                  (SEQ ID NO: 77)
-GGFG-,
                                  (SEQ ID NO: 78)
-GGPI-,
                                  (SEQ ID NO: 79)
-GGVCit-,
                                  (SEQ ID NO: 80)
-GGVK-,

-GG(D-)P-I-,
and
                                  (SEQ ID NO: 81)
-GGPL-.
```

More preferred examples are -GGVA- (SEQ ID NO: 76), -GGVCit- (SEQ ID NO: 79), and —VA-.

La' represents any one selected from the following group:
—C(=O)—$(CH_2CH_2)n^6$-C(=O)—, —C(=O)—$(CH_2CH_2)n^6$-C(=O)—NH—$(CH_2CH_2)n^7$-C(=O)—, —C(=O)—$(CH_2CH_2)n^6$-C(=O)—NH—$(CH_2CH_2O)$$n^7$-$CH_2$—C(=O)—, —C(=O)—$(CH_2CH_2)n^6$-NH—C(=O)—$(CH_2CH_2O)n^7$-$CH_2CH_2$—C(=O)—, —$(CH_2)n^8$-O—C(=O)—, $(CH_2)n^{12}$-C(=O)—, and, —$(CH_2CH_2)n^{13}$-C(=O)—NH—$(CH_2CH_2O)n^{14}$-$CH_2CH_2$—C(=O)—

In the formulas, $n^6$ represents an integer of 1 to 3 (preferably, 1 or 2), $n^7$ represents an integer of 1 to 5 (preferably, an integer of 2 to 4, more preferably, 2 or 4), $n^8$ represents an integer of 0 to 2 (preferably, 0 or 1), $n^{12}$ represents an integer of 2 to 7 (preferably, an integer of 2 to 5, more preferably, 2 or 5), $n^{13}$ represents an integer of 1 to 3 (preferably, 1), and $n^{14}$ represents an integer of 6 to 10 (preferably, 8).

La' preferably represents any one selected from the following group:
—C(=O)—CH$_2$CH$_2$—C(=O)—, —C(=O)—(CH$_2$CH$_2$)$_2$—C(=O)—, —C(=O)—CH$_2$CH$_2$—C(=O)—NH—(CH$_2$CH$_2$)$_2$—C(=O)—, —C(=O)—CH$_2$CH$_2$—C(=O)—NH—(CH$_2$CH$_2$O)$_2$—CH$_2$—C(=O)—, —C(=O)—CH$_2$CH$_2$—NH—C(=O)—(CH$_2$CH$_2$O)$_4$—CH$_2$CH$_2$—C(=O)—, —CH$_2$—OC(=O)—, —OC(=O)—, (CH$_2$)$_2$—C(=O)—, —(CH$_2$)$_5$—C(=O)—, and —CH$_2$CH$_2$—C(=O)—NH—(CH$_2$CH$_2$O)$_8$—CH$_2$CH$_2$—C(=O)—.

La' is more preferably —C(=O)—CH$_2$CH$_2$—C(=O)—, —C(=O)—(CH$_2$CH$_2$)$_2$—C(=O)—, or —(CH$_2$)$_5$—C(=O)—.

J is not limited to a particular structure and may be any cyclic structure including an alkyne structure that reacts with an azide group to form a 1,2,3-triazole ring, and examples thereof may include, but are not limited to, compounds represented by the following formulas:

[Formula 69]

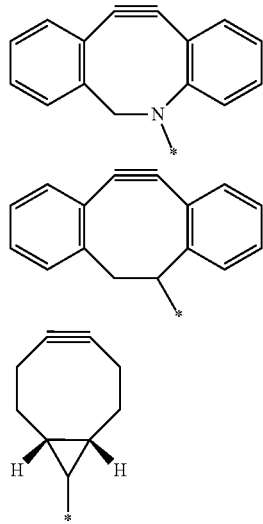

In the structural formulas for J shown above, each asterisk represents bonding to —(C=O) or —(CH$_2$)n$^1$ at the left end of La'.

Alternatively, J may be a compound that bonds to a side chain of an amino acid residue (e.g., cysteine, or lysine) of antibody Ab, or a halogen atom, and examples of J may include, but are not limited to, a maleimidyl group represented by the following formula:

[Formula 70]

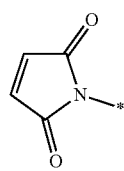

In the maleimidyl group shown above, the asterisk represents bonding to —(CH$_2$)n$^{12}$ or —(CH$_2$CH$_2$)n$^{13}$ at the left end of La'.

$R^{16}$ is preferably represented by J-La'-Lp'—NH—B'—CH$_2$—O(C=O)—*, wherein

B' is a 1,4-phenyl group;

Lp' represents any one selected from the following group:

-GGVA-, (SEQ ID NO: 76)

-GG-(D-)VA-,

-VA-,

-GGFG-, (SEQ ID NO: 77)

-GGPI-, (SEQ ID NO: 78)

-GGVCit-, (SEQ ID NO: 79)

-GGVK-, (SEQ ID NO: 80)

-GG(D-)P-I-, and

-GGPL-. (SEQ ID NO: 81)

La' represents any one selected from the following group:
—C(=O)—CH$_2$CH$_2$—C(=O)—, —C(=O)—(CH$_2$CH$_2$)$_2$—C(=O)—, —C(=O)—CH$_2$CH$_2$—C(=O)—NH—(CH$_2$CH$_2$)$_2$—C(=O)—, —C(=O)—CH$_2$CH$_2$—C(=O)—NH—(CH$_2$CH$_2$O)$_2$—CH$_2$—C(=O)—, —C(=O)—CH$_2$CH$_2$—NH—C(=O)—(CH$_2$CH$_2$O)$_4$—CH$_2$CH$_2$—C(=O)—, —OC(=O)—, —CH$_2$—OC(=O)—, (CH$_2$)$_5$—C(=O)—, and —CH$_2$CH$_2$—C(=O)—NH—(CH$_2$CH$_2$O)$_8$—CH$_2$CH$_2$—C(=O)—; and J represents any of the structural formulas:

[Formula 71]

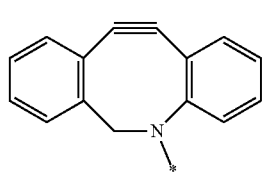

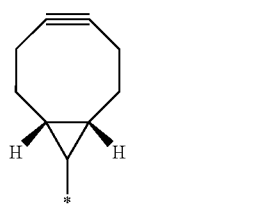

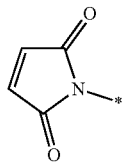

wherein, in the structural formulas for J, each asterisk represents bonding to La'.

R$^{16}$ is more preferably any one selected from the following group:

J$^1$-C(=O)—CH$_2$CH$_2$—C(=O)-GGVA-NH—B'—CH$_2$—OC(=O)— ("GGVA" disclosed as SEQ ID NO: 76), J$^1$-C(=O)—CH$_2$CH$_2$—C(=O)-GG-(D-)VA (SEQ ID NO: 95) —NH—B'—CH$_2$—OC(=O)—, J$^1$-C(=O)—CH$_2$CH$_2$—C(=O)—VA-NH—B'—CH$_2$—OC(=O)—, J$^1$-C(=O)—(CH$_2$CH$_2$)$_2$—C(=O)—VA-NH—B'—CH$_2$—OC(=O)—, J$^1$-C(=O)—CH$_2$CH$_2$—C(=O)-GGPI—NH—B'—CH$_2$—OC(=O)— ("GGPI" disclosed as SEQ ID NO: 78), J$^1$-C(=O)—CH$_2$CH$_2$—C(=O)-GGFG-NH—B'—CH$_2$—OC(=O)— ("GGFG" disclosed as SEQ ID NO: 77), J$^1$-C(=O)—CH$_2$CH$_2$—C(=O)-GGVCit-NH—B'—CH$_2$—OC(=O)— ("GGVCit" disclosed as SEQ ID NO: 79), J$^1$-C(=O)—CH$_2$CH$_2$—C(=O)-GGVK—NH—B'—CH$_2$—OC(=O)— ("GGVK" disclosed as SEQ ID NO: 80), J$^1$-C(=O)—CH$_2$CH$_2$—C(=O)-GGPL-NH—B'—CH$_2$—OC(=O)— ("GGPL" disclosed as SEQ ID NO: 81), J$^1$-C(=O)—CH$_2$CH$_2$—C(=O)—NH—(CH$_2$CH$_2$)$_2$—C(=O)—VA-NH—B'—CH$_2$—OC(=O)—, J$^1$-C(=O)—CH$_2$CH$_2$—C(=O)—NH—(CH$_2$CH$_2$O)$_2$—CH$_2$—C(=O)—VA-NH—B'—CH$_2$—OC(=O)—, J$^1$-C(=O)—CH$_2$CH$_2$—NH—C(=O)—(CH$_2$CH$_2$O)$_4$—CH$_2$CH$_2$—C(=O)—VA-NH—B'—CH$_2$—OC(=O)—, J$^2$-OC(=O)-GGVA-NH—B'—CH$_2$—OC(=O)— ("GGVA" disclosed as SEQ ID NO: 76), J$^3$-CH$_2$—OC(=O)-GGVA-NH—B'—CH$_2$—OC(=O)— ("GGVA" disclosed as SEQ ID NO: 76), J$^4$-(CH$_2$)$_5$—C(=O)-GGVA-NH—B'—CH$_2$—OC(=O)— ("GGVA" disclosed as SEQ ID NO: 76), J$^4$-(CH$_2$)$_5$—C(=O)—VA-NH—B'—CH$_2$—OC(=O)—, and J$^4$-CH$_2$CH$_2$—C(=O)—NH—(CH$_2$CH$_2$O)$_8$—CH$_2$CH$_2$—C(=O)—VA-NH—B'—CH$_2$—OC(=O)— wherein J$^1$, J$^2$, J$^3$, and J$^4$ represent structural formulas represented by the following:

[Formula 72]

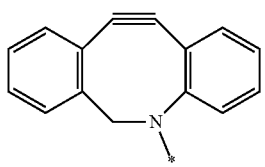

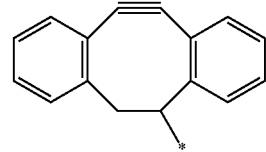

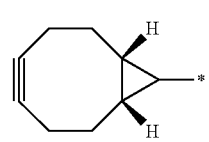

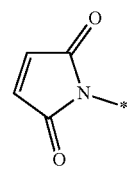

wherein, in the structural formulas for J$^1$, J$^2$, J$^3$ and J$^4$, each asterisk represents bonding to a group neighboring to J$^1$, J$^2$, J$^3$, or J$^4$, and B' is a 1,4-phenyl group.

R$^{16}$ is most preferably any of the following:

J$^1$-C(=O)—CH$_2$CH$_2$—C(=O)-GGVA-NH—B'—CH$_2$—OC(=O)— ("GGVA" disclosed as SEQ ID NO: 76), J$^1$-C(=O)—CH$_2$CH$_2$—C(=O)—VA-NH—B'—CH$_2$—OC(=O)—, J$^1$-C(=O)—(CH$_2$CH$_2$)$_2$—C(=O)—VA-NH—B'—CH$_2$—OC(=O)—, J$^1$-C(=O)—CH$_2$CH$_2$—C(=O)-GGVCit-NH—B'—CH$_2$—OC(=O)— ("GGVCit" disclosed as SEQ ID NO: 79), J$^1$-C(=O)—CH$_2$CH$_2$—C(=O)—NH—(CH$_2$CH$_2$)$_2$—C(=O)—VA-NH—B'—CH$_2$—OC(=O)—, J$^1$-C(=O)—CH$_2$CH$_2$—C(=O)—NH—(CH$_2$CH$_2$O)$_2$—CH$_2$—C(=O)—VA-NH—B'—CH$_2$—OC(=O)—, J$^1$-C(=O)—CH$_2$CH$_2$—NH—C(=O)—(CH$_2$CH$_2$O)$_4$—CH$_2$CH$_2$—C(=O)—VA-NH—B'—CH$_2$—OC(=O)—, J$^4$-(CH$_2$)$_5$—C(=O)—VA-NH—B'—CH$_2$—OC(=O)— wherein
B' is a 1,4-phenyl group, and
$J^1$ and $J^4$ are represented by the following structural formulas for J:

[Formula 73]

$J^1$

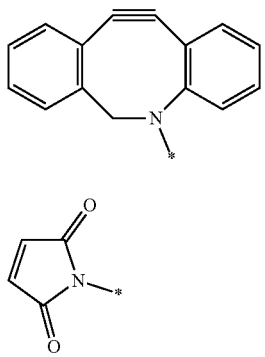

$J^4$ wherein, in the structural formulas for $J^1$ and $J^4$,
each asterisk representes bonding to a group neighboring to $J^1$ or $J^4$.
$R^{17}$ is a hydroxy group or a C1 to C3 alkoxy group, and preferably a hydroxy group or a methoxy group.
$R^{17}$ may be hydrogensulfite adduct ($OSO_3M$, wherein M is a metal cation).

Since $R^{17}$ bonds to an asymmetric carbon atom, a steric configuration represented by partial structure (VIa) or (VIb) below is provided. Each wavy line represents bonding to W in the intermediate and free drug represented by general formula (VI).

[Formula 74]

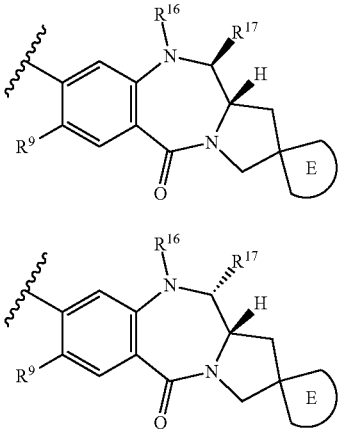

VI(a)

VI(b)

The free drug is preferably one compound selected from the following group:

[Formula 75]

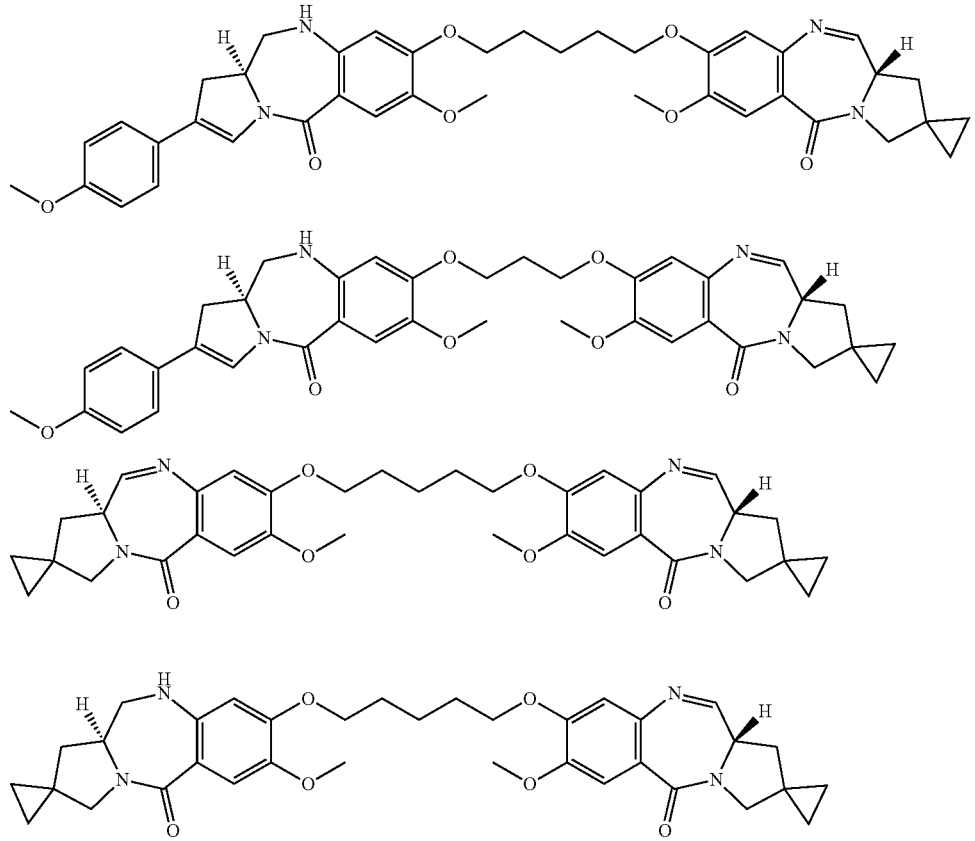

The free drug is in some cases released in tumor cells with a part of linker L bonded, but is a superior drug that exerts superior antitumor effect even in such state. The free drug, after migrating to tumor cells, is in some cases further oxidized to cause dehydrogenation of $R^{16}$ and $R^{17}$, but exerts superior antitumor effect even in such state.

The production intermediate is preferably one compound selected from the following group:

[Formula 76]

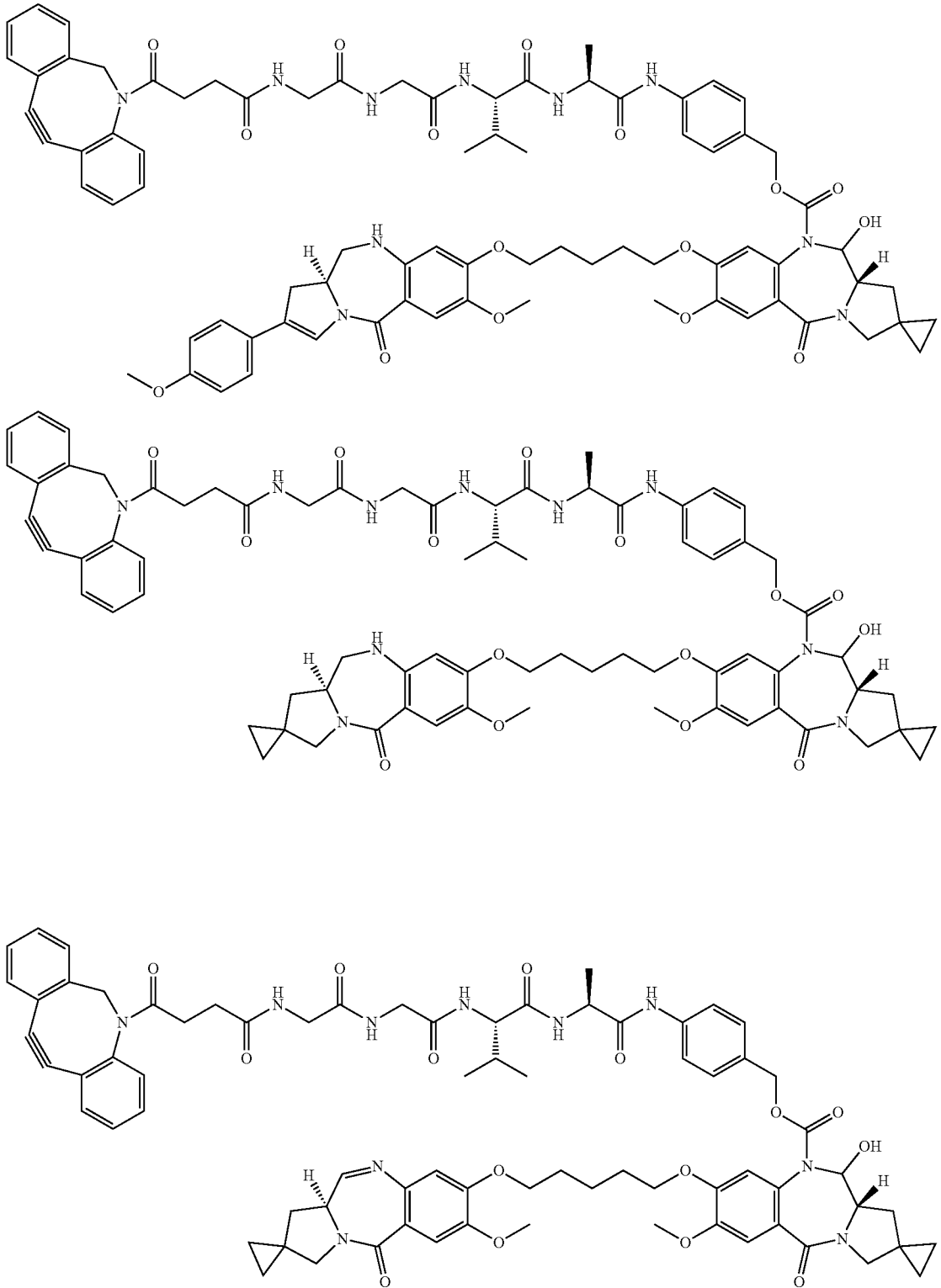

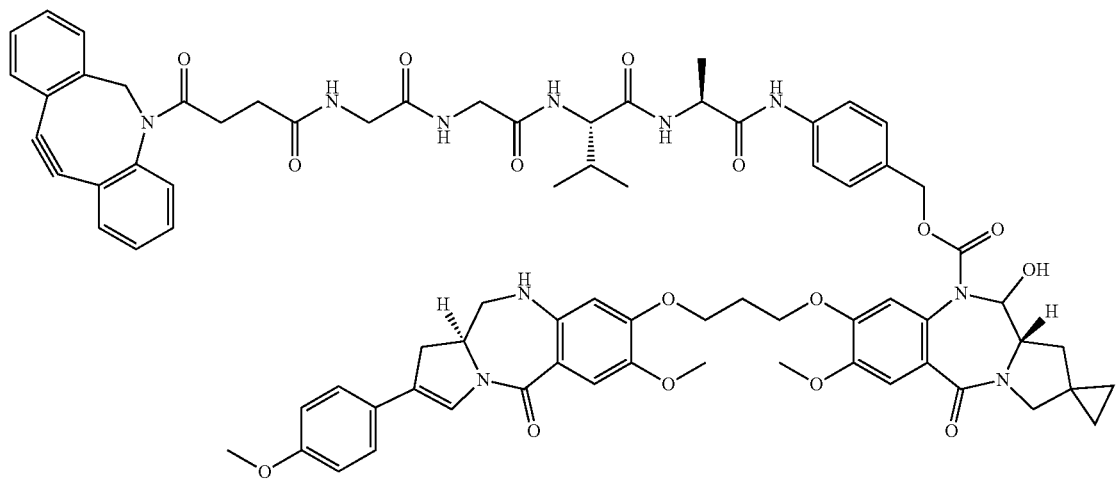
[Formula 77]
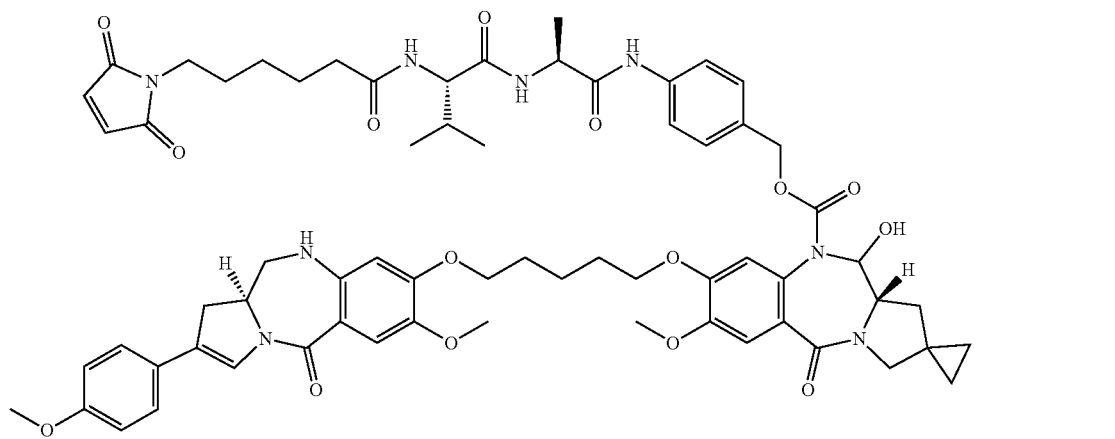
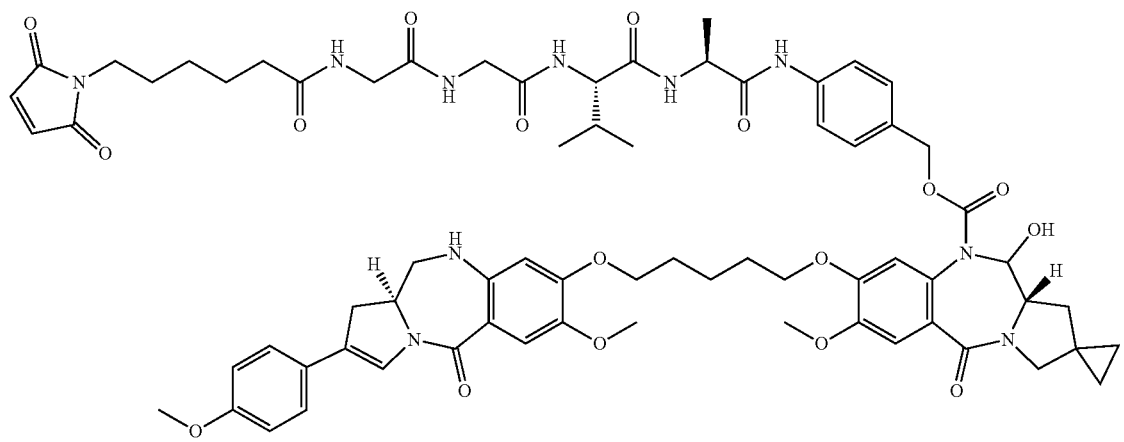

The production intermediate is preferably one compound selected from the following group:
[Formula 78]
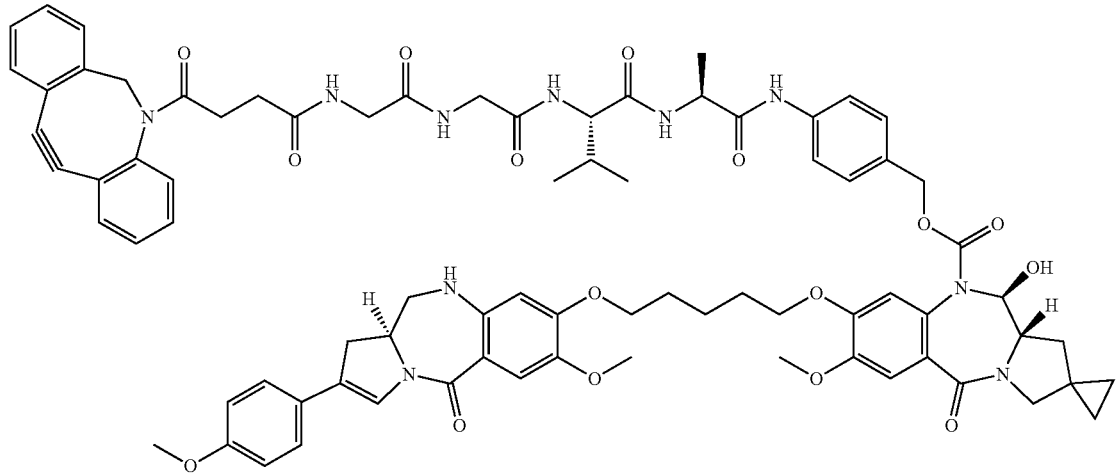
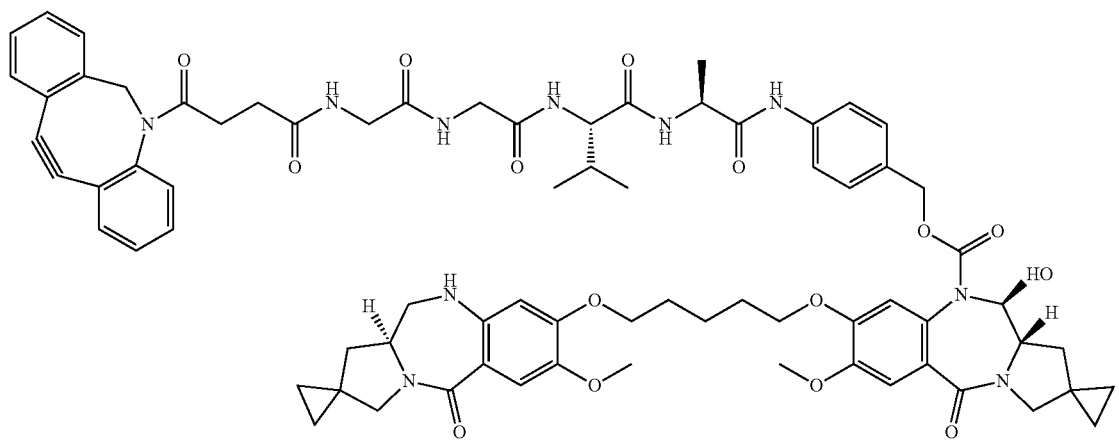
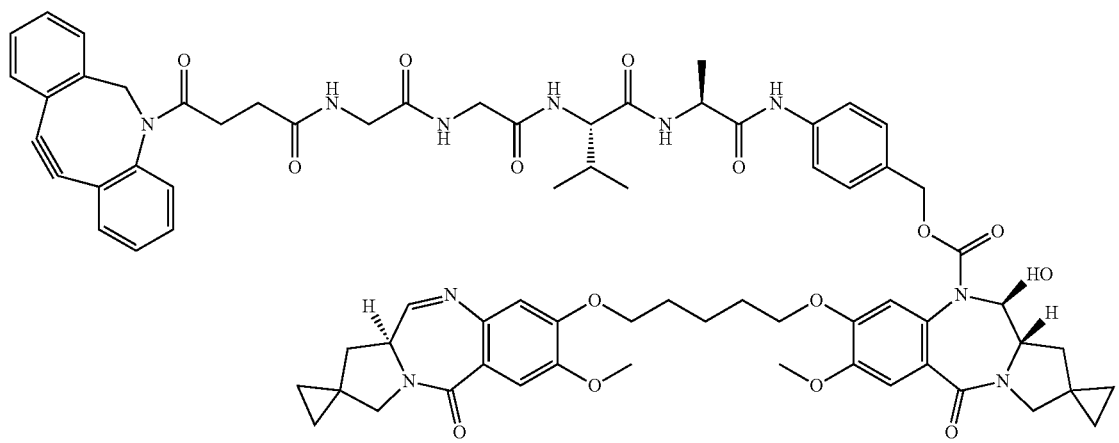

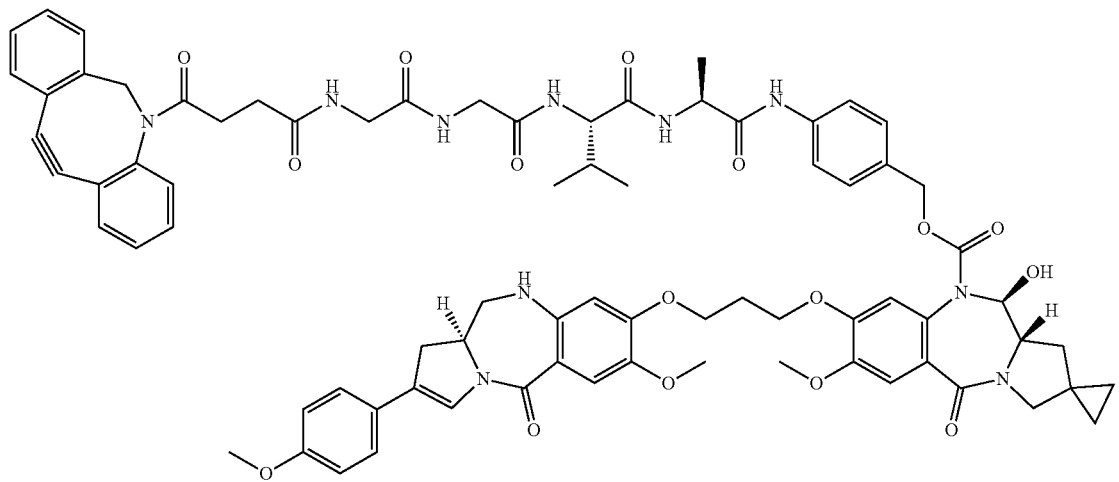
[Formula 79]
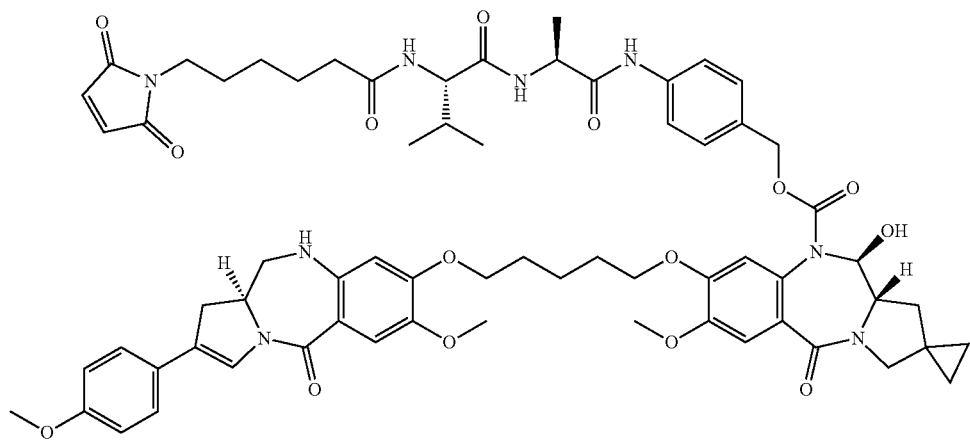
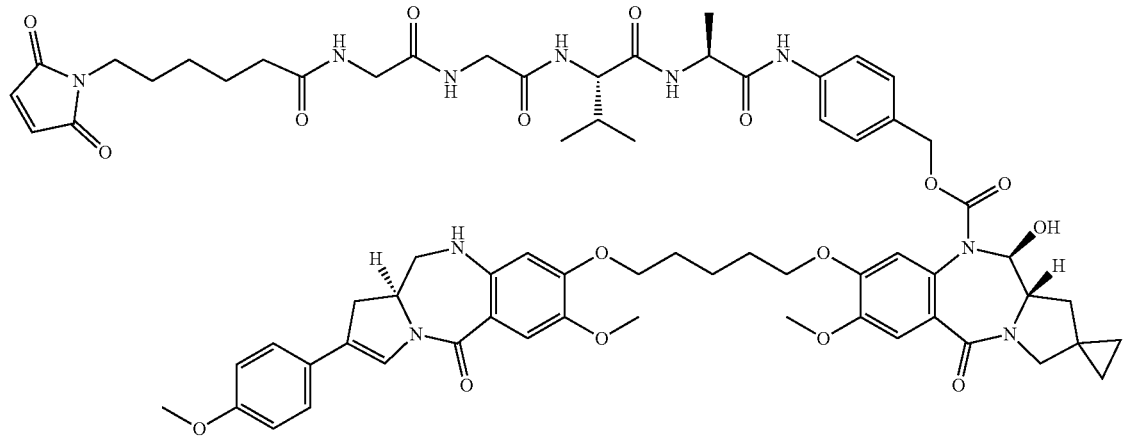

[Formula 80]
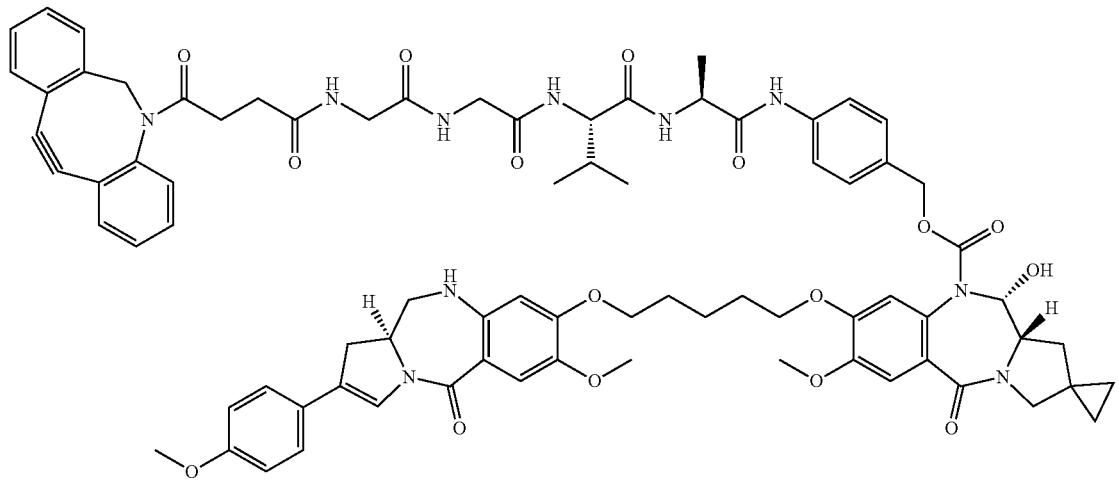
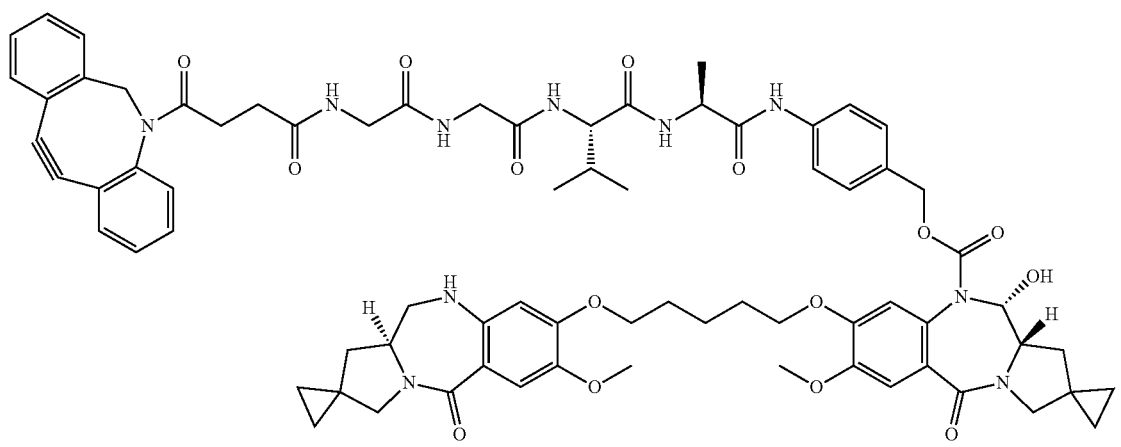
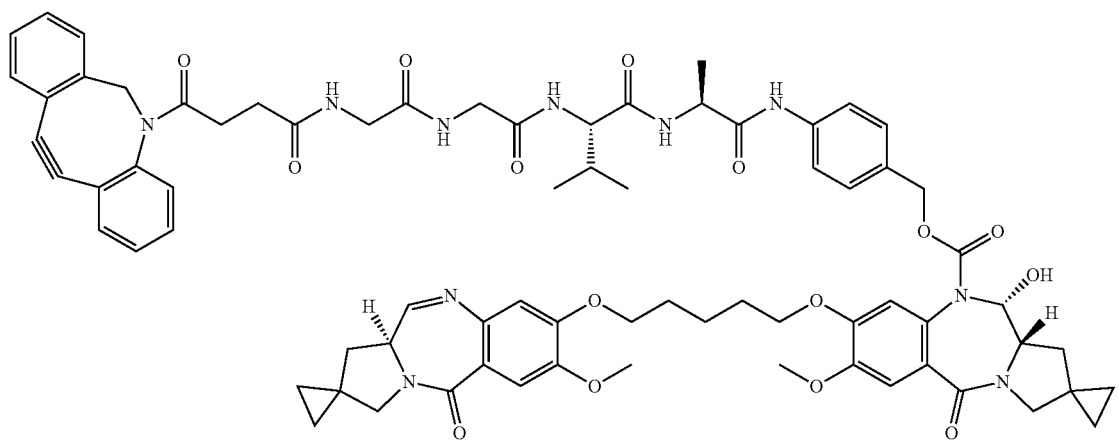

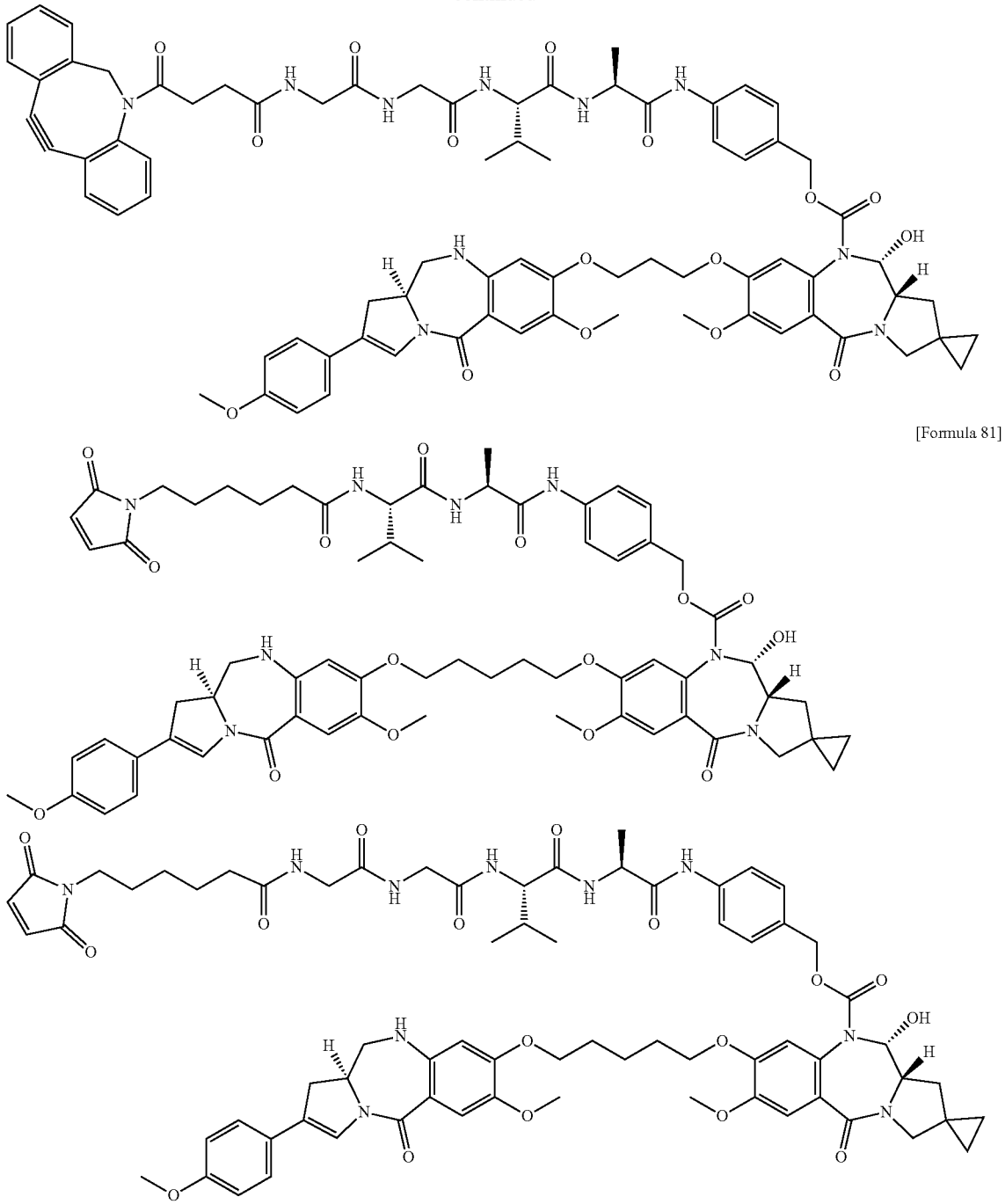

[Formula 81]

<Antibody>

In the present invention, "cancer" and "tumor" are used for the same meaning.

In the present invention, a "gene" refers to nucleotides or a nucleotide sequence including a nucleotide sequence encoding amino acids of protein or a complementary strand thereof. The meaning of a "gene" encompasses, for example, a polynucleotide, an oligonucleotide, DNA, mRNA, cDNA, and RNA as a nucleotide sequence including a nucleotide sequence encoding amino acids of protein or a complementary strand thereof. Examples of the "CLDN6 gene" of the present invention include DNA, mRNA, cDNA, and cRNA including a nucleotide sequence encoding the amino acid sequence of CLDN6 protein.

In the present invention, "nucleotides", "polynucleotide", and "nucleotide sequence" have the same meaning as that of "nucleic acids", and the meaning of "nucleotides" and "nucleotide sequence" encompasses, for example, DNA, RNA, a probe, an oligonucleotide, a polynucleotide, and a primer.

In the present invention, "polypeptide", "peptide", and "protein" are used interchangeably.

In the present invention, "CLDN6" is used for the same meaning as CLDN6 protein.

In the present invention, "cells" include cells in an animal individual and cultured cells.

In the present invention, "cellular cytotoxic activity" refers to causing pathological change to cells in any way, which includes causing, not only direct traumas, but also all types of damage in the structure and function of cells such as cleavage of DNA, formation of a nucleotide dimer, cleavage of a chromosome, damage of the mitotic apparatus, and lowered activity of various enzymes.

In the present invention, a "functional fragment of an antibody" is also referred to as an "antigen-binding fragment of an antibody", and means a partial fragment of an antibody with binding activity to an antigen, and examples thereof may include, but not limited to, Fab, F(ab')2, Fv, scFv, diabodies, linear antibodies, and multispecific antibodies formed from antibody fragments. In addition, the meaning of an antigen-binding fragment of an antibody encompasses Fab', a monovalent fragment of a variable region of an antibody obtained by treating F(ab')2 under reducing conditions. However, there is no limitation to those molecules as long as the molecules have binding ability to an antigen. Those antigen-binding fragments include not only those obtained by treating a full-length molecule of an antibody protein with an appropriate enzyme, but also protein produced in an appropriate host cell by using a genetically engineered antibody gene.

The functional fragment of the present invention includes a functional fragment that has well conserved asparagine (Asn297) to be modified with an N-linked glycan in the IgG heavy chain Fc region and amino acids around Asn297, while retains binding activity to an antigen.

In the present invention, an "epitope" refers to a partial peptide or partial three-dimensional structure of an antigen to which a particular antibody (e.g., an anti-CLDN6 antibody) binds (a partial peptide or partial three-dimensional structure of CLDN6). An epitope as such a partial peptide (e.g., a partial peptide of CLDN6) can be determined by using any method well known to those skilled in the art, such as immunoassay.

A "CDR" in the present invention refers to a complementarity determining region. It is known that each of heavy chains and light chains of an antibody molecule have three CDRs. CDRs, which are also called a hypervariable region, are located in variable regions of heavy chains and light chains of an antibody and is a site with particularly high variation of the primary structure. Three CDRs are separately located in the primary structure of the polypeptide chain of each of heavy chains and light chains. Regarding CDRs of antibodies, herein, CDRs of a heavy chain refer to CDRH1, CDRH2, and CDRH3 from the amino terminus of the heavy chain amino acid sequence, and CDRs of a light chain refer to CDRL1, CDRL2, and CDRL3 from the amino terminus of the light chain amino acid sequence. These sites are located in the proximity of each other in the three-dimensional structure, determining specificity to an antibody to bind.

In the present invention, "hybridize under stringent conditions" refers to hybridization in the commercially available hybridization solution ExpressHyb Hybridization Solution (Clontech) at 68° C., or hybridization using a filter with DNA fixed thereto in the presence of 0.7 to 1.0 M NaCl at 68° C. and washing at 68° C. with 0.1 to 2×SSC solution (1×SSC solution contains 150 mM NaCl and 15 mM sodium citrate), or hybridization under conditions equivalent thereto.

In the present invention, "one to several" refers to 1 to 10, one to nine, one to eight, one to seven, one to six, one to five, one to four, one to three, or one or two.

In the present invention, an antibody capable of recognizing or binding to CLDN6 and that capable of recognizing or binding to CLDN6 and CLDN9 are occasionally called as an "anti-CLDN6 antibody" and an "anti-CLDN6/CLDN9 antibody", respectively. Such antibodies include chimeric antibodies, humanized antibodies, and human antibodies. An antibody capable of recognizing or binding to CLDN6 and CLDN9 is occasionally called as an "anti-CLDN6 antibody".

The antibody to be used for the antibody-drug conjugate of the present invention refers to immunoglobulin, and is a molecule including an antigen-binding site which immunospecifically binds to an antigen. The antibody of the present invention may be of any class of IgG, IgE, IgM, IgD, IgA, and IgY, and preferred is IgG. The subclass may be any of IgG1, IgG2, IgG3, IgG4, IgA1, and IgA2, and preferred are IgG1, IgG2, and IgG4. If IgG1 or IgG4 is used, the effector function may be adjusted by substituting some of amino acid residues in the constant region (see WO 88/07089, WO 94/28027, WO 94/29351).

The antibody may be derived from any species, which preferably include, but not limited to, a human, a rat, a mouse, and a rabbit. If the antibody is derived from species other than human species, it is preferably chimerized or humanized using a well known technique. The antibody of the present invention may be a polyclonal antibody or a monoclonal antibody, and is preferably a monoclonal antibody. Examples of monoclonal antibodies may include, but not limited to, monoclonal antibodies derived from non-human animals such as rat antibodies, mouse antibodies, and rabbit antibodies; chimeric antibodies; humanized antibodies; human antibodies; functional fragments of them; and modified variants of them.

The antibody of the present invention is preferably an antibody capable of targeting a tumor cell. Specifically, the antibody, to which a drug having antitumor activity is conjugated via a linker, preferably has one or more properties of recognizing a tumor cell, binding to a tumor cell, being incorporated and internalizing in a tumor cell, and damaging a tumor cell.

The binding activity of the antibody against tumor cells can be confirmed using flow cytometry. The incorporation of the antibody into tumor cells can be confirmed using (1) an assay of visualizing an antibody incorporated in cells under a fluorescence microscope using a secondary antibody (fluorescently labeled) binding to the therapeutic antibody (Cell Death and Differentiation (2008) 15, 751-761), (2) an assay of measuring a fluorescence intensity incorporated in cells using a secondary antibody (fluorescently labeled) binding to the therapeutic antibody (Molecular Biology of the Cell, Vol. 15, 5268-5282, December 2004), or (3) a Mab-ZAP assay using an immunotoxin binding to the therapeutic antibody wherein the toxin is released upon incorporation into cells to inhibit cell growth (Bio Techniques 28: 162-165, January 2000). As the immunotoxin, a recombinant complex protein of a diphtheria toxin catalytic domain and protein G may be used.

In the present invention, "high internalization ability" refers to the situation that the survival rate (which is a relative rate to the cell survival rate without addition of the antibody as 100%) of targeted antigen-expressing cells (e.g., CLDN6-expressing cells) with addition of the antibody and a saporin-labeled anti-mouse or rat IgG antibody is preferably 70% or less, and more preferably 60% or less. [0121]

Since the compound conjugated in the antibody-drug conjugate of the present invention exerts an antitumor effect, it is preferred but not essential that the antibody itself should have an antitumor effect. For the purpose of specifically and selectively exerting the cytotoxicity of the antitumor compound against tumor cells, it is important and also preferred that the antibody should have the property of internalizing to migrate into tumor cells. To exert antitumor effect, it is important and also preferred that the antibody should have the property of internalizing and migrating into tumor cells, from the viewpoint that the drug specifically and selectively damages tumor cells. The antitumor activity of the antibody refers to the cellular cytotoxic activity or anticellular effect against tumor cells. The antitumor activity may be confirmed by using any known in vitro or in vivo evaluation system.

Examples of such an antibody may include, but not limited to, antibodies to tumor-related antigens, including an anti-CLDN6 antibody, an anti-CLDN6/CLDN9 antibody, an anti-HER2 antibody, an anti-DLL3 (Delta like protein 3) antibody, an anti-A33 antibody, an anti-CanAg antibody, an anti-CD19 antibody, an anti-CD20 antibody, an anti-CD22 antibody, an anti-CD30 antibody, an anti-CD33 antibody, an anti-CD56 antibody, an anti-CD70 antibody, an anti-CD98 antibody, an anti-TROP2 antibody, an anti-CEA antibody, an anti-Cripto antibody, an anti-EphA2 antibody, an anti-FGFR2 antibody (e.g., WO 201315206), an anti-G250 antibody, an anti-MUC1 antibody (e.g., WO 2011012309), an anti-GPNMB antibody, an anti-integrin antibody, an anti-PSMA antibody, an anti-tenascin-C antibody, an anti-SLC44A4 antibody, an anti-mesothelin antibody, an anti-EGFR antibody, and an anti-DR5 antibody.

The antibody of the present invention is preferably an anti-CLDN6 antibody, an anti-CLDN6/CLDN9 antibody, an anti-HER2 antibody, an anti-CD98 antibody, or an anti-TROP2 antibody, and more preferably an anti-CLDN6 antibody or an anti-HER2 antibody (e.g., trastuzumab, a trastuzumab variant).

The antibody of the present invention may be obtained using a method usually carried out in the art, which involves immunizing animals with an antigenic polypeptide and collecting and purifying antibodies produced in vivo. The origin of the antigen is not limited to humans, and the animals may be immunized with an antigen derived from a non-human animal such as a mouse, a rat or the like. In this case, the cross-reactivity of antibodies binding to the obtained heterologous antigen with human antigens can be tested to screen for an antibody applicable to a human disease.

Alternatively, antibody-producing cells which produce antibodies against the antigen are fused with myeloma cells according to a method known in the art (e.g., Nature (1975) 256, p. 495-497, Monoclonal Antibodies, p. 365-367, Plenum Press, N.Y. (1980)) to establish hybridomas, from which monoclonal antibodies can in turn be obtained (described later).

The antigen can be obtained by genetically engineering host cells to produce a gene encoding the antigenic protein.

The chimeric antibody and humanized antibody of the present invention may be obtained in accordance with a known method (e.g., Proc. Natl. Acad. Sci. U.S.A., 81, 6851-6855, (1984), Nature (1986) 321, p. 522-525, WO 90/07861).

The anti-HER2 antibody (e.g., U.S. Pat. No. 5,821,337), anti-TROP2 antibody (e.g., WO 2003/074566), and anti-CD98 antibody (e.g., WO 2015/146132) may be obtained by using a known approach.

Now, the anti-CLDN6 antibody used in the present invention will be described. An embodiment described below is an example of representative embodiments of the present invention, and the scope of the present invention is not interpreted as being narrower by the embodiment.

1. CLDN6 and CLDN9

CLDN6, a four-transmembrane protein belonging to the claudin family and consisting of 220 amino acids, has the N terminus and C terminus in a cell.

The amino acid sequence of and DNA sequence for human CLDN6 are published in public databases, and can be referred to, for example, from accession numbers of NP_067018 (SEQ ID NO: 1 (FIG. 11)) and NM_021195 (SEQ ID NO: 2 (FIG. 11)) (both in NCBI).

In the amino acid sequence of human CLDN6 protein (hereinafter, referred to as "CLDN6 amino acid sequence"), the extracellular region is composed of an extracellular domain (EC1) consisting of amino acid residues 29 to 81 of SEQ ID NO: 1 in Sequence Listing and an extracellular domain (EC2) consisting of amino acid residues 138 to 160 of SEQ ID NO: 1 in Sequence Listing.

CLDN9, a four-transmembrane protein belonging to the claudin family and consisting of 217 amino acids, has the N terminus and C terminus in a cell. CLDN9 is highly homologous to CLDN6.

The amino acid sequence of and DNA sequence for human CLDN9 are published in public databases, and can be referred to, for example, from accession numbers of NP_066192 (SEQ ID NO: 3 (FIG. 12)) and NM_020982 (SEQ ID NO: 4 (FIG. 12)) (both in NCBI).

2. Anti-CLDN6 Antibody

An example of the anti-CLDN6 antibody of the present invention is an anti-CLDN6 antibody that recognizes a higher order structure including two extracellular regions, specifically, an amino acid sequence of the 29- to 81-positions and amino acid sequence of the 138- to 160-positions from the N terminus of CLDN6 as represented by SEQ ID NO: 1 in Sequence Listing, and has internalization activity.

The anti-CLDN6 antibody of the present invention is an antibody capable of targeting tumor cells, and specifically has a property of recognizing a tumor cell, a property of binding to a tumor cell, a property of being incorporated and internalizing in a tumor cell, and so on. Accordingly, the anti-CLDN6 antibody according to the present invention can be used for an antibody-drug conjugate by conjugating via a linker with a compound having antitumor activity.

The anti-CLDN6 antibody of the present invention may have antitumor activity.

The anti-CLDN6 antibody may be obtained using a method usually carried out in the art, which involves immunizing animals with an antigenic polypeptide and collecting and purifying antibodies produced in vivo. CLDN6 is a four-transmembrane protein, and hence protein retaining the three-dimensional structure may be used as an antigen, and examples of such methods may include, but not limited to, cell immunization.

Alternatively, antibody-producing cells which produce antibodies against the antigen are fused with myeloma cells according to the method known in the art to establish hybridomas, from which monoclonal antibodies can in turn be obtained.

Now, a method for obtaining an antibody against CLDN6 will be specifically described.

1) Preparation of Antigen

CLDN6 may be directly purified for use from tumor tissue or tumor cells of a human, or a cell membrane fraction of the cells may be prepared for use as CLDN6. Alternatively, CLDN6 may be obtained by synthesizing CLDN6 in vitro (e.g., Rapid Translation System (RTS) produced by Roche Diagnostics K.K.), or allowing host cells to produce CLDN6 through gene engineering.

To obtain the antigen through gene engineering, cDNA for CLDN6 is incorporated into a vector capable of expressing the cDNA, and CLDN6 is synthesized in a solution containing an enzyme, substrate, and energy substance required for transcription and translation, or host cells of another prokaryote or eukaryote are transformed to allow the cells to express CLDN6. Alternatively, CLDN6-expressing cells obtained through the gene engineering or a cell line expressing CLDN6 may be used as CLDN6 protein.

The antigen may be obtained as a secretory protein by allowing an appropriate host-vector system to express a fusion protein including the extracellular region of the membrane protein CLDN6 and the constant region of an antibody linked together.

The above-described transformant itself may be used as an antigen.

Further, a cell line that expresses CLDN6 may be used as the antigen. Examples of such cell lines may include cells of the human pancreatic cancer cell line NOR-P1; the human ovarian cancer cell lines NIH:OVCAR-3, OV-90, and OAW28; the human ovarian teratoma cell line PA-1; the human liver cancer cell line HuH-7; the human gastational choriocarcinoma cell line JEG-3; and human pluripotent embryonic carcinoma cell line NTERA-2 clone D1, but are not limited thereto and any cell line that expresses CLDN6 is acceptable.

The CLDN9 protein to be used in the present invention may be prepared for use in the same manner.

2) Production of Anti-CLDN6 Monoclonal Antibody

The anti-CLDN6 antibody used in the present invention is not limited to a particular antibody, and, for example, an antibody specified by any of the amino acid sequences listed in the present Sequence Listing can be preferably used. The anti-CLDN6 antibody to be used in the present invention is desired to have the following properties.

(1) An antibody having the following properties (a) and (b).
 (a) Recognizing or binding to the CLDN family.

The antibody of the present invention recognizes the CLDN family. In other words, the antibody of the present invention binds to the CLDN family. The antibody of the present invention preferably binds to CLDN6, and more preferably specifically binds to CLDN6. Further, the antibody of the present invention may recognize CLDN9 or bind to CLDN9.

In the present invention, "specific recognition", that is, "specific binding" refers to binding being not nonspecific adsorption. Examples of determination criteria on whether binding is specific or not may include, but not limited to, dissociation constants (hereinafter, referred to as "KD"). A preferred KD value of the antibody of the present invention to CLDN6 and/or CLDN9 is $1\times10^{-5}$ M or less, $5\times10^{-6}$ M or less, $2\times10^{-6}$ M or less, or $1\times10^{-6}$ M or less, and more preferably $5\times10^{-7}$ M or less, $2\times10^{-7}$ M or less, or $1\times10^{-7}$ M or less.

Binding between an antigen and an antibody in the present invention may be measured or determined by an analysis method such as an ELISA method, an RIA method, and surface plasmon resonance (hereinafter, referred to as "SPR"). Binding between an antigen expressed on a cell surface and an antibody may be measured, for example, by a flow cytometry method.

(b) Having activity to internalize in CLDN6- and/or CLDN9-expressing cells through binding to CLDN6 and/or CLDN9.

(2) The antibody according to (1), wherein CLDN6 and/or CLDN9 are/is human CLDN6 and/or human CLDN9.

The method of the present invention for obtaining the antibody against CLDN6 typically involves the following steps, but is not limited to the following.

(Method Using Hybridoma)
(a) Purification of a biopolymer for use as the antigen or preparation of antigen-expressing cells, and administration of the biopolymer or antigen-expressing cells to an animal;
(b) collection of tissue (e.g., a lymph node) including antibody-producing cells from the animal for which immunoreaction has been induced;
(c) preparation of myeloma cells (e.g., mouse myeloma SP2/0-ag14 cells);
(d) cell fusion of antibody-producing cells and myeloma cells;
(e) selection of a hybridoma group producing the targeted antibody;
(f) division into single cell clones (cloning);
(g) an optional step of culture of the hybridoma for mass production of an monoclonal antibody or rearing of an animal to which the hybridoma was transplanted; and
(h) examination of the physiological activity (internalization activity) and the binding specificity of the thus-produced monoclonal antibody, or testing of properties as a labeling reagent.

Examples of methods to be used here for measuring antibody titers may include, but not limited to, flow cytometry and a Cell-ELISA method.

Examples of the thus-obtained monoclonal anti-CLDN6 antibody may include, but not limited to, the mouse anti-CLDN6 antibodies B1 and C7. In the present invention, the "B1" and the "C7" are occasionally called as the "B1 antibody" and the "C7 antibody", respectively.

The nucleotide sequence for and the amino acid sequence of the heavy chain variable region of the B1 antibody are respectively represented by SEQ ID NO: 20 (FIG. 19) and SEQ ID NO: 21 (FIG. 19) in Sequence Listing. The nucleotide sequence for and the amino acid sequence of the light chain variable region of the B1 antibody are respectively represented by SEQ ID NO: 18 (FIG. 18) and SEQ ID NO: 19 (FIG. 18) in Sequence Listing.

The amino acid sequences of CDRH1, CDRH2, CDRH3, CDRL1, CDRL2, and CDRL3 of the B1 antibody are represented by SEQ ID NO: 9 (FIG. 15), SEQ ID NO: 10 (FIG. 15), SEQ ID NO: 11 (FIG. 15), SEQ ID NO: 5 (FIG. 13), SEQ ID NO: 6 (FIG. 13), and SEQ ID NO: 7 (FIG. 13), respectively.

The nucleotide sequence for and the amino acid sequence of the heavy chain variable region of the C7 antibody are respectively represented by SEQ ID NO: 24 (FIG. 21) and SEQ ID NO: 25 (FIG. 21) in Sequence Listing. The nucleotide sequence for and the amino acid sequence of the light chain variable region of the C7 antibody are respectively represented by SEQ ID NO: 22 (FIG. 20) and SEQ ID NO: 23 (FIG. 20) in Sequence Listing.

The amino acid sequences of CDRH1, CDRH2, CDRH3, CDRL1, CDRL2, and CDRL3 of the C7 antibody are represented by SEQ ID NO: 15 (FIG. 17), SEQ ID NO: 16 (FIG. 17), SEQ ID NO: 17 (FIG. 17), SEQ ID NO: 12 (FIG. 16), SEQ ID NO: 13 (FIG. 16), and SEQ ID NO: 14 (FIG. 16), respectively.

Further, even if a monoclonal antibody was independently obtained by steps (a) to (h) in "Production of anti-CLDN6 antibody" again, or a monoclonal antibody was separately obtained by using another method, an antibody having internalization activity equivalent to that of the B1 antibody or C7 antibody can be obtained. An example of such antibodies is an antibody that binds to an epitope for the B1 antibody or C7 antibody. If a monoclonal antibody newly produced binds to a partial peptide or partial three-dimensional structure to which the B1 antibody or C7 antibody binds, it can be determined that the monoclonal antibody binds to an epitope for the B1 antibody or C7 antibody. By confirming that the monoclonal antibody competes with the B1 antibody or C7 antibody for binding to CLDN6 (i.e., the monoclonal antibody interferes with binding between the B1 antibody or C7 antibody and CLDN6), it can be determined, even when the specific sequence or structure of an epitope has not been determined, that the monoclonal antibody binds to an epitope for the anti-CLDN6 antibody. If epitope identity has been confirmed, the monoclonal antibody is strongly expected to have antigen-binding ability, biological activity, and/or internalization activity equivalent to that of the B1 antibody or C7 antibody.

The antibody of the present invention includes, in addition to the monoclonal antibody against CLDN6, a gene recombinant antibody obtained by artificial modification for the purpose of decreasing heterologous antigenicity to humans such as a chimeric antibody, a humanized antibody, and a human antibody. These antibodies can be produced using a known method.

(1) Chimeric Antibody

Examples of the chimeric antibody may include, but not limited to, an antibody in which antibody variable and constant regions are derived from different species, for example, a chimeric antibody in which a mouse- or rat-derived antibody variable region is connected to a human-derived antibody constant region (see Proc. Natl. Acad. Sci. USA, 81, 6851-6855, (1984)).

A chimeric antibody derived from the mouse anti-human CLDN6 antibody B1 antibody, as an example of the chimeric antibody of the present invention, is an antibody comprising a heavy chain comprising a heavy chain variable region consisting of an amino acid sequence represented by SEQ ID NO: 21 (FIG. 19) and a light chain comprising a light chain variable region represented by SEQ ID NO: 19 (FIG. 18), which may comprising any human-derived constant region.

Specific examples of the chimeric antibody derived from the mouse anti-human CLDN6 antibody B1 antibody may include, but not limited to, the chimeric antibody chB1 antibody (hereinafter, also called as "chB1") derived from the mouse anti-human CLDN6 antibody B1 antibody. Examples of the chB1 antibody, in terms of the amino acid sequence, may include, but not limited to, an antibody comprising a heavy chain having an amino acid sequence consisting of amino acid residues 20 to 471 of SEQ ID NO: 32 (FIG. 24) in Sequence Listing and a light chain having an amino acid sequence consisting of amino acid residues 21 to 234 of SEQ ID NO: 28 (FIG. 22) in Sequence Listing.

In the heavy chain sequence represented by SEQ ID NO: 32 (FIG. 24) in Sequence Listing, the amino acid sequence consisting of amino acid residues 1 to 19 is the signal sequence, the amino acid sequence consisting of amino acid residues 20 to 141 is the heavy chain variable region, and the amino acid sequence consisting of amino acid residues 142 to 471 is the heavy chain constant region. In the light chain sequence represented by SEQ ID NO: 28 (FIG. 22) in Sequence Listing, the amino acid sequence consisting of amino acid residues 1 to 20 is the signal sequence, the amino acid sequence consisting of amino acid residues 21 to 127 is the light chain variable region, and the amino acid sequence consisting of amino acid residues 128 to 234 is the light chain constant region.

The amino acid sequences of the heavy chain and light chain variable regions of the chB1 antibody are respectively represented by SEQ ID NO: 34 (FIG. 25) and SEQ ID NO: 30 (FIG. 23) in Sequence Listing.

The heavy chain amino acid sequence of the chB1 antibody is encoded by a nucleotide sequence represented by SEQ ID NO: 33 (FIG. 24) in Sequence Listing. A nucleotide sequence consisting of nucleotide residues 1 to 57 of a nucleotide sequence represented by SEQ ID NO: 33 in Sequence Listing is encoding the signal sequence of the chB1 antibody heavy chain, a nucleotide sequence consisting of nucleotide residues 58 to 423 of a nucleotide sequence represented by SEQ ID NO: 33 in Sequence Listing is encoding the heavy chain variable region of the chB1 antibody, and a nucleotide sequence consisting of nucleotide residues 424 to 1413 of a nucleotide sequence represented by SEQ ID NO: 33 in Sequence Listing is encoding the heavy chain constant region of the chB1 antibody.

The nucleotide sequence for the heavy chain variable region of the chB1 antibody is represented by SEQ ID NO: 35 (FIG. 25) in Sequence Listing.

The light chain amino acid sequence of the chB1 antibody is encoded by a nucleotide sequence represented by SEQ ID NO: 29 (FIG. 22) in Sequence Listing. A nucleotide sequence consisting of nucleotide residues 26 to 85 of a nucleotide sequence represented by SEQ ID NO: 29 in Sequence Listing is encoding the signal sequence of the chB1 antibody light chain, a nucleotide sequence consisting of nucleotide residues 86 to 406 of a nucleotide sequence represented by SEQ ID NO: 29 in Sequence Listing is encoding the light chain variable region of the chB1 antibody, and a nucleotide sequence consisting of nucleotide residues 407 to 727 of a nucleotide sequence represented by SEQ ID NO: 29 in Sequence Listing is encoding the light chain constant region of the chB1 antibody.

The nucleotide sequence for the light chain variable region of the chB1 antibody is represented by SEQ ID NO: 31 (FIG. 23) in Sequence Listing.

(2) Humanized Antibody

Examples of the humanized antibody may include, but not limited to, an antibody obtained by incorporating only the complementarity determining regions (CDRs) into a human-derived antibody (see Nature (1986) 321, p. 522-525), an antibody obtained by grafting a part of the amino acid residues of a framework as well as the CDR sequences to a human antibody by a CDR-grafting method (WO 90/07861), and an antibody in which a part of the CDR amino acid sequences has been modified with the binding ability to an antigen maintained.

If the humanized antibody is derived from the B1 antibody or C1 antibody, however, the humanized antibody may be any humanized antibody, without limited to a particular humanized antibody, that retains all the six CDR sequences of the B1 antibody or C1 antibody and has CLDN6-binding activity, and in addition the humanized antibody may be any humanized antibody, without limited to a particular humanized antibody, such that its humanized antibody variant in which one to several (preferably, one or two, more preferably, one) CDR amino acid sequences have been modified also recognizes CLDN6 protein, or has the CLDN6 protein-binding activity of the original antibody.

Examples of the humanized anti-CLDN6 antibody of the present invention or a functional fragment thereof may include, but not limited to, an antibody comprising a heavy chain having a variable region comprising:

CDRH1 consisting of an amino acid sequence represented by SEQ ID NO: 9 (FIG. 15) in Sequence Listing, or an amino acid sequence obtained by substituting one to several (preferably, one or two) amino acids in the aforementioned amino acid sequence;

CDRH2 consisting of an amino acid sequence represented by SEQ ID NO: 10 (FIG. 15) in Sequence Listing, or an amino acid sequence obtained by substituting one to several (preferably, one or two) amino acids in the aforementioned amino acid sequence; and CDRH3 consisting of an amino acid sequence represented by SEQ ID NO: 11 (FIG. 15) in Sequence Listing, or an amino acid sequence obtained by substituting one to several (preferably, one or two) amino acids in the aforementioned amino acid sequence; and a light chain having a variable region comprising:

CDRL1 consisting of an amino acid sequence represented by SEQ ID NO: 5 (FIG. 13) in Sequence Listing, or an amino acid sequence obtained by substituting one to several (preferably, one or two) amino acids in the aforementioned amino acid sequence;

CDRL2 consisting of an amino acid sequence represented by SEQ ID NO: 6 (FIG. 13) in Sequence Listing, or an amino acid sequence obtained by substituting one to several (preferably, one or two) amino acids in the aforementioned amino acid sequence; and CDRL3 consisting of an amino acid sequence represented by SEQ ID NO: 7 (FIG. 13) in Sequence Listing, or an amino acid sequence obtained by substituting one to several (preferably, one or two) amino acids in the aforementioned amino acid, and recognizing the CLDN6 protein of the present invention or retaining the CLDN6 protein-binding activity of the antibody, or a functional fragment of the antibody.

Preferred examples of CDR amino acid substitution in the humanized anti-CLDN6 antibody or functional fragment thereof may include, but not limited to, substitution of one to several (preferably, one or two) amino acids in CDRL3 as described above, and an example thereof is CDRL3 represented by SEQ ID NO: 8 (FIG. 14) in Sequence Listing, which is obtained by substituting amino acid residues 4 and 5 of SEQ ID NO: 7 in Sequence Listing.

Examples of the heavy chain variable region of the humanized antibody comprising the above-described CDRHs may include, but not limited to, an amino acid sequence represented by SEQ ID NO: 54 (FIG. 35) in Sequence Listing, an amino acid sequence represented by SEQ ID NO: 58 (FIG. 37) in Sequence Listing, and an amino acid sequence represented by SEQ ID NO: 62 (FIG. 39) in Sequence Listing, and examples of the light chain variable region of the humanized antibody comprising the above-described CDRLs may include, but not limited to, an amino acid sequence represented by SEQ ID NO: 38 (FIG. 27) in Sequence Listing, an amino acid sequence represented by SEQ ID NO: 42 (FIG. 29) in Sequence Listing, and an amino acid sequence represented by SEQ ID NO: 46 (FIG. 31) in Sequence Listing.

Preferred examples of humanized antibodies including a combination of the above heavy chain variable region and light chain variable region may include, but not limited to:

a humanized antibody comprising a heavy chain variable region consisting of an amino acid sequence represented by SEQ ID NO: 54 (FIG. 35) in Sequence Listing and a light chain variable region consisting of an amino acid sequence represented by SEQ ID NO: 38 (FIG. 27) in Sequence Listing;

a humanized antibody comprising a heavy chain variable region consisting of an amino acid sequence represented by SEQ ID NO: 58 (FIG. 37) in Sequence Listing and a light chain variable region consisting of an amino acid sequence represented by SEQ ID NO: 42 (FIG. 29) in Sequence Listing;

a humanized antibody comprising a heavy chain variable region consisting of an amino acid sequence represented by SEQ ID NO: 54 (FIG. 35) in Sequence Listing and a light chain variable region consisting of an amino acid sequence represented by SEQ ID NO: 46 (FIG. 31) in Sequence Listing;

a humanized antibody comprising a heavy chain variable region consisting of an amino acid sequence represented by SEQ ID NO: 58 (FIG. 37) in Sequence Listing and a light chain variable region consisting of an amino acid sequence represented by SEQ ID NO: 50 (FIG. 33) in Sequence Listing; and a humanized antibody comprising a heavy chain variable region consisting of an amino acid sequence represented by SEQ ID NO: 62 (FIG. 39) in Sequence Listing and a light chain variable region consisting of an amino acid sequence represented by SEQ ID NO: 46 (FIG. 31) in Sequence Listing.

Examples of full-length sequences of humanized antibodies including a combination of the above heavy chain variable region and light chain variable region may include, but not limited to:

a humanized antibody comprising a heavy chain consisting of an amino acid sequence consisting of amino acid residues 20 to 471 of SEQ ID NO: 52 (FIG. 34) in Sequence Listing and a light chain consisting of an amino acid sequence consisting of amino acid residues 21 to 234 of SEQ ID NO: 36 (FIG. 26) in Sequence Listing (H1L1);

a humanized antibody comprising a heavy chain consisting of an amino acid sequence consisting of amino acid residues 20 to 471 of SEQ ID NO: 56 (FIG. 36) in Sequence Listing and a light chain consisting of an amino acid sequence consisting of amino acid residues 21 to 234 of SEQ ID NO: 40 (FIG. 28) in Sequence Listing (H2L2);

a humanized antibody comprising a heavy chain consisting of an amino acid sequence consisting of amino acid residues 20 to 471 of SEQ ID NO: 52 (FIG. 34) in Sequence Listing and a light chain consisting of an amino acid sequence consisting of amino acid residues 21 to 234 of SEQ ID NO: 44 (FIG. 30) in Sequence Listing (H1L3);

a humanized antibody comprising a heavy chain consisting of an amino acid sequence consisting of amino acid residues 20 to 471 of SEQ ID NO: 56 (FIG. 36) in Sequence Listing and a light chain consisting of an amino acid sequence consisting of amino acid residues 21 to 234 of SEQ ID NO: 48 (FIG. 32) in Sequence Listing (H2L4); and a humanized antibody comprising a heavy chain consisting of an amino acid sequence consisting of amino acid residues 20 to 471 of SEQ ID NO: 60 (FIG. 38) in Sequence Listing and a light chain consisting of an amino acid sequence consisting of amino acid residues 21 to 234 of SEQ ID NO: 44 (FIG. 30) in Sequence Listing (H3L3).

In the heavy chain amino acid sequence represented by SEQ ID NO: 52 (FIG. 34), 56 (FIG. 36), or 60 (FIG. 38) in Sequence Listing, an amino acid sequence consisting of amino acid residues 1 to 19 is the signal sequence, an amino acid sequence consisting of amino acid residues 20 to 141 is the heavy chain variable region, and an amino acid sequence consisting of amino acid residues 142 to 471 is the heavy chain constant region.

In the light chain amino acid sequence represented by SEQ ID NO: 36 (FIG. 26), 40 (FIG. 28), 44 (FIG. 30), or 48 (FIG. 32), an amino acid sequence consisting of amino acid residues 1 to 20 is the signal sequence, an amino acid sequence consisting of amino acid residues 21 to 127 is the light chain variable region, and an amino acid sequence consisting of amino acid residues 128 to 234 is the light chain constant region.

The nucleotide sequence encoding the heavy chain amino acid sequence of the humanized antibody H1L1 and that encoding the light chain amino acid sequence of the humanized antibody H1L1 are a polynucleotide represented by SEQ ID NO: 53 (FIG. 34) and a polynucleotide represented by SEQ ID NO: 37 (FIG. 26), respectively;

the nucleotide sequence encoding the heavy chain amino acid sequence of the humanized antibody H2L2 and that encoding the light chain amino acid sequence of the humanized antibody H2L2 are a polynucleotide represented by SEQ ID NO: 57 (FIG. 36) and a polynucleotide represented by SEQ ID NO: 41 (FIG. 28), respectively;

the nucleotide sequence encoding the heavy chain amino acid sequence of the humanized antibody H1L3 and that encoding the light chain amino acid sequence of the humanized antibody H1L3 are a polynucleotide represented by SEQ ID NO: 53 (FIG. 34) and a polynucleotide represented by SEQ ID NO: 45 (FIG. 30), respectively;

the nucleotide sequences encoding the heavy chain amino acid sequence of the humanized antibody H2L4 and that encoding the light chain amino acid sequence of the humanized antibody H2L4 are a polynucleotide represented by SEQ ID NO: 57 (FIG. 36) and a polynucleotide represented by SEQ ID NO: 49 (FIG. 32), respectively; and the nucleotide sequence encoding the heavy chain amino acid sequence of the humanized antibody H3L3 and that encoding the light chain amino acid sequence of the humanized antibody H3L3 are a polynucleotide represented by SEQ ID NO: 61 (FIG. 38) and a polynucleotide represented by SEQ ID NO: 45 (FIG. 30), respectively.

The nucleotide sequence encoding the amino acid sequence of the heavy chain variable region of the humanized antibody H1L1 and that encoding the light chain variable region of the humanized antibody H1L1 are a polynucleotide represented by SEQ ID NO: 55 (FIG. 35) and a polynucleotide represented by SEQ ID NO: 39 (FIG. 27), respectively;

the nucleotide sequence encoding the amino acid sequence of the heavy chain variable region of the humanized antibody H2L2 and that encoding the light chain variable region of the humanized antibody H2L2 are a polynucleotide represented by SEQ ID NO: 59 (FIG. 37) and a polynucleotide represented by SEQ ID NO: 43 (FIG. 29), respectively;

the nucleotide sequence encoding the amino acid sequence of the heavy chain variable region of the humanized antibody H1L3 and that encoding the light chain variable region of the humanized antibody H1L3 are a polynucleotide represented by SEQ ID NO: 55 (FIG. 35) and a polynucleotide represented by SEQ ID NO: 47 (FIG. 31), respectively;

the nucleotide sequence encoding the amino acid sequence of the heavy chain variable region of the humanized antibody H2L4 and that encoding the light chain variable region of the humanized antibody H2L4 are a polynucleotide represented by SEQ ID NO: 59 (FIG. 37) and a polynucleotide represented by SEQ ID NO: 51 (FIG. 33), respectively; and the nucleotide sequence encoding the amino acid sequence of the heavy chain variable region of the humanized antibody H3L3 and that encoding the light chain variable region of the humanized antibody H3L3 are a polynucleotide represented by SEQ ID NO: 63 (FIG. 39) and a polynucleotide represented by SEQ ID NO: 47 (FIG. 31), respectively.

In the nucleotide sequence represented by SEQ ID NO: 53 (FIG. 34), 57 (FIG. 36), or 61 (FIG. 38) in Sequence Listing, a nucleotide sequence consisting of nucleotide resides 1 to 57 is encoding the signal sequence of the humanized antibody heavy chain, a nucleotide sequence consisting of nucleotide resides 58 to 423 is encoding the amino acid sequence of the variable region of the humanized antibody heavy chain, and a nucleotide sequence consisting of nucleotide resides 424 to 1413 is encoding the constant region of the antibody heavy chain.

In the nucleotide sequence represented by SEQ ID NO: 37 (FIG. 26), 41 (FIG. 28), 45 (FIG. 30), or 49 (FIG. 32) in Sequence Listing, a nucleotide sequence consisting of nucleotide resides 1 to 60 is encoding the signal sequence of the humanized antibody light chain, a nucleotide sequence consisting of nucleotide residues 61 to 381 is encoding the amino acid sequence of the variable region of the humanized antibody light chain, and a nucleotide sequence consisting of nucleotide residues 382 to 702 is encoding the constant region of the antibody light chain.

As long as having binding activity to CLDN6, any antibody that has an identity or homology of 80% or higher, preferably of 90% or higher, more preferably of 95% or higher, even more preferably of 97% or higher, the most preferably of 99% or higher, to the amino acid sequence of any of the antibodies including the above combinations of a heavy chain variable region and a light chain variable region and the antibodies including the above combinations of a heavy chain and a light chain is also included in the antibody of the present invention.

As long as having binding activity to CLDN6, any antibody that includes CDRs consisting of the amino acid sequences of the CDRs of any of the antibodies including the above combinations of a heavy chain variable region and a light chain variable region and the antibodies including the above combinations of a heavy chain and a light chain, wherein the amino acid sequence of the antibody excluding the amino acid sequences of the CDRs has an amino acid identity or homology of 80% or higher, preferably of 90% or higher, more preferably of 95% or higher, even more preferably of 97% or higher, the most preferably of 99% or higher, is also included in the antibody of the present invention.

Further, an antibody having biological activity equivalent to each of the above antibodies may be selected through combining amino acid sequences obtained by substituting, deleting, or adding one or several amino acid residues in the amino acid sequence of the heavy chain or light chain. The substitution of an amino acid herein is preferably conservative amino acid substitution (WO 2013154206).

The conservative amino acid substitution is substitution that occurs in an amino acid group with related amino acid side chains. Such amino acid substitution is preferably carried out to such a degree that the properties of the substance having the original amino acid sequence are not decreased.

Homology between two amino acid sequences may be determined by using default parameters of Blast algorithm version 2.2.2 (Altschul, Stephen F., Thomas L. Madden, Alejandro A. Schaaffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402) Blast algorithm may be used by accessing www.ncbi.nlm.nih.gov/blast on the Internet.

(3) Human Antibody

Further examples of the antibody of the present invention may include, but not limited to, human antibodies capable of binding to CLDN6 and/or CLDN9. The human anti-CLDN6 and/or CLDN9 antibody refers to a human antibody having only an antibody gene sequence derived from a human chromosome. The human anti-CLDN6 antibody may be obtained by using a method with a human antibody-producing mouse having a human chromosome fragment including the genes of a heavy chain and light chain of a human antibody (see Nature Genetics (1997) 16, p. 133-143; Nucl. Acids Res. (1998) 26, p. 3447-3448; Animal Cell Technology: Basic and Applied Aspects vol. 10, p. 69-73, Kluwer Academic Publishers, 1999; Proc. Natl. Acad. Sci. USA (2000) 97, p. 722-727, etc.).

Specifically, such a human antibody-producing mouse may be created by producing a knockout animal or transgenic animal as a gene recombinant animal with the gene loci for the heavy chain and light chain of endogenous immunoglobulin destroyed, instead, with the gene loci for the heavy chain and light chain of human immunoglobulin introduced therein, for example, via a yeast artificial chromosome (YAC) vector, and interbreeding of such animals.

Alternatively, such an antibody may be obtained as follows: a eukaryotic cell is transformed with cDNA encoding the heavy chain and light chain of a human antibody, preferably with a vector including the cDNA, through a gene recombinant technique, and the transformed cell producing a gene recombinant human monoclonal antibody is cultured, and the antibody is obtained from the culture supernatant.

For the host, for example, a eukaryotic cell, preferably a mammalian cell such as a CHO cell, a lymphocyte, and a myeloma cell may be used.

In addition, a method of obtaining a phage display-derived human antibody sorted out of a human antibody library (see Investigative Ophthalmology & Visual Science (2002) 43 (7), p. 2301-2308; Briefings in Functional Genomics and Proteomics (2002), 1 (2), p. 189-203; Ophthalmology (2002) 109 (3), p. 427-431, etc.) is known.

For example, a phage display method (Nature Biotechnology (2005), 23, (9), p. 1105-1116) may be used, in which the variable region of a human antibody is expressed as a single chain antibody (scFv) on phage surfaces, and phages that bind to the antigen are selected.

Analysis of phage genes selected because of binding to the antigen can determine the DNA sequence encoding the variable region of the human antibody that binds to the antigen.

Once the DNA sequence of scFv that binds to the antigen has been clarified, the human antibody can be obtained by producing an expression vector including the sequence and introducing the expression vector into an appropriate host for expression (WO92/01047, WO92/20791, WO93/06213, WO93/11236, WO93/19172, WO95/01438, WO95/15388, Annu. Rev. Immunol (1994) 12, p. 433-455, Nature Biotechnology (2005) 23(9), p.1105-1116)

Chimeric antibodies, humanized antibodies, human antibodies, and so on obtained by using the above method may be evaluated for binding activity to an antigen, for example, by using a known method to screen for a preferred antibody.

Another example of indicators in comparing characteristics among antibodies is stability of antibodies. Differential scanning calorimetry (DSC) is an apparatus capable of quickly and accurately measuring thermal denaturation midpoints (Tm), a good indicator for relative structural stability of protein. Difference in thermal stability can be compared through comparison of Tm values measured with DSC. Storage stability of antibodies is known to be correlated with thermal stability of antibodies to some degree (Pharmaceutical Development and Technology (2007) 12, p. 265-273), and hence thermal stability may be used as an indicator to screen for a preferred antibody. Examples of other indicators for screening for an antibody may include, but not limited to, a high yield in appropriate host cells and a low agglutinating property in aqueous solution. It is needed to screen for the most suitable antibody for administration to humans through comprehensive determination based on the above-described indicators, for example, because an antibody with the highest yield does not necessarily exhibit the highest thermal stability.

The antibody of the present invention includes "antibodies that bind to a site to which the anti-CLDN6 antibody provided by the present invention binds". That is, the present invention includes antibodies that bind to a site on CLDN6 protein that B1 or C7 of the present invention recognizes.

The antibody of the present invention includes modified variants of the antibody. The modified variant refers to a variant obtained by subjecting the antibody of the present invention to chemical or biological modification. Examples of the chemically modified variant may include, but not limited to, variants including a linkage of a chemical moiety to an amino acid skeleton, and variants with chemical modification of an N-linked or O-linked carbohydrate chain. Examples of the biologically modified variant may include, but not limited to, variants obtained by post-translational modification (e.g., N-linked or O-linked glycosylation, N- or C-terminal processing, deamidation, isomerization of aspartic acid, oxidation of methionine), and variants in which a methionine residue has been added to the N terminus by being expressed in a prokaryotic host cell. Further, an antibody labeled so as to enable the detection or isolation of the antibody of the present invention or an antigen, for example, an enzyme-labeled antibody, a fluorescence-labeled antibody, and an affinity-labeled antibody are also included in the meaning of the modified variant. Such a modified variant of the antibody of the present invention is useful for improving the stability and blood retention of the antibody, reducing the antigenicity thereof, detecting or isolating an antibody or an antigen, and so on.

Further, by regulating the modification of a glycan which is linked to the antibody of the present invention (glycosylation, defucosylation, etc.), the antibody-dependent cellular cytotoxic activity can be enhanced. As the technique for regulating the modification of a glycan of antibodies, WO 1999/54342, WO 2000/61739, WO 2002/31140, etc., are known. However, the technique is not limited thereto. In the antibody of the present invention, antibodies in which the modification of a glycan is regulated are also included.

Such modification may be applied at any position or a desired position in an antibody or a functional fragment of the antibody, and the same type or two or more different types of modification may be applied at one or two or more positions.

In the present invention, the meaning of a "modified variant of an antibody fragment" also includes a "fragment of a modified variant of an antibody".

If an antibody gene is temporarily isolated and then introduced into an appropriate host to produce an antibody, an appropriate combination of a host and an expression vector can be used. Specific examples of the antibody gene may include, but not limited to, combination of a gene encoding the heavy chain sequence or the like of an antibody described herein and a gene encoding the light chain sequence or the like of an antibody described herein. To transform host cells, a heavy chain sequence gene or the like and a light chain sequence gene or the like may be inserted into the same expression vector, or inserted into separate expression vectors.

If eukaryotic cells are used as a host, animal cells, plant cells, and eukaryotic microorganisms may be used. Particularly, examples of animal cells may include, but not limited to, mammalian cells, such as COS cells (Cell (1981) 23, p. 175-182, ATCC CRL-1650), as monkey cells, the mouse fibroblast NIH3T3 (ATCC No. CRL-1658), a dihydrofolate reductase-deficient strain (Proc. Natl. Acad. Sci. U.S.A. (1980) 77, p. 4126-4220) of Chinese hamster ovary cells (CHO cells, ATCC CCL-61), and FreeStyle 293F cells (Invitrogen).

If prokaryotic cells are used, for example, Escherichia coli or Bacillus subtilis may be used.

A targeted antibody gene is introduced into these cells by transformation, and the transformed cells are cultured in vitro to afford an antibody. Sequence difference among antibodies may result in different yields in the culture, and hence antibodies that allow easy production of a medicine may be selected out of antibodies having equivalent binding activity by using yields as an indicator. Accordingly, the antibody of the present invention includes antibodies obtained by using a method for producing the antibody, the method including the steps of: culturing the transformed host cell; and collecting a targeted antibody or a functional fragment of the antibody from a culture obtained in the step of culturing.

The antibody gene is preferably a polynucleotide including a polynucleotide described in any one of (a) to (e):

(a) a combination of a polynucleotide encoding the heavy chain amino acid sequence and a polynucleotide encoding the light chain amino acid sequence of an antibody of any one of the B1 or C7 antibody, the chB1 antibody, and the humanized antibodies H1L1, H2L2, H1L3, H2L4, and H3L3;

(b) a combination of a polynucleotide encoding a heavy chain amino acid sequence including the sequences of CDRH1 to CDRH3 and a polynucleotide encoding a light chain amino acid sequence including the sequences of CDRL1 to CDRL3 of an antibody of any one of the B1 or C7 antibody, the chB1 antibody, and the humanized antibodies H1L1, H2L2, H1L3, H2L4, and H3L3;

(c) a combination of a polynucleotide encoding a heavy chain amino acid sequence comprising the amino acid sequence of the heavy chain variable region and a polynucleotide encoding a light chain amino acid sequence comprising the amino acid sequence of the light chain variable region of an antibody of any one of the B1 or C7 antibody, the chB1 antibody, and the humanized antibodies H1L1, H2L2, H1L3, H2L4, and H3L3;

(d) a polynucleotide that is hybridizable with nucleotides consisting of a polynucleotide complementary to the polynucleotide according to any one of (a) to (c) under stringent conditions and is encoding the amino acid sequence of an antibody capable of binding to CDLN6; and (e) a polynucleotide encoding the amino acid sequence of a polypeptide obtained by substituting, deleting, adding, or inserting 1 to 50, 1 to 45, 1 to 40, 1 to 35, 1 to 30, 1 to 25, 1 to 20, 1 to 15, 1 to 10, one to eight, one to six, one to five, one to four, one to three, one or two, or one amino acid(s) in the polynucleotide according to any one of (a) to (c), and is encoding the amino acid sequence of an antibody capable of binding to CDLN6.

The present invention includes a nucleotide encoding the antibody of the present invention or a functional fragment of the antibody, or a modified variant of the antibody or functional fragment; a recombinant vector including the gene inserted therein; and a cell including the gene or the vector introduced therein.

The present invention includes a method for producing an antibody or a functional fragment of the antibody, or a modified variant of the antibody or functional fragment, the method including the steps of: culturing the cell; and collecting from the culture an antibody or a functional fragment of the antibody, or a modified variant of the antibody or functional fragment.

It is known that a lysine residue at the carboxyl terminus of the heavy chain of an antibody produced in a cultured mammalian cell is deleted (Journal of Chromatography A, 705: 129-134 (1995)), and it is also known that two amino acid residues, glycine and lysine, at the carboxyl terminus of the heavy chain of an antibody produced in a cultured mammalian cell are deleted and a proline residue newly located at the carboxyl terminus is amidated (Analytical Biochemistry, 360: 75-83 (2007)). However, such deletion and modification of the heavy chain sequence do not affect the antigen-binding ability and the effector function (the activation of complement, antibody-dependent cellular cytotoxicity, etc.) of the antibody. Therefore, in the antibody according to the present invention, antibodies subjected to such modification and functional fragments of the antibody are also included, and deletion variants in which one or two amino acids have been deleted at the carboxyl terminus of the heavy chain, variants obtained by amidation of deletion variants (for example, a heavy chain in which the carboxyl terminal proline residue has been amidated), and the like are also included. The type of deletion variants having a deletion at the carboxyl terminus of the heavy chain of the antibody according to the present invention is not limited to the above variants as long as the antigen-binding ability and the effector function are conserved. The two heavy chains constituting the antibody according to the present invention may be of one type selected from the group consisting of a full-length heavy chain and the above-described deletion variant, or may be of two types in combination selected therefrom. The ratio of the amount of each deletion variant can be affected by the type of cultured mammalian cells which produce the antibody according to the present invention and the culture conditions; however, an antibody in which one amino acid residue at the carboxyl terminus has been deleted in both of the two heavy chains in the antibody according to the present invention can be preferably exemplified as a main component of molecules of the antibody.

Examples of isotypes of the anti-CLDN6 antibody of the present invention may include, but not limited to, IgG (IgG1, IgG2, IgG3, IgG4), and preferred examples thereof include IgG1, IgG2, and IgG4.

If IgG1 is used as the isotype of the antibody of the present invention, the effector function may be adjusted by substituting some amino acid residues in the constant region. Examples of variants of IgG1 with the effector function lowered or attenuated may include, but not limited to, IgG1 LALA (IgG1-L234A, L235A) and IgG1 LAGA (IgG1-L235A, G237A), and a preferred variant of IgG1 is IgG1 LALA. The L234A, L235A indicates substitution of leucine with alanine at the 234- and 235-positions specified by EU-index numbering (Proc. Natl. Acad. Sci. U.S.A., Vol. 63, No. 1 (May 15, 1969), pp. 78-85), and the G237A indicates substitution of glycine with alanine at the 237-position specified by EU-index numbering.

Typical examples of bioactivity of antibodies may include, but not limited to, antigen-binding activity, activity to internalize in cells expressing an antigen by binding to the antigen, activity to neutralize antigen activity, activity to enhance antigen activity, antibody-dependent cellular cytotoxicity (ADCC), complement-dependent cytotoxicity (CDC), and antibody-dependent cellular phagocytosis (ADCP), and the function of the antibody according to the present invention is binding activity to CLDN6, and preferably activity to internalize in CLDN6-expression cells by binding to CLDN6. In addition to cellular internalization activity, the antibody of the present invention may have activities of ADCC, CDC, and/or ADCP in combination.

The antibody obtained may be purified to a homogeneous state. For separation/purification of the antibody, separation/purification methods commonly used for protein can be used. For example, the antibody may be separated/purified by appropriately selecting and combining column chromatography, filter filtration, ultrafiltration, salting-out, dialysis, preparative polyacrylamide gel electrophoresis, isoelectric focusing, and so on (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but separation/purification methods are not limited thereto.

Examples of chromatography may include, but not limited to, affinity chromatography, ion-exchange chromatography, hydrophobic chromatography, gel filtration chromatography, reversed-phase chromatography, and adsorption chromatography.

These chromatographies may be carried out using liquid chromatography such as HPLC and FPLC.

Examples of columns for affinity chromatography may include, but not limited to, a Protein A column and a Protein G column.

Alternatively, the antibody may be purified by utilizing binding activity to an antigen with a carrier to which the antigen has been immobilized.

It is desirable that the anti-HER2 antibody of the present invention be, for example, that having any of the following properties, but the anti-HER2 antibody is not limited thereto.
(1) An anti-HER2 antibody having the following properties:
   (a) specifically binding to HER2; and
   (b) internalizing into HER2-expressing cells by binding to HER2.

(2) The antibody according to (1), binding to the extracellular domain of HER2.
(3) The antibody according to (1) or (2), being a monoclonal antibody.
(4) The antibody according to any one of (1) to (3), having activities or activity of antibody-dependent cellular cytotoxicity (ADCC) and/or complement-dependent cytotoxicity (CDC).
(5) The antibody according to any one of (1) to (4), being a mouse monoclonal antibody, a chimeric monoclonal antibody, or a humanized monoclonal antibody.
(6) The antibody according to any one of (1) to (3), wherein the heavy chain constant region is a heavy chain constant region of human IgG1, and comprises a mutation that causes lowering of activities or activity of ADCC and/or CDC.
(7) The antibody according to (6), wherein the heavy chain constant region is a heavy chain constant region of human IgG1, and leucine at the 234- and 235-positions specified by EU Index numbering is substituted with alanine.
(8) The antibody according to any one of (1) to (4), being a humanized monoclonal antibody comprising a heavy chain consisting of an amino acid sequence represented by SEQ ID NO: 65 and a light chain consisting of an amino acid sequence represented by SEQ ID NO: 64.
(9) The antibody according to any one of (1) to (3), (6), and (7), being a humanized monoclonal antibody comprising a heavy chain consisting of an amino acid sequence consisting of amino acid residues 20 to 469 of SEQ ID NO: 75 and a light chain consisting of an amino acid sequence consisting of amino acid residues 21 to 234 of SEQ ID NO: 73.
(10) The antibody according to any one of (1) to (9), wherein one or two amino acids are deleted at the carboxyl terminus of the heavy chain.
(11) The antibody according to any one of (1) to (3), (8), and (10), comprising a heavy chain consisting of an amino acid sequence consisting of amino acid residues 1 to 449 of SEQ ID NO: 65 and a light chain consisting of an amino acid sequence consisting of amino acid residues 1 to 214 of SEQ ID NO: 64.
(12) The antibody according to any one of (1) to (3), (6), (7), (9), and (10), comprising a heavy chain consisting of an amino acid sequence consisting of amino acid residues 20 to 468 of SEQ ID NO: 75 and a light chain consisting of an amino acid sequence consisting of amino acid residues 21 to 234 of SEQ ID NO: 73.
(13) An antibody obtained by using a method for producing the antibody according to any one of (1) to (12), the method including the steps of: culturing a host cell transformed with an expression vector containing a polynucleotide encoding the antibody; and collecting the targeted antibody from a culture obtained from the step of culturing.

<Glycan Remodeling>

Recently has been reported a method for remodeling heterogeneous glycoprotein of an antibody by enzymatic reaction or the like to homogeneously introduce a glycan having a functional group (ACS Chemical Biology 2012, 7, 110, ACS Medicinal Chemistry Letters 2016, 7, 1005). An attempt with use of this glycan remodeling technique has been made to site-specifically introduce a drug to synthesize a homogeneous ADC (Bioconjugate Chemistry 2015, 26, 2233, Angew. Chem. Int. Ed. 2016, 55, 2361-2367, US 2016361436).

In the glycan remodeling of the present invention, using hydrolase, heterogeneous glycans added to a protein (e.g., an antibody) are cleaved off to leave only GlcNAc at each terminus thereby producing a homogenous protein moiety with GlcNAc (hereinafter, referred to as an "acceptor"). Subsequently, an arbitrary glycan separately prepared (hereinafter, referred to as a "donor") is provided, and the acceptor and the donor are linked together by using transglycosidase. Thereby, a homogeneous glycoprotein with arbitrary glycan structure can be synthesized.

In the present invention, a "glycan" refers to a structural unit of two or more monosaccharides bonded together via glycosidic bonds. Specific monosaccharides and glycans are occasionally abbreviated, for example, as "GlcNAc-", "MSG-", and so on. When any of these abbreviations is used in a structural formula, the abbreviation is shown with an intention that an oxygen atom or nitrogen atom involved in a glycosidic bond at the reducing terminal to another structural unit is not included in the abbreviation indicating the glycan, unless specifically defined.

In the present invention, a monosaccharide as a basic unit of a glycan is indicated for convenience so that in the ring structure, the position of a carbon atom bonding to an oxygen atom constituting the ring and directly bonding to a hydroxy group (or an oxygen atom involved in a glycosidic bond) is defined as the 1-position (the 2-position only for sialic acids), unless otherwise specified. The names of compounds in Examples are each provided in view of the chemical structure as a whole, and that rule is not necessarily applied.

When a glycan is indicated as a sign (e.g., GLY, SG, MSG, GlcNAc) in the present invention, the sign is intended, unless otherwise defined, to include carbon atoms ranging to the reducing terminal and not to include N or O involved in an N- or O-glycosidic bond.

In the present invention, unless specifically stated, a partial structure when a glycan is linking to a side chain of an amino acid is indicated in such a manner that the side chain portion is indicated in parentheses, for example, "(SG-)Asn".

The antibody-drug conjugate of the present invention is represented by the following formula:

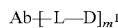  [Formula 82]

wherein antibody Ab or a functional fragment of the antibody may bond from a side chain of an amino acid residue thereof (e.g., cysteine, lysine) directly to L, or bond via a glycan or remodeled glycan of Ab to L, and preferably bonds via a glycan or remodeled glycan of Ab to L, and more preferably bonds via a remodeled glycan of Ab to L.

Glycans in Ab of the present invention are N-linked glycans or O-linked glycans, and preferably N-linked glycans.

N-linked glycans and O-linked glycans bond to an amino acid side chain of an antibody via an N-glycosidic bond and an O-glycosidic bond, respectively.

Ab of the present invention is IgG, and preferably IgG1, IgG2, or IgG4.

IgG has a well conserved N-linked glycan on an asparagine residue at the 297-position of the Fc region of the heavy chain (hereinafter, referred to as "Asn297 or N297"), and the N-linked glycan is known to contribute to the activity and kinetics of the antibody molecule. (Biotechnol. Prog., 2012, 28, 608-622, Sanglier-Cianferani, S., Anal. Chem., 2013, 85, 715-736)

The amino acid sequence in the constant region of IgG is well conserved, and each amino acid is specified by Eu index numbering in Edelman et al. (Proc. Natl. Acad. Sci. U.S.A., Vol. 63, No. 1 (May 15, 1969), pp. 78-85). For example, Asn297, to which an N-linked glycan is added in the Fc region, corresponds to the 297-position in Eu index numbering, and each amino acid is uniquely specified by Eu index numbering, even if the actual position of the amino acid has varied through fragmentation of the molecule or deletion of a region.

In the antibody-drug conjugate of the present invention, the antibody or functional fragment of the antibody more preferably bonds to L via a glycan bonding to a side chain of Asn297 thereof (hereinafter, referred to as "N297 glycan"), and the antibody or functional fragment of the antibody even more preferably bonds via the N297 glycan to L, wherein the N297 glycan is a remodeled glycan.

The following formula illustrates the situation that the antibody-drug conjugate of the present invention or a functional fragment of the antibody bonds via the N297 glycan to L. [Formula 83]

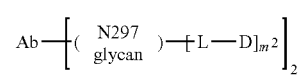  [Formula 83]

An antibody having the remodeled glycan is referred to as a glycan-remodeled antibody.

SGP, an abbreviation for sialyl glycopeptide, is a representative N-linked complex glycan. SGP can be separated/purified from the yolk of a hen egg, for example, by using a method described in WO 2011/0278681. Purified products of SGP are commercially available (Tokyo Chemical Industry Co., Ltd., FUSHIMI Pharmaceutical Co., Ltd.), and may be purchased. For example, disialooctasaccharide (Tokyo Chemical Industry Co., Ltd.), a glycan formed by deleting one GlcNAc at the reducing terminal in the glycan moiety of SG (hereinafter, referred to as "SG (10)", is commercially available.

In the present invention, a glycan structure formed by deleting a sialic acid at a non-reducing terminal only in either one of the branched chains of β-Man in SG (10) refers to MSG (9), and a structure having a sialic acid only in the 1-3 branched chain is called as MSG1, and a structure having a sialic acid only in the 1-6 branched chain is called as MSG2.

The remodeled glycan of the present invention is N297-(Fuc)MSG1, N297-(Fuc)MSG2, or a mixture of N297-(Fuc)MSG1 and N297-(Fuc)MSG2, or N297-(Fuc)SG, and is preferably N297-(Fuc)MSG1, N297-(Fuc)MSG2, or N297-(Fuc)SG, and is more preferably N297-(Fuc)MSG1 or N297-(Fuc)MSG2.

N297-(Fuc)MSG1 is represented by the following structural formula or sequence formula:

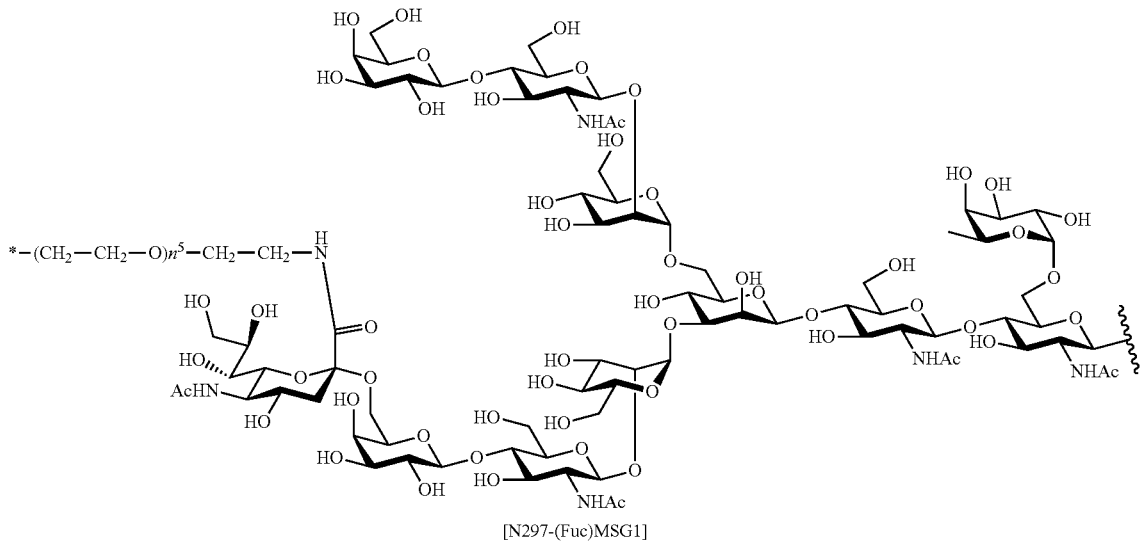

[Formula 84]

[N297-(Fuc)MSG1]

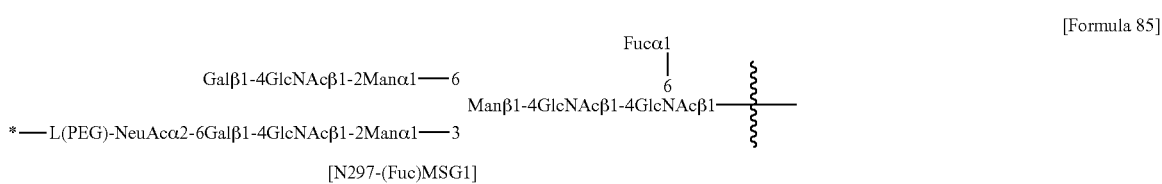

[Formula 85]

[N297-(Fuc)MSG1]

In the formulas, each wavy line represents bonding to Asn297 of the antibody,

L(PEG) represents —(CH$_2$CH$_2$—O)n$^5$-CH$_2$CH$_2$—NH—, wherein the amino group at the right end represents amide-bonding to carboxylic acid at the 2-position of a sialic acid at the non-reducing terminal in the 1-3 branched chain of β-Man in the N297 glycan, each asterisk represents bonding to linker L, in particular, a nitrogen atom at the 1- or 3-position of the 1,2,3-triazole ring of Lb in linker L, and n$^5$ is an integer of 2 to 10, and preferably an integer of 2 to 5.

N297-(Fuc)MSG2 is represented by the following structural formula or sequence formula:

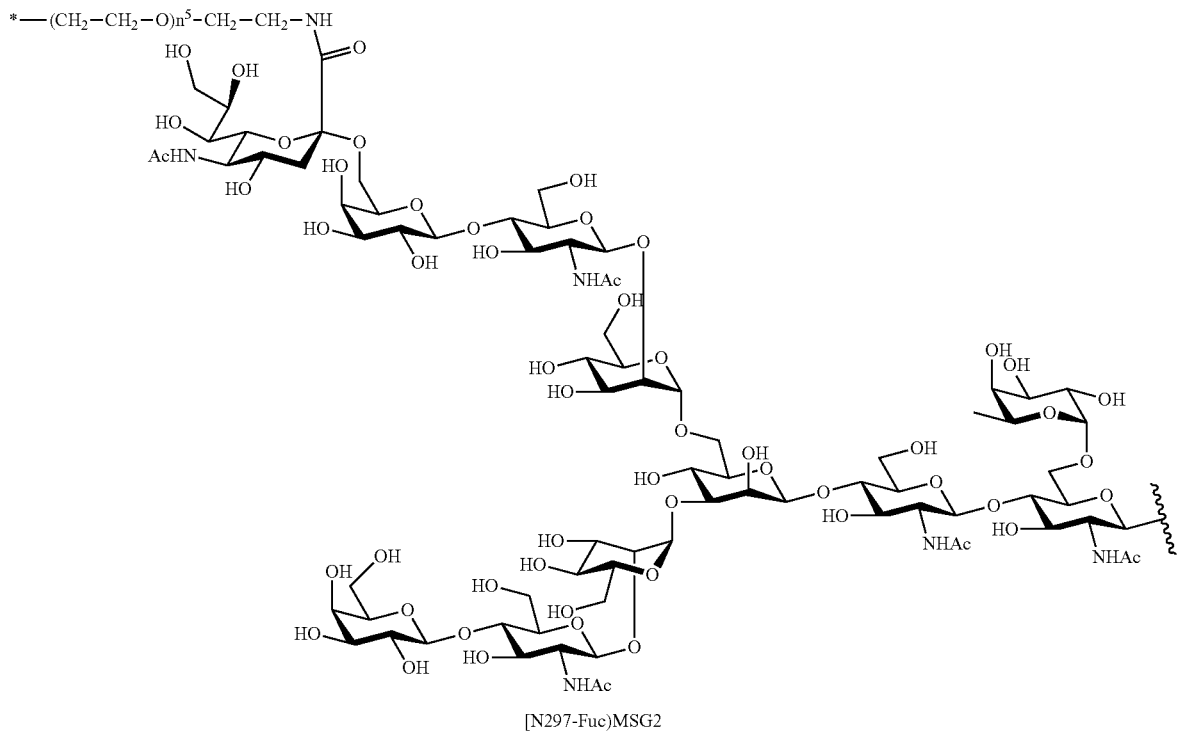

[N297-Fuc)MSG2

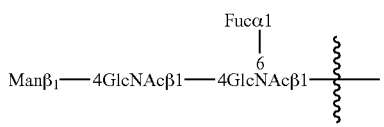

[N297-(Fuc)MSG1)

In the formulas, each wavy line represents bonding to Asn297 of the antibody,

L(PEG) represents —(CH$_2$CH$_2$—O)n$^5$-CH$_2$CH$_2$—NH—, wherein the amino group at the right end represents amide-bonding to carboxylic acid at the 2-position of a sialic acid at the non-reducing terminal in the 1-6 branched chain of β-Man in the N297 glycan, each asterisk represents bonding to linker L, in particular, a nitrogen atom at the 1- or 3-position of the 1,2,3-triazole ring of Lb in linker L, and n$^5$ is an integer of 2 to 10, and preferably an integer of 2 to 5.

N297-(Fuc)SG is represented by the following structural formula or sequence formula:

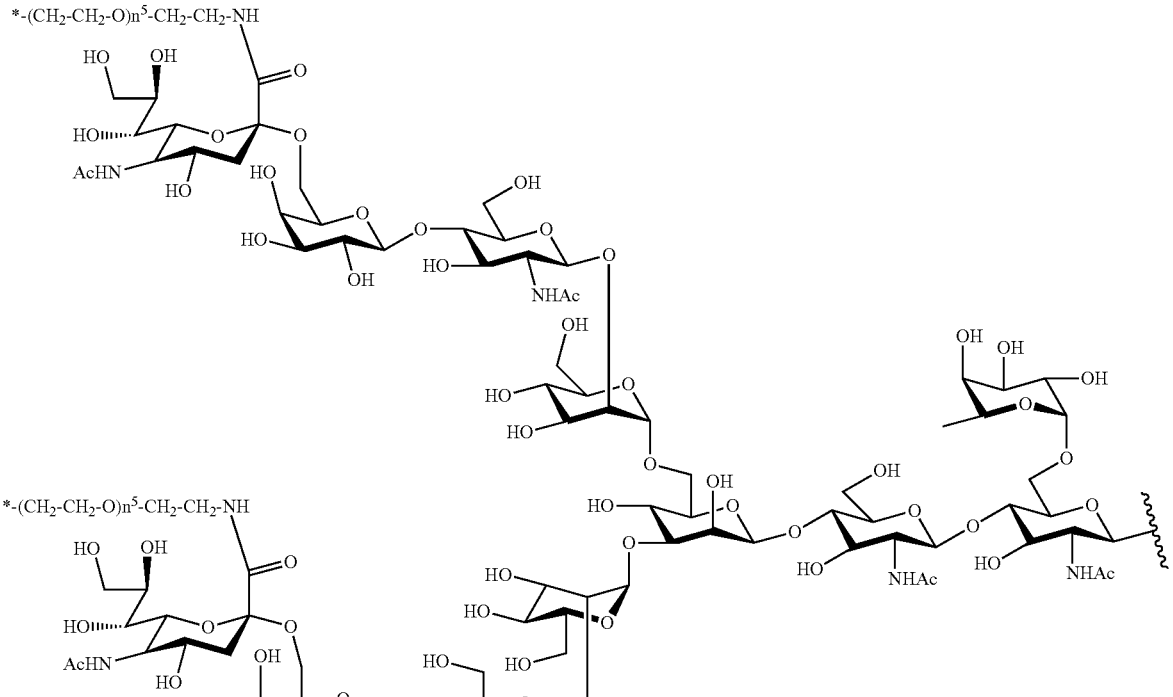

[Formula 88]

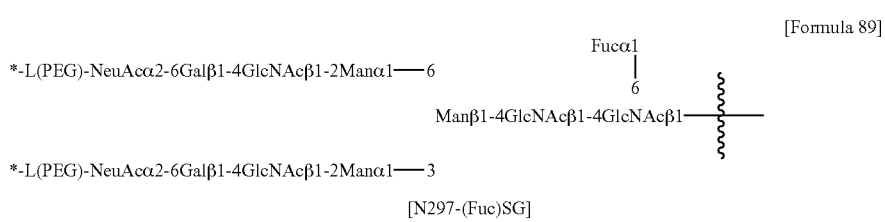

[Formula 89]

[N297-(Fuc)SG]

In the formulas, each wavy line represents bonding to Asn297 of the antibody,

L(PEG) represents —(CH$_2$CH$_2$—O)n$^5$-CH$_2$CH$_2$—NH—, wherein the amino group at the right end represents amide-bonding to carboxylic acid at the 2-position of a sialic acid at the non-reducing terminal in each of the 1-3 and 1-6 branched chains of β-Man in the N297 glycan, each asterisk represents bonding to linker L, in particular, a nitrogen atom at the 1- or 3-position of the 1,2,3-triazole ring of Lb in linker L, and n$^5$ is an integer of 2 to 10, and preferably an integer of 2 to 5.

If N297 glycan of the antibody in the antibody-drug conjugate of the present invention is N297-(Fuc)MSG1, N297-(Fuc)MSG2, or a mixture of them, the antibody-drug conjugate is a molecule to which two molecules of linker L and two molecules of drug D have been conjugated (m$^2$=1) since the antibody is a dimer (see FIG. 1).

For example, Example 74: ADC8 is in the case that N297 glycan is N297-(Fuc)MSG1, and Example 67: ADC1 is in the case that N297 glycan is a mixture of N297-(Fuc)MSG1 and N297-(Fuc)MSG2.

If N297 glycan of the antibody in the antibody-drug conjugate of the present invention is N297-(Fuc)SG, the antibody-drug conjugate is a molecule to which four molecules of linker L and four molecules of drug D have been conjugated (m$^2$=2) since the antibody is a dimer. For example, Example 72: ADC6 is in the case that N297 glycan is N297-(Fuc)SG.

N297 glycan is preferably N297-(Fuc)MSG1, N297-(Fuc)MSG2, or N297-(Fuc)SG, and more preferably N297-(Fuc)MSG1 or N297-(Fuc)MSG2.

If N297 glycan of the antibody in the antibody-drug conjugate of the present invention is N297-(Fuc)MSG1, N297-(Fuc)MSG2, or N297-(Fuc)SG, a homogeneous ADC can be obtained.

The present invention provides a method for producing a remodeled antibody or a functional fragment of the antibody, the method including the following steps of:
 i) culturing the host cell (e.g., an animal cell (such as a CHO cell)) according to any one of [46] to [48] and collecting a targeted antibody from a culture obtained;
 ii) treating the antibody obtained in step i) with hydrolase to produce an antibody with N297 glycan being (Fucα1,6)GlcNAc ((Fucα1,6)GlcNAc-antibody) (FIG. 3A);
  preferably further purifying the (Fucα1,6)GlcNAc-antibody through a step including purification of the reaction solution with a hydroxyapatite column; and
 any one of iii)-1 and iii)-2 (FIG. 3B):
 iii)-1 reacting the (Fucα1,6)GlcNAc-antibody with a glycan donner molecule in the presence of transglycosidase to synthesize a glycan-remodeled antibody with an azide group introduced to a sialic acid, the glycan donner molecule obtained by introducing a PEG linker having an azide group ($N_3$-L(PEG)) to the carbonyl group of carboxylic acid at the 2-position of a sialic acid in MSG (9) or SG (10) and oxazolinating the reducing terminal; and
 iii)-2 reacting the (Fucα1,6)GlcNAc-antibody with a glycan donner molecule in the presence of transglycosidase to synthesize a glycan-remodeled antibody with an azide group introduced to a sialic acid, the glycan donner molecule obtained by introducing a PEG linker having an azide group ($N_3$-L(PEG)) to the carbonyl group of carboxylic acid at the 2-position of a sialic acid in (MSG-)Asn or (SG-)Asn with an α-amino group optionally protected or modified and to the carbonyl group of carboxylic acid in the Asn, utilizing hydrolase, and then oxazolinating the reducing terminal.

The present invention includes glycan-remodeled antibodies and functional fragments of the antibodies, and modified variants of the antibodies and functional fragments obtained by using the production method.

The production intermediate of the present antibody-drug conjugate has an alkyne structure reactive with an azide group, such as DBCO (dibenzocyclooctyne). Therefore, the antibody-drug conjugate of the present invention can be produced by reacting the production intermediate with an MSG1-type, MSG2-type, or SG-type glycan-remodeled antibody or a functional fragment of the antibody, where the antibody, in which a PEG linker having an azide group has been introduced to a sialic acid of a glycan, is obtained through steps i) to iii).

With regard to N297 glycan in the present invention, fucosylated GlcNAc ((Fucα1,6)GlcNAc) at the reducing terminal is preferably derived from an antibody produced in an animal cell, and a portion of the glycan located to the non-reducing terminal side of (Fucα1,6)GlcNAc preferably has been remodeled into the above-described glycan structure as MSG (MSG1, MSG2) or SG. In each case, carboxylic acid bonding to the 2-position of a sialic acid at the non-reducing terminal is used for bonding to L(PEG).

Figure 2A:
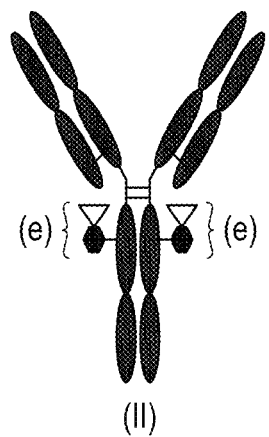
FIGS. 2A and 2B are schematic diagrams illustrating the structures of a (Fucα1,6)GlcNAc-antibody (the molecule of FIG. 2A in (II) of FIGS. 2A and 2B), which is a production intermediate of the drug-conjugate of the present invention, and an MSG-type glycan-remodeled antibody (the molecule of (III) in FIG. 2B of FIGS. 2A and 2B). In each of the diagrams, the Y-shaped diagram represents antibody Ab as in FIG. 1.
Figure 3A:
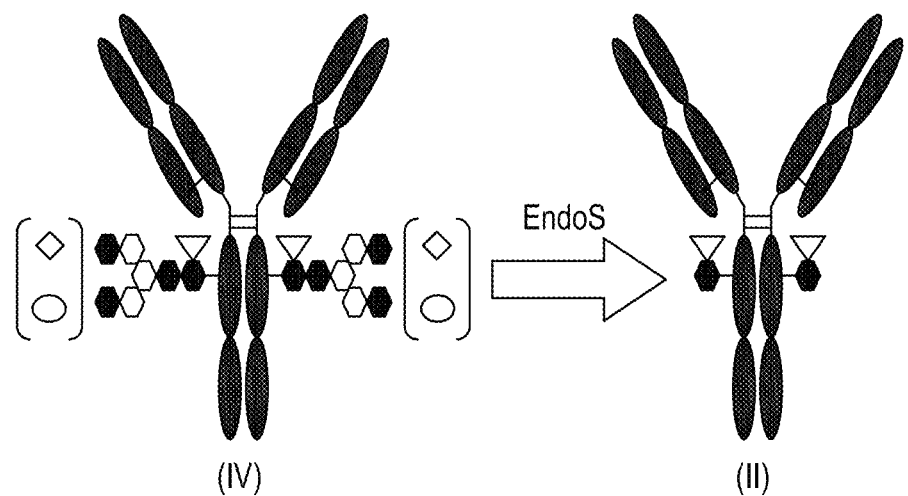
FIGS. 3A and 3B are schematic diagrams for the step of producing an MSG-type glycan-remodeled antibody from an antibody produced in an animal cell. As in FIGS. 2A and 2B, molecules (II) and (III) in this Figure represent an (Fucα1,6)GlcNAc-antibody and an MSG-type glycan-remodeled antibody, respectively. Molecule (IV) is an antibody produced in an animal cell, and is a mixture of molecules with heterogeneous N297 glycan moieties.
Figure 3B:
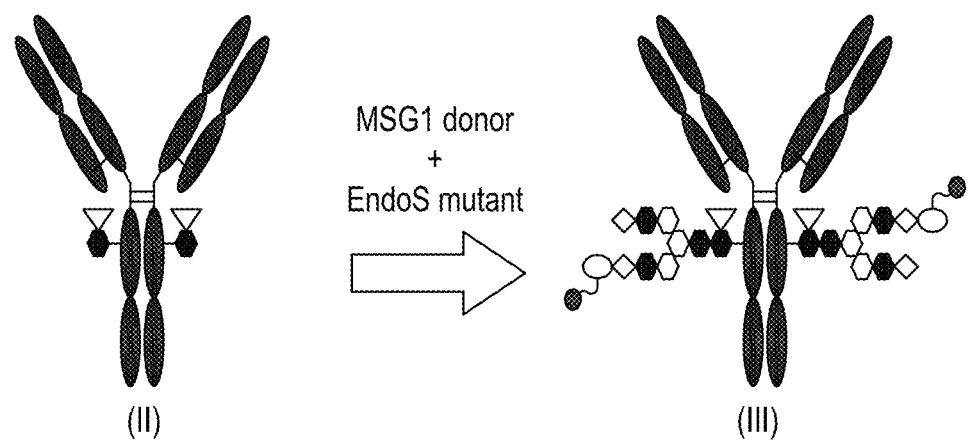

Such a glycan-remodeled antibody having MSG- (MSG1-, MSG2-) or SG-type N297 glycan may be produced by using a method as illustrated in FIGS. 3A and 3B, for example, in accordance with a method described in WO 2013/120066. If an antibody is produced as a gene-recombinant protein by using an animal cell as a host in accordance with a known method (step i), the N297 glycan has, as a base structure, a fucosylated N-linked glycan structure, whereas a mixture of antibody molecules having glycans of various structures with various modifications for the structure of the non-reducing terminal or constituent saccharides or fragments of such antibody molecules is provided (IV in FIG. 3A). Treatment of such an antibody produced with an animal cell with hydrolase such as EndoS causes hydrolysis of the glycosidic bond at GlcNAcβ1-4GlcNAc in the chitobiose structure at the reducing terminal, providing antibody molecules of single glycan structure having only (Fucα1,6)GlcNAc as N297 glycan (referred to as "(Fucα1, 6)GlcNAc-antibody", see FIG. 2A) (FIG. 3A) (step ii)).

For the enzyme for the hydrolysis reaction of N297 glycan, for example, EndoS or a variant enzyme retaining the hydrolysis activity may be used.

Figure 2B:
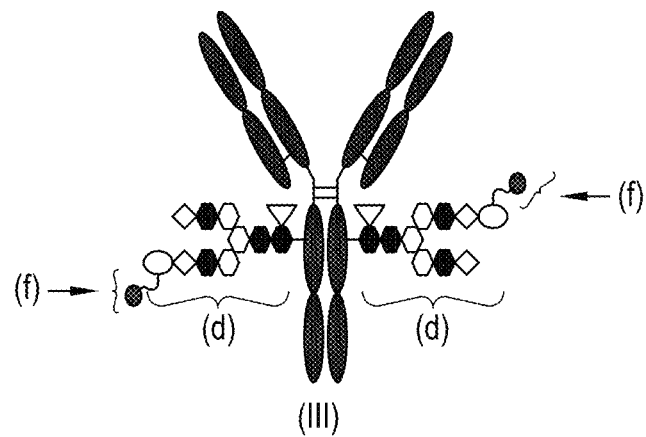

By reacting the (Fucα1,6)GlcNAc-antibody obtained in the above hydrolysis reaction, as a glycan acceptor molecule, and an MSG- (MSG1-, MSG2-) or SG-type glycan donor molecule with use of transglycosidase (e.g., WO 2017010559) such as EndoS D233Q and EndoS D233Q/Q303L variants, an antibody of the above-described structure including MSG-(MSG1-, MSG2-) or SG type N297 glycan (see FIG. 2B) can be obtained (FIG. 3B) (step iii)-1, iii)-2).

If the number of conjugated drug molecules per antibody molecule, $m^2$, in the antibody-drug conjugate is 1, a glycan donor molecule having MSG, MSG1, or MSG2 as glycan is employed. For such glycan, commercially available monosialo-Asn free (1S2G/1G2S-10NC-Asn, GlyTech, Inc., hereinafter, referred to as "(MSG-)Asn") as a raw material may be separated in accordance with a method described in Example 56 to obtain (MSG-)Asn1 or (MSG2-)Asn, which may be employed, or a mixture of them may be employed without separation.

If the number of conjugated drug molecules per antibody molecule, $m^2$, in the antibody-drug conjugate is 2, a glycan donor molecule including SG (10) as glycan is used for the transglycosylation reaction. For such SG (10) glycan, for example, that obtained from SGP through hydrolysis or the like may be used, or SG (10) glycan such as commercially available disialooctasaccharide (Tokyo Chemical Industry Co., Ltd.) may be used.

MSG- (MSG1-, MSG2-) or SG-type glycan included in the donor molecule has a PEG linker having an azide group ($N_3$-L(PEG)) at the 2-position of a sialic acid therein. To introduce a PEG linker having an azide group ($N_3$-L(PEG)) to the 2-position of a sialic acid, a reaction known in the field of synthetic organic chemistry (e.g., condensation reaction) may be used for MSG (MSG (9)), MSG1, or MSG2, or disialooctasaccharide (SG (10)) and the PEG linker having an azide group ($N_3$-L(PEG)) $N_3$—($CH_2CH_2$—O)$n_5$-$CH_2CH_2$—$NH_2$, wherein $n^5$ is an integer of 2 to 10, and preferably represents an integer of 2 to 5. Specifically, carboxylic acid at the 2-position of a sialic acid and the amino group at the right end of $N_3$—($CH_2CH_2$—O)$n_5$-$CH_2CH_2$—$NH_2$ undergo condensation reaction to form an amide bond.

Alternatively, MSG- (MSG1-, MSG2-) or SG-type glycan may be obtained by introducing a PEG linker having an azide group ($N_3$—($CH_2CH_2$—O)$n_5$-$CH_2CH_2$—$NH_2$) to carboxylic acid at the 2-position of a sialic acid of a raw material such as (MSG1-)Asn, (MSG2-)Asn, and (SG-)Asn (GlyTech, Inc.) with an α-amino group optionally protected or modified, and to carboxylic acid of the Asn with use of condensation reaction, and utilizing hydrolase such as EndoM and EndoRp (iii)-2). Examples of protective groups for α-amino groups may include, but not limited to, an acetyl (Ac) group, a t-butoxycarbonyl (Boc) group, a benzoyl (Bz) group, a benzyl (Bzl) group, a carbobenzoxy (Cbz)

group, and a 9-fluorenylmethoxycarbonyl (Fmoc) group. The protective group for α-amino groups is preferably an Fmoc group.

Examples of modifying groups for α-amino groups include modifying groups that enhance solubility in water with a hydroxyacetyl group, a PEG structure, or the like.

An α-amino group of (MSG1-)Asn, (MSG-2)Asn, or (SG-)Asn is preferably protected with any of the protective groups. If an α-amino group is protected with a protective group (e.g., an Fmoc group), the protective group may be removed, as necessary, after introduction of a PEG linker having an azide group and before causing action of hydrolase.

It is preferred to use an activated form such as an oxazolinated form formed by treatment with 2-chloro-1,3-dimethyl-1H-benzimidazol-3-ium-chloride for GlcNAc at the reducing terminal of MSG (MSG1, MSG2) or SG-type glycan included in the molecule.

Various enzymes for use in transglycosylation reaction (transglycosidase) may be employed that have activity of transferring complex glycan to N297 glycan; however, EndoS D233Q, a modified product for which hydrolysis reaction is suppressed by substituting Asp at the 233-position of EndoS with Gln, is a preferred transglycosidase. Transglycosylation reaction using EndoS D233Q is described, for example, in WO 2013/120066. Alternatively, a modified enzyme such as EndoS D233Q/Q303L (WO 2017010559), which is obtained by further adding a mutation to EndoS D233Q, may be used.

The purification operation for the antibody after the glycan remodeling for the antibody (glycohydrolysis and transglycosylation reaction) is intended to separate low-molecular-weight compounds and enzymes used for the reaction, and gel filtration chromatography, ion-exchange chromatography, affinity chromatography, and so on are typically used for such purification, and additional purification with a hydroxyapatite column may be further carried out. That is, the present invention provides a method for producing a drug-conjugate, the method including, subsequent to the step of purifying an intermediate from reaction solution after glycohydrolysis of an antibody, the additional step of purifying with a hydroxyapatite column. According to an example of reports on glycan remodeling (J. Am. Chem. Soc. 2012, 134, 12308-12318., Angew. Chem. Int. Ed. 2016, 55, 2361-2367), reaction solution after treatment of an antibody with hydrolase is purified only with a Protein A column (affinity chromatography column); however, this purification method has been proved to be incapable of completely removing hydrolase (e.g., EndoS), and affect the subsequent transglycosylation reaction because of the residual enzyme. In view of such a result, examination was made on purification methods to find that when purification of reaction solution after treatment of an antibody with hydrolase was carried out using a Protein A column and a hydroxyapatite column (CHT column, Bio-Rad Laboratories, Inc.) in the order presented, the reaction efficiency of the subsequent glycosylation reaction was enhanced, without the influence of a residual enzyme.

The antibody-drug conjugate of the present invention is the most preferably one antibody-drug conjugate selected from the following group:

[Formula 90]

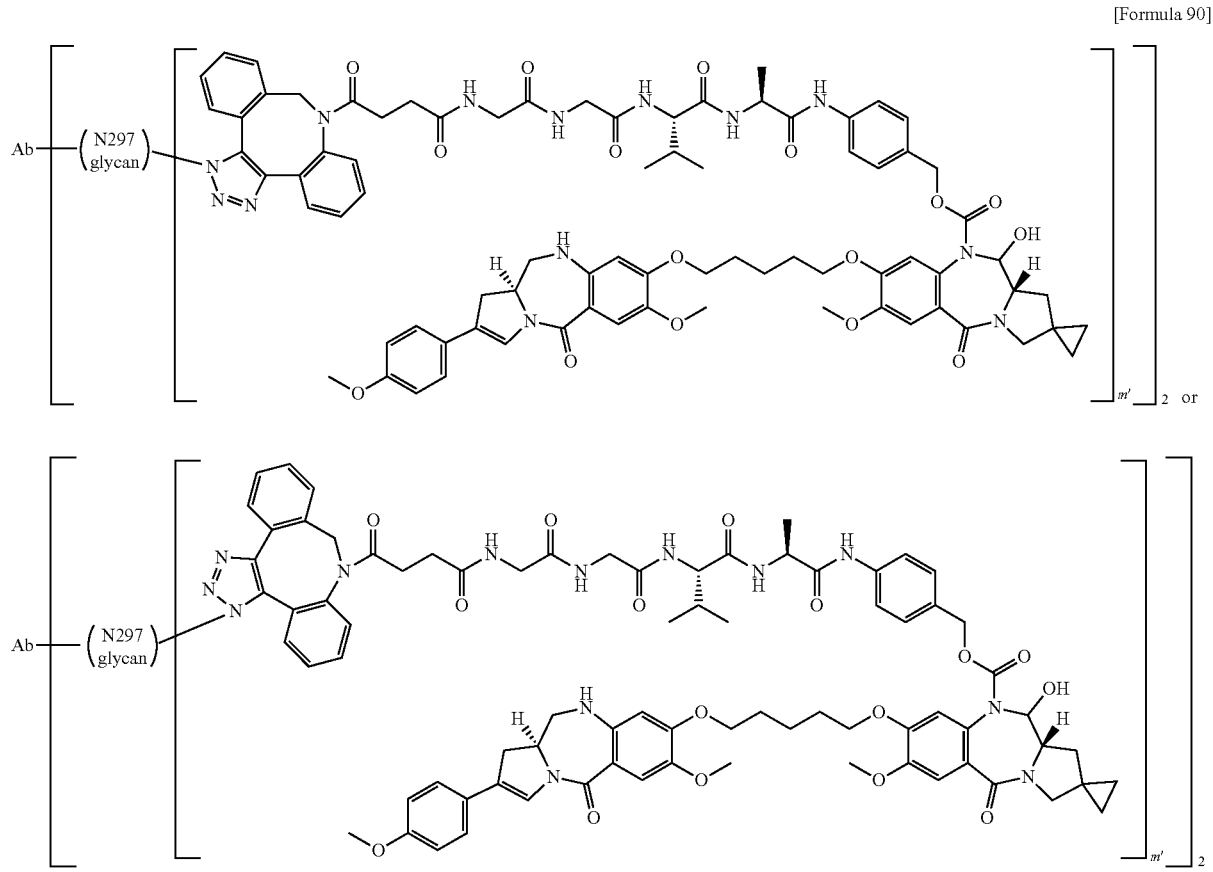

[Formula 91]
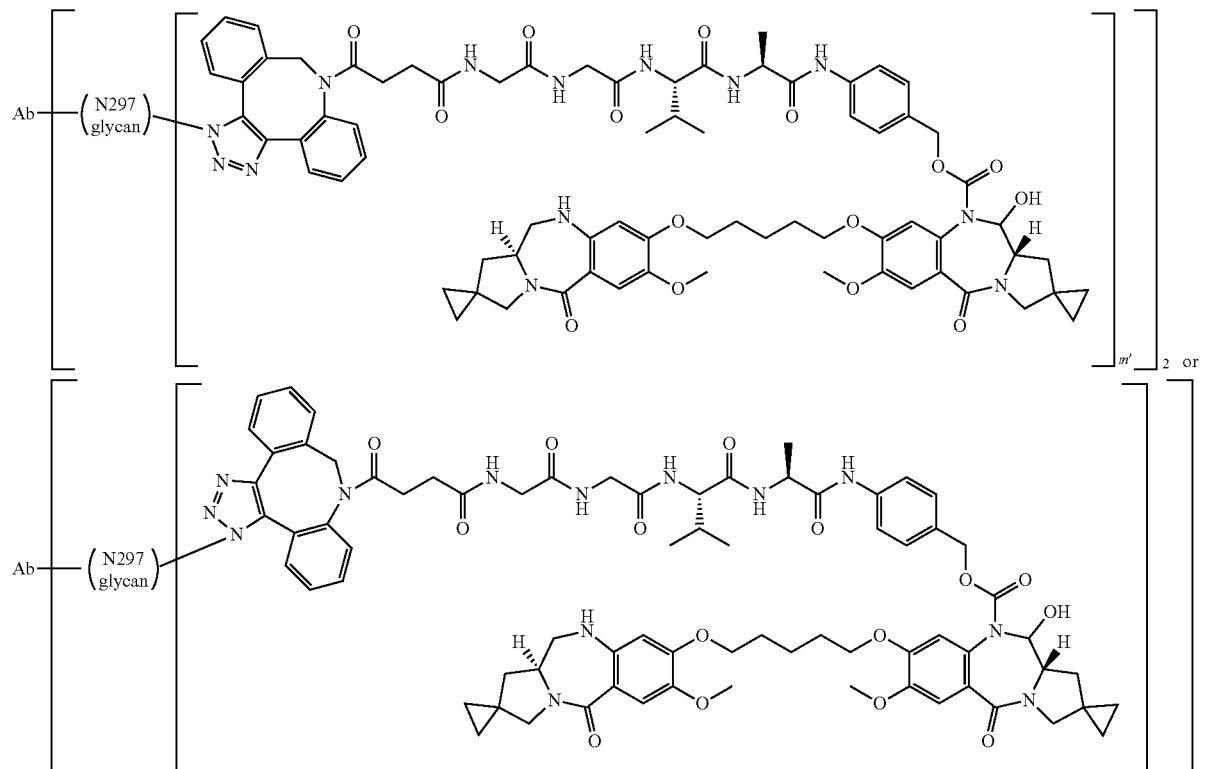
[Formula 92]
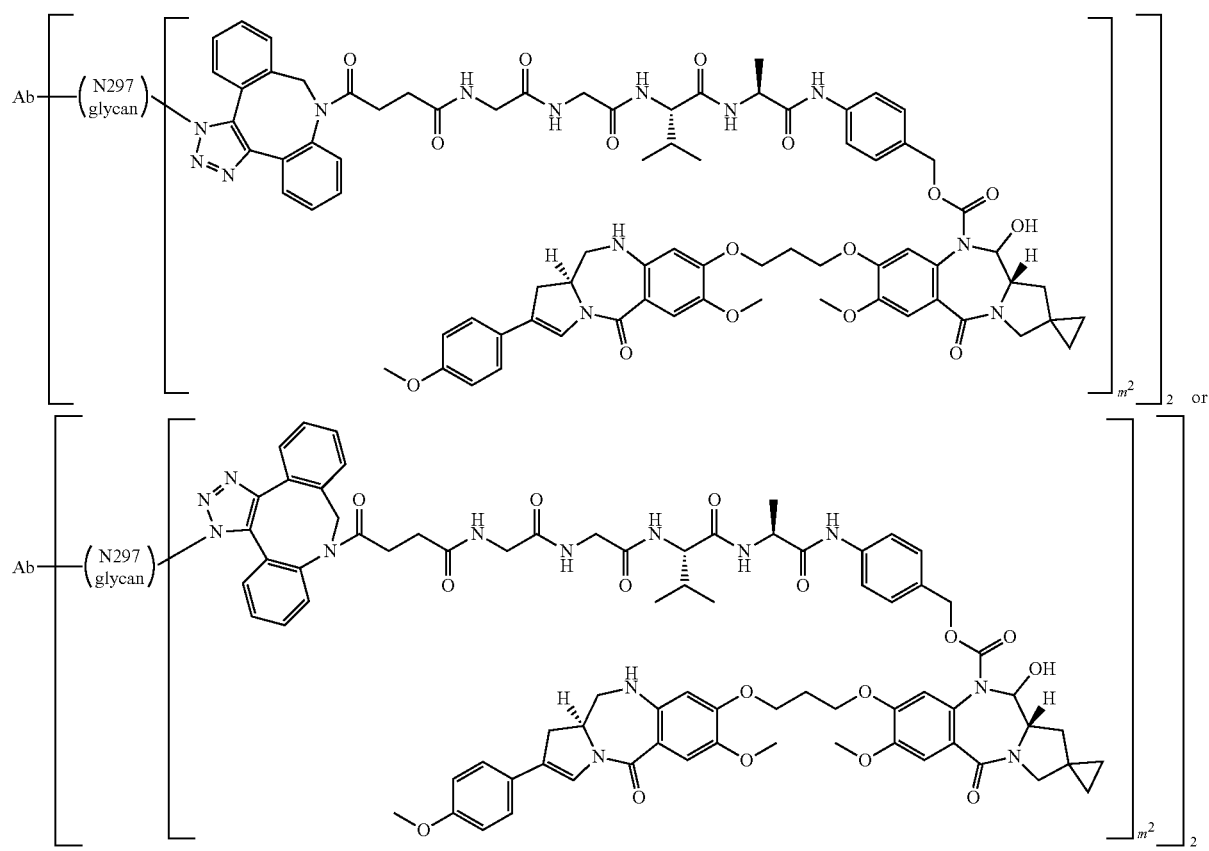

[Formula 93]
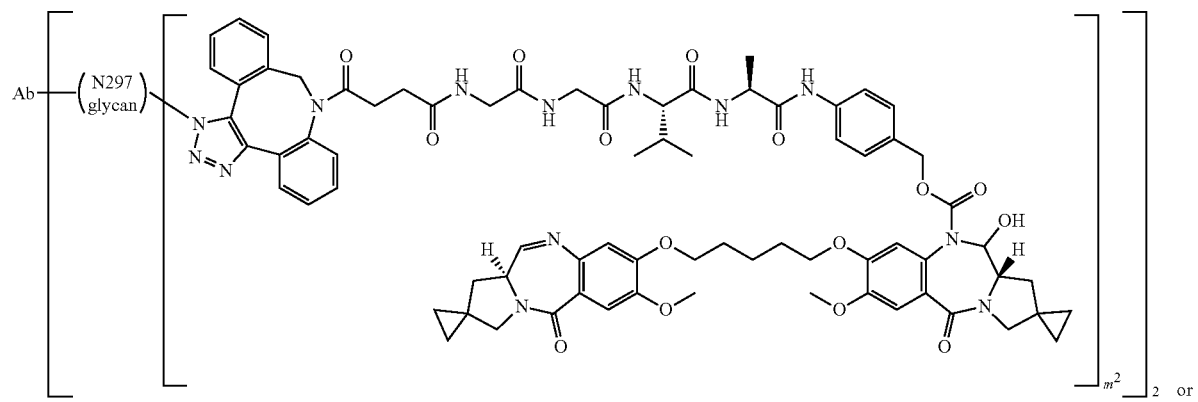
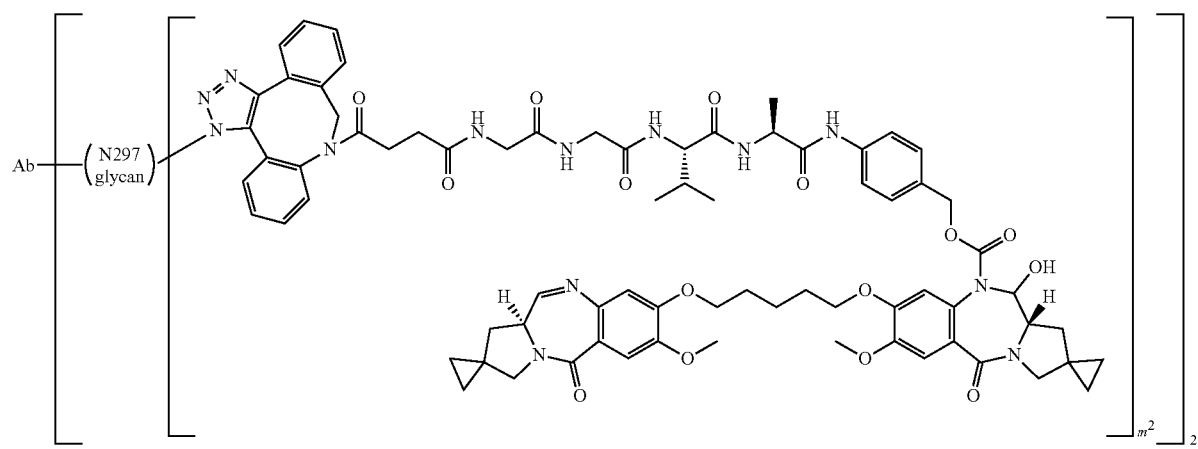
[Formula 94]
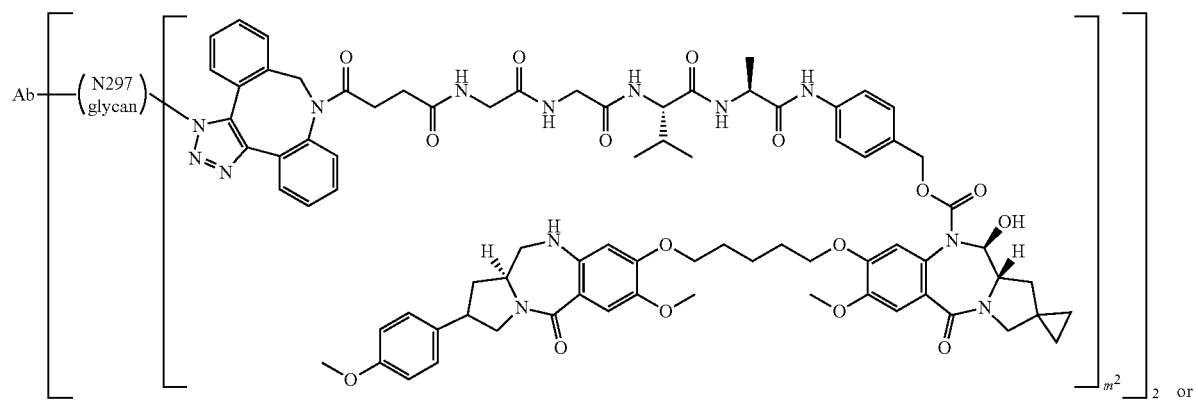

-continued
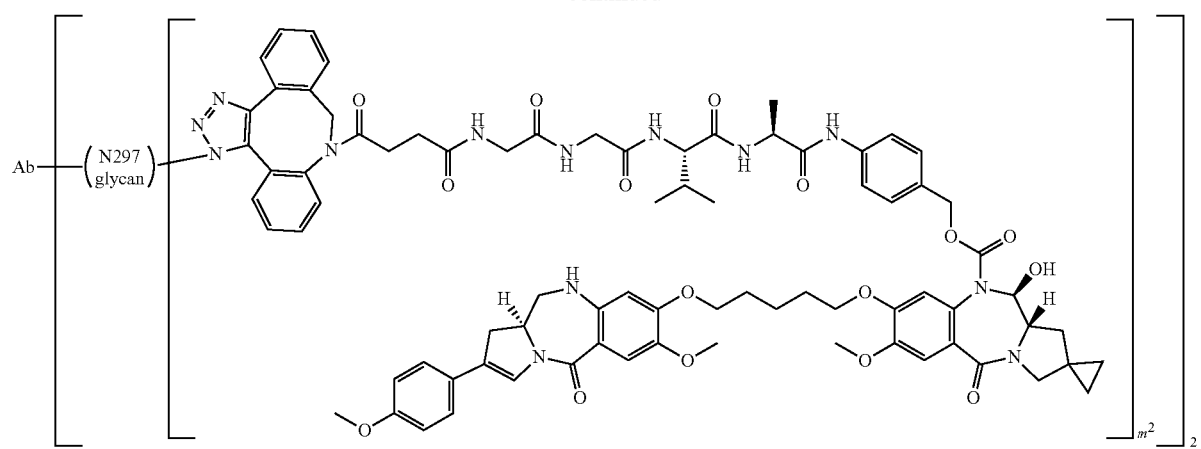
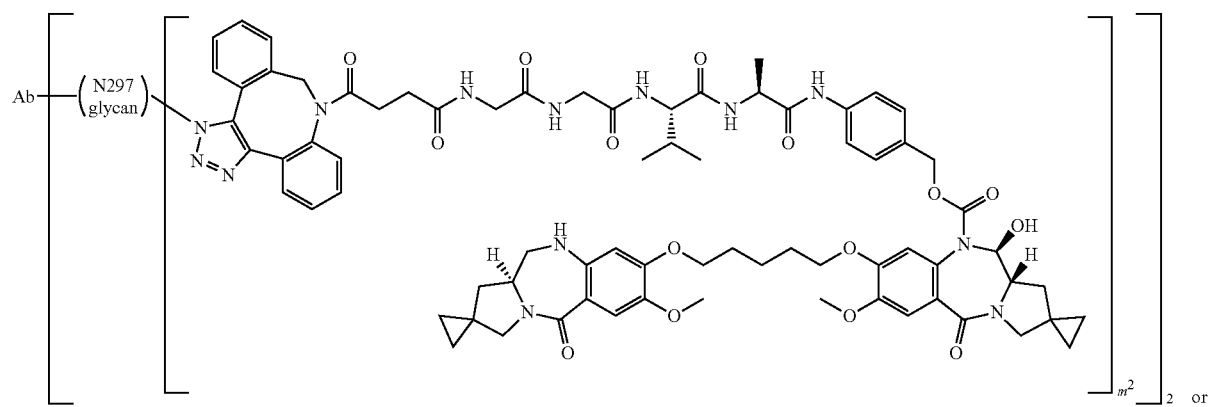
[Formula 95]
or
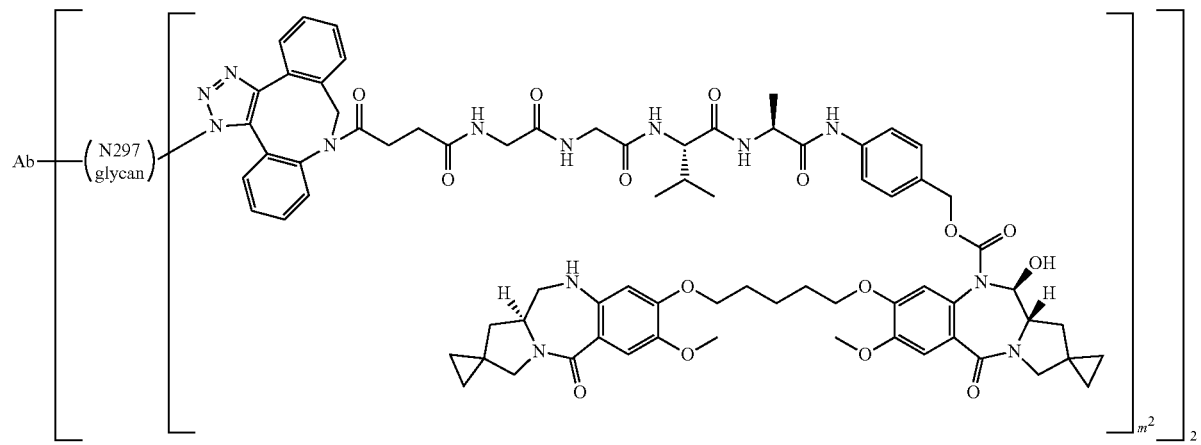

-continued
[Formula 96]
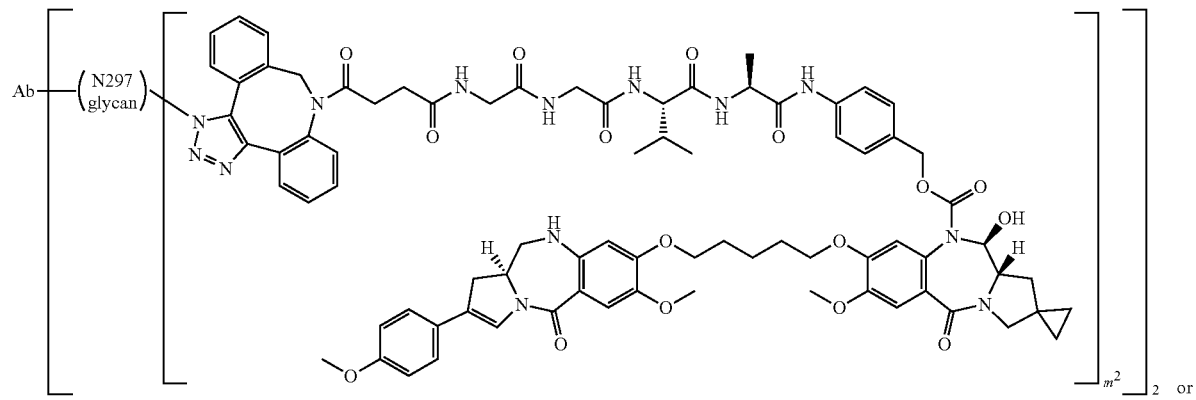
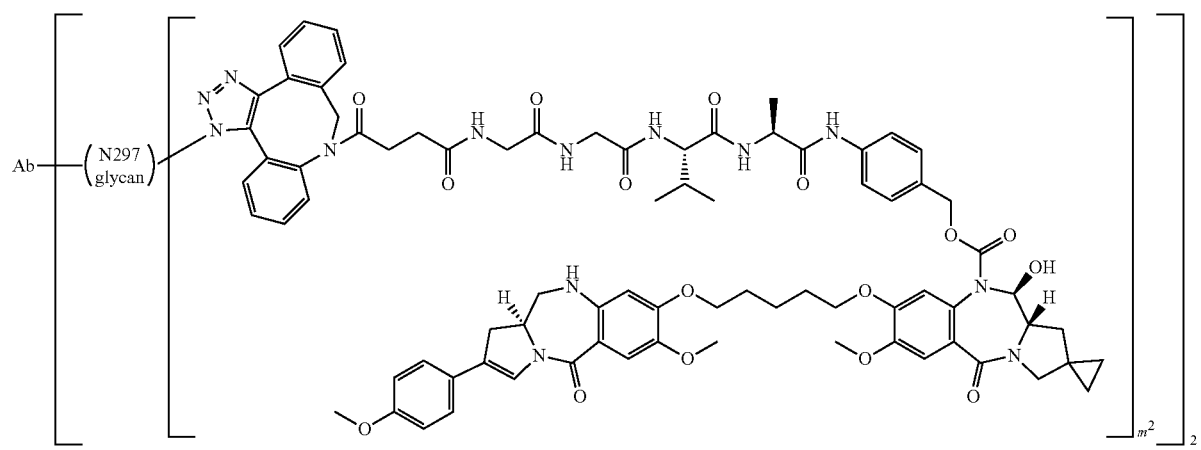
[Formula 97]
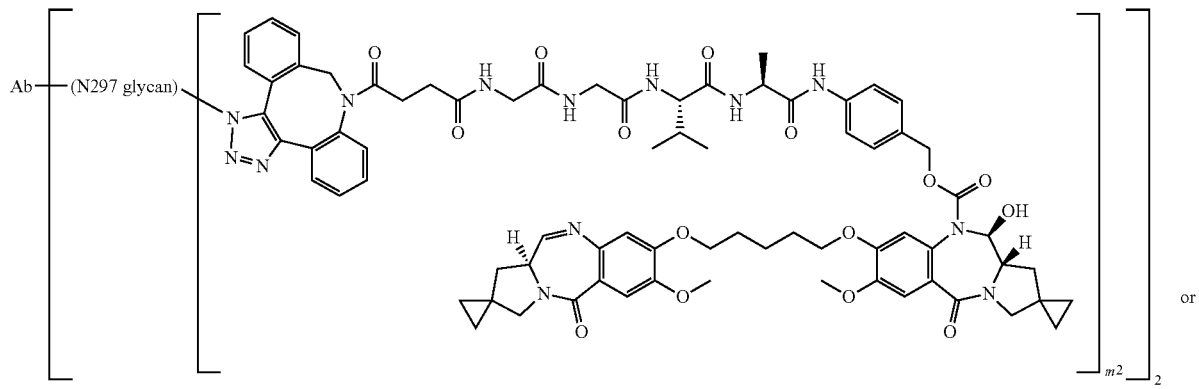

-continued
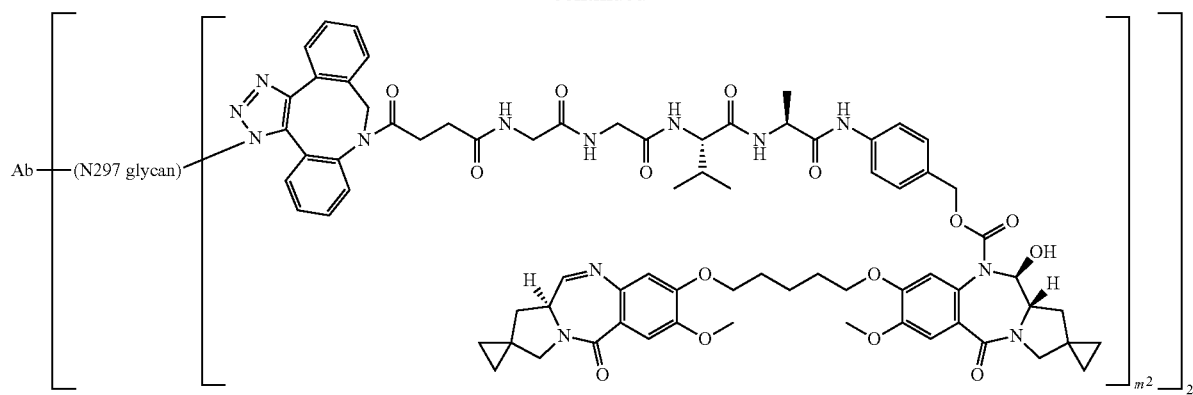
[Formula 98]
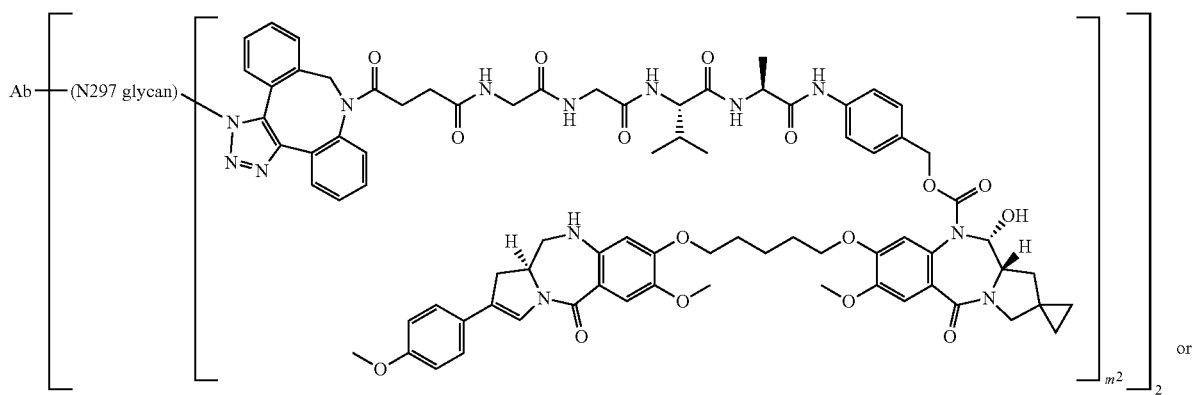
or
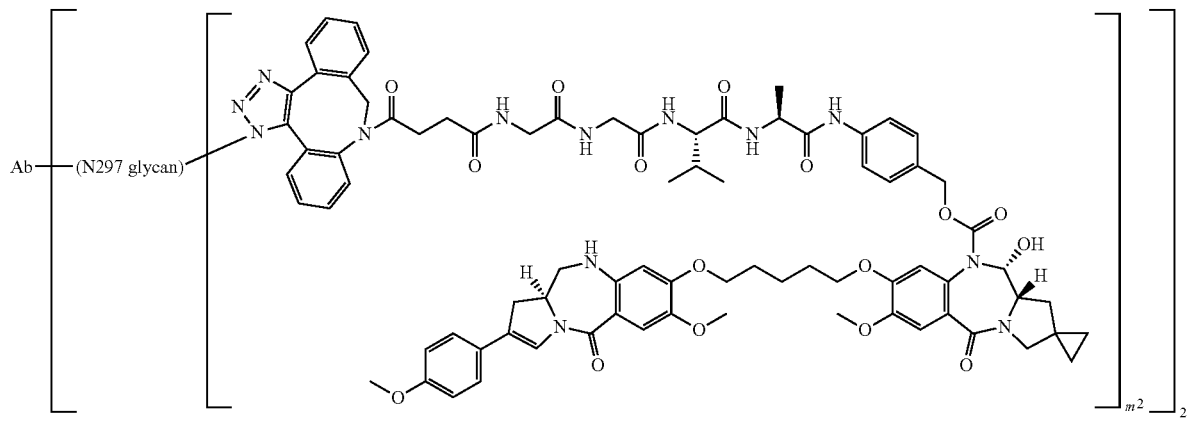
[Formula 99]
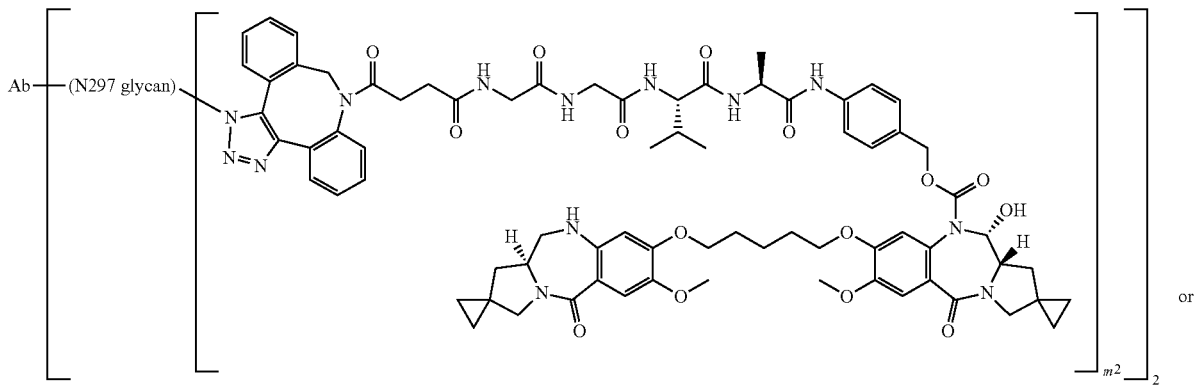
or -continued
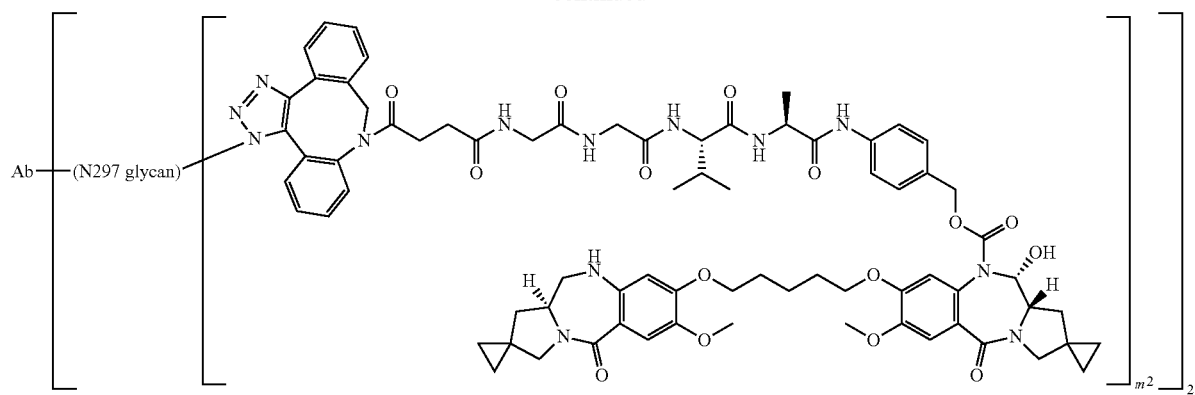
[Formula 100]
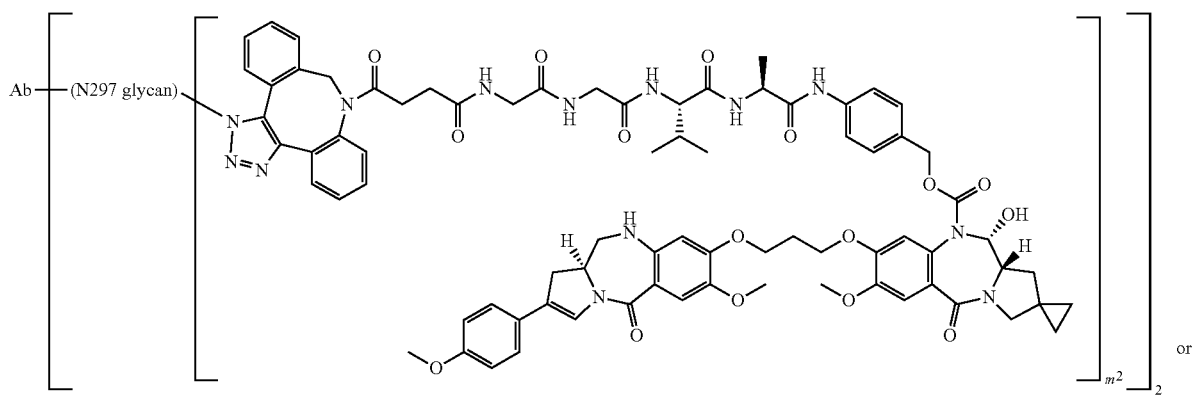
or
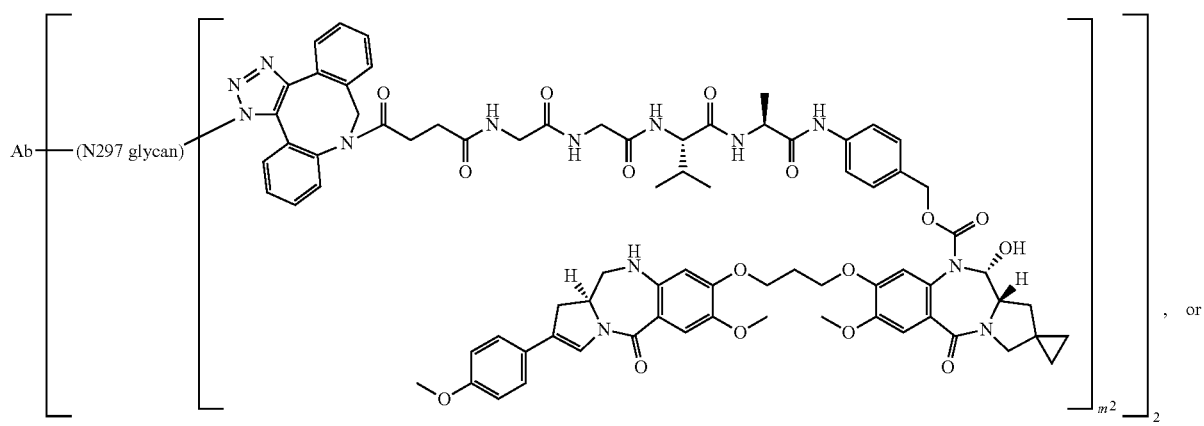
, or
[Formula 101]
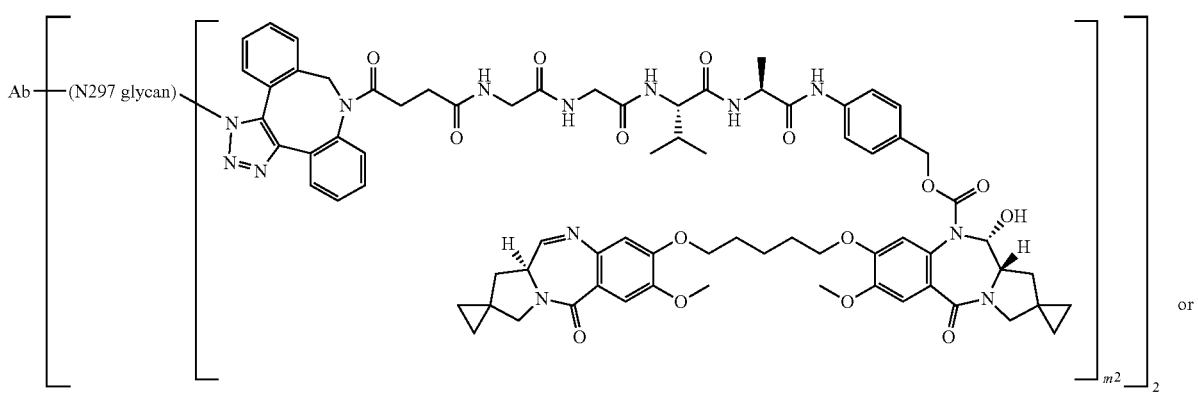
or -continued

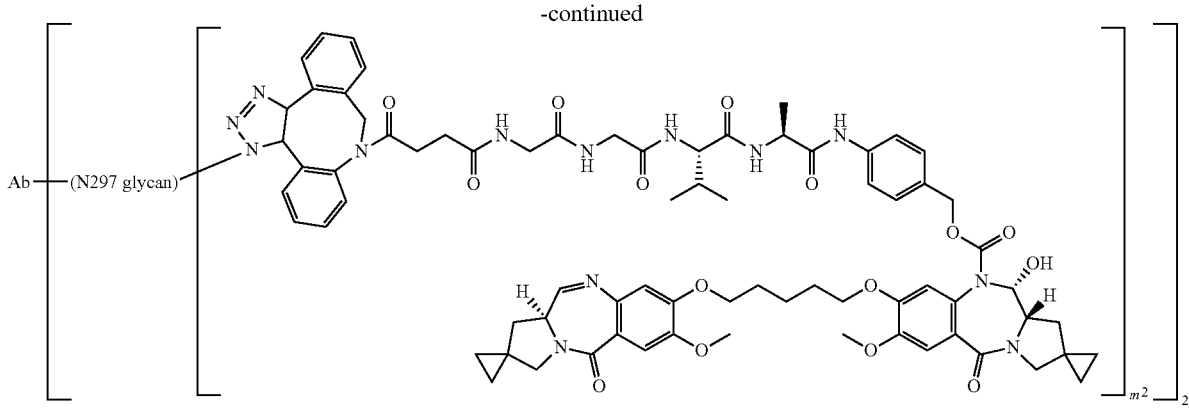

In each of the structural formulas above, $m^2$ represents 1 or 2 (preferably, $m^2$ is 1), antibody Ab is an IgG antibody (preferably, IgG1, IgG2, or IgG4, more preferably, IgG1), or a functional fragment of the antibody, N297 glycan represents any one of N297-(Fuc)MSG1, N297-(Fuc)MSG2, and a mixture of them, and N297-(Fuc)SG (preferably, N297-(Fuc)MSG1), L(PEG) represents —NH—CH$_2$CH$_2$—(O—CH$_2$CH$_2$)$_3$—*, wherein the amino group at the left end represents amide-bonding to carboxylic acid at the 2-position of a sialic acid at the non-reducing terminal of each or either one of the 1-3 and 1-6 branched chains (preferably, the 1-3 branched chain) of β-Man in N297 glycan, and the asterisk represents bonding to a nitrogen atom at the 1- or 3-position of the triazole ring of Lb in linker L.

Although structures with two or four units ($m^2$=1 or 2) of "—(N297 glycan)-L-D" in each of which N297 glycan bonds to the nitrogen atom at the 1-position of the triazole ring of Lb in L in one conjugate molecule ("(N297 glycan)-(N1Lb)L-D") or structures with two or four units ($m^2$=1 or 2) of "—(N297 glycan)-L-D" in each of which N297 glycan bonds to the nitrogen atom at the 3-position of the triazole ring of Lb in L in one conjugate molecule ("(N297 glycan)-(N3Lb)L-D") are illustrated as the most preferred antibody-drug conjugate for convenience, antibody-drug conjugates having both "(N297 glycan)-(N1Lb)L-D" (if $m^2$=1, then one unit, if $m^2$=2, then one, two, or three units) and "(N297 glycan)-(N3Lb)L-D" (if $m^2$=1, then one unit, if $m^2$=2, then three, two, or one unit) in one conjugate molecule are also included. In other words, either one of "(N297 glycan)-(N1Lb)L-D" and "(N297 glycan)-(N3Lb)L-D" exists or both of them coexist in one conjugate molecule.

Further, Ab is preferably an anti-CLDN6 antibody, an anti-CLDN6/CLDN9 antibody, an anti-HER2 antibody, an anti-DLL3 antibody, an anti-FAP antibody, an anti-CDH11 antibody, an anti-A33 antibody, an anti-CanAg antibody, an anti-CD19 antibody, an anti-CD20 antibody, an anti-CD22 antibody, an anti-CD30 antibody, an anti-CD33 antibody, an anti-CD56 antibody, an anti-CD70 antibody, an anti-CD98 antibody, an anti-TROP2 antibody, an anti-CEA antibody, an anti-Cripto antibody, an anti-EphA2 antibody, an anti-FGFR2 antibody, an anti-G250 antibody, an anti-MUC1 antibody, an anti-GPNMB antibody, an anti-integrin antibody, an anti-PSMA antibody, an anti-tenascin-C antibody, an anti-SLC44A4 antibody, an anti-mesothelin antibody, an anti-EGFR antibody, or an anti-DR5 antibody, more preferably an anti-CLDN6 antibody, an anti-CLDN6/CLDN9 antibody, an anti-HER2 antibody, an anti-CD98 antibody, or an anti-TROP2 antibody, and even more preferably the anti-CLDN6 antibody (e.g., Example 106, 107, 108, 109) or anti-HER2 antibody (e.g., trastuzumab, a trastuzumab variant).

The antibody-drug conjugate of the present invention and the anti-CLDN6 antibody- or anti-HER2 antibody-drug conjugate of the present invention exhibit strong tumor activity (in vivo antitumor activity, in vitro anticellular activity) and satisfactory in vivo kinetics and physical property, and have high safety, and hence are useful as a pharmaceutical.

There may exist stereoisomers, optical isomers due to an asymmetric carbon atom, geometric isomers, tautomers, or optical isomers such as d-forms, 1-forms and atropisomers for the antibody-drug conjugate of the present invention, and a free drug or production intermediate of the antibody-drug conjugate, and these isomers, optical isomers, and mixtures of them are all included in the present invention. PBD derivative (V) or (VI) of the present invention has an asymmetric carbon at the 11-position, and thus there exist optical isomers. Herein, these isomers and mixtures of these isomers are all represented by a single formula, namely, general formula (V) or (VI). Accordingly, (V) or (VI) includes all the optical isomers and mixtures of the optical isomers at any ratio. The absolute steric configuration at the 11-position of (V) or (VI) can be determined through X-ray crystal structure analysis or NMR such as a Mosher method for its crystalline product or intermediate, or a derivative thereof. Then, the absolute steric configuration may be determined by using a crystalline product or intermediate derivatized with a reagent having an asymmetric center whose steric configuration is known. As desired, stereoisomers of the synthesized compound according to the present invention may be obtained by isolating with a common optical resolution method or separation method.

The number of conjugated drug molecules per antibody molecule is an important factor having influence on efficacy and safety for the antibody-drug conjugate of the present invention. Antibody-drug conjugates are produced with reaction conditions, such as the amounts of raw materials and reagents to be reacted, specified so as to give a constant number of conjugated drug molecules, but, in contrast to chemical reaction of low-molecular-weight compounds, a mixture with different numbers of conjugated drug molecules is typically obtained. Numbers of conjugated drug molecules per antibody molecule are specified as the average value, namely, the average number of conjugated drug molecules (DAR: Drug to Antibody Ratio). The number of pyrrolobenzodiazepine derivative molecules conjugated to an antibody molecule is controllable, and 1 to 10 pyrrolobenzodiazepine derivative molecules can be conjugated as the average number of conjugated drug molecules per antibody molecule (DAR), but preferably the number is one to eight, and more preferably one to five.

If the antibody bonds via a remodeled glycan of the antibody to L in the antibody-drug conjugate of the present invention, the number of conjugated drug molecules per antibody molecule in the antibody-drug conjugate, $m^2$, is an integer of 1 or 2. If the glycan is N297 glycan and the glycan is N297-(Fuc)MSG1, N297-(Fuc)MSG2, or a mixture of N297-(Fuc)MSG1 and N297-(Fuc)MSG2, $m^2$ is 1, and DAR is in the range of 1 to 3 (preferably, in the range of 1.0 to 2.5, more preferably, in the range of 1.2 to 2.2). If the N297 glycan is N297-(Fuc)SG, $m^2$ is 2, and DAR is in the range of 3 to 5 (preferably, in the range of 3.2 to 4.8, more preferably, in the range of 3.5 to 4.2).

Those skilled in the art could engineer the reaction method to conjugate a required number of drug molecules to each antibody molecule on the basis of the description in Examples herein, and obtain an antibody with a controlled number of conjugated pyrrolobenzodiazepine derivative molecules.

The antibody-drug conjugate, free drug, or production intermediate of the present invention may absorb moisture, allow adhesion of adsorbed water, or become a hydrate when being left to stand in the atmosphere or recrystallized, and such compounds and salts containing water are also included in the present invention.

The antibody-drug conjugate, free drug, or production intermediate of the present invention may be converted into a pharmaceutically acceptable salt, as desired, if having a basic group such as an amino group. Examples of such salts may include, but not limited to, hydrogen halide salts such as hydrochlorides and hydroiodides; inorganic acid salts such as nitrates, perchlorates, sulfates, and phosphates; lower alkanesulfonates such as methanesulfonates, trifluoromethanesulfonates, and ethanesulfonates; arylsufonates such as benzenesulfonates and p-toluenesulfonates; organic acid salts such as formates, acetates, malates, fumarates, succinates, citrates, tartrates, oxalates, and maleates; and amino acid salts such as ornithinates, glutamates, and aspartates.

If the antibody-drug conjugate, free drug, or production intermediate of the present invention has an acidic group such as a carboxy group, a base addition salt can be generally formed. Examples of pharmaceutical acceptable salts may include, but not limited to, alkali metal salts such as sodium salts, potassium salts, and lithium salts; alkali earth metal salts such as calcium salts and magnesium salts; inorganic salts such as ammonium salts; and organic amine salts such as dibenzylamine salts, morpholine salts, phenylglycine alkyl ester salts, ethylenediamine salts, N-methylglucamates, diethylamine salts, triethylamine salts, cyclohexylamine salts, dicyclohexylamine salts, N,N'-dibenzylethylenediamine salts, diethanolamine salts, N-benzyl-N-(2-phenylethoxy)amine salts, piperazine salts, tetramethylammonium salts, and tris(hydroxymethyl)aminomethane salts.

The antibody-drug conjugate, free drug, or production intermediate of the present invention may exist as a hydrate, for example, by absorbing moisture in the air. The solvate of the present invention is not limited to a particular solvate and may be any pharmaceutically acceptable solvate, and specifically hydrates, ethanol solvates, 2-propanol solvates, and so on are preferred. The antibody-drug conjugate, free drug, or production intermediate of the present invention may be its N-oxide form if a nitrogen atom is present therein, and these solvates and N-oxide forms are included in the scope of the present invention.

The present invention includes compounds labeled with various radioactive or nonradioactive isotopes. The antibody-drug conjugate, free drug, or production intermediate of the present invention may contain one or more constituent atoms with non-natural ratios of atomic isotopes. Examples of atomic isotopes may include, but not limited to, deuterium ($^2$H), tritium (3H), iodine-125 ($^{125}$I), and carbon-14 ($^{14}$C). The compound of the present invention may be radiolabeled with a radioactive isotope such as tritium ($^3$H), iodine-125 ($^{125}$I), and carbon-14 ($^{14}$C). The radiolabeled compound is useful as a therapeutic or prophylactic agent, a reagent for research such as an assay reagent, and a diagnostic agent such as a diagnostic agent for in vivo imaging. Isotopic variants of the antibody-drug conjugate of the present invention are all included in the scope of the present invention, regardless of whether they are radioactive or not.

[Production Methods]

Next, representative methods for producing the antibody-drug conjugate of the present invention and free drugs or production intermediates thereof will be described. In the following, compound numbers shown in reaction formulas are used to identify compounds from each other. Specifically, reference in the form of "compound of formula (1)", "compound (1)", and so on will be made. Compounds with the other numbers will be indicated in the same manner.

1. Production Method 1

Compound (1) of the present invention may be produced in accordance with scheme A to scheme Q described in the following.

[Formula 102]

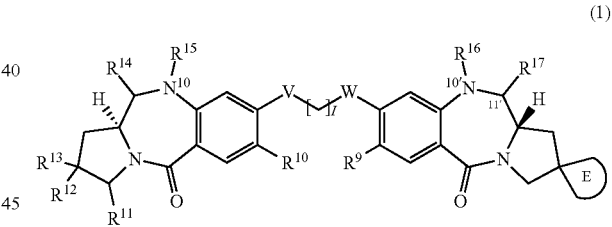

(1)

Scheme A to scheme M are each a method for producing a production intermediate for the antibody-drug conjugate of the present invention.

Scheme N to scheme Q are each a method for producing a free drug of the present invention.

In each step in scheme A to scheme Q below, a desired reaction may be carried out by using a known technique of organic chemistry.

Solvent to be used in reaction of each step in scheme A to scheme Q below is not limited to a particular solvent and may be any solvent that dissolves starting raw materials to some degree without inhibiting the reaction or having adverse effect on the reaction.

In each step in scheme A to scheme Q below, reaction temperature depends on solvent, starting raw materials, reagents, and so on, and reaction time depends on solvent, starting raw materials, reagents, reaction temperature, and so on.

In each step in scheme A to scheme Q below, a targeted compound is collected by using a conventional method from a reaction mixture after the completion of reaction. For example, a reaction mixture is appropriately neutralized; if any insoluble matter is present the insoluble matter is removed through filtration; an organic solvent immiscible with water, such as ethyl acetate, is then added to the resultant; an organic layer containing the targeted compound is separated and washed with water or the like, and dried over anhydrous magnesium sulfate, anhydrous sodium sulfate, or the like; and the resultant is filtered and the solvent is then distilled off to afford the targeted product. The targeted product obtained may be subjected to separation/purification, as necessary, by appropriately combining conventional methods, for example, typical methods conventionally used for separation/purification of organic compounds such as recrystallization, reprecipitation, and chromatography (e.g., appropriately combining adsorption column chromatography methods with a carrier such as silica gel, alumina, a Florisil of magnesium-silica gel type, and $SO_3H$-silica (produced by FUJI SILYSIA CHEMICAL LTD.); methods with a synthesized adsorbent such as partition column chromatography with a carrier such as Sephadex LH-20 (produced by Pharmacia), Amberlite XAD-11 (produced by Rohm and Haas Company), and DIAION HP-20 (produced by Mitsubishi Chemical Corporation); methods using ion-exchange chromatography; normal phase/reversed-phase column chromatography methods (preferably, high performance liquid chromatography) with silica gel or alkylated silica gel, and eluting with an appropriate eluent). In the case of a targeted compound insoluble in solvent, a crude product of solid obtained may be washed with solvent and purified. A targeted compound in each step may be used for the subsequent reaction without purification.

In each step in scheme A to scheme Q below, J, La', Lp', B', E, V, W, $R^9$, $R^{10}$, $R^{11}$, $R^{12}$, $R^{13}$, $R^{14}$, $R^{15}$, $R^{16}$, $R^{17}$, l, $n^7$, $n^6$, and $m^1$ have the same meanings as described above. (Lp')' represents any of dipeptide residues of —VA-, —FG-, —PI—, —VCit-, —VK—,-(D-)PI—, —PL- , -(D-)VA-, and -GF-. If a hydroxy group or an amino group is present on a substituent of $R^{13}$, a protective group may be used for $(R^{13})'$, and if there is no protective group, $(R^{13})'$ represents $R^{13}$. $(R^{17})'$ represents either a hydroxy group protected with a protective group such as a tert-butyldimethylsilyloxy group, or $R^{17}$.

$PRO^1$, $PRO^4$, $PRO^6$, $PRO^8$, and $PRO^9$ each represent a protective group for an amino group. Preferably, $PRO^1$, $PRO^4$, $PRO^8$, and $PRO^9$ each are, for example, an allyloxycarbonyl group, a 2,2,2-trichloroethyloxycarbonyl group, a trimethylsilylethoxymethoxy group, a benzyloxycarbonyl group, or a 9-fluorenylmethyloxycarbonyl group. $PRO^6$ is preferably, for example, a 2-(trimethylsilyl)ethoxymethyl group or a methoxymethy group.

$PRO^2$, $PRO^3$, $PRO^5$, $PRO^7$, $PRO^{10}$, $PRO^{11}$, and $PRO^{12}$ each represent a protective group used in the field of synthetic organic chemistry for a hydroxy group, a phenol group, and a carboxyl group. Preferably, $PRO^2$, $PRO^3$, $PRO^5$, $PRO^7$, $PRO^{10}$, $PRO^{11}$, and $PRO^{12}$ are each an acetyl group, a benzyl group, a tert-butyldimethylsilyl (TBDMS) group, a triisopropylsilyl group, or a tert-butyl group.

$X^2$ represents a leaving group used in the field of synthetic organic chemistry. Preferably, $X^2$ is a chlorine atom, a bromine atom, an iodine atom, a methanesulfonyl group, or a p-toluenesulfonyl group.

$R^a$ and $R^c$ each represent a substituent bonding to a carboxyl group, and is preferably, for example, a methyl group, an ethyl group, a benzyl group, or a tert-butyl group.

$R^b$ represents a leaving group to form enol sulfonate, and is preferably, for example, a trifluoromethanesulfonyl group.

Amino groups and hydroxy groups without explicit description on protection in scheme A to scheme Q may be protected, as necessary, by using a protective group. Deprotection may be carried out, as necessary, and protection may be followed by deprotection to replace with another protective group.

Scheme A

The production method is a method for producing compound (12a), a synthesized intermediate needed for production of compound (1).

[Formula 103]

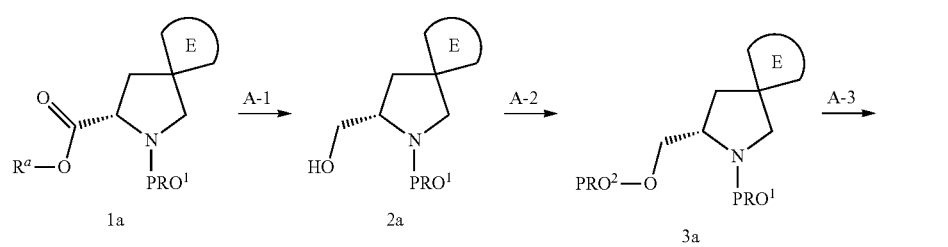

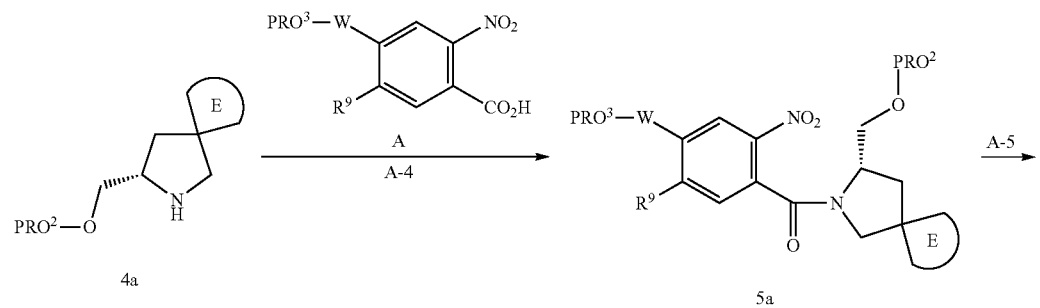

-continued

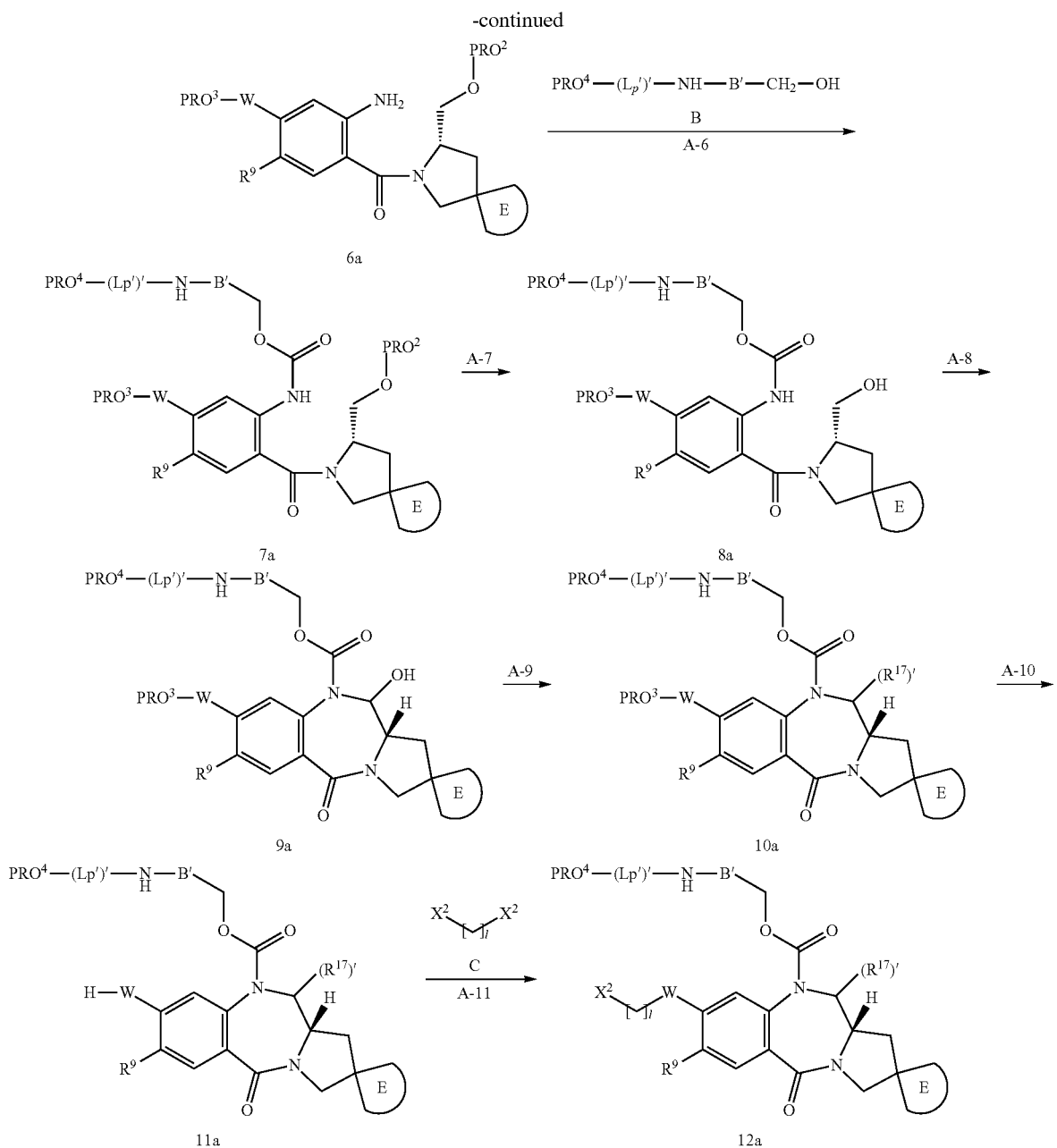

Step A-1 (1a)→(2a): Reduction Reaction

The step is carried out by treating compound (1a) with a reducing agent (e.g., lithium aluminium hydride, diborane, lithium borohydride, sodium borohydride, a borane-tetrahydrofuran complex, or sodium bis(2-methoxyethoxy)aluminum hydride) in solvent (diethyl ether, tetrahydrofuran (THF), dichloromethane, ethanol, or the like, or mixed solvent thereof) at −78° C. to the boiling point of the solvent used for the reaction, preferably at −78° C. to 50° C. The amount of moles of the reducing agent to be used is 1 mol to an excessive amount of moles, preferably 1 to 5 mol, relative to compound (1a). As necessary, a Lewis acid (e.g., lithium chloride, calcium chloride, tin chloride, a trifluoroborane-ether complex) is added to the reaction. The reaction time is 1 minute to 60 hours, and preferably 5 minutes to 24 hours.

Step A-2 (2a)→(3a): Introduction of Protective Group (e.g., Tert-Butyldimethylsilyl Group)

When PRO² is a TBDMS group, the step is carried out by reacting compound (2a) with a silylating reagent (e.g., tert-butyldimethylsilyl chloride, tert-butyldimethylsilyl trifluoromethanesulfonate) in solvent (dichloromethane, acetonitrile, tetrahydrafuran, N,N-dimethylformamide (DMF), or the like, or mixed solvent thereof) at −20° C. to 120° C., preferably at 0° C. to 100° C. As necessary, a base (e.g., imidazole, pyridine, 2,6-lutidine, 4-dimethylaminopyridine, sodium hydride) is added to the reaction. The amount of moles of the silylating agent to be used is 1 mol to an excessive amount of moles, preferably 1 to 5 mol, relative to compound (2a), and the amount of moles of the base to be used is 1 mol to an excessive amount of moles, preferably 1 to 5 mol, relative to compound (2a). The reaction time is 1 minute to 72 hours, and preferably 5 minutes to 24 hours.

Step A-3 (3a)→(4a): Deprotection Reaction

When PRO$^1$ is a benzyloxycarbonyl group, the step is carried out by subjecting compound (3a) to catalytic hydrogenation in solvent (ethanol, propanol, methanol, ethyl acetate, THF, 1,4-dioxane, or the like, or mixed solvent thereof) in the presence of a transition metal catalyst (e.g., palladium carbon) at 0° C. to the boiling point of the solvent used for the reaction, preferably at 0° C. to 50° C. The step is typically carried out under the hydrogen atmosphere; however, cyclohexene, 1,4-cyclohexadiene, or the like may be used as a hydrogen donor, as necessary. The reaction time is 10 minutes to 100 hours, and preferably 30 minutes to 72 hours.

Step A-4 (4a)→(5a): Condensation Reaction

The step is carried out by reacting compound (4a) and a carboxylic acid (compound (A)) in solvent (benzene, toluene, diethyl ether, dichloromethane, THF, DMF, water, or the like, or mixed solvent thereof) in the presence of a condensing agent such as N,N-dicyclohexylcarbodiimide, 1-ethyl-3-(3-dimethylaminopropyl)carbodiimide, 0-(7-azabenzotriazol-1-yl)-N,N,N',N'-tetramethyluronium hexafluoroborate, N-ethoxycarbonyl-2-ethoxy-1,2-dihydroquinoline, and 4-(4,6-dimethoxy-1,3,5-triazin-2-yl)-4-methylmorpholinium chloride at −30° C. to the boiling point of the solvent used for the reaction, preferably at 0° C. to 50° C. The amount of moles of the carboxylic acid (compound (A)) to be used is 0.3 to 5 mol, preferably 0.4 to 2 mol, per mole of compound (4a), and the amount of moles of the condensing agent to be used is 1 mol to an excessive amount of moles, preferably 1 to 5 mol, per mole of compound (4a). As necessary, a base (e.g., triethylamine, diisopropylethylamine, N-methylmorpholine, 4-dimethylaminopyridine) and an additive (e.g., 1-hydroxybenzotriazole, 1-hydroxy-7-azabenzotriazole) are added to the reaction. The amount of moles of the base to be used is a catalytic amount to an excessive amount of moles, preferably 0.2 to 3 mol, per mole of compound (4a). The amount of moles of the additive to be used is a catalytic amount to an excessive amount, preferably 0.01 to 3 mol, per mole of compound (4a). The reaction time is 10 minutes to 72 hours, and preferably 30 minutes to 24 hours.

When the carboxylic acid (compound (A)) is to be converted into an acid halide and subjected to condensation reaction, the step is carried out by reacting compound (4a) and the acid halide of the carboxylic acid (compound (A)) in solvent (benzene, toluene, diethyl ether, dichloromethane, tetrahydrofuran, dichloromethane, or the like, or mixed solvent thereof) in the presence of a base (e.g., triethylamine, diisopropylethylamine, N-methylmorpholine, 4-dimethylaminopyridine) at −78° C. to the boiling point of the solvent used for the reaction, preferably at −50° C. to 100° C. The amount of moles of the acid halide to be used is 0.3 mol to 5 mol, preferably 0.4 mol to 2 mol, per mole of compound (4a), and the amount of moles of the base to be used is a catalytic amount to an excessive amount of moles, preferably 0.2 to 5 mol, per mole of compound (4a). The reaction time is 10 minutes to 72 hours, and preferably 30 minutes to 24 hours.

To prepare the acid halide compound of the carboxylic acid (compound (A)), the carboxylic acid (compound (A)) is treated with oxalyl chloride, thionyl chloride, or the like in solvent (benzene, toluene, dichloromethane, dichloroethane, or the like, or mixed solvent thereof) at 0° C. to the boiling point of the solvent used for the reaction, preferably at 0° C. to 100° C. As necessary, a catalytic amount of N,N-dimethylformamide or the like is added to the reaction. The amount of moles of oxalyl chloride or thionyl chloride to be used is 1 mol to an excessive amount of moles, preferably 1 to 10 mol, relative to the carboxylic acid (compound (A)). The reaction time is 10 minutes to 72 hours, and preferably 30 minutes to 24 hours.

Step A-5 (5a)→(6a): Reduction Reaction

The step is carried out by subjecting compound (5a) to catalytic hydrogenation in solvent (ethanol, propanol, methanol, ethyl acetate, THF, 1,4-dioxane, DMF, or the like, or mixed solvent thereof) in the presence of a transition metal catalyst (palladium carbon, nickel, or the like) at 0° C. to the boiling point of the solvent used for the reaction, preferably at 0° C. to 50° C. The step is typically carried out under the hydrogen atmosphere; however, cyclohexene, 1,4-cyclohexadiene, hydrazine, or the like may be used as a hydrogen donor. The reaction time is 10 minutes to 72 hours, and preferably 30 minutes to 24 hours.

Reduction of the nitro group may be carried out in the following conditions.

The step is carried out by reacting compound (5a) and a reducing agent (e.g., iron, zinc, tin chloride) in solvent (ethanol, methanol, diethyl ether, ethyl acetate, or water, or mixed solvent thereof) at 0° C. to the boiling point of the solvent used for the reaction, preferably at 0° C. to 90° C. As necessary, an acid (e.g., acetic acid, formic acid, ammonium chloride) is added to the reaction. The amount of moles of the reducing agent to be used is 1 mol to an excessive amount of moles, preferably 1 to 100 mol, per mole of compound (5a), and the amount of moles of the acid to be added is 1 mol to an excessive amount of moles per mole of compound (5a). The reaction time is 10 minutes to 72 hours, and preferably 30 minutes to 24 hours.

Step A-6 (6a)→(7a): Carbamatization Reaction

The step is carried out by reacting compound (6a) and triphosgene (isocyanating agent) in solvent (THF, dichloromethane, DMF, or the like, or mixed solvent thereof) at −30° C. to the boiling point of the solvent used for the reaction, preferably at 0° C. to 50° C. to generate an isocyanate intermediate in the system, followed by treating with an alcohol represented by general formula (B). As necessary, a base (e.g., triethylamine, diisopropylethylamine, sodium carbonate, sodium hydroxide) is added to the reaction. The amount of moles of triphosgene (isocyanating agent) to be used is 0.3 mol to an excessive amount of moles, preferably 0.35 to 3 mol, per mole of compound (6a), and the amount of moles of the base to be added is 0.5 to 5 mol per mole of compound (6a). The reaction time until the isocyanate intermediate has formed is 10 minutes to 24 hours, and preferably 30 minutes to 1 hour. The reaction time for the reaction between the isocyanate intermediate and alcohol (B) is 10 minutes to 72 hours, and preferably 1 hour to 24 hours.

Alcohol (B) to be used in the present step may be produced according to scheme L described later.

Step A-7 (7a)→(8a): Deprotection Reaction

When PRO$^2$ is a TBDMS group, the step is carried out by reacting compound (7a) and any of an acid (e.g., acetic acid), a desilylating reagent (e.g., hydrofluoric acid-pyridine, hydrofluoric acid-triethylamine, a hydrofluorate, hydrofluoric acid, tetra(n-butylammonium) fluoride), and a mixture of the acid and desilylating reagent in solvent (dichloromethane, chloroform, acetonitrile, methanol, ethanol, THF, water, or the like, or mixed solvent thereof) at −20° C. to 100° C., preferably at 0° C. to 50° C. The amount of moles of the acid to be used is 1 mol to an excessive amount of moles per mole of compound (7a), and the amount of the acid or desilylating reagent to be used is 1 mol to an excessive amount of moles, and preferably 1 to 10 mol, per mole of compound (7a). The reaction time is 10 minutes to 72 hours, and preferably 30 minutes to 24 hours.

Step A-8 (8a)→(9a): Oxidation Reaction

The step is carried out by reacting compound (8a) and an oxidizing agent (e.g., a chlorosulfonium salt, a Dess-Martin reagent, tetrabutylammonium ruthenate, pyridinium chlorochromate, a nitroxy radical oxidation catalyst) in solvent (acetone, dichloromethane, pyridine, or the like, or mixed solvent thereof) at −78° C. to the boiling point of the solvent used for the reaction, preferably at −78° C. to 30° C. As necessary, a base (e.g., triethylamine, diisopropylethylamine, sodium hydrogen carbonate, sodium carbonate, sodium hydroxide) and a reoxidizing agent (e.g., N-methylmorpholine N-oxide, iodobenzene diacetate, sodium hypochlorite) or additive (e.g., tetrabutylammonium bromide, potassium bromide) is added to the reaction. The amount of moles of the oxidizing agent to be used is 0.005 mol to an excessive amount of moles, preferably 0.005 to 10 mol, per mole of compound (8a). The amount of moles of the base or reoxidizing agent to be added is 1 to 10 mol per mole of compound (8a), and the amount of moles of the additive to be added is 0.02 to 1 mol per mole of compound (8a). The reaction time is 10 minutes to 72 hours, and preferably 30 minutes to 24 hours.

Step A-9 (9a)→(10a): Introduction of Protective Group

When (R$^{17}$)' is a tert-butyldimethylsilyloxy group, production is carried out according to step A-2.

Step A-10 (10a)→(11a): Deprotection Reaction

When PRO$^1$ is a triisopropylsilyl group, production is carried out by treating compound (10a) with lithium acetate in solvent (DMF, water, or the like, or a mixture thereof) at 0° C. to the boiling point of the solvent used for the reaction, preferably at 0° C. to 50° C. The amount of moles of lithium acetate to be used is 1 mol to an excessive amount of moles, preferably 1 to 5 mol, per mole of compound (10a). The reaction time is 10 minutes to 72 hours, and preferably 30 minutes to 24 hours.

Step A-11 (1La)→(12a): Alkylation Reaction

The production is carried out by reacting compound (11a) and alkylating agent (C) (e.g., 1,5-dibromopentane, 1,3-dibromopropane) in solvent (THF, DMF, or N,N-dimethylacetamide, or mixed solvent thereof) at −20° C. to the boiling point of the solvent used for the reaction, preferably at 0° C. to the boiling point. As necessary, a base (e.g., potassium carbonate, cesium carbonate) is added to the reaction. The amount of moles of the alkylating agent to be used is 1 mol to an excessive amount of moles, preferably 1 to 10 mol, per mole of compound (11a), and the amount of moles of the base to be used is 0.4 mol to an excessive amount of moles, preferably 0.5 to 5 mol, per mole of compound (11a). The reaction time is 1 minute to 60 hours, and preferably 5 minutes to 24 hours.

Scheme B

The production method is a method for producing compound (10b), an intermediate needed for producing compound (1) in which R$^{11}$ and R$^{12}$ are combined, together with the carbon atoms to which R$^{11}$ and R$^{12}$ are bound, to form a double bond and R" and R$^{15}$ are each hydrogen. TEKO

[Formula 104]

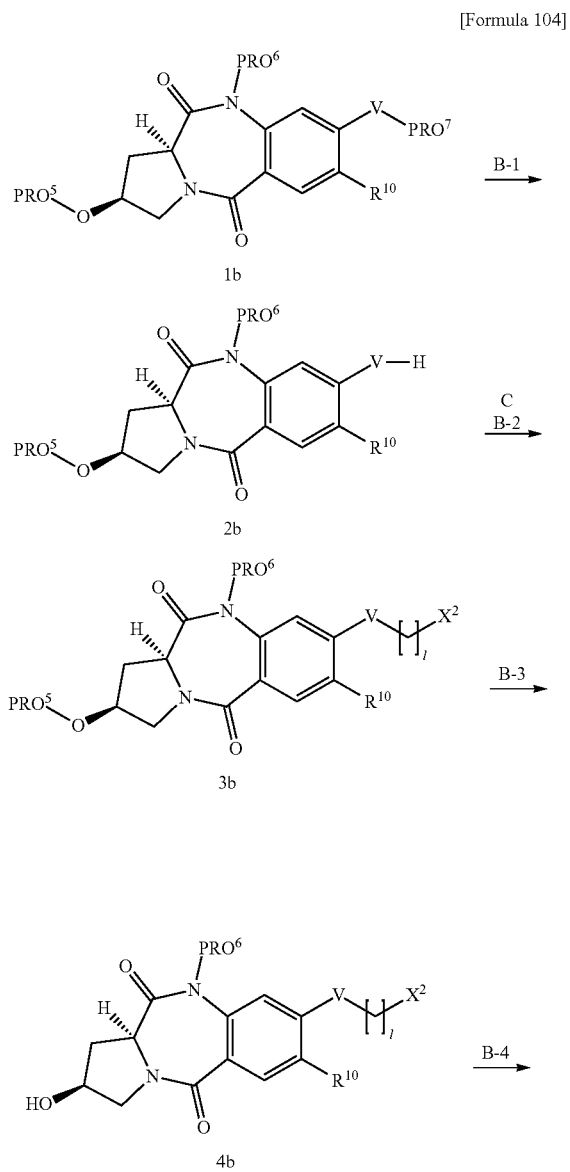

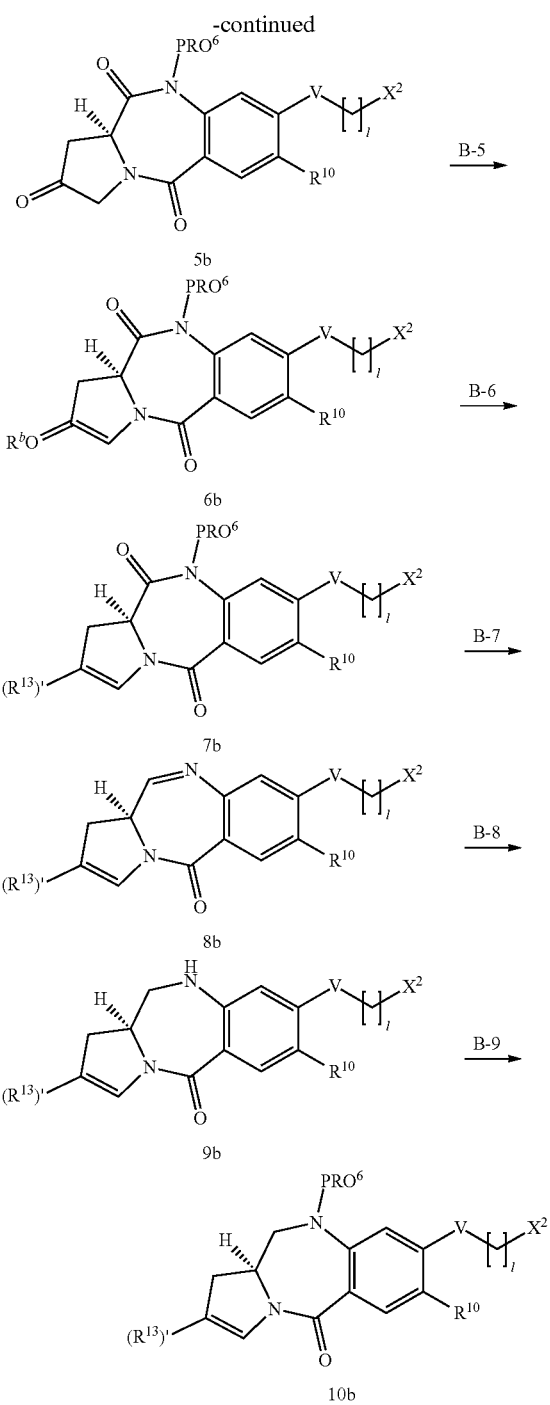

Step B-1 (Lb)→(2b): Deprotection Reaction

When PRO⁷ is a triisopropylsilyl group, production is carried out according to step A-10 of scheme A.

When PRO⁷ is a benzyl group, production is carried out according to step A-3 of scheme A.

Step B-2 (2b)→(3b): Alkylation Reaction

Production is carried out according to step A-11 of scheme A.

Step B-3 (3b)→(4b): Deprotection Reaction

When PRO¹ is a TBDMS group, production is carried out according to step A-7 of scheme A.

When PRO⁵ is an acetyl group, the step is carried out by reacting compound (3b) and an appropriate base (e.g., potassium carbonate, sodium methoxide, sodium hydroxide) in solvent (methanol, ethanol, THF, water, or the like, or mixed solvent thereof) at −20° C. to the boiling point of the solvent used for the reaction, preferably at 0° C. to 50° C. The amount of moles of the base to be used is a catalytic amount to an excessive amount of moles, and preferably 0.1 to 10 mol. The reaction time is 10 minutes to 72 hours, and preferably 30 minutes to 24 hours.

Step B-4 (4b)→(5b): Oxidation Reaction

The production is carried out according to step A-8 of scheme A.

Step B-5 (5b)→(6b): Enol Sulfonylation Reaction

When $R^b$ is a trifluoromethanesulfonyl group, the step is carried out by reacting compound (5b) and trifluoromethanesulfonic anhydride or the like in solvent (e.g., dichloromethane) at −78° C. to the boiling point of the solvent used for the reaction, preferably at −78° C. to 30° C. As necessary, a base (e.g., 2,6-lutidine) is added to the reaction. The amount of moles of trifluoromethanesulfonic anhydride to be used is 1 mol to an excessive amount of moles, preferably 1 to 5 mol, per mole of compound (5b). The amount of moles of the base to be used is 1 mol to 10 mol. The reaction time is 10 minutes to 24 hours, and preferably 30 minutes to 6 hours.

Step B-6 (6b)→(7b): Cross Coupling Reaction (e.g., Suzuki-Miyaura Reaction) with Transition Metal Catalyst The step is carried out by using compound (6b) and an organic boron compound (e.g., 4-methoxyphenylboronic acid) in solvent (ethanol, toluene, 1,4-dioxane, DMF, tetrahydrafuran, water, or the like, or mixed solvent thereof) in the presence of a transition metal catalyst (e.g., tetrakis (triphenylphosphine)palladium, dichlorobis(benzonitrile) palladium (II)) at 0° C. to the boiling point of the solvent used for the reaction, preferably at 0° C. to 120° C. As necessary, a base (e.g., sodium carbonate, potassium carbonate, cesium carbonate, sodium hydrogen carbonate, sodium hydroxide) or an additive (e.g., silver oxide, triphenylarsine) is added to the reaction. The amount of moles of the palladium catalyst to be used is 0.01 mol to 1 mol, preferably 0.01 mol to 0.5 mol, per mole of compound (6b). The amount of moles of the organic boron compound to be used is 1 mol to an excessive amount of moles, preferably 1 mol to 10 mol, per mole of compound (6b), the amount of moles of the base to be used is 1 mol to 5 mol per mole of compound (6b), and the amount of moles of the additive to be used is 0.1 mol to 5 mol per mole of compound (6b). The reaction time is 10 minutes to 72 hours, and preferably 30 minutes to 24 hours.

Step B-7 (7b)→(8b): Reduction Reaction

When PRO⁶ is a 2-(trimethylsilyl)ethoxymethyl group, for example, the step is carried out by treating compound (7b) with a reducing agent (e.g., lithium borohydride, sodium borohydride) in solvent (diethyl ether, THF, dichloromethane, ethanol, or the like, or mixed solvent thereof) at −78° C. to the boiling point of the solvent used for the reaction, preferably at −78° C. to 50° C. The amount of moles of the reducing agent to be used is 1 mol to an excessive amount of moles, preferably 1 to 30 mol, relative to 1 mol of compound (7b). The reaction time is 1 minute to 24 hours, and preferably 5 minutes to 6 hours. Compound (8b) can be produced by adding silica gel to a solution (dichloromethane, ethanol, water, or mixed solvent thereof) of the crude product obtained from the reduction reaction followed by treating with stirring. The silica gel to be used is in an excessive amount relative to compound (7b). The treatment time is 12 hours to 150 hours, and preferably 12 hours to 100 hours.

Step B-8 (8b)→(9b): Reduction of Imino Group

The step is carried out by treating compound (8b) with a reducing agent (e.g., sodium borohydride, cyanoborohydride, sodium triacetoxyborohydride, 2-picoline borane, pyridine borane) in solvent (THF, dichloromethane, N,N-dimethylforamide, or the like, or mixed solvent thereof) at −78° C. to the boiling point of the solvent used for the reaction, preferably at −78° C. to 50° C. The amount of moles of the reducing agent to be used is 1 mol to an excessive amount of moles, preferably 1 to 5 mol, relative to 1 mol of compound (8b). The reaction time is 1 minute to 60 hours, and preferably 5 minutes to 24 hours.

Step B-9 (9b)→(10b): Introduction of Protective Group

When PRO$^1$ is an allyloxycarbonyl group, the step is carried out by reacting compound (9b) and allyl chloroformate, diallyl dicarbonate, or the like in solvent (benzene, toluene, pyridine, diethyl ether, dichloromethane, THF, 1,4-dioxane, water, or the like, or mixed solvent thereof) at −30° C. to the boiling point of the solvent used for the reaction, preferably at 0° C. to 50° C. As necessary, a base (e.g., triethylamine, diisopropylethylamine, pyridine, sodium carbonate, potassium carbonate, sodium hydroxide) is added to the reaction. The amount of moles of allyl chloroformate to be used is 1 mol to an excessive amount of moles, preferably 1 mol to 10 mol, per mole of compound (9b), and the amount of moles of the base to be used is 1 mol to an excessive amount of moles, preferably 1 to 10 mol, per mole of compound (9b). The reaction time is 10 minutes to 72 hours, and preferably 10 minutes to 48 hours.

When PRO$^1$ is a 2,2,2-trichloroethoxycarbonyl group, the step is carried out by reacting compound (9b) and 2,2,2-trichloroethyl chloroformate in solvent (benzene, toluene, pyridine, diethyl ether, dichloromethane, THF, 1,4-dioxane, water, or the like, or mixed solvent thereof) at −30° C. to the boiling point of the solvent used for the reaction, preferably at 0° C. to 50° C. As necessary, a base (e.g., triethylamine, diisopropylethylamine, pyridine, sodium carbonate, sodium hydroxide) is added to the reaction. The amount of moles of 2,2,2-trichloroethyl chloroformate to be used is 1 mol to an excessive amount of moles, preferably 1 mol to 10 mol, per mole of compound (9b), and the amount of moles of the base to be used is 1 mol to an excessive amount, preferably 1 to 10 mol, per mole of compound (9b). The reaction time is 10 minutes to 72 hours, and preferably 30 minutes to 48 hours.

Scheme C

The production method is a method for producing compound (14c), an intermediate needed for producing compound (1) in which R$^{11}$ and R$^{12}$ are combined, together with the carbon atoms to which R$^{11}$ and R$^{12}$ are bond, to thereto form a double bond and R$^{14}$ and R$^{15}$ are each hydrogen. Compound (10b) may be produced by using the production method.

[Formula 105]

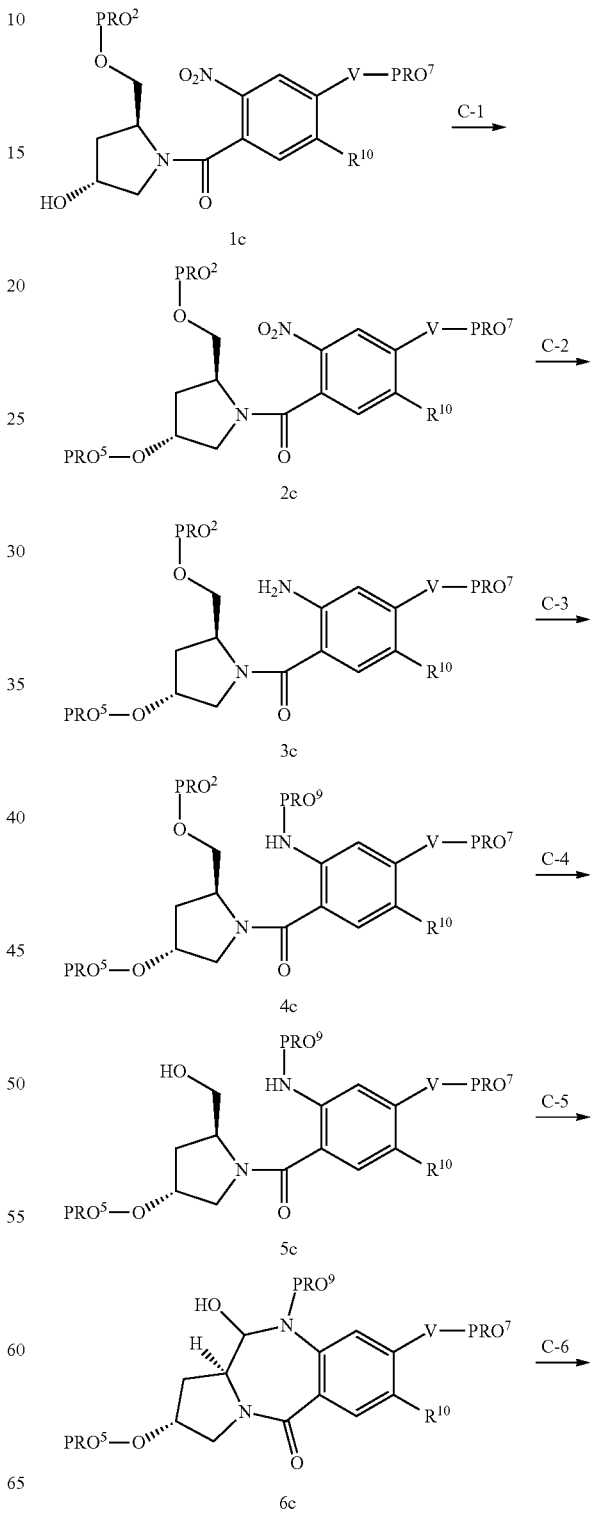

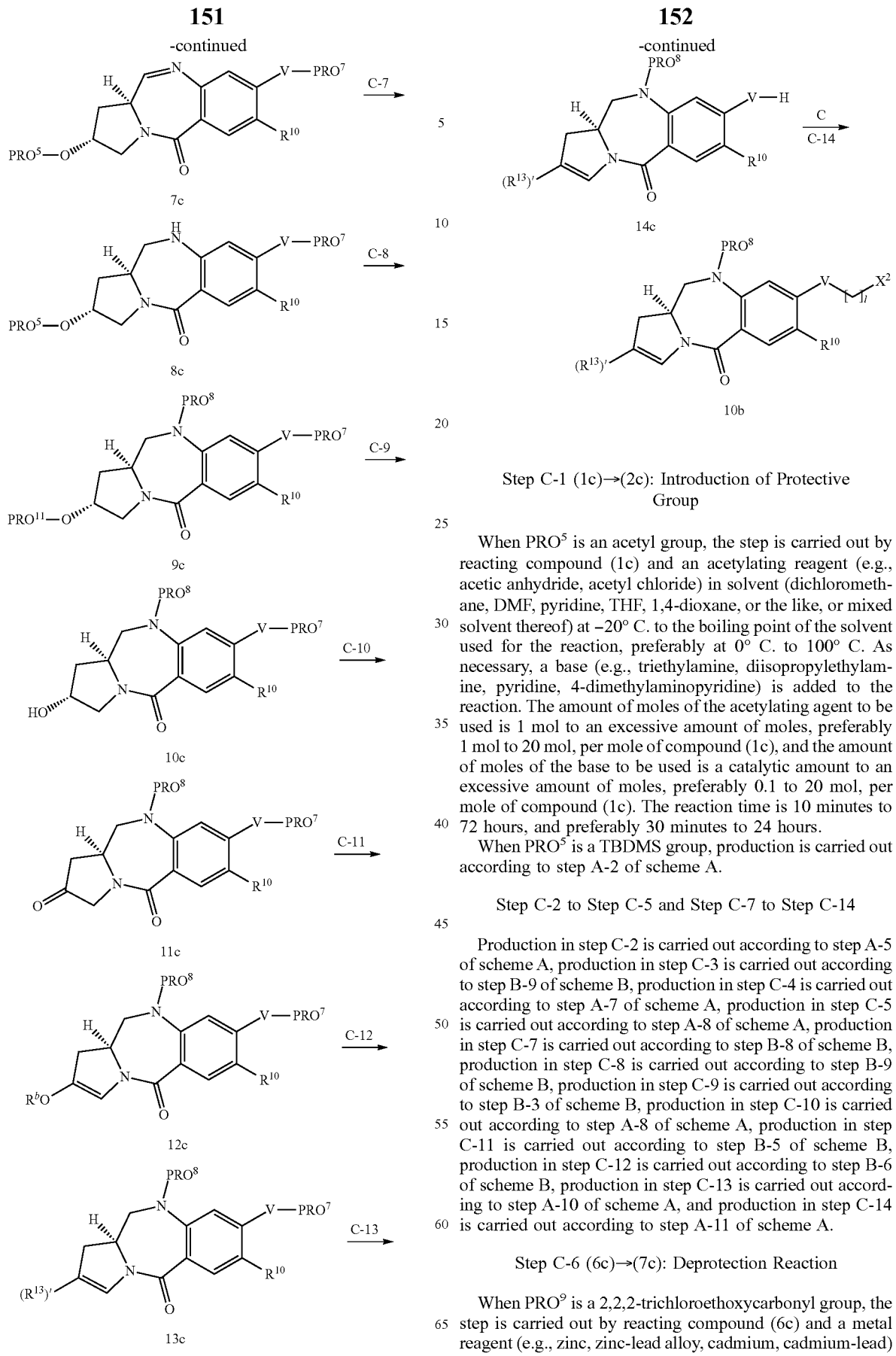

Step C-1 (1c)→(2c): Introduction of Protective Group

When PRO$^5$ is an acetyl group, the step is carried out by reacting compound (1c) and an acetylating reagent (e.g., acetic anhydride, acetyl chloride) in solvent (dichloromethane, DMF, pyridine, THF, 1,4-dioxane, or the like, or mixed solvent thereof) at −20° C. to the boiling point of the solvent used for the reaction, preferably at 0° C. to 100° C. As necessary, a base (e.g., triethylamine, diisopropylethylamine, pyridine, 4-dimethylaminopyridine) is added to the reaction. The amount of moles of the acetylating agent to be used is 1 mol to an excessive amount of moles, preferably 1 mol to 20 mol, per mole of compound (1c), and the amount of moles of the base to be used is a catalytic amount to an excessive amount of moles, preferably 0.1 to 20 mol, per mole of compound (1c). The reaction time is 10 minutes to 72 hours, and preferably 30 minutes to 24 hours.

When PRO$^5$ is a TBDMS group, production is carried out according to step A-2 of scheme A.

Step C-2 to Step C-5 and Step C-7 to Step C-14

Production in step C-2 is carried out according to step A-5 of scheme A, production in step C-3 is carried out according to step B-9 of scheme B, production in step C-4 is carried out according to step A-7 of scheme A, production in step C-5 is carried out according to step A-8 of scheme A, production in step C-7 is carried out according to step B-8 of scheme B, production in step C-8 is carried out according to step B-9 of scheme B, production in step C-9 is carried out according to step B-3 of scheme B, production in step C-10 is carried out according to step A-8 of scheme A, production in step C-11 is carried out according to step B-5 of scheme B, production in step C-12 is carried out according to step B-6 of scheme B, production in step C-13 is carried out according to step A-10 of scheme A, and production in step C-14 is carried out according to step A-11 of scheme A.

Step C-6 (6c)→(7c): Deprotection Reaction

When PRO$^9$ is a 2,2,2-trichloroethoxycarbonyl group, the step is carried out by reacting compound (6c) and a metal reagent (e.g., zinc, zinc-lead alloy, cadmium, cadmium-lead) in solvent (THF, acetic acid, an aqueous solution of ammonium acetate, water, or the like, or mixed solvent thereof) at −20° C. to the boiling point of the solvent, preferably at 0° C. to 40° C. The amount of moles of the metal reagent to be used is 1 mol to an excessive amount of moles, preferably 1 to 10 mol, per mole of compound (6c). The reaction time is 10 minutes to 72 hours, and preferably 30 minutes to 24 hours.

When PRO$^9$ is an allyloxycarbonyl group, the step is carried out by using compound (6c), a palladium catalyst (e.g., tetrakis(triphenylphosphine)palladium), and a scavenger for allyl groups (e.g., pyrrolidine, morpholine, barbituric acid) in solvent (dichloromethane, DMF, THF, or the like, or a mixture thereof) at 0° C. to the boiling point of the solvent used for the reaction, preferably at 0° C. to 30° C. The amount of moles of the palladium catalyst to be used is 0.005 mol to 1 mol, preferably 0.005 mol to 0.5 mol, per mole of compound (6c). The amount of moles of the scavenger for allyl groups to be used is 1 mol to an excessive amount of moles, preferably 1 mol to 10 mol. The reaction time is 10 minutes to 72 hours, and preferably 30 minutes to 24 hours.

Scheme D

Compound (13c) may be produced by using the scheme.

[Formula 106]

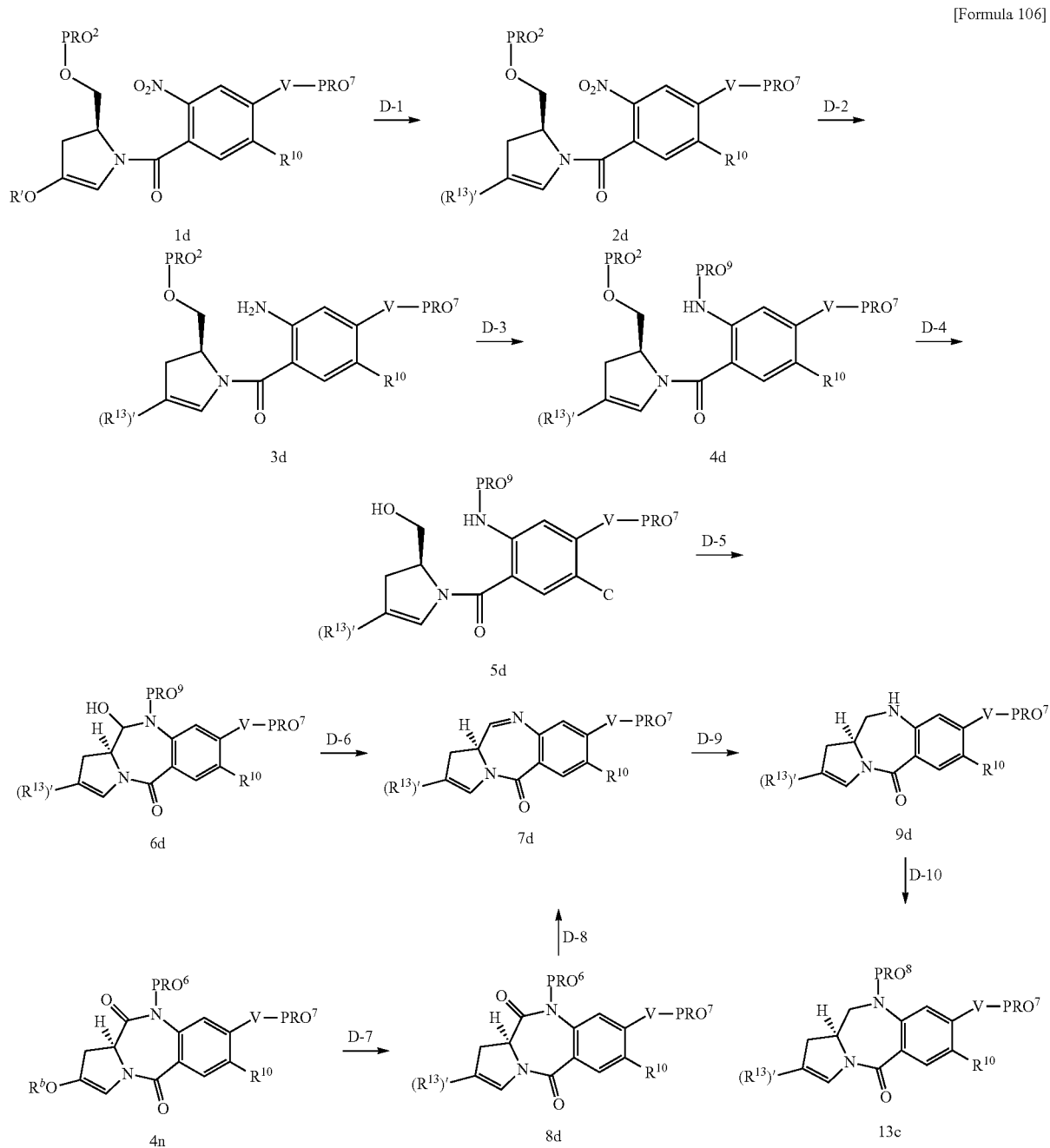

Step D-1 to Step D-6, Step D-9, and Step D-10

Production in step D-1 is carried out according to step B-6 of scheme B, production in step D-2 is carried out according to step A-5 of scheme A, production in D-3 is carried out according to step B-9 of scheme B, production in step D-4 is carried out according to step A-7 of scheme A, production in step D-5 is carried out according to step A-8 of scheme A, production in step D-6 is carried out according to step C-6 of scheme C, production in step D-9 is carried out according to step B-8 of scheme B, and production in step D-10 is carried out according to step B-9 of scheme B.

Step D-7 and Step D-8

Alternatively, compound (7d) may be produced according to step D-7, which is the same as step B-6 of scheme B, and step D-8, which is the same as step B-7 of scheme B.
Scheme E Scheme E is a method for producing compound (4e) by bonding compounds (11a) and (12a) produced in scheme A and compounds (10b) and (14c) produced in scheme B or scheme C.

Step E-1

The step is a step of producing compound (1e) through coupling reaction of compound (11a) produced in scheme A and compound (10b) produced in scheme B.

Production is carried out by subjecting compound (11a) to coupling reaction with compound (10b) in solvent (THF, DMF, N,N-dimethylacetamide, or mixed solvent thereof) in the presence of a base (e.g., potassium carbonate, cesium carbonate) at −20° C. to the boiling point of the solvent used for the reaction, preferably at 0° C. to 50° C. The amount of moles of compound (10b) to be used is 1 mol to an excessive amount of moles, preferably 0.7 to 1.5 mol, relative to 0.5 mol of compound (11a). The amount of moles of the base to be used is 1 mol to 5 mol relative to 0.5 mol of compound (11a). The reaction time is 1 minute to 60 hours, and preferably 5 minutes to 24 hours.

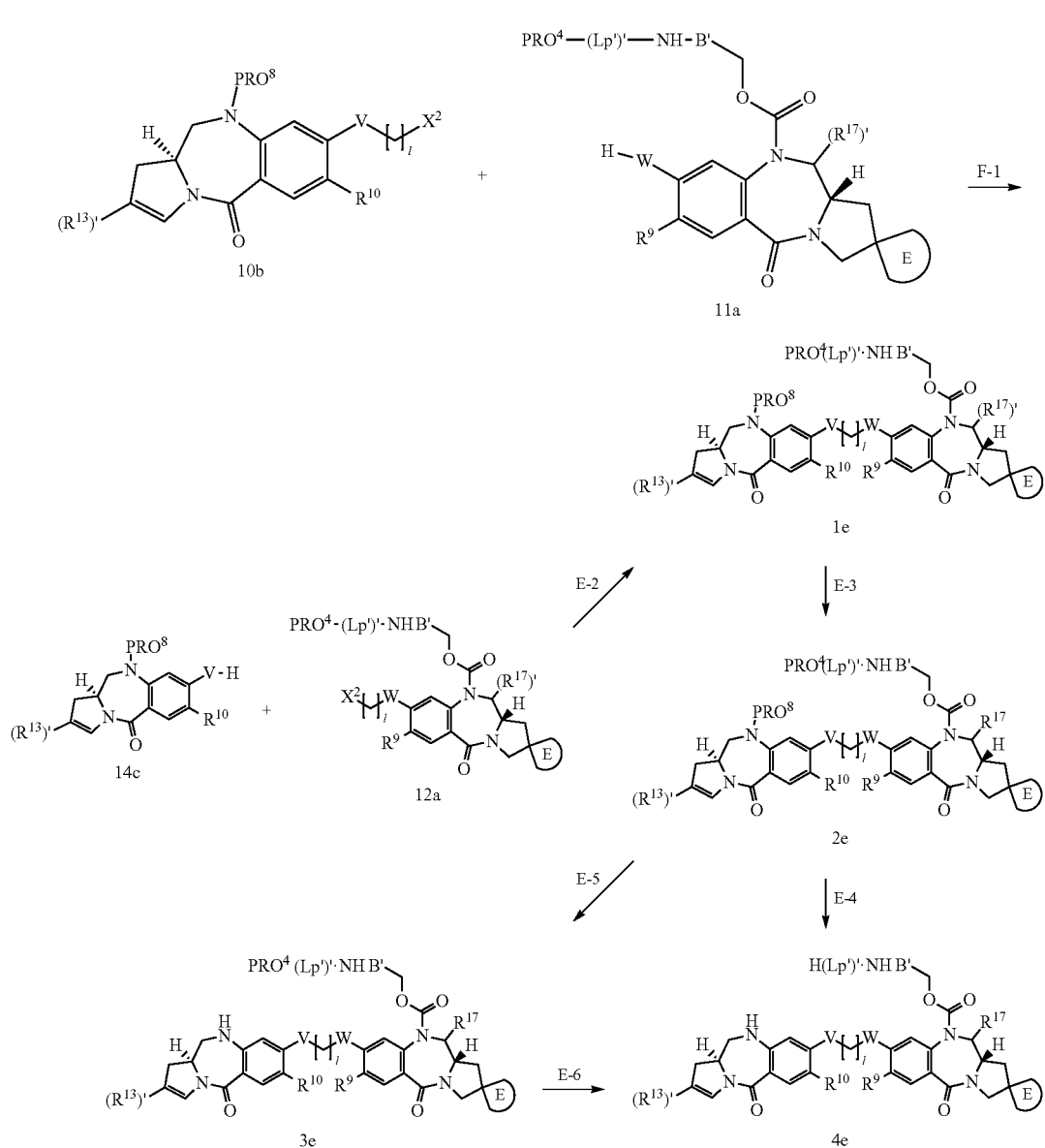

[Formula 107]

Step E-2

Alternatively, compound (1e) may be produced by subjecting compound (12a) produced in scheme A and compound (14c) produced in scheme C to coupling reaction as in step E-1.

Step E-3

Production in step E-3 is carried out according to step A-7 of scheme A.

Step E-4

The step is a step of producing compound (4e), when the protective groups $PRO^4$ and $PRO^1$ in compound (2e) are the same, by subjecting compound (2e) to deprotection reaction as in step C-6 of scheme C.

When the protective groups $PRO^4$ and $PRO^5$ in compound (2e) are different, compound (4e) can be produced by stepwise deprotection reaction through step E-5 and step E-6.

Production in step E-5 and step E-6 is carried out according to step C-6 of scheme C.

Scheme F

Alternatively, compound (4e) may be produced from intermediate compound (10f) in the synthesis method. The production method represents a method for producing compound (10f) and compound (4e).

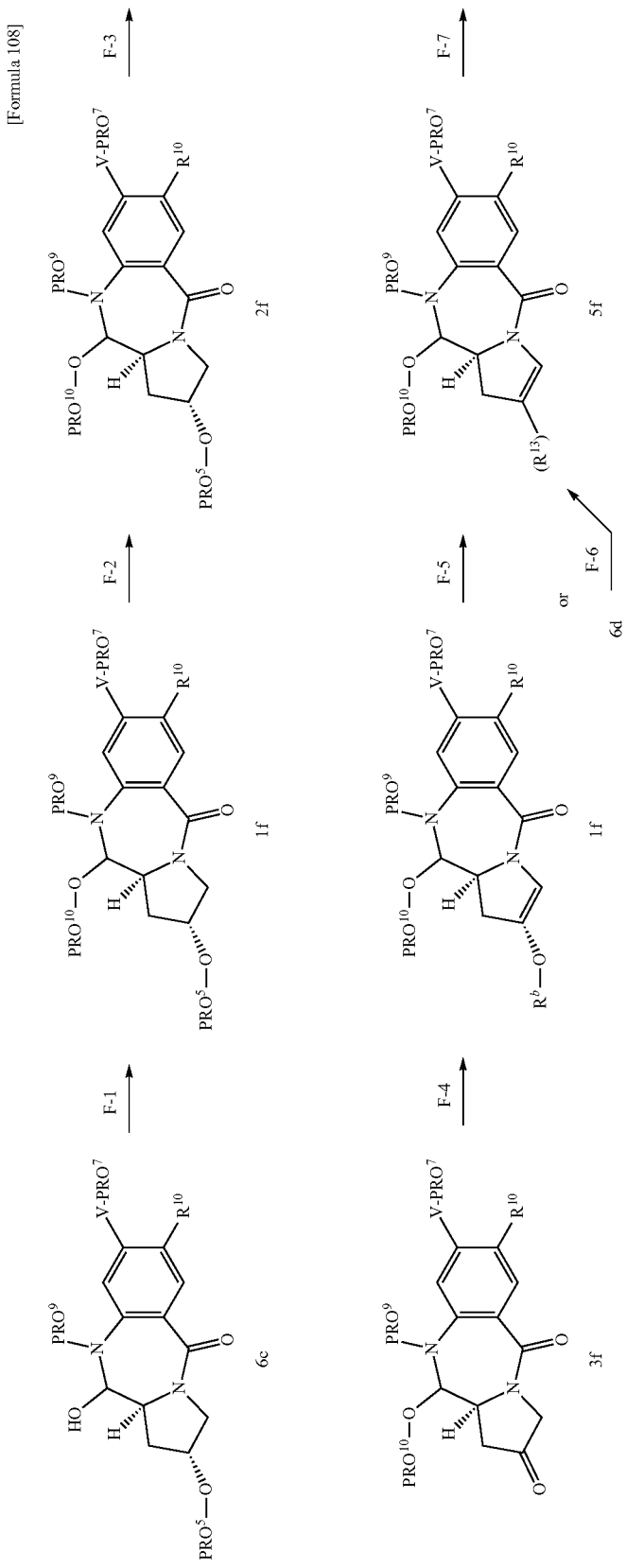

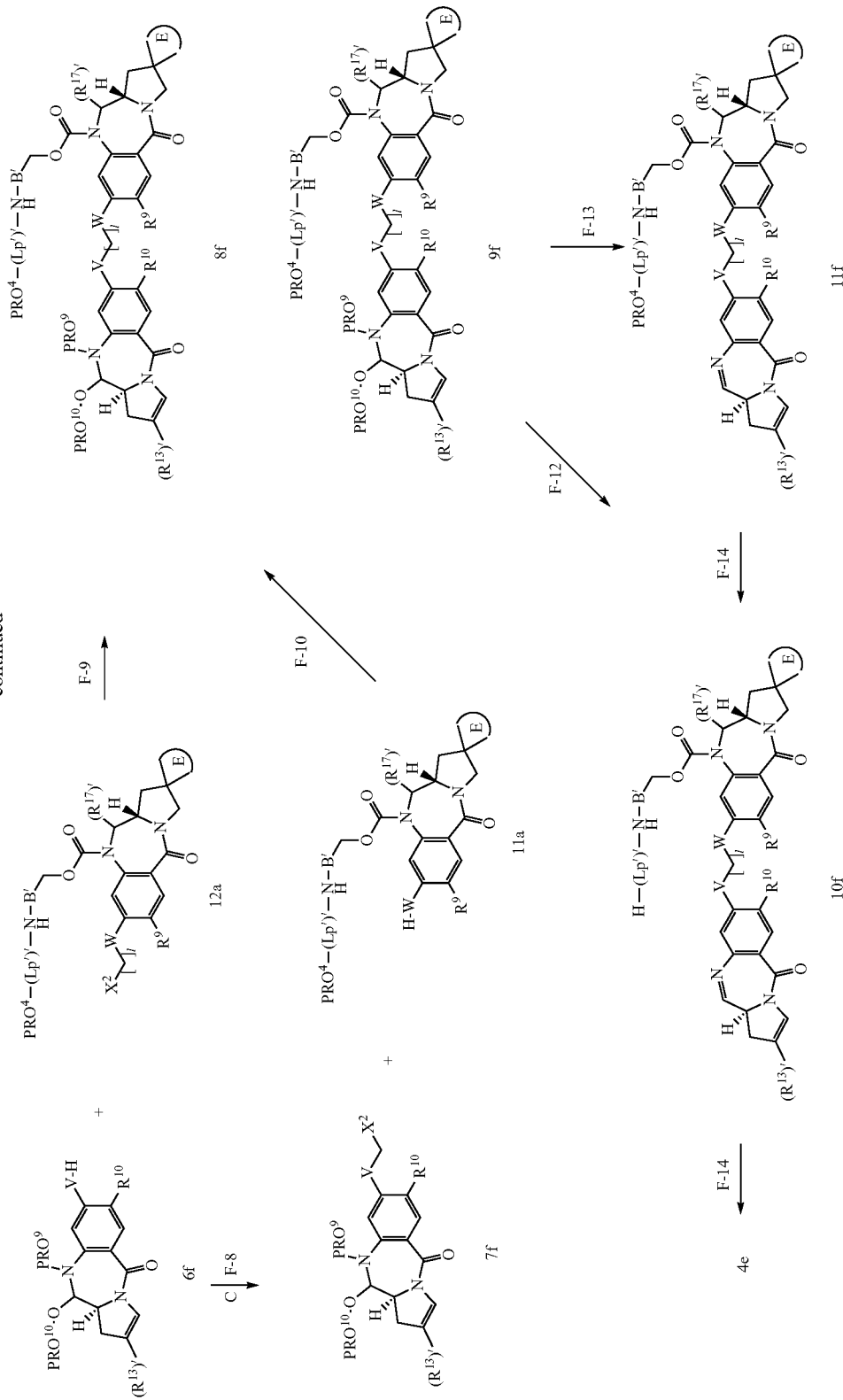

163

Step F-1 to Step F-10, and Step F-15

Production in step F-1 is carried out according to step A-2 of scheme A, production in step F-2 is carried out according to step B-3 of scheme B, production in step F-3 is carried out according to step A-8 of scheme A, production in step F-4 is carried out according to step B-5 of scheme B, production in step F-5 is carried out according to step B-6 of scheme B, production in step F-6 is carried out according to construction method A-2 of scheme A, production in step F-7 is carried out according to step A-10 of scheme A, production in step F-8 is carried out according to step A-11 of scheme A, production in step F-9 is carried out according to step E-1 of scheme E, production in step F-10 is carried out according to step E-1 of scheme E, and production in step F-15 is carried out according to step B-8 of scheme B.

Step F-11

When PRO$^{10}$ and the protective group for the hydroxy group in (R")' are each a TBDMS group, production is carried out according to step A-7 of scheme A.

Step F-12

The step is a step of producing compound (10f), when the protective groups PRO$^4$ and PRO$^9$ in compound (9f) are the same, by subjecting compound (9f) to deprotection reaction as in step C-6 of scheme C.

Step F-13 and Step F-14

When the protective groups PRO$^4$ and PRO$^9$ in compound (9f) are different, compound (10f) can be produced in stepwise deprotection reaction through step F-13 and step F-14. Production in step F-13 and step F-14 is carried out according to step C-6 of scheme C.

Scheme G

The production method is a method for producing compound (11g), an intermediate for producing compound (1) in which R$^{11}$ represents a hydrogen atom, R$^{12}$ and R$^{13}$ are combined to form a spiro ring, and R$^{14}$ and R$^{15}$ each represent a hydrogen atom.

164

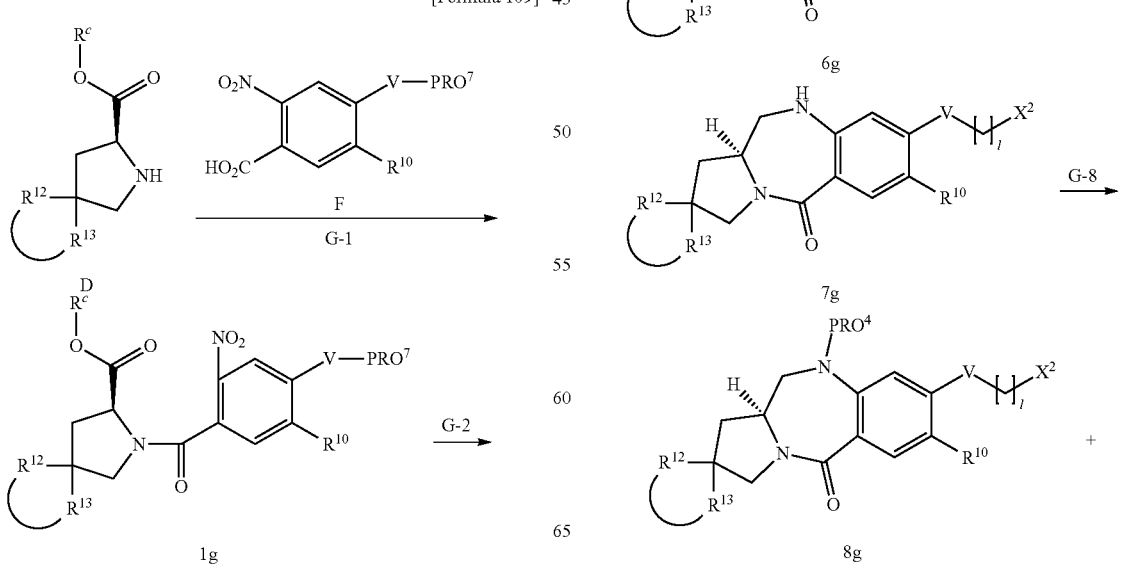

Steps G-1 and G-2, and Steps G-5 to G-11

Production in step G-1 is carried out according to step A-4 of scheme A, production in step G-2 is carried out according to step A-5 of scheme A, production in step G-5 is carried out according to step A-11 of scheme A, production in step G-6 is carried out according to step B-7 of scheme B, production in step G-7 is carried out according to step B-8 of scheme B, production in step G-8 is carried out according to step B-9 of scheme B, production in step G-9 is carried out according to step E-1 of scheme E, production in step G-10 is carried out according to step A-7 of scheme A, and production in step G-11 is carried out according to step C-6 of scheme C.

Step G-3: Introduction of Protective Group

The step is carried out by reacting compound (2g) and a chloromethoxy ether-based reagent (e.g., 2-(chloromethoxy) ethyltrimethylsilane, chloromethyl methyl ether, benzyl chloromethyl ether) in solvent (THF, DMF, dioxane, or the like, or mixed solvent thereof) at −78° C. to the boiling point of the solvent, preferably at 0° C. to 50° C. As necessary, a base (sodium hydride, n-butyl lithium, hexamethyldisilazane lithium) is added to the reaction. The amount of moles of the reagent to be used is 1 mol to an excessive amount of moles, preferably 1 to 5 mol, per mole of compound (2g). The amount of moles of the base to be used is 1 mol to an excessive amount of moles, preferably 1 to 5 mol, per mole of compound (2g). The reaction time is 10 minutes to 72 hours, and preferably 30 minutes to 24 hours.

Step G-4

When $PRO^7$ is a benzyl group, production is carried out according to step A-3 of scheme A.

When $PRO^7$ is a triisopropylsilyl group, production is carried out according to step A-10 of scheme A.

Scheme H

The production method is a method for producing compound (9h), an intermediate for producing compound (1) in which $R^{11}$ represents a hydrogen atom, $R^{12}$ and $R^{13}$ are combined to form a spiro ring, and $R^{14}$ and $R^{15}$ are combined to represent an imine bond (C=N). In the production method, the spiro ring formed by $R^{12}$ and $R^{13}$ is synonymous with E, and hence represented by E.

[Formula 110]

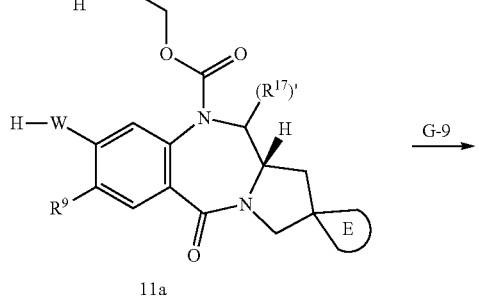

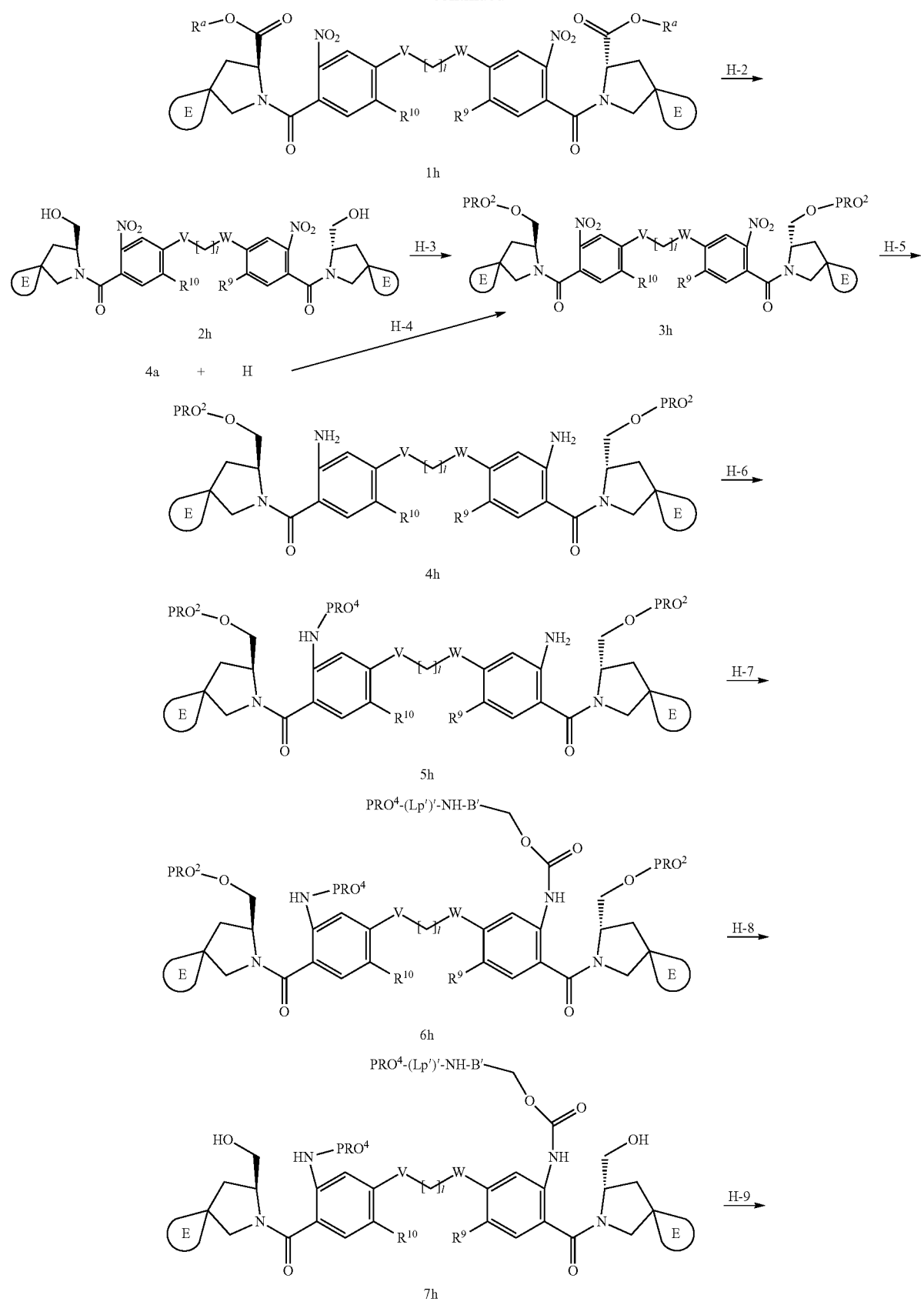

-continued

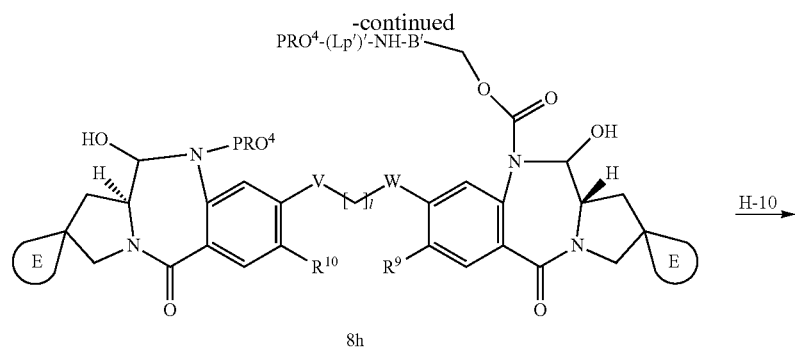

Step H-1 to Step H-10

Production in step H-1 is carried out according to step A-4 of scheme A, production in step H-2 is carried out according to step A-1 of scheme A, production in step H-3 is carried out according to step C-1 of scheme C, production in step H-4 is carried out according to step A-4 of scheme A, production in step H-5 is carried out according to step A-5 of scheme A, production in step H-6 is carried out according to step B-9 of scheme B, production in step H-7 is carried out according to step A-6 of scheme A, production in step H-8 is carried out according to step B-3 of scheme B, production in step H-9 is carried out according to step A-8 of scheme A, and production in step H-10 is carried out according to step C-6 of scheme C.

Scheme I

The production method is a method for producing compound (11i), an intermediate for producing compound (1) in which $R^{11}$ and $R^{12}$ are combined to form a benzene ring, $R^{13}$ is a single bond, and $R^{14}$ and $R^{15}$ are combined to form imine.

[Formula 111]

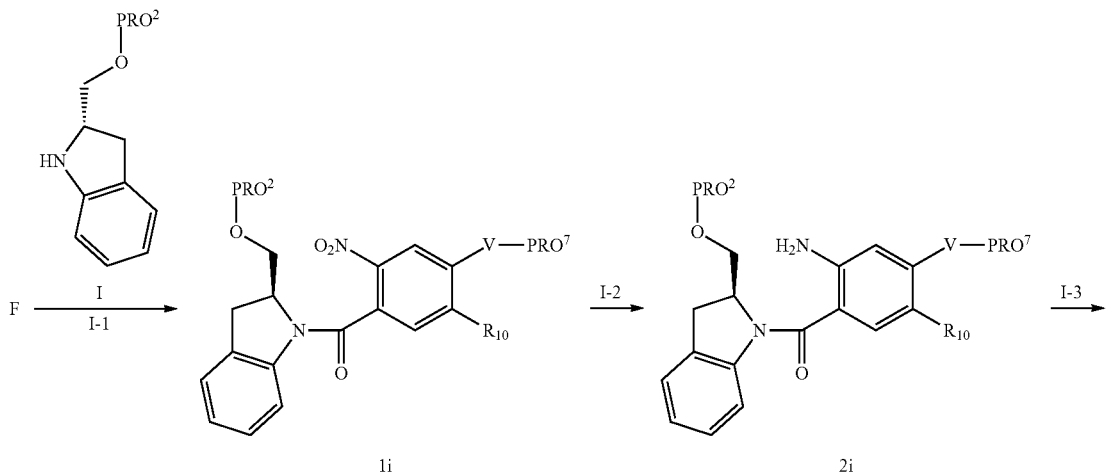

-continued
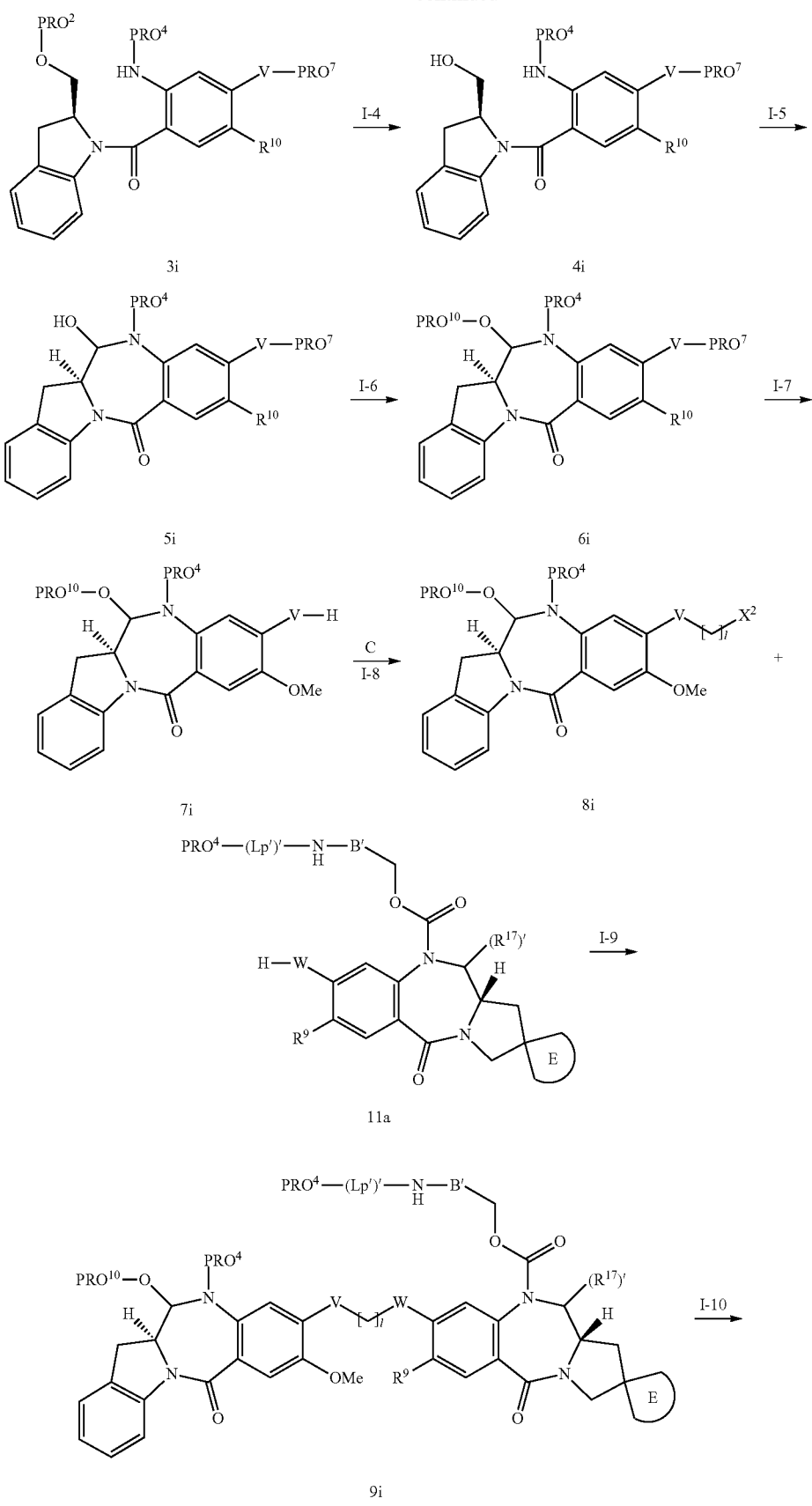

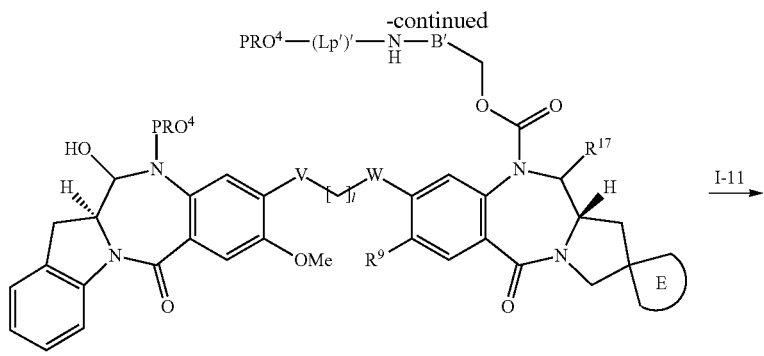

10i

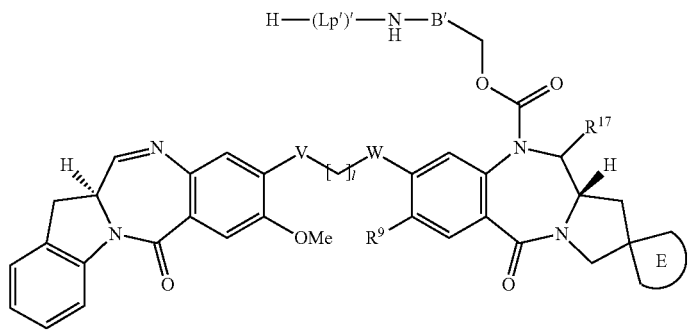

11i

Step I-1 to Step I-11

Production in step I-1 is carried out according to step A-4 of scheme A, production in step I-2 is carried out according to step A-5 of scheme A, production in step I-3 is carried out according to step B-9 of scheme B, production in step I-4 is carried out according to step A-7 of scheme A, production in step I-5 is carried out according to step A-8 of scheme A, production in step I-6 is carried out according to step A-2 of scheme A, production in step I-7 is carried out according to step A-10 of scheme A, production in step I-8 is carried out according to step A-11 of scheme A, production in step I-9 is carried out according to step E-1 of scheme E, production in step I-10 is carried out according to step A-7 of scheme A, and production in step I-11 is carried out according to step C-6 of scheme C.

Scheme J

The production method is a method for producing compound (12j), an intermediate for producing compound (1) in which $R^{12}$ and $R^{13}$ are combined to form $CH_2=$, R'' is hydrogen, and $R^{14}$ and $R^{15}$ are combined to form imine.

[Formula 112]

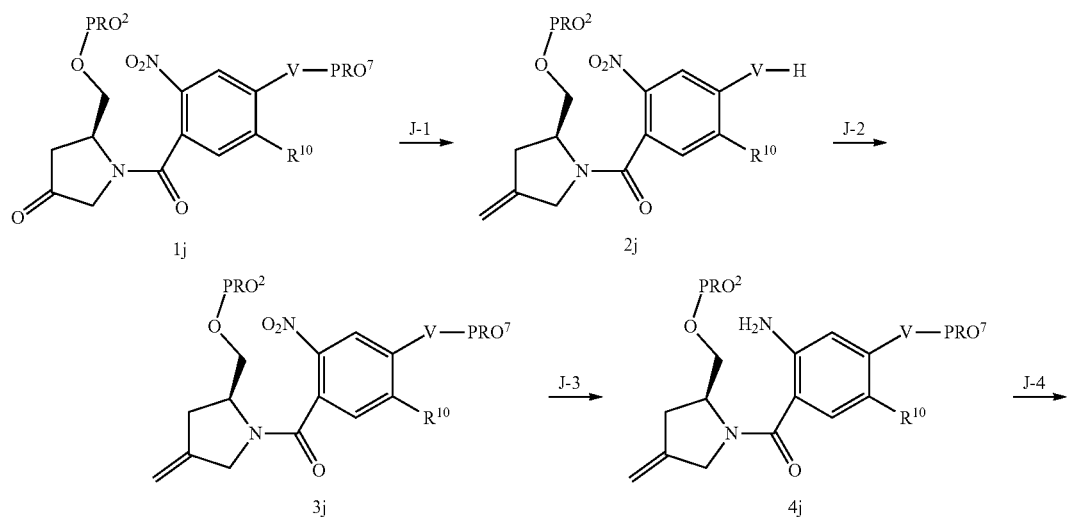

-continued
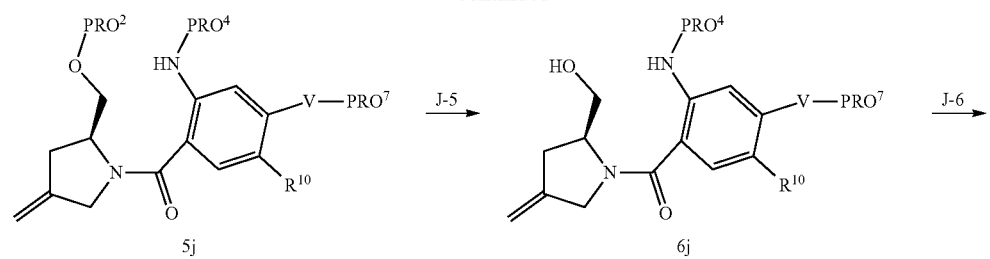
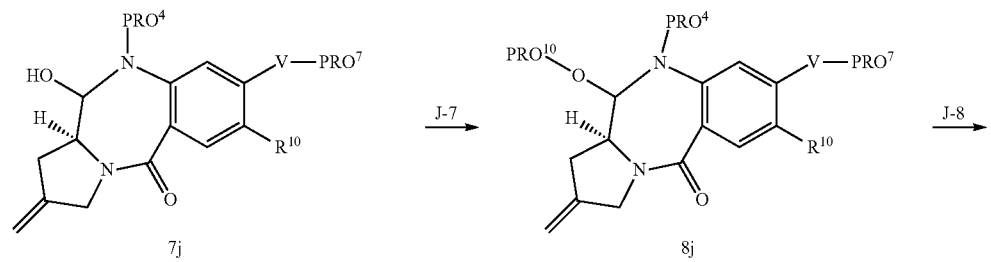
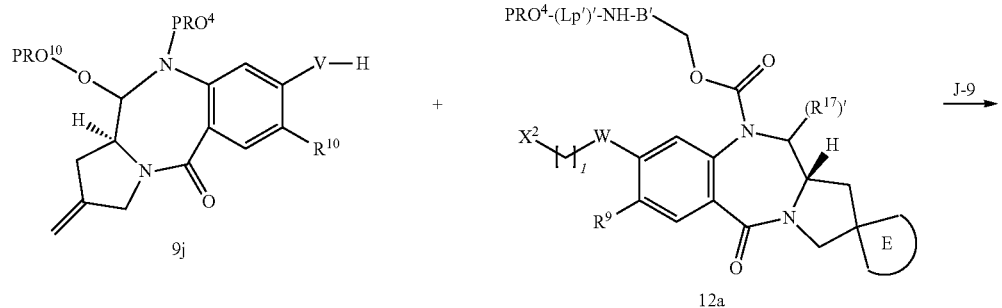
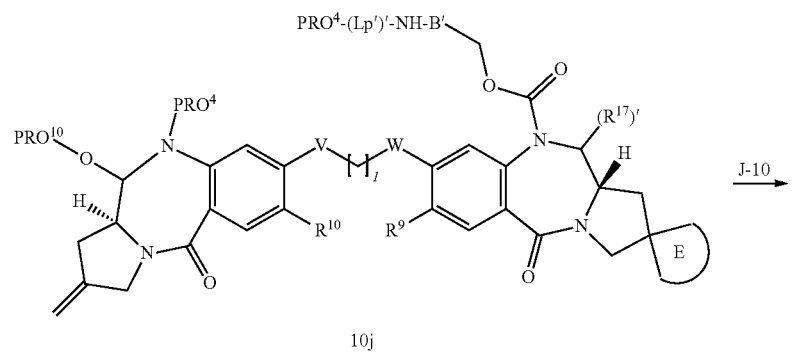
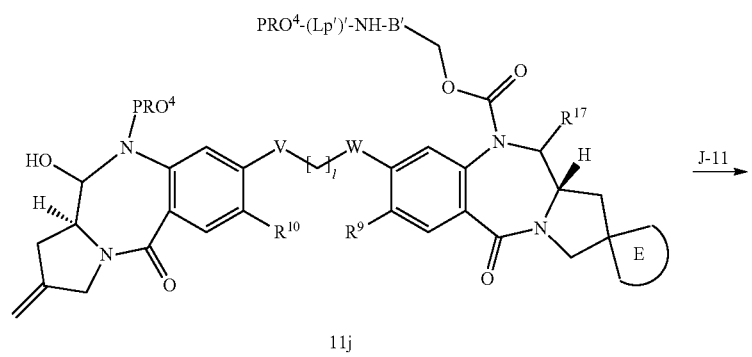

-continued

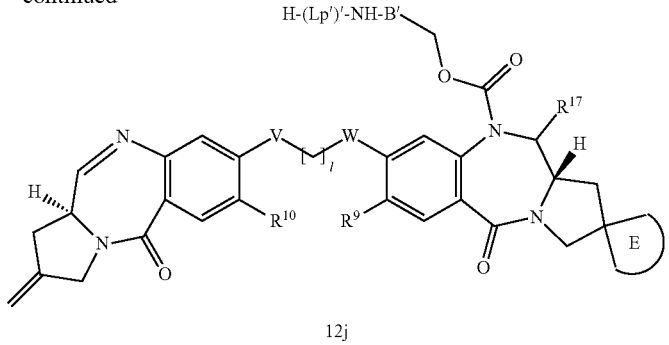

12j

Step J-1

The step is a step of producing compound (2j) by subjecting compound (1j) to Wittig reaction.

Step J-2: Introduction of Protective Group

When PRO$^7$ is a triisopropylsilyl group, the step is carried out by reacting compound (2j) and a silylating reagent (e.g., triisopropylsilyl chloride, triisopropylsilyl triflate) in solvent (dichloromethane, acetonitrile, THF, DMF, or the like, or mixed solvent thereof) at −20° C. to 120° C., preferably at 0° C. to 100° C. As necessary, a base (e.g., imidazole, pyridine, 2,6-lutidine, 4-dimethylaminopyridine, sodium hydride) is added to the reaction. The amount of moles of the silylating agent to be used is 1 mol to an excessive amount of moles, preferably 1 to 3 mol, per mole of compound (2a), and the amount of moles of the base to be used is 1 mol to an excessive amount of moles, preferably 1 to 5 mol, per mole of compound (2a). The reaction time is 10 minutes to 72 hours, and preferably 30 minutes to 24 hours.

Step J-3 to Step J-11

Production in step J-3 is carried out according to step A-5 of scheme A, production in step J-4 is carried out according to step B-9 of scheme B, production in step J-5 is carried out according to step A-7 of scheme A, production in step J-6 is carried out according to step A-8 of scheme A, production in step J-7 is carried out according to step A-2 of scheme A, production in step J-8 is carried out according to step A-10 of scheme A, production in step J-9 is carried out according to step E-1 of scheme E, production in step J-10 is carried out according to step A-7 of scheme A, and production in step J-11 is carried out according to step C-6 of scheme C.

Scheme K

Scheme K is a method for producing compound (7k), an intermediate needed for producing compound (1) in which R$^{11}$ and R$^{12}$ are combined, together with the carbon atoms to which R$^{11}$ and R$^{12}$ are bond, to form a double bond thereto, R$^{13}$ is a hydroxymethyl group, and R$^{14}$ and R$^{15}$ together form imine.

[Formula 113]

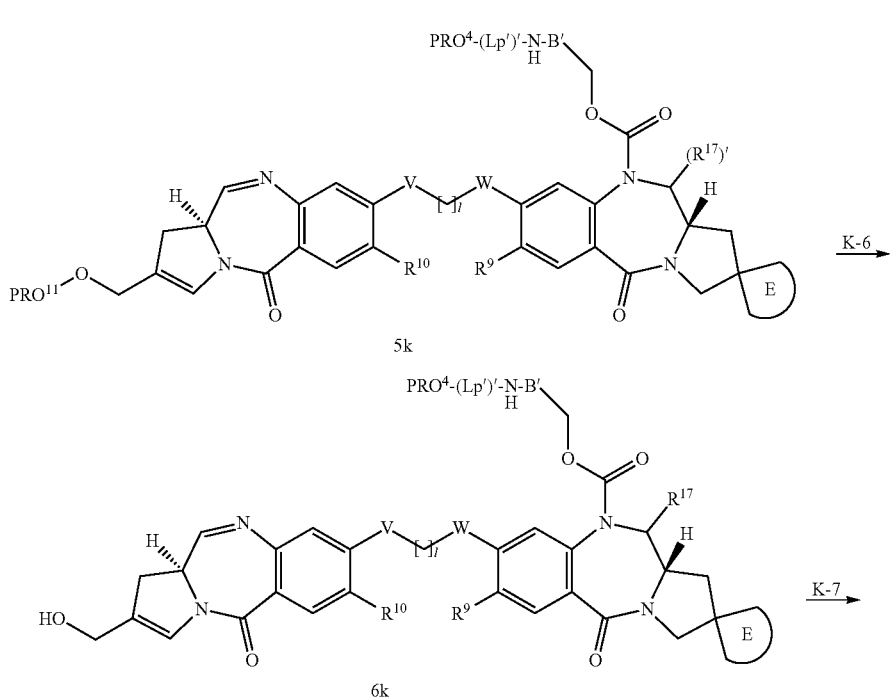

-continued

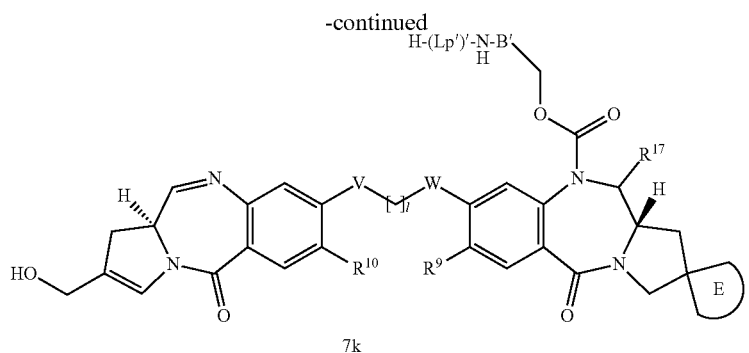

7k

Step K-1

The step is a step of producing compound (1k) by subjecting compound (6b) to carbonylation reaction.

Step K-2

The step is a step of producing compound (2k) by subjecting compound (1k) to aldehyde-selective reduction reaction.

Step K-3 to Step K-7

Production in step K-3 is carried out according to step A-2 of scheme A, production in step K-4 is carried out according to step B-7 of scheme B, production in step K-5 is carried out according to step E-1 of scheme E, production in step K-6 is carried out according to step A-7 of scheme A, and production in step K-7 is carried out according to step C-6 of scheme C.

Scheme L

Scheme L is a representative method for producing compound (B).

[Formula 114]

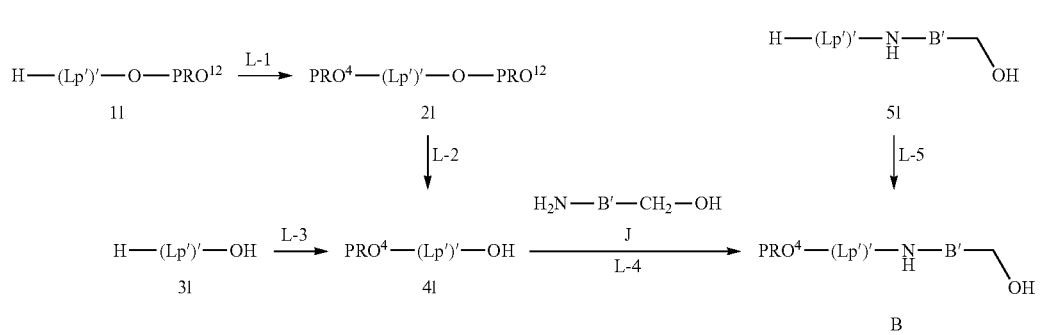

The peptide residues represented by general formula (Lp')' can be produced through condensation reaction of amino acids.

$PRO^4$ is protecting the N terminus of the peptide residues (Lp')' and $PRO^{12}$ is protecting the C terminus.

Step L-1

Production in step L-1 is carried out according to step B-9 of scheme B.

Step L-2: Deprotection Reaction

When $PRO^{12}$ is a tert-butyl group, the step is carried out by reacting compound (21) and an acid (e.g., trifluoroacetic acid, p-toluenesulfonic acid, hydrochloric acid, acetic acid) in solvent (dichloromethane or the like) at 0° C. to the boiling point of the solvent used for the reaction, preferably at 0° C. to 40° C. The amount of moles of the acid to be used is a catalytic amount to an excessive amount of moles per mole of compound (21). The reaction time is 10 minutes to 72 hours, and preferably 30 minutes to 24 hours.

Step L-3 and Step L-4

Production in step L-3 is carried out according to step B-9 of scheme B, and production in step L-4 is carried out according to step A-4 of scheme A.

Step L-5

Alternatively, compound (B) may be produced in step L-5 according to step B-9 of scheme B.

Scheme M

Scheme M is a method for producing compound (2).

Compound (2) shown in the production method is synonymous with compound (1) such that $R^{16}$ in the production intermediate of the present invention is J-La'-Lp'—NH—B'—$CH_2$—O(C=O)—*.

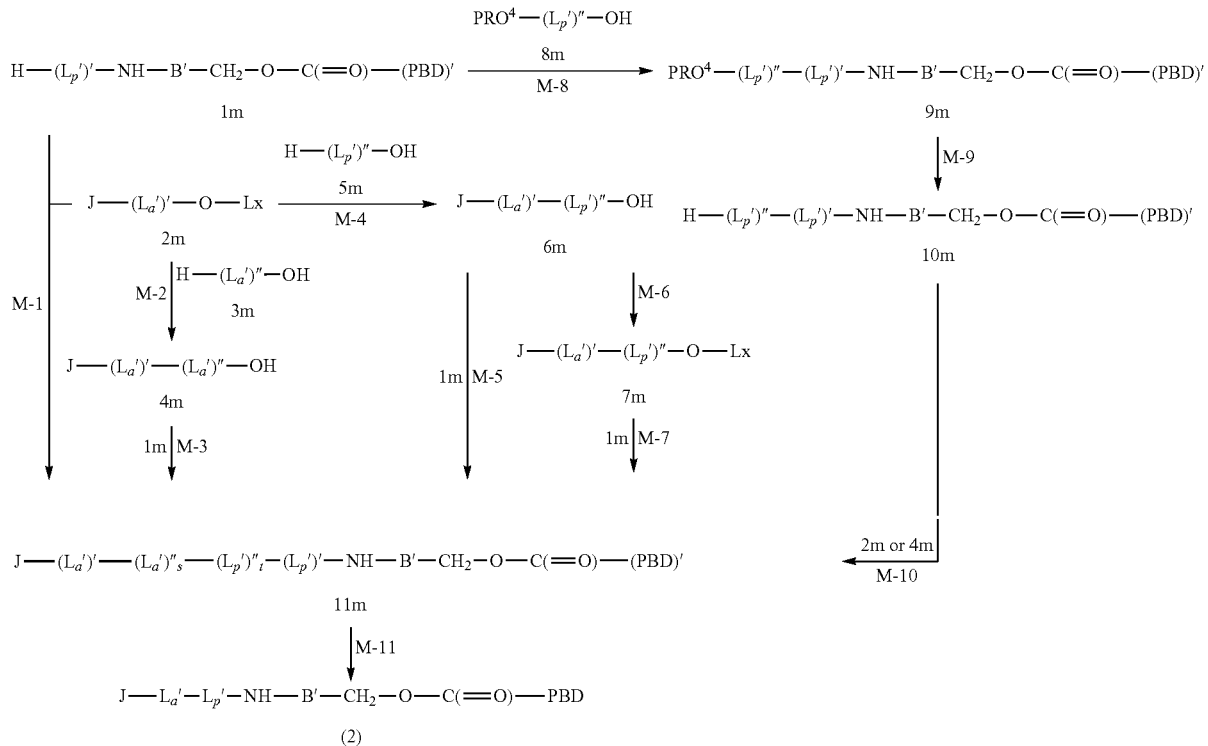

[Formula 115]

Compound (1m) shown in the production method represents compound (4e), (4f), (11g), (9h), (11), (12j), (7k), or (8k) produced in any of schemes E to K.

(PBD)' shown in the production method represents:

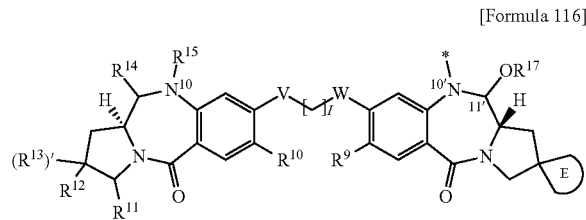

[Formula 116]

and PBD represents:

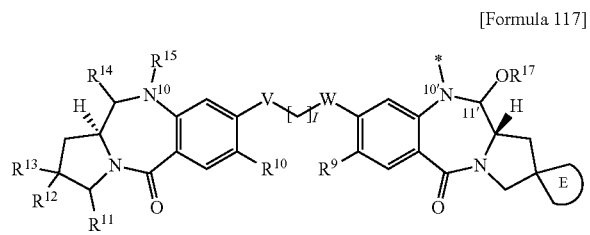

[Formula 117]

wherein (PBD)' may be protected with a substituent (e.g., a hydroxy group) on $R^{13}$ in PBD, and when lacking a protective group, (PBD)' is synonymous with PBD ($R^{13}$=($R^{13}$)')

In the peptide residues represented by $(Lp')''_t$-$(Lp')'$ in the production method, a functional group (e.g., an amino group) on a side chain of the amino acid residues represented by Lp' may be protected with a protective group, and when a protective group is unsubstituted, $(Lp')''_t$-$(Lp')'$ is synonymous with Lp'.

(Lp')' represents an amino acid sequence of two amino acids as shown below, and when a functional group (an amino group, a hydroxy group) is present in a side chain, (Lp')' may be protected: —VA-, (D-)VA-, -FG-, —PI—, -VCit-, —VK—, —PL-, -(D-)P—I—, or -GF-.

(Lp')" represents an amino acid sequence of two to four amino acids as shown below, and when a functional group (an amino group, a hydroxy group) is present in a side chain, (Lp')" may be protected:
GG-, -EGG-, -DG-, -(D-)DG-, -EG-, -GGF—, —SG-, -KG-, -DGG-, -GGF—, -DDGG- (SEQ ID NO: 92), —KDGG- (SEQ ID NO: 93), or -GGFG- (SEQ ID NO: 77).

(La')' represents any one selected from the following group:
—C(=O)—(CH$_2$CH$_2$)n$^6$-C(=O), —C(=O)—(CH$_2$CH$_2$)n$^6$-NH—C(=O)—(CH$_2$CH$_2$O)n$^7$-CH$_2$CH$_2$—C(=O)—, —(CH$_2$)n$^8$-O—C(=O)—, —(CH$_2$)n$^{12}$-C(=O)—, and, (CH$_2$CH$_2$)n$^{13}$-C(=O)—NH—(CH$_2$CH$_2$O)n$^{14}$-CH$_2$CH$_2$—C(=O)—

(La')" represents any one selected from the following group:
—NH—(CH$_2$CH$_2$)n$^7$-C(=O)— and —NH—(CH$_2$CH$_2$O)n$^7$-CH$_2$—C(=O)—, and s and t each independently represent 0 or 1. For example, s and t are each 0 in step M-1, s is 1 and t is 0 in step M-3, and s is 0 and t is 1 in step M-5.

(La')'-(La')"$_s$ is synonymous with La'.

When having a protective group, $(Lp')''_t$-$(Lp')'$ is converted to Lp' through deprotection, and is synonymous with Lp' when having no protective group.

Lx shown in the production method represents a hydrogen atom or a leaving group (e.g., hydroxysuccinimide).

PBD or (PBD)' in each of 1m, 9m, 10m, 11m, and compound (2) shown in the production method represents bonding at the asterisk (the N10'-position) to C(=O)— at the right end of —O—C(=O)—.

Step M-1

The step is a method of producing compound (11m) by subjecting compound (1m) produced in any of schemes E to K and compound (2m) to condensation reaction.

When Lx=H and compound (2m) is a carboxylic acid, compound (2m) can be produced according to step A-4 of scheme A.

When Lx is a leaving group (e.g., hydroxysuccinimide, a p-nitrophenoxy group), the step is carried out by reacting compound (1m) and compound (2m) in solvent (benzene, toluene, diethyl ether, dichloromethane, THF, DMF, methanol, water, or the like, or mixed solvent thereof) at −30° C. to the boiling point of the solvent used for the reaction, preferably at 0° C. to 50° C. The amount of moles of compound (2m) to be used is 0.9 mol to an excessive amount of moles, preferably 0.9 to 2 mol, per mole of compound (1m). As necessary, a base (e.g., triethylamine, N,N-diisopropylethylamine, N-methylmorpholine, 4-dimethylaminopyridine, diazabicycloundecene) is added to the reaction. The amount of moles of the base to be used is 1 mol to an excessive amount, preferably 1 to 5 mol, per mole of compound (1m). The reaction time is 10 minutes to 72 hours, and preferably 30 minutes to 36 hours.

Step M-2 to Step M-5 and Step M-8

Production in step M-2 is carried out according to step M-1, production in step M-3 is carried out according to A-4 of scheme A, production in step M-4 is carried out according to step M-1, production in step M-5 is carried out according to step A-4 of scheme A, and production in step M-8 is carried out according to step A-4 of scheme A.

Step M-6

The step is a step of producing active ester intermediate (7m) by subjecting compound (6m) to condensation reaction.

The step is carried out by reacting compound (6m) and hydroxysuccinimide or the like in solvent (benzene, toluene, diethyl ether, dichloromethane, THF, DMF, or the like, or mixed solvent thereof) in the presence of a condensing agent such as N,N-dicyclohexylcarbodiimide and 1-ethyl-3-(3-dimethylaminopropyl)carbodiimide at −30° C. to the boiling point of the solvent used for the reaction, preferably at 0° C. to 50° C. The amount of moles of the condensing agent to be used is 1 mol to an excessive amount of moles, preferably 1 to 5 mol, per mole of compound (6m). The amount of moles of hydroxysuccinimide to be used is 1 mol to an excessive amount of moles, preferably 1 mol to 5 mol, per mole of compound (6m). The reaction time is 10 minutes to 72 hours, and preferably 30 minutes to 24 hours.

Step M-7

The step is a step of producing compound (11m) by subjecting compound (1m) and compound (7m) to condensation reaction as in step M-1.

Step M-9

The step is a step of producing compound (10m) by subjecting compound (9m) to deprotection reaction. When $PRO^4$ is a 9-fluorenylmethyloxycarbonyl group, the step is carried out by reacting compound (9m) and a base (e.g., 1,8-diazabicyclo[5.4.0]-7-undecene, piperidine) in solvent (THF, dichloromethane, DMF, or the like, or mixed solvent thereof) at −20° C. to the boiling point of the solvent, preferably at 0° C. to 40° C. The amount of moles of the base to be used is 1 mol to an excessive amount of moles, preferably 1 to 10 mol, per mole of compound (9m). The reaction time is 1 minute to 72 hours, and preferably 5 minutes to 24 hours.

Step M-10

The step is a step of producing compound (11m) by subjecting compound (10m) and compound (2m) or (4m) to condensation reaction as in step A-4 of scheme A.

Step M-11

The step is a step of producing compound (2), when $(Lp')''_r$-(Lp')' or PBD' in compound (11m) has a protective group, by deprotecting compound (11m). Production is carried out according to step B-3 of scheme B and step C-6 of scheme C.

When (Lp')' or PBD' has no protective group, step M-11 is omitted, and in this case compound (11m) is synonymous with compound (2).

Scheme N

Scheme N represents a synthesis method for a compound, as the free drug represented by (1) in which $R^{11}$ and $R^{12}$ are combined, together with the carbon atoms to which R" and $R^{12}$ are bound, to form a double bond, $R^{14}$ and $R^{15}$ are each hydrogen, and $R^{16}$ and $R^{17}$ are combined to form an imine bond.

[Formula 118]

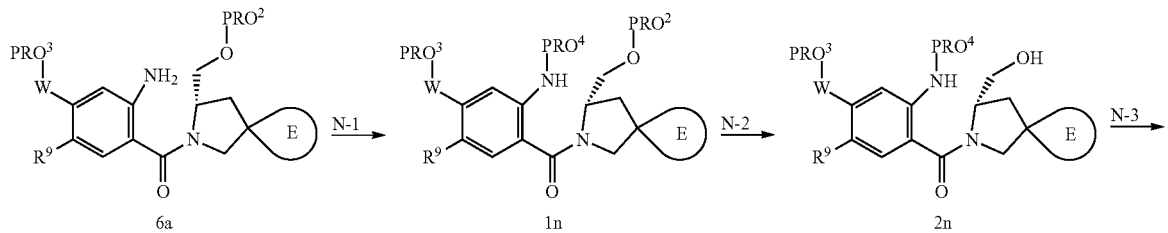

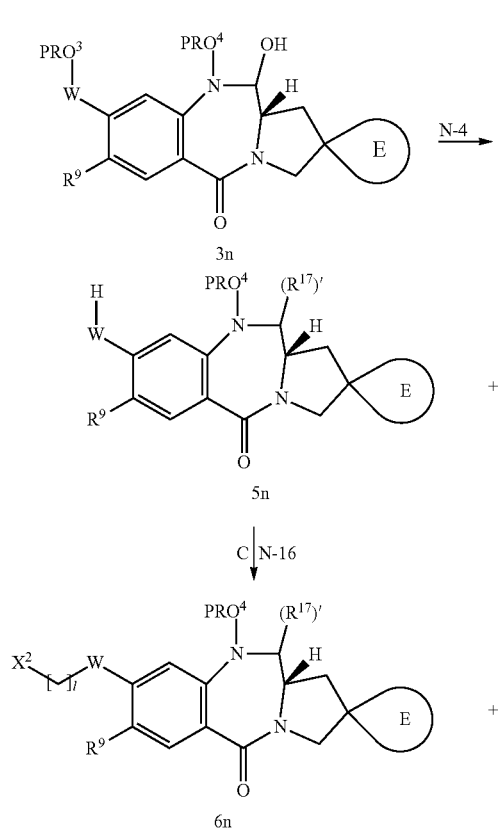

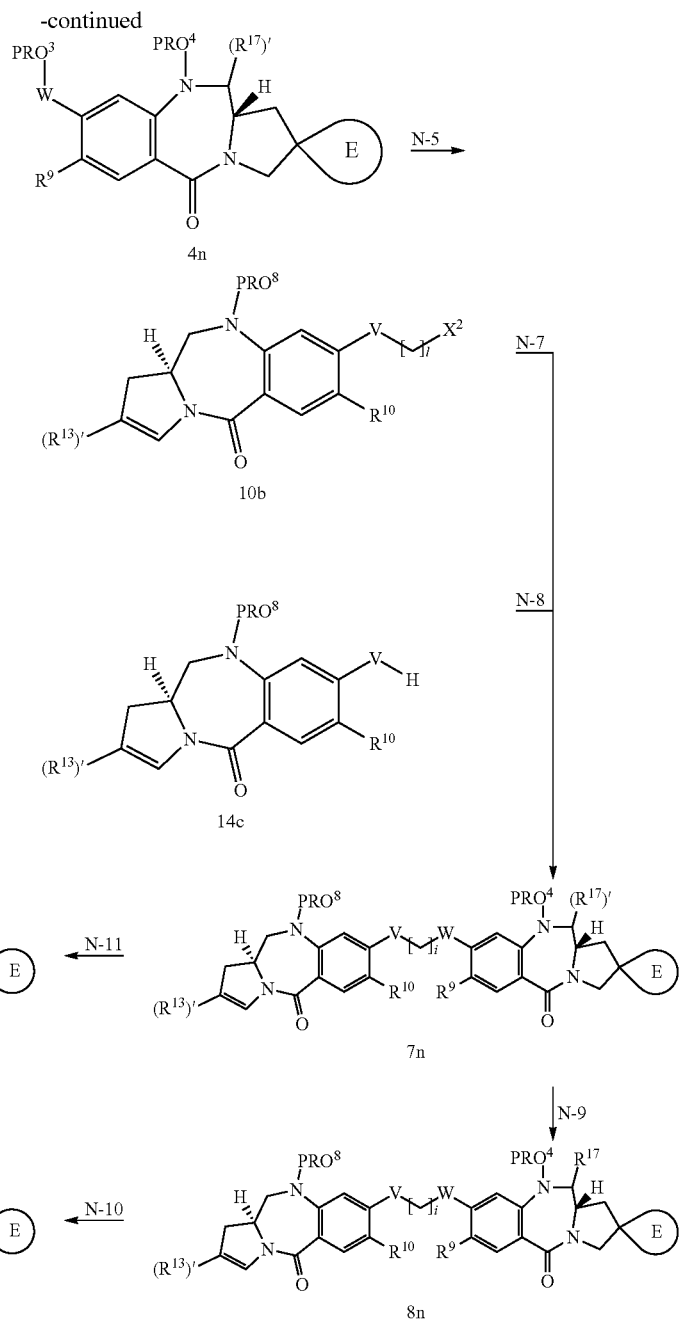

Step N-1 to Step N-8

Production in step N-1 is carried out according to step B-9 of scheme B, production in step N-2 is carried out according to step A-7 of scheme A, production in step N-3 is carried out according to step A-8 of scheme A, production in step N-4 is carried out according to step A-2 of scheme A, production in step N-5 is carried out according to step A-10 of scheme A, production in step N-6 is carried out according to step A-11 of scheme A, production in step N-7 is carried out according to step E-1 of scheme E, and production in step N-8 is carried out according to step E-1 of scheme E.

When $(R^{13})' = R^{13}$, production is carried out according to step N-9 and step N-10 shown in the following.

Step N-9

Production in step N-9 is carried out according to step A-7 of scheme A.

Step N-10

When the protective groups $PRO^4$ and $PRO^5$ are the same, production is carried out according to step E-4 of scheme E. When the protective groups $PRO^4$ and $PRO^5$ are different, production is carried out according to steps E-5 and E-6 of scheme E.

When $(R^{13})'$ has a protective group, production is carried out according to step N-11 and step N-12 shown in the following.

Step N-11

Production is carried out according to step B-3 of scheme B.

Step N-12

When the protective groups PRO⁴ and PRO⁵ are the same, production is carried out according to steps E-3 and E-4 of scheme E. When the protective groups PRO⁴ and PRO⁸ are different, production is carried out according to steps E-3, E-5, and E-6 of scheme E.

Scheme O

Scheme O is a method for producing compound (6o), as the free drug represented by (1) in which $R^{11}$ and $R^{12}$ are combined, together with the carbon atoms to which $R^{11}$ and $R^{12}$ are bound, to form a double bond, $R^{14}$ and $R^{15}$ are combined to form an imine bond (C=N), and $R^{16}$ and $R^{17}$ together form an imine bond (C=N).

[Formula 119]

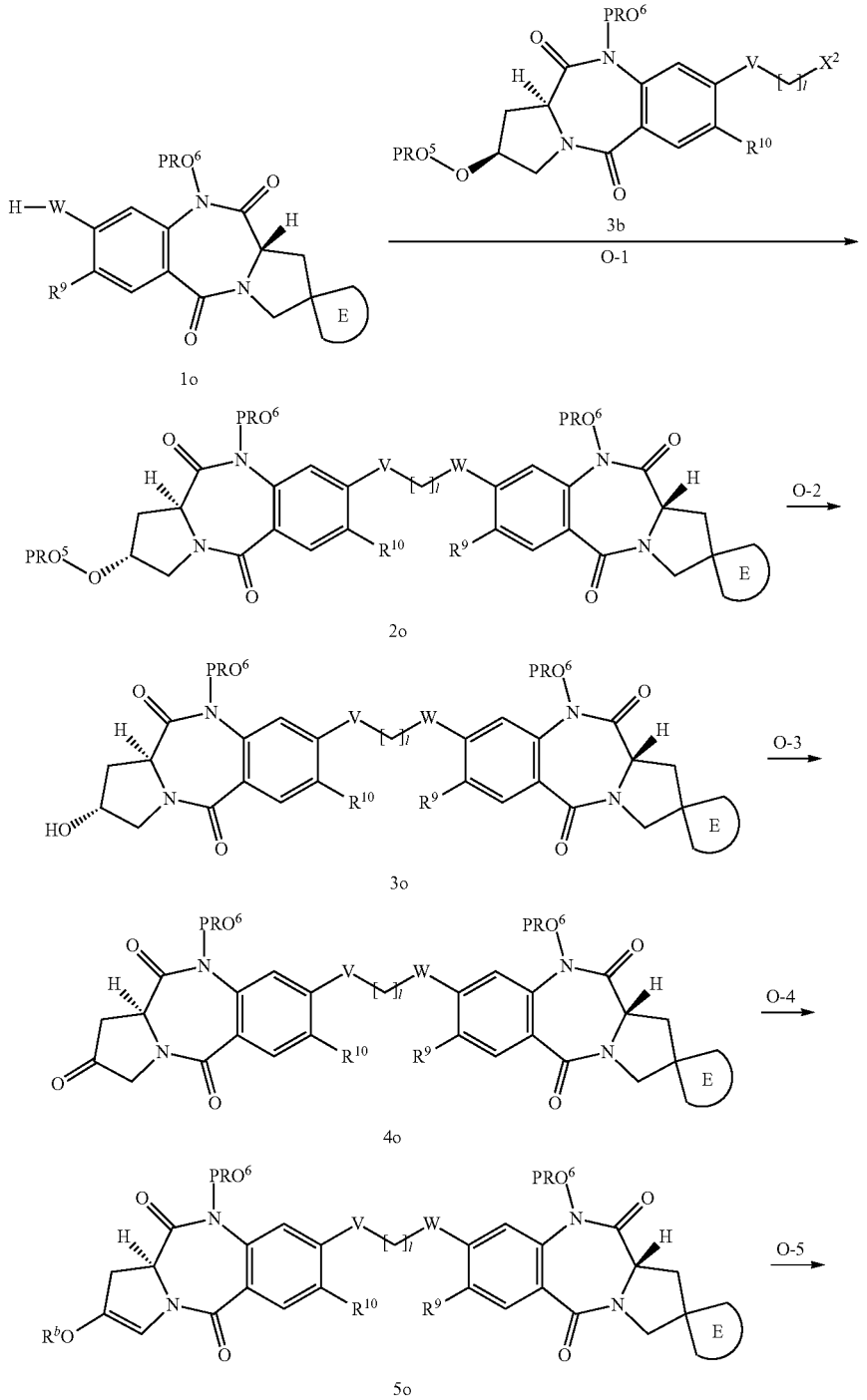

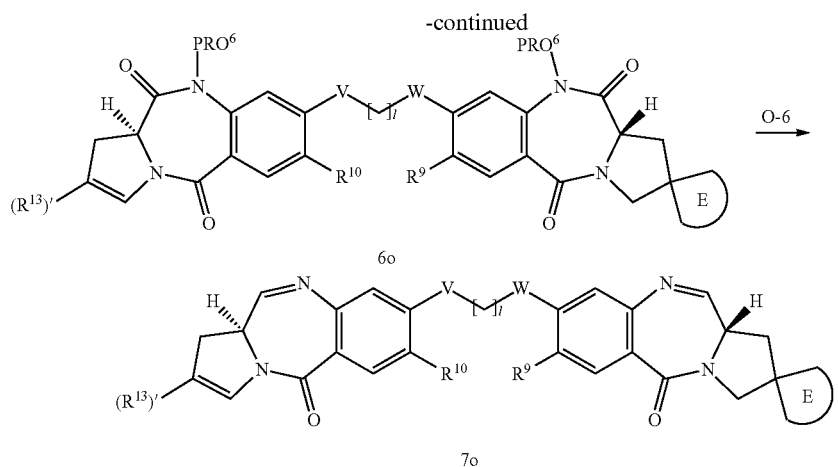

6o

7o

Step O-1 to Step O-6

Production in step O-1 is carried out according to step E-1 of scheme E, production in step O-2 is carried out according to step B-3 of scheme B, production in step O-3 is carried out according to step A-8 of scheme A, production in step O-4 is carried out according to step B-5 of scheme B, production in step O-5 is carried out according to step B-6 of scheme B, and production in step O-6 is carried out according to step B-7 of scheme B.

Scheme P

The production method is a method for producing a compound as the free drug represented by (1) in which $R^{11}$ represents a hydrogen atom, $R^{12}$ and $R^{13}$ are combined to form a spiro ring, $R^{14}$ and $R^{15}$ are combined to form an imine bond (C=N), and $R^{16}$ and $R^{17}$ together form an imine bond (C=N). In the production method, the spiro ring formed by $R^{12}$ and $R^{13}$ in compound (4h) as a starting raw material is synonymous with E, and hence represented by E.

[Formula 120]

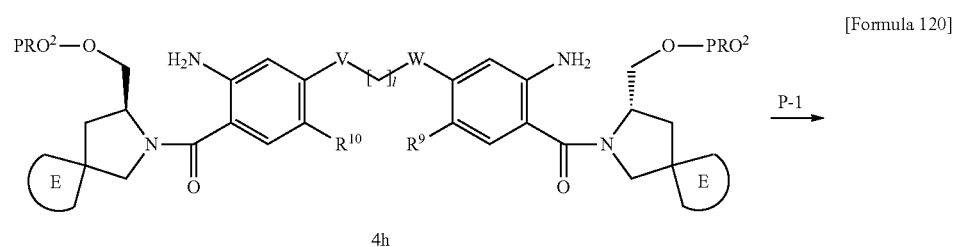

4h

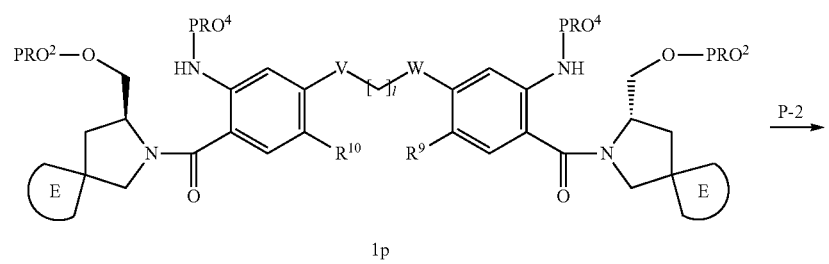

1p

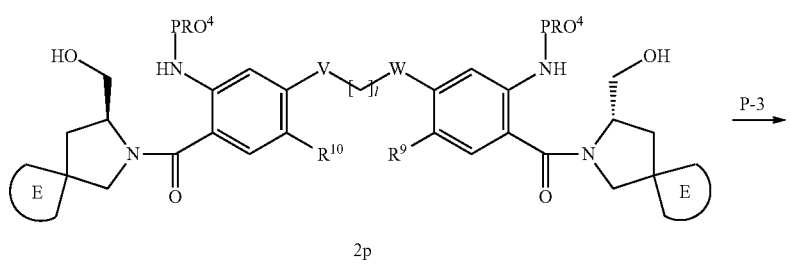

2p

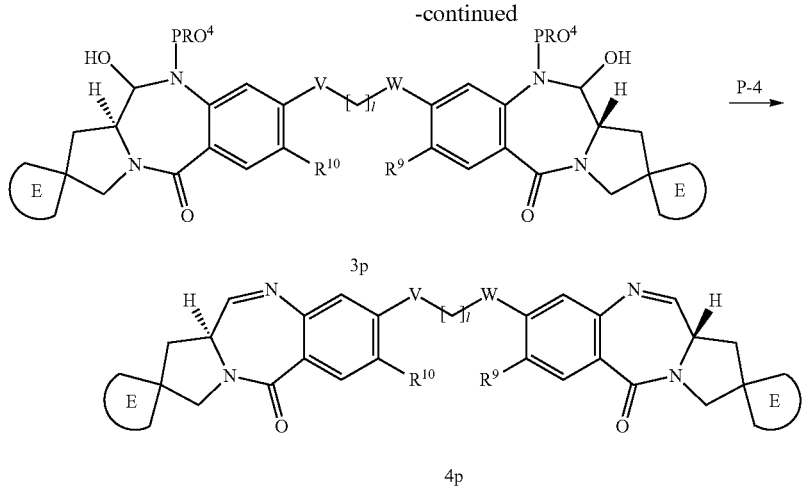

Step P-1 to Step P-4

Production in step P-1 is carried out according to step B-9 of scheme B, production in step P-2 is carried out according to step B-3 of scheme B, production in step P-3 is carried out according to step A-8 of scheme A, and production in step P-4 is carried out according to step C-6 of scheme C.

Scheme Q

The production method is a method for producing a compound as the free drug represented by (1) in which $R^D$, $R^{14}$, and $R''$ each represent a hydrogen atom, $R^{12}$ and $R^{13}$ are combined to form a spiro ring, and $R^{16}$ and $R^{17}$ are combined to form an imine bond (C=N).

[Formula 121]

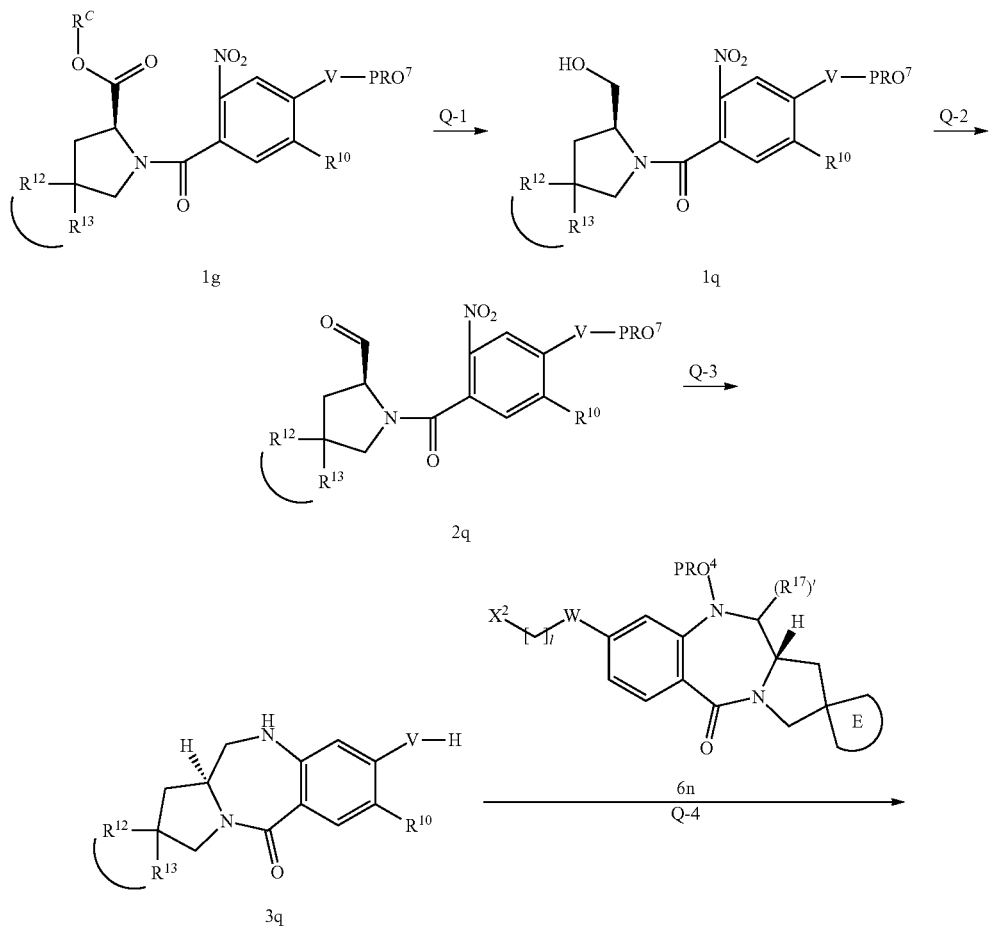

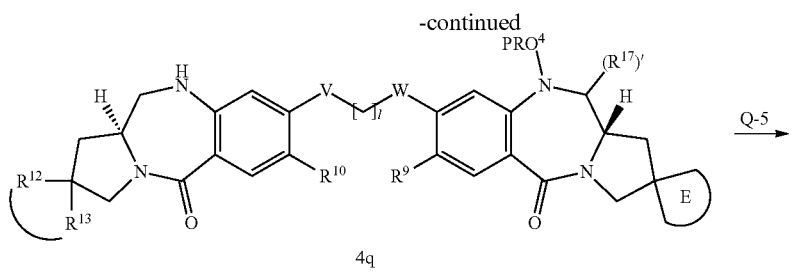
4q
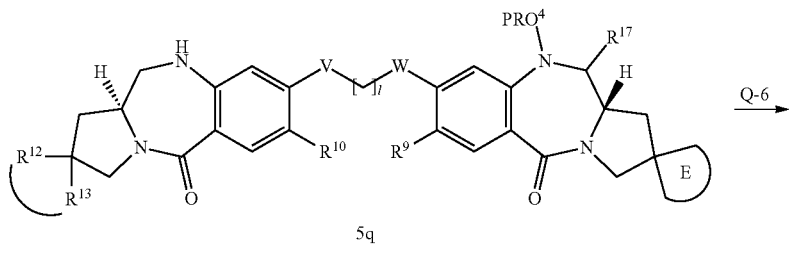
5q
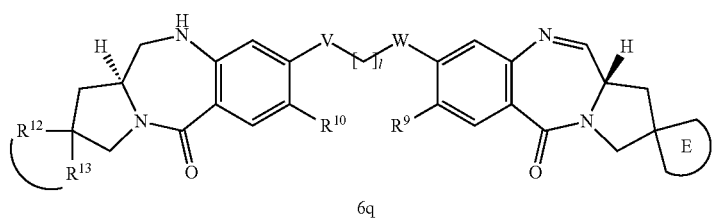
6q
[Formula 121]
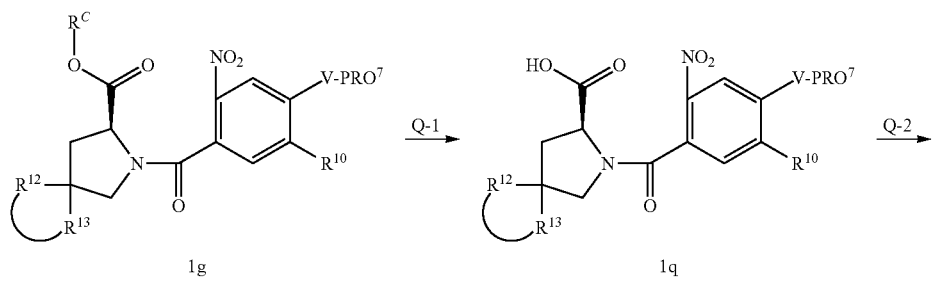
1g    1q
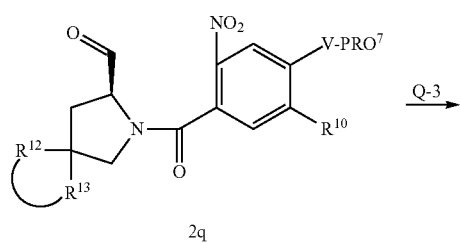
2q

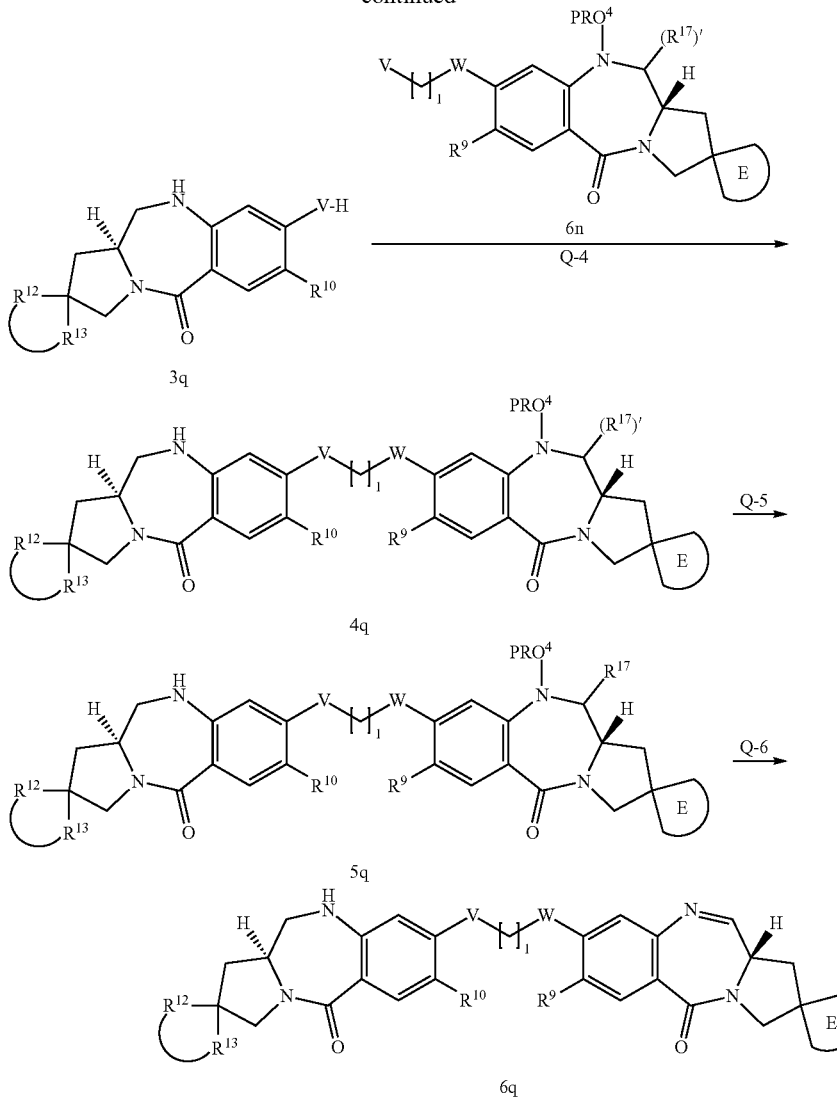

Step Q-1 to Step Q-6

Production in step Q-1 is carried out according to step A-1 of scheme A, production in step Q-2 is carried out according to step A-8 of scheme A, production in step Q-3 is carried out according to step A-5 of scheme A, production in step Q-4 is carried out according to step E-1 of scheme E, production in step Q-5 is carried out according to step A-7 of scheme A, and production in step Q-6 is carried out according to step C-6 of scheme C.

The protective group for optionally protected amino groups and hydroxy groups in the above description refers to a protective group cleavable with a chemical method such as hydrogenolysis, hydrolysis, electrolysis, and photolysis, and represents a protective group commonly used in synthetic organic chemistry (e.g., see Protective groups in Organic Synthesis, 3rd Edition, John Wiley & Sons, Inc. (1999)).

The "protective group" for optionally protected hydroxy groups (e.g., an alkylcarbonyl group, a silyl group, or an aralkyl group), the "protective group" for optionally protected carboxy groups (e.g., a $C_1$-$C_6$ alkyl group or an aralkyl group), and the "protective group" for optionally protected amino groups (e.g., an alkoxycarbonyl group) are not limited to a particular protective group and may be any protective group used for hydroxy groups, carboxy groups, and amino groups for use in the field of synthetic organic chemistry.

Steps requiring protection or deprotection are carried out according to any known method (e.g., a method described in "Protective groups in Organic Synthesis" (by Theodora W. Greene, Peter G. M. Wuts, 1999, published by Wiley-Interscience Publication)).

Scheme R: Preparation of Antibody

Figure 50:
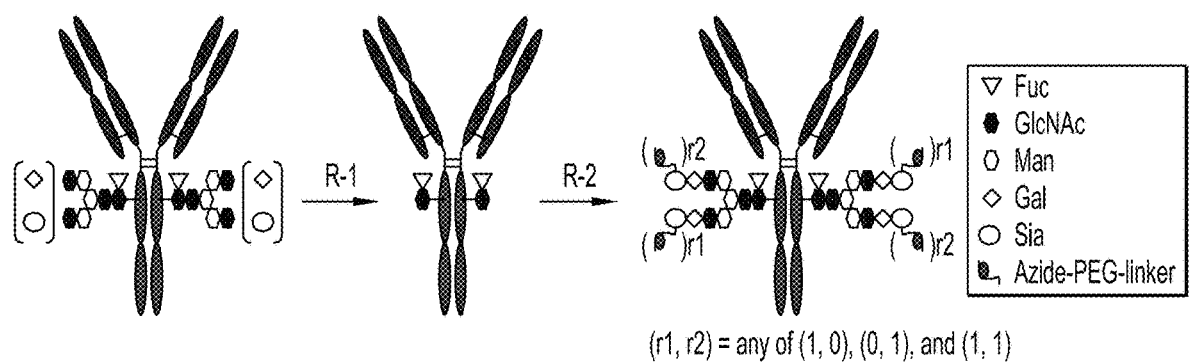
FIG. 50 shows Formula 122, which is a glycan-remodeled antibody which may be produced by using a method as illustrated in FIGS. 3A and 3B, for example, according to a method described in WO 2013/120066.

A glycan-remodeled antibody may be produced by using a method as illustrated in FIGS. 3A and 3B, for example, according to a method described in WO 2013/120066 (see FIG. 50).

Step R-1: Hydrolysis of Glycosidic Bond at GlcNAcβ1-4GlcNAc of Chitobiose Structure at Reducing Terminal The step is a step of preparing a glycan-truncated antibody by cleaving N-linked glycan bonding to asparagine at the 297-position of the amino acid sequence of a targeted antibody (N297-linked glycan) with use of a known enzymatic reaction.

A targeted antibody (20 mg/mL) in buffer solution (e.g., 50 mM phosphate buffer solution) is subjected to hydrolysis reaction of the glycosidic bond between GlcNAcβ1 and 4GlcNAc in the chitobiose structure at the reducing terminal with use of hydrolase such as the enzyme EndoS at 0° C. to 40° C. The reaction time is 10 minutes to 72 hours, and preferably 1 hour to 6 hours. The amount of the wild-type enzyme EndoS to be used is 0.1 to 10 mg, preferably 0.1 to 3 mg, to 100 mg of the antibody. After the completion of the reaction, purification with affinity chromatography and/or purification with a hydroxyapatite column, each described later, are/is carried out to produce a (Fucα1,6)GlcNAc antibody with the glycan hydrolyzed between GlcNAcβ1 and 4GlcNAc.

Step R-2: Transglycosylation Reaction

The step is a step of producing a glycan-remodeled antibody by bonding the (Fucα1,6)GlcNAc antibody to MSG- (MSG1-, MSG2-) or SG-type glycan oxazoline form (hereinafter, referred to as "azide glycan oxazoline form") having a PEG linker including an azide group with use of enzymatic reaction.

The glycan-truncated antibody in buffer solution (e.g., phosphate buffer solution) is subjected to transglycosylation reaction by reacting with an azide glycan oxazoline form in the presence of a catalytic amount of transglycosidase such as EndoS (D233Q/Q303L) at 0° C. to 40° C. The reaction time is 10 minutes to 72 hours, and preferably 1 hour to 6 hours. The amount of the enzyme EndoS (D233Q/Q303L) to be used is 1 to 10 mg, preferably 1 to 3 mg, to 100 mg of the antibody, and the amount of the azide glycan oxazoline form to be used is 2 equivalents to an excessive equivalent, preferably 2 equivalents to 20 equivalents.

After the completion of the reaction, purification with affinity chromatography and purification with a hydroxyapatite column are carried out to afford a purified glycan-remodeled antibody.

The azide glycan oxazoline form may be prepared according to methods described in Examples 55 to 57. By using a reaction known in the field of synthetic organic chemistry (e.g., condensation reaction), $N_3$—$(CH_2CH_2$—$O)n_5$-$CH_2CH_2$—$NH_2$, a PEG linker including an azide group ($N_3$-L(PEG)), may be introduced to MSG (MSG1, MSG2) or disialooctasaccharide (Tokyo Chemical Industry Co., Ltd.). Specifically, carboxylic acid at the 2-position of a sialic acid and the amino group at the right end of $N_3$— $(CH_2CH_2$—$O)n_5$-$CH_2CH_2$—$NH_2$ undergo condensation reaction to form an amide bond.

Examples of the condensing agent in using condensation reaction may include, but not limited to, N,N'-dicyclohexylcarbodiimide (DCC), 1-ethyl-3-(3-dimethylaminopropyl) carbodiimide (EDCI), carbonyldiimidazole (CDI), 2-(2H-benzotriazol-2-yl)-4-(1,1,3,3-tetramethylbutyl)phenol (BOP), 1H-benzotriazol-1-yloxytripyrrolidinophosphonium hexafluorophosphate (PyBOP), and O-(7-azabenzotriazol-1-yl)-N,N,N',N'-tetramethyluronium hexafluorophosphate (HATU), and examples of the solvent for the reaction may include, but not limited to, dichloromethane, DMF, THF, ethyl acetate, and mixed solvent thereof.

The reaction temperature is typically −20° C. to 100° C. or the boiling point of the solvent, and preferably in the range of −5° C. to 50° C. As necessary, an organic base such as triethylamine, diisopropylethylamine, N-methylmorpholine, and 4-dimethylaminopyridine or an inorganic base such as potassium carbonate, sodium carbonate, potassium hydrogen carbonate, and sodium hydrogen carbonate may be added. Further, for example, 1-hydroxybenzotriazole or N-hydroxysuccinimide may be added as a reaction accelerator.

MSG, MSG1, or MSG2 may be obtained by hydrolysis of the (MSG-)Asn or separated/purified (MSG1-)Asn or (MSG2-)Asn (Example 56) with hydrolase such as EndoM.

Oxazolination may be prepared from GlcNAc at the reducing terminal of MSG-(MSG1-, MSG2-) or SG-type glycan according to a known article (J. Org Chem., 2009, 74(5), 2210-2212. Helv. Chim. Acta, 2012, 95, 1928-1936).

In preparing the glycan-remodeled antibody, concentration of an aqueous solution of an antibody, measurement of concentration, and buffer exchange may be carried out according to common operations A to C in the following.
Common Operation A: Concentration of Aqueous Solution of Antibody A solution of an antibody or antibody-drug conjugate was placed in a container of an Amicon Ultra (30,000 to 50,000 MWCO, Millipore Corporation), and the solution of an antibody or antibody-drug conjugate, which is described later, was concentrated through a centrifugation operation (centrifugation at 2000 G to 4000 G for 5 to 20 minutes) using a centrifuge (Allegra X-15R, Beckman Coulter, Inc.).
Common Operation B: Measurement of Antibody Concentration Measurement of antibody concentration was carried out by using a UV measurement apparatus (Nanodrop 1000, Thermo Fisher Scientific Inc.) according to a method specified by the manufacturer. Then, 280 nm absorption coefficients, being different among antibodies (1.3 mL mg$^{-1}$ cm$^{-1}$ to 1.8 mL mg$^{-1}$ cm$^{-1}$), were used.
Common Operation C: Buffer Exchange for Antibody A buffer solution (e.g., phosphate buffered saline (pH 6.0), phosphate buffer (pH 6.0)) was added to an aqueous solution of an antibody, which was concentrated according to common operation A. This operation was carried out several times, and the antibody concentration was then measured by using common operation B, and adjusted to 10 mg/mL with a buffer solution (e.g., phosphate buffered saline (pH 6.0), phosphate buffer (pH 6.0)).
Scheme S: Conjugation The production method is a method for producing an antibody-drug conjugate by conjugating the above-described glycan-remodeled antibody to production intermediate (2) through SPAAC (strain-promoted alkyne azide cycloaddition: J. AM. CHEM. SOC. 2004, 126, 15046-15047) reaction. In the formula, Ab represents the glycan-remodeled antibody.

[Formula 123]

Ab + J—$L_a'$—$L_p'$—NH—B'—$CH_2$—O(C=O)—PBD ⟶

(2)

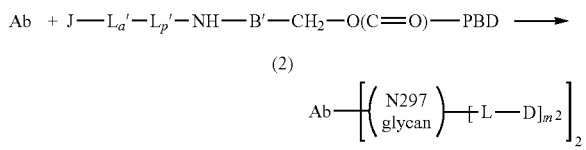

SPAAC reaction proceeds by mixing a buffer solution (sodium acetate solution, sodium phosphate, sodium borate solution, or the like, or a mixture thereof) of antibody Ab and a solution dissolving compound (2) in an appropriate solvent (dimethyl sulfoxide (DMSO), dimethylformamide (DMF), dimethylacetamide (DMA), N-methyl-2-pyrrolidone (NMP), propylene glycol (PG), or the like, or a mixture thereof).

The amount of moles of compound (2) to be used is 2 mol to an excessive amount of moles, preferably 1 mol to 30 mol, per mole of the antibody, and the ratio of the organic solvent is preferably 1 to 200% v/v to the buffer of the antibody. The reaction temperature is 0° C. to 37° C., and preferably 10° C. to 25° C., and the reaction time is 1 to 150 hours, and preferably 6 hours to 100 hours. The pH in the reaction is preferably 5 to 9.

Antibody-drug conjugate compounds (ADCs) can be identified from each other through buffer exchange, purification, and measurement of antibody concentration and average number of conjugated drug molecules per antibody molecule according to common operations A to C described above and common operations D to F described later.

Common Operation D: Purification of Antibody-Drug Conjugate

An NAP −25 column was equilibrated with acetic acid buffer solution (10 mM, pH 5.5; herein, referred to as ABS) containing commercially available sorbitol (5%). To this NAP-25 column, an aqueous reaction solution of an antibody-drug conjugate (about 1.5 to 2.5 mL) was applied, and eluted with a buffer in an amount specified by the manufacturer to separate and collect an antibody fraction. The fraction separated and collected was again applied to the NAP-25 column, and a gel filtration purification operation to elute with a buffer was repeated twice or three times in total to afford the antibody-drug conjugate with an unbound drug-linker, dimethyl sulfoxide, and propylene glycol removed. As necessary, the concentration of the solution of the antibody-drug conjugate was adjusted through common operations A to C.

Common Operation E: Measurement of Antibody Concentration of Antibody-Drug Conjugate The concentration of the conjugated drug in an antibody-drug conjugate can be calculated by using the Lambert-Beer's law shown below. Expression (I) using the Lambert-Beer's law is as follows.

[Expression 1]

$$A_{280} = \varepsilon_{280}(L \cdot mol^{-1} \cdot cm^{-1}) \cdot C(mol \cdot L^{-1}) \cdot l(cm) \quad \text{Expression (I)}$$

Absorbance =

Molar absorption coefficient × Molarity × Optical path length

Here, A280 denotes absorbance of an aqueous solution of an antibody-drug conjugate at 280 nm, ε280 denotes the molar absorption coefficient of an antibody-drug conjugate at 280 nm, and C (mol·L$^{-1}$) denotes the molarity of an antibody-drug conjugate. From expression (I), the molarity of an antibody-drug conjugate, C (mol·L$^{-1}$), can be determined by using expression (II) below.

[Expression 2]

$$C(mol \cdot L^{-1}) = \frac{A_{280}}{\varepsilon_{280}(L \cdot mol^{-1} \cdot cm^{-1}) \cdot l(cm)} \quad \text{Expression (II)}$$

Further, the both sides are multiplied by the molar mass of the antibody-drug conjugate, MW (g·mol$^{-1}$), to determine the weight concentration of the antibody-drug conjugate, C' (mg·mL$^{-1}$) (expression (III)).

[Expression 3]

$$C'(mg \cdot mL^{-1}) = MW(g \cdot mol^{-1}) \cdot C(mol \cdot L^{-1}) = \frac{A_{280} \cdot MW(g \cdot mol^{-1})}{\varepsilon_{280}(L \cdot mol^{-1} \cdot cm^{-1}) \cdot l(cm)} \quad \text{Expression (III)}$$

Values used for the expression and applied to Examples will be described.

The absorbance A280 used was a measured value of UV absorbance of an aqueous solution of an antibody-drug conjugate at 280 nm. For molar mass, MW (g·mol$^{-1}$), an estimated value of the molecular weight of an antibody was calculated from the amino acid sequence of the antibody, and used as an approximate value of the molar mass of an antibody-drug conjugate. The optical path length, 1 (cm), used in measurement was 1 cm.

The molar absorption coefficient, E280, of the antibody-drug conjugate can be determined by using expression (IV) below.

[Expression 4]

| $\varepsilon_{260} =$ | $\varepsilon_{Ab.280}$ + | $\varepsilon_{DL.280}$ × Number | Expression (IV) |
|---|---|---|---|
| Molar absorption Coefficient of antibody | Molar absorption Coefficient of Drug | of conjugated drug Molecules | |

Here, $\varepsilon_{Ab, 280}$ denotes the molar absorption coefficient of an antibody at 280 nm, and $\varepsilon_{DL, 280}$ denotes the molar absorption coefficient of a drug at 280 nm.

By using a known calculation method (Protein Science, 1995, vol. 4, 2411-2423), $\varepsilon_{Ab, 280}$ can be estimated from the amino acid sequence of an antibody. In Examples, the molar absorption coefficient of trastuzumab used was $\varepsilon_{Ab, 280}$=215400 (calculated estimated value). The molar absorption coefficient of the CLDN6 antibody used was $\varepsilon_{Ab, 280}$=221340 (calculated estimated value), the molar absorption coefficient of the TROP2 antibody used was $\varepsilon_{Ab, 280}$=226400 (calculated estimated value), the molar absorption coefficient of the CD98 antibody used was $\varepsilon_{Ab, 280}$=240400 (calculated estimated value), the molar absorption coefficient of the LPS antibody used was $\varepsilon_{Ab, 280}$=230300 (calculated estimated value), and the molar absorption coefficient of the trastuzumab variant used was $\varepsilon_{Ab, 280}$=215057 (calculated estimated value).

$\varepsilon_{DL, 280}$ was calculated for use from a measured value obtained in each UV measurement. Specifically, the absorbance of a solution dissolving a conjugate precursor (drug) with a certain molarity was measured, and expression (I), the Lambert-Beer's law, was applied thereto, and the resulting value was used.

Common Operation F: Measurement of Average Number of Conjugated Drug Molecules Per Antibody Molecule in Antibody-Drug Conjugate The average number of conjugated drug molecules per antibody molecule in an antibody-drug conjugate can be determined through high-performance liquid chromatography (HPLC) with the following method.

[F-1. Preparation of Sample for HPLC Analysis (Reduction of Antibody-Drug Conjugate)]

A solution of an antibody-drug conjugate (about 1 mg/mL, 60 µL) is mixed with an aqueous solution of dithiothreitol (DTT) (100 mM, 15 µL). The mixture is incubated at 37° C. for 30 minutes to prepare a sample in which the disulfide bond between the L chain and H chain of the antibody-drug conjugate cleaved, and this sample is used for HPLC analysis.

[F-2. HLPC Analysis]

HPLC analysis is carried out under the following conditions.

HPLC system: Agilent 1290 HPLC system (Agilent Technologies)
Detector: Ultraviolet absorption spectrometer (measurement wavelength: 280 nm, 329 nm)
Column: BEH Phenyl (2.1×50 mm, 1.7 m, Waters Acquity)
Column temperature: 75° C.
Mobile phase A: 0.1% trifluoroacetic acid (TFA)-15% isopropyl alcohol aqueous solution
Mobile phase B: 0.075% TFA-15% isopropyl alcohol acetonitrile solution
Gradient program: 14%-36% (0 min to 15 min), 36%-80% (15 min to 17 min), 80%-14% (17 min to 17.1 min), 14%-14% (17.1 min to 23 min)
Sample injection volume: 5μL

[F-3. Data Analysis]

[F-3-1] An L chain with a conjugated drug molecule (L chain with one conjugated drug molecule: $L_1$) and H chain with a conjugated drug molecule(s) (H chain with one conjugated drug molecule: $H_1$, H chain with two conjugated drug molecules: $H_2$, H chain with three conjugated drug molecules: $H_3$) have hydrophobicity increased in proportion to the number of conjugated drug molecules and have longer retention time as compared to the L chain ($L_0$) and H chain ($H_0$) of an antibody without any conjugated drug molecule, and hence $L_0$, $L_1$, $H_0$, $H_1$, $H_2$, and $H_3$ are eluted in the presented order. While the order of $L_1$ and $H_0$ is inversed in some cases, $H_0$, which has no conjugated drug molecule, does not absorb at a wavelength of 329 nm characteristic to drugs. Therefore, $L_1$ and $H_0$ can be distinguished by checking absorption at a wavelength of 329 nm. Through comparison of retention time between $L_0$ and $H_0$, each peak detected can be assigned to $L_0$, $L_1$, $H_0$, $H_1$, $H_2$, or $H_3$.

[F-3-2] Since each drug-linker absorbs UV, peak area values are corrected by using the following expression with the molar absorption coefficients of an L chain, H chain, and drug-linker according to the number of conjugated drug-linker molecules.

[Expression 5]

Corrected L chain peak area $(Li) =$ $$\text{Peak area} \times \frac{\text{Molar absorption coefficient of } L \text{ chain}}{\text{Molar absorption coefficient of } L \text{ chain} + \text{Number of conjugated drug molecules} \times \text{Molar absorption coefficient of drug-linker}}$$

Corrected H chain peak area $(Hi) =$ $$\text{Peak area} \times \frac{\text{Molar absorption coefficient of } H \text{ chain}}{\text{Molar absorption coefficient of } H \text{ chain} + \text{Number of conjugated drug molecules} \times \text{Molar absorption coefficient of drug-linker}}$$

Here, for the molar absorption coefficients (280 nm) of the L chain and H chain of each antibody, values estimated from the amino acid sequences of the L chain and H chain of the antibody by using a known calculation method (Protein Science, 1995, vol. 4, 2411-2423) may be used. In the case of trastuzumab, 26150 was used as the molar absorption coefficient of the L chain estimated from the amino acid sequence, and 81290 was used as the molar absorption coefficient of the H chain estimated from the amino acid sequence. In the case of the CLDN6 antibody, similarly, 33140 was used as the molar absorption coefficient of the L chain, and 77280 was used as the molar absorption coefficient of the H chain; in the case of the TROP2 antibody, 26210 was used as the molar absorption coefficient of the L chain, and 68990 was used as the molar absorption coefficient of the H chain; in the case of the CD98 antibody, 41680 was used as the molar absorption coefficient of the L chain, and 78500 was used as the molar absorption coefficient of the H chain; in the case of the LPS antibody, 31710 was used as the molar absorption coefficient of the L chain, and 77470 was used as the molar absorption coefficient of the H chain; in the case of the trastuzumab variant, 26251 was used as the molar absorption coefficient of the L chain, and 81488 was used as the molar absorption coefficient of the H chain; and the molar absorption coefficient (280 nm) measured for compound (1), as a conjugate precursor, was used as the molar absorption coefficient (280 nm) of each drug-linker.

[F-3-3] The peak area ratio (%) of each chain to the total of corrected peak areas is calculated by using the following expression.

[Expression 6]

$$L \text{ chain peak area ratio} = \frac{A_{Li}}{A_{L0} + A_{L1}} \times 100$$

$$H \text{ chain peak area ratio} = \frac{A_{Hi}}{A_{H0} + A_{H1} + A_{H2} + A_{H3}} \times 100$$

$A_{Li}, A_{Hi}: L_i, H_i$ Respective corrected peak areas

[F-3-4] The average number of conjugated drug molecules per antibody molecule in an antibody-drug conjugate is calculated by using the following expression.

Average number of conjugated drug molecules=($L_0$ peak area ratio×0+$L_0$ peak area ratio×1+$H_0$ peak area ratio×0+$H_1$ peak area ratio×1+$H_2$ peak area ratio×2+$H_3$ peak area ratio×3)/100×2

<Medicine>

The antibody-drug conjugate of the present invention exhibits cellular cytotoxic activity to cancer cells, and hence may be used as a medicine, in particular, a therapeutic agent and/or prophylactic agent for cancer.

Examples of cancers to which the antibody-drug conjugate of the present invention is applied may include lung cancer (e.g., non-small cell lung cancer, small cell lung cancer), kidney cancer, urothelial cancer, colorectal cancer, prostate cancer, glioblastoma multiforme, ovarian cancer (e.g., surface epithelial tumor, stromal tumor, germ cell tumor), pancreatic cancer, breast cancer, melanoma, liver cancer, bladder cancer, gastric cancer, esophageal cancer or the like, endometrial cancer, testicular cancer (seminoma, non-seminoma), uterine cervix cancer, placental choriocarcinoma, brain tumor, and head-and-neck cancer, and metastatic forms of them, but are not limited thereto as long as cancer cells as a therapeutic target are expressing protein recognizable for the antibody in the antibody-drug conjugate.

The antibody-drug conjugate of the present invention can be preferably administered to mammals, and are more preferably administered to humans.

Substances used in a pharmaceutical composition containing the antibody-drug conjugate of the present invention may be suitably selected and applied from formulation additives or the like that are generally used in the field in view of the dose or concentration for administration.

The antibody-drug conjugate of the present invention may be administered as a pharmaceutical composition containing one or more pharmaceutically applicable components. For example, the pharmaceutical composition typically contains one or more pharmaceutical carriers (e.g., sterilized liquid (including water and oil (petroleum oil and oil of animal origin, plant origin, or synthetic origin (such as peanut oil, soybean oil, mineral oil, and sesame oil)))). Water is a more typical carrier when the pharmaceutical composition above is intravenously administered. Saline solution, an aqueous dextrose solution, and an aqueous glycerol solution can be also used as a liquid carrier, in particular, for an injection solution. Suitable pharmaceutical vehicles are known in the art. If desired, the composition above may also contain a trace amount of a moisturizing agent, an emulsifying agent, or a pH buffering agent. Examples of suitable pharmaceutical carriers are disclosed in "Remington's Pharmaceutical Sciences" by E. W. Martin. The formulations correspond to the administration mode.

Various delivery systems are known and they may be used for administering the antibody-drug conjugate of the present invention. Examples of the administration route may include, but not limited to, intradermal, intramuscular, intraperitoneal, intravenous, and subcutaneous routes. The administration may be made by injection or bolus injection, for example. According to a specific preferred embodiment, the administration of the above ligand-drug conjugate form is done by injection. Parenteral administration is a preferred administration route.

According to a representative embodiment, the pharmaceutical composition is prescribed, as a pharmaceutical composition suitable for intravenous administration to humans, according to conventional procedures. The composition for intravenous administration is typically a solution in a sterile and isotonic aqueous buffer. If necessary, the medicine may contain a solubilizing agent and a local anesthetic to alleviate pain at an injection site (e.g., lignocaine). Generally, the ingredients above are provided either individually as a dried lyophilized powder or an anhydrous concentrate contained in each container which is obtained by sealing in an ampoule or a sachet with indication of the amount of the active agent, or as a mixture in a unit dosage form. When the pharmaceutical composition is to be administered by injection, it may be administered from an injection bottle containing water or saline of sterile pharmaceutical grade. When the medicine is administered by injection, an ampoule of sterile water or saline for injection may be provided so that the aforementioned ingredients are admixed with each other before administration.

The pharmaceutical composition of the present invention may be a pharmaceutical composition containing only the present antibody-drug conjugate, or a pharmaceutical composition containing the antibody-drug conjugate and at least one cancer treating agent other than the antibody-drug conjugate. The antibody-drug conjugate of the present invention may be administered in combination with other cancer treating agents, and thereby the anti-cancer effect may be enhanced. Other anti-cancer agents used for such purpose may be administered to an individual simultaneously with, separately from, or subsequently to the antibody-drug conjugate, and may be administered while varying the administration interval for each. Examples of such cancer treating agents may include abraxane, carboplatin, cisplatin, gemcitabine, irinotecan (CPT-11), paclitaxel, pemetrexed, sorafenib, vinblastin, agents described in International Publication No. WO 2003/038043, LH-RH analogues (e.g., leuprorelin, goserelin), estramustine phosphate, estrogen antagonists (e.g., tamoxifen, raloxifene), and aromatase inhibitors (e.g., anastrozole, letrozole, exemestane), but are not limited thereto as long as they are agents having an antitumor activity.

The pharmaceutical composition can be formulated into a lyophilization formulation or a liquid formulation as a formulation having the selected composition and required purity. When formulated as a lyophilization formulation, it may be a formulation containing suitable formulation additives that are used in the art. Also for a liquid formulation, it may be formulated as a liquid formulation containing various formulation additives that are used in the art.

The composition and concentration of the pharmaceutical composition may vary depending on the administration method. However, the antibody-drug conjugate contained in the pharmaceutical composition of the present invention can exhibit a pharmaceutical effect even at a small dosage when the antibody-drug conjugate has a higher affinity for an antigen, that is, a higher affinity (lower Kd value) in terms of the dissociation constant (Kd value) for the antigen. Thus, for determining the dosage of the antibody-drug conjugate, the dosage may be set in view of the situation relating to the affinity of the antibody-drug conjugate with the antigen. When the antibody-drug conjugate of the present invention is administered to a human, for example, about 0.001 to 100 mg/kg can be administered once or administered in several portions with intervals of 1 to 180 days.

The antibody of the present invention or a functional fragment of the antibody may be used as a medicine. In this case, the above description of "antibody-drug conjugate" in the above chapter <Medicine> may be appropriately read as a description of the "antibody or functional fragment of the antibody".

Further, the free drug of the present invention (novel PBD derivative compound), a salt of the free drug, and hydrates of them may be used as a medicine. In this case, the above description of "antibody-drug conjugate" in the above chapter <Medicine> may be appropriately read as a description of the "free drug (novel PBD derivative compound), a salt of the free drug, and hydrates of them".

EXAMPLES

The present invention will be specifically described with reference to Examples shown below; however, the present invention is not limited to Examples. Examples should not be interpreted as limitation in any sense. Reagents, solvents, and starting materials without any description herein can be readily obtained from commercially available sources of supply.

Reference Example 1: Trastuzumab-tesirine

Step 1: Conjugation of Antibody and Drug-Linker

To a 5 mM solution of trastuzumab (Reference Example 3) in ethylenediamine tetraacetate-phosphate buffered saline (pH 6.5) (9.91 mg/mL, 0.70 mL), an aqueous solution of dipotassium phosphate (1.0 M, 0.0112 mL) and an aqueous solution of tris(2-carboxyethyl)phosphine hydrochloride (10 mM, 0.0086 mL) were added at 20° C., and reacted at 20° C. for 60 minutes and then at room temperature for 30 minutes. A solution of tesirine (0.36 mg) synthesized with reference to a literature (Med. Chem. Lett. 2016, 7, 983-987)

in dimethylacetamide (0.0415 mL) was added to the reaction solution, and reacted at room temperature for 1 hour. An aqueous solution of N-acetylcysteine (100 mM, 0.0024 mL) was added to the reaction solution, and reacted for 30 minutes to terminate the reaction. Purification operation: The solution was purified by using common operation D to afford 3.5 mL of a solution of the targeted compound.

Characterization: The following characteristic values were obtained by using common operations E and F.

Antibody concentration: 1.40 mg/mL, antibody yield: 4.90 mg (71%), average number of conjugated drug molecules per antibody molecule (n): 2.0

Reference Example 2: Anti-CLDN6 (H1L1)-tesirine

Step 1: Conjugation of Antibody and Drug-Linker

To a 5 mM solution of an anti-CLDN6 (H1L1) antibody in ethylenediamine tetraacetate-phosphate buffered saline (pH 6.5) (9.87 mg/mL, 0.45 mL), an aqueous solution of dipotassium phosphate (1.0 M, 0.0072 mL) and an aqueous solution of tris(2-carboxyethyl)phosphine hydrochloride (10 mM, 0.0041 mL) were added at 20° C., and reacted at 20° C. for 90 minutes. A solution of tesirine (0.15 mg) synthesized with reference to a literature (Med. Chem. Lett. 2016, 7, 983-987) in N,N-dimethylacetamide (0.0277 mL) was added to the reaction solution, and reacted at 20° C. for 1 hour. An aqueous solution of N-acetylcysteine (100 mM, 0.001 mL) was added to the reaction solution, and reacted for 30 minutes to terminate the reaction.

Purification operation: The solution was purified by using common operation D to afford 3.5 mL of a solution of the targeted compound.

Characterization: The following characteristic values were obtained by using common operations E and F.

Antibody concentration: 1.56 mg/mL, antibody yield: 3.90 mg (88%), average number of conjugated drug molecules per antibody molecule (n): 2.1

Reference Example 3: Anti-HER2 Antibody Trastuzumab

The anti-HER2 antibody was produced with reference to U.S. Pat. No. 5,821,337. The amino acid sequences of the light chain and heavy chain of trastuzumab are represented by SEQ ID NO: 64 and SEQ ID NO: 65, respectively.

Reference Example 4: Anti-LPS Antibody h #1G5-H1L1

The anti-LPS antibody was produced with reference to WO 2015/046505. The amino acid sequences of the light chain and heavy chain of h #1G5-H1L1 are represented by SEQ ID NO: 66 and SEQ ID NO: 67, respectively.

Reference Example 5: Anti-TROP2 Antibody hRS7

The anti-TROP2 antibody was produced with reference to WO 2003/074566 and WO 2015/098099 (Reference Example 1). The amino acid sequences of the light chain and heavy chain of hRS7 are represented by SEQ ID NO: 68 and SEQ ID NO: 69, respectively.

Reference Example 6: Anti-CD98 Antibody hM23-H1L1

The anti-CD98 antibody was produced with reference to WO 2015/146132. The amino acid sequences of the light chain and heavy chain of hM23-H1L1 are represented by SEQ ID NO: 70 and SEQ ID NO: 71, respectively.

[Synthesis of Production Intermediate]

Example 1: Intermediate 1

[Formula 124]

-continued
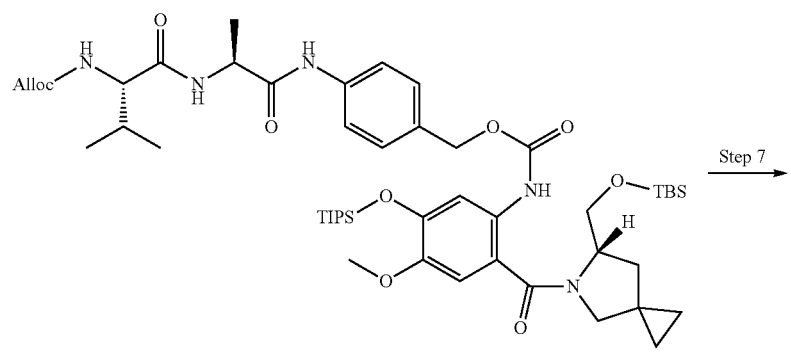
1-7
Step 7 →
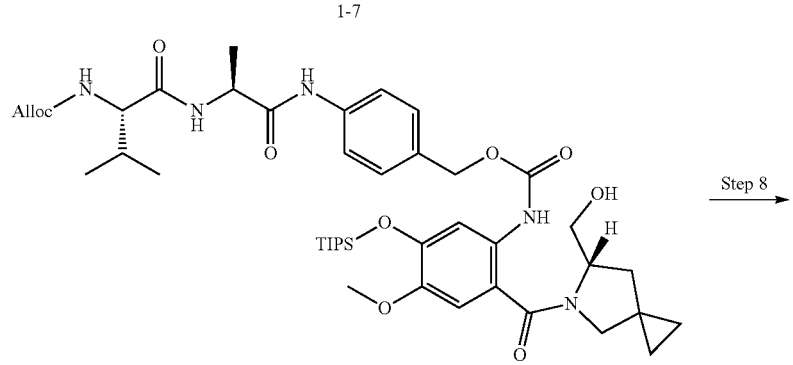
1-8
Step 8 →
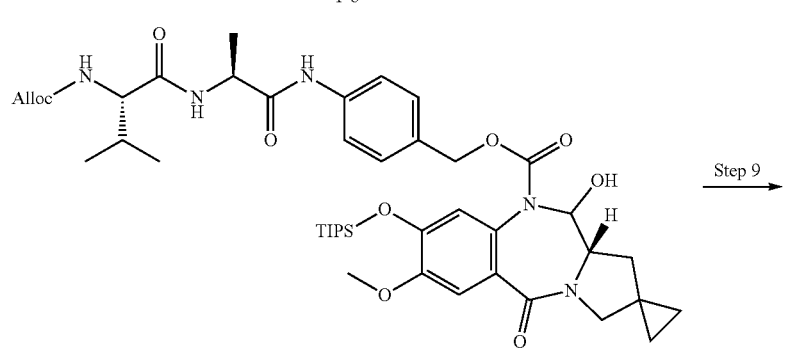
1-9
Step 9 →
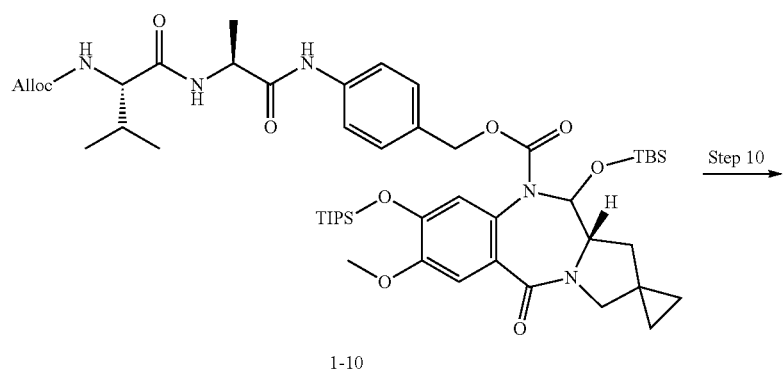
1-10
Step 10 →

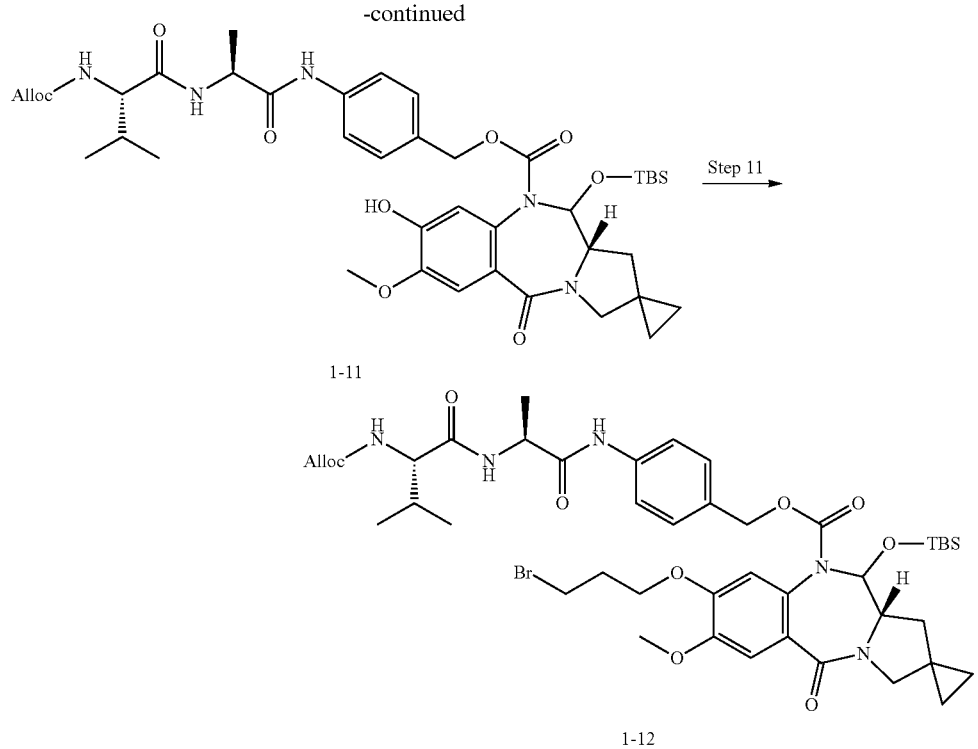

1-11

1-12

Step 1: Benzyl (6S)-6-(hydroxymethyl)-5-azaspiro[2.4]heptane-5-carboxylate

To a solution of 5-benzyl 6-methyl (6S)-5-azaspiro[2.4]heptane-5,6-dicarboxylate (104 mmol, WO 2012087596) in THF (500 mL), lithium borohydride (4.30 g, 178 mmol) was added in small portions at 0° C. The resultant was stirred at 0° C. for 30 minutes, and then stirred at room temperature for 2 hours. Water (180 mL) and 2 N hydrochloric acid (186 mL) were added at 0° C., and the resultant was distillated under reduced pressure. The resulting residue was extracted with ethyl acetate four times, and the organic layer was washed with brine and then dried over anhydrous sodium sulfate. The resultant was distillated under reduced pressure, and the resulting residue (27.9 g, 90%) was directly used for the subsequent reaction.

Step 2: Benzyl (6S)-6-({[tert-butyl(dimethyl)silyl]oxy}methyl)-5-azaspiro[2.4]heptane-5-carboxylate To a solution of the compound obtained in step 1 (27.9 g, 107 mmol) and imidazole (14.5 g, 214 mmol) in dichloromethane (300 mL), tert-butyldimethylsilyl chloride (24.2 g, 160 mmol) was added at room temperature, and the resultant was stirred at room temperature for 18 hours. The reaction solution was washed with a saturated aqueous citric acid, a saturated aqueous sodium hydrogen carbonate, and brine, dried over anhydrous sodium sulfate, and then distillated under reduced pressure. The resulting residue was purified by silica gel column chromatography [hexane:ethyl acetate=100:0 (v/v) to 50:50 (v/v)] to afford the desired compound (32.5 g, 81%).
$^1$H-NMR (CDCl$_3$) δ:7.39-7.34 (5H, m), 5.23-5.11 (2H, m), 4.10-3.48 (4H, m), 3.16-3.14 (1H, m), 2.15-2.04 (1H, m), 1.81-1.77 (1H, m), 0.91-0.88 (9H, m), 0.65-0.55 (4H, m), 0.08-0.01 (6H, m).

MS(APCI)m/z:376(M+H)$^+$

Step 3: (6S)-6-({[tert-Butyl(dimethyl)silyl]oxy}methyl)-5-azaspiro[2.4]heptane

To a solution of the compound obtained in step 2 (32.5 g, 86.5 mmol) in ethanol (400 mL), 7.5% palladium carbon catalyst (moisture content: 54%, 5.00 g) was added at room temperature, and the resultant was stirred under the hydrogen atmosphere at room temperature for 6 hours. The reaction solution was filtered through a Celite, and the filtrate was distillated under reduced pressure to afford the desired compound (21.3 g, quantitative).
$^1$H-NMR (CDCl$_3$) δ:3.79-3.77 (1H, m), 3.71-3.69 (1H, m), 3.65-3.60 (1H, m), 3.01-2.98 (2H, m), 1.81-1.71 (2H, m), 0.90 (9H, s), 0.65-0.57 (4H, m), 0.08 (3H, s), 0.07 (3H, s).
MS(APCI, ESI)m/z:242(M+H)$^+$ Step 4: [(6S)-6-({[tert-Butyl(dimethyl)silyl]oxy}methyl)-5-azaspiro[2.4]hept-5-yl](5-methoxy-2-nitro-4-{[tri(propan-2-yl)silyl]oxy}phenyl)methanone To a solution of 5-methoxy-2-nitro-4-{tri(propan-2-yl)silyl]oxy}benzoic acid (52.2 g, 141 mmol, US 20150283262) and 1-hydroxybenzotriazole monohydrate (23.8 g, 155 mmol) in dichloromethane (500 mL), N,N'-dicyclohexylcarbodiimide (35.0 g, 170 mmol) was added under ice-cooling. The reaction mixture was stirred at room temperature. After the carboxylic acid disappeared, a solution of the compound obtained in step 3 (34.1 g, 141 mmol) and triethylamine (29.4 mL, 212 mmol) in dichloromethane (100 mL) was slowly added dropwise thereto. After the reaction solution was stirred at room temperature overnight, saturated aqueous sodium hydrogen carbonate was added to the reaction mixture, and the reaction mixture was extracted with chloroform. The organic layer was washed with water and brine, and dried over anhydrous magnesium sulfate. The resultant was distillated under reduced pressure, and to the resulting residue ethyl acetate and diethyl ether were added, and the solid contents were removed through filtration, and the filtrate was distillated under reduced pressure, and the resulting residue was purified by silica gel column chromatography [hexane:ethyl acetate=100:0 (v/v) to 25:75 (v/v)] to afford the desired compound (55.0 g, 66%).

$^1$H-NMR (CDCl$_3$) δ:7.72-7.66 (1H, m), 6.80-6.73 (1H, m), 4.53-4.49 (1H, m), 4.04-3.95 (1H, m), 3.91-3.88 (3H, m), 3.59-3.54 (1H, m), 3.36-3.25 (0.5H,m), 3.01-2.96 (1.5H, m), 2.24-2.20 (0.3H,m), 2.09-2.05 (0.7H,m), 2.00-1.97 (0.7H,m), 1.69-1.67 (0.3H,m), 1.32-1.24 (3H, m), 1.12-1.05 (18H, m), 0.93-0.91 (6H, m), 0.79-0.77 (3H, m), 0.71-0.62 (2H, m), 0.57-0.40 (2H, m), 0.12-0.10 (4H, m), 0.11-0.15 (2H, m).

MS(APCI, ESI)m/z:593(M+H)$^+$

Step 5: (2-Amino-5-methoxy-4-{[tri(propan-2-yl)silyl]oxy}phenyl)[(6S)-6-({[tert-butyl(dimethyl)silyl]oxy}methyl)-5-azaspiro[2.4]hept-5-yl]methanone To a solution of the compound obtained in step 4 (55.0 g, 92.8 mmol) in ethanol (300 mL), 7.5% palladium carbon (10.0 g) was added under the nitrogen atmosphere. The nitrogen balloon was immediately replaced with a hydrogen balloon, and the reaction mixture was vigorously stirred under the hydrogen atmosphere at room temperature. After the raw materials disappeared, the reaction mixture was filtered, and the filtrate was distillated under reduced pressure to afford the desired compound (52.2 g, 100%), which was directly used for the subsequent reaction.

$^1$H-NMR (CDCl$_3$) δ:6.71 (1H, s), 6.25 (1H, s), 4.55-4.28 (2H, m), 3.97 (1H, m), 3.75-3.62 (3H, m), 3.70 (3H, s), 3.09-3.07 (1H, m), 2.24-2.19 (1H, m), 1.81-1.68 (1H, m), 1.27-1.22 (3H, m), 1.09-1.05 (18H, m), 0.90 (9H, s), 0.65-0.46 (4H, m), 0.07-0.03 (6H, m).

MS(APCI, ESI)m/z:563(M+H)$^+$

Step 6: N-[(Prop-2-en-1-yloxy)carbonyl]-L-valyl-N-[4-({[(2-{[(6S)-6-({[tert-butyl(dimethyl)silyl]oxy}methyl)-5-azaspiro[2.4]hept-5-yl]carbonyl}-4-methoxy-5-{[tri(propan-2-yl)silyl]oxy}phenyl)carbamoyl]oxy}methyl)phenyl]-L-alaninamide To a solution of the compound obtained in step 5 (18.6 g, 33.0 mmol) and triethylamine (6.26 mL, 45.2 mmol) in THF (300 mL), triphosgene (4.22 g, 14.2 mmol) was slowly added on an ethanol-ice bath. After the addition, a mixed solution of N-[(prop-2-en-1-yloxy)carbonyl]-L-valyl-N-[4-(hydroxymethyl)phenyl]-L-alaninamide (11.4 g, 30.2 mmol, WO 2011130598) and triethylamine (6.26 mL, 45.2 mmol) in THF (100 mL) and N,N-dimethylformamide (30 mL) was slowly added dropwise to the ice-cooled reaction mixture. After the dropwise addition, the ice bath was removed, and the reaction mixture was stirred under the nitrogen atmosphere at 40° C. After the raw materials disappeared, water was added to the reaction mixture, and the reaction mixture was extracted with ethyl acetate. The organic layer was washed with brine, and dried over anhydrous sodium sulfate. After filtration followed by distillation under reduced pressure, the resulting residue was purified by silica gel column chromatography [hexane:ethyl acetate=100:0 (v/v) to 40:60 (v/v)] to afford the desired compound (23.5 g, 74%).

$^1$H-NMR (CDCl$_3$) δ:8.99 (1H, m), 8.58 (1H, s), 7.80 (1H, s), 7.55-7.53 (2H, m), 7.34-7.32 (2H, m), 6.77-6.75 (2H, m), 5.94-5.87 (1H, m), 5.40-5.38 (1H, m), 5.33-5.29 (1H, m), 5.23-5.21 (1H, m), 5.13 (1H, m), 5.10 (2H, m), 4.69-4.64 (1H, m), 4.62-4.52 (2H, m), 4.06-4.03 (1H, m), 3.98 (1H, m), 3.76-3.65 (6H, m), 3.04 (1H, m), 2.28-2.26 (1H, m), 2.18-2.13 (1H, m), 1.46 (3H, m), 1.32-1.25 (3H, m), 1.11-1.09 (18H, m), 0.99-0.84 (15H, m), 0.65-0.40 (4H, m), 0.08-0.00 (6H, m).

MS(APCI, ESI)m/z:966(M+H)$^+$

Step 7: N-[(Prop-2-en-1-yloxy)carbonyl]-L-valyl-N-[4-({[(2-{[(6S)-6-(hydroxymethyl)-5-azaspiro[2.4]hept-5-yl]carbonyl}-4-methoxy-5-{[tri(propan-2-yl)silyl]oxy}phenyl)carbamoyl]oxy}methyl)phenyl]-L-alaninamide To a solution of the compound obtained in step 6 (23.5 g, 24.3 mmol in THF (50 mL), methanol (50 mL) and water (44 mL), acetic acid (200 mL) was added at room temperature. The reaction mixture was stirred at room temperature. After the raw materials disappeared, the reaction mixture was extracted with ethyl acetate. The organic layer was washed with water and brine, and dried over anhydrous sodium sulfate. After filtration followed by distillation under reduced pressure, the resulting residue was purified by silica gel column chromatography [hexane:ethyl acetate=100:0 (v/v) to 0:100 (v/v)] to afford the desired compound (18.0 g, 87%).

$^1$H-NMR (CDCl$_3$) δ:8.64-8.62 (1H, m), 8.50 (1H, m), 7.69 (1H, m), 7.55-7.53 (2H, m), 7.34-7.32 (2H, m), 6.79-6.75 (3H, m), 5.91-5.89 (1H, m), 5.39 (1H, m), 5.32-5.29 (1H, m), 5.23-5.21 (1H, m), 4.68-4.54 (4H, m), 4.31 (1H, m), 4.06-4.04 (1H, m), 3.81-3.79 (3H, m), 3.76 (3H, s), 3.63-3.61 (1H, m), 3.13-3.11 (1H, m), 2.16-2.13 (1H, m), 1.87-1.81 (2H, m), 1.46-1.43 (3H, m), 1.30-1.24 (3H, m), 1.12-1.08 (18H, m), 0.98-0.91 (6H, m), 0.63-0.45 (4H, m).

MS(APCI, ESI)m/z:852(M+H)$^+$

Step 8: N-[(Prop-2-en-1-yloxy)carbonyl]-L-valyl-N-{4-[({[(11a'S)-11'-hydroxy-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide To a solution of dimethyl sulfoxide (3.75 mL, 52.8 mmol) in dichloromethane (300 mL), oxalyl chloride (2.17 mL, 25.3 mmol) was slowly added dropwise under the nitrogen atmosphere at −78° C. After the dropwise addition, the reaction mixture was stirred at −78° C. A solution of the compound obtained in step 7 (18.0 g, 21.1 mmol) in dichloromethane (50.0 mL) was slowly added to the reaction mixture. Triethylamine (14.6 mL, 105 mmol) was added to the reaction solution at −78° C. After the addition, the refrigerant bath was removed, and the temperature was slowly raised to room temperature. After the raw materials disappeared, water was added to the reaction mixture, and the reaction mixture was extracted with chloroform (200 mL). The organic layer was washed with water and brine, and dried over anhydrous magnesium sulfate. After filtration followed by distillation under reduced pressure, the resulting residue was purified by silica gel column chromatography [hexane:ethyl acetate=100:0 (v/v) to 0:60 (v/v)] to afford the desired compound (16.5 g, 92%).

$^1$H-NMR (CDCl$_3$) δ:8.51-8.36 (1H, m), 7.54-7.38 (2H, m), 7.22-7.07 (3H, m), 6.73-6.64 (1H, m), 5.94-5.87 (2H, m), 5.33-5.22 (3H, m), 5.09 (1H, m), 4.97 (1H, m), 4.64-4.58 (4H, m), 4.02-4.00 (1H, m), 3.86-3.83 (3H, m), 3.75-3.70 (1H, m), 3.61-3.54 (2H, m), 3.38-3.29 (1H, m), 2.40 (1H, m), 2.16-2.14 (1H, m), 1.74-1.71 (1H, m), 1.44 (3H, m), 1.18-1.16 (3H, m), 1.05-1.00 (18H, m), 0.97-0.92 (6H, m), 0.72-0.60 (4H, m).

MS(APCI, ESI)m/z:850(M+H)⁺

Step 9: N-[(Prop-2-en-1-yloxy)carbonyl]-L-valyl-N-{4-[({[(11a'S)-11'-{[tert-butyl(dimethyl)silyl]oxy}-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide To a solution of the compound obtained in step 8 (12.0 g, 14.1 mmol) and 2,6-lutidine (6.58 mL, 56.5 mmol) in dichloromethane (200 mL), tert-butyldimethylsilyl trifluoromethylsulfonate (9.73 mL, 42.3 mmol) was slowly added dropwise under the nitrogen atmosphere at 0° C. After stirring under ice-cooling for 10 minutes, the ice bath was removed, and stirring was performed at room temperature. After the raw materials disappeared, water was added to the reaction mixture, and the reaction mixture was extracted with chloroform. The organic layer was washed with water and brine, and dried over anhydrous sodium sulfate. After filtration followed by distillation under reduced pressure, the resulting residue was purified by silica gel column chromatography [hexane:ethyl acetate=100:0(v/v) to 25:75(v/v)] to afford the desired compound (8.12 g, 60%).

¹H-NMR (CDCl₃) δ:8.67-8.45 (1H, m), 7.50-7.44 (2H, m), 7.19 (1H, s), 7.13 (2H, m), 6.95 (2H, m), 6.62-6.57 (2H, m), 6.01 (1H, m), 5.95-5.86 (1H, m), 5.33-5.13 (3H, m), 4.82 (1H, m), 4.65-4.54 (3H, m), 4.03-4.01 (1H, m), 3.84-3.82 (3H, m), 3.73-3.66 (1H, m), 3.50-3.48 (1H, m), 3.27 (1H, m), 2.37-2.33 (1H, m), 2.19-2.13 (1H, m), 1.54-1.43 (3H, m), 1.22-1.13 (3H, m), 1.10-1.00 (18H, m), 0.97-0.91 (6H, m), 0.81 (9H, s), 0.76-0.59 (4H, m), 0.19-0.09 (6H, m).

MS(APCI, ESI)m/z:964(M+H)⁺

Step 10: N-[(Prop-2-en-1-yloxy)carbonyl]-L-valyl-N-{4-[({[(11a'S)-11'-{[tert-butyl(dimethyl)silyl]oxy}-8'-hydroxy-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide To a solution of the compound obtained in step 9 (8.12 g, 8.42 mmol) in N,N-dimethylformamide (90 mL) and water (2 mL), lithium acetate (0.611 g, 9.26 mmol) was added, and the resultant was stirred at room temperature. After the raw materials disappeared, water was added to the reaction mixture, which was extracted with ethyl acetate. The organic layer was washed with water and brine, and dried over anhydrous sodium sulfate. After filtration followed by distillation under reduced pressure, the resulting residue was purified by silica gel column chromatography [hexane:ethyl acetate=100:0 (v/v) to 0:100 (v/v)] to afford the desired compound (5.48 g, 81%).

¹H-NMR (CDCl₃) δ:8.76-8.60 (1H, m), 8.02-7.56 (1H, m), 7.45-7.44 (2H, m), 7.21 (1H, s), 7.10-7.09 (2H, m), 6.81-6.74 (1H, m), 6.65 (1H, s), 6.23 (1H, s), 6.01-5.99 (1H, m), 5.95-5.84 (1H, m), 5.41-5.20 (2H, m), 5.16 (1H, m), 4.84 (1H, m), 4.67-4.54 (4H, m), 4.05-4.03 (1H, m), 3.87 (3H, s), 3.71 (1H, m), 3.55-3.51 (1H, m), 3.26 (1H, m), 2.35 (1H, m), 2.18-2.12 (1H, m), 1.55-1.42 (3H, m), 0.97-0.92 (6H, m), 0.81 (9H, s), 0.76-0.61 (4H, m), 0.20-0.06 (6H, m).

MS(APCI, ESI)m/z:808(M+H)⁺

Step 11: N-[(Prop-2-en-1-yloxy)carbonyl]-L-valyl-N-{4-[({[(11a'S)-8'-(3-bromopropoxy)-11'-{[tert-butyl(dimethyl)silyl]oxy}-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 10 (2.40 g, 2.97 mmol) was reacted in the same manner as in step 1 of Example 4 to afford the desired compound (2.73 g, 99%).

¹H-NMR (DMSO-D₆) δ:10.01-9.86 (1H, m), 8.24-8.04 (2H, m), 7.64-7.54 (2H, m), 7.32-7.14 (4H, m), 6.59-6.48 (1H, m), 5.94-5.88 (2H, m), 5.32-4.76 (5H, m), 4.44-4.38 (3H, m), 3.87-3.81 (5H, m), 3.64-3.55 (2H, m), 3.41 (1H, m), 3.14 (1H, m), 2.45-2.09 (4H, m), 1.97-1.94 (1H, m), 1.44-1.30 (4H, m), 0.89-0.53 (9H, m), 0.79 (9H, s), 0.13-0.06 (6H, m).

MS(APCI, ESI)m/z:930[⁸¹Br,(M+H)⁺], 928[⁷⁹Br,(M+H)⁺].

Example 2: Intermediate 2

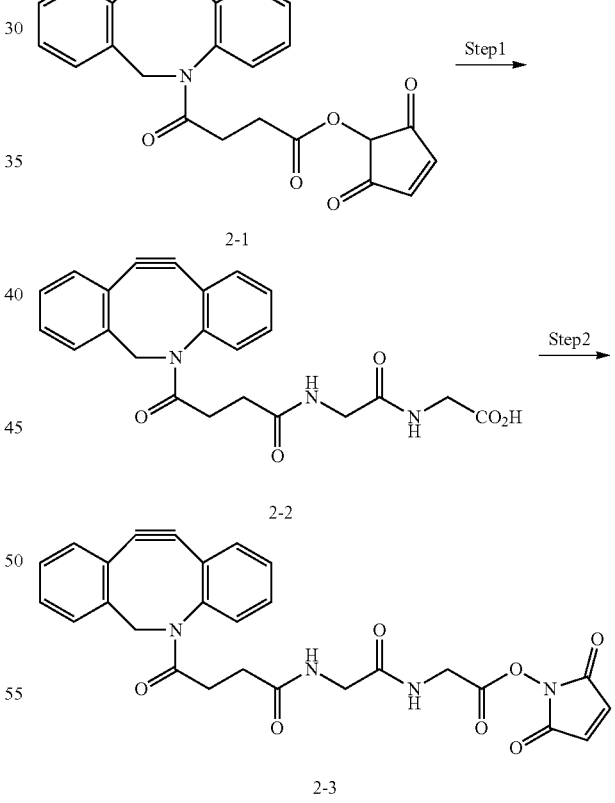

[Formula 125]

Step 1: N-[4-(11,12-Didehydrodibenzo[b,f]azocin-5(6H)-yl)-4-oxobutanoyl]glycylglycine To a mixture of glycylglycine (0.328 g, 2.49 mmol), N,N-diisopropylethylamine (0.433 mL, 2.49 mmol) and N,N-dimethylformamide (20 mL), 1-{[4-(11,12-didehydrodibenzo[b,f]azocin-5(6H)-yl)-4-oxobutanoyl]oxy}pyrrolidin-2,5-dione (1.00 g, 2.49 mmol, Click Chemistry Tools) and water (10 mL) were added at room temperature, and the resultant was stirred at room temperature overnight. The resultant was distillated under reduced pressure, and the resulting residue was purified by silica gel column chromatography [chloroform:CMW=100:0(v/v) to 0:100(v/v)] to afford the desired compound (0.930 g, 89%). CMW refers to an organic layer for distribution with chloroform:methanol:water=7:3:1(v/v/v).

$^1$H-NMR (DMSO-D$_6$) δ:12.58 (1H, s), 8.14-8.12 (1H, m), 8.08-8.07 (1H, m), 7.69-7.68 (1H, m), 7.62-7.61 (1H, m), 7.53-7.45 (3H, m), 7.40-7.29 (3H, m), 5.05-5.01 (1H, m), 3.73-3.72 (2H, m), 3.66-3.60 (3H, m), 2.66-2.60 (1H, m), 2.33-2.24 (1H, m), 2.08-2.04 (1H, m), 1.81-1.77 (1H, m).

MS(APCI, ESI)m/z:420[(M+H)$^+$].

Step 2: 2,5-Dioxopyrrolidin-1-yl N-[4-(11,12-didehydrodibenzo[b,f]azocin-5(6H)-yl)-4-oxobutanoyl] glycyl glycinate To a solution of the compound obtained in step 1 (0.612 g, 1.46 mmol)) and N-hydroxysuccinimide (0.168 g, 1.459 mmol) in dichloromethane (6 mL), 1-ethyl-3-(3-dimethylaminopropyl)carbodiimide hydrochloride (0.420 g, 2.19 mmol) was added, and the resultant was stirred at room temperature for 21 hours. The resultant was distillated under reduced pressure, and the resulting residue was purified by silica gel column chromatography [chloroform:CMW=100:0(v/v) to 0:100(v/v)] to afford the desired compound (0.375 g, 50%). CMW refers to an organic layer for distribution with chloroform:methanol:water=7:3:1(v/v/v).

Example 3: Drug-Linker 1

[Formula 126]

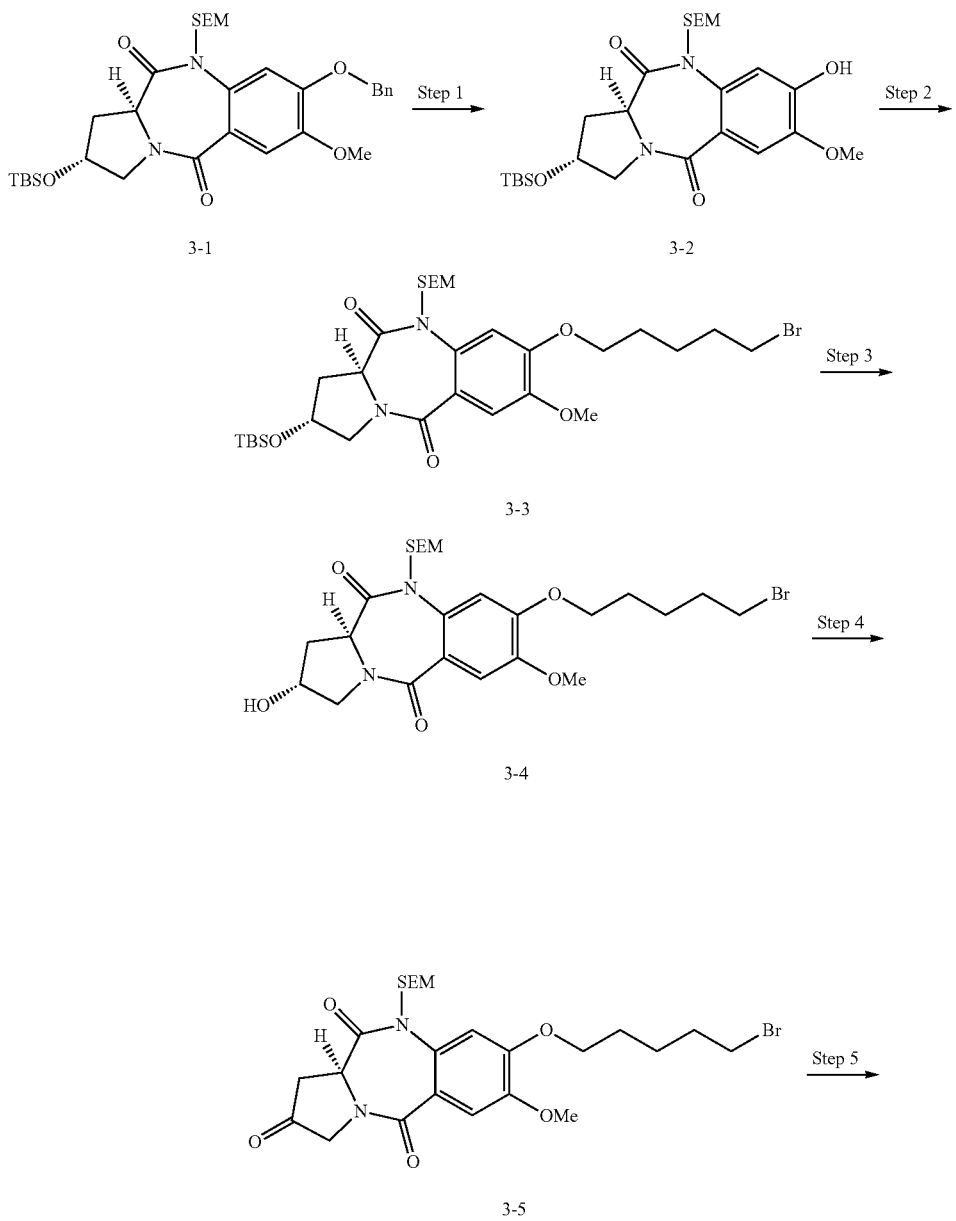

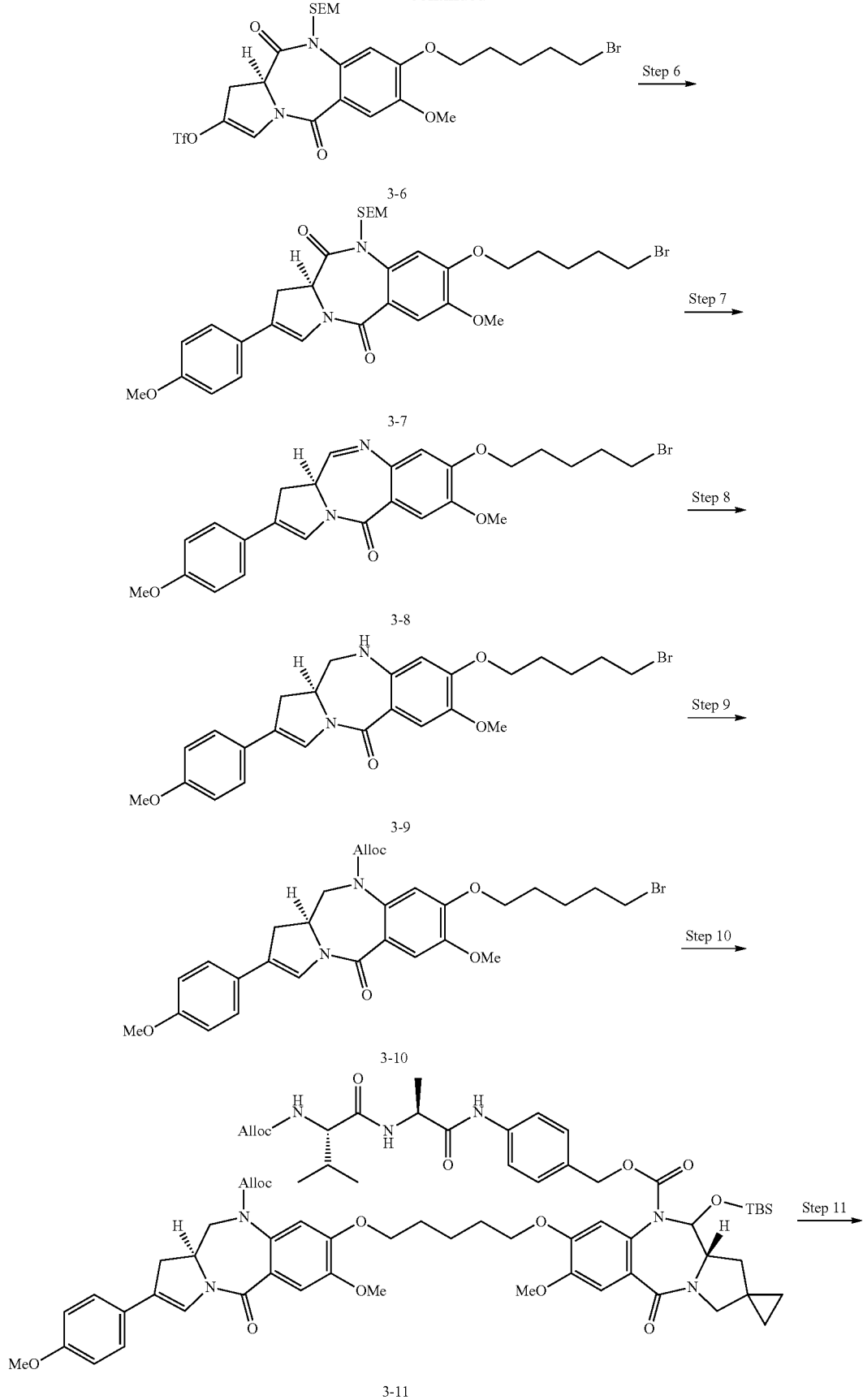

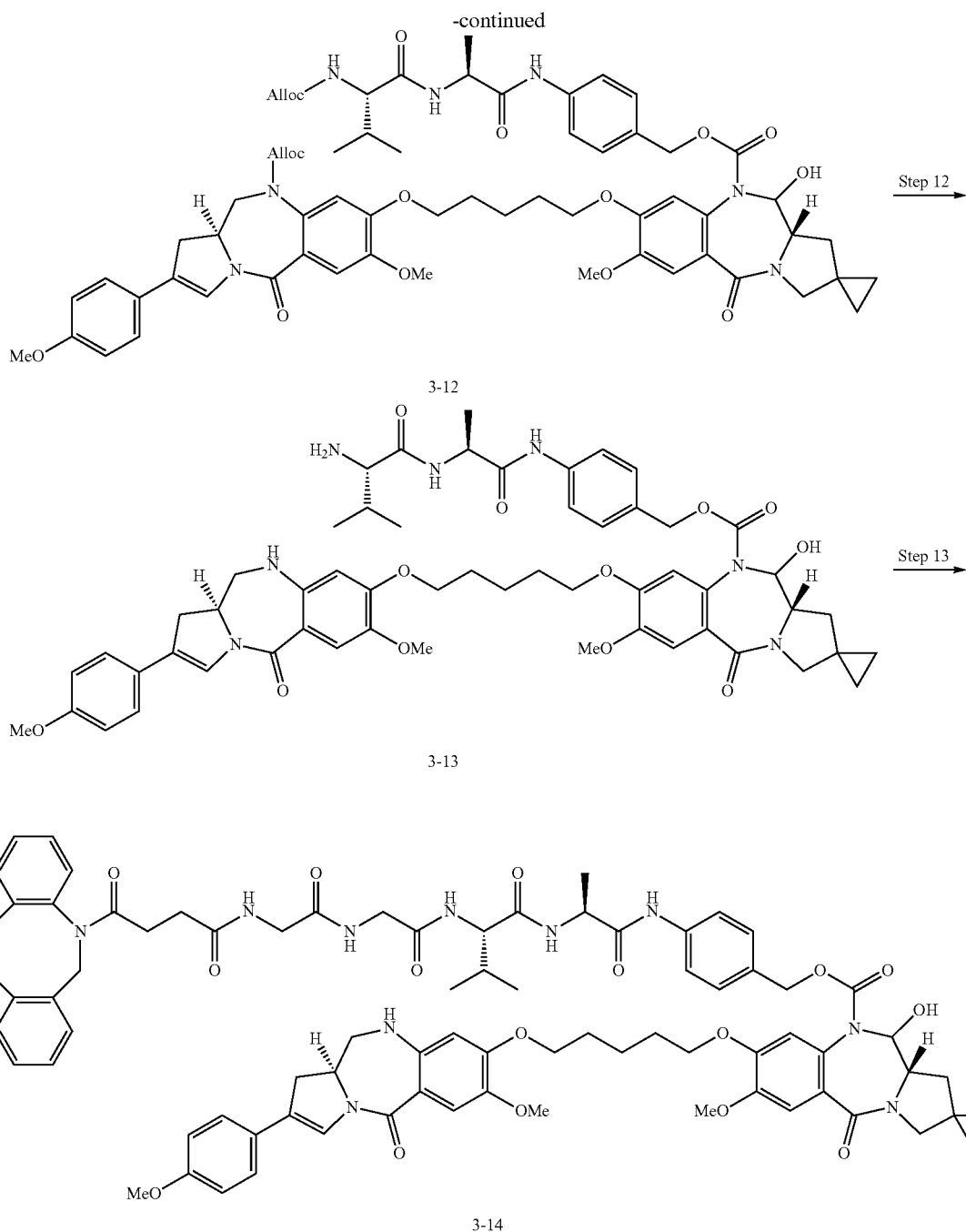

Step 1:(2R,11aS)-2-{[tert-Butyl(dimethyl)silyl]oxy}-8-hydroxy-7-methoxy-10-{[2-(trimethylsilyl)ethoxy]methyl}-2,3-dihydro-1H-pyrrolo[2,1-c][1,4]benzodiazepin-5,11(10H, 11aH)-dione To a solution of (2R,11aS)-8-(benzyloxy)-2-{[tert-butyl(dimethyl)silyl]oxy}-7-methoxy-10-{[2-(trimethylsilyl)ethoxy]methyl}-2,3-dihydro-1H-pyrrolo[2,1-c][1,4]benzodiazepin-5,11(10H,11aH)-dione (25.5 g, 41.6 mmol, WO 2016149546) in THF (150 mL) and ethanol (150 mL), 5% palladium carbon (moisture content: 54%, 10.0 g) was added under the nitrogen atmosphere, and the reaction solution was then stirred under the hydrogen atmosphere at room temperature for 3 days. Chloroform was added to the reaction solution, which was filtered through a Celite, and the filtrate was then distillated under reduced pressure. The resulting residue was purified by silica gel column chromatography [hexane:ethyl acetate=100:0 (v/v) to 50:50 (v/v)] to afford the desired compound (19.4 g, 89%).

$^1$H-NMR (CDCl$_3$) δ:7.36 (1H, s), 7.25 (1H, s), 6.01 (1H, s), 5.45-5.43 (1H, m), 4.69-4.67 (1H, m), 4.60-4.55 (1H, m), 4.23-4.21 (1H, m), 3.96 (3H, s), 3.76-3.68 (2H, m), 3.63-3.61 (1H, m), 3.56-3.53 (1H, m), 2.88-2.83 (1H, m), 2.03-2.00 (1H, m), 1.00-0.98 (2H, m), 0.87 (9H, s), 0.10 (6H, s), 0.02 (9H, s).

MS(APCI, ESI)m/z:523(M+H)$^+$

Step 2: (2R,11aS)-8-[(5-Bromopentyl)oxy]-2-{[tert-butyl(dimethyl)silyl]oxy}-7-methoxy-10-{[2-(trimethylsilyl)ethoxy]methyl}-2,3-dihydro-1H-pyrrolo[2,1-c][1,4]benzodiazepin-5,11(10H,11aH)-dione To a solution of the compound obtained in step 1 (10.8 g, 20.7 mmol) in N,N-dimethylformamide (30 mL), 1,5-dibromopentane (23.8 g, 103 mmol) and potassium carbonate (3.43 g, 24.8 mmol) were added at room temperature. After stirring at room temperature for 3 hours, water was added to the reaction solution, which was extracted with ethyl acetate. The organic layer obtained was washed with brine and dried over sodium sulfate, and distillated under reduced pressure. The resulting residue was purified by silica gel column chromatography [hexane:ethyl acetate=90:10 (v/v) to 50:50 (v/v)] to afford the desired compound (14.5 g, quantitative).
$^1$H-NMR (CDCl$_3$) δ:7.34 (1H, s), 7.21 (1H, s), 5.52-5.49 (1H, m), 4.63-4.62 (1H, m), 4.58-4.55 (1H, m), 4.24-4.22 (1H, m), 4.07-4.04 (2H, m), 3.92 (3H, s), 3.82-3.64 (3H, m), 3.56-3.53 (1H, m), 3.45-3.43 (2H, m), 2.86-2.84 (1H, m), 2.04-2.00 (1H, m), 1.97-1.87 (4H, m), 1.66-1.62 (2H, m), 1.01-0.98 (2H, m), 0.87 (9H, s), 0.10 (6H, s), 0.04 (9H, s).
MS(APCI, ESI)m/z:673[$^{81}$Br,(M+H)$^+$], 671[$^{79}$Br,(M+H)$^+$].

Step 3: (2R,11aS)-8-[(5-Bromopentyl)oxy]-2-hydroxy-7-methoxy-10-{[2-(trimethylsilyl)ethoxy]methyl}-2,3-dihydro-1H-pyrrolo[2,1-c][1,4]benzodiazepin-5,11(10H,11aH)-dione To a solution of the compound obtained in step 2 (21.5 mmol) in THF (40 mL), a 1 mol/L THF solution of tetrabutylammonium fluoride (28.0 mL, 28.0 mmol) was added at 0° C. After stirring at room temperature for 30 minutes, water was added to the reaction solution, which was extracted with ethyl acetate, and the organic layer obtained was washed with brine. The resultant was dried over sodium sulfate, and then distillated under reduced pressure. The resulting residue was purified by silica gel column chromatography [chloroform:methanol=97.5:2.5 (v/v) to 92.5:7.5 (v/v)] to afford the desired compound (11.3 g, 94%).
$^1$H-NMR (CDCl$_3$) δ:7.34 (1H, s), 7.21 (1H, s), 5.53-5.50 (1H, m), 4.69-4.64 (2H, m), 4.32-4.30 (1H, m), 4.10-4.00 (2H, m), 3.91 (3H, s), 3.88-3.75 (2H, m), 3.73-3.64 (2H, m), 3.45-3.44 (2H, m), 2.99-2.96 (1H, m), 2.15-2.09 (1H, m), 1.99-1.85 (5H, m), 1.68-1.62 (2H, m), 1.01-0.95 (2H, m), 0.04 (9H, s).
MS(APCI, ESI)m/z:559[$^{81}$Br,(M+H)$^+$], 557[$^{79}$Br,(M+H)$^+$].

Step 4: (11aS)-8-[(5-Bromopentyl)oxy]-7-methoxy-10-{[2-(trimethylsilyl)ethoxy]methyl}-1H-pyrrolo[2,1-c][1,4]benzodiazepin-2,5,11 (3H,10H,11aH)-trione The compound obtained in step 3 (11.3 g, 20.2 mmol), tetrabutylammonium bromide (0.325 g, 1.01 mmol), and potassium bromide (0.240 g, 2.02 mmol) were dissolved in a saturated aqueous sodium hydrogen carbonate (60 mL)/dichloromethane (60 mL), to which nor-AZADO (0.0279 g, 0.202 mmol) and sodium hypochlorite pentahydrate (2.03 g, 27.2 mmol) were added at 0° C., and the resultant was stirred at 0° C. for 30 minutes. Because the raw materials remained, sodium hypochlorite pentahydrate (1.00 g, 13.4 mmol) was added thereto at 0° C., and the resultant was stirred at 0° C. for 15 minutes. Sodium hypochlorite pentahydrate (0.300 g, 4.03 mmol) was further added thereto at 0° C., and the resultant was stirred at 0° C. for 15 minutes, and the disappearance of the raw materials was confirmed by TLC. An aqueous solution of sodium thiosulfate was added to the reaction solution, which was extracted with chloroform, and the organic layer obtained was dried over sodium sulfate. The resultant was distilled under reduced pressure, and the resulting residue was purified by silica gel column chromatography [hexane:ethyl acetate=75:25(v/v) to 40:60(v/v)] to afford the desired compound (9.74 g, 87%).
$^1$H-NMR (CDCl$_3$) δ:7.33 (1H, s), 7.24 (1H, s), 5.56-5.53 (1H, m), 4.71-4.69 (1H, m), 4.66-4.63 (1H, m), 4.27-4.22 (1H, m), 4.12-4.02 (2H, m), 3.93-3.88 (4H, m), 3.82-3.75 (1H, m), 3.69-3.67 (1H, m), 3.61-3.56 (1H, m), 3.46-3.44 (2H, m), 2.82-2.77 (1H, m), 1.97-1.89 (4H, m), 1.68-1.64 (2H, m), 1.05-0.93 (2H, m), 0.04 (9H, s).
MS(APCI, ESI)m/z:557[$^{81}$Br,(M+H)$^+$], 555[$^{79}$Br,(M+H)$^+$].

Step 5: (11aS)-8-[(5-Bromopentyl)oxy]-7-methoxy-5,11-dioxo-10-{[2-(trimethylsilyl)ethoxy]methyl}-5,10,11,11a-tetrahydro-1H-pyrrolo[2,1-c][1,4]benzodiazepin-2-yl trifluoromethanesulfonate To a solution of the compound obtained in step 4 (9.74 g, 17.5 mmol) in dichloromethane (160 mL), 2,6-lutidine (8.17 mL, 70.1 mmol) was added at −40° C., and the resultant was stirred at −40° C. for 10 minutes. Anhydrous trifluoromethanesulfonic acid (8.85 mL, 52.6 mmol) was added to the reaction solution at −40° C., and the resultant was stirred at −40° C. for 30 minutes. To the reaction solution, a 10% aqueous solution of citric acid was added, which was extracted with chloroform, and the organic layer obtained was dried over sodium sulfate. The resultant was distilled under reduced pressure, and the resulting residue was purified by silica gel column chromatography [hexane:ethyl acetate=95:5 (v/v) to 70:35 (v/v)] and then purified by NH2 silica gel chromatography [hexane:ethyl acetate=95:5 (v/v) to 65:35 (v/v)] to afford the desired compound (7.10 g, 59%).
$^1$H-NMR (CDCl$_3$) δ:7.32 (1H, s), 7.24 (1H, s), 7.15-7.14 (1H, m), 5.56-5.53 (1H, m), 4.70-4.68 (1H, m), 4.66-4.63 (1H, m), 4.11-4.01 (2H, m), 3.94-3.90 (4H, m), 3.84-3.75 (1H, m), 3.73-3.68 (1H, m), 3.46-3.44 (2H, m), 3.18-3.14 (1H, m), 1.96-1.88 (4H, m), 1.69-1.61 (2H, m), 1.02-0.92 (2H, m), 0.04 (9H, s).
MS(APCI, ESI)m/z:689[$^{81}$Br,(M+H)$^+$], 687[$^{79}$Br,(M+H)$^+$].

Step 6: (11aS)-8-[(5-Bromopentyl)oxy]-7-methoxy-2-(4-methoxyphenyl)-10-{[2-(trimethylsilyl)ethoxy]methyl}-1H-pyrrolo[2,1-c][1,4]benzodiazepin-5,11 (10H,11aH)-dione To a mixture of the compound obtained in step 5 (2.00 g, 2.91 mmol), 4-methoxyphenylboronic acid (0.884 g, 5.82 mmol), tetrakis(triphenylphosphine)palladium (0) (0.336 g, 0.291 mmol) and sodium carbonate (1.23 g, 11.6 mmol), toluene (20 mL), ethanol (10 mL) and water (10 mL) were added at room temperature. The reaction solution was stirred at room temperature for 30 minutes, and the reaction solution was then extracted with ethyl acetate, and the extract was washed with water and brine. The organic layer was dried over sodium sulfate, and then distillated under reduced pressure. The resulting residue was purified by silica gel column chromatography [hexane:ethyl acetate=90:10 (v/v) to 50:50 (v/v)] to afford the desired compound (1.71 g, 91%).

¹H-NMR (CDCl₃) δ:7.38-7.37 (3H, m), 7.33 (1H, s), 7.25 (1H, s), 6.89-6.88 (2H, m), 5.56-5.54 (1H, m), 4.71-4.68 (1H, m), 4.65-4.62 (1H, m), 4.09-4.04 (2H, m), 3.96-3.91 (4H, m), 3.85-3.66 (5H, m), 3.46-3.45 (2H, m), 3.16-3.12 (1H, m), 1.99-1.94 (4H, m), 1.69-1.64 (2H, m), 1.00-0.98 (2H, m), 0.04 (9H, s).

MS(APCI, ESI)m/z:647[⁸¹Br,(M+H)⁺], 645[⁷⁹Br,(M+H)⁺].

Step 7: (11aS)-8-[(5-Bromopentyl)oxy]-7-methoxy-2-(4-methoxyphenyl)-1,11a-dihydro-5H-pyrrolo[2,1-c][1,4]benzodiazepin-5-one The compound obtained in step 6 (0.789 g, 1.22 mmol) was dissolved in ethanol (10 mL) and THF (10 mL), and 2.0 M tetrahydrofuran solution of lithium borohydride (6.11 mL, 12.2 mmol) was added thereto at 0° C., and the resultant was stirred at 0° C. for 3 hours. Water was added to the reaction solution, which was extracted with chloroform, and the organic layer obtained was dried over sodium sulfate. The resultant was distilled under reduced pressure, and the resulting residue was dissolved in dichloromethane (10 mL), ethanol (20 mL) and water (10 mL), to which silica gel (4 g) was added at room temperature, and the resultant was stirred at room temperature for 4 days. The silica gel was removed through filtration, and water was added thereto, and the resultant was extracted with chloroform. The organic layer obtained was dried over sodium sulfate. The resultant was distilled under reduced pressure, and the resulting residue was purified by silica gel column chromatography [hexane:ethyl acetate=60:40 (v/v) to 25:75 (v/v)] to afford the desired compound (0.496 g, 81%).

¹H-NMR (CDCl₃) δ:7.90-7.89 (1H, m), 7.53 (1H, s), 7.40-7.40 (1H, m), 7.35-7.34 (2H, m), 6.92-6.90 (2H, m), 6.83-6.81 (1H, m), 4.43-4.40 (1H, m), 4.13-4.06 (2H, m), 3.96 (3H, s), 3.84 (3H, s), 3.61-3.57 (1H, m), 3.47-3.36 (3H, m), 2.00-1.92 (4H, m), 1.67-1.63 (2H, m).

MS(APCI, ESI)m/z:501[⁸¹Br,(M+H)⁺], 499[⁷⁹Br,(M+H)⁺].

Step 8: (11aS)-8-[(5-Bromopentyl)oxy]-7-methoxy-2-(4-methoxyphenyl)-1,10,11,11a-tetrahydro-5H-pyrrolo[2,1-c][1,4]benzodiazepin-5-one To a solution of the compound obtained in step 7 (0.496 g, 0.992 mmol) in dichloromethane (20 mL), sodium triacetoxyborohydride (0.421 g, 1.99 mmol) was added at 0° C. After stirring at room temperature for 2 hours, a saturated aqueous sodium hydrogen carbonate was added thereto, and the resultant was extracted with chloroform. The organic layer was dried over sodium sulfate, and distilled under reduced pressure, and the resulting residue was then purified by silica gel column chromatography [hexane:ethyl acetate=60:40 (v/v) to 25:75 (v/v)] to afford the desired compound (0.426 g, 86%).

¹H-NMR (CDCl₃) δ:7.53-7.53 (2H, m), 7.32-7.30 (2H, m), 6.89-6.87 (2H, m), 6.05 (1H, s), 4.33-4.27 (2H, m), 4.00-3.98 (2H, m), 3.86 (3H, s), 3.82 (3H, s), 3.57-3.55 (2H, m), 3.42-3.38 (3H, m), 2.76-2.72 (1H, m), 1.96-1.88 (4H, m), 1.65-1.62 (2H, m).

MS(APCI, ESI)m/z:503[⁸¹Br,(M+H)⁺], 501[⁷⁹Br,(M+H)⁺].

Step 9: Prop-2-en-1-yl (11aS)-8-[(5-bromopentyl)oxy]-7-methoxy-2-(4-methoxyphenyl)-5-oxo-11,11a-dihydro-1H-pyrrolo[2,1-c][1,4]benzodiazepin-10(5H)-carboxylate To a solution of the compound obtained in step 8 (0.426 g, 0.849 mmol) in dichloromethane (30 mL), pyridine (0.102 mL 1.27 mmol) and allyl chloroformate (0.374 mL, 3.54 mmol) were added at 0° C., and the resultant was stirred at 0° C. for 15 minutes. To the reaction solution, a 10% aqueous solution of citric acid was added, which was extracted with chloroform, and the organic layer obtained was washed with a saturated aqueous sodium hydrogen carbonate, and then dried over sodium sulfate. The resultant was distilled under reduced pressure, and the resulting residue was purified by silica gel column chromatography [hexane:ethyl acetate=90:10 (v/v) to 50:50 (v/v)] to afford the desired compound (0.465 g, 94%).

¹H-NMR (CDCl₃) δ:7.38 (1H, s), 7.31-7.29 (2H, m), 7.26-7.25 (1H, m), 6.89-6.87 (2H, m), 6.71 (1H, s), 5.80-5.78 (1H, m), 5.14-5.11 (2H, m), 4.65-4.62 (1H, m), 4.39-4.26 (3H, m), 4.03-4.01 (2H, m), 3.92 (3H, s), 3.82 (3H, s), 3.66-3.64 (1H, m), 3.46-3.44 (2H, m), 3.30-3.27 (1H, m), 2.72-2.68 (1H, m), 1.96-1.88 (4H, m), 1.68-1.60 (2H, m).

MS(APCI, ESI)m/z:587[⁸¹Br,(M+H)⁺], 585[⁷⁹Br,(M+H)⁺].

Step 10: N-[(Prop-2-en-1-yloxy)carbonyl]-L-valyl-N-{4-[({[(11a'S)-11'-{[tert-butyl(dimethyl)silyl]oxy}-7'-methoxy-8'-{[5-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)pentyl]oxy}-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide To a solution of the compound obtained in step 10 of Example 1 (0.130 g, 0.161 mmol) and the compound obtained in step 9 (0.104 g, 0.177 mmol) in N,N-dimethylformamide (3 mL), potassium carbonate (0.0266 g, 0.193 mmol) was added at room temperature, and the resultant was stirred at room temperature overnight. The reaction solution was diluted with ethyl acetate, and washed with water and brine, and then dried over sodium sulfate. The resultant was distilled under reduced pressure, and the resulting residue was then purified by NH2-silica gel column chromatography [hexane:ethyl acetate=70:30 (v/v) to 0:100 (v/v)] to afford the desired compound (0.184 g, 87%).

¹H-NMR (CDCl₃) δ:8.76 (1H, s), 7.58-7.56 (2H, m), 7.39 (1H, s), 7.32-7.30 (2H, m), 7.26-7.24 (2H, m), 7.19-7.17 (3H, m), 6.90-6.88 (2H, m), 6.78 (1H, s), 6.68-6.66 (1H, m), 6.37 (1H, s), 5.99-5.93 (3H, m), 5.34-5.20 (6H, m), 4.66-4.01 (11H, m), 3.90 (3H, s), 3.89 (3H, s), 3.78-3.54 (9H, m), 3.31-3.28 (2H, m), 2.73-2.69 (1H, m), 2.38-2.35 (1H, m), 2.19-2.13 (1H, m), 1.82-1.80 (2H, m), 1.46-1.29 (6H, m), 0.98-0.90 (6H, m), 0.83 (9H, s), 0.69-0.63 (4H, m), 0.19-0.16 (6H, m).

MS(APCI, ESI)m/z:1312(M+H)⁺

Step 11: N-[(Prop-2-en-1-yloxy)carbonyl]-L-valyl-N-{4-[({[(11a'S)-11'-hydroxy-7'-methoxy-8'-{[5-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)pentyl]oxy}-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide To a solution of the compound obtained in step 10 (0.1837 g, 0.140 mmol) and acetic acid (0.048 mL, 0.840 mmol) in THF (5.00 mL), a 1 mol/L tetrahydrofuran solution of tetrabutylammonium fluoride (0.700 mL, 0.700 mmol) was added at room temperature, and the resultant was stirred at room temperature for 3 hours. The reaction solution was diluted with ethyl acetate, and the organic layer was washed with a saturated aqueous sodium hydrogen carbonate and brine, and then dried over sodium sulfate. The resultant was distilled under reduced pressure, and the resulting residue was purified by silica gel chromatography [chloroform:methanol=99.5:0.5(v/v) to 95:5(v/v)] to afford the desired compound (0.178 g, quantitative).

$^1$H-NMR (CDCl$_3$) δ:8.86 (1H, s), 7.60-7.59 (2H, m), 7.39 (1H, s), 7.32-7.20 (7H, m), 6.90-6.88 (2H, m), 6.78 (1H, s), 6.68 (1H, s), 6.38 (1H, s), 5.90-5.87 (3H, m), 5.39-5.22 (6H, m), 4.72-4.02 (11H, m), 3.90 (3H, s), 3.88 (3H, s), 3.83 (3H, s), 3.70-3.63 (6H, m), 3.32-3.29 (3H, m), 2.73-2.69 (1H, m), $^1$H-NMR (CD$_3$OD, 50° C.) δ:7.84 (1H, s), 7.56-7.48 (2H, m), 7.44-7.32 (4H, m), 7.26-7.13 (3H, m), 6.89 (2H, d, J=8.5 Hz), 6.78-6.66 (1H, m), 6.26 (1H, s), 5.96 (1H, d, J=9.7 Hz, H$_{11}$), 5.27 (1H, d, J=12.1 Hz), 4.96-4.78 (1H, m), 4.63-4.58 (2H, m), 4.49 (1H, q, J=6.9 Hz), 4.28-4.19 (1H, m), 4.07-3.89 (4H, m), 3.85 (3H, s), 3.79 (3H, s), 3.76 (3H, s), 3.67 (1H, d, J=11.5 Hz), 3.61 (1H, d, J=13.3 Hz), 3.5 4 (1H, dd, J=9.7, 8.2 Hz, H$_{11'a}$), 3.43-3.31 (2H, m), 3.21 (1H, d, J=11.5 Hz), 3.14 (1H, d, J=4.8 Hz), 2.78 (1H, dd, J=16.6, 4.5 Hz), 2.43 (1H, dd, J=13.0, 8.2 Hz, H$_{1'b}$), 2.05-1.93 (1H, m), 1.91-1.75 (4H, m), 1.73-1.55 (2H, m), 1.69 (1H, d, J=13.3 Hz, H$_{1'a}$), 1.40 (3H, d, J=7.3 Hz), 0.96 (3H, d, J=6.7 Hz), 0.89 (3H, d, J=7.3 Hz), 0.76-0.58 (4H, m).

[Formula 127]

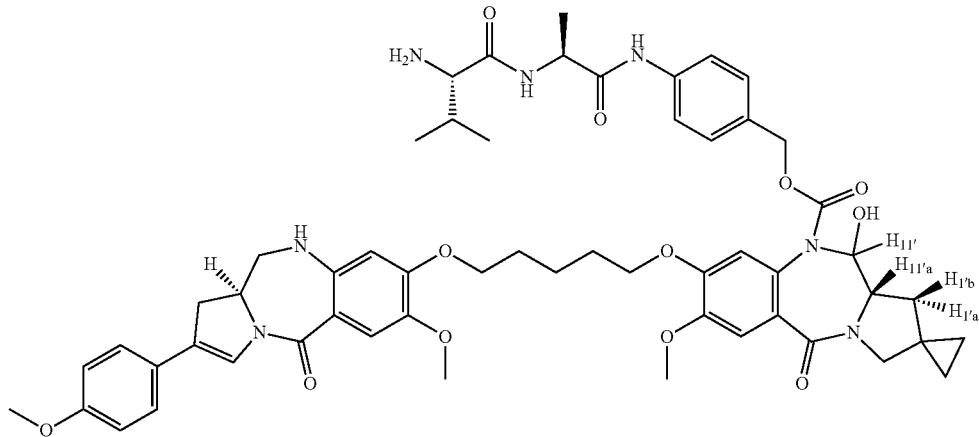

3-13

2.43-2.40 (1H, m), 2.12-2.06 (1H, m), 1.77-1.74 (2H, m), 1.39-1.25 (6H, m), 0.96-0.89 (6H, m), 0.73-0.66 (4H, m).

MS(APCI, ESI)m/z:1198(M+H)$^+$

Step 12: L-Valyl-N-{4-[({[(11a'S)-11'-hydroxy-7'-methoxy-8'-[(5-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}pentyl)oxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide To a solution of the compound obtained in step 11 (0.140 mmol) in dichloromethane (2 mL), pyrrolidine (0.0579 mL, 0.700 mmol) and tetrakis(triphenylphosphine)palladium (0) (0.0162 g, 0.0140 mmol) were added at room temperature, and the resultant was stirred at room temperature for 15 minutes. After distillation under reduced pressure, the resulting residue was purified by silica gel chromatography [chloroform:methanol=99.5:0.5(v/v) to 92.5:7.5(v/v)] to afford the desired compound (0.143 g, 99%).

$^1$H-NMR (CDCl$_3$) δ:9.12 (1H, s), 7.94-7.92 (1H, m), 7.57-7.53 (4H, m), 7.33-7.31 (2H, m), 7.20-7.18 (3H, m), 6.90-6.88 (2H, m), 6.36 (1H, s), 6.07 (1H, s), 5.91-5.88 (1H, m), 5.47-5.44 (1H, m), 5.21-5.13 (1H, m), 4.66-4.58 (3H, m), 4.32 (1H, s), 4.03-3.49 (17H, m), 3.38-3.29 (4H, m), 3.15-3.14 (1H, m), 2.77-2.73 (1H, m), 2.57 (2H, s), 2.43-2.40 (1H, m), 2.32-2.27 (1H, m), 1.81-1.39 (8H, m), 0.98-0.96 (3H, m), 0.85-0.83 (3H, m), 0.75-0.62 (4H, m).

MS(APCI, ESI)m/z:1030(M+H)$^+$

Step 13: N-[4-(11,12-Didehydrodibenzo[b,f]azocin-5 (6H)-yl)-4-oxobutanoyl]glycylglycyl-L-valyl-N-{4-[({[(11a'S)-11'-hydroxy-7'-methoxy-8'-[(5-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}pentyl)oxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

To a mixture of the compound obtained in step 1 of Example 2 (0.0640 g, 0.153 mmol) and N-ethoxycarbonyl-2-ethoxy-1,2-dihydroquinoline (0.0446 g, 0.180 mmol), dichloromethane (2 mL) was added at room temperature, and the resultant was stirred at room temperature for 15 minutes. To the reaction solution, a solution of the compound obtained in step 13 (0.143 g, 0.139 mmol) in dichloromethane (2 mL) was added, and the resultant was stirred at room temperature for 5 hours, and then distillated under reduced pressure. The resulting residue was purified by silica gel column chromatography [chloroform:methanol=99.5:0.5 (v/v) to 92.5:7.5 (v/v)] to afford the desired compound (0.103 g, 52%).

Table 1: Peak positions of proton NMR and MS for drug-linker 1

$^1$H-NMR (DMSO-D$_6$) δ:9.93 (1H, s), 8.21-8.16 (2H, m), 8.07-8.04 (1H, m), 7.83-7.64 (2H, m), 7.60-7.55 (3H, m), 7.51-7.28 (10H,m), 7.19-7.16 (2H, m), 7.10-7.04 (1H, m), 6.92-6.90 (2H, m), 6.76-6.70 (1H, m), 6.39 (1H, s), 5.77-5.75 (1H, m), 5.21-5.18 (1H, m), 5.03-4.99 (1H, m), 4.82-4.79 (1H, m), 4.37-4.35 (1H, m), 4.21-4.20 (2H, m), 4.02-3.24 (26H, m), 3.16-3.13 (1H, m), 2.79-2.59 (2H, m), 2.39-2.28 (2H, m), 2.05-1.97 (2H, m), 1.91-1.77 (4H, m), 1.57-1.54 (3H, m), 1.28-1.23 (3H, m), 0.85-0.80 (6H, m), 0.67-0.61 (4H, m).
MS(APCI, ESI)m/z:1431(M+H)$^+$
Example 4: Drug-Linker 2
[Formula 128]
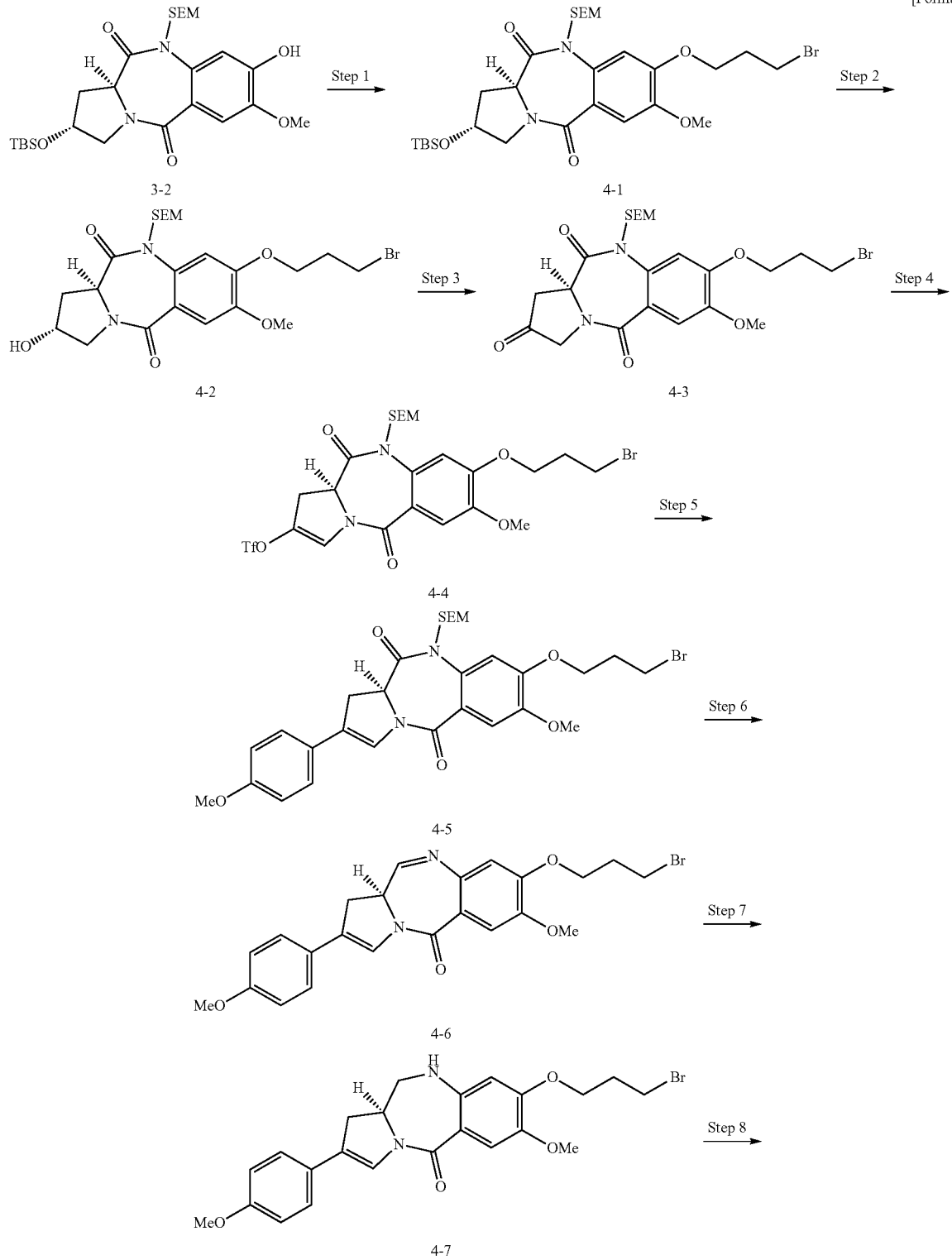

-continued
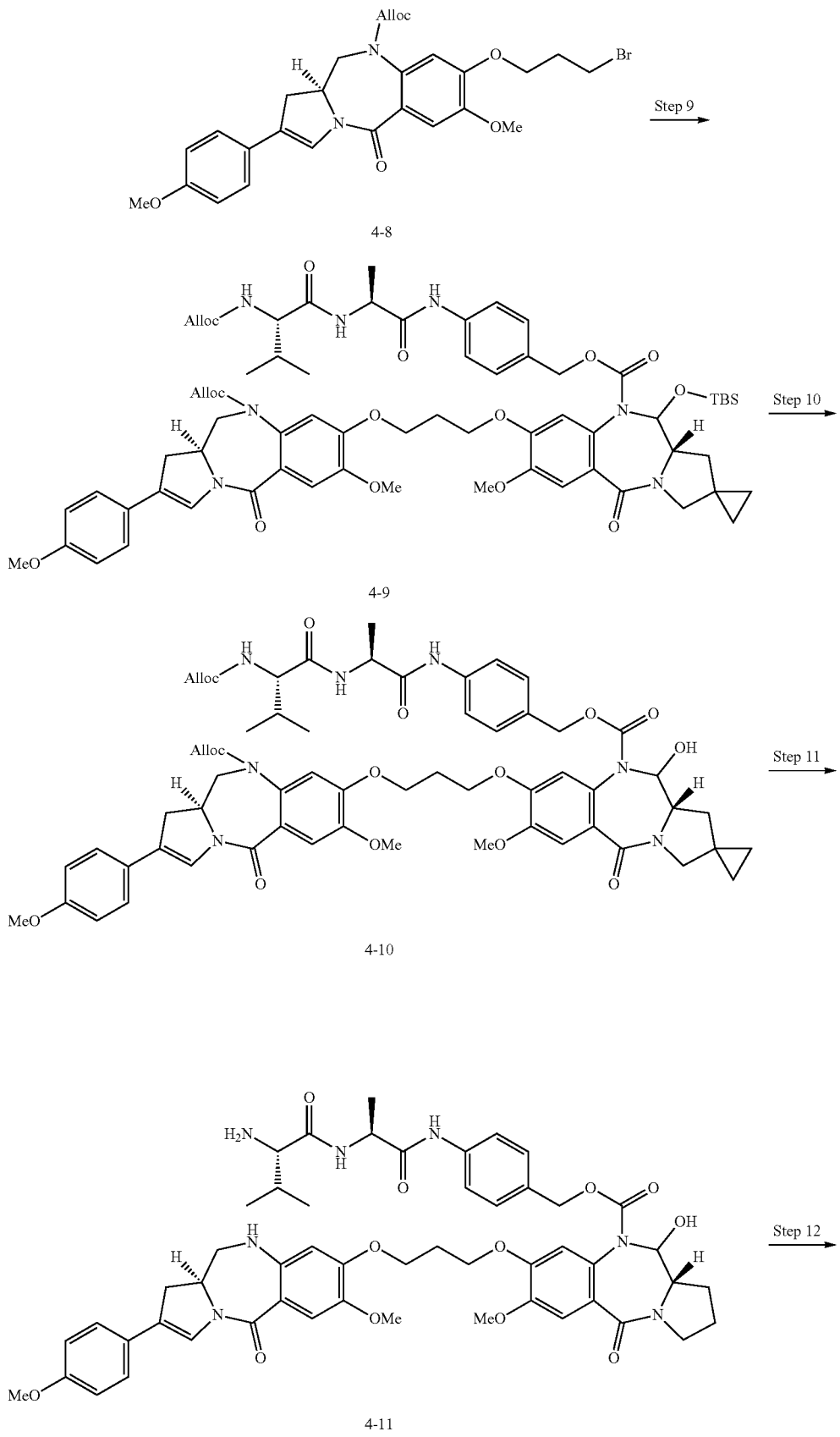
4-8
4-9
4-10
4-11

-continued

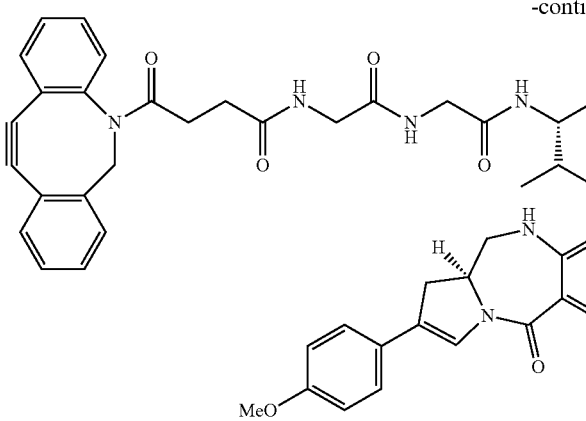

4-12

Step 1: (2R,11aS)-8-(3-Bromopropoxy)-2-{[tert-butyl(dimethyl)silyl]oxy}-7-methoxy-10-{[2-(trimethylsilyl)ethoxy]methyl}-2,3-dihydro-1H-pyrrolo[2,1-c][1,4]benzodiazepin-5,11(10H,11aH)-dione The compound obtained in step 1 of Example 3 (5.06 g, 9.67 mmol) and 1,3-dibromopropane (4.93 mL, 48.4 mmol) were reacted in the same manner as in step 2 of Example 3 to afford the desired compound (4.85 g, 78%).

$^1$H-NMR (CDCl$_3$) δ:7.35 (1H, s), 7.26 (1H, s), 5.52-5.50 (1H, m), 4.65-4.63 (1H, m), 4.61-4.55 (1H, m), 4.25-4.14 (3H, m), 3.92 (3H, s), 3.82-3.62 (5H, m), 3.57-3.54 (1H, m), 2.86-2.84 (1H, m), 2.41-2.39 (2H, m), 2.06-1.99 (1H, m), 1.03-0.97 (2H, m), 0.87 (9H, s), 0.10 (6H, s), 0.04 (9H, s).
MS(APCI, ESI)m/z:645[$^{81}$Br,(M+H)$^+$], 643[$^{79}$Br,(M+H)$^+$].

Step 2: (2R,11aS)-8-(3-Bromopropoxy)-2-hydroxy-7-methoxy-10-{[2-(trimethylsilyl)ethoxy]methyl}-2,3-dihydro-1H-pyrrolo[2,1-c][1,4]benzodiazepin-5,11(10H,11aH)-dione The compound obtained in step 1 (4.85 g, 7.54 mmol) was reacted in the same manner as in step 3 of Example 3 to afford the desired compound (4.05 g, quantitative).

$^1$H-NMR (CDCl$_3$) δ:7.35 (1H, s), 7.26 (1H, s), 5.53-5.51 (1H, m), 4.66-4.61 (2H, m), 4.32-4.30 (1H, m), 4.21-4.16 (2H, m), 3.91-3.85 (4H, m), 3.82-3.74 (1H, m), 3.71-3.59 (4H, m), 2.99-2.96 (1H, m), 2.43-2.37 (2H, m), 2.15-2.09 (2H, m), 1.04-0.96 (2H, m), 0.04 (9H, s).
MS(APCI, ESI)m/z:531[$^{81}$Br,(M+H)$^+$], 529[$^{79}$Br,(M+H)$^+$].

Step 3: (11aS)-8-(3-Bromopropoxy)-7-methoxy-10-{[2-(trimethylsilyl)ethoxy]methyl}-1H-pyrrolo[2,1-c][1,4]benzodiazepin-2,5,11 (3H,10H,11aH)-trione The compound obtained in step 2 (7.54 mmol) was reacted in the same manner as in step 4 of Example 3 to afford the desired compound (3.73 g, 93%).

$^1$H-NMR (CDCl$_3$) δ:7.34 (1H, s), 7.29 (1H, s), 5.56-5.53 (1H, m), 4.72-4.69 (1H, m), 4.67-4.61 (1H, m), 4.23-4.17 (3H, m), 3.97-3.88 (4H, m), 3.82-3.75 (1H, m), 3.74-3.56 (4H, m), 2.82-2.77 (1H, m), 2.43-2.38 (2H, m), 1.06-0.94 (2H, m), 0.08-0.00 (9H, m).

Step 4: (11aS)-8-(3-Bromopropoxy)-7-methoxy-5,11-dioxo-10-{[2-(trimethylsilyl)ethoxy]methyl}-5,10,11,11a-tetrahydro-1H-pyrrolo[2,1-c][1,4]benzodiazepin-2-yl trifluoromethanesulfonate The compound obtained in step 3 (3.73 g, 7.08 mmol) was reacted in the same manner as in step 5 of Example 3 to afford the desired compound (3.27 g, 70%).

$^1$H-NMR (CDCl$_3$) δ:7.33 (1H, s), 7.29 (1H, s), 7.15-7.15 (1H, m), 5.56-5.54 (1H, m), 4.70-4.65 (2H, m), 4.21-4.18 (2H, m), 3.94-3.91 (4H, m), 3.81-3.79 (1H, m), 3.70-3.64 (3H, m), 3.19-3.15 (1H, m), 2.47-2.38 (2H, m), 1.02-1.00 (2H, m), 0.04 (9H, s).
MS(APCI, ESI)m/z:661[$^{81}$Br,(M+H)$^+$], 659[$^{79}$Br,(M+H)$^+$].

Step 5: (11aS)-8-(3-Bromopropoxy)-7-methoxy-2-(4-methoxyphenyl)-10-{[2-(trimethylsilyl)ethoxy]methyl}-1H-pyrrolo[2,1-c][1,4]benzodiazepin-5,11 (10H,11aH)-dione The compound obtained in step 4 (3.27 g, 4.96 mmol) was reacted in the same manner as in step 6 of Example 3 to afford the desired compound (2.49 g, 81%).

$^1$H-NMR (DMSO-D$_6$) δ:7.49-7.47 (2H, m), 7.40 (1H, s), 7.31-7.24 (2H, m), 6.93-6.88 (2H, m), 5.33-5.31 (1H, m), 5.25-5.18 (1H, m), 4.81-4.80 (1H, m), 4.23-4.10 (2H, m), 3.85 (3H, s), 3.77 (3H, s), 3.70-3.59 (3H, m), 3.52-3.40 (2H, m), 3.15-3.08 (1H, m), 2.33-2.27 (2H, m), 0.86-0.74 (2H, m), −0.07 (9H, s).
MS(APCI, ESI)m/z:619[$^{81}$Br,(M+H)$^+$], 617[$^{79}$Br,(M+H)$^+$].

Step 6: (11aS)-8-(3-Bromopropoxy)-7-methoxy-2-(4-methoxyphenyl)-1,11a-dihydro-5H-pyrrolo[2,1-c][1,4]benzodiazepin-5-one The compound obtained in step 5 (2.49 g, 4.04 mmol) was reacted in the same manner as in step 7 of Example 3 to afford the desired compound (1.59 g, 84%).
MS(APCI, ESI)m/z:473[$^{81}$Br,(M+H)$^+$], 471[$^{79}$Br,(M+H)$^+$].

Step 7: (11aS)-8-(3-Bromopropoxy)-7-methoxy-2-(4-methoxyphenyl)-1,10,11,11a-tetrahydro-5H-pyrrolo[2,1-c][1,4]benzodiazepin-5-one The compound obtained in step 6 (1.59 g, 3.38 mmol) was reacted in the same manner as in step 8 of Example 3 to afford the desired compound (1.39 g, 87%).

¹H-NMR (CDCl₃) δ:7.54 (1H, s), 7.54-7.51 (1H, m), 7.32-7.29 (2H, m), 6.89-6.87 (2H, m), 6.10 (1H, s), 4.32-4.28 (2H, m), 4.14-4.13 (2H, m), 3.85 (3H, s), 3.82 (3H, s), 3.63-3.62 (2H, m), 3.57-3.55 (2H, m), 3.40-3.36 (1H, m), 2.76-2.72 (1H, m), 2.40-2.37 (2H, m).
MS(APCI, ESI)m/z:475[⁸¹Br,(M+H)⁺], 473[⁷⁹Br,(M+H)⁺].

Step 8: Prop-2-en-1-yl (11aS)-8-(3-bromopropoxy)-7-methoxy-2-(4-methoxyphenyl)-5-oxo-11,11a-dihydro-1H-pyrrolo[2,1-c][1,4]benzodiazepin-10(5H)-carboxylate The compound obtained in step 7 (1.40 g, 2.95 mmol) was reacted in the same manner as in step 9 of Example 3 to afford the desired compound (0.885 g, 54%).
¹H-NMR (CDCl₃) δ:7.34 (1H, s), 7.27-7.25 (2H, m), 7.22 (1H, s), 6.86-6.84 (2H, m), 6.73 (1H, s), 5.76-5.74 (1H, m), 5.11-5.09 (2H, m), 4.62-4.59 (2H, m), 4.33-4.31 (1H, m), 4.16-4.13 (3H, m), 3.88 (3H, s), 3.79 (3H, s), 3.60-3.59 (3H, m), 3.27-3.23 (1H, m), 2.69-2.65 (1H, m), 2.37-2.34 (2H, m).
MS(APCI, ESI)m/z:559[⁸¹Br,(M+H)⁺], 557[⁷⁹Br,(M+H)⁺].

Step 9: N-{[(Prop-2-en-1-yl)oxy]carbonyl}-L-valyl-N-[4-({[(11'aS)-11'-{[tert-butyl(dimethyl)silyl]oxy}-7'-methoxy-8'-(3-{[(11aS)-7-methoxy-2-(4-methoxyphenyl)-5-oxo-10-{[(prop-2-en-1-yl)oxy]carbonyl}-5,10,11,11a-tetrahydro-1H-pyrrolo[2,1-c][1,4]benzodiazepin-8-yl]oxy}propoxy)-5'-oxo-11',11'a-dihydro-1'H,3'H-spiro[cyclopropane-1,2'-pyrrolo[2,1-c][1,4]benzodiazepine]-10'(5'H)—carbonyl]oxy}methyl)phenyl]-L-alaninamide The compound obtained in step 8 (0.0381 g, 0.0683 mmol) was reacted in the same manner as in step 10 of Example 3 to afford the desired compound (0.0712 g, 81%).
MS(APCI, ESI)m/z:1284(M+H)⁺.

Step 10: N-{[(Prop-2-en-1-yl)oxy]carbonyl}-L-valyl-N-[4-({[(11'aS)-11'-hydroxy-7'-methoxy-8'-(3-{[(11aS)-7-methoxy-2-(4-methoxyphenyl)-5-oxo-10-{[(prop-2-en-1-yl)oxy]carbonyl}-5,10,11,11a-tetrahydro-1H-pyrrolo[2,1-c][1,4]benzodiazepin-8-yl]oxy}propoxy)-5'-oxo-11',11'a-dihydro-1'H,3'H-spiro[cyclopropane-1,2'-pyrrolo[2,1-c][1,4]benzodiazepine]-10'(5'H)-carbonyl]oxy}methyl)phenyl]-L-alaninamide The compound obtained in step 9 (0.0712 g, 0.0554 mmol) was reacted in the same manner as in step 11 of Example 3 to afford the desired compound (0.0671 g, quantitative).
MS(APCI, ESI)m/z:1170(M+H)⁺.

Step 11: L-Valyl-N-[4-({[(11'aS)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11'a-dihydro-1'H,3'H-spiro[cyclopropane-1,2'-pyrrolo[2,1-c][1,4]benzodiazepine]-10'(5'H)-carbonyl]oxy}methyl)phenyl]-L-alaninamide The compound obtained in step 10 (0.0571 mmol) was reacted in the same manner as in step 12 of Example 3 to afford the desired compound (0.0574 g, 99%).
¹H-NMR (CDCl₃) δ:9.16 (1H, s), 7.93-7.91 (1H, m), 7.55-7.52 (1H, m), 7.50-7.47 (3H, m), 7.35-7.32 (2H, m), 7.21 (1H, s), 7.13-7.11 (2H, m), 6.90-6.87 (2H, m), 6.40 (1H, s), 6.08 (1H, s), 5.90-5.87 (1H, m), 5.37-5.34 (1H, m), 4.73-4.53 (3H, m), 4.23-4.08 (5H, m), 3.89 (3H, s), 3.82 (3H, s), 3.78-3.72 (5H, m), 3.57-3.51 (3H, m), 3.38-3.30 (3H, m), 2.76-2.71 (1H, m), 2.36-2.24 (4H, m), 1.78-1.42 (6H, m), 1.00-0.98 (3H, m), 0.87-0.84 (3H, m), 0.74-0.62 (4H, m).
MS(APCI, ESI)m/z:1002(M+H)⁺.

Step 12: N-[4-(11,12-Didehydrodibenzo[b,f]azocin-5(6H)-yl)-4-oxobutanoyl]glycylglycyl-L-valyl-N-[4-({[(11'aS)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11'a-dihydro-1'H,3'H-spiro[cyclopropane-1,2'-pyrrolo[2,1-c][1,4]benzodiazepine]-10'(5'H)-carbonyl]oxy}methyl)phenyl]-L-alaninamide ("GGVA" Disclosed as SEQ ID NO: 76)

The compound obtained in step 11 (0.189 g, 0.189 mmol) was reacted in the same manner as in step 13 of Example 3 to afford the desired compound (0.169 g, 64%).
MS(APCI, ESI)m/z:1402(M+H)⁺.

Example 5: Drug-Linker 3

[Formula 129]

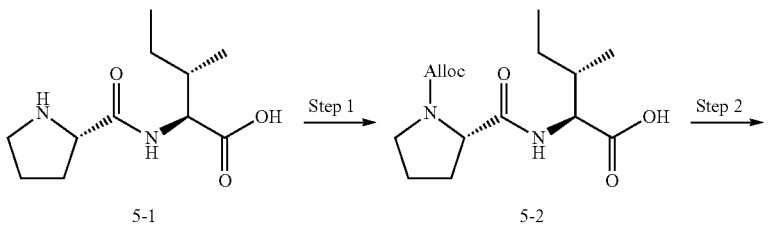

-continued
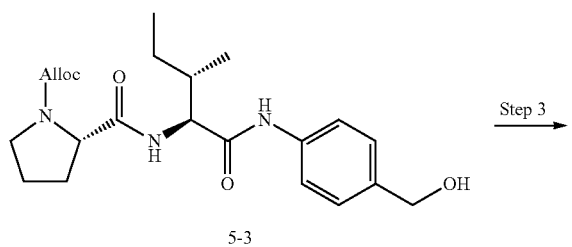
5-3
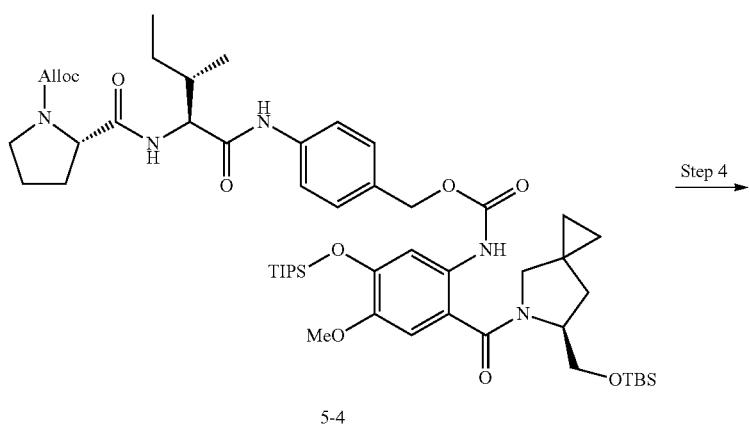
5-4
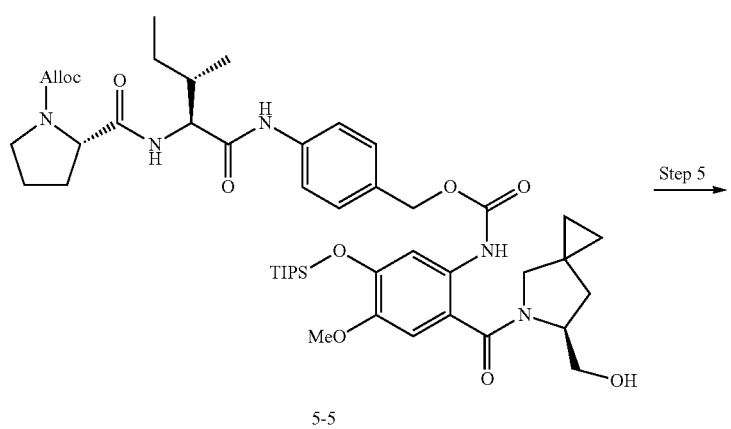
5-5
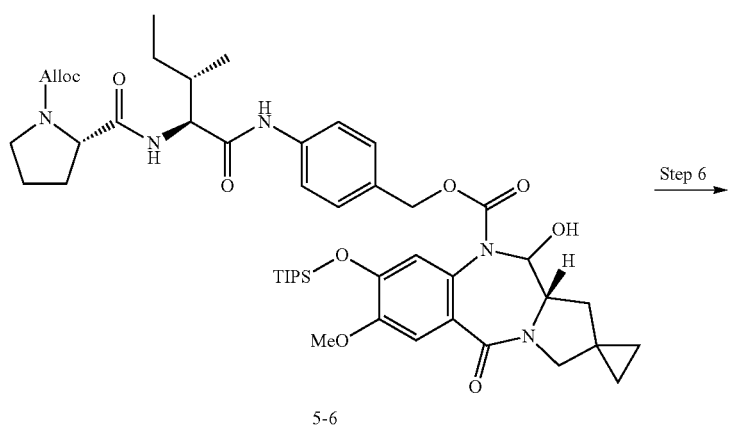
5-6

-continued
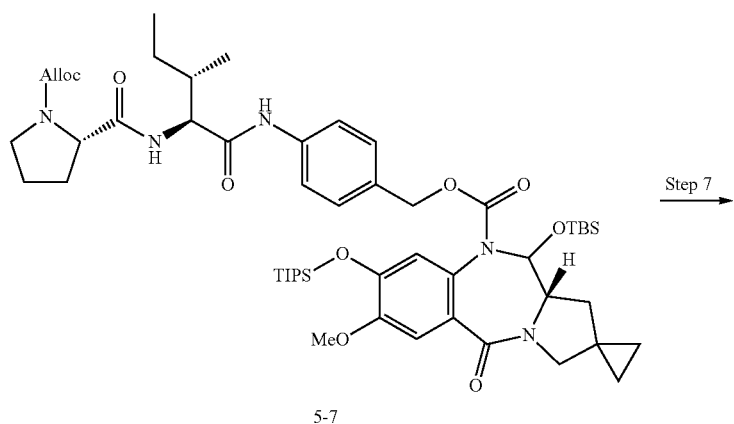
5-7
Step 7 →
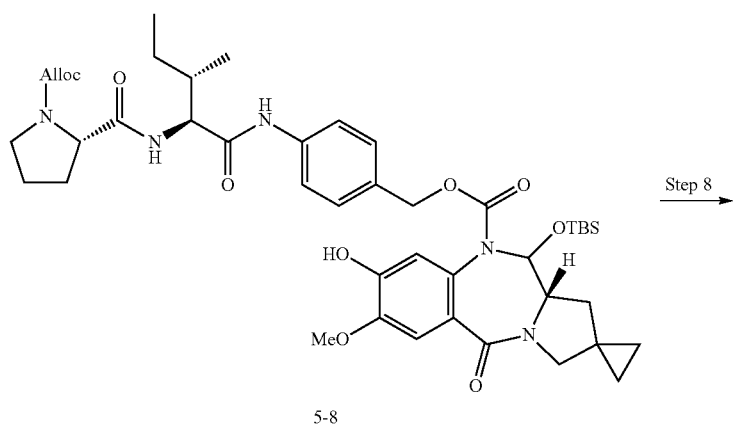
5-8
Step 8 →
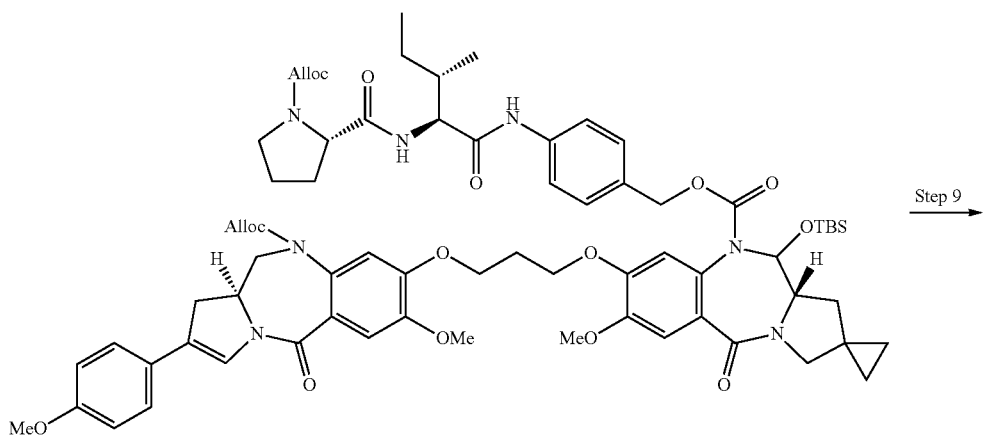
5-9
Step 9 →

-continued
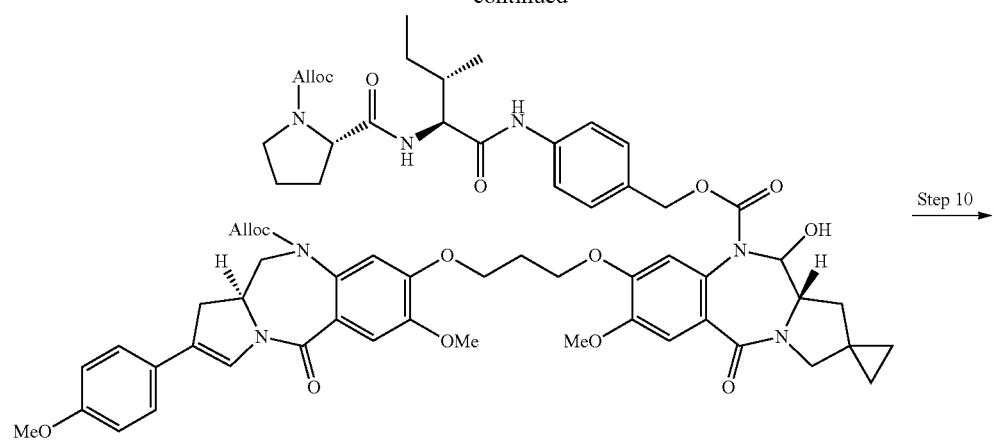
5-10
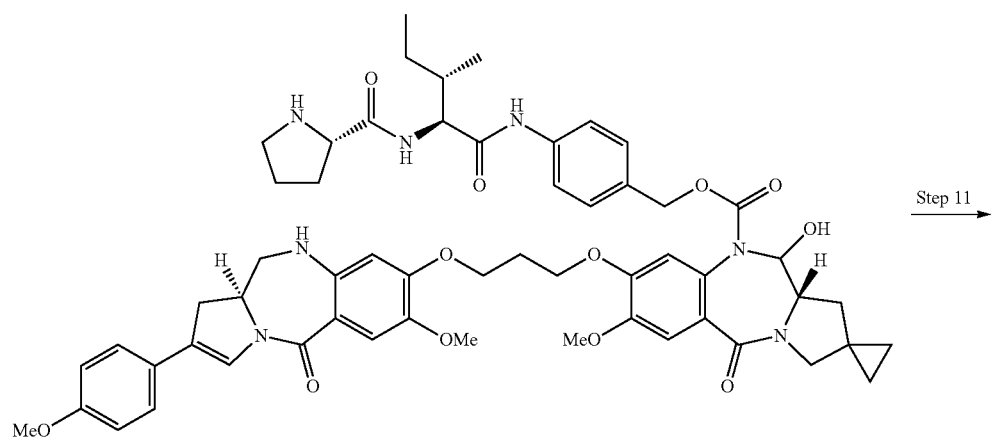
5-11
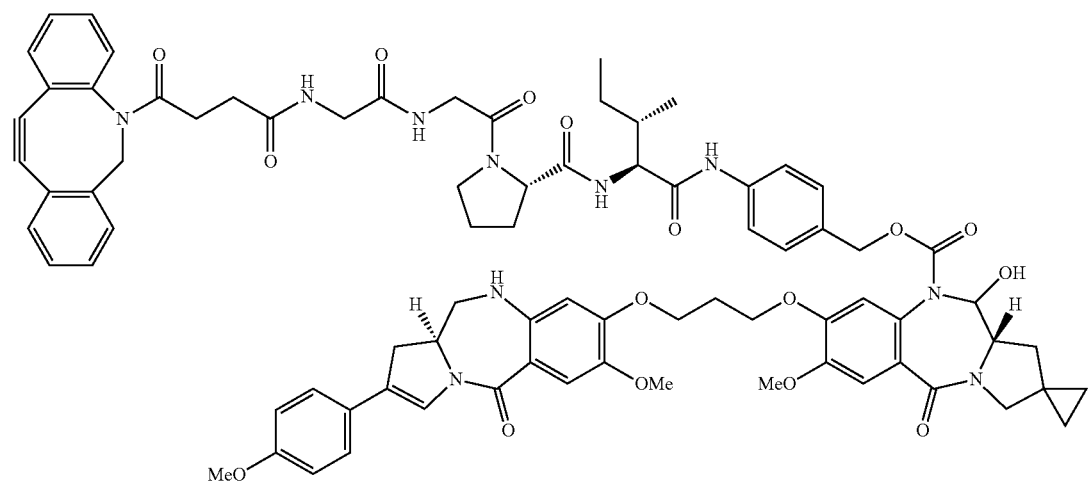
5-12

Step 1: 1-[(Prop-2-en-1-yloxy)carbonyl]-L-prolyl-L-isoleucine

To a 1 mol/L aqueous solution of sodium hydroxide (8.80 mL, 8.80 mmol) with a solution of L-prolyl-L-isoleucine (1.00 g, 4.40 mmol) in 1,4-dioxane (30 mL), allyl chloroformate (0.690 mL, 6.53 mmol) was slowly added dropwise at 0° C. The reaction mixture was stirred at room temperature for 5 hours, and an aqueous solution of potassium hydrogen sulfate was then added to the reaction mixture to adjust the pH to around 4, and the reaction mixture was extracted with chloroform. The organic layer was washed with brine, and dried over anhydrous sodium sulfate. The resultant was filtered and then concentrated under reduced pressure, and hexane was added to the residue. A solid generated was collected through filtration, and dried to afford the desired compound (1.20 g, 88%).

MS(APCI, ESI)m/z:311(M−H)—

Step 2: 1-[(Prop-2-en-1-yloxy)carbonyl]-L-prolyl-N-[4-(hydroxymethyl)phenyl]-L-isoleucinamide To THF solution (100 mL) of the compound obtained in step 1 (13.7 g, 43.4 mmol) and 4-aminobenzyl alcohol (6.00 g, 48.7 mmol), N-ethoxycarbonyl-2-ethoxy-1,2-dihydroquinoline (12.0 g, 48.7 mmol) was added at room temperature. The reaction solution was stirred at room temperature for 23 hours, to which diethyl ether (200 mL) was added, and a solid generated was then collected through filtration, and the compound (13.2 g, 65%) obtained was directly used for the subsequent reaction.

Step 3: 1-[(Prop-2-en-1-yloxy)carbonyl]-L-prolyl-N-[4-({[(2-{[(6S)-6-({[tert-butyl(dimethyl)silyl]oxy}methyl)-5-azaspiro[2.4]hept-5-yl]carbonyl}-4-methoxy-5-{[tri(propan-2-yl)silyl]oxy}phenyl)carbamoyl]oxy}methyl)phenyl]-L-isoleucinamide The compound obtained in step 2 (6.87 g, 16.5 mmol) was reacted in the same manner as in step 6 of Example 1 to afford the desired compound (7.46 g, 56%).

$^1$H-NMR (CDCl$_3$) δ:8.99-8.97 (1H, m), 8.45-8.42 (1H, m), 7.81-7.49 (3H, m), 7.36-7.33 (2H, m), 6.81-6.77 (2H, m), 5.96-5.91 (1H, m), 5.32-5.23 (2H, m), 5.13-5.10 (2H, m), 4.73-4.30 (6H, m), 4.00-3.98 (1H, m), 3.78-3.52 (7H, m), 3.06-3.02 (1H, m), 2.37-2.12 (5H, m), 2.06-1.92 (1H, m), 1.77-1.48 (2H, m), 1.32-1.27 (3H, m), 1.11-1.09 (18H, m), 1.03-0.91 (15H, m), 0.66-0.44 (4H, m), 0.09-0.04 (6H, m).

Step 4: 1-[(Prop-2-en-1-yloxy)carbonyl]-L-prolyl-N-[4-({[(2-{[(6S)-6-(hydroxymethyl)-5-azaspiro[2.4]hept-5-yl]carbonyl}-4-methoxy-5-{[tri(propan-2-yl)silyl]oxy}phenyl)carbamoyl]oxy}methyl)phenyl]-L-isoleucinamide The compound obtained in step 3 (7.46 g, 7.41 mmol) was reacted in the same manner as in step 7 of Example 1 to afford the desired compound (6.07 g, 92%).

MS(APCI, ESI)m/z:892(M+H)$^+$

Step 5: 1-[(Prop-2-en-1-yloxy)carbonyl]-L-prolyl-N-{4-[({[(11a'S)-11'-hydroxy-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-isoleucinamide The compound obtained in step 4 (6.07 g, 6.80 mmol) was reacted in the same manner as in step 8 of Example 1 to afford the desired compound (4.18 g, 69%).

MS(APCI, ESI)m/z:890(M+H)$^+$

Step 6: 1-[(Prop-2-en-1-yloxy)carbonyl]-L-prolyl-N-{4-[({[(11a'S)-11'-{[tert-butyl(dimethyl)silyl]oxy}-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-isoleucinamide The compound obtained in step 5 (4.18 g, 4.70 mmol) was reacted in the same manner as in step 9 of Example 1 to afford the desired compound (4.26 g, 90%).

MS(APCI, ESI)m/z:1004(M+H)$^+$

Step 7: 1-[(Prop-2-en-1-yloxy)carbonyl]-L-prolyl-N-{4-[({[(11a'S)-11'-{[tert-butyl(dimethyl)silyl]oxy}-8'-hydroxy-7'-methoxy-5'-oxo-11',11a'-dihydro-1'H-spirocyclopropane-1,2'-pyrrolo[2,1-c][1,4]benzodiazepine]-10'(5'H)-yl]carbonyl}oxy)methyl]phenyl}-L-isoleucinamide The compound obtained in step 6 (4.26 g, 4.70 mmol) was reacted in the same manner as in step 10 of Example 1 to afford the desired compound (2.48 g, 69%).

$^1$H-NMR (CDCl$_3$) δ:8.44-8.41 (1H, m), 7.53-7.37 (1H, m), 7.24-7.23 (1H, m), 7.14-7.11 (2H, m), 6.82 (1H, s), 6.67-6.65 (1H, m), 6.11-6.07 (1H, m), 5.99-5.95 (2H, m), 5.33-5.02 (4H, m), 4.84-4.41 (5H, m), 3.94 (3H, s), 3.73-3.70 (1H, m), 3.59-3.52 (4H, m), 3.29-3.26 (1H, m), 2.39-2.24 (5H, m), 1.99-1.97 (2H, m), 1.56-1.53 (1H, m), 1.10-0.64 (19H, m), 0.20-0.16 (3H, m), 0.09-0.07 (3H, m).

MS(APCI, ESI)m/z:848(M+H)$^+$

Step 8: 1-[(Prop-2-en-1-yloxy)carbonyl]-L-prolyl-N-{4-[({[(11a'S)-7'-methoxy-8'-[3-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)propoxy]-5'-oxo-11'-[(trimethylsilyl)oxy]-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-isoleucinamide The compound obtained in step 7 (0.200 g, 0.236 mmol) was reacted in the same manner as in step 9 of Example 4 to afford the desired compound (0.308 g, 99%).

MS(APCI, ESI)m/z:1324(M+H)$^+$

Step 9: 1-[(Prop-2-en-1-yloxy)carbonyl]-L-prolyl-N-{4-[({[(11a'S)-11'-hydroxy-7'-methoxy-8'-[3-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)propoxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-isoleucinamide The compound obtained in step 8 (0.308 g, 0.233 mmol) was reacted in the same manner as in step 11 of Example 3 to afford the desired compound (0.261 g, 93%).
MS(APCI, ESI)m/z:1210(M+H)$^+$

Step 10: L-Prolyl-N-{4-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-isoleucinamide The compound obtained in step 9 (0.261 g, 0.216 mmol) was reacted in the same manner as in step 12 of Example 3 to afford the desired compound (0.183 g, 81%).
$^1$H-NMR (CDCl$_3$) δ:9.06 (1H, s), 8.33-8.31 (1H, m), 7.53-7.47 (4H, m), 7.33-7.31 (2H, m), 7.21 (1H, s), 7.11-7.09 (2H, m), 6.89-6.87 (2H, m), 6.40 (1H, s), 6.08 (1H, s), 5.91-5.88 (1H, m), 5.35-5.32 (1H, m), 4.69-4.66 (2H, m), 4.45-4.28 (3H, m), 4.15-4.05 (3H, m), 3.87 (3H, s), 3.82 (3H, s), 3.78 (3H, s), 3.74-3.72 (3H, m), 3.64-3.47 (3H, m), 3.37-3.30 (2H, m), 3.04-3.00 (1H, m), 2.94-2.88 (1H, m), 2.75-2.72 (1H, m), 2.42-2.39 (1H, m), 2.13-2.05 (4H, m), 1.92-1.55 (6H, m), 1.20-1.14 (1H, m), 0.98-0.96 (3H, m), 0.91-0.89 (3H, m), 0.70-0.66 (4H, m).
MS(APCI, ESI)m/z:1042(M+H)$^+$

Step 11: N-[4-(11,12-Didehydrodibenzo[b,f]azocin-5 (6H)-yl)-4-oxobutanoyl]glycylglycyl-L-prolyl-N-{4-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-isoleucinamide ("GGPI" Disclosed as SEQ ID NO: 78)

The compound obtained in step 10 (0.0474 g, 0.455 mmol) was reacted in the same manner as in step 13 of Example 3 to afford the desired compound (0.0495 g, 75%).
MS(APCI, ESI)m/z:1443(M+H)$^+$ Example 6: Drug-Linker 4

[Formula 130]

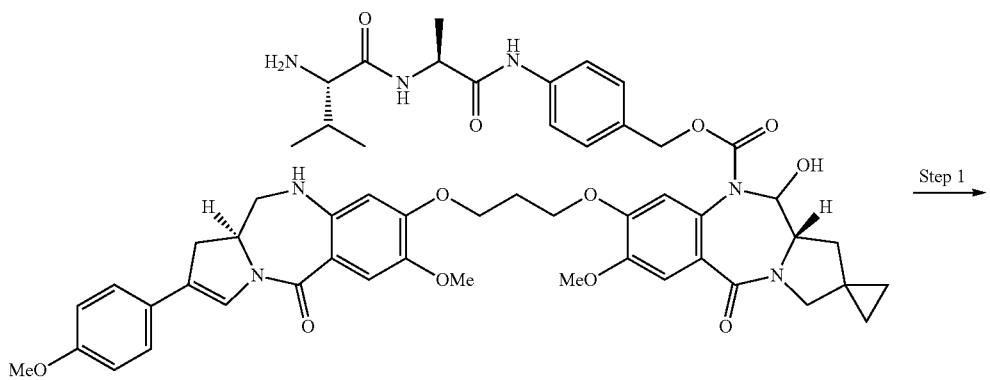

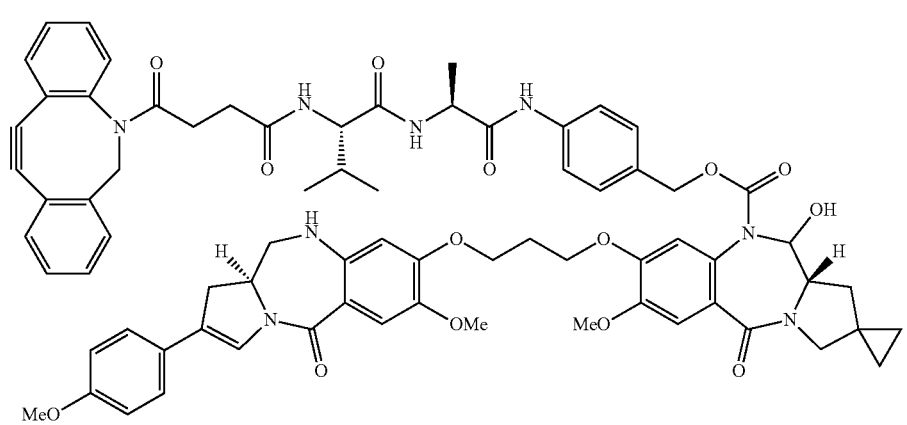

Step 1: To a solution of the compound obtained in step 11 of Example 4 (0.0564 g, 0.0563 mmol) and triethylamine (0.00936 mL, 0.0675 mmol) in N,N-dimethylformamide (5 mL), 1-{[4-(11,12-didehydrodibenzo[b,f]azocin-5(6H)-yl)-4-oxobutanoyl]oxy}pyrrolidin-2,5-dione (0.0249 g, 0.0619 mmol) was added at room temperature. The resultant was stirred at room temperature for 2 hours, and then distillated under reduced pressure, and the resulting residue was purified by silica gel column chromatography [chloroform:methanol=99.5:0.5 (v/v) to 90:10 (v/v)] to afford the desired compound (0.0490 g, 68%).

MS(APCI, ESI)m/z:1289(M+H)$^+$

Example 7: Drug-Linker 5

[Formula 131]

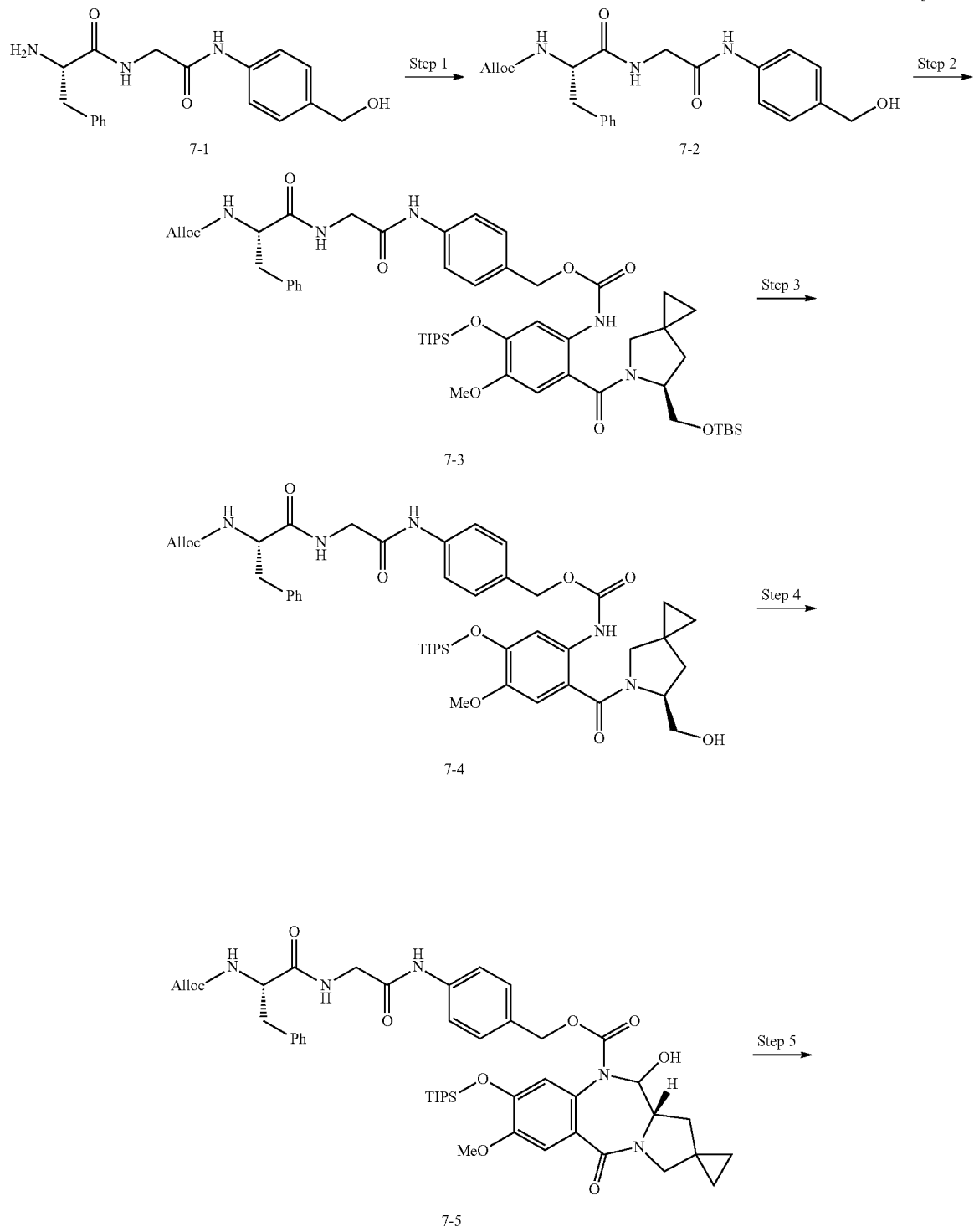

-continued
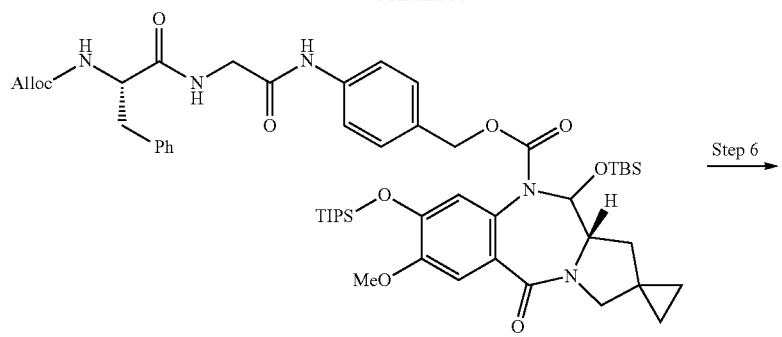
7-6
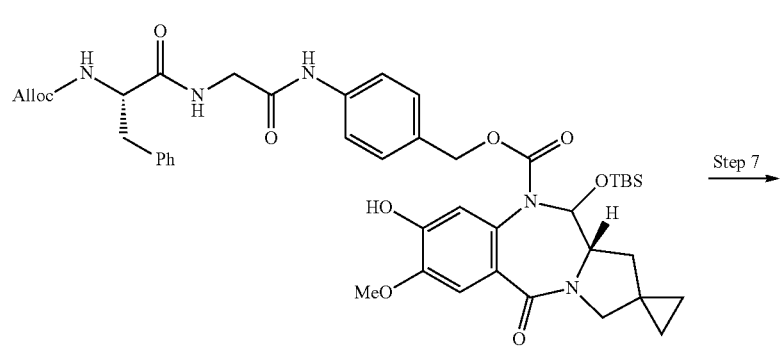
7-7
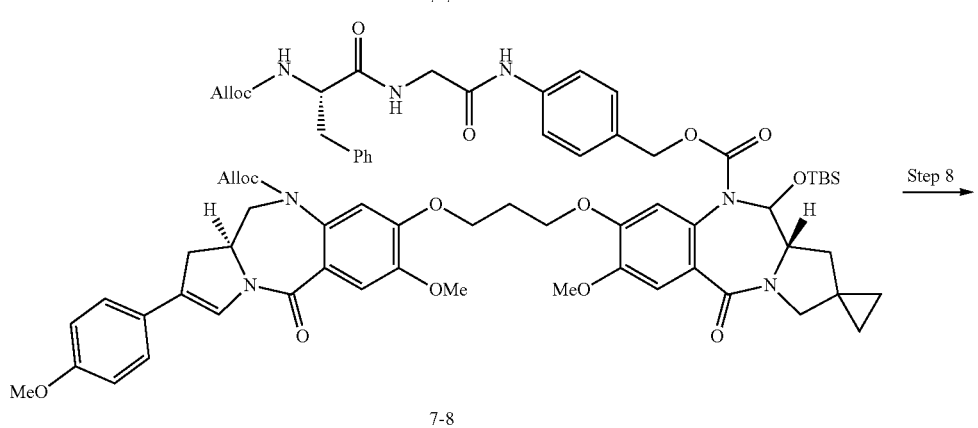
7-8
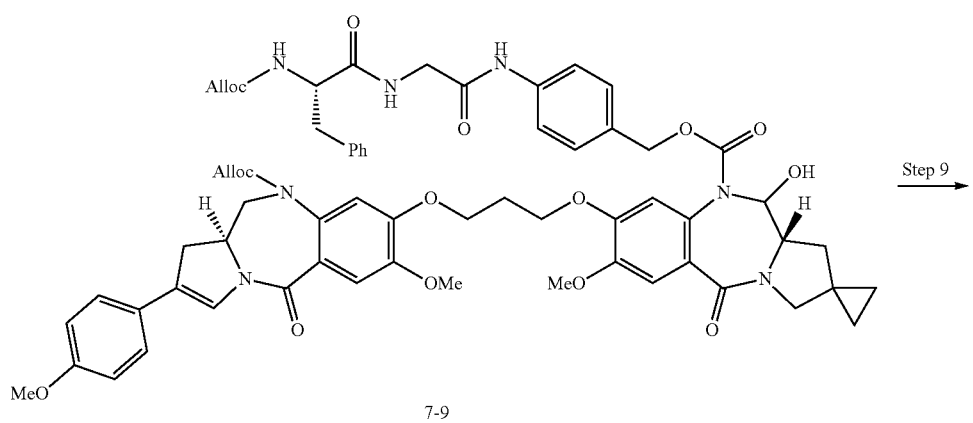
7-9

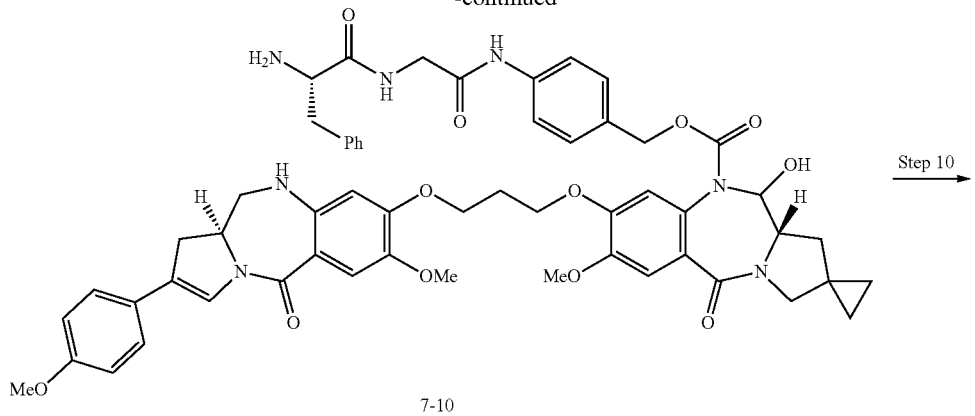

7-10

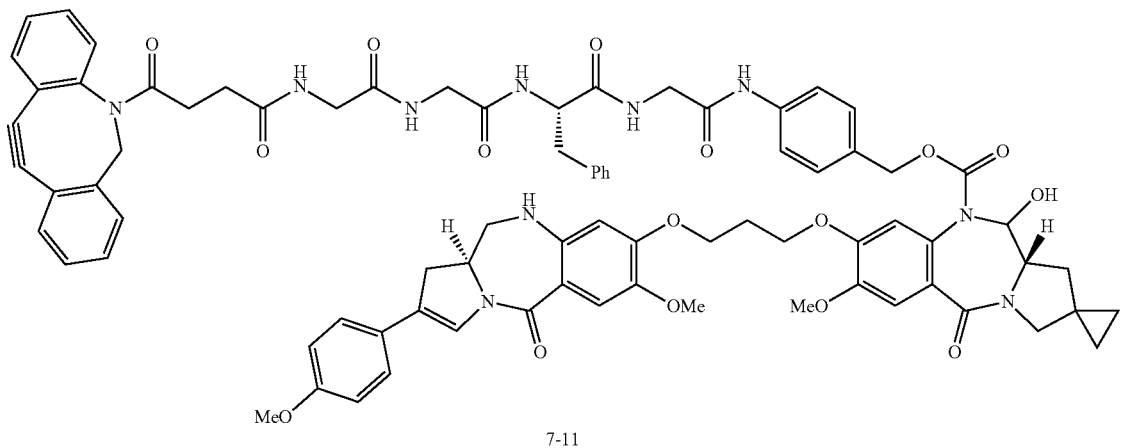 [SMILES: COc1ccc(C2=CN3C(=O)c4cc(OC)c(OCCCOc5cc6c(cc5OC)C(=O)N5CC7(CC7)C[C@H]5C(O)N6C(=O)OCc5ccc(NC(=O)CNC(=O)[C@H](Cc6ccccc6)NC(=O)CNC(=O)CNC(=O)CCC(=O)N6Cc7ccccc7C#Cc7ccccc76)cc5)cc4NC[C@@H]3C2)cc1]

7-11

Step 1: N-[(Prop-2-en-1-yloxy)carbonyl]-L-phenyl-alanyl-N-[4-(hydroxymethyl)phenyl]glycinamide To a solution of starting material 7-1 (1.24 g, 3.80 mmol, Bioorganic & Medicinal Chemistry 2015, 3, 3237-3247) and potassium carbonate (0.945 g, 6.84 mmol) in THF (18 mL) and water (12 mL), allyl chloroformate (0.482 mL, 4.560 mmol) was added at 0° C., and added at room temperature for 1 hour. After extraction with ethyl acetate, the extract was washed with water and brine, and dried over sodium sulfate. The resultant was distillated under reduced pressure, and the resulting residue was then dissolved in a small amount of ethyl acetate, to which diethyl ether was added. A solid generated (1.30 g, 83%) was collected through filtration, and directly used for the subsequent reaction.

Step 2: N-[(Prop-2-en-1-yloxy)carbonyl]-L-phenyl-alanyl-N-[4-({[(2-{[(6S)-6-({[tert-butyl(dimethyl)silyl]oxy}methyl)-5-azaspiro[2.4]hept-5-yl]carbonyl}-4-methoxy-5-{[tri(propan-2-yl)silyl]oxy}phenyl)carbamoyl]oxy}methyl)phenyl]glycinamide The compound obtained in step 1 (1.30 g, 3.16 mmol) was reacted in the same manner as in step 6 of Example 1 to afford the desired compound (1.32 g, 54%).

$^1$H-NMR (CDCl$_3$) δ:9.01 (1H, s), 8.38 (1H, s), 7.80 (1H, s), 7.60-7.58 (2H, m), 7.32-7.29 (5H, m), 7.19-7.18 (2H, m), 6.76 (1H, s), 6.55 (1H, s), 5.89-5.83 (1H, m), 5.24-5.13 (5H, m), 4.56-4.55 (3H, m), 4.34-4.33 (1H, m), 4.10-4.06 (1H, m), 3.98-3.94 (2H, m), 3.75-3.72 (5H, m), 3.16-3.08 (3H, m), 2.28-2.25 (1H, m), 1.70-1.68 (1H, m), 1.30-1.27 (3H, m), 1.11-1.09 (18H, m), 0.90 (9H, s), 0.65-0.48 (4H, m), 0.05-0.02 (6H, m).

MS(APCI, ESI)m/z:1000(M+H)$^+$

Step 3: N-[(Prop-2-en-1-yloxy)carbonyl]-L-phenyl-alanyl-N-[4-({[(2-{[(6S)-6-(hydroxymethyl)-5-azaspiro[2.4]hept-5-yl]carbonyl}-4-methoxy-5-{[tri(propan-2-yl)silyl]oxy}phenyl)carbamoyl]oxy}methyl)phenyl]glycinamide The compound obtained in step 2 (1.32 g, 1.32 mmol) was reacted in the same manner as in step 7 of Example 1 to afford the desired compound (1.23 g, quantitative).

$^1$H-NMR (CDCl$_3$) δ:8.48-8.38 (2H, m), 7.71 (1H, s), 7.61-7.59 (2H, m), 7.36-7.27 (5H, m), 7.20-7.18 (2H, m), 6.76 (1H, s), 6.55-6.52 (1H, m), 5.89-5.83 (1H, m), 5.28-5.13 (5H, m), 4.56-4.55 (3H, m), 4.34-4.33 (1H, m), 4.22-4.20 (1H, m), 4.10-4.06 (1H, m), 3.98-3.94 (1H, m), 3.78-3.75 (5H, m), 3.64-3.62 (1H, m), 3.17-3.07 (3H, m), 1.84-1.83 (2H, m), 1.30-1.26 (3H, m), 1.11-1.09 (18H, m), 0.61-0.49 (4H, m).

MS(APCI, ESI)m/z:886(M+H)$^+$

Step 4: N-[(Prop-2-en-1-yloxy)carbonyl]-L-phenyl-alanyl-N-{4-[({[(11a'S)-11'-hydroxy-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-yl]carbonyl}oxy)methyl]phenyl}glycinamide The compound obtained in step 3 (1.32 mmol) was reacted in the same manner as in step 8 of Example 1 to afford the desired compound (0.660 g, 57%).

$^1$H-NMR (CDCl$_3$) δ:8.34 (1H, s), 7.53-7.51 (2H, m), 7.26-7.18 (8H, m), 6.66-6.57 (2H, m), 5.88-5.80 (2H, m), 5.27-5.21 (3H, m), 5.11-5.07 (1H, m), 4.99-4.96 (1H, m), 4.55-4.54 (2H, m), 4.36-4.34 (1H, m), 4.13-3.92 (2H, m), 3.83 (3H, s), 3.73-3.70 (1H, m), 3.57-3.55 (1H, m), 3.46-3.44 (1H, m), 3.32-3.29 (1H, m), 3.18-3.15 (1H, m), 3.09-3.05 (1H, m), 2.42-2.38 (1H, m), 1.75-1.72 (1H, m), 1.25-1.02 (21H, m), 0.73-0.60 (4H, m).

MS(APCI, ESI)m/z:884(M+H)$^+$

Step 5: N-[(Prop-2-en-1-yloxy)carbonyl]-L-phenyl-alanyl-N-{4-[({[(11a'S)-11'-{[tert-butyl(dimethyl)silyl]oxy}-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-yl]carbonyl}oxy)methyl]phenyl}glycinamide The compound obtained in step 4 (0.834 g, 0.943 mmol) was reacted in the same manner as in step 9 of Example 1 to afford the desired compound (0.555 g, 59%).

$^1$H-NMR (CDCl$_3$) δ:8.26-8.23 (1H, m), 7.51-7.50 (2H, m), 7.29-7.28 (3H, m), 7.18-7.13 (5H, m), 6.64-6.62 (1H, m), 6.52-6.49 (1H, m), 6.02-6.00 (1H, m), 5.88-5.83 (1H, m), 5.25-5.17 (4H, m), 4.84-4.81 (1H, m), 4.55-4.55 (2H, m), 4.34-4.33 (1H, m), 4.06-3.97 (2H, m), 3.84 (3H, s), 3.71-3.68 (1H, m), 3.50-3.48 (1H, m), 3.28-3.05 (3H, m), 2.36-2.33 (1H, m), 1.56-1.53 (1H, m), 1.28-1.01 (21H, m), 0.81-0.61 (13H, m), 0.19 (3H, s), 0.09 (3H, s).

MS(APCI, ESI)m/z:998(M+H)$^+$

Step 6: N-[(Prop-2-en-1-yloxy)carbonyl]-L-phenyl-alanyl-N-{4-[({[(11a'S)-11'-{[tert-butyl(dimethyl)silyl]oxy}-8'-hydroxy-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}glycinamide The compound obtained in step 5 (0.555 g, 0.556 mmol) was reacted in the same manner as in step 10 of Example 1 to afford the desired compound (0.451 g, 96%).

$^1$H-NMR (CDCl$_3$) δ:8.42-8.40 (1H, m), 7.50-7.46 (2H, m), 7.28-7.26 (3H, m), 7.20-7.18 (3H, m), 7.10-7.08 (2H, m), 6.67-6.65 (2H, m), 6.16-6.13 (1H, m), 6.02-5.99 (1H, m), 5.88-5.82 (1H, m), 5.28-5.18 (4H, m), 4.87-4.84 (1H, m), 4.54-4.53 (1H, m), 4.38-4.36 (1H, m), 4.10-4.07 (1H, m), 3.93-3.90 (4H, m), 3.72-3.69 (1H, m), 3.54-3.52 (1H, m), 3.25-3.17 (2H, m), 3.08-3.04 (1H, m), 2.36-2.33 (1H, m), 1.57-1.54 (1H, m), 0.81-0.61 (13H, m), 0.19 (3H, s), 0.10 (3H, s).

MS(APCI, ESI)m/z:842(M+H)$^+$

Step 7: N-[(Prop-2-en-1-yloxy)carbonyl]-L-phenyl-alanyl-N-{4-[({[(11a'S)-11'-{[tert-butyl(dimethyl)silyl]oxy}-7'-methoxy-8'-[3-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)propoxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}glycinamide The compound obtained in step 6 (0.115 g, 0.137 mmol) was reacted in the same manner as in step 9 of Example 4 to afford the desired compound (0.160 g, 89%) MS(APCI, ESI)m/z:1318(M+H)$^+$ Step 8: N-[(Prop-2-en-1-yl)carbonyl]-L-phenylalanyl-N-{4-[({[(11a'S)-11'-hydroxy-7'-methoxy-8'-[3-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)propoxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}glycinamide The compound obtained in step 7 (0.160 g, 0.121 mmol) was reacted in the same manner as in step 11 of Example 3 to afford the desired compound (0.136 g, 93%).
MS(APCI, ESI)m/z:1204(M+H)$^+$ Step 9: L-Phenylalanyl-N-{4-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}glycinamide The compound obtained in step 8 (0.136 g, 0.113 mmol) was reacted in the same manner as in step 12 of Example 3 to afford the desired compound (0.0372 g, 32%).

$^1$H-NMR (CDCl$_3$) δ:8.84-8.81 (1H, m), 8.07-8.05 (1H, m), 7.53-7.39 (4H, m), 7.34-7.19 (8H, m), 7.12-7.10 (2H, m), 6.90-6.87 (2H, m), 6.44-6.42 (1H, m), 6.10-6.08 (1H, m), 5.90-5.88 (1H, m), 5.38-5.35 (1H, m), 4.76-4.72 (1H, m), 4.57-4.44 (1H, m), 4.32-4.29 (1H, m), 4.17-4.01 (5H, m), 3.89-3.52 (17H, m), 3.41-3.25 (3H, m), 2.72-2.69 (2H, m), 2.43-2.40 (1H, m), 2.19-2.16 (2H, m), 1.78-1.74 (1H, m), 1.59-1.56 (1H, m), 0.72-0.66 (4H, m).
MS(APCI, ESI)m/z:1036(M+H)$^+$

Step 10: N-[4-(11,12-Didehydrodibenzo[b,f]azocin-5 (6H)-yl)-4-oxobutanoyl]glycylglycyl-L-phenylalanyl-N-{4-[({[(11a'S)-11'-hydroxy-7'-methoxy-8'-(3- {[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}glycinamide ("GGFG" Disclosed as SEQ ID NO: 77)

The compound obtained in step 9 (0.0372 g, 0.0359 mmol) was reacted in the same manner as in step 13 of Example 3 to afford the desired compound (0.0170 g, 33%).
MS(APCI, ESI)m/z:1437(M+H)$^+$

Example 8: Drug-Linker 6

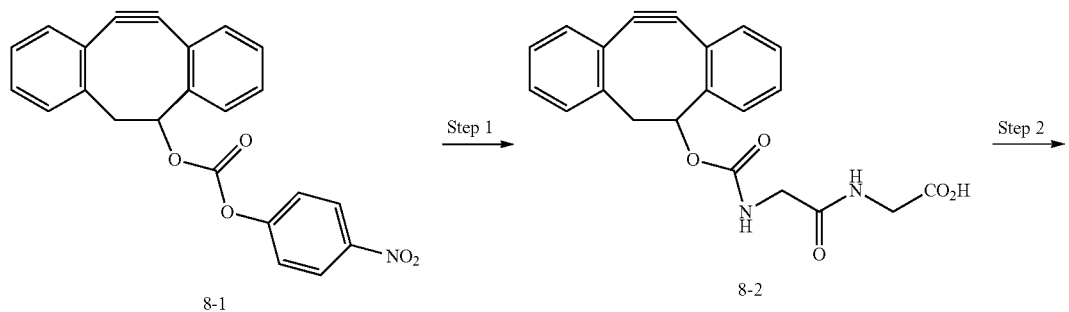

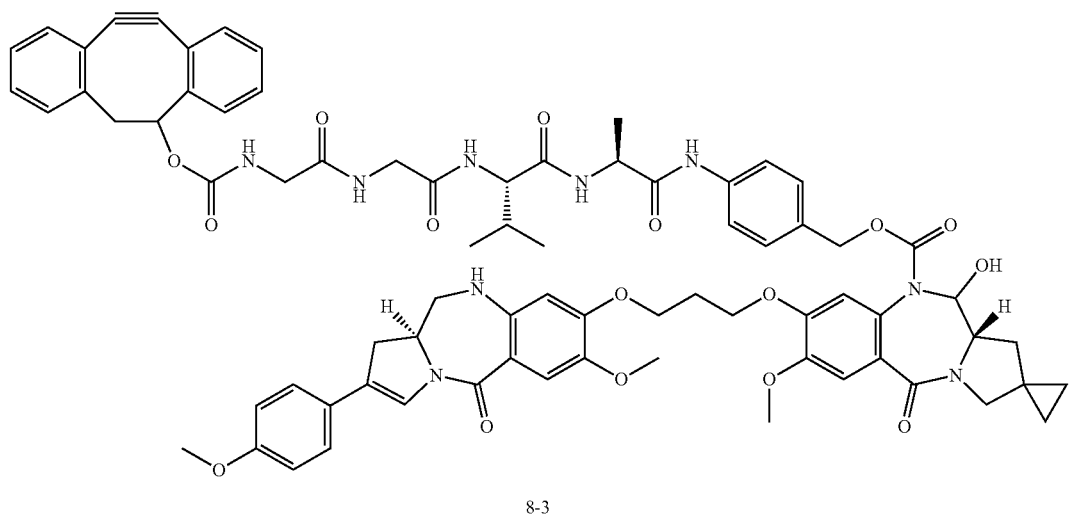

Step 1: N-[(11,12-Didehydro-5,6-dihydrodibenzo[a,e][8]annulen-5-yloxy)carbonyl]glycylglycine To a solution of 11,12-didehydro-5,6-dihydrodibenzo[a,e][8]annulen-5-yl 4-nitrophenylcarbamate (0.437 g, 1.14 mmol) and N,N-diisopropylethylamine (0.198 mL, 1.14 mmol) in N,N-dimethylformamide (6 mL), glycylglycine (0.150 g, 1.14 mmol) and water (3 mL) were added at room temperature, and the resultant was stirred at room temperature overnight. The resultant was distillated under reduced pressure, and the resulting residue was purified by silica gel column chromatography [chloroform:CMW=100:0(v/v) to 0:100(v/v)] to afford the desired compound (0.324 g, 75%).

MS(APCI, ESI)m/z:378(M+H)$^+$

Step 2: N-[(11,12-Didehydro-5,6-dihydrodibenzo[a,e][8]annulen-5-yloxy)carbonyl]glycylglycyl-L-valyl-N-{4-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 1 (0.0306 g, 0.0305 mmol) was reacted in the same manner as in step 13 of Example 3 to afford the desired compound (0.0361 g, 87%).

MS(APCI, ESI)m/z:1362(M+H)$^+$

Example 9: Drug-Linker 7
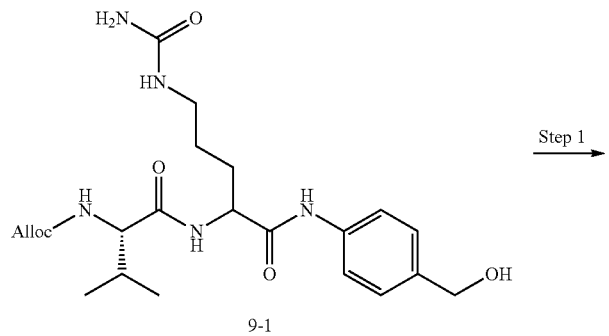
9-1
Step 1
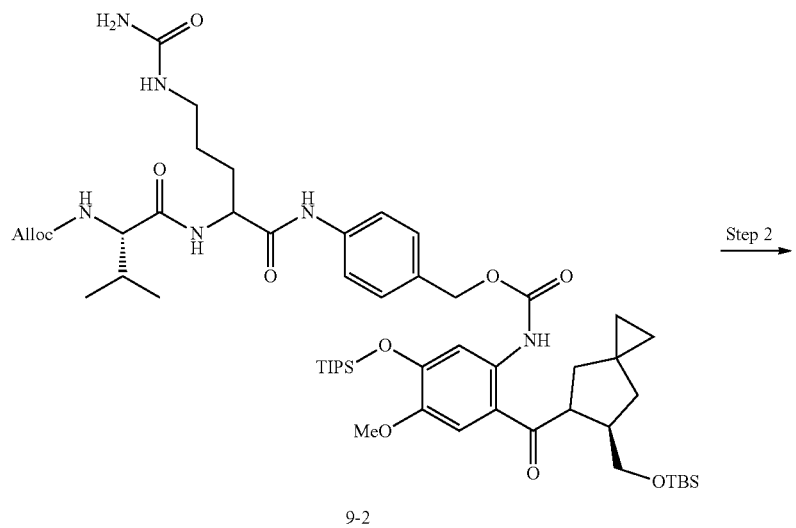
9-2
Step 2
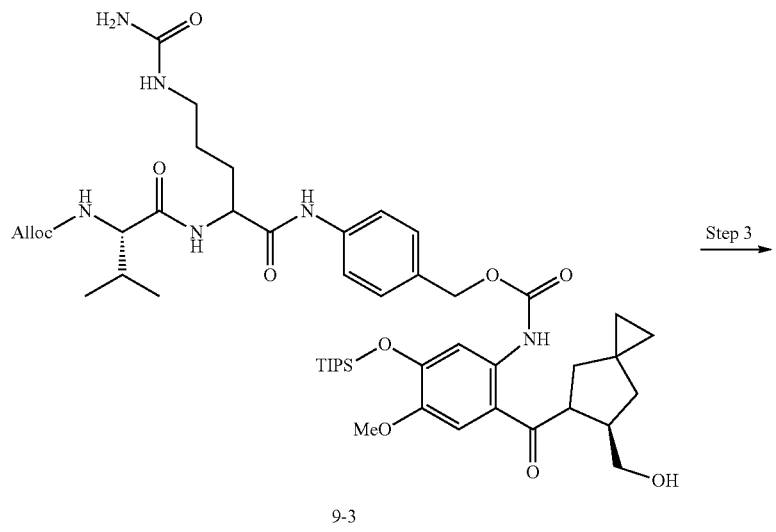
9-3
Step 3
[Formula 133]

-continued
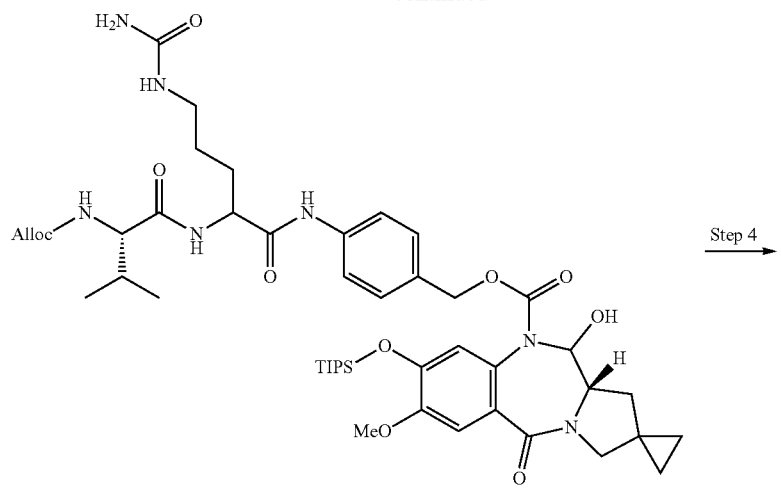
9-4
Step 4
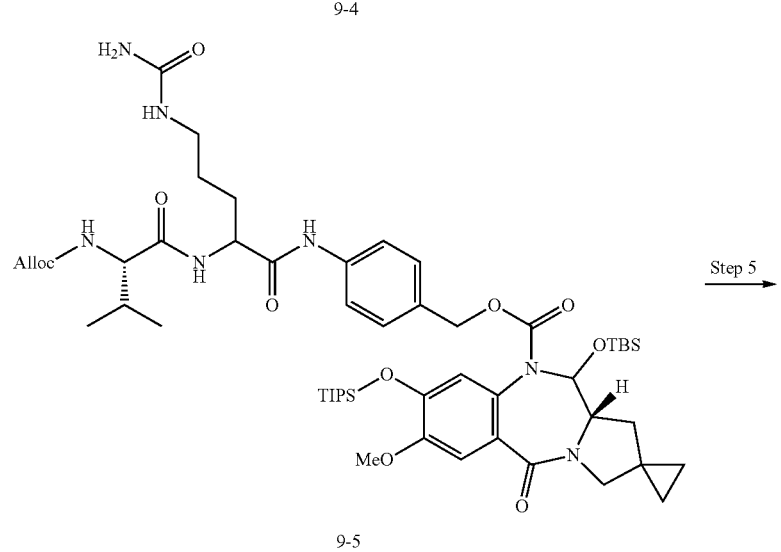
9-5
Step 5
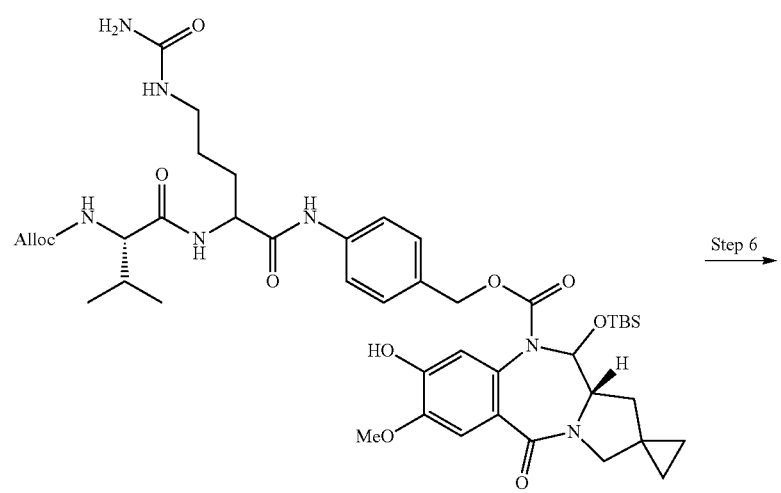
9-6
Step 6

-continued
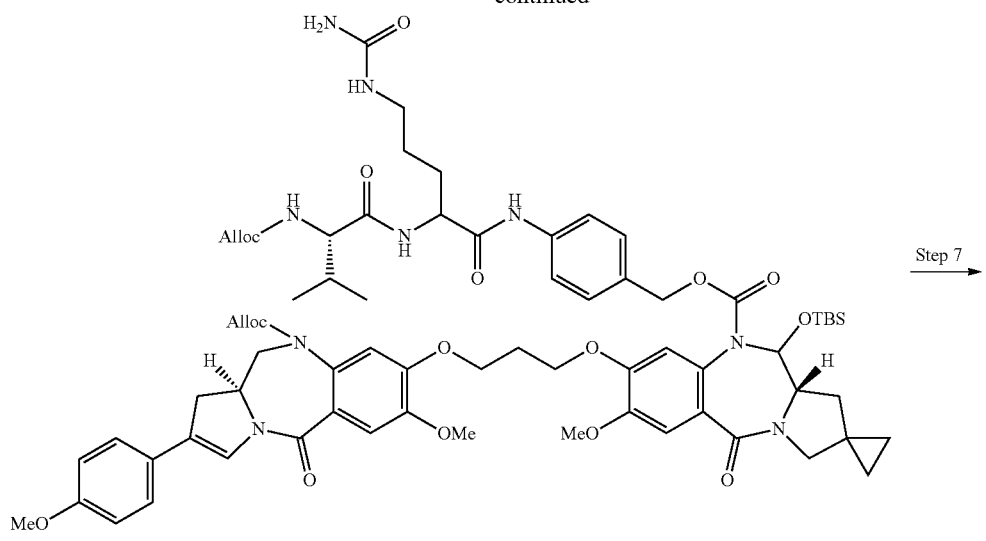
9-7
Step 7
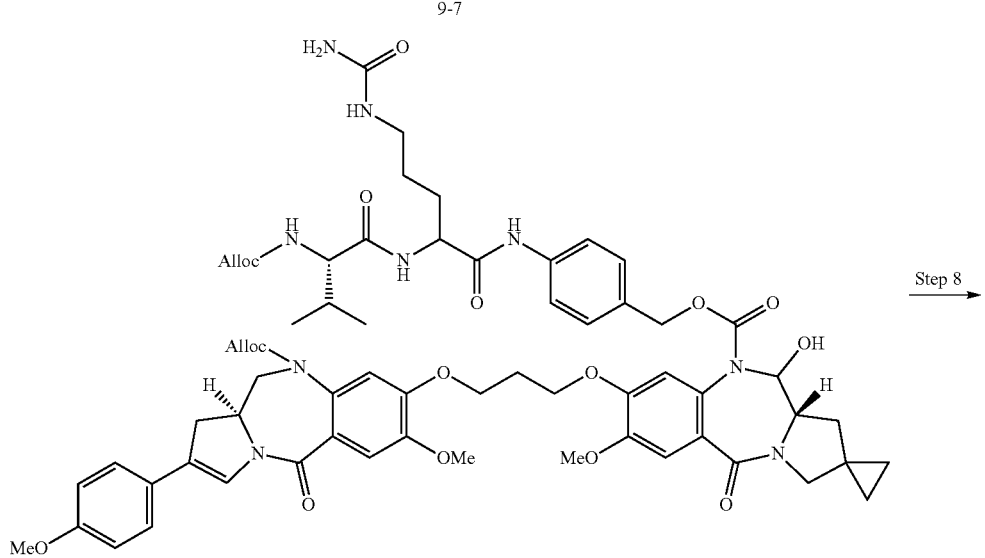
9-8
Step 8
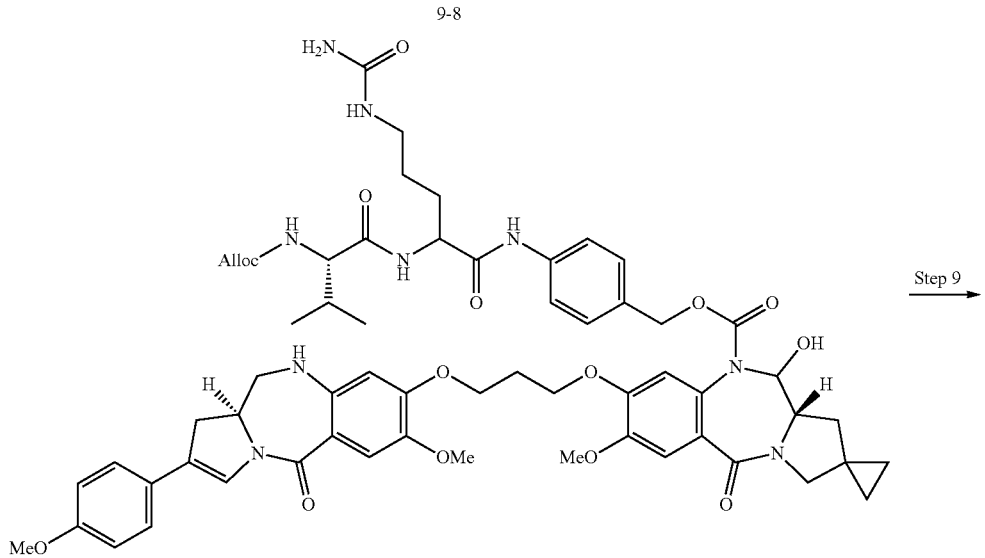
9-9
Step 9

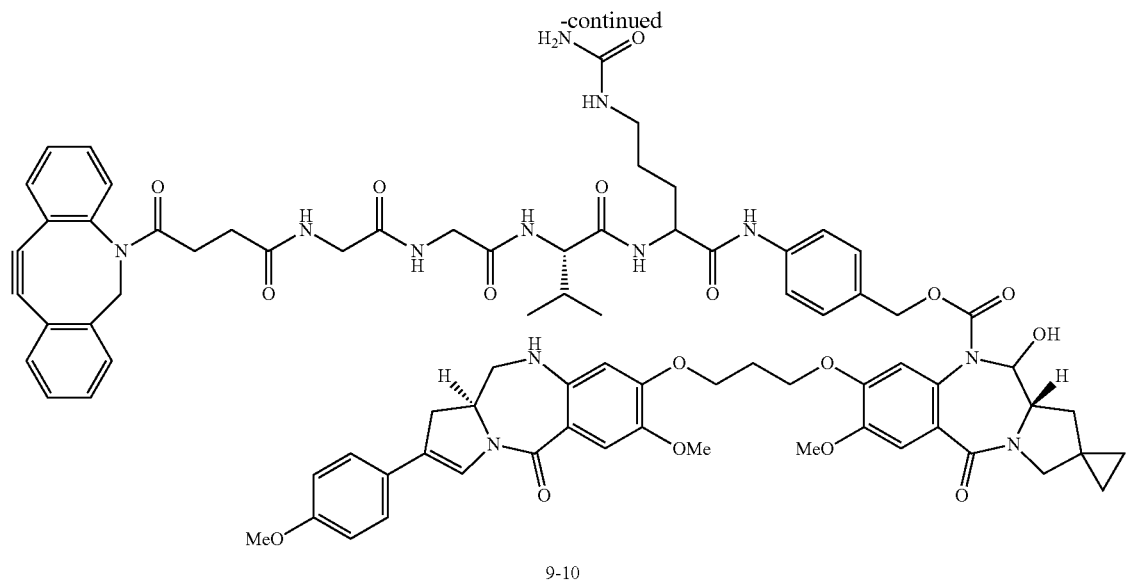

9-10

Step 1: N-[(Prop-2-en-1-yloxy)carbonyl]-L-valyl-N-[4-({[(2-{[(6S)-6-({[tert-butyl(dimethyl)silyl]oxy}methyl)-5-azaspiro[2.4]hept-5-yl]carbonyl}-4-methoxy-5-{[tri(propan-2-yl)silyl]oxy}phenyl)carbamoyl]oxy}methyl)phenyl]-$N^5$-carbamoyl-L-ornithinamide Starting material 9-1 was reacted in the same manner as in step 6 of Example 1 to afford the desired compound (1.37 g, 45%).

$^1$H-NMR (DMSO-$D_6$) δ:10.06 (1H, s), 9.16 (1H, s), 8.10-8.06 (1H, m), 7.62-7.60 (2H, m), 7.33-7.31 (2H, m), 7.27-7.24 (2H, m), 6.84-6.81 (1H, m), 5.94-5.89 (2H, m), 5.41 (2H, s), 5.32-5.28 (1H, m), 5.18-5.16 (1H, m), 5.03 (2H, s), 4.48-4.42 (3H, m), 4.30 (1H, s), 3.93-3.73 (6H, m), 3.47-3.14 (3H, m), 3.00-2.95 (2H, m), 2.00-1.89 (2H, m), 1.65-1.60 (2H, m), 1.42-1.39 (2H, m), 1.26-1.19 (3H, m), 1.04-1.01 (18H, m), 0.88-0.75 (15H, m), 0.51-0.49 (4H, m), 0.05-0.17 (6H, m).

MS(APCI, ESI)m/z:1052(M+H)$^+$

Step 2: N-[(Prop-2-en-1-yloxy)carbonyl]-L-valyl-$N^5$-carbamoyl-N-[4-({[(2-{[(6S)-6-(hydroxymethyl)-5-azaspiro[2.4]hept-5-yl]carbonyl}-4-methoxy-5-{[tri(propan-2-yl)silyl]oxy}phenyl)carbamoyl]oxy}methyl)phenyl]-L-ornithinamide The compound obtained in step 1 (1.37 g, 1.31 mmol) was reacted in the same manner as in step 7 of Example 1 to afford the desired compound (1.00 g, 82%).

$^1$H-NMR (DMSO-$D_6$) δ:10.07 (1H, s), 9.13 (1H, s), 8.11-8.09 (1H, m), 7.62-7.60 (2H, m), 7.34-7.31 (2H, m), 7.26-7.23 (2H, m), 6.92-6.90 (1H, m), 5.97-5.86 (2H, m), 5.41 (2H, s), 5.32-5.28 (1H, m), 5.19-5.16 (1H, m), 5.04 (2H, s), 4.80 (1H, s), 4.48-4.41 (3H, m), 4.27 (1H, s), 3.93-3.87 (1H, m), 3.74 (3H, s), 3.61-3.58 (2H, m), 3.39-3.30 (2H, m), 3.03-2.97 (3H, m), 2.00-1.84 (2H, m), 1.65-1.60 (2H, m), 1.44-1.37 (2H, m), 1.26-1.19 (3H, m), 1.05-1.04 (18H, m), 0.87-0.83 (6H, m), 0.53-0.42 (4H, m).

MS(APCI, ESI)m/z:938(M+H)$^+$

Step 3: N-[(Prop-2-en-1-yloxy)carbonyl]-L-valyl-$N^5$-carbamoyl-N-{4-[({[(11a'S)-11'-hydroxy-7'-methoxy-5'-oxy-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-ornithinamide To a mixture of the compound obtained in step 2 (1.00 g, 1.07 mmol), dichloromethane (80 mL), and dimethylformamide (10 mL), Dess-Martin periodinane (0.455 g, 1.07 mmol) was added at 0° C. After stirring at 0° C. for 1 hour, Dess-Martin periodinane (0.455 g, 1.07 mmol) was again added thereto, and the resultant was stirred at 0° C. for 1 hour. To the reaction solution, a saturated aqueous sodium hydrogen carbonate was added, and the resultant was extracted with chloroform, and the extract was then washed with brine. The resultant was distillated under reduced pressure, to which ethyl acetate was then added, and a solid was collected through filtration. The filtrate was distillated under reduced pressure, and the resulting residue was purified by silica gel column chromatography [hexane:ethyl acetate=50:50 to hexane:ethyl acetate=0:100(v/v)] and combined with the solid to afford the desired compound (0.671 g, 67%).

$^1$H-NMR (DMSO-$D_6$) δ:10.05 (1H, s), 8.11-8.09 (1H, m), 7.56-7.54 (2H, m), 7.25-7.23 (1H, m), 7.13-7.09 (3H, m), 6.62 (1H, s), 6.53 (1H, s), 5.94-5.88 (2H, m), 5.78-5.76 (1H, m), 5.40 (2H, s), 5.32-5.28 (1H, m), 5.17-5.14 (2H, m), 4.81-4.78 (1H, m), 4.48-4.41 (3H, m), 3.92-3.90 (1H, m), 3.79 (3H, s), 3.54-3.51 (1H, m), 3.16-3.14 (1H, m), 3.02-2.89 (2H, m), 2.37-2.34 (2H, m), 1.97-1.92 (1H, m), 1.63-1.57 (3H, m), 1.43-1.37 (2H, m), 1.08-1.01 (21H, m), 0.87-0.83 (6H, m), 0.67-0.61 (4H, m).

MS(APCI, ESI)m/z:938(M+H)$^+$

Step 4: N-[(Prop-2-en-1-yloxy)carbonyl]-L-valyl-N-{4-[({[(11a'S)-11'-{[tert-butyl(dimethyl)silyl]oxy}-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-yl]carbonyl}oxy)methyl]phenyl}-N⁵-carbamoyl-L-ornithinamide Using a mixed solvent of dichloromethane (80 mL) and dimethylformamide (5 mL), the compound obtained in step 3 (0.671 g, 0.712 mmol) was reacted in the same manner as in step 9 of Example 1 to afford the desired compound (0.335 g, 44%).

¹H-NMR (DMSO-D₆) δ:10.04 (1H, s), 8.12-8.10 (1H, m), 7.56-7.54 (2H, m), 7.26-7.24 (1H, m), 7.14-7.11 (3H, m), 6.51 (1H, s), 5.94-5.91 (3H, m), 5.40-5.16 (5H, m), 4.79-4.76 (1H, m), 4.47-4.44 (3H, m), 3.92-3.90 (1H, m), 3.80 (3H, s), 3.55-3.52 (1H, m), 3.17-3.14 (1H, m), 3.00-2.96 (3H, m), 2.56-2.30 (1H, m), 2.06-1.17 (6H, m), 1.10-0.99 (21H, m), 0.78-0.61 (19H, m), 0.17 (3H, s), 0.07 (3H, s).

MS(APCI, ESI)m/z:1050(M+H)⁺

Step 5: N-[(Prop-2-en-1-yloxy)carbonyl]-L-valyl-N-{4-[({[(11a'S)-11'-{[tert-butyl(dimethyl)silyl]oxy}-8'-hydroxy-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-N⁵-carbamoyl-L-ornithinamide The compound obtained in step 4 (0.355 g, 0.712 mmol) was reacted in the same manner as in step 10 of Example 1 to afford the desired compound (0.264 g, 93%).

¹H-NMR (DMSO-D₆) δ:10.07-10.03 (1H, m), 9.89-9.86 (1H, m), 8.12-8.10 (1H, m), 7.63-7.54 (2H, m), 7.35-7.26 (1H, m), 7.14-7.12 (2H, m), 7.06 (1H, s), 6.62-6.59 (1H, m), 5.97-5.87 (3H, m), 5.43-5.40 (2H, m), 5.32-5.28 (1H, m), 5.17-5.14 (2H, m), 4.86-4.82 (1H, m), 4.46-4.42 (3H, m), 3.91-3.89 (1H, m), 3.81 (3H, s), 3.54-3.51 (1H, m), 3.42-3.40 (1H, m), 3.09-2.96 (3H, m), 2.40-2.34 (1H, m), 1.98-1.97 (1H, m), 1.68-1.59 (2H, m), 1.42-1.38 (3H, m), 0.77-0.64 (19H, m), 0.16 (3H, s), 0.08 (3H, s).

MS(APCI, ESI)m/z:894(M+H)⁺

Step 6: N-[(Prop-2-en-1-yloxy)carbonyl]-L-valyl-N-{4-[({[(11a'S)-11'-{[tert-butyl(dimethyl)silyl]oxy}-7'-methoxy-8'-[3-({(11aS)-7-methoxy-2-(4-methoxyphenyl)-5-oxo-10-[(prop-2-en-1-yloxy)carbonyl-5,10,11,11a-tetrahydro-1H-pyrrolo[2,1-c][1,4]benzodiazepin-8-yl}oxy)propoxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-N⁵-carbamoyl-L-ornithinamide The compound obtained in step 5 (0.113 g, 0.126 mmol) was reacted in the same manner as in step 9 of Example 4 to afford the desired compound (0.149 g, 86%).

MS(APCI, ESI)m/z:1370(M+H)⁺

Step 7: N-[(Prop-2-en-1-yloxy)carbonyl]-L-valyl-N⁵-carbamoyl-N-{4-[({[(11a'S)-11'-hydroxy-7'-methoxy-8'-[3-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)propoxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-ornithinamide The compound obtained in step 6 (0.149 g, 0.109 mmol) was reacted in the same manner as in step 11 of Example 3 to afford the desired compound (0.119 g, 87%).

MS(APCI, ESI)m/z:1256(M+H)⁺

Step 8: L-Valyl-N⁵-carbamoyl-N-{4-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-ornithinamide The compound obtained in step 7 (0.050 g, 0.0398 mmol) was reacted in the same manner as in step 12 of Example 3 to afford the desired compound (0.0347 g, 80%).

¹H-NMR (CDCl₃) δ:9.43 (1H, s), 7.96-7.94 (1H, m), 7.51-7.46 (4H, m), 7.33-7.31 (2H, m), 7.22 (1H, s), 7.13-7.11 (2H, m), 6.90-6.87 (2H, m), 6.46 (1H, s), 6.11 (1H, s), 5.92-5.89 (1H, m), 5.42-5.39 (2H, m), 4.78-4.67 (4H, m), 4.31-4.29 (1H, m), 4.11-4.04 (3H, m), 3.92-3.70 (13H, m), 3.60-3.23 (8H, m), 3.07-3.05 (1H, m), 2.75-2.70 (1H, m), 2.43-2.39 (1H, m), 2.19-2.16 (3H, m), 1.73-1.48 (6H, m), 0.98-0.96 (3H, m), 0.83-0.81 (3H, m), 0.71-0.65 (4H, m).

MS(APCI, ESI)m/z:1088(M+H)⁺

Step 9: N-[4-(11,12-Didehydrodibenzo[b,f]azocin-5(6H)-yl)-4-oxobutanoyl]glycylglycyl-L-valyl-N⁵-carbamoyl-N-{4-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-ornithinamide ("GGVOrn" Disclosed as SEQ ID NO: 94)

The compound obtained in step 8 (0.0347 g, 0.0319 mmol) was reacted in the same manner as in step 13 of Example 3 to afford the desired compound (0.00650 g, 14%).

MS(APCI, ESI)m/z:1489(M+H)⁺

Example 10: Drug-Linker 8
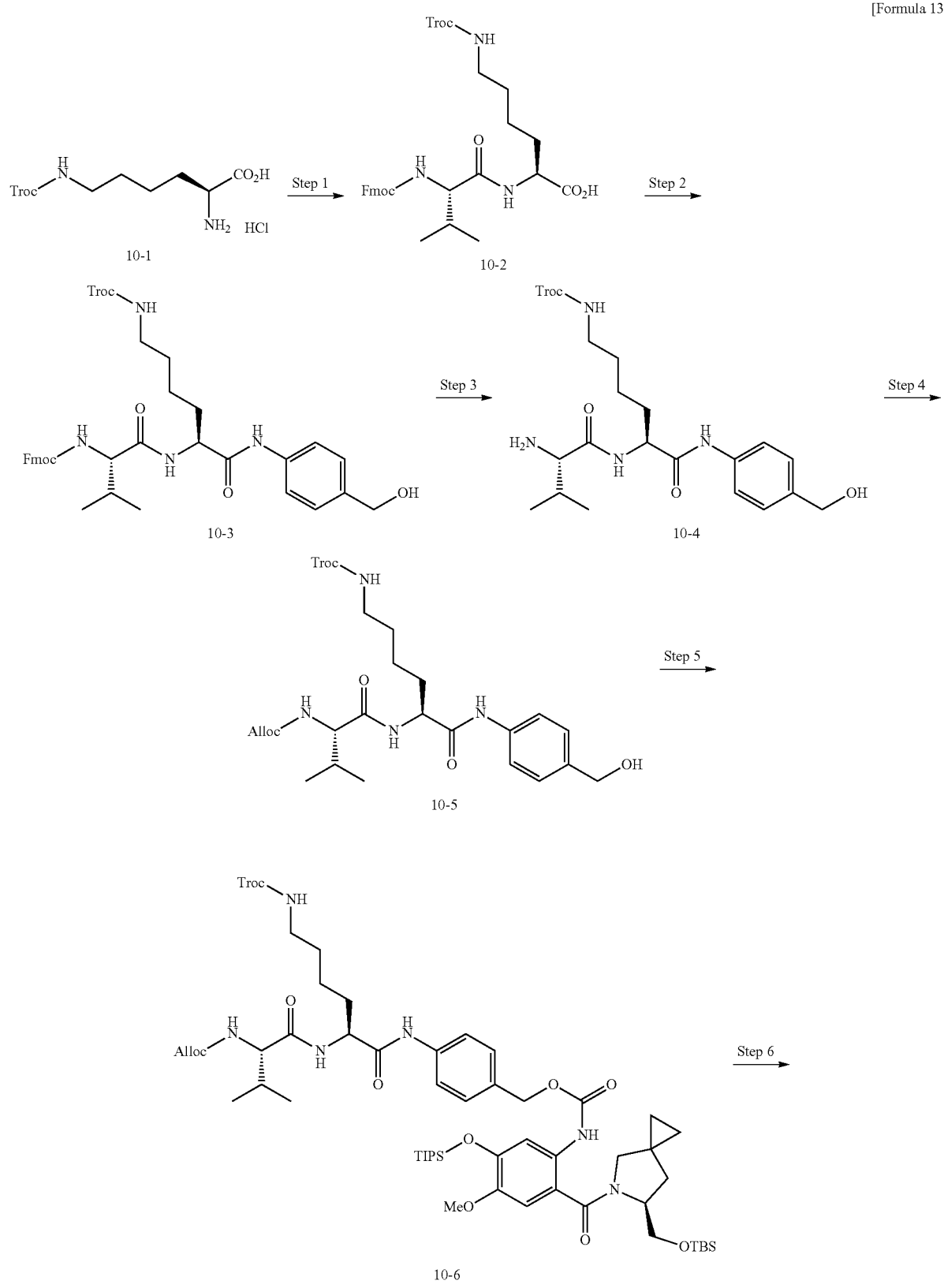

-continued
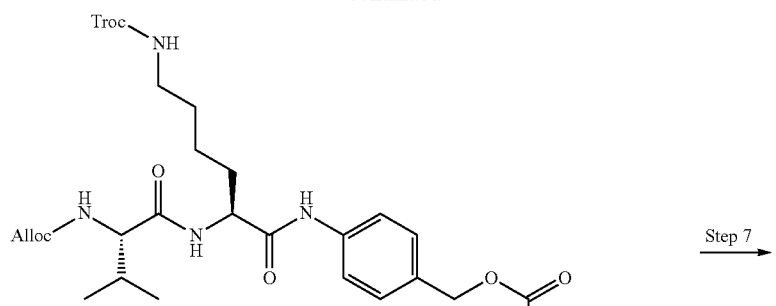
10-7
Step 7 →
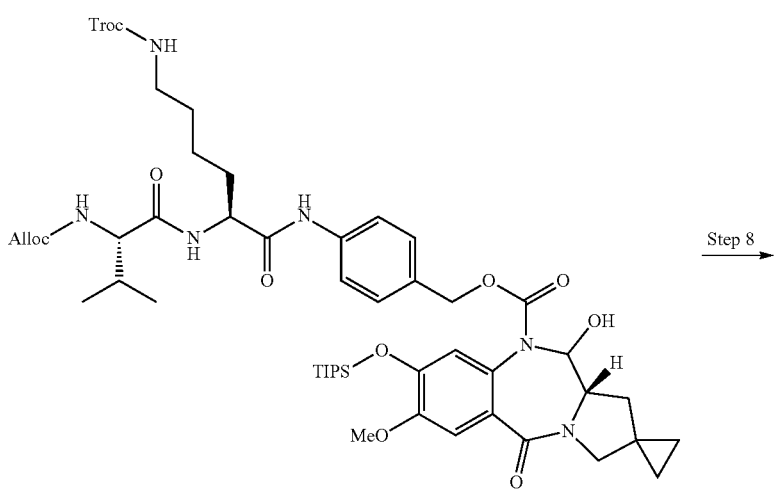
10-8
Step 8 →
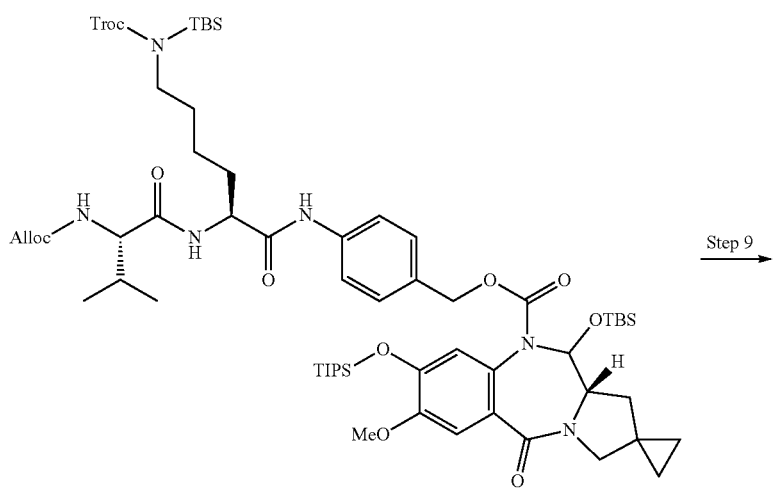
10-9
Step 9 →

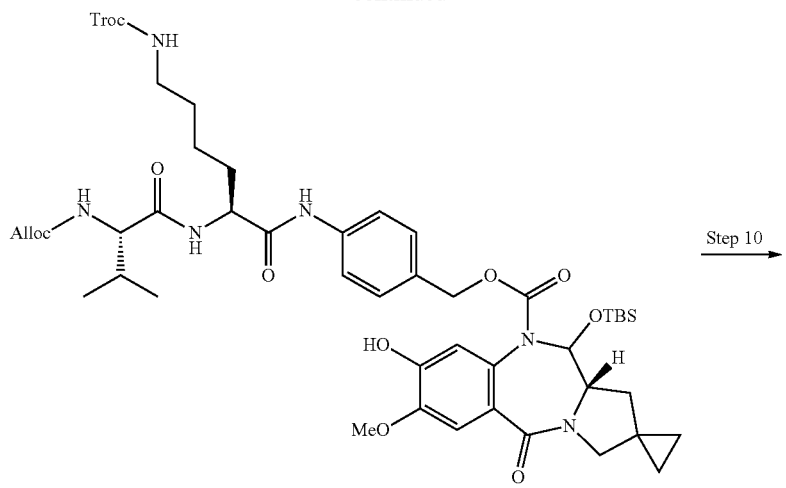

-continued
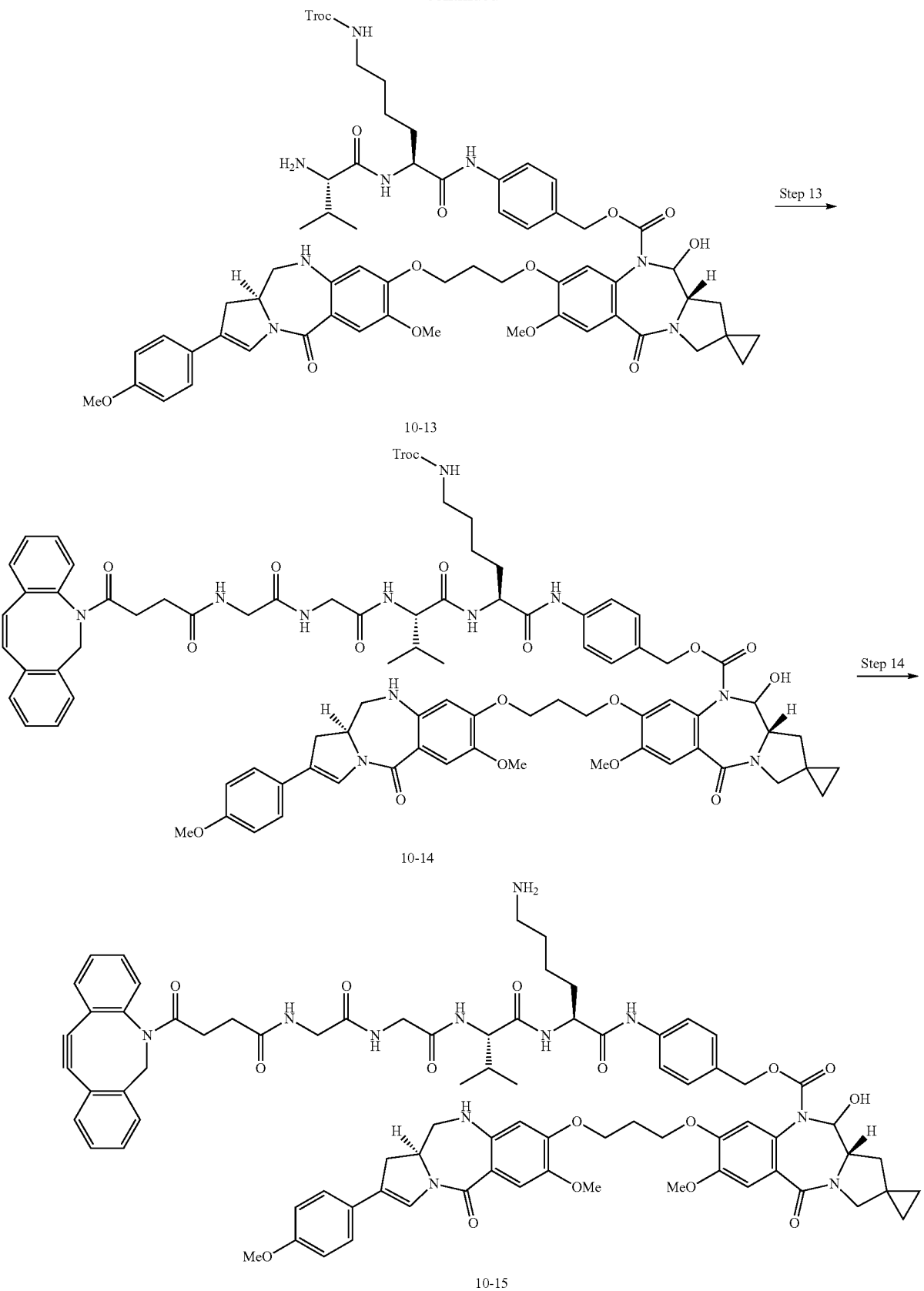
10-13
Step 13 →
10-14
Step 14 →
10-15

Step 1: N-[(9H-Fluoren-9-ylmethoxy)carbonyl]-L-valyl-N⁶-[(2,2,2-trichloroethoxy)carbonyl]-L-lysine To a solution of starting material 10-1 (2.78 g, 7.75 mmol, Bioscience, Biotechnology, and Biochemistry 2012, 76, 205) in 1,2-dimethoxyethane (30 mL), water (30 mL), and THF (15 mL), sodium hydrogen carbonate (1.30 g, 15.5 mmol) and 2,5-dioxopyrrolidin-1-yl N-[(9H-fluoren-9-ylmethoxy)carbonyl]-L-valinate (3.39 g, 7.76 mmol) were added at room temperature. The reaction solution was stirred at room temperature for five days, and then extracted with a mixed liquid of chloroform and methanol (10:1, v/v). The organic layer was washed with water and brine, and then distillated under reduced pressure. The resulting residue was washed with diethyl ether, and a solid was removed through filtration. The filtrate was distillated under reduced pressure, and the resulting residue was purified by silica gel column chromatography [hexane:ethyl acetate=30:70 (v/v) to 0:100 (v/v)] to afford the desired compound (2.13 g, 43%).

¹H-NMR (CDCl₃) δ:7.78-7.76 (2H, m), 7.60-7.58 (2H, m), 7.41-7.39 (2H, m), 7.32-7.30 (2H, m), 6.85-6.83 (1H, m), 5.58-5.56 (1H, m), 5.32-5.30 (1H, m), 4.72-4.57 (3H, m), 4.46-4.34 (2H, m), 4.23-4.21 (1H, m), 4.05-4.03 (1H, m), 3.22-3.15 (2H, m), 2.06-1.88 (3H, m), 1.52-1.51 (2H, m), 1.40-1.38 (2H, m), 0.97-0.96 (6H, m).

MS(APCI, ESI)m/z:642(M+H)⁺

Step 2: N-[(9H-Fluoren-9-ylmethoxy)carbonyl]-L-valyl-N-[4-(hydroxymethyl)phenyl]-N⁶-[(2,2,2-trichloroethoxy)carbonyl]-L-lysinamide The compound obtained in step 1 (2.11 g, 3.29 mmol) was reacted in the same manner as in step 2 of Example 5, and the resulting compound (2.24 g, 91%) was directly used for the subsequent reaction.

Step 3: L-Valyl-N-[4-(hydroxymethyl)phenyl]-N⁶-[(2,2,2-trichloroethoxy)carbonyl]-L-lysinamide To a solution of the compound obtained in step 2 (2.24 g, 3.00 mmol) in N,N-dimethylformamide (20 mL), piperidine (0.5934 mL, 5.994 mmol) was added at room temperature, and the resultant was stirred at room temperature for 1 hour. The resultant was distillated under reduced pressure, and the resulting residue (1.576 g, quantitative) was directly used for the subsequent reaction.

Step 4: N-[(Prop-2-en-1-yloxy)carbonyl]-L-valyl-N-[4-(hydroxymethyl)phenyl]-N⁶-[(2,2,2-trichloroethoxy)carbonyl]-L-lysinamide The compound obtained in step 3 (1.58 g, 3.00 mmol) was reacted in the same manner as in step 1 of Example 7, and the resulting compound (1.50 g, 82%) was directly used for the subsequent reaction.

Step 5: N-[(Prop-2-en-1-yloxy)carbonyl]-L-valyl-N-[4-({[(2-{[(6S)-6-({[tert-butyl(dimethyl)silyl]oxy}methyl)-5-azaspiro[2.4]hept-5-yl]carbonyl}-4-methoxy-5-{[tri(propan-2-yl)silyl]oxy}phenyl)carbamoyl]oxy}methyl)phenyl]-N⁶-[(2,2,2-trichloroethoxy)carbonyl]-L-lysinamide The compound obtained in step 4 (1.57 g, 2.57 mmol) was reacted in the same manner as in step 6 of Example 1 to afford the desired compound (1.691 g, 71%).

¹H-NMR (CDCl₃) δ:9.04-9.02 (1H, m), 8.48-8.45 (1H, m), 7.81 (1H, s), 7.55-7.53 (2H, m), 7.35-7.33 (2H, m), 6.76 (1H, s), 6.68-6.66 (1H, m), 5.94-5.86 (1H, m), 5.32-5.23 (4H, m), 5.14-5.10 (2H, m), 4.79-4.76 (1H, m), 4.69-4.67 (1H, m), 4.57-4.54 (4H, m), 4.03-4.02 (2H, m), 3.75-3.72 (5H, m), 3.29-3.22 (2H, m), 3.04-3.02 (1H, m), 2.27-2.01 (4H, m), 1.83-1.58 (3H, m), 1.46-1.44 (2H, m), 1.31-1.27 (3H, m), 1.11-1.09 (18H, m), 1.00-0.90 (15H, m), 0.65-0.48 (4H, m), 0.06-0.03 (6H, m).

MS(APCI, ESI)m/z:1219(M+Na)⁺

Step 6: N-[(Prop-2-en-1-yloxy)carbonyl]-L-valyl-N-[4-({[(2-{[(6S)-6-(hydroxymethyl)-5-azaspiro[2.4]hept-5-yl]carbonyl}-4-methoxy-5-{[tri(propan-2-yl)silyl]oxy}phenyl)carbamoyl]oxy}methyl)phenyl]-N⁶-[(2,2,2-trichloroethoxy)carbonyl]-L-lysinamide The compound obtained in step 5 (1.69 g, 1.41 mmol) was reacted in the same manner as in step 7 of Example 1 to afford the desired compound (1.43 g, 94%).

¹H-NMR (CDCl₃) δ:8.57-8.52 (2H, m), 7.70 (1H, s), 7.56-7.54 (2H, m), 7.35-7.33 (2H, m), 6.76-6.75 (2H, m), 5.91-5.90 (1H, m), 5.40-5.26 (4H, m), 5.12 (2H, s), 4.78-4.75 (1H, m), 4.69-4.66 (1H, m), 4.58-4.55 (4H, m), 4.37-4.34 (1H, m), 4.04-4.02 (1H, m), 3.80-3.77 (5H, m), 3.65-3.62 (1H, m), 3.28-3.11 (3H, m), 2.13-2.04 (2H, m), 1.81-1.78 (3H, m), 1.60-1.58 (2H, m), 1.45-1.43 (2H, m), 1.33-1.25 (3H, m), 1.11-1.09 (18H, m), 0.98-0.94 (6H, m), 0.58-0.51 (4H, m).

MS(APCI, ESI)m/z:1083(M+H)⁺

Step 7: N-[(Prop-2-en-1-yloxy)carbonyl]-L-valyl-N-{4-[({[(11a'S)-11'-hydroxy-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-yl]carbonyl}oxy)methyl]phenyl}-N⁶-[(2,2,2-trichloroethoxy)carbonyl]-L-lysinamide The compound obtained in step 6 (1.43 g, 1.32 mmol) was reacted in the same manner as in step 3 of Example 9 to afford the desired compound (0.714 g, 50%).

¹H-NMR (CDCl₃) δ:8.49-8.46 (1H, m), 7.52-7.45 (2H, m), 7.19-7.18 (3H, m), 6.72-6.68 (2H, m), 5.90-5.87 (2H, m), 5.33-5.23 (4H, m), 5.10-5.07 (1H, m), 4.98-4.95 (1H, m), 4.78-4.76 (1H, m), 4.69-4.66 (1H, m), 4.58-4.53 (3H, m), 4.01 (1H, s), 3.83-3.81 (4H, m), 3.73-3.70 (1H, m), 3.57-3.55 (2H, m), 3.29-3.25 (3H, m), 2.42-2.39 (1H, m), 2.15-2.13 (1H, m), 2.03-2.01 (2H, m), 1.74-1.71 (2H, m), 1.44-1.42 (2H, m), 1.23-1.17 (3H, m), 1.03-0.93 (24H, m), 0.67-0.64 (4H, m).

MS(APCI, ESI)m/z:1081(M+H)⁺

Step 8: N-[(Prop-2-en-1-yloxy)carbonyl]-L-valyl-N⁶-[tert-butyl(dimethyl)silyl]-N-{4-[({[(11a'S)-11'-{[tert-butyl(dimethyl)silyl]oxy}-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-yl]carbonyl}oxy)methyl]phenyl}-N⁶-[(2,2,2-trichloroethoxy)carbonyl]-L-lysinamide The compound obtained in step 7 (0.714 g, 0.660 mmol) was reacted in the same manner as in step 9 of Example 1 to afford the desired compound (0.476 g, 60%).

¹H-NMR (CDCl₃) δ:8.63-8.51 (1H, m), 7.49-7.48 (2H, m), 7.18-7.14 (3H, m), 6.61-6.53 (2H, m), 5.99-5.94 (2H, m), 5.33-5.17 (4H, m), 4.81-4.78 (3H, m), 4.59-4.57 (3H, m), 4.03-4.01 (1H, m), 3.88-3.85 (4H, m), 3.70-3.67 (2H, m), 3.50-3.47 (1H, m), 3.24-3.17 (3H, m), 2.37-2.34 (1H, m), 2.13-2.07 (2H, m), 1.59-1.54 (3H, m), 1.38 (2H, s), 1.16-0.92 (35H, m), 0.81-0.76 (9H, m), 0.67-0.64 (4H, m), 0.34-0.31 (6H, m), 0.19 (3H, s), 0.09 (3H, s).

Step 9: N-[(Prop-2-en-1-yloxy)carbonyl]-L-valyl-N⁶-[tert-butyl(dimethyl)silyl]-N-{4-[({[(11'S,11a'S)-11'-{[tert-butyl(dimethyl)silyl]oxy}-8'-hydroxy-7'-methoxy-5'-oxo-11',11a'-dihydro-1'H-spiro [cyclopropane-1,2'-pyrrolo[2,1-c][1,4] benzodiazepine]-10'(5'H)-yl]carbonyl}oxy)methyl] phenyl}-N⁶- [(2,2,2-trichloroethoxy)carbonyl]-L-lysinamide The compound obtained in step 8 (0.476 g, 0.398 mmol) was reacted in the same manner as in step 10 of Example 1 to afford the desired compound (0.283 g, 68%).

¹H-NMR (CDCl₃) δ:8.48 (1H, s), 7.51-7.47 (2H, m), 7.25-7.24 (2H, m), 7.12-7.10 (2H, m), 6.70-6.67 (2H, m), 6.09-6.07 (1H, m), 5.98-5.92 (2H, m), 5.33-5.20 (5H, m), 4.82-4.71 (3H, m), 4.59-4.56 (3H, m), 4.03-4.00 (1H, m), 3.91 (3H, s), 3.72-3.69 (1H, m), 3.54-3.52 (1H, m), 3.28-3.25 (3H, m), 2.37-2.34 (1H, m), 2.18-2.16 (1H, m), 2.05-1.99 (1H, m), 1.78-1.75 (1H, m), 1.56-1.53 (2H, m), 1.43-1.41 (2H, m), 0.98-0.94 (6H, m), 0.82-0.75 (9H, m), 0.67-0.64 (4H, m), 0.19 (3H, s), 0.10 (3H, s).

MS(APCI, ESI)m/z:1039(M+H)⁺

Step 10: N-[(Prop-2-en-1-yloxy)carbonyl]-L-valyl-N-{4-[({[(11a'S)-11'-{[tert-butyl(dimethyl)silyl] oxy}-7'-methoxy-8'-[3-({(11aS)-7-methoxy-2-(4-methoxyphenyl)-5-oxo-10-[(prop-2-en-1-yloxy) carbonyl]-5,10,11,11a-tetrahydro-1H-pyrrolo[2,1-c] [1,4]benzodiazepin-8-yl}oxy)propoxy]-5'-oxo-11', 11a'-dihydro-1'H-spiro[cyclopropane-1,2'-pyrrolo[2, 1-c][1,4]benzodiazepine]-10'(5'H)-yl]carbonyl}oxy) methyl]phenyl}-N⁶-[(2,2,2-trichloroethoxy) carbonyl]-L-lysinamide The compound obtained in step 9 (0.119 g, 0.114 mmol) was reacted in the same manner as in step 9 of Example 4 to afford the desired compound (0.134 g, 77%).

Step 11: N-[(Prop-2-en-1-yloxy)carbonyl]-L-valyl-N-{4-[({[(11a'S)-11'-hydroxy-7'-methoxy-8'-[3-({ (11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)propoxy]-5'-oxo-11',11a'-dihydro-1'H-spiro [cyclopropane-1,2'-pyrrolo[2,1-c][1,4]benzodiaz-epine]-10'(5'H)-yl]carbonyl}oxy)methyl]phenyl}-N⁶- [(2,2,2-trichloroethoxy)carbonyl]-L-lysinamide The compound obtained in step 10 (0.134 g, 0.0881 mmol) was reacted in the same manner as in step 11 of Example 3 to afford the desired compound (0.120 g, 97%).

MS(APCI, ESI)m/z:1423(M+Na)⁺

Step 12: L-Valyl-N-{4-[({[(11a'S)-11'-hydroxy-7'-methoxy-8'-(3-{[(11aS)-7-methoxy-2-(4-methoxy-phenyl)-5-oxo-5,10,11,11a-tetrahydro-1H-pyrrolo[2, 1-c][1,4]benzodiazepin-8-yl]oxy}propoxy)-5'-oxo-11',11a'-dihydro-1'H-spiro[cyclopropane-1,2'-pyrrolo [2,1-c][1,4]benzodiazepine]-10'(5'H)-yl] carbonyl}oxy)methyl]phenyl}-N⁶- [(2,2,2-trichloroethoxy)carbonyl]-L-lysinamide The compound obtained in step 11 (0.120 g, 0.0855 mmol) was reacted in the same manner as in step 12 of Example 3 to afford the desired compound (0.0813 g, 77%).

¹H-NMR (CDCl₃) δ:9.10 (1H, s), 7.94-7.92 (1H, m), 7.58 (1H, s), 7.47-7.45 (3H, m), 7.35-7.33 (2H, m), 7.21 (2H, s), 7.13-7.11 (2H, m), 6.90-6.88 (2H, m), 6.43 (1H, s), 6.11 (1H, s), 5.90-5.88 (1H, m), 5.51 (1H, s), 5.39-5.36 (1H, m), 4.73-4.70 (3H, m), 4.52-4.51 (2H, m), 4.32 (1H, s), 4.13-4.08 (3H, m), 3.89 (3H, s), 3.80-3.76 (9H, m), 3.60-3.50 (4H, m), 3.34-3.24 (5H, m), 2.76-2.72 (1H, m), 2.44-2.12 (4H, m), 1.94-1.27 (7H, m), 1.00-0.98 (3H, m), 0.84-0.82 (3H, m), 0.70-0.66 (4H, m).

MS(APCI, ESI)m/z:1233(M+H)⁺

Step 13: N-[4-(11,12-Didehydrodibenzo[b,f]azo-cin-5 (6H)-yl)-4-oxobutanoyl]glycylglycyl-L-valyl-N-{4-[({[(11a'S)-11'-hydroxy-7'-methoxy-8'-(3-{ [(11aS)-7-methoxy-2-(4-methoxyphenyl)-5-oxo-5, 10,11,11a-tetrahydro-1H-pyrrolo[2,1-c][1,4] benzodiazepin-8-yl]oxy}propoxy)-5'-oxo-11',11a'-dihydro-1'H-spiro[cyclopropane-1,2'-pyrrolo[2,1-c] [1,4]benzodiazepine]-10'(5'H)-yl]carbonyl}oxy) methyl]phenyl}-N⁶- [(2,2,2-trichloroethoxy) carbonyl]-L-lysinamide ("GGVK" disclosed as SEQ ID NO: 80)

The compound obtained in step 12 (0.0813 g, 0.0659 mmol) was reacted in the same manner as in step 13 of Example 3 to afford the desired compound (0.0721 g, 67%).

MS(APCI, ESI)m/z:1656(M+Na)⁺

Step 14: N-[4-(11,12-Didehydrodibenzo[b,f]azo-cin-5 (6H)-yl)-4-oxobutanoyl]glycylglycyl-L-valyl-N-{4-[({[(11a'S)-11'-hydroxy-7'-methoxy-8'-(3-{ [(11aS)-7-methoxy-2-(4-methoxyphenyl)-5-oxo-5, 10,11,11a-tetrahydro-1H-pyrrolo[2,1-c][1,4] benzodiazepin-8-yl]oxy}propoxy)-5'-oxo-11',11a'-dihydro-1'H-spiro[cyclopropane-1,2'-pyrrolo[2,1-c] [1,4]benzodiazepine]-10'(5'H)-yl]carbonyl}oxy) methyl]phenyl}-L-lysinamide ("GGVK" Disclosed as SEQ ID NO: 80)

The compound obtained in step 13 (0.0721 g, 0.0441 mmol) was reacted in the same manner as in step 6 of Example 21 to afford the desired compound (0.0348 g, 54%).

MS(APCI, ESI)m/z:1460(M+H)⁺

Example 11: Drug-Linker 9
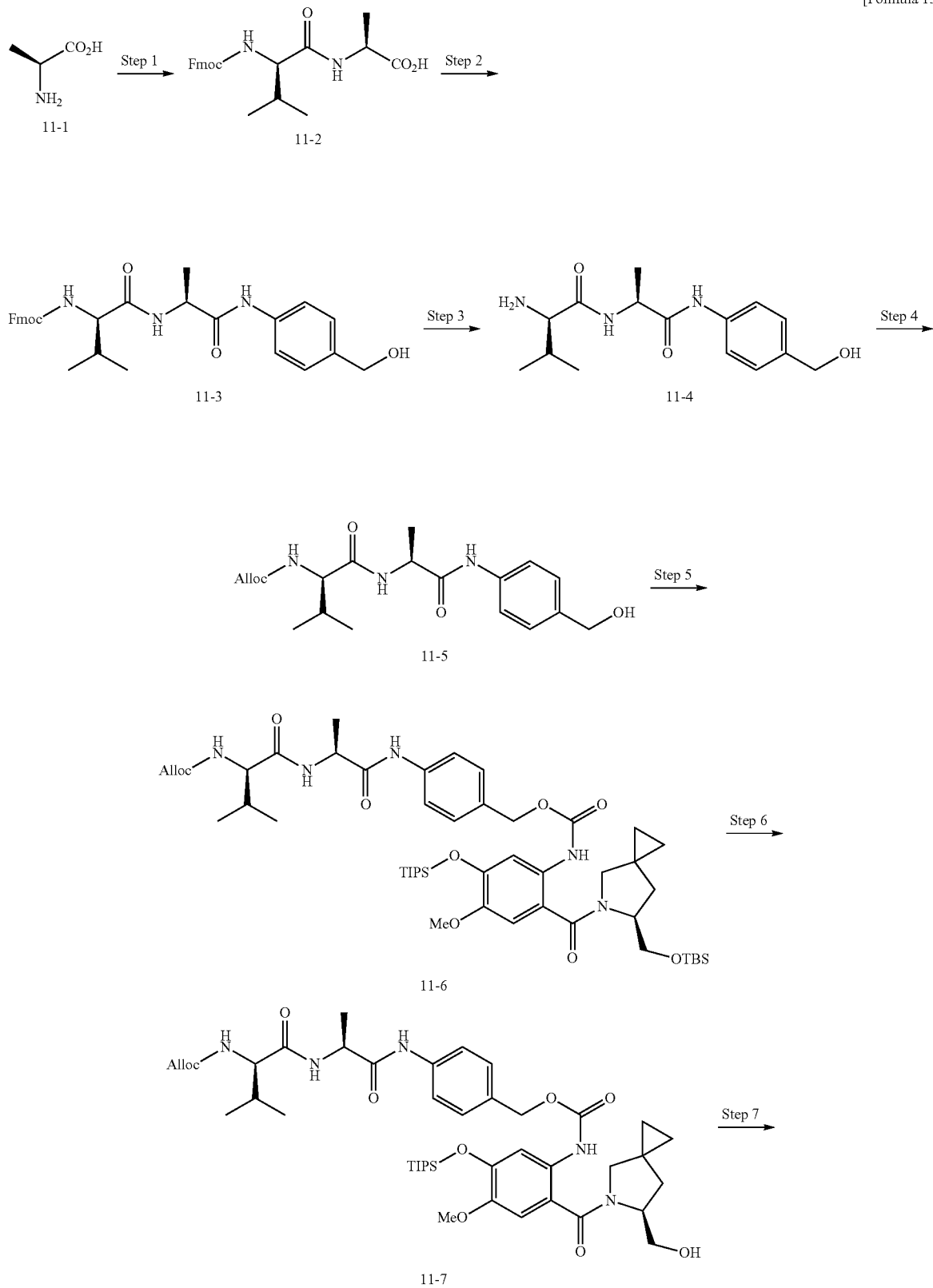
[Formula 135]

-continued
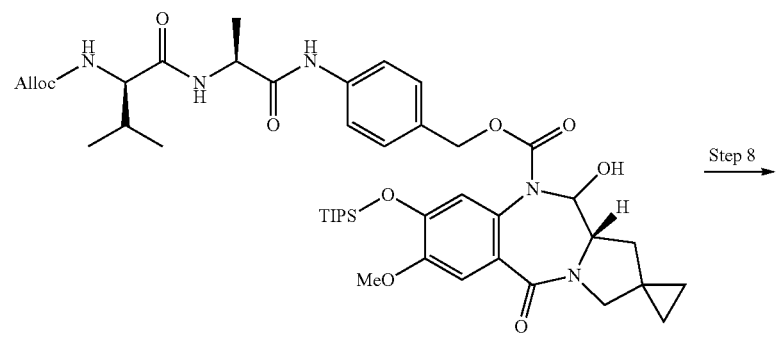
11-8
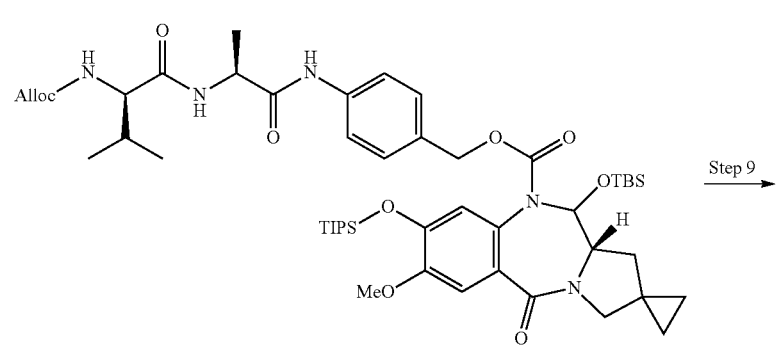
11-9
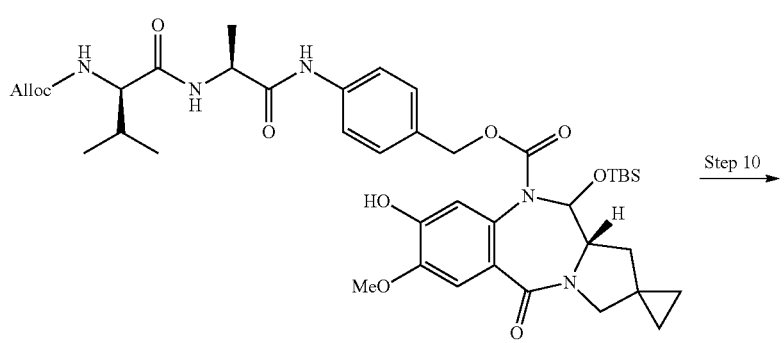
11-10
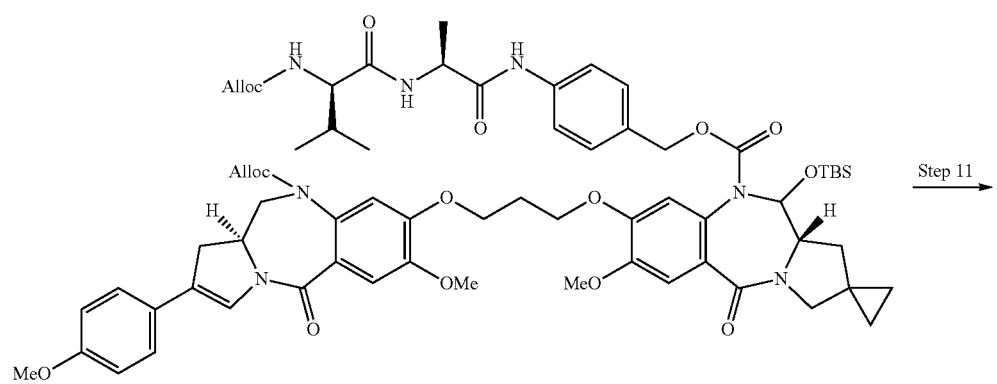
11-11

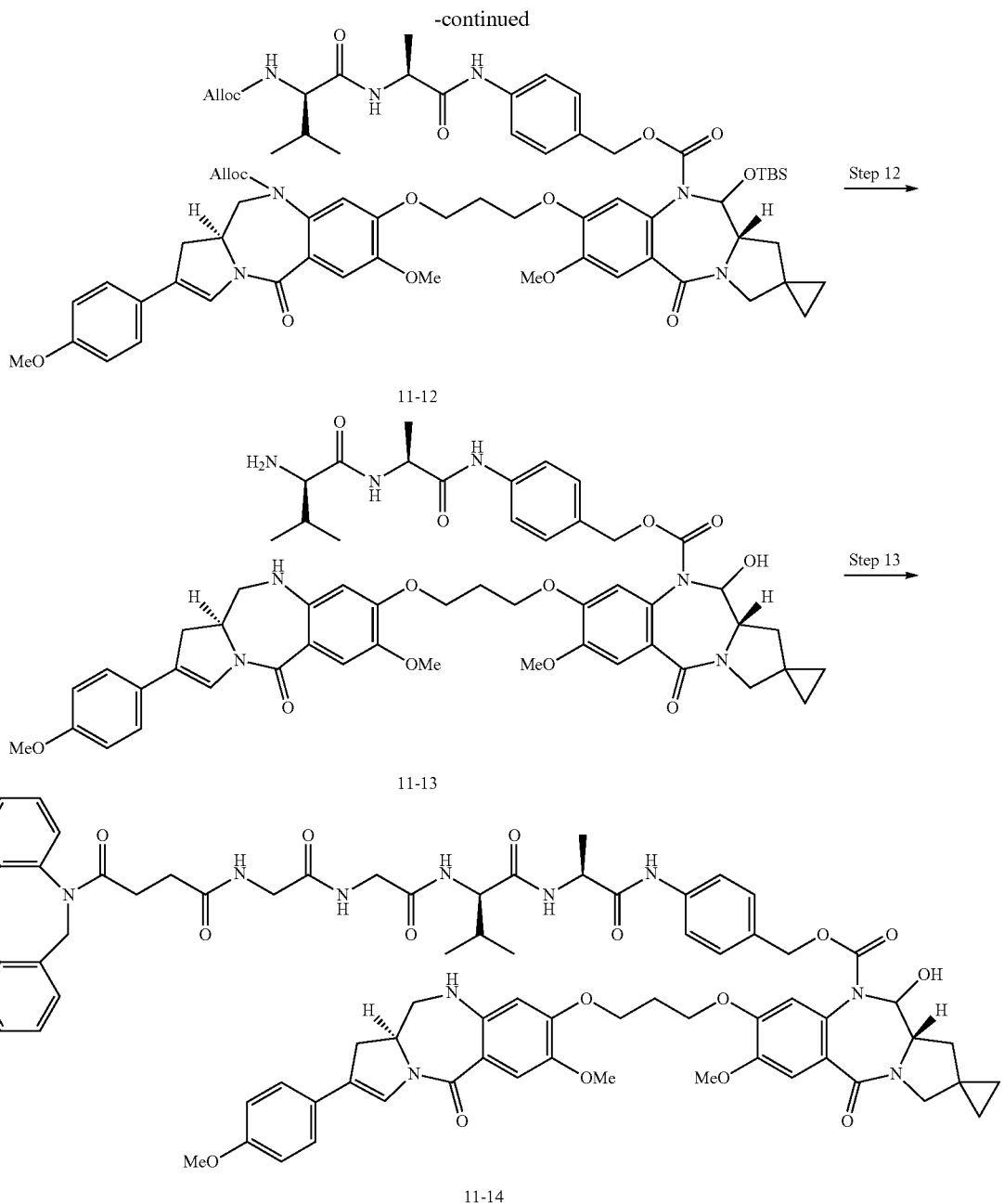

11-12

11-13

11-14

Step 1: N-[(9H-Fluoren-9-ylmethoxy)carbonyl]-D-valyl-L-alanine

L-alanine (0.0721 g, 0.0441 mmol) was reacted in the same manner as in step 1 of Example 10, except that 2,5-dioxopyrrolidin-1-yl N-[(9H-fluoren-9-ylmethoxy)carbonyl]-D-valinate (0.528 g, 5.92 mmol) was used in place of 2,5-dioxopyrrolidin-1-yl N-[(9H-fluoren-9-ylmethoxy)carbonyl]-L-valinate. The resulting compound (0.0348 g, 54%) was directly used for the subsequent reaction.

$^1$H-NMR (DMSO-D$_6$) δ:10.55 (1H, s), 8.23-8.21 (1H, m), 7.91-7.89 (2H, m), 7.76-7.75 (2H, m), 7.42-7.40 (3H, m), 7.33-7.31 (2H, m), 4.31-4.20 (4H, m), 3.93-3.91 (1H, m), 1.97-1.93 (1H, m), 1.27-1.25 (3H, m), 0.86-0.84 (6H, m).

MS(APCI, ESI)m/z:411(M+H)$^+$

Step 2: N-[(9H-Fluoren-9-ylmethoxy)carbonyl]-D-valyl-N-[4-(hydroxymethyl)phenyl]-L-alaninamide The compound obtained in step 1 (2.05 g, 4.99 mmol) was reacted in the same manner as in step 2 of Example 5, and the resulting compound (2.19 g, 85%) was directly used for the subsequent reaction.

Step 3: D-Valyl-N-[4-(hydroxymethyl)phenyl]-L-alaninamide

The compound obtained in step 2 (2.19 g, 4.25 mmol) was reacted in the same manner as in step 3 of Example 10, and the resulting compound (0.966 g, 76%) was directly used for the subsequent reaction.

Step 4: N-[(Prop-2-en-1-yloxy)carbonyl]-D-valyl-N-[4-(hydroxymethyl)phenyl]-L-alaninamide The compound (0.966 g, 3.29 mmol) obtained in step 3 was reacted in the same manner as in step 1 of Example 7, and the resulting compound (1.11 g, 89%) was directly used for the subsequent reaction.

Step 5: N-[(Prop-2-en-1-yloxy)carbonyl]-D-valyl-N-[4-({[(2-{[(6S)-6-({[tert-butyl(dimethyl)silyl]oxy}methyl)-5-azaspiro[2.4]hept-5-yl]carbonyl}-4-methoxy-5-{[tri(propan-2-yl)silyl]oxy}phenyl)carbamoyl]oxy}methyl)phenyl]-L-alaninamide The compound obtained in step 4 (1.11 g, 2.93 mmol) was reacted in the same manner as in step 6 of Example 1 to afford the desired compound (1.75 g, 80%).
$^1$H-NMR (CDCl$_3$) δ:9.02 (1H, s), 8.55 (1H, s), 7.81 (1H, s), 7.57-7.54 (2H, m), 7.34-7.32 (2H, m), 6.76 (1H, s), 6.52-6.50 (1H, m), 5.91-5.86 (1H, m), 5.30-5.22 (3H, m), 5.13-5.10 (2H, m), 4.65-4.59 (4H, m), 3.99-3.97 (1H, m), 3.87-3.85 (1H, m), 3.75-3.72 (5H, m), 3.04-3.02 (1H, m), 2.28-2.13 (2H, m), 1.70-1.68 (1H, m), 1.49-1.47 (3H, m), 1.31-1.27 (3H, m), 1.11-1.09 (18H, m), 1.00-0.90 (15H, m), 0.65-0.48 (4H, m), 0.06-0.03 (6H, m).
MS(APCI, ESI)m/z:966(M+H)$^+$

Step 6: N-[(Prop-2-en-1-yloxy)carbonyl]-D-valyl-N-[4-({[(2-{[(6S)-6-(hydroxymethyl)-5-azaspiro[2.4]hept-5-yl]carbonyl}-4-methoxy-5-{[tri(propan-2-yl)silyl]oxy}phenyl)carbamoyl]oxy}methyl)phenyl]-L-alaninamide The compound obtained in step 5 (1.75 g, 1.81 mmol) was reacted in the same manner as in step 7 of Example 1 to afford the desired compound (1.53 g, 99%).
$^1$H-NMR (CDCl$_3$) δ:8.66 (1H, s), 8.50 (1H, s), 7.69 (1H, s), 7.57-7.54 (2H, m), 7.34-7.32 (2H, m), 6.75-6.71 (2H, m), 5.90-5.85 (1H, m), 5.40-5.38 (1H, m), 5.29-5.21 (2H, m), 5.12 (2H, s), 4.71-4.50 (4H, m), 4.34-4.31 (1H, m), 3.89-3.77 (6H, m), 3.64-3.61 (1H, m), 3.13-3.10 (1H, m), 2.17-2.09 (1H, m), 1.87-1.84 (2H, m), 1.48-1.46 (3H, m), 1.32-1.28 (3H, m), 1.11-1.09 (18H, m), 0.97-0.94 (6H, m), 0.63-0.49 (4H, m).
MS(APCI, ESI)m/z:852(M+H)$^+$

Step 7: N-[(Prop-2-en-1-yloxy)carbonyl]-D-valyl-N-{4-[({[(11'S,11a'S)-11'-hydroxy-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 6 (1.53 g, 1.79 mmol) was reacted in the same manner as in step 3 of Example 9 to afford the desired compound (1.24 g, 81%).
$^1$H-NMR (CDCl$_3$) δ:8.51 (1H, s), 7.51-7.49 (2H, m), 7.18-7.15 (3H, m), 6.65 (1H, s), 6.56-6.54 (1H, m), 5.90-5.85 (2H, m), 5.31-5.19 (3H, m), 5.10-5.07 (1H, m), 4.97-4.94 (1H, m), 4.67-4.50 (3H, m), 3.90-3.88 (1H, m), 3.84 (3H, s), 3.73-3.70 (1H, m), 3.58-3.56 (2H, m), 3.31-3.28 (1H, m), 2.42-2.39 (1H, m), 2.18-2.15 (1H, m), 1.74-1.71 (1H, m), 1.48-1.46 (3H, m), 1.19-0.88 (27H, m), 0.69-0.65 (4H, m).
MS(APCI, ESI)m/z:850(M+H)$^+$

Step 8: N-[(Prop-2-en-1-yloxy)carbonyl]-D-valyl-N-{4-[({[(11a'S)-11'-{[tert-butyl(dimethyl)silyl]oxy-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 7 (1.24 g, 1.45 mmol) was reacted in the same manner as in step 9 of Example 1 to afford the desired compound (0.979 g, 70%).
$^1$H-NMR (CDCl$_3$) δ:8.48 (1H, s), 7.51-7.49 (2H, m), 7.19 (1H, s), 7.14-7.12 (2H, m), 6.62 (1H, s), 6.53-6.51 (1H, m), 6.01-5.99 (1H, m), 5.91-5.85 (1H, m), 5.30-5.28 (2H, m), 5.21-5.15 (2H, m), 4.82-4.79 (1H, m), 4.68-4.51 (3H, m), 3.88-3.84 (4H, m), 3.71-3.69 (1H, m), 3.50-3.47 (1H, m), 3.28-3.25 (1H, m), 2.37-2.34 (1H, m), 2.20-2.13 (1H, m), 1.52-1.47 (4H, m), 1.21-0.94 (27H, m), 0.80-0.77 (9H, m), 0.67-0.64 (4H, m), 0.19 (3H, s), 0.08 (3H, s).
MS(APCI, ESI)m/z:964(M+H)$^+$

Step 9: N-[(Prop-2-en-1-yloxy)carbonyl]-D-valyl-N-{4-[({[(11a'S)-11'-{[tert-butyl(dimethyl)silyl]oxy}-8'-hydroxy-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 8 (0.979 g, 1.02 mmol) was reacted in the same manner as in step 10 of Example 1 to afford the desired compound (0.769 g, 94%).
$^1$H-NMR (CDCl$_3$) δ:8.71 (1H, s), 7.37-7.35 (2H, m), 7.23 (1H, s), 7.04-7.02 (2H, m), 6.86-6.84 (1H, m), 6.74-6.72 (1H, m), 6.65 (1H, s), 6.05-5.85 (2H, m), 5.64-5.62 (1H, m), 5.32-5.20 (3H, m), 4.82-4.78 (1H, m), 4.70-4.52 (3H, m), 4.00-3.98 (1H, m), 3.93-3.90 (3H, m), 3.73-3.70 (1H, m), 3.55-3.53 (1H, m), 3.27-3.23 (1H, m), 2.38-2.18 (2H, m), 1.60-1.46 (4H, m), 1.00-0.92 (6H, m), 0.80 (9H, s), 0.68-0.63 (4H, m), 0.20 (3H, s), 0.10 (3H, s).
MS(APCI, ESI)m/z:808(M+H)$^+$

Step 10: N-[(Prop-2-ene)-1-yloxy)carbonyl]-D-valyl-N-{4-[({[(11a'S)-11'-{[tert-butyl(dimethyl)silyl]oxy}-7'-methoxy-8'-[3-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)propoxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 9 (0.100 g, 0.124 mmol) was used reacted in the same manner as in step 9 of Example 4 to afford the desired compound (0.148 g, 94%).
MS(APCI, ESI)m/z:1284(M+H)$^+$

Step 11: N-[(Prop-2-en-1-yloxy)carbonyl]-D-valyl-N-{4-[({[(11a'S)-11'-hydroxy-7'-methoxy-8'-[3-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)propoxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 10 (0.148 g, 0.124 mmol) was used and reacted in the same manner as in step 11 of Example 3 to afford the desired compound (0.132 g, 98%).
MS(APCI, ESI)m/z:1170(M+H)$^+$ Step 12: D-Valyl-N-{4-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 11 (0.132 g, 0.113 mmol) was used and reacted in the same manner as in step 12 of Example 3 to afford the desired compound (0.0963 g, 85%)

$^1$H-NMR (CDCl$_3$) δ:9.12 (1H, s), 7.85-7.84 (1H, m), 7.54-7.52 (1H, m), 7.49 (1H, s), 7.44-7.42 (2H, m), 7.34-7.32 (2H, m), 7.21 (1H, s), 7.13-7.11(2H,m), 6.90-6.88 (2H, m), 6.41 (1H, s), 6.10 (1H, s), 5.90-5.87 (1H, m), 5.35-5.32 (1H, m), 4.74-4.71 (1H, m), 4.60-4.56 (2H, m), 4.30 (1H, s), 4.13-4.10 (4H, m), 3.89 (3H, s), 3.83 (3H, s), 3.80 (3H, s), 3.74-3.71 (1H, m), 3.60-3.49 (4H, m), 3.39-3.35 (1H, m), 3.31-3.27 (2H, m), 2.75-2.72 (1H, m), 2.44-2.18 (4H, m), 1.78-1.44 (6H, m), 0.98-0.97 (3H, m), 0.74-0.68 (7H, m).
MS(APCI, ESI)m/z:1002(M+H)$^+$

Step 13: N-[4-(11,12-Didehydrodibenzo[b,f]azocin-5 (6H)-yl)-4-oxobutanoyl]glycylglycyl-D-valyl-N-{4-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 12 (0.0455 g, 0.0454 mmol) was used and reacted in the same manner as in step 13 of Example 3 to afford the desired compound (0.0416 g, 65%).
MS(APCI, ESI)m/z:1403(M+H)$^+$ Example 12: Drug-Linker 10

[Formula 136]

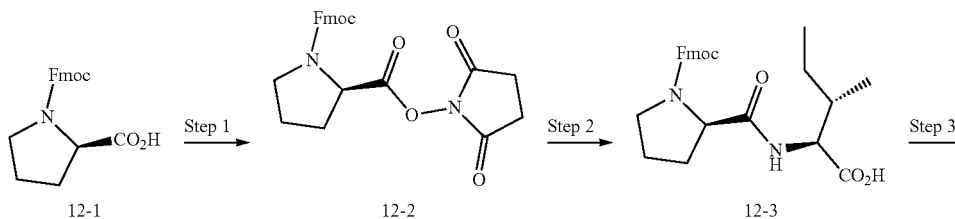

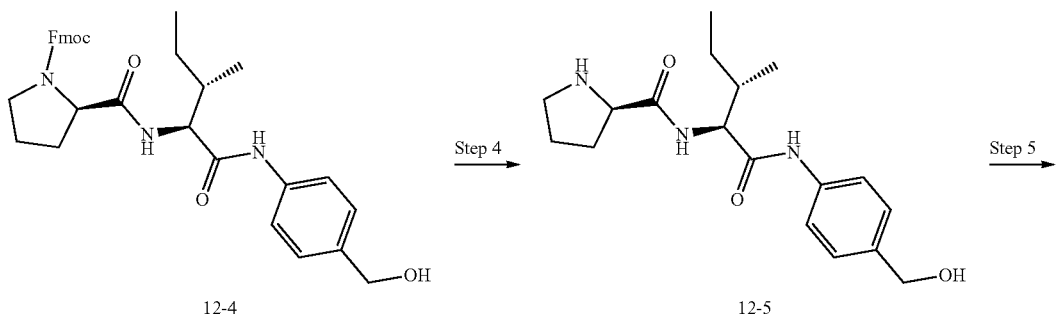

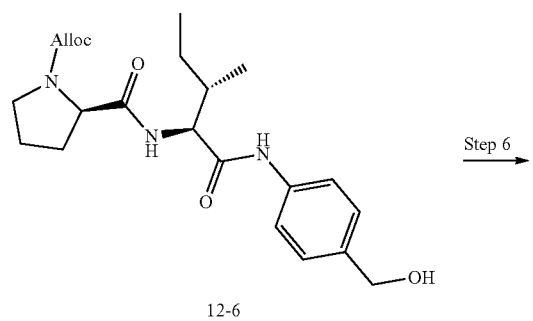

-continued
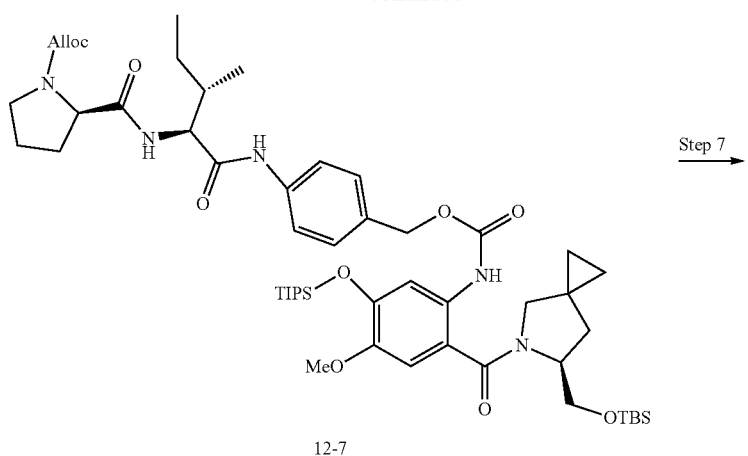
12-7
Step 7
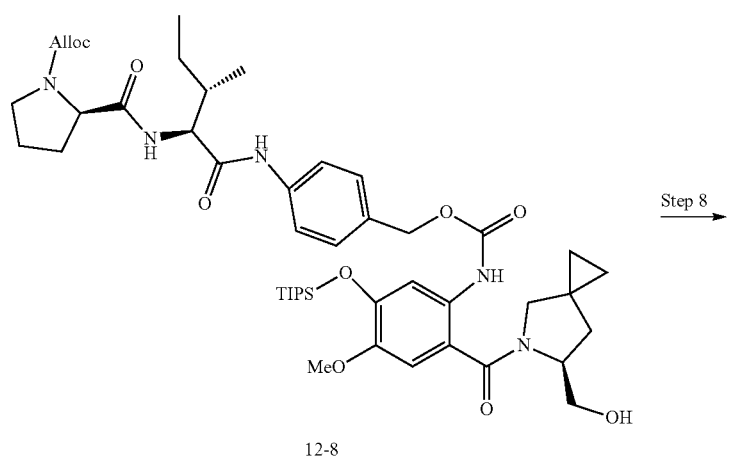
12-8
Step 8
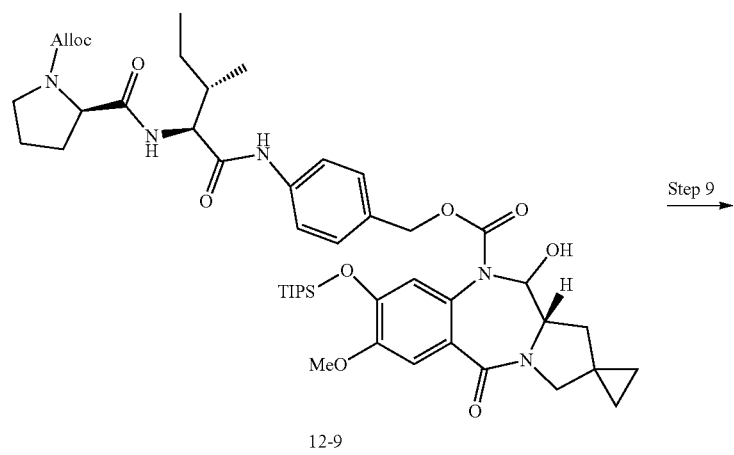
12-9
Step 9

-continued
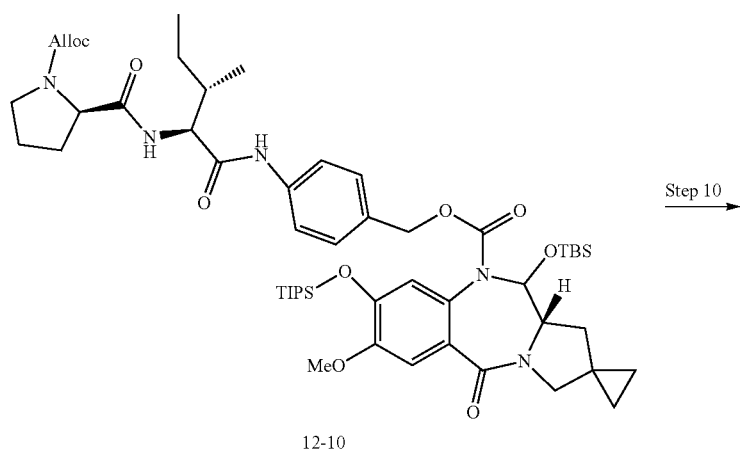
12-10
Step 10 →
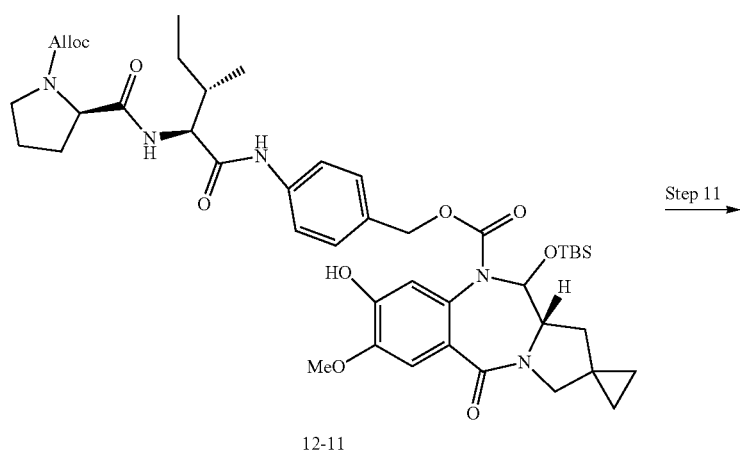
12-11
Step 11 →
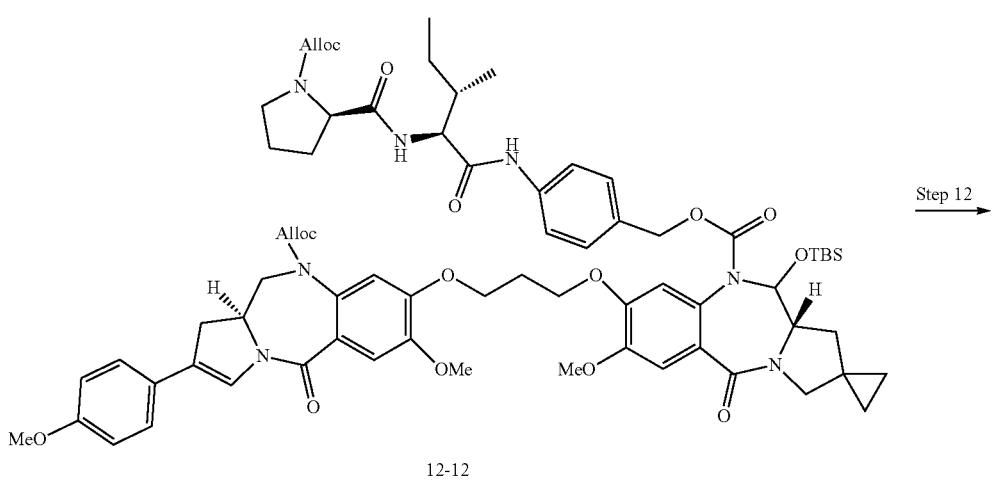
12-12
Step 12 →

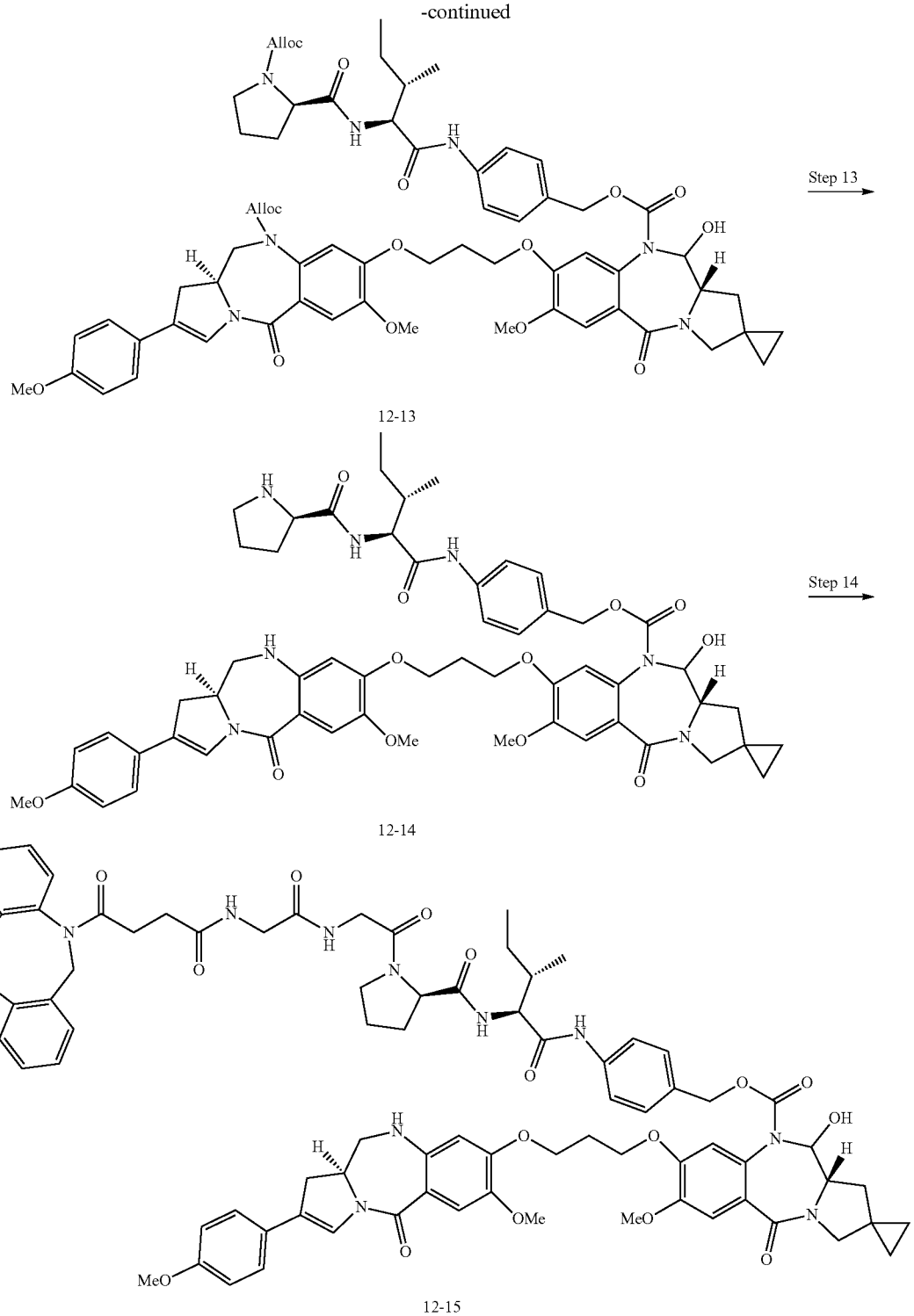

Step 1: Compound 12-2

To starting material 12-1 (2.01 g, 5.94 mmol) in dichloromethane (50 mL), 1-(3-dimethylaminopropyl)-3-ethylcarbodiimide hydrochloride (1.37 g, 7.13 mmol) was added at room temperature, and the resultant was stirred at room temperature for 10 minutes, and N-hydroxysuccinimide (0.821 g, 7.13 mmol) was then added thereto at 0° C. The reaction solution was stirred at room temperature overnight, and the solvent was then distilled off under reduced pressure. Ethyl acetate and water were added to the resulting residue, and the organic layer was washed with water, a 10% aqueous solution of citric acid, a saturated aqueous sodium hydrogen carbonate, and brine, and dried over sodium sulfate. The resultant was distilled under reduced pressure, and the resulting residue was purified by silica gel column chromatography [hexane:ethyl acetate=90:10 (v/v) to 50:50 (v/v)] to afford the desired compound (2.11 g, 82%).
MS(APCI, ESI)m/z:435(M+H)⁺

Step 2: Compound 12-3

The compound obtained in step 1 (2.11 g, 4.85 mmol) was reacted in the same manner as in step 1 of Example 10, except that L-isoleucine was used in place of N⁶- [(2,2,2-trichloroethoxy)carbonyl]-L-lysine hydrochloride, to afford the desired compound (2.16 g, 99%).
MS(APCI, ESI)m/z:451(M+H)⁺

Step 3: Compound 12-4

The compound obtained in step 2 (2.16 g, 4.85 mmol) was reacted in the same manner as in step 2 of Example 5 to afford the desired compound (1.48 g, 56%).

Step 4: Compound 12-5

The compound obtained in step 3 (1.48 g, 2.67 mmol) was reacted in the same manner as in step 3 of Example 10 to afford the desired compound (0.794 g, 89%).

Step 5: Compound 12-6

The compound obtained in step 4 (0.794 g, 2.38 mmol) was reacted in the same manner as in step 1 of Example 7 to afford the desired compound (0.886 g, 89%).

Step 6: Compound 12-7

The compound obtained in step 5 (0.794 g, 2.12 mmol) was reacted in the same manner as in step 6 of Example 1 to afford the desired compound (1.19 g, 72%).
MS(APCI, ESI)m/z:1006(M+H)⁺

Step 7: Compound 12-8

The compound obtained in step 6 (1.19 g, 1.18 mmol) was reacted in the same manner as in step 7 of Example 1 to afford the desired compound (1.07 g, quantitative).
MS(APCI, ESI)m/z:892(M+H)⁺

Step 8: Compound 12-9

The compound obtained in step 7 (1.18 mmol) was reacted in the same manner as in step 8 of Example 1 to afford the desired compound (0.800 g, 76%).
MS(APCI, ESI)m/z:890(M+H)⁺

Step 9: Compound 12-10

The compound obtained in step 8 (0.800 g, 0.899 mmol) was reacted in the same manner as in step 9 of Example 1 to afford the desired compound (0.567 g, 90%).
MS(APCI, ESI)m/z:1004(M+H)⁺

Step 10: Compound 12-11

The compound obtained in step 9 (0.567 g, 0.564 mmol) was reacted in the same manner as in step 10 of Example 1 to afford the desired compound (0.454 g, 94%).
MS(APCI, ESI)m/z:848(M+H)⁺

Step 11: Compound 12-12

The compound obtained in step 10 (0.100 g, 0.118 mmol) was reacted in the same manner as in step 9 of Example 4 to afford the desired compound (0.159 g, quantitative).
MS(APCI, ESI)m/z:1324(M+H)⁺

Step 12: Compound 12-13

The compound obtained in step 11 (0.118 mmol) was reacted in the same manner as in step 11 of Example 3 to afford the desired compound (0.139 g, 97%).
MS(APCI, ESI)m/z:1210(M+H)⁺

Step 13: Compound 12-14

The compound obtained in step 12 (0.139 g, 0.114 mmol) was reacted in the same manner as in step 12 of Example 3 to afford the desired compound (0.0667 g, 56%).
¹H-NMR (CDCl₃) δ:8.81 (1H, s), 8.21-8.19 (1H, m), 7.55-7.44 (4H, m), 7.33-7.31 (2H, m), 7.22 (1H, s), 7.13-7.11 (2H, m), 6.90-6.87 (2H, m), 6.39 (1H, s), 6.11 (1H, s), 5.89-5.87 (1H, m), 5.35-5.32 (1H, m), 4.80-4.58 (2H, m), 4.30 (1H, s), 4.22-4.07 (5H, m), 3.89 (3H, s), 3.81-3.72 (9H, m), 3.58-3.53 (3H, m), 3.38-3.31 (2H, m), 2.98-2.93 (2H, m), 2.76-2.72 (1H, m), 2.42-2.39 (1H, m), 2.18-2.12 (3H, m), 1.94-1.51 (7H, m), 1.31-1.13 (1H, m), 0.97-0.90 (6H, m), 0.71-0.66 (4H, m).
MS(APCI, ESI)m/z:1042(M+H)⁺

Step 14: N-[4-(11,12-Didehydrodibenzo[b,f]azo-cin-5 (6H)-yl)-4-oxobutanoyl]glycylglycyl-D-prolyl-N-{4-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-isoleucinamide The compound obtained in step 13 (0.0314 g, 0.0301 mmol) was reacted in the same manner as in step 13 of Example 3 to afford the desired compound (0.0300 g, 69%).
MS(APCI, ESI)m/z:1443(M+H)⁺

Example 13: Drug-Linker 11

[Formula 137]

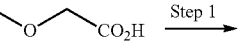

13-1

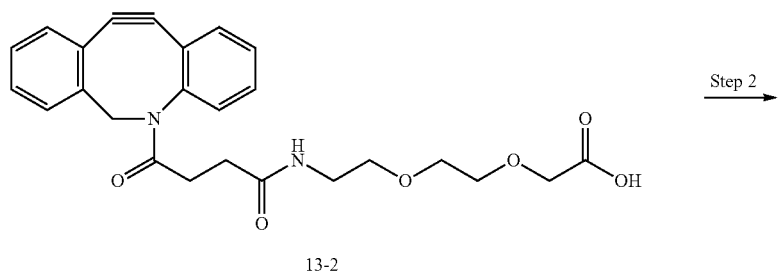

13-2

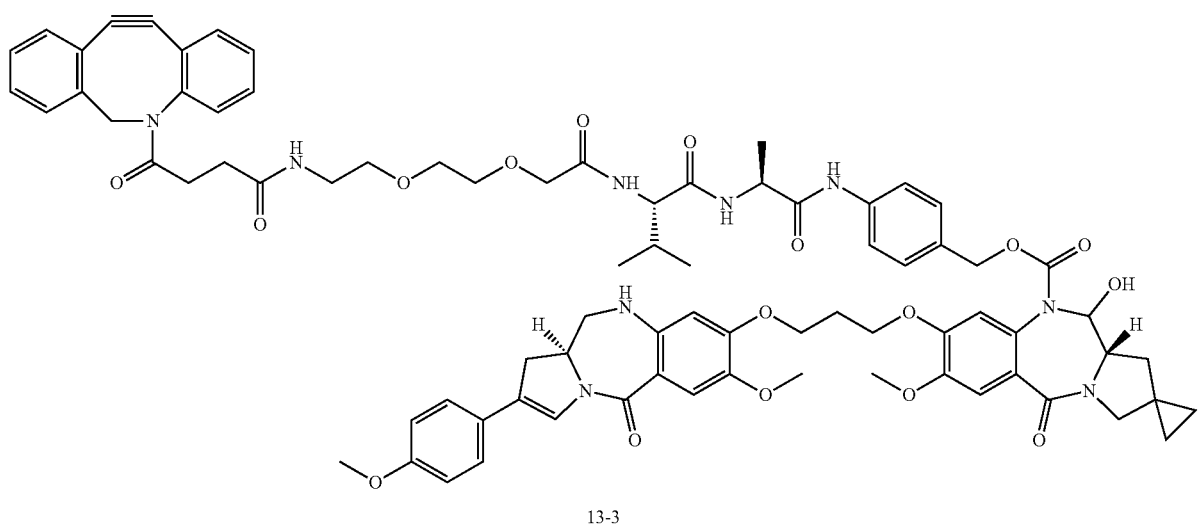

13-3

Step 1: [2-(2-{[4-(11,12-Didehydrodibenzo[b,f]azocin-5 (6H)-yl)-4-oxobutanoyl]amino}ethoxy)ethoxy]acetate To a solution of starting material 13-1 (3.00 g, 7.78 mmol, Tokyo Chemical Industry Co., Ltd.) in N,N-dimethylformamide (10 mL), 1,8-diazabicyclo[5.4.0]-7-undecene (1.16 mL, 7.78 mL) was added, and the resultant was stirred at room temperature for 2 hours, and 1-{[4-(11,12-didehydrodibenzo[b,f]azocin-5 (6H)-yl)-4-oxobutanoyl]oxy}pyrrolidin-2,5-dione (1.10 g, 2.72 mmol) and triethylamine (1.94 mL, 14.0 mmol) was then added thereto at room temperature. The reaction solution was distillated under reduced pressure, and the resulting residue was then purified by silica gel column chromatography [chloroform:methanol=100:0 (v/v) to chloroform:methanol=90:10 (v/v)] to afford the desired compound (0.410 g, 12%).

$^1$H-NMR (CDCl$_3$) δ:7.68-7.66 (1H, m), 7.55-7.53 (1H, m), 7.44-7.24 (6H, m), 6.58-6.56 (1H, m), 5.16-5.12 (1H, m), 4.16-4.11 (2H, m), 3.80-3.57 (5H, m), 3.48-3.44 (2H, m), 3.30-3.18 (2H, m), 2.90-2.86 (1H, m), 2.52-2.45 (1H, m), 2.26-2.22 (1H, m), 2.02-1.98 (1H, m).

MS(APCI, ESI)m/z:451(M+H)$^+$

Step 2: N-{[2-(2-{[4-(11,12-Didehydrodibenzo[b,f]azocin-5 (6H)-yl)-4-oxobutanoyl]amino}ethoxy)ethoxy]acetyl}-L-valyl-N-{4-[({[(11a'S)-11'-hydroxy-7'-methoxy-8'-(3- {[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 1 (0.050 g, 0.0499 mmol) was reacted in the same manner as in step 13 of Example 3 to afford the desired compound (0.0590 g, 82%).

MS(APCI, ESI)m/z:1434(M+H)$^+$

Example 14: Drug-Linker 12

[Formula 138]

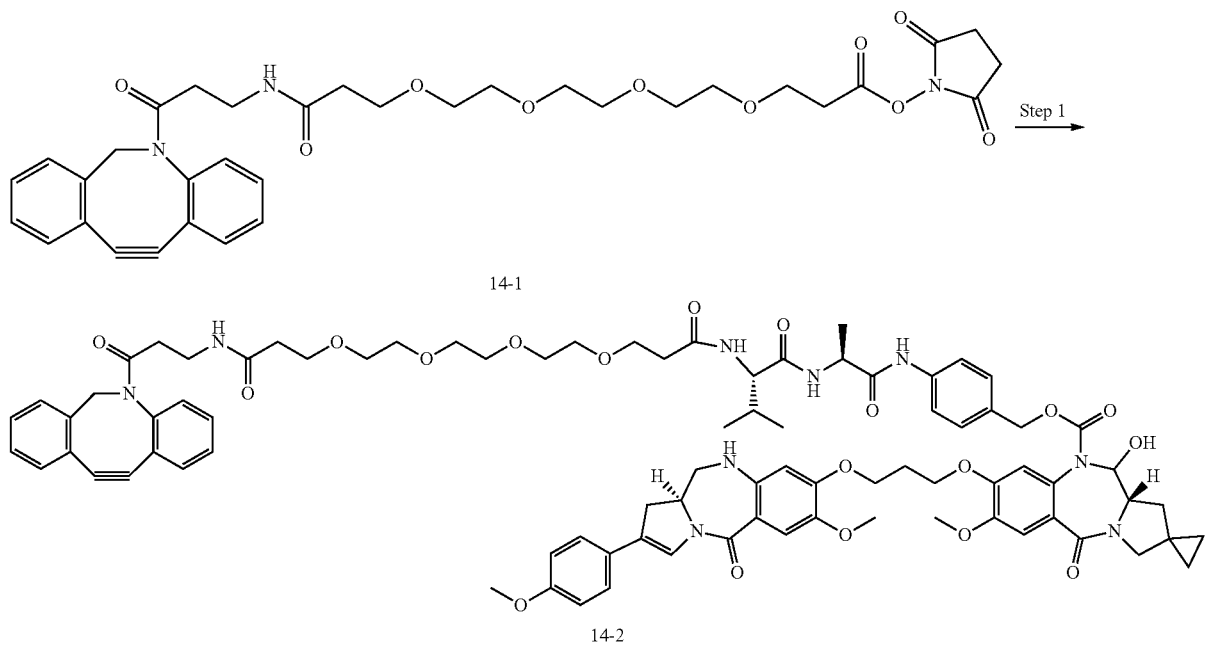

Step 1: N-[20-(11,12-Didehydrodibenzo[b,f]azocin-5 (6H)-yl)-16,20-dioxo-4,7,10,13-tetraoxa-17-azaicosan-1-oyl]-L-valyl-N-{4-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide A solution of the compound obtained in step 11 of Example 4 (0.0500 g, 0.0499 mmol), starting material 14-1 (0.050 g, 0.0499 mmol, commercially available from Alfa Aesar), and triethylamine (0.00830 mL, 0.0599 mmol) in dichloromethane (3 mL) was stirred at room temperature overnight. The resultant was distillated under reduced pressure, and the resulting residue was then purified by silica gel column chromatography [chloroform:methanol=100:0 (v/v) to chloroform:methanol=90:10 (v/v)] to afford the desired compound (0.0490 g, 64%).

MS (APCI, ESI)m/z:1536 (M+H)$^+$

Example 15: Drug-Linker 13

[Formula 139]

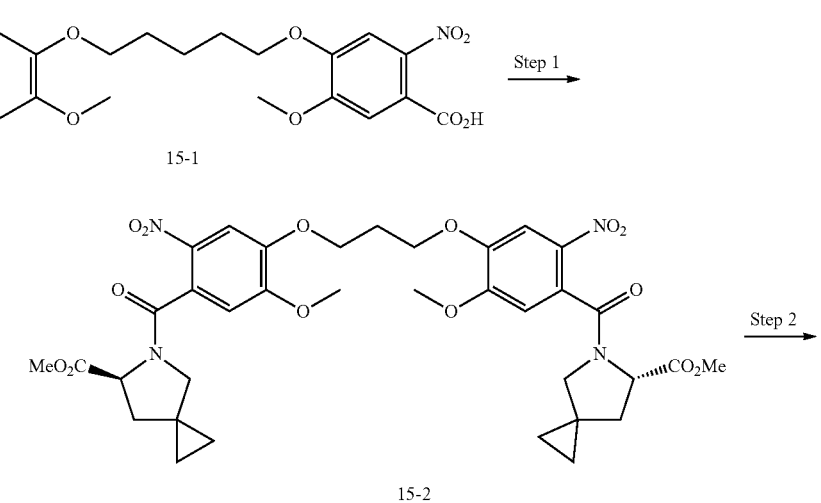

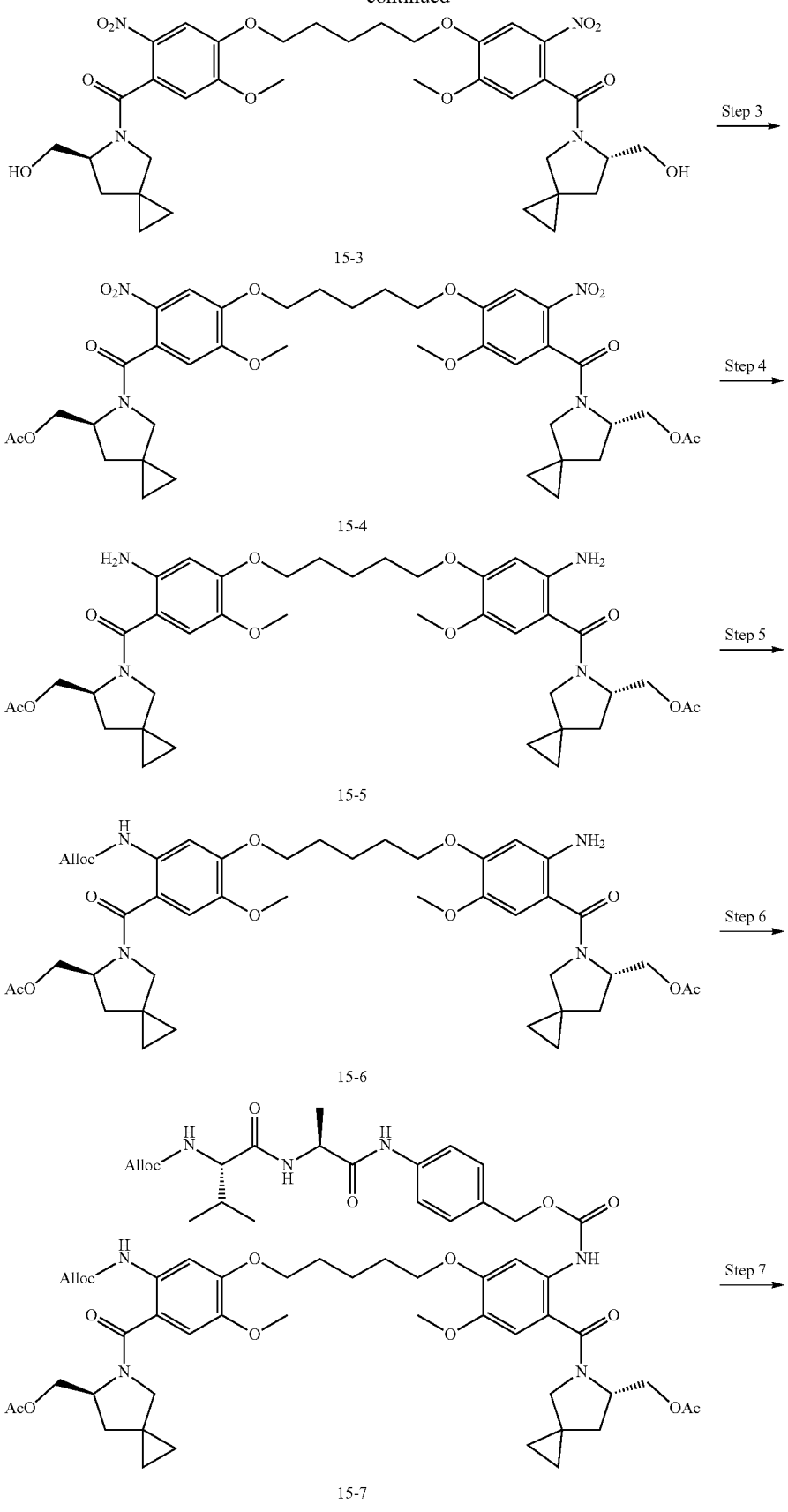

-continued
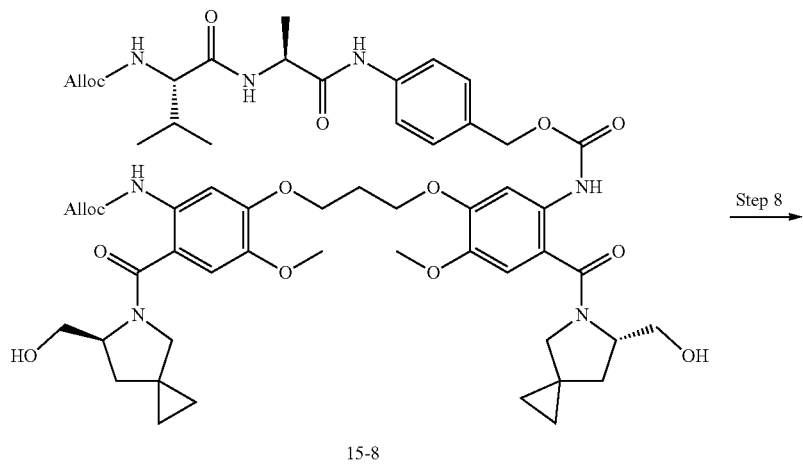
15-8
Step 8 →
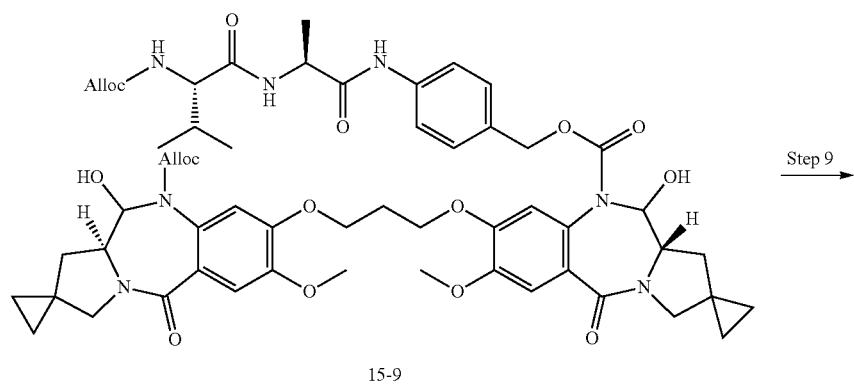
15-9
Step 9 →
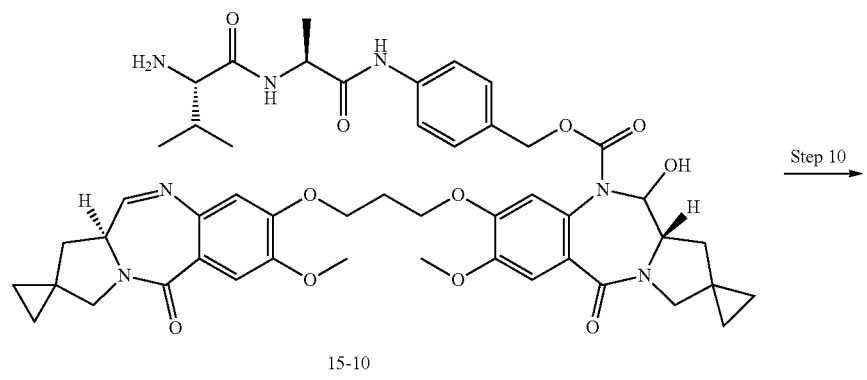
15-10
Step 10 →

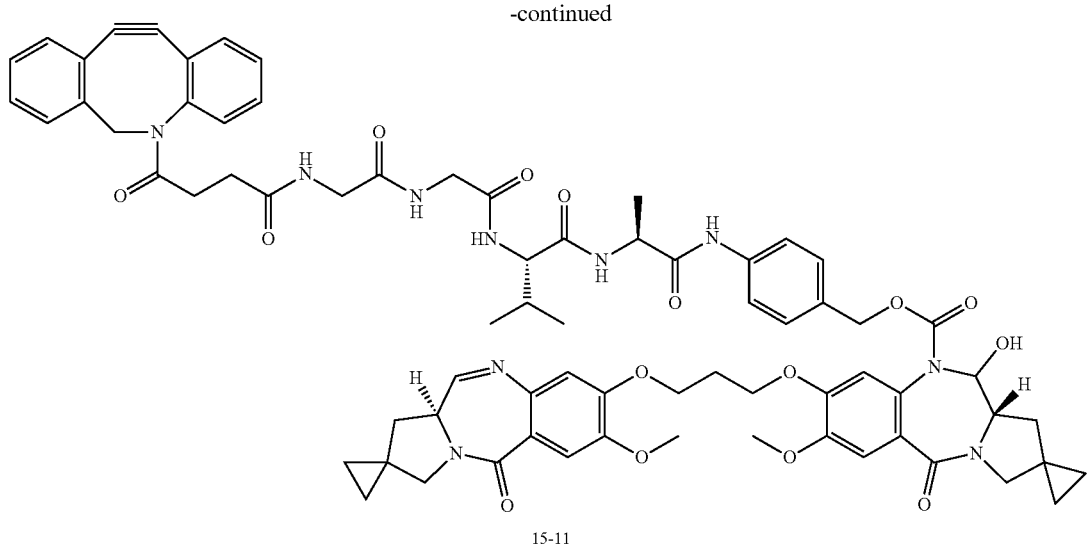

15-11

Step 1: Dimethyl (6S,6'S)-5,5'-{1,5-pentanediylbis[oxy(5-methoxy-2-nitrobenzen-4,1-diyl)carbonyl]}bis(5-azaspiro[2.4]heptane-6-carboxylate)

To a solution of starting material 15-1 (5.41 g, 10.9 mmol, Journal of Medicinal Chemistry 2004, 47, 1161) in dichloromethane (50 mL), oxalyl chloride (5.63 mL, 65.7 mmol) was added at 0° C., and N,N-dimethylformamide (0.0844 mL, 1.09 mmol) was added dropwise thereto. The temperature of the reaction solution was raised to room temperature, and the reaction solution was stirred for 2 hours. The resultant was distilled under reduced pressure, and the resulting residue was dissolved in dichloromethane (100 mL), which was added dropwise to dichloromethane solution (100 mL) of methyl (6S)-5-azaspiro[2.4]heptane-6-carboxylate hydrochloride (4.28 g, 24.1 mmol, Tetrahedron Letters 2012. 53. 3847) and triethylamine (6.07 mL, 43.8 mmol) under the nitrogen atmosphere at −40° C. The temperature of the reaction solution was raised to 0° C., and the reaction solution was stirred for 2 hours. To the reaction mixture, 1 N hydrochloric acid (100 mL) was added, and the organic layer was washed with water and brine, and dried over anhydrous sodium sulfate. The resultant was distilled under reduced pressure to afford the desired compound (8.40 g, quantitative).

$^1$H-NMR (DMSO-D$_6$) δ:7.71 (2H, s), 6.88 (2H, s), 4.63 (2H, m), 4.15-4.12 (4H, m), 3.94 (6H, s), 3.71 (6H, s), 3.25 (2H, m), 3.10 (2H, m), 2.31-2.28 (2H, m), 1.90-1.83 (6H, m), 1.60-1.58 (2H, m), 0.71-0.49 (8H, m).

MS(APCI, ESI)m/z:769(M+H)$^+$.

Step 2: {1,5-Pentanediylbis[oxy (5-methoxy-2-nitrobenzen-4,1-diyl)]}bis{[(6S)-6-(hydroxymethyl)-5-azaspiro[2.4]hept-5-yl]methanone}

To a solution of the compound obtained in step 1 (8.40 g, 10.9 mmol) in THF (100 mL), lithium borohydride (714 mg, 32.8 mmol) was added, and the resultant was stirred at 0° C. for 30 minutes, and the temperature was raised to room temperature, and stirring was performed for 1 hour. After 1 N hydrochloric acid was added at 0° C., the resultant was extracted with ethyl acetate, and washed with brine, and then dried over anhydrous sodium sulfate. The solvent was distilled off under reduced pressure to afford the desired compound (7.70 g, 99%).

$^1$H-NMR (DMSO-D$_6$) δ:7.67 (2H, s), 7.05 (2H, s), 4.86-4.74 (2H, m), 4.22-4.12 (6H, m), 3.92 (6H, s), 3.83-3.73 (2H, m), 3.62-3.51 (2H, m), 3.29 (1H, m), 3.11 (2H, m), 2.96 (1H, m), 2.12-2.03 (2H, m), 1.82-1.77 (6H, m), 1.59-1.56 (2H, m), 0.67-0.41 (8H, m).

MS(APCI, ESI)m/z:713(M+H)$^+$.

Step 3: Pentan-1,5-diylbis[oxy (5-methoxy-2-nitrobenzen-4,1-diyl)carbonyl (6S)-5-azaspiro[2.4]heptan-5,6-diylmethanediyl]diacetate The compound obtained in step 2 (7.70 g, 10.8 mmol) was dissolved in pyridine (20 mL) and acetic anhydride (10 mL, 105.9 mmol), which was stirred at room temperature. The resultant was distillated under reduced pressure to afford the desired compound (8.38 g, 97%).

$^1$H-NMR (DMSO-D$_6$) δ:7.68 (2H, s), 7.03 (2H, s), 4.47-4.46 (2H, m), 4.36-4.27 (4H, m), 4.13-4.11 (6H, m), 3.92 (6H, s), 3.16 (2H, m), 2.98 (2H, m), 2.17 (1H, m), 2.06 (6H, s), 1.84 (4H, m), 1.68 (1H, m), 1.58 (2H, m), 0.64-0.45 (8H, m).

MS(APCI, ESI)m/z:797(M+H)$^+$.

Step 4: 1,5-Pentanediylbis[oxy (2-amino-5-methoxybenzen-4,1-diyl)carbonyl (6S)-5-azaspiro[2.4]heptan-5,6-diylmethanediyl]diacetate To a solution of the compound obtained in step 3 (8.28 g, 10.4 mmol) in N,N-dimethylformamide (100 mL), 5% palladium carbon (moisture content: 54%, 1.00 g) was added, and the reaction solution was then vigorously stirred under the hydrogen atmosphere at room temperature for 6 hours. The resultant was filtered through a Celite, and the filtrate was then distillated under reduced pressure, and the resulting residue was purified by silica gel column chromatography [chloroform:methanol=100:0(v/v) to 90:10(v/v)] to afford the desired compound (5.05 g, 66%).

$^1$H-NMR (DMSO-D$_6$) δ:6.66 (2H, s), 6.36 (2H, s), 5.11 (4H, s), 4.49 (2H, s), 4.19 (4H, m), 3.90 (4H, m), 3.62 (6H, s), 3.48-3.46 (2H, m), 3.33 (2H, s), 3.23-3.20 (2H, m), 2.01 (6H, s), 1.78-1.74 (6H, m), 1.55 (2H, m), 0.61-0.58 (4H, m), 0.49-0.48 (4H, m).

MS(APCI, ESI)m/z:737(M+H)$^+$.

Step 5: {(6S)-5-[4-({5-[4-({(6S)-6-[(Acetyloxy)methyl]-5-azaspiro[2.4]hept-5-yl}carbonyl)-5-amino-2-methoxyphenoxy]pentyl}oxy)-5-methoxy-2-{[(prop-2-en-1-yloxy)carbonyl]amino}benzoyl]-5-azaspiro[2.4]hept-6-yl}methyl acetate (monoallyloxycarbonyl form)

To a solution of the compound obtained in step 4 (5.05 g, 6.85 mmol) in dichloromethane (100 mL), pyridine (1.10 mL, 13.7 mmol) was added, and allyl chloroformate (0.725 mL, 6.85 mmol) was added thereto under the nitrogen atmosphere at −78° C., and the resultant was stirred for 2 hours. The resultant was distillated under reduced pressure, and the resulting residue was purified by silica gel column chromatography [hexane:ethyl acetate=70:30 (v/v) to 100:0 (v/v), chloroform:methanol=100:0 (v/v) to 90:10 (v/v)] to afford the bisallyloxycarbonyl form (1.36 g, 22%) and monoallyloxycarbonyl form (2.63 g, 47%) as the desired compound.

Pentan-1,5-diylbis[oxy (5-methoxy-2-{[(prop-2-en-1-yloxy)carbonyl]amino}benzen-4,1-diyl)carbonyl (6S)-5-azaspiro[2.4]heptan-5,6-diylmethanediyl]diacetate (bisallyloxycarbonyl form):

$^1$H-NMR (DMSO-D$_6$) δ:9.14 (2H, s), 7.14 (2H, s), 6.85 (2H, s), 5.94 (2H, m), 5.33 (2H, m), 5.21 (2H, m), 4.55 (4H, m), 4.47 (1H,s), 4.23 (3H, s), 3.96 (4H, m), 3.74 (6H, s), 3.34 (6H, s), 3.31 (2H, m), 3.21 (2H, m), 2.04 (6H, s), 1.79 (4H,m), 1.67 (2H, m), 1.56 (2H, m), 0.56-0.48 (8H, m).

MS(APCI, ESI)m/z:905(M+H)$^+$.

Monoallyloxycarbonyl form:

$^1$H-NMR (DMSO-D$_6$)

δ:9.14 (1H, s), 7.14 (1H, s), 6.85 (1H, s), 6.65 (1H, s), 6.35 (1H, s), 5.95 (1H, m), 5.33 (1H, m), 5.22 (1 H,m), 5.11 (2H, s), 4.55 (2H, m), 4.48 (2H, s), 4.23-4.14 (4H, m), 3.96 (2H, m), 3.90 (2H, m), 3.74 (3H, s), 3.63 (3H, s), 3.49 (1H, m), 3.38-3.30 (4H, m), 3.21 (1H, m), 2.04 (3H, s), 2.01 (3H, s), 1.77 (5H, m), 1.68 (1H, m), 1.56 (2H, m), 0.63-0.48 (8H, m).

MS(APCI, ESI)m/z:821(M+H)$^+$.

Step 6: N-[(2-Propen-1-yloxy)carbonyl]-L-valyl-N-{4-[({2-({(6S)-6-[(acetyloxy)methyl]-5-azaspiro[2.4]hept-5-yl}carbonyl)-5-({5-[4-({(6S)-6-[(acetyloxy)methyl]-5-azaspiro[2.4]hept-5-yl}carbonyl)-2-methoxy-5-{[(2-propen-1-yloxy)carbonyl]amino}phenoxy]pentyl}oxy)-4-methoxyphenyl]carbamoyl}oxy)methyl]phenyl}-L-alaninamide The monoallyloxycarbonyl form obtained in step 5 (2.00 g, 2.44 mmol) was reacted in the same manner as in step 6 of Example 1 to afford the desired compound (2.64 g, 89%).

$^1$H-NMR (DMSO-D$_6$) δ:10.02 (1H, s), 9.14 (2H, s), 8.18 (1H, m), 7.59 (2H, m), 7.33 (2H, m), 7.27 (1H, m), 7.14 (2H, s), 6.8 5(2H,s), 5.99-5.86 (2H, m), 5.31(2H,n), 5.19 (2H, m), 5.03 (2H, s), 4.55 (2H, m), 4.48(2H,n), 4.41 (2H, m), 4.23-4.21 (3H, m), 3.94-3.91 (4H, m), 3.88-3.86 (2H, m), 3.74 (3H, s), 3.74 (3H, s), 3.34 (4H, s), 3.32-3.30 (2H, m), 3.20-3.18 (2H, m), 2.03 (6H, s), 1.96 (1H, m), 1.79 (4H, s), 1.66 (1H, m), 1.55 (2H, s), 1.30 (3H, m), 0.88(3H,m), 0.83 (3H, m), 0.54-0.49 (8H, m).

MS(APCI, ESI)m/z:1224(M+H)$^+$.

Step 7: N-[(2-Propen-1-yloxy)carbonyl]-L-valyl-N-[4-({[(2-{[(6S)-6-(hydroxymethyl)-5-azaspiro[2.4]hept-5-yl]carbonyl}-5-{[5-(4-{[(6S)-6-(hydroxymethyl)-5-azaspiro[2.4]hept-5-yl]carbonyl}-2-methoxy-5-{[(2-propen-1-yloxy)carbonyl]amino}phenoxy)pentyl]oxy}-4-methoxyphenyl)carbamoyl]oxy}methyl)phenyl]-L-alaninamide To a solution of the compound obtained in step 6 (2.64 g, 2.16 mmol) in methanol (10 mL), potassium carbonate (1.49 g, 10.8 mmol) was added, and the resultant was stirred at room temperature for 3 hours. A saturated aqueous ammonium chloride (100 mL) was added to the reaction mixture, which was extracted with ethyl acetate. The organic layer was dried over anhydrous sodium sulfate. The resultant was distillated under reduced pressure to afford the desired compound (2.21 g, 90%).

$^1$H-NMR (DMSO-D$_6$) δ:10.04 (1H, s), 9.18 (1H, s), 8.18 (1H, m), 7.59 (2H, m), 7.33 (2H, m), 7.26 (1H, m), 7.22 (1H, s), 7.1 4(2H,s), 6.89 (2H, s), 5.98-5.86 (2H, m), 5.31 (2H, m), 5.19 (2H, m), 5.04 (2H, s), 4.80 (2H, m), 4.55 (2H, m), 4.48 (2H, m), 4.41 (1H, m), 4.26 (2H, s), 3.96-3.94 (4H, m), 3.90-3.85 (1H, m), 3.74 (6H, s), 3.59 (2H, m), 3.33 (6H, s), 3.09 (1H, m), 1.93-1.83 (8H, m), 1.57-1.54 (2H, m), 1.30 (3H, m), 0.88 (3H, m), 0.83 (3H, m), 0.52-0.43 (8H, m).

MS(APCI, ESI)m/z:1140(M+H)$^+$.

Step 8: N-[(2-Propen-1-yloxy)carbonyl]-L-valyl-N-{4-[({[(11a'S)-11'-hydroxy-8'-{[5-({(11a'S)-11'-hydroxy-7'-methoxy-5'-oxo-10'-[(2-propen-1-yloxy)carbonyl]-5',10',11',11a'-tetrahydro-1'H-spiro[cyclopropane-1,2'-pyrrolo[2,1-c][1,4]benzodiazepine]-8'-yl}oxy)pentyl]oxy}-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide To a solution of the compound obtained in step 7 (2.03 g, 1.78 mmol) in dichloromethane (50 mL), Dess-Martin periodinane (1.59 g, 3.74 mmol) was added, and the resultant was stirred at room temperature overnight. A saturated aqueous sodium hydrogen carbonate (100 mL) was added to the reaction mixture, which was extracted with chloroform.

The organic layer was dried over anhydrous sodium sulfate. The resultant was distillated under reduced pressure, and the resulting residue was purified by silica gel column chromatography [chloroform:methanol=100:0(v/v) to 90:10 (v/v)] to afford the desired compound (2.05 g, quantitative).

$^1$H-NMR (DMSO-D$_6$) δ:9.99 (1H, s), 8.16 (1H, m), 7.54 (2H, m), 7.32-7.22 (3H, m), 7.08-7.04 (2H, m), 6.80-6.72 (2H, m), 6.55 (2H, s), 5.94-5.86 (2H, m), 5.75 (2H, m), 5.31-5.04 (2H, m), 4.81 (1H, m), 4.62 (1H, m), 4.48-4.38 (4H, m), 4.00-3.87 (4H, m), 3.79-3.76 (7H, m), 3.54 (2H, m), 3.42-3.40 (2H, m), 3.33 (4H, s), 3.14 (2H, m), 2.35 (2H, m), 1.80-1.78 (4H, m), 1.59-1.56 (4H, m), 1.29 (3H, m), 0.87 (3H, m), 0.83 (3H, m), 0.70-0.59 (8H, m).

MS(APCI, ESI)m/z:1136(M+H)$^+$.

Step 9: L-Valyl-N-{4-[({[(11a'S)-11'-hydroxy-7'-methoxy-8'-[(5-{[(11a'S)-7'-methoxy-5'-oxo-5',11a'-dihydro-1'H-spiro[cyclopropane-1,2'-pyrrolo[2,1-c][1,4]benzodiazepine]-8'-yl]oxy}pentyl)oxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 8 (2.05 g, 1.80 mmol) was reacted in the same manner as in step 12 of Example 3 to afford the desired compound (1.02 g, 60%).

¹H-NMR (DMSO-D₆) δ:10.08 (1H, s), 7.57 (2H, m), 7.32-7.20 (3H, m), 7.05 (2H, s), 6.68-6.60 (3H, m), 5.74 (1H, m), 4.99-4.58 (4H, m), 3.99-3.94 (4H, m), 3.78-3.73 (6H, m), 3.66-3.38 (4H, m), 3.15-3.01 (3H, m), 2.40-2.34 (3H, m), 1.89-1.81 (6H, m), 1.57-1.53 (4H, m), 1.28 (3H, m), 0.88 (3H, m), 0.78 (3H, m), 0.64-0.55 (8H, m).
MS(APCI, ESI)m/z:950(M+H)⁺.

Step 10: N-[4-(11,12-Didehydrodibenzo[b,f]azocin-5 (6H)-yl)-4-oxobutanoyl]glycylglycyl-L-valyl-N-{4-[({[(11a'S)-11'-hydroxy-7'-methoxy-8'-[(5-{[(11a'S)-7'-methoxy-5'-oxo-5',11a'-dihydro-1'H-spiro[cyclopropane-1,2'-pyrrolo[2,1-c][1,4]benzodiazepine]-8'-yl]oxy}pentyl)oxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 9 (0.710 g, 0.747 mmol) and the compound obtained in step 1 of Example 2 (0.313 g, 0.747 mmol) were dissolved in mixed solvent of dichloromethane (1.5 mL) and methanol (0.1 mL). Thereto, 4-(4,6-dimethoxy-1,3,5-triazin-2-yl)-4-methylmorpholinium chloride (0.264 g, 0.897 mmol) was added, and the resultant was stirred at room temperature for 1 hour. The resultant was distillated under reduced pressure, and the resulting residue was purified by silica gel column chromatography [chloroform:methanol=100:0 (v/v) to 80:20 (v/v)] to afford the desired compound (0.671 g, 66%).

Table 2: Peak positions of proton NMR and MS for drug-linker 13

¹H-NMR (DMSO-D₆) δ:9.91 (1H, s), 8.32 (1H, s), 8.23-7.91 (3H, m), 7.81-7.19 (14H, m), 7.04 (1H, m), 6.80-6.62 (3H, m), 5.77-5.75 (1H, m), 5.20 (1H, m), 5.01 (1H, m), 4.79 (1H, m), 4.46-4.35 (1H, m), 4.04 (4H, m), 3.86-3.38 (18H, m), 3.22-3.15 (2H, m), 2.67-2.63 (1H, m), 2.46-2.23 (3H, m), 2.09-1.91 (2H, m), 1.80-1.78 (5H, m), 1.57 (3H, m), 1.27 (3H, s), 1.11-1.04 (1H, m), 0.87-0.79 (6H, m), 0.63-0.55 (6H, m).
MS(APCI, ESI)m/z:1351(M+H)⁺.

Example 16: Drug-Linker 14

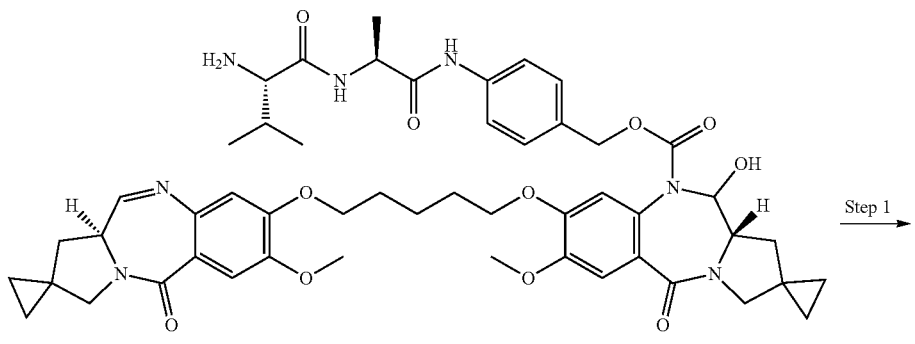

Step 1

15-10

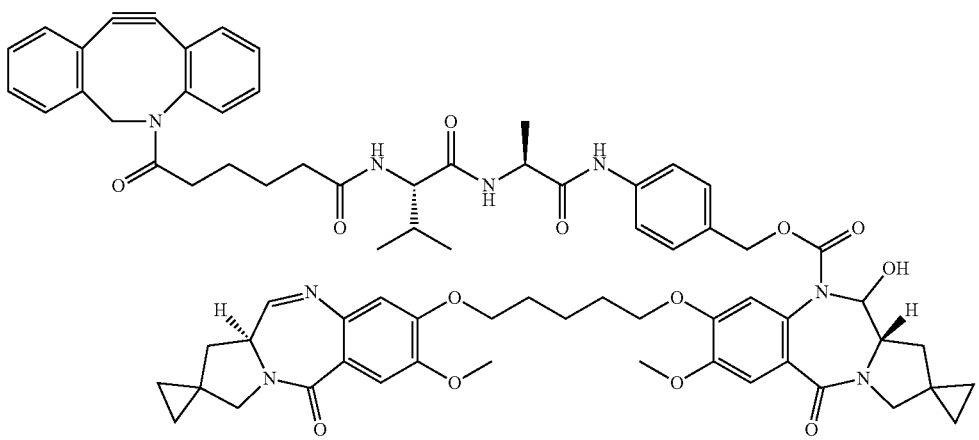

16-1

Step 1: N-[6-(11,12-Didehydrodibenzo[b,f]azocin-5 (6H)-yl)-6-oxohexanoyl]-L-valyl-N-{4-[({[(11a'S)-11'-hydroxy-7'-methoxy-8'-[(5-{[(11a'S)-7'-methoxy-5'-oxo-5',11a'-dihydro-1'H-spiro[cyclopropane-1,2'-pyrrolo[2,1-c][1,4]benzodiazepine]-8'-yl]oxy}pentyl)oxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 9 of Example 15 (0.100 g, 0.105 mmol) and azadibenzocyclooctynoic acid (0.0351 g, 0.105 mmol) were reacted in the same manner as in step 10 of Example 15 to afford the desired compound (0.0702 g, 53%).

$^1$H-NMR (DMSO-D$_6$) δ:9.92 (1H, s), 8.14 (1H, m), 7.92-7.19 (16H, m), 7.04 (1H, m), 6.86-6.72 (1H, m), 6.60-6.58 (1H, m), 5.76 (1H, m), 5.20 (1H, m), 5.03 (1H, m), 4.81-4.78 (1H, m), 4.43-4.37 (2H, m), 4.11-3.41 (14H, m), 3.21-3.15 (3H, m), 2.43-2.37 (2H, m), 2.19-2.15 (1H, m), 2.03-1.92 (3H, m), 1.77-1.75 (5H, m), 1.55 (4H, s), 1.26-1.18 (6H, m), 1.09-1.04 (1H, m), 0.87-0.77 (6H, m), 0.69-0.50 (8H, m).

MS(APCI, ESI)m/z:1265(M+H)$^+$.

Example 17: Drug-Linker 15

[Formula 141]

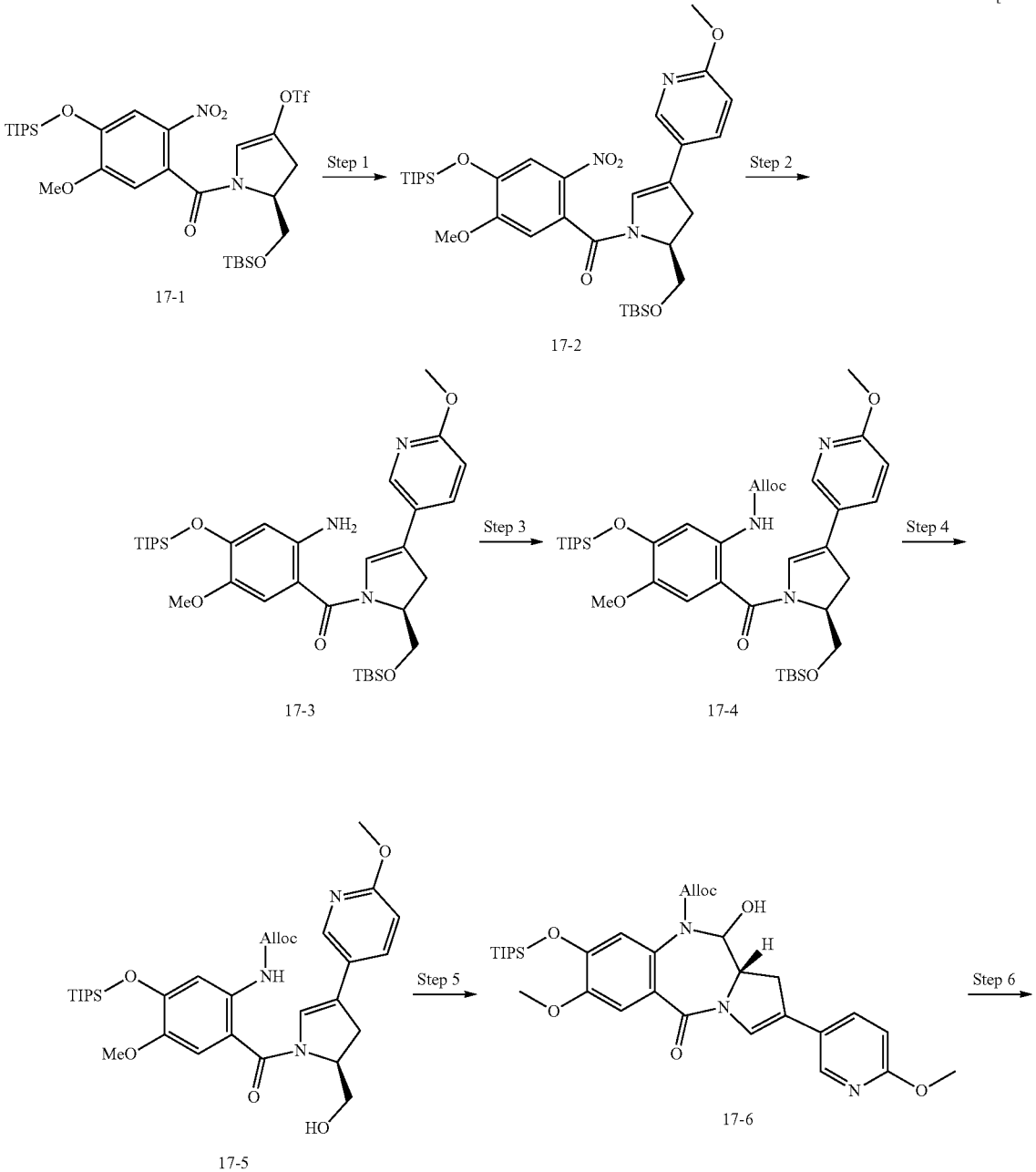

-continued
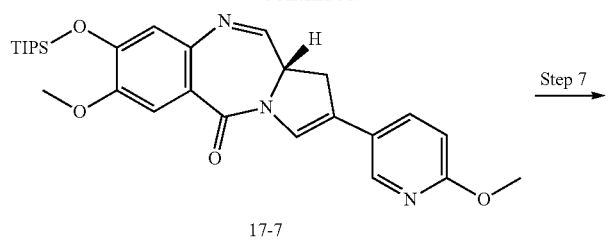
17-7
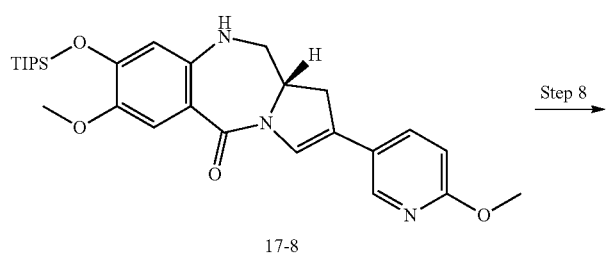
17-8
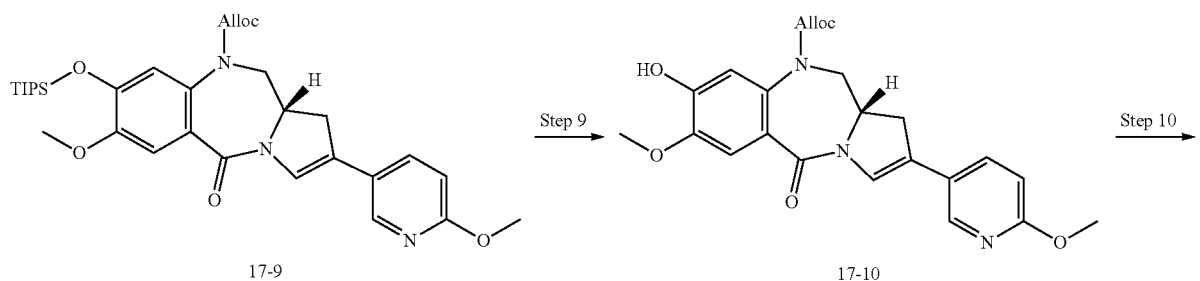
17-9 17-10
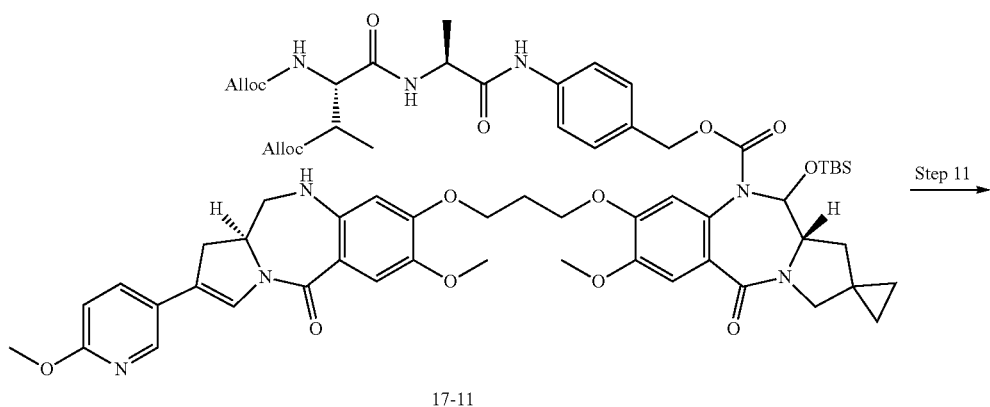
17-11
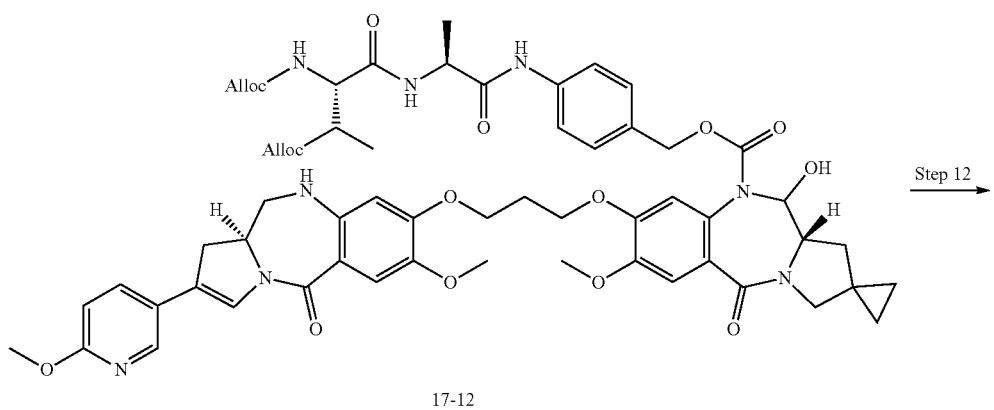
17-12

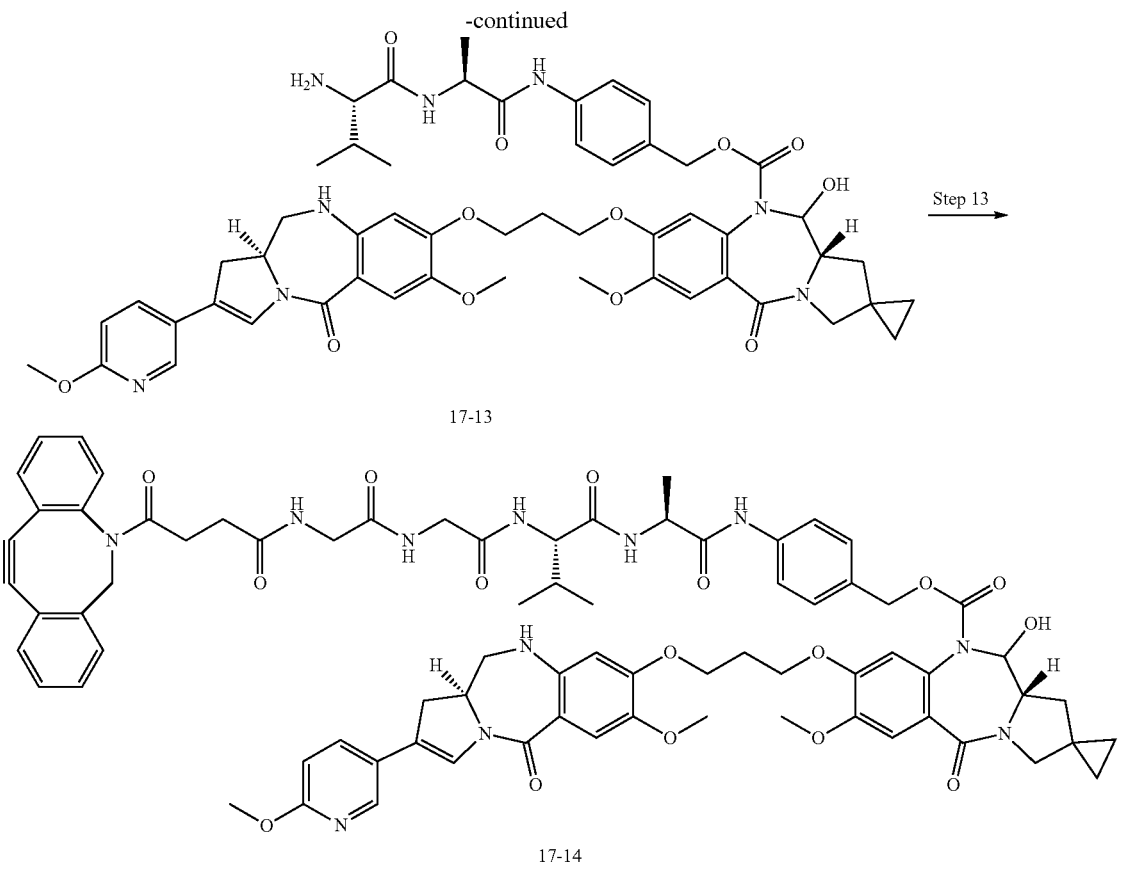

17-13

17-14

Step 1: Compound 17-2

Starting raw material 17-1 (2.00 g, 2.81 mmol, WO 2013053872) and 2-methoxy-5-(4,4,5,5-tetramethyl-1,3,2-dioxaborolan-2-yl)pyridine (2.00 g, 8.51 mmol) were reacted in the same manner as in step 6 of Example 3 to afford the desired compound (1.89 g, quantitative).

MS(APCI, ESI)m/z:672(M+H)$^+$.

Step 2: Compound 17-3

The compound obtained in step 1 (1.89 g, 2.81 mmol) was dissolved in a mixed solvent of ethanol (30 mL and formic acid (1.5 mL). Zinc powder (3.68 g) was added thereto, and the resultant was stirred at room temperature for 1 hour. The resultant was filtered through a Celite, and a saturated aqueous sodium hydrogen carbonate (100 mL) was added to the filtrate, which was extracted with ethyl acetate. The organic layer was dried over anhydrous sodium sulfate. The resultant was distillated under reduced pressure to afford the desired compound (1.81 g, quantitative).

MS(APCI, ESI)m/z:642(M+H)$^+$.

Step 3: Compound 17-4

The compound obtained in step 2 (1.81 g, 2.82 mmol) was reacted in the same manner as in step 9 of Example 3 to afford the desired compound (1.76 g, 86%).

MS(APCI, ESI)m/z:726(M+H)$^+$.

Step 4: Compound 17-5

The compound obtained in step 3 (1.76 g, 2.42 mmol) was reacted in the same manner as in step 7 of Example 1 to afford the desired compound (1.05 g, 71%).

MS(APCI, ESI)m/z:612(M+H)$^+$.

Step 5: Compound 17-6

The compound obtained in step 4 (1.05 g, 1.71 mmol) was reacted in the same manner as in step 3 of Example 9 to afford the desired compound (0.686 g, 66%).

MS(APCI, ESI)m/z:610(M+H)$^+$.

Step 6: Compound 17-7

The compound obtained in step 5 (0.481 g, 0.789 mmol) was reacted in the same manner as in step 12 of Example 3 to afford the desired compound (0.288 g, 72%).

MS(APCI, ESI)m/z:508(M+H)$^+$.

Step 7: Compound 17-8

The compound obtained in step 6 (0.288 g, 0.567 mmol) was reacted in the same manner as in step 8 of Example 3 to afford the desired compound (0.268 g, 93%).

MS(APCI, ESI)m/z:510(M+H)$^+$.

Step 8: Compound 17-9

The compound obtained in step 7 (0.267 g, 0.525 mmol) was reacted in the same manner as in step 9 of Example 3 to afford the desired compound (0.278 g, 89%).

MS(APCI, ESI)m/z:594(M+H)$^+$.

Step 9: Compound 17-10

The compound obtained in step 8 (0.278 g, 0.468 mmol) was reacted in the same manner as in step 10 of Example 1 to afford the desired compound (0.207 g, quantitative).
MS(APCI, ESI)m/z:438(M+H)$^+$.

Step 10: Compound 17-11

Using the compound obtained in step 11 of Example 1 (0.307 g, 0.331 mmol), the compound obtained in step 9 (0.0964 g, 0.220 mmol) was reacted in the same manner as in step 10 of Example 3 to afford the desired compound (0.224 g, 79%).
MS(APCI, ESI)m/z:1285(M+H)$^+$.

Step 11: Compound 17-12

The compound obtained in step 10 (0.294 g, 0.228 mmol) was reacted in the same manner as in step 11 of Example 3 to afford the desired compound (0.284 g, quantitative).
MS(APCI, ESI)m/z:1171(M+H)$^+$.

Step 12: Compound 17-13

The compound obtained in step 11 (0.284 g, 0.242 mmol) was reacted in the same manner as in step 12 of Example 3 to afford the desired compound (0.114 g, 47%).
MS(APCI, ESI)m/z:1003(M+H)$^+$.

Step 13: N-[4-(11,12-Didehydrodibenzo[b,f]azocin-5 (6H)-yl)-4-oxobutanoyl]glycylglycyl-L-valyl-N-{4-[({[(11a'S)-11'-hydroxy-7'-methoxy-8'-(3-{[7-methoxy-2-(6-methoxy-3-pyridinyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy) methyl]phenyl}-L-alaninamide ("GGVA" Disclosed as SEQ ID NO: 76)

The compound obtained in step 12 (0.114 g, 0.113 mmol) was reacted in the same manner as in step 13 of Example 3 to afford the desired compound (0.0121 g, 8%).

$^1$H-NMR (CDCl$_3$) δ:8.75 (1H, s), 8.24-8.09 (2H, m), 7.85-6.98 (13H, m), 6.75-6.73 (2H, m), 6.57-6.47 (1H, m), 6.18 (1H, s), 5.89 (1H, s), 5.37-4.96 (3H, m), 4.67-4.60 (3H, m), 4.41-4.06 (6H, m), 3.92 (3H, s), 3.86-3.82 (3H, m), 3.74-3.70 (3H, m), 3.59-3.45 (3H, m), 3.32-3.23 (2H, m), 2.81-2.64 (3H, m), 2.28-2.04 (4H, m), 1.49-1.38 (4H, m), 1.23-1.22 (2H, m), 1.09-1.01 (3H, m), 0.96-0.90 (5H, m), 0.69-0.64 (6H, m).

MS(APCI, ESI)m/z:1404(M+H)$^+$.

Example 18: Drug-Linker 16

[Formula 142]

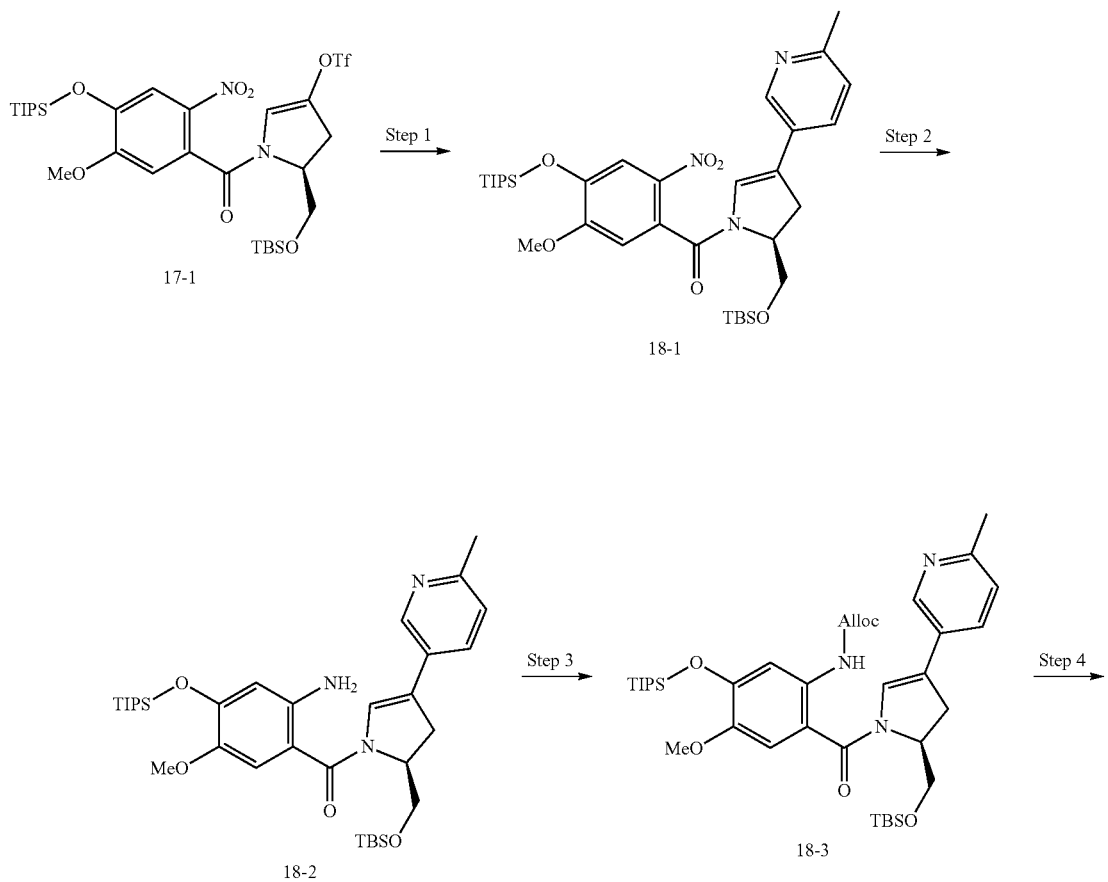

-continued
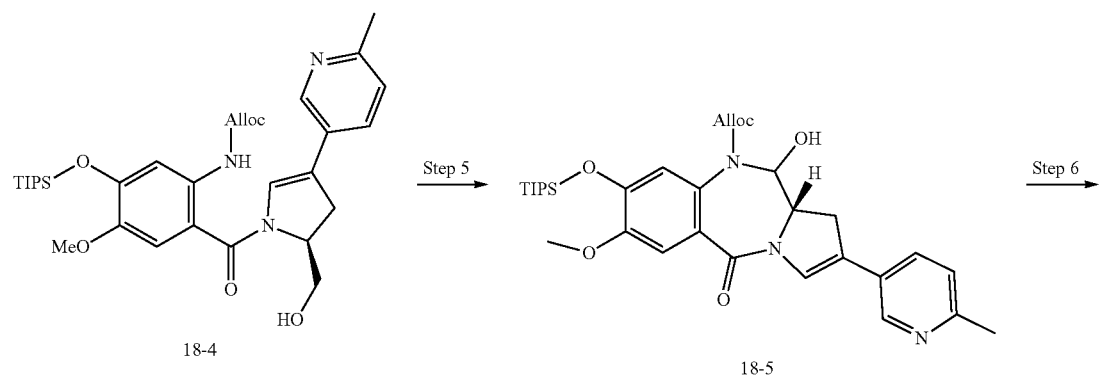
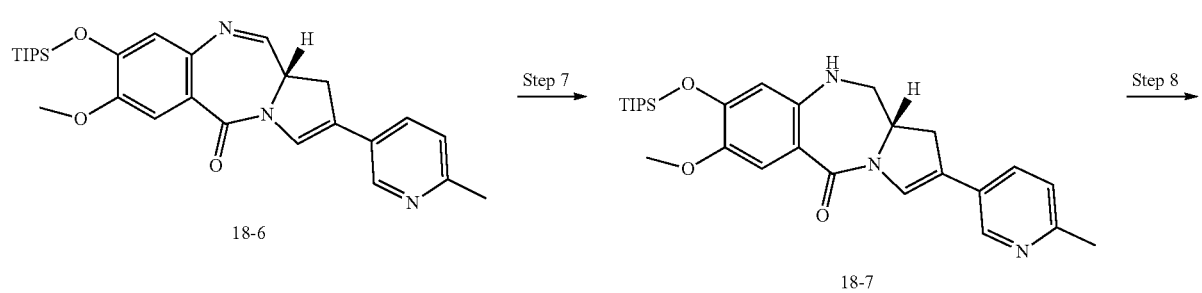
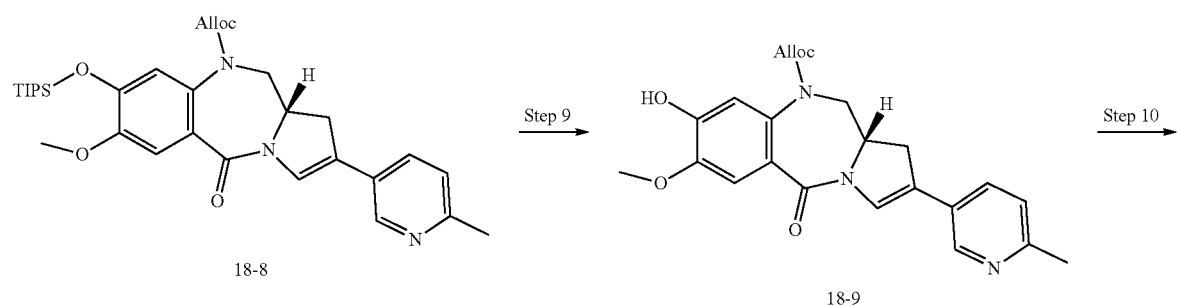
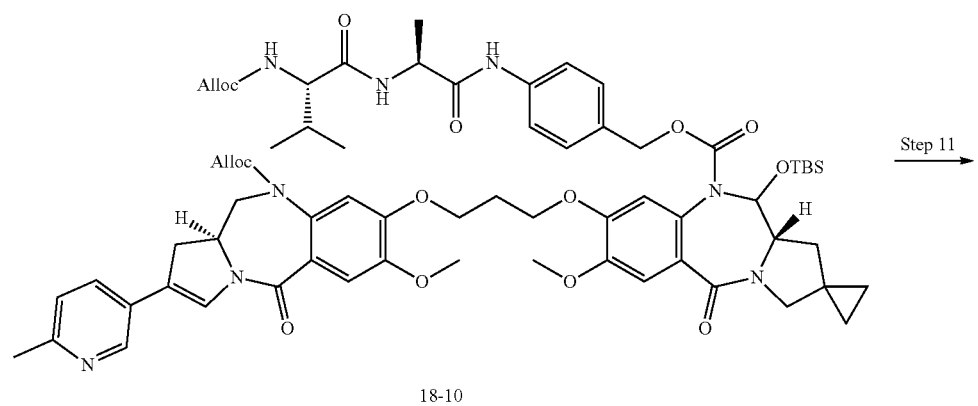

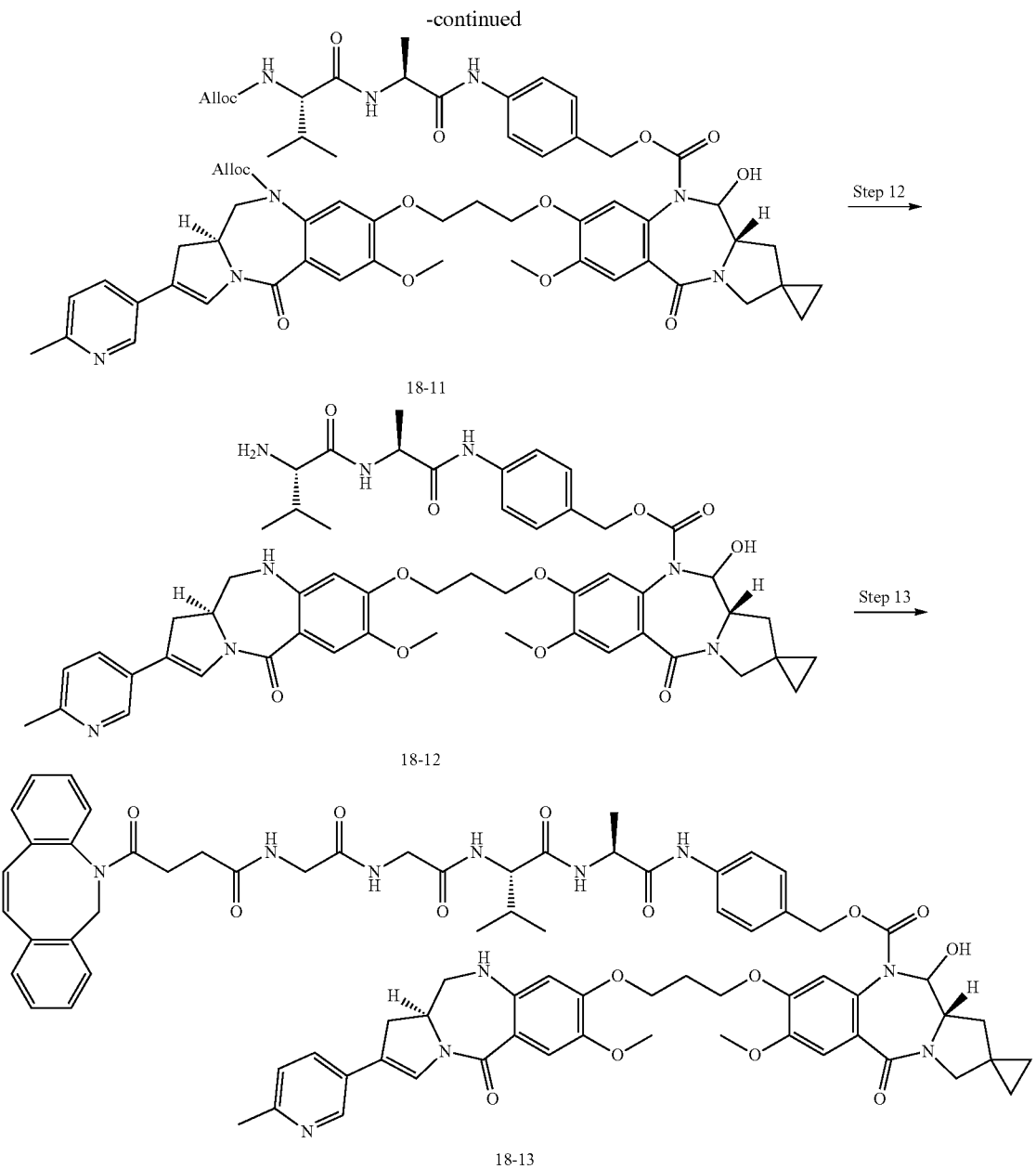

Step 1: Compound 18-1

Starting raw material 17-1 (2.00 g, 2.81 mmol) and 2-methyl-5-pyridinylboronic acid (1.00 g, 7.30 mmol) were used and subjected to Suzuki-Miyaura coupling reaction in the same manner as in step 6 of Example 3 to afford the desired compound (0.901 g, 49%).

MS(APCI, ESI)m/z:656(M+H)$^+$.

Step 2: Compound 18-2

The compound obtained in step 1 (1.98 g, 3.02 mmol) was reacted in the same manner as in step 2 of Example 17 to afford the desired compound (1.86 g, 98%).

MS(APCI, ESI)m/z:626(M+H)$^+$.

Step 3: Compound 18-3

The compound obtained in step 2 (1.86 g, 2.97 mmol) was reacted in the same manner as in step 9 of Example 3 to afford the desired compound (1.36 g, 65%).

MS(APCI, ESI)m/z:710(M+H)$^+$.

Step 4: Compound 18-4

The compound obtained in step 3 (1.36 g, 2.42 mmol) was reacted in the same manner as in step 7 of Example 1 to afford the desired compound (0.991 g, 87%).

MS(APCI, ESI)m/z:596(M+H)$^+$.

Step 5: Compound 18-5

The compound obtained in step 4 (0.991 g, 1.66 mmol) was reacted in the same manner as in step 3 of Example 9 to afford the desired compound (0.608 g, 62%).

MS(APCI, ESI)m/z:594(M+H)$^+$.

Step 6: Compound 18-6

The compound obtained in step 5 (0.405 g, 0.682 mmol) was reacted in the same manner as in step 12 of Example 3 to afford the desired compound (0.239 g, 71%).

$^1$H-NMR (DMSO-D$_6$) δ:8.60 (1H, m), 8.02 (1H, m), 7.87 (1H, m), 7.67 (1H, s), 7.62 (1H, m), 7.57-7.54 (1H, m), 7.40 (1H, s), 7.25 (1H, m), 6.74 (1H, s), 4.53-4.49 (1H, m), 3.85 (3H, s), 3.52 (2H, m), 2.46 (3H, s), 1.30-1.24 (3H, m), 1.07-1.06 (18H, m), observed as a water adduct of the desired compound.

MS(APCI, ESI)m/z:492(M+H)$^+$.

Step 7: Compound 18-7

The compound obtained in step 6 (0.239 g, 0.485 mmol) was reacted in the same manner as in step 8 of Example 3 to afford the desired compound (0.180 g, 75%).

MS(APCI, ESI)m/z:494(M+H)$^+$.

Step 8: Compound 18-8

The compound obtained in step 7 (0.180 g, 0.364 mmol) was reacted in the same manner as in step 9 of Example 3 to afford the desired compound (0.179 g, 85%).

MS(APCI, ESI)m/z:578(M+H)$^+$.

Step 9: Compound 18-9

The compound obtained in step 8 (0.179 g, 0.309 mmol) was reacted in the same manner as in step 10 of Example 1 to afford the desired compound (0.137 g, quantitative).

MS(APCI, ESI)m/z:422(M+H)$^+$.

Step 10: Compound 18-10

The compound obtained in step 9 (0.0780 g, 0.185 mmol) was reacted in the same manner as in step 10 of Example 3, except that the compound obtained in step 11 of Example 1 (0.258 g, 0.278 mmol) was used in place of the compound obtained in step 10 of Example 1, to afford the desired compound (0.213 g, 91%).

MS(APCI, ESI)m/z:1269(M+H)$^+$.

Step 11: Compound 18-11

The compound obtained in step 10 (0.213 g, 0.168 mmol) was reacted in the same manner as in step 11 of Example 3 to afford the desired compound (0.182 g, 94%).

$^1$H-NMR (DMSO-D$_6$) δ:10.00-9.85 (1H, m), 8.54 (1H, s), 8.32 (1H, m), 8.16 (1H, s), 7.82 (1H, m), 7.65-7.56 (3H, m), 7.35-7.06 (6H, m), 6.79 (1H, m), 6.57 (1H, s), 5.87-5.80 (3H, m), 5.26-5.09 (5H, m), 4.85-4.83 (1H, m), 4.56-4.40 (5H, m), 4.13 (5H, m), 3.92-3.87 (2H, m), 3.80 (5H, s), 3.58-3.54 (1H, m), 3.21-3.09 (3H, m), 2.81 (1H, m), 2.45 (3H, s), 2.36-2.34 (1H, m), 2.16-2.10 (2H, m), 1.98-1.92 (1H, m), 1.57 (2H, m), 1.30-1.28 (4H, m), 0.92-0.84 (7H, m), 0.67-0.62 (4H, m).

MS(APCI, ESI)m/z:1155(M+H)$^+$.

Step 12: Compound 18-12

The compound obtained in step 11 (0.182 g, 0.157 mmol) was reacted in the same manner as in step 12 of Example 3 to afford the desired compound (0.0751 g, 48%).

$^1$H-NMR (DMSO-D$_6$) δ:10.15 (1H, s), 8.54 (1H, m), 8.50 (1H, s), 7.78 (1H, m), 7.67 (1H, s), 7.57 (2H, m), 7.30 (1H, s), 7.21-7.19 (3H, m), 7.05 (1H, s), 6.77 (1H, s), 6.60-6.56 (2H, m), 6.35 (1H, s), 5.91-5.83 (2H, m), 5.76 (1H, m), 5.29-5.13 (4H, m), 4.84 (1H, m), 4.54-4.49 (1H, m), 4.19-4.03 (4H, m), 3.79 (3H, s), 3.65 (3H, s), 3.57-3.53 (2H, m), 3.42-3.40 (1H, m), 3.28-3.26 (1H, m), 3.14 (1H, m), 2.81 (1H, m), 2.44 (3H, s), 2.37-2.33 (1H, m), 2.21-2.01 (3H, m), 1.57 (1H, m), 1.30-1.26 (3H, m), 0.93-0.83 (6H, m), 0.67-0.61 (4H, m).

MS(APCI, ESI)m/z:987(M+H)$^+$.

Step 13: N-[4-(11,12-Didehydrodibenzo[b,f]azocin-5 (6H)-yl)-4-oxobutanoyl]glycylglycyl-L-valyl-N-{4-[({[(11a'S)-11'-hydroxy-7'-methoxy-8'-(3-{[7-methoxy-2-(6-methyl-3-pyridinyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 12 (0.0751 g, 0.0761 mmol) was reacted in the same manner as in step 13 of Example 3 to afford the desired compound (0.0117 g, 11%).

$^1$H-NMR (CDCl$_3$) δ:8.75 (1H, s), 8.48-8.46 (1H, m), 7.69-7.56 (4H, m), 7.47-6.89 (14H, m), 6.45 (1H, m), 6.24-6.19 (1H, m), 5.91 (1H, m), 5.37 (1H, m), 5.01 (1H, m), 4.67-4.59 (3H, m), 4.30-3.19 (22H, m), 2.88-2.63 (3H, m), 2.55 (3H, s), 2.42-2.34 (2H, m), 2.27-2.04 (4H, m), 1.51-1.34 (4H, m), 1.12-1.06 (3H, m), 0.99-0.84 (3H, m), 0.71-0.66 (4H, m).

MS(APCI, ESI)m/z:1388(M+H)$^+$.

Example 19: Drug-Linker 17

[Formula 143]

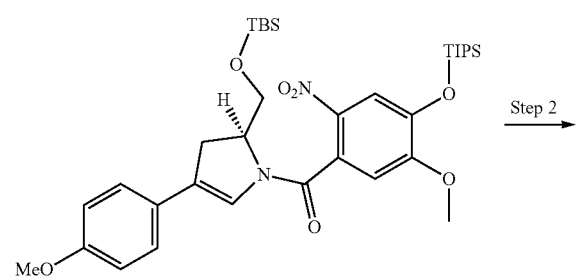

323    324
-continued
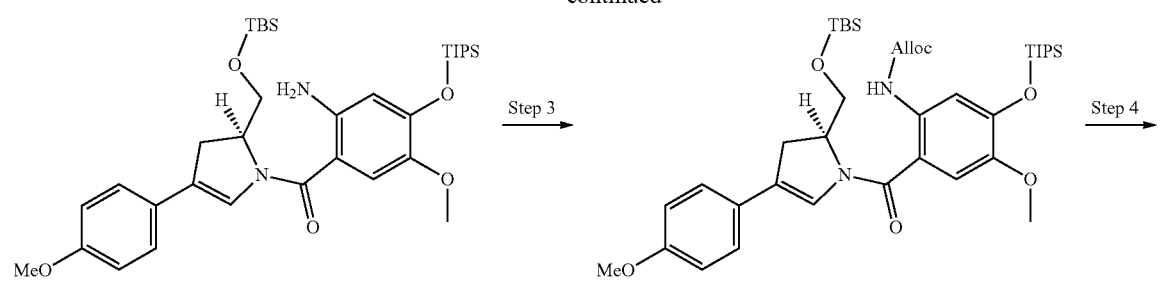
19-2 → Step 3 → 19-3 → Step 4 →
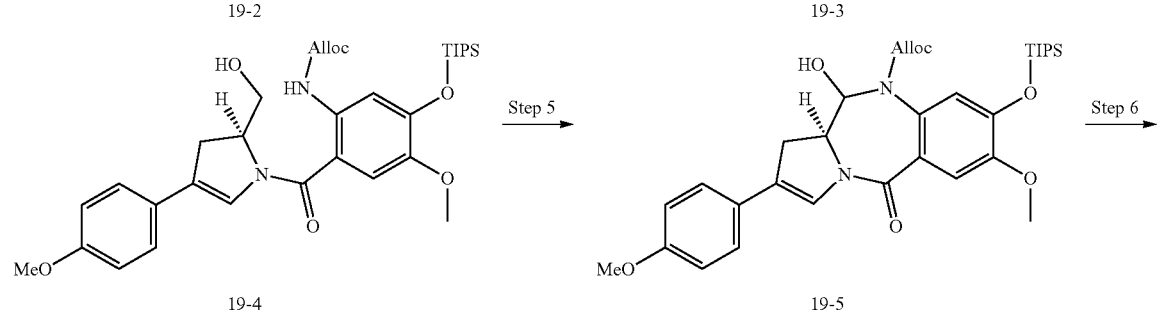
19-4 → Step 5 → 19-5 → Step 6 →
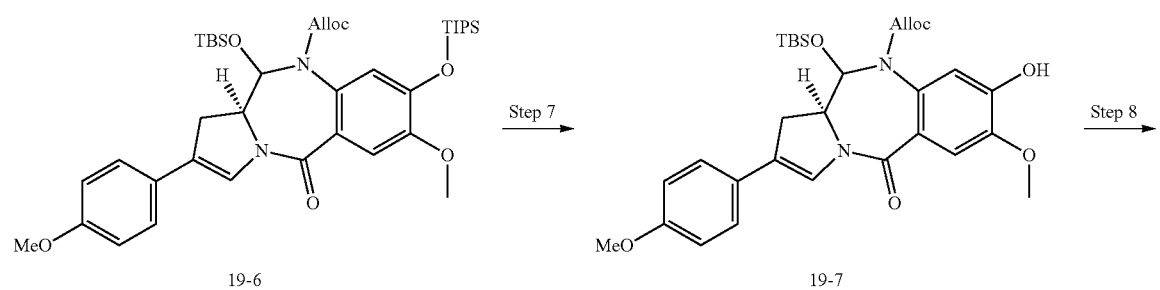
19-6 → Step 7 → 19-7 → Step 8 →
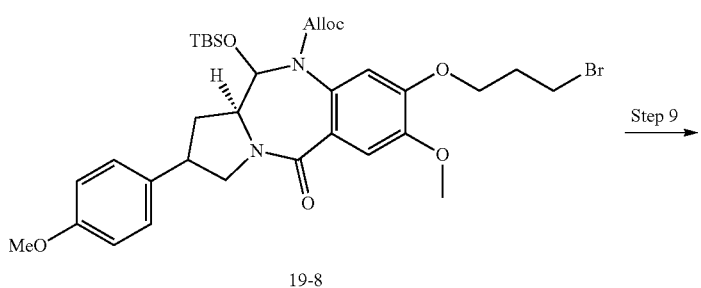
19-8 → Step 9 →
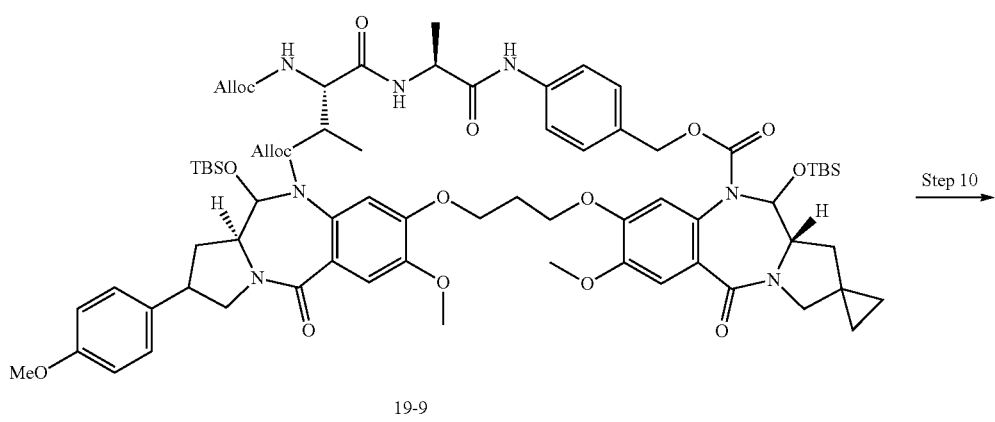
19-9 → Step 10 →

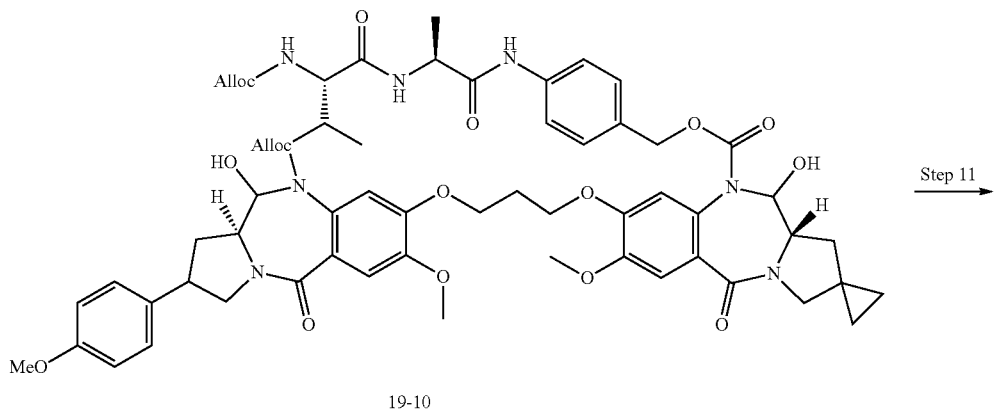
19-10
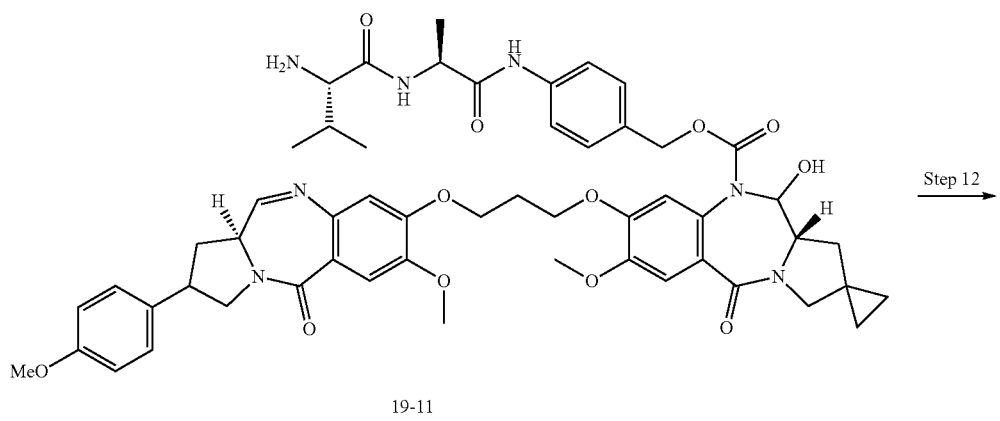
19-11
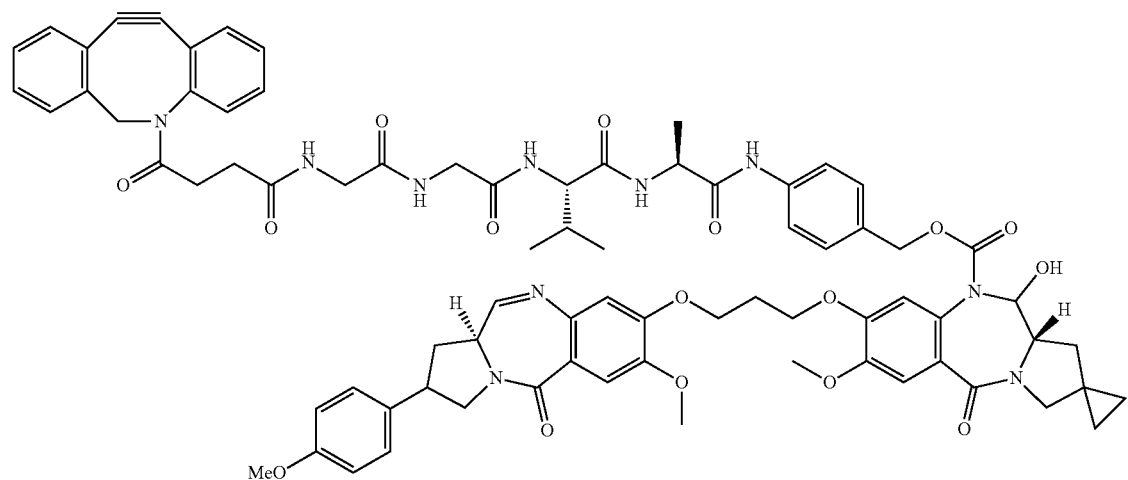
19-12

Step 1: [(2S)-2-({[tert-Butyl(dimethyl)silyl]oxy}methyl)-4-(4-methoxyphenyl)-2,3-dihydro-1H-pyrrol-1-yl](5-methoxy-2-nitro-4-{[tri(propan-2-yl)silyl]oxy}phenyl)methanone Starting material 17-1 (2.00 g, 2.81 mmol) was reacted in the same manner as in step 6 of Example 3 to afford the desired compound (1.31 g, 93%).
$^1$H-NMR (CDCl$_3$) δ:7.75-7.73 (1H, m), 7.12 (2H, m), 6.82-6.76 (4H, m), 6.13-6.11 (1H, m), 4.80-4.70 (1H, m), 3.93-3.91 (3H, m), 3.79-3.75 (4H, m), 3.21-3.15 (1H, m), 3.01-2.93 (1H, m), 1.34-1.25 (3H, m), 1.12 (18H, m), 0.89 (9H, s), 0.13-0.18 (6H, m).
MS(APCI, ESI)m/z:671(M+H)$^+$

Step 2: (2-Amino-5-methoxy-4-{[tri(propan-2-yl)silyl]oxy}phenyl)[(2S)-2-({[tert-butyl(dimethyl)silyl]oxy}methyl)-4-(4-methoxyphenyl)-2,3-dihydro-1H-pyrrol-1-yl]methanone The compound obtained in step 1 (1.31 g, 1.95 mmol) was reacted in the same manner as in step 2 of Example 17 to afford the desired compound (1.12 g, 90%).
$^1$H-NMR (CDCl$_3$) δ:7.21-7.18 (2H, m), 6.85-6.81 (2H, m), 6.79-6.76 (2H, m), 6.28 (1H, s), 4.42 (2H, m), 3.98-3.93 (1H, m), 3.90-3.86 (1H, m), 3.80 (3H, s), 3.71 (3H, s), 3.11 (1H, m), 2.98 (1H, m), 1.32-1.23 (4H, m), 1.12-1.10 (18H, m), 0.85 (9H, s), 0.08-0.02 (6H, m).

Step 3: Prop-2-en-1-yl (2-{[(2S)-2-({[tert-butyl(dimethyl)silyl]oxy}methyl)-4-(4-methoxyphenyl)-2,3-dihydro-1H-pyrrol-1-yl]carbonyl}-4-methoxy-5-{[tri(propan-2-yl)silyl]oxy}phenyl)carbamate The compound obtained in step 2 (1.12 g, 1.59 mmol) was reacted in the same manner as in step 9 of Example 3 to afford the desired compound (0.890 g, 77%).
$^1$H-NMR (CDCl$_3$) δ:8.57 (1H, m), 7.77 (1H, m), 7.18 (2H, m), 6.86-6.78 (4H, m), 5.95-5.90 (1H, m), 5.32 (1H, m), 5.20 (1H, m), 4.79-4.77 (1H, m), 4.64-4.57 (2H, m), 4.00-3.98 (1H, m), 3.93-3.91 (1H, m), 3.80 (3H, s), 3.76 (3H, s), 3.14-3.09 (1H, m), 3.00 (1H, m), 1.36-1.25 (3H, m), 1.14-1.11 (18H, m), 0.85 (9H, s), 0.11-0.03 (6H, m).
MS(APCI, ESI)m/z:725(M+H)$^+$

Step 4: Prop-2-en-1-yl (2-{[(2S)-2-(hydroxymethyl)-4-(4-methoxyphenyl)-2,3-dihydro-1H-pyrrol-1-yl]carbonyl}-4-methoxy-5-{[tri(propan-2-yl)silyl]oxy}phenyl)carbamate The compound obtained in step 3 (0.890 g, 1.23 mmol) was reacted in the same manner as in step 7 of Example 1 to afford the desired compound (0.696 g, 93%).
$^1$H-NMR (CDCl$_3$) δ:8.54-8.36 (1H, m), 7.71 (1H, m), 7.18-7.17 (2H, m), 6.86-6.84 (3H, m), 6.77 (1H, m), 5.94-5.90 (1H, m), 5.32 (1H, m), 5.21 (1H, m), 4.87-4.85 (1H, m), 4.61 (2H, m), 4.50 (1H, m), 3.96-3.84 (2H, m), 3.80 (3H, s), 3.76 (3H, s), 3.28 (1H, m), 2.64 (1H, m), 1.36-1.25 (3H, m), 1.13 (18H, m).
MS(APCI, ESI)m/z:611(M+H)$^+$

Step 5: Prop-2-en-1-yl (11aS)-11-hydroxy-7-methoxy-2-(4-methoxyphenyl)-5-oxo-8-{[tri(propan-2-yl)silyl]oxy}-11,11a-dihydro-1H-pyrrolo[2,1-c][1,4]benzodiazepin-10(5H)-carboxylate The compound obtained in step 4 (0.696 g, 1.14 mmol) was reacted in the same manner as in step 8 of Example 1 to afford the desired compound (0.532 g, 77%).
$^1$H-NMR (CDCl$_3$) δ:7.36 (1H, s), 7.31-7.29 (2H, m), 7.22 (1H, s), 6.90-6.87 (2H, m), 6.72 (1H, m), 5.82-5.76 (2H, m), 5.19-5.14 (2H, m), 4.60 (1H, m), 4.49-4.46 (1H, m), 3.98-3.96 (1H, m), 3.86 (3H, s), 3.82 (3H, s), 3.44 (1H, m), 3.36 (1H, m), 3.05 (1H, m), 1.28-1.21 (3H, m), 1.10-1.07 (18H, m).
MS(APCI, ESI)m/z:609(M+H)$^+$

Step 6: Prop-2-en-1-yl (11aS)-11-{[tert-butyl(dimethyl)silyl]oxy}-7-methoxy-2-(4-methoxyphenyl)-5-oxo-8-{[tri(propan-2-yl)silyl]oxy}-11,11a-dihydro-1H-pyrrolo[2,1-c][1,4]benzodiazepin-10(5H)-carboxylate The compound obtained in step 5 (0.532 g, 0.874 mmol) was reacted in the same manner as in step 9 of Example 1 to afford the desired compound (0.532 g, 95%). 1H-NMR (CDCl$_3$) δ:7.35 (1H, s), 7.29 (2H, m), 7.23 (1H, s), 6.89 (2H, m), 6.70 (1H, s), 5.90 (1H, m), 5.76 (1 H,m), 5.14-5.10 (2H, m), 4.60 (1H, m), 4.38 (1H, m), 3.93-3.85 (1H, m), 3.87 (3H, s), 3.82 (3H, s), 3.32 (1H, m), 2.82-2.78 (1H, m), 1.29-1.22 (3H, m), 1.12-1.07 (18H, m), 0.89 (9H, s), 0.27 (3H, s), 0.20 (3H, s).
MS(APCI, ESI)m/z:723(M+H)$^+$

Step 7: Prop-2-en-1-yl (11aS)-11-{[tert-butyl(dimethyl)silyl]oxy}-8-hydroxy-7-methoxy-2-(4-methoxyphenyl)-5-oxo-11,11a-dihydro-1H-pyrrolo[2,1-c][1,4]benzodiazepin-10(5H)-carboxylate The compound obtained in step 6 (0.532 g, 0.756 mmol) was reacted like step 10 of Example 1 to afford the desired compound (0.359 g, 86%).
$^1$H-NMR (CDCl$_3$) δ:7.34 (1H, s), 7.30-7.27 (3H, m), 6.90-6.88 (2H, m), 6.76 (1H, s), 5.93-5.90 (2H, m), 5.81-5.73 (1H, m), 5.12-5.08 (2H, m), 4.61 (1H, m), 4.42 (1H, m), 3.97 (3H, s), 3.93-3.88 (1H, m), 3.83 (3H, s), 3.31 (1H, m), 2.83-2.79 (1H, m), 0.91 (9H, s), 0.27 (3H, s), 0.22 (3H, s).
MS(APCI, ESI)m/z:567(M+H)$^+$

Step 8: Prop-2-en-1-yl (11aS)-8-(3-bromopropoxy)-11-{[tert-butyl(dimethyl)silyl]oxy}-7-methoxy-2-(4-methoxyphenyl)-5-oxo-11,11a-dihydro-1H-pyrrolo[2,1-c][1,4]benzodiazepin-10(5H)-carboxylate The compound obtained in step 7 (0.405 g, 0.715 mmol) was reacted in the same manner as in step 1 of Example 4 to afford the desired compound (0.490 g, 99%).
$^1$H-NMR (CDCl$_3$) δ:7.35 (1H, s), 7.29 (2H, m), 6.89 (2H, m), 6.69 (1H, s), 5.94 (1H, m), 5.82-5.75 (1H, m), 5.13-5.08 (1H, m), 5.13-5.08 (2H, m), 4.65 (1H, m), 4.41 (1H, m), 4.20-4.13 (2H, m), 3.94-3.88 (1H, m), 3.92 (3H, s), 3.83 (3H, s), 3.62 (2H, m), 3.32 (1H, m), 2.83-2.80 (1H, m), 2.41-2.36 (2H, m), 0.91 (9H, s), 0.27 (3H, s), 0.24 (3H, s).
MS(APCI, ESI)m/z:687(M+H)$^+$

Step 9: N-[(Prop-2-en-1-yloxy)carbonyl]-L-valyl-N-{4-[({[(11a'S)-8'-[3-({(11aS)-11-{[tert-butyl(dimethyl)silyl]oxy}-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)propoxy]-11'-hydroxy-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 8 (0.490 g, 0.713 mmol) was reacted in the same manner as in step 10 of Example 3 to afford the desired compound (0.600 g, 60%).
MS(APCI, ESI)m/z:1414(M+H)$^+$ Step 10: N-[(Prop-2-en-1-yloxy)carbonyl]-L-valyl-N-{4-[({[(11a'S)-11'-hydroxy-8'-[3-({(11aS)-11-hydroxy-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)propoxy]-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 9 (0.600 g, 0.424 mmol) was reacted in the same manner as in step 11 of Example 3 to afford the desired compound (0.500 g, 99%).
MS(APCI, ESI)m/z:1184(M−H)+

Step 11: L-Valyl-N-{4-[({[(11a'S)-11'-hydroxy-7'-methoxy-8'-(3-{[(11aS)-7-methoxy-2-(4-methoxyphenyl)-5-oxo-5,11a-dihydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 9 (0.500 g, 0.421 mmol) was reacted in the same manner as in step 12 of Example 3 to afford the desired compound (0.113 g, 27%).
¹H-NMR (CDCl₃) δ:8.94 (1H, s), 7.70 (1H, s), 7.56-7.53 (2H, m), 7.46-7.44 (2H, m), 7.36 (1H, s), 7.31 (2H, m), 7.23 (1H, s), 7.03 (2H, m), 6.90-6.88 (2H, m), 6.68 (1H, m), 6.57 (1H, s), 6.40 (1H, s), 5.92 (1H, m), 5.43 (1H, m), 4.67 (1H, m), 4.55-4.53 (1H, m), 4.46 (1H, m), 4.35-4.33 (1H, m), 4.28-4.24 (1H, m), 4.15-4.13 (1H, m), 3.88 (3H, s), 3.87 (3H, s), 3.83 (3H, s), 3.77-3.72 (1H, m), 3.62-3.60 (1H, m), 3.52-3.47 (2H, m), 3.34 (1H, m), 3.30-3.28 (1H, m), 3.00-2.91 (2H, m), 2.50-2.41 (2H, m), 2.24-2.22 (1H, m), 2.10-2.08 (1H, m), 1.77-1.75 (1H, m), 1.40-1.37 (1H, m), 1.16 (3H, m), 0.82 (3H, m), 0.76-0.62 (4H, m), 0.69 (3H, m).
MS(APCI, ESI)m/z:1000(M+H)+

Step 12: N-[4-(11,12-Didehydrodibenzo[b,f]azocin-5 (6H)-yl)-4-oxobutanoyl]glycylglycyl-L-valyl-N-{4-[({[(11a'S)-11'-hydroxy-7'-methoxy-8'-(3-{[(11aS)-7-methoxy-2-(4-methoxyphenyl)-5-oxo-5,11a-dihydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 11 (0.157 g, 0.157 mmol) was reacted in the same manner as in step 13 of Example 3 to afford the desired compound (0.120 g, 49%).
MS(APCI, ESI)m/z:1401(M+H)+

Example 20: Drug-Linker 18

[Formula 144]

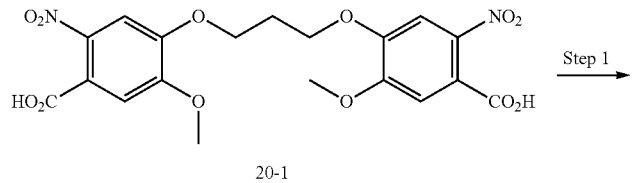

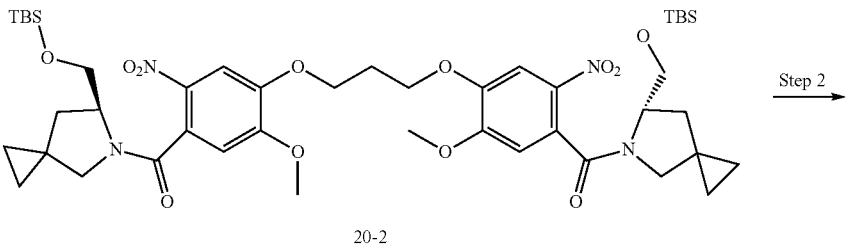

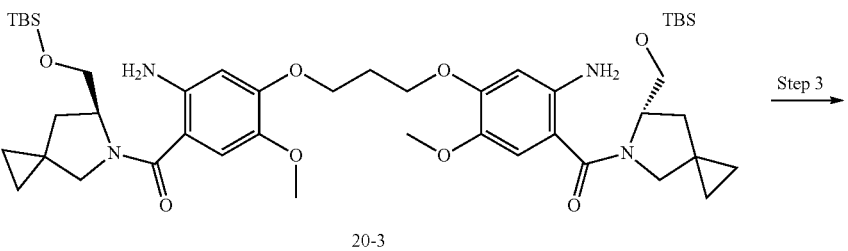

-continued
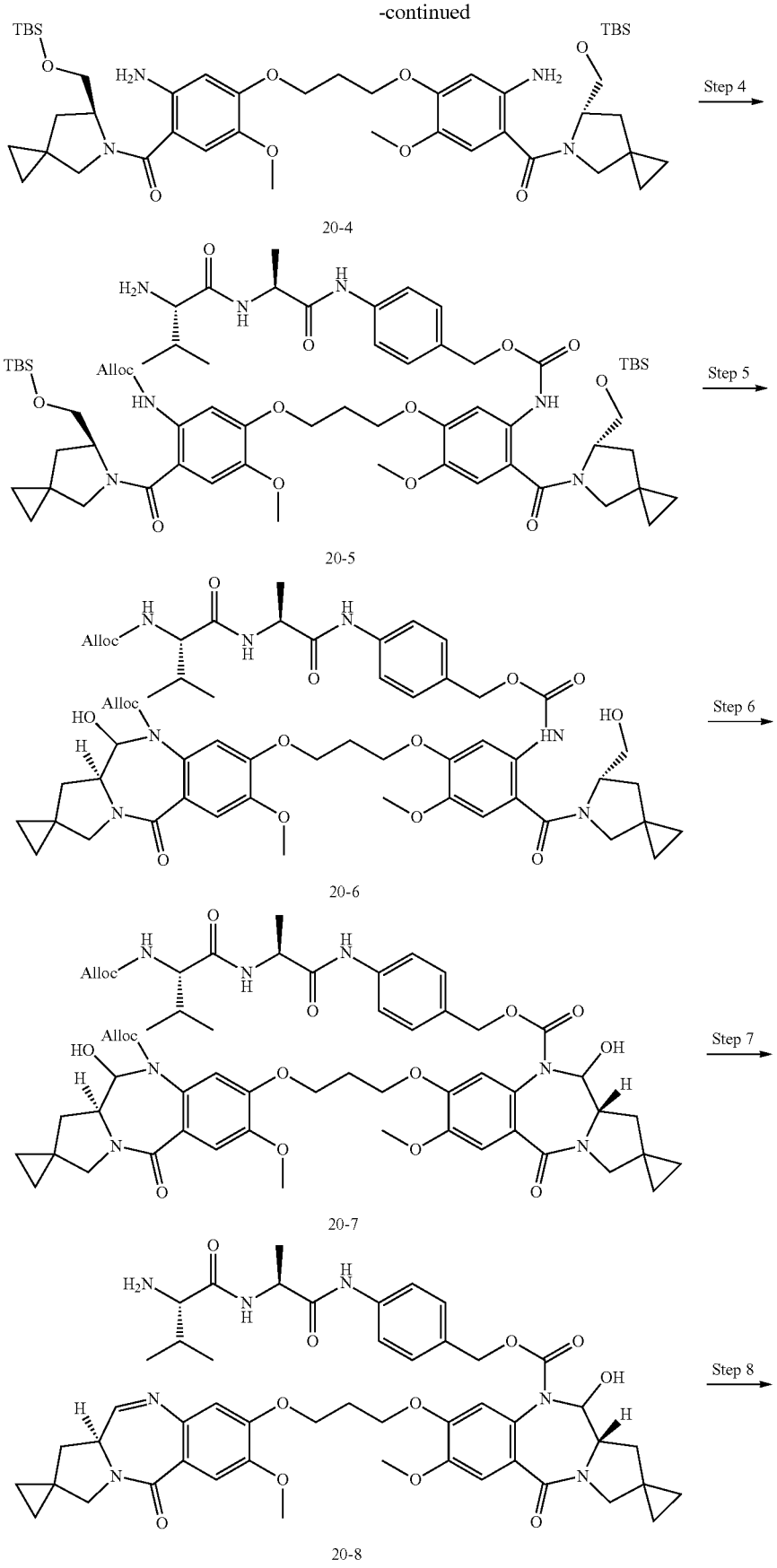
20-4
20-5
20-6
20-7
20-8

-continued

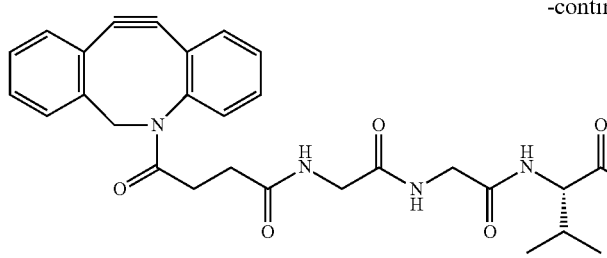
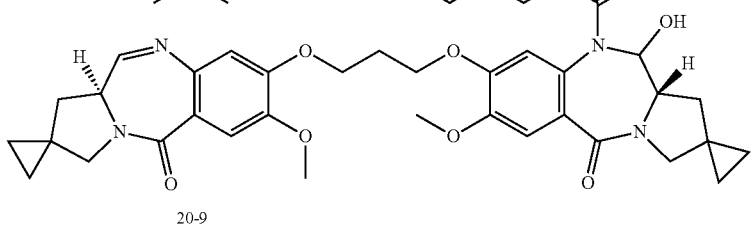

20-9

Step 1: {Propan-1,3-diylbis[oxy (5-methoxy-2-nitrobenzen-4,1-diyl)]}bis{[(6S)-6-({[tert-butyl(dimethyl)silyl]oxy}methyl)-5-azaspiro[2.4]hept-5-yl]methanone}

Starting raw material 20-1 (3.00 g, 6.43 mmol, Journal of the American Chemical Society 1992, 13, 4939) and the compound obtained in step 3 of Example 1 (3.42 g, 14.2 mmol) were reacted in the same manner as in step 1 of Example 15 to afford the desired compound (3.74 g, 64%).

$^{1}$H-NMR (CDCl$_{3}$) δ:7.79-7.70 (2H, m), 6.83-6.75 (2H, m), 4.52-4.50 (1.5H,m), 4.35-4.29 (4.5H,m), 4.03 (0.5H,m), 3.97-3.92 (6H, m), 3.88 (0.5H,m), 3.60-3.52 (1H, m), 3.38-3.33 (0.5H,m), 3.26-3.24 (0.5H,m), 3.04-2.93 (3H, m), 2.45-2.39 (2H, m), 2.25-2.21 (1H, m), 2.09-1.98 (1H, m), 1.68 (1H, m), 1.56 (1H, m), 0.93-0.90 (14H, m), 0.77-0.74 (4H, m), 0.71-0.62 (4H, m), 0.57-0.49 (4H, m), 0.44-0.40 (2H, m), 0.11 (9H, m), −0.14 (3H, m).

MS(APCI, ESI)m/z:912(M+H)$^{+}$

Step 2: {Propan-1,3-diylbis[oxy (2-amino-5-methoxybenzen-4,1-diyl)]}bis{[(6S)-6-({[tert-butyl(dimethyl)silyl]oxy}methyl)-5-azaspiro[2.4]hept-5-yl]methanone}}

The compound obtained in step 1 (3.74 g, 4.10 mmol) was reacted in the same manner as in step 4 of Example 15 to afford the desired compound (2.97 g, 85%).

$^{1}$H-NMR (CDCl$_{3}$) δ:7.79-7.69 (2H, m), 6.82-6.75 (2H, m), 4.54-4.47 (1.5H,m), 4.36-4.26 (4.5H,m), 4.03 (0.5H,m), 3.98-3.92 (6H, m), 3.88 (0.5H,m), 3.61-3.51 (1H, m), 3.39-3.32 (0.5H,m), 3.28-3.21 (0.5H,m), 3.05-2.93 (3H, m), 2.45-2.39 (2H, m), 2.24-2.21 (1H, m), 2.08-2.06 (1H, m), 2.00-1.99 (1H, m), 1.69-1.66 (1H, m), 1.57-1.54 (5H, m), 0.94-0.88 (14H, m), 0.78-0.74 (4H, m), 0.71-0.62 (4H, m), 0.57-0.49 (4H, m), 0.44-0.40 (2H, m), 0.13-0.10 (9H, m), −0.11-0.17 (3H, m).

MS(APCI, ESI)m/z:853(M+H)$^{+}$

Step 3: Prop-2-en-1-yl (5-[3-(5-amino-4-{[(6S)-6-({[tert-butyl(dimethyl)silyl]oxy}methyl)-5-azaspiro[2.4]hept-5-yl]carbonyl}-2-methoxyphenyl)propoxy]-2-{[(6S)-6-({[tert-butyl(dimethyl)silyl]oxy}methyl)-5-azaspiro[2.4]hept-5-yl]carbonyl}-4-methoxyphenyl)carbamate The compound obtained in step 2 (2.97 g, 3.48 mmol) was reacted in the same manner as in step 5 of Example 15 to afford the desired compound (0.549 g, 17%). 1H-NMR (CDCl$_{3}$) δ:9.18 (1H, m), 7.88 (1H, m), 6.80 (1H, m), 6.73 (1H, s), 6.31 (1H, s), 5.96 (1H, m), 5.36 (1H,m), 5.24 (1H, m), 4.68-4.59 (4H, m), 4.59-4.43 (2H, m), 4.27-4.25 (2H, m), 4.20-4.18 (2H, m), 4.00 (2H, m), 3.79-3.72 (9H, m), 3.05 (1H, m), 2.35 (2H, m), 2.32-2.19 (2H, m), 1.78-1.50 (4H, m), 0.99-0.89 (20H, m), 0.67-0.54 (4H, m), 0.50-0.48 (2H, m), 0.05 (12H, m).

MS(APCI, ESI)m/z:1021(M+H)$^{+}$

Step 4: N-[(Prop-2-en-1-yloxy)carbonyl]-L-valyl-N-[4-({[(2-{[(6S)-6-({[tert-butyl(dimethyl)silyl]oxy}methyl)-5-azaspiro[2.4]hept-5-yl]carbonyl}-5-[3-(4-{[(6S)-6-({[tert-butyl(dimethyl)silyl]oxy}methyl)-5-azaspiro[2.4]hept-5-yl]carbonyl}-2-methoxy-5-{[(prop-2-en-1-yloxy)carbonyl]amino}phenoxy)propoxy]-4-methoxyphenyl)carbamoyl]oxy}methyl)phenyl]-L-alaninamide The compound obtained in step 3 (0.549 g, 0.586 mmol) was reacted in the same manner as in step 6 of Example 1 to afford the desired compound (0.402 g, 51%).

MS (APCI, ESI)m/z:1341 (M+H)$^{+}$

Step 5: N-[(Prop-2-en-1-yloxy)carbonyl]-L-valyl-N-[4-({[(2-{[(6S)-6-(hydroxymethyl)-5-azaspiro[2.4]hept-5-yl]carbonyl}-5-[3-(4-{[(6S)-6-(hydroxymethyl)-5-azaspiro[2.4]hept-5-yl]carbonyl}-2-methoxy-5-{[(prop-2-en-1-yloxy)carbonyl]amino}phenoxy)propoxy]-4-methoxyphenyl)carbamoyl]oxy}methyl)phenyl]-L-alaninamide The compound obtained in step 4 (0.402 g, 0.300 mmol) was reacted in the same manner as in step 7 of Example 1 to afford the desired compound (0.282 g, 85%).

MS (APCI, ESI)m/z:1120 (M+H)$^{+}$

Step 6: N-[(Prop-2-en-1-yloxy)carbonyl]-L-valyl-N-{4-[({[(11a'S)-11'-hydroxy-8'-[3-({(11a'S)-11'-hydroxy-7'-methoxy-5'-oxo-10'-[(prop-2-en-1-yloxy)carbonyl]-5',10',11',11a'-tetrahydro-1'H-spiro[cyclopropane-1,2'-pyrrolo[2,1-c][1,4]benzodiazepine]-8'-yl}oxy)propoxy]-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 5 (0.282 g, 0.253 mmol) was reacted in the same manner as in step 8 of Example 1 to afford the desired compound (0.0600 g, 21%).
MS (APCI, ESI)m/z:1106 (M−H)+

Step 7: L-Valyl-N-{4-[({[(11a'S)-11'-hydroxy-7'-methoxy-8'-(3-{[(11a'S)-7'-methoxy-5'-oxo-5',11a'-dihydro-1'H-spiro[cyclopropane-1,2'-pyrrolo[2,1-c][1,4]benzodiazepine]-8'-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 6 (0.0600 g, 0.0541 mmol) was reacted in the same manner as in step 12 of Example 3 to afford the desired compound (0.0347 g, 70%).
MS (APCI, ESI)m/z:922 (M+H)+

Step 8: N-[4-(11,12-Didehydrodibenzo[b,f]azocin-5(6H)-yl)-4-oxobutanoyl]glycylglycyl-L-valyl-N-{4-[({[(11a'S)-11'-hydroxy-7'-methoxy-8'-(3-{[(11a'S)-7'-methoxy-5'-oxo-5',11a'-dihydro-1'H-spiro[cyclopropane-1,2'-pyrrolo[2,1-c][1,4]benzodiazepine]-8'-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 7 (0.0347 g, 0.0376 mmol) was reacted in the same manner as in step 13 of Example 3 to afford the desired compound (0.00770 g, 16%).

MS (APCI, ESI)m/z:1323 (M+H)+

Example 21: Drug-Linker 19

[Formula 145]

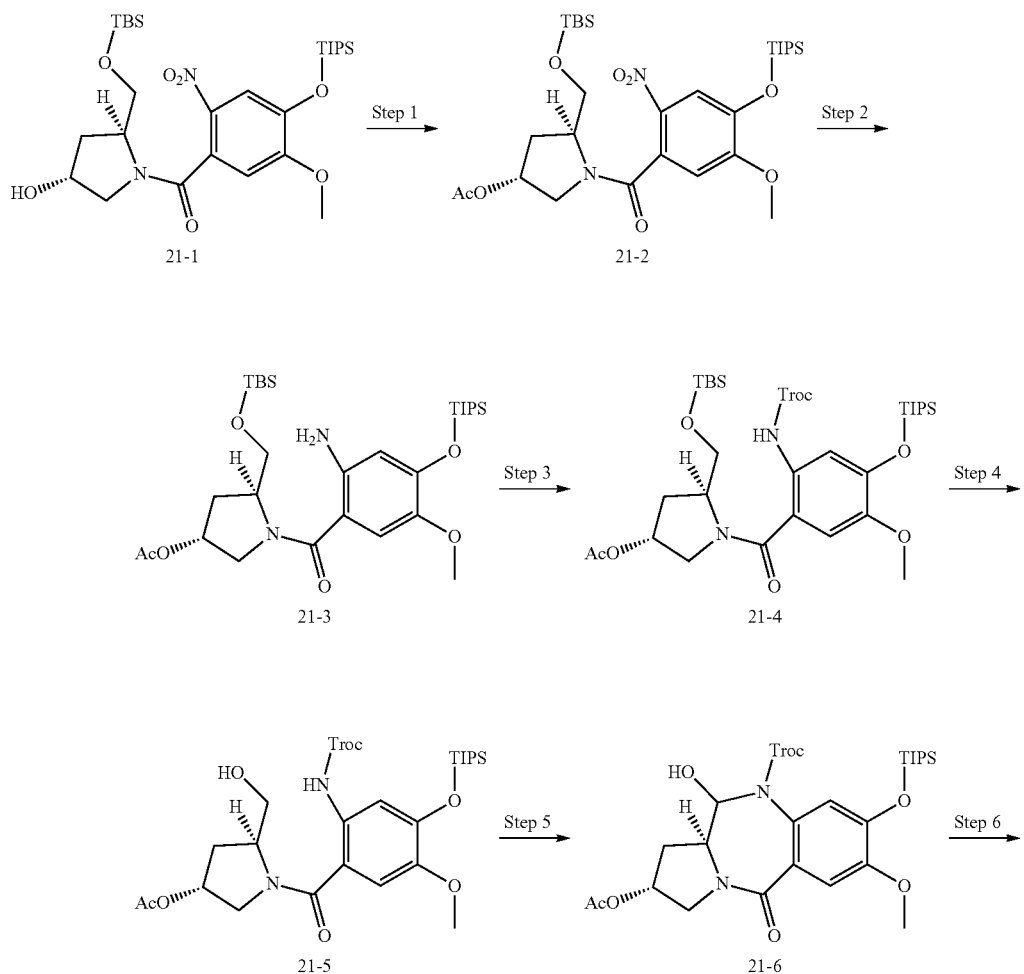

-continued
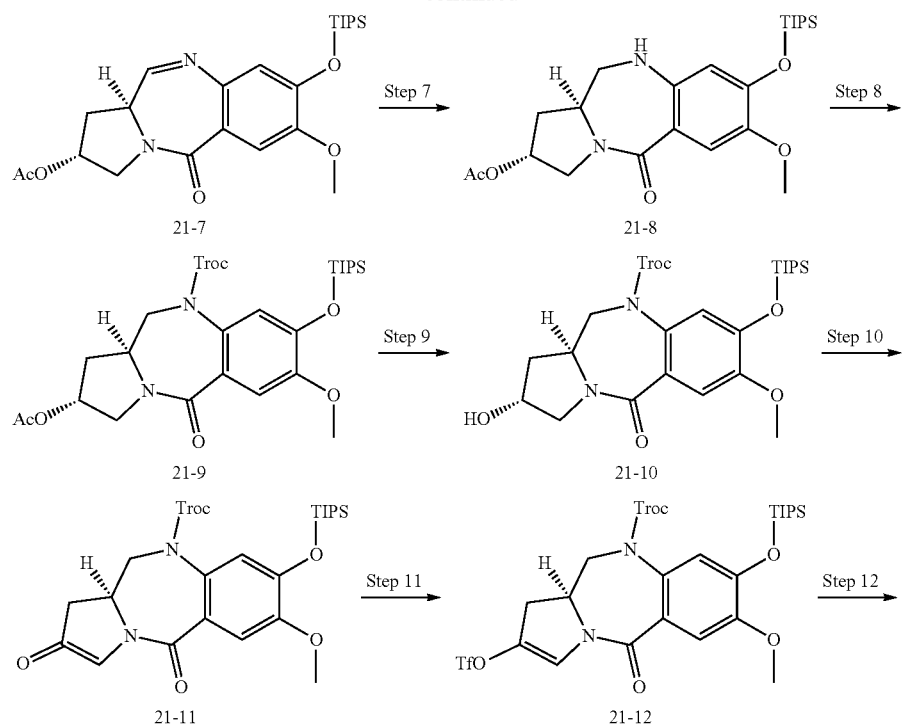
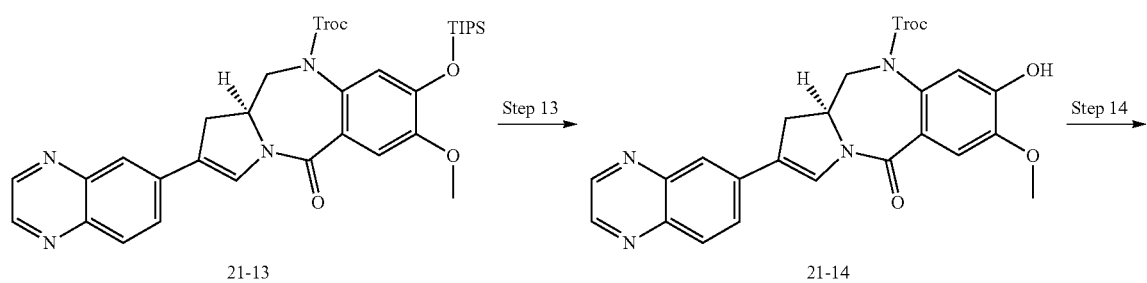
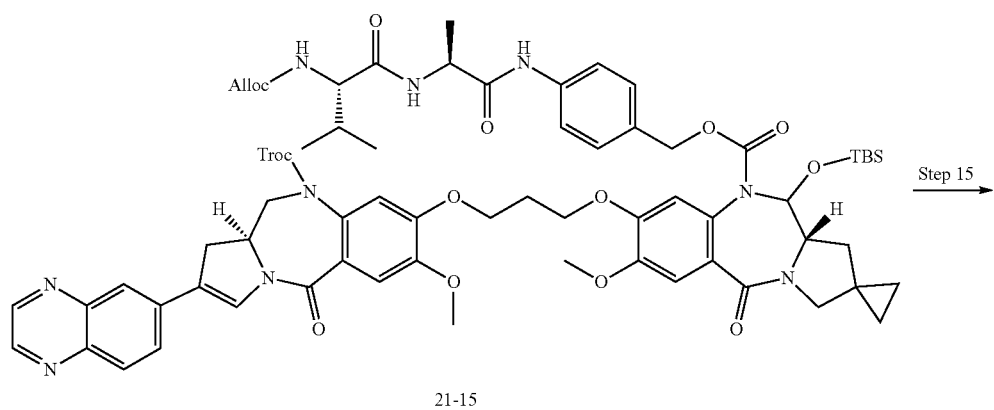

-continued
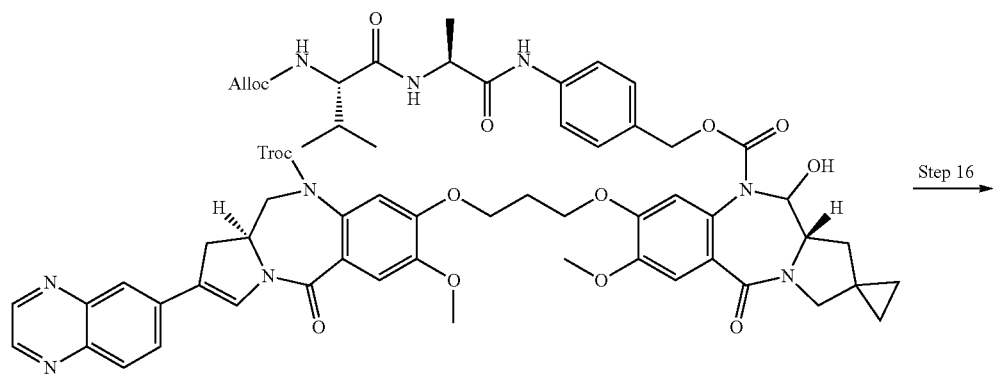
21-16
Step 16 →
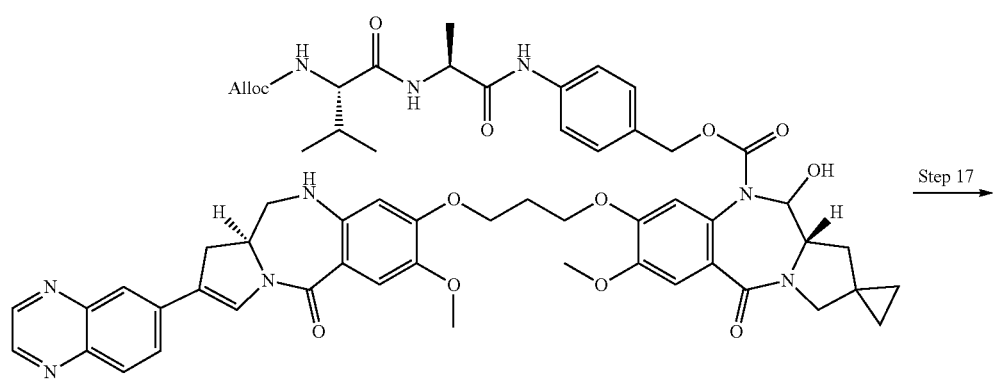
21-17
Step 17 →
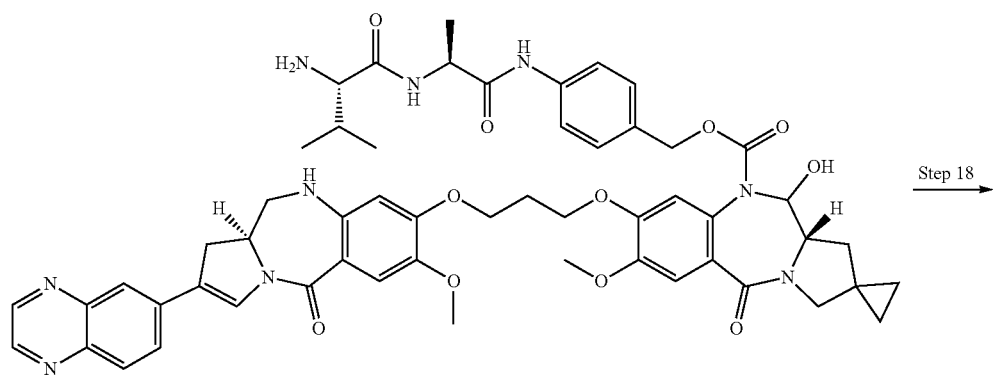
21-18
Step 18 →

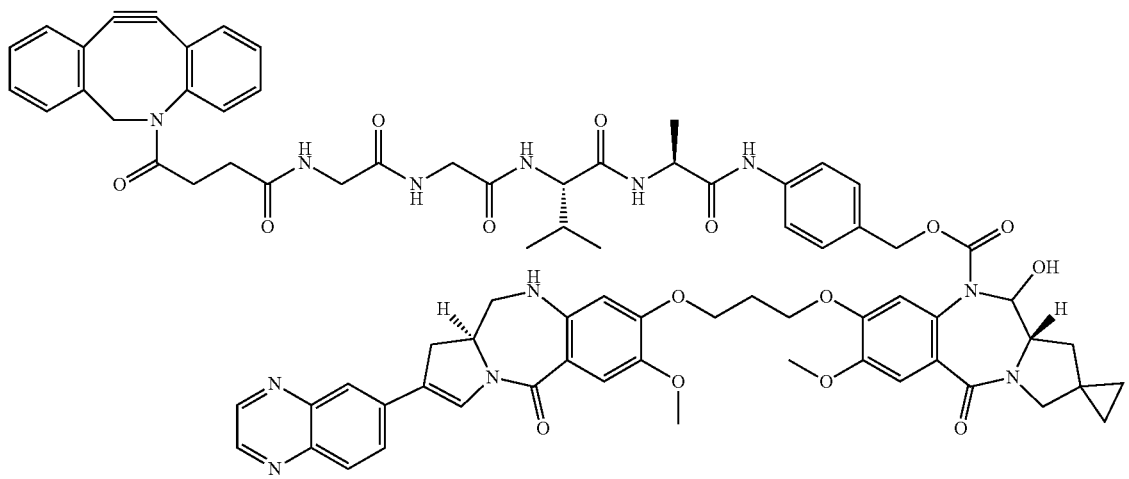

21-19

Step 1: Compound 21-2

To a solution of starting raw material 21-1 (11.8 g, 20.2 mmol, WO 2013053872) and pyridine (1.79 mL, 22.2 mmol) in THF (50 mL), acetic anhydride (2.10 mL, 22.3 mmol) was slowly added under ice-cooling. Subsequently, 4-dimethylaminopyridine (0.459 g, 3.76 mmol) was added thereto, and the resultant was stirred at room temperature. After the raw materials disappeared, water was added to the reaction mixture, which was extracted with ethyl acetate. The organic layer was washed with water and brine, and dried over anhydrous sodium sulfate. The resultant was filtered and then distillated under reduced pressure, and the resulting residue was purified by silica gel column chromatography [hexane:ethyl acetate=90:10 (v/v) to 60:40 (v/v)] to afford the desired compound (12.3 g, 97%).

MS(APCI, ESI)m/z:625(M+H)$^+$

Step 2: Compound 21-3

The compound obtained in step 1 (12.3 g, 19.7 mmol) was reacted in the same manner as in step 4 of Example 15 to afford the desired compound (11.3 g, 97%)

MS(APCI, ESI)m/z:595(M+H)$^+$

Step 3: Compound 21-4

The compound obtained in step 2 (11.3 g, 19.0 mmol) was reacted in the same manner as in step 9 of Example 3, except that 2,2,2-trichloroethyl chloroformate (2.93 mL, 21.9 mmol) was used in place of allyl chloroformate, to afford the desired compound (12.4 g, 85%).

MS(APCI, ESI)m/z:769(M+H)$^+$

Step 4: Compound 21-5

The compound obtained in step 3 (12.4 g, 16.1 mmol) was reacted in the same manner as in step 7 of Example 1 to afford the desired compound (9.90 g, 94%).

MS(APCI, ESI)m/z:655(M+H)$^+$

Step 5: Compound 21-6

The compound obtained in step 4 (9.90 g, 15.1 mmol) was reacted in the same manner as in step 8 of Example 1 to afford the desired compound (8.19 g, 83%).

MS(APCI, ESI)m/z:653(M+H)$^+$

Step 6: Compound 21-7

To the compound obtained in step 5 (3.00 g, 4.59 mmol) in tetrahydrofuran (10 mL) and a 10% aqueous solution of ammonium acetate (10 mL), 10% Cd/Pb (3.00 g, 24.0 mmol, 90 mass %) was added, and the resultant was vigorously stirred under the nitrogen atmosphere.

After the raw materials disappeared, the reaction mixture was filtered. The filtrate was extracted with dichloromethane. The organic layer was washed with brine, and dried over anhydrous sodium sulfate. The resultant was filtered, and then distillated under reduced pressure, and the resulting compound (2.10 g, 99%) was directly used for the subsequent reaction.

MS(APCI, ESI)m/z:461(M+H)$^+$

Step 7: Compound 21-8

The compound obtained in step 6 (2.10 g, 4.56 mmol) was reacted in the same manner as in step 8 of Example 3 to afford the desired compound (2.09 g, 99%).

MS(APCI, ESI)m/z:463(M+H)$^+$

Step 8: Compound 21-9

The compound obtained in step 7 (2.09 g, 4.52 mmol) was reacted in the same manner as in step 3 of Example 21 to afford the desired compound (2.88 g, 100%).

$^1$H-NMR (CDCl$_3$) δ:7.23 (1H, s), 6.81 (1H, s), 5.40-5.37 (1H, m), 4.95 (1H, m), 4.41 (1H, m), 4.21 (1H, m), 4.05 (1H, m), 3.96-3.92 (1H, m), 3.86 (3H, s), 3.79-3.75 (1H, m), 3.64

(1H, m), 2.34-2.28 (1H, m), 2.18-2.13 (1H, m), 2.05 (3H, s), 1.30-1.19 (3H, m), 1.11-1.04 (18H, m).
MS(APCI, ESI)m/z:637(M+H)+

Step 9: Compound 21-10

To a mixed solution of the compound obtained in step 8 (2.28 g, 4.51 mmol) in methanol (15 mL) and tetrahydrofuran (5 mL), a solution of potassium carbonate (0.624 g, 4.52 mmol) in water (15 mL) was slowly added dropwise, and the resultant was stirred at room temperature. After the raw materials disappeared, water was added to the reaction mixture, which was extracted with ethyl acetate. The organic layer was washed with brine, and dried over anhydrous sodium sulfate. The resultant was filtered, and then distillated under reduced pressure, and the resulting residue was purified by silica gel column chromatography [hexane:ethyl acetate=90:10 (v/v) to 0:100 (v/v)] to afford the desired compound (2.08 g, 77%).
$^1$H-NMR (CDCl$_3$) δ:7.18 (1H, s), 6.80 (1H, s), 4.96 (1H, m), 4.64-4.59 (1H, m), 4.40 (1H, m), 4.18 (1H, m), 4.00-3.92 (2H, m), 3.82 (3H, s), 3.65 (2H, m), 2.28-2.20 (2H, m), 2.04-1.97 (1H, m), 1.27-1.20 (3H, m), 1.09-1.05 (18H, m).
MS(APCI, ESI)m/z:595(M+H)+

Step 10: Compound 21-11

To a solution of the compound obtained in step 9 (2.08 g, 3.49 mmol) and 2,2,6,6-tetramethyl-1-piperidyloxy radical (0.109 g, 0.698 mmol) in dichloromethane (50 mL), iodobenzene diacetate (2.00 g, 6.21 mmol) was slowly added under ice-cooling. The reaction mixture was stirred at room temperature for 2 hours. After the raw materials disappeared, water was added to the reaction mixture, and the reaction mixture was extracted with dichloromethane. The organic layer was washed with water and brine, and dried over anhydrous magnesium sulfate. The resultant was filtered, and then distillated under reduced pressure, and the resulting residue was purified by silica gel column chromatography [hexane:ethyl acetate=90:10 (v/v) to 60:40 (v/v)] to afford the desired compound (1.94 g, 94%).
$^1$H-NMR (CDCl$_3$) δ:7.21 (1H, s), 6.84 (1H, s), 4.96 (1H, m), 4.44 (1H, m), 4.34-4.23 (3H, m), 3.99-3.92 (1H, m), 3.86 (3H, s), 3.68-3.62 (1H, m), 2.94 (1H, m), 2.50-2.46 (1H, m), 1.29-1.21 (3H, m), 1.21-1.21 (18H, m).
MS(APCI, ESI)m/z:593(M+H)+

Step 11: Compound 21-12

The compound obtained in step 10 (1.94 g, 3.27 mmol) was reacted in the same manner as in step 5 of Example 3 to afford the desired compound (2.17 g, 92%).
$^1$H-NMR (CDCl$_3$) δ:7.22-7.18 (2H, m), 6.84 (1H, s), 4.95 (1H, m), 4.45-4.39 (2H, m), 4.23-4.15 (1H, m), 3.85 (3H, s), 3.64 (1H, m), 3.36-3.30 (1H, m), 2.74-2.68 (1H, m), 1.29-1.19 (3H, m), 1.11-1.04 (18H, m).

Step 12: Compound 21-13

The compound obtained in step 11 (0.837 g, 1.15 mmol) and quinoxaline-6-boronic acid pinacol ester (1.18 g, 4.61 mmol) were reacted in the same manner as in step 6 of Example 3 to afford the desired compound (0.713 g, 88%).
$^1$H-NMR (CDCl$_3$) δ:8.82-8.77 (2H, m), 8.05 (1H, m), 7.95 (1H, m), 7.79-7.75 (2H, m), 7.25 (1H, s), 6.88 (1H, s), 4.96 (1H, m), 4.49-4.40 (2H, m), 4.37-4.28 (1H, m), 3.88 (3H, s), 3.75 (1H, m), 3.48 (1H, m), 2.90 (1H, m), 1.30-1.22 (3H, m), 1.13-1.06 (18H, m).
MS(APCI, ESI)m/z:705(M+H)+

Step 13: Compound 21-14

The compound obtained in step 12 (0.713 g, 1.01 mmol) was reacted in the same manner as in step 10 of Example 1 to afford the desired compound (0.400 g, 72%).
$^1$H-NMR (CDCl$_3$) δ:8.81-8.80 (2H, m), 8.05 (1H, m), 7.95 (1H, m), 7.80-7.75 (2H, m), 7.29 (1H, s), 6.96 (1H, s), 6.10 (1H, m), 5.07 (1H, m), 4.45-4.32 (3H, m), 3.98 (3H, s), 3.80-3.73 (1H, m), 3.51-3.46 (1H, m), 2.91 (1H, m).
MS(APCI, ESI)m/z:549(M+H)+

Step 14: Compound 21-15 Using the compound obtained in step 11 of Example 1 (0.321 g, 0.346 mmol), the compound obtained in step 13 (0.200 g, 0.364 mmol) was subjected to coupling reaction in the same manner as in step 10 of Example 3 to afford the desired compound (0.475 g, 99%).

$^1$H-NMR (CDCl$_3$) δ:8.83-8.79 (2H, m), 8.65-8.55 (1H, m), 8.09-7.98 (2H, m), 7.92-7.82 (2H, m), 7.47-7.31 (2H, m), 7.24-7.19 (1H, m), 7.14-7.02 (2H, m), 6.97-6.88 (1H, m), 6.80-6.66 (1H, m), 6.55-6.47 (1H, m), 6.06-6.00 (1H, m), 5.97-5.85 (1H, m), 5.51-5.09 (3H, m), 4.82-4.71 (2H, m), 4.63-4.52 (2H, m), 4.48-4.30 (2H, m), 4.26-4.17 (2H, m), 4.16-4.09 (1H, m), 4.08-3.98 (3H, m), 3.9-3.73 (6H, m), 3.53-3.44 (2H, m), 3.28-3.26 (1H, m), 2.94-2.91 (1H, m), 2.40-2.33 (2H, m), 2.21-2.13 (1H, m), 2.07-2.03 (4H, m), 1.67-1.50 (2H, m), 1.46-1.39 (2H, m), 1.29-1.24 (2H, m), 1.00-0.60 (18H, m), 0.22-0.06 (6H, m).
MS(APCI, ESI)m/z:1395(M+H)+

Step 15: Compound 21-16

The compound obtained in step 14 (0.475 g, 0.340 mmol) was reacted in the same manner as in step 11 of Example 3 to afford the desired compound (0.310 g, 71%).
$^1$H-NMR (CDCl$_3$) δ:8.83-8.79 (2H, m), 8.72 (1H, m), 8.07-8.01 (2H, m), 7.88 (2H, m), 7.41-7.39 (2H, m), 7.23 (1H, m), 7.13 (2H, m), 6.84 (1H, m), 6.56 (1H, s), 5.95-5.88 (2H, m), 5.48-5.47 (1H, m), 5.32-5.10 (3H, m), 4.87-4.72 (2H, m), 4.61-4.55 (2H, m), 4.47-4.20 (3H, m), 4.07-4.03 (2H, m), 3.90 (3H, s), 3.83 (3H, s), 3.80-3.72 (3H, m), 3.58 (1H, m), 3.49 (1H, m), 3.31 (1H, m), 2.92 (1H, m), 2.41 (1H, m), 2.36-2.29 (1H, m), 2.19-2.11 (1H, m), 1.77-1.72 (1H, m), 1.68-1.66 (3H, m), 1.65-1.63 (1H, m), 1.42-1.41 (3H, m), 0.97 (3H, m), 0.93 (3H, m), 0.76-0.61 (4H, m).
MS(APCI, ESI)m/z:1282(M+H)+

Step 16: Compound 21-17

The compound obtained in step 15 (0.310 g, 0.242 mmol) was reacted in the same manner as in step 6 of Example 21 to afford the desired compound (0.168 g, 63%).
$^1$H-NMR (CDCl$_3$) δ:8.85-8.76 (3H, m), 8.04-7.99 (3H, m), 7.86 (1H, s), 7.49-7.41 (3H, m), 7.25-7.06 (3H, m), 6.96-6.83 (1H, m), 6.49 (1H, m), 6.13 (1H, s), 5.51-5.45 (2H, m), 5.34-5.28 (2H, m), 5.21 (1H, m), 4.80-4.37 (4H, m), 4.17-4.02 (6H, m), 3.88 (3H, s), 3.84-3.70 (6H, m), 3.68-3.50 (5H, m), 3.31 (1H, m), 2.93-2.90 (1H, m), 2.42 (1H, m), 2.29-2.12 (3H, m), 1.78-1.75 (1H, m), 1.44 (3H, m), 0.97 (3H, m), 0.94 (3H, m), 0.79-0.60 (4H, m).
MS(APCI, ESI)m/z:1108(M+H)+

Step 17: Compound 21-18

The compound obtained in step 16 (0.168 g, 0.152 mmol) was reacted in the same manner as in step 12 of Example 3 to afford the desired compound (0.112 g, 72%).

¹H-NMR (CDCl₃) δ:9.18 (1H, m), 8.78 (2H, m), 8.04-8.02 (2H, m), 7.95-7.93 (2H, m), 7.77 (1H, s), 7.50-7.44 (3H, m), 7.23-7.21 (1H, m), 7.11 (2H, m), 6.44 (1H, m), 6.11 (1H, m), 5.90 (1H, m), 5.34 (1H, m), 4.74-4.63 (3H, m), 4.42 (1H, m), 4.16-4.03 (3H, m), 3.89 (3H, s), 3.80 (3H, s), 3.74-3.72 (1H, m), 3.65-3.51 (4H, m), 3.32-3.28 (3H, m), 2.92 (1H, m), 2.41 (1H, m), 2.34-2.28 (1H, m), 2.20-2.18 (2H, m), 1.76 (4H, m), 1.43 (3H, m), 1.00 (3H, m), 0.84 (3H, m), 0.75-0.62 (4H, m).

MS(APCI, ESI)m/z:1024(M+H)⁺

Step 18: N-[4-(11,12-Didehydrodibenzo[b,f]azocin-5 (6H)-yl)-4-oxobutanoyl]glycylglycyl-L-valyl-N-{4-[({[(11a'S)-11'-hydroxy-7'-methoxy-8'-(3-{[(11aS)-7-methoxy-5-oxo-2-(quinoxaline-6-yl)-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 18 (0.112 g, 0.109 mmol) was reacted in the same manner as in step 13 of Example 3 to afford the desired compound (0.110 g, 71%).

MS (APCI, ESI)m/z:1425 (M+H)⁺

Example 22: Drug-Linker 20

[Formula 146]

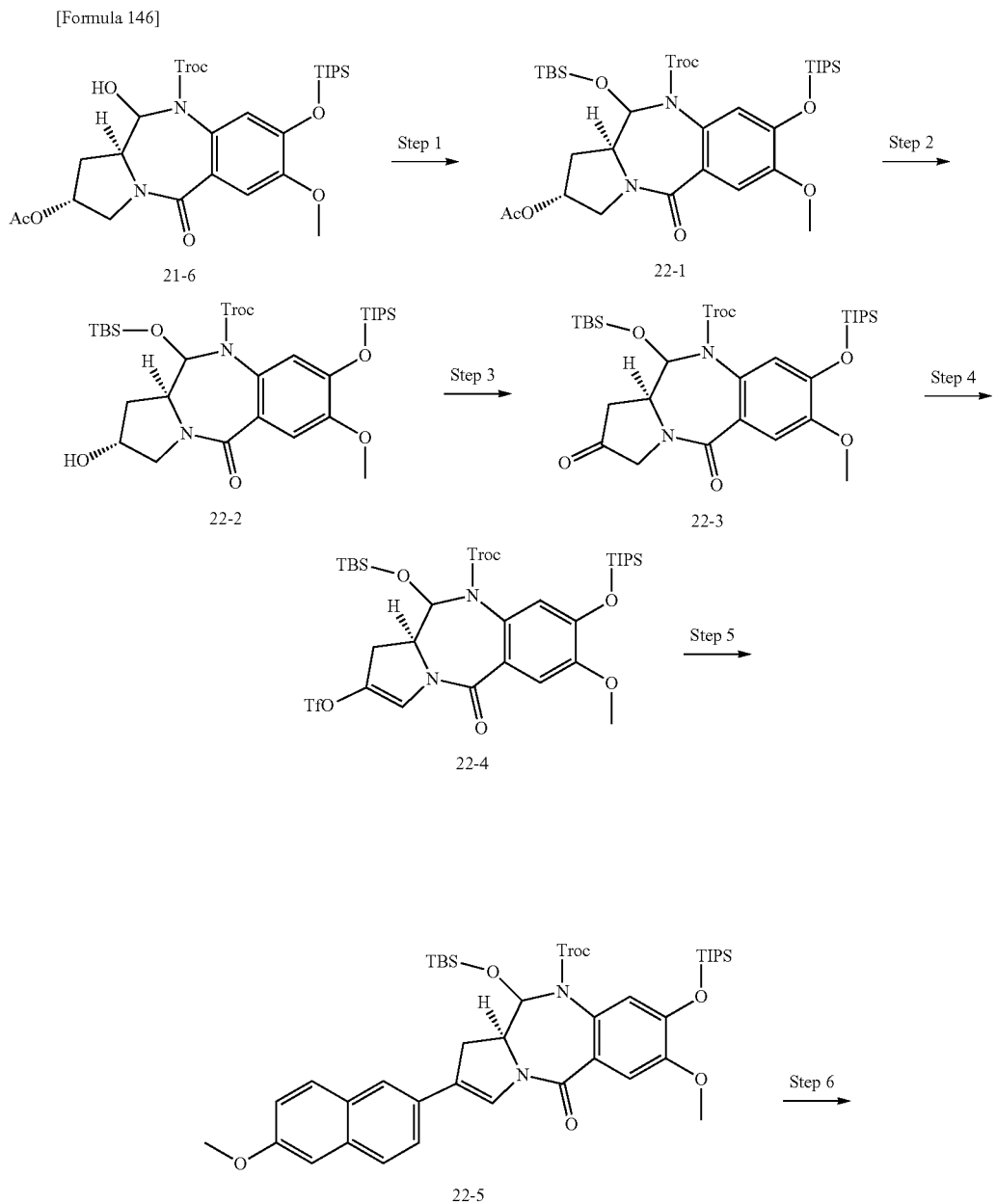

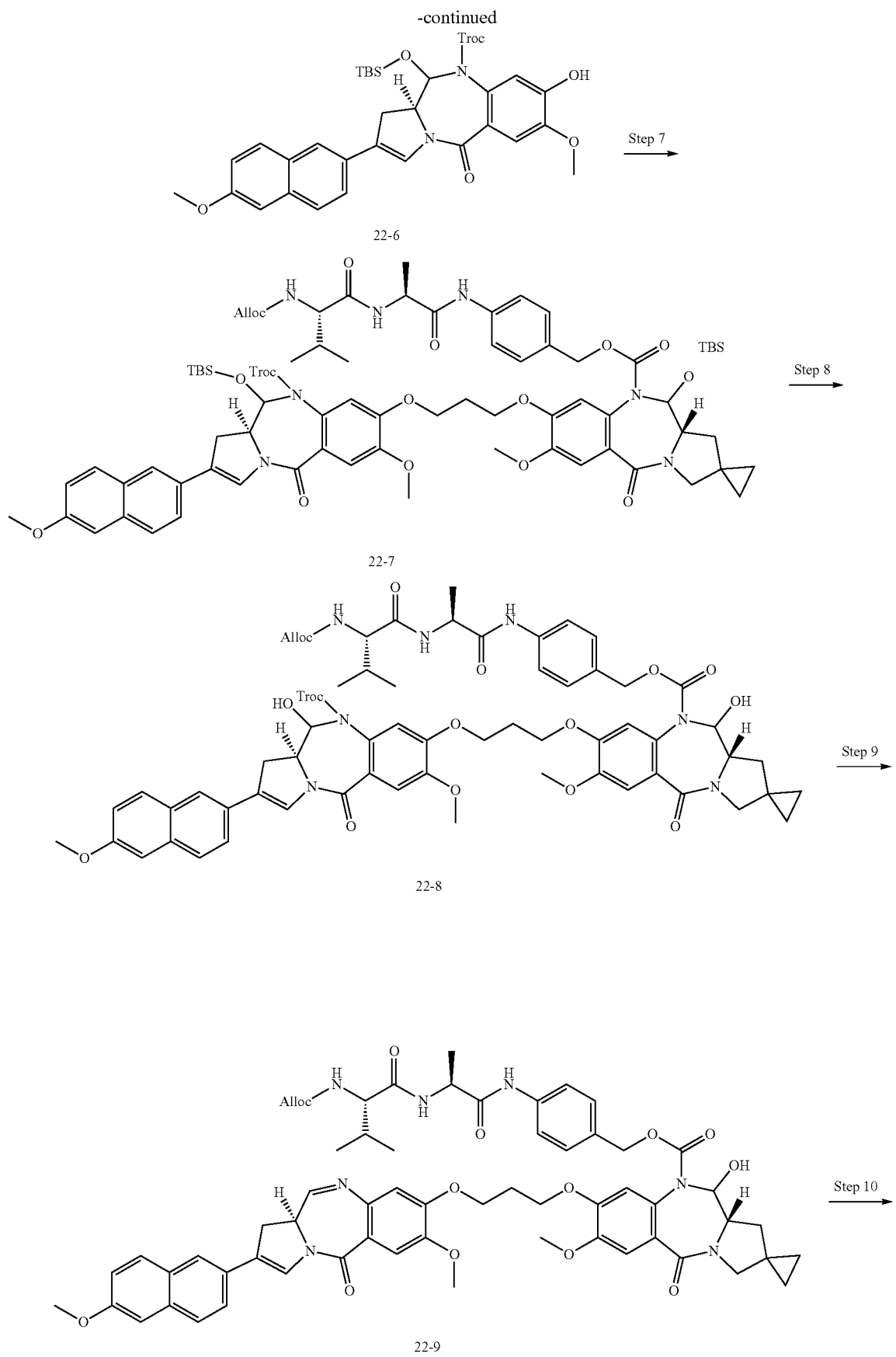

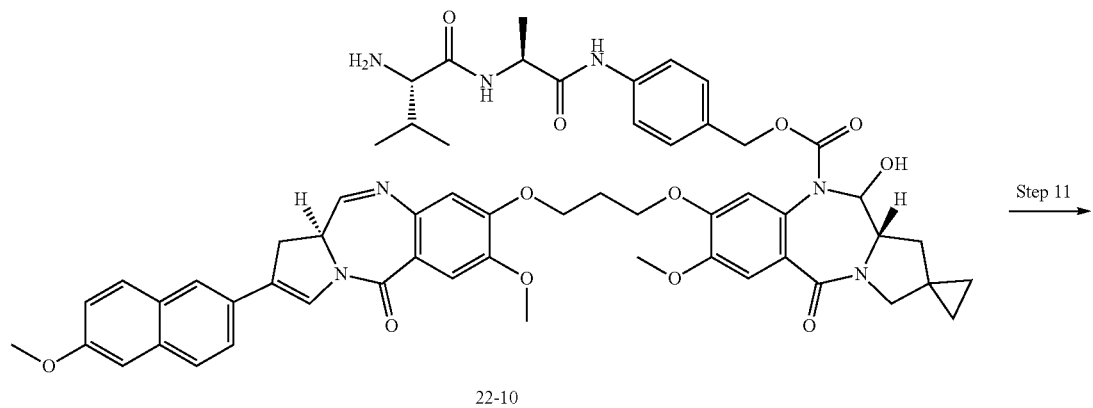
22-10
Step 11 →
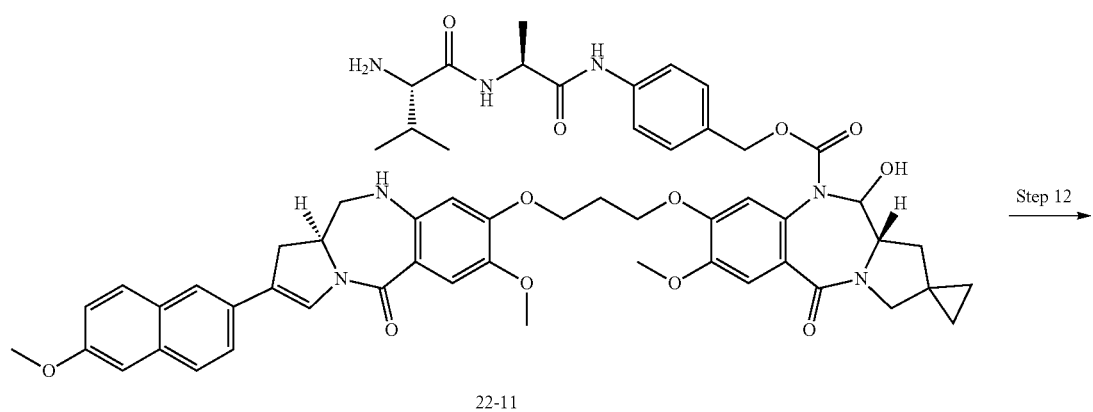
22-11
Step 12 →
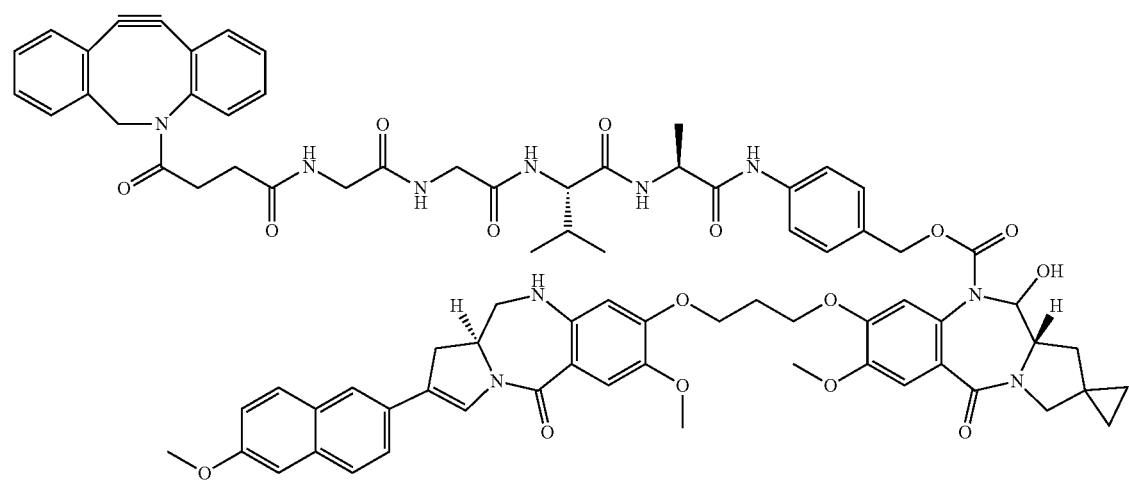
22-12

Step 1: Compound 22-1

The compound obtained in step 5 of Example 21 (5.11 g, 7.81 mmol) was reacted in the same manner as in step 9 of Example 1 to afford the desired compound (5.70 g, 95.00).
MS(APCI, ESI)m/z:767(M+H)$^+$

Step 2: Compound 22-2

The compound obtained in step 1 (5.70 g, 7.42 mmol) was reacted in the same manner as in step 9 of Example 21 to afford the desired compound (5.07 g, 94%).
MS(APCI, ESI)m/z:725(M+H)$^+$

Step 3: Compound 22-3

The compound obtained in step 2 (5.07 g, 6.98 mmol) was reacted in the same manner as in step 10 of Example 21 to afford the desired compound (4.44 g, 88%).
MS(APCI, ESI)m/z:723(M+H)$^+$

Step 4: Compound 22-4

The compound obtained in step 3 (4.44 g, 6.13 mmol) was reacted in the same manner as in step 5 of Example 3 to afford the desired compound (4.85 g, 92%).
$^1$H-NMR (CDCl$_3$):7.24-7.16 (1H, m), 6.78 (1H, s), 5.92 (1H, m), 5.05 (1H, m), 4.34 (1H, m), 3.91-3.87 (2H, m), 3.86 (3H, s), 3.35-3.29 (1H, m), 2.80 (1H, m), 1.28-1.22 (3H, m), 1.10-1.05 (18H, m), 0.86 (9H, s), 0.28 (3H, s), 0.21 (3H, s).

Step 5: Compound 22-5

The compound obtained in step 4 (1.20 g, 1.40 mmol) and 6-methoxy-2-naphthylboronic acid (0.850 g, 4.21 mmol) were used and reacted in the same manner as in step 6 of Example 3 to afford the desired compound (1.06 g, 88%).
$^1$H-NMR (CDCl$_3$) δ:7.72-7.69 (2H, m), 7.59-7.51 (3H, m), 7.30 (1H, s), 7.16-7.07 (2H, m), 6.82 (1H, s), 5.94 (1H, m), 5.06 (1H, m), 4.34 (1H, m), 3.99-3.95 (1H, m), 3.93 (3H, s), 3.88 (3H, s), 3.46 (1H, m), 2.94 (1H, m), 1.30-1.23 (3H, m), 1.12-1.07 (18H, m), 0.93 (9H, s), 0.31 (3H, s), 0.23 (3H, s).

Step 6: Compound 22-6

The compound obtained in step 5 (1.06 g, 1.23 mmol) was reacted in the same manner as in step 10 of Example 1 to afford the desired compound (0.6126 g, 71%).
MS(APCI, ESI)m/z:707(M+H)$^+$

Step 7: Compound 22-7

The compound obtained in step 6 (0.205 g, 0.290 mmol) and the compound obtained in step 11 of Example 1 (0.255 g, 0.274 mmol) were subjected to coupling reaction in the same manner as in step 10 of Example 3 to afford the desired compound (0.375 g, 83%).
$^1$H-NMR (CDCl$_3$) δ:8.68 (1H, s), 7.72 (2H, m), 7.67-7.55 (3H, m), 7.36-7.21 (4H, m), 7.16-7.06 (4H, m), 6.82-6.79 (2H, m), 6.53 (1H, s), 6.03-6.02 (1H, m), 5.97-5.89 (2H, m), 5.36-5.30 (2H, m), 5.23-5.16 (3H, m), 4.83-4.80 (1H, m), 4.75-4.72 (1H, m), 4.61-4.55 (3H, m), 4.33-4.29 (1H, m), 4.17-4.11 (2H, m), 4.06-4.01 (2H, m), 3.94 (3H, s), 3.92-3.90 (2H, m), 3.81 (3H, s), 3.72-3.70 (1H, m), 3.51-3.47 (2H, m), 3.26 (1H, m), 2.99-2.95 (1H, m), 2.42-2.32 (2H, m), 2.20-2.13 (1H, m), 1.55-1.40 (4H, m), 0.97-0.92 (18H, m), 0.84-0.81 (9H, m), 0.69-0.63 (4H, m), 0.30-0.05 (12H, m).

Step 8: Compound 22-8

The compound obtained in step 7 (0.375 g, 0.241 mmol) was reacted in the same manner as in step 11 of Example 3 to afford the desired compound (0.236 g, 74%).
$^1$H-NMR (CDCl$_3$) δ:8.70 (1H, s), 7.72-7.68 (3H, m), 7.63-7.58 (2H, m), 7.43-7.41 (2H, m), 7.27-7.22 (2H, m), 7.16-7.12 (2H, m), 6.91-6.86 (2H, m), 6.56 (1H, s), 5.95-5.84 (2H, m), 5.49 (1H, m), 5.34-5.14 (4H, m), 4.78 (1H, m), 4.64-4.53 (4H, m), 4.27-4.24 (2H, m), 4.17-4.02 (3H, m), 3.97-3.88 (2H, m), 3.93 (3H, s), 3.89 (3H, s), 3.88 (3H, s), 3.75-3.72 (2H, m), 3.61-3.48 (3H, m), 3.33-3.30 (2H, m), 3.23-3.19 (1H, m), 2.44-2.39 (2H, m), 2.29-2.27 (2H, m), 2.17-2.11 (1H, m), 1.76-1.72 (1H, m), 1.43 (3H, m), 0.95 (3H, m), 0.92 (3H, m), 0.77-0.61 (4H, m).

Step 9: Compound 22-9

The compound obtained in step 8 (0.236 g, 0.178 mmol) was reacted in the same manner as in step 6 of Example 21 to afford the desired compound (0.201 g, 99%).
MS(APCI, ESI)m/z:1134(M+H)$^+$

Step 10: Compound 22-10

The compound obtained in step 9 (0.201 g, 0.177 mmol) was reacted in the same manner as in step 12 of Example 3 to afford the desired compound (0.180 g, 97%).
$^1$H-NMR (CDCl$_3$) δ:9.17 (1H, s), 7.90 (1H, s), 7.72-7.68 (2H, m), 7.63-7.53 (4H, m), 7.44-7.42 (2H, m), 7.25-7.22 (1H, m), 7.16-7.12 (3H, m), 7.02-6.99 (2H, m), 6.76-6.74 (1H, m), 6.59 (1H, s), 6.41 (1H, s), 5.94-5.87 (2H, m), 5.42 (1H, m), 4.66 (1H, m), 4.56-4.49 (2H, m), 4.40-4.38 (1H, m), 4.29-4.24 (1H, m), 4.17-4.11 (1H, m), 3.93 (3H, s), 3.89 (3H, s), 3.87 (3H, s), 3.85-3.70 (2H, m), 3.65-3.59 (2H, m), 3.37-3.31 (2H, m), 3.06 (1H, m), 2.46-2.41 (2H, m), 2.20 (1H, m), 2.10-2.06 (1H, m), 1.76-1.74 (2H, m), 1.17 (3H, m), 0.88-0.63 (4H, m), 0.78 (3H, m), 0.67 (3H, m).
MS(APCI, ESI)m/z:1050(M+H)$^+$

Step 11: Compound 22-11

The compound obtained in step 10 (0.0870 g, 0.0828 mmol) was reacted in the same manner as in step 8 of Example 3 to afford the desired compound (0.0650 g, 75%).
$^1$H-NMR (CDCl$_3$) δ:9.19 (1H, s), 7.92 (1H, m), 7.73-7.64 (4H, m), 7.55-7.44 (4H, m), 7.22 (1H, s), 7.15-7.09 (4H, m), 6.43 (1H, s), 6.09 (1H, s), 5.90 (2H, m), 5.34 (1H, m), 4.72 (1H, m), 4.65-4.63 (1H, m), 4.36-4.34 (1H, m), 4.17-4.02 (4H, m), 3.92 (3H, s), 3.89 (3H, s), 3.80 (3H, s), 3.78-3.72 (3H, m), 3.60-3.46 (5H, m), 3.31-3.27 (2H, m), 2.89-2.85 (1H, m), 2.41 (1H, m), 2.33-2.26 (1H, m), 2.21-2.15 (2H, m), 1.77-1.75 (1H, m), 1.43 (3H, m), 0.98 (3H, m), 0.83 (3H, m), 0.76-0.61 (4H, m).
MS(APCI, ESI)m/z:1051(M+H)$^+$ Step 12: N-[4-(11,12-Didehydrodibenzo[b,f]azocin-5 (6H)-yl)-4-oxobutanoyl]glycylglycyl-L-valyl-N-{4-[({[(11a'S)-11'-hydroxy-7'-methoxy-8'-(3-{[(11aS)-7-methoxy-2-(6-methoxynaphthalen-2-yl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 11 (0.065 g, 0.062 mmol) was reacted in the same manner as in step 13 of Example 3 to afford the desired compound (0.048 g, 54%).
MS (APCI, ESI)m/z:1453 (M+H)$^+$ Example 23: Drug-Linker 21

[Formula 147]

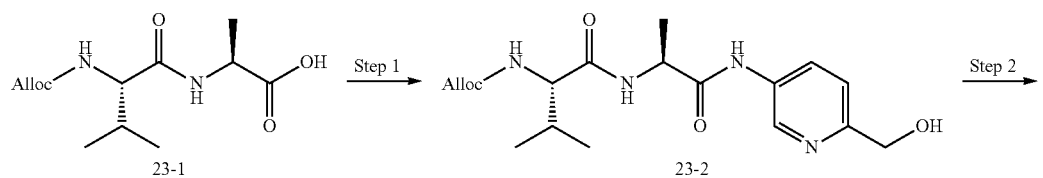

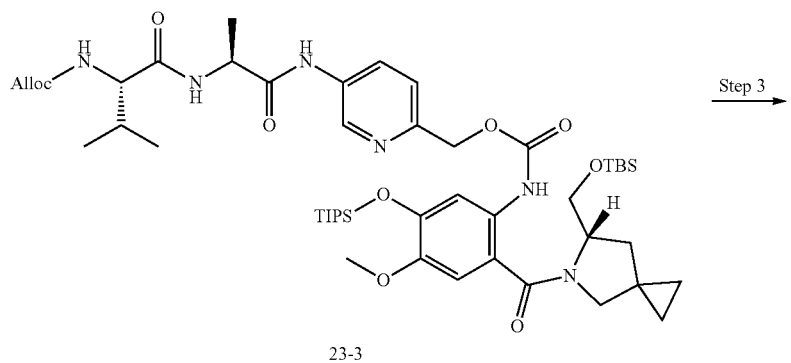

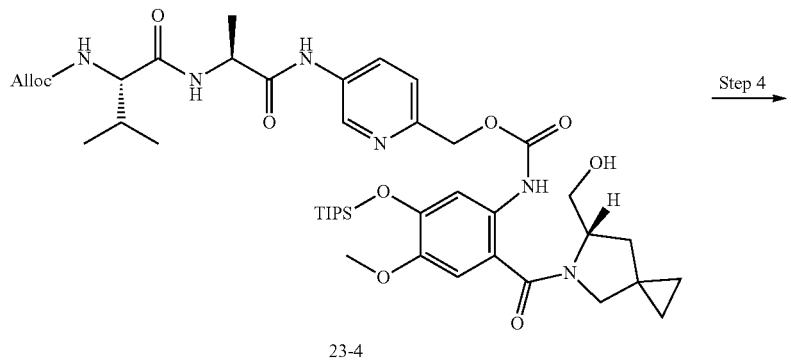

-continued
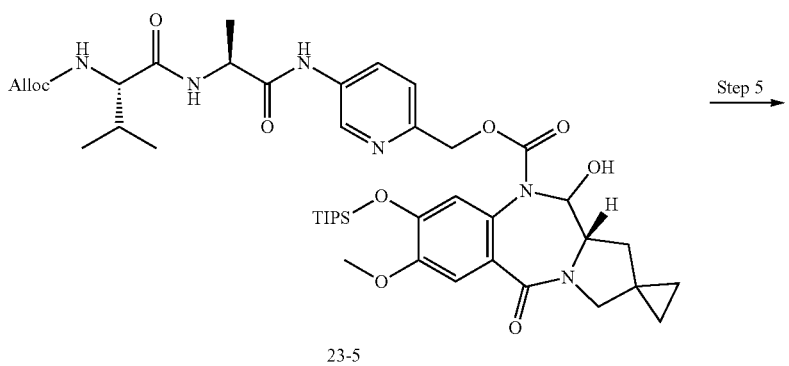
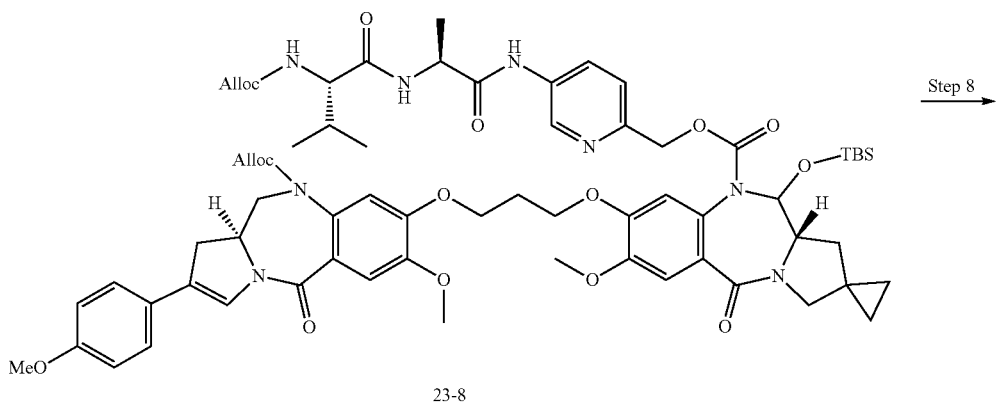

-continued
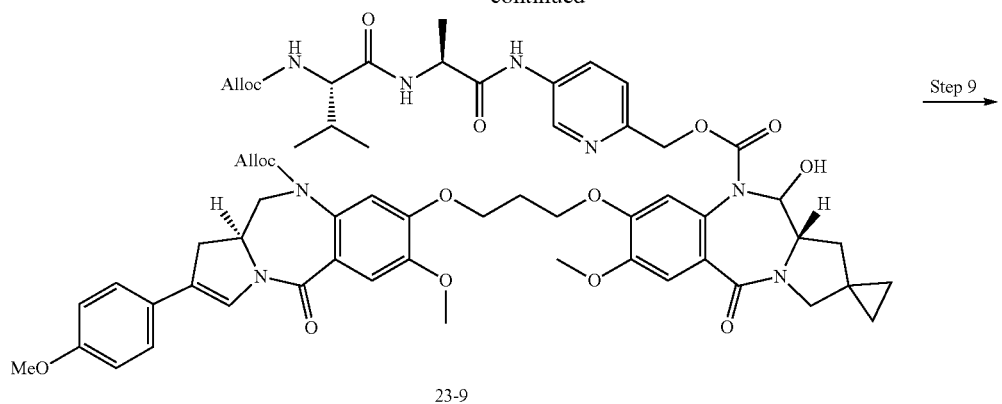
23-9
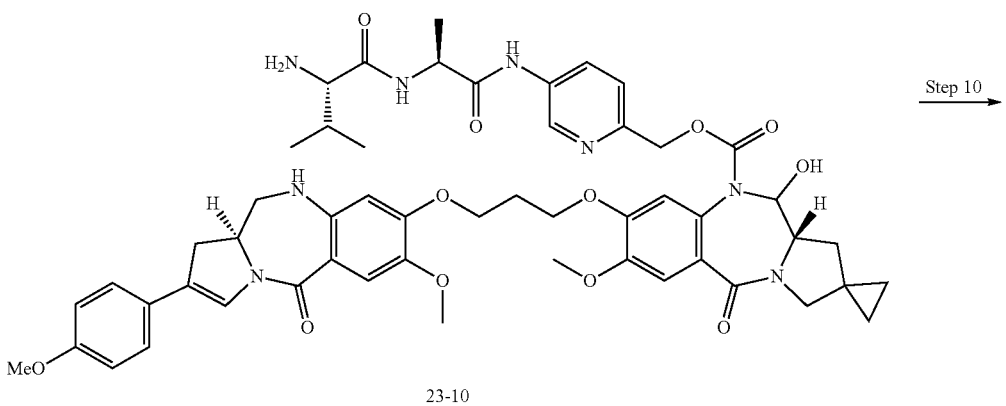
23-10
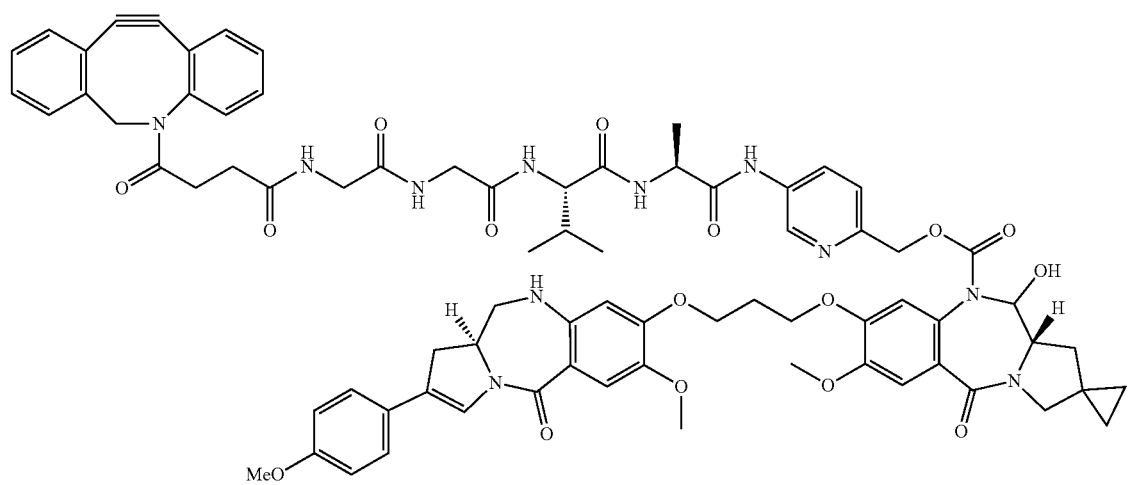
23-11

Step 1: Compound 23-2 Starting raw material 23-1 (14.8 g, 54.4 mmol, WO 2011130613) was reacted in the same manner as in step 2 of Example 5 to afford the desired compound (12.2 g, 63%).

MS(APCI, ESI)m/z:379(M+H)$^+$

Step 2: Compound 23-3

The compound obtained in step 1 (3.78 g, 10.0 mmol) was reacted in the same manner as in step 6 of Example 1 to afford the desired compound (3.86 g, 40%).
MS(APCI, ESI)m/z:967(M+H)$^+$ Step 3: Compound 23-4

The compound obtained in step 2 (3.860 g, 3.99 mmol) was reacted in the same manner as in step 7 of Example 1 to afford the desired compound (3.11 g, 920%).
$^1$H-NMR (CDCl$_3$) δ:9.03 (1H, m), 8.70-8.63 (2H, m), 8.17-8.13 (1H, m), 7.68 (1H, s), 7.35 (1H, m), 6.82-6.76 (2H, m), 5.93-5.83 (1H, m), 5.49-5.42 (1H, m), 5.32-5.17 (4H, m), 4.73-4.52 (5H, m), 4.03 (1H, m), 3.86 (1H, s), 3.80-3.75 (2H, m), 3.77 (3H, s), 3.65-3.63 (1H, m), 3.12-3.10 (1H, m), 2.20-2.14 (1H, m), 1.93-1.88 (1H, m), 1.45 (3H, m), 1.31-1.23 (3H, m), 1.10-1.08 (18H, m), 0.98 (3H, m), 0.94 (3H, m), 0.64-0.47 (4H, m).

Step 4: Compound 23-5

The compound obtained in step 3 (3.11 g, 3.65 mmol) was reacted in the same manner as in step 8 of Example 1 to afford the desired compound (2.58 g, 84%).
$^1$H-NMR (CDCl$_3$) δ:9.02-8.88 (1H, m), 8.69-8.59 (1H, m), 8.17-8.02 (1H, m), 7.22-7.17 (1H, m), 7.02 (1H, m), 6.79-6.78 (2H, m), 6.63 (1H, m), 5.95-5.87 (2H, m), 5.33-5.11 (4H, m), 4.65-4.53 (3H, m), 4.01 (1H, m), 3.83 (3H, s), 3.73 (1H, m), 3.59 (1H, m), 3.32 (1H, m), 2.43-2.39 (1H, m), 2.18-2.16 (1H, m), 1.75-1.67 (2H, m), 1.48-1.43 (3H, m), 1.20-1.14 (3H, m), 1.10-0.94 (24H, m), 0.73-0.60 (4H, m).

Step 5: Compound 23-6

The compound obtained in step 4 (2.58 g, 3.03 mmol) was reacted in the same manner as in step 9 of Example 1 to afford the desired compound (2.75 g, 94%). 1H-NMR (CDCl$_3$) δ:8.78 (1H, m), 8.58 (1H, m), 8.03 (1H, m), 7.21 (1H, s), 6.97 (1H, m), 6.73 (1H, s), 6.59-6.55 (1H, m), 6.02 (1H, m), 5.93-5.85 (1H, m), 5.32-5.04 (4H, m), 4.72-4.55 (3H, m), 3.99 (1H, m), 3.84 (3H, s), 3.73-3.70 (1H, m), 3.53 (1H, m), 3.28 (1H, m), 2.36 (1H, m), 2.21-2.14 (1H, m), 1.55-1.53 (1H, m), 1.47-1.44 (4H, m), 1.23-1.16 (3H, m), 1.10-1.00 (18H, m), 0.98 (3H, m), 0.94 (3H, m), 0.83 (9H, s), 0.81-0.60 (4H, m), 0.21-0.19 (3H, m), 0.18-0.16 (3H, m).

Step 6: Compound 23-7

The compound obtained in step 5 (2.75 g, 2.85 mmol) was reacted in the same manner as in step 10 of Example 1 to afford the desired compound (2.28 g, 99%).
MS(APCI, ESI)m/z:809(M+H)$^+$ Step 7: Compound 23-8

The compound obtained in step 6 (0.340 g, 0.420 mmol) was reacted in the same manner as in step 9 of Example 4 to afford the desired compound (0.530 g, 98%).
MS(APCI, ESI)m/z:1285(M+H)$^+$ Step 8: Compound 23-9

The compound obtained in step 7 (0.530 g, 0.412 mmol) was reacted in the same manner as in step 11 of Example 3 to afford the desired compound (0.362 g, 75%).
MS(APCI, ESI)m/z:1171(M+H)$^+$ Step 9: Compound 23-10

The compound obtained in step 8 (0.444 g, 0.379 mmol) was reacted in the same manner as in step 12 of Example 3 to afford the desired compound (0.347 g, 91%).
MS(APCI, ESI)m/z:1103(M+H)$^+$ Step 10: N-[4-(11,12-Didehydrodibenzo[b,f]azocin-5 (6H)-yl)-4-oxobutanoyl]glycylglycyl-L-valyl-N-{6-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]pyridine-3-yl}-L-alaninamide ("GGVA" Disclosed as SEQ ID NO: 76)

The compound obtained in step 9 (0.100 g, 0.0997 mmol) was reacted in the same manner as in step 13 of Example 3 to afford the desired compound (0.067 g, 48%).
MS (APCI, ESI)m/z:1404 (M+H)$^+$ Example 24: Drug-Linker 22

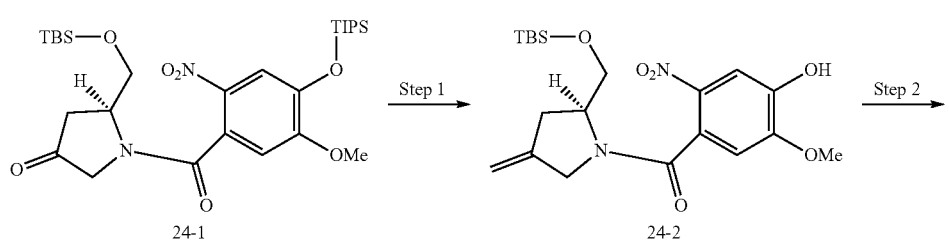

[Formula 148]

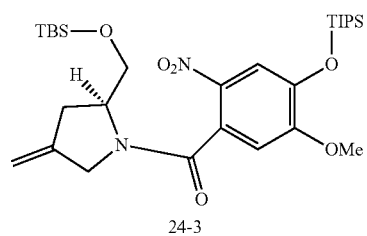
24-3
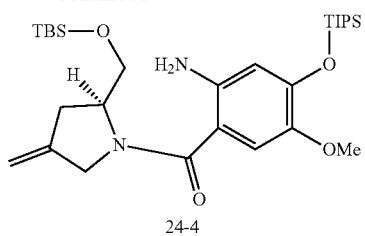
24-4
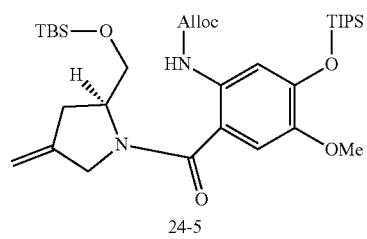
24-5
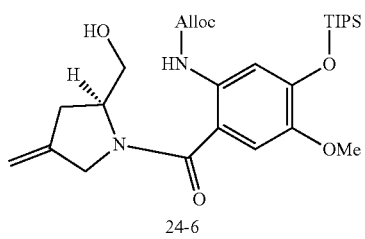
24-6
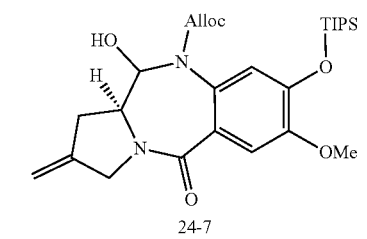
24-7
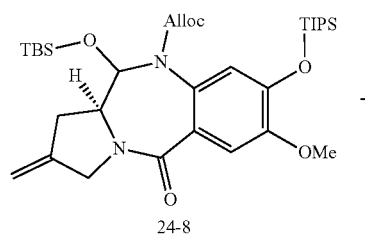
24-8
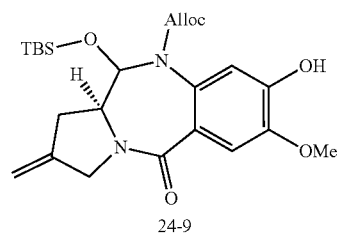
24-9
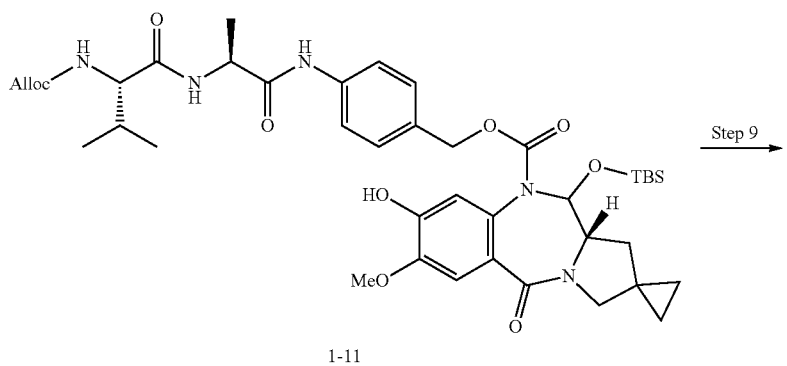
1-11
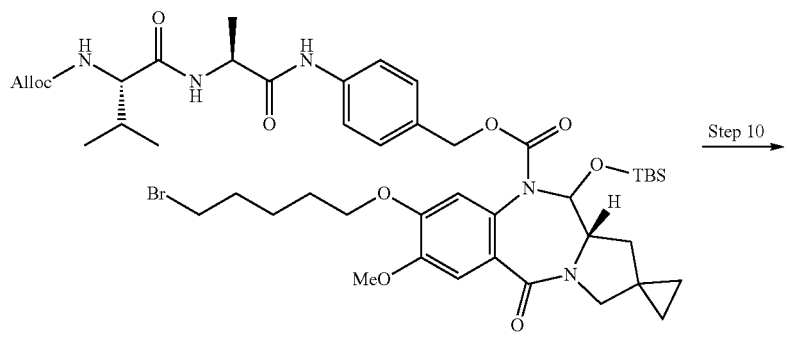
24-10

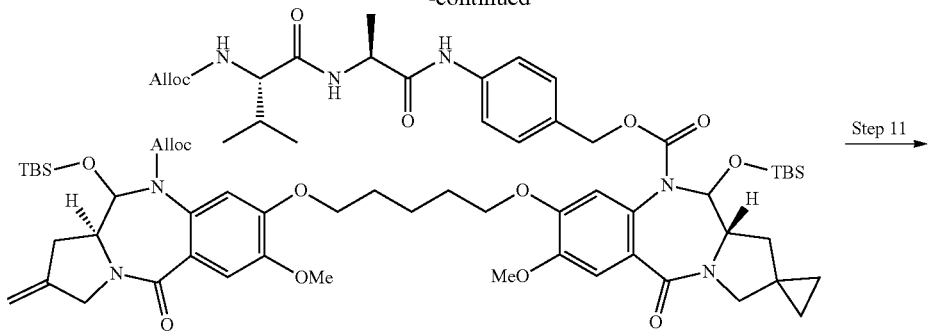

24-11

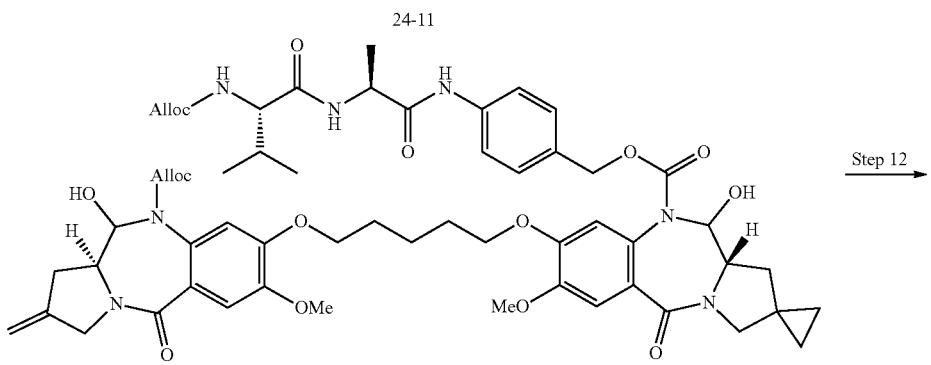

24-12

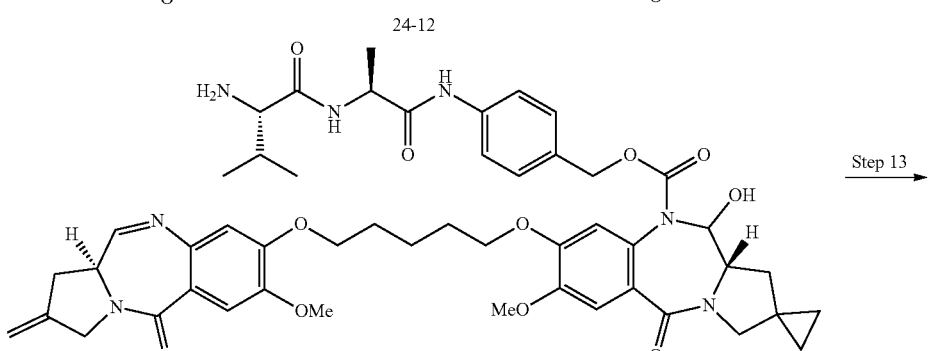

24-13

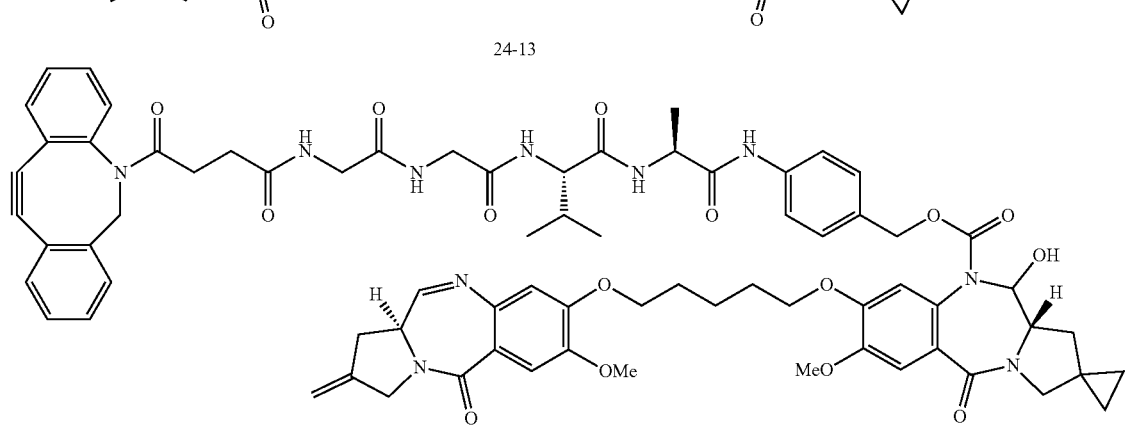

24-14

Step 1: Compound 24-2

To a suspension solution of methyltriphenylphosphonium bromide (7.28 g, 20.4 mmol) in tetrahydrofuran (30 mL), potassium tert-butoxide (2.06 g, 18.3 mmol) was added in small portions under the nitrogen atmosphere at 0° C., and the resultant was then stirred for 2 hours. A solution of compound 24-1 (1.18 g, 2.04 mmol, WO 2013053872) in THF (10 mL) was added dropwise thereto over 2 minutes, and the resultant was stirred at 0° C. for 28 hours. Water and an aqueous solution of citric acid was added to the reaction solution (pH=4.0), which was then extracted with ethyl acetate. The organic layer was washed with brine, and dried over sodium sulfate. The resultant was distillated under reduced pressure, and the resulting residue was purified by silica gel column chromatography [hexane:ethyl acetate=100:0 (v/v) to 0:100 (v/v)] to afford the desired compound (0.450 g, 52%).

MS(APCI, ESI)m/z:423(M+H)$^+$.

Step 2: Compound 24-3

To a solution of the compound obtained in step 1 (0.668 g, 1.58 mmol) in N,N-dimethylformamide (10 mL), imidazole (0.211 g, 3.16 mmol) was added under the nitrogen atmosphere. Thereafter, triisopropylsilyl chloride (0.502 mL, 2.37 mmol) was added dropwise thereto, and the resultant was stirred at room temperature for 6 hours. To the reaction solution, a 10% aqueous solution of citric acid was added, which was twice extracted with ethyl acetate. The organic layer was washed with brine, dried over anhydrous sodium sulfate, and then distillated under reduced pressure. The resulting residue was purified by silica gel chromatography [hexane:ethyl acetate=100:0 (v/v) to 50:50 (v/v)] to afford the desired compound (0.520 g, 57%).

MS(APCI, ESI)m/z:579(M+H)$^+$.

Step 3: Compound 24-4

The compound obtained in step 2 (0.520 g, 0.898 mmol) was reacted in the same manner as in step 2 of Example 17 to afford the desired compound (0.478 g, 97%).

MS(APCI, ESI)m/z:547(M−H)$^+$.

Step 4: Compound 24-5 Under the nitrogen atmosphere, the compound obtained in step 3 (0.478 g, 0.871 mmol) was reacted in the same manner as in step 9 of Example 3. After distillation under reduced pressure, the resulting residue (0.570 g) was directly used for the subsequent reaction.

Step 5: Compound 24-6

The compound obtained in step 4 (0.570 g) was reacted in the same manner as in step 7 of Example 1 to afford the desired compound (0.446 g, 95%).

MS(APCI, ESI)m/z:519(M+H)$^+$.

Step 6: Compound 24-7

The compound obtained in step 5 (0.446 g, 0.859 mmol) was reacted in the same manner as in step 8 of Example 1 to afford the desired compound (0.196 g, 44%).

$^1$H-NMR (CDCl$_3$) δ:7.19 (1H, s), 6.68 (1H, s), 5.78-5.76 (1H, m), 5.55 (1H, m), 5.19-5.13 (4H, m), 4.61-4.58 (1H, m), 4.49-4.46 (1H, m), 4.29 (1H, m), 4.15 (1H, m), 3.85 (3H, s), 3.61 (1H, m), 3.38 (1H, s), 2.93-2.90 (1H, m), 2.71 (1H, m), 1.30-1.18 (3H, m), 1.12-1.06 (18H, m).

MS(APCI, ESI)m/z:517(M+H)$^+$.

Step 7: Compound 24-8

The compound obtained in step 6 (0.195 g, 0.377 mmol) was reacted in the same manner as in step 9 of Example 1 to afford the desired compound (0.230 g, 97%).

$^1$H-NMR (CDCl$_3$) δ:7.19 (1H, s), 6.66 (1H, s), 5.75-5.65 (1H, m), 5.66 (1H, m), 5.12-5.10 (4H, m), 4.59 (1H, m), 4.35 (1H, m), 4.28 (1H, m), 4.11 (1H, m), 3.86 (3H, s), 3.53 (1H, m), 2.90-2.84 (1H, m), 2.48 (1H, m), 1.26-1.19 (3H, m), 1.09-1.06 (18H, m), 0.86 (9H, s), 0.23 (3H, s), 0.17 (3H, s).

Step 8: Compound 24-9

The compound obtained in step 7 (0.230 g, 0.365 mmol) was reacted in the same manner as in step 10 of Example 1. In this present step, a liquid separation operation was performed after the completion of the reaction, and a crude product (0.238 g, quantitative) obtained by distilling off the organic solvent under reduced pressure was used for the subsequent reaction.

Step 9: Compound 24-10

The compound obtained in the previous step and the compound obtained in step 10 of Example 1 (0.251 g, 0.311 mmol) were reacted in the same manner as in step 2 of Example 3 to afford the desired compound (0.185 g, 62%).

MS(APCI, ESI)m/z:958[$^{81}$Br,(M+H)$^+$], 956[$^{79}$Br,(M+H)$^+$].

Step 10: Compound 24-11

The compound obtained in step 8 (0.0660 g, 0.139 mmol) and the compound obtained in step 9 (0.133 g, 0.139 mmol) were reacted in the same manner as in step 10 of Example 3 to afford the desired compound (0.123 g, 66%).

MS(APCI, ESI)m/z:1350(M+H)$^+$.

Step 11: Compound 24-12

The compound obtained in step 10 (0.123 g, 0.0910 mmol) was reacted in the same manner as in step 11 of Example 3 to afford the desired compound (0.0950 g, 92%).

$^1$H-NMR (CDCl$_3$) δ:8.65 (1H, s), 7.59 (2H, m), 7.31-7.29 (2H, m), 7.23-7.21 (3H, m), 6.89-6.86 (1H, m), 6.78 (1H, s), 6.38 (1H, s), 5.92-5.88 (2H, m), 5.81-5.79 (1H, m), 5.61-5.52 (2H, m), 5.31 (2H, m), 5.23 (1H,n), 5.13-5.10 (4H, m), 5.05-5.02 (1H, m), 4.69-4.67 (2H, m), 4.58-4.55 (2H, m), 4.49-4.46 (1H, m), 4.30 (2H, m), 4.16 (1H, m), 3.98-3.96 (3H, m), 3.93 (3H, s), 3.89 (3H, s), 3.81-3.78 (2H, m), 3.74 (1H, m), 3.69-3.66 (1H, m), 3.61 (1H, m), 3.43-3.41 (1H, m), 3.32 (1H, m), 2.89-2.87 (1H, m), 2.73 (1H, m), 2.42 (1H, m), 2.10-2.08 (1H, m), 1.80-1.73 (4H, m), 1.53-1.50 (2H, m), 1.25-1.24 (3H, m), 0.93-0.89 (6H, m), 0.75-0.63 (4H, m).

MS(APCI, ESI)m/z:1122(M+H)$^+$.

Step 12: Compound 24-13

The compound obtained in step 11 (0.0950 g, 0.0847 mmol) was reacted in the same manner as in step 12 of Example 3 to afford the desired compound (0.0610 g, 76%).

$^1$H-NMR (CDCl$_3$) δ:9.12-8.96 (1H, m), 7.82-7.60 (4H, m), 7.22-7.19 (3H, m), 6.94-6.66 (1H, m), 6.40-6.34 (2H, m), 5.89-5.86 (1H, m), 5.55 (1H, m), 5.40-5.07 (3H, m), 4.60-4.42 (4H, m), 4.23-4.09 (5H, m), 3.91-3.88 (8H, m), 3.81-3.75 (8H, m), 3.60 (1H, m), 3.32-3.30 (2H, m), 3.24-3.22 (1H, m), 3.12-3.09 (1H, m), 2.65-2.61 (1H, m), 2.41 (1H, m), 2.12-2.11 (1H, m), 1.89-1.84 (9H, m), 1.75 (3H, m), 1.40-1.38 (2H, m), 1.25-1.21 (3H, m), 0.99 (3H, m), 0.84 (3H, m), 0.74-0.66 (6H, m).

MS(APCI, ESI)m/z:936(M+H)⁺.

Step 13: N-[4-(11,12-Didehydrodibenzo[b,f]azocin-5 (6H)-yl)-4-oxobutanoyl]glycylglycyl-L-valyl-N-{4-[({[(11a'S)-11'-hydroxy-7'-methoxy-8'-[(5-{[(11aS)-7-methoxy-2-methylidene-5-oxo-2,3,5,11a-tetrahydro-1H-pyrrolo[2,1-c][1,4]benzodiazepin-8-yl]oxy}pentyl)oxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 12 (0.0600 g, 0.0629 mmol) was reacted in the same manner as in step 13 of Example 3 to afford the desired compound (0.075 g, 89%).

¹H-NMR (DMSO-D₆) δ:9.91 (1H, s), 8.21-8.16 (2H, m), 8.07-8.03 (1H, m), 7.74-7.65 (3H, m), 7.60-7.44 (6H, m), 7.39-7.29 (5H, m), 7.21-7.19 (2H, m), 7.03 (1H, s), 6.85 (1H, s), 6.72 (1H, s), 6.58-6.56 (1H, m), 5.77-5.74 (1H, m), 5.19-5.16 (3H, m), 5.03-5.00 (1H, m), 4.82-4.79 (1H, m), 4.36-4.33 (1H, m), 4.21-4.19 (1H, m), 4.14-4.11 (2H, m), 4.00-3.95 (3H, m), 3.80-3.73 (10H,m), 3.65-3.52 (4H, m), 3.41-3.38 (2H, m), 3.15-3.30 (1H, m), 3.14 (1H, m), 3.04-3.01 (1H, m), 2.68-2.66 (1H, m), 2.32-2.28 (2H, m), 2.05-1.98 (2H, m), 1.78-1.77 (5H, m), 1.57-1.54 (3H, m), 1.28-1.25 (3H, m), 0.86-0.81 (6H, m), 0.67-0.62 (4H, m).
MS(APCI, ESI)m/z:1337(M+H)⁺.

Example 25: Drug-Linker 23

[Formula 149]

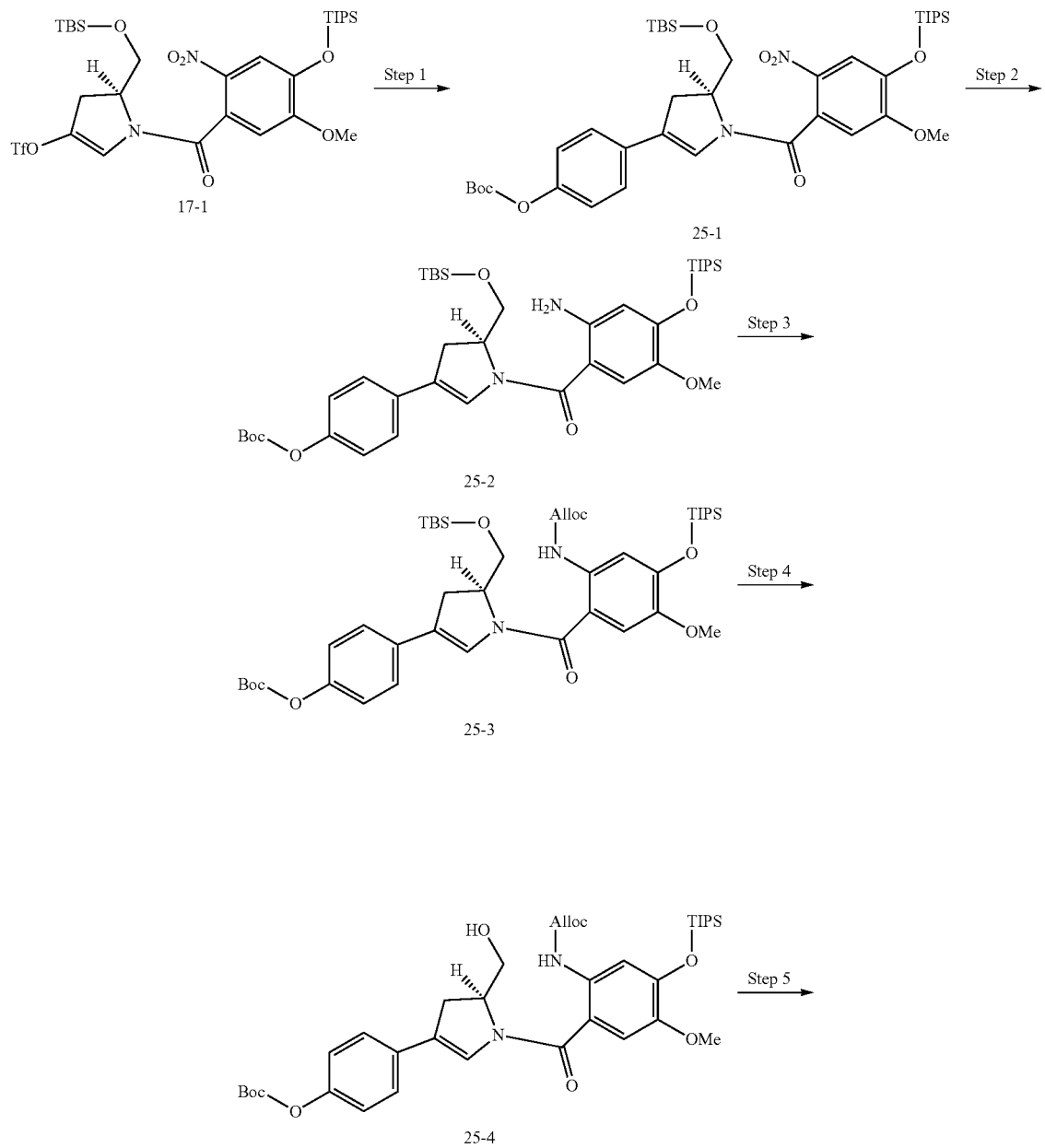

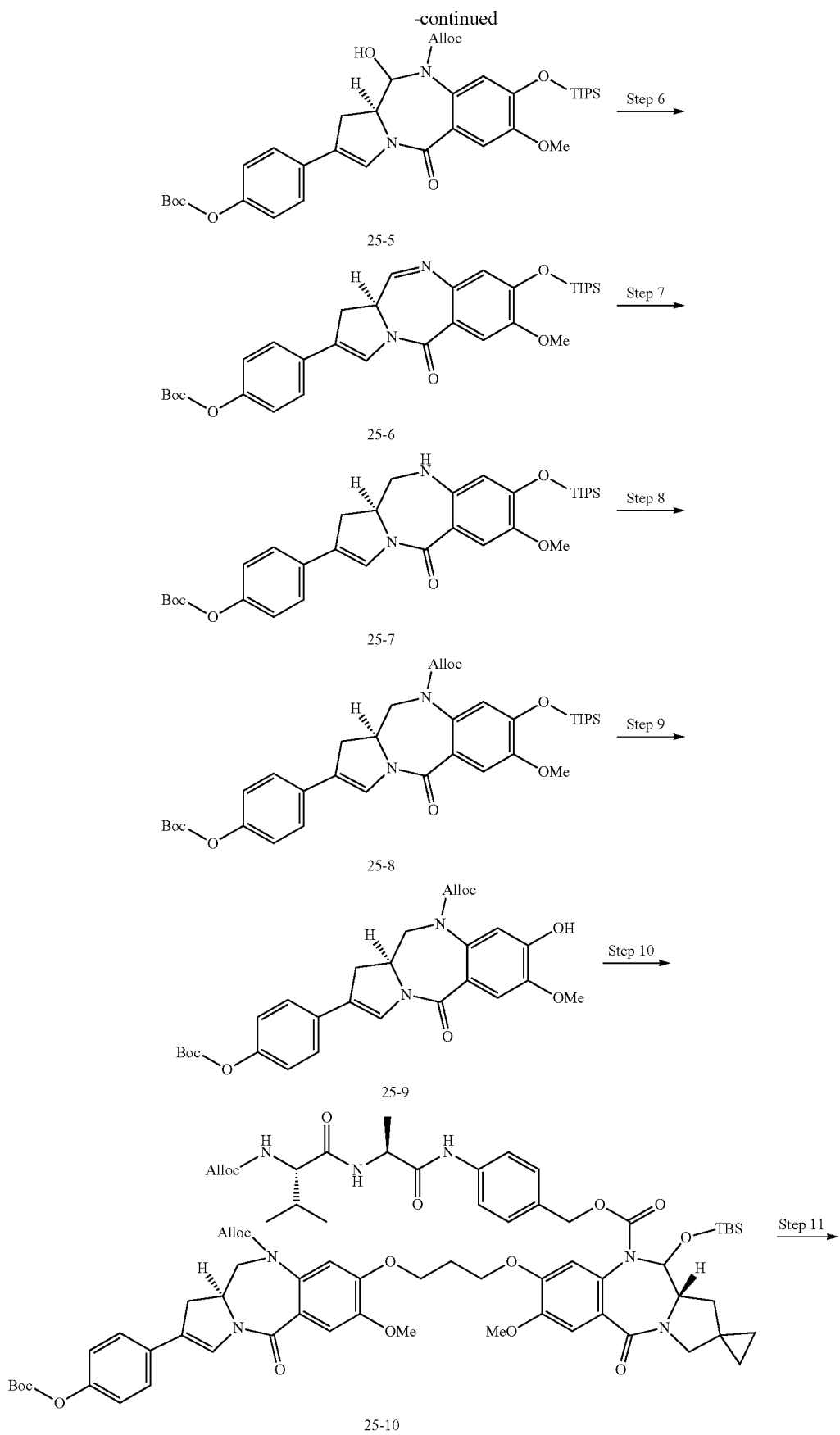

-continued
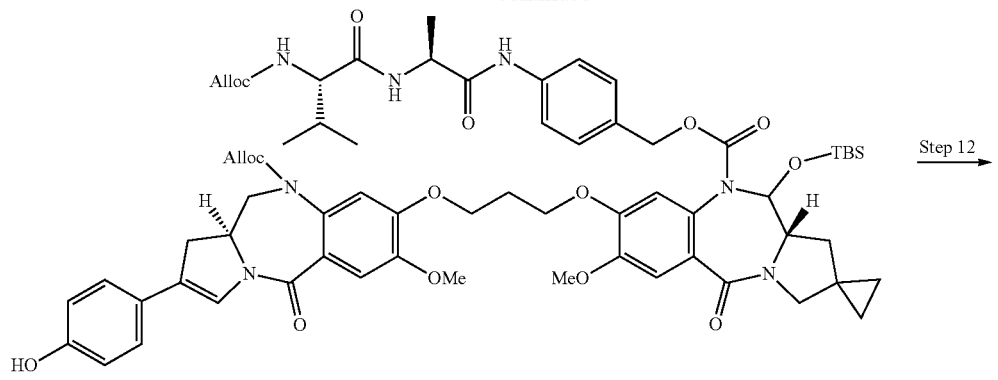
25-11
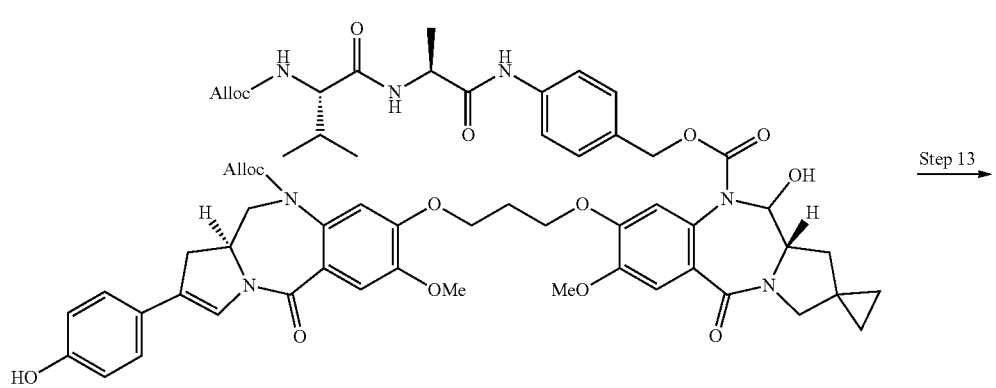
25-12
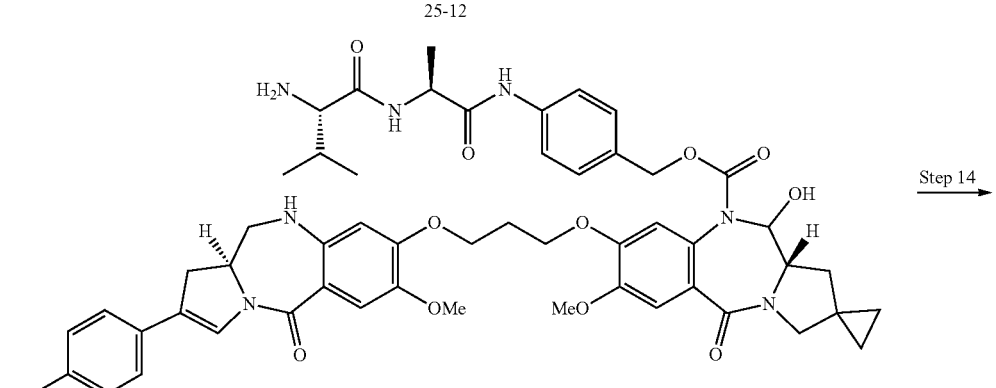
25-13
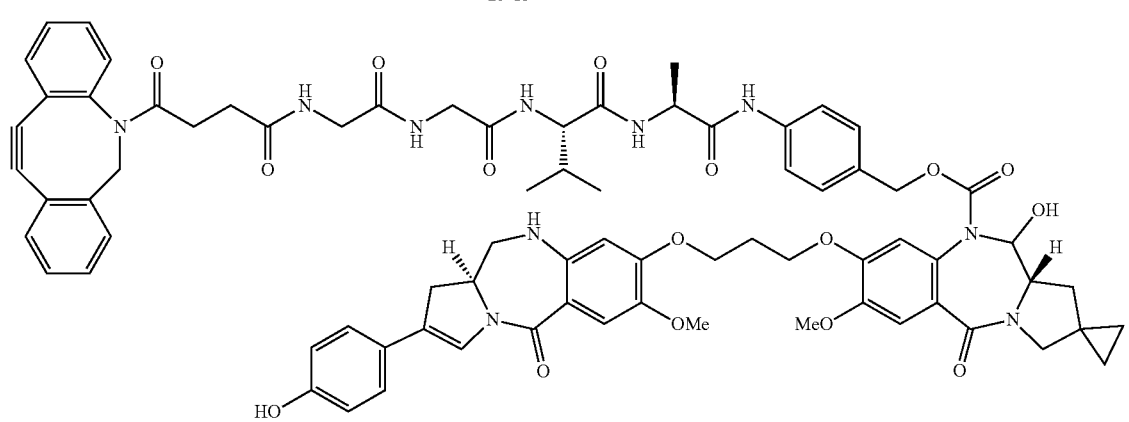
25-14

Step 1: Compound 25-1

Starting material 17-1 (3.81 g, 5.34 mmol) and tert-butyl 4-(4,4,5,5-tetramethyl-1,3,2-dioxaboran-2-yl)phenylcarbonate (5.13 g, 16.0 mmol) were reacted in the same manner as in step 6 of Example 3 to afford the desired compound (3.05 g, 75%).
MS(APCI, ESI)m/z:757(M+H)$^+$

Step 2: Compound 25-2

The compound obtained in step 1 (3.05 g, 4.09 mmol) was reacted in the same manner as in step 2 of Example 17 to afford the desired compound (2.67 g, 91%).
MS(APCI, ESI)m/z:727(M+H)$^+$.

Step 3: Compound 25-3

The compound obtained in step 2 (2.67 g, 3.67 mmol) was reacted in the same manner as in step 9 of Example 3. In this step, a liquid separation operation was performed after the completion of the reaction, and a crude product (3.00 g, quantitative) obtained by concentrating the organic solvent under reduced pressure was directly used for the subsequent reaction.

Step 4: Compound 25-4

The compound obtained in step 3 (3.05 g) was reacted in the same manner as in step 7 of Example 1 to afford the desired compound (2.67 g, quantitative).
$^1$H-NMR (CDCl$_3$) δ:8.34 (1H, m), 7.70 (1H, m), 7.24 (2H, m), 7.12 (2H, m), 6.86 (1H, s), 6.84 (1H, s), 5.95-5.89 (1H, m), 5.31 (1H, m), 5.21 (1H, m), 4.87-4.86 (1H, m), 4.61-4.61 (2H, m), 4.41 (1H, m), 3.93-3.90 (2H, m), 3.76 (3H, s), 3.29 (1H, m), 2.68-2.66 (1H, m), 1.55 (9H, s), 1.33-1.26 (3H, m), 1.13-1.11 (18H, m).
MS(APCI, ESI)m/z:697(M+H)$^+$.

Step 5: Compound 25-5

The compound obtained in step 4 (1.22 g, 1.75 mmol) was reacted in the same manner as in step 3 of Example 9 to afford the desired compound (0.838 g, 69%).
$^1$H-NMR (CDCl$_3$) δ:7.45 (1H, s), 7.37 (2H, m), 7.22 (1H, s), 7.15 (2H, m), 7.11-7.09 (1H, m), 6.72 (1H, s), 5.82-5.79 (1H, m), 5.19-5.16 (2H, m), 4.61-4.59 (2H, m), 4.50-4.47 (1H, m), 4.00 (1H, m), 3.86 (3H, s), 3.41-3.28 (1H, m), 3.09-3.05 (1H, m), 1.57 (9H, s), 1.29-1.25 (3H, m), 1.14-1.07 (18H, m).
MS(APCI, ESI)m/z:695(M+H)$^+$.

Step 6: Compound 25-6

The compound obtained in step 5 (0.838 g, 1.21 mmol) was reacted in the same manner as in step 12 of Example 3 to afford the desired compound (0.745 g, quantitative).
$^1$H-NMR (CDCl$_3$) δ:7.88 (1H, m), 7.50 (1H, s), 7.48-7.48 (1H, m), 7.40 (2H, m), 7.18 (2H, m), 6.86 (1H, s), 4.45-4.43 (1H, m), 3.90 (3H, s), 3.60-3.56 (1H, m), 3.38 (1H, m), 1.57 (9H, s), 1.31-1.26 (3H, m), 1.11-1.10 (18H, m).
MS(APCI, ESI)m/z:593(M+H)$^+$.

Steps 7 to 9: Compound 25-9

The compound obtained in step 6 (0.745 g, 1.26 mmol) was reacted in the same manner as in steps 8 and 9 of Example 3 and step 10 of Example 1 to afford the desired compound (0.516 g, yields in three steps: 78%).
$^1$H-NMR (CDCl$_3$) δ:7.46 (1H, s), 7.35 (2H, m), 7.27-7.25 (2H, m), 7.15 (2H, m), 6.82 (1H, s), 5.93 (1H, s), 5.84-5.81 (1H, m), 5.12 (1H, m), 4.61 (1H, m), 4.49-4.46 (1H, m), 4.35-4.32 (1H, m), 4.23-4.21 (1H, m), 3.96 (3H, s), 3.65-3.62 (1H, m), 3.29 (1H, m), 2.71 (1H, m), 1.57 (9H, s).
MS(APCI, ESI)m/z:523(M+H)$^+$.

Step 10: Compound 25-10

The compound obtained in step 9 (0.105 g, 0.200 mmol) and the compound obtained in step 11 of Example 1 (0.186 g, 0.200 mmol) were subjected to coupling reaction in the same manner as in step 10 of Example 3 to afford the desired compound (0.248 g, 90%).
$^1$H-NMR (CDCl$_3$) δ:8.72-8.50 (1H, m), 7.52 (1H, s), 7.40-7.38 (4H, m), 7.23-7.21 (2H, m), 7.16 (2H, m), 7.09 (1H, m), 6.84-6.82 (2H, m), 6.51-6.49 (1H, m), 6.02 (1H, m), 5.92-5.90 (1H, m), 5.30-5.21 (5H, m), 4.71-4.61 (6H, m), 4.36-4.24 (5H, m), 4.02-4.00 (3H, m), 3.93-3.88 (1H, m) 3.87 (3H, s), 3.81 (3H, s), 3.71 (2H, m), 3.51-3.49 (1H, m), 3.32-3.28 (2H, m), 2.72 (1H, m), 2.37-2.34 (3H, m), 2.16-2.13 (1H, m), 1.66 (9H, s), 1.50-1.46 (4H, m), 0.97-0.93 (7H, m), 0.82 (9H, s), 0.68-0.65 (4H, m), 0.20 (3H, s), 0.14 (3H, s).
MS(APCI, ESI)m/z:1370(M+H)$^+$.

Step 11: Compound 25-11

To a solution of the compound obtained in step 10 (0.248 g, 0.181 mmol) in dichloromethane (3 mL), piperidine (3 mL) was added, and the resultant was stirred at room temperature for 2 hours. The reaction solution was diluted with an aqueous solution of citric acid, and twice extracted with ethyl acetate. The organic layer was washed with brine, and dried over sodium sulfate. After filtration, the organic solvent was distilled off under reduced pressure, and the resulting residue was purified by silica gel column chromatography [chloroform:methanol=100:0 (v/v) to 90:10 (v/v)] to afford the desired compound (0.153 g, 93%).
$^1$H-NMR (CDCl$_3$) δ:8.77-8.69 (1H, m), 7.40-7.36 (3H, m), 7.23-7.21 (4H, m), 7.07 (2H, m), 6.88-6.86 (1H, m), 6.82 (2H, m), 6.51 (1H, s), 6.03 (1H, m), 5.92-5.90 (1H, m), 5.30-5.21 (4H, m), 4.75-4.72 (2H, m), 4.58-4.55 (3H, m), 4.37-4.35 (1H, m), 4.23-4.21 (3H, m), 4.01-3.99 (2H, m), 3.86 (3H, s), 3.79 (3H, s), 3.72 (2H, m), 3.66-3.64 (1H, m), 3.51-3.48 (1H, m), 3.28 (2H, m), 2.67 (1H, m), 2.37-2.12 (4H, m), 1.55-1.52 (2H, m), 1.45-1.42 (4H, m), 0.95-0.91 (6H, m), 0.81 (9H, s), 0.81-0.78 (2H, m), 0.68-0.65 (3H, m), 0.20-0.15 (6H, m).
MS(APCI, ESI)m/z:1270(M+H)$^+$.

Step 12: Compound 25-12

The compound obtained in step 11 (0.175 g, 0.138 mmol) was reacted in the same manner as in step 11 of Example 3 to afford the desired compound (0.162 g, quantitative).
MS (APCI, ESI)m/z:1156 (M+H)$^+$.

Step 13: Compound 25-13

The compound obtained in step 12 (0.116 g, 0.100 mmol) was reacted in the same manner as in step 12 of Example 3 to afford the desired compound (0.0410 g, 41%).
MS (APCI, ESI)m/z:988 (M+H)$^+$.

Step 14: N-[4-(11,12-Didehydrodibenzo[b,f]azocin-5 (6H)-yl)-4-oxobutanoyl]glycylglycyl-L-valyl-N-{4-[({[(11a'S)-11'-hydroxy-8'-(3-{[(11aS)-2-(4-hydroxyphenyl)-7-methoxy-5-oxo-5,10,11,11a-tetrahydro-1H-pyrrolo[2,1-c][1,4]benzodiazepin-8-yl]oxy}propoxy)-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 13 (0.00500 g, 0.00506 mmol) and the compound obtained in step 2 of Example 2 (0.0100 g, 0.0202 mmol) were dissolved in dichloromethane (0.3 mL) and methanol (0.3 mL), and N,N-diisopropylethylamine (3.5 μL, 0.0202 mmol) was added thereto, and the resultant was stirred at room temperature for 1 hour. The reaction solution was distillated under reduced pressure, and the resulting residue was purified by silica gel column chromatography [chloroform:CMW=100:0(v/v) to 0:100(v/v)] to afford the desired compound (0.00350 g, 50%).

MS (APCI, ESI)m/z:1389 (M+H)$^+$.

Example 26: Drug-Linker 24

[Formula 150]

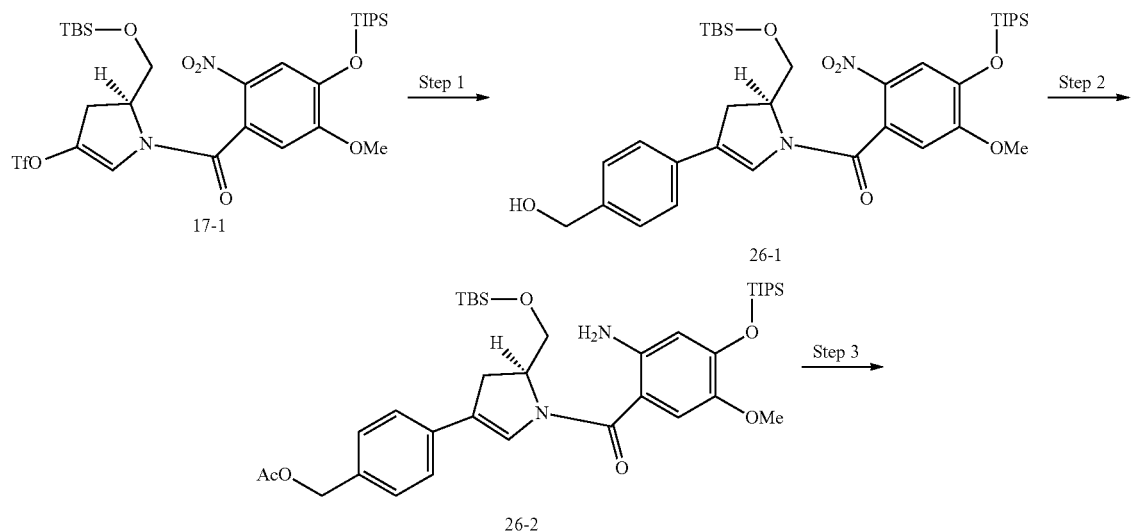

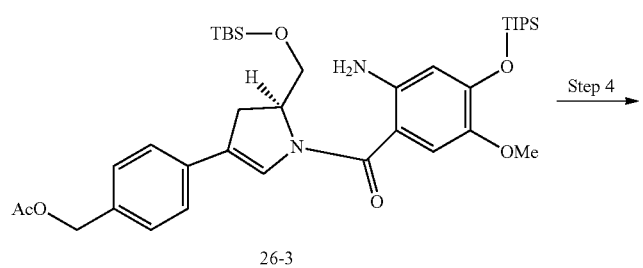

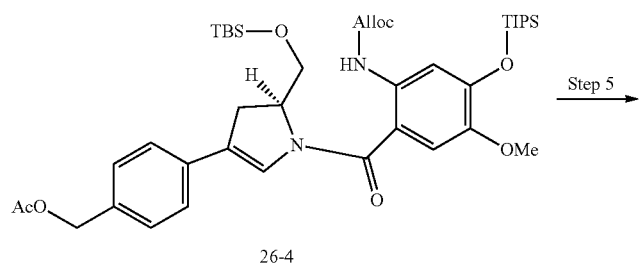

-continued
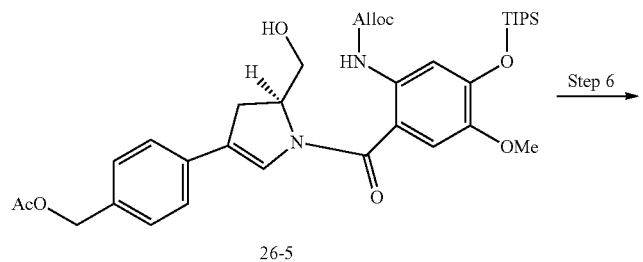
26-5
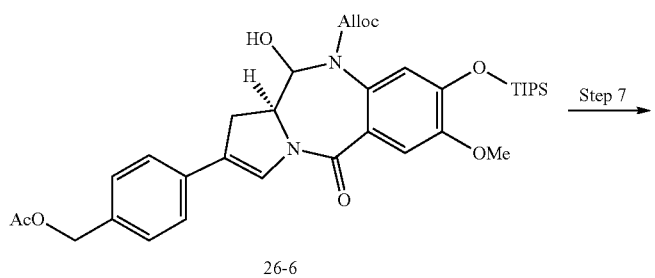
26-6
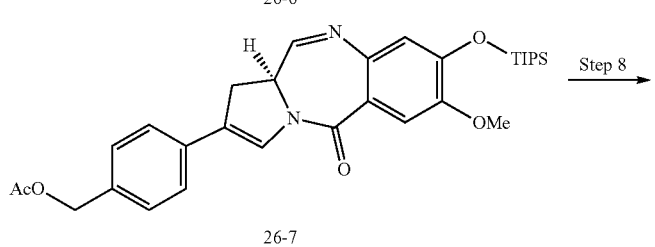
26-7
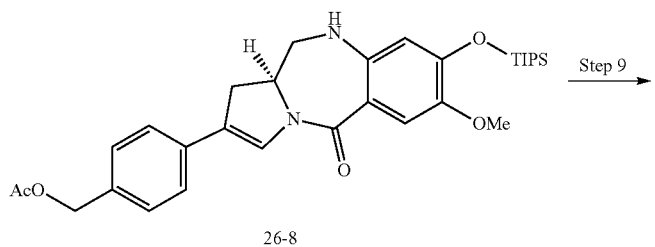
26-8
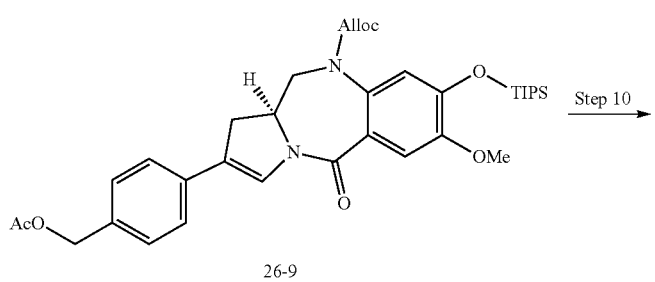
26-9
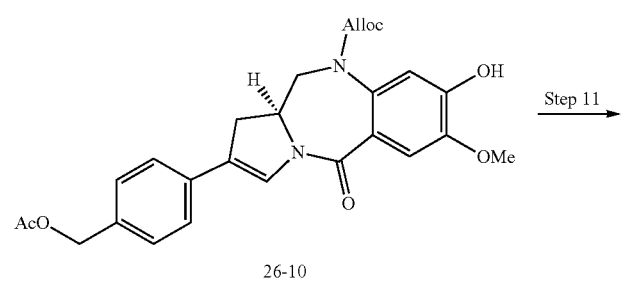
26-10

-continued
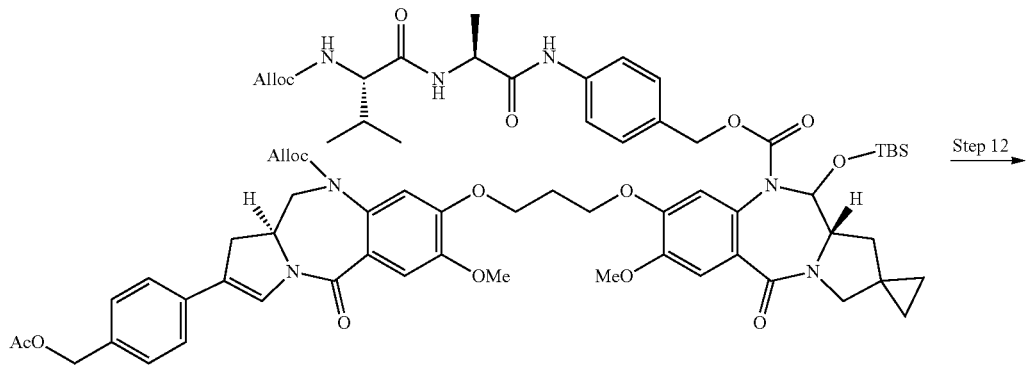
26-11
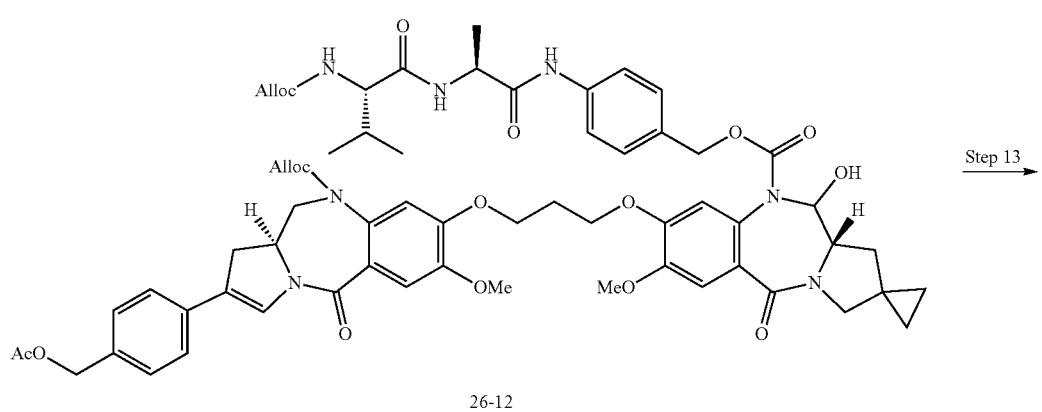
26-12
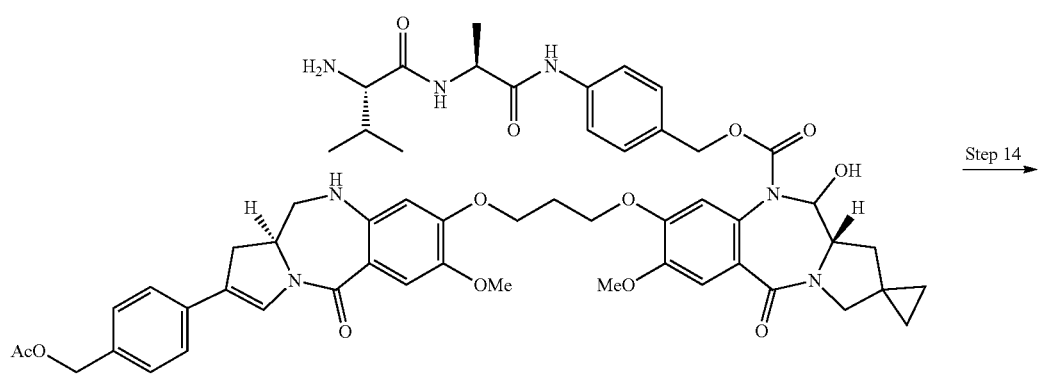
26-13
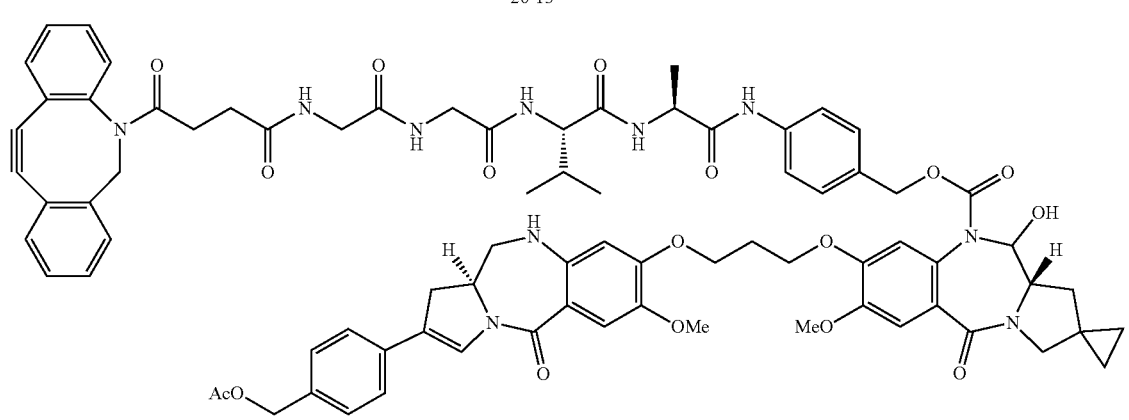
26-14

Step 1: Compound 26-1

Starting material 17-1 (3.93 g, 5.51 mmol) and 4-(hydroxymethyl)phenylboronic acid were reacted in the same manner as in step 6 of Example 3 to afford the desired compound (3.09 g, 84%).

MS(APCI, ESI)m/z:671(M+H)+.

Step 2: Compound 26-2

A solution of the compound obtained in step 1 (3.09 g, 4.61 mmol) in dichloromethane (100 mL) was ice-cooled, to which triethylamine (1.60 mL, 11.5 mmol) was added, and acetyl chloride (0.491 mL, 6.91 mmol) was then added dropwise thereto, and the resultant was stirred at room temperature for 2 hours. The reaction solution was diluted with an aqueous solution of citric acid, and three times extracted with chloroform. The organic layer was washed with a saturated aqueous sodium carbonate and brine, and dried over anhydrous sodium sulfate, and the solvent was then distilled off under reduced pressure. The resulting compound (3.75 g, quantitative) was directly used for the subsequent reaction.

Step 3: Compound 26-3

The compound obtained in step 2 (3.28 g, 4.60 mmol) was reacted in the same manner as in step 2 of Example 17 to afford the desired compound (2.09 g, 67%).

MS(APCI, ESI)m/z:682(M+H)+.

Step 4: Compound 26-4

The compound obtained in step 3 (1.01 g, 1.48 mmol) was reacted in the same manner as in step 9 of Example 3. The resultant was distilled under reduced pressure, and the resulting compound (1.19 g, quantitative) was directly used for the subsequent reaction.

Step 5: Compound 26-5

The compound obtained in step 4 (1.19 g, 1.55 mmol) was reacted in the same manner as in step 7 of Example 1 to afford the desired compound (0.885 g, 87%). 1H-NMR (CDCl$_3$) δ:8.34 (1H, m), 7.71 (1H, s), 7.31 (2H, m), 7.24 (2H, m), 6.91 (1H, s), 6.84 (1H, s), 5.97-5.88 (1H, m), 5.35-5.29 (1H, m), 5.22-5.20 (1H, m), 5.07 (2H, s), 4.88-4.87 (1H, m), 4.62-4.61 (3H, m), 4.33-4.31 (1H, m), 3.94-3.91 (2H, m), 3.76 (3H, s), 3.33-3.29 (1H, m), 2.68 (1H, m), 1.33-1.29 (4H, m), 1.15-1.12 (18H, m).

MS(APCI, ESI)m/z:653(M+H)+.

Steps 6 and 7: Compound 26-7

The compound obtained in step 5 (0.885 g, 1.36 mmol) was treated in the same manner as in step 3 of Example 9 and step 12 of Example 3 to afford the desired compound (0.515 g, 85%).

MS (APCI, ESI)m/z:549 (M+H)+.

Step 8-10: Compound 26-10

The compound obtained in step 7 (0.515 g, 0.983 mmol) was reacted in the same manner as in steps 8 and 9 of Example 3 and step 10 of Example 1 to afford the desired compound (0.448 g, quantitative).

$^1$H-NMR (CDCl$_3$):7.51 (1H, s), 7.37-7.30 (4H, m), 7.26-7.25 (1H, m), 6.82 (1H, s), 5.94 (1H, s), 5.86-5.79 (1H, m), 5.15-5.13 (1H, m), 5.09 (3H, s), 4.61 (1H, m), 4.48-4.46 (1H, m), 4.35-4.32 (1H, m), 4.25-4.23 (1H, m), 3.96 (3H, s), 3.64 (1H, d, m), 3.33-3.29 (1H, m), 2.73 (1H, m), 2.11 (3H, s).

MS(APCI, ESI)m/z:479(M+H)+.

Step 11: Compound 26-11

The compound obtained in step 10 (0.0690 g, 0.144 mmol) and the compound obtained in step 11 of Example 1 (0.134 g, 0.144 mmol) were reacted in the same manner as in step 10 of Example 3 to afford the desired compound (0.118 g, 62%).

MS(APCI, ESI)m/z:1325(M+H)+.

Steps 12 and 13: Compound 26-13

The compound obtained in step 11 (0.134 g, 0.101 mmol) was reacted in the same manner as in steps 11 and 12 of Example 3 to afford the desired compound (0.0950 g, yield in two steps: 90%) $^1$H-NMR (CDCl$_3$) δ:9.14 (1H, s), 7.91 (1H, m), 7.69 (1H, s), 7.47 (4H, m), 7.40-7.38 (2H, m), 7.34-7.32 (2H, m), 7.21 (1H, s), 7.18 (2H, m), 7.13 (2H, m), 6.40 (1H, s), 6.08 (1H, s), 5.88 (1H, m), 5.36 (1H,m), 5.09 (2H, s), 4.72 (1H, m), 4.62-4.59 (2H, m), 4.35-4.32 (1H, m), 4.12-4.07 (4H, m), 3.89 (3H, s), 3.80 (3H, s), 3.74-3.71 (2H, m), 3.58-3.53 (3H, m), 3.41-3.38 (1H, m), 3.31-3.29 (2H, m), 2.78-2.74 (1H, m), 2.41 (1H, m), 2.31-2.31 (1H, m), 2.18-2.15 (1H, m), 2.11 (3H, s), 1.76 (1H, m), 1.44-1.42 (3H, m), 0.99 (3H, m), 0.83 (3H, m), 0.71-0.66 (4H, m).

MS(APCI, ESI)m/z:1044(M+H)+.

Step 14: N-[4-(11,12-Didehydrodibenzo[b,f]azocin-5 (6H)-yl)-4-oxobutanoyl]glycylglycyl-L-valyl-N-{4-[({[(11a'S)-8'-(3-{[(11aS)-2-{4-[(acetyloxy) methyl]phenyl}-7-methoxy-5-oxo-5,10,11,11a-tetrahydro-1H-pyrrolo[2,1-c][1,4]benzodiazepin-8-yl]oxy}propoxy)-11'-hydroxy-7'-methoxy-5'-oxo-11', 11a'-dihydro-1'H-spiro[cyclopropane-1,2'-pyrrolo[2, 1-c][1,4]benzodiazepine]-10'(5'H)-yl]carbonyl}oxy) methyl]phenyl}-L-alaninamide ("GGVA" Disclosed as SEQ ID NO: 76)

The compound obtained in step 13 (0.0700 g, 0.0670 mmol) was reacted in the same manner as in step 13 of Example 3 to afford the desired compound (0.0520 g, 54%).

MS (APCI, ESI)m/z:1445 (M+H)+.

Example 27: Drug-Linker 25

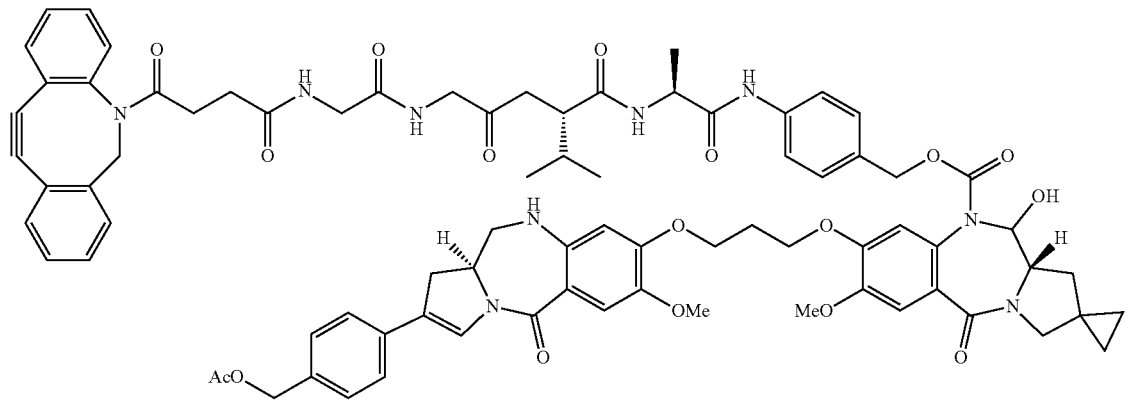

26-14

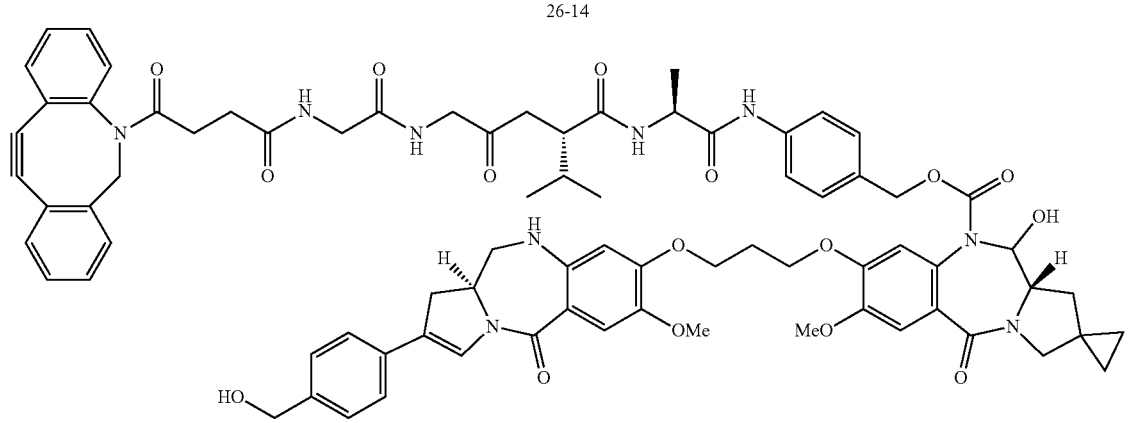

27-1

Step 1: N-[4-(11,12-Didehydrodibenzo[b,f]azocin-5 (6H)-yl)-4-oxobutanoyl]glycylglycyl-L-valyl-N-{4-[({[(11a'S)-11'-hydroxy-8'-[3-({(11aS)-2-[4-(hydroxymethyl)phenyl]-7-methoxy-5-oxo-5,10,11,11a-tetrahydro-1H-pyrrolo[2,1-c][1,4]benzodiazepin-8-yl}oxy)propoxy]-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

To a solution of the compound obtained in step 14 of Example 26 (0.0230 g, 0.0159 mmol) in methanol (2 mL), 1 N sodium hydroxide solution (0.0175 mL, 0.0175 mmol) was added, and the resultant was stirred at room temperature for 1 hour. Thereto, 1 N sodium hydroxide solution (0.0175 mL, 0.0175 mmol) was further added, and the resultant was stirred at room temperature for 30 minutes. To the reaction solution, 1 N hydrochloric acid aqueous solution (0.0350 mL) and water were added, and the resultant was three times extracted with chloroform. The organic layer was dried over sodium sulfate, and distillated under reduced pressure, and the resulting residue was then purified by silica gel column chromatography [chloroform:CMW=100:0(v/v) to 0:100(v/v)] to afford the desired compound (0.0190 g, 85%).

MS (APCI, ESI)m/z:1403 (M+H)$^+$.

Example 28: Drug-Linker 26

[Formula 152]

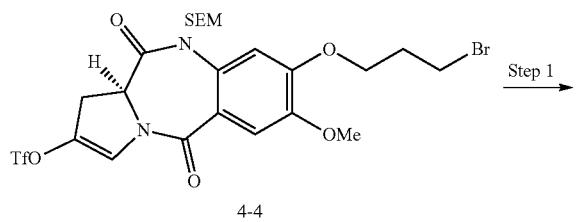

4-4

-continued
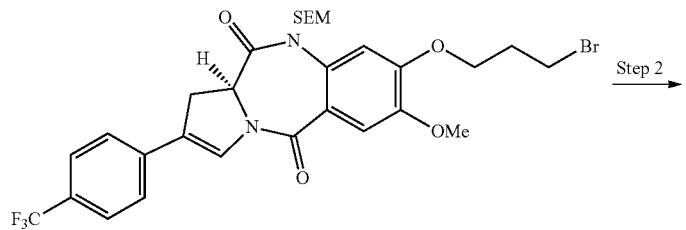
28-1
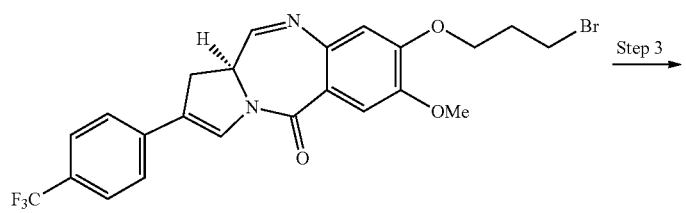
28-2
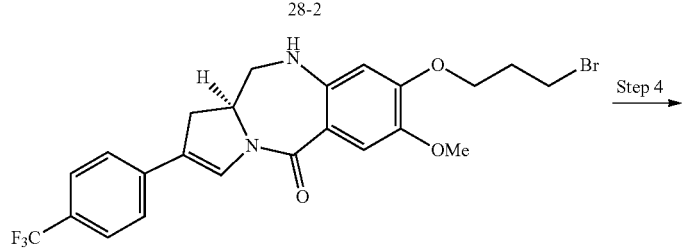
28-3
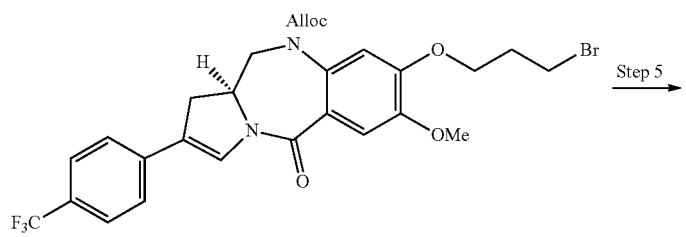
28-4
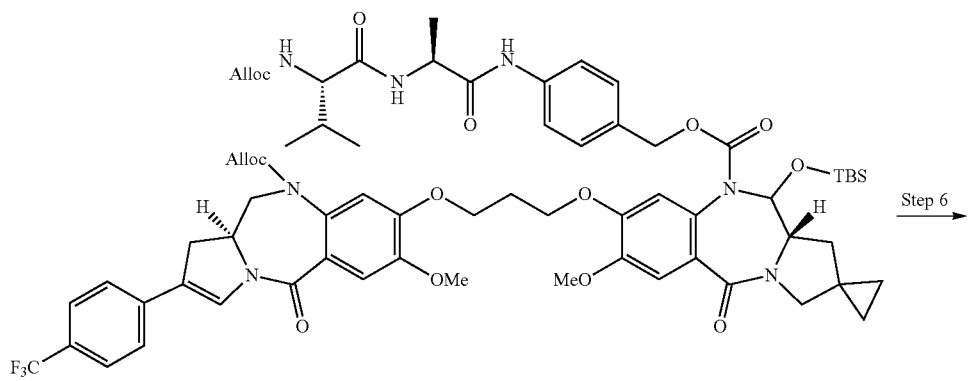
28-5

-continued
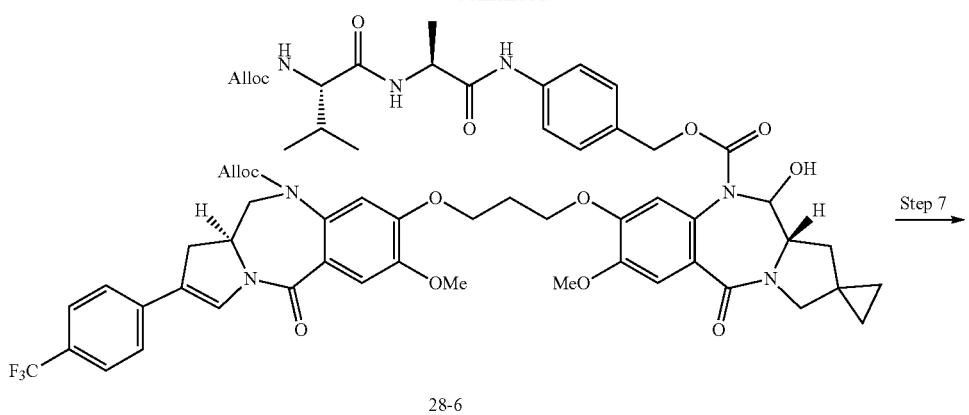
28-6
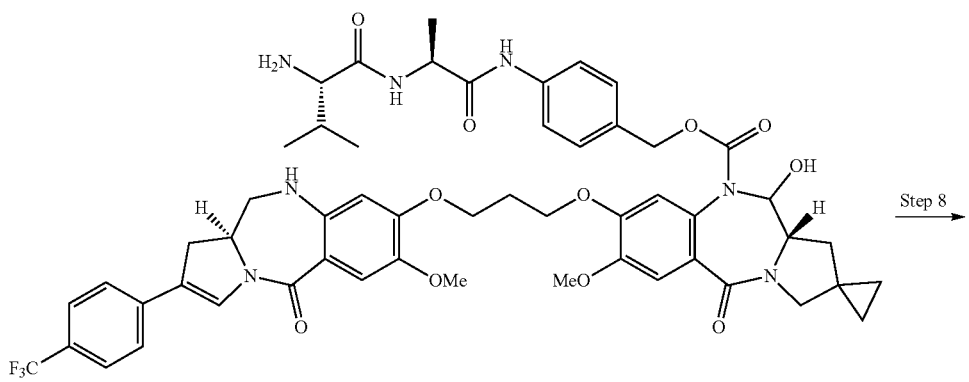
28-7
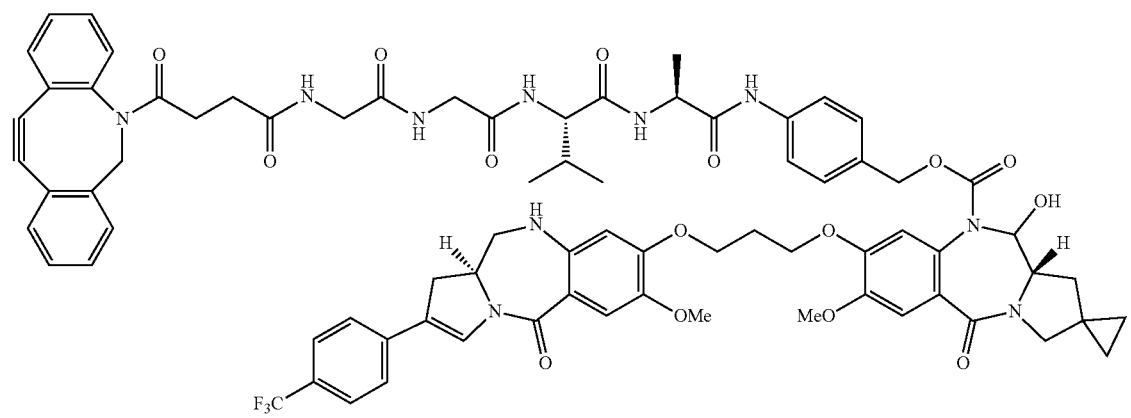
28-8

Step 1: Compound 28-1

The compound obtained in step 4 of Example 4 (1.12 g, 1.70 mmol) and 4-(4,4,5,5-tetramethyl-1,3,2-dioxaboran-2-yl)trifluoromethylbenzene (0.924 g, 3.40 mmol) were reacted in the same manner as in step 6 of Example 3 to afford the desired compound (0.918 g, 83%).
MS(APCI, ESI)m/z:657[$^{81}$Br,(M+H)$^+$], 655[$^{79}$Br,(M+H)$^+$].

Step 2: Compound 28-2

The compound obtained in step 1 (0.918 g, 1.40 mmol) was reacted in the same manner as in step 7 of Example 3 to afford the desired compound (0.425 g, 60%).
MS(APCI, ESI)m/z:511[$^{81}$Br,(M+H)$^+$], 509[$^{79}$Br,(M+H)$^+$].

Step 3: Compound 28-3

The compound obtained in step 2 (0.425 g, 0.834 mmol) was reacted in the same manner as in step 8 of Example 3. After a liquid separation operation, the resultant was distillated under reduced pressure, and the resulting compound (0.410 g) was directly used for the subsequent reaction.

Step 4: Compound 28-4

The compound obtained in step 2 (0.425 g, 0.834 mmol) was reacted in the same manner as in step 8 of Example 3 and step 9 of Example 3 to afford the desired compound (0.420 g, 85%). MS(APCI, ESI)m/z:597[$^{81}$Br,(M+H)$^+$], 595 [$^{79}$Br,(M+H)$^+$].

Step 5: Compound 28-5

The compound obtained in step 4 (0.0960 g, 0.160 mmol) was reacted in the same manner as in step 10 of Example 3 to afford the desired compound (0.212 g, 99%).
MS(APCI, ESI)m/z:1321(M+H)$^+$.

Step 6: Compound 28-6

The compound obtained in step 5 (0.210 g, 0.159 mmol) was reacted in the same manner as in step 11 of Example 3 to afford the desired compound (0.162 g, 84%).
MS(APCI, ESI)m/z:1208(M+H)$^+$.

Step 7: Compound 28-7

The compound obtained in step 6 (0.160 g, 0.132 mmol) was used and reacted in the same manner as in step 12 of Example 3 to afford the desired compound (0.103 g, 75%).
MS(APCI, ESI)m/z:1039(M+H)$^+$.

Step 8: N-[4-(11,12-Didehydrodibenzo[b,f]azocin-5 (6H)-yl)-4-oxobutanoyl]glycylglycyl-L-valyl-N-{4-[({[(11a'S)-11'-hydroxy-7'-methoxy-8'-[3-({(11aS)-7-methoxy-5-oxo-2-[4-(trifluoromethyl)phenyl]-5,10,11,11a-tetrahydro-1H-pyrrolo[2,1-c][1,4]benzodiazepin-8-yl}oxy)propoxy]-5'-oxo-11',11a'-dihydro-1'H-spiro[cyclopropane-1,2'-pyrrolo[2,1-c][1,4]benzodiazepine]-10'(5'H)-yl]carbonyl}oxy) methyl]phenyl}-L-alaninamide ("GGVA" Disclosed as SEQ ID NO: 76)

Starting raw material 4-4 and the compound obtained in step 7 (0.101 g, 0.0971 mmol) were reacted in the same manner as in step 13 of Example 3 to afford the desired compound (0.107 g, 76%).
MS (APCI, ESI)m/z:1441 (M+H)$^+$.

Example 29: Drug-Linker 27

[Formula 153]

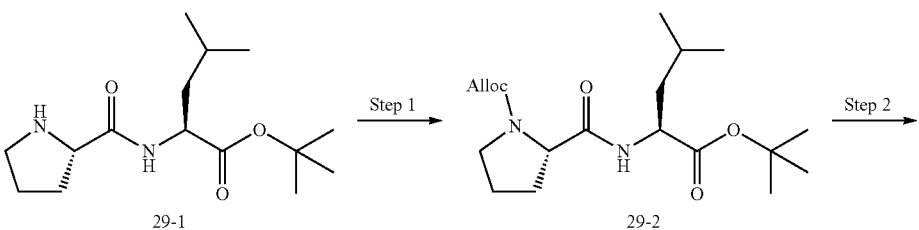

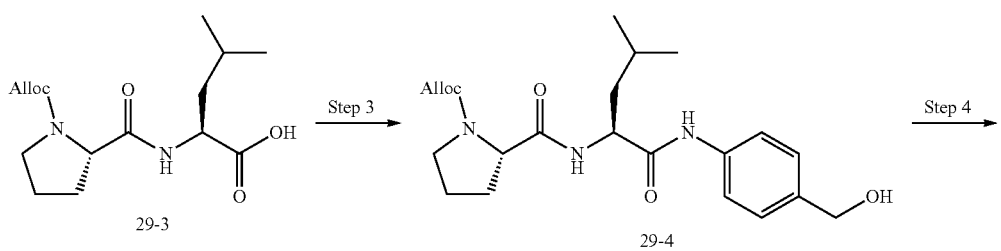

-continued
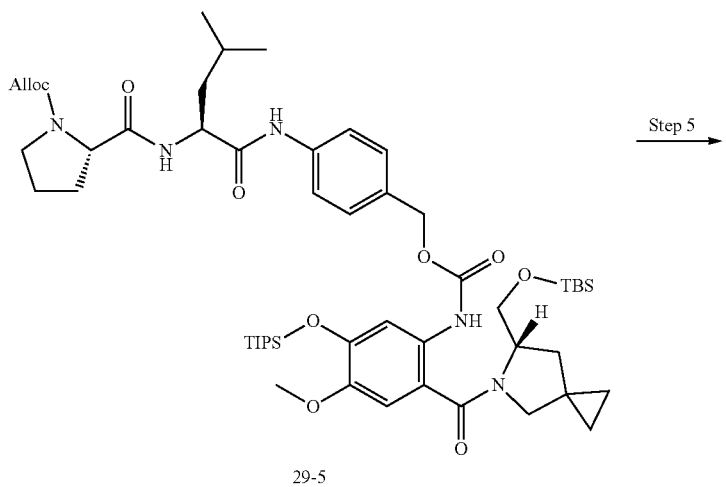
29-5
Step 5
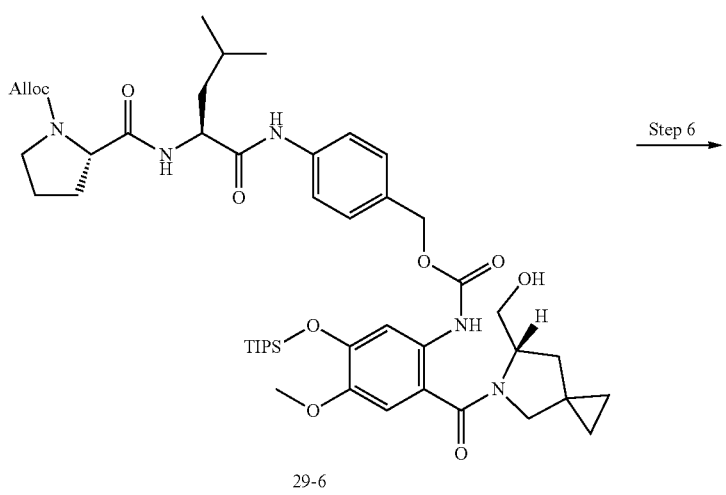
29-6
Step 6
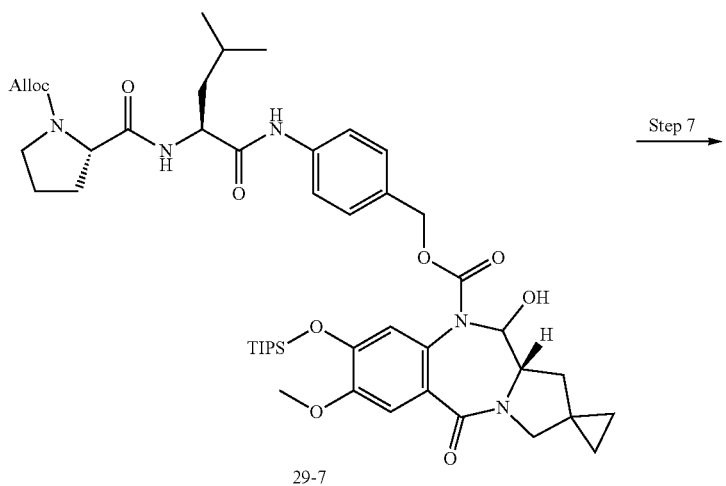
29-7
Step 7

-continued
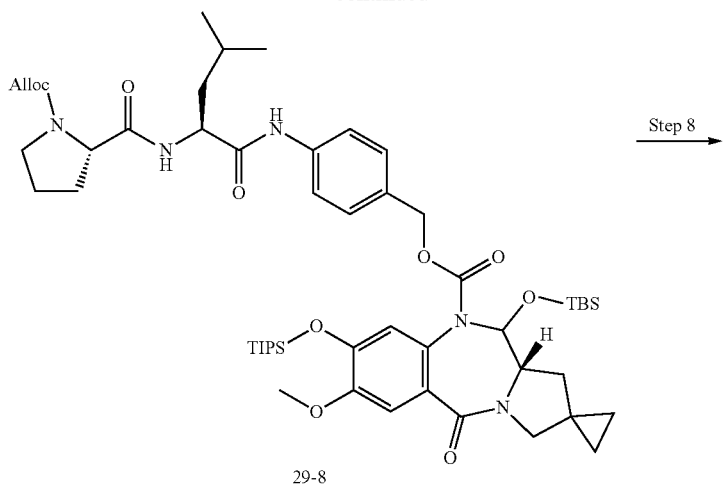
29-8
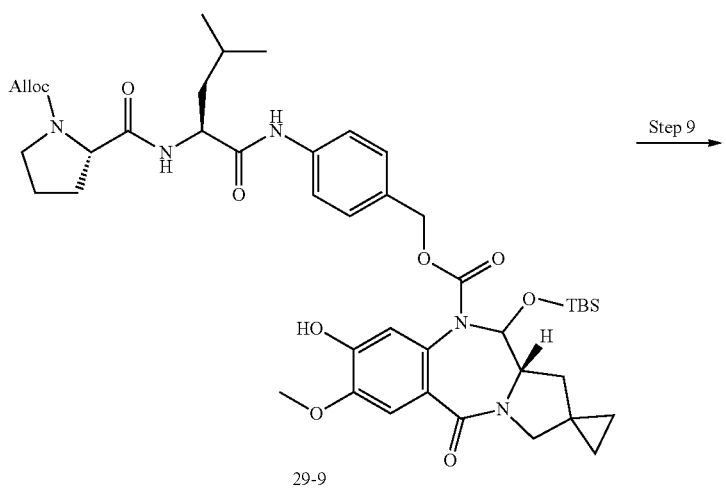
29-9
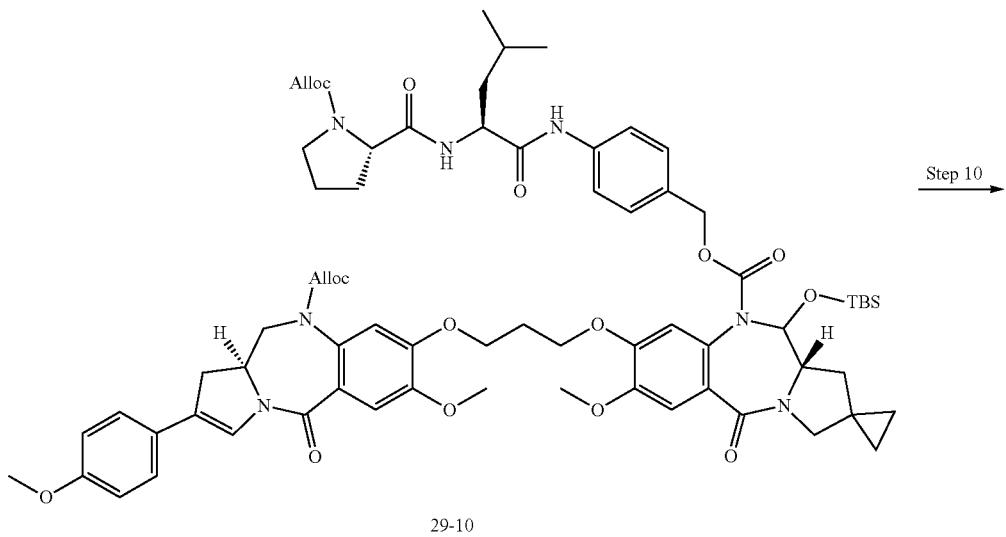
29-10

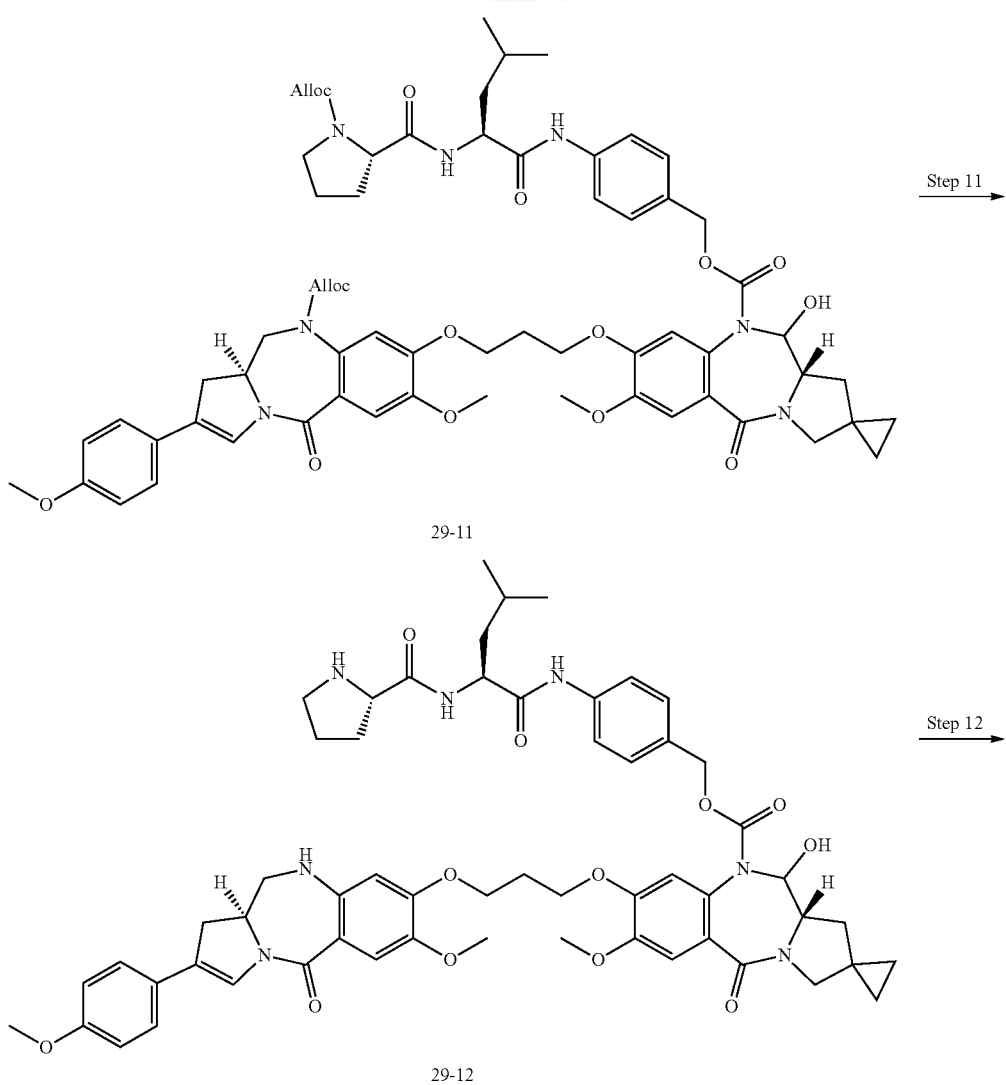
29-11
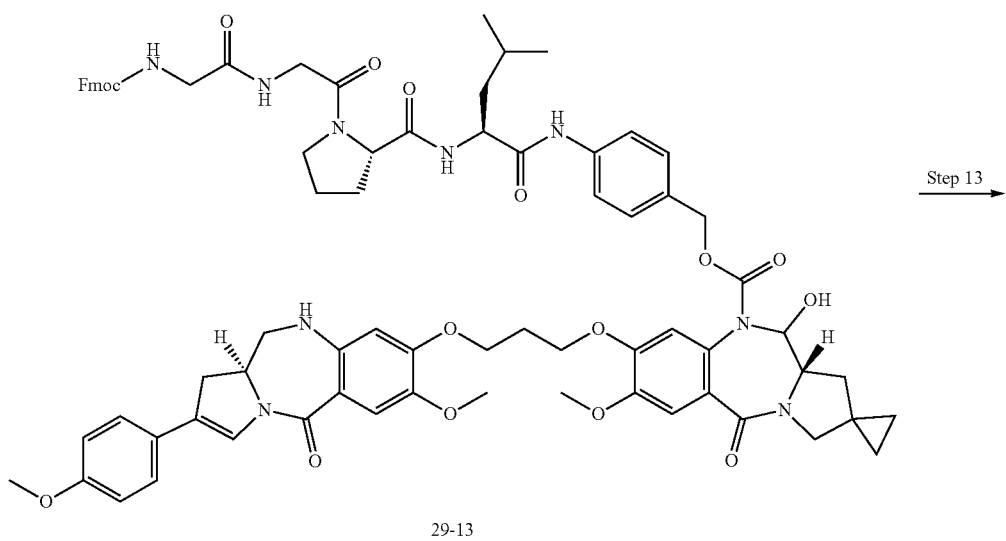
29-12
29-13

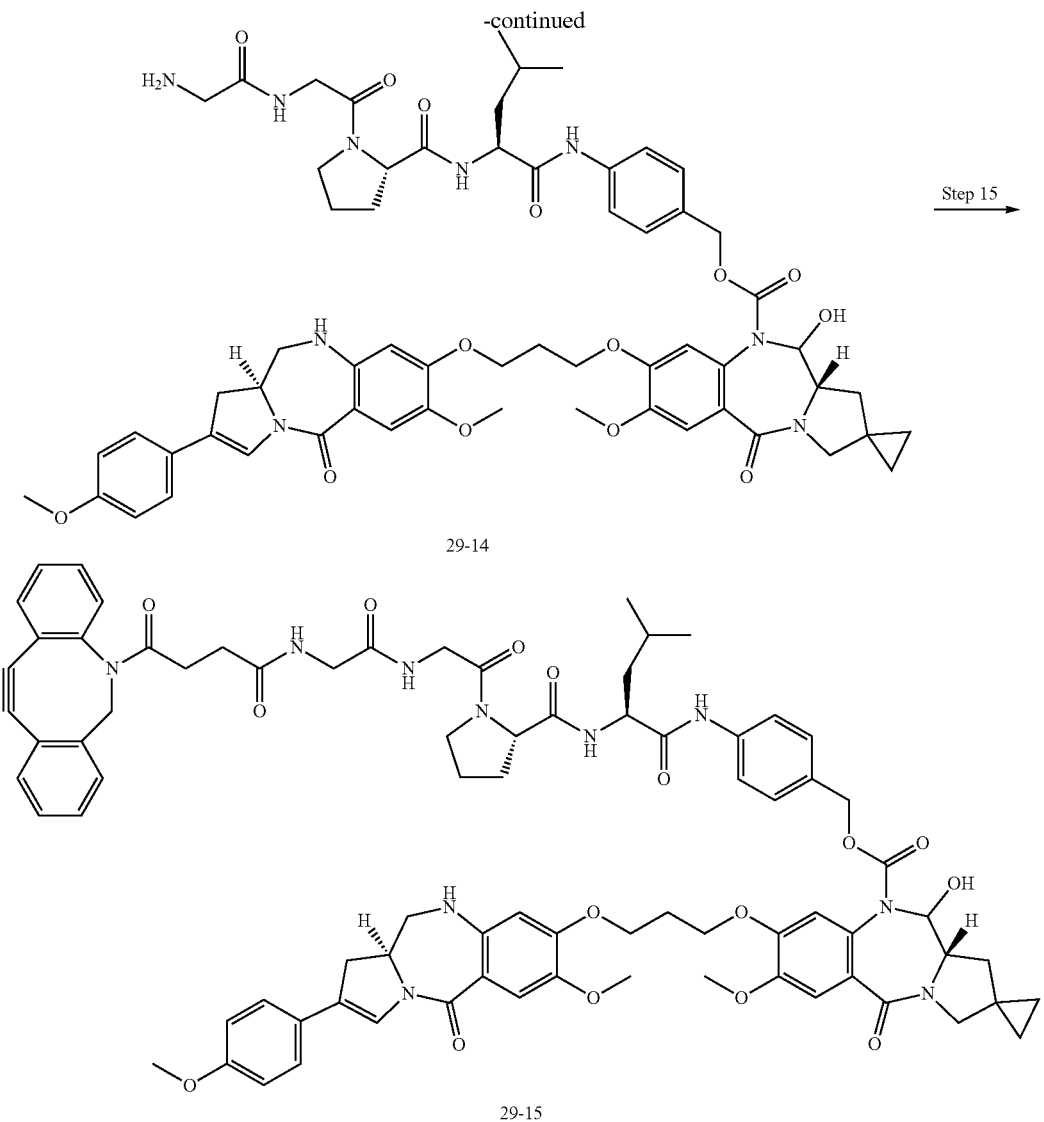

29-14

29-15

Step 1: tert-Butyl 1-[(prop-2-en-1-yloxy)carbonyl]-L-prolyl-L-leucinate tert-Butyl-L-prolyl-L-leucinate (4.64 g, 16.3 mmol) was reacted in the same manner as in step 9 of Example 3, except that triethylamine (3.41 mL, 24.5 mmol) was used in place of pyridine. After the completion of the reaction, a liquid separation operation was performed, and the organic solvent was distilled off under reduced pressure, and the resulting compound (5.79 g, 96%) was directly used for the subsequent reaction.

Step 2: 1-[(Prop-2-en-1-yloxy)carbonyl]-L-prolyl-L-leucine

To a solution of the compound obtained in step 1 (5.79 g, 15.7 mmol) in dichloromethane (60 mL), trifluoroacetic acid (20 mL) was added, and the resultant was stirred at room temperature for 1 hour. Toluene was added to the reaction solution, which was distillated under reduced pressure, and the resulting compound (2.69 g, 55%) was directly used for the subsequent reaction.

Step 3: 1-[(Prop-2-en-1-yloxy)carbonyl]-L-prolyl-N-[4-(hydroxymethyl)phenyl]-L-leucinamide To a solution of the compound obtained in step 2 (6.10 g, 19.5 mmol) in THF (100 mL), N-ethoxycarbonyl-2-ethoxy-1,2-dihydroquinoline (5.07 g, 20.5 mmol) was added, and the resultant was stirred at room temperature for 1 hour. Thereto, 4-aminobenzyl alcohol (2.16 g, 20.5 mmol) was added, and the resultant was stirred overnight. The reaction solution was distillated under reduced pressure, and the resulting residue was dissolved in ethyl acetate. The resultant was washed with dilute hydrochloric acid, a saturated aqueous sodium hydrogen carbonate, and brine, and the organic layer was dried over anhydrous sodium sulfate. After filtration, the solvent was distilled off under reduced pressure, and the resulting residue was purified by silica gel column chromatography [hexane:ethyl acetate=90:10 (v/v) to 0:100 (v/v)] to afford the desired compound (1.60 g, 20%).

$^1$H-NMR (CDCl$_3$) δ:8.62-8.33 (1H, m), 7.68-7.49 (2H, m), 7.31-7.30 (2H, m), 6.66-6.43 (1H, m), 5.97-5.70 (1H, m), 5.39-4.96 (2H, m), 4.64-4.53 (5H, m), 4.40-4.35 (1H, m), 3.57-3.50 (2H, m), 2.20-2.19 (2H, m), 1.98-1.97 (3H, m), 1.66-1.64 (3H, m), 0.97-0.94 (6H, m).

MS(APCI, ESI)m/z:418(M+H)+.

Step 4: 1-[(Prop-2-en-1-yloxy)carbonyl]-L-prolyl-N-[4-({[(2-{[(6S)-6-({[tert-butyl(dimethyl)silyl]oxy}methyl)-5-azaspiro[2.4]hept-5-yl]carbonyl}-4-methoxy-5-{[tri(propan-2-yl)silyl]oxy}phenyl)carbamoyl]oxy}methyl)phenyl]-L-leucinamide The compound obtained in step 3 (0.838 g, 2.01 mmol) was reacted in the same manner as in step 6 of Example 1 to afford the desired compound (0.535 g, 37%).

$^1$H-NMR (CDCl$_3$) δ:8.98 (1H, m), 8.62 (1H, s), 7.80 (1H, s), 7.65-7.50 (2H, m), 7.33-7.31 (2H, m), 6.76 (1H, s), 6.67-6.34 (1H, m), 5.95-5.92 (1H, m), 5.33-5.25 (1H, m), 5.30-5.27 (1H, m), 5.12 (2H, s), 4.66-4.63 (3H, m), 4.58-4.55 (3H, m), 4.38-4.36 (1H, m), 3.99-3.96 (1H, m), 3.73 (3H, s), 3.70-3.65 (2H, m), 3.57-3.55 (2H, m), 3.04-3.02 (1H, m), 2.21-2.20 (3H, m), 1.98-1.95 (3H, m), 1.74-1.62 (3H, m), 1.32-1.30 (3H, m), 1.11-1.09 (16H, m), 0.97-0.94 (6H, m), 0.90 (9H, s), 0.60-0.52 (4H, m), 0.05-0.04 (6H, m).

Steps 5 and 6: 1-[(Prop-2-en-1-yloxy)carbonyl]-L-prolyl-N-{4-[({[(11a'S)-11'-hydroxy-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-leucinamide The compound obtained in step 4 (0.535 g, 0.531 mmol) was reacted in the same manner as in step 7 of Example 1 and step 3 of Example 9 to afford the desired compound (0.367 g, 78%).

$^1$H-NMR (CDCl$_3$) δ:8.60 (1H, s), 7.58-7.42 (2H, m), 7.19-7.16 (3H, m), 6.69-6.64 (2H, m), 5.89-5.87 (2H, m), 5.32-5.24 (2H, m), 5.10 (1H, m), 4.93 (1H, m), 4.65-4.63 (1H, m), 4.57-4.54 (2H, m), 4.37-4.34 (1H, m), 3.84 (3H, s), 3.72 (1H, m), 3.57-3.55 (3H, m), 3.40-3.38 (1H, m), 3.31 (1H, m), 2.41 (1H, m), 2.20-2.18 (2H, m), 1.98-1.95 (3H, m), 1.73 (1H, m), 1.66-1.63 (1H, m), 1.16-1.10 (4H, m), 1.05-0.99 (18H, m) 0.97-0.93 (6H, m), 0.71-0.64 (4H, m).

MS(APCI, ESI)m/z:890(M+H)+.

Step 7: 1-[(Prop-2-en-1-yloxy)carbonyl]-L-prolyl-N-{4-[({[(11a'S)-11'-{[tert-butyl(dimethyl)silyl]oxy}-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-leucinamide The compound obtained in step 6 (0.367 g, 0.412 mmol) was used and reacted in the same manner as in step 9 of Example 1 to afford the desired compound (0.181 g, 44%).

$^1$H-NMR (CDCl$_3$) δ:8.54 (1H, s), 7.52-7.45 (2H, m), 7.19 (1H, s), 7.14 (2H, m), 6.71-6.68 (1H, m), 6.61 (1H, s), 6.01 (1H, m), 5.94-5.92 (1H, m), 5.34-5.17 (2H, m), 4.77 (1H, m), 4.64-4.56 (3H, m), 4.38-4.35 (1H, m), 3.85 (3H, s), 3.72-3.69 (1H, m), 3.55-3.46 (3H, m), 3.27 (1H, m), 2.35 (1H, m), 2.21-2.18 (2H, m), 1.97-1.95 (3H, m), 1.54-1.51 (2H, m), 1.16-1.09 (5H, m), 1.02-1.01 (18H, m), 0.97-0.93 (6H, m), 0.81 (9H, s), 0.68-0.63 (4H, m), 0.19 (3H, s), 0.09 (3H, s).

Step 8: 1-[(Prop-2-en-1-yloxy)carbonyl]-L-prolyl-N-{4-[({[(11a'S)-11'-{[tert-butyl(dimethyl)silyl]oxy}-8'-hydroxy-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-leucinamide The compound obtained in step 7 (0.181 g, 0.180 mmol) was treated in the same manner as in step 10 of Example 1 to afford the desired compound (0.153 g, quantitative).

$^1$H-NMR (CDCl$_3$) δ:8.57-8.27 (1H, m), 7.69-7.41 (2H, m), 7.23 (1H, s), 7.12 (2H, m), 6.69-6.66 (1H, m), 6.64 (1H, s), 5.99-5.92 (3H, m), 5.34-5.19 (3H, m), 4.81 (1H, m), 4.63-4.57 (4H, m), 4.38-4.36 (1H, m), 3.94 (3H, s), 3.71 (1H, m), 3.54-3.52 (3H, m), 3.27 (1H, m), 2.35 (1H, m), 2.19 (2H, m), 1.97-1.95 (3H, m), 1.55-1.52 (2H, m), 0.97-0.93 (6H, m), 0.81 (9H, s), 0.76-0.61 (4H, m), 0.21 (3H, s), 0.09 (3H, s).

MS(APCI, ESI)m/z:848(M+H)+.

Step 9: 1-[(Prop-2-en-1-yloxy)carbonyl]-L-prolyl-N-{4-[({[(11a'S)-11'-{[tert-butyl(dimethyl)silyl]oxy}-7'-methoxy-8'-[3-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)propoxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-leucinamide The compound obtained in step 8 (0.153 g, 0.180 mmol) was reacted in the same manner as in step 9 of Example 4 to afford the desired compound (0.137 g, 57%).

$^1$H-NMR (CDCl$_3$) δ:8.79 (1H, s), 7.54-7.51 (1H, m), 7.39-7.37 (2H, m), 7.30-7.29 (2H, m), 7.23-7.21 (3H, m), 7.13-7.11 (2H, m), 6.88 (2H, m), 6.82-6.80 (1H, m), 6.50-6.48 (1H, m), 6.03-6.01 (1H, m), 5.92-5.89 (1H, m), 5.75-5.72 (1H, m), 5.28-5.26 (3H, m), 5.06-5.03 (2H, m), 4.74-4.71 (1H, m), 4.62-4.60 (4H, m), 4.36-4.34 (2H, m), 4.22-4.19 (3H, m), 4.01-3.99 (1H, m), 3.88 (3H, s), 3.84-3.81 (6H, m), 3.71 (2H, m), 3.53-3.50 (4H, m), 3.28-3.25 (2H, m), 2.72-2.68 (1H, m), 2.37-2.34 (4H, m), 2.19-2.16 (3H, m), 1.97-1.94 (2H, m), 1.49-1.43 (2H, m), 0.95-0.92 (7H, m), 0.81 (9H, s), 0.68-0.65 (4H, m), 0.19 (3H, s), 0.13 (3H, s).

MS(APCI, ESI)m/z:1324(M+H)+.

Step 10: 1-[(Prop-2-en-1-yloxy)carbonyl]-L-prolyl-N-{4-[({[(11a'S)-11'-hydroxy-7'-methoxy-8'-[3-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)propoxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-leucinamide The compound obtained in step 9 (0.136 g, 0.103 mmol) was reacted in the same manner as in step 11 of Example 3 to afford the desired compound (0.116 g, 93%).

$^1$H-NMR (CDCl$_3$) δ:8.83 (1H, s), 7.57-7.52 (1H, m), 7.39-7.37 (2H, m), 7.30-7.29 (2H, m), 7.24-7.20 (5H, m), 6.88 (2H, m), 6.81 (1H, s), 6.54-6.51 (1H, m), 5.90-5.88 (2H, m), 5.76-5.74 (1H, m), 5.55-5.53 (1H, m), 5.33-5.05 (3H, m), 4.74-4.76 (1H, m), 4.63-4.60 (4H, m), 4.35-4.33 (2H, m), 4.22-4.19 (3H, m), 4.04-4.03 (1H, m), 3.88 (3H, s), 3.85-3.83 (6H, m), 3.72 (2H, m), 3.62-3.56 (4H, m), 3.32-

3.29 (2H, m), 2.70 (1H, m), 2.45-2.38 (2H, m), 2.30-2.27 (2H, m), 2.20-2.10 (3H, m), 1.94-1.89 (4H, m), 1.75-1.71 (2H, m), 0.95 (7H, m), 0.72-0.66 (4H, m).

MS(APCI, ESI)m/z:1210(M+H)+.

Step 11: L-Prolyl-N-{4-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-leucinamide The compound obtained in step 10 (0.116 g, 0.0958 mmol) was reacted in the same manner as in step 12 of Example 3 to afford the desired compound (0.0530 g, 53%).

$^1$H-NMR (CDCl$_3$) δ:9.15 (1H, s), 8.11 (1H, m), 7.50-7.45 (4H, m), 7.32-7.31 (2H, m), 7.21 (1H, s), 7.13 (2H, m), 6.89 (2H, m), 6.37 (1H, s), 6.08 (1H, s), 5.88 (1H, m), 5.38 (1H,m), 4.69 (1H, m), 4.63-4.60 (1H, m), 4.53-4.51 (1H, m), 4.31-4.28 (1H, m), 4.13-4.08 (3H, m), 3.89 (3H, s), 3.83 (3H, s), 3.81 (3H, s), 3.75-3.70 (4H, m), 3.57-3.55 (3H, m), 3.37-3.33 (2H, m), 3.01-2.99 (1H, m), 2.90-2.86 (1H, m), 2.76-2.73 (1H, m), 2.41 (1H, m), 2.17-2.15 (3H, m), 1.90-1.87 (1H, m), 1.74 (4H, m), 1.25 (2H, m), 0.97-0.91 (7H, m), 0.67 (4H, m).

MS(APCI, ESI)m/z:1042(M+H)+.

Step 12: N-[(9H-Fluoren-9-yloxy)carbonyl]glycylglycyl-L-prolyl-N-{4-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-leucinamide ("GGPL" disclosed as SEQ ID NO: 81)

To a solution of the compound obtained in step 11 (0.0410 g, 0.0393 mmol) and N-[(9H-fluoren-9-ylmethoxy)carbonyl]glycylglycine (0.0410 g, 0.0393 mmol) in N,N-dimethylformamide (1 mL), 1-hydroxybenzotriazole monohydrate (0.000602 g, 0.00393 mmol) and 1-ethyl-3-(3-dimethylaminopropyl)carbodiimide hydrochloride (0.00905 g, 0.0472 mmol) were added, and the resultant was stirred at room temperature for 1 hour.

The resultant was distilled under reduced pressure, and the resulting residue was purified by silica gel column chromatography (chloroform:methanol=100:0 to 90:10) to afford the desired compound (0.0520 g, 94%).

$^1$H-NMR (CDCl$_3$) δ:8.57 (1H, s), 7.77-7.75 (3H, m), 7.63-7.61 (2H, m), 7.51-7.48 (2H, m), 7.40-7.38 (3H, m), 7.31-7.29 (4H, m), 7.21-7.11 (5H, m), 6.88 (2H, m), 6.47 (1H, s), 6.08 (1H, s), 5.93 (1H, m), 5.21-5.19 (1H, m), 5.13 (1H, m), 4.78 (1H, m), 4.66-4.59 (1H, m), 4.53-4.51 (1H, m), 4.42-4.39 (1H, m), 4.33-4.31 (1H, m), 4.19-4.11 (6H, m), 4.10-3.86 (4H, m), 3.82 (3H, s), 3.76 (3H, s), 3.73-3.71 (3H, m), 3.56-3.51 (7H, m), 3.32-3.29 (2H, m), 2.73-2.69 (1H, m), 2.40 (1H, m), 2.29-2.27 (3H, m), 2.06-2.04 (4H, m), 1.73-1.70 (2H, m), 1.25 (2H, m), 0.96-0.93 (6H, m), 0.66 (4H, m).

MS(APCI, ESI)m/z:1378(M+H)+.

Step 13: Glycylglycyl-L-prolyl-N-{4-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-leucinamide ("GGPL" disclosed as SEQ ID NO: 81)

To a solution of the compound obtained in step 12 (0.0520 g, 0.0377 mmol) in N,N-dimethylformamide (2 mL), 1,8-diazabicyclo[5.4.0]-7-undecene (67 µL, 0.0453 mmol) was added, and the resultant was stirred at room temperature for 1 hour. The resultant was distillated under reduced pressure, and the resulting residue was purified by silica gel column chromatography [chloroform:CMW=100:0(v/v) to 0:100(v/v)] to afford the desired compound (0.0420 g, 92%).

$^1$H-NMR (CDCl$_3$) δ:8.64 (1H, s), 7.74 (1H, m), 7.66-7.64 (1H, m), 7.50 (1H, s), 7.45 (1H, s), 7.33-7.30 (3H, m), 7.24-7.21 (2H, m), 7.18-7.16 (3H, m), 6.89 (2H, m), 6.51 (1H, s), 6.15 (1H, s), 5.89 (1H, m), 5.27 (1H, m), 4.82-4.78 (1H, m), 4.74 (1H, m), 4.56-4.54 (1H, m), 4.49-4.47 (1H, m), 4.23-4.20 (3H, m), 4.13-4.10 (3H, m), 3.96-3.92 (1H, m), 3.90 (3H, s), 3.83 (3H, s), 3.76 (3H, s), 3.72 (2H, m), 3.62-3.56 (5H, m), 3.40-3.36 (1H, m), 3.31 (1H, m), 3.04 (1H, m), 2.90-2.86 (1H, m), 2.75-2.71 (1H, m), 2.42-2.39 (1H, m), 2.36 (2H, s), 2.29-2.27 (3H, m), 2.07-2.05 (3H, m), 1.97-1.95 (1H, m), 1.75-1.72 (2H, m), 0.94 (6H, m), 0.69 (4H, m).

MS(APCI, ESI)m/z:1156(M+H)+.

Step 14: N-[4-(11,12-Didehydrodibenzo[b,f]azocin-5(6H)-yl)-4-oxobutanoyl]glycylglycyl-L-prolyl-N-{4-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-leucinamide ("GGPL" disclosed as SEQ ID NO: 81)

To a solution of the compound obtained in step 13 (0.0400 g, 0.0346 mmol) in N,N-dimethylformamide (1 mL), 1-{[4-(11,12-didehydrodibenzo[b,f]azocin-5(6H)-yl)-4-oxobutanoyl]oxy}pyrrolidin-2,5-dione (0.0140 g, 0.0346 mmol, Click Chemistry Tools) and diisopropylamine (0.0240 mL, 0.138 mmol) were added, and the resultant was stirred at room temperature for 18 hours. The reaction solution was distilled under reduced pressure, and the resulting residue was purified by silica gel column chromatography [chloroform:methanol=100:0(v/v) to 90:10(v/v)] to afford the desired compound (0.0230 g, 46%).

MS (APCI, ESI)m/z:1443 (M+H)+.

Example 30: Drug-Linker 28

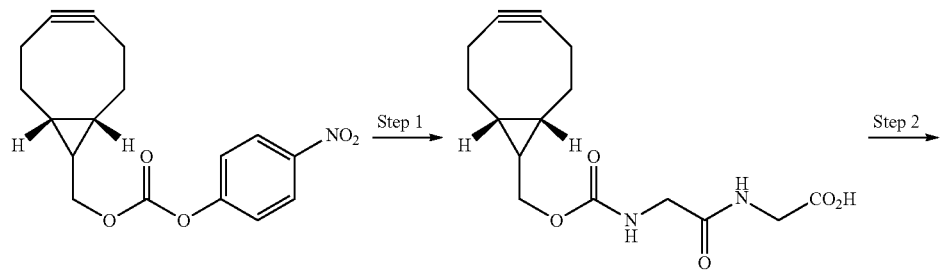

[Formula 154]

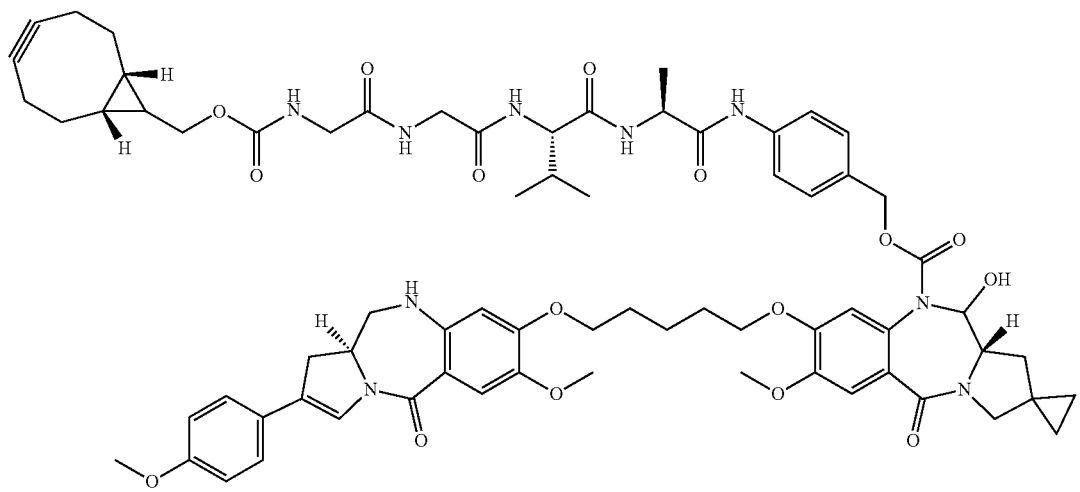

30-3

Step 1: N-{[(1R,8S)-Bicyclo[6.1.0]non-4-in-9-yl-methoxy]carbonyl}glycylglycine To a solution of starting material 30-1 (0.215 g, 0.682 mmol, Chemistry-A European Journal 2016, 22, 639) in N,N-dimethylformamide (4 mL), N,N-diisopropylethylamine (0.119 mL, 0.682 mmol), glycyl-glycine (0.0900 g, 0.682 mmol), and water (2 mL) were added, and the resultant was stirred at room temperature overnight. The reaction solution was distillated under reduced pressure, and the resulting residue was purified by silica gel column chromatography [chloroform:CMW=100:0(v/v) to 0:100(v/v)] to afford the desired compound (0.205 g, 98%).

MS(APCI, ESI)m/z:309(M+H)$^+$.

Step 2: N-{[(1R,8S)-Bicyclo[6.1.0]non-4-in-9-yl-methoxy]carbonyl}glycylglycyl-L-valyl-N-{4-[({[(11a'S)-11'-hydroxy-7'-methoxy-8'-[(5-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}pentyl)oxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 1 (0.0180 g, 0.0587 mmol) was reacted in the same manner as in step 13 of Example 3 to afford the desired compound (0.0420 g, 60%).

¹H-NMR (DMSO-D₆) δ:9.93 (1H, s), 8.25 (1H, m), 8.05 (1H, s), 7.85 (1H, m), 7.60-7.54 (2H, m), 7.45 (1H, s), 7.39-7.37 (3H, m), 7.29 (1H, s), 7.20 (1H, m), 7.04 (1H, s), 6.91 (2H, m), 6.72 (1H, s), 6.56-6.53 (2H, m), 6.31 (1H, s), 5.76-5.74 (1H, m), 5.19 (1H, m), 4.80 (1H, m), 4.38-4.36 (1H, m), 4.23-4.21 (2H, m), 4.04 (2H, m), 3.95-3.92 (3H, m), 3.78-3.76 (9H, m), 3.66 (3H, s), 3.60 (2H, m), 3.55-3.52 (2H, m), 3.45-3.38 (2H, m), 3.26-3.23 (1H, m), 3.14 (1H, m), 2.77-2.74 (1H, m), 2.35-2.33 (1H, m), 2.20-2.11 (6H,m), 1.99-1.96 (1H, m), 1.81-1.78 (4H, m), 1.56-1.54 (5H, m), 1.29-1.26 (4H, m), 0.87-0.82 (9H, m), 0.67-0.62 (4H, m).
MS(APCI, ESI)m/z:1320(M+H)⁺.
Example 31: Drug-Linker 29
[Formula 155]
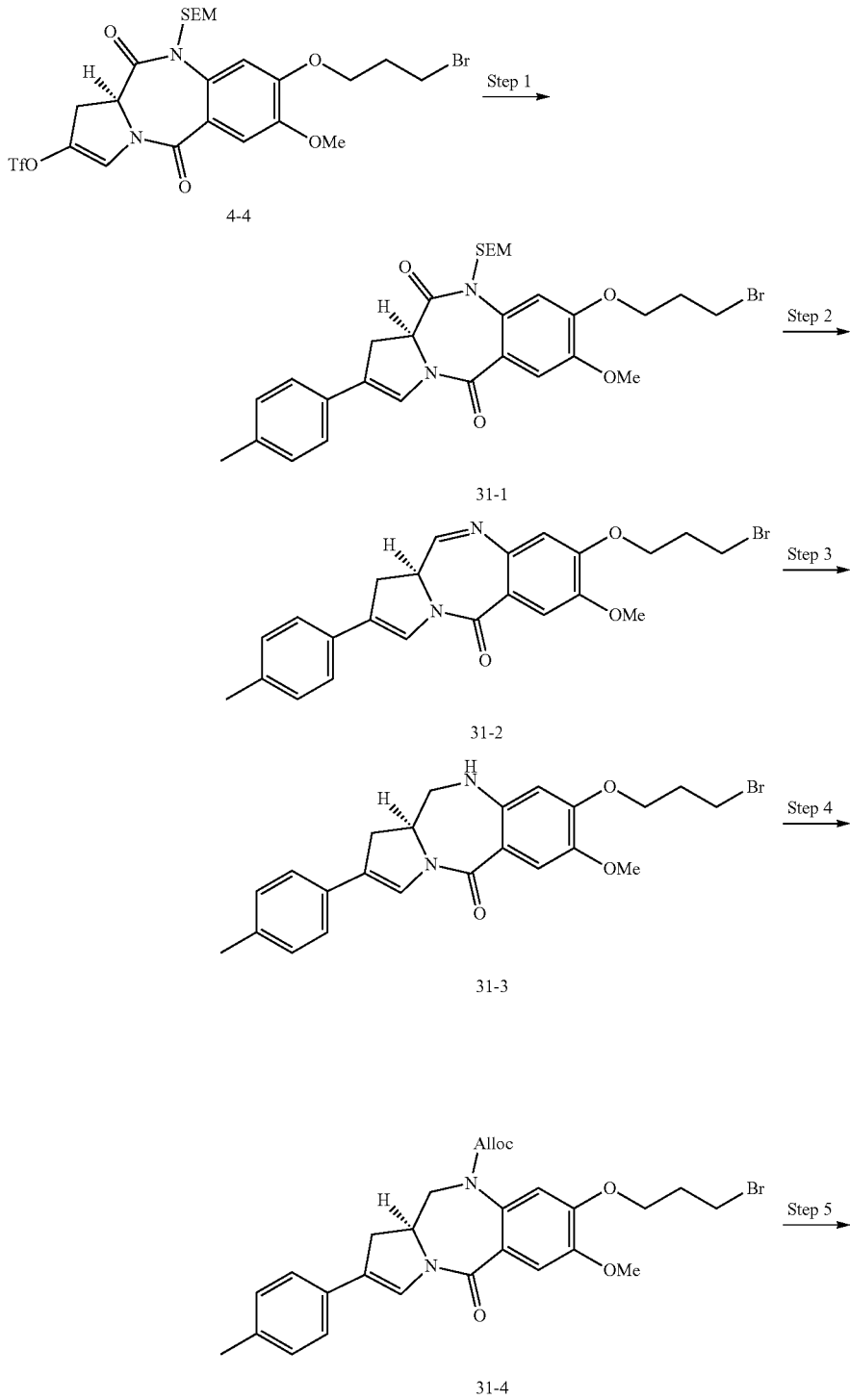

-continued
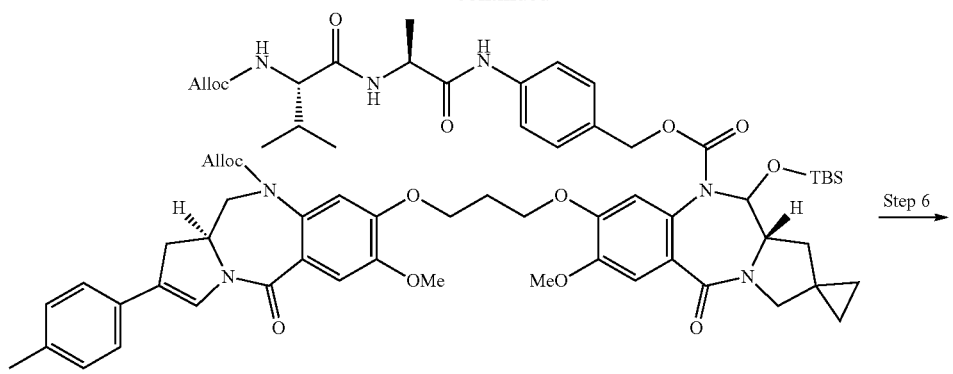
31-5
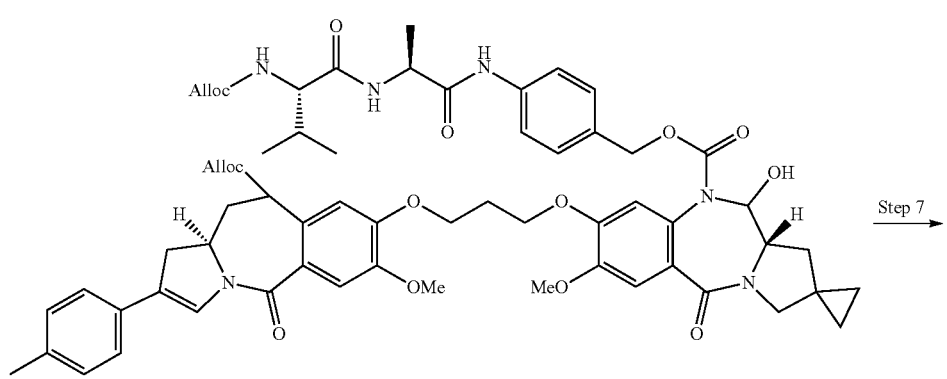
31-6
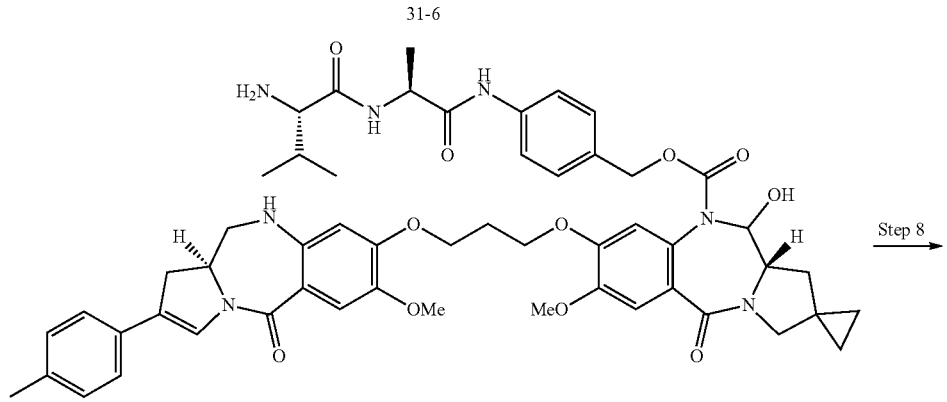
31-7
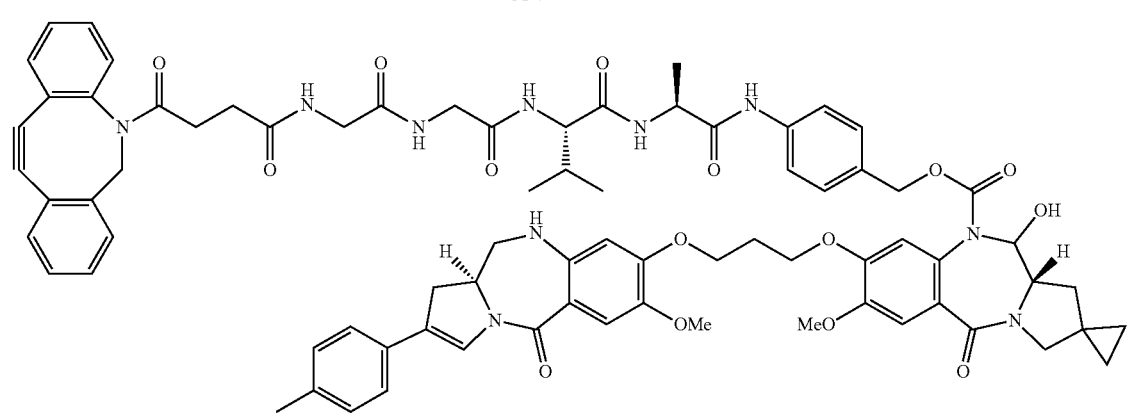
31-8

409

Step 1: Compound 31-1

The compound obtained in step 4 of Example 4 (1.00 g, 1.52 mmol) and 4-methylphenylboronic acid (0.309 g, 2.27 mmol) were reacted in the same manner as in step 6 of Example 3 to afford the desired compound (0.653 g, 72%).

Step 2: Compound 31-2

The compound obtained in step 1 (0.653 g, 1.09 mmol) was reacted in the same manner as in step 7 of Example 3 to afford the desired compound (0.377 g, 76%).
MS(APCI, ESI)m/z:457[$^{81}$Br,(M+H)$^+$], 455[$^{79}$Br,(M+H)$^+$].

Step 3: Compound 31-3

The compound obtained in step 2 (0.377 g, 0.828 mmol) was reacted in the same manner as in step 8 of Example 3 to afford the desired compound (0.311 g, 82%).
MS(APCI, ESI)m/z:459[$^{81}$Br,(M+H)$^+$], 457[$^{79}$Br,(M+H)$^+$].

Step 4: Compound 31-4

The compound obtained in step 3 (0.311 g, 0.68 mmol) was reacted in the same manner as in step 9 of Example 3 to afford the desired compound (0.320 g, 87%).
MS(APCI, ESI)m/z:543[$^{81}$Br,(M+H)$^+$], 541[$^{79}$Br,(M+H)$^+$].

Step 5: Compound 31-5

The compound obtained in step 4 (0.0737 g, 0.136 mmol) was reacted in the same manner as in step 10 of Example 3 to afford the desired compound (0.145 g, 92%).
MS(APCI, ESI)m/z:1272(M+H)$^+$.

410

Step 6: Compound 31-6

The compound obtained in step 5 (0.145 g, 0.114 mmol) was reacted in the same manner as in step 11 of Example 3 to afford the desired compound (0.122 g, 93%).
MS(APCI, ESI)m/z:1158(M+H)$^+$.

Step 7: Compound 31-7

The compound obtained in step 6 (0.122 g, 0.114 mmol) was reacted in the same manner as in step 12 of Example 3 to afford the desired compound (0.0598 g, 53%).
MS(APCI, ESI)m/z:990(M+H)$^+$.

Step 8: N-[4-(11,12-Didehydrodibenzo[b,f]azocin-5(6H)-yl)-4-oxobutanoyl]glycylglycyl-L-valyl-N-{4-[({[(11a'S)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 7 (0.0300 g, 0.0304 mmol) was reacted in the same manner as in step 13 of Example 3 to afford the desired compound (0.0184 g, 44%).
MS (APCI, ESI)m/z:1391 (M+H)$^+$.

Example 32: Drug-Linker 30

[Formula 156]

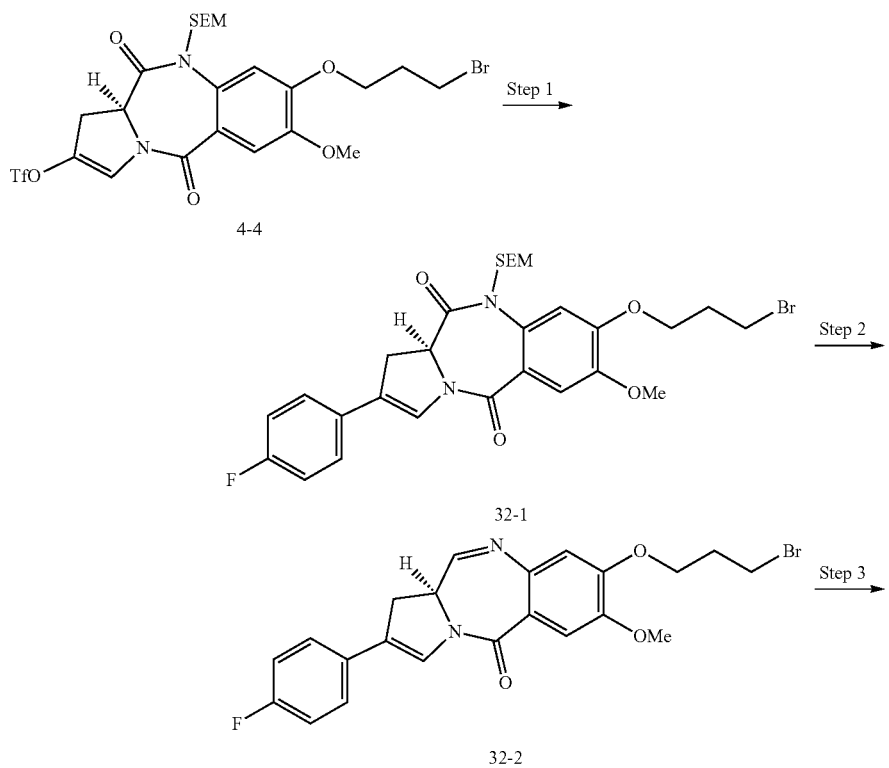

-continued
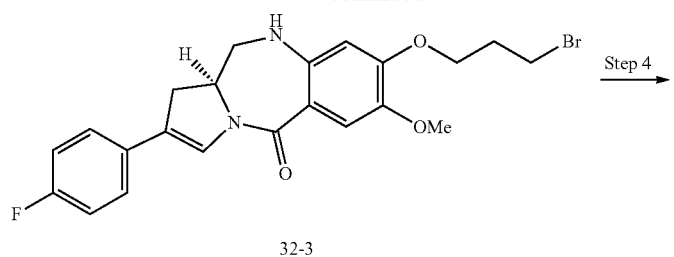
32-3
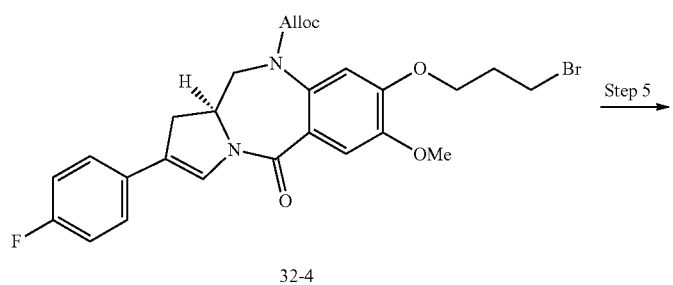
32-4
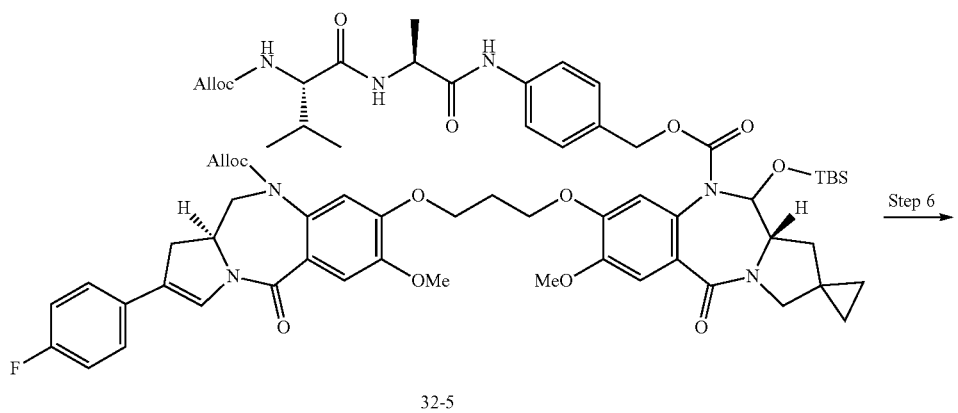
32-5
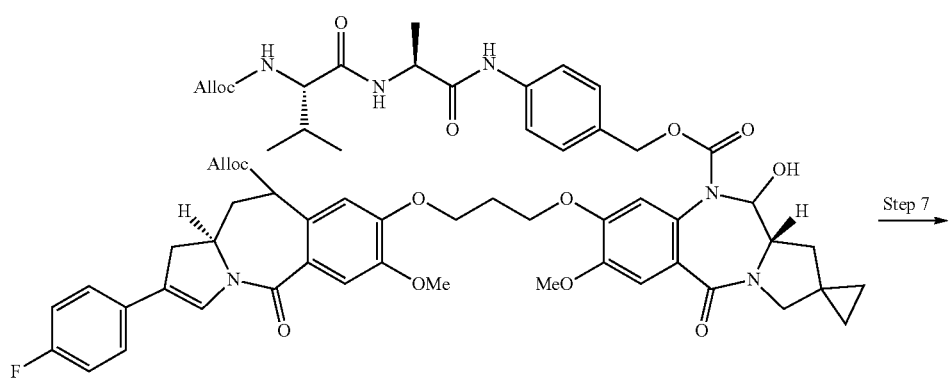
32-6

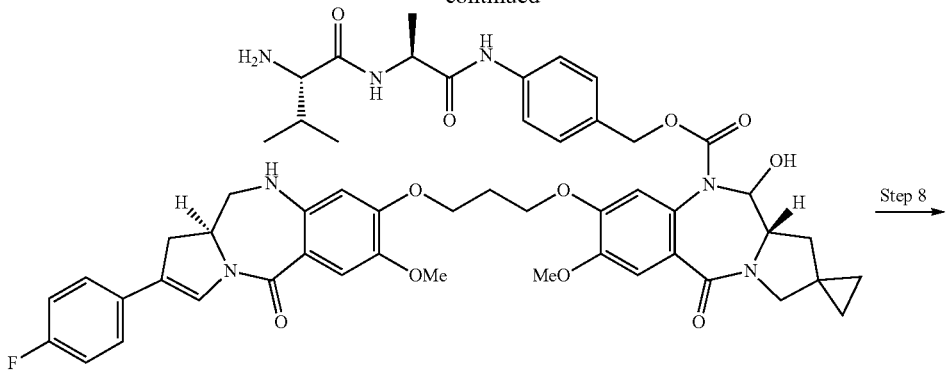

32-7

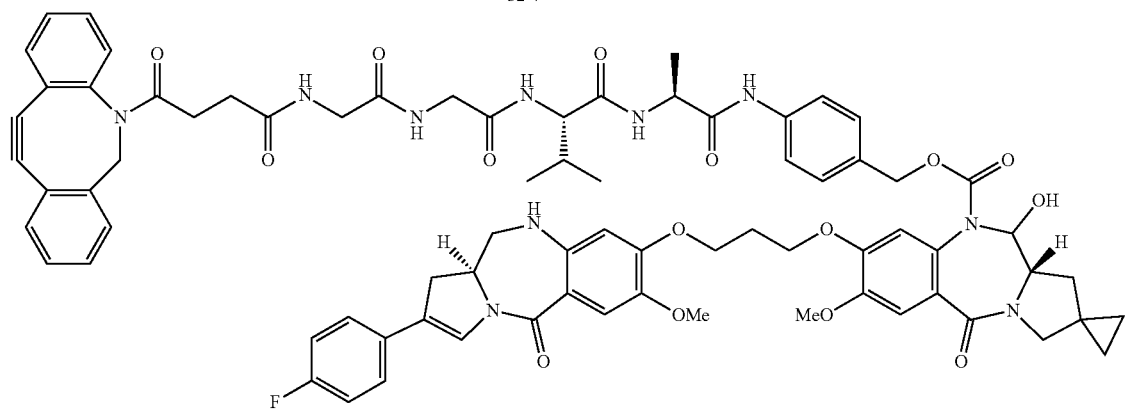

32-8

Step 1: Compound 32-1

The compound obtained in step 4 of Example 4 (1.00 g, 1.52 mmol) and 4-fluorophenylboronic acid (0.318 g, 2.27 mmol) were reacted in the same manner as in step 6 of Example 3 to afford the desired compound (0.623 g, 68%).

Step 2: Compound 32-2

The compound obtained in step 1 (0.623 g, 1.03 mmol) was reacted in the same manner as in step 7 of Example 3 to afford the desired compound (0.244 g, 52%).

MS(APCI, ESI)m/z:461[$^{81}$Br,(M+H)$^+$], 459[$^{79}$Br,(M+H)$^+$].

Step 3: Compound 32-3

The compound obtained in step 2 (0.244 g, 0.531 mmol) was reacted in the same manner as in step 8 of Example 3 to afford the desired compound (0.144 g, 59%).

MS(APCI, ESI)m/z:463[$^{81}$Br,(M+H)$^+$], 461[$^{79}$Br,(M+H)$^+$].

Step 4: Compound 32-4

The compound obtained in step 3 (0.144 g, 0.312 mmol) was reacted in the same manner as in step 9 of Example 3 to afford the desired compound (0.139 g, 82%).

MS(APCI, ESI)m/z:547[$^{81}$Br,(M+H)$^+$], 545[$^{79}$Br,(M+H)$^+$].

Step 5: Compound 32-5

The compound obtained in step 4 (0.0742 g, 0.136 mmol) was reacted in the same manner as in step 10 of Example 3 to afford the desired compound (0.138 g, 88%).

MS(APCI, ESI)m/z:1284(M+H)$^+$.

Step 6: Compound 32-6

The compound obtained in step 5 (0.138 g, 0.108 mmol) was reacted in the same manner as in step 11 of Example 3 to afford the desired compound (0.109 g, 87%).

MS(APCI, ESI)m/z:1170(M+H)$^+$.

Step 7: Compound 32-7

The compound obtained in step 6 (0.109 g, 0.101 mmol) was reacted in the same manner as in step 12 of Example 3 to afford the desired compound (0.0613 g, 61%).

MS(APCI, ESI)m/z:1002(M+H)$^+$.

Step 8: N-[4-(11,12-Didehydrodibenzo[b,f]azocin-5 (6H)-yl)-4-oxobutanoyl]glycylglycyl-L-valyl-N-{4-[({[(11a'S)-8'-(3-{[(11aS)-2-(4-fluorophenyl)-7-methoxy-5-oxo-5,10,11,11a-tetrahydro-1H-pyrrolo[2,1-c][1,4]benzodiazepin-8-yl]oxy}propoxy)-11'-hydroxy-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 7 (0.0300 g, 0.0333 mmol) was reacted in the same manner as in step 13 of Example 3 to afford the desired compound (0.0191 g, 45%).
MS (APCI, ESI)m/z:1402 (M+H)⁺.

Example 33: Drug-Linker 31

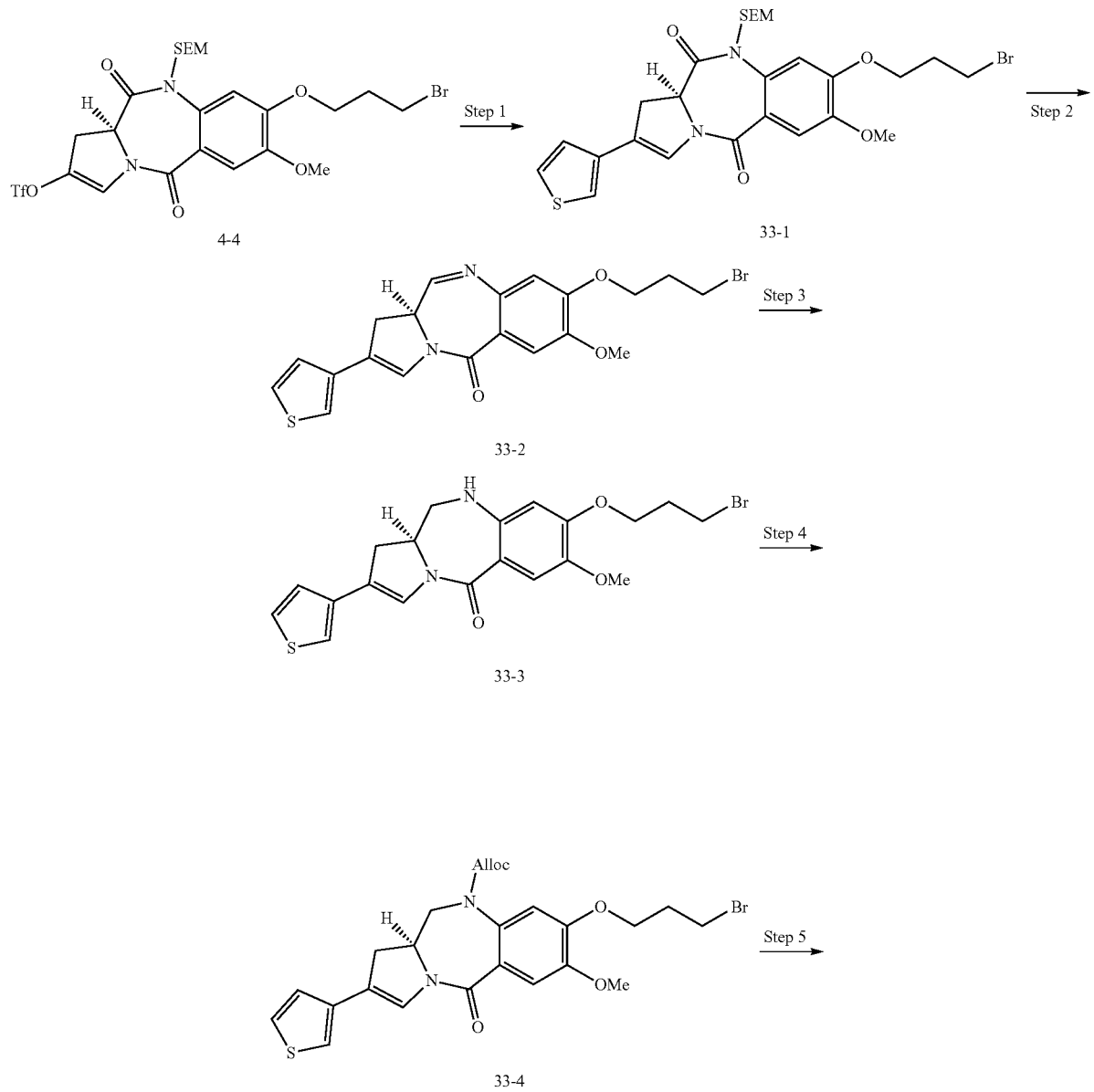

[Formula 157]

-continued
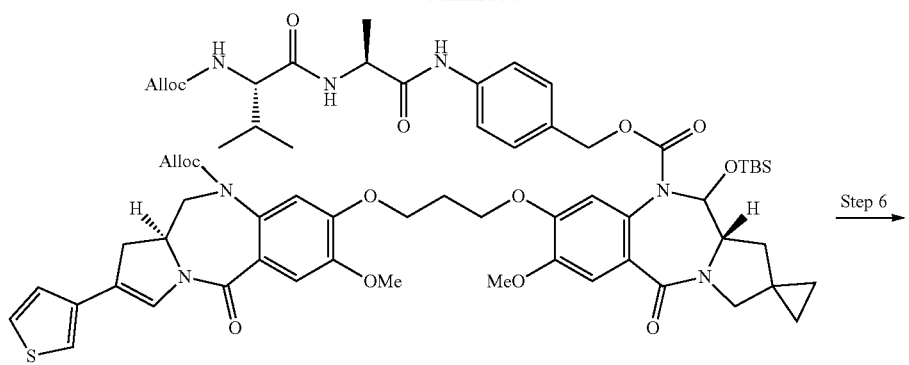
33-5
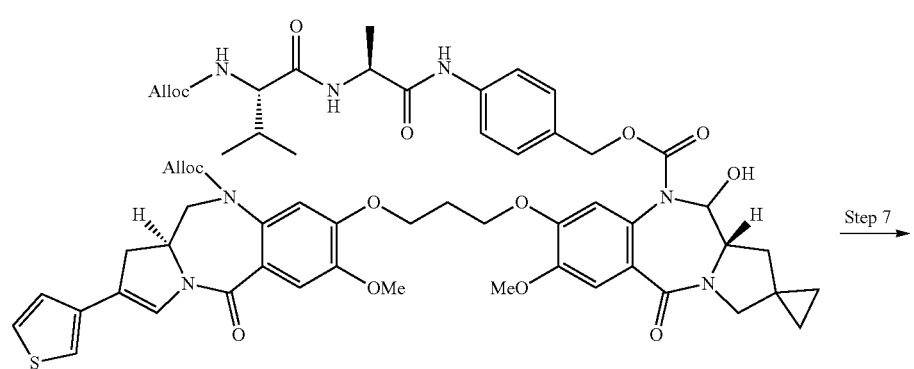
33-6
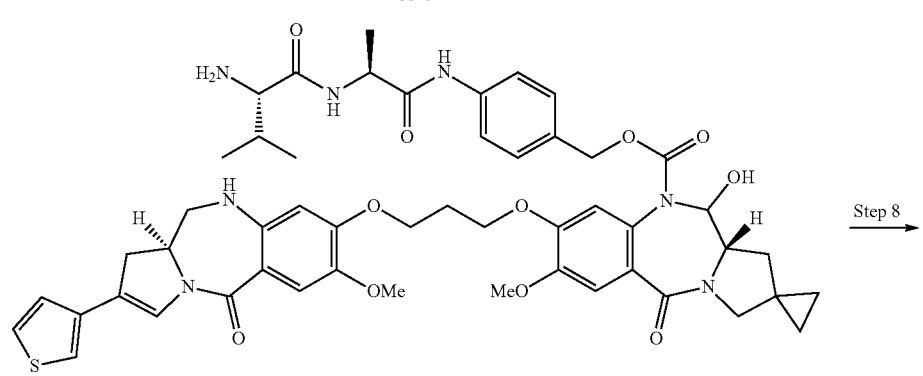
33-7
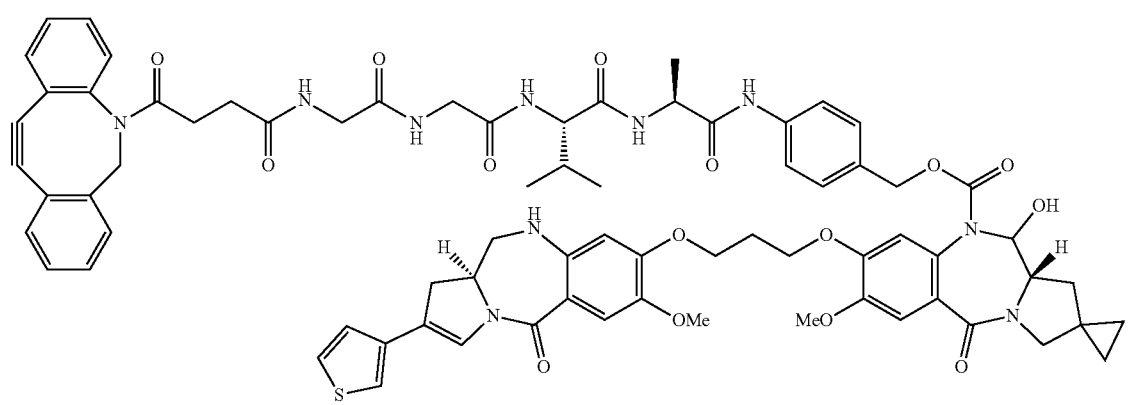
33-8

Step 1: Compound 33-1

The compound obtained in step 4 of Example 4 (1.00 g, 1.52 mmol) and thiophene-3-boronic acid (0.582 g, 4.55 mmol) were used and reacted in the same manner as in step 6 of Example 3 to afford the desired compound (0.611 g, 68%).

Step 2: Compound 33-2

The compound obtained in step 1 (0.611 g, 1.03 mmol) was used and reacted in the same manner as in step 7 of Example 3 to afford the desired compound (0.397 g, 86%).
MS(APCI, ESI)m/z:449[$^{81}$Br,(M+H)$^+$], 447[$^{79}$Br,(M+H)$^+$].

Step 3: Compound 33-3

The compound obtained in step 2 (0.397 g, 0.887 mmol) was used and reacted in the same manner as in step 8 of Example 3 to afford the desired compound (0.341 g, 86%).
MS(APCI, ESI)m/z:451[$^{81}$Br,(M+H)$^+$], 449[$^{79}$Br,(M+H)$^+$].

Step 4: Compound 33-4

The compound obtained in step 3 (0.341 g, 0.759 mmol) was used and reacted in the same manner as in step 9 of Example 3 to afford the desired compound (0.368 g, 91%).
MS(APCI, ESI)m/z:535[$^{81}$Br,(M+H)$^+$], 533[$^{79}$Br,(M+H)$^+$].

Step 5: Compound 33-5

The compound obtained in step 4 (0.0726 g, 0.136 mmol) was used and reacted in the same manner as in step 10 of Example 3 to afford the desired compound (0.125 g, 80%).
MS (APCI, ESI)m/z:1260 (M+H)$^+$.

Step 6: Compound 33-6

The compound obtained in step 5 (0.125 g, 0.0992 mmol) was used and reacted in the same manner as in step 11 of Example 3 to afford the desired compound (0.109 g, 96%).
MS (APCI, ESI)m/z:1146 (M+H)$^+$.

Step 7: Compound 33-7

The compound obtained in step 6 (0.109 g, 0.0951 mmol) was used and reacted in the same manner as in step 12 of Example 3 to afford the desired compound (0.0723 g, 78%).
$^1$H-NMR (CDCl$_3$) δ:9.13-9.04 (1H, m), 7.89-7.87 (1H, m), 7.47-7.42 (4H, m), 7.27-7.23 (3H, m), 7.18 (1H, s), 7.12-7.08 (2H, m), 6.97-6.96 (1H, m), 6.42-6.37 (1H, m), 6.08-6.04 (1H, m), 5.86-5.84 (1H, m), 5.34-5.31 (1H, m), 4.65-4.58 (3H, m), 4.23-3.95 (5H, m), 3.85 (3H, s), 3.75-3.69 (6H, m), 3.57-3.47 (3H, m), 3.34-3.29 (3H, m), 2.72-2.68 (1H, m), 2.38-2.29 (2H, m), 2.15-2.14 (2H, m), 1.72-1.69 (1H, m), 1.40-1.38 (3H, m), 0.96-0.95 (3H, m), 0.80-0.61 (7H, m).

Step 8: N-[4-(11,12-Didehydrodibenzo[b,f]azocin-5(6H)-yl)-4-oxobutanoyl]glycylglycyl-L-valyl-N-{4-[({[(11a'S)-11'-hydroxy-7'-methoxy-8'-(3-{[(11aS)-7-methoxy-5-oxo-2-(thiophen-3-yl)-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 7 (0.0300 g, 0.0307 mmol) was used and reacted in the same manner as in step 13 of Example 3 to afford the desired compound (0.0101 g, 24%).
MS (APCI, ESI)m/z:1379 (M+H)$^+$.

Example 34: Drug-Linker 32

[Formula 158]

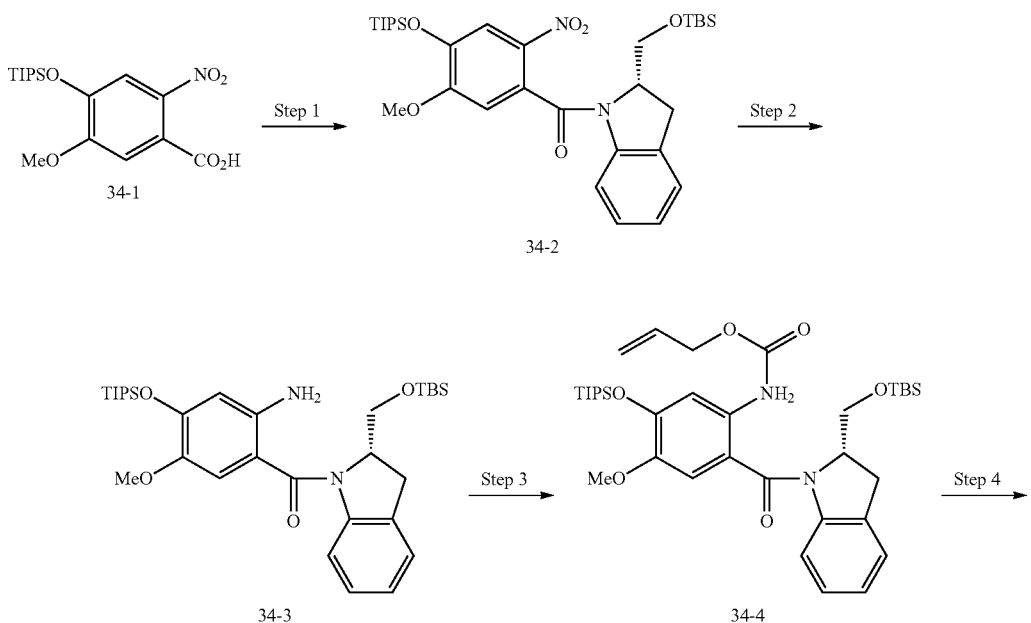

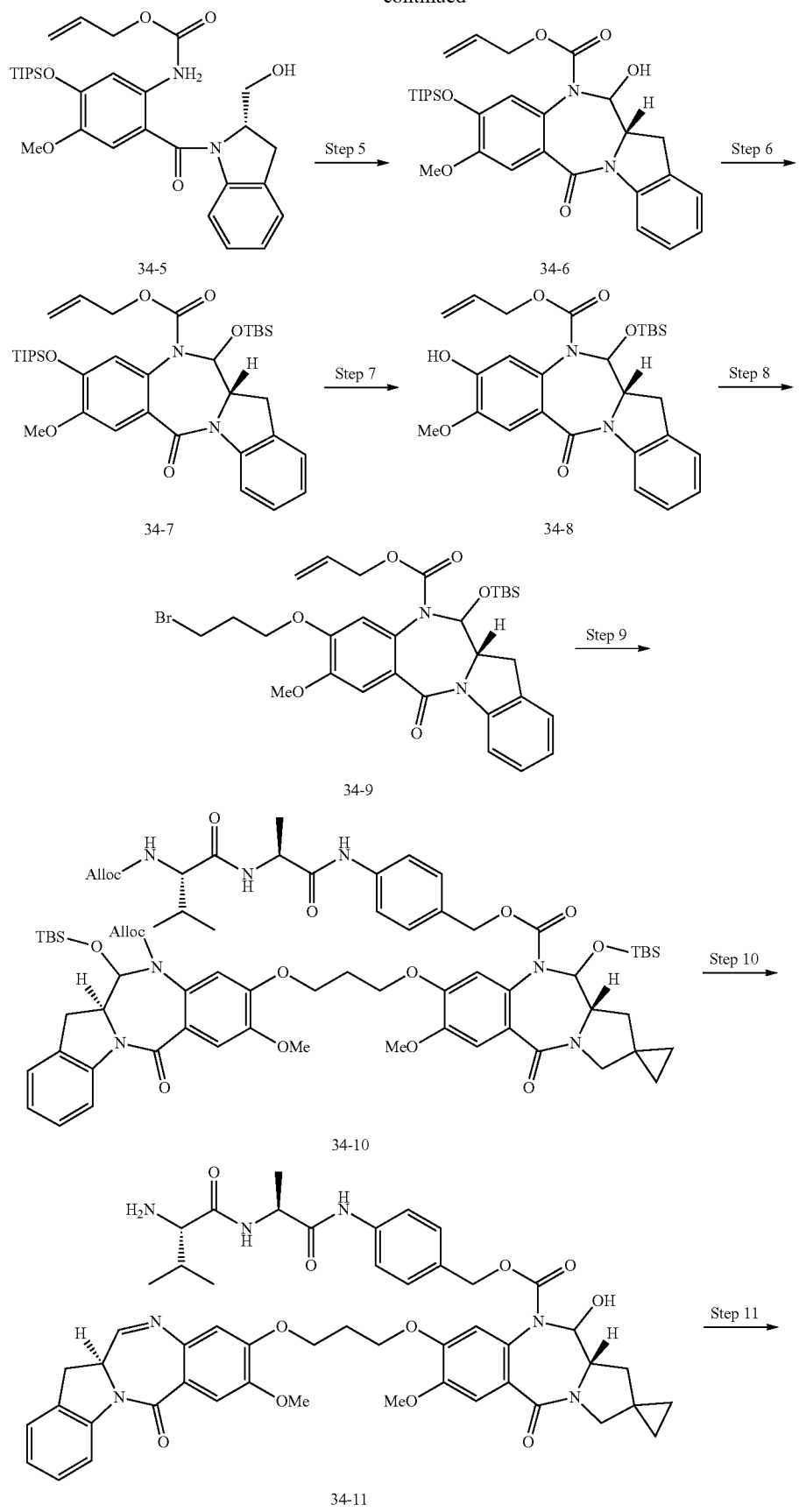

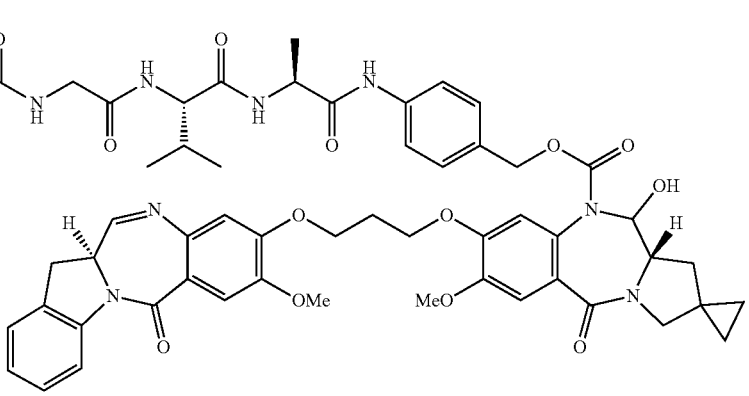

34-12

Step 1: Compound 34-2

To a solution of starting material 34-1 (4.00 g, 10.8 mmol, US 20150283262) in dichloromethane (100 mL), N,N-dimethylformamide (0.2 mL) and oxalyl chloride (2.75 g, 21.7 mmol) were added at 0° C., afollowed by stirring at room temperature for 30 minutes.

After the solvent was distilled off under reduced pressure, the residue was dried under reduced pressure, and dissolved in dichloromethane (60 mL). Thereto, (2S)-2-({[tert-butyl (dimethyl)silyl]oxy}methyl)-2,3-dihydro-1H-indole (4.28 g, 16.2 mmol, Journal of the American Chemical Society 2006, 128, 14264) and triethylamine (1.64 g, 16.2 mmol) were added at 0° C., followed by stirring at room temperature for 15 minutes. Water was added to the reaction solution, which was extracted with dichloromethane. The organic layer obtained was washed with brine, and dried over magnesium sulfate, and then distillated under reduced pressure. The resulting residue was purified by silica gel column chromatography [hexane:ethyl acetate=100:0 (v/v) to 80:20 (v/v)] to afford the desired compound (6.10 g, 92%).

MS (APCI, ESI)m/z:615 (M+H)$^+$

Step 2: Compound 34-3

To a solution of the compound obtained in step 1 (6.10 g, 9.90 mmol) in ethanol (100 mL), 5% palladium carbon (moisture content: 54%, 1.00 g) was added under the nitrogen atmosphere, and the reaction solution was then stirred under the hydrogen atmosphere at room temperature for 4 hours. After the reaction solution was filtered through a Celite, the filtrate was distillated under reduced pressure to afford the desired compound (5.80 g, quantitative).

MS(APCI, ESI)m/z:585(M+H)$^+$

Step 3: Compound 34-4

The compound obtained in step 2 (2.90 g, 5.00 mmol) was reacted in the same manner as in step 9 of Example 3 to afford the desired compound (3.20 g, 96%).

$^1$H-NMR (CDCl$_3$):8.26 (1H, s), 7.78 (1H, s), 7.18-7.17 (1H, m), 6.94-6.83 (3H, m), 5.94-5.90 (1H, m), 5.35-5.19 (2H, m), 4.74 (1H, m), 4.65-4.60 (2H, m), 3.76-3.61 (6H, m), 3.31-3.27 (1H, m), 3.10 (1H, m), 1.35-1.17 (3H, m), 1.10 (18H, m), 0.79-0.70 (9H, m), −0.03 (3H, s), −0.08 (3H, s).

Step 4: Compound 34-5

The compound obtained in step 3 (3.20 g, 4.80 mmol) was reacted in the same manner as in step 7 of Example 1 to afford the desired compound (2.32 g, 87%).

MS(APCI, ESI)m/z:555(M+H)$^+$

Step 5: Compound 34-6

The compound obtained in step 4 (2.32 g, 4.18 mmol) was reacted in the same manner as in step 8 of Example 1 to afford the desired compound (1.68 g, 73%).

MS(APCI, ESI)m/z:553(M+H)$^+$

Step 6: Compound 34-7

The compound obtained in step 5 (1.68 g, 3.04 mmol) was reacted in the same manner as in step 9 of Example 1 to afford the desired compound (2.32 g, quantitative).

$^1$H-NMR (CDCl$_3$) δ:8.16 (1H, m), 7.28-7.20 (3H, m), 7.09-7.07 (1H, m), 6.70 (1H, s), 5.80-5.76 (2H, m), 5.14-5.12 (2H, m), 4.60 (1H, m), 4.37 (1H, m), 4.01-3.99 (1H, m), 3.87 (3H, s), 3.45-3.41 (1H, m), 2.99-2.95 (1H, m), 1.28-1.23 (3H, m), 1.10-1.07 (18H, m), 0.92 (9H, s), 0.26 (3H, s), 0.19 (3H, s).

Step 7: Compound 34-8

The compound obtained in step 6 (2.32 g, 3.48 mmol) was reacted in the same manner as in step 10 of Example 1 to afford the desired compound (1.42 g, 80%).

MS(APCI, ESI)m/z:511(M+H)$^+$

Step 8: Compound 34-9

The compound obtained in step 7 (0.720 g, 1.41 mmol) was reacted in the same manner as in step 1 of Example 4 to afford the desired compound (0.580 g, 65%).

MS(APCI, ESI)m/z:633[$^{81}$Br,(M+H)$^+$], 631[$^{79}$Br,(M+H)$^+$].

Step 9: Compound 34-10

The compound obtained in step 8 (0.235 g, 0.371 mmol) was reacted in the same manner as in step 3 of Example 10 to afford the desired compound (0.347 g, 83%).

MS(APCI, ESI)m/z:1359(M+H)$^+$

Step 10: Compound 34-11

The compound obtained in step 9 (0.347 g, 0.255 mmol) was reacted in the same manner as in step 11 of Example 3 to afford a silyl-deprotected form (0.265 g, 92%). The silyl-deprotected form (0.265 g, 0.234 mmol) was reacted in the same manner as in step 12 of Example 1 to afford the desired compound (0.086 g, 39%).

MS (APCI, ESI)m/z:944 (M+H)$^+$

Step 11: N-[4-(11,12-Didehydrodibenzo[b,f]azocin-5 (6H)-yl)-4-oxobutanoyl]glycylglycyl-L-valyl-N-{4-[({[(11a'S)-11'-hydroxy-7'-methoxy-8'-(3-{[(5aS)-10-methoxy-12-oxo-5a,12-dihydro-5H-indolo[2,1-c][1,4]benzodiazepin-9-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 10 (0.0860 g, 0.0911 mmol) was reacted in the same manner as in step 13 of Example 3 to afford the desired compound (0.0800 g, 65%).

MS (APCI, ESI)m/z:1345 (M+H)$^+$

Example 35: Drug-Linker 33

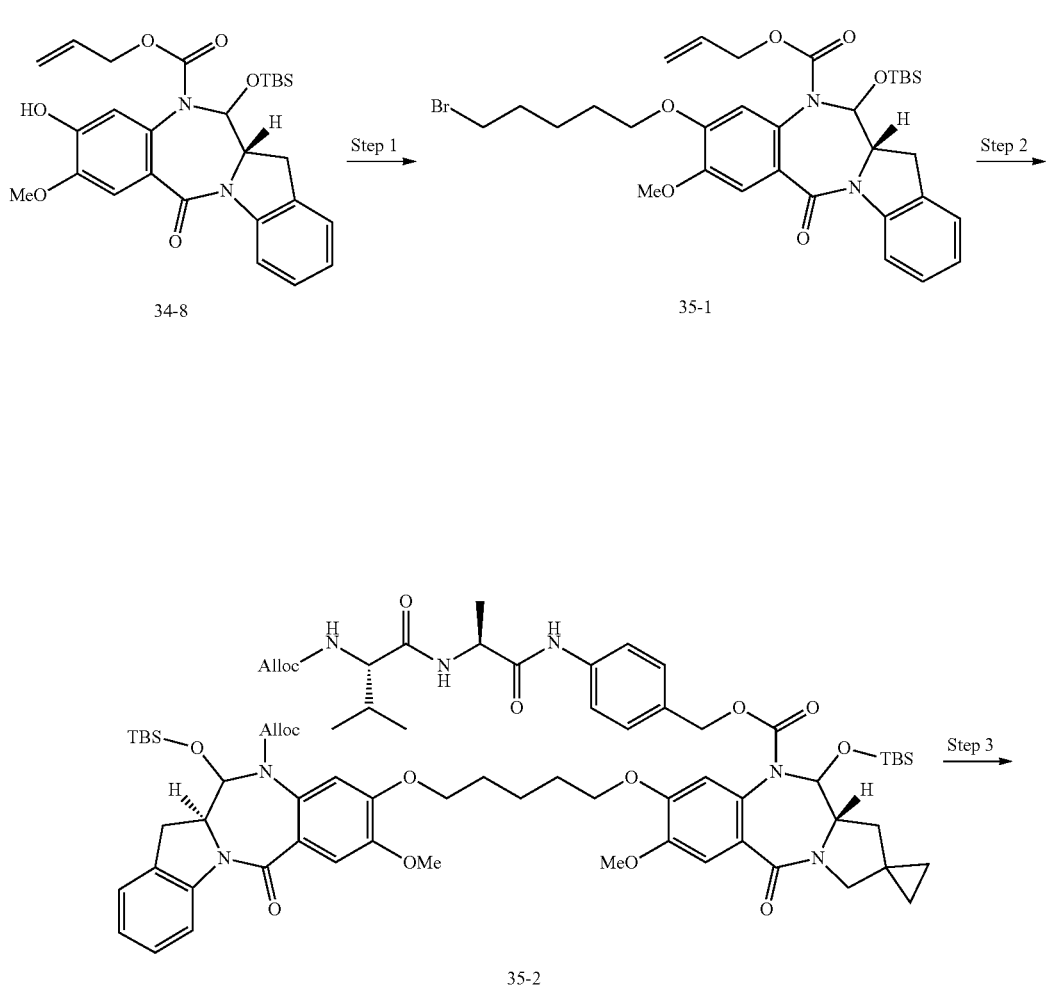

[Formula 159]

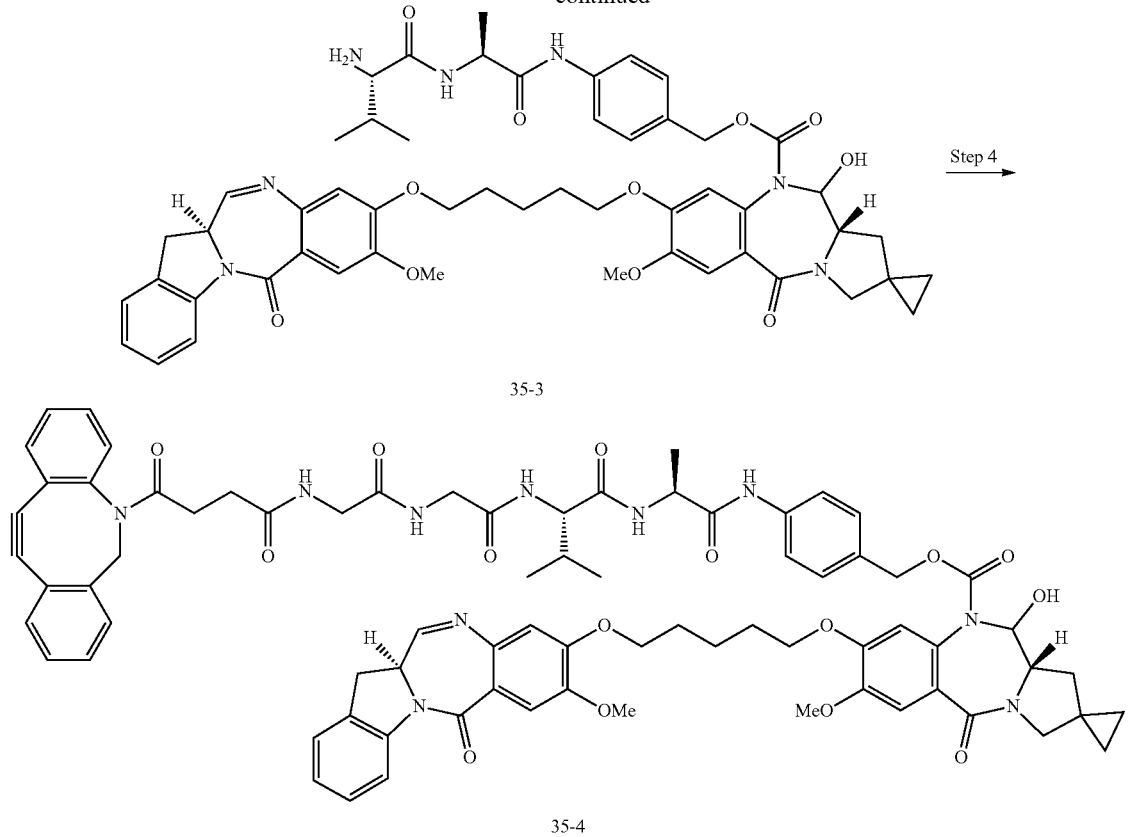

35-3

35-4

Step 1: Compound 35-1

The compound obtained in step 7 of Example 34 (0.700 g, 1.37 mmol) was reacted in the same manner as in step 2 of Example 3 to afford the desired compound (0.790 g, 87%).
MS(APCI, ESI)m/z:661[$^{81}$Br,(M+H)$^+$], 659[$^{79}$Br,(M+H)$^+$].

Step 2: Compound 35-2

The compound obtained in step 1 (0.245 g, 0.371 mmol) was reacted in the same manner as in step 10 of Example 3 to afford the desired compound (0.368 g, 86%).
MS (APCI, ESI)m/z:1387 (M+H)$^+$

Step 3: Compound 35-3

The compound obtained in step 2 (0.368 g, 0.265 mmol) was reacted in the same manner as in steps 11 and 12 of Example 3 to afford the desired compound (0.180 g, 81%).
MS (APCI, ESI)m/z:972 (M+H)$^+$

Step 4: N-[4-(11,12-Didehydrodibenzo[b,f]azocin-5(6H)-yl)-4-oxobutanoyl]glycylglycyl-L-valyl-N-{4-[({[(11a'S)-11'-hydroxy-7'-methoxy-8'-[(5-{[(5aS)-10-methoxy-12-oxo-5a,12-dihydro-5H-indolo[2,1-c][1,4]benzodiazepin-9-yl]oxy}pentyl)oxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 3 (0.0700 g, 0.0720 mmol) was reacted in the same manner as in step 13 of Example 3 to afford the desired compound (0.0440 g, 44%).
MS (APCI, ESI)m/z:1373 (M+H)$^+$

Example 36: Drug-Linker 34

[Formula 160]

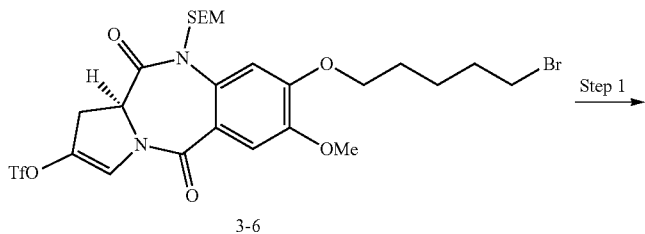

3-6

-continued
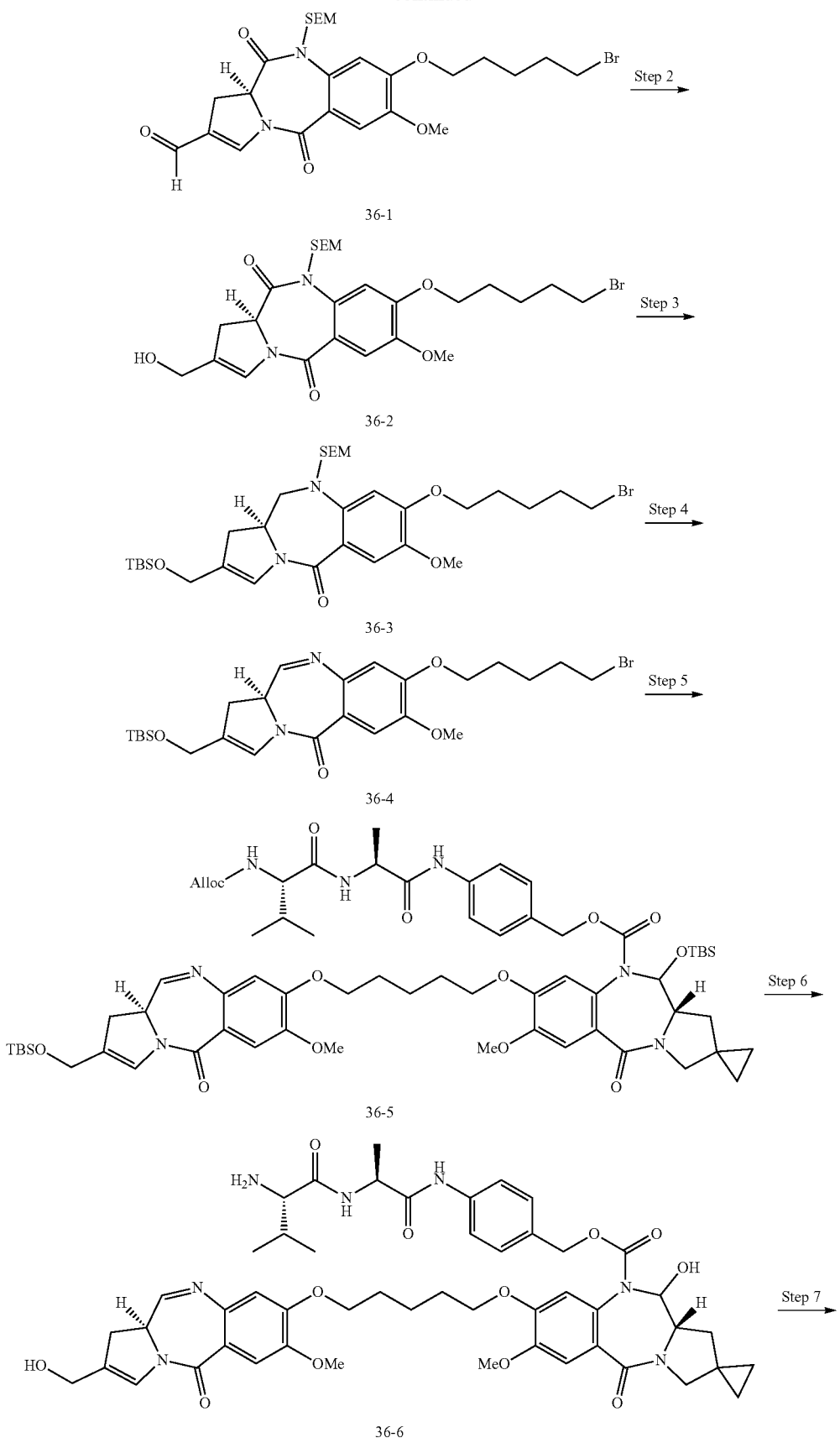
36-1
36-2
36-3
36-4
36-5
36-6

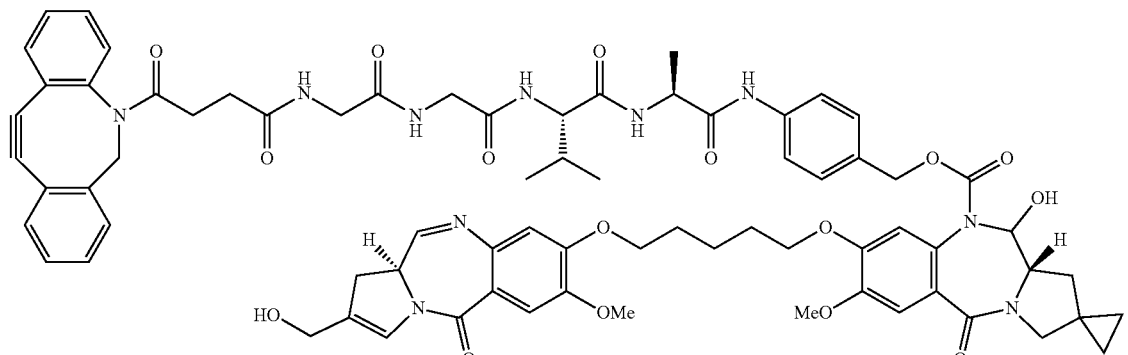

36-7

Step 1: (11aS)-8-[(5-Bromopentyl)oxy]-7-methoxy-5,11-dioxo-10-{[2-(trimethylsilyl)ethoxy]methyl}-5,10,11,11a-tetrahydro-1H-pyrrolo[2,1-c][1,4]benzodiazepin-2-carbaldehyde The compound obtained in step 5 of Example 3 (3.54 g, 5.15 mmol) was dissolved in N,N-dimethylformamide (52 mL), to which N-formylsaccharin (5.44 g, 25.7 mmol), palladium acetate (0.0578 g, 0.257 mmol), 1,4-bis(diphenylphosphino)butane (0.154 g, 0.360 mmol), sodium carbonate (2.73 g, 25.7 mmol), and triethylsilane (1.20 g, 10.3 mmol) were added, and the resultant was stirred at room temperature for 19 hours. Water was added to the reaction solution, and the reaction solution was extracted with ethyl acetate, and the extract was washed with water and brine. The organic layer was dried over magnesium sulfate, and then distilled under reduced pressure. The resulting residue was purified by silica gel column chromatography [hexane:ethyl acetate=100:0 (v/v) to 40:60 (v/v)] to afford the desired compound (0.760 g, 26%).

$^1$H-NMR (CDCl$_3$) δ:9.74 (1H, s), 7.79 (1H, s), 7.32 (1H, s), 7.24 (1H, s), 5.54 (1H, m), 4.76-4.69 (2H, m), 4.07-4.05 (2H, m), 3.93 (3H, s), 3.83-3.65 (3H, m), 3.45 (2H, m), 3.02-2.98 (1H, m), 1.95-1.91 (4H, m), 1.69-1.58 (2H, m), 1.02-0.92 (2H, m), 0.06-0.03 (9H, m).

Step 2: (11aS)-8-[(5-Bromopentyl)oxy]-2-(hydroxymethyl)-7-methoxy-10-{[2-(trimethylsilyl)ethoxy]methyl}-1H-pyrrolo[2,1-c][1,4]benzodiazepin-5,11(10H,11aH)-dione The compound obtained in step 1 (0.760 g, 1.34 mmol) was dissolved in dichloromethane (14 mL), to which sodium borohydride (0.101 g, 2.68 mmol) was added at −78° C., and the temperature was then raised to room temperature. To the reaction solution, 1 N hydrochloric acid was added, and the organic layer was washed with water and brine.

The organic layer was dried over magnesium sulfate, and then distilled under reduced pressure. The resulting residue was purified by silica gel column chromatography [hexane:ethyl acetate=100:0 (v/v) to 0:100 (v/v)] to afford the desired compound (0.432 g, 57%).

$^1$H-NMR (CDCl$_3$):7.35 (1H, s), 7.23 (1H, s), 6.93 (1H, s), 5.53 (1H, m), 4.67 (1H, m), 4.57-4.54 (1H, m), 4.32-4.31 (2H, m), 4.10-4.01 (2H, m), 3.92 (3H, s), 3.83-3.57 (3H, m), 3.45 (2H, m), 2.90-2.88 (1H, m), 1.99-1.88 (4H, m), 1.69-1.61 (2H, m), 1.00-0.98 (2H, m), 0.03 (9H, s).

MS(APCI, ESI)m/z:571[$^{81}$Br,(M+H)$^+$], 569[$^{79}$Br,(M+H)$^+$].

Step 3: (11aS)-8-[(5-Bromopentyl)oxy]-2-({[tert-butyl(dimethyl)silyl]oxy}methyl)-7-methoxy-10-{[2-(trimethylsilyl)ethoxy]methyl}-1H-pyrrolo[2,1-c][1,4]benzodiazepin-5,11(10H,11 aH)-dione The compound obtained in step 2 (0.432 g, 0.758 mmol) was dissolved in N,N-dimethylformamide (8 mL), to which imidazole (0.0775 g, 1.14 mmol) and tert-butyldimethylsilyl chloride (0.137 g, 0.910 mmol) were added at room temperature, and the resultant was stirred at room temperature for 10 minutes. Water was added to the reaction solution, and the reaction solution was extracted with ethyl acetate. The organic layer was washed with water and brine, and dried over magnesium sulfate. After distillation under reduced pressure, the resulting residue was purified by silica gel column chromatography [hexane:ethyl acetate=100:0 (v/v) to 30:70 (v/v)] to afford the desired compound (0.485 g, 94%).

$^1$H-NMR (CDCl$_3$) δ:7.35 (1H, s), 7.22 (1H, s), 6.87 (1H, m), 5.53 (1H, m), 4.68 (1H, m), 4.54-4.52 (1H, m), 4.33-4.28 (2H, m), 4.11-4.00 (2H, m), 3.92 (3H, s), 3.80-3.78 (1H, m), 3.69-3.66 (1H, m), 3.52-3.50 (1H, m), 3.45 (2H, m), 2.86-2.82 (1H, m), 1.99-1.87 (4H, m), 1.68-1.60 (2H, m), 1.00-0.98 (2H, m), 0.91 (9H, s), 0.09 (6H, s), 0.04 (9H, s).

MS(APCI, ESI)m/z:685[$^{81}$Br,(M+H)$^+$], 683[$^{79}$Br,(M+H)$^+$].

Step 4: (11aS)-8-[(5-Bromopentyl)oxy]-2-({[tert-butyl(dimethyl)silyl]oxy}methyl)-7-methoxy-1,11a-dihydro-5H-pyrrolo[2,1-c][1,4]benzodiazepin-5-one The compound obtained in step 3 (0.103 g, 0.151 mmol) was reacted in the same manner as in step 7 of Example 3 to afford the desired compound (0.0590 g, 73%).

$^1$H-NMR (CDCl$_3$):7.83 (1H, m), 7.51 (1H, s), 6.92 (1H, m), 6.79 (1H, s), 4.32-4.30 (3H, m), 4.12-4.04 (2H, m), 3.93 (3H, s), 3.86-3.84 (1H, m), 3.46-3.39 (2H, m), 3.26-3.23 (1H, m), 3.07-3.03 (1H, m), 1.97-1.85 (4H, m), 1.68-1.63 (2H, m), 0.92 (9H, s), 0.09 (6H, s).

MS(APCI, ESI)m/z:539[$^{81}$Br,(M+H)$^+$], 537[$^{79}$Br,(M+H)$^+$].

Step 5: N-[(Prop-2-en-1-yloxy)carbonyl]-L-valyl-N-{4-[({[(11a'S)-11'-{[tert-butyl(dimethyl)silyl]oxy}-8'-[(5-{[(11aS)-2-({[tert-butyl(dimethyl)silyl]oxy}methyl)-7-methoxy-5-oxo-5,11a-dihydro-1H-pyrrolo[2,1-c][1,4]benzodiazepin-8-yl]oxy}pentyl)oxy]-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 4 (0.251 g, 0.467 mmol) was reacted in the same manner as in step 10 of Example 3 to afford the desired compound (0.300 g, 51%).

Step 6: L-Valyl-N-{4-[({[(11a'S)-11'-hydroxy-8'-[(5-{[(11aS)-2-(hydroxymethyl)-7-methoxy-5-oxo-5,11a-dihydro-1H-pyrrolo[2,1-c][1,4]benzodiazepin-8-yl]oxy}pentyl)oxy]-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 5 (0.300 g, 0.237 mmol) was reacted in the same manner as in steps 11 and 12 of Example 33 to afford the desired compound (0.0540 g, 53%).

MS (APCI, ESI)m/z:952 (M+H)$^+$

Step 7: N-[4-(11,12-Didehydrodibenzo[b,f]azocin-5(6H)-yl)-4-oxobutanoyl]glycylglycyl-L-valyl-N-{4-[({[(11a'S)-11'-hydroxy-8'-[(5-{[(11aS)-2-(hydroxymethyl)-7-methoxy-5-oxo-5,11a-dihydro-1H-pyrrolo[2,1-c][1,4]benzodiazepin-8-yl]oxy}pentyl)oxy]-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 6 (0.0500 mg, 0.0525 mmol) was reacted in the same manner as in step 13 of Example 3 to afford the desired compound (0.0340 mg, 48%).

MS (APCI, ESI)m/z:1351 (M−H)$^-$

Example 37: Drug-Linker 35

[Formula 161]

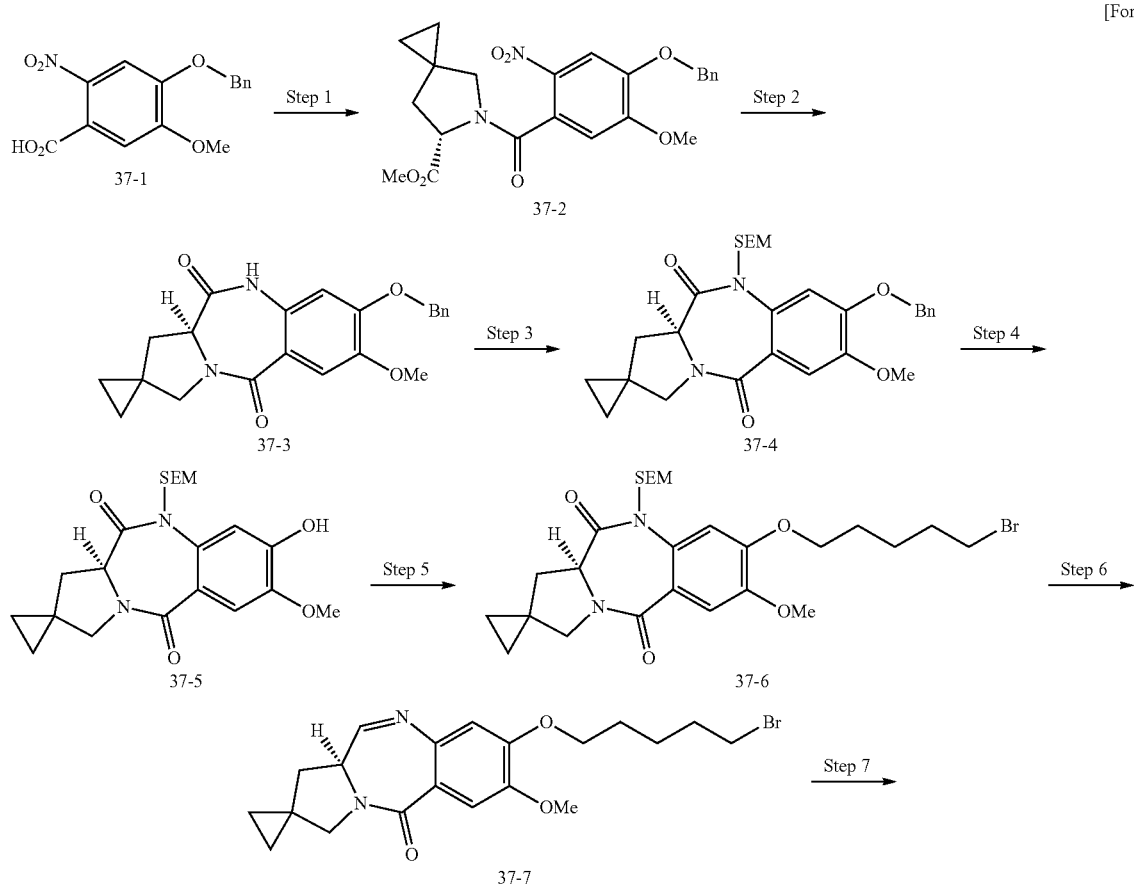

-continued
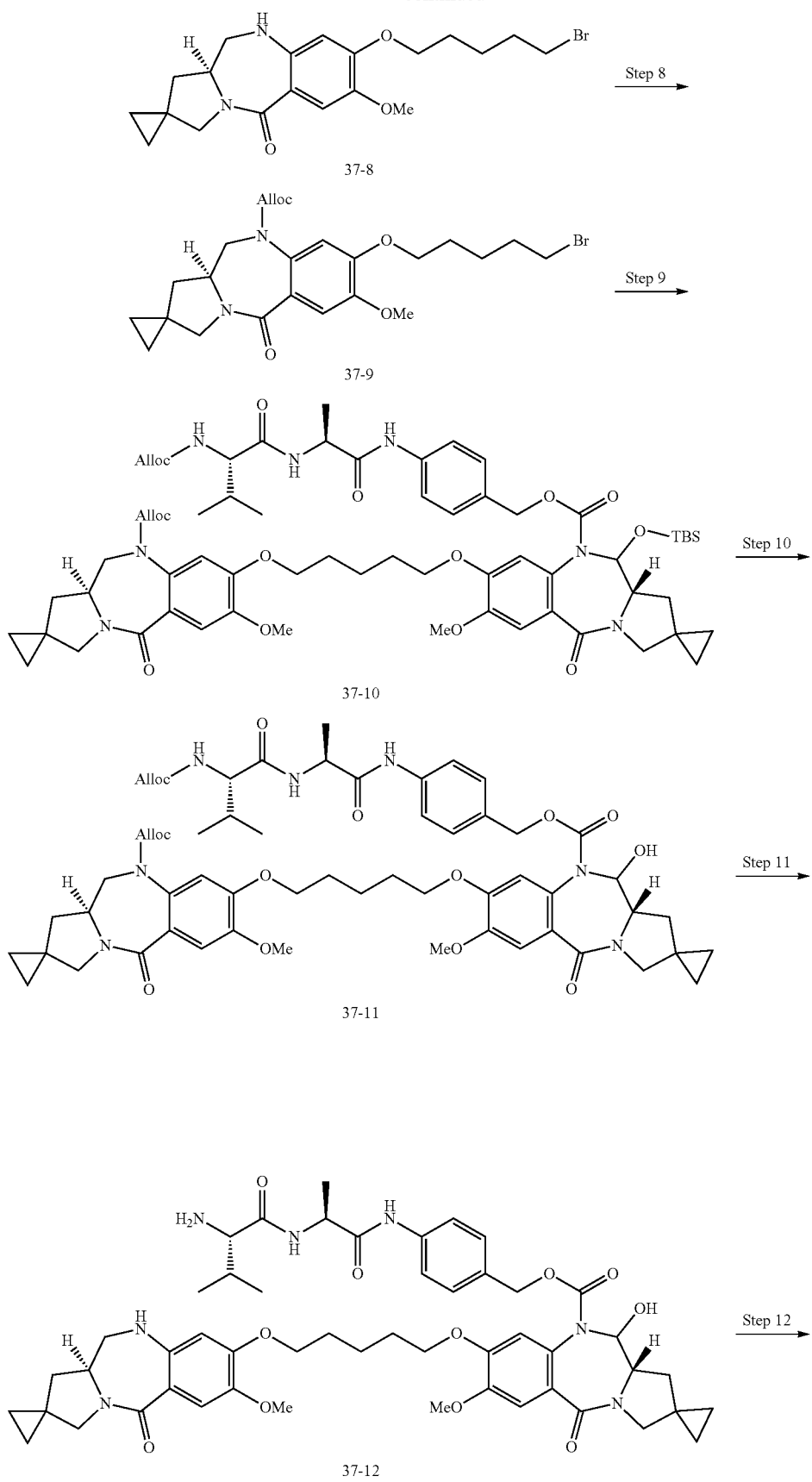

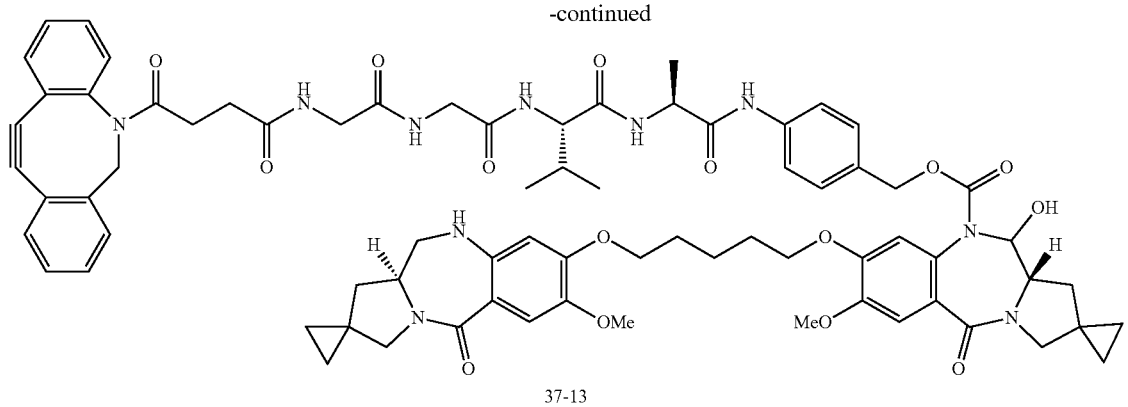

37-13

Step 1: Methyl (6S)-5-[4-(benzyloxy)-5-methoxy-2-nitrobenzoyl]-5-azaspiro[2.4]heptane-6-carboxylate To a solution of 4-(benzyloxy)-5-methoxy-2-nitrobenzoic acid (6.07 g, 20.0 mmol, Tetrahedron 1995, 51, 5617) and N,N-dimethylformamide (1.08 mL, 13.9 mmol) in dichloromethane (100 mL), oxalyl chloride (3.43 mL, 40.0 mmol) was added dropwise under ice-cooling over 5 minutes. The reaction solution was stirred at room temperature for 5 hours, and then distillated under reduced pressure, and the resulting residue was dissolved in dichloromethane (20 mL), which was distillated under reduced pressure. After this operation was repeated three times, the residue was suspended in dichloromethane (5 mL), to which excessive amounts of diethyl ether and hexane were added, and the following filtration and drying under reduced pressure afforded the crude acyl chloride. The acyl chloride obtained was dissolved in dichloromethane and cooled to −40° C. (dry ice-acetonitrile bath), to which methyl (6S)-5-azaspiro[2.4]heptane-6-carboxylate hydrochloride (4.22 g, 22.0 mmol, Tetrahedron Letters 2012. 53. 3847) and triethylamine (3.36 mL, 24.2 mmol) were gradually added. The temperature of the reaction mixture was raised to room temperature overnight.

To the reaction mixture, 1 N hydrochloric acid was added, and the reaction mixture was extracted with dichloromethane. The organic layer was washed with water, a saturated aqueous sodium hydrogen carbonate, and brine, and dried over anhydrous sodium sulfate. The resultant was distillated under reduced pressure, and the resulting residue was purified by silica gel column chromatography [hexane:ethyl acetate=100:0 to 50:50] to afford the desired compound (6.55 g, 80%).

MS (APCI, ESI)m/z:441 (M+H)⁺

Step 2: (11a'S)-8'-(Benzyloxy)-7'-methoxy-1'H-spiro[cyclopropane-1,2'-pyrrolo[2,1-c][1,4]benzodiazepine]-5',11'(10'H,11a'H)-dione To a solution of the compound obtained in step 1 (6.55 g, 16.0 mmol) in ethanol (150 mL) and THF (150 mL), Raney nickel (7.00 g) was added under the nitrogen atmosphere. Hydrazine monohydrate (7 mL) was added to the reaction mixture, and the temperature was gradually raised to 50° C. After stirring at 50° C. for 2 hours, Raney nickel (3.00 g) and hydrazine monohydrate (3 mL) were added thereto, and the resultant was stirred for 1 hour. THF (100 mL) was added to the reaction mixture, which was filtered through a Celite.

The resultant was distillated under reduced pressure, and the resulting residue was purified by silica gel column chromatography [hexane:ethyl acetate=100:0(v/v) to 25:75(v/v)] to afford the desired compound (4.42 g, 73%).

¹H-NMR (CDCl₃) δ:7.82 (1H, s), 7.48 (1H, s), 7.42-7.35 (4H, m), 7.32-7.31 (1H, m), 6.44 (1H, s), 5.16 (2H, s), 4.16-4.10 (1H, m), 3.93 (3H, s), 3.78-3.76 (1H, m), 3.39-3.37 (1H, m), 2.45-2.43 (1H, m), 2.24-2.21 (1H, m), 0.83-0.61 (4H, m).

MS(APCI, ESI)m/z:379(M+H)⁺

Step 3: (11a'S)-8'-(Benzyloxy)-7'-methoxy-10'-{[2-(trimethylsilyl)ethoxy]methyl}-1'H-spiro[cyclopropane-1,2'-pyrrolo[2,1-c][1,4]benzodiazepine]-5',11'(10'H,11a'H)-dione To a solution of the compound obtained in step 2 (10.0 g, 26.4 mmol) in THF (150 mL), a 2.6 mol/L normal-hexane solution of normal-butyllithium (12.0 mL, 31.8 mmol) was added slowly dropwise at −40° C. The reaction solution was stirred at −40° C. for 15 minutes, and 2-(chloromethoxy)ethyltrimethylsilane (5.57 mL, 31.7 mmol) was then added slowly dropwise thereto. After the reaction solution was stirred at room temperature for 3 hours, water was added thereto, and the resultant was extracted with ethyl acetate. The organic layer was washed with water and brine, and dried over anhydrous sodium sulfate. After distillation under reduced pressure, the resulting residue was purified by silica gel column chromatography [hexane:ethyl acetate=100:0(v/v) to 30:70(v/v)] to afford the desired compound (11.8 g, 88%).

¹H-NMR (CDCl₃) δ:7.45-7.44 (2H, m), 7.37-7.32 (4H, m), 7.28 (1H, s), 5.48-5.46 (1H, m), 5.21 (2H, s), 4.50-4.48 (1H, m), 4.22-4.20 (1H, m), 3.95 (3H, s), 3.73-3.70 (2H, m), 3.62-3.60 (1H, m), 3.41-3.38 (1H, m), 2.45-2.43 (1H, m), 2.23-2.20 (1H, m), 0.98-0.96 (2H, m), 0.83-0.68 (4H, m), 0.04 (9H, s).

MS(APCI, ESI)m/z:509(M+H)⁺

Step 4: (11a'S)-8'-Hydroxy-7'-methoxy-10'-{[2-(trimethylsilyl)ethoxy]methyl}-1'H-spiro[cyclopropane-1,2'-pyrrolo[2,1-c][1,4]benzodiazepine]-5',11'(10'H,11a'H)-dione To a solution of the compound obtained in step 3 (18.7 g, 36.8 mmol) in THF (50 mL) and ethanol (100 mL), a 5% palladium carbon catalyst (5.00 g) was added under the nitrogen atmosphere. The nitrogen balloon was immediately replaced with a hydrogen balloon, and the reaction mixture was stirred under the hydrogen atmosphere for 6 hours. The reaction mixture was diluted by addition of chloroform and filtered through a Celite, and the filtrate was then distillated under reduced pressure, and the resulting residue was purified by silica gel column chromatography [hexane:ethyl acetate=100:0(v/v) to 25:75(v/v)] to afford the desired compound (15.1 g, 98%).

$^1$H-NMR (CDCl$_3$):7.38 (1H, s), 7.28 (1H, s), 6.01 (1H, s), 5.49-5.47 (1H, m), 4.70-4.68 (1H, m), 4.24-4.22 (1H, m), 3.96 (3H, s), 3.76-3.71 (2H, m), 3.66-3.64 (1H, m), 3.42-3.39 (1H, m), 2.47-2.45 (1H, m), 2.23-2.21 (1H, m), 1.01-0.99 (2H, m), 0.89-0.63 (4H, m), 0.03 (9H, s).

MS(APCI, ESI)m/z:419(M+H)$^+$

Step 5: (11a'S)-8'-[(5-Bromopentyl)oxy]-7'-methoxy-10'-{[2-(trimethylsilyl)ethoxy]methyl}-1'H-spiro[cyclopropane-1,2'-pyrrolo[2,1-c][1,4]benzodiazepine]-5',11'(10'H,11a'H)-dione The compound obtained in step 4 (2.77 g, 6.62 mmol) was reacted in the same manner as in step 2 of Example 3 to afford the desired compound (3.31 g, 88%).

$^1$H-NMR (CDCl$_3$):7.36 (1H, s), 7.25 (1H, s), 5.55 (1H, m), 4.65 (1H, m), 4.24-4.23 (1H, m), 4.11-4.03 (2H, m), 3.93 (3H, s), 3.85-3.78 (1H, m), 3.72-3.69 (2H, m), 3.46-3.39 (3H, m), 2.47-2.44 (1H, m), 2.25-2.22 (1H, m), 1.95-1.91 (4H, m), 1.67-1.59 (1H, m), 1.03-0.95 (2H, m), 0.90-0.85 (1H, m), 0.70-0.66 (4H, m), 0.05 (9H, s).

Step 6: (11a'S)-8'-[(5-Bromopentyl)oxy]-7'-methoxy-1',11a'-dihydro-5'H-spiro[cyclopropane-1,2'-pyrrolo[2,1-c][1,4]benzodiazepine]-5'-one The compound obtained in step 5 (3.31 g, 5.83 mmol) was reacted in the same manner as in step 7 of Example 3 to afford the desired compound (1.11 g, 45%).

$^1$H-NMR (CDCl$_3$):7.81 (1H, m), 7.53 (1H, s), 6.82 (1H, s), 4.13-4.06 (2H, m), 3.97 (3H, s), 3.88-3.83 (1H, m), 3.69 (1H, m), 3.52-3.39 (3H, m), 2.55-2.52 (1H, m), 2.06-1.89 (5H, m), 1.67-1.63 (2H, m), 0.76-0.72 (4H, m).

Step 7: (11a'S)-8'-[(5-Bromopentyl)oxy]-7'-methoxy-1',10',11',11a'-tetrahydro-5'H-spiro[cyclopropane-1,2'-pyrrolo[2,1-c][1,4]benzodiazepine]-5'-one The compound obtained in step 6 (2.56 g, 6.08 mmol) was reacted in the same manner as in step 8 of Example 3 to afford the desired compound (1.15 g, 45%).

$^1$H-NMR (CDCl$_3$) δ:7.60 (1H, s), 6.07 (1H, s), 4.11-4.04 (1H, m), 3.99 (2H, m), 3.87-3.84 (1H, m), 3.85 (3H, s), 3.73 (1H, m), 3.58-3.53 (2H, m), 3.47-3.42 (3H, m), 2.03-1.78 (6H, m), 1.65-1.63 (2H, m), 0.77-0.56 (4H, m).

Step 8: Prop-2-en-1-yl (11a'S)-8'-[(5-bromopentyl)oxy]-7'-methoxy-5'-oxo-11',11a'-dihydro-1'H-spiro[cyclopropane-1,2'-pyrrolo[2,1-c][1,4]benzodiazepine]-10'(5'H)-carboxylate The compound obtained in step 7 (1.15 g, 2.72 mmol) was reacted in the same manner as in step 9 of Example 3 to afford the desired compound (1.14 g, 82%).

$^1$H-NMR (CDCl$_3$):7.23 (1H, s), 6.69 (1H, s), 5.79 (1H, s), 5.13-5.10 (2H, m), 4.68-4.66 (1H, m), 4.48-4.45 (2H, m), 4.01 (2H, m), 3.92 (3H, s), 3.76 (1H, m), 3.54-3.37 (3H, m), 2.39 (1H, m), 1.95-1.90 (4H, m), 1.68-1.61 (3H, m), 1.44 (1H, m), 0.75-0.66 (4H, m).

Step 9: N-[(Prop-2-en-1-yloxy)carbonyl]-L-valyl-N-{4-[({[(11a'S)-11'-{[tert-butyl(dimethyl)silyl]oxy}-7'-methoxy-8'-{[5-({(11a'S)-7'-methoxy-5'-oxo-10'-[(prop-2-en-1-yloxy)carbonyl]-5',10',11',11a'-tetrahydro-1'H-spiro[cyclopropane-1,2'-pyrrolo[2,1-c][1,4]benzodiazepine]-8'-yl}oxy)pentyl]oxy}-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 8 (0.374 g, 0.737 mmol) was reacted in the same manner as in step 10 of Example 3 to afford the desired compound (0.589 g, 65%).

MS (APCI, ESI)m/z:1234 (M+H)$^+$

Step 10: N-[(Prop-2-en-1-yloxy)carbonyl]-L-valyl-N-{4-[({[(11a'S)-11'-hydroxy-7'-methoxy-8'-{[5-({(11a'S)-7'-methoxy-5'-oxo-10'-[(prop-2-en-1-yloxy)carbonyl]-5',10',11',11a'-tetrahydro-1'H-spiro[cyclopropane-1,2'-pyrrolo[2,1-c][1,4]benzodiazepine]-8'-yl}oxy)pentyl]oxy}-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 5 (0.589 g, 0.477 mmol) was reacted in the same manner as in step 11 of Example 3 to afford the desired compound (0.382 g, 71%).

$^1$H-NMR (CDCl$_3$) δ:8.90 (1H, s), 7.55 (2H, m), 7.25-7.21 (2H, m), 6.74 (2H, m), 6.38 (1H, s), 5.90-5.87 (5H, m), 5.33-5.09 (8H, m), 4.66-4.60 (8H, m), 3.98-3.91 (10H,m), 3.77-3.30 (12H, m), 2.42-2.36 (2H, m), 1.77-1.39 (6H, m), 0.91-0.70 (14H, m).

Step 11: L-Valyl-N-{4-[({[(11a'S)-11'-hydroxy-7'-methoxy-8'-[(5-{[(11a'S)-7'-methoxy-5'-oxo-5',10',11',11a'-tetrahydro-1'H-spiro[cyclopropane-1,2'-pyrrolo[2,1-c][1,4]benzodiazepine]-8'-yl]oxy}pentyl)oxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 10 (0.382 g, 0.341 mmol) was reacted in the same manner as in step 12 of Example 3 to afford the desired compound (0.200 g, 62%).

MS (APCI, ESI)m/z:952 (M+H)$^+$

Step 12: N-[4-(11,12-Didehydrodibenzo[b,f]azocin-5 (6H)-yl)-4-oxobutanoyl]glycylglycyl-L-valyl-N-{4-[({[(11a'S)-11'-hydroxy-7'-methoxy-8'-[(5-{[(11a'S)-7'-methoxy-5'-oxo-5',10',11',11a'-tetrahydro-1'H-spiro[cyclopropane-1,2'-pyrrolo[2,1-c][1,4]benzodiazepine]-8'-yl]oxy}pentyl)oxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 11 (0.0560 g, 0.0588 mmol) was reacted in the same manner as in step 13 of Example 3 to afford the desired compound (0.0500 g, 63%).

MS (APCI, ESI)m/z:1354 (M+H)$^+$

Example 38: Drug-Linker 36

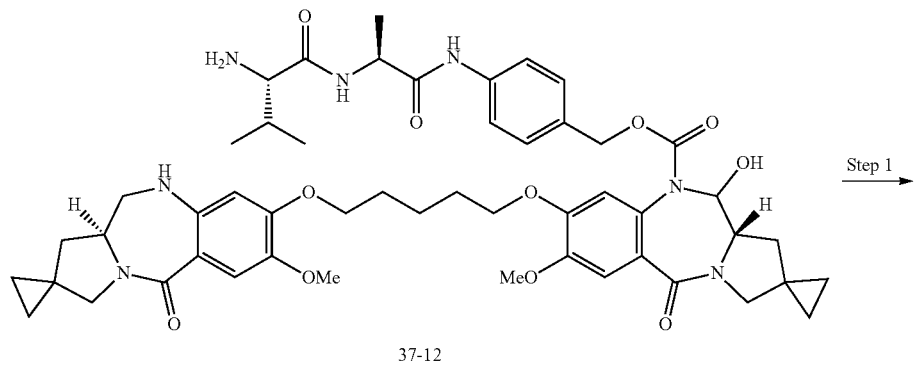

37-12

[Formula 162]

Step 1 →

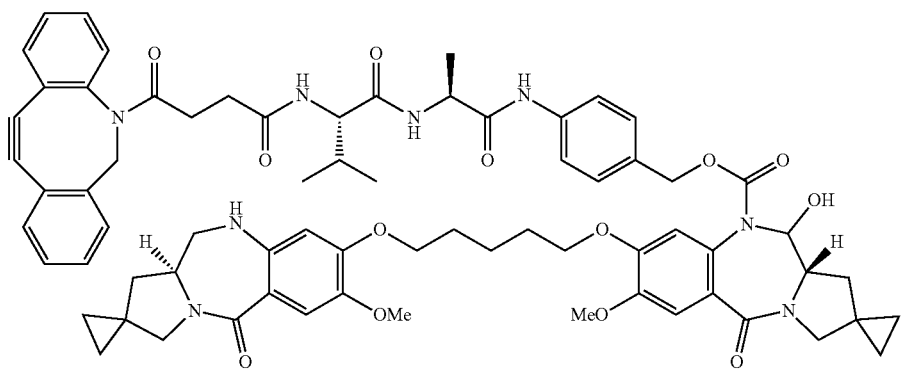

38-1

Step 1: N-[4-(11,12-Didehydrodibenzo[b,f]azocin-5(6H)-yl)-4-oxobutanoyl]-L-valyl-N-{4-[({[(11a'S)-11'-hydroxy-7'-methoxy-8'-[(5-{[(11a'S)-7'-methoxy-5'-oxo-5',10',11',11a'-tetrahydro-1'H-spiro[cyclopropane-1,2'-pyrrolo[2,1-c][1,4]benzodiazepine]-8'-yl]oxy}pentyl)oxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 11 of Example 37 (0.0410 g, 0.0430 mmol) was reacted in the same manner as in step 1 of Example 6 to afford the desired compound (0.0210 g, 39%).

MS (APCI, ESI)m/z:1240 (M+H)⁺

Example 39: Drug-Linker 37

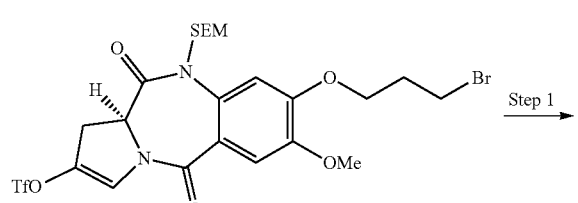

4-4

[Formula 163]

Step 1 →

-continued
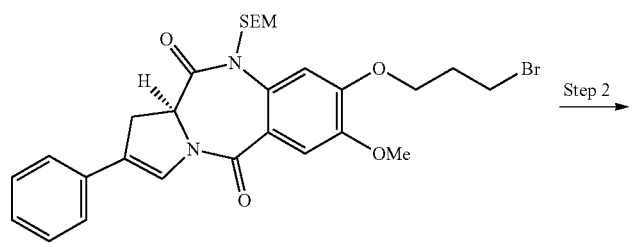
39-1
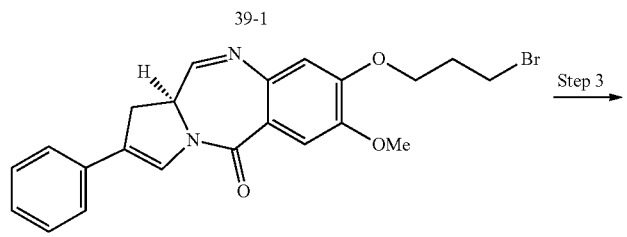
39-2
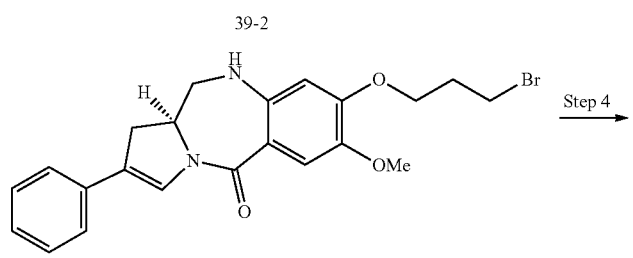
39-3
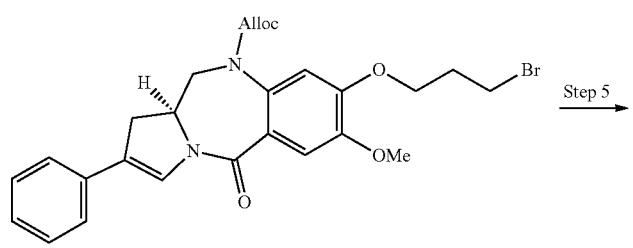
39-4
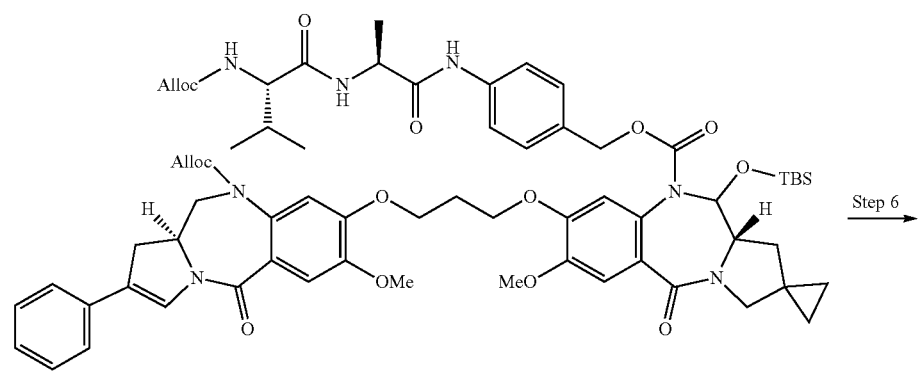
39-5

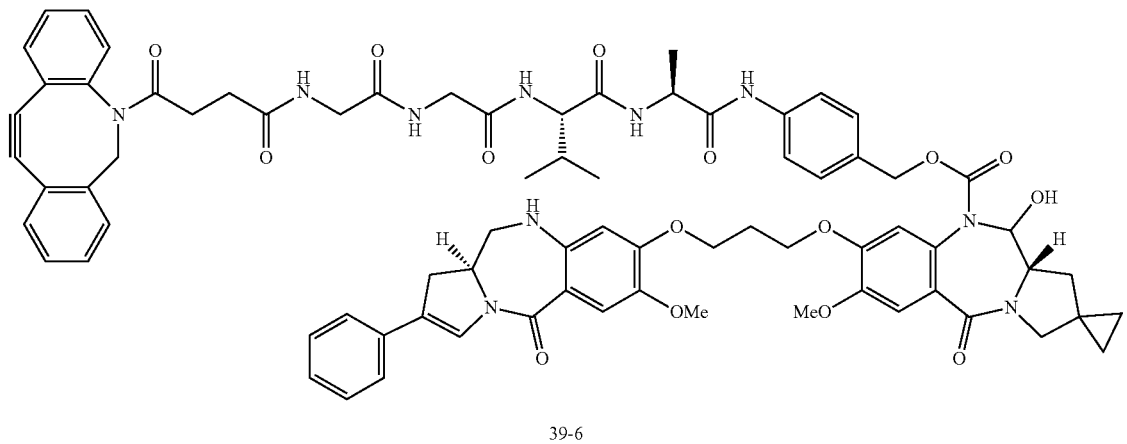 [SMILES: COc1cc2c(cc1OCCCOc1cc3c(cc1OC)C(=O)N1CC4(CC4)C[C@H]1C(O)N3C(=O)OCc1ccc(NC(=O)[C@H](C)NC(=O)[C@@H](NC(=O)CNC(=O)CNC(=O)CCC(=O)N3Cc4ccccc4C#Cc4ccccc43)C(C)C)cc1)NC[C@@H]1CC(c3ccccc3)=CN1C2=O]

39-6

Step 1: Compound 39-1

The compound obtained in step 4 of Example 4 (1.00 g, 1.52 mmol) and phenylboronic acid (0.370 g, 3.03 mmol) were used and reacted in the same manner as in step 6 of Example 3 to afford the desired compound (0.726 g, 81%).

MS(APCI, ESI)m/z:589[$^{81}$Br,(M+H)$^+$], 587[$^{79}$Br,(M+H)$^+$].

Step 2: Compound 39-2

The compound obtained in step 1 (0.726 g, 1.24 mmol) was reacted in the same manner as in step 7 of Example 3 to afford the desired compound (0.344 g, 63%).

MS(APCI, ESI)m/z:443[$^{81}$Br,(M+H)$^+$], 441[$^{79}$Br,(M+H)$^+$].

Step 3: Compound 39-3

The compound obtained in step 2 (0.344 g, 0.779 mmol) was reacted in the same manner as in step 8 of Example 3 to afford the desired compound (0.248 g, 72%).

MS(APCI, ESI)m/z:445[$^{81}$Br,(M+H)$^+$], 443[$^{79}$Br,(M+H)$^+$].

Step 4: Compound 39-4

The compound obtained in step 3 (0.248 g, 0.559 mmol) was reacted in the same manner as in step 9 of Example 3 to afford the desired compound (0.267 g, 90%).

MS(APCI, ESI)m/z:529[$^{81}$Br,(M+H)$^+$], 527[$^{79}$Br,(M+H)$^+$].

Step 5: Compound 39-5

The compound obtained in step 4 (0.100 g, 0.190 mmol) was reacted in the same manner as in step 10 of Example 3 to afford the desired compound (0.201 g, 85%).

MS(APCI, ESI)m/z:1255(M+H)$^+$.

Step 6: N-[4-(11,12-Didehydrodibenzo[b,f]azocin-5(6H)-yl)-4-oxobutanoyl]glycylglycyl-L-valyll-N-{4-[({[(11a'S)-11'-hydroxy-7'-methoxy-8'-(3-{[(11aS)-7-methoxy-5-oxo-2-phenyl-5,10,11,11a-tetrahydro-1H-pyrrolo[2,1-c][1,4]benzodiazepin-8-yl]oxy}propoxy)-5'-oxo-11',11a'-dihydro-1'H-spiro[cyclopropane-1,2'-pyrrolo[2,1-c][1,4]benzodiazepine]-10'(5'H)-yl]carbonyl}oxo)methyl]phenyl}-L-alaninamide ("GGVA" Disclosed as SEQ ID NO: 76)

The compound obtained in step 5 (0.201 g, 0.160 mmol) was reacted in the same manner as in steps 11, 12, and 13 of Example 3 to afford the desired compound (0.080 g, 36%).

MS (APCI, ESI)m/z:1372 (M+H)$^+$.

Example 40: Drug-Linker 38

[Formula 164]

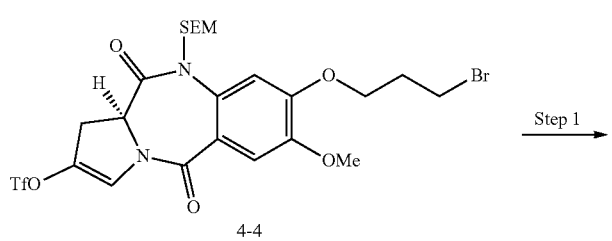

4-4

Step 1

-continued
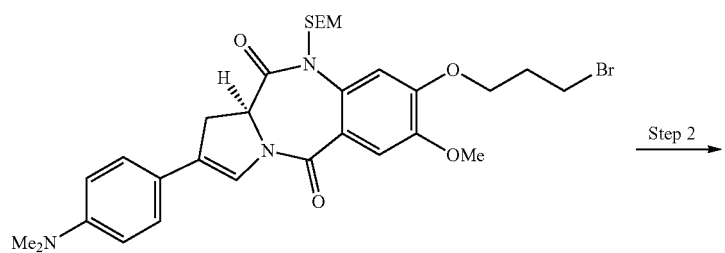
40-1
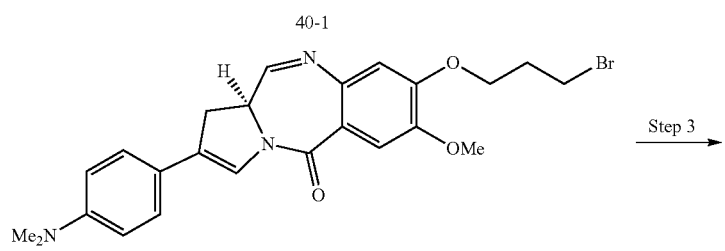
40-2
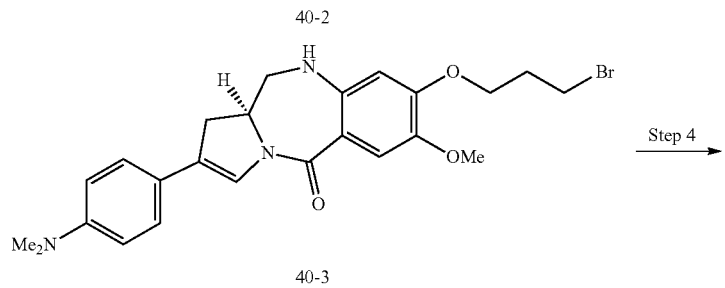
40-3
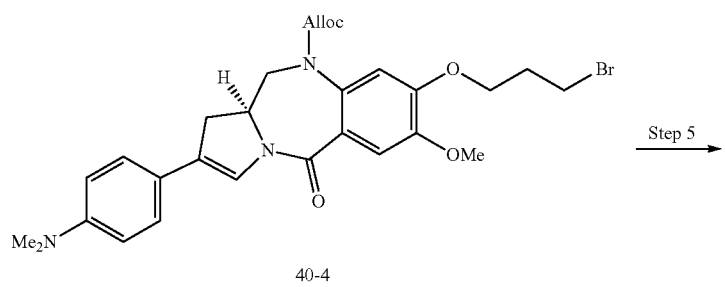
40-4
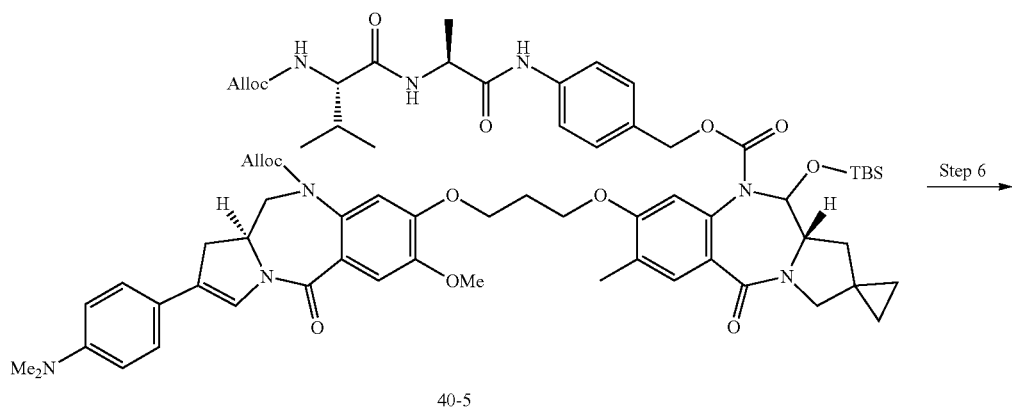
40-5

-continued

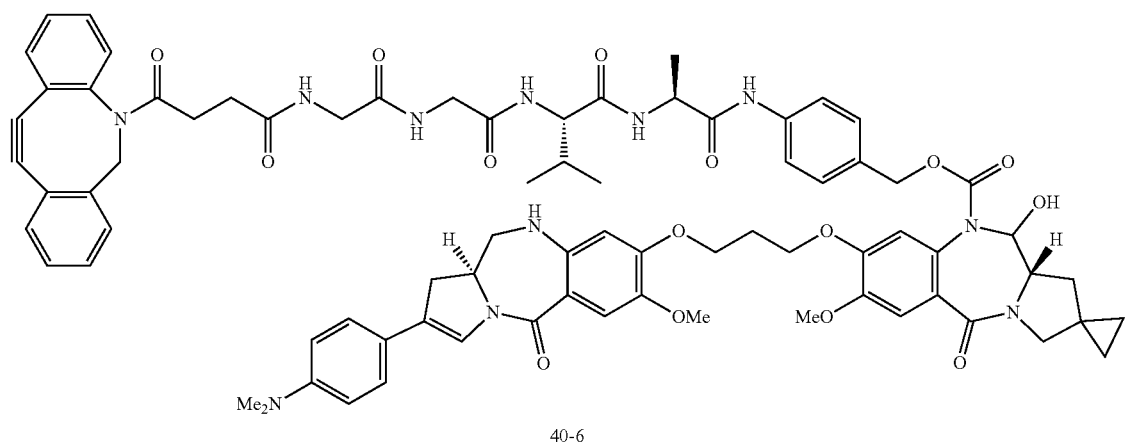

40-6

Step 1: Compound 40-1

The compound obtained in step 4 of Example 4 (1.48 g, 2.24 mmol) and 4-(dimethylamino)phenylboronic acid (0.741 g, 4.49 mmol) were reacted in the same manner as in step 6 of Example 3 to afford the desired compound (0.520 g, 37%).

MS(APCI, ESI)m/z:632[$^{81}$Br,(M+H)$^+$], 630[$^{79}$Br,(M+H)$^+$].

Step 2: Compound 40-2

The compound obtained in step 1 (0.520 g, 0.825 mmol) was reacted in the same manner as in step 7 of Example 3 to afford the desired compound (0.167 g, 42%).

Step 3: Compound 40-3

The compound obtained in step 2 (0.167 g, 0.345 mmol) was reacted in the same manner as in step 8 of Example 3 to afford the desired compound (0.0650 g, 39%).

MS(APCI, ESI)m/z:488[$^{81}$Br,(M+H)$^+$], 486[$^{79}$Br,(M+H)$^+$].

Step 4: Compound 40-4

The compound obtained in step 3 (0.0650 g, 0.134 mmol) was reacted in the same manner as in step 9 of Example 3 to afford the desired compound (0.0690 g, 90%).

MS(APCI, ESI)m/z:572[$^{81}$Br,(M+H)$^+$], 570[$^{79}$Br,(M+H)$^+$].

Step 5: Compound 40-5

The compound obtained in step 4 (0.0690 g, 0.121 mmol) was reacted in the same manner as in step 10 of Example 3 to afford the desired compound (0.0660 g, 42%).

MS(APCI, ESI)m/z:1297(M+H)$^+$.

Step 6: N-[4-(11,12-Didehydrodibenzo[b,f]azocin-5(6H)-yl)-4-oxobutanoyl]glycylglycyl-L-valyl-N-{4-[({[(11a'S)-8'-[3-({(11aS)-2-[4-(dimethylamino)phenyl]-7-methoxy-5-oxo-5,10,11,11a-tetrahydro-1H-pyrrolo[2,1-c][1,4]benzodiazepin-8-yl}oxy)propoxy]-11'-hydroxy-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 5 (0.0660 g, 0.0509 mmol) was reacted in the same manner as in steps 11, 12, and 13 of Example 3 to afford the desired compound (0.0350 g, 49%).

MS (APCI, ESI)m/z:1417 (M+H)$^+$.

Example 41: Drug-Linker 39

[Formula 165]

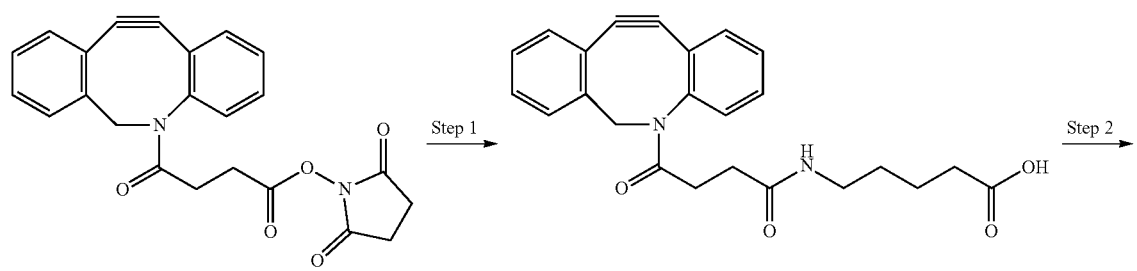

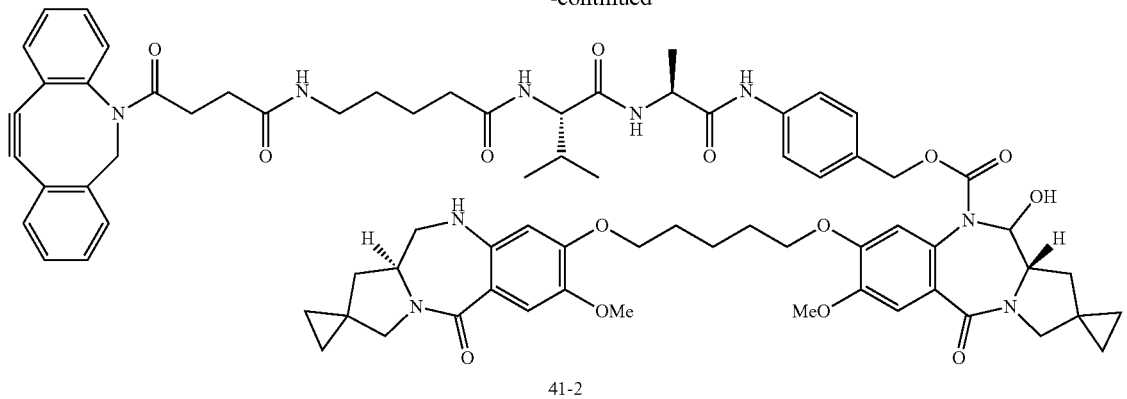

41-2

Step 1: N,N-Dimethylformamide Adduct of 5-{[4-(11,12-didehydrodibenzo[b,f]azocin-5 (6H)-yl)-4-oxobutanoyl]amino}valeric acid In N,N-dimethylformamide (10 mL), 5-aminovaleric acid (0.436 g, 3.72 mmol) was dissolved, to which 1-{[4-(11,12-didehydrodibenzo[b,f]azocin-5 (6H)-yl)-4-oxobutanoyl]oxy}pyrrolidin-2,5-di one (1.36 g, 3.38 mmol) and triethylamine (0.937 mL, 6.76 mmol) were added at room temperature, and the resultant was stirred at room temperature for 1.5 hours. To the reaction solution, 1 N hydrochloric acid was added, which was extracted with chloroform, and the organic layer obtained was washed with water and brine and then dried over magnesium sulfate. After distillation under reduced pressure, the resulting residue was purified by silica gel column chromatography [organic layer for distribution with chloroform-chloroform:methanol:water=7:3:1 (v/v/v)] to afford the desired compound (0.730 g, 45%) as a solid.

$^1$H-NMR (CDCl$_3$) δ:8.06 (1H, s), 7.71 (1H, m), 7.54-7.52 (1H, m), 7.46-7.32 (6H, m), 6.04 (1H, m), 5.18 (1H, m), 3.72 (1H, m), 3.17-3.10 (2H, m), 3.00 (3H, s), 2.92 (3H, s), 2.84-2.80 (1H, m), 2.45-2.34 (3H, m), 2.28-2.24 (1H, m), 2.03-1.99 (1H, m), 1.66-1.58 (2H, m), 1.47-1.40 (2H, m).
MS(APCI, ESI)m/z:405(M+H)$^+$

Step 2: N-(5-{[4-(11,12-Didehydrodibenzo[b,f]azocin-5 (6H)-yl)-4-oxobutanoyl]amino}pentanoyl)-L-valyl-N-{4-[({[(11a'S)-11'-hydroxy-7'-methoxy-8'-[(5-{[(11a'S)-7'-methoxy-5'-oxo-5',10',11',11a'-tetrahydro-1'H-spiro[cyclopropane-1,2'-pyrrolo[2,1-c][1,4]benzodiazepine]-8'-yl]oxy}pentyl)oxy]-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide The compound obtained in step 1 (0.0176 g, 0.0368 mmol) was reacted in the same manner as in step 13 of Example 3 to afford the desired compound (0.00880 g, 18%).
MS (APCI, ESI)m/z:1339 (M+H)$^+$ Example 42: Drug-Linker 40

[Formula 166]

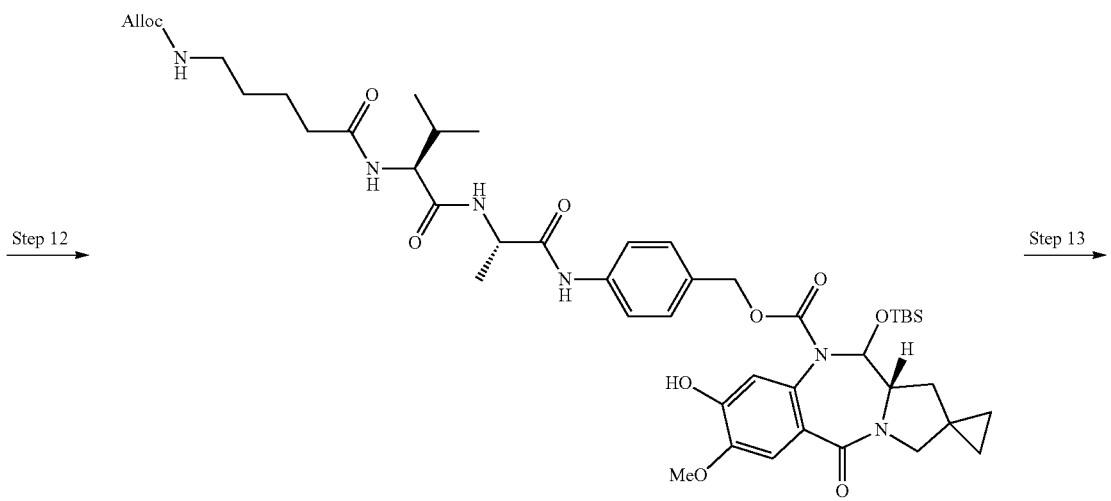

42-12

453 454
-continued
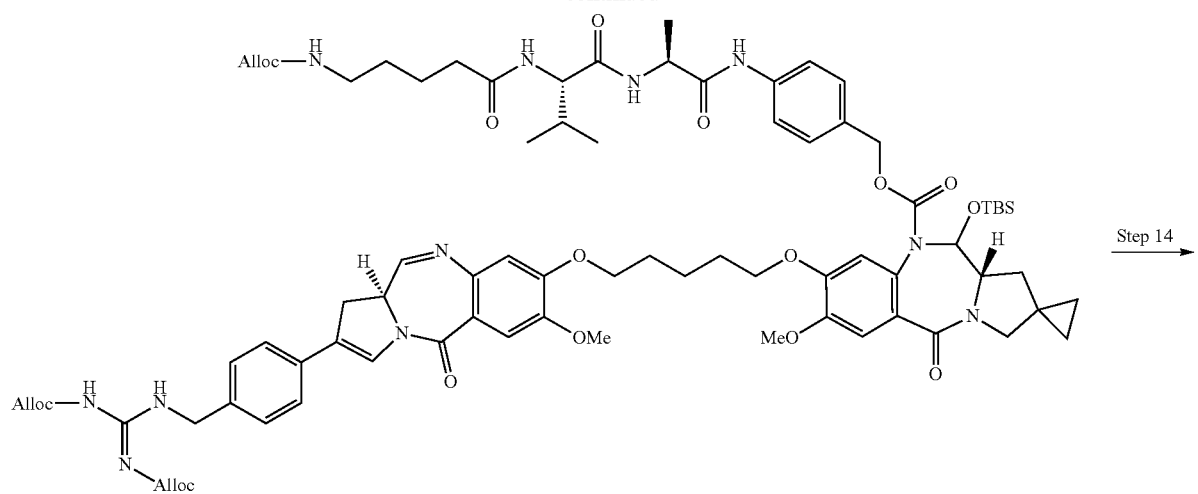
42-13
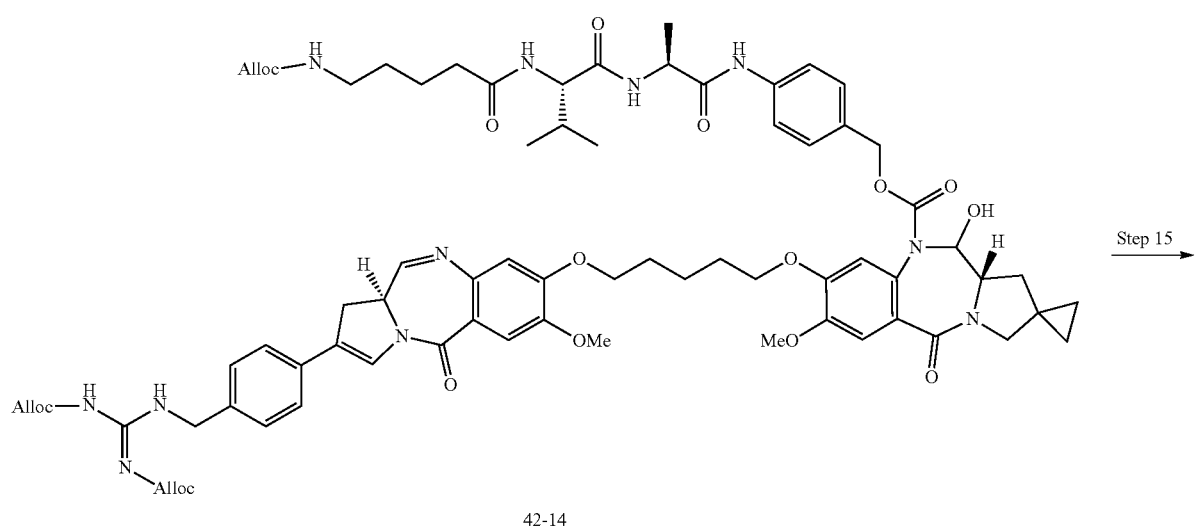
42-14
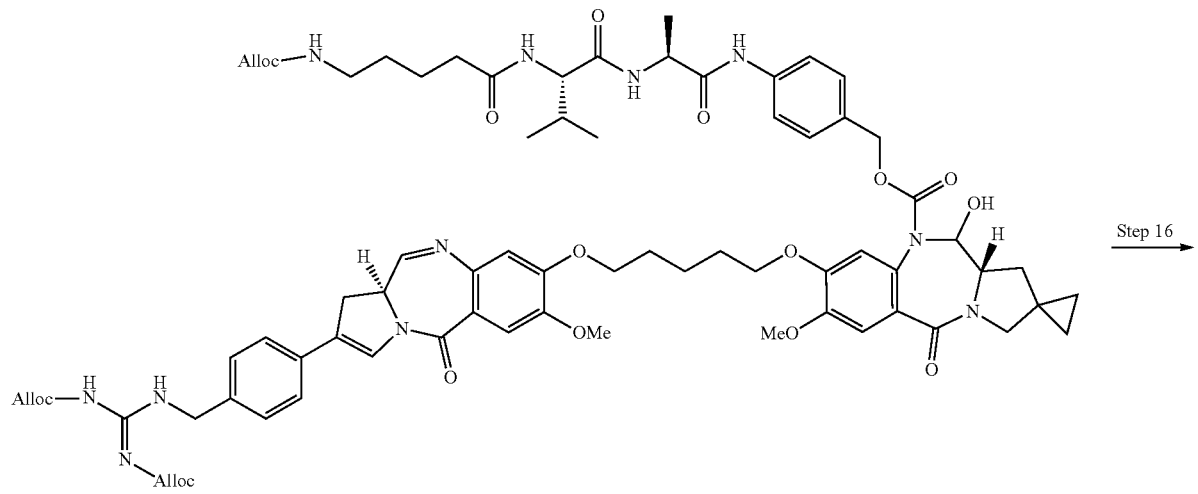
42-15
Step 14 →
Step 15 →
Step 16 →

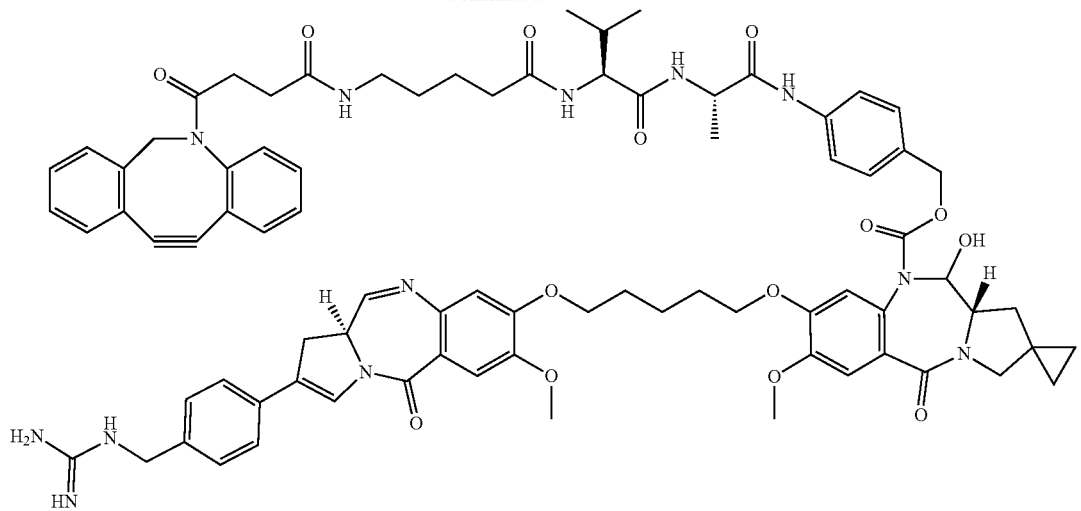
42-16
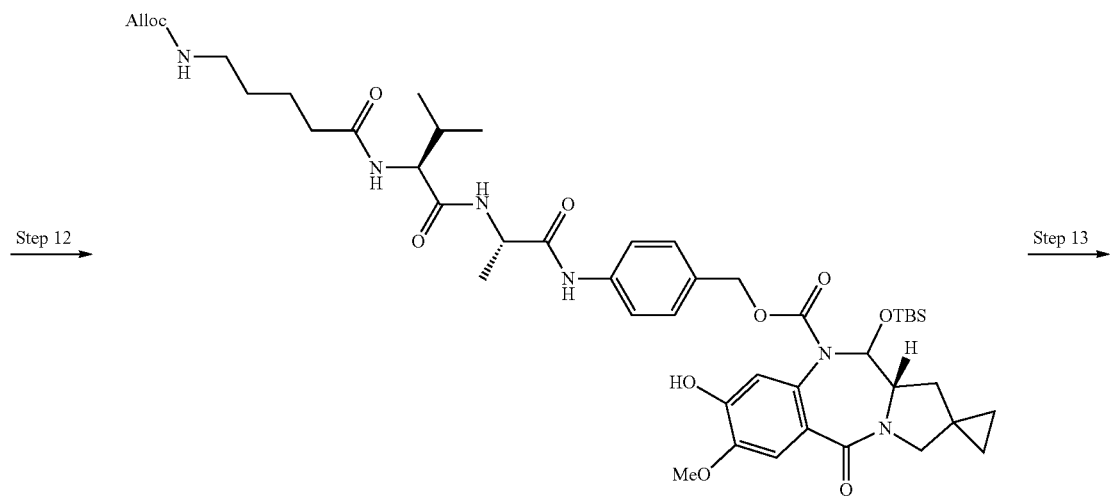
42-12
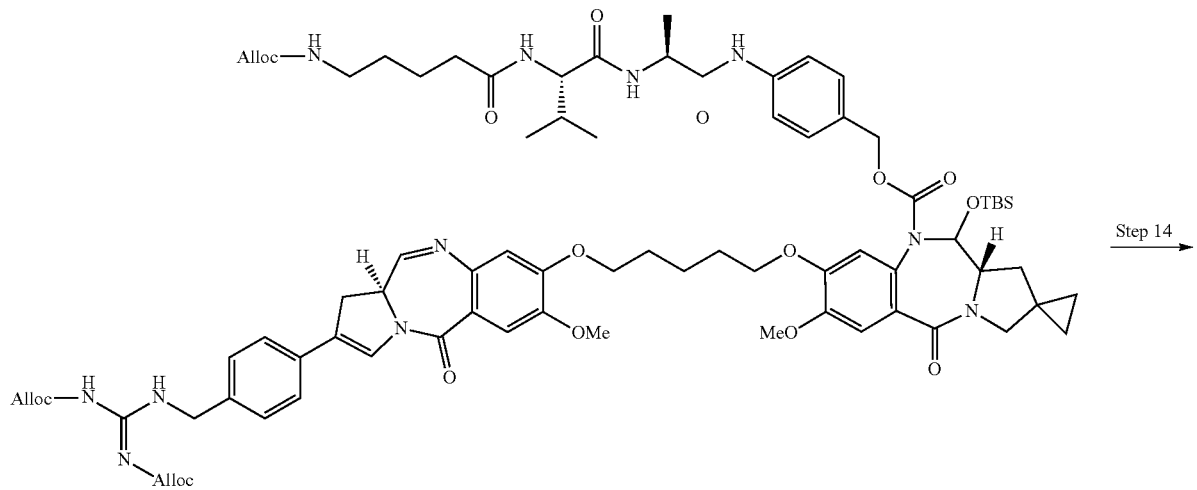
42-13

457 458
-continued
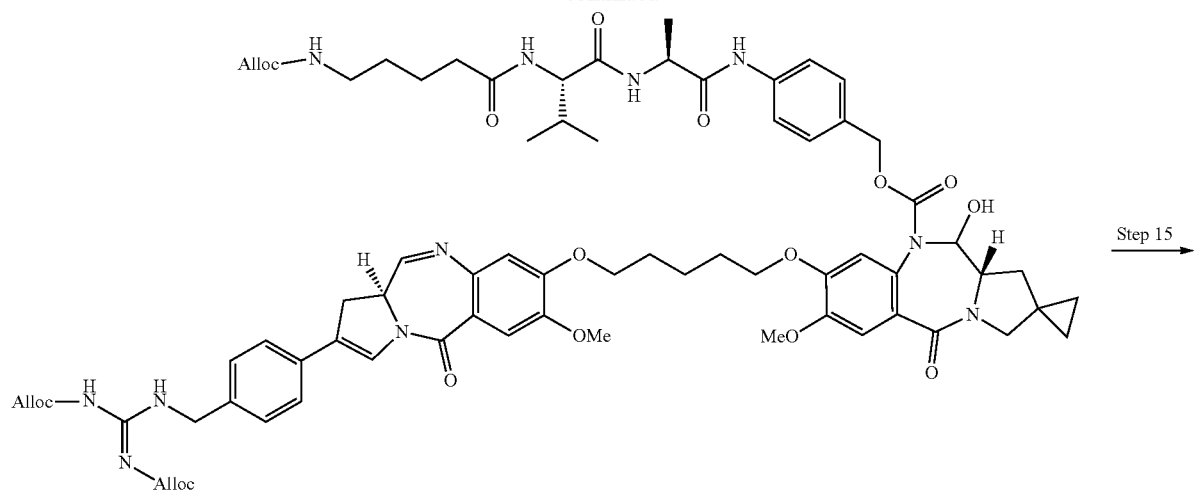
42-14
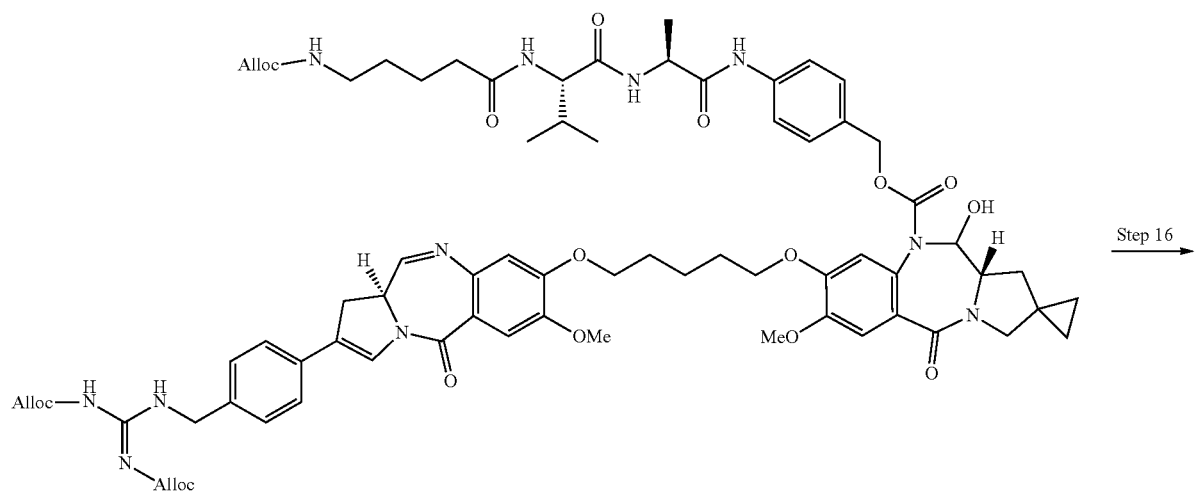
42-15
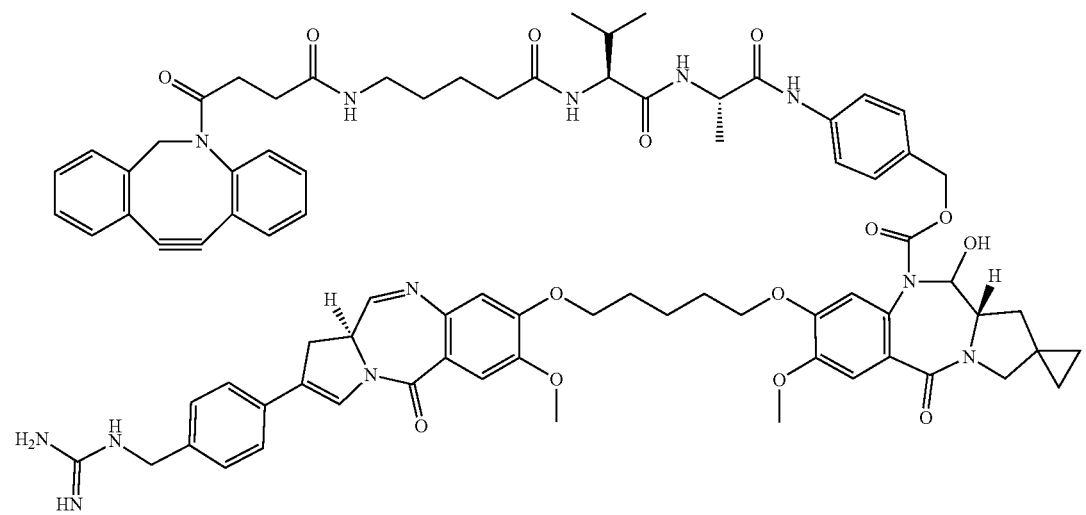
42-16

Step 1: Compound 42-1

The compound obtained in step 1 of Example 3 (5.00 g, 9.66 mmol) was reacted in the same manner as in step 3 of Example 3 to afford the desired compound (3.95 g, 100%).
MS(APCI, ESI)m/z:409(M+H)$^+$

Step 2: Compound 42-2

The compound obtained in step 1 (3.95 g, 9.67 mmol) was reacted in the same manner as in step 2 of Example 24 to afford the desired compound (4.78 g, 87%).
MS(APCI, ESI)m/z:565(M+H)$^+$

Step 3: Compound 42-3

The compound obtained in step 2 (4.78 g, 8.43 mmol) was reacted in the same manner as in step 4 of Example 3 to afford the desired compound (2.36 g, 50%). MS(APCI, ESI)m/z:563(M+H)$^+$

Step 4: Compound 42-4

The compound obtained in step 3 (1.53 g, 2.72 mmol) was reacted in the same manner as in step 5 of Example 3 to afford the desired compound (1.27 g, 69%).
$^1$H-NMR (CDCl$_3$):7.31 (2H, s), 7.15 (1H, m), 5.52 (1H, m), 4.65 (1H, m), 4.57 (1H, m), 3.95-3.89 (1H, m), 3.87 (3H, s), 3.75-3.58 (2H, m), 3.18-3.14 (1H, m), 1.33-1.25 (3H, m), 1.10 (18H, m), 1.00-0.96 (2H, m), 0.03 (9H, s).

Step 5: Compound 42-5

The compound obtained in step 4 (0.255 g, 0.367 mmol) and 4-(aminomethyl)phenylboronic acid (0.344 g, 1.84 mmol) were reacted in the same manner as in step 6 of Example 3 to afford the desired compound (0.148 g, 62%).
MS(APCI, ESI)m/z:652(M+H)$^+$

Step 6: Compound 42-6

To a solution of the compound (0.142 g, 0.218 mmol) obtained in step 5 and diprop-2-en-1-yl [(Z)-(methylsulfanyl)methylidene]biscarbamate (0.079 g, 0.079 mmol, WO 9920628) in dimethylformamide (2.2 mL), triethylamine (0.090 mL, 0.653 mmol) and mercury chloride (II) (0.083 g, 0.305 mmol) were added at room temperature. After the reaction solution was stirred at room temperature for 30 minutes, the reaction solution was diluted by addition of ethyl acetate, and mercury salts were removed through filtration. The organic layer obtained was washed with 0.1 N phosphate buffer and brine. The organic layer was dried over sodium sulfate, and then distillated under reduced pressure. The resulting residue was purified by silica gel column chromatography [hexane:ethyl acetate=100:0 (v/v) to 60:40 (v/v)] to afford the desired compound (0.157 g, 83%).
MS(APCI, ESI)m/z:863(M+H)$^+$

Step 7: Compound 42-7

To a solution of the compound obtained in step 6 (0.153 g, 0.177 mmol) in THF (1.8 mL), a 1 mol/L tetrahydrofuran solution of tetrabutylammonium fluoride (0.266 mL, 0.266 mmol) was added at room temperature. After stirring at room temperature for 50 minutes, 0.1 N phosphate buffer (pH 7.0) was added to the reaction solution, which was extracted with ethyl acetate, and the organic layer obtained was washed with 0.1 N phosphate buffer (pH 7.0). The resultant was dried over sodium sulfate, and then distillated under reduced pressure. The resulting residue was purified by silica gel column chromatography [hexane:ethyl acetate=100:0 (v/v) to 0:100 (v/v)] to afford the desired compound (0.115 g, 92%).
MS(APCI, ESI)m/z:706(M+H)$^+$

Step 8: Compound 42-8

To a solution of the compound obtained in step 7 (0.115 g, 0.163 mmol) in N,N-dimethylformamide (1.0 mL), 1,5-dibromopentane (0.088 mL, 0.652 mmol) and cesium carbonate (0.032 g, 0.098 mmol) were added at room temperature. After stirring at room temperature for 2 hours, 0.1 N phosphate buffer (pH 7.0) was added to the reaction solution, which was extracted with ethyl acetate. The organic layer obtained was washed with 0.1 N phosphate buffer (pH 7.0) and brine and dried over sodium sulfate, and then distillated under reduced pressure. The resulting residue was purified by silica gel column chromatography [hexane:ethyl acetate=100:0 (v/v) to 50:50 (v/v)] to afford the desired compound (0.111 g, 80%).
MS(APCI, ESI)m/z:856[$^{81}$Br,(M+H)$^+$], 854[$^{79}$Br,(M+H)$^+$]

Step 9: Compound 42-9

The compound obtained in step 8 (0.105 g, 0.123 mmol) was reacted in the same manner as in step 7 of Example 3 to afford the desired compound (0.036 g, 41%).
MS(APCI,ESI)m/z:772[$^{81}$Br,(M+H)$^+$], 770[$^{79}$Br,(M+H)$^+$]

Step 10: Compound 42-10

The compound obtained in step 9 (0.163 g, 0.169 mmol) was reacted in the same manner as in step 12 of Example 3 to afford the desired compound (0.132 g, 88%).
MS (APCI, ESI)m/z:880(M+H)$^+$

Step 11: Compound 42-11

To a solution of the compound obtained in step 10 (0.13 g, 0.147 mmol), 5-{[(prop-2-en-1-yloxy)carbonyl]amino}pentanoic acid (0.0386 g, 0.192 mmol), and 1-hydroxybenzotriazole monohydrate (0.038 g, 0.251 mmol) in dichloromethane (3 mL), triethylamine (0.035 mL, 0.251 mmol) and 1-ethyl-3-(3-dimethylaminopropyl)carbodiimide hydrochloride (0.048 g, 0.251 mmol) were added at room temperature, and the resultant was stirred at room temperature for 1 hour. To the reaction solution, 0.1 N phosphate buffer (pH 7.0) was added, and the resultant was extracted with ethyl acetate. The organic layer obtained was washed with 0.1 N phosphate buffer (pH 7.0), and ethyl acetate was distilled off under reduced pressure. The resultant was azeotroped with toluene, and the resulting residue was purified by silica gel column chromatography [hexane:ethyl acetate=100:0 (v/v) to 50:50 (v/v)] to afford the desired compound (0.150 g, 95%).
MS(APCI, ESI)m/z:1063(M+H)$^+$

Step 12: Compound 42-12

To a solution of the compound obtained in step 11 (0.150 g, 0.141 mmol) in N,N-dimethylformamide (3.5 mL), an aqueous solution of lithium acetate (1.52 M, 0.088 mL) was added at room temperature. After stirring at room temperature for 1.5 hours, water was added to the reaction solution, which was extracted with ethyl acetate. The organic layer was washed with water, and then distillated under reduced pressure. The resulting residue was purified by silica gel column chromatography [chloroform:methanol=100:0 (v/v) to 95:5 (v/v)] to afford the desired compound (0.135 g, 96%).

MS(APCI, ESI)m/z:907(M+H)$^+$

Step 13: Compound 42-13

To a solution of the compound obtained in step 12 (0.048 g, 0.053 mmol) and the compound obtained in step 9 (0.034 g, 0.048 mmol) in N,N-dimethylformamide (0.5 mL), cesium carbonate (0.011 g, 0.034 mmol) was added at room temperature. Stirring was performed at room temperature for 1.5 hours, and then at 45° C. for 5 hours. To the reaction solution, 0.1 N phosphate buffer (pH 7.0) was added, and the resultant was extracted with ethyl acetate. The organic layer obtained was washed with 0.1 N phosphate buffer (pH 7.0) and dried over sodium sulfate, and then distillated under reduced pressure. The resulting residue was purified by silica gel column chromatography [chloroform:methanol=100:0 (v/v) to 97:3 (v/v)] to afford the desired compound (0.038 g, 52%).

MS (APCI, ESI)m/z:1534 (M+H)$^+$

Step 14: Compound 42-14

The compound obtained in step 13 (0.038 g, 0.247 mmol) was reacted in the same manner as in step 11 of Example 3. After the reaction solution was subjected to liquid separation, the organic solvent was distilled off under reduced pressure, and the resulting compound was directly used for the subsequent reaction.

MS (APCI, ESI)m/z:1420 (M+H)$^+$

Step 15: Compound 42-15

To a solution of the compound obtained in step 14 (0.034 g, 0.140 mmol) in dimethylformamide (2 mL), pyrrolidine (0.048 mL, 0.574 mmol) and tetrakis(triphenylphosphine) palladium (0) (0.0054 g, 0.0046 mmol) were added at room temperature, and the resultant was stirred at room temperature for 50 minutes. After the organic solvent was distilled off under reduced pressure, the resulting residue was dissolved in dimethyl sulfoxide and purified by reversed-phase column chromatography (column: Develosil Combi-RP-5 (Nomura Chemical Co., Ltd.), 20 mm×100 mm: a 0.1% formic acid aqueous solution: 0.1% formic acid acetonitrile solution=79.2:20.8 to 51.4:48.6, flow rate: 25 mL/min, temperature: 25° C.) to afford the desired compound (0.020 g, 72%).

MS (APCI, ESI)m/z:1168 (M+H)$^+$

Step 16: Compound 42-16

To a solution of the compound obtained in step 15 (0.002 g, 0.0017 mmol) in dimethylformamide (0.5 mL), triethylamine (0.007 mL, 0.051 mmol) and commercially available 1-{[4-(11,12-didehydrobenzo[b,f]azocin-5 (6H)-yl)-4-oxobutanoyl]oxopyrrolidin-2,5-dione (0.083 g, 0.0205 mmol) were added, and the resultant was stirred at room temperature for 10 hours. The organic solvent was distilled off under reduced pressure, and the resulting residue was dissolved in dimethyl sulfoxide and purified by reversed-phase column chromatography (column: Develosil Combi-RP-5 (Nomura Chemical Co., Ltd.), 20 mm×100 mm: a 0.1% formic acid aqueous solution: 0.1% formic acid acetonitrile solution=62.5:37.5 to 34.7:65.3, flow rate: 25 mL/min, temperature: 25° C.) and silica gel column chromatography [organic layer for distribution with chloroform-chloroform:methanol:water=7:3:1 (v/v/v)] to afford the desired compound (0.033 g, 14%).

MS (APCI, ESI)m/z:1455 (M+H)$^+$

Example 43: Drug-Linker 41

[Formula 167]

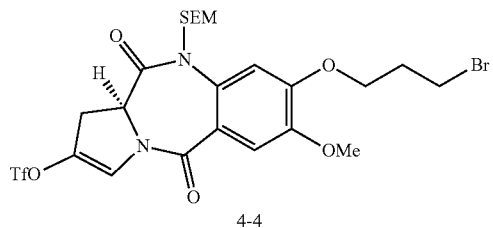

4-4

Step 1 →

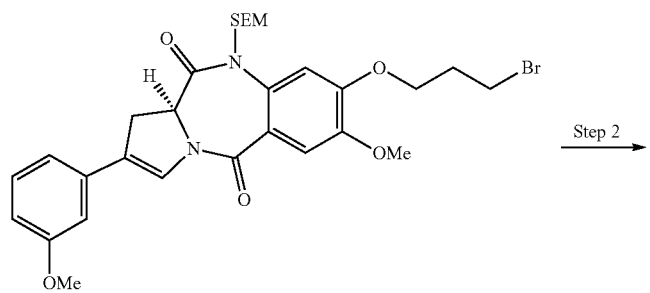

43-1

Step 2 →

-continued
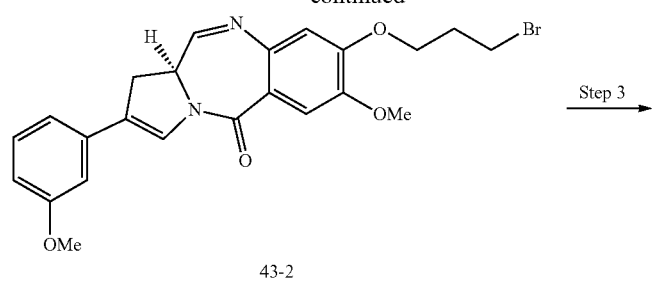
43-2
Step 3 →
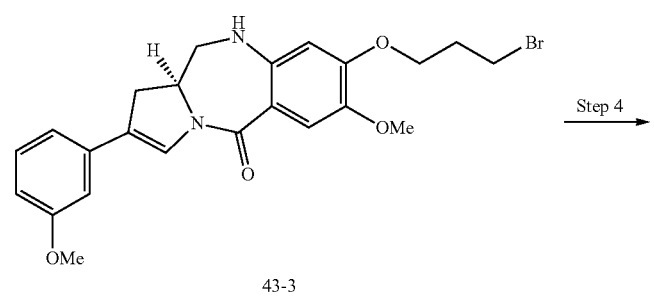
43-3
Step 4 →
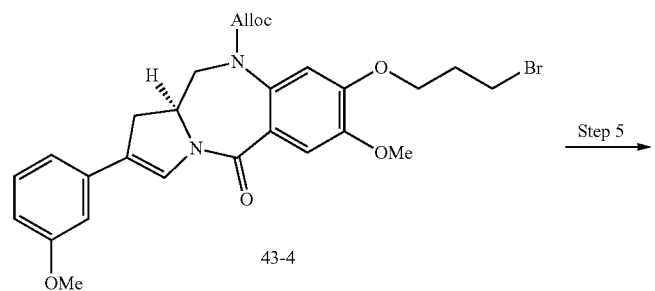
43-4
Step 5 →
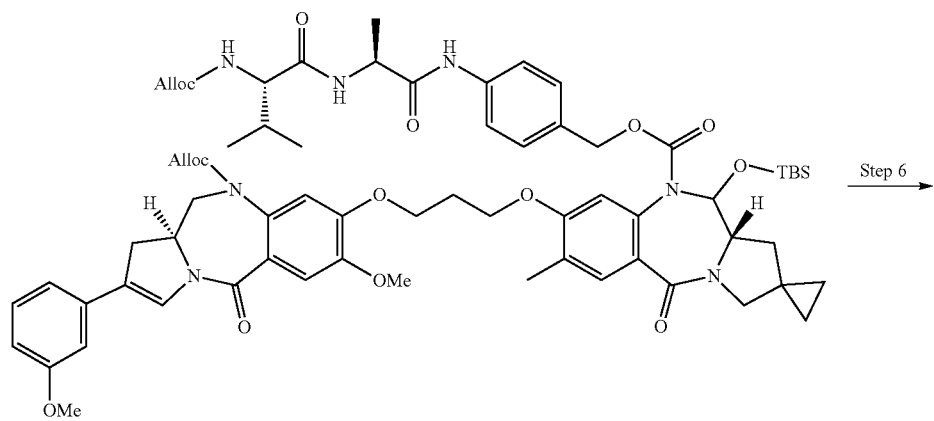
43-5
Step 6 →

-continued
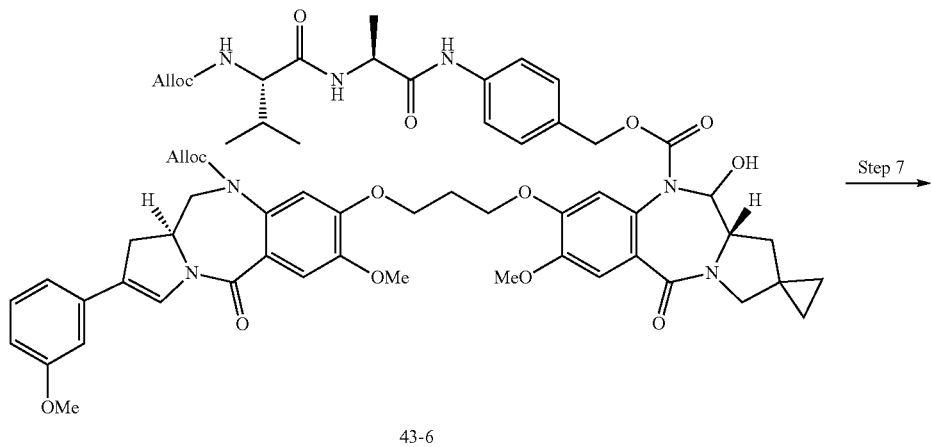
43-6
Step 7 →
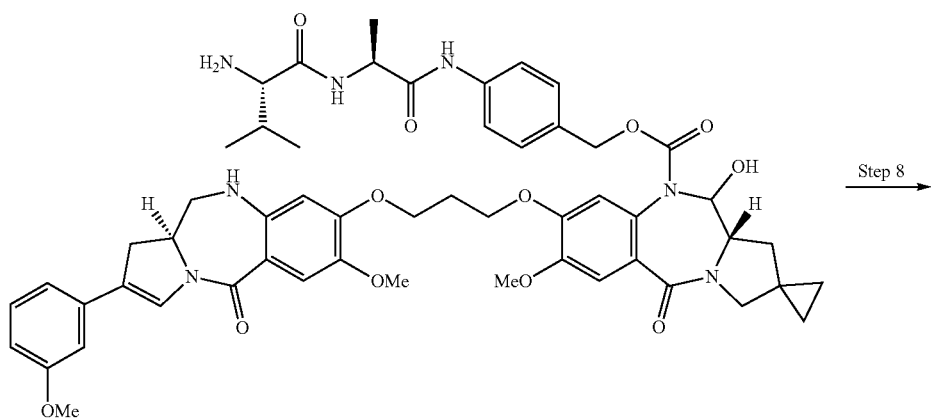
43-7
Step 8 →
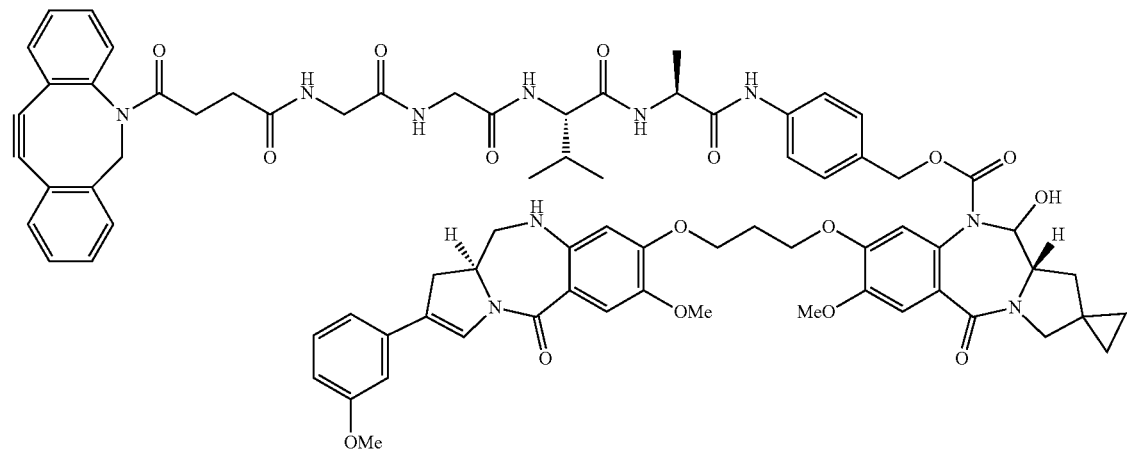
43-8

Step 1: Compound 43-1

The compound obtained in step 4 of Example 4 (0.72 g, 1.09 mmol) and 3-methoxyphenylboronic acid (0.332 g, 2.18 mmol) were reacted in the same manner as in step 6 of Example 3 to afford the desired compound (0.526 g, 78%).
MS(APCI, ESI)m/z:619[$^{81}$Br,(M+H)$^+$], 617[$^{79}$Br,(M+H)$^+$]

Step 2: Compound 43-2

The compound obtained in step 1 (0.526 g, 0.851 mmol) was reacted in the same manner as in step 7 of Example 3 to afford the desired compound (0.195 g, 49%).
MS(APCI, ESI)m/z:473[$^{81}$Br,(M+H)$^+$], 471[$^{79}$Br,(M+H)$^+$]

Step 3: Compound 43-3

The compound obtained in step 2 (0.195 g, 0.414 mmol) was reacted in the same manner as in step 8 of Example 3 to afford the desired compound (0.195 g, quantitative).
MS(APCI, ESI)m/z:475[$^{81}$Br,(M+H)$^+$], 473[$^{79}$Br,(M+H)$^+$]

Step 4: Compound 43-4

The compound obtained in step 3 (0.413 mmol) was reacted in the same manner as in step 9 of Example 3 to afford the desired compound (0.106 g, 46%).
MS(APCI, ESI)m/z:559[$^{81}$Br,(M+H)$^+$], 557[$^{79}$Br,(M+H)$^+$]

Step 5: Compound 43-5

The compound obtained in step 4 (0.069 g, 0.124 mmol) was reacted in the same manner as in step 10 of Example 3 to afford the desired compound (0.128 g, 80%).
MS(APCI, ESI)m/z:1284(M+H)$^+$

Step 6: Compound 43-6

The compound obtained in step 5 (0.128 g, 0.099 mmol) was reacted in the same manner as in step 11 of Example 3 to afford the desired compound (0.105 g, 90%).
MS(APCI, ESI)m/z:1170(M+H)$^+$

Step 7: Compound 43-7

The compound obtained in step 6 (0.105 g, 0.089 mmol) was reacted in the same manner as in step 12 of Example 3 to afford the desired compound (0.072 g, 80%).
MS(APCI, ESI)m/z:1002(M+H)$^+$

Step 8: N-[4-(11,12-Didehydrodibenzo[b,f]azocin-5 (6H)-yl)-4-oxobutanoyl]glycylglycyl-L-valyl-N-{4-[({[(11a'S)-11'-hydroxy-7'-methoxy-8'-(3-{[(11aS)-7-methoxy-2-(3-methoxyphenyl)-5-oxo-5,10,11,11a-tetrahydro-1H-pyrrolo[2,1-c][1,4]benzodiazepin-8-yl]oxy}propoxy)-5'-oxo-11',11a'-dihydro-1'H-spiro [cyclopropane-1,2'-pyrrolo[2,1-c][1,4] benzodiazepine]-10'(5'H)-yl]carbonyl}oxy)methyl] phenyl}-L-alaninamide ("GGVA" Disclosed as SEQ ID NO: 76)

The compound obtained in step 7 (0.072 g, 0.072 mmol) was reacted in the same manner as in step 13 of Example 3 to afford the desired compound (0.053 g, 52%).
MS (APCI, ESI)m/z:1403 (M+H)$^+$

Example 44: Drug-Linker 42

[Formula 168]

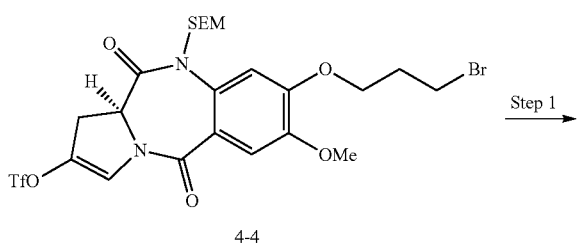

4-4

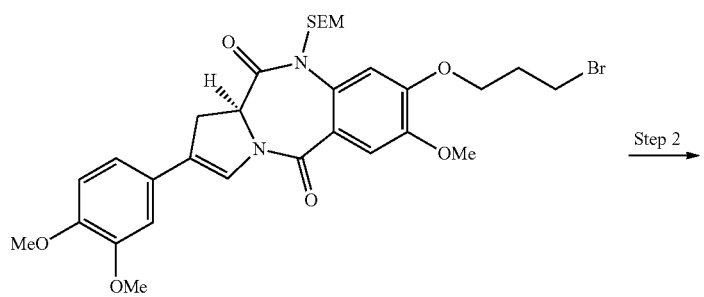

44-1

-continued
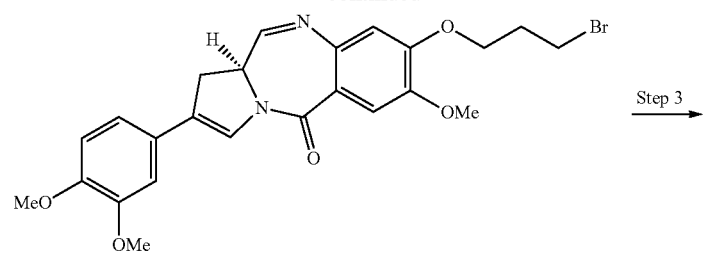
44-2
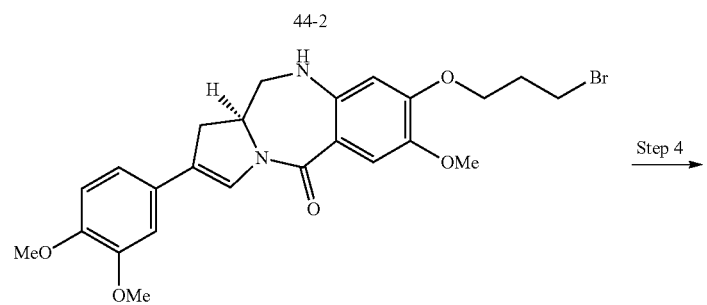
44-3
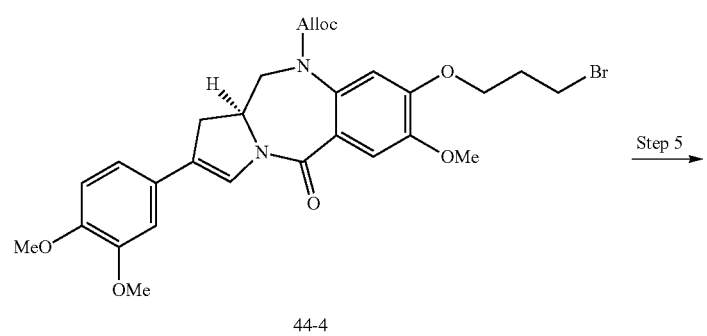
44-4
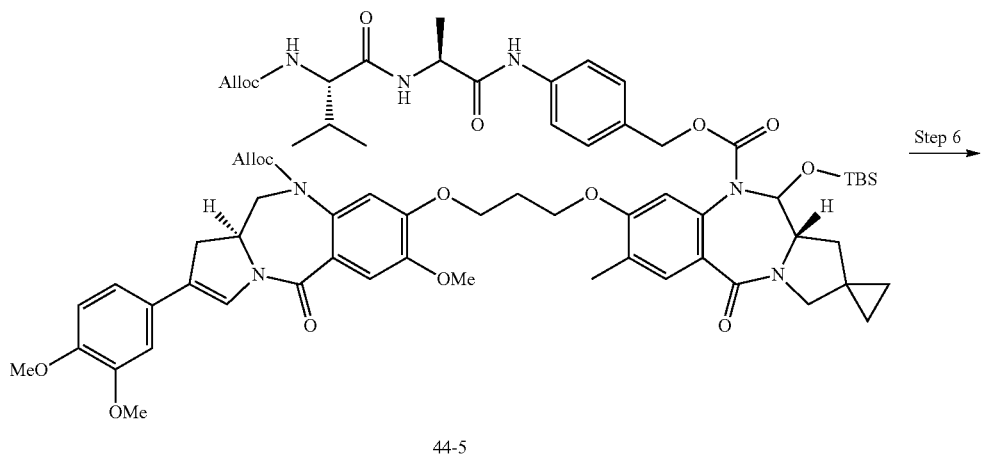
44-5

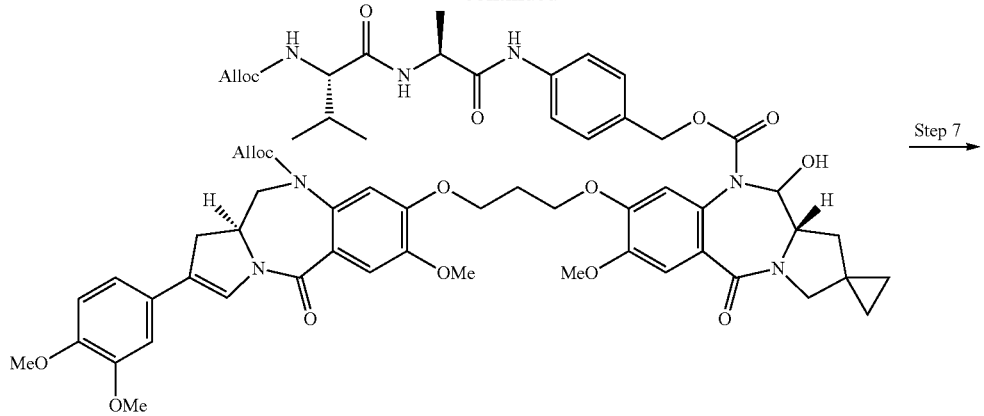

Step 7

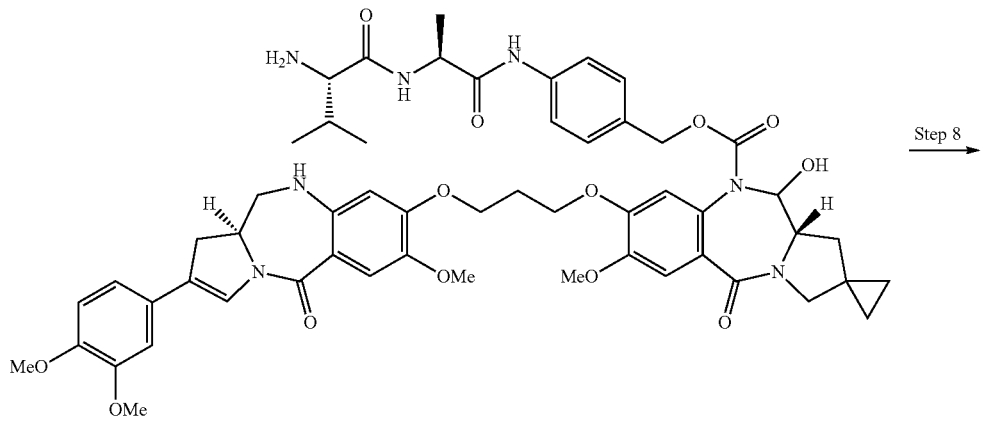

44-6

Step 8

44-7

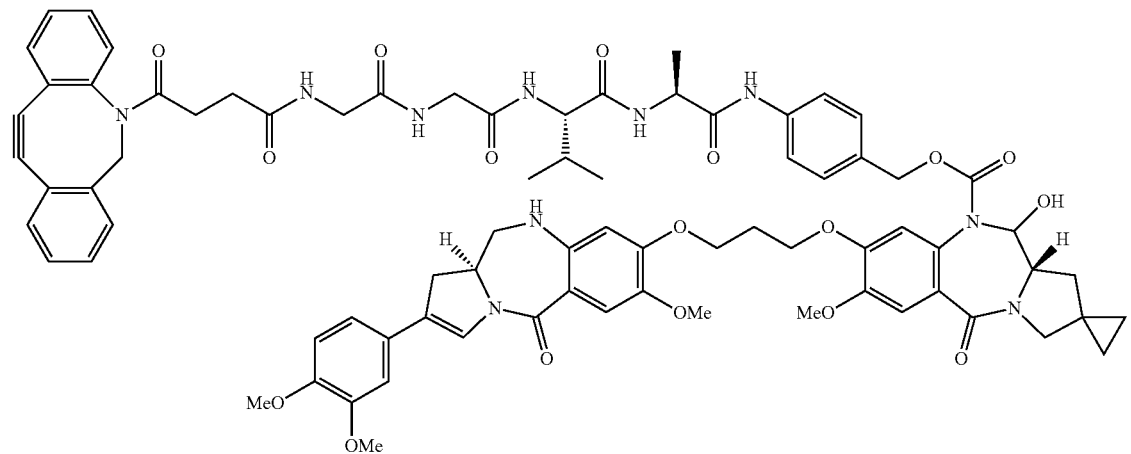

44-8

Step 1: Compound 44-1

The compound obtained in step 4 of Example 4 (0.68 g, 1.03 mmol) and 3,4-dimethoxyphenylboronic acid (0.375 g, 2.06 mmol) were reacted in the same manner as in step 6 of Example 3 to afford the desired compound (0.506 g, 750).

MS(APCI, ESI)m/z:649[$^{81}$Br,(M+H)$^+$], 647[$^{79}$Br,(M+H)$^+$]

Step 2: Compound 44-2

The compound obtained in step 1 (0.506 g, 0.781 mmol) was reacted in the same manner as in step 7 of Example 3 to afford the desired compound (0.199 g, 50%).

MS(APCI, ESI)m/z:503[$^{81}$Br,(M+H)$^+$], 501[$^{79}$Br,(M+H)$^+$]

Step 3: Compound 44-3

The compound obtained in step 2 (0.169 g, 0.337 mmol) was reacted in the same manner as in step 8 of Example 3 to afford the desired compound (0.231 g, quantitative).
MS(APCI, ESI)m/z:505[$^{81}$Br,(M+H)$^+$], 503[$^{79}$Br,(M+H)$^+$]

Step 4: Compound 44-4

The compound obtained in step 3 (0.337 mmol) was reacted in the same manner as in step 9 of Example 3 to afford the desired compound (0.170 g, 86%).
MS(APCI, ESI)m/z:589[$^{81}$Br,(M+H)$^+$], 587[$^{79}$Br,(M+H)$^+$]

Step 5: Compound 44-5

The compound obtained in step 4 (0.076 g, 0.136 mmol) was reacted in the same manner as in step 10 of Example 3 to afford the desired compound (0.116 g, 71%).
MS(APCI, ESI)m/z:1314(M+H)$^+$

Step 6: Compound 44-6

The compound obtained in step 5 (0.116 g, 0.088 mmol) was reacted in the same manner as in step 11 of Example 3 to afford the desired compound (0.108 g, quantitative).
MS(APCI, ESI)m/z:1200(M+H)$^+$

Step 7: Compound 44-7

The compound obtained in step 6 (0.090 mol) was reacted in the same manner as in step 12 of Example 3 to afford the desired compound (0.066 g, 71%).
MS(APCI, ESI)m/z:1032(M+H)$^+$

Step 8: N-[4-(11,12-Didehydrodibenzo[b,f]azocin-5(6H)-yl)-4-oxobutanoyl]glycylglycyl-L-valyl-N-{4-[({[(11a'S)-8'-(3-{[(11aS)-2-(3,4-dimethoxyphenyl)-7-methoxy-5-oxo-5,10,11,11a-tetrahydro-1H-pyrrolo[2,1-c][1,4]benzodiazepin-8-yl]oxy}propoxy)-11'-hydroxy-7'-methoxy-5'-oxo-11',11a'-dihydro-1'H-spiro[cyclopropane-1,2'-pyrrolo[2,1-c][1,4]benzodiazepine]-10'(5'H)-yl]carbonyl}oxy)methyl]phenyl}-L-alaninamide ("GGVA" Disclosed as SEQ ID NO: 76)

The compound obtained in step 7 (0.066 g, 0.064 mmol) was reacted in the same manner as in step 13 of Example 3 to afford the desired compound (0.053 g, 58%).
MS (APCI, ESI)m/z:1434 (M+H)$^+$
[Synthesis of Drug D]

Example 45: Drug 1

[Formula 169]

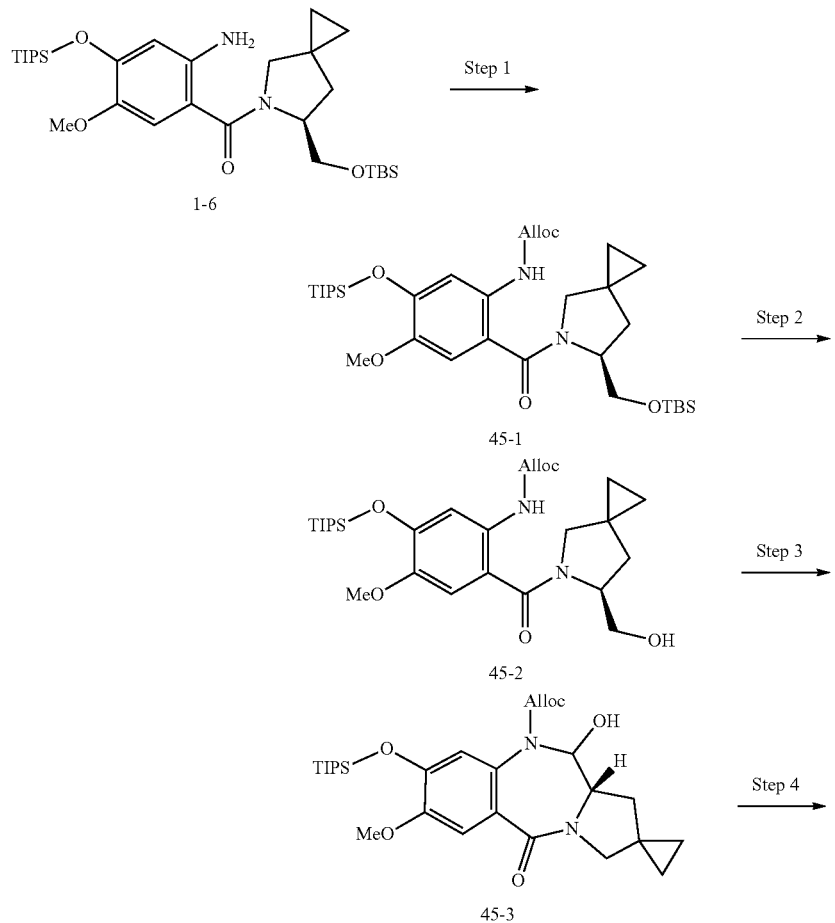

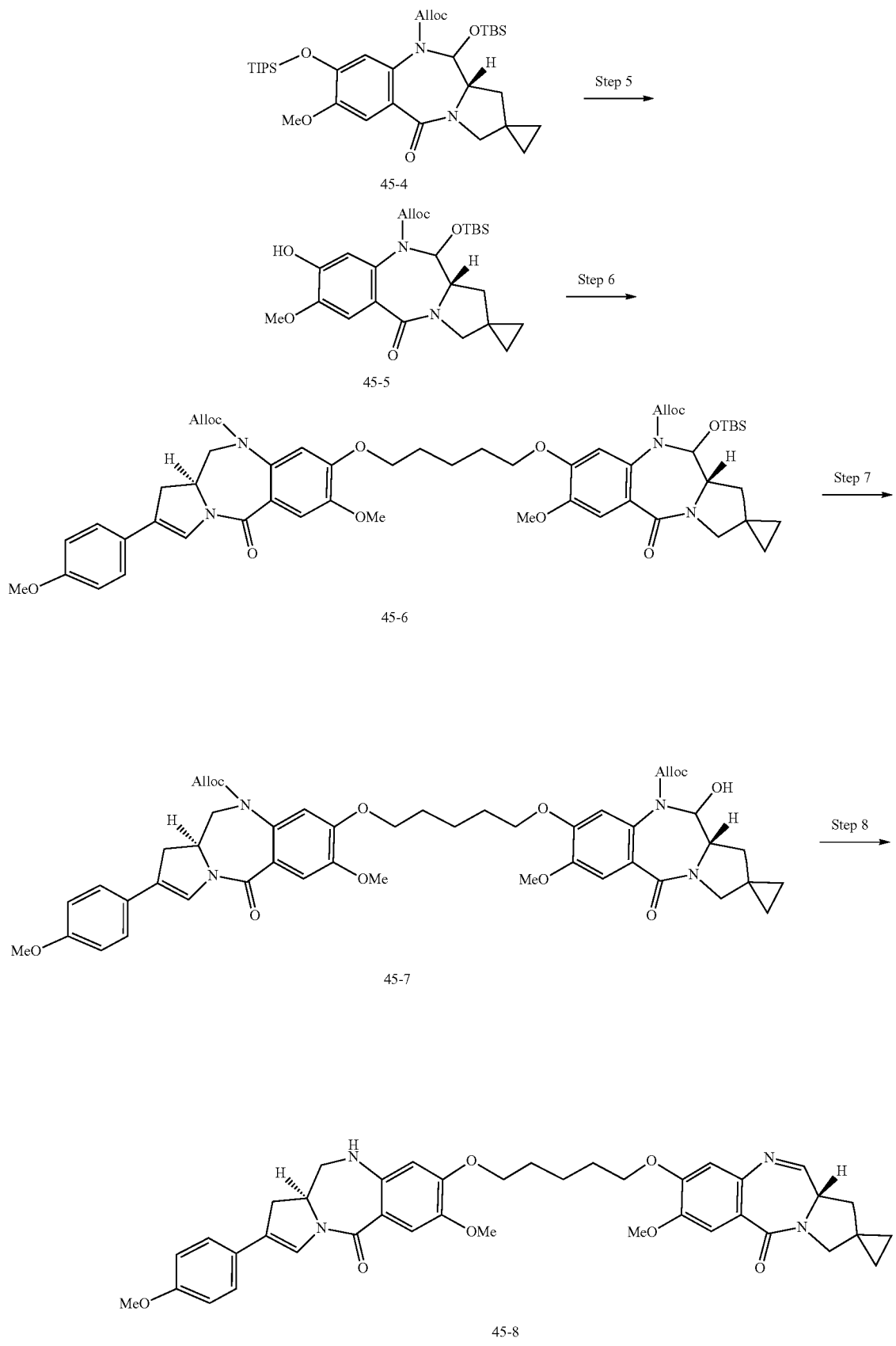

Step 1: Prop-2-en-1-yl (2-{[(6S)-6-({[tert-butyl(dimethyl)silyl]oxy}methyl)-5-azaspiro[2.4]hept-5-yl]carbonyl}-4-methoxy-5-{[tri(propan-2-yl)silyl]oxy}phenyl)carbamate The compound obtained in step 5 of Example 1 (4.59 g, 8.15 mmol) was reacted in the same manner as in step 9 of Example 3 to afford the desired compound (4.86 g, 92%).

$^1$H-NMR (CDCl$_3$) δ:8.97 (1H, s), 7.77 (1H, s), 6.77 (1H, s), 5.97-5.94 (1H, m), 5.39-5.21 (2H, m), 4.67-4.59 (3H, m), 4.00-3.98 (1H, m), 3.74-3.66 (5H, m), 3.05-3.03 (1H, m), 2.30-2.28 (1H, m), 1.72-1.70 (1H, m), 1.30-1.27 (3H, m), 1.11-1.05 (18H, m), 0.99-0.91 (9H, m), 0.61-0.53 (4H, m), 0.10-0.06 (6H, m).

MS(APCI, ESI)m/z:647(M+H)$^+$

Step 2: Prop-2-en-1-yl (2-{[(6S)-6-(hydroxymethyl)-5-azaspiro[2.4]hept-5-yl]carbonyl}-4-methoxy-5-{[tri(propan-2-yl)silyl]oxy}phenyl)carbamate The compound obtained in step 1 (4.86 g, 7.51 mmol) was reacted in the same manner as in step 7 of Example 1 to afford the desired compound (3.42 g, 86%).

$^1$H-NMR (CDCl$_3$):8.52 (1H, s), 7.71 (1H, s), 6.77 (1H, s), 6.00-5.94 (1H, m), 5.35-5.27 (2H, m), 4.65-4.64 (3H, m), 4.33-4.31 (1H, m), 3.82-3.77 (5H, m), 3.68-3.66 (1H, m), 3.15-3.13 (1H, m), 1.89-1.86 (2H, m), 1.30-1.26 (3H, m), 1.14-1.10 (18H, m), 0.66-0.51 (4H, m).

MS(APCI, ESI)m/z:533(M+H)$^+$

Step 3: Prop-2-en-1-yl (11a'S)-11'-hydroxy-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-carboxylate The compound obtained in step 2 (6.68 g, 12.5 mmol) was reacted in the same manner as in step 8 of Example 1 to afford the desired compound (6.44 g, 97%).

$^1$H-NMR (CDCl$_3$):7.20 (1H, s), 6.69 (1H, s), 5.89-5.78 (2H, m), 5.18-5.15 (2H, m), 4.62-4.60 (1H, m), 4.49-4.47 (1H, m), 3.85 (3H, s), 3.74-3.71 (1H, m), 3.59-3.57 (1H, m), 3.33-3.30 (2H, m), 2.43-2.40 (1H, m), 1.76-1.73 (1H, m), 1.28-1.20 (3H, m), 1.09-1.07 (18H, m), 0.74-0.65 (4H, m).

MS(APCI, ESI)m/z:531(M+H)$^+$

Step 4: Prop-2-en-1-yl (11a'S)-11'-{[tert-butyl(dimethyl)silyl]oxy}-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10'(5'H)-carboxylate The compound obtained in step 3 (3.24 g, 6.10 mmol) was reacted in the same manner as in step 9 of Example 1 to afford the desired compound (3.86 g, 98%).

$^1$H-NMR (CDCl$_3$):7.20 (1H, s), 6.67 (1H, s), 6.01-5.98 (1H, m), 5.79-5.73 (1H, m), 5.14-5.10 (2H, m), 4.64-4.61 (1H, m), 4.37-4.34 (1H, m), 3.86 (3H, s), 3.72-3.69 (1H, m), 3.52-3.50 (1H, m), 3.29-3.26 (1H, m), 2.38-2.34 (1H, m), 1.55-1.51 (1H, m), 1.28-1.24 (3H, m), 1.15-1.07 (18H, m), 0.81-0.66 (13H, m), 0.21 (3H, s), 0.18 (3H, s).

MS(APCI, ESI)m/z:645(M+H)$^+$

Step 5: Prop-2-en-1-yl (11a'S)-11'-{[tert-butyl(dimethyl)silyl]oxy}-8'-hydroxy-7'-methoxy-5'-oxo-11',11a'-dihydro-1'H-spiro[cyclopropane-1,2'-pyrrolo[2,1-c][1,4]benzodiazepine]-10'(5'H)-carboxylate The compound obtained in step 4 (4.49 g, 6.96 mmol) was reacted in the same manner as in step 10 of Example 1 to afford the desired compound (3.24 g, 95%).

$^1$H-NMR (CDCl$_3$):7.25 (1H, s), 6.73 (1H, s), 6.02-6.00 (1H, m), 5.91 (1H, s), 5.77-5.75 (1H, m), 5.11-5.09 (2H, m), 4.64-4.62 (1H, m), 4.41-4.40 (1H, m), 3.95 (3H, s), 3.72-3.70 (1H, m), 3.54-3.53 (1H, m), 3.29-3.26 (1H, m), 2.36-2.34 (1H, m), 1.56-1.54 (1H, m), 0.79-0.67 (13H, m), 0.21 (3H, s), 0.20 (3H, s).

MS(APCI, ESI)m/z:489(M+H)$^+$

Step 6: Prop-2-en-1-yl (11a'S)-11'-{[tert-butyl(dimethyl)silyl]oxy}-7'-methoxy-8'-{[5-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)pentyl]oxy}-5'-oxo-11',11a'-dihydro-1'H-spiro[cyclopropane-1,2'-pyrrolo[2,1-c][1,4]benzodiazepine]-10'(5'H)-carboxylate The compound obtained in step 5 (0.080 g, 0.164 mmol) was reacted in the same manner as in step 10 of Example 3 to afford the desired compound (0.160 g, 98%).

$^1$H-NMR (DMSO-D$_6$) δ:7.44-7.42 (3H, m), 7.12-7.10 (2H, m), 7.05-7.03 (1H, m), 6.92-6.90 (2H, m), 6.61-6.59 (1H, m), 5.87-5.81 (3H, m), 5.10-5.07 (4H, m), 4.66-4.55 (3H, m), 4.43-4.39 (2H, m), 4.21-3.94 (5H, m), 3.83 (3H, s), 3.81 (3H, s), 3.76 (3H, s), 3.65-3.62 (1H, m), 3.56-3.54 (1H, m), 3.42-3.39 (1H, m), 3.22-3.14 (2H, m), 2.77-2.73 (1H, m), 2.42-2.33 (1H, m), 1.81-1.79 (4H, m), 1.55-1.44 (3H, m), 0.82 (9H, s), 0.72-0.53 (4H, m), 0.19 (3H, s), 0.17 (3H, s).

MS(APCI, ESI)m/z:993(M+H)$^+$

Step 7: Prop-2-en-1-yl (11a'S)-11'-hydroxy-7'-methoxy-8'-{[5-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)pentyl]oxy}-5'-oxo-11',11a'-dihydro-1'H-spiro[cyclopropane-1,2'-pyrrolo[2,1-c][1,4]benzodiazepine]-10'(5'H)-carboxylate The compound obtained in step 6 (160 mg, 0.161 mmol) was reacted in the same manner as in step 11 of Example 3 to afford the desired compound (141 mg, quantitative).

$^1$H-NMR (DMSO-D$_6$) δ:7.44-7.42 (3H, m), 7.08-7.06 (3H, m), 6.92-6.90 (2H, m), 6.82-6.79 (1H, m), 6.56-6.54 (1H, m), 5.77-5.74 (3H, m), 5.09 (4H, s), 4.58-4.55 (3H, m), 4.43-4.41 (2H, m), 4.16-4.01 (5H, m), 3.81-3.81 (6H, m), 3.76 (3H, s), 3.64 (1H, s), 3.56-3.53 (1H, m), 3.42-3.38 (1H, m), 3.25-3.13 (2H, m), 2.74-2.70 (1H, m), 2.37-2.34 (1H, m), 1.82-1.79 (4H, m), 1.59-1.56 (3H, m), 0.66-0.62 (4H, m).

MS(APCI, ESI)m/z:879(M+H)$^+$

Step 8: (11a'S)-7'-Methoxy-8'-[(5-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}pentyl)oxy]-1',11a'-dihydro-5'H-spiro[cyclopropane-1,2'-pyrrolo[2,1-c][1,4]benzodiazepine]-5'-one The compound obtained in step 7 (141 mg, 0.161 mmol) was reacted in the same manner as in step 12 of Example 3 to afford the desired compound (109.8 mg, 99%).

$^1$H-NMR (DMSO-D$_6$) δ:7.92-7.91 (1H, m), 7.45 (1H, s), 7.39-7.37 (2H, m), 7.33 (1H, s), 7.29 (1H, s), 6.92-6.89 (2H, m), 6.85 (1H, s), 6.56-6.54 (1H, m), 6.31 (1H, s), 4.19-4.12 (2H, m), 4.05-3.99 (1H, m), 3.95-3.93 (2H, m), 3.82-3.79 (4H, m), 3.76 (3H, s), 3.66 (3H, s), 3.52-3.46 (3H, m), 3.30-3.21 (2H, m), 2.78-2.74 (1H, m), 2.45-2.42 (1H, m), 2.06-2.05 (1H, m), 1.89-1.82 (4H, m), 1.60-1.58 (2H, m), 0.80-0.63 (4H, m).
MS(APCI, ESI)m/z:693(M+H)$^+$
Example 46: Drug 2
[Formula 170]
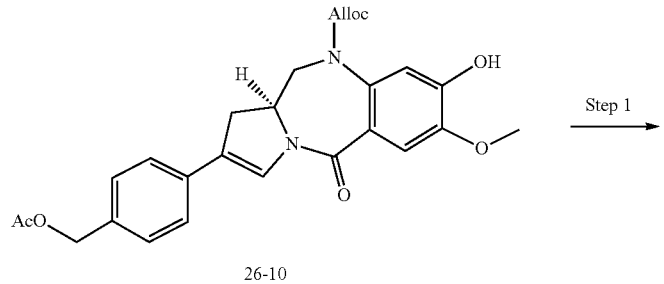
26-10
Step 1
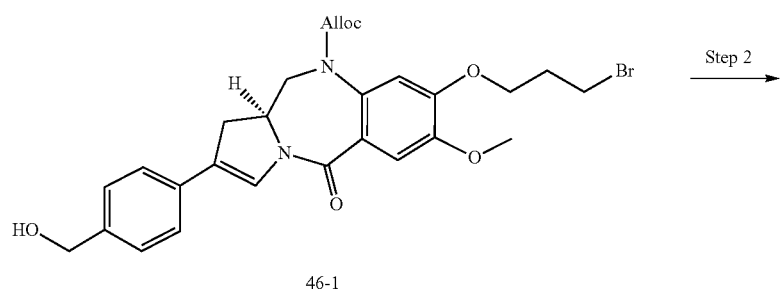
46-1
Step 2
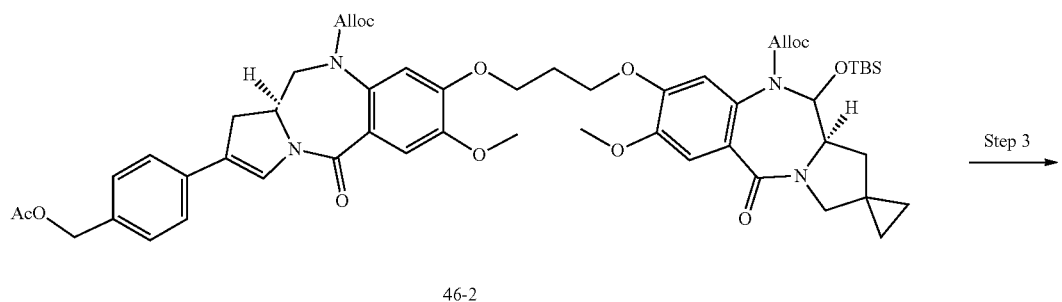
46-2
Step 3
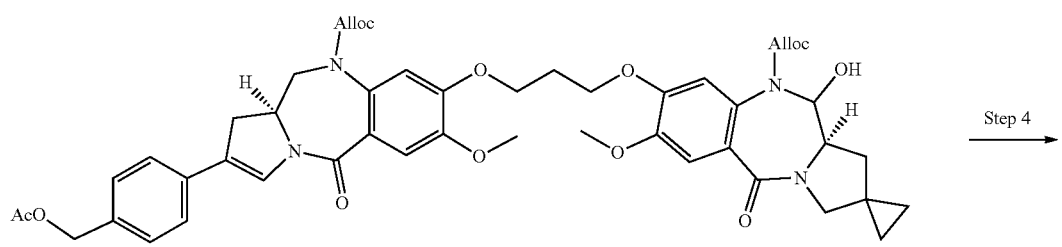
46-3
Step 4

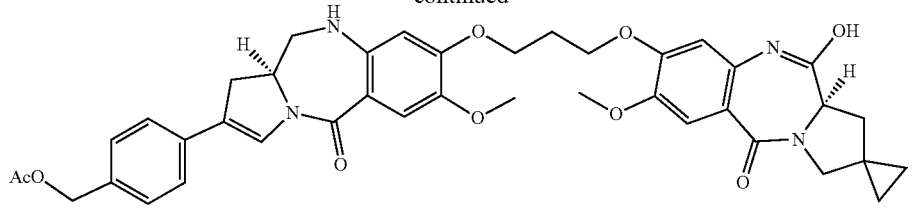

46-4

Step 1: Compound 46-1

The compound obtained in step 10 of Example 26 (0.246 g, 0.514 mmol) was used and reacted in the same manner as in step 1 of Example 4 to afford the desired compound (0.122 g, 40%).
MS(APCI, ESI)m/z:601[$^{81}$Br,(M+H)$^+$], 599[$^{79}$Br,(M+H)$^+$].

Step 2: Compound 46-2

The compound obtained in step 1 (0.122 g, 0.204 mmol) was reacted in the same manner as in step 6 of Example 45 to afford the desired compound (0.176 g, 86%).

Step 3: Compound 46-3

The compound obtained in step 2 (0.0870 g, 0.0864 mmol) was reacted in the same manner as in step 11 of Example 3 to afford the desired compound (0.0660 g, 86%).
MS(APCI, ESI)m/z:892(M+H)$^+$

Step 4: 4-[(11aS)-7-Methoxy-8-(3-{[(11a'S)-7'-methoxy-5'-oxo-5',11a'dihydro-1'H-spiro[cyclopropane-1,2'-pyrrolo[2,1-c][1,4]benzodiazepine]-8'-yl]oxy}propoxy)-5-oxo-5,10,11,11a-tetrahydro-1H-pyrrolo[2,1-c][1,4]benzodiazepin-2-yl]benzyl acetate The compound obtained in step 3 (0.0660 g, 0.0793 mmol) was reacted in the same manner as in step 12 of Example 3 to afford the desired compound (0.0444 g, 85%).
$^1$H-NMR (CDCl$_3$) δ:7.80-7.79 (1H, m), 7.66-7.65 (1H, m), 7.52-7.50 (2H, m), 7.39-7.33 (5H, m), 6.86-6.85 (1H, m), 6.14-6.13 (1H, m), 5.09 (2H, s), 4.32-4.23 (6H, m), 3.95-3.95 (3H, m), 3.85-3.82 (4H, m), 3.71-3.68 (2H, m), 3.55-3.49 (3H, m), 3.42-3.33 (1H, m), 2.79-2.72 (1H, m), 2.54-2.50 (1H, m), 2.40-2.36 (2H, m), 2.02-1.98 (1H, m), 1.26-1.24 (1H, m), 0.76-0.72 (4H, m).
MS(APCI, ESI)m/z:706(M+H)$^+$

Example 47: Drug 3

[Formula 171]

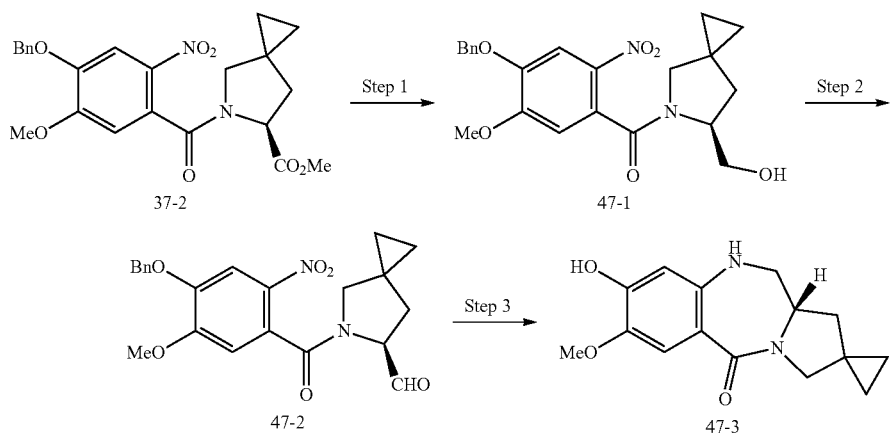

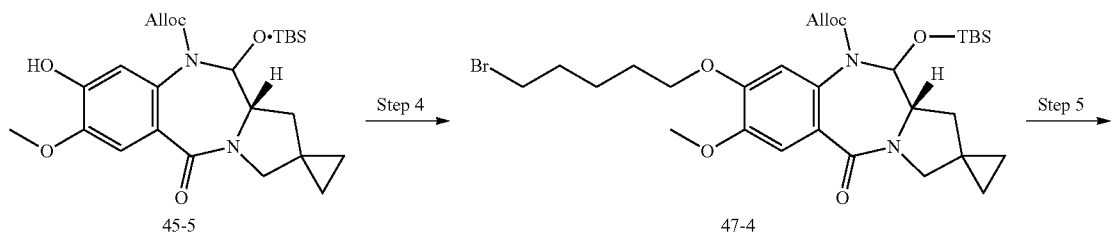

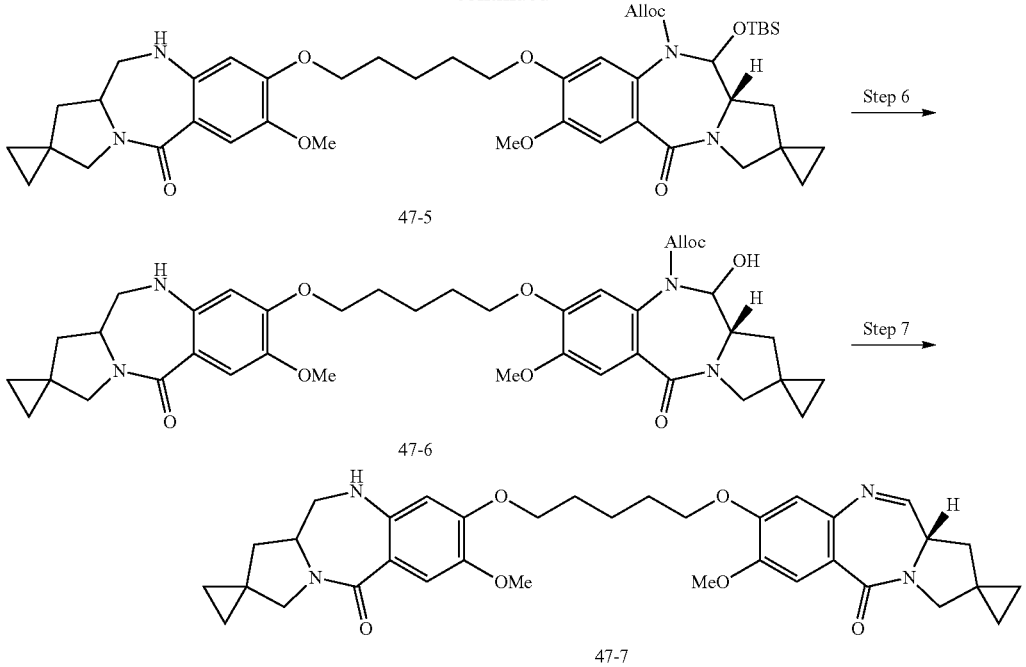

47-5

47-6

47-7

Step 1: [4-(Benzyl)-5-methoxy-2-nitrophenyl][(6S)-6-(hydroxymethyl)-5-azaspiro[2.4]hept-5-yl]methanone To a solution of the compound obtained in step 1 of Example 37 (6.49 g, 14.7 mmol) in tetrahydrofuran (147 mL), lithium borohydride (0.642 g, 29.5 mmol) was added at 0° C., and the resultant was stirred at room temperature for 2 hours. To the reaction solution, 1 N hydrochloric acid was added, which was extracted with ethyl acetate. The organic layer obtained was washed with brine and dried over magnesium sulfate, and then distillated under reduced pressure. The resulting residue (6.94 g, quantitative) was used for the subsequent step without purification.

MS (APCI, ESI)m/z:413 (M+H)$^+$

Step 2: (6S)-5-[4-(Benzyloxy)-5-methoxy-2-nitrobenzoyl]-5-azaspiro[2.4]heptane-6-carbaldehyde The compound obtained in step 1 (4.50 g, 11.0 mmol) was reacted in the same manner as in step 8 of Example 1 to afford the desired compound (1.94 g, 43%).

MS (APCI, ESI)m/z:411 (M+H)$^+$

Step 3: (11a'S)-8'-Hydroxy-7'-methoxy-1',10',11',11a'-tetrahydro-5'H-spiro[cyclopropane-1,2'-pyrrolo[2,1-c][1,4]benzodiazepine]-5'-one To a mixed solution of the compound obtained in step 2 (1.94 g, 4.73 mmol) in tetrahydrofuran (25 mL), ethyl acetate (25 mL), and methanol (25 mL), 5% palladium carbon (moisture content: 54%, 1.0 g) was added under the nitrogen atmosphere, and the reaction solution was then stirred under the hydrogen atmosphere at room temperature for 22 hours.

After the reaction solution was filtered through a Celite, the filtrate was distillated under reduced pressure. The resulting residue was purified by silica gel column chromatography [hexane:ethyl acetate=80:20 (v/v) to 0:100 (v/v)] to afford the desired compound (1.20 g, 93%).

$^1$H-NMR (CDCl$_3$):7.55 (1H, s), 6.16 (1H, s), 5.86 (1H, s), 4.08-4.02 (2H, m), 3.86 (3H, s), 3.72-3.69 (1H, m), 3.57-3.37 (3H, m), 2.04-2.01 (1H, m), 1.78-1.75 (1H, m), 0.79-0.53 (4H, m).

MS(APCI, ESI)m/z:275(M+H)$^+$

Step 4: Prop-2-en-1-yl (11a'S)-8'-[(5-bromopentyl)oxy]-11'-{[tert-butyl(dimethyl)silyl]oxy}-7'-methoxy-5'-oxo-11',11a'-dihydro-1'H-spiro[cyclopropane-1,2'-pyrrolo[2,1-c][1,4]benzodiazepine]-10'(5'H)-carboxylate The compound obtained in step 3 of Example 45 (0.300 g, 0.614 mmol) was reacted in the same manner as in step 2 of Example 3 to afford the desired compound (0.388 g, 99%).

$^1$H-NMR (CDCl$_3$):7.24 (1H, s), 6.60 (1H, s), 6.02-5.98 (1H, m), 5.80-5.75 (1H, m), 5.11-5.06 (2H, m), 4.68-4.64 (1H, m), 4.40-4.38 (1H, m), 4.02-3.98 (2H, m), 3.92 (3H, s), 3.72-3.69 (1H, m), 3.54-3.52 (1H, m), 3.46-3.41 (2H, m), 3.29-3.26 (1H, m), 2.38-2.34 (1H, m), 1.94-1.87 (4H, m), 1.65-1.62 (2H, m), 1.55-1.55 (1H, m), 0.86 (9H, s), 0.75-0.67 (4H, m), 0.24-0.22 (6H, m).

MS(APCI, ESI)m/z:639[$^{81}$Br,(M+H)$^+$], 637[$^{79}$Br,(M+H)$^+$].

Step 5: Prop-2-en-1-yl (11a'S)-11'-{[tert-butyl(dimethyl)silyl]oxy}-7'-methoxy-8'-[(5-{[(11a'S)-7'-methoxy-5'-oxo-5',10',11',11a'-tetrahydro-1'H-spiro[cyclopropane-1,2'-pyrrolo[2,1-c][1,4]benzodiazepine]-8'-yl]oxy}pentyl)oxy]-5'-oxo-11',11a'-dihydro-1'H-spiro[cyclopropane-1,2'-pyrrolo[2,1-c][1,4]benzodiazepine]-10'(5'H)-carboxylate The compound obtained in step 4 (0.203 g, 0.318 mmol) was reacted with the compound obtained in step 3 (0.131 g, 0.478 mmol) in the same manner as in step 10 of Example 3 to afford the desired compound (0.0880 g, 33%).

MS (APCI, ESI)m/z:831 (M+H)⁺

Step 6: Prop-2-en-1-yl (11a'S)-11'-hydroxy-7'-methoxy-8'-[(5-{[(11a'S)-7'-methoxy-5'-oxo-5',10',11',11a'-tetrahydro-1'H-spiro[cyclopropane-1,2'-pyrrolo[2,1-c][1,4]benzodiazepine]-8'-yl]oxy}pentyl)oxy]-5'-oxo-11',11a'-dihydro-1'H-spiro[cyclopropane-1,2'-pyrrolo[2,1-c][1,4]benzodiazepine]-10'(5'H)-carboxylate The compound obtained in step 5 (0.0880 g, 0.106 mmol) was reacted in the same manner as in step 11 of Example 3 to afford the desired compound (0.0500 g, 66%).

MS (APCI, ESI)m/z:717 (M+H)⁺

Step 7: (11a'S)-7'-Methoxy-8'-[(5-{[(11a'S)-7'-methoxy-5'-oxo-5',11a'-dihydro-1'H-spiro[cyclopropane-1,2'-pyrrolo[2,1-c][1,4]benzodiazepine]-8'-yl]oxy}pentyl)oxy]-1',10',11',11a'-tetrahydro-5'H-spiro[cyclopropane-1,2'-pyrrolo[2,1-c][1,4]benzodiazepine]-5'-one The compound obtained in step 6 (0.0500 g, 0.0698 mmol) was reacted in the same manner as in step 12 of Example 3 to afford the desired compound (0.0330 g, 77%).

¹H-NMR (CDCl₃):7.80 (1H, m), 7.58 (1H, s), 7.52 (1H, s), 6.81 (1H, s), 6.05 (1H, s), 4.17-3.97 (5H, m), 3.94 (3H, s), 3.87 (1H, m), 3.84 (3H, s), 3.72-3.68 (3H, m), 3.51-3.45 (5H, m), 2.54-2.51 (1H, m), 2.03-1.90 (6H, m), 1.75-1.68 (2H, m), 0.66 (8H, m).

MS(APCI, ESI)m/z:615(M+H)⁺

Example 48: Drug 4

[Formula 172]

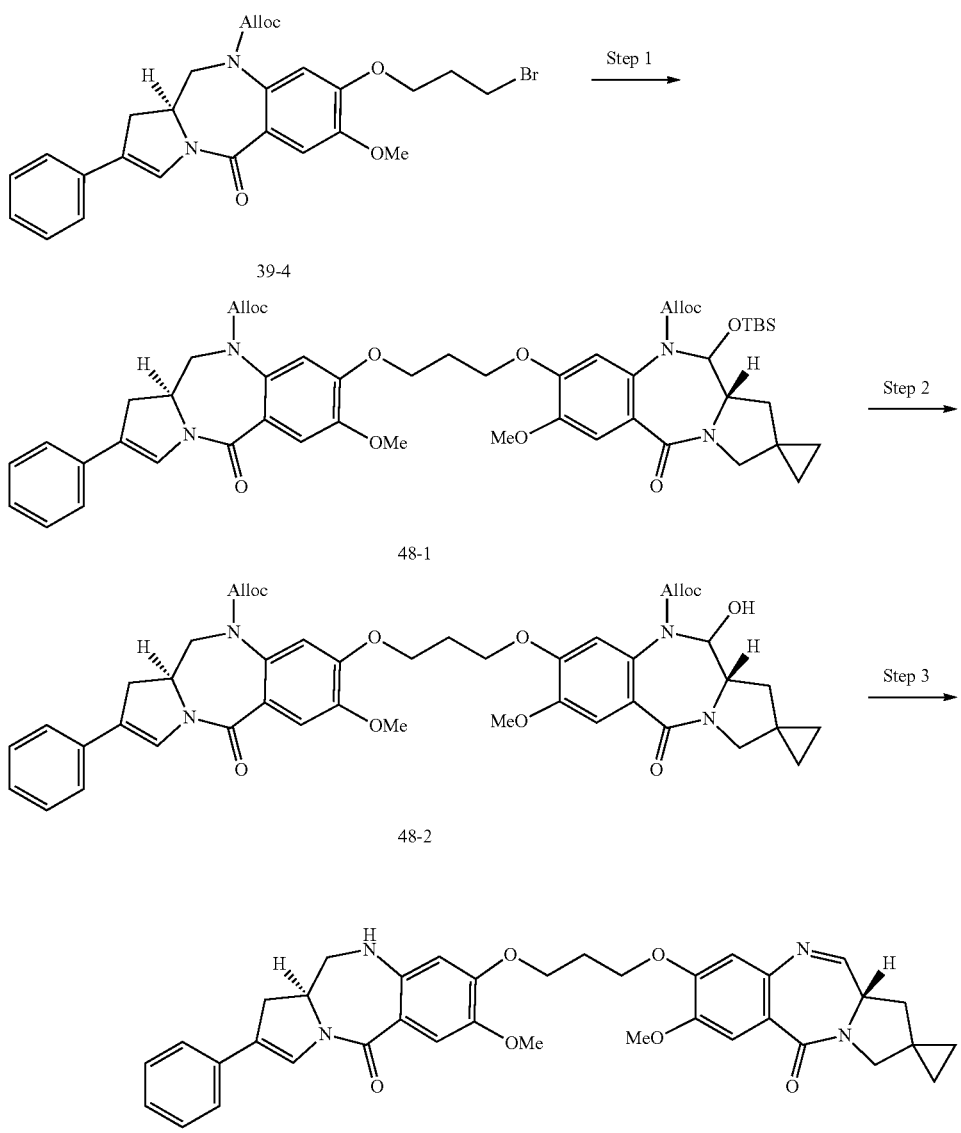

Step 1: Compound 48-1

The compound obtained in step 4 of Example 39 (0.165 g, 0.313 mmol) was reacted in the same manner as in step 6 of Example 45 to afford the desired compound (0.270 g, 92%).
MS (APCI, ESI)m/z:935 (M+H)+.

Step 2: Compound 48-2

The compound obtained in step 1 (0.270 g, 0.289 mmol) was reacted in the same manner as in step 11 of Example 3 to afford the desired compound (0.208 g, 88%).
MS (APCI, ESI)m/z:821 (M+H)+.

Step 3: (11a'S)-7'-Methoxy-8'-(3-{[(11aS)-7-methoxy-5-oxo-2-phenyl-5,10,11,11a-tetrahydro-1H-pyrrolo[2,1-c][1,4]benzodiazepin-8-yl]oxy}propoxy)-1',11a'-dihydro-5'H-spiro[cyclopropane-1,2'-pyrrolo[2,1-c][1,4]benzodiazepine]-5'-one The compound obtained in step 2 (0.208 g, 0.253 mmol) was reacted in the same manner as in step 12 of Example 3 to afford the desired compound (0.130 g, 80%).
MS (APCI, ESI)m/z:635 (M+H)+.

Example 49: Drug 5

[Formula 173]

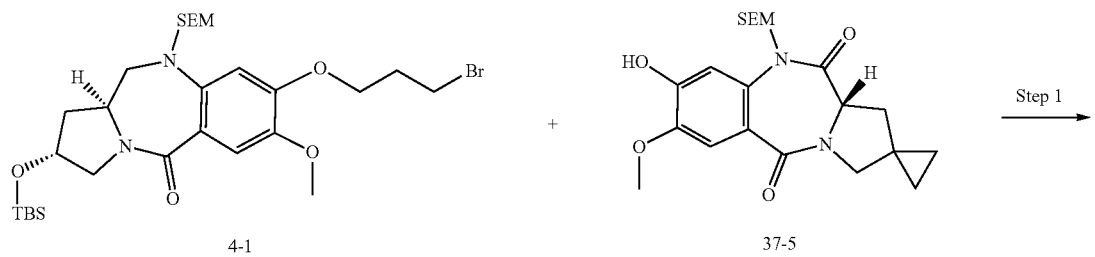

4-1 + 37-5 → Step 1

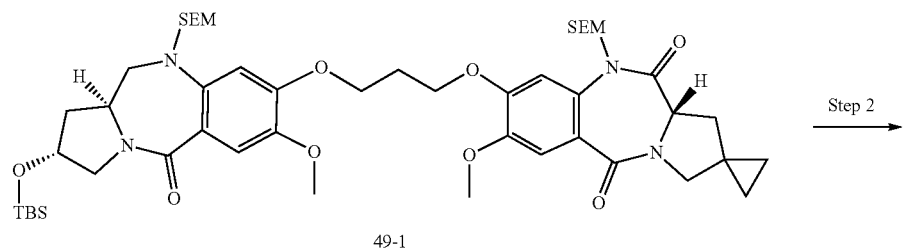

49-1 → Step 2

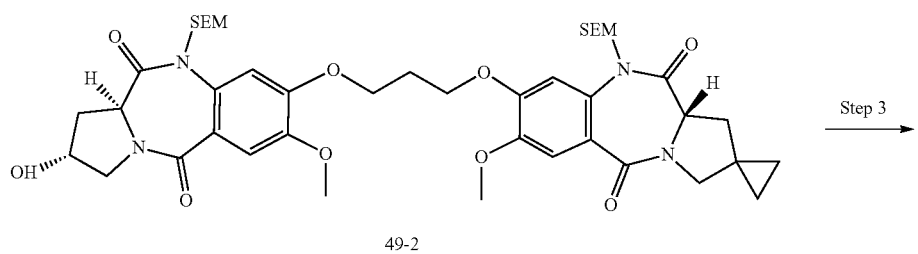

49-2 → Step 3

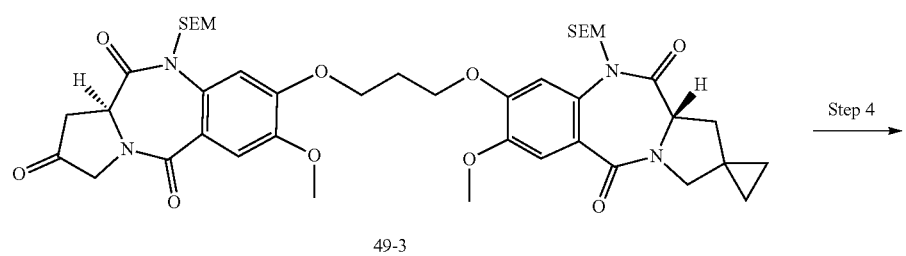

49-3 → Step 4

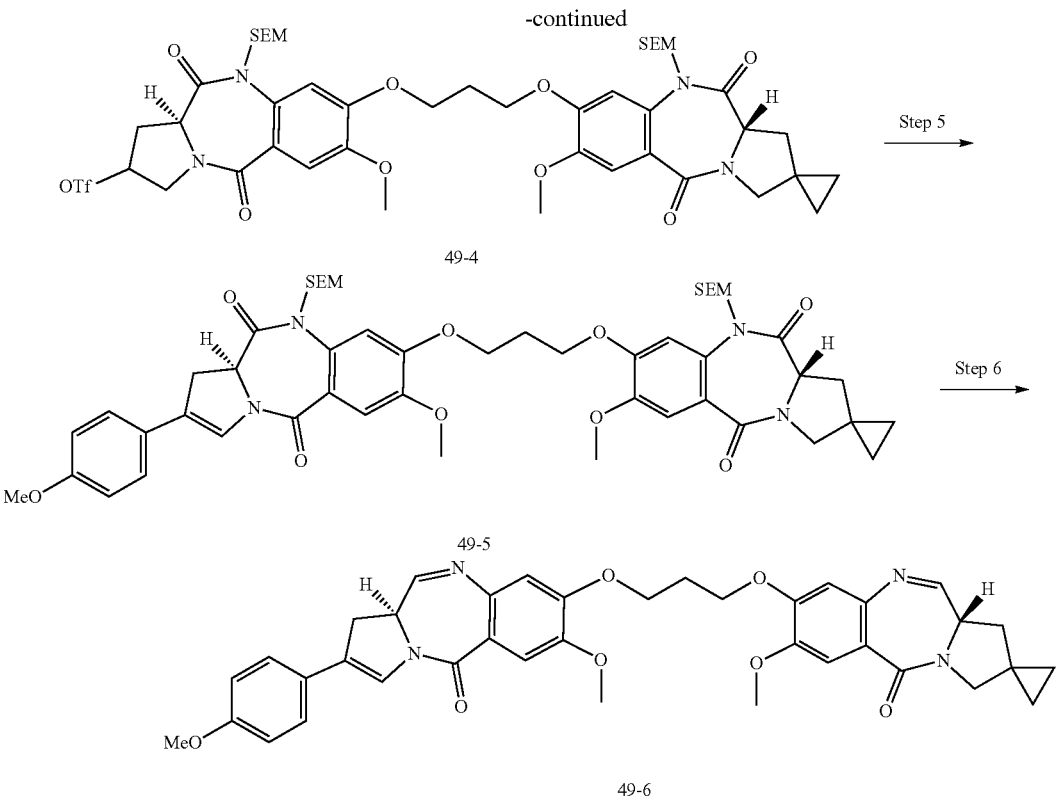

Step 1: Compound 49-1

Compound 4-1 (8.52 g, 13.2 mmol) and compound 37-5 (6.09 g, 14.5 mmol), obtained in step 4 of Example 37, were used and reacted in the same manner as in step 10 of Example 3 to afford the desired compound (10.7 g, 83%).

$^1$H-NMR (CDCl$_3$):7.36 (1H, s), 7.34 (1H, s), 7.26 (1H, s), 7.23 (1H, s), 5.53-5.46 (2H, m), 4.72-4.69 (2H, m), 4.59-4.55 (1H, m), 4.28-4.20 (6H, m), 3.90-3.89 (6H, m), 3.80-3.63 (6H, m), 3.57-3.54 (1H, m), 3.42-3.39 (1H, m), 2.87-2.82 (1H, m), 2.47-2.40 (3H, m), 2.24-2.20 (1H, m), 2.04-1.99 (1H, m), 0.99-0.95 (4H, m), 0.87 (9H, s), 0.70-0.63 (4H, m), 0.09 (6H, s), 0.02-0.00 (18H, m).

Step 2: Compound 49-2

The compound obtained in step 1 (10.7 g, 10.9 mmol) was reacted in the same manner as in step 3 of Example 3 to afford the desired compound (9.45 g, 100%).

$^1$H-NMR (CDCl$_3$) δ:7.36-7.34 (2H, m), 7.26 (1H, s), 7.23 (1H, s), 5.53-5.47 (2H, m), 4.72-4.64 (3H, m), 4.30-4.20 (6H, m), 3.89 (6H, s), 3.85-3.62 (7H, m), 3.42-3.39 (1H, m), 2.99-2.93 (1H, m), 2.47-2.39 (3H, m), 2.25-2.07 (3H, m), 0.99-0.95 (4H, m), 0.89-0.86 (1H, m), 0.70-0.64 (3H, m), 0.02-0.00 (18H, m).

Step 3: Compound 49-3

The compound obtained in step 2 (9.45 g, 10.9 mmol) was reacted in the same manner as in step 4 of Example 3 to afford the desired compound (9.14 g, 97%).

$^1$H-NMR (CDCl$_3$) δ:7.37 (1H, s), 7.33 (1H, s), 7.27-7.26 (2H, m), 5.54-5.51 (2H, m), 4.77-4.70 (2H, m), 4.64-4.61 (1H, m), 4.31-4.20 (6H, m), 3.91 (3H, s), 3.90 (3H, s), 3.80-3.65 (6H, m), 3.60-3.55 (1H, m), 3.42-3.39 (1H, m), 2.83-2.75 (1H, m), 2.47-2.41 (3H, m), 2.25-2.20 (1H, m), 1.00-0.95 (4H, m), 0.92-0.85 (1H, m), 0.71-0.63 (3H, m), 0.02-0.01 (18H, m).

Step 4: Compound 49-4

The compound obtained in step 3 (4.27 g, 4.94 mmol) was reacted in the same manner as in step 5 of Example 3 to afford the desired compound (3.16 g, 64%).

$^1$H-NMR (CDCl$_3$):7.37 (1H, s), 7.32 (1H, s), 7.27-7.25 (2H, m), 7.15-7.14 (1H, m), 5.53-5.50 (2H, m), 4.77-4.70 (2H, m), 4.64-4.60 (1H, m), 4.30-4.20 (6H, m), 3.90 (6H, s), 3.81-3.66 (4H, m), 3.42-3.39 (1H, m), 3.18-3.13 (1H, m), 2.47-2.41 (3H, m), 2.25-2.20 (1H, m), 0.99-0.94 (4H, m), 0.89-0.86 (1H, m), 0.69-0.64 (3H, m), 0.02-0.00 (18H, m).

Step 5: Compound 49-5

The compound obtained in step 4 (1.00 g, 1.00 mmol) was reacted in the same manner as in step 6 of Example 3 to afford the desired compound (0.900 g, 94%).

$^1$H-NMR (CDCl$_3$) δ:7.69-7.65 (1H, m), 7.57-7.53 (1H, m), 7.49-7.45 (1H, m), 7.39-7.36 (4H, m), 7.33 (1H, s), 7.27 (1H, s), 6.90-6.88 (2H, m), 5.53-5.50 (2H, m), 4.77-4.71 (2H, m), 4.62-4.59 (1H, m), 4.30-4.20 (5H, m), 3.91 (3H, s), 3.91 (3H, s), 3.82 (3H, s), 3.80-3.65 (4H, m), 3.42-3.39 (1H, m), 3.16-3.10 (1H, m), 2.47-2.41 (3H, m), 2.25-2.20 (1H, m), 1.00-0.96 (4H, m), 0.89-0.85 (1H, m), 0.70-0.63 (3H, m), 0.02-0.01 (18H, m).

Step 6: (11a'S)-7'-Methoxy-8'-(3-{[(11aS)-7-methoxy-2-(4-methoxyphenyl)-5-oxo-5,11a-dihydro-1H-pyrrolo[2,1-c][1,4]benzodiazepin-8-yl]oxy}propoxy)-1',11a'-dihydro-5'H-spiro[cyclopropane-1,2'-pyrrolo[2,1-c][1,4]benzodiazepine]-5'-one sodium sulfate. After filtration followed by distillation under reduced pressure, the resulting residue was purified by silica gel column chromatography [chloroform:methanol=100:0 (v/v) to 92:8 (v/v)] to afford the desired compound (0.308 g, 49%).

MS (APCI, ESI)m/z:663 (M+H)+

Example 50: Drug 6

[Formula 174]

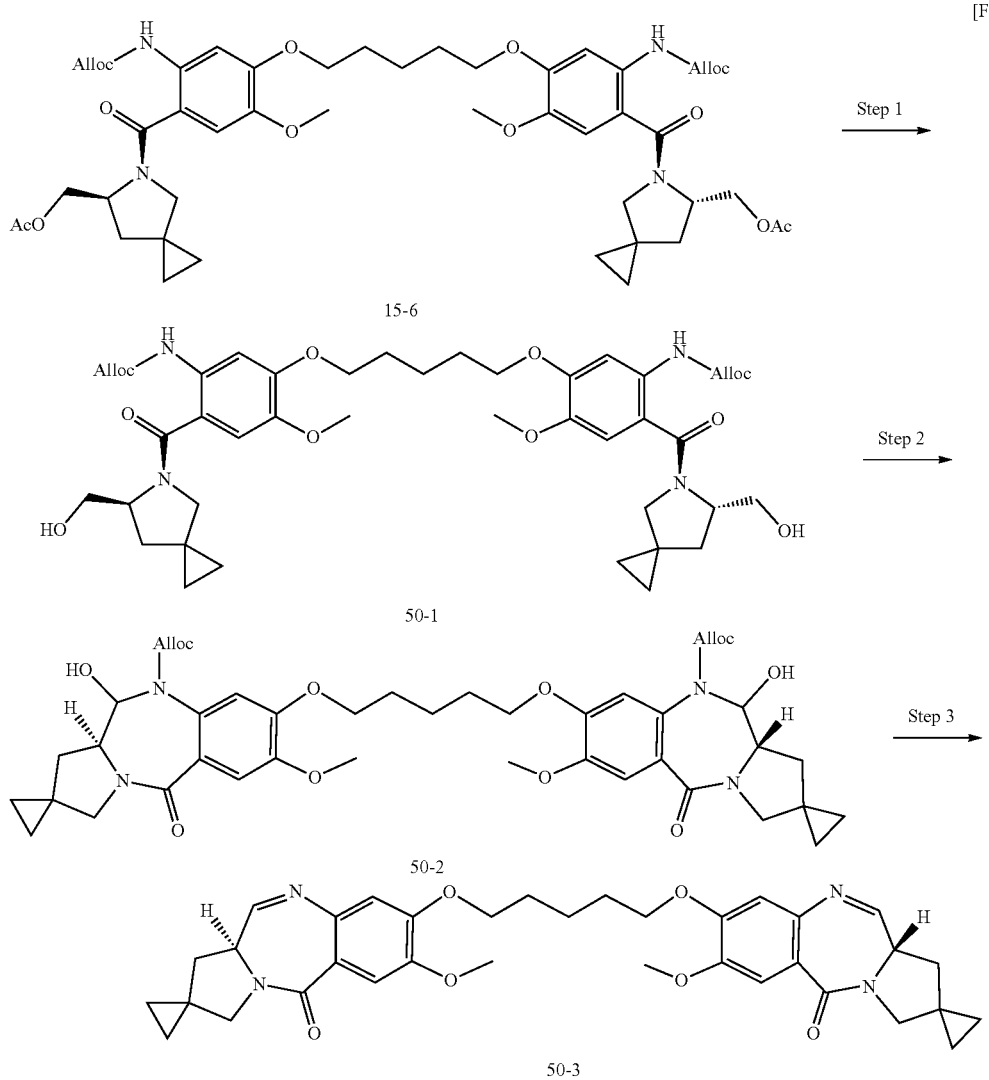

To a solution of the compound obtained in step 5 (0.900 g, 0.942 mmol) in THF (30 mL) and ethanol (3 mL), lithium borohydride (0.456 g, 18.8 mmol) was slowly added at 0° C. After the reaction mixture was stirred at room temperature for 1.5 hours, water was added to the reaction mixture, which was vigorously stirred. The reaction mixture was extracted with chloroform. The organic layer was distillated under reduced pressure, and the resulting residue was dissolved in dichloromethane (10 mL), ethanol (20 mL), and water (5 mL). Silica gel (15.0 g) was added to the reaction mixture, which was stirred under the nitrogen atmosphere for 3 days. The reaction mixture was filtered, and the organic layer was washed with brine and dried over anhydrous Step 1: Di-2-propen-1-yl {1,5-pentanediylbis[oxy(6-{[(6S)-6-(hydroxymethyl)-5-azaspiro[2.4]hept-5-yl]carbonyl}-4-methoxybenzen-3,1-diyl)]}biscarbamate Bisallyloxycarbonyl form 15-6 (0.460 g, 0.508 mmol), obtained in step 5 of Example 15, was dissolved in methanol (10 mL), and potassium carbonate (351 mg, 2.54 mmol) was then added thereto, and the resultant was stirred at room temperature for 30 minutes. Thereto, 50 mL of a saturated aqueous ammonium chloride was added, and the resultant was extracted with ethyl acetate. The organic layer was dried over anhydrous sodium sulfate. The resultant was distillated under reduced pressure to afford the desired compound (0.421 g, quantitative).

$^1$H-NMR (DMSO-D$_6$) δ:9.19 (2H, s), 7.22 (2H, s), 6.89 (2H, s), 5.97-5.92 (2H, m), 5.33 (2H, m), 5.22 (2H, m), 4.81 (2H, m), 4.55 (4H, m), 4.26 (2H, s), 3.96 (4H, m), 3.74 (6H, s), 3.62 (2H, m), 3.56 (2H, s), 3.37 (2H, m), 3.11 (2H, m), 1.88-1.78 (8H, m), 1.56-1.54 (2H, m), 0.54-0.43 (8H, m).

MS(APCI, ESI)m/z:821(M+H)$^+$.

Step 2: Diprop-2-en-1-yl (11a'S,11a''''S)-8',8''-[pentan-1,5-diylbis(oxy)]bis(11'-hydroxy-7'-methoxy-5'-oxo-11',11a'-dihydro-1'H-spiro[cyclopropane-1,2'-pyrrolo[2,1-c][1,4]benzodiazepine]-10'(5'H)-carboxylate)

The compound obtained in step 1 (0.421 g, 0.513 mmol) was reacted in the same manner as in step 8 of Example 15 to afford the desired compound (0.326 g, 78%).

$^1$H-NMR (DMSO-D$_6$) δ:7.07 (2H, s), 6.80 (2H, s), 6.55 (2H, m), 5.84-5.81 (2H, m), 5.75 (2H, m), 5.09-5.05 (4H, m), 4.62 (2H,mz), 4.40 (2H, m), 3.98 (4H, m), 3.81 (6H, s), 3.54 (2H, m), 3.43-3.37 (2H, m), 3.14 (2H, m), 2.35 (2H, m), 1.81-1.79 (4H, m), 1.59-1.56 (4H, m), 0.70-0.59 (8H, m).

MS(APCI, ESI)m/z:817(M+H)$^+$.

Step 3: (11a'S,11a''''S)-8',8''-[1,5-Pentanediylbis(oxy)]bis(7'-methoxy-1',11a'-dihydro-5'H-spiro[cyclopropane-1,2'-pyrrolo[2,1-c][1,4]benzodiazepine]-5'-one)

The compound obtained in step 2 (0.326 g, 0.399 mmol) was reacted in the same manner as in step 12 of Example 3 to afford the desired compound (0.208 g, 85%).

$^1$H-NMR (DMSO-D$_6$) δ:7.91 (2H, m), 7.32 (2H, s), 6.84 (2H, s), 4.11 (2H, m), 4.06 (2H, m), 3.82 (6H, s), 3.51-3.31 (6H, m), 2.43 (2H, m), 2.05 (2H, m), 1.82-1.80 (4H, m), 1.60-1.58 (2H, m), 0.79-0.77 (2H, m), 0.68-0.64 (6H, m).

MS(APCI, ESI)m/z:613(M+H)$^+$.

Example 51: Drug 7

[Formula 175]

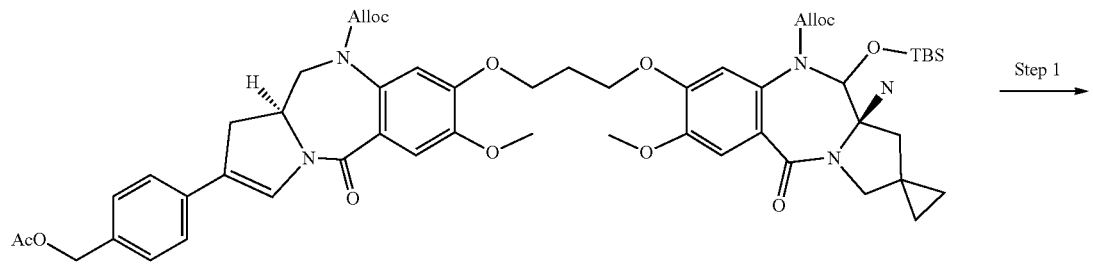

46-2

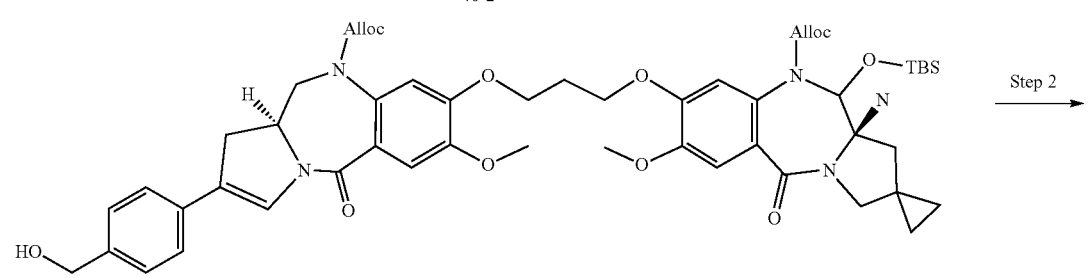

51-1

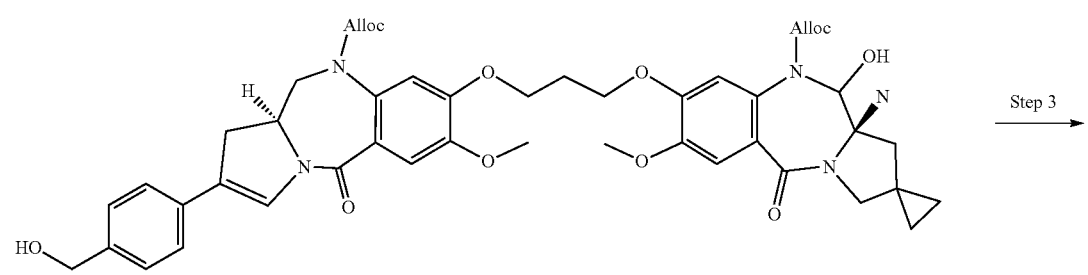

51-2

-continued

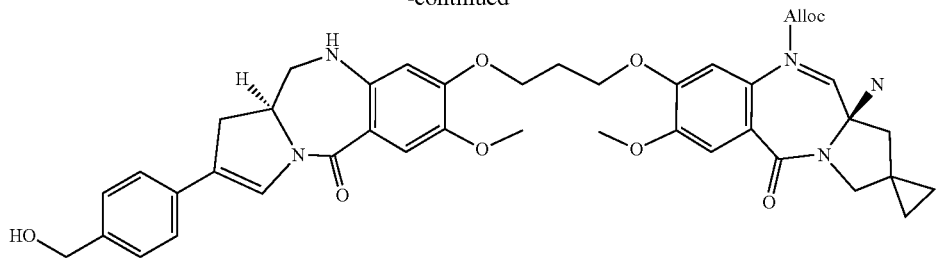

51-3

Step 1: Compound 51-1

Compound 46-2 (0.0870 g, 0.0863 mmol) was reacted in the same manner as in step 1 of Example 27 to afford the desired compound (0.0660 mg, 79%).

$^1$H-NMR (CDCl$_3$) δ:7.50 (1H, s), 7.36-7.34 (4H, m), 7.27-7.24 (2H, m), 6.80 (1H, s), 6.64 (1H, s), 6.03 (1H, m), 5.80-5.74 (2H, m), 5.10-5.06 (3H, m), 4.70 (2H, m), 4.67-4.60 (2H, m), 4.41-4.37 (3H, m), 4.23-4.20 (6H, m), 3.90 (3H, s), 3.89 (3H, s), 3.72 (1H, m), 3.65-3.62 (1H, m), 3.51 (1H, m), 3.34-3.26 (2H, m), 2.75-2.71 (1H, m), 2.39-2.35 (3H, m), 1.74 (1H, m), 1.56-1.52 (1H, m), 0.85 (9H, s), 0.80-0.62 (4H, m), 0.22 (3H, s), 0.21 (3H, s).

MS (APCI, ESI)m/z:965 (M+H)$^+$.

Step 2: Compound 51-2

The compound obtained in step 1 (0.0660 g, 0.0683 mmol) was reacted in the same manner as in step 11 of Example 3 to afford the desired compound (0.0590 g, quantitative).

MS(APCI, ESI)m/z:851(M+H)$^+$.

Step 3: (11a'S)-8'-[3-({(11aS)-2-[4-(Hydroxymethyl)phenyl]-7-methoxy-5-oxo-5,10,11,11a-tetrahydro-1H-pyrrolo[2,1-c][1,4]benzodiazepin-8-yl}oxy)propoxy]-7'-methoxy-1',11a'-dihydro-5'H-spiro[cyclopropane-1,2'-pyrrolo[2,1-c][1,4]benzodiazepine]-5'-one The compound obtained in step 2 (0.0590 g, 0.0693 mmol) was reacted in the same manner as in step 12 of Example 3 to afford the desired compound (0.0290 g, 63%).

$^1$H-NMR (CDCl$_3$) δ:7.80-7.79 (1H, m), 7.64-7.64 (1H, m), 7.52-7.51 (2H, m), 7.36-7.33 (4H, m), 6.85 (1H, m), 6.14 (1H, m), 4.69 (2H, m), 4.30-4.26 (6H, m), 3.95-3.95 (3H, m), 3.86-3.84 (3H, m), 3.67 (1H, m), 3.56-3.54 (2H, m), 3.50-3.48 (2H, m), 3.39-3.30 (1H, m), 2.80-2.73 (1H, m), 2.52 (1H, m), 2.41-2.39 (2H, m), 2.00 (1H, m), 1.73-1.72 (1H, m), 0.76-0.70 (4H, m).

MS(APCI, ESI)m/z:665(M+H)$^+$.

Example 52: Drug 8

[Formula 176]

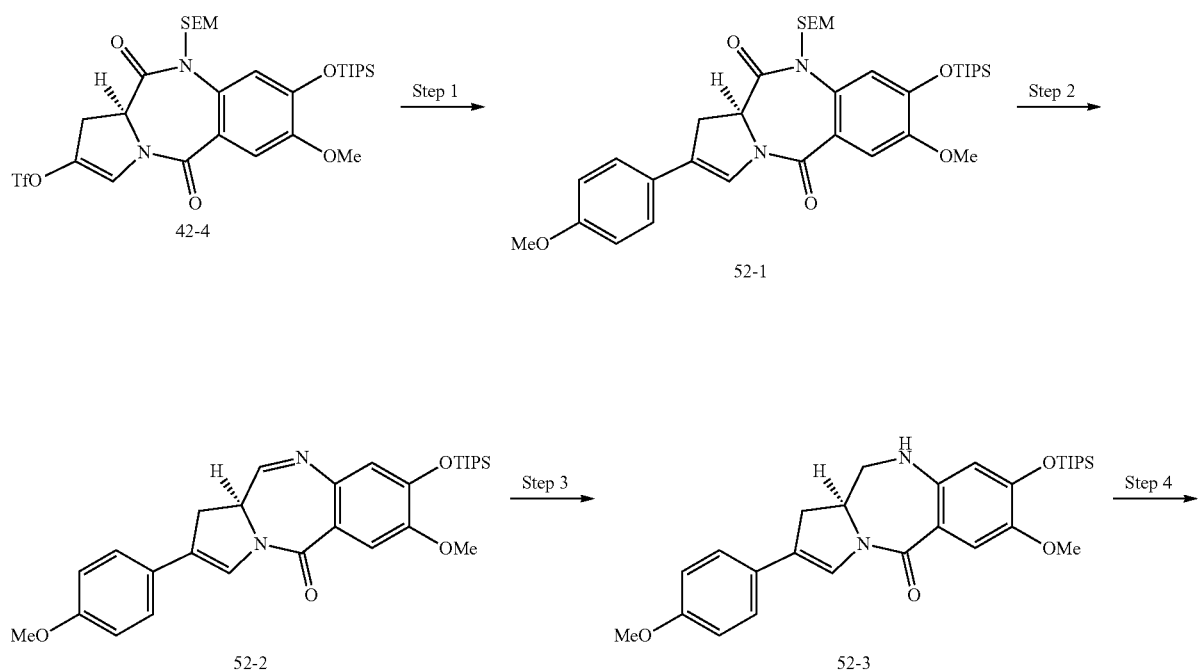

497 498
-continued
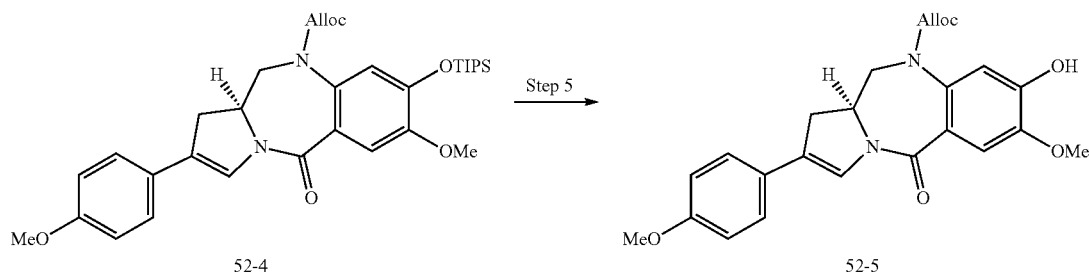
52-4 → 52-5
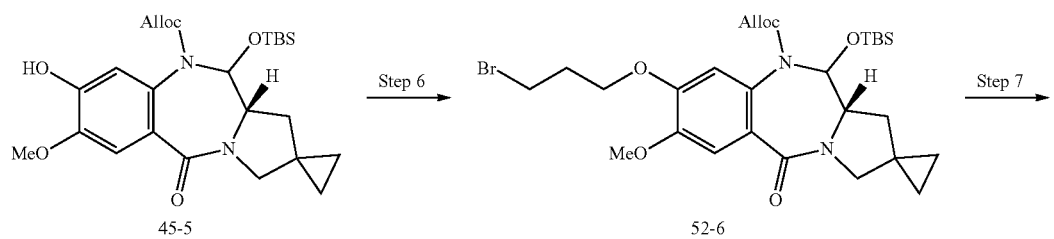
45-5 → 52-6 → 
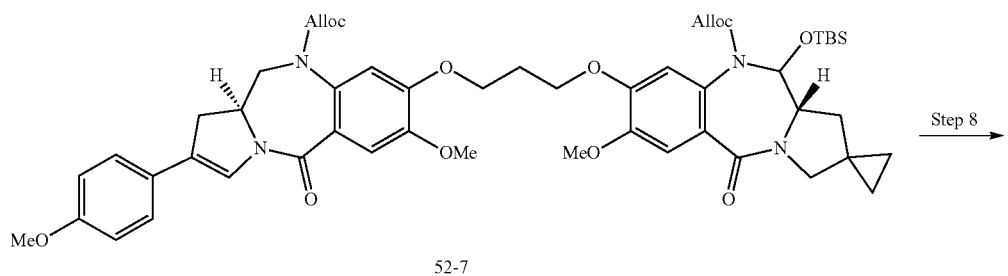
52-7
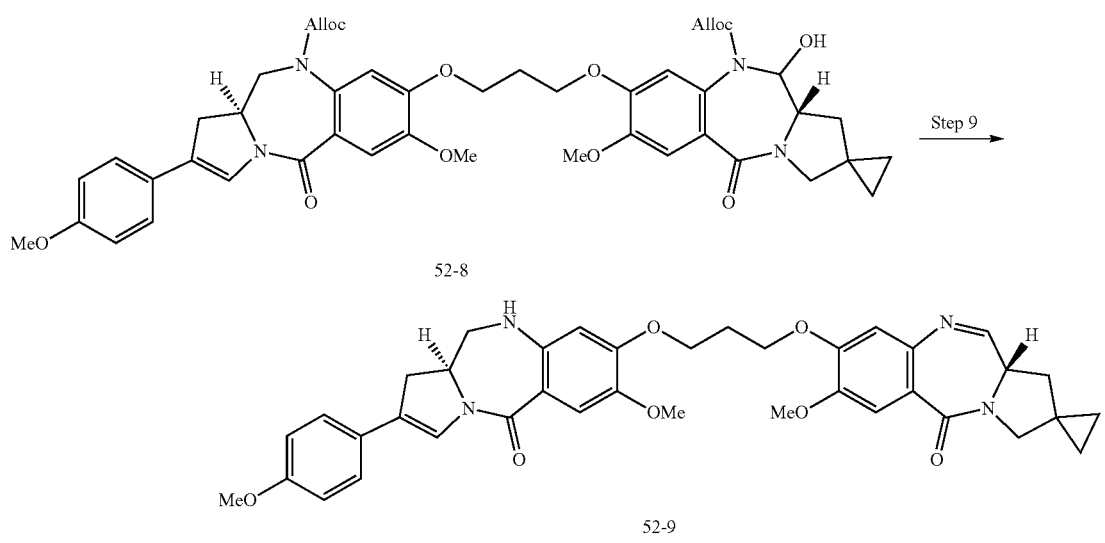
52-8
52-9

Step 1: (11aS)-7-Methoxy-2-(4-methoxyphenyl)-10-{[2-(trimethylsilyl)ethoxy]methyl}-8-{[tri(propan-2-yl)silyl]oxy}-1H-pyrrolo[2,1-c][1,4]benzodiazepin-5,11(10H,11aH)-dione The compound obtained in step 4 of Example 42 (0.519 g, 0.747 mmol) was reacted in the same manner as in step 6 of Example 3 to afford the desired compound (0.511 g, quantitative).
¹H-NMR (CDCl₃) δ:7.41-7.31 (5H, m), 6.91-6.85 (2H, m), 5.52 (1H, m), 4.64 (1H, m), 4.57 (1H, m), 3.97-3.90 (1H, m), 3.88 (3H, s), 3.83 (3H, s), 3.75-3.56 (2H, m), 3.19-3.09 (1H, m), 1.36-1.23 (3H, m), 1.11 (18H, m), 1.02-0.97 (2H, m), 0.03 (9H, s).
MS (APCI, ESI) m/z:653[(M+H)⁺]

Step 2: (11aS)-7-Methoxy-2-(4-methoxyphenyl)-8-{[tri(propan-2-yl)silyl]oxy}-1,11a-dihydro-5H-pyrrolo[2,1-c][1,4]benzodiazepin-5-one The compound obtained in step 1 (0.178 g, 0.272 mmol) was reacted in the same manner as in step 7 of Example 3 to afford the desired compound (0.094 g, 68%).
¹H-NMR (CDCl₃):7.87 (1H, m), 7.51 (1H, s), 7.41-7.39 (1H, m), 7.36-7.33 (2H, m), 6.93-6.89 (2H, m), 6.86 (1H, s), 4.44-4.38 (1H, m), 3.90 (3H, s), 3.83 (3H, s), 3.61-3.53 (1H, m), 3.41-3.34 (1H, m), 1.33-1.25 (3H, m), 1.11-1.06 (18H, m).
MS (APCI, ESI)m/z:507(M+H)⁺

Step 3: (11aS)-7-Methoxy-2-(4-methoxyphenyl)-8-{[tri(propan-2-yl)silyl]oxy}-1,10,11,11a-tetrahydro-5H-pyrrolo[2,1-c][1,4]benzodiazepin-5-one The compound obtained in step 2 (0.063 g, 0.124 mmol) was used and reacted in the same manner as in step 8 of Example 3 to afford the desired compound (0.046 g, 72%).
¹H-NMR (CDCl₃) δ:7.53-7.48 (2H, m), 7.33-7.29 (2H, m), 6.90-6.86 (2H, m), 6.13-6.11 (1H, m), 4.36-4.29 (1H, m), 4.11 (1H, s), 3.82 (3H, s), 3.79 (3H, s), 3.59-3.50 (2H, m), 3.40-3.31 (1H, m), 2.78-2.68 (1H, m), 1.31-1.20 (3H, m), 1.13-1.02 (18H, m).
MS (APCI,ESI)m/z:509(M+H)⁺

Step 4: Prop-2-en-1-yl (11aS)-7-methoxy-2-(4-methoxyphenyl)-5-oxo-8-{[tri(propan-2-yl)silyl]oxy}-11,11a-dihydro-1H-pyrrolo[2,1-c][1,4]benzodiazepin-10(5H)-carboxylate The compound obtained in step 3 (0.046 g, 0.090 mmol) was used and reacted in the same manner as in step 9 of Example 3 to afford the desired compound (0.03 g, 56%).
¹H-NMR (CDCl₃) δ:7.39-7.36 (1H, m), 7.31-7.28 (2H, m), 7.22 (1H, s), 6.90-6.86 (3H, m), 6.75-6.72 (1H, m), 5.82-5.69 (1H, m), 5.18-5.08 (2H, m), 4.59-4.52 (1H, m), 4.48-4.39 (1H, m), 4.39-4.29 (1H, m), 4.23-4.12 (1H, m), 3.86 (3H, s), 3.82 (3H, s), 3.64-3.58 (1H, m), 3.32-3.25 (1H, m), 2.73-2.65 (1H, m), 1.30-1.20 (2H, m), 1.12-1.06 (18H, m).
MS (APCI, ESI)m/z:593 (M+H)⁺

Step 5: Prop-2-en-1-yl (11aS)-8-hydroxy-7-methoxy-2-(4-methoxyphenyl)-5-oxo-11,11a-dihydro-1H-pyrrolo[2,1-c][1,4]benzodiazepin-10(5H)-carboxylate The compound obtained in step 4 (0.030 g, 0.050 mmol) was reacted in the same manner as in step 10 of Example 1 to afford the desired compound (0.015 g, 0.034 mmol).

¹H-NMR (CDCl₃) δ:7.39-7.25 (4H, m), 6.92-6.78 (3H, m), 6.03-5.92 (1H, m), 5.86-5.68 (1H, m), 5.20-5.07 (2H, m), 4.66-4.57 (1H, m), 4.52-4.40 (1H, m), 4.40-4.27 (1H, m), 4.27-4.16 (1H, m), 3.95 (3H, s), 3.82 (3H, s), 3.66-3.59 (1H, m), 3.32-3.21 (1H, m), 2.74-2.64 (1H, m).
MS(APCI, ESI)m/z:437(M+H)⁺

Step 6: Prop-2-en-1-yl (11a'S)-8'-(3-bromopropoxy)-11'-{[tert-butyl(dimethyl)silyl]oxy}-7'-methoxy-5'-oxo-11',11a'-dihydro-1'H-spiro[cyclopropane-1,2'-pyrrolo[2,1-c][1,4]benzodiazepine]-10'(5'H)-carboxylate The compound obtained in step 5 of Example 45 (0.131 g, 0.268 mmol) was reacted in the same manner as in step 1 of Example 4 to afford the desired compound (0.086 g, 52%).
¹H-NMR (CDCl₃) δ:7.24 (1H, s), 6.65 (1H, s), 6.02 (1H, m), 5.87-5.71 (1H, m), 5.15-5.04 (2H, m), 4.72-4.62 (1H, m), 4.44-4.32 (1H, m), 4.23-4.07 (3H, m), 3.92 (3H, s), 3.77-3.47 (4H, m), 3.28 (1H, m), 2.37 (3H, m), 1.57-1.52 (1H, m), 0.86 (9H, m), 0.82-0.57 (4H, m), 0.21 (6H, m).
MS(APCI, ESI)m/z:611[⁸¹Br,(M+H)⁺], 609[⁷⁹Br,(M+H)⁺]

Step 7: Prop-2-en-1-yl (11a'S)-11'-{[tert-butyl(dimethyl)silyl]oxy}-7'-methoxy-8'-[3-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)propoxy]-5'-oxo-11',11a'-dihydro-1'H-spiro[cyclopropane-1,2'-pyrrolo[2,1-c][1,4]benzodiazepine]-10'(5'H)-carboxylate The compound obtained in step 5 (0.015 g, 0.034 mmol) and the compound obtained in step 6 (0.030 g, 0.048 mmol) were reacted in the same manner as in step 10 of Example 3 to afford the desired compound (0.032 g, 96%).
MS (APCI, ESI)m/z:965 (M+H)⁺

Step 8: Prop-2-en-1-yl (11a'S)-11'-hydroxy-7'-methoxy-8'-[3-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy)propoxy]-5'-oxo-11',11a'-dihydro-1'H-spiro[cyclopropane-1,2'-pyrrolo[2,1-c][1,4]benzodiazepine]-10'(5'H)-carboxylate The compound obtained in step 7 (0.031 g, 0.032 mmol) was reacted in the same manner as in step 11 of Example 3 to afford the desired compound (0.026 g, 95%).
MS (APCI, ESI)m/z:851 (M+H)⁺

Step 9: (11a'S)-7'-Methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-1',11a'-dihydro-5'H-spiro[cyclopropane-1,2'-pyrrolo[2,1-c][1,4]benzodiazepine]-5'-one The compound obtained in step 8 (0.026 g, 0.030 mmol) was reacted in the same manner as in step 12 of Example 3 to afford the desired compound (0.018 g, 88%).
¹H-NMR (CDCl₃) δ:7.80 (1H, m), 7.54-7.51 (3H, m), 7.33-7.29 (2H, m), 6.91-6.85 (3H, m), 6.14 (1H, s), 4.35-4.17 (6H, m), 3.95 (3H, s), 3.85 (3H, s), 3.82 (3H, s), 3.76-3.25 (5H, m), 2.79-2.69 (1H, m), 2.52 (1H, m), 2.45-2.35 (1H, m), 2.03-1.96 (1H, m), 1.28-1.23 (2H, m), 0.78-0.69 (4H, m).
MS(APCI, ESI)m/z:665(M+H)⁺
Example 53: Drug 9
Step 1: Compound 53-1
The compound obtained in step 4 of Example 43 (0.027 g, 0.048 mmol) was reacted in the same manner as in step 6 of Example 45 to afford the desired compound (0.037 g, 79%).
MS (APCI, ESI)m/z:965 (M+H)⁺
[Formula 177]
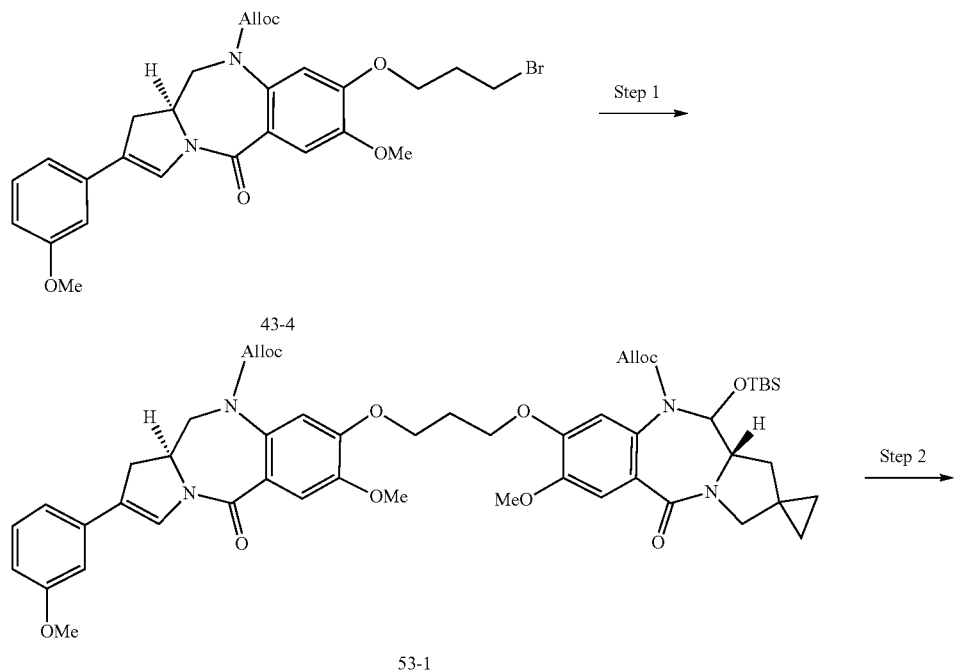
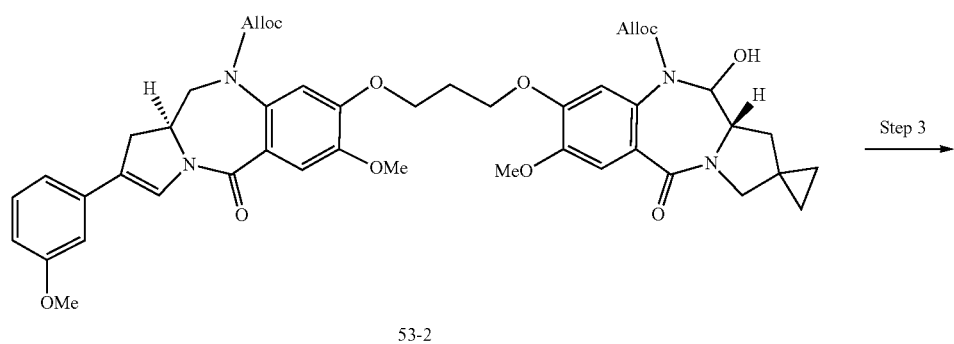

Step 2: Compound 53-2

The compound obtained in step 1 (0.037 g, 0.038 mmol) was reacted in the same manner as in step 11 of Example 3 to afford the desired compound (35 mg, quantitative).
MS (APCI, ESI)m/z:851[(M+H)⁺]

Step 3: (11a'S)-7'-Methoxy-8'-(3-{[(11aS)-7-methoxy-2-(3-methoxyphenyl)-5-oxo-5,10,11,11a-tetrahydro-1H-pyrrolo[2,1-c][1,4]benzodiazepin-8-yl]oxy}propoxy)-1',11a'-dihydro-5'H-spiro[cyclopropane-1,2'-pyrrolo[2,1-c][1,4]benzodiazepine]-5'-one The compound obtained in step 2 (0.038 mmol) was reacted in the same manner as in steps 6 to 8 of Example 45 to afford the desired compound (25 mg, 99%).

$^1$H-NMR (CDCl$_3$) δ:7.81-7.78 (1H, m), 7.65-7.62 (1H, m), 7.53-7.49 (2H, m), 7.24 (1H, m), 6.96 (1H, m), 6.91-6.88 (1H, m), 6.85 (1H, m), 6.78 (1H, m), 6.14 (1H, m), 4.41-4.18 (5H, m), 3.97-3.92 (3H, m), 3.88-3.84 (3H, m), 3.83 (3H, s), 3.76-3.25 (5H, m), 2.78-2.71 (1H, m), 2.52 (1H, m), 2.45-2.35 (2H, m), 2.03-1.96 (1H, m), 1.29-1.21 (2H, m), 0.78-0.69 (4H, m).

MS(APCI, ESI)m/z:664(M+H)⁺

Example 54: Drug 10

[Formula 178]

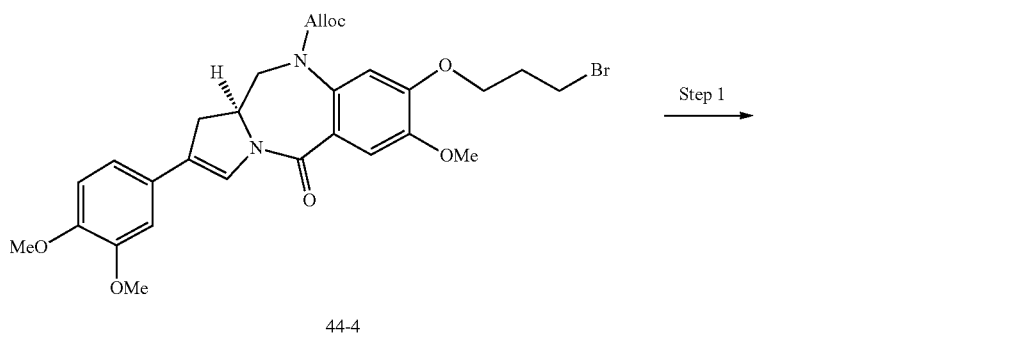

44-4

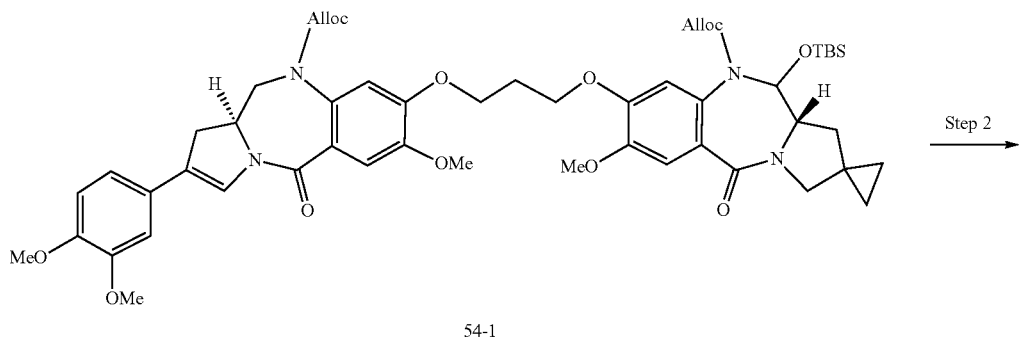

54-1

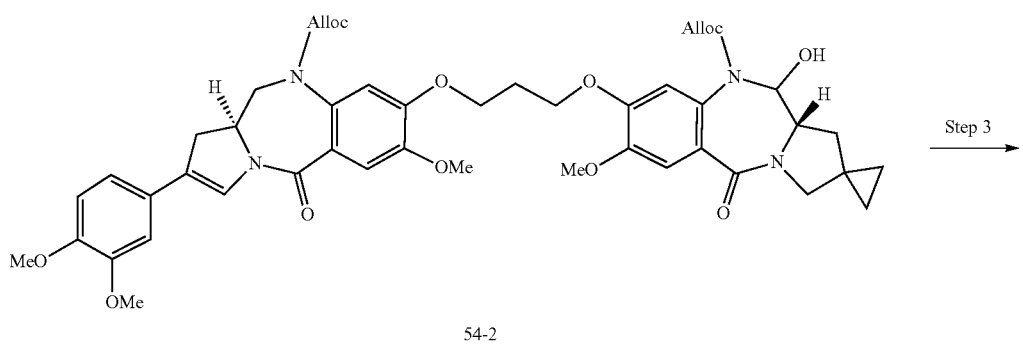

54-2

-continued

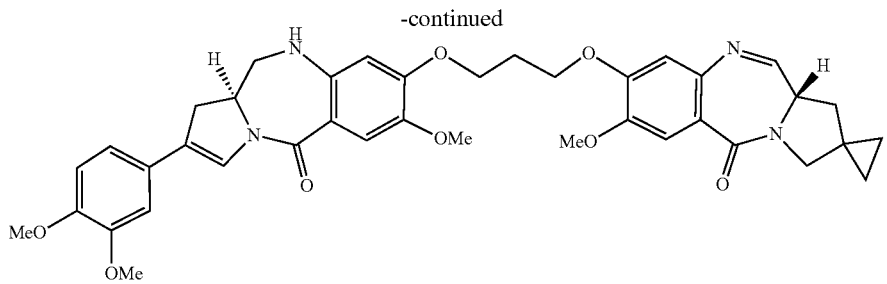

54-3

Step 1: Compound 54-1

The compound obtained in step 4 of Example 44 (0.027 g, 0.046 mmol) was reacted in the same manner as in step 6 of Example 45 to afford the desired compound (0.037 g, 81%).

MS (APCI, ESI)m/z:995 (M+H)$^+$

Step 2: Compound 54-2

The compound obtained in step 1 (0.037 g, 0.037 mmol) was reacted in the same manner as in step 11 of Example 3 to afford the desired compound (0.034 g, quantitative).

MS (APCI, ESI)m/z:881 (M+H)$^+$

Step 3: (11a'S)-8'-(3-{[(11aS)-2-(3,4-Dimethoxyphenyl)-7-methoxy-5-oxo-5,10,11,11a-tetrahydro-1H-pyrrolo[2,1-c][1,4]benzodiazepin-8-yl]oxy}propoxy)-7'-methoxy-1',11a'-dihydro-5'H-spiro[cyclopropane-1,2'-pyrrolo[2,1-c][1,4]benzodiazepine]-5'-one The compound obtained in step 2 (0.037 mmol) was reacted in the same manner as in step 12 of Example 3 to afford the desired compound (0.027 g, quantitative).

$^1$H-NMR (CDCl$_3$) δ:7.81-7.78 (1H, m), 7.55-7.49 (3H, m), 6.99-6.96 (1H, m), 6.87-6.82 (3H, m), 6.14 (1H, m), 4.41-3.28 (22H, m), 2.77-2.71 (1H, m), 2.57-2.48 (1H, m), 2.45-2.34 (2H, m), 2.04-1.96 (1H, m), 1.43-1.11 (2H, m), 0.79-0.67 (4H, m).

MS(APCI, ESI)m/z:695(M+H)$^+$

Synthesis of Glycan Donor

Figure 51:
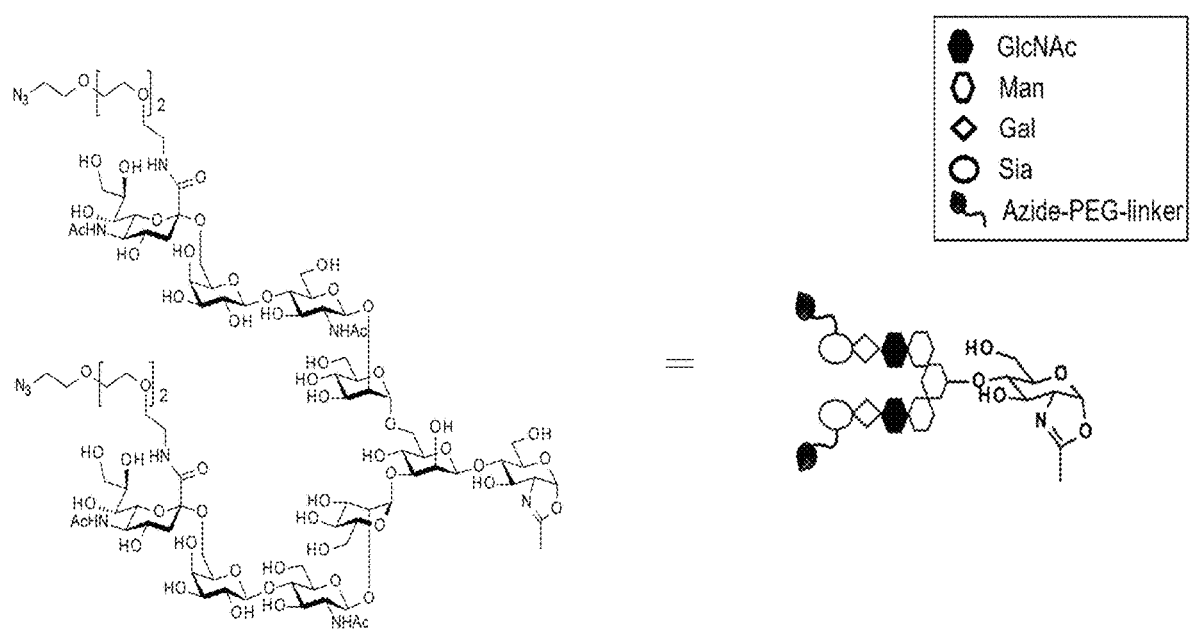
FIG. 51 shows Formula 179, wherein the schematic diagram in the right of the structural formula represents the corresponding structure in the schematic diagram of an intermediate having a linker structure to which an azide group has been introduced as represented by the reaction formula of Example 58.

Example 55: [N$_3$-PEG (3)]$_2$-SG (10)-Ox (in FIG. 51, the schematic diagram in the right of the structural formula represents the corresponding structure in the schematic diagram of an intermediate having a linker structure to which an azide group has been introduced as represented by the reaction formula of Example 58.)

Step 1: [N$_3$-PEG (3)]$_2$-SG (10)

Into a 5 mL sampling tube (Ina-Optica Co., Ltd), an aqueous solution (0.5 mL) of 11-azide-3,6,9-trioxaundecane-1-amine (0.096 mL, 0.485 mmol) and disialooctasaccharide (50 mg, 0.24 mmol) were added, and the resultant was stirred for 1 hour and then freeze-dried. Into the 5 mL sampling tube after freeze-drying, an N,N-dimethylformamide solution (0.6 mL) of O-(7-azabenzotriazol-1-yl)-N,N,N',N'-tetramethyluronium hexafluorophosphate (92 mg, 0.24 mmol) and diisopropylethylamine (0.042 mL, 0.24 mmol) were added, followed by stirring at 37° C. for 4 hours. After the completion of the reaction, the reaction solution was transferred into a centrifuge tube (50 mL) into which diethyl ether (20 mL) had been added in advance. The solid matter was precipitated by using a small centrifuge (Hitachi Koki Co., Ltd., CF16RX) and the supernatant was removed. Diethyl ether (20 mL) was added and the resultant was decanted. Subsequently, acetonitrile (20 mL) was added and the resultant was decanted, and then dried under reduced pressure to afford a crude product. The resulting solid matter was dissolved in an appropriate amount of a 0.2% trifluoroacetic acid aqueous solution, and subjected to separation/purification by reversed-phase HPLC. The eluent was a 0.1% trifluoroacetic acid aqueous solution and a 0.1% trifluoroacetic acid acetonitrile solution, the apparatus used was a Purif-Rp2 (produced by Shoko Scientific Co., Ltd.), and the column used was an Inertsil ODS-3 (produced by GL Sciences, Inc.). Fractions containing the desired compound UV-detected (220 nm) during the elution were collected together, and freeze-dried to afford the desired compound (42 mg).

Step 2: [N$_3$-PEG (3)]$_2$-SG (10)-Ox

Into a 5 mL sampling tube (produced by Ina-Optica Co., Ltd), the compound synthesized in step 1 (40 mg) and an aqueous solution (200 μL) of 2-chloro-1,3-dimethyl-1H-benzimidazol-3-ium-chloride (produced by FUSHIMI Pharmaceutical Co., Ltd. 17.9 mg, 0.083 mmol) was added. To the reaction solution after being ice-cooled, an aqueous solution (200 μL) of tripotassium phosphate (52.6 mg, 0.25 mmol) was added, followed by stirring under ice-cooling for 2 hours. The resulting reaction solution was subjected to ultrafiltration with an Amicon Ultra (Ultracel 30K, produced by Merck Millipore) to remove the solid matter. The filtered solution was purified by gel filtration chromatography. The apparatus used was a Purif-Rp2 (produced by Shoko Scientific Co., Ltd.), the column used was a HiPrep 26/10 Desalting (produced by GE Healthcare), the mobile phase used was 0.03%-NH$_3$ aqueous solution, and the flow rate was 10 mL/min and the fraction volume was 10 mL. Fractions containing the desired compound UV-detected (220 nm) during the elution were collected together, to which a 1 N aqueous solution of sodium hydroxide (33 μL, 0.033 mmol) was added, and the resultant was freeze-dried to afford the desired compound (34 mg).

Figure 52:
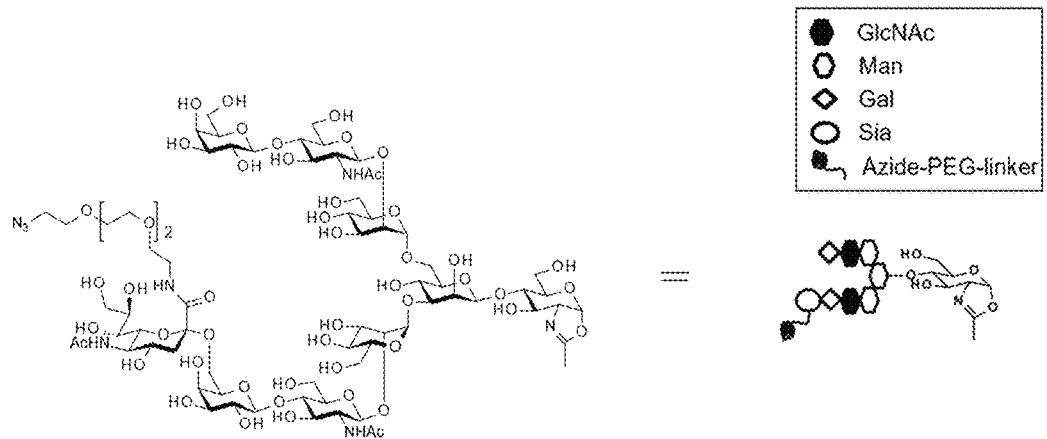
FIG. 52 shows Formula 180, wherein the schematic diagram in the right of the structural formula represents the corresponding structure in the schematic diagram of an intermediate having a linker structure to which an azide group has been introduced as represented by the reaction formula of each of Examples 60, 61, 62, 63, 64, 65, and 66.

Example 56: [N3-PEG (3)]-MSG1-Ox (In FIG. 52, the schematic diagram in the right of the structural formula represents the corresponding structure in the schematic diagram of an intermediate having a linker structure to which an azide group has been introduced as represented by the reaction formula of each of Examples 60, 61, 62, 63, 64, 65, and 66.)

Step 1: (MSG1-)Asn

The commercially available product monosialo-Asn free (1S2G/1G2S-10NC-Asn, produced by GlyTech, Inc.) (referred to as "(MSG-)Asn") (500 mg) was subjected to separation/purification by reversed-phase HPLC under conditions below to separate into (MSG1-)Asn eluted as the 1st main peak (retention time: around 15 to 19 min) and (MSG2-)Asn eluted as the 2nd main peak (retention time: around 21 to 26 min). The eluent used was a 0.1% formic acid aqueous solution, the apparatus used was an ELS-PDA trigger preparative system (produced by JASCO Corporation), the column used was an Inertsil ODS-3 (10 um, 30ϕ×250 mm, produced by GL Sciences, Inc.), and the flow rate was 30 mL/min. Fractions belonging to the first peak UV-detected (210 nm) during the elution were collected together, and freeze-dried to afford the desired compound (238 mg).

Step 2: MSG1

The compound obtained in step 1 (229 mg) was dissolved in 200 mM phosphate buffer solution (pH 6.25) (1145 μL), to which an aqueous solution (100 μL) of EndoM (produced by Tokyo Chemical Industry Co., Ltd., 1 U/mL)) was added, and the resultant was incubated at 35° C. for 6 days. After the completion of the reaction, the reaction solution was subjected to ultrafiltration with a VIVASPIN 15R (Hydrosart membrane, 30K, 6,000 g), and the filtered solution obtained was subjected to separation/purification by reversed-phase HPLC. The eluent used was a 0.1% trifluoroacetic acid aqueous solution, the apparatus used was an ELS-PDA trigger preparative system (produced by JASCO Corporation), and the column used was an Inertsil ODS-3 (produced by GL Sciences, Inc.). Fractions containing the desired compound UV-detected (210 nm) during the elution were collected together, and freeze-dried to afford the desired compound (117 mg).

Step 3: [$N_3$-PEG (3)]-MSG1

The compound synthesized in step 2 (169 mg) was reacted in the same manner as in step 1 of Example 55 to afford the desired compound (94.2 mg).

Step 4 [$N_3$-PEG (3)]-MSG1-Ox

The compound (100 mg) synthesized in step 3 was reacted in the same manner as in step 2 of Example 55 to afford the desired compound (89 mg).

Figure 53:
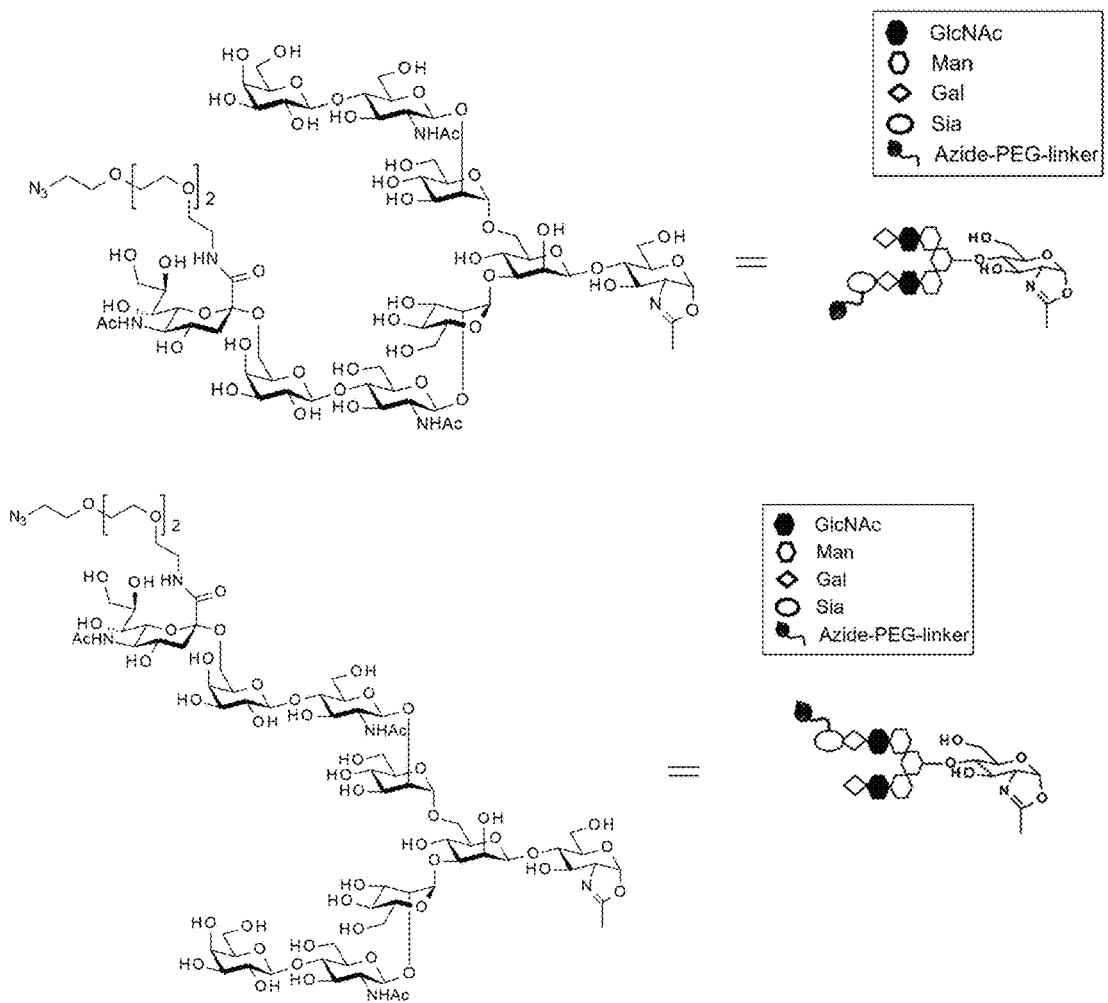
FIG. 53 shows Formula 181, wherein the schematic diagram in the right of the structural formula represents the corresponding structure in the schematic diagram of an intermediate having a linker structure to which an azide group has been introduced as represented by the reaction formula of Example 59.

Example 57: [$N_3$-PEG (3)]-MSG-Ox (In FIG. 53, the schematic diagram in the right of the structural formula represents the corresponding structure in the schematic diagram of an intermediate having a linker structure to which an azide group has been introduced as represented by the reaction formula of Example 59.)

Step 1: Preparation of (MSG-)Asn

The commercially available product 1S2G/1G2S-10NC-Asn-Fmoc (produced by GlyTech, Inc.) (referred to as "Fmoc-(MSG-)Asn") (1000 mg) was dissolved in ethanol/water (1/1) (10 mL), to which a 1 N aqueous solution of sodium hydroxide (1.75 mL, 4 equivalents) was added, followed by stirring at room temperature for 3 hours. After the completion of the reaction, the reaction solution was subjected to ultrafiltration with an Amicon Ultra (30K, produced by Millipore Corporation) to remove the solid matter, and 1 N hydrochloric acid (832 μL, 1.9 equivalents) was added to the filtered solution obtained. The solvent was removed with the high-speed evaporator V-10 (produced by Biotage). Acetonitrile was added thereto, and the solvent was removed with the high-speed evaporator V-10 (produced by Biotage), and the resultant was then subjected to separation/purification by reversed-phase HPLC. The eluent was a 0.1% trifluoroacetic acid aqueous solution and a 0.1% trifluoroacetic acid acetonitrile solution, the apparatus used was a Purif-Rp2 (produced by Shoko Scientific Co., Ltd.), and the column used was an Inertsil ODS-3 (produced by GL Sciences, Inc.). Fractions containing the desired compound UV-detected (220 nm) during the elution were collected together, and freeze-dried. This was dissolved again in pure water, and a pH test paper strip indicated that the solution was acidic. Hence, 18% aqueous ammonia (150 μL) was added thereto and it was confirmed with a pH test paper strip that the solution had become basic, and the solution was freeze-dried again. The desired compound obtained (840 mg) was directly used for the subsequent reaction.

Step 2: Synthesis of MSG

The compound obtained in step 1 (840 mg) was dissolved in 200 mM phosphate buffer solution (pH 6.25) (6000 μL), to which an aqueous solution (200 μL) of EndoM (produced by Tokyo Chemical Industry Co., Ltd., 1 U/mL)) was added, and the resultant was incubated at 28° C. for 26 hours. Because the reaction had not completed, an aqueous solution (50 μL) of EndoM (produced by Tokyo Chemical Industry Co., Ltd., 1 U/mL)) was added, and the resultant was incubated at 28° C. for 2 hours, and then left to stand at room temperature until the completion of the reaction. After the completion of the reaction, the reaction solution was subjected to ultrafiltration with an Amicon Ultra (30K, produced by Millipore Corporation). Trifluoroacetic acid (80 μL) was added to the filtered solution obtained, which was subjected to separation/purification by reversed-phase HPLC. The eluent was a 0.10% trifluoroacetic acid aqueous solution and a 0.1% trifluoroacetic acid acetonitrile solution, the apparatus used was a Purif-Rp2 (produced by Shoko Scientific Co., Ltd.), and the column used was an Inertsil ODS-3 (produced by GL Sciences, Inc.). Fractions containing the desired compound UV-detected (220 nm) during the elution were collected together, and freeze-dried. This was dissolved again in pure water in order to remove the residual trifluoroacetic acid, and thus the desired compound (618 mg) was obtained as a colorless solid.

ESI-MS: Calcd for $C_{66}H_{110}N_4O_{49}$: $[M+H]^+$ 1743.62, Found 1743.63

Step 3: Synthesis of [$N_3$-PEG (3)]-MSG

In accordance with the procedure of step 1 of Example 55 using the compound obtained in step 2 (120 mg), the desired compound (88.6 mg) was obtained.

ESI-MS: Calcd for $C_{73}H_{124}N_8O_{51}$: $[M+2H]^{2+}$ 965.37, Found 965.37

Step 4 Synthesis of [N₃-PEG (3)]-MSG-Ox

In accordance with the procedure of step 2 of Example 55 using the compound obtained in step 4 (100 mg), the desired compound (88 mg) was obtained.

Preparation of Glycan-Remodeled Antibody

Example 58: Sugar Chain Remodeling 1 (T-SG)

Figure 54:
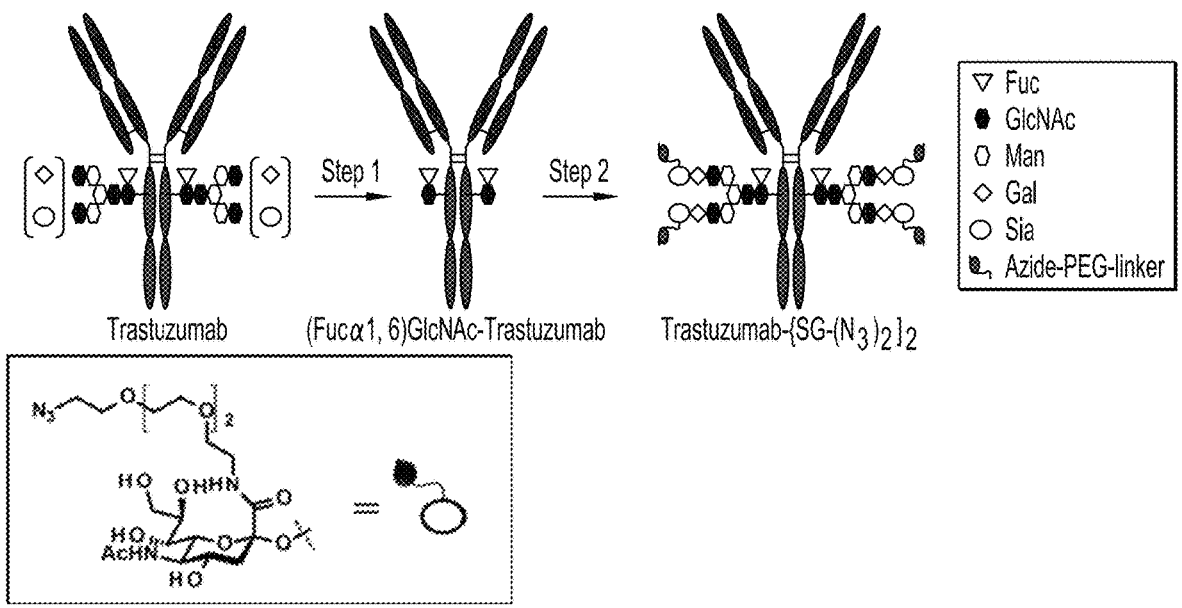
FIG. 54 shows Formula 182 which represents a linker structure in which an azide group has been introduced to a sialic acid at the non-reducing terminal of an SG-type N297 glycan. In Example 58, linker structures of intermediates formed by introducing an azide group to an N297 glycan are all the same as the structure represented by the formula.

(See FIG. 54. This formula represents a linker structure in which an azide group has been introduced to a sialic acid at the non-reducing terminal of an SG-type N297 glycan. In Example 58, linker structures of intermediates formed by introducing an azide group to an N297 glycan are all the same as the structure represented by the formula.)

Step 1: Preparation of (Fucα1,6)GlcNAc-Trastuzumab

The 22 mg/mL trastuzumab solution (25 mM histidine solution (pH 6.0), 5% sorbitol solution) (45.5 mL) prepared in Reference Example 3 was halved and according to common operation C, buffer exchange to 50 mM phosphate buffer (pH 6.0) was conducted twice separately. To the resulting 28.1 mg/mL (18 mL) and 28.0 mg/mL (18 mL) trastuzumab solution (50 mM phosphate buffer (pH 6.0)), 1.26 mL and 1.27 mL of wild-type EndoS solution (2.0 mg/mL, PBS) were respectively added, and the solutions were incubated at 37° C. for 4 hours. The progress of the reaction was checked by Experion electrophoresis station (produced by Bio-Rad Laboratories, Inc.). After the completion of the reaction, purification by affinity chromatography and purification with a hydroxyapatite column were performed in accordance with the following methods.
(1) Purification by Affinity Chromatography
  Purification apparatus: AKTA pure150 (produced by GE Healthcare)
  Column: HiTrap rProtein A FF (5 mL) (produced by GE Healthcare)
  Flow rate: 5 mL/min (1.25 mL/min in charging)

Each reaction solution obtained above was purified in multiple separate operations. Two columns were linked together into one column, and in connecting to the column the reaction solution was added to the upper part of the column, and 2 CV of binding buffer (20 mM phosphate buffer (pH 6.0)) was flowed at 1.25 mL/min and 5 CV thereof was further flowed at 5 mL/min. In intermediate washing, 15 CV of washing solution (20 mM phosphate buffer (pH 7.0), 0.5 M sodium chloride solution) was flowed. In elution, 6 CV of elution buffer (ImmunoPure IgG Eution buffer, produced by Pierce) was flowed. The eluate was immediately neutralized with 1 M Tris buffer (pH 9.0). Fractions UV-detected (280 nm) during the elution were checked by using the micro-volume spectrophotometer Xpose (produced by Trinean NV) and an Experion electrophoresis station (produced by Bio-Rad Laboratories, Inc.). Fractions containing the desired compound were subjected to buffer exchange to 5 mM phosphate buffer/50 mM 2-morpholinoethanesulfonic acid (MES) solution (pH 6.8) by using common operation C.

(2) Purification by Hydroxyapatite Chromatography
  Purification apparatus: AKTA avant25 (produced by GE Healthcare)
  Column: Bio-Scale Mini CHT Type I cartridge (5 mL) (produced by Bio-Rad Laboratories, Inc.)
  Flow rate: 5 mL/min (1.25 mL/min in charging)

Two columns were linked together into one column, and the solution obtained in (1) was purified in multiple separate operations. The solution was added to the upper part of the column, and 2 CV of solution A (5 mM phosphate buffer, 50 mM 2-morpholinoethanesulfonic acid (MES) solution (pH 6.8)) was flowed at 1.25 mL/min and 3 CV thereof was further flowed at 5 mL/min. Thereafter, elution was performed with solution A and solution B (5 mM phosphate buffer/50 mM 2-morpholinoethanesulfonic acid (MES) solution (pH 6.8), 2 M sodium chloride solution). The elution conditions were solution A:solution B=100:0 to 0:100 (15 CV). Further, 5 CV of washing solution (500 mM phosphate buffer (pH 6.5)) was flowed.

Fractions containing the desired compound were subjected to buffer exchange by using common operation C to afford a 25.5 mg/A D mL (Fucα1,6)GlcNAc-Trastuzumab solution (50 mM phosphate buffer (pH 6.0)) (35 mL).

Step 2: Preparation of Trastuzumab[SG-(N₃)₂]₂

To the 23.9 mg/mL (Fucα1,6)GlcNAc-Trastuzumab solution (50 mM phosphate buffer (pH 6.0)) obtained in step 1 (3.37 mL), a solution (0.258 mL) of the compound synthesized in step 2 of Example 55 (12.9 mg) in 50 mM phosphate buffer (pH 6.0) and 4.90 mg/mL EndoS D233Q/Q303L solution (PBS) (0.328 mL) were added, and the resultant was incubated at 30° C. for 4.5 hours. These operations were performed in two lots. The progress of the reaction was checked by using an Experion electrophoresis station (produced by Bio-Rad Laboratories, Inc.). After the completion of the reaction, purification by affinity chromatography and purification by hydroxyapatite chromatography were performed as in step 1, and fractions containing the desired compound were then subjected to buffer exchange to phosphate buffered saline (pH 6.0) by using common operation C to afford a 10.0 mg/mL Trastuzumab [SG-(N₃)₂]₂ solution (phosphate buffered saline (pH 6.0)) (15.5 mL).

Example 59: Sugar Chain Remodeling 2 (T-MSG)

Figure 55:
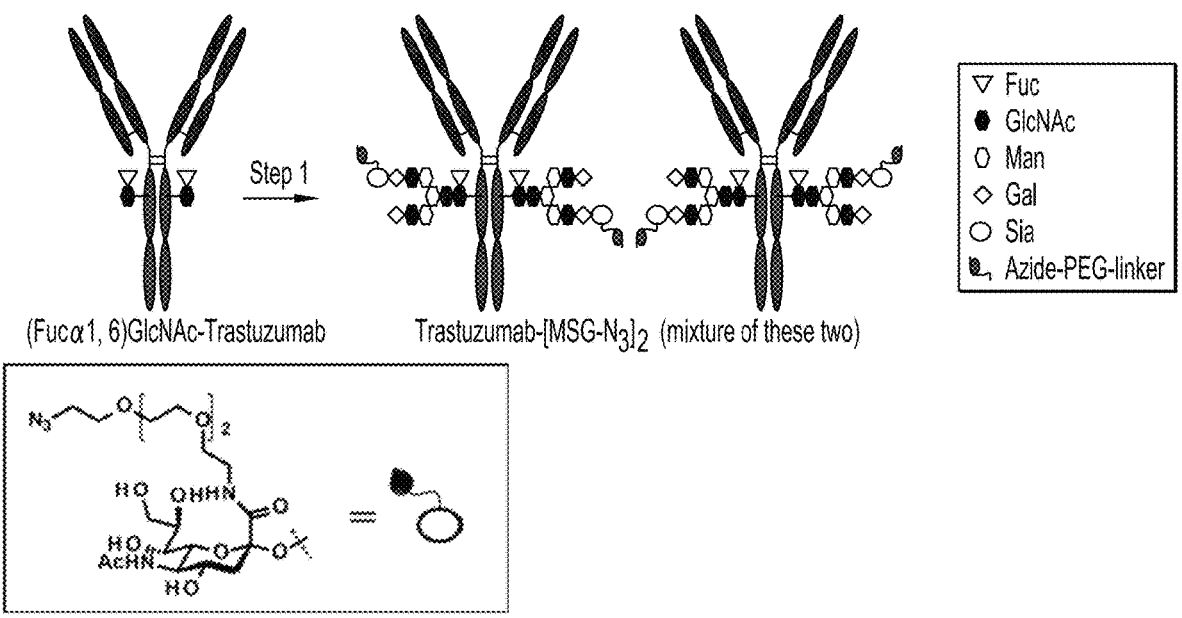
FIG. 55 shows Formula 183, which represents a linker structure in which an azide group has been introduced to a sialic acid at the non-reducing terminal of an MSG-type N297 glycan. In Example 59, linker structures of intermediates formed by introducing an azide group to an N297 glycan are all the same as the structure represented by the formula.

(See FIG. 55. This formula represents a linker structure in which an azide group has been introduced to a sialic acid at the non-reducing terminal of an MSG-type N297 glycan. In Example 59, linker structures of intermediates formed by introducing an azide group to an N297 glycan are all the same as the structure represented by the formula.)

Step 1: Trastuzumab[MSG-N₃]₂

The following operations were performed in five lots. The compound obtained in step 1 of Example 58 (20 mg/mL, 15.0 mL) was used together with the compound obtained in step 4 of Example 57 (25.5 mg) as a glycan donor, and incubated at 30° C. for 3 hours, and the operations same as in step 2 of Example 59 were performed. With the five lots combined, a 14.4 mg/mL Trastuzumab [MSG-N$_3$]$_2$ solution (phosphate buffered saline (pH 6.0)) (93.5 mL) was obtained.

Example 60: Sugar Chain Remodeling 3 (T-MSG1)

Figure 56:
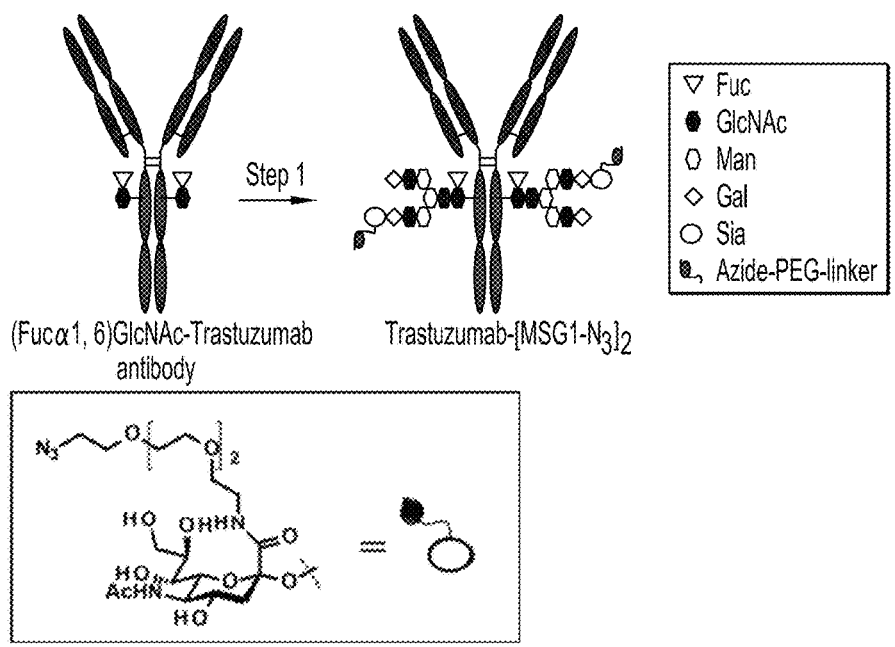
FIG. 56 shows Formula 184, which represents a linker structure in which an azide group has been introduced to a sialic acid at the non-reducing terminal of an MSG1-type N297 glycan. In Example 60, linker structures of intermediates formed by introducing an azide group to an N297 glycan are all the same as the structure represented by the formula. The same holds true for Examples 61 to 66.

(See FIG. 56. This formula represents a linker structure in which an azide group has been introduced to a sialic acid at the non-reducing terminal of an MSG1-type N297 glycan. In Example 60, linker structures of intermediates formed by introducing an azide group to an N297 glycan are all the same as the structure represented by the formula. The same holds true for Examples 61 to 66.)

Step 1: Trastuzumab[MSG1-N$_3$]$_2$

The following operations were performed in two lots. The compound obtained in step 1 of Example 58 (25.5 mL, 7.8 mL) was used together with the compound obtained in step 4 of Example 56 (25.5 mg) as a glycan donor, and incubated at 30° C. for 3 hours, and the operations same as in step 2 of Example 59 were performed. With the two lots combined, a 10.6 mg/mL Trastuzumab[MSG1-N$_3$]$_2$ solution (phosphate buffered saline (pH 6.0)) (31 mL) was obtained.

Example 61: Sugar chain remodeling 4 (CLDN6-MSG1 (H1L1))

Step 1: (Fucα1,6)GlcNAc-anti-CLDN6 antibody (H1L1)

Figure 57:
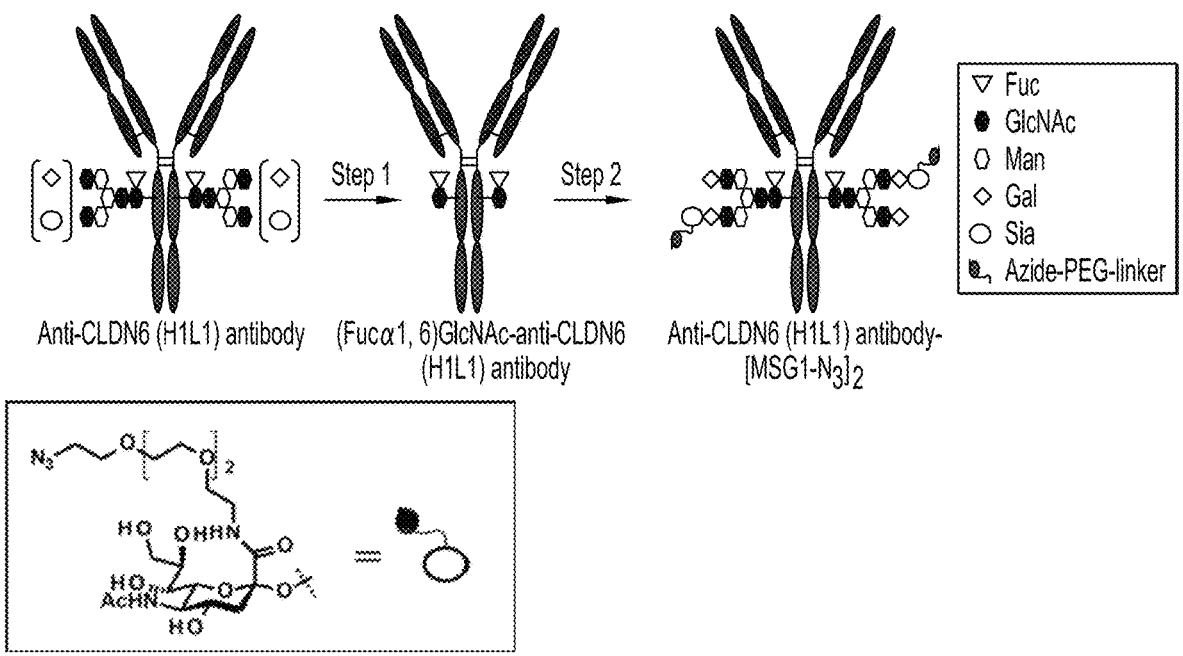
FIG. 57 shows Formula 185, Step 1: (Fucα1,6)GlcNAc-anti-CLDN6 antibody (H1L1). The operations same as in step 1 of Example 58 were performed using a ca. 37.7 mg/mL anti-CLDN6 antibody solution (25 mM histidine solution (pH 6.0), 5% sorbitol solution) prepared in Example 136 (2.5 mL) to afford a 19.2 mg/mL (Fucα1,6)GlcNAc-anti-CLDN6 antibody (H1L1) solution (50 mM phosphate buffer (pH 6.0)) (4.8 mL).

The operations same as in step 1 of Example 58 were performed using a ca. 37.7 mg/mL anti-CLDN6 antibody solution (25 mM histidine solution (pH 6.0), 5% sorbitol solution) prepared in Example 136 (2.5 mL) to afford a 19.2 mg/mL (Fucα1,6)GlcNAc-anti-CLDN6 antibody (H1L1) solution (50 mM phosphate buffer (pH 6.0)) (4.8 mL) (see FIG. 57).

Step 2: Anti-CLDN6 Antibody (H1L1)-[MSG1-N$_3$]$_2$

The operations same as in step 1 of Example 60 were performed using the 19.2 mg/mL (Fucα1,6)GlcNAc-anti-CLDN6 (H1L1) antibody solution (50 mM phosphate buffer (pH 6.0)) obtained in step 1 (4.8 mL) to afford a 10.2 mg/mL anti-CLDN6 antibody (H1L1)-[MSG1-N$_3$]$_2$ solution (phosphate buffered saline (pH 6.0)) (7.2 mL).

Example 62: Sugar Chain Remodeling 5 (CLDN6-MSG1 (H2L2))

Step 1: (Fucα1,6)GlcNAc-anti-CLDN6 antibody (H2L2)

Figure 58:
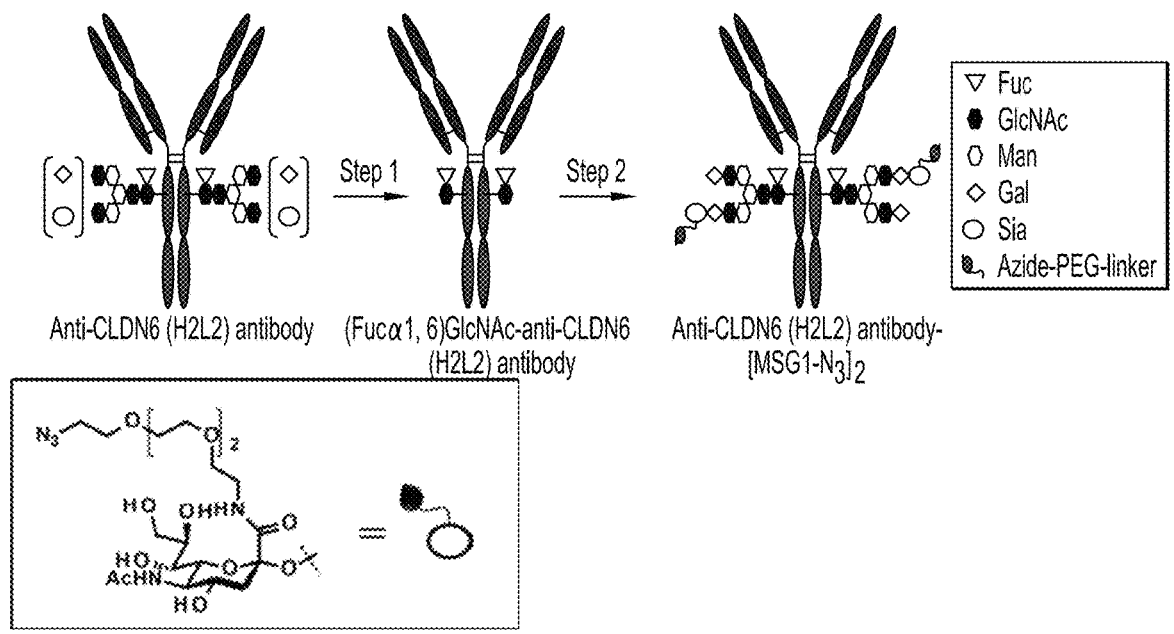
FIG. 58 shows Formula 186, Step 1: (Fucα1,6)GlcNAc-anti-CLDN6 antibody (H2L2). The operations same as in step 1 of Example 58 were performed using a ca. 20 mg/mL anti-CLDN6 antibody solution (25 mM histidine solution (pH 6.0), 5% sorbitol solution) prepared in Example 136 (6 mL) to afford a 21.84 mg/mL (Fucα1,6)GlcNAc-anti-CLDN6 antibody (H2L2) solution (50 mM phosphate buffer (pH 6.0)) (5.7 mL).

The operations same as in step 1 of Example 58 were performed using a ca. 20 mg/mL anti-CLDN6 antibody solution (25 mM histidine solution (pH 6.0), 5% sorbitol solution) prepared in Example 136 (6 mL) to afford a 21.84 mg/mL (Fucα1,6)GlcNAc-anti-CLDN6 antibody (H2L2) solution (50 mM phosphate buffer (pH 6.0)) (5.7 mL) (see FIG. 58).

Step 2: Anti-CLDN6 Antibody (H2L2)-[MSG1-N$_3$]$_2$

The operations same as in step 1 of Example 60 were performed using the 21.8 mg/mL (Fucα1,6)GlcNAc-anti-CLDN6 (H2L2) antibody solution (50 mM phosphate buffer (pH 6.0)) obtained in step 1 (5.7 mL) to afford a 10.2 mg/mL anti-CLDN6 antibody (H2L2)-[MSG1-N$_3$]$_2$ solution (phosphate buffered saline (pH 6.0)) (11.1 mL).

Example 63: Sugar Chain Remodeling 6 (CLDN6-MSG1 (H1L3))

Step 1: (Fucα1,6)GlcNAc-anti-CLDN6 antibody (H1L3)

Figure 59:
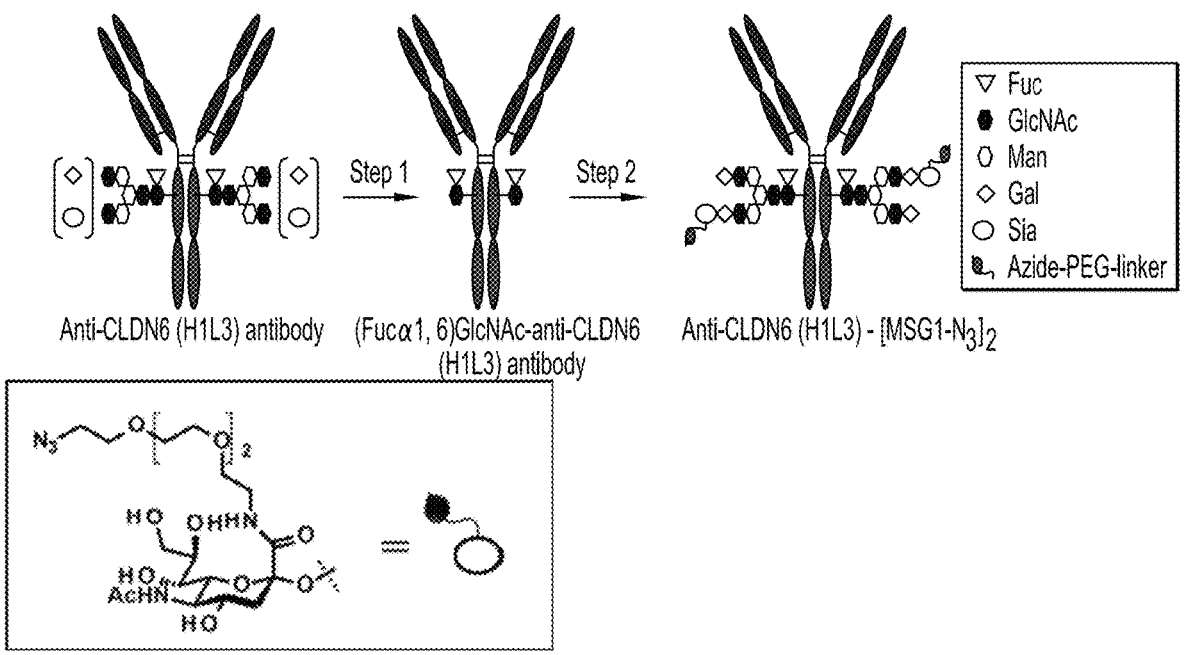
FIG. 59 shows Formula 187, Step 1: (Fucα1,6)GlcNAc-anti-CLDN6 antibody (H1L3). The operations same as in step 1 of Example 58 were performed using a ca. 39.4 mg/mL anti-CLDN6 antibody solution (25 mM histidine solution (pH 6.0), 5% sorbitol solution) prepared in Example 136 (3 mL) to afford a 39.2 mg/mL (Fucα1,6)GlcNAc-anti-CLDN6 antibody (H1L3) solution (50 mM phosphate buffer (pH 6.0)) (4.5 mL).

The operations same as in step 1 of Example 58 were performed using a ca. 39.4 mg/mL anti-CLDN6 antibody solution (25 mM histidine solution (pH 6.0), 5% sorbitol solution) prepared in Example 136 (3 mL) to afford a 39.2 mg/mL (Fucα1,6)GlcNAc-anti-CLDN6 antibody (H1L3) solution (50 mM phosphate buffer (pH 6.0)) (4.5 mL) (see FIG. 59).

Step 2: Anti-CLDN6 Antibody (H1L3)-[MSG1-N$_3$]$_2$

The operations same as in step 1 of Example 60 were performed using the 39.2 mg/mL (Fucα1,6)GlcNAc-anti-CLDN6 (H1L3) antibody solution (50 mM phosphate buffer (pH 6.0)) obtained in step 1 (4.5 mL) to afford a 9.83 mg/mL anti-CLDN6 antibody (H1L3)-[MSG1-N$_3$]$_2$ solution (phosphate buffered saline (pH 6.0)) (7.2 mL).

Example 64: Sugar chain remodeling 7 (CD98-MSG1)

Step 1: (Fucα1,6)GlcNAc-anti-CD98 antibody

Figure 60:
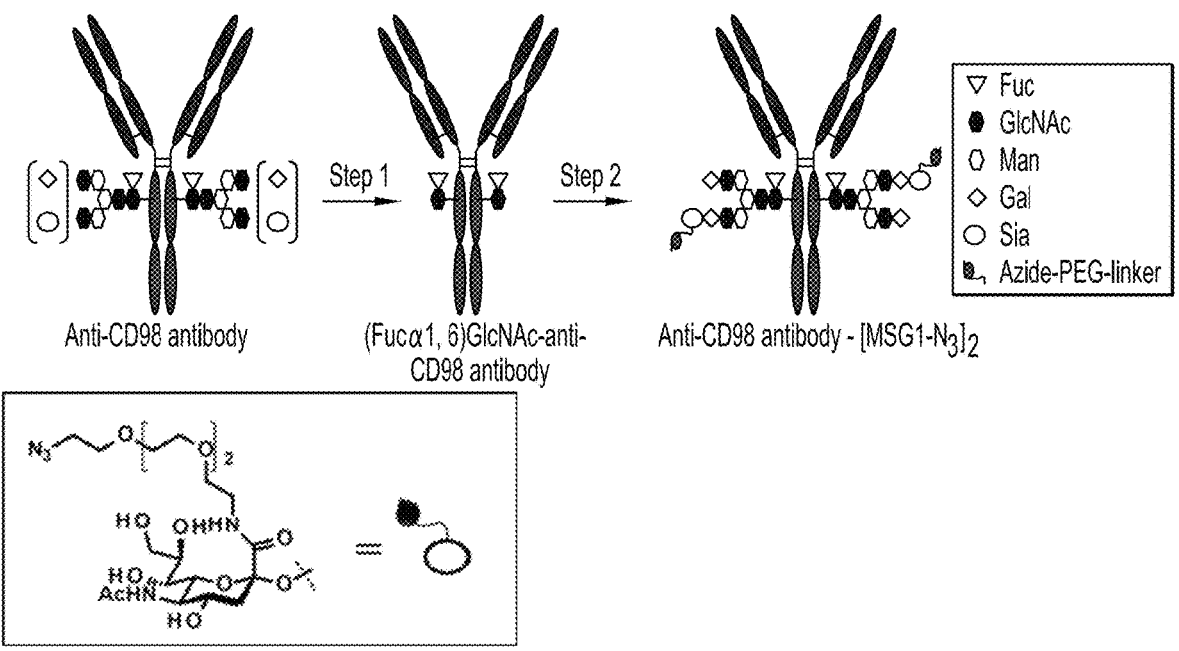
FIG. 60 shows Formula 188, Step 1: (Fucα1,6)GlcNAc-anti-CD98 antibody. The operations same as in step 1 of Example 58 were performed using a ca. 20 mg/mL anti-CD98 antibody solution (25 mM histidine solution (pH 6.0), 5% sorbitol solution) prepared in Reference Example 6 (6 mL) to afford a 21.7 mg/mL (Fucα1,6)GlcNAc-anti-CD98 antibody solution (50 mM phosphate buffer (pH 6.0)) (4.7 mL).

The operations same as in step 1 of Example 58 were performed using a ca. 20 mg/mL anti-CD98 antibody solution (25 mM histidine solution (pH 6.0), 5% sorbitol solution) prepared in Reference Example 6 (6 mL) to afford a 21.7 mg/mL (Fucα1,6)GlcNAc-anti-CD98 antibody solution (50 mM phosphate buffer (pH 6.0)) (4.7 mL) (see FIG. 60).

Step 2: Anti-CD98 Antibody-[MSG1-N$_3$]$_2$

The operations same as in step 1 of Example 60 were performed using the 21.7 mg/mL (Fucα1,6)GlcNAc-anti-CD98 antibody solution (50 mM phosphate buffer (pH 6.0)) obtained in step 1 (4.7 mL) to afford a 10.1 mg/mL anti-CD98 antibody-[MSG1-N$_3$]$_2$ solution (phosphate buffered saline (pH 6.0)) (7.6 mL).

Example 65: Sugar Chain Remodeling 8 (TROP2-MSG1)

Step 1: (Fucα1,6)GlcNAc-anti-Trop2 Antibody

Figure 61:
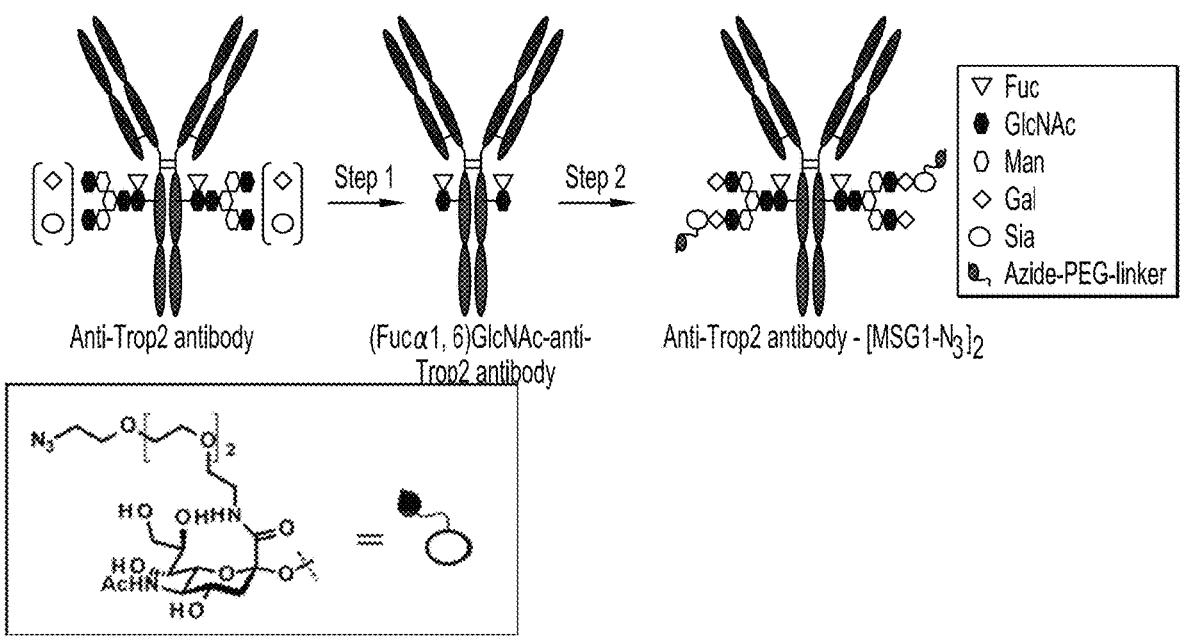
FIG. 61 shows Formula 189, Step 1: (Fucα1,6)GlcNAc-anti-Trop2 antibody. The operations same as in step 1 of Example 58 were performed using a ca. 20 mg/mL anti-Trop2 antibody solution (25 mM histidine solution (pH 6.0), 5% sorbitol solution) obtained in Reference Example 5 (6 mL) to afford a 21.69 mg/mL (Fucα1,6)GlcNAc-anti-Trop2 antibody solution (50 mM phosphate buffer (pH 6.0)) (3.3 mL).

The operations same as in step 1 of Example 58 were performed using a ca. 20 mg/mL anti-Trop2 antibody solution (25 mM histidine solution (pH 6.0), 5% sorbitol solution) obtained in Reference Example 5 (6 mL) to afford a 21.69 mg/mL (Fucα1,6)GlcNAc-anti-Trop2 antibody solution (50 mM phosphate buffer (pH 6.0)) (3.3 mL) (see FIG. 61).

Step 2: Anti-Trop2 Antibody-[MSG1-N$_3$]$_2$

The operations same as in step 1 of Example 60 were performed using the 21.69 mg/mL (Fucα1,6)GlcNAc-anti- Trop2 antibody solution (50 mM phosphate buffer (pH 6.0)) obtained in step 1 (3.35 mL) to afford a 10.3 mg/mL anti-Trop2 Antibody-[MSG1-N$_3$]$_2$ solution (phosphate buffered saline (pH 6.0)) (6.4 mL).

Example 66: Sugar Chain Remodeling 9 (LPS-MSG1)

Step 1: (Fucα1,6)GlcNAc-anti-LPS Antibody

Figure 62:
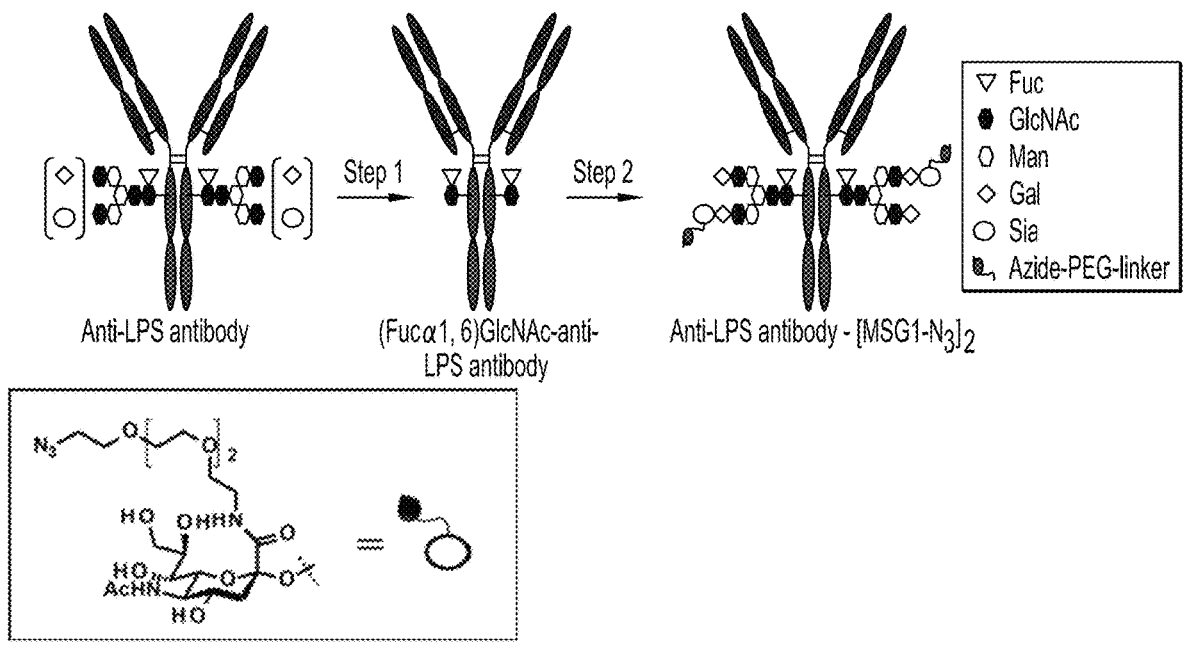
FIG. 62 shows Formula 190, Step 1: (Fucα1,6)GlcNAc-anti-LPS antibody. The operations same as in step 1 of Example 58 were performed using a ca. 17 mg/mL anti-LPS antibody solution (25 mM histidine solution (pH 6.0), 5% sorbitol solution) prepared in Reference Example 4 (6.6 mL) to afford a 21.03 mg/mL (Fucα1,6)GlcNAc-anti-LPS antibody solution (50 mM phosphate buffer (pH 6.0)) (5.4 mL).

The operations same as in step 1 of Example 58 were performed using a ca. 17 mg/mL anti-LPS antibody solution (25 mM histidine solution (pH 6.0), 5% sorbitol solution) prepared in Reference Example 4 (6.6 mL) to afford a 21.03 mg/mL (Fucα1,6)GlcNAc-anti-LPS antibody solution (50 mM phosphate buffer (pH 6.0)) (5.4 mL) (see FIG. 62).

Step 2: Anti-LPS Antibody-[MSG1-N$_3$]$_2$

The operations same as in step 1 of Example 60 were performed using the 21.03 mg/mL (Fucα1,6)GlcNAc-anti-LPS antibody solution (50 mM phosphate buffer (pH 6.0)) obtained in step 1 (5.4 mL) to afford a 9.89 mg/mL anti-LPS antibody-[MSG1-N$_3$]$_2$ solution (phosphate buffered saline (pH 6.0)) (7.9 mL).

[Synthesis of ADC]

Figure 63:
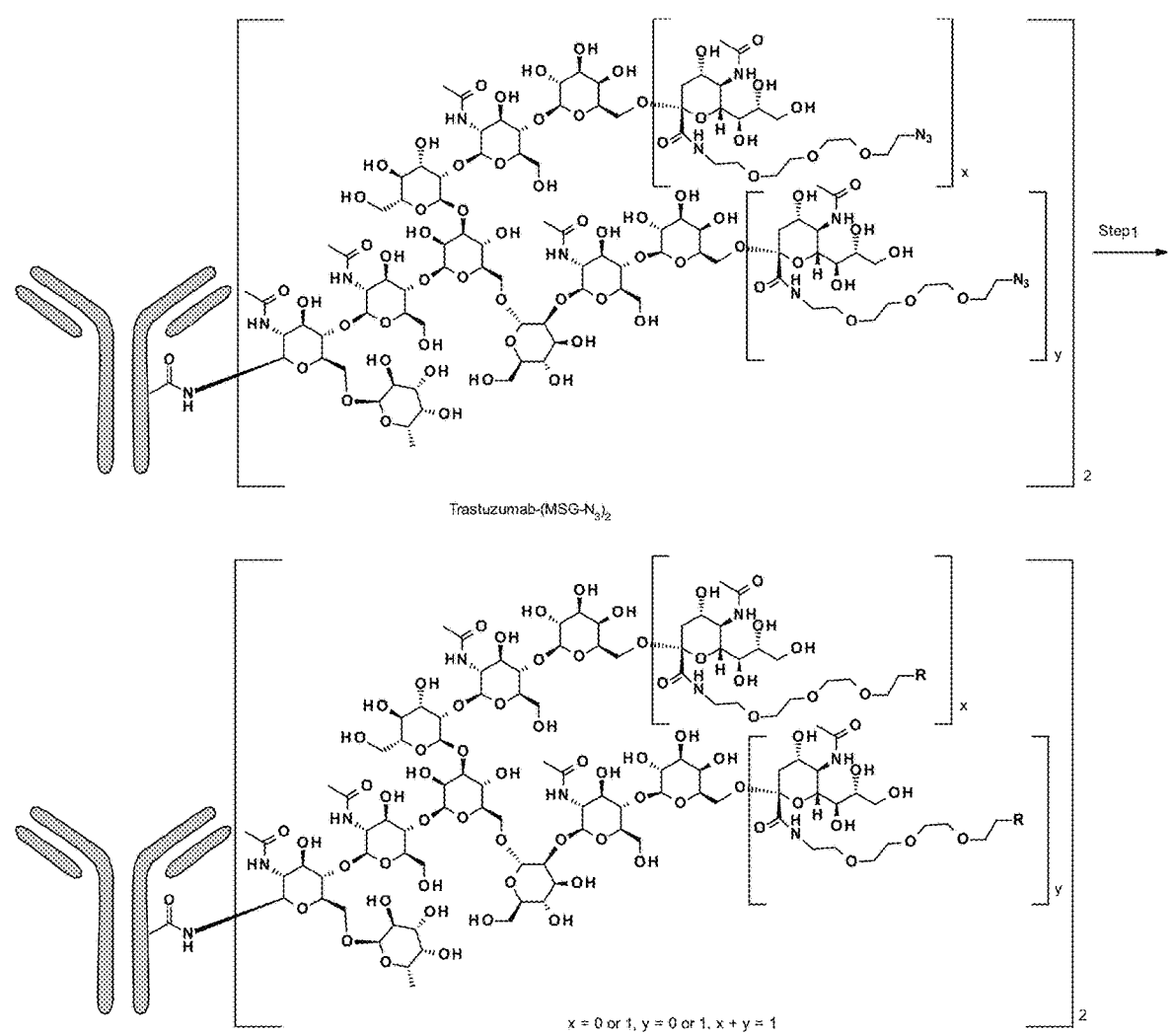
FIG. 63 shows Formula 191, wherein the ADCs described in Examples 67 to 71, 77 to 80, 82 to 88, 92 to 95, 109 to 114, and 120 were synthesized, as illustrated in the following reaction formula, by conjugating the antibody obtained in step 1 of Example 59 with a drug-linker. In the formula, R differs among drug-linkers used in those Examples.

ADCs described in Examples 67 to 71, 77 to 80, 82 to 88, 92 to 95, 109 to 114, and 120 were synthesized, as illustrated in the following reaction formula, by conjugating the antibody obtained in step 1 of Example 59 with a drug-linker. In the formula, R differs among drug-linkers used in those Examples (see FIG. 63).

Figure 64:
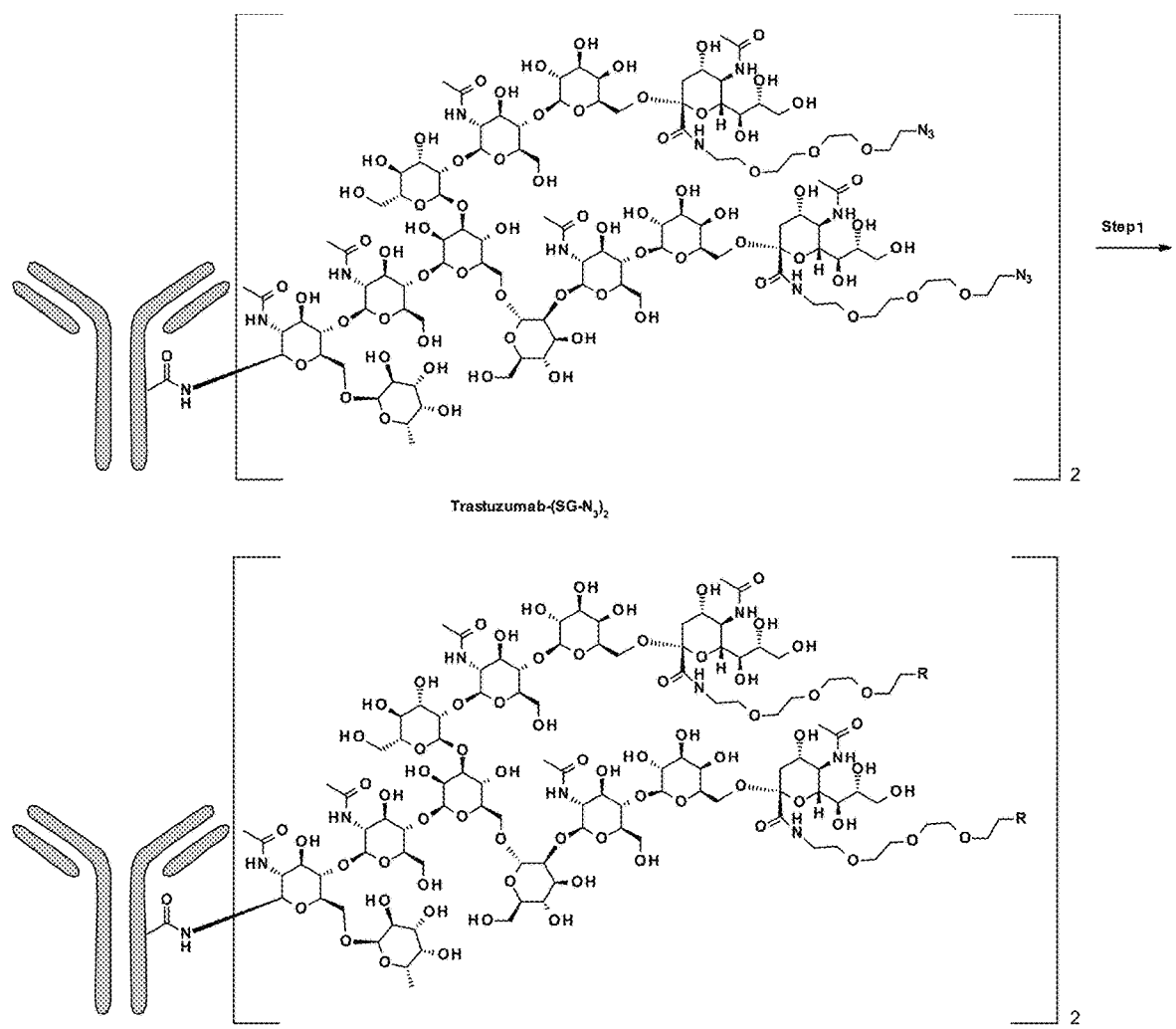
FIG. 64 shows Formula 192, wherein the ADCs described in Examples 72, 73, 75, and 91 were synthesized, as illustrated in the following reaction formula, by conjugating the antibody obtained in step 2 of Example 58 with a drug-linker. In the formula, R differs among drug-linkers used in those Examples.

ADCs described in Examples 72, 73, 75, and 91 were synthesized, as illustrated in the following reaction formula, by conjugating the antibody obtained in step 2 of Example 58 with a drug-linker. In the formula, R differs among drug-linkers used in those Examples (see FIG. 64).

Figure 65:
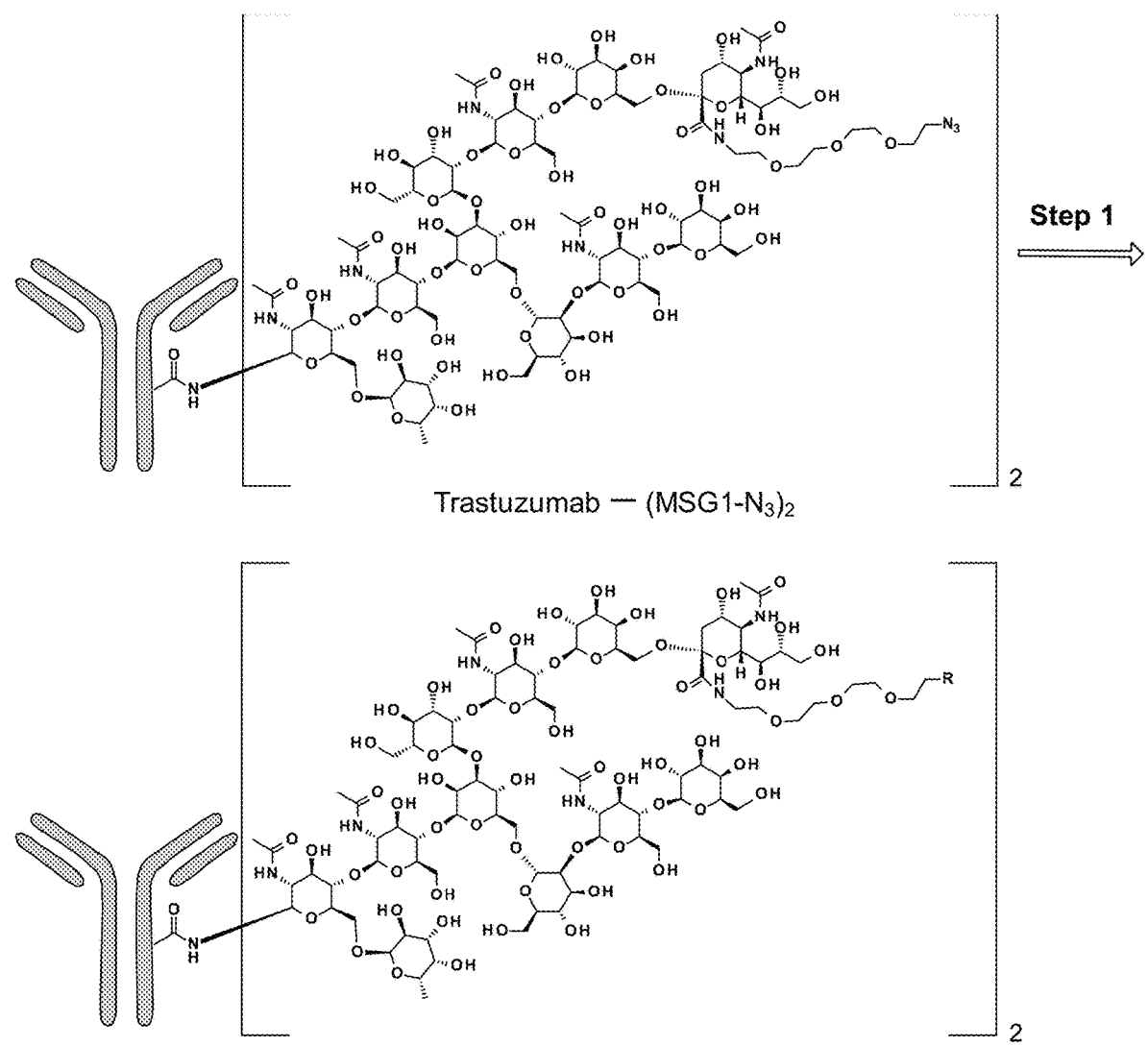
FIG. 65 shows Formula 193, wherein the ADCs described in Examples 74, 81, 89, 90, 96 to 105, 115, and 118 were synthesized, as illustrated in the following reaction formula, by conjugating the antibody obtained in step 1 of Example 60 with a drug-linker. In the formula, R group differs among drug-linkers used in those Examples.

ADCs described in Examples 74, 81, 89, 90, 96 to 105, 115, and 118 were synthesized, as illustrated in the following reaction formula, by conjugating the antibody obtained in step 1 of Example 60 with a drug-linker. In the formula, R group differs among drug-linkers used in those Examples (see FIG. 65).

Example 67: ADC1

The triazole ring to be formed in step 1 has geometric isomers, and the compound obtained in step 1 of Example 67 has a linker as a mixture of the two structures shown as R (FIG. 66).

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 13 of Example 24 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 14.00 mL of a solution of the desired compound. This solution was concentrated by using common operation A to afford 0.75 mL of a solution of the desired compound.

Characterization: The following characteristic values were obtained by using common operations E and F.

Antibody concentration: 11.4 mg/mL, antibody yield: 8.56 mg (86%), average number of conjugated drug molecules per antibody molecule (n): 1.9

Example 68: ADC2

[Formula 195]

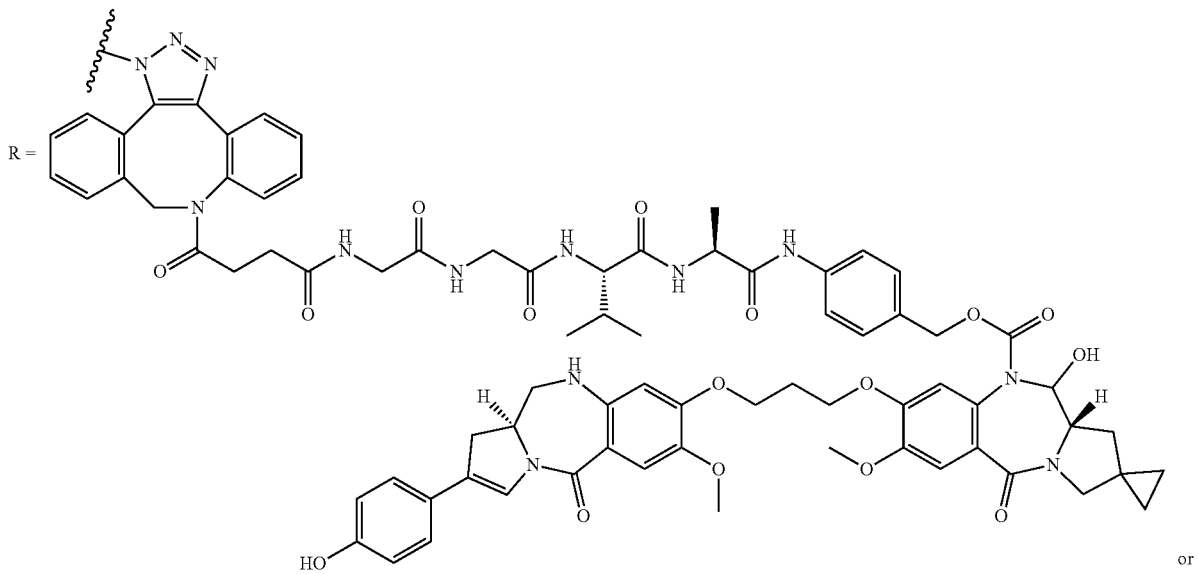

or

-continued

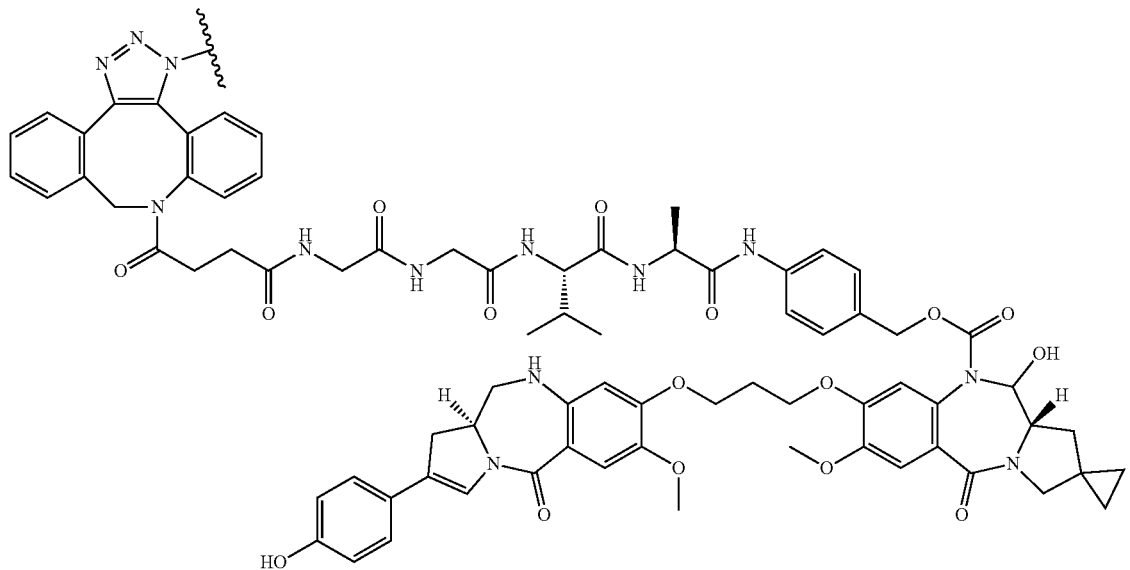

(The triazole ring to be formed in step 1 has geometric isomers, and the compound obtained in step 1 of Example 68 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 14 of Example 25 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.00 mL of a solution of the desired compound.

Characterization: The following characteristic values were obtained by using common operations E and F.

Antibody concentration: 1.48 mg/mL, antibody yield: 8.88 mg (89%), average number of conjugated drug molecules per antibody molecule (n): 1.9

Example 69: ADC3

[Formula 196]

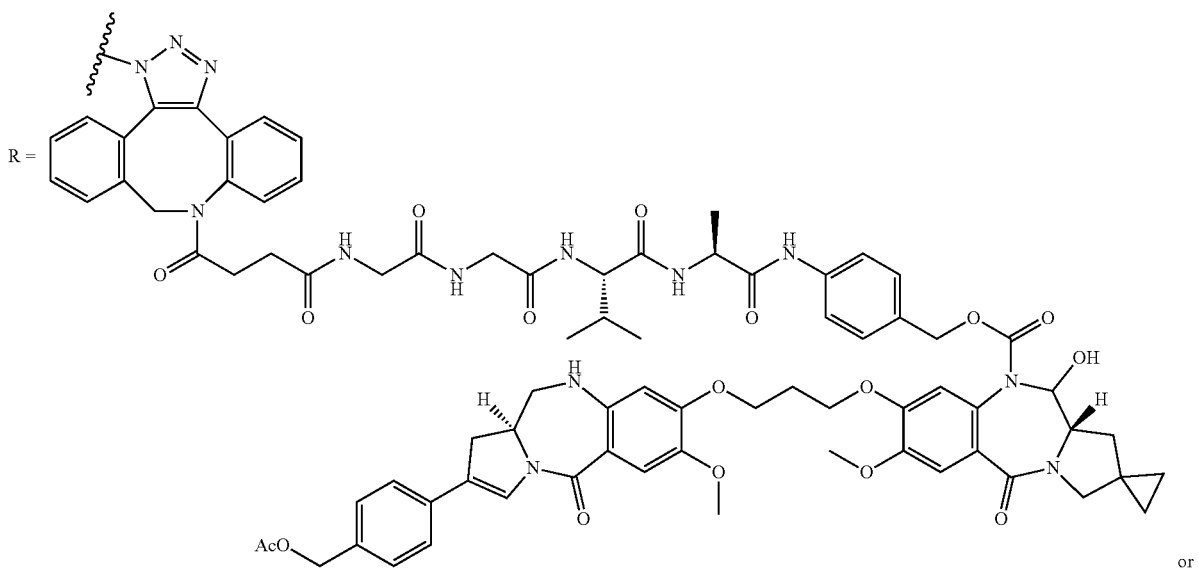

or

-continued

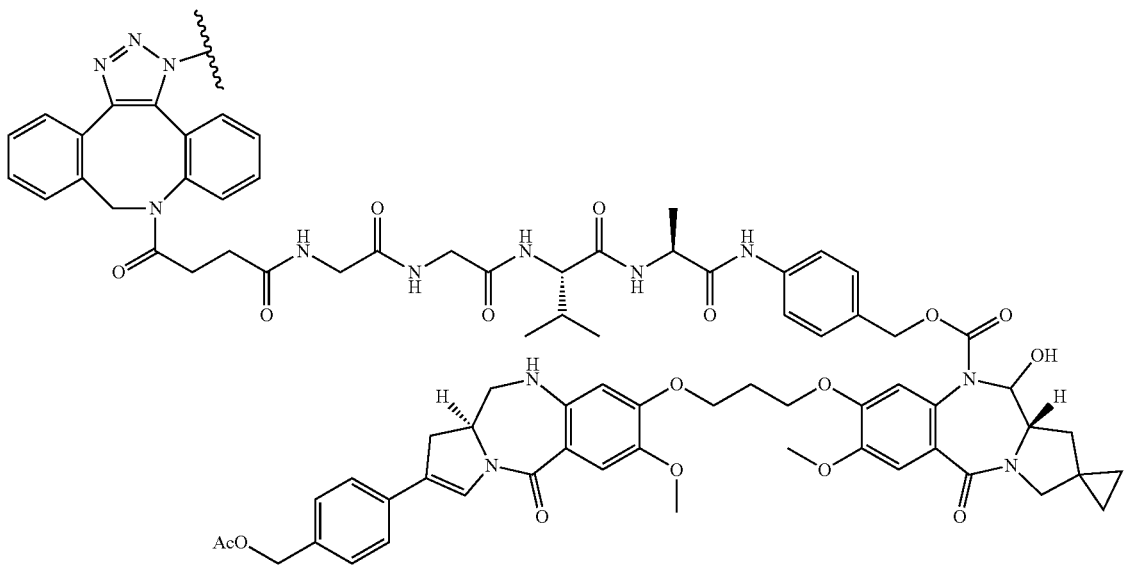

(The triazole ring to be formed in step 1 has geometric isomers, and the compound obtained in step 1 of Example 69 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 14 of Example 26 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.00 mL of a solution of the desired compound.

Characterization: The following characteristic values were obtained by using common operations E and F.

Antibody concentration: 1.45 mg/mL, antibody yield: 8.67 mg (89%), average number of conjugated drug molecules per antibody molecule (n): 1.9

Example 70: ADC4

[Formula 197]

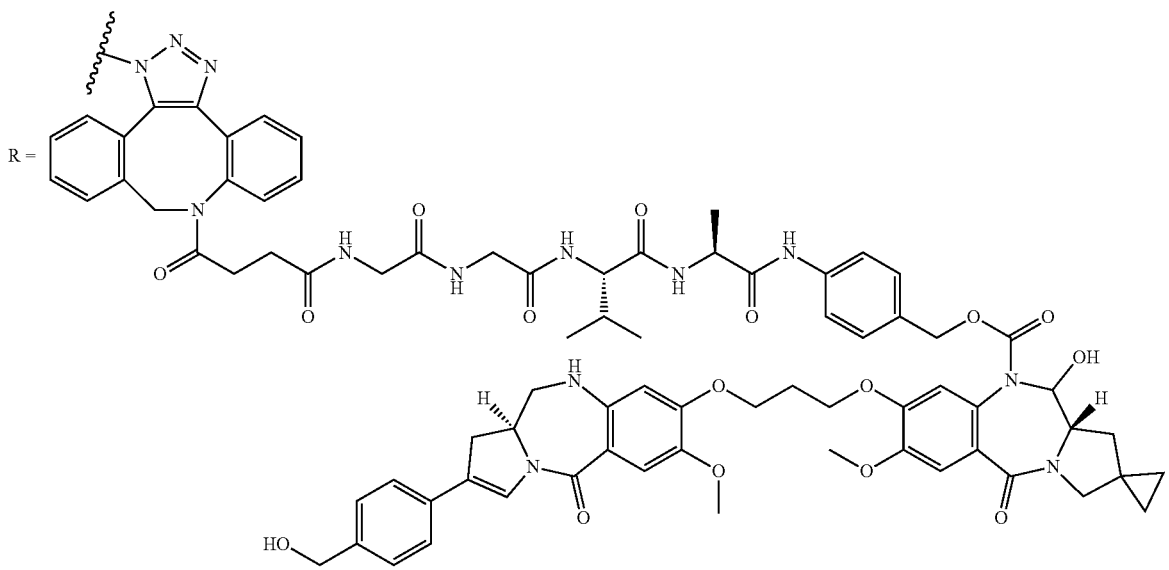

or

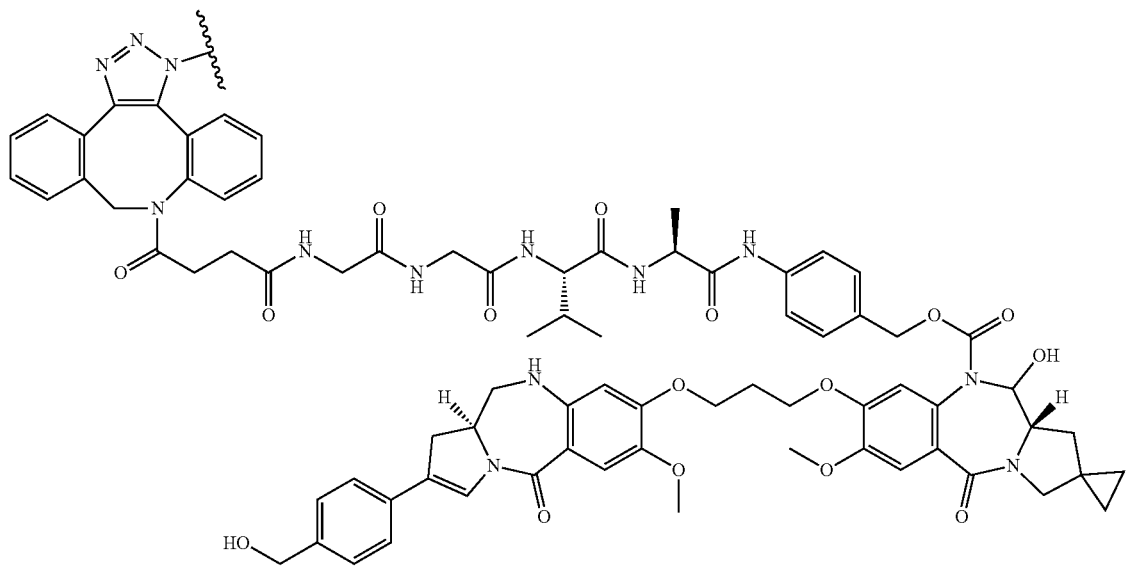

(The triazole ring to be formed in step 1 has geometric isomers, and the compound obtained in step 1 of Example 70 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 1 of Example 27 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.00 mL of a solution of the desired compound.

Characterization: The following characteristic values were obtained by using common operations E and F.

Antibody concentration: 1.30 mg/mL, antibody yield: 7.80 mg (78%), average number of conjugated drug molecules per antibody molecule (n): 1.9

Example 71: ADC5

[Formula 198]

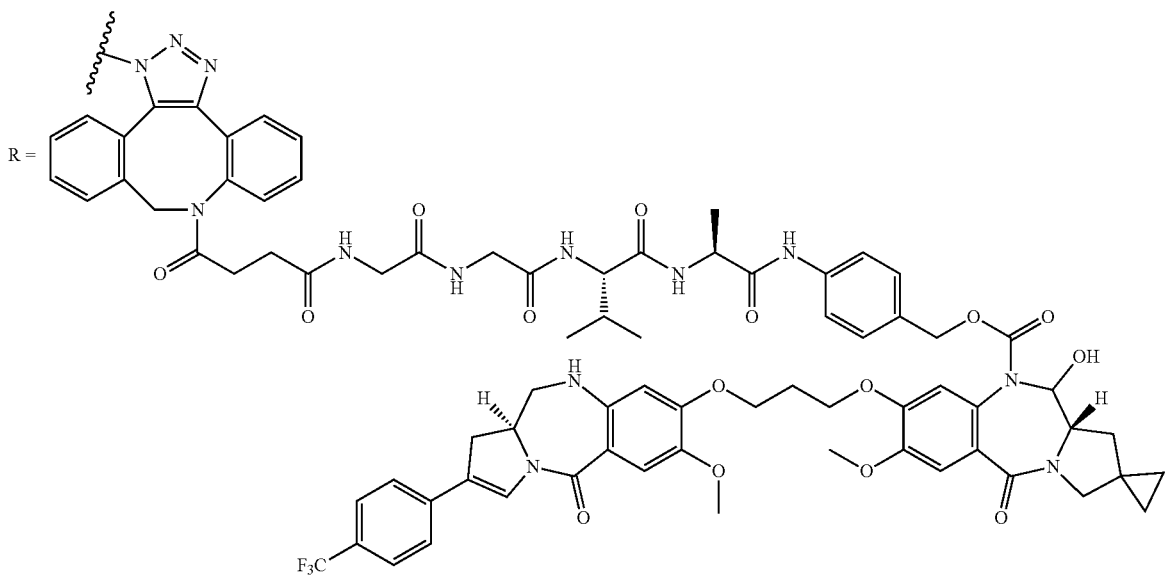

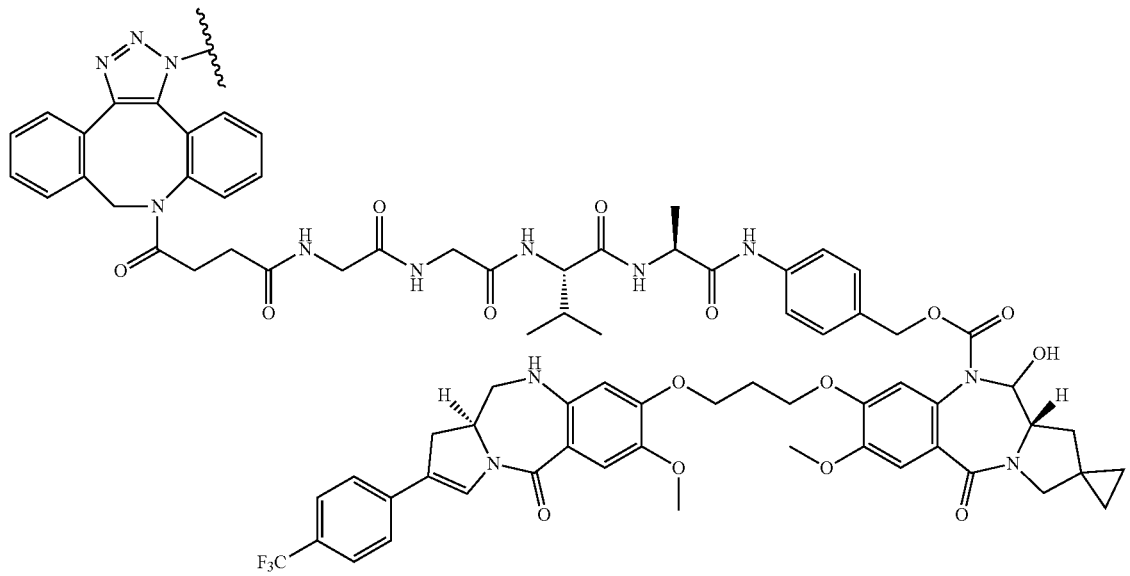

(The triazole ring to be formed in step 1 has geometric isomers, and the compound obtained in step 1 of Example 71 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 8 of Example 28 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.00 mL of a solution of the desired compound.

Characterization: The following characteristic values were obtained by using common operations E and F.

Antibody concentration: 1.08 mg/mL, antibody yield: 6.48 mg (65%), average number of conjugated drug molecules per antibody molecule (n): 1.6

Example 72: ADC6

[Formula 199]

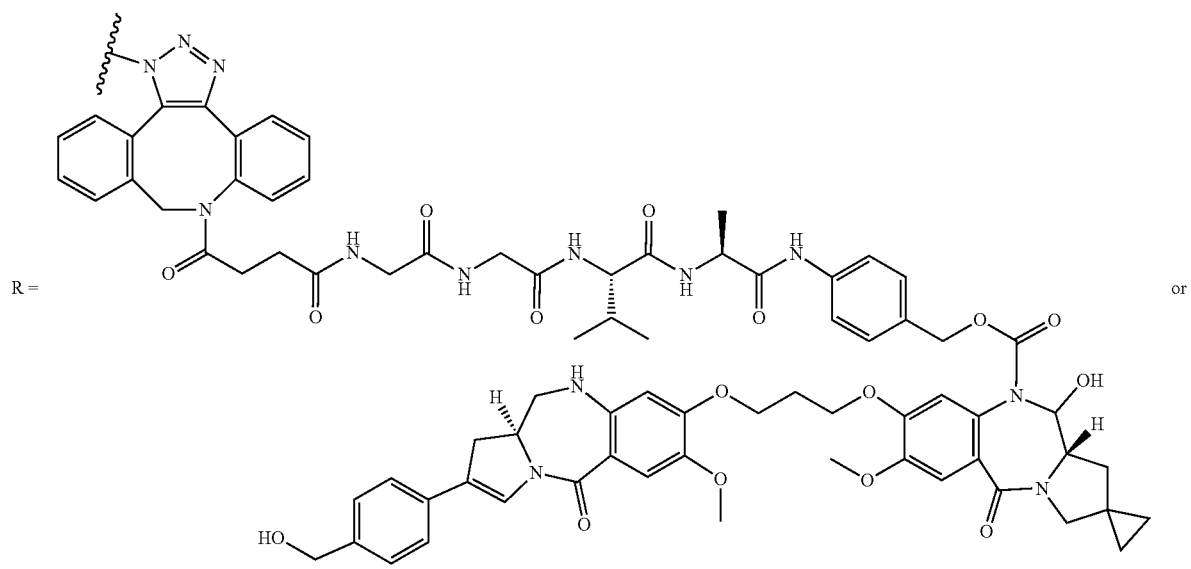

R =    or

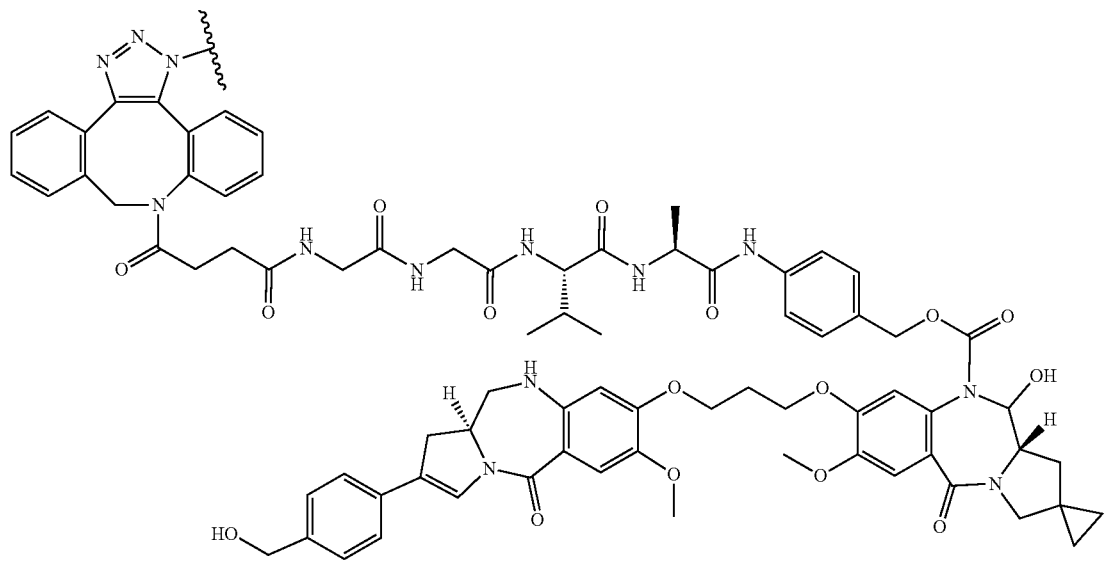

(The triazole ring to be formed in step 1 has geometric isomers, and the compound obtained in step 1 of Example 72 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 2 of Example 58, 1,2-propanediol (0.835 mL) and a 10 mM dimethyl sulfoxide solution of the compound obtained in step 1 of Example 27 (0.165 mL; 24 equivalents per antibody molecule) were added at room temperature, and the resultant was reacted using a tube rotator (MTR-103, AS ONE Corporation) at room temperature for 48 hours.

Purification operation: The solution was purified by using common operation D to afford 4.50 mL of a solution of the desired compound.

Characterization: The following characteristic values were obtained by using common operations E and F.

Antibody concentration: 1.75 mg/mL, antibody yield: 7.86 mg (79%), average number of conjugated drug molecules per antibody molecule (n): 3.8

Example 73: ADC7

[Formula 200]

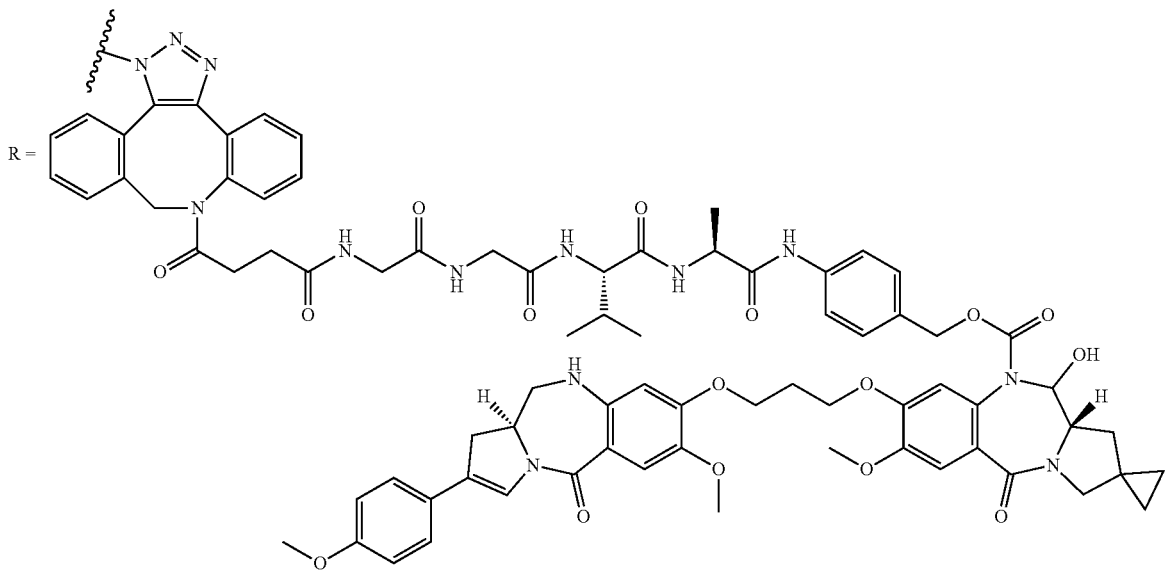

or

-continued

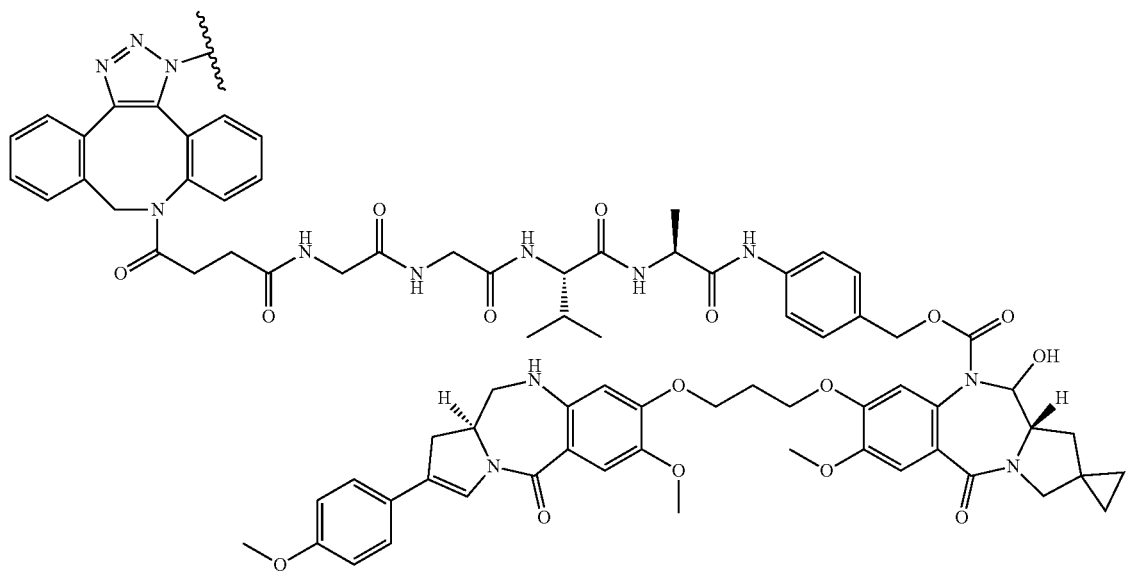

(The triazole ring to be formed in step 1 has geometric isomers, and the compound obtained in step 1 of Example 73 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 2 of Example 58, 1,2-propanediol (0.835 mL) and a 10 mM dimethyl sulfoxide solution of the compound obtained in step 12 of Example 4 (0.165 mL; 24 equivalents per antibody molecule) were added at room temperature, and the resultant was reacted using a tube rotator (MTR-103, AS ONE Corporation) at room temperature for 48 hours.

Purification operation: The solution was purified by using common operation D to afford 4.50 mL of a solution of the desired compound.

Characterization: The following characteristic values were obtained by using common operations E and F.

Antibody concentration: 1.66 mg/mL, antibody yield: 7.48 mg (75%), average number of conjugated drug molecules per antibody molecule (n): 3.8

Example 74: ADC8

[Formula 201]

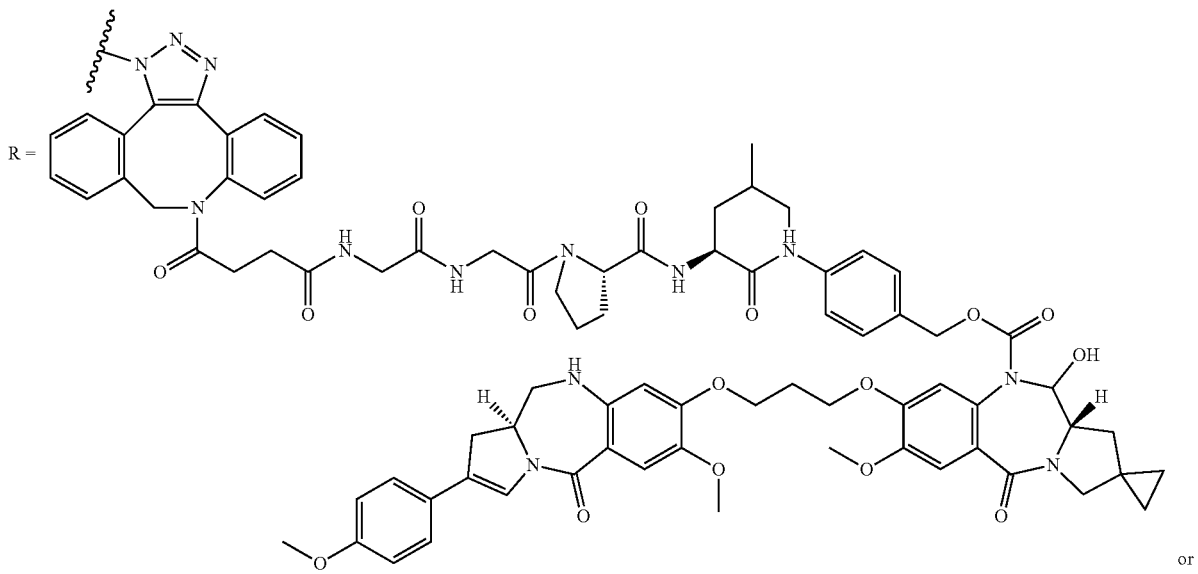

or

-continued

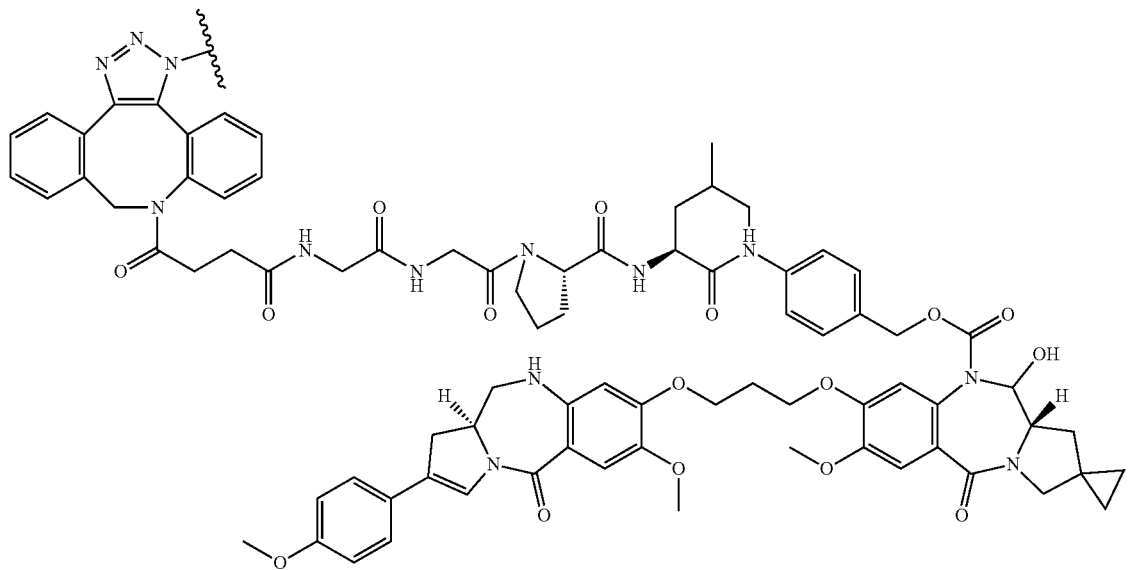

(The triazole ring to be formed in step 1 has geometric isomers, and the compound obtained in step 1 of Example 74 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 60, 1,2-propanediol (0.917 mL) and a 10 mM dimethyl sulfoxide solution of the compound obtained in step 14 of Example 29 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.00 mL of a solution of the desired compound.

Characterization: The following characteristic values were obtained by using common operations E and F.

Antibody concentration: 1.36 mg/mL, antibody yield: 8.17 mg (82%), average number of conjugated drug molecules per antibody molecule (n): 1.8

Example 75: ADC9

[Formula 202]

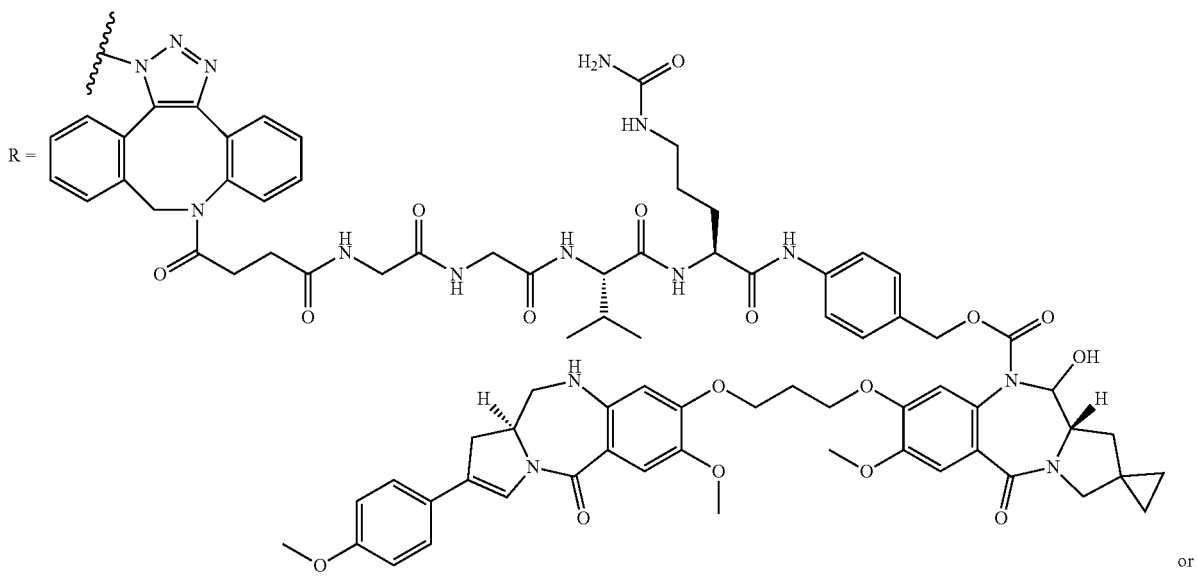

or

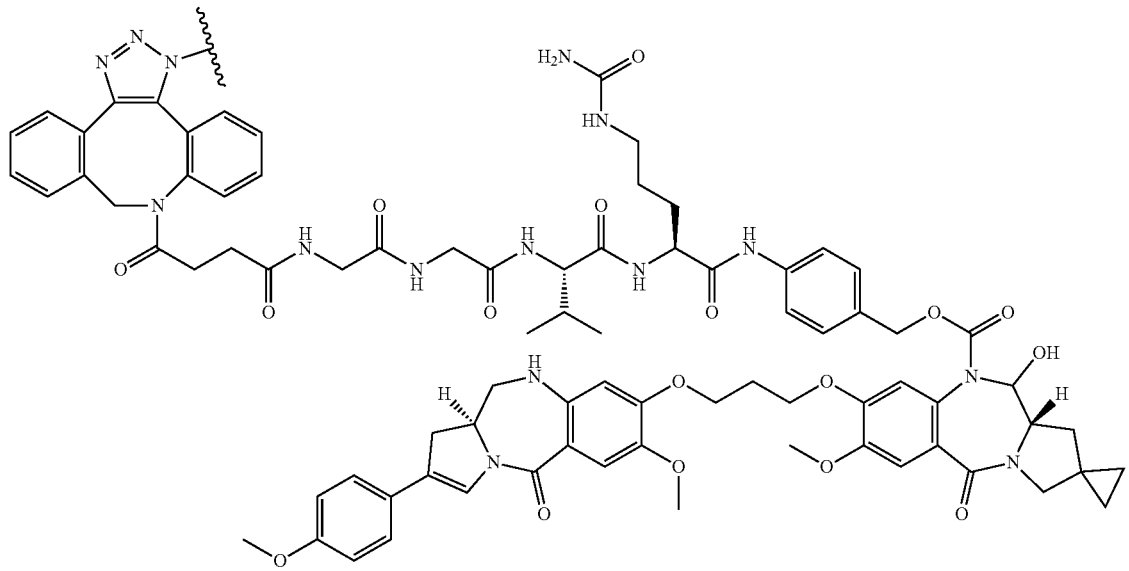

(The triazole ring to be formed in step 1 has geometric isomers, and the compound obtained in step 1 of Example 75 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 2 of Example 58, 1,2-propanediol (0.835 mL) and a 10 mM dimethyl sulfoxide solution of the compound obtained in step 9 of Example 9 (0.165 mL; 24 equivalents per antibody molecule) were added at room temperature, and the resultant was reacted using a tube rotator (MTR-103, AS ONE Corporation) at room temperature for 48 hours.

Purification operation: The solution was purified by using common operation D to afford 8.50 mL of a solution of the desired compound.

Characterization: The following characteristic values were obtained by using common operations E and F.

Antibody concentration: 0.86 mg/mL, antibody yield: 7.35 mg (73%), average number of conjugated drug molecules per antibody molecule (n): 3.6

Example 76: ADC10

[Formula 203]

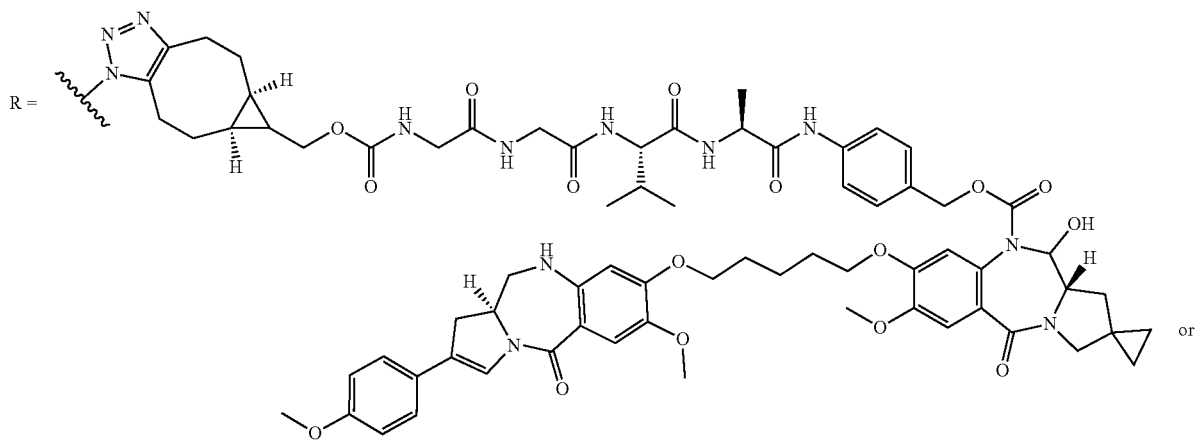

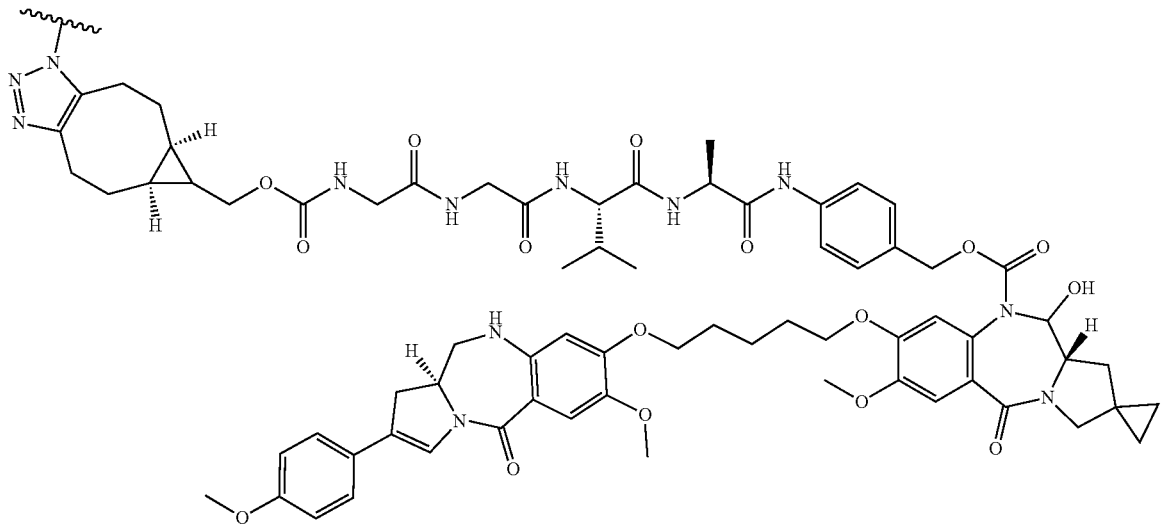

(The triazole ring to be formed in step 1 has geometric isomers, and the compound obtained in step 1 of Example 76 has a linker as a mixture of the two structures shown above as R.)

Step 1: Conjugation of Antibody and Drug-Linker

As illustrated in the reaction formula in Example 106, to a phosphate buffered saline (pH 6.0) solution of the antibody (10.2 mg/mL, 0.400 mL) obtained in step 2 of Example 61, 1,2-propanediol (0.200 mL), a 10 mM dimethyl sulfoxide solution of the compound obtained in step 2 of Example 30 (0.0549 mL; 20 equivalents per antibody molecule), and dimethyl sulfoxide (0.145 mL) were added at room temperature, and the resultant was reacted using a tube rotator (MTR-103, AS ONE Corporation) at room temperature for 72 hours.

Purification operation: The solution was purified by using common operation D to afford 2.50 mL of a solution of the desired compound.

Characterization: The following characteristic values were obtained by using common operations E and F.

Antibody concentration: 1.19 mg/mL, antibody yield: 2.98 mg (75%), average number of conjugated drug molecules per antibody molecule (n): 1.8

Example 77: ADC11

[Formula 204]

R =

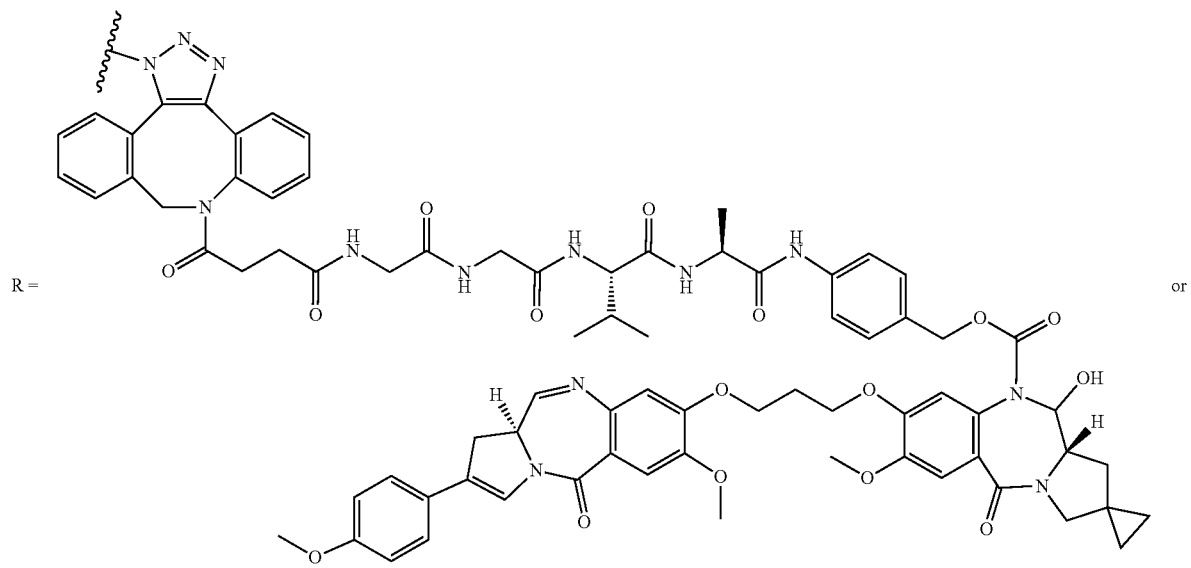

or

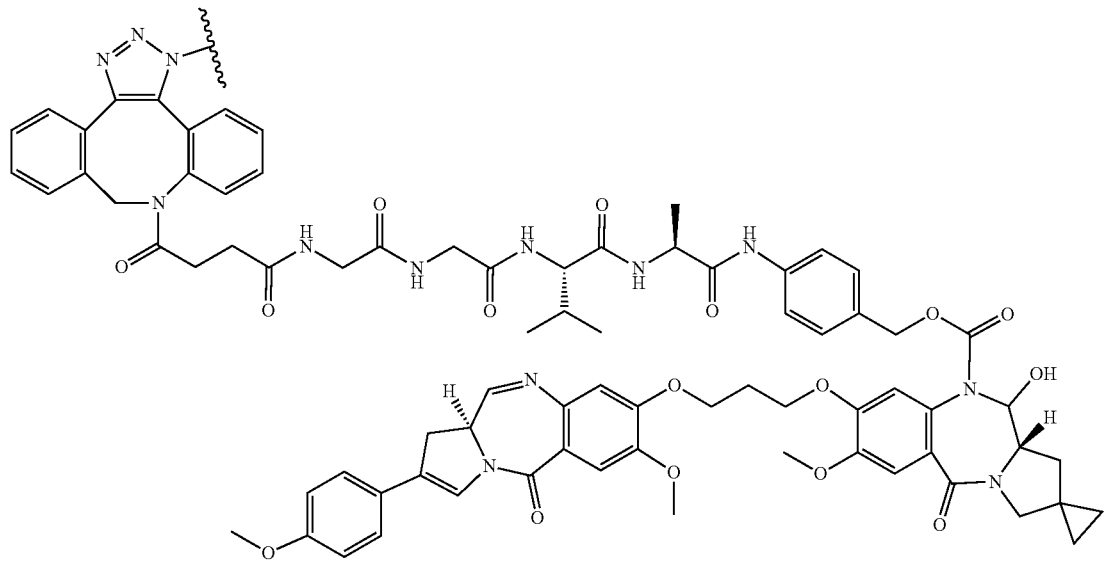

(The triazole ring to be formed in step 1 has geometric isomers, and the compound obtained in step 1 of Example 77 has a linker as a mixture of the two structures shown above as R.)

Step 1: Conjugation of Antibody and Drug-Linker

To a phosphate buffered saline (pH 6.0) solution of the antibody (9.88 mg/mL, 0.500 mL) obtained in step 1 of Example 59, 1,2-propanediol (0.459 mL) and a 10 mM dimethyl sulfoxide solution of the compound obtained in step 12 of Example 19 (0.0408 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D, and the resulting solution was concentrated by using common operation A to afford 0.470 mL of a solution of the desired compound.

Characterization: The following characteristic values were obtained by using common operations E and F.

Antibody concentration: 8.31 mg/mL, antibody yield: 3.90 mg (79%), average number of conjugated drug molecules per antibody molecule (n): 1.8

Example 78: ADC12

[Formula 205]

R =

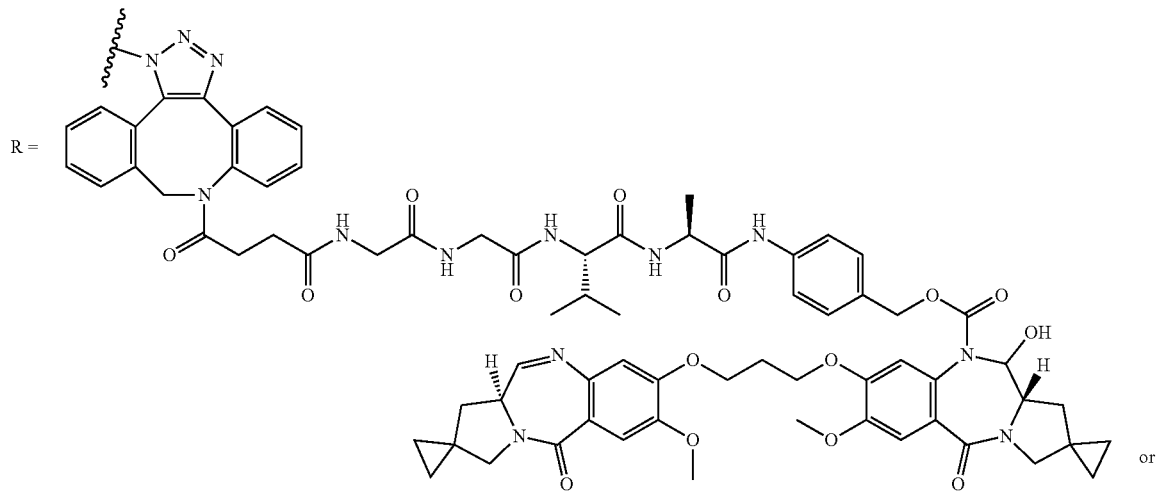

or

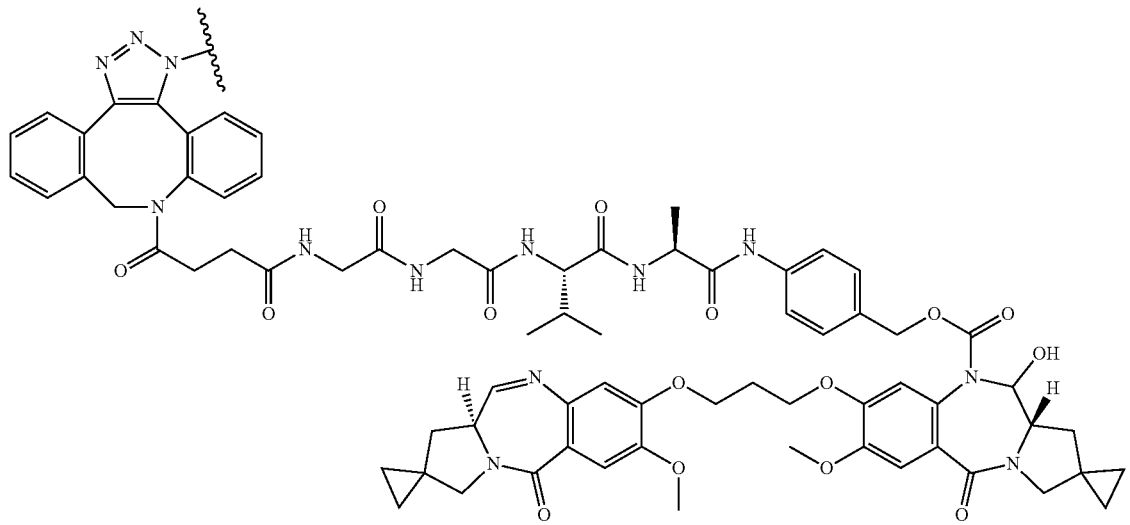

(The triazole ring to be formed in step 1 has geometric isomers, and the compound obtained in step 1 of Example 78 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 8 of Example 20 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D, and the resulting solution was then concentrated by using common operation A to afford 0.75 mL of a solution of the desired compound.

Characterization: The following characteristic values were obtained by using common operations E and F.

Antibody concentration: 8.70 mg/mL, antibody yield: 6.94 mg (69%), average number of conjugated drug molecules per antibody molecule (n): 1.7

Example 79: ADC13

[Formula 206]

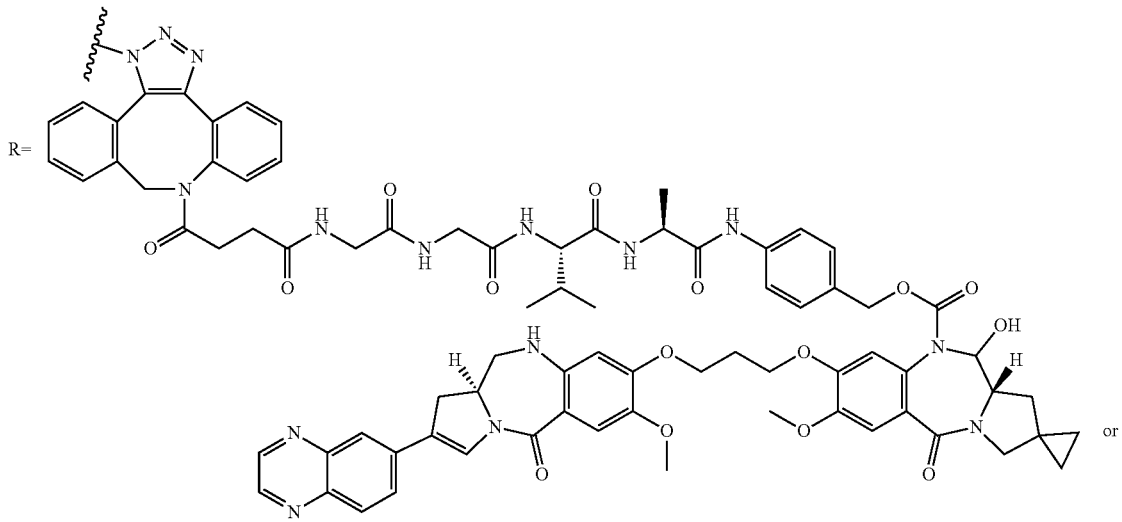

or

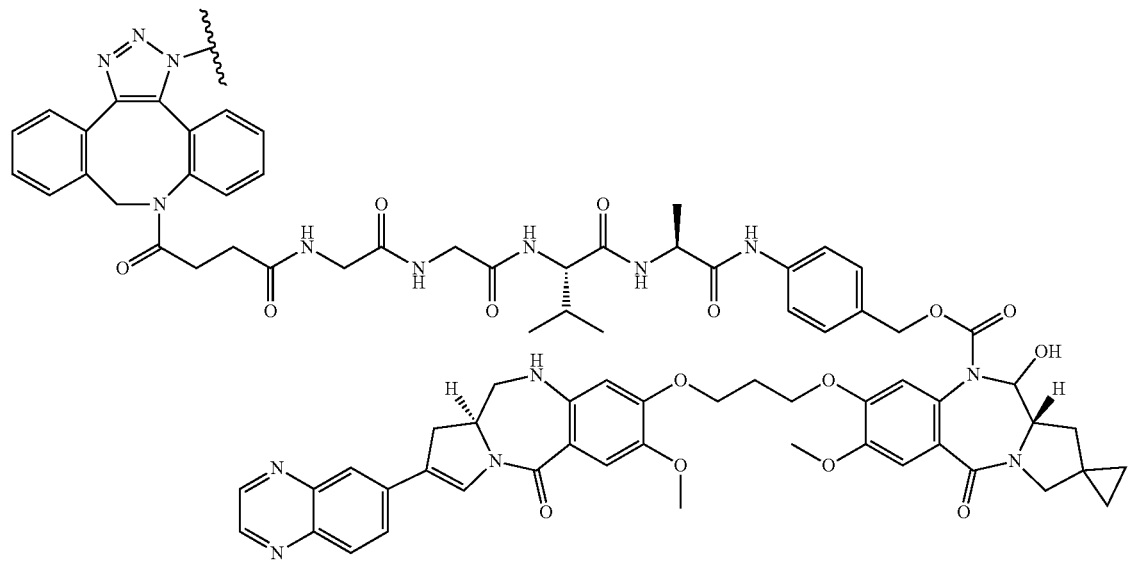

(The triazole ring to be formed in step 1 has geometric isomers, and the compound obtained in step 1 of Example 79 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 18 of Example 21 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.00 mL of a solution of the desired compound.

Characterization: The following characteristic values were obtained by using common operations E and F.

Antibody concentration: 0.96 mg/mL, antibody yield: 5.77 mg (58%), average number of conjugated drug molecules per antibody molecule (n): 1.9

Example 80: ADC14

[Formula 207]

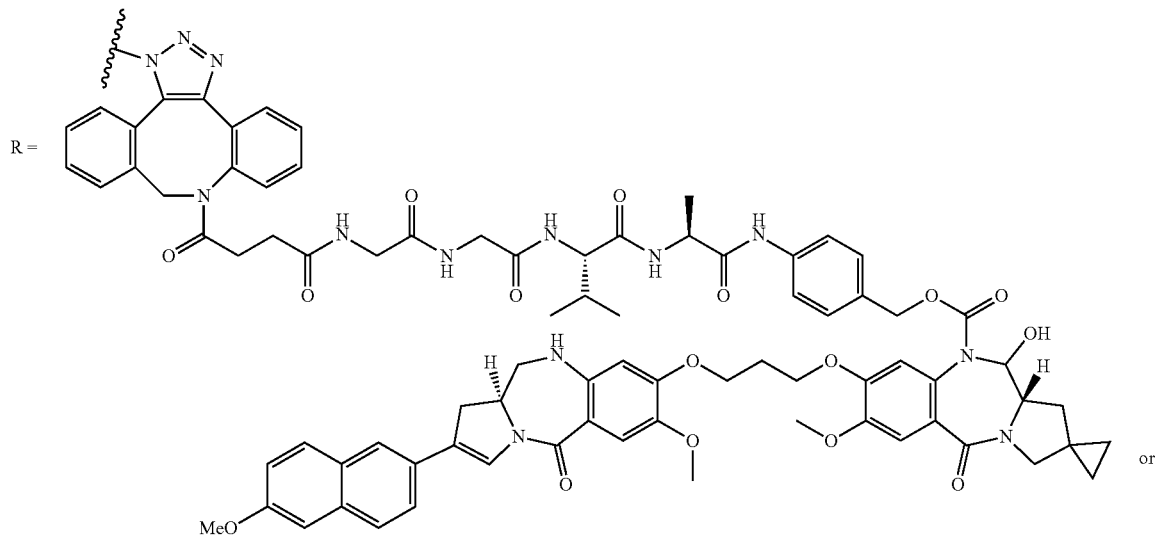

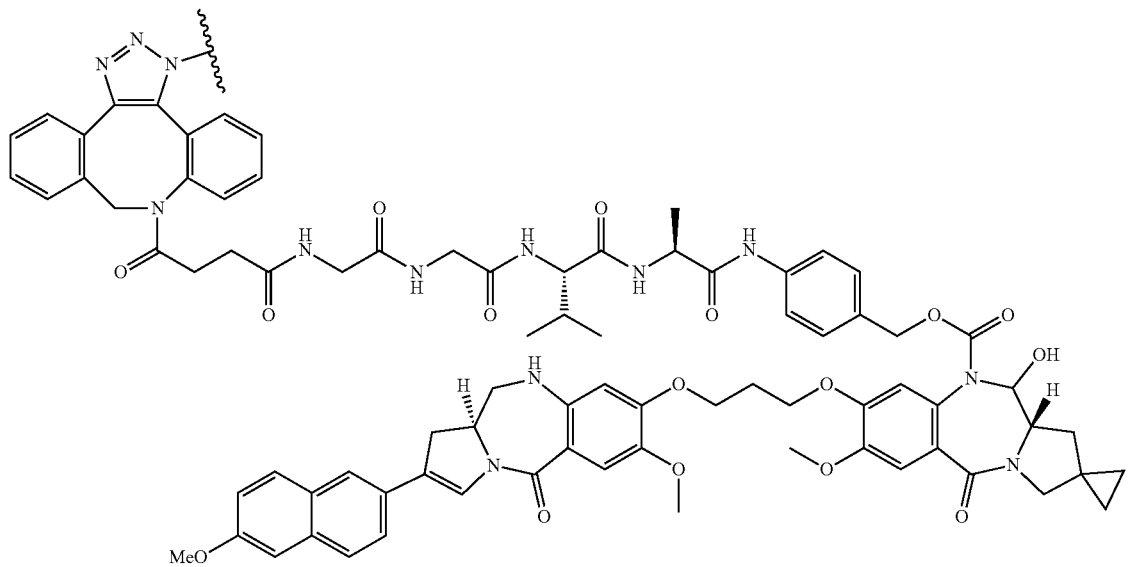

(The triazole ring to be formed in step 1 has geometric isomers, and the compound obtained in step 1 of Example 80 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 12 of Example 22 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.00 mL of a solution of the desired compound.

Characterization: The following characteristic values were obtained by using common operations E and F.

Antibody concentration: 1.28 mg/mL, antibody yield: 7.70 mg (77%), average number of conjugated drug molecules per antibody molecule (n): 1.8

Example 81: ADC15

[Formula 208]

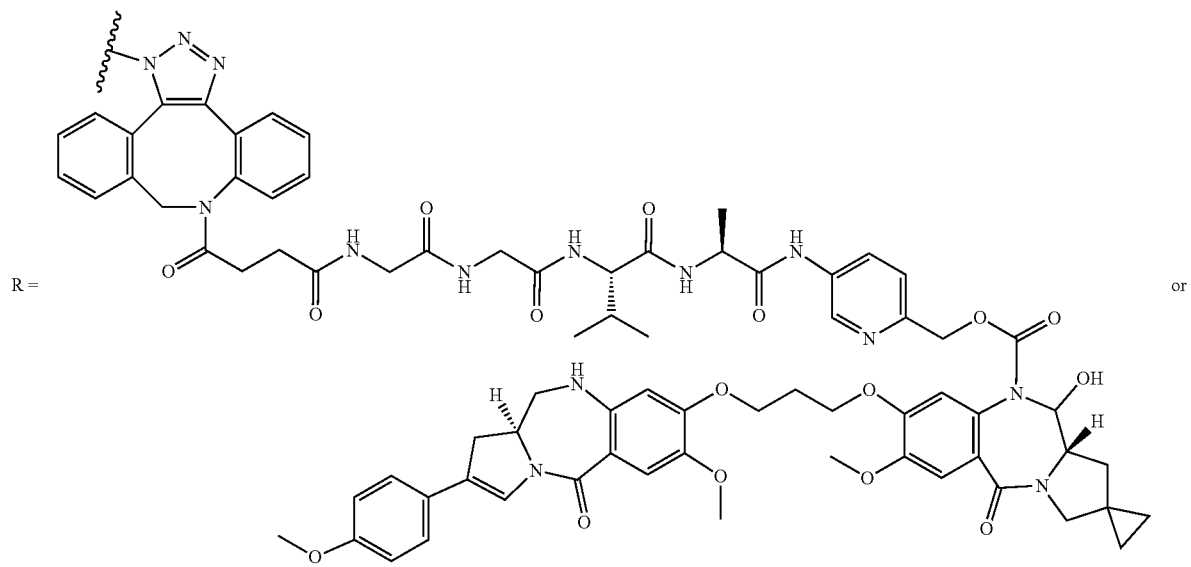

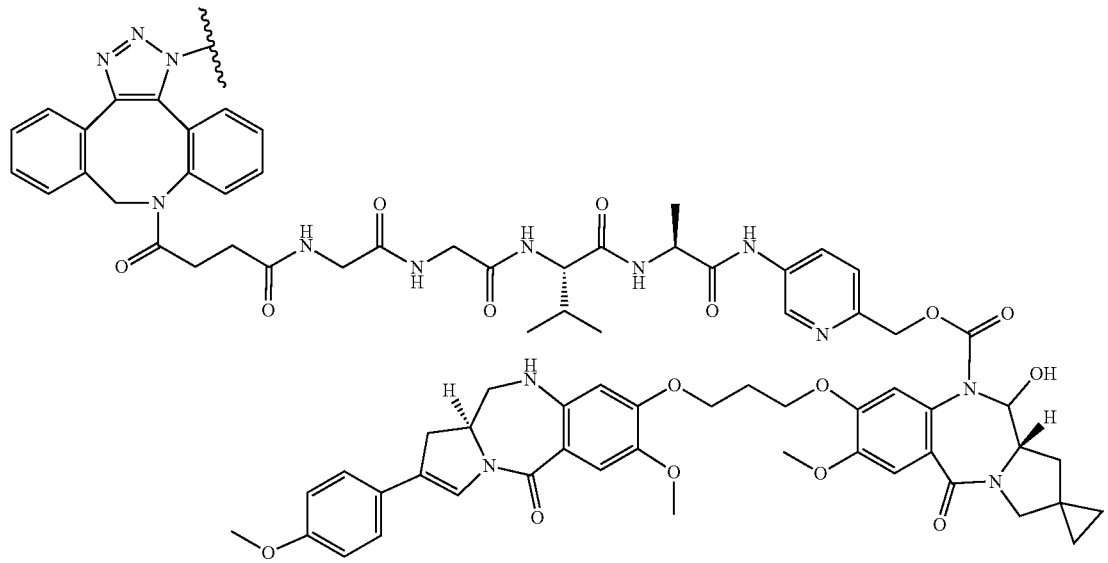

(The triazole ring to be formed in step 1 has geometric isomers, and the compound obtained in step 1 of Example 81 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 60, 1,2-propanediol (0.917 mL) and a 10 mM dimethyl sulfoxide solution of the compound obtained in step 10 of Example 23 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.00 mL of a solution of the desired compound.

Characterization: The following characteristic values were obtained by using common operations E and F.

Antibody concentration: 1.60 mg/mL, antibody yield: 9.60 mg (96%), average number of conjugated drug molecules per antibody molecule (n): 1.9

Example 82: ADC16

[Formula 209]

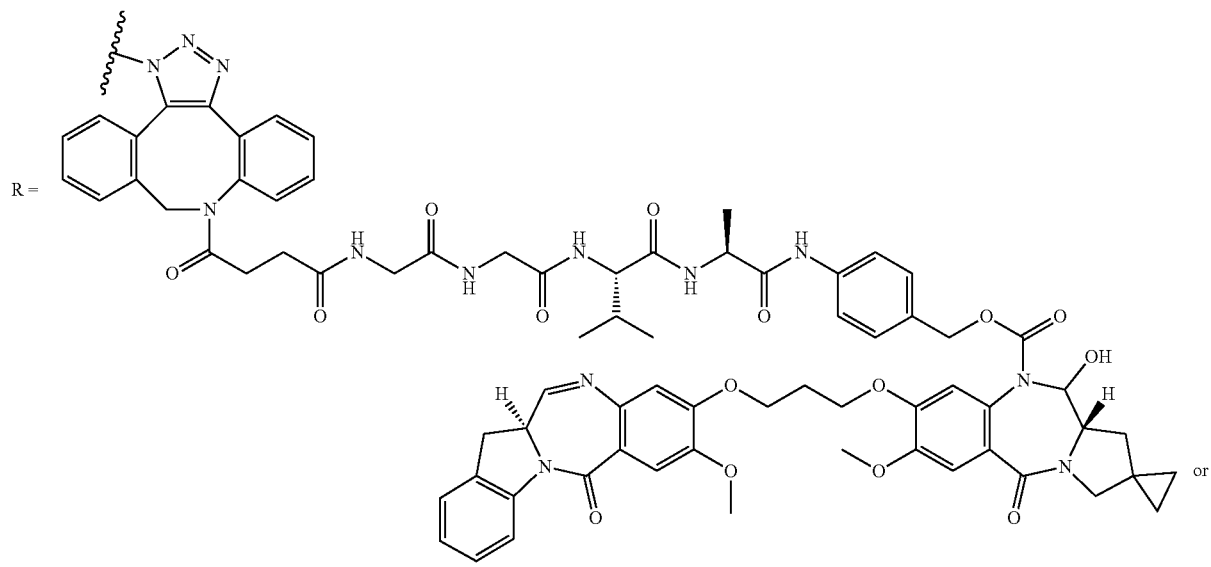

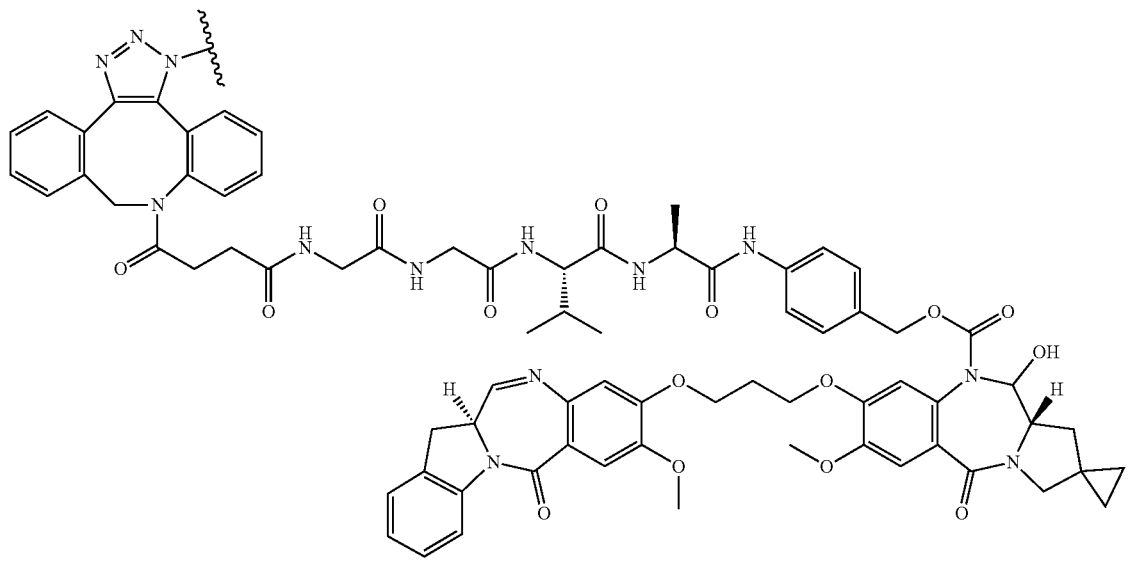

(The triazole ring to be formed in step 1 has geometric isomers, and the compound obtained in step 1 of Example 82 has a linker as a mixture of the two structures shown above as R.)

Step 1: Conjugation of Antibody and Drug-Linker

To a phosphate buffered saline (pH 6.0) solution of the antibody (9.88 mg/mL, 0.500 mL) obtained in step 1 of Example 59, 1,2-propanediol (0.459 mL) and a 10 mM dimethyl sulfoxide solution of the compound obtained in step 11 of Example 34 (0.0408 mL; 12 equivalents per antibody molecule) were added at room temperature, and the resultant was reacted using a tube rotator (MTR-103, AS ONE Corporation) at room temperature for 1 day.

Purification operation: The solution was purified by using common operation D to afford 10.5 mL of a solution of the desired compound. This solution was concentrated by using common operation A to afford 0.500 mL of a solution of the desired compound.

Characterization: The following characteristic values were obtained by using common operations E and F.

Antibody concentration: 6.94 mg/mL, antibody yield: 3.47 mg (70%), average number of conjugated drug molecules per antibody molecule (n): 1.8

Example 83: ADC17

[Formula 210]

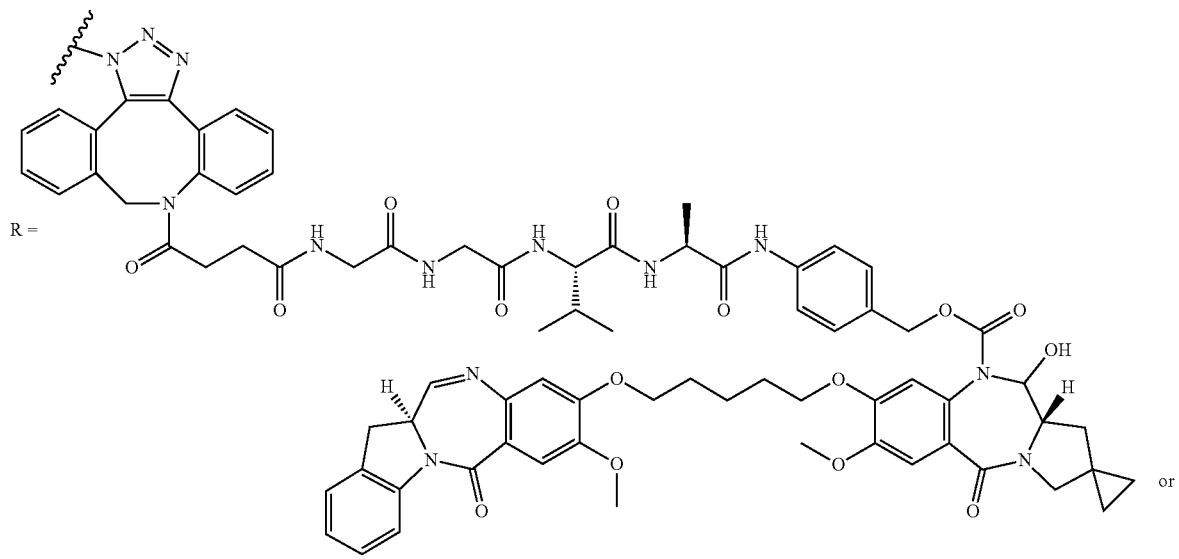

-continued

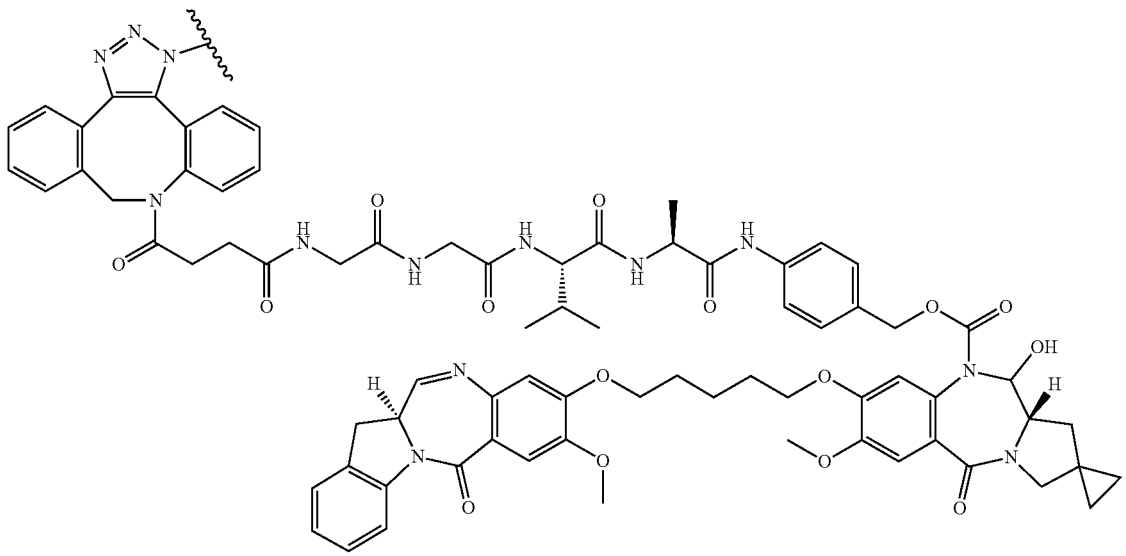

(The triazole ring to be formed in step 1 has geometric isomers, and the compound obtained in step 1 of Example 83 has a linker as a mixture of the two structures shown above as R.)

Step 1: Conjugation of Antibody and Drug-Linker

To a phosphate buffered saline (pH 6.0) solution of the antibody (9.88 mg/mL, 0.500 mL) obtained in step 1 of Example 59, 1,2-propanediol (0.459 mL) and a 10 mM dimethyl sulfoxide solution of the compound obtained in step 4 of Example 35 (0.0408 mL; 12 equivalents per antibody molecule) were added at room temperature, and the resultant was reacted using a tube rotator (MTR-103, AS ONE Corporation) at room temperature for 1 day.

Purification operation: The solution was purified by using common operation D, and the resulting solution was concentrated by using common operation A to afford 0.500 mL of a solution of the desired compound.

Characterization: The following characteristic values were obtained by using common operations E and F.

Antibody concentration: 8.07 mg/mL, antibody yield: 4.03 mg (82%), average number of conjugated drug molecules per antibody molecule (n): 1.8

Example 84: ADC18

[Formula 211]

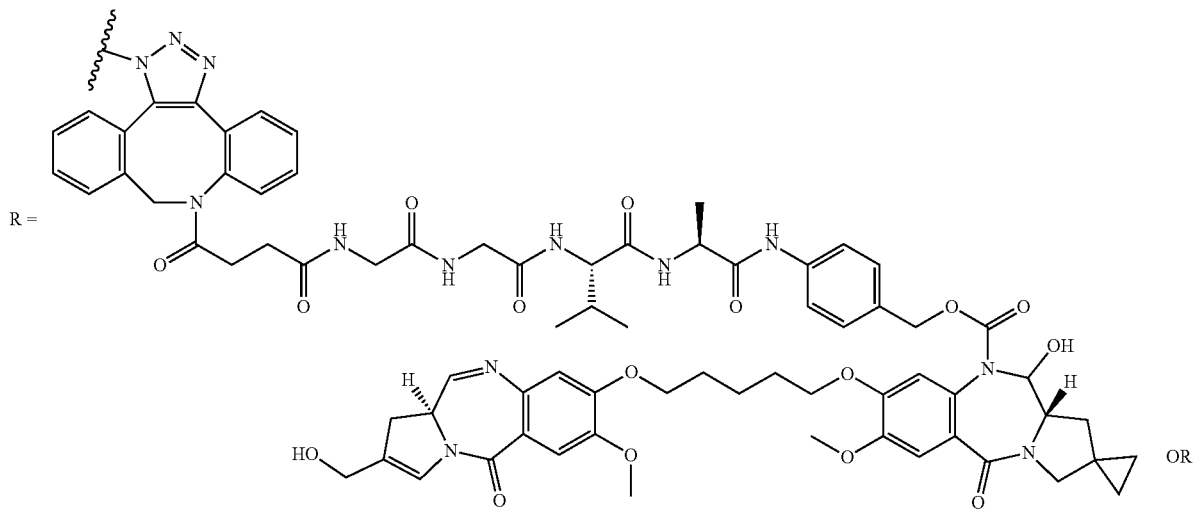

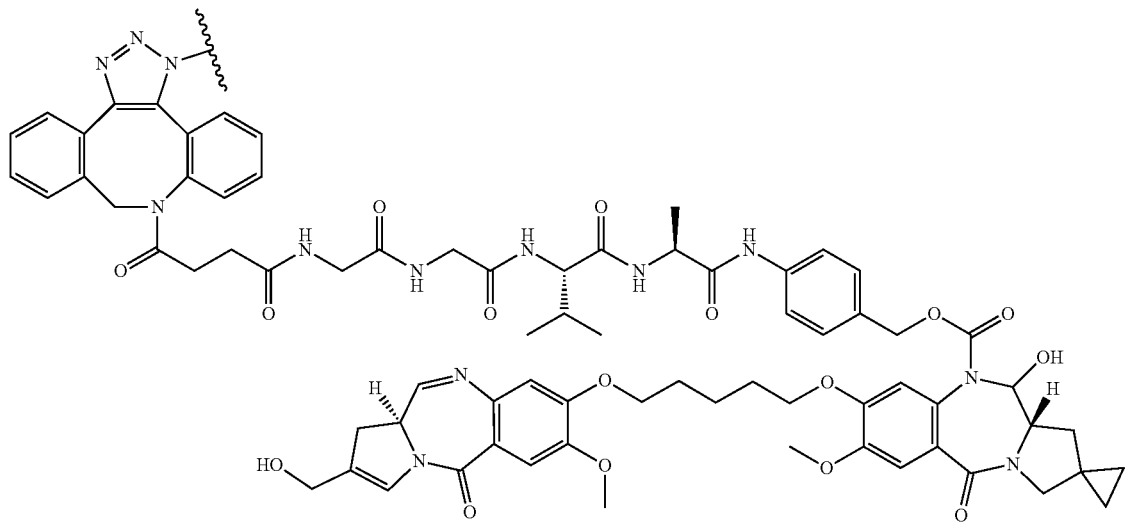

(The triazole ring to be formed in step 1 has geometric isomers, and the compound obtained in step 1 of Example 86 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 7 of Example 36 (0.0825 mL; 12 equivalents per antibody molecule) were added at room temperature, and the resultant was reacted using a tube rotator (MTR-103, AS ONE Corporation) at room temperature for 1 day.

Purification operation: The solution was purified by using common operation D to afford 14.0 mL of a solution of the desired compound. This solution was concentrated by using common operation A to afford 0.700 mL of a solution of the desired compound.

Characterization: The following characteristic values were obtained by using common operations E and F.

Antibody concentration: 12.9 mg/mL, antibody yield: 9.00 mg (90%), average number of conjugated drug molecules per antibody molecule (n): 1.9

Example 85: ADC19

[Formula 212]

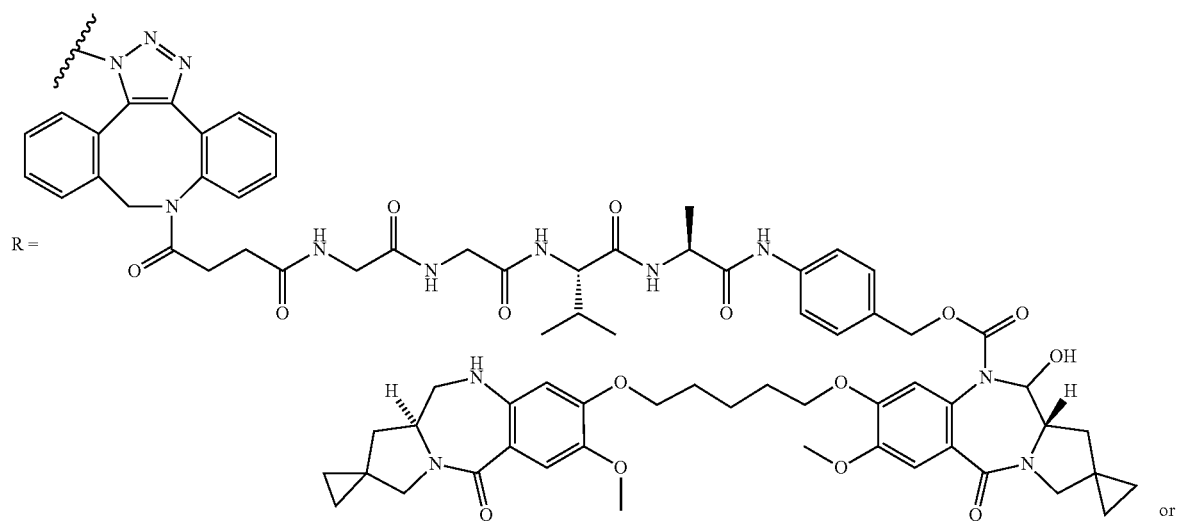

or

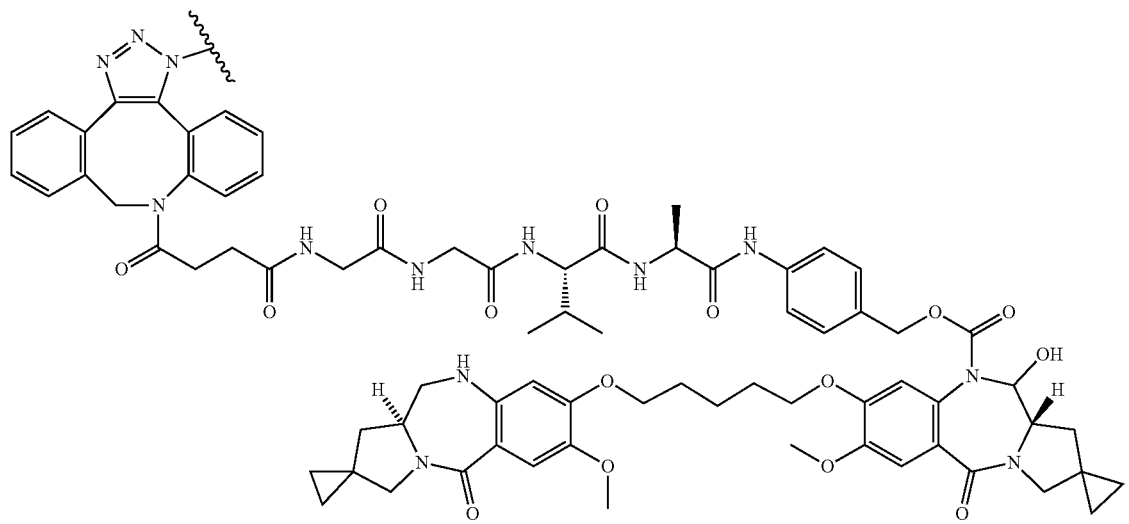

(The triazole ring to be formed in step 1 has geometric isomers, and the compound obtained in step 1 of Example 85 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 12 of Example 37 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.0 mL of a solution of the desired compound.

Characterization: The following characteristic values were obtained by using common operations E and F.

Antibody concentration: 1.33 mg/mL, antibody yield: 7.97 mg (80%), average number of conjugated drug molecules per antibody molecule (n): 1.9

Example 86: ADC20

[Formula 213]

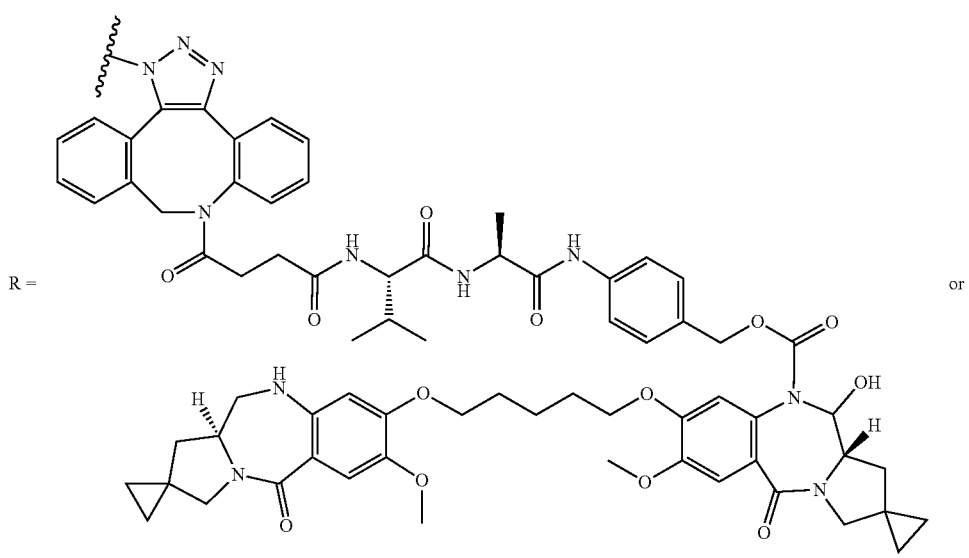

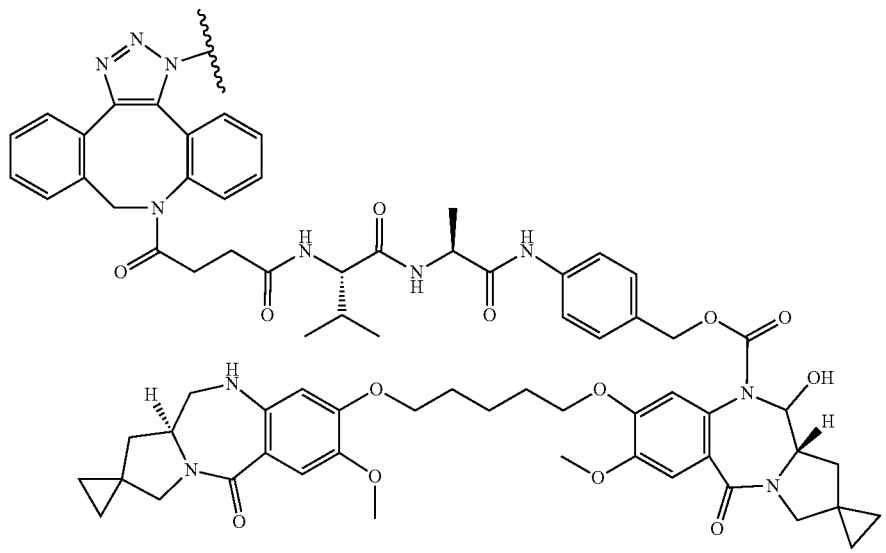

(The triazole ring to be formed in step 1 has geometric isomers, and the compound obtained in step 1 of Example 86 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 1 of Example 38 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.0 mL of a solution of the desired compound.

Characterization: The following characteristic values were obtained by using common operations E and F.

Antibody concentration: 1.56 mg/mL, antibody yield: 9.37 mg (94%), average number of conjugated drug molecules per antibody molecule (n): 2.0

Example 87: ADC21

[Formula 214]

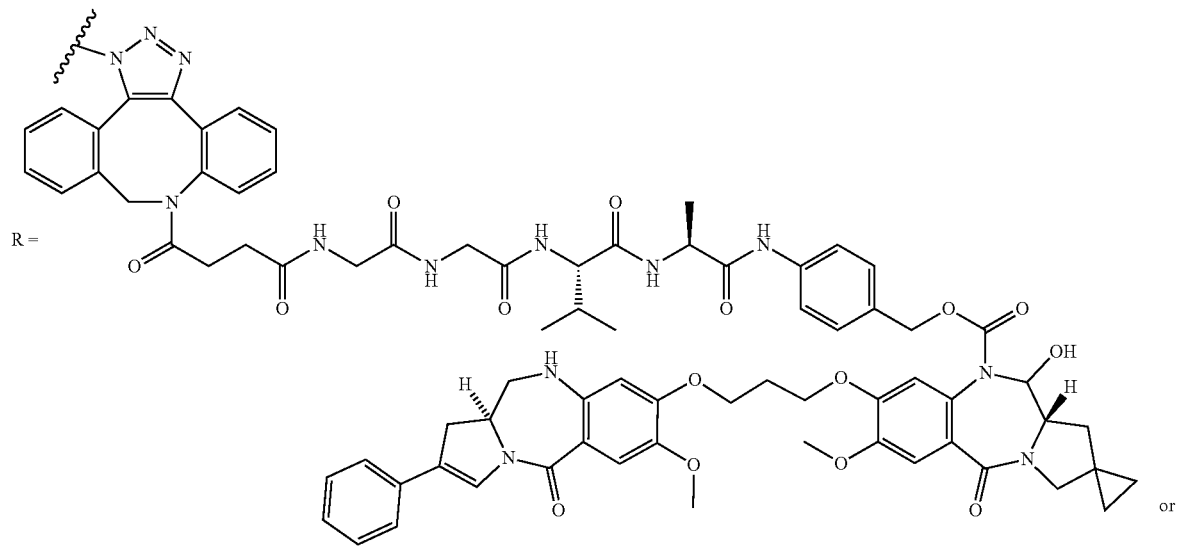

or

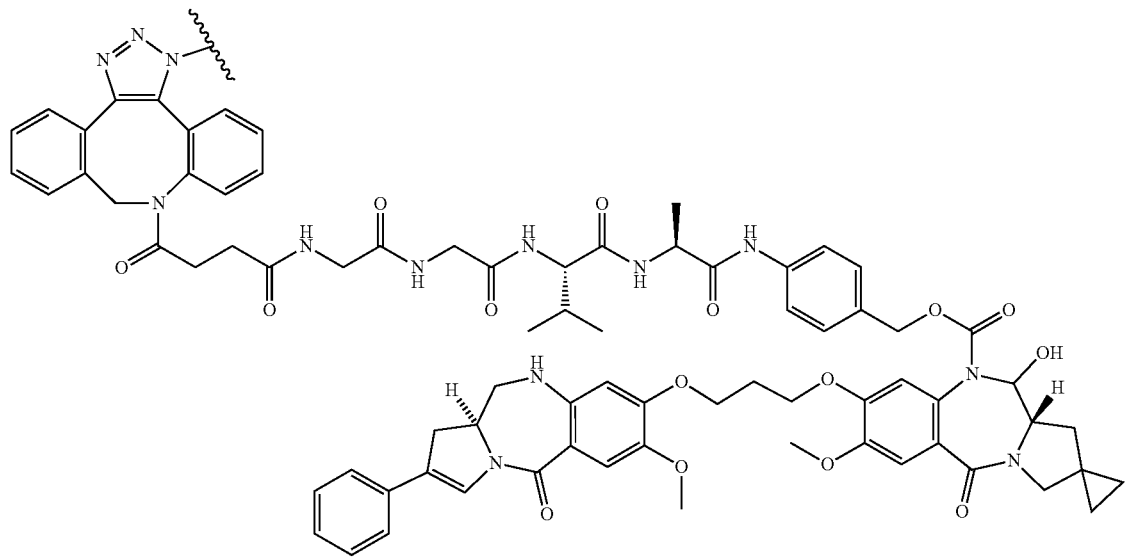

(The triazole ring to be formed in step 1 has geometric isomers, and the compound obtained in step 1 of Example 87 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 6 of Example 39 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.0 mL of a solution of the desired compound.

Characterization: The following characteristic values were obtained by using common operations E and F.

Antibody concentration: 1.89 mg/mL, antibody yield: 11.4 mg (quantitative), average number of conjugated drug molecules per antibody molecule (n): 1.9

Example 88: ADC22

[Formula 215]

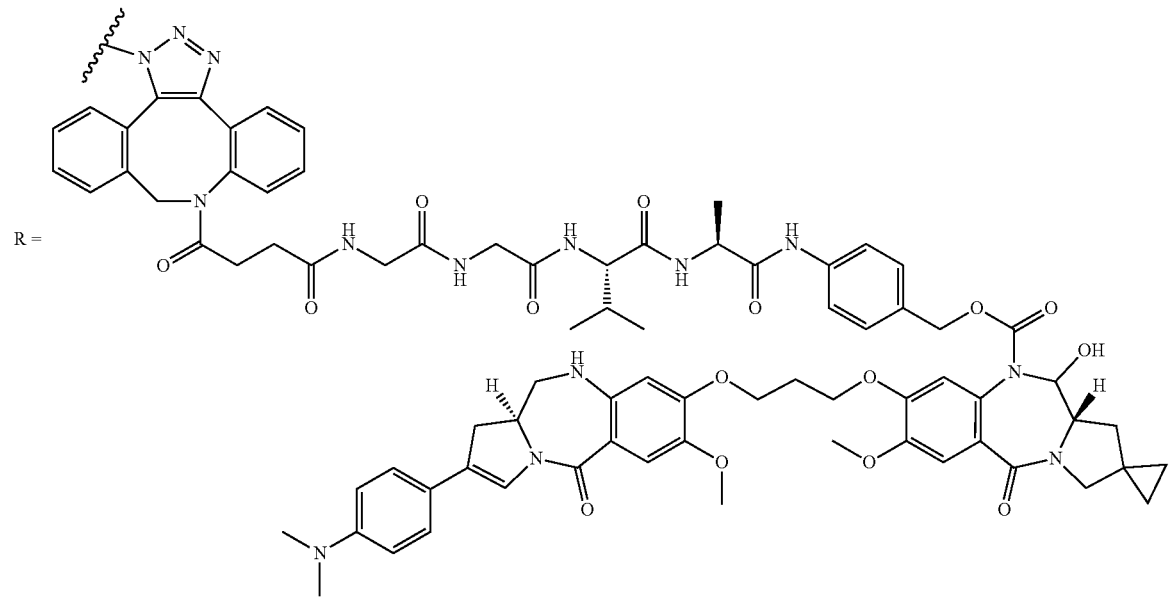

or

-continued

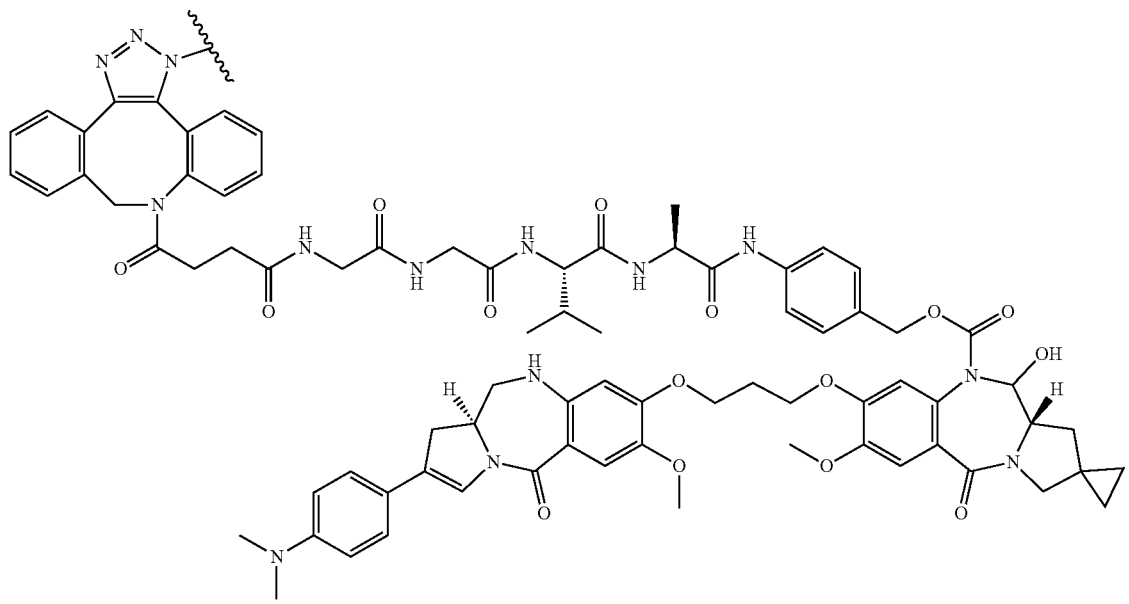

(The triazole ring to be formed in step 1 has geometric isomers, and the compound obtained in Example 88 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 6 of Example 40 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.0 mL of a solution of the desired compound.

Characterization: The following characteristic values were obtained by using common operations E and F.

Antibody concentration: 1.47 mg/mL, antibody yield: 8.84 mg (88%), average number of conjugated drug molecules per antibody molecule (n): 1.9

Example 89: ADC23

[Formula 216]

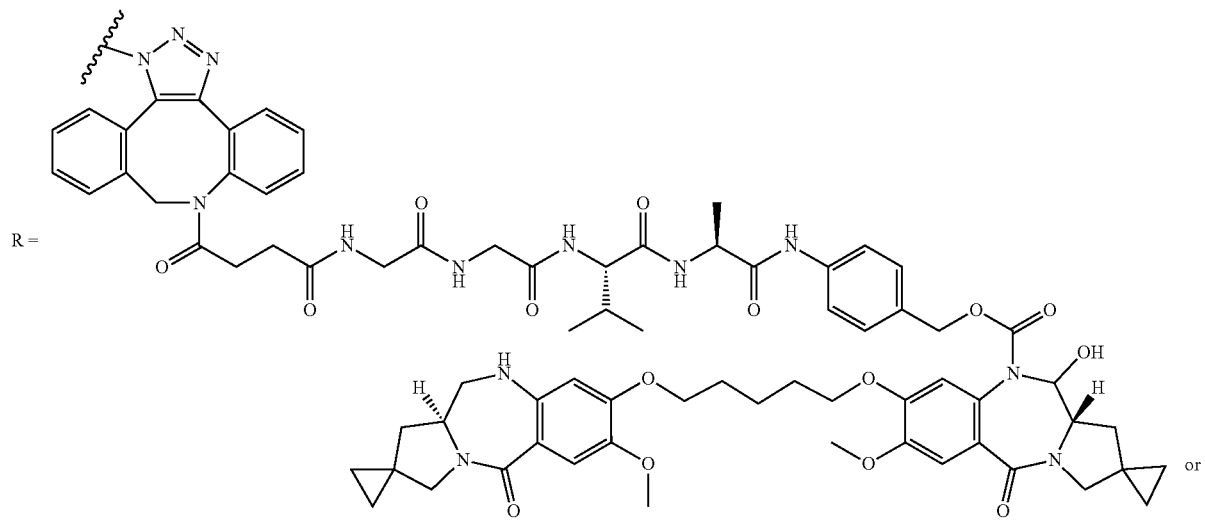

R = or

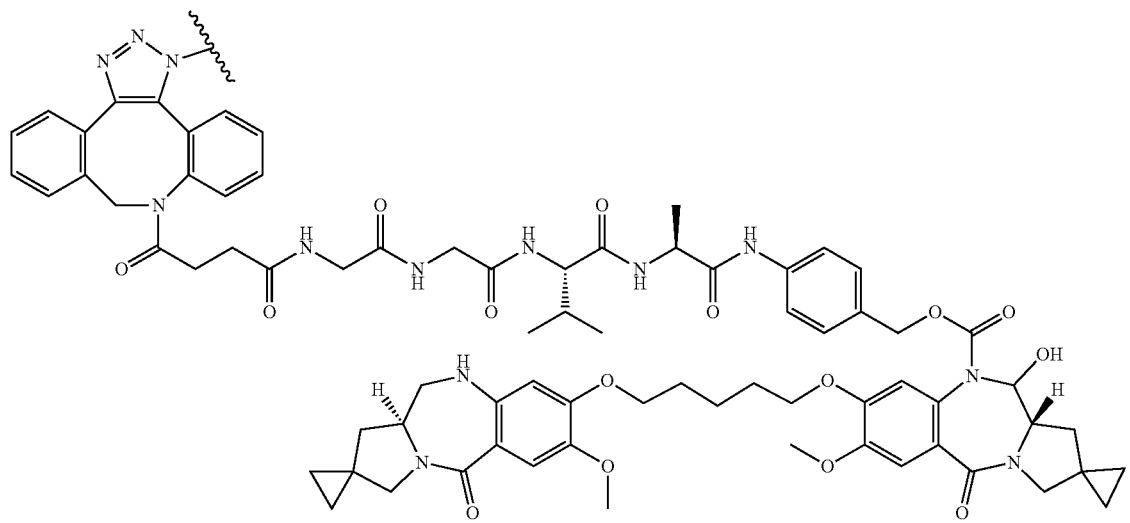

(The triazole ring to be formed in step 1 has geometric isomers, and the compound obtained in step 1 of Example 89 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 60, 1,2-propanediol (0.917 mL) and a 10 mM dimethyl sulfoxide solution of the compound obtained in step 12 of Example 37 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.0 mL of a solution of the desired compound.

Characterization: The following characteristic values were obtained by using common operations E and F.

Antibody concentration: 1.46 mg/mL, antibody yield: 8.76 mg (88%), average number of conjugated drug molecules per antibody molecule (n): 1.9

Example 90: ADC24

[Formula 217]

R =

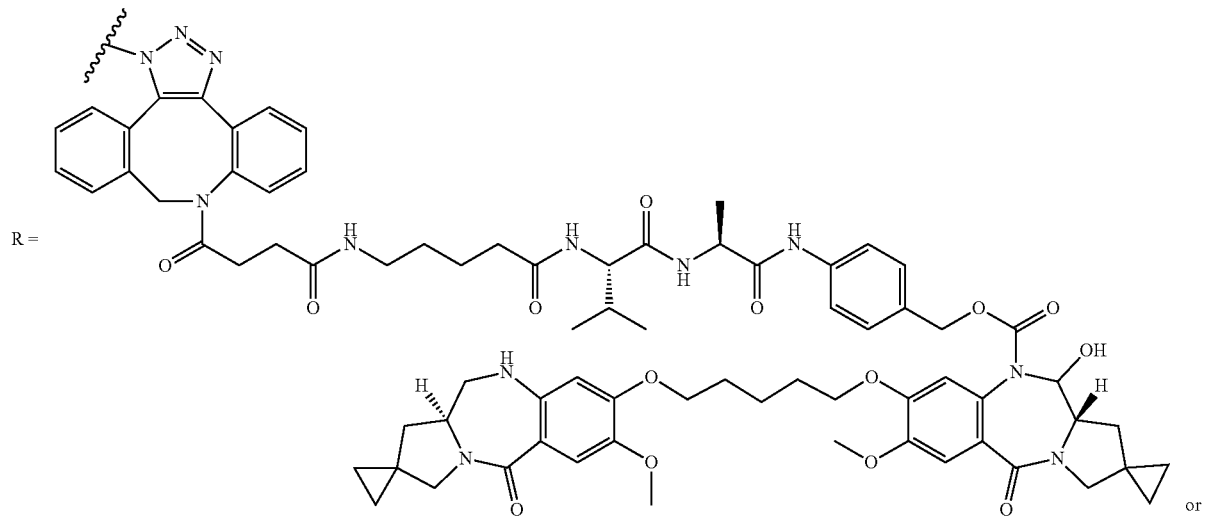

or

-continued

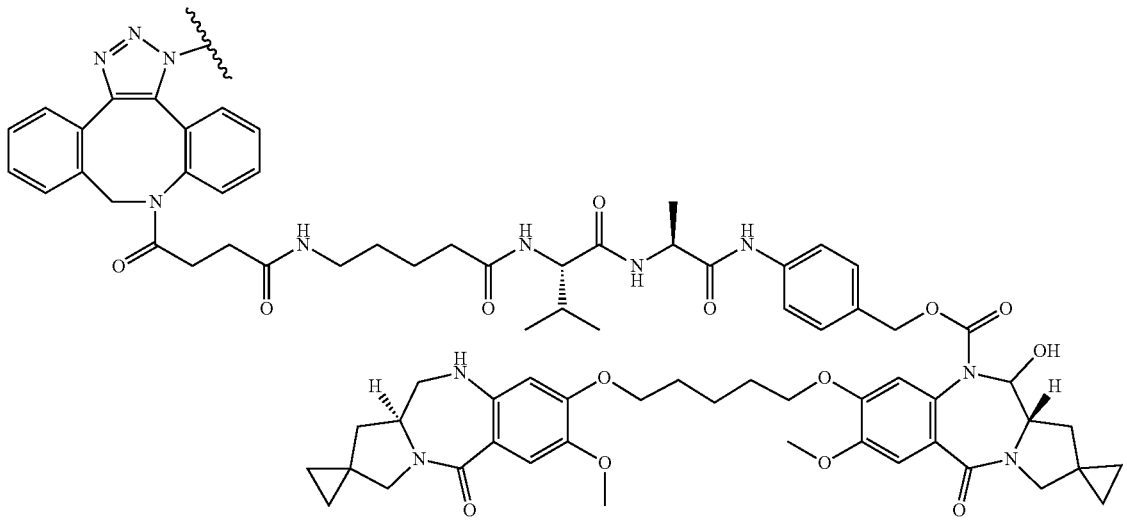

(The triazole ring to be formed in step 1 has geometric isomers, and the compound obtained in step 1 of Example 90 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 60, 1,2-propanediol (0.917 mL) and a 10 mM dimet hyl sulfoxide solution of the compound obtained in step 2 of Example 41 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.0 mL of a solution of the desired compound.

Characterization: The following characteristic values were obtained by using common operations E and F.

Antibody concentration: 1.53 mg/mL, antibody yield: 9.17 mg (92%), average number of conjugated drug molecules per antibody molecule (n): 1.9

Example 91: ADC25

[Formula 218]

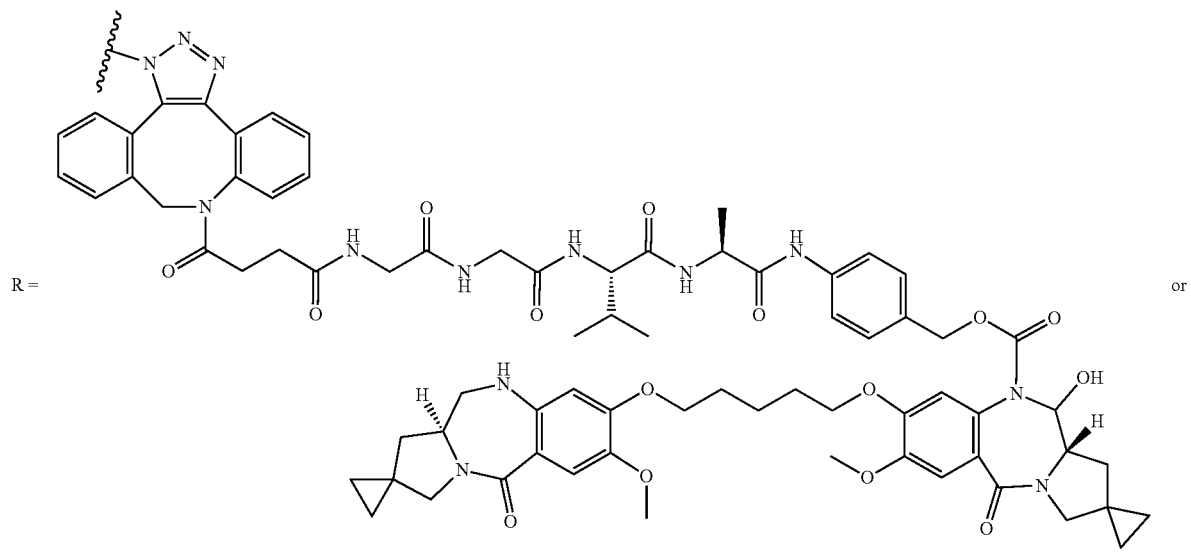

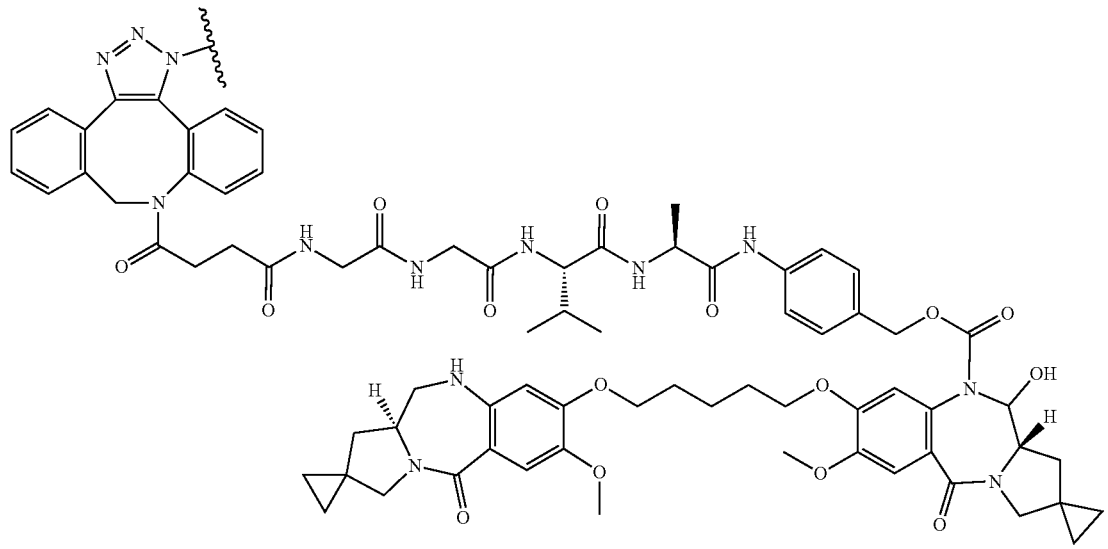

(The triazole ring to be formed in step 1 has geometric isomers, and the compound obtained in Example 91 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 2 of Example 58, 1,2-propanediol (0.835 mL) and a 10 mM dimethyl sulfoxide solution of the compound obtained in step 12 of Example 37 (0.165 mL; 24 equivalents per antibody molecule) were added at room temperature, and the resultant was reacted using a tube rotator (MTR-103, AS ONE Corporation) at room temperature for 2 days.

Purification operation: The solution was purified by using common operation D to afford 10.5 mL of a solution of the desired compound. Characterization: The following characteristic values were obtained by using common operations E and F.

Antibody concentration: 0.73 mg/mL, antibody yield: 7.70 mg (77%), average number of conjugated drug molecules per antibody molecule (n): 3.8

Example 92: ADC26

[Formula 219]

R =

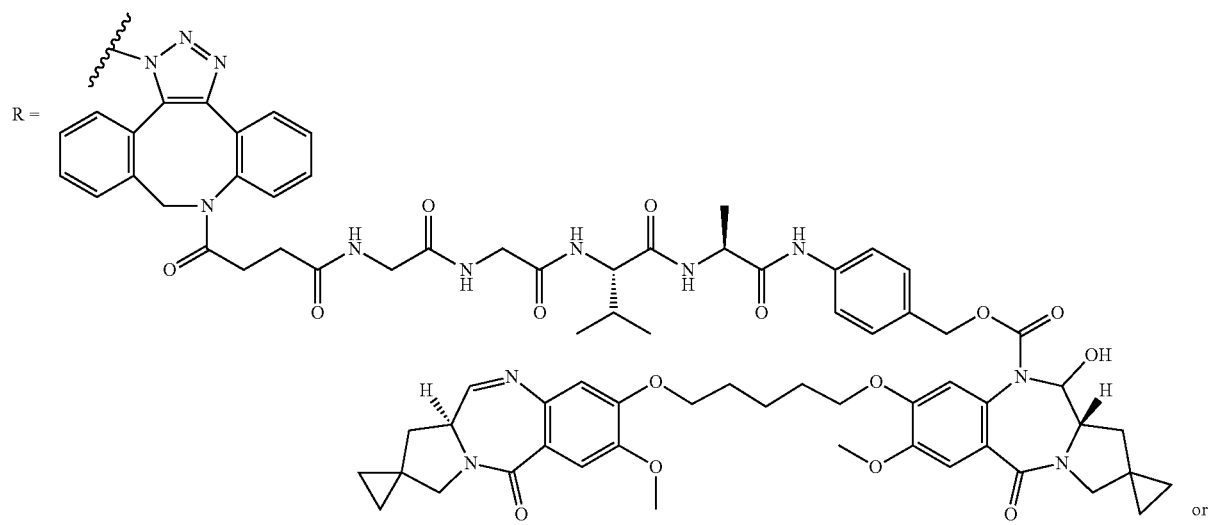

or

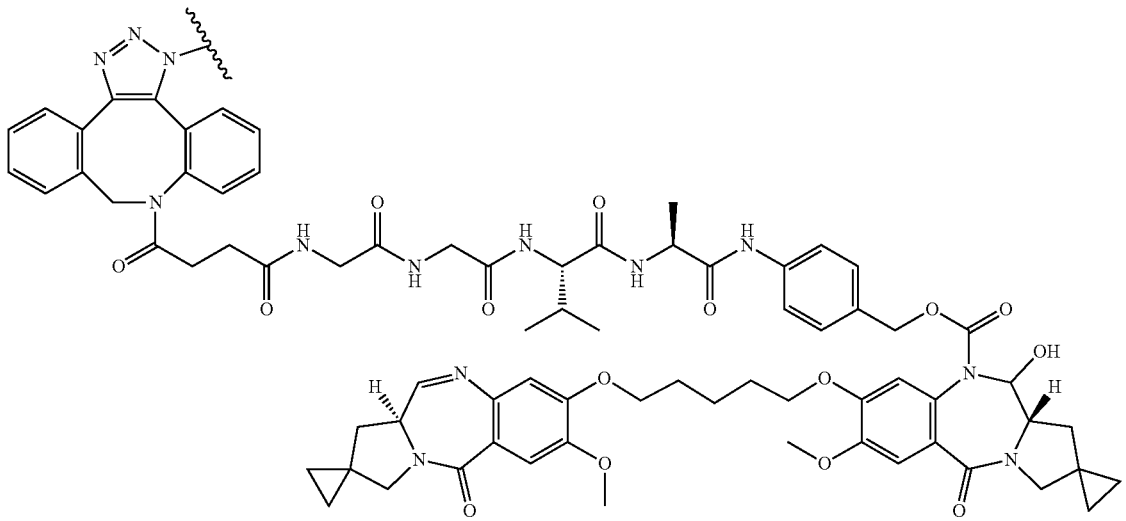

(The triazole ring to be formed in step 1 has geometric isomers, and the compound obtained in step 1 of Example 92 has a linker as a mixture of the two structures shown above as R.)

Step 1. Conjugation of Antibody and Drug-Linker

To a phosphate buffered saline (pH 6.0) solution of the antibody (9.88 mg/mL, 0.500 mL) obtained in step 1 of Example 59, 1,2-propanediol (0.459 mL) and a 10 mM dimethyl sulfoxide solution of the compound obtained in step 10 of Example 15 (0.0408 mL; 12 equivalents per antibody molecule) were added at room temperature, and the resultant was reacted using a tube rotator (MTR-103, AS ONE Corporation) at room temperature for 1 day.

Purification operation: The solution was purified by using common operation D to afford 6.00 mL of a solution of the desired compound. This solution was concentrated by using common operation A to afford 0.420 mL of a solution of the desired compound.

Characterization: The following characteristic values were obtained by using common operations E and F.

Antibody concentration: 7.27 mg/mL, antibody yield: 3.54 mg (72%), average number of conjugated drug molecules per antibody molecule (n): 1.8

Example 93: ADC27

[Formula 220]

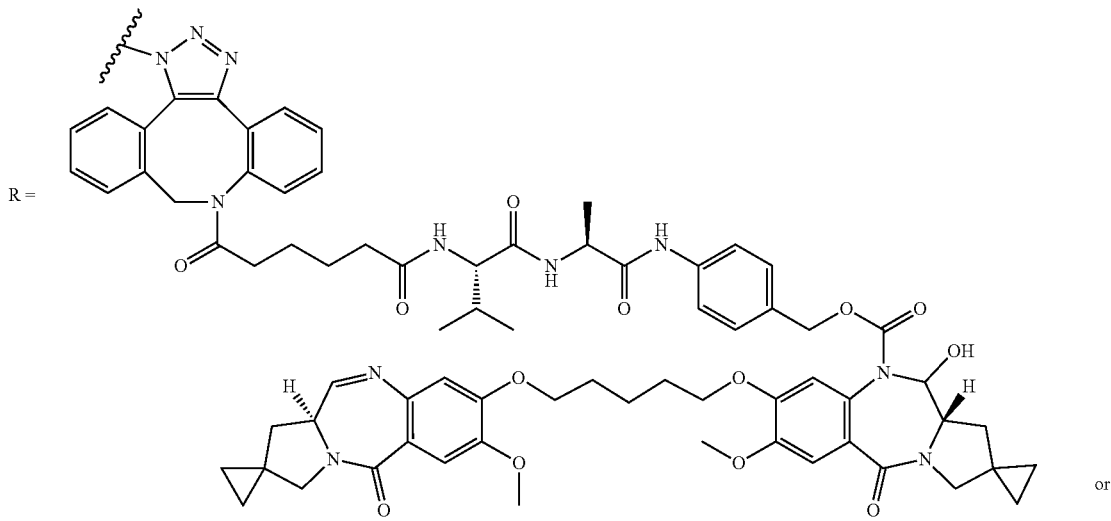

or

-continued

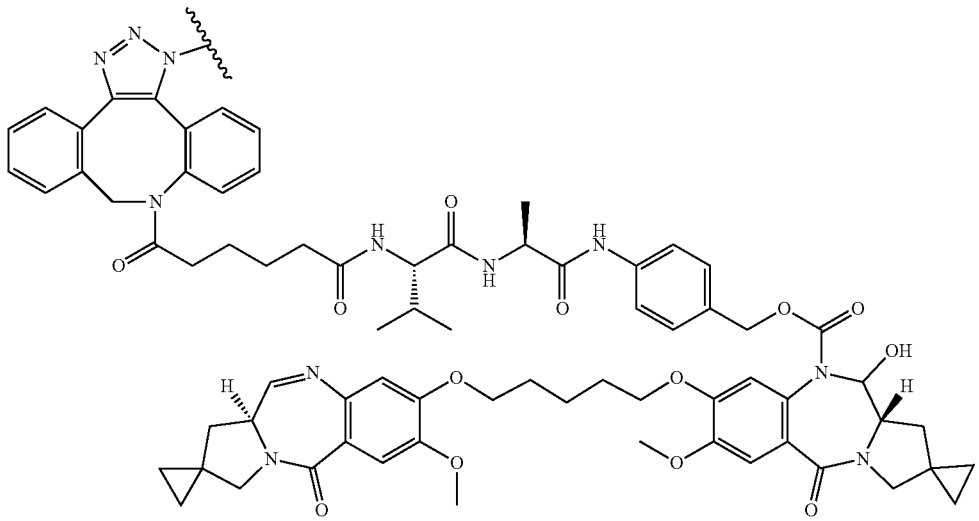

(The triazole ring to be formed in step 1 has geometric isomers, and the compound obtained in step 1 of Example 93 has a linker as a mixture of the two structures shown above as R.)

Step 1: Conjugation of Antibody and Drug-Linker

To a phosphate buffered saline (pH 6.0) solution of the antibody (9.88 mg/mL, 1.00 mL) obtained in step 1 of Example 59, 1,2-propanediol (0.917 mL) and a 10 mM dimethyl sulfoxide solution of the compound obtained in step 1 of Example 16 (0.0825 mL; 12 equivalents per antibody molecule) were added at room temperature, and the resultant was reacted using a tube rotator (MTR-103, AS ONE Corporation) at room temperature for 1 day.

Purification operation: The solution was purified by using common operation D to afford 10.5 mL of a solution of the desired compound. This solution was concentrated by using common operation A to afford 0.850 mL of a solution of the desired compound.

Characterization: The following characteristic values were obtained by using common operations E and F.

Antibody concentration: 8.90 mg/mL, antibody yield: 7.56 mg (77%), average number of conjugated drug molecules per antibody molecule (n): 1.8

Example 94: ADC28

[Formula 221]

R =

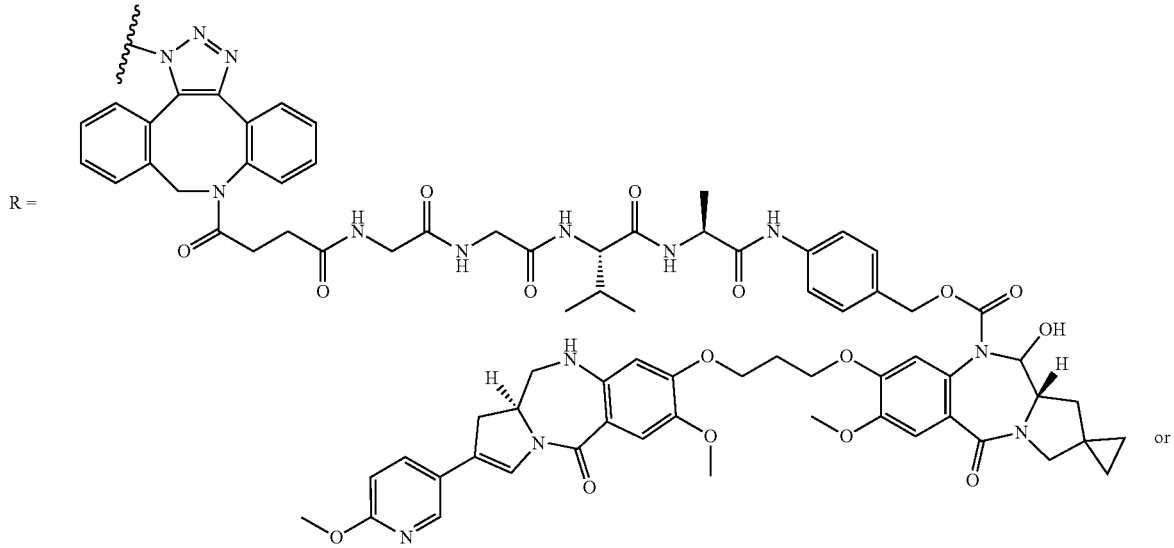

or

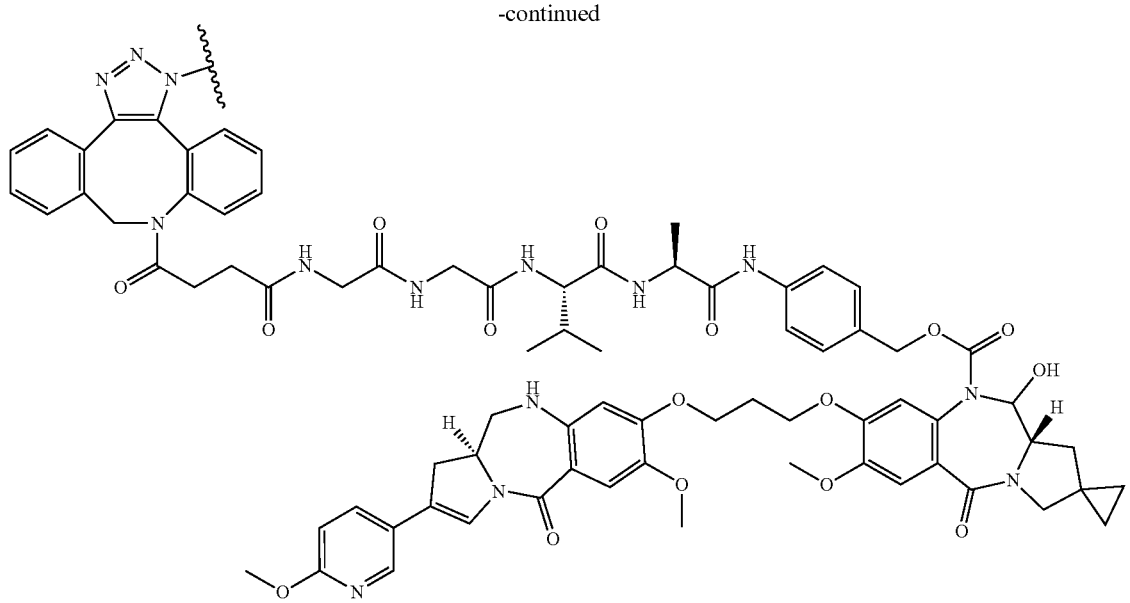

(The triazole ring to be formed in step 1 has geometric isomers, and the compound obtained in step 1 of Example 94 has a linker as a mixture of the two structures shown above as R.)

Step 1: Conjugation of Antibody and Drug-Linker

To a phosphate buffered saline (pH 6.0) solution of the antibody (10.2 mg/mL, 1.00 mL) obtained in step 1 of Example 59, 1,2-propanediol (0.917 mL) and a 10 mM dimethyl sulfoxide solution of the compound obtained in step 13 of Example 17 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.00 mL of a solution of the desired compound.

Characterization: The following characteristic values were obtained by using common operations E and F.

Antibody concentration: 1.24 mg/mL, antibody yield: 7.43 mg (73%), average number of conjugated drug molecules per antibody molecule (n): 1.5

Example 95: ADC29

[Formula 222]

R=

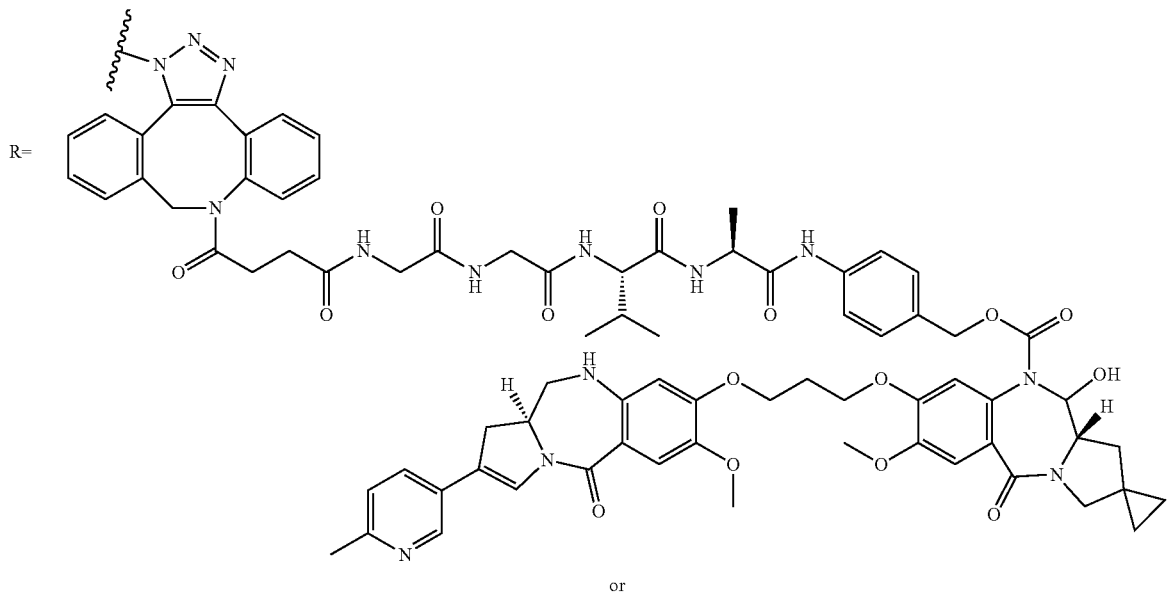

or

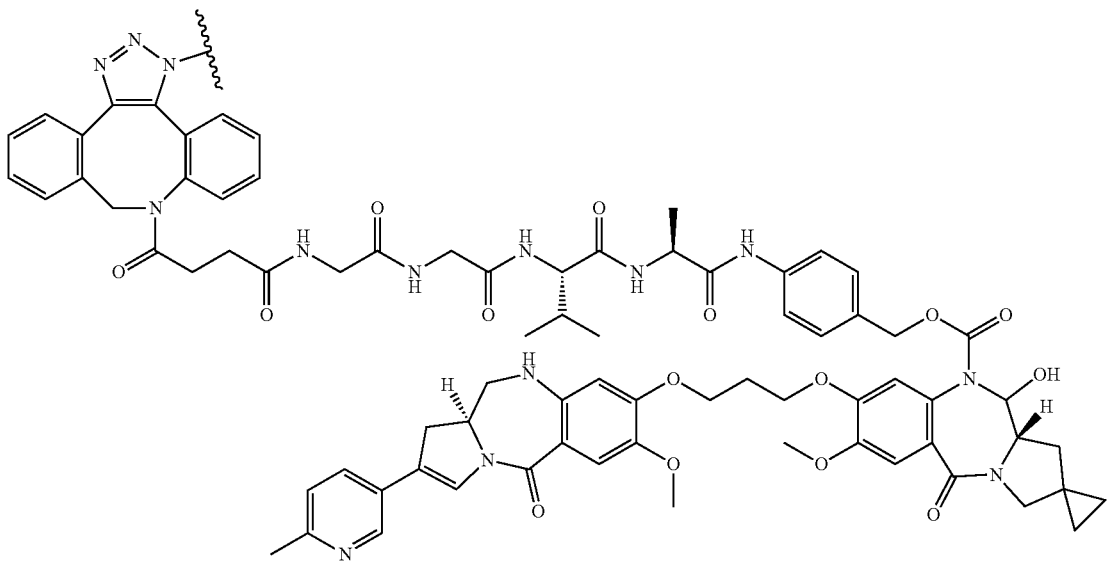

(The triazole ring to be formed in step 1 has geometric isomers, and the compound obtained in step 1 of Example 95 has a linker as a mixture of the two structures shown above as R.)

Step 1: Conjugation of Antibody and Drug-Linker

To a phosphate buffered saline (pH 6.0) solution of the antibody (10.2 mg/mL, 1.00 mL) obtained in step 1 of Example 59, 1,2-propanediol (0.917 mL) and a 10 mM dimethyl sulfoxide solution of the compound obtained in step 13 of Example 18 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.00 mL of a solution of the desired compound.

Characterization: The following characteristic values were obtained by using common operations E and F.

Antibody concentration: 1.29 mg/mL, antibody yield: 7.76 mg (76%), average number of conjugated drug molecules per antibody molecule (n): 1.9

Example 96: ADC30

[Formula 223]

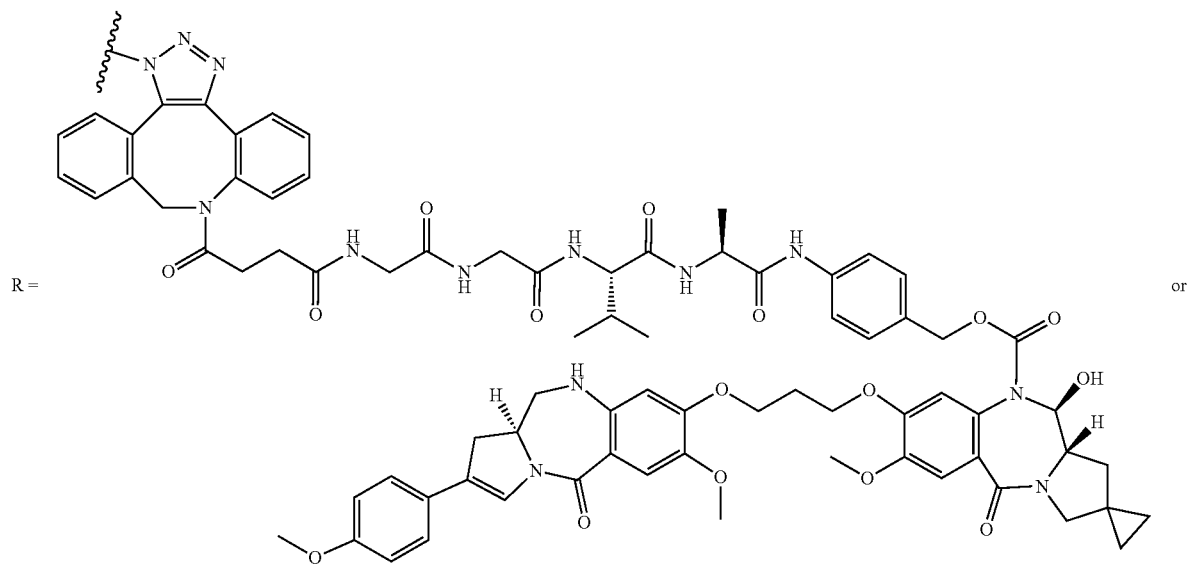

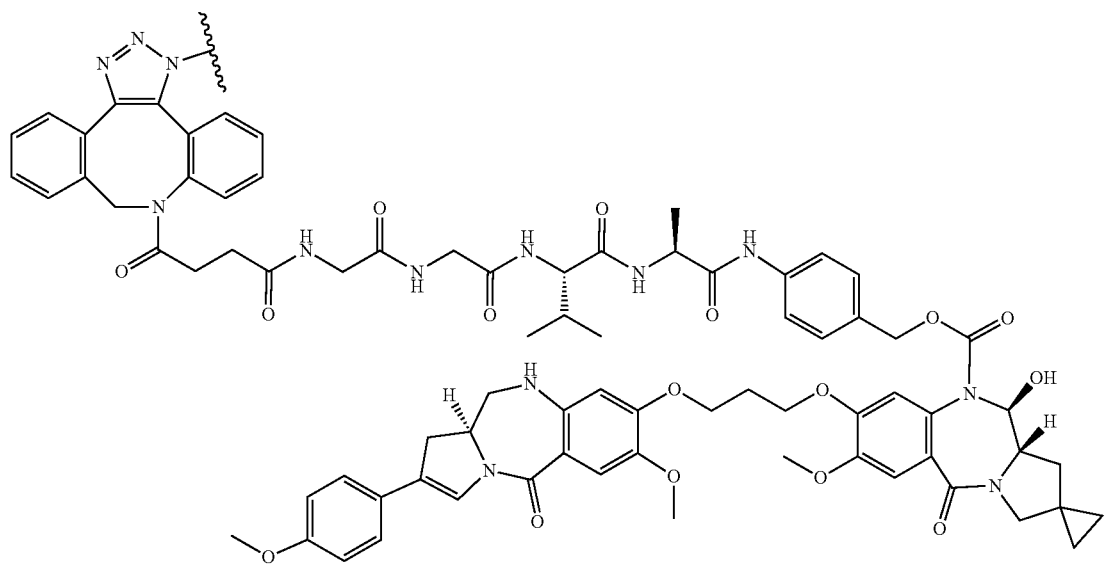

(The triazole ring to be formed in step 1 has geometric isomers, and the compound obtained in step 1 of Example 96 has a linker as a mixture of the two structures shown above as R.)

Step 1: Conjugation of Antibody and Drug-Linker

To a phosphate buffered saline (pH 6.0) solution of the antibody (10.0 mg/mL, 5.00 mL) obtained in step 1 of Example 60, 1,2-propanediol (4.59 mL) and a 10 mM dimethyl sulfoxide solution of the compound obtained in step 12 of Example 4 (0.413 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 30.0 mL of a solution of the desired compound.

Characterization: The following characteristic values were obtained by using common operations E and F.

Antibody concentration: 1.30 mg/mL, antibody yield: 38.9 mg (78%), average number of conjugated drug molecules per antibody molecule (n): 1.9

Example 97: ADC31

[Formula 224]

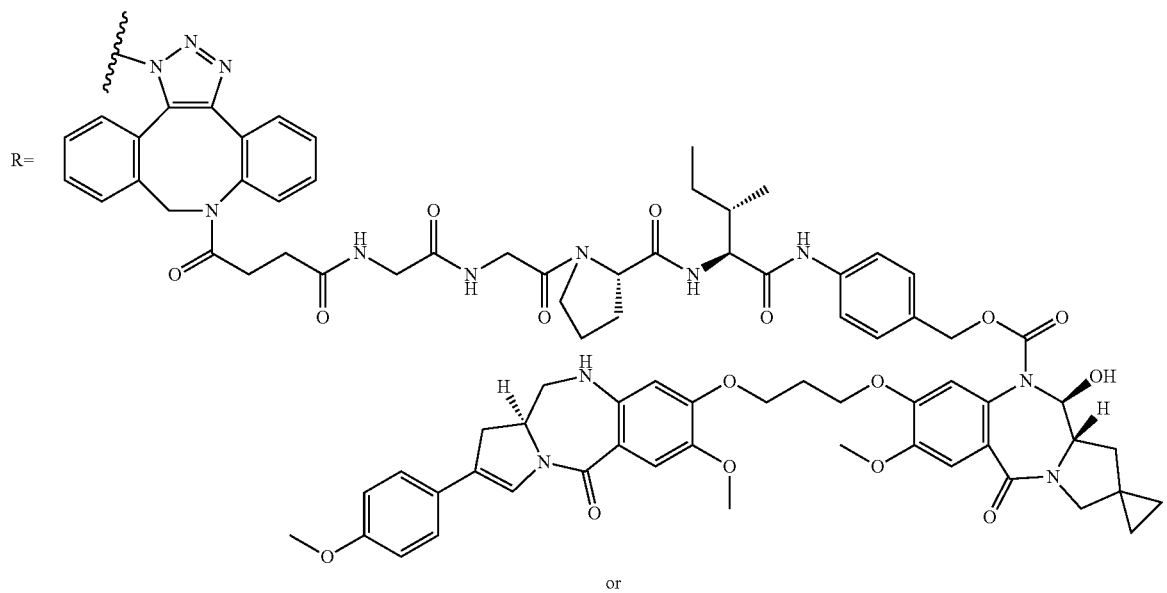

or

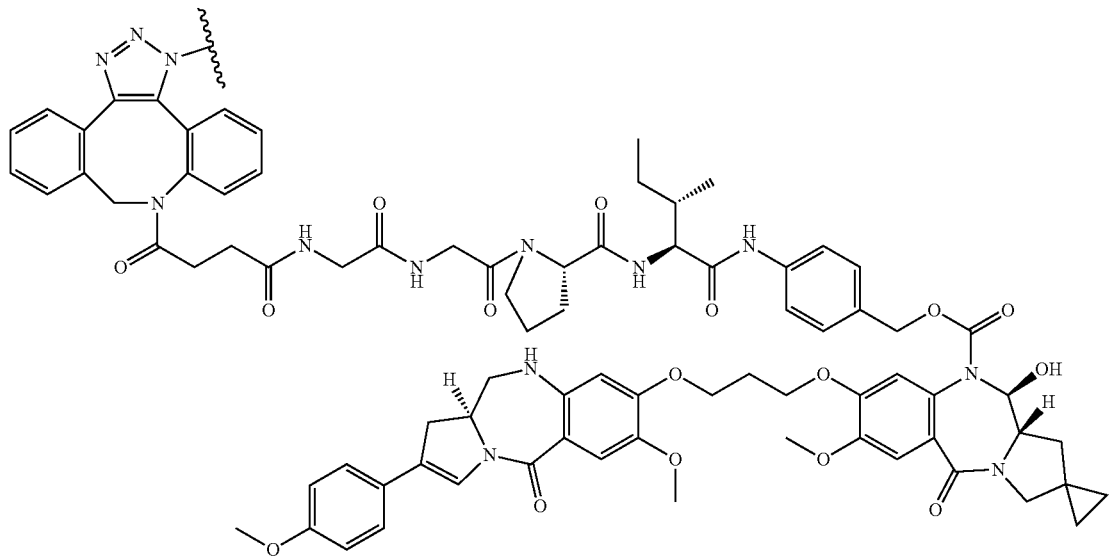

(The triazole ring to be formed in step 1 has geometric isomers, and the compound obtained in step 1 of Example 97 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 60, 1,2-propanediol (0.917 mL) and a 10 mM dimethyl sulfoxide solution of the compound obtained in step 11 of Example 5 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.0 mL of a solution of the desired compound.

Characterization: The following characteristic values were obtained by using common operations E and F.

Antibody concentration: 1.47 mg/mL, antibody yield: 8.82 mg (88%), average number of conjugated drug molecules per antibody molecule (n): 1.8

Example 98: ADC32

[Formula 225]

R=

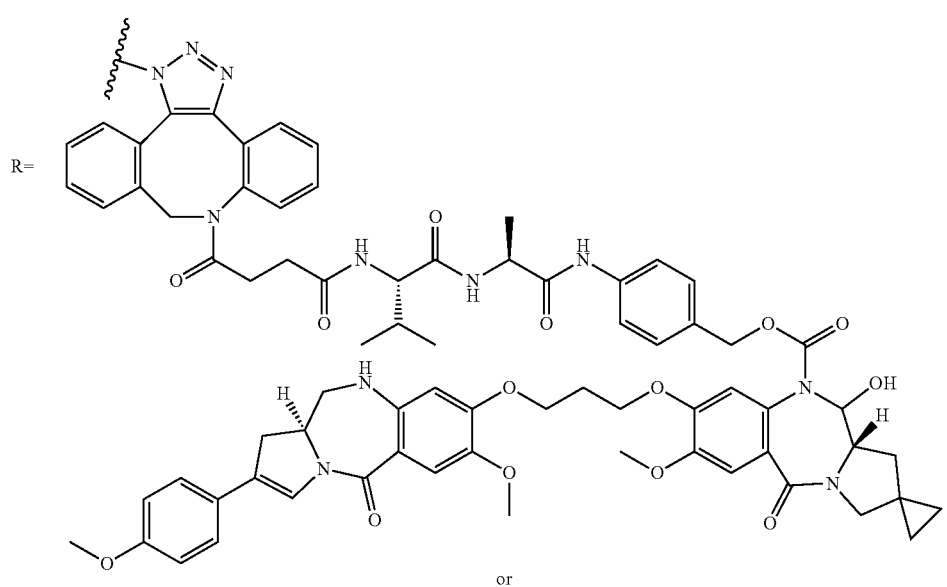

or

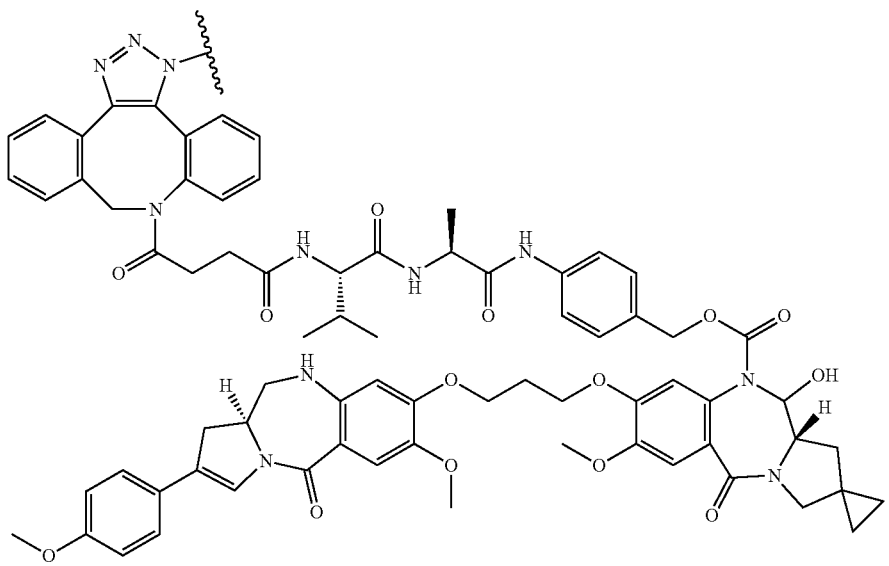

(The triangle ring to be formed in step 1 has geometric isomers, and the compound obtained in step 1 of Example 98 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 60, 1,2-propanediol (0.917 mL) and a 10 mM dimethyl sulfoxide solution of the compound obtained in step 1 of Example 6 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.0 mL of a solution of the desired compound.

Characterization: The following characteristic values were obtained by using common operations E and F.

Antibody concentration: 1.35 mg/mL, antibody yield: 8.10 mg (81%), average number of conjugated drug molecules per antibody molecule (n): 1.8

Example 99: ADC33

[Formula 226]

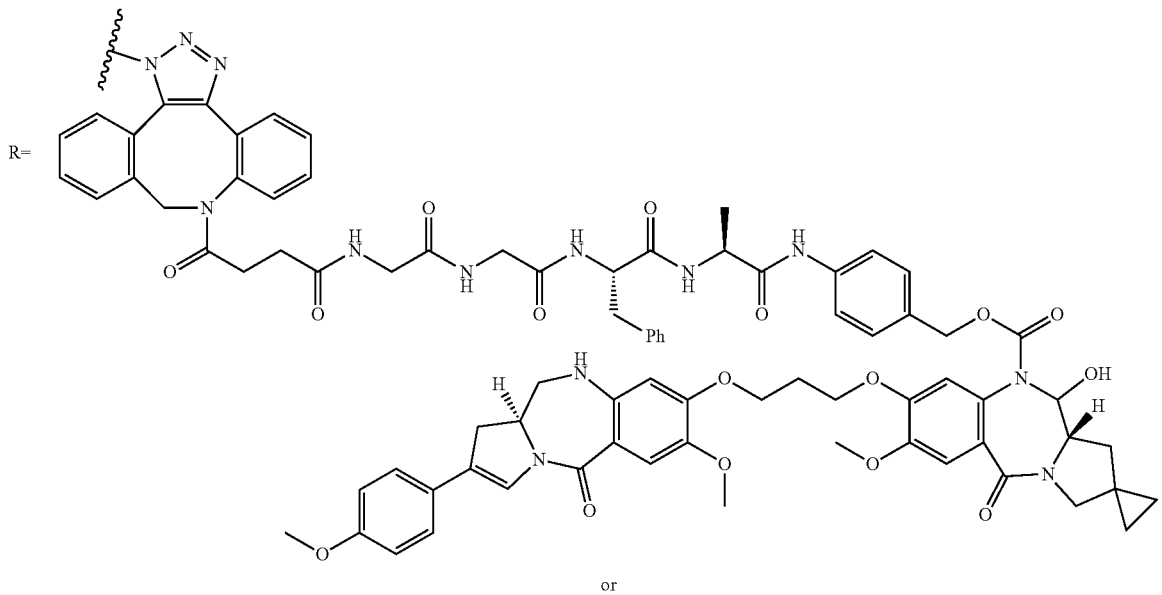

or

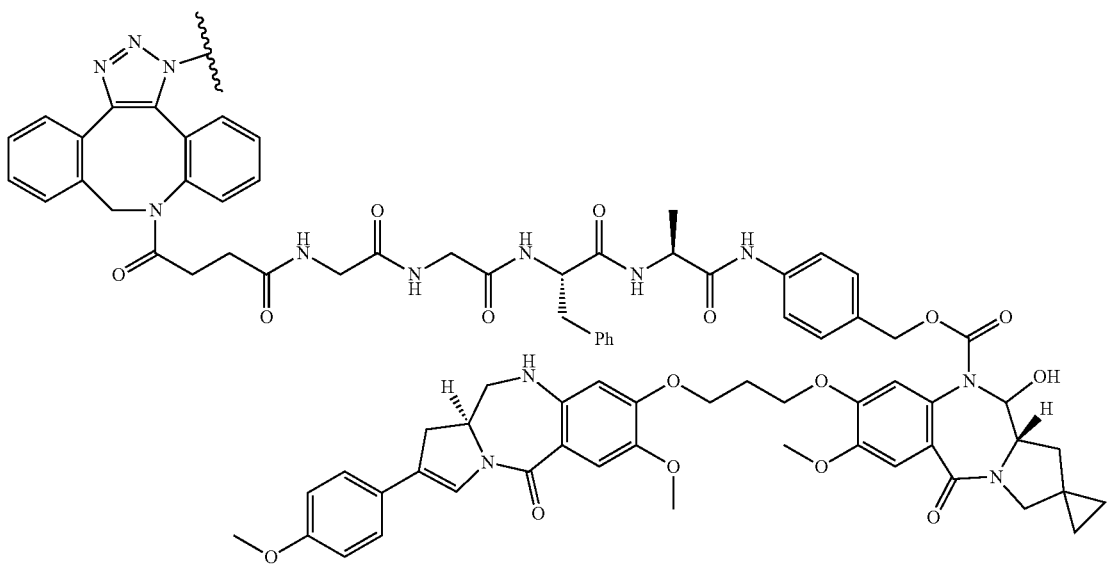

(The triazole ring to be formed in step 1 has geometric isomers, and the compound obtained in step 1 of Example 99 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 60, 1,2-propanediol (0.917 mL) and a 10 mM dimethyl sulfoxide solution of the compound obtained in step 10 of Example 7 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.0 mL of a solution of the desired compound.

Characterization: The following characteristic values were obtained by using common operations E and F.

Antibody concentration: 1.41 mg/mL, antibody yield: 8.44 mg (84%), average number of conjugated drug molecules per antibody molecule (n): 1.8

Example 100: ADC34

[Formula 227]

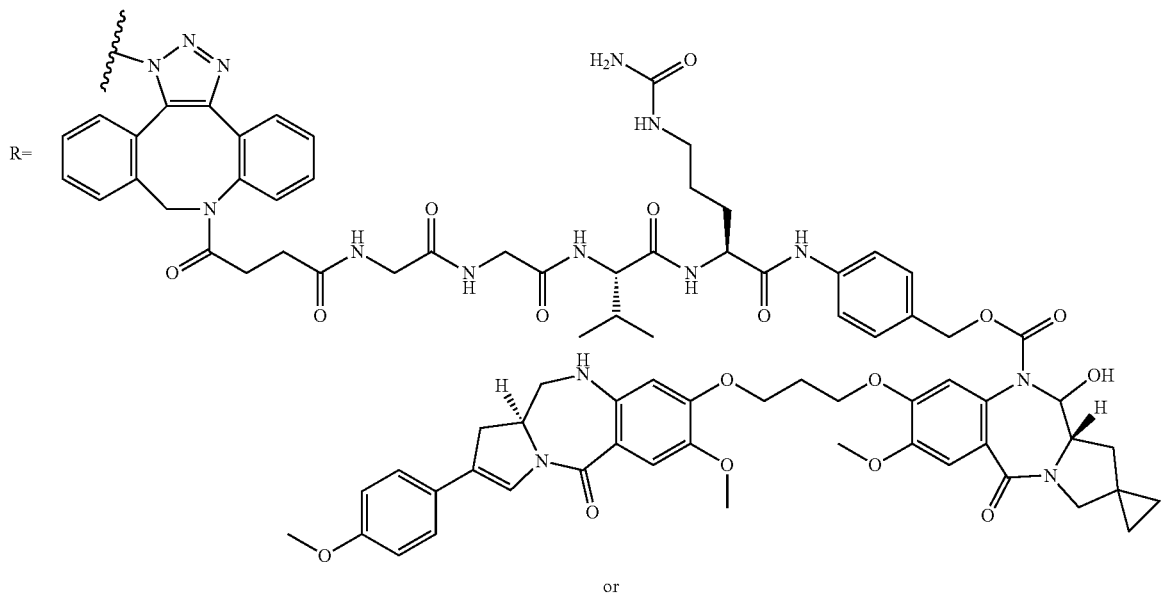

or

-continued

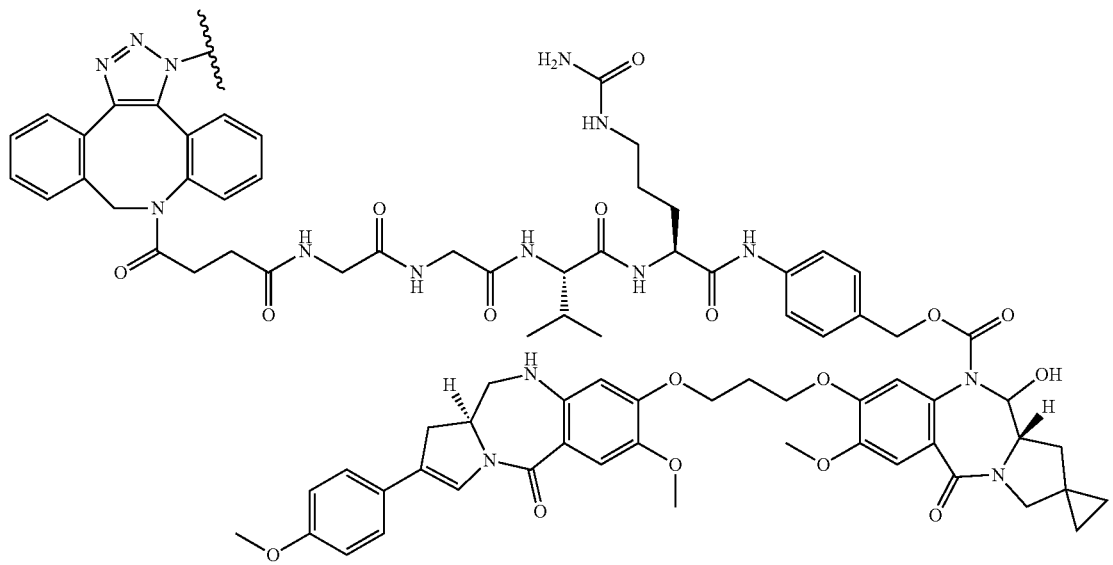

(The triazole ring to be formed in step 1 has geometric isomers, and the compound obtained in step 1 of Example 100 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 60, 1,2-propanediol (0.917 mL) and a 10 mM dimethyl sulfoxide solution of the compound obtained in step 9 of Example 9 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.0 mL of a solution of the desired compound.

Characterization: The following characteristic values were obtained by using common operations E and F.

Antibody concentration: 1.47 mg/mL, antibody yield: 8.79 mg (88%), average number of conjugated drug molecules per antibody molecule (n): 1.8

Example 101: ADC35

[Formula 228]

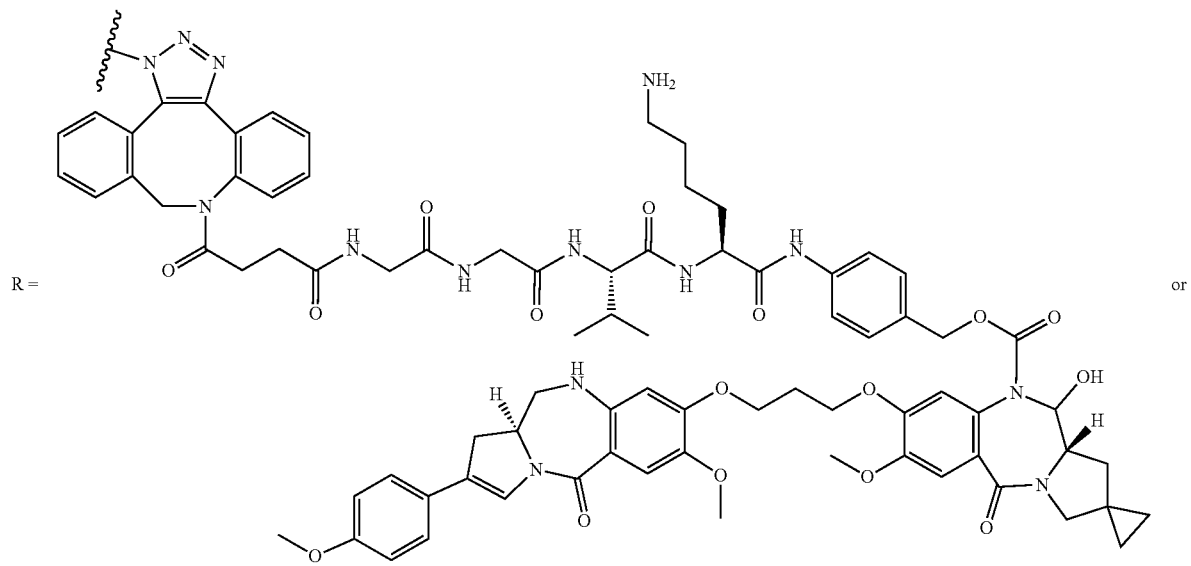

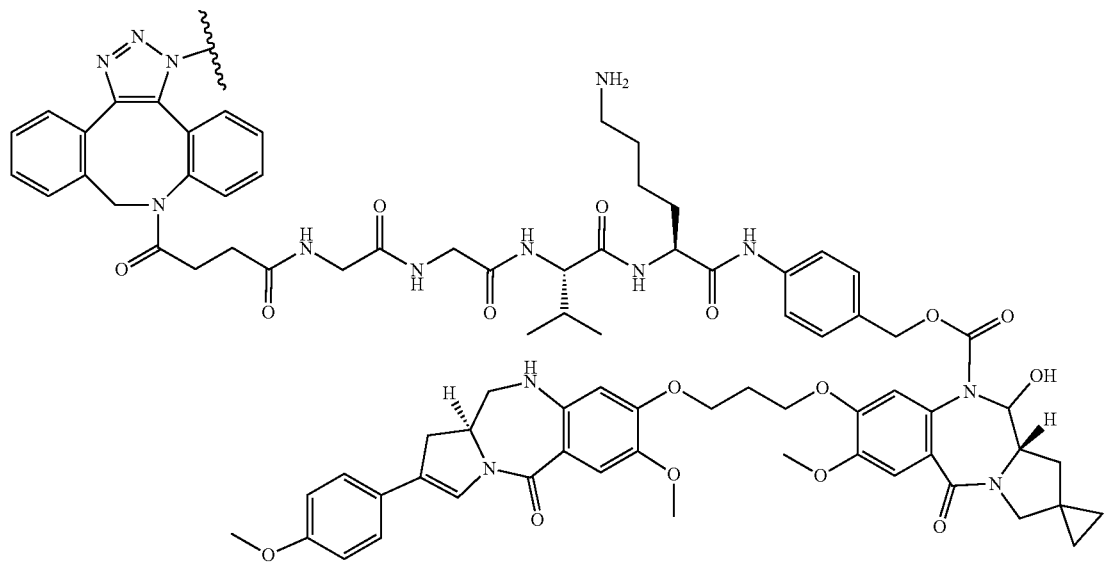

(The triazole ring to be formed in step 1 has geometric isomers, and the compound obtained in step 1 of Example 101 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 60, 1,2-propanediol (0.917 mL) and a 10 mM dimethyl sulfoxide solution of the compound obtained in step 14 of Example 10 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.0 mL of a solution of the desired compound.

Characterization: The following characteristic values were obtained by using common operations E and F.

Antibody concentration: 1.67 mg/mL, antibody yield: 10.0 mg (quantitative), average number of conjugated drug molecules per antibody molecule (n): 1.8

Example 102: ADC36

[Formula 229]

R=

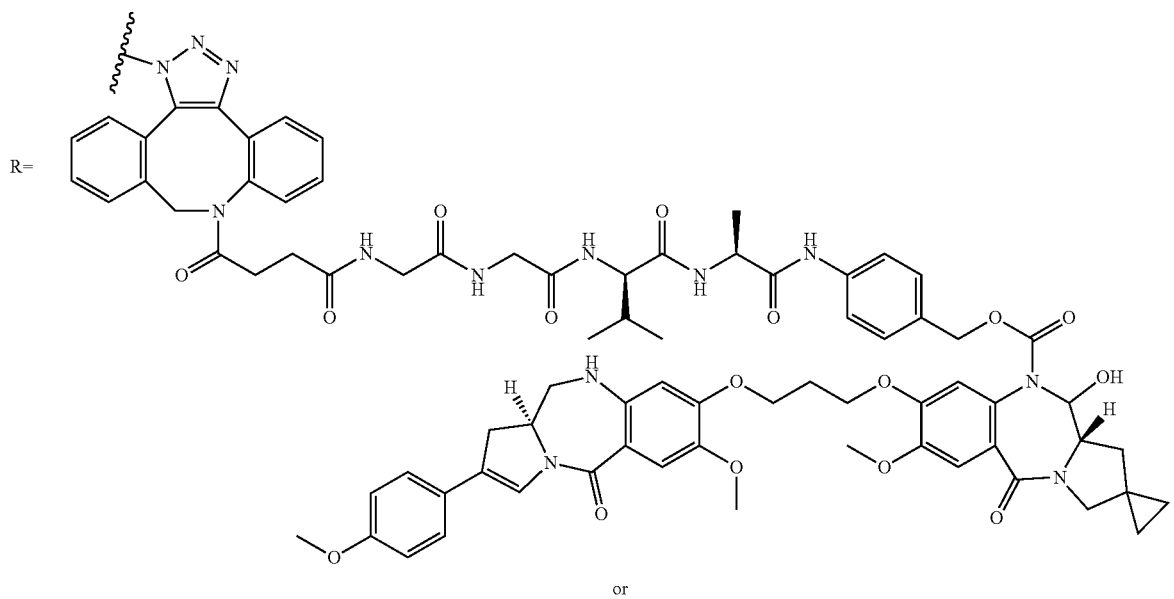

or

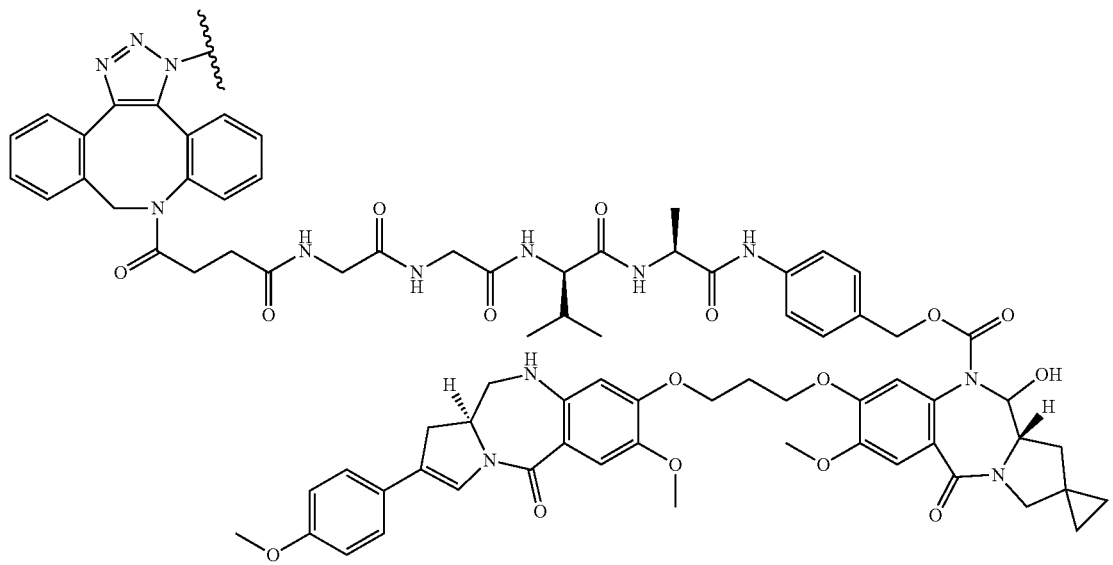

(The triazole ring to be formed in step 1 has geometric isomers, and the compound obtained in step 1 of Example 103 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 60, 1,2-propanediol (0.917 mL) and a 10 mM dimethyl sulfoxide solution of the compound obtained in step 13 of Example 11 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.0 mL of a solution of the desired compound.

Characterization: The following characteristic values were obtained by using common operations E and F.

Antibody concentration: 1.40 mg/mL, antibody yield: 8.39 mg (84%), average number of conjugated drug molecules per antibody molecule (n): 1.8

Example 103: ADC37

[Formula230]

R=

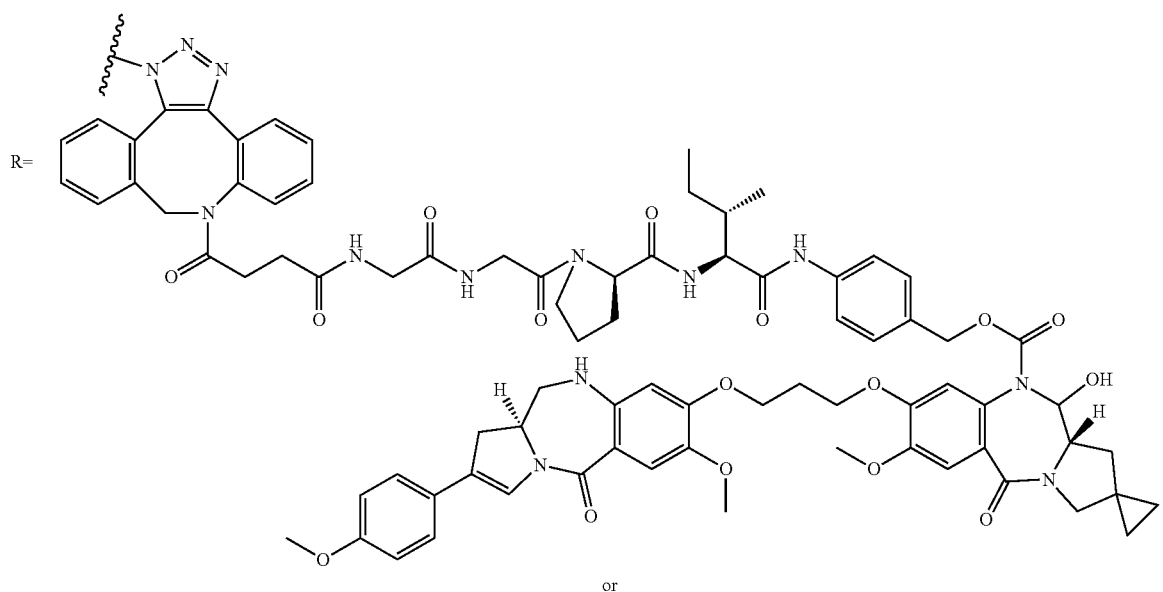

or

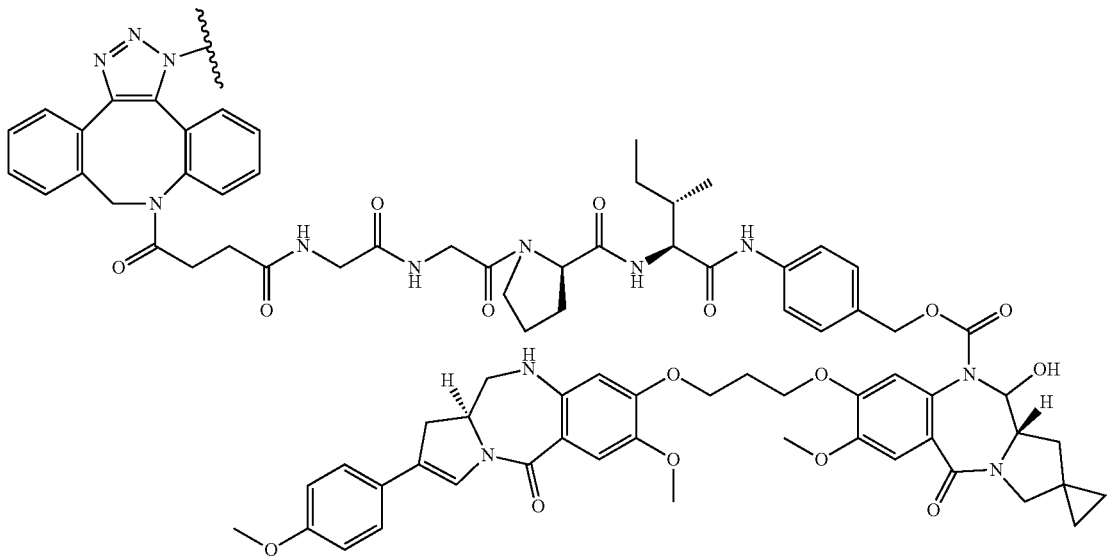

(The triazole ring to be formed in step 1 has geometric isomers, and the compound obtained in step 1 of Example 103 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 60, 1,2-propanediol (0.917 mL) and a 10 mM dimethyl sulfoxide solution of the compound obtained in step 14 of Example 12 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.0 mL of a solution of the desired compound.

Characterization: The following characteristic values were obtained by using common operations E and F.

Antibody concentration: 1.41 mg/mL, antibody yield: 8.49 mg (85%), average number of conjugated drug molecules per antibody molecule (n): 1.8

Example 104: ADC:38

[Formula 231]

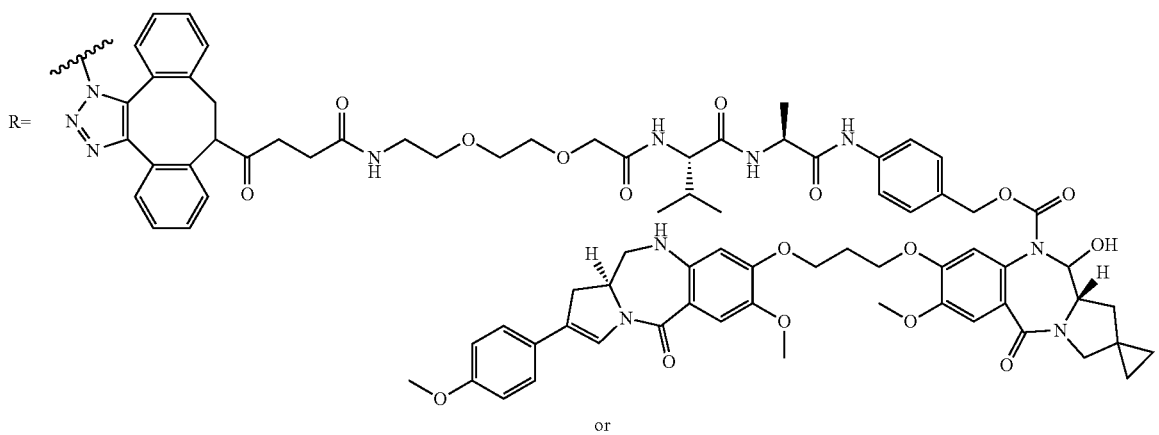

or

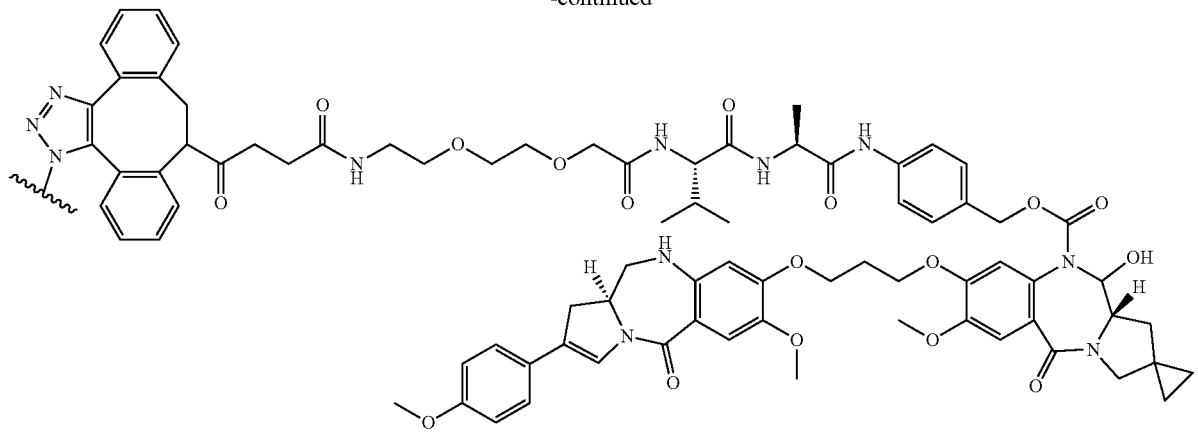

(The triazole ring to be formed in step 1 has geometric isomers, and the compound obtained in step 1 of Example 104 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 60, 1,2-propanediol (0.917 mL) and a 10 mM dimethyl sulfoxide solution of the compound obtained in step 2 of Example 13 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.0 mL of a solution of the desired compound.

Characterization: The following characteristic values were obtained by using common operations E and F.

Antibody concentration: 1.63 mg/mL, antibody yield: 9.80 mg (98%), average number of conjugated drug molecules per antibody molecule (n): 1.8

Example 105: ADC39

[Formula 232]

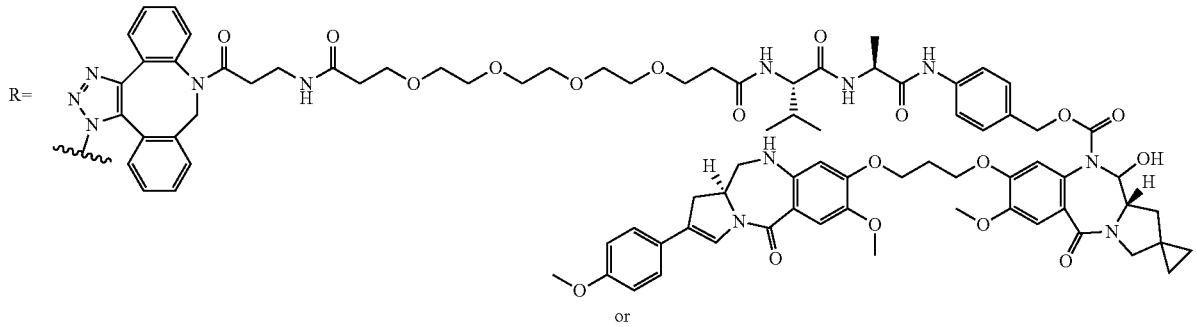

or

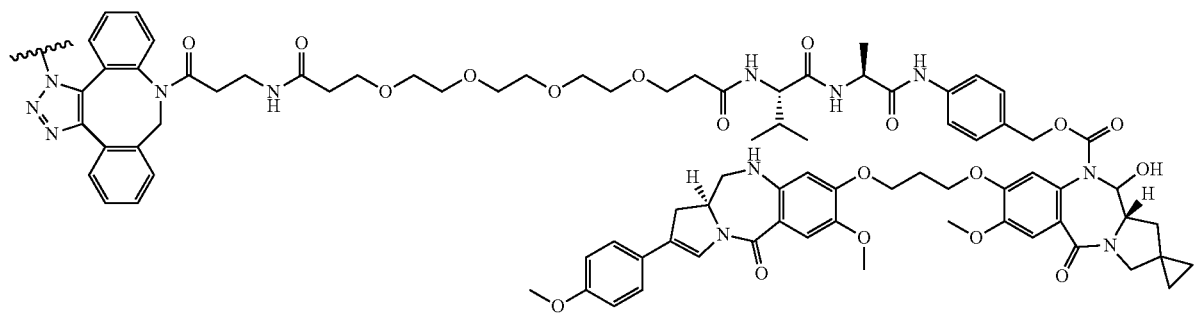

(The triazole ring to be formed in step 1 has geometric isomers, and the compound obtained in step 1 of Example 105 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 60, 1,2-propanediol (0.917 mL) and a 10 mM dimethyl sulfoxide solution of the compound obtained in step 1 of Example 14 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.0 mL of a solution of the desired compound.

Characterization: The following characteristic values were obtained by using common operations E and F.

Antibody concentration: 1.72 mg/mL, antibody yield: 10.3 mg (quantitative), average number of conjugated drug molecules per antibody molecule (n): 1.9

Example 106: ADC40

Figure 67:
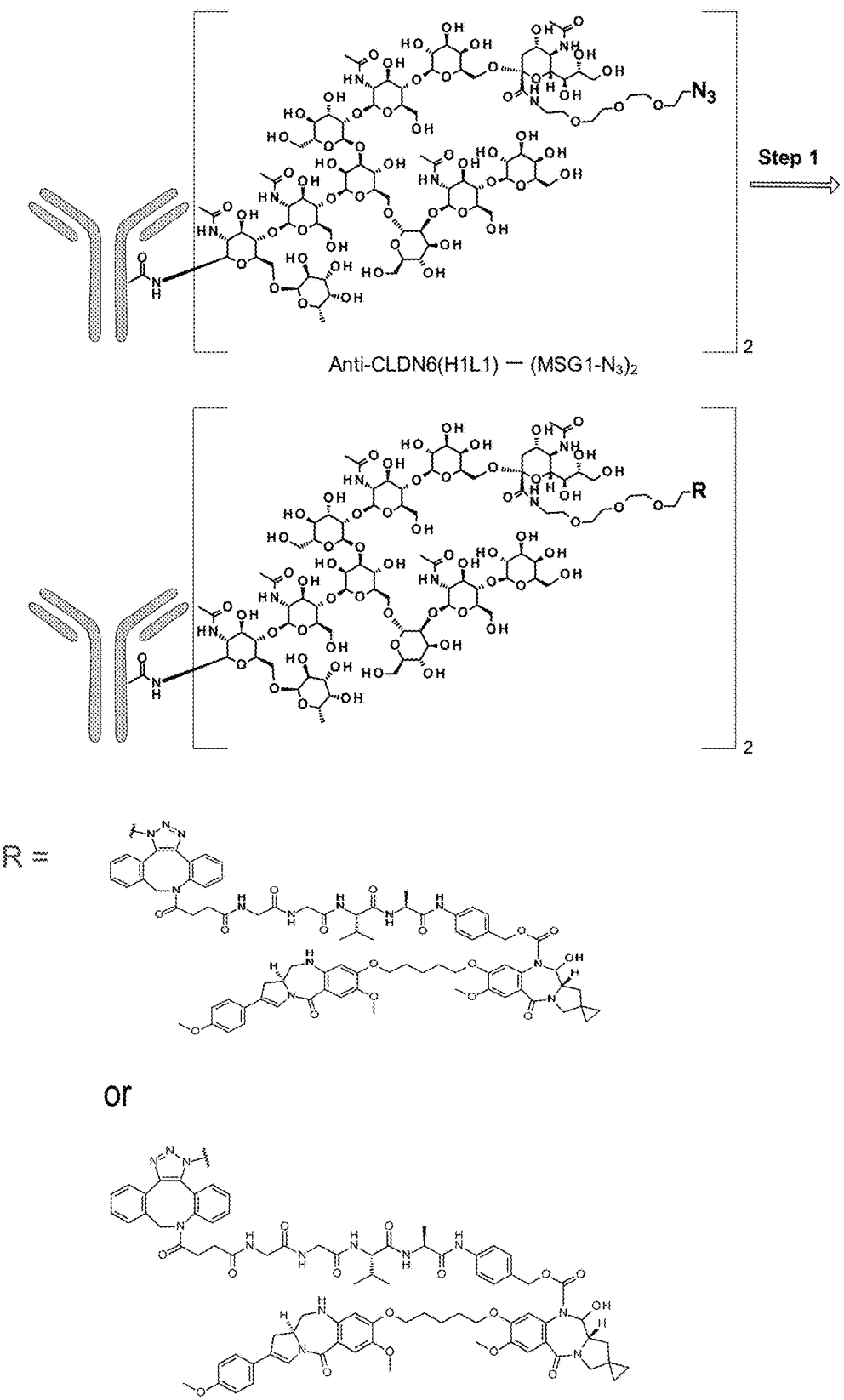
FIG. 67 shows Formula 233, wherein the triazole ring to be formed in step 1 has geometric isomers, and the compound obtained in step 1 of Example 106 has a linker as a mixture of the two structures shown as R.

(The triazole ring to be formed in step 1 has geometric isomers, and the compound obtained in step 1 of Example 106 has a linker as a mixture of the two structures shown above as R) (see FIG. 67).

Step 1: Conjugation of Antibody and Drug-Linker

To a phosphate buffered saline (pH 6.0) solution of the antibody (10.2 mg/mL, 2.50 mL) obtained in step 2 of Example 61, 1,2-propanediol (2.29 mL) and a 10 mM dimethyl sulfoxide solution of the compound obtained in step 13 of Example 3 (0.206 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 14.5 mL of a solution of the desired compound.

Characterization: The following characteristic values were obtained by using common operations E and F.

Antibody concentration: 1.54 mg/mL, antibody yield: 22.3 mg (89%), average number of conjugated drug molecules per antibody molecule (n): 1.9

Example 107: ADC41

(The triazole ring to be formed in step 1 has geometric isomers, and the compound obtained in step 1 of Example 107 has a linker as a mixture of the two structures shown above as R) (see FIG. 68).

Step 1: Conjugation of Antibody and Drug-Linker

To a phosphate buffered saline (pH 6.0) solution of the antibody (9.96 mg/mL, 2.50 mL) obtained in step 2 of Example 62, 1,2-propanediol (2.29 mL) and a 10 mM dimethyl sulfoxide solution of the compound obtained in step 13 of Example 3 (0.206 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 14.5 mL of a solution of the desired compound. Characterization: The following characteristic values were obtained by using common operations E and F.

Antibody concentration: 1.52 mg/mL, antibody yield: 22.0 mg (88%), average number of conjugated drug molecules per antibody molecule (n): 1.9

Example 108: ADC42

(The triazole ring to be formed in step 1 has geometric isomers, and the compound obtained in step 1 of Example 108 has a linker as a mixture of the two structures shown above as R) (see FIG. 69).

Step 1: Conjugation of Antibody and Drug-Linker

To a phosphate buffered saline (pH 6.0) solution of the antibody (9.83 mg/mL, 2.50 mL) obtained in step 2 of Example 63, 1,2-propanediol (2.29 mL) and a 10 mM dimethyl sulfoxide solution of the compound obtained in step 13 of Example 3 (0.206 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 14.5 mL of a solution of the desired compound.

Characterization: The following characteristic values were obtained by using common operations E and F.

Antibody concentration: 1.45 mg/mL, antibody yield: 21.0 mg (84%), average number of conjugated drug molecules per antibody molecule (n): 1.9

Example 109: ADC43

R=

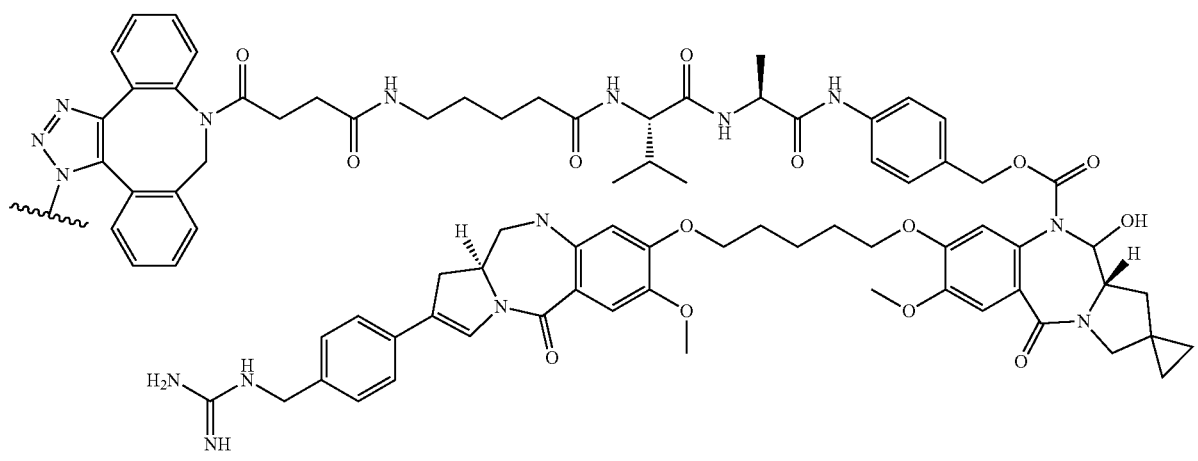

or

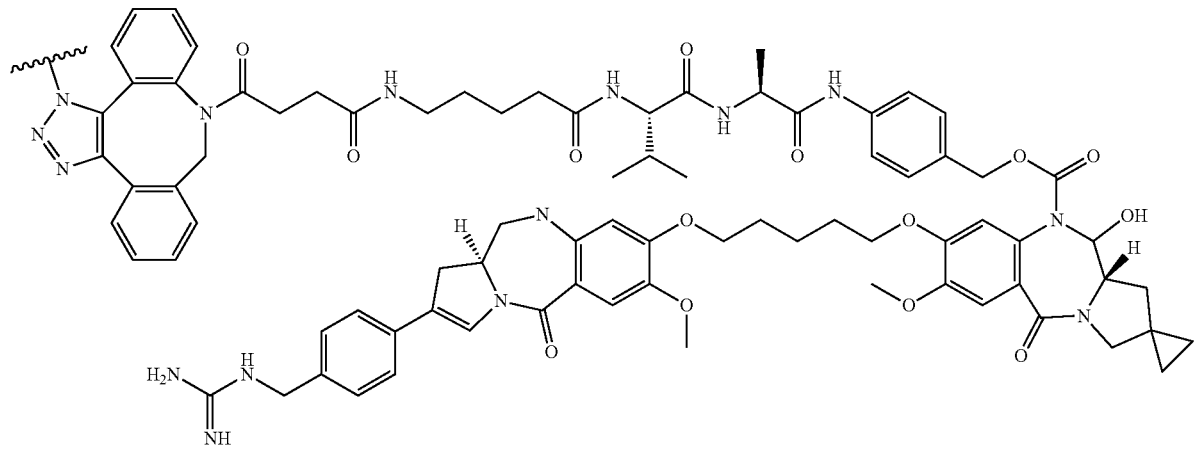

(The triazole ring to be formed in step 1 has geometric isomers, and the compound obtained in step 1 of Example 109 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 16 of Example 42 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 3.0 mL of a solution of the desired compound.

Characterization: The following characteristic values were obtained by using common operations E and F.

Antibody concentration: 1.30 mg/mL, antibody yield: 7.79 mg (78%), average number of conjugated drug molecules per antibody molecule (n): 1.9

Example 110: ADC44

[Formula 237]

R=

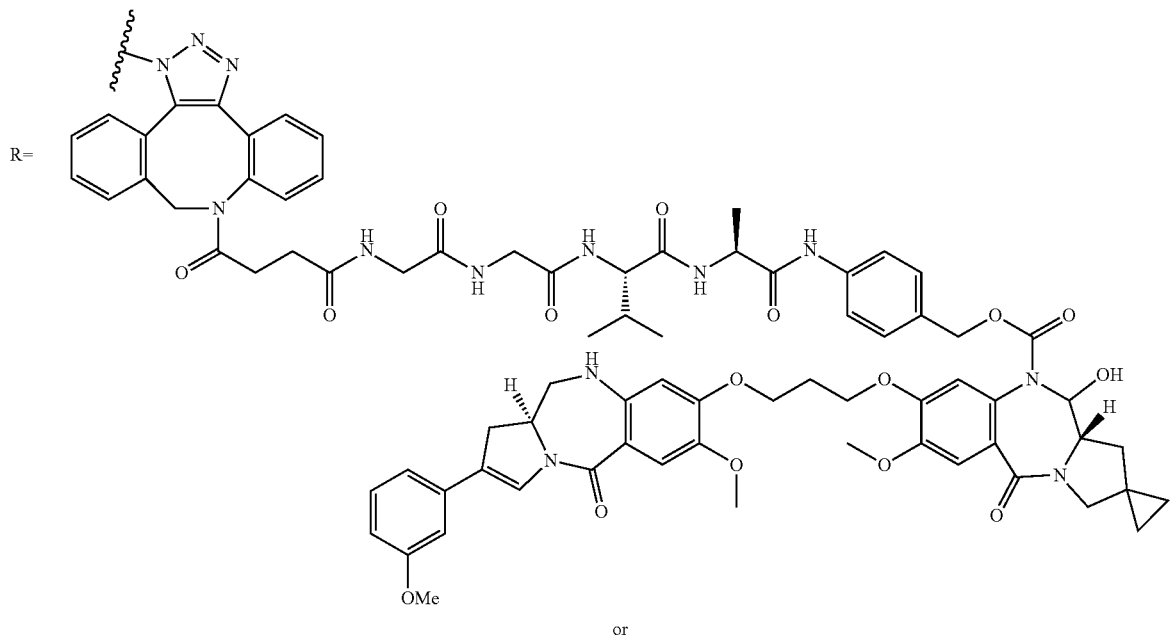

or

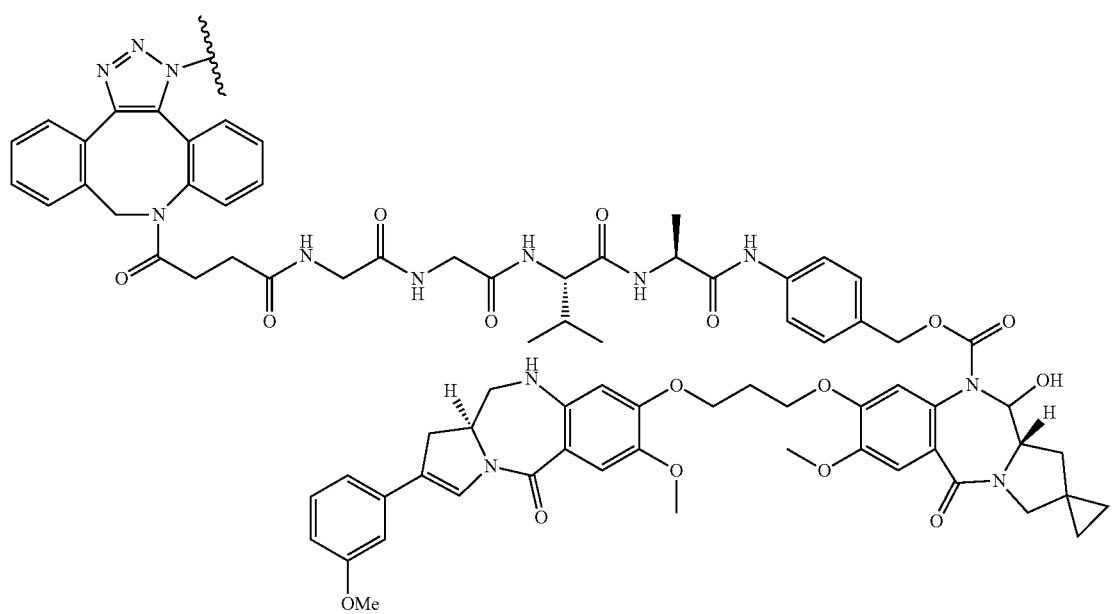

(The triazole ring to be formed in step 1 has geometric isomers, and the compound obtained in step 1 of Example 110 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 8 of Example 43 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.0 mL of a solution of the desired compound.

Characterization: The following characteristic values were obtained by using common operations E and F.

Antibody concentration: 0.93 mg/mL, antibody yield: 5.58 mg (56%), average number of conjugated drug molecules per antibody molecule (n): 1.9

Example 111: ADC45

R=

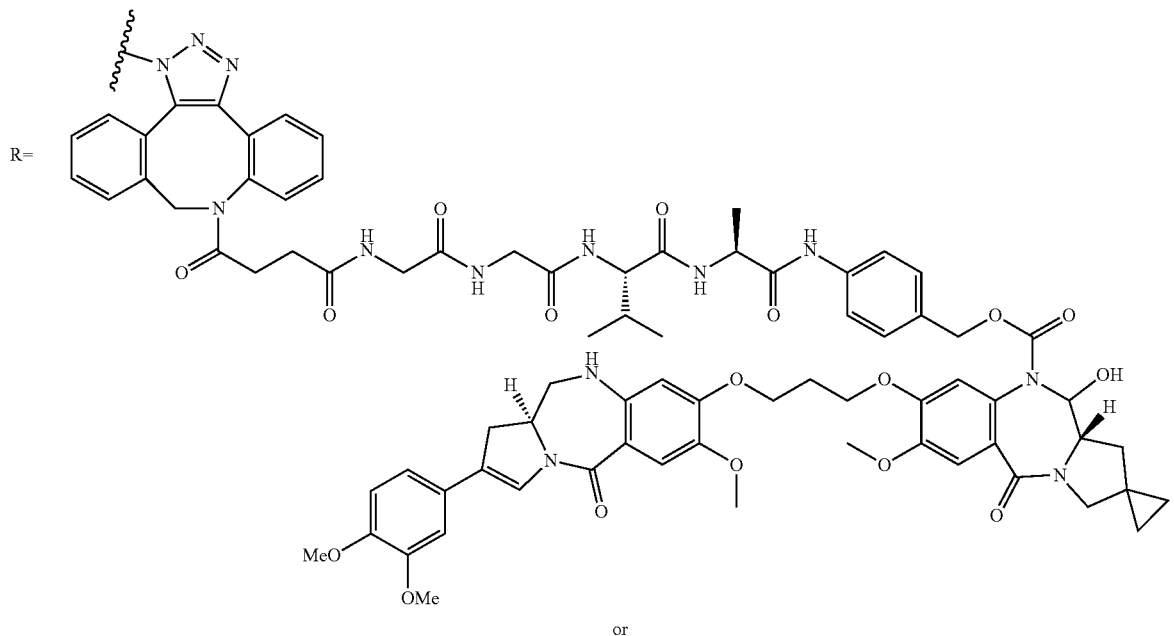

or

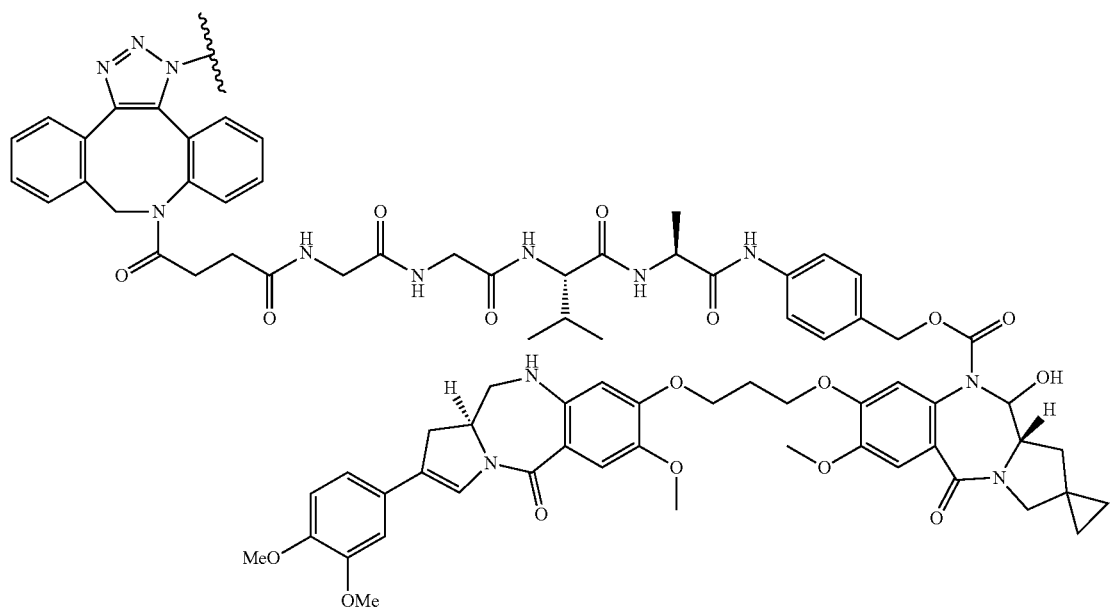

(The triazole ring to be formed in step 1 has geometric isomers, and the compound obtained in step 1 of Example 111 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 8 of Example 44 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6.0 mL of a solution of the desired compound.

Characterization: The following characteristic values were obtained by using common operations E and F.

Antibody concentration: 0.99 mg/mL, antibody yield: 5.95 mg (59%), average number of conjugated drug molecules per antibody molecule (n): 1.9

Example 112: ADC46

R=

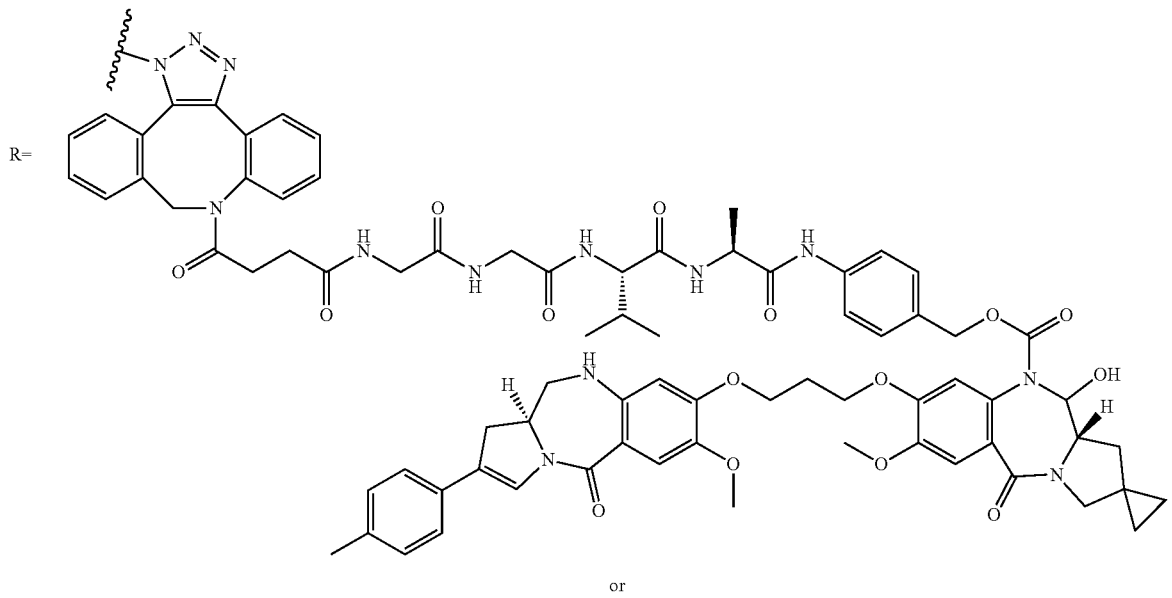

or

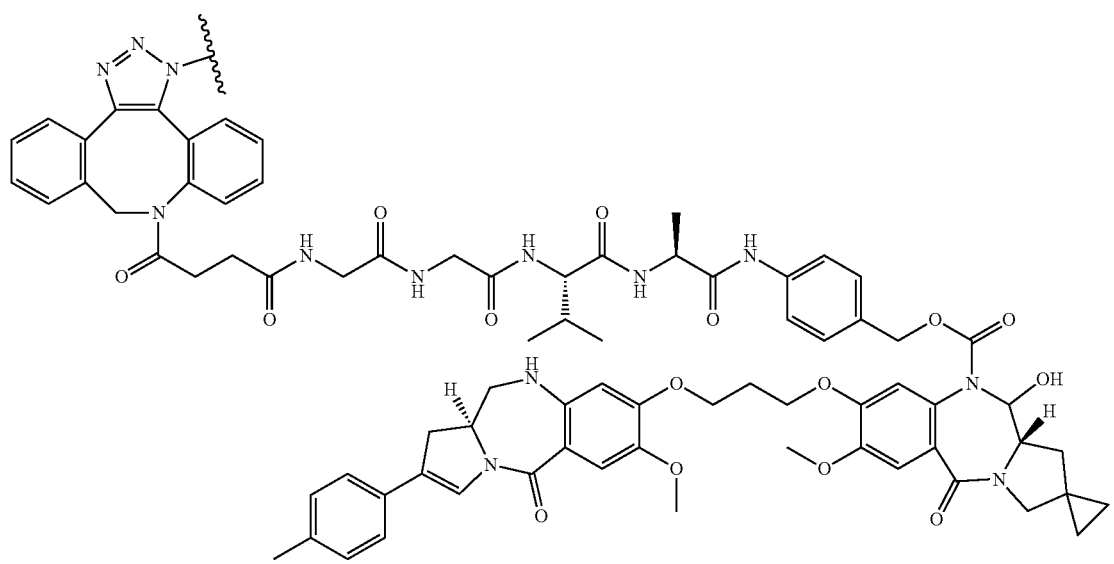

(The triazole ring to be formed in step 1 has geometric isomers, and the compound obtained in step 1 of Example 112 has a linker as a mixture of the two structures shown above as R.)

Step 1: Conjugation of Antibody and Drug-Linker

To a phosphate buffered saline (pH 6.0) solution of the antibody (10.2 mg/mL, 1.00 mL) obtained in step 1 of Example 59, 1,2-propanediol (0.917 mL) and a 10 mM dimethyl sulfoxide solution of the compound obtained in step 8 of Example 31 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.00 mL of a solution of the desired compound.

Characterization: The following characteristic values were obtained by using common operations E and F.

Antibody concentration: 1.49 mg/mL, antibody yield: 8.94 mg (89%), average number of conjugated drug molecules per antibody molecule (n): 1.9

Example 113: ADC47

[Formula 240]

R = 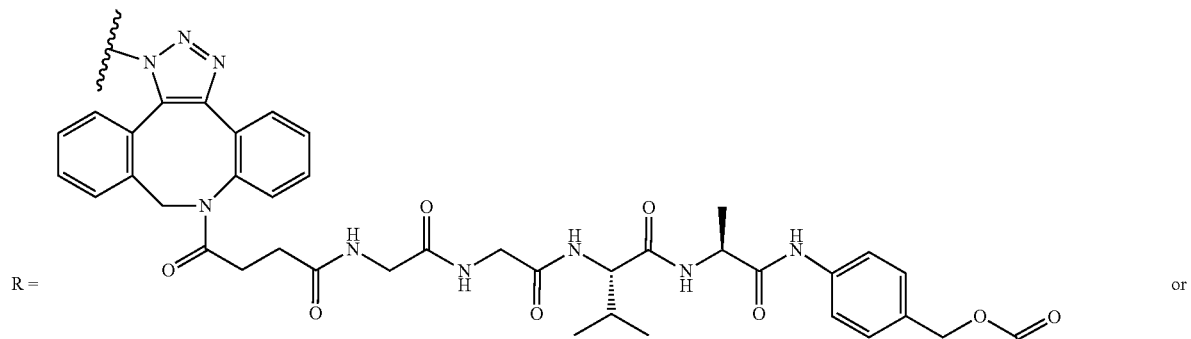

or

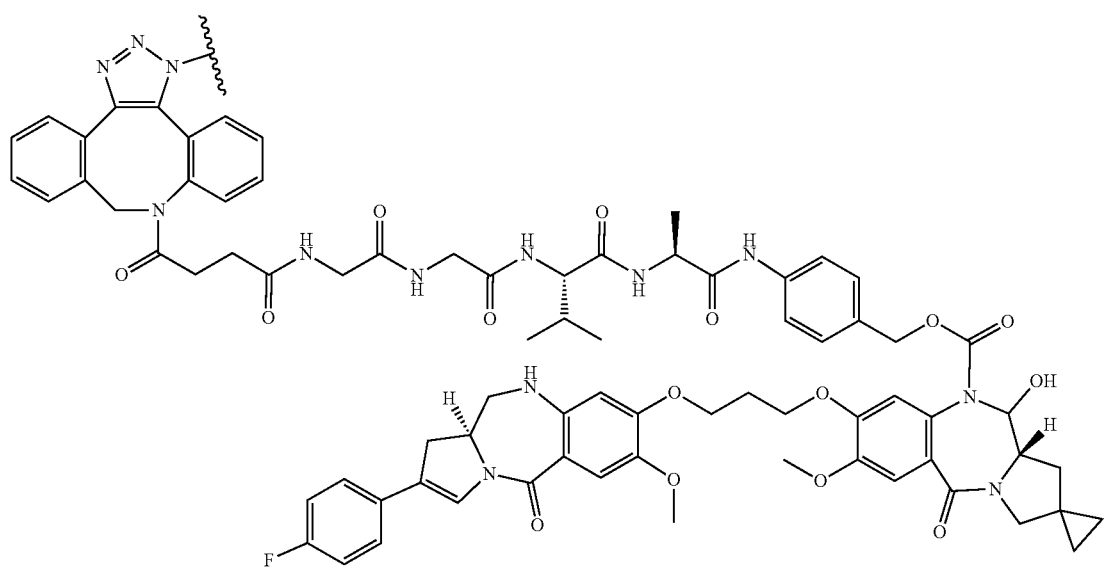

(The triazole ring to be formed in step 1 has geometric isomers, and the compound obtained in step 1 of Example 113 has a linker as a mixture of the two structures shown above as R.)

Step 1: Conjugation of Antibody and Drug-Linker

To a phosphate buffered saline (pH 6.0) solution of the antibody (10.2 mg/mL, 1.00 mL) obtained in step 1 of Example 59, 1,2-propanediol (0.917 mL) and a 10 mM dimethyl sulfoxide solution of the compound obtained in step 8 of Example 32 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.00 mL of a solution of the desired compound.

Characterization: The following characteristic values were obtained by using common operations E and F.

Antibody concentration: 1.45 mg/mL, antibody yield: 8.73 mg (87%), average number of conjugated drug molecules per antibody molecule (n): 1.9

Example 114: ADC48

[Formula 241]

R =

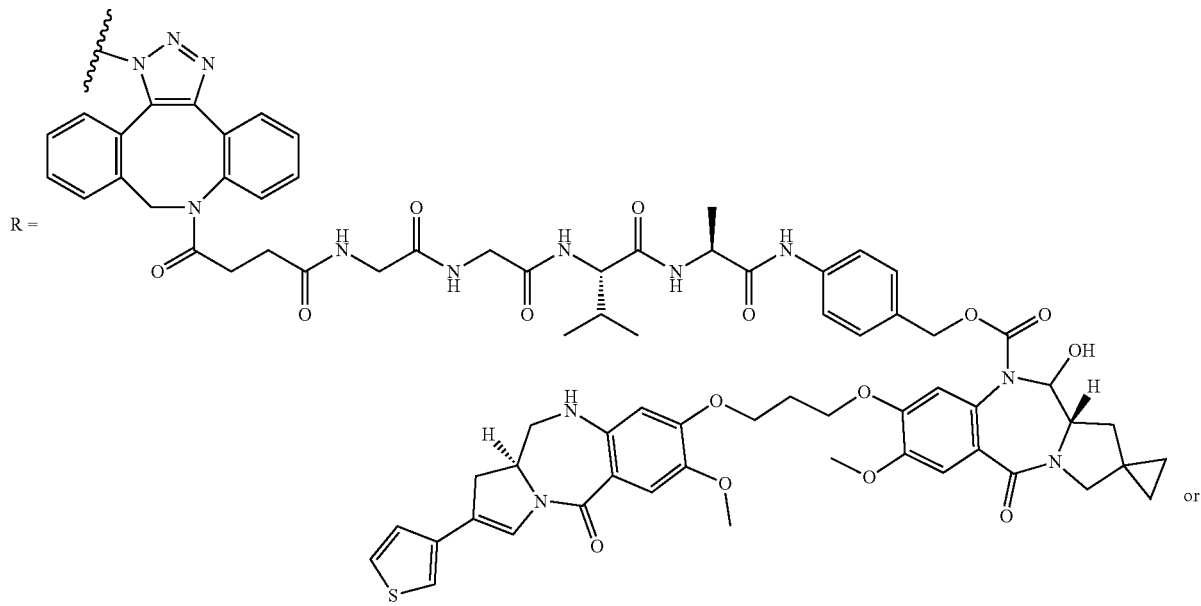

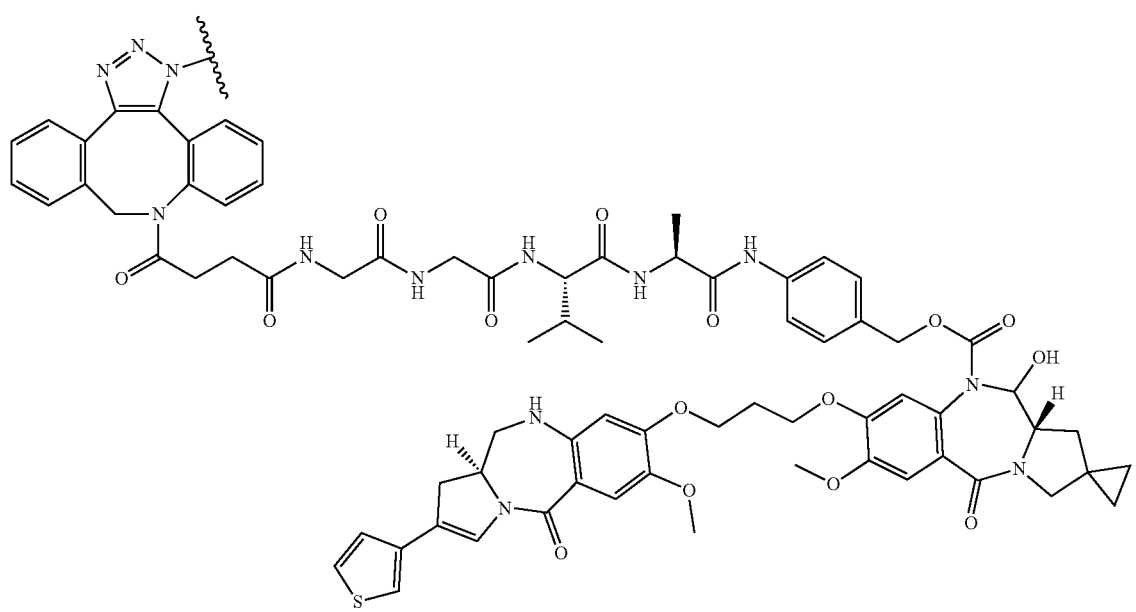

or (The triazole ring to be formed in step 1 has geometric isomers, and the compound obtained in step 1 of Example 114 has a linker as a mixture of the two structures shown above as R.)

Step 1: Conjugation of Antibody and Drug-Linker

To a phosphate buffered saline (pH 6.0) solution of the antibody (10.2 mg/mL, 1.00 mL) obtained in step 1 of Example 59, 1,2-propanediol (0.917 mL) and a 10 mM dimethyl sulfoxide solution of the compound obtained in step 8 of Example 33 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.00 mL of a solution of the desired compound.

Characterization: The following characteristic values were obtained by using common operations E and F.

Antibody concentration: 1.45 mg/mL, antibody yield: 8.70 mg (87%), average number of conjugated drug molecules per antibody molecule (n): 1.9

Example 115: ADC49

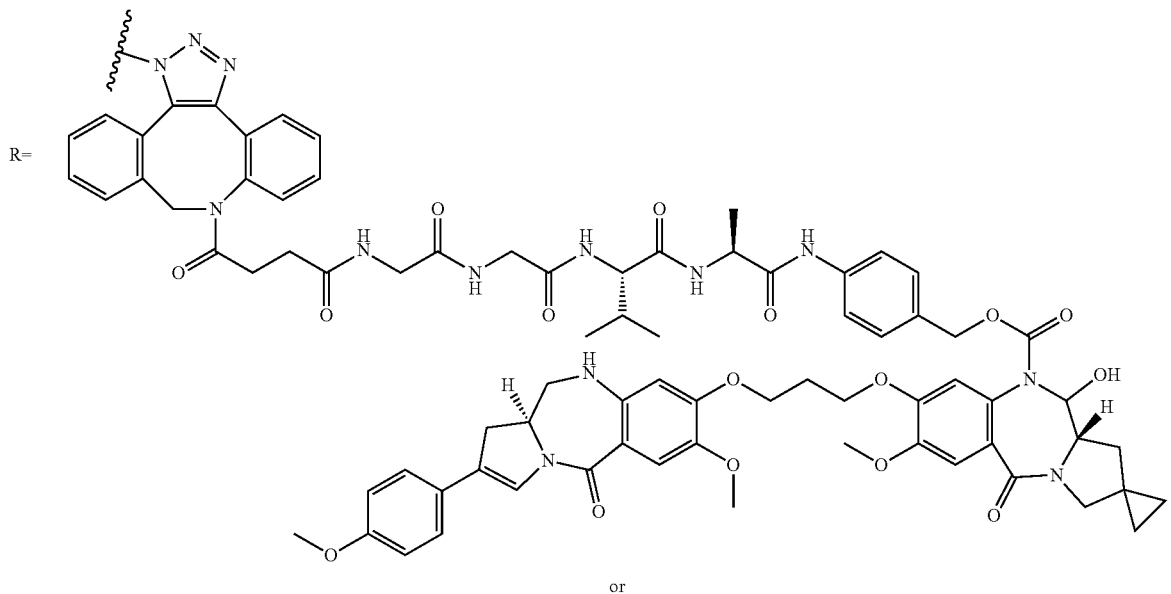

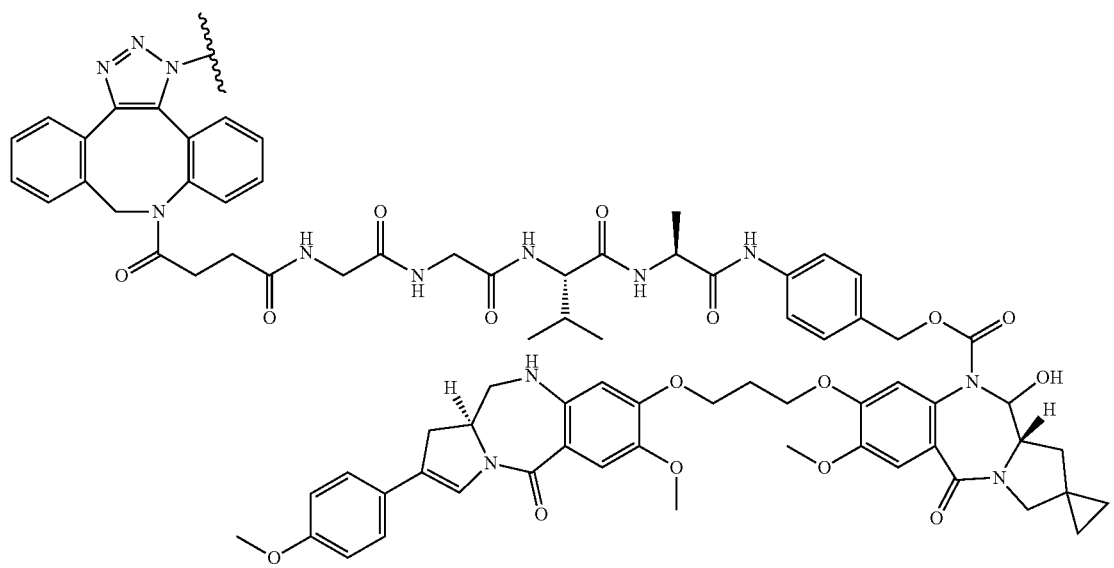

(The triazole ring to be formed in step 1 has geometric isomers, and the compound obtained in step 1 of Example 115 has a linker as a mixture of the two structures shown above as R.)

Step 1: Conjugation of Antibody and Drug-Linker

To a phosphate buffered saline (pH 6.0) solution of the antibody (10.2 mg/mL, 1.00 mL) obtained in step 1 of Example 60, 1,2-propanediol (0.917 mL) and a 10 mM dimethyl sulfoxide solution of the compound obtained in step 13 of Example 3 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.00 mL of a solution of the desired compound.

Characterization: The following characteristic values were obtained by using common operations E and F.

Antibody concentration: 1.41 mg/mL, antibody yield: 8.45 mg (85%), average number of conjugated drug molecules per antibody molecule (n): 1.9

605

Example 116: ADC50

(The triazole ring to be formed in step 1 has geometric isomers, and the compound obtained in step 1 of Example 116 has a linker as a mixture of the two structures shown above as R) (see FIG. 70).

Step 1: Conjugation of Antibody and Drug-Linker

To a phosphate buffered saline (pH 6.0) solution of the antibody (10 mg/mL, 1.00 mL) obtained in step 2 of Example 65, 1,2-propanediol (0.917 mL) and a 10 mM dimethyl sulfoxide solution of the compound obtained in step 13 of Example 3 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.00 mL of a solution of the desired compound.

Characterization: The following characteristic values were obtained by using common operations E and F.

Antibody concentration: 1.47 mg/mL, antibody yield: 8.8 mg (88%), average number of conjugated drug molecules per antibody molecule (n): 1.9

606

Example 117: ADC51

(The triazole ring to be formed in step 1 has geometric isomers, and the compound obtained in step 1 of Example 117 has a linker as a mixture of the two structures shown as R) (see FIG. 71).

Step 1: Conjugation of Antibody and Drug-Linker

To a phosphate buffered saline (pH 6.0) solution of the antibody (10.2 mg/mL, 1.00 mL) obtained in step 2 of Example 64, 1,2-propanediol (0.917 mL) and a 10 mM dimethyl sulfoxide solution of the compound obtained in step 13 of Example 3 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.00 mL of a solution of the desired compound.

Characterization: The following characteristic values were obtained by using common operations E and F.

Antibody concentration: 1.36 mg/mL, antibody yield: 8.19 mg (82%), average number of conjugated drug molecules per antibody molecule (n): 1.8

Example 118: ADC52

[Formula 245]

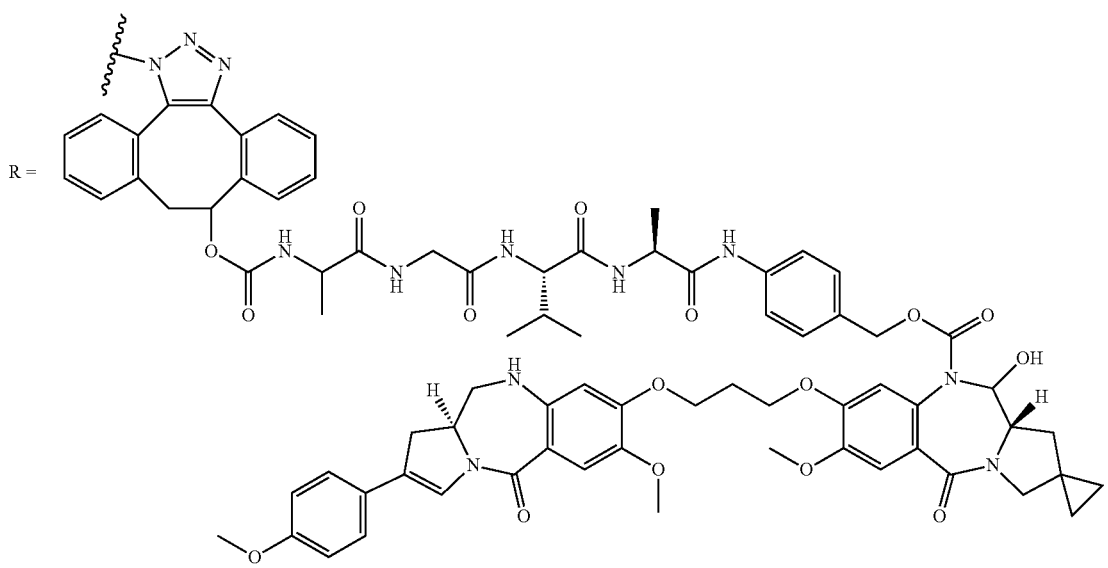

or 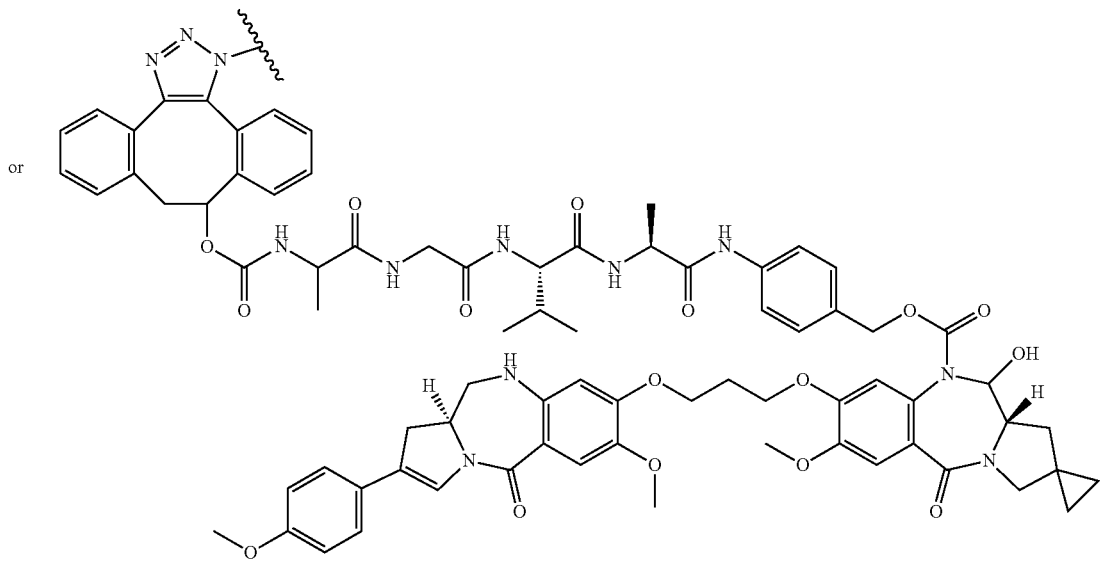

(The triazole ring to be formed in step 1 has geometric isomers, and the compound obtained in step 1 of Example 118 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 60, 1,2-propanediol (0.917 mL) and a 10 mM dimethyl sulfoxide solution of the compound obtained in step 2 of Example 8 (0.0825 mL; 12 equivalents per antibody molecule) were added at room temperature, and the resultant was reacted using a tube rotator (MTR-103, AS ONE Corporation) at room temperature for 3 days.

Purification operation: The solution was purified by using common operation D to afford 6.00 mL of a solution of the desired compound.
Characterization: The following characteristic values were obtained by using common operations E and F.
Antibody concentration: 1.06 mg/mL, antibody yield: 6.35 mg (63%), average number of conjugated drug molecules per antibody molecule (n): 1.2

Example 119: ADC53

(The triazole ring to be formed in step 1 has geometric isomers, and the compound obtained in step 1 of Example 119 has a linker as a mixture of the two structures shown above as R) (see FIG. 72).

Step 1: Conjugation of Antibody and Drug-Linker

To a phosphate buffered saline (pH 6.0) solution of the antibody (9.89 mg/mL, 0.40 mL) obtained in step 2 of Example 66, 1,2-propanediol (0.367 mL) and a 10 mM dimethyl sulfoxide solution of the compound obtained in step 13 of Example 3 (0.0328 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 2.50 mL of a solution of the desired compound.
Characterization: The following characteristic values were obtained by using common operations E and F.
Antibody concentration: 1.16 mg/mL, antibody yield: 2.89 mg (72%), average number of conjugated drug molecules per antibody molecule (n): 1.8

Example 120: ADC54

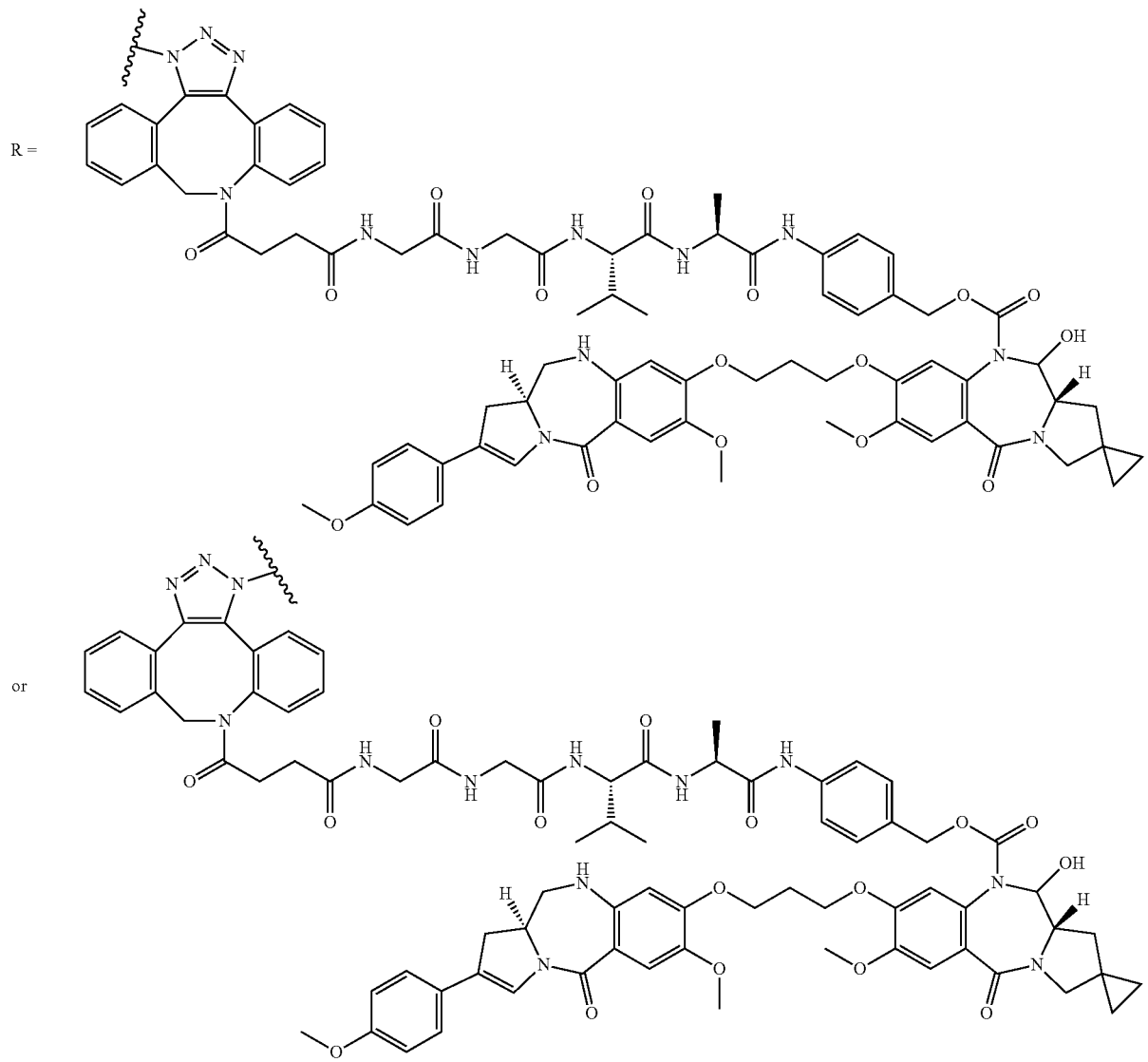

[Formula 247]

R = or (The triazole ring to be formed in step 1 has geometric isomers, and the compound obtained in step 1 of Example 120 has a linker as a mixture of the two structures shown above as R.)

Step 1: Conjugation of Antibody and Drug-Linker

To a phosphate buffered saline (pH 6.0) solution of the antibody (10.0 mg/mL, 1.00 mL) obtained in step 1 of Example 59, 1,2-propanediol (0.917 mL) and a 10 mM dimethyl sulfoxide solution of the compound obtained in step 12 of Example 4 (0.0825 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 6 mL of a solution of the desired compound.

Characterization: The following characteristic values were obtained by using common operations E and F.
Antibody concentration: 1.49 mg/mL, antibody yield: 8.94 mg (89%), average number of conjugated drug molecules per antibody molecule (n): 1.8

Example 121: Anticellular Effect of Antibody-Drug Conjugate (1)

NCI-N87 (American Type Culture Collection; ATCC CRL-5822), a human gastric cancer cell line of HER2 antigen-positive cells, was cultured in RPMI1640 Medium (Thermo Fisher Scientific; hereinafter, referred to as RPMI medium) containing 10% fetal bovine serum (Hyclone). MDA-MB-468 (ATCC HTB-132), HER2 antigen-negative cells, was cultured in Leibovitz's L-15 Medium (Thermo Fisher Scientific; hereinafter, referred to as Leibovitz's medium) containing 10% fetal bovine serum (Hyclone).

NCI-N87 and MDA-MB-468 cells were prepared with RPMI medium and Leibovitz's medium, respectively, to reach $2.5 \times 10^4$ cells/mL, and 80 µL portions of them were added to a 96-well cell culture microplate. After addition of the cells, NCI-N87 was cultured at 37° C. and 5% $CO_2$ overnight, and MDA-MB-468 was cultured at 37° C. overnight, without setting of $CO_2$ concentration.

On the next day, 20 µL portions of an anti-HER2 antibody-drug conjugate diluted with RPMI medium or Leibovitz's medium to 100 nM, 10 nM, 1 nM, 0.1 nM, 0.01 nM, and 0.001 nM were added to the microplate. To each well without any antibody-drug conjugate, 20 µL of RPMI medium or Leibovitz's medium was added. NCI-N87 was cultured at 37° C. and 5% $CO_2$ for 6 days, and MDA-MB-468 was cultured at 37° C. for 6 days, without setting of $CO_2$ concentration. After culturing, the microplate was taken out of the incubator, and left to stand at room temperature for 30 minutes. CellTiter-Glo Luminescent Cell Viability Assay (Promega Corporation) in an amount equivalent to that of the culture solution was added, and stirred using a plate mixer. The microplate was left to stand at room temperature for 10 minutes, and thereafter the amount of emission was measured by using a plate reader (PerkinElmer). Cell survival rates were calculated by using the following formula.

Cell survival rate (%)=$a \div b \times 100$ a: Mean value of amounts of emission from wells with test substance
b: Mean value of amounts of emission from wells with medium $IC_{50}$ values were calculated by using the following formula.

$IC_{50}(nM)$=antilog$((50-d) \times (LOG_{10}(b)-LOG_{10}(a)) \div (d-c) + LOG_{10}(b))$ a: Concentration of test substance, a
b: Concentration of test substance, b
c: Cell survival rate when test substance of concentration a was added
d: Cell survival rate when test substance of concentration b was added a and b satisfy a>b at points sandwiching a cell survival rate of 50%.

The antibody-drug conjugates ADC17, ADC18, ADC1, ADC54, ADC20, ADC34, ADC23, ADC24, and ADC25 each exhibited an anticellular effect of $IC_{50}<0.001$ (nM) on the NCI-N87 cells. The antibody-drug conjugates ADC26, ADC27, ADC16, ADC11, ADC12, ADC2, ADC3, ADC4, ADC43, ADC5, ADC21, ADC48, ADC44, ADC6, ADC7, ADC28, ADC29, ADC13, ADC14, ADC30, ADC31, ADC32, ADC33, ADC35, ADC36, ADC8, ADC9, ADC38, and ADC39 each exhibited an anticellular effect of 0.001 $IC_{50}<0.1$ (nM). None of the antibody-drug conjugates exhibited anticellular effect on the MDA-MB-468 cells ($IC_{50}>0.1$ (nM)).

Example 122: Anticellular Effect of Antibody-Drug Conjugate (2)

NCI-N87 (American Type Culture Collection; ATCC CRL-5822), a human gastric cancer cell line of HER2 antigen-positive cells, was cultured in RPMI1640 Medium (Thermo Fisher Scientific; hereinafter, referred to as RPMI medium) containing 10% fetal bovine serum (Hyclone). JIMT-1 (Deutsche Sammlung von Mikroorganismen und Zellkulturen GmbH; DSMZ ACC 589), a human breast cancer cell line of HER2 antigen-positive cells, was cultured in Dulbecco's Modified Eagle Medium (Thermo Fisher Scientific; hereinafter, referred to as DMEM medium) containing 10% fetal bovine serum (Hyclone). NCI-N87 cells were prepared with RPMI medium to reach $5.0 \times 10^4$ cells/mL and JIMT-1 cells were prepared with DMEM medium to reach $1.3 \times 10^4$ cells/mL, and 80 µL portions of them were added to a 96-well cell culture microplate, and the cells were cultured at 37° C. and 5% $CO_2$ overnight.

On the next day, 20 µL portions of the anti-HER2 antibody-drug conjugate ADC49 or anti-LPS Antibody-drug conjugate ADC53 diluted with RPMI medium or DMEM medium to 400 nM, 80 nM, 16 nM, 3.2 nM, 0.64 nM, 0.13 nM, 0.026 nM, 0.0051 nM, and 0.0010 nM were added to the microplate. To each well without any antibody-drug conjugate, 20 µL of RPMI medium or DMEM medium was added. The cells were cultured at 37° C. and 5% $CO_2$ for 6 days. After culturing, the microplate was taken out of the incubator, and left to stand at room temperature for 30 minutes. CellTiter-Glo Luminescent Cell Viability Assay (Promega Corporation) in an amount equivalent to that of the culture solution was added, and stirred using a plate mixer. The microplate was left to stand at room temperature for 10 minutes, and thereafter the amount of emission was measured by using a plate reader (PerkinElmer). Cell survival rates were calculated by using the following formula.

Cell survival rate (%)=$a \div b \times 100$ a: Mean value of amounts of emission from wells with test substance
b: Mean value of amounts of emission from wells with medium $IC_{50}$ values were calculated by using the following formula.

$IC_{50}(nM)$=antilog$((50-d) \times (LOG_{10}(b)-LOG_{10}(a)) \div (d-c) + LOG_{10}(b))$ a: Concentration of test substance, a
b: Concentration of test substance, b
c: Cell survival rate when test substance of concentration a was added
d: Cell survival rate when test substance of concentration b was added a and b satisfy a>b at points sandwiching a cell survival rate of 50%.

The anti-HER2 antibody-drug conjugate ADC49 exhibited an anticellular effect of $0.001<IC50<0.1$ (nM) on both of the NCI-N87 and JIMT-1 cells. The anti-LPS Antibody-drug conjugate ADC53 exhibited, by contrast, no anticellular effect on both cells ($IC_{50}>0.1$ (nM)).

Example 123: Anticellular Effect of Antibody-Drug Conjugate (3)

OV-90 (ATCC CRL-11732), a human ovarian cancer cell line of CLDN6 antigen-positive cells, was cultured in 1:1 mixed medium (hereinafter, referred to as the medium) of Medium199 (Thermo Fisher Scientific) and MCDB 105 Medium (Sigma-Aldrich Co. LLC) containing 15% fetal bovine serum (Hyclone). OV-90 cells were prepared with the medium to reach $1.9 \times 10^4$ cells/mL, and 80 µL portions of them were added to a 96-well cell culture microplate, and the cells were cultured at 37° C. and 5% $CO_2$ overnight.

On the next day, 20 µL portions of the anti-CLDN6 antibody-drug conjugate ADC40, ADC41, or ADC42 diluted with the medium to 50 nM, 10 nM, 2.0 nM, 400 pM, 80 pM, 16 pM, 3.2 pM, 0.64 pM, and 0.13 pM were added to the microplate. To each well without any antibody-drug conjugate, 20 µL of the medium was added. The cells were cultured at 37° C. and 5% $CO_2$ for 6 days. After culturing, the microplate was taken out of the incubator, and left to stand at room temperature for 30 minutes. CellTiter-Glo Luminescent Cell Viability Assay (Promega Corporation) in an amount equivalent to that of the culture solution was added, and stirred using a plate mixer. The microplate was left to stand at room temperature for 10 minutes, and thereafter the amount of emission was measured by using a plate reader (PerkinElmer). Cell survival rates were calculated by using the following formula.

Cell survival rate (%)=$a \div b \times 100$ a: Mean value of amounts of emission from wells with test substance
b: Mean value of amounts of emission from wells with medium $IC_{50}$ values were calculated by using the following formula.

$IC_{50}$(nM)=antilog$((50-d) \times (LOG_{10}(b)-LOG_{10}(a)) \div (d-c)+LOG_{10}(b))$ a: Concentration of test substance, a
b: Concentration of test substance, b
c: Cell survival rate when test substance of concentration a was added
d: Cell survival rate when test substance of concentration b was added
a and b satisfy a>b at points sandwiching a cell survival rate of 50%.

The anti-CLDN6 antibody-drug conjugates ADC40, ADC41, and ADC42 each exhibited an anticellular effect of $0.001 < IC_{50} < 0.1$ (nM) on the OV-90 cells.

Example 124: Antitumor Test for Antibody-Drug Conjugate (1)

Mouse: Four- to five-week-old female BALB/c nude mice (Charles River Laboratories Japan, Inc.) were habituated under SPF conditions for 4 to 7 days before being used for experiment. To the mice, sterilized pellets (FR-2, Funabashi Farms Co., Ltd.) were fed and sterilized tap water (prepared by adding 5 to 15 ppm sodium hypochlorite solution) was provided.

Assay and calculation formula: In all of the studies, the major axis and minor axis of a tumor were measured twice or three times a week by using an electronic digital caliper (CD-15CX, Mitutoyo Corp.), and the tumor volume (mm³) was calculated. The calculation formula is as shown below.

Tumor volume (mm³)=Major axis (mm)×[Minor axis (mm)]²×1/2

Each of the antibody-drug conjugates and antibodies was diluted with 10 mM acetate buffer, 5% sorbitol, pH 5.5 (NACALAI TESQUE, INC.; ABS buffer), and a liquid volume of 10 mL/kg was administered into the tail vein. As a control group (Vehicle group), ABS buffer was administered in the same manner.

NCI-N87 cells (ATCC CRL-5822) were suspended in physiological saline (Otsuka Pharmaceutical Factory, Inc.), and $1 \times 10^7$ cells were subcutaneously transplanted to the right flank of each female nude mouse (Day 0), and the mice were randomly grouped on Day 7. The anti-HER2 antibody-drug conjugate ADC26, ADC19, or ADC54 was administered into the tail vein on Day 7 at a dose of 0.3 mg/kg for ADC26 and at a dose of 1 mg/kg for ADC19 and ADC54. As a control group (Vehicle group), ABS buffer was administered in the same manner.

Figure 4:
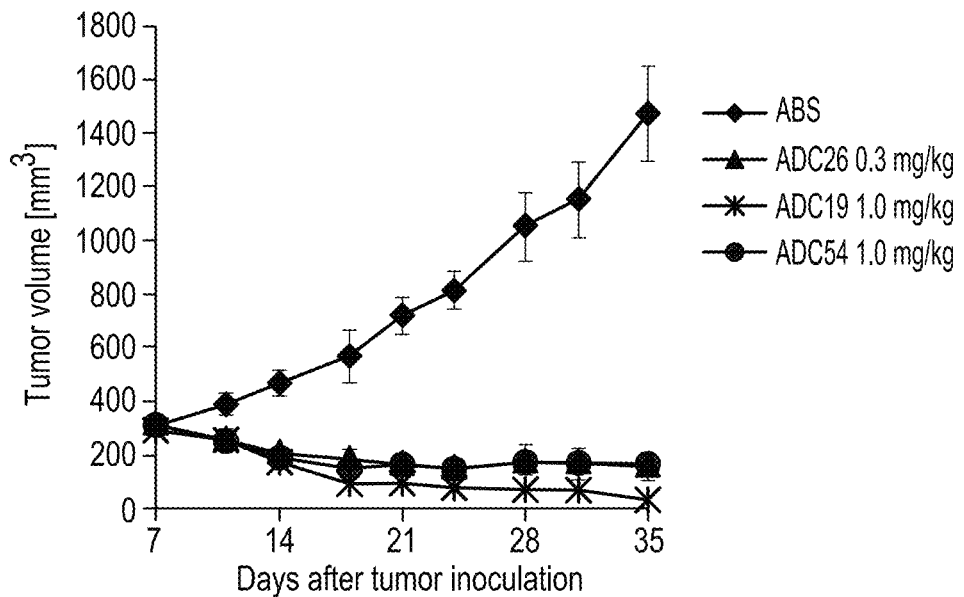
FIG. 4 shows the effects of the anti-HER2 antibody-drug conjugates ADC26, ADC19, and ADC54 on subcutaneously transplanted NCI-N87 cells, a human gastric cancer cell line.

FIG. 4 shows the results. The anti-HER2 antibody-drug conjugates ADC26, ADC19, and ADC54 were found to have strong antitumor effect causing regression of tumor. No weight loss was found for any of the mice with administration of any of the anti-HER2 antibody-drug conjugates.

In the following evaluation examples relating to antitumor test, the method used in the present evaluation example was conducted, unless otherwise stated.

Example 125: Antitumor Test for Antibody-Drug Conjugate (2)

NCI-N87 cells (ATCC CRL-5822) were suspended in Dulbecco's phosphate buffered saline (Sigma-Aldrich Co. LLC), and $1 \times 10^7$ cells were subcutaneously transplanted to the right flank of each female nude mouse (Day 0), and the mice were randomly grouped on Day 4. The anti-HER2 antibody-drug conjugate ADC49, the anti-HER2 antibody trastuzumab (Reference Example 3), or the anti-LPS Antibody-drug conjugate ADC53 was administered into the tail vein on Day 4 at a dose of 0.33 mg/kg for all cases. As a control group (Vehicle group), ABS buffer was administered in the same manner.

Figure 5:
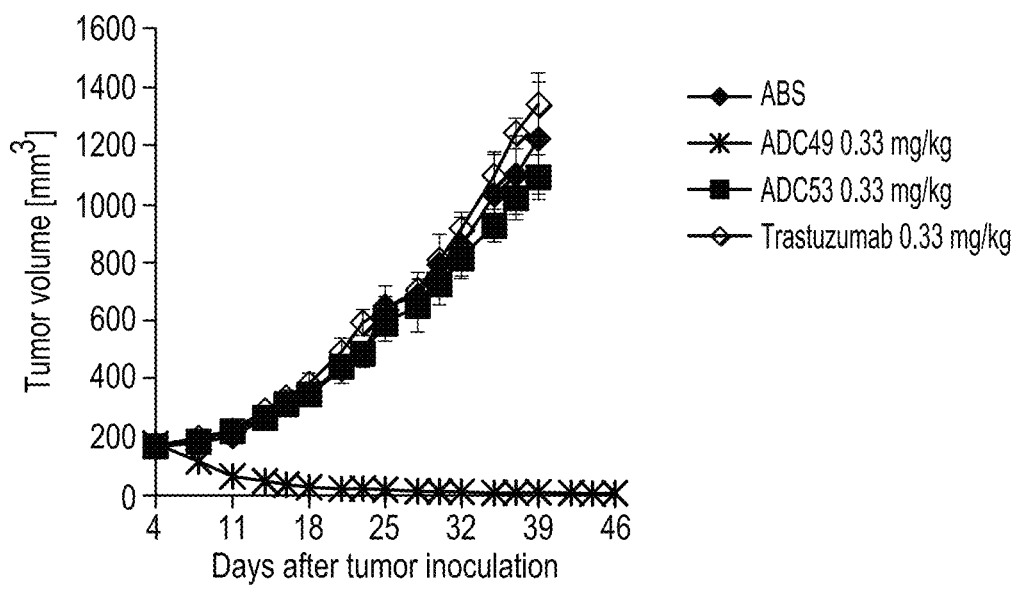
FIG. 5 shows the effects of the anti-HER2 antibody-drug conjugate ADC49, trastuzumab, and the anti-LPS antibody-drug conjugate ADC53 on subcutaneously transplanted NCI-N87 cells, a human gastric cancer cell line.

FIG. 5 shows the results. The anti-HER2 antibody-drug conjugate ADC49 was found to have strong antitumor effect causing regression of tumor. By contrast, the anti-HER2 antibody trastuzumab and the anti-LPS Antibody-drug conjugate ADC53 did not suppress tumor growth. No weight loss caused by administration of the antibody-drug conjugate ADC49 or ADC53, or the anti-HER2 antibody was found for the mice.

Example 126: Antitumor Test for Antibody-Drug Conjugate (3)

KPL-4 cells (Dr. Junichi Kurebayashi, Kawasaki Medical School, British Journal of Cancer, (1999) 79 (5/6). 707-717) were suspended in Dulbecco's phosphate buffered saline (Sigma-Aldrich Co. LLC), and $1.5 \times 10^7$ cells were subcutaneously transplanted to the right flank of each female nude mouse (Day 0), and the mice were randomly grouped on Day 14. The anti-HER2 antibody-drug conjugate ADC49, the anti-LPS Antibody-drug conjugate ADC53, or trastuzumab tesirine (Reference Example 1) was administered into the tail vein on Day 14 at a dose of 0.4 mg/kg. As a control group (Vehicle group), ABS buffer was administered in the same manner.

Figure 6:
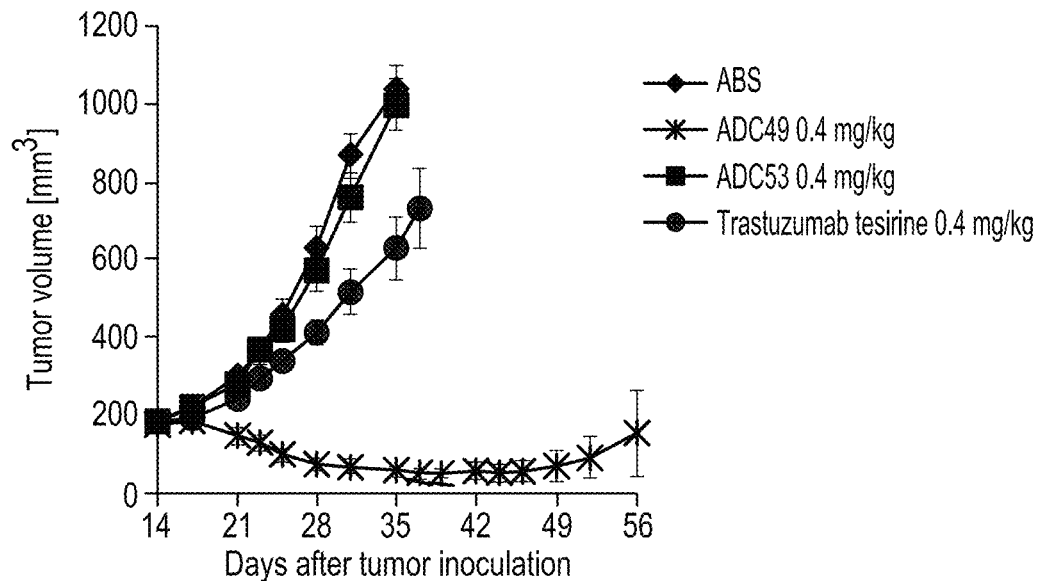
FIG. 6 shows the effects of the anti-HER2 antibody-drug conjugate ADC49, the anti-LPS antibody-drug conjugate ADC53, and trastuzumab-tesirine (Reference Example 1) on subcutaneously transplanted KPL-4 cells, a human breast cancer cell line.

FIG. 6 shows the results. The anti-HER2 antibody-drug conjugate ADC49 was found to have strong antitumor effect causing regression of tumor. By contrast, regression of tumor was not found for ADC53 and trastuzumab tesirine. No weight loss caused by administration of ADC49 or trastuzumab tesirine was found for the mice.

Example 127: Antitumor Test for Antibody-Drug Conjugate (4)

JIMT-1 cells (DSMZ ACC 589) were suspended in physiological saline (Otsuka Pharmaceutical Factory, Inc.), and $5 \times 10^6$ cells were subcutaneously transplanted to the right flank of each female nude mouse (Day 0), and the mice were randomly grouped on Day 10. The anti-HER2 antibody-drug conjugate ADC49 or trastuzumab tesirine (Reference Example 1) was administered into the tail vein on Day 10 at a dose of 0.4 mg/kg. As a control group (Vehicle group), ABS buffer was administered in the same manner.

Figure 7:
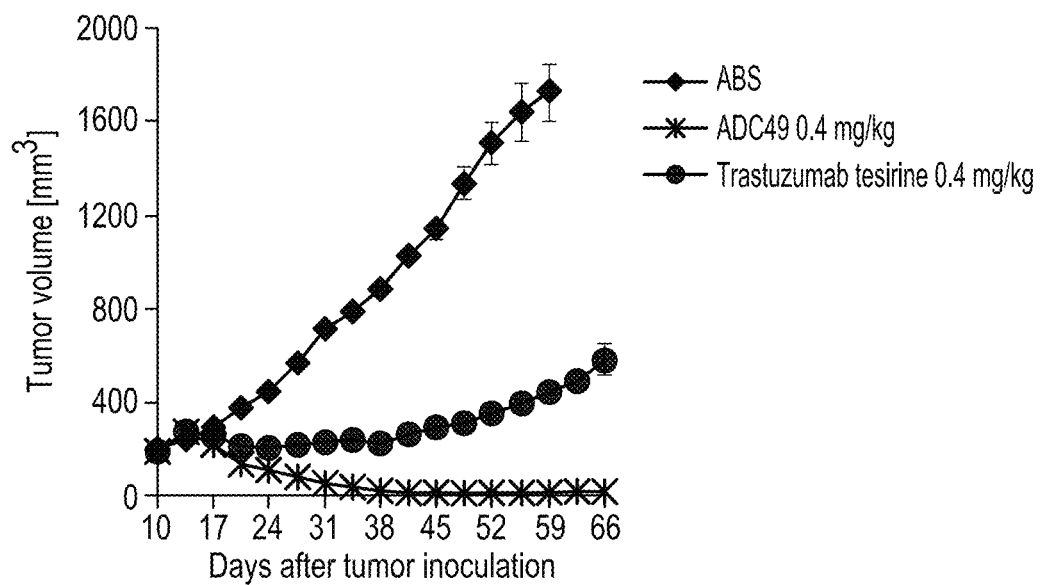
FIG. 7 shows the effect of the anti-HER2 antibody-drug conjugate ADC49 and trastuzumab-tesirine (Reference Example 1) on subcutaneously transplanted JIMT-1 cells, a human breast cancer cell line.

FIG. 7 shows the results. The anti-HER2 antibody-drug conjugate ADC49 was found to have strong antitumor effect causing regression of tumor. For trastuzumab tesirine, by contrast, antitumor effect was found but regression of tumor was not found. No weight loss caused by administration of ADC49 or trastuzumab tesirine was found for the mice.

Example 128: Antitumor Test for Antibody-Drug Conjugate (5)

OV-90 cells (ATCC CRL-11732) were suspended in Matrigel (Corning Incorporated), and $2.5 \times 10^6$ cells were subcutaneously transplanted to the right flank of each female nude mouse (Day 0), and the mice were randomly grouped on Day 15. The anti-CLDN6 antibody-drug conjugate ADC40 or anti-CLDN6 antibody (H1L1) tesirine was administered into the tail vein on Day 15 at a dose of 0.33 mg/kg. As a control group (Vehicle group), ABS buffer was administered in the same manner.

Figure 8:
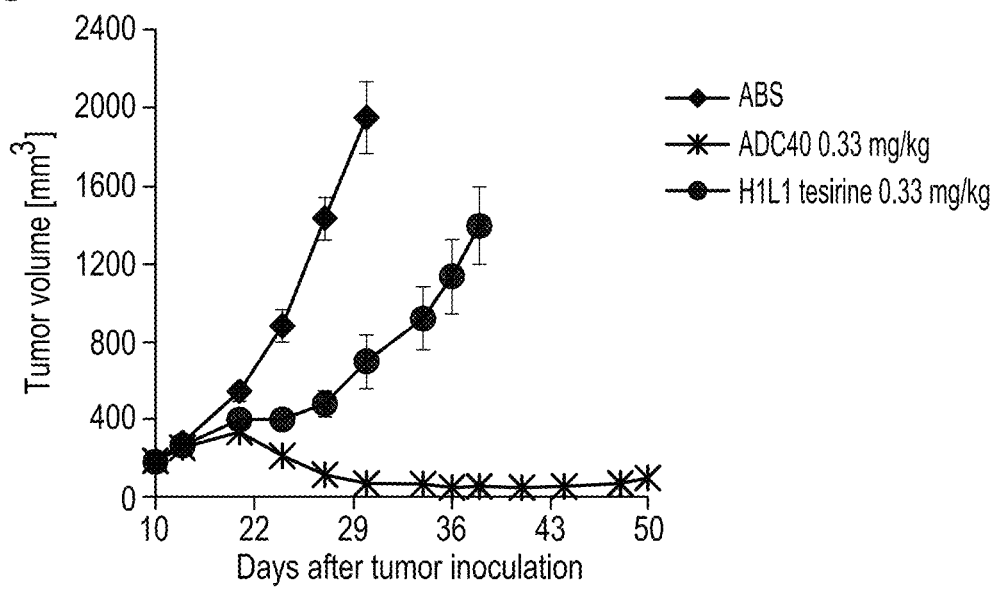
FIG. 8 shows the effects of the anti-CLDN6 antibody-drug conjugate ADC40 and an anti-CLDN6 antibody (H1L1)-tesirine (Reference Example 1) on subcutaneously transplanted OV-90 cells, a human ovarian cancer cell line.

FIG. 8 shows the results. The anti-CLDN6 antibody-drug conjugate ADC40 was found to have strong antitumor effect causing regression of tumor. By contrast, regression of tumor was not found for the anti-CLDN6 antibody (H1L1)-tesirine. No weight loss caused by administration of ADC40 or H1L1-tesirine was found for the mice.

Example 129: Antitumor Test for Antibody-Drug Conjugate (6)

NIH:OVCAR-3 cells (ATCC HTB-161) were suspended in Matrigel (Corning Incorporated), and $1 \times 10^7$ cells were subcutaneously transplanted to the right flank of each female nude mouse (Day 0), and the mice were randomly grouped on Day 25. The anti-CLDN6 antibody-drug conjugate ADC40 or anti-CLDN6 antibody (H1L1)-tesirine was administered into the tail vein on Day 25 at a dose of 0.33 mg/kg. As a control group (Vehicle group), ABS buffer was administered in the same manner.

Figure 9:
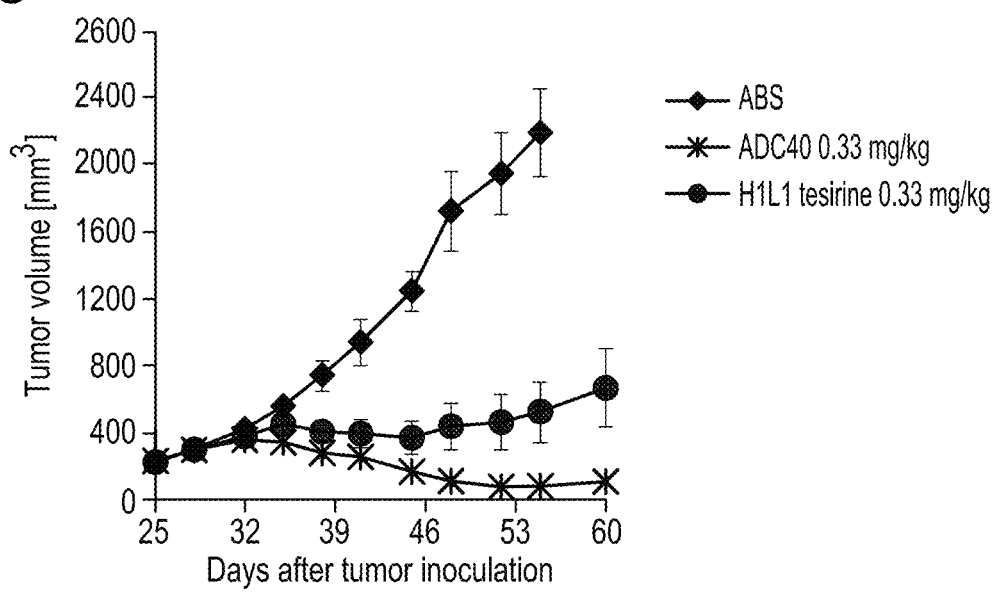
FIG. 9 shows the effects of the anti-CLDN6 antibody-drug conjugate ADC40 and an anti-CLDN6 antibody (H1L1)-tesirine (Reference Example 1) on subcutaneously transplanted NIH:OVCAR-3 cells, a human ovarian cancer cell line.

FIG. 9 shows the results. The anti-CLDN6 antibody-drug conjugate ADC40 was found to have strong antitumor effect causing regression of tumor. For H1L1-tesirine, by contrast, antitumor effect was found but regression of tumor was not found. No weight loss caused by administration of ADC40 or H1L1-tesirine was found for the mice.

Example 130: Antitumor Test for Antibody-Drug Conjugate (7)

FaDu cells (ATCC HTB-43) were suspended in physiological saline (Otsuka Pharmaceutical Factory, Inc.), and $3 \times 10^6$ cells were subcutaneously transplanted to the right flank of each female nude mouse (Day 0), and the mice were randomly grouped on Day 10. The anti-TROP2 antibody-drug conjugate ADC50 or the anti-LPS Antibody-drug conjugate ADC53 was administered into the tail vein on Day 10 at a dose of 0.4 mg/kg. As a control group (Vehicle group), ABS buffer was administered in the same manner.

FIG. 10 shows the results. The anti-TROP2 antibody-drug conjugate ADC50 was found to have strong antitumor effect causing regression of tumor. By contrast, the anti-LPS Antibody-drug conjugate ADC53 did not suppress tumor growth. No weight loss caused by administration of ADC50 or ADC53 was found for the mice.

Example 131: Mouse Anti-CLDN6 Antibody B1-Producing Hybridoma (218B1) and Mouse Anti-CLDN6 Antibody C7-Producing Hybridoma (218C7)

131-1. Immunization of Mice and Acquisition of Hybridomas 1-1) Preparation of Cells for Immunization of Mice In RPMI-1640 (Roswell Park Memorial Institute-1640) 10% FBS (fetal bovine serum) (+) medium (10 mL or 20 mL), $2 \times 10^6$ or $5 \times 10^6$ NOR-P1 cells (human pancreatic cancer cell line, RIKEN RCB-2139) were cultured for 5 days and then collected, and washed twice with PBS (phosphate buffered saline) and resuspended in PBS (300 μL).

1-2) Immunization of Mice

Each BALB/c mouse (12-week-old) was intraperitoneally immunized with NOR-P1 cells ($2 \times 10^6$ cells) at intervals of about 1 week for the first to fifth immunization. About 2 weeks after the fifth immunization, each BALB/c mouse was intraperitoneally immunized with NOR-P1 cells ($5 \times 10^6$ cells). About 3 weeks after the sixth immunization, each BALB/c mouse was intraperitoneally immunized with NOR-P1 cells ($2 \times 10^6$ cells). Each BALB/c mouse was intraperitoneally immunized with $2 \times 10^6$ NOR-P1 cells at intervals of about 2 weeks for the 8th to 10th immunization. About 3 weeks after the 10th immunization (11th immunization) and 3 days thereafter (12th immunization, final immunization), each BALB/c mouse was intraperitoneally immunized with $5 \times 10^6$ NOR-P1 cells. Splenocytes were isolated 3 days after the final immunization.

1-3) Preparation of Splenocytes from Immunized Mice

The spleen was isolated from each immunized mouse, triturated, and suspended in RPMI1640 10% FBS (+) medium. The cell suspension was passed through a Cell Strainer (70 m, BD Falcon), and then centrifuged at 1500 rpm at room temperature for 5 minutes to discard the supernatant. Tris-NH$_4$Cl solution (20 mM Tris-HCl pH 7.2, 77.6 mM NH$_4$Cl; 20 mL) was added thereto, and the resultant was treated at room temperature for 5 minutes. PBS (20 mL) was added thereto, and the resultant was centrifuged at 1500 rpm at room temperature for 5 minutes. After the supernatant was discard, RPMI1640 FBS (+) medium (10 mL) was added to the residue.

1-4) Preparation of Myeloma Cells

P3U1 cells (mouse myeloma cell line) was cultured in RPMI1640 FBS (+) medium for 5 days, and then collected and resuspended in RPMI1640 FBS (+) medium (20 mL).

1-5) Cell Fusion

Splenocytes and myeloma cells were mixed together at 5:1, and centrifuged at 1500 rpm at room temperature for 5 minutes. The cells were washed twice with RPMI1640 FBS (−) medium (10 mL), and then centrifuged (1500 rpm, 5 minutes). The group of cells in the precipitated fraction obtained was sufficiently loosened, and polyethylene glycol-1500 (PEG-1500; 1 mL) was then gradually added thereto with stirring over about 1 minute. After stirring for 3 minutes 30 seconds, the resultant was left to stand at room temperature for 30 seconds. Thereafter, RPMI medium 10% Low IgG FBS (+) (10 mL) was added to the cell solution over 1 minute. The cell suspension was centrifuged (1500 rpm, 5 minutes), and the cells in the precipitated fraction obtained were gently loosened, and then gently suspended in HAT medium (RPMI1640 medium containing 10% Low IgG FBS, HAT Media Supplement, and 5% BriClone; 200 mL). The suspension was aliquoted into a 96-well culture plate at 200 μL/well, and cultured in an incubator at 37° C. and 5% CO$_2$ for 6 days.

1-6) Screening of Hybridomas/Preparation of Probe

DT3C, a recombinant complex protein, was produced for the purpose of assaying internalization of antibodies and immunotoxin activity. This DT3C is a protein formed by fusing the catalytic domain of diphtheria toxin (DT) and the antibody-binding domain of streptococcal protein G through genetic engineering. DT3C specifically binds to the Fc region of antibodies, and induce cell death through protein synthesis inhibition when being incorporated in a cell. Use of this system allows simultaneous observation of the internalization of an antibody and the cytocidal effect of immunotoxin (Yamaguchi, M. et al., Biochemical and Biophysical Research Communications 454 (2014) 600-603).

1-7) Screening of Hybridomas with DT3C

To a 96-well plate, 4 µg/mL DT3C (25 µL) was added, and the culture supernatant of the hybridoma obtained in step 1-5 (25 µL) was further added, and the resultant was incubated at room temperature for 30 minutes. NOR-P1 cells (50 µL) were seeded at $2\times10^5$ cells/mL (RPMI medium 10% Low IgG FBS (+)), and cultured in a $CO_2$ incubator at 37° C. for 3 days. Through microscopic observation after culturing, wells with the number of adhering cells being about 25% or less of that in using a negative control antibody were determined to be positive. Selected clones were subjected to one or two subcloning steps to establish eight monoclonal hybridoma cell lines.

131-2: Identification of Antigen to which Antibody Produced by Hybridoma Binds

Antigens were identified for two clones, 218B1 and 218C7, of antibodies produced by the hybridomas prepared in Example 131-1.

2-1) Immunoprecipitation of Biotin-Labeled Cell Surface Protein with 218B1 Antibody and 218C7 Antibody Culture supernatant of $2\times10^6$ NTERA-2 cells (human testicular cancer cell line, ATCC CRL-1973) was removed, and the residue was washed twice with PBS. EZ-Link Sulfo-NHS-Biotin (Thermo Fisher Scientific) was suspended in PBS to a concentration of 0.1 mg/mL. After PBS was removed, Biotin/PBS solution was added, and the resultant was incubated on a shaker for 30 minutes, and then washed twice with 100 mM glycine/PBS solution (25 mL) and then washed once with PBS (10 mL). The washed cells were resuspended in 200 µL of lysis buffer (150 mM NaCl, 50 mM Tris-HCl pH 7.4, 1% DDM, Protease inhibitor, Complete EDTA free (F. Hoffmann-La Roche, Ltd.) 1 particle/50 mL), and treated at 4° C. for 30 minutes. The resultant was centrifuged (13000 rpm, 20 minutes, 4° C.) to prepare a cell lysate. To the cell lysate, Protein G Sepharose/lysis buffer (50% slurry; 30 µL) obtained by substituting the buffer of Protein G Sepharose (Protein G Sepharose 4 Fast Flow (GE Healthcare)) with the lysis buffer was added, and the resultant was rotated at 4° C. for 30 minutes and then centrifuged at 4° C. for 1 minute, and the supernatant was collected. To this supernatant the 218B1 antibody or 218C7 antibody (about 3 g) was added, and the resultant was rotated at 4° C. for 30 minutes, to which Protein G Sepharose/lysis buffer (50% slurry; 60 µL) was then added, and the resultant was rotated at 4° C. for 1 hour. The Protein G Sepharose was washed six times with the lysis buffer (1 mL), and then resuspended in 1×SDS sample buffer (Bio-Rad Laboratories, Inc.). After the suspension was treated at 100° C. for 5 minutes, the solution was collected as a sample for SDS-PAGE (polyacrylamide gel electrophoresis).

2-2) SDS-PAGE and Western Blotting

The SDS-PAGE sample prepared in 2-1) was stacked with SuperSep Ace 5-20% (Wako Pure Chemical Industries, Ltd.) at 50 mV for 30 minutes, and then subjected to electrophoresis at 200 mV for 1 hour, and blotted from the gel onto a membrane at 12 mV for 47 minutes. The membrane was washed with PBS-T (PBS (-)-0.02% Tween 20), and then blocked for 1 hour. The membrane was washed three times with PBS-T for 5 minutes, and then reacted with a Streptavidin-horseradish peroxidase conjugate (GE Healthcare; 2000-fold diluted with PBS-T in use) for 1 hour. The membrane was washed twice with PBS-T for 5 minutes, and a targeted band was then detected by using an enhanced chemiluminescence (ECL) method. A band indicating a molecular weight of 18 kDa was detected for any of the case with the 218B1 antibody and the case with the 218C7 antibody, regardless of the presence or absence of DTT added.

2-3) Mass Spectrometry of Immunoprecipitated Product of Cell Protein with 218B1 Antibody and 218C7 Antibody $2\times10^7$ NTERA-2 cells were collected and washed twice with PBS. The cells were collected by using a cell scraper, and centrifuged at 1500 rpm for 5 minutes. After the supernatant was removed, the cells were resuspended in 2 mL of the lysis buffer, and treated at 4° C. for 30 minutes. The resultant was centrifuged (13000 rpm, 20 minutes, 4° C.) to prepare a cell lysate. Protein G Sepharose/lysis buffer (50% slurry; 180 µL) was added to the cell lysate, and the resultant was rotated at 4° C. for 30 minutes and then centrifuged at 4° C. for 1 hour, and the supernatant was collected. The 218B1 antibody (about 9 µg) was added to the supernatant, and the resultant was rotated at 4° C. for 30 minutes, to which Protein G Sepharose/lysis buffer (50% slurry; 180 µL) was then added, and the resultant was rotated at 4° C. for 1 hour. The Protein G Sepharose was washed six times with the lysis buffer (1 mL), and then resuspended in 1×SDS sample buffer. After the suspension was treated at 100° C. for 5 minutes, the solution was collected as a sample for SDS-PAGE. SDS-PAGE was carried out in the same manner as in 2-2), and the electrophoresis gel was stained with CBB. The part corresponding to 18 kDa was cut out of the electrophoresis gel, and subjected to mass spectrometry. The mass spectrometry found that the gel piece contained claudin-6.

2-4) FACS Analysis

Since the antigen for the 218B1 antibody and 218C7 antibody was estimated to be claudin-6 from the mass spectrometry, forced expression analysis by cDNA transfection was carried out. FACS analysis results showed that the 218B1 antibody and 218C7 antibody exhibited strong positive reaction for human claudin-6-expressing CHO-K1 cells, demonstrating that the antigen for the 218B1 antibody and 218C7 antibody is claudin-6.

Example 132: Purification of Antibody from Hybridoma Culture Supernatant

The mouse anti-CLDN6 antibody B1-producing hybridoma (218B1) and mouse anti-CLDN6 antibody C7-producing hybridoma (218C7) produced in Example 131 were cultured in Hybridoma-SFM (Thermo Fisher Scientific) containing 10% Fetal Bovine Serum, Ultra-Low IgG (Thermo Fisher Scientific). The culture supernatant was collected by centrifugation, and filtered through a filter of 0.45 m (produced by Corning Incorporated). The antibody was purified from the culture supernatant through rProtein A affinity chromatography (at 4 to 6° C.) in one step. The step of buffer displacement after rProtein A affinity chromatography was carried out at 4 to 6° C. First, the culture supernatant was applied to a column packed with MabSelectSuRe (produced by GE Healthcare Bioscience) equilibrated with PBS. After the culture solution completely entered the column, the column was washed with PBS in an amount twice or more the column volume. Subsequently, elution was carried out with a 2 M solution of arginine hydrochloride (pH 4.0), and a fraction containing the antibody was collected. The fraction was subjected to liquid displacement to PBS (−) by dialysis (Thermo Scientific, Slide-A-Lyzer Dialysis Cassette). Finally, the fraction was concentrated with a Centrifugal UF Filter Device VIVASPIN20 (molecular weight cutoff: UF10K, Sartorius AG, at 4° C.) to adjust the IgG concentration to 1 mg/mL or more. The fraction was filtered through a Minisart-Plus filter (Sartorius AG), and the resultant was used as a purified sample.

Example 133: In Vitro Evaluation of Mouse Anti-CLDN6 Antibodies B1 and C7

Figure 40:
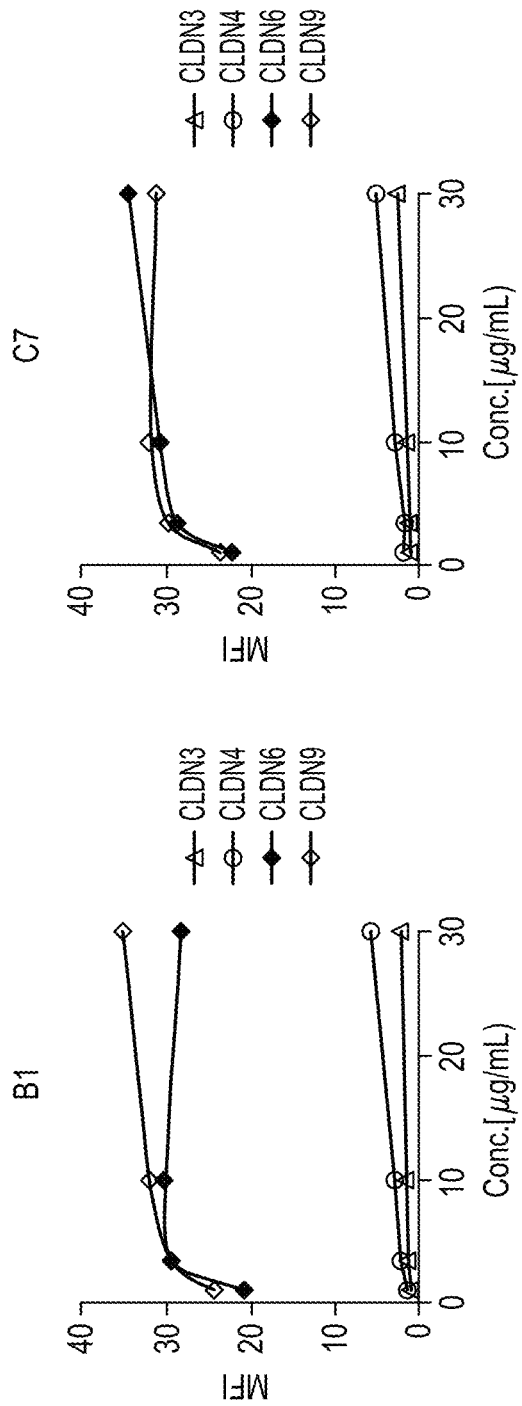
FIG. 40 shows the binding abilities of a B1 antibody and a C7 antibody to human CLDN6 and the family molecules CLDN3, CLDN4, and CLDN9 measured by flow cytometry.

133-1: Evaluation of Binding Ability of Mouse Anti-CLDN6 Antibodies by Flow Cytometry Binding activity of the mouse anti-CLDN6 antibodies produced in Example 132 to human CLDN6 and its family molecules, CLDN3, CLDN4, and CLDN9, was evaluated by using a flow cytometry method. Human CLDN3/pCMV6-Entry, human CLDN4/pCMV6-Entry, human CLDN6/pCMV-Entry, human CLDN9/pCMV6-Entry, or pCMV6-Entry purchased from OriGene Technologies, Inc. was transiently transferred into 293T cells (Thermo Fisher Scientific, HCL4517) by using Lipofectamine 2000 (Thermo Fisher Scientific), and the cells were cultured under conditions of 37° C. and 5% $CO_2$ overnight, and then a cell suspension was prepared. The transfected 293T cell suspension was centrifuged to remove the supernatant, and a mouse anti-CLDN6 antibody (clone number: B1 or C7) or a mouse IgG1 control antibody (R&D Systems, Inc.) was then added and suspended to a final concentration of 30 μg/mL, 10 μg/mL, 3.3 μg/mL, or 1.1 μg/mL, and the resultant was left to stand at 4° C. for 1 hour. The cells were washed twice with Dulbecco's phosphate buffered saline (Sigma-Aldrich Co. LLC) containing 5% fetal bovine serum (Hyclone) (hereinafter, referred to as 5% FBS-containing PBS), and FLUORESCEIN-CONJUGATED GOAT IGG FRACTION TO MOUSE IGG (WHOLE MOLECULE) (MP Biomedicals, Inc.) 500-fold diluted with 5% FBS-containing PBS was then added thereto, and the cells were suspended and left to stand at 4° C. for 1 hour. After washing twice with 5% FBS-containing PBS, detection was carried out by using a flow cytometer (FC500; Beckman Coulter, Inc.). Data analysis was carried out by using FlowJo (Tree Star, Inc.). To confirm each transfection, the cells were permeabilized with 0.25% Tween 20-containing PBS, and then a mouse anti-FLAG antibody (Sigma-Aldrich Co. LLC) was used. FIG. 40 shows the results. In each graph in FIG. 40, the ordinate represents FITC fluorescence intensity indicating the amount of the binding antibody and the abscissa represents antibody concentrations. The mouse anti-CLDN6 antibodies produced bound to human CLDN6 and human CLDN9 to a similar degree, and did not bind to human CLDN3 or human CLDN4. The mouse control IgG1 did not bind to any of the cells.

133-2: Internalization Activity of Antibodies

Internalization activity of the mouse anti-CLDN6 antibodies B1 and C7 was evaluated by using the anti-mouse IgG reagent, to which a toxin that inhibits protein synthesis (saporin) had been conjugated, Mab-ZAP (Advanced Targeting Systems). In this evaluation, Mab-ZAP is incorporated into cells in a manner depending on the internalization activity of a mouse anti-CLDN6 antibody, and saporin, which inhibits protein synthesis, is released in the cells to suppress cell growth.

Figure 41:
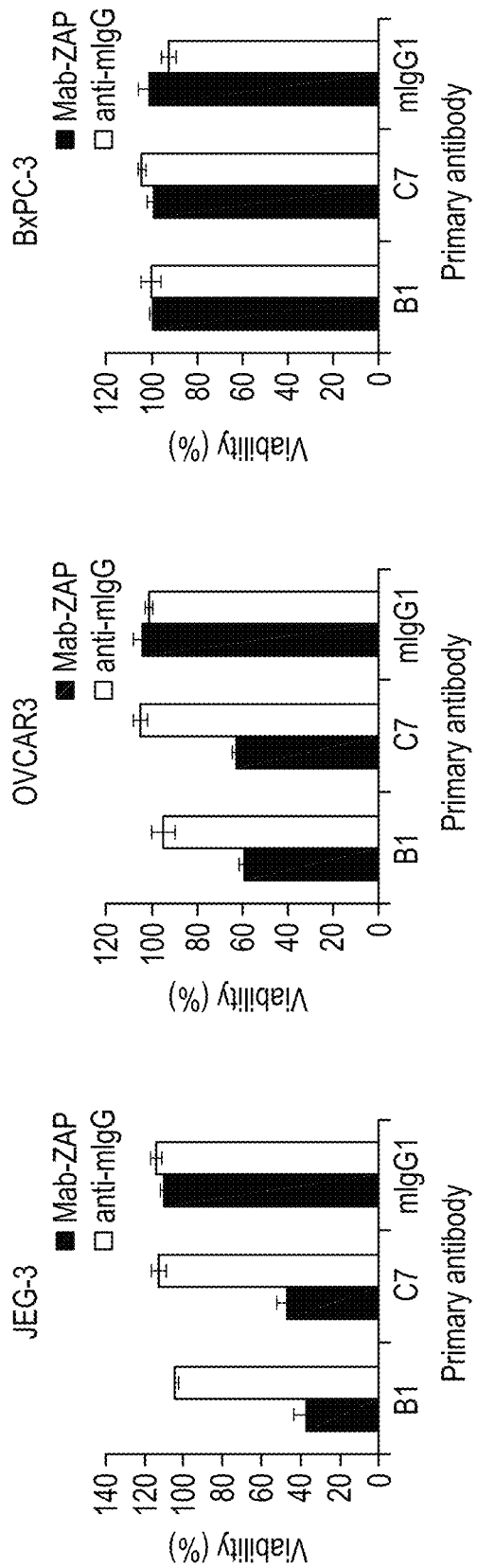
FIG. 41 shows the antibody internalization activities of a B1 antibody and C7 antibody measured by Mab-ZAP.

JEG-3(ATCC HTB-36), a human choriocarcinoma cell line of human CLDN6-positive cells, NIH:OVCAR-3 (ATCC HTB-161), a human ovarian cancer cell line of human CLDN6-positive cells, or BxPC-3 (ATCC CRL-1687), a human pancreatic cancer cell line of human CLDN6-negative cells, was seeded in a 96-well cell culture microplate at 2×10' cells/well, and cultured under conditions of 37° C. and 5% $CO_2$ overnight. On the next day, a mixed solution obtained by mixing each mouse anti-CLDN6 antibody or mouse IgG1 antibody (R&D Systems, Inc.) to a final concentration of 1 nM, with Mab-ZAP (final concentration: 0.5 nM) or AffiniPure Goat Anti-Mouse IgG, Fcγ Fragment Specific (Jackson ImmunoResearch Laboratories Inc.) (final concentration: 0.5 nM), without conjugated toxin, was added, and the cells were cultured under conditions of 37° C. and 5% $CO_2$ for 5 days. The number of surviving cells was determined through quantification of ATP activity by using CellTiter-Glo Luminescent Cell Viability Assay (Promega Corporation). The cell growth-suppressing effect by addition of each anti-CLDN6 antibody was determined as a relative survival rate to the value for the well without the mixed solution as 100%. FIG. 41 shows the results. The mouse anti-CLDN6 antibodies (B1, C7) were found to have cell growth-suppressing effect on the human CLDN6-positive cell lines JEG-3 and NIH:OVCAR-3. On the other hand, they were found to have no cell growth-suppressing effect on the human CLDN6-negative cell line BxPC-3. The mouse IgG1 antibody was found to have no cell growth-suppressing effect on any of the cell lines. These results suggest that the anti-CLDN6 antibodies (B1, C7) produced have internalization activity and are each suitable as an antibody for antibody-drug conjugates.

Example 134: Nucleotide Sequencing of cDNA Encoding Variable Region of Each of Mouse Anti-CLDN6 Antibodies B1 and C7

134-1: Nucleotide Sequencing of cDNA Encoding Variable Region of B1 Antibody
134-1-1: Preparation of Total RNA of B1 Antibody-Producing Hybridoma To amplify cDNA encoding the variable region of the B1 antibody, total RNA was prepared from the B1 antibody-producing hybridoma by using TRIzol Reagent (Ambion).
134-1-2: Amplification and Sequencing of cDNA Encoding Light Chain Variable Region of B1 Antibody Through 5'-RACE PCR Amplification of cDNA encoding the light chain variable region was carried out by using about 1 g of the total RNA prepared in Example 134-1-1 and a SMARTer RACE 5/3' Kit (Clontech). As a primer to amplify cDNA encoding the variable region of the light chain gene of the B1 antibody through PCR, UPM (Universal Primer A Mix: attached to the SMARTer RACE 5'/3' Kit) and a primer designed on the basis of the sequence of a known mouse light chain constant region were used.

The cDNA encoding the variable region of the light chain amplified through 5'-RACE PCR was cloned into a plasmid, and subsequently sequence analysis was carried out for the nucleotide sequence of the cDNA encoding the variable region of the light chain.

The determined nucleotide sequence of the cDNA encoding the variable region of the light chain of the B1 antibody is represented by SEQ ID NO: 18, and the corresponding amino acid sequence is represented by SEQ ID NO: 19.

134-1-3: Amplification and Sequencing of cDNA Encoding Heavy Chain Variable Region of B1 Antibody Through 5'-RACE PCR Amplification of cDNA encoding the heavy chain variable region was carried out by using about 1 g of the total RNA prepared in Example 134-1-1 and a SMARTer RACE 5/3' Kit (Clontech). As a primer to amplify cDNA encoding the variable region of the heavy chain gene of the LB1 antibody through PCR, UPM (Universal Primer A Mix: attached to the SMARTer RACE 5'/3' Kit) and a primer designed on the basis of the sequence of a known mouse heavy chain constant region were used.

The cDNA encoding the variable region of the heavy chain amplified through 5'-RACE PCR was cloned into a plasmid, and subsequently sequence analysis was carried out for the nucleotide sequence of the cDNA encoding the variable region of the heavy chain.

The determined nucleotide sequence of the cDNA encoding the variable region of the heavy chain of the B1 antibody is represented by SEQ ID NO: 20, and the corresponding amino acid sequence is represented by SEQ ID NO: 21.

134-2: Nucleotide Sequencing of cDNA Encoding Variable Region of C7 Antibody

Nucleotide sequencing was carried out in the same manner in Example 134-1. The determined nucleotide sequence of the cDNA encoding the variable region of the light chain of the C7 antibody is represented by SEQ ID NO: 22, and the corresponding amino acid sequence is represented by SEQ ID NO: 23. The nucleotide sequence of the cDNA encoding the variable region of the heavy chain of the C7 antibody is represented by SEQ ID NO: 24, and the corresponding amino acid sequence is represented by SEQ ID NO: 25.

Example 135: Production of Chimeric Anti-CLDN6 Antibody chB1

135-1: Construction of Expression Vector for Chimeric Anti-CLDN6 Antibody chB1

135-1-1: Construction of Expression Vector pCMA-LK for Chimeric and Humanized Light Chains About 5.4 kb of a fragment obtained by digesting the plasmid pcDNA3.3-TOPO/LacZ (Invitrogen) with the restriction enzymes XbaI and PmeI was linked to a DNA fragment including a DNA sequence encoding the human light chain signal sequence and human κ chain constant region, as represented by SEQ ID NO: 26, by using an In-Fusion HID PCR Cloning Kit (Clontech) to prepare pcDNA3.3/LK. A neomycin expression unit was removed from the pcDNA3.3/LK to construct pCMA-LK.

135-1-2: Construction of Expression Vector pCMA-G1LALA for Chimeric and Humanized IgG1LALA-Type Heavy Chains A DNA fragment obtained by digesting the pCMA-LK with XbaI and PmeI to remove the light chain signal sequence and human κ chain constant region was linked to a DNA fragment including a DNA sequence encoding the human heavy chain signal sequence and human IgG1LALA constant region, as represented by SEQ ID NO: 27, by using an In-Fusion HD PCR Cloning Kit (Clontech) to construct pCMA-G1LALA.

135-1-3: Construction of Chimeric chB1 Heavy Chain Expression Vector

The DNA fragment consisting of nucleotide residues 36 to 440 of the nucleotide sequence for the chB1 heavy chain, as represented by SEQ ID NO: 33, was synthesized (GeneArt). The pCMA-G1LALA was cleaved with the restriction enzyme BlpI, and the synthesized DNA fragment was inserted into the cleaved portion by using an In-Fusion HD PCR Cloning Kit (Clontech) to construct a chB1 heavy chain expression vector. The amino acid sequence of the chB1 heavy chain is represented by SEQ ID NO: 32.

135-1-4: Construction of Chimeric chB1 Light Chain Expression Vector

A DNA fragment including a DNA sequence encoding the chB1 light chain, as represented by SEQ ID NO: 29, was synthesized (GeneArt). By using an In-Fusion HD PCR Cloning Kit (Clontech), the synthesized DNA fragment was linked to a DNA fragment obtained by digesting the pCMA-LK with XbaI and PmeI for removal of the light chain signal sequence and human κ chain constant region to construct a chB1 light chain expression vector. The amino acid sequence of the chB1 light chain is represented by SEQ ID NO: 28.

135-2: Production and Purification of Chimeric Anti-CLDN6 Antibody chB1

135-2-1: Production of Chimeric Antibody chB1

FreeStyle 293F cells (Invitrogen) were passaged and cultured in accordance with the instruction manual. Into a 3 L Fernbach Erlenmeyer Flask (Corning Incorporated), 1.2× $10^9$ FreeStyle 293F cells (Invitrogen) in the logarithmic growth phase were seeded, and diluted with FreeStyle293 expression medium (Invitrogen) to adjust to 2.0×$10^6$ cells/mL. To 40 mL of Opti-Pro SFM medium (Invitrogen), 0.24 mg of the heavy chain expression vector, 0.36 mg of the light chain expression vector, and 1.8 mg of polyethyleneimine (Polyscience, Inc., #24765) were added and gently stirred, and further left to stand for 5 minutes, and then added to the FreeStyle 293F cells. After shaking culture at 90 rpm in an incubator at 37° C. and 8% $CO_2$ for 4 hours, 600 mL of EX-CELL VPRO medium (SAFC Biosciences, Inc.), 18 mL of GlutaMAX I (Gibco), and 30 mL of Yeastolate Ultrafiltrate (Gibco) were added, and the resultant was subjected to shaking culture at 90 rpm in an incubator at 37° C. and 8% $CO_2$ for 7 days, and the resulting culture supernatant was filtered through a Disposable Capsule Filter (ADVANTEC, #CCS-045-E1H). The chimeric anti-CLDN6 antibody obtained was designated as "chB1".

135-2-2: Purification of Chimeric Antibody chB1

The antibody was purified from the culture supernatant obtained in Example 135-2-1 through rProtein A affinity chromatography in one step. The culture supernatant was applied to a column packed with MabSelectSuRe (produced by GE Healthcare Bioscience) equilibrated with PBS, and the column was then washed with PBS in an amount twice or more the column volume. Subsequently, elution was carried out with a 2 M solution of arginine hydrochloride (pH 4.0), and a fraction containing the antibody was collected. The antibody was subjected to buffer displacement to PBS (−) by dialysis (Thermo Scientific, Slide-A-Lyzer Dialysis Cassette). The fraction was concentrated with a Centrifugal UF Filter Device VIVASPIN20 (molecular weight cutoff: UF10K, Sartorius AG) to adjust the IgG concentration to 1 mg/mL or more. Finally, the fraction was filtered through a Minisart-Plus filter (Sartorius AG), and the resultant was used as a purified sample.

Example 136: Production of Humanized Anti-CLDN6 Antibody 136-1: Design of Humanized Form of Anti-CLDN6 Antibody 136-1-1: Molecular Modeling of Variable Region of Chimeric Antibody chB1

A method known as homology modeling (Methods in Enzymology, 203, 121-153 (1991)) was used for molecular modeling of the variable region of chB1. Molecular modeling was carried out by using the commercially available protein conformational analysis program BioLuminate (Schrodinger, Inc.) with a structure (PDB ID: 1XIW), as a template, registered in Protein Data Bank (Nuc. Acid Res. 35, D301-D303 (2007)) with high sequence identity to the variable regions of the heavy chain and light chain of chB1.

136-1-2: Design of Humanized Amino Acid Sequence chB1 was humanized by CDR grafting (Proc. Natl. Acad. Sci. USA 86, 10029-10033 (1989)). The consensus sequence of human gamma chain subgroup 1 and that of human kappa chain subgroup 1 specified in Kabat et al. (Sequences of Proteins of Immunological Interest, 5th Ed. Public Health Service National Institutes of Health, Bethesda, MD. (1991)) had high identity to the framework regions of the chB1, and hence were respectively selected as acceptors for the heavy chain and the light chain. Donor residues to be transferred on the acceptors were selected through analysis of the three-dimensional model, for example, with reference to criteria provided by Queen et al. (Proc. Natl. Acad. Sci. USA 86, 10029-10033 (1989)). Because the CDRL3 was rich in hydrophobic amino acids, a humanized light chain with mutation in the CDRL3 was additionally designed.

136-2: Humanization of chB1 Heavy Chain

The three heavy chains designed were designated as hH1, hH2, and hH3. The heavy chain full-length amino acid sequence of hH1 is represented by SEQ ID NO: 52 (FIG. 34). The nucleotide sequence encoding the amino acid sequence of SEQ ID NO: 52 is represented by SEQ ID NO: 53 (FIG. 34). The heavy chain full-length amino acid sequence of hH2 is represented by SEQ ID NO: 56 (FIG. 36). The nucleotide sequence encoding the amino acid sequence of SEQ ID NO: 56 is represented by SEQ ID NO: 57 (FIG. 36). The heavy chain full-length amino acid sequence of hH3 is represented by SEQ ID NO: 60 (FIG. 38). The nucleotide sequence encoding the amino acid sequence of SEQ ID NO: 60 is represented by SEQ ID NO: 61 (FIG. 38).

FIG. 45 shows comparison among the amino acid sequences of chB1_H, which is the heavy chain of the chimeric human anti-CLDN6 antibody chB1 demonstrated in Example 135, and the humanized antibody heavy chains hH1, hH2, and hH3. Each in the sequences of hH1, hH2 and hH3 denotes an amino acid residue identical to that of chB1_H at the position, and each position with a letter symbol of an amino acid residue indicates that the amino acid residue is a substituted amino acid residue.

136-3: Humanization of chB1 Light Chain

The four light chains designed were designated as hL1, hL2, hL3, and hL4. The light chain full-length amino acid sequence of hL1 is represented by SEQ ID NO: 36 (FIG. 26). The nucleotide sequence encoding the amino acid sequence of SEQ ID NO: 36 is represented by SEQ ID NO: 37 (FIG. 26). The light chain full-length amino acid sequence of hL2 is represented by SEQ ID NO: 40 (FIG. 28). The nucleotide sequence encoding the amino acid sequence of SEQ ID NO: 40 is represented by SEQ ID NO: 41 (FIG. 28). The light chain full-length amino acid sequence of hL3 is represented by SEQ ID NO: 44 (FIG. 30). The nucleotide sequence encoding the amino acid sequence of SEQ ID NO: 44 is represented by SEQ ID NO: 45 (FIG. 30). The light chain full-length amino acid sequence of hL4 is represented by SEQ ID NO: 48 (FIG. 32). The nucleotide sequence encoding the amino acid sequence of SEQ ID NO: 48 is represented by SEQ ID NO: 49 (FIG. 32).

FIG. 46 shows comparison among the amino acid sequences of chB1_L, which is the light chain of the chimeric human anti-CLDN6 antibody chB1 demonstrated in Example 135, and the humanized antibody light chains hL1, hL2, hL3, and hL4. Each "-" in the sequences of hL1, hL2, hL3, and hL4 denotes an amino acid residue identical to that of chB1_L at the position, and each position with a letter symbol of an amino acid residue indicates that the amino acid residue is a substituted amino acid residue.

136-4: Design of Humanized Antibody with Combination of Heavy Chain and Light Chain An antibody consisting of hH1 and hL1 is referred to as "H1L1 antibody" or "H1L1".

An antibody consisting of hH2 and hL2 is referred to as "H2L2 antibody" or "H2L2". An antibody consisting of hH1 and hL3 is referred to as "H1L3 antibody" or "H1L3". An antibody consisting of hH2 and hL4 is referred to as "H2L4 antibody" or "H2L4". An antibody consisting of hH3 and hL3 is referred to as "H3L3 antibody" or "H3L3".

136-5: Production of Humanized Anti-CLDN6 Antibody 136-5-1: Construction of Humanized Heavy Chain Expression Vector 136-5-1-1: Construction of hH1 Expression Vector The DNA fragment consisting of nucleotide residues 36 to 440 of the nucleotide sequence of SEQ ID NO: 53 for hH1 was synthesized (GeneArt). An hH1 expression vector was constructed in the same manner as in Example 135-1-3.

136-5-1-2: Construction of hH2 Expression Vector

The DNA fragment consisting of nucleotide residues 36 to 440 of the nucleotide sequence of SEQ ID NO: 57 for hH2 was synthesized (GeneArt). An hH2 expression vector was constructed in the same manner as in Example 135-1-3.

136-5-1-3: Construction of hH3 Expression Vector

The DNA fragment consisting of nucleotide residues 36 to 440 of the nucleotide sequence of SEQ ID NO: 61 for hH2 was synthesized (GeneArt). An hH3 expression vector was constructed in the same manner as in Example 135-1-3.

136-5-2: Construction of Humanized Light Chain Expression Vector 136-5-2-1: Construction of hL1 Expression Vector The DNA fragment consisting of nucleotide residues 37 to 402 of the nucleotide sequence of SEQ ID NO: 37 for hL1 was synthesized (GeneArt). The pCMA-LK was cleaved with the restriction enzyme BsiWI, and the synthesized DNA fragment was inserted into the cleaved portion by using an In-Fusion HD PCR Cloning Kit (Clontech) to construct an hL1 expression vector.

136-5-2-2: Construction of hL2 Expression Vector

The DNA fragment consisting of nucleotide residues 37 to 402 of the nucleotide sequence of SEQ ID NO: 41 for hL2 was synthesized (GeneArt). An hL2 expression vector was constructed in the same manner as in Example 136-5-2-1.

136-5-2-3: Construction of hL3 Expression Vector

The DNA fragment consisting of nucleotide residues 37 to 402 of the nucleotide sequence of SEQ ID NO: 45 for hL3 was synthesized (GeneArt). An hL3 expression vector was constructed in the same manner as in Example 136-5-2-1.

136-5-2-4: Construction of hL4 Expression Vector

The DNA fragment consisting of nucleotide residues 37 to 402 of the nucleotide sequence of SEQ ID NO: 49 for hL4 was synthesized (GeneArt). An hL4 expression vector was constructed in the same manner as in Example 136-5-2-1.

136-5-3: Preparation of Humanized Antibodies 136-5-3-1: Production of Humanized Antibodies H1L1, H2L2, H1L3, H2L4, and H3L3

They were produced in the same manner as in Example 135-2-1. H1L1, H2L2, H1L3, H2L4, and H3L3 were produced by using the combinations of a heavy chain expression vector and a light chain expression vector corresponding to the combinations of a heavy chain and a light chain shown in Example 136-4.

136-5-3-2: Two-Step Purification of Humanized Antibodies H1L1, H2L2, H1L3, H2L4, and H3L3

The culture supernatant obtained in Example 136-5-3-1 was purified in two steps through rProtein A affinity chromatography and ceramic hydroxyapatite. The culture supernatant was applied to a column packed with MabSelectSuRe (produced by GE Healthcare Bioscience) equilibrated with PBS, and the column was then washed with PBS in an amount twice or more the column volume. Subsequently, the antibody was eluted with a 2 M solution of arginine hydrochloride (pH 4.0). A fraction containing the antibody was subjected to buffer displacement to PBS by dialysis (Thermo Scientific, Slide-A-Lyzer Dialysis Cassette), 5-fold diluted with a buffer of 5 mM sodium phosphate/50 mM MES/pH 7.0, and then applied to a ceramic hydroxyapatite column (Bio-Rad Laboratories Japan, Inc., Bio-Scale CHT Type-1 Hydroxyapatite Column) equilibrated with a buffer of 5 mM NaPi/50 mM MES/30 mM NaCl/pH 7.0. Linear concentration gradient elution was carried out with sodium chloride, and a fraction containing the antibody was collected. The fraction was subjected to buffer displacement to HBSor (25 mM histidine/5% sorbitol, pH 6.0) by dialysis (Thermo Scientific, Slide-A-Lyzer Dialysis Cassette). The antibody was concentrated with a Centrifugal UF Filter Device VIVASPIN20 (molecular weight cutoff: UF10K, Sartorius AG) to adjust the IgG concentration to 50 mg/mL. Finally, the fraction was filtered through a Minisart-Plus filter (Sartorius AG), and the resultant was used as a purified sample.

Figure 42:
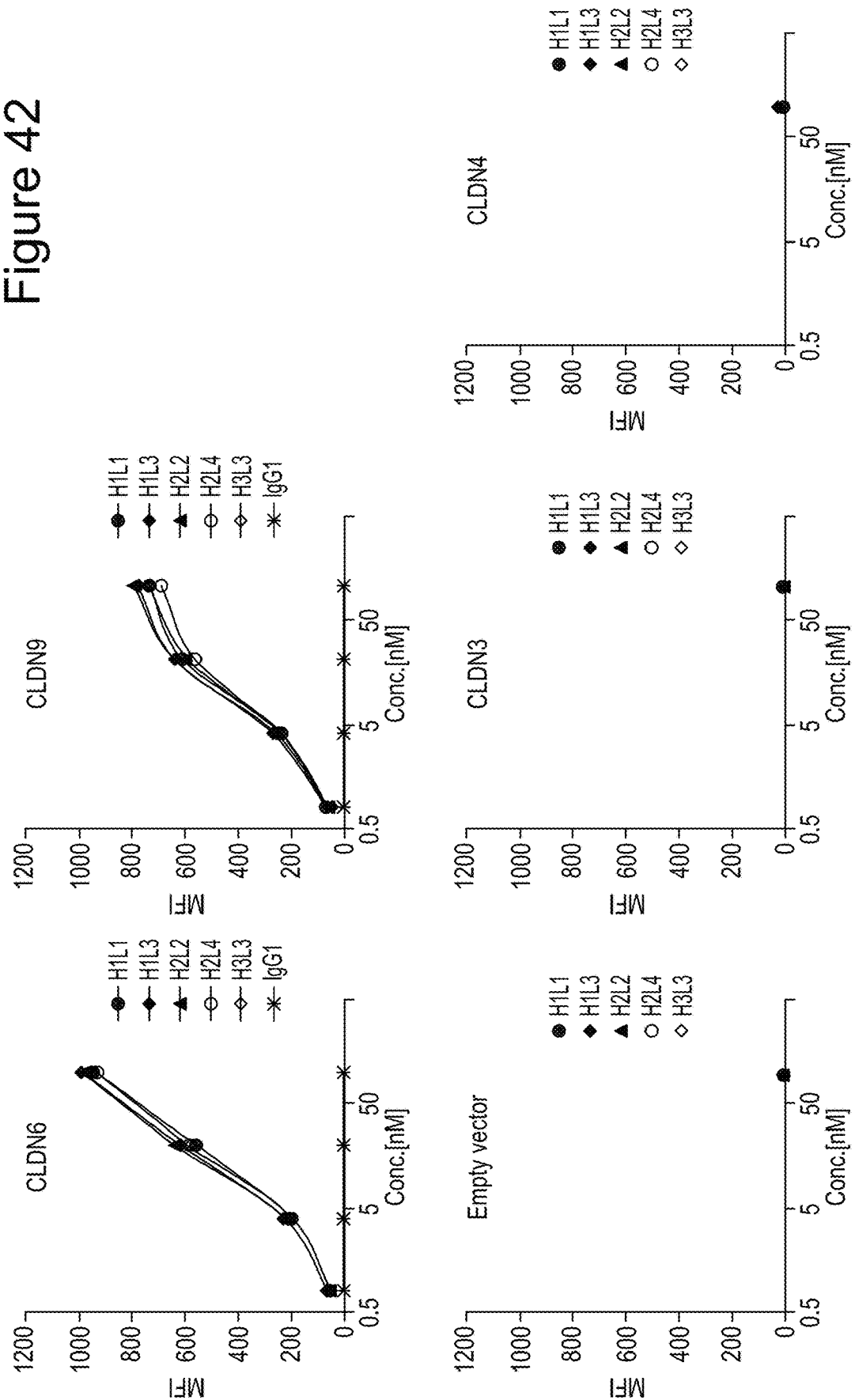
FIG. 42 shows the binding abilities of the humanized anti-CLDN6 antibodies H1L1, H2L2, H1L3, H2L4, and H3L3 to CLDN6 and the family molecules measured by flow cytometry.

Example 137: Evaluation of Binding Ability of Humanized Anti-CLDN6 Antibody by Flow Cytometry The binding activity of the humanized anti-CLDN6 antibody produced in Example 136 to human CLDN6 and its family molecules, CLDN3, CLDN4, and CLDN9, was evaluated by using a flow cytometry method. Used were 293T cells transiently transfected in the same manner as in Example 133-1. To cells into which a human CLDN6 or human CLDN9 gene had been transferred, the humanized anti-CLDN6 antibody H1L1, H2L2, H1L3, H2L4, or H3L3, or a human IgG1 control antibody (Calbiochem) was added and suspended to a final concentration of 100 nM, 20 nM, 4 nM, or 0.8 nM, and the resultant was left to stand at 4° C. for 30 minutes. To cells into which a human CLDN3 or human CLDN4 gene, or an empty vector had been transferred, the humanized anti-CLDN6 antibody H1L1, H2L2, H1L3, H2L4, or H3L3 was added and suspended to a final concentration of 100 nM, and the resultant was left to stand at 4° C. for 30 minutes. The cells were washed with Dulbecco's phosphate buffered saline (Sigma-Aldrich Co. LLC) containing 5% fetal bovine serum (Hyclone) (hereinafter, referred to as 5% FBS-containing PBS), and FITC AffiniPureF (ab')2 Fragment Goat Anti-Human IgG (H+L) (Jackson ImmunoResearch Laboratories Inc.) 150-fold diluted with 5% FBS-containing PBS was then added thereto, and the cells were suspended and left to stand at 4° C. for 30 minutes. After washing with 5% FBS-containing PBS, detection was carried out by using a flow cytometer (FC500; Beckman Coulter, Inc.). Data analysis was carried out by using FlowJo (Tree Star, Inc.), and mean fluorescence intensity (MFI) of FITC, which indicates the amount of the binding antibody, was calculated. FIG. 42 shows the results. In each graph in FIG. 42, the abscissa represents antibody concentrations and the ordinate represents MFI. The humanized anti-CLDN6 antibody produced bound to human CLDN6 and human CLDN9 to a similar degree, and did not bind to human CLDN3 or human CLDN4. The human control IgG1 did not bind to any of the cells.

Example 138: Production of Trastuzumab Variant 138-1: Construction of Heavy Chain Expression Vector for Trastuzumab-LALA The DNA fragment consisting of nucleotide residues 36 to 434 of the nucleotide sequence of SEQ ID NO: 74 for the heavy chain of trastuzumab-LALA was synthesized (GeneArt). An expression vector was constructed in the same manner as in Example 135-1-3. The amino acid sequence of the heavy chain of trastuzumab-LALA is represented by SEQ ID NO: 75.

138-2: Construction of Light Chain Expression Vector for Trastuzumab-LALA

The DNA fragment consisting of nucleotide residues 37 to 402 of the nucleotide sequence of SEQ ID NO: 72 for the light chain of trastuzumab-LALA was synthesized (GeneArt). An expression vector was constructed in the same manner as in Example 136-5-2-1. The amino acid sequence of the light chain of trastuzumab-LALA is represented by SEQ ID NO: 73.

138-3: Production of Trastuzumab Variant

A trastuzumab variant was produced in the same manner as in Example 135-2-1.

138-4: Purification of Trastuzumab Variant

Trastuzumab-LALA was purified from the culture supernatant obtained in Example 138-3 in the same manner as in Example 135-2-2, except that buffer displacement was carried out not to PBS (−) but to 50 mM phosphate buffer solution (pH 6.0).

Example 139: Sugar Chain Remodeling (Trastuzumab Variant-MSG1)

Step 1: (Fucα1,6)GlcNAc-trastuzumab Variant

The operation in step 1 of Example 58 was carried out with a ca. 22.3 mg/mL trastuzumab variant solution (50 mM phosphate buffer (pH 6.0)) (2.7 mL) prepared in Example 138 to afford a 6.1 mg/mL (Fucα1,6)GlcNAc-trastuzumab variant solution (50 mM phosphate buffer (pH 6.0)) (6.1 mL).

Step 2: Trastuzumab Variant-[MSG1-$N_3$]$_2$

The operation in step 1 in Example 60 was carried out with the 6.1 mg/mL (Fucα1,6)GlcNAc-trastuzumab variant solution (50 mM phosphate buffer (pH 6.0)) (6.1 mL) obtained in step 1 to afford a 10.2 mg/mL trastuzumab variant-[MSG1-$N_3$]$_2$ solution (phosphate buffered saline (pH 6.0)) (3.7 mL).

Example 140: ADC55

[Formula 248]

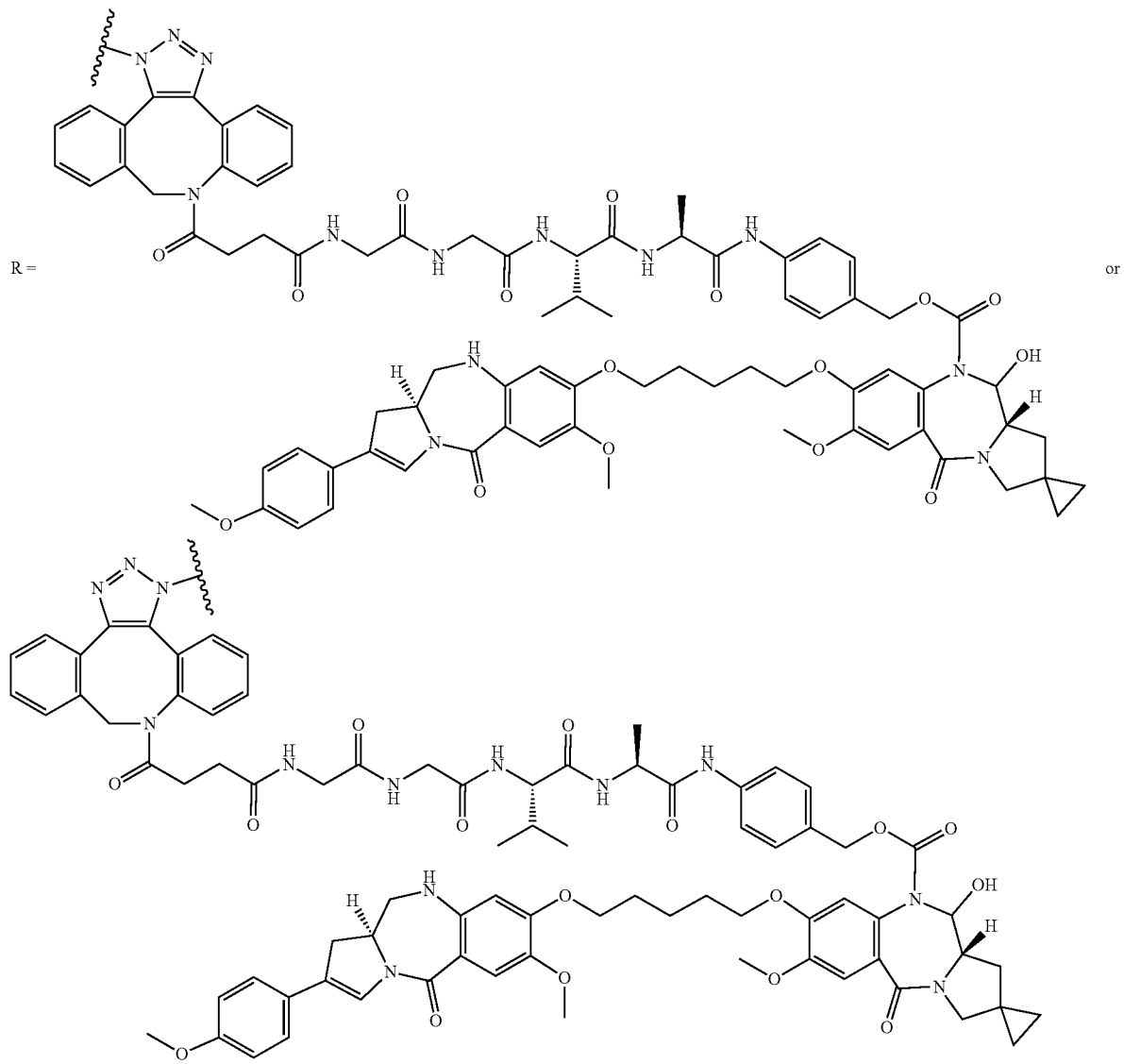

(The compound to be obtained in step 1 has geometric isomers of the triazole ring as illustrated in this formula, and the compound obtained in step 1 of Example 140 retains a linker as a mixture of the two structures shown above as R.)

Step 1: Conjugation of Antibody and Drug-Linker

To a solution of the antibody obtained in step 2 of Example 139 in phosphate buffered saline (pH 6.0) (10.2 mg/mL, 0.40 mL), a solution of phosphate buffered saline (pH 6.0) (0.40 mL), 1,2-propanediol (0.767 mL), dimethylformamide (0.20 mL), and a 10 mM dimethylformamide solution of the compound obtained in step 13 of Example 3 (0.033 mL; 12 equivalents per antibody molecule) were added at room temperature, and the resultant was reacted at room temperature with a tube rotator (MTR-103, AS ONE Corporation) for 48 hours.

Purification operation: The solution was purified by using common operation D to afford 7.00 mL of a solution containing the targeted compound.
Characterization: The following characteristic values were obtained by using common operations E and F.
Antibody concentration: 0.39 mg/mL, antibody yield: 1.38 mg (35%), average number of conjugated drug molecules per antibody molecule (n): 1.8

Example 141: Anticellular Effect of Anti-HER2 Antibody-Drug Conjugate

KPL-4 cells (Dr. Junichi Kurebayashi, Kawasaki Medical School), a human breast cancer cell line of HER2 antigen-positive cells, were prepared with RPMI1640 Medium (Thermo Fisher Scientific; hereinafter, referred to as RPMI medium) containing 10% fetal bovine serum (Hyclone) to reach 6.25×10³ cells/mL, and 80 µL portions of them were added to a 96-well cell culture microplate. After addition of the cells, the cells were cultured at 37° C. and 5% $CO_2$ overnight.

On the next day, 20 µL portions of an anti-HER2 antibody-drug conjugate diluted with RPMI medium to 100 nM, 20 nM, 4 nM, 0.8 nM, 0.16 nM, 0.032 nM, 6.4 pM, 1.3 pM, and 0.26 pM were added to the microplate. To each well without any antibody-drug conjugate, 20 µL of RPMI medium was added. KPL-4 was cultured at 37° C. and 5% $CO_2$ for 6 days. After culturing, the microplate was taken out of the incubator, and left to stand at room temperature for 30 minutes. CellTiter-Glo Luminescent Cell Viability Assay (Promega Corporation) in an amount equivalent to that of the culture solution was added, and stirred using a plate mixer. The microplate was left to stand at room temperature for 10 minutes, and thereafter the amount of emission was measured by using a plate reader (PerkinElmer). Cell survival rates were calculated in the same manner as in Example 123.

The anti-HER2 antibody-drug conjugates ADC49 and ADC55 each exhibited an anticellular effect of $0.001 < IC_{50} < 0.01$ (nM) on the KPL-4 cells.

Example 142: Antitumor Test for Anti-HER2 Antibody-Drug Conjugate (1)

Antitumor effect of the anti-HER2 antibody-drug conjugates was measured by using the same experiment animals and method as in Example 124.

KPL-4 cells (Dr. Junichi Kurebayashi, Kawasaki Medical School) were suspended in Dulbecco's phosphate buffered saline (Sigma-Aldrich Co. LLC), and 1.5×10⁷ cells were subcutaneously transplanted to the right flank of each female nude mouse (Day 0), and the mice were randomly grouped on Day 14. The anti-HER2 antibody-drug conjugate ADC49 or the anti-HER2 antibody-drug conjugate ADC55 was administered into the tail vein on Day 14 at a dose of 0.33 mg/kg. As a control group (Vehicle group), ABS buffer was administered in the same manner.

Figure 47:
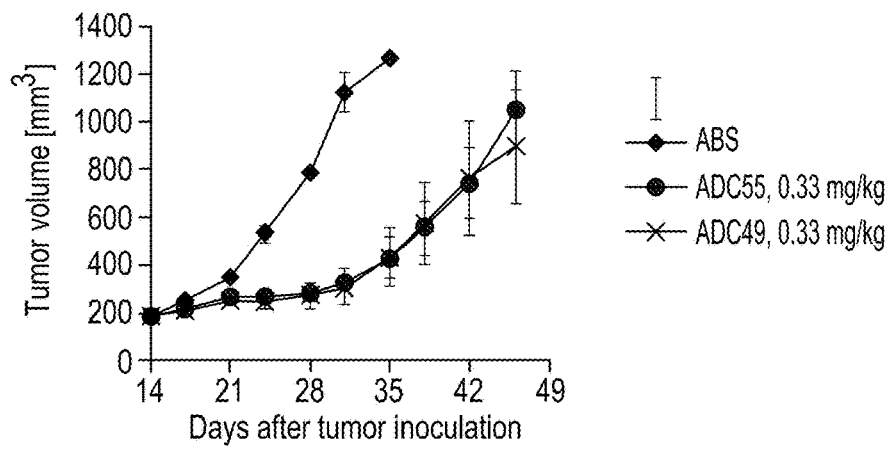
FIG. 47 shows the effects of the anti-HER2 antibody-drug conjugates ADC49 and ADC55 on subcutaneously transplanted KPL-4 cells, a human breast cancer cell line.

FIG. 47 shows the results. ADC49 and ADC55 exhibited comparable antitumor activity with administration of 0.33 mg/kg. No weight loss caused by administration of ADC49 or ADC55 was found for the mice.

Example 143: Antitumor Test for Anti-HER2 Antibody-Drug Conjugate (2)

JIMT-1 cells (DSMZ ACC 589) were suspended in physiological saline (Otsuka Pharmaceutical Factory, Inc.), and 5×10⁶ cells were subcutaneously transplanted to the right flank of each female nude mouse (Day 0), and the mice were randomly grouped on Day 11. ADC55 was administered into the tail vein on Day 11 at a dose of 0.4 mg/kg or 0.2 mg/kg. As a control group (Vehicle group), ABS buffer was administered in the same manner.

Figure 48:
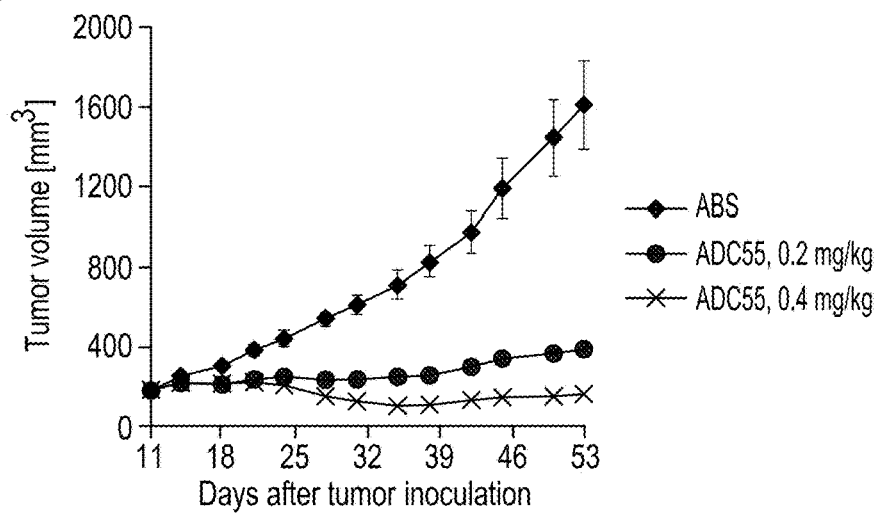
FIG. 48 shows the effect of the anti-HER2 antibody-drug conjugate ADC55 on subcutaneously transplanted JIMT-1 cells, a human breast cancer cell line.

FIG. 48 shows the results. ADC55 was found to have strong antitumor effect causing regression of tumor in administration of 0.4 mg/kg. No weight loss caused by administration of ADC55 was found for the mice with any dose of administration.

Example 144: Antitumor Test for Anti-HER2 Antibody-Drug Conjugate (3)

CFPAC-1 cells (ATCC CRL-1918) were suspended in physiological saline (Otsuka Pharmaceutical Factory, Inc.), and 5×10⁶ cells were subcutaneously transplanted to the right flank of each female nude mouse (Day 0), and the mice were randomly grouped on Day 10. The anti-HER2 antibody-drug conjugate ADC49 or ADC55, or the anti-LPS Antibody-drug conjugate ADC53 was administered into the tail vein on Day 10 at a dose of 0.4 mg/kg. As a control group (Vehicle group), ABS buffer was administered in the same manner.

Figure 49:
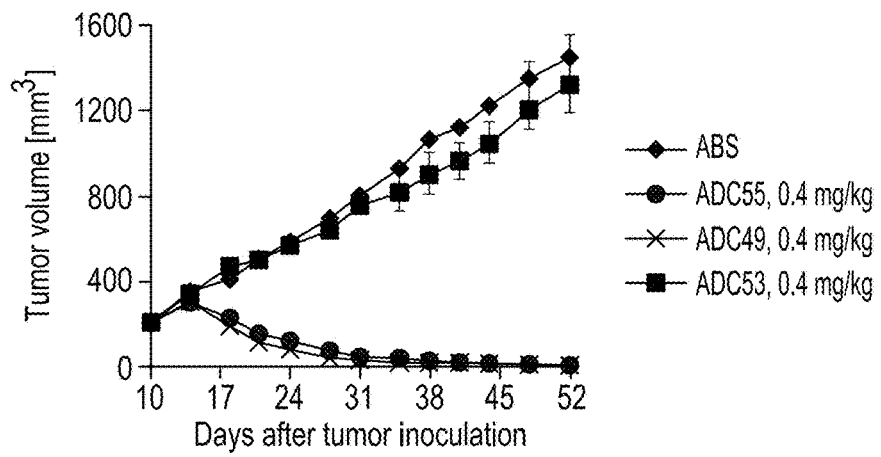
FIG. 49 shows the effects of the anti-HER2 antibody-drug conjugates ADC49 and ADC55, and the anti-LPS antibody-drug conjugate ADC53 on subcutaneously transplanted CFPAC-1 cells, a human pancreatic cancer cell line.

FIG. 49 shows the results. Strong antitumor effect causing regression of tumor was found for any mice to which ADC49 or ADC55 had been administered. No weight loss caused by administration of ADC49, ADC55, or ADC53 was found for the mice.

Example 145: Drug-Linker 43

[Formula 249]

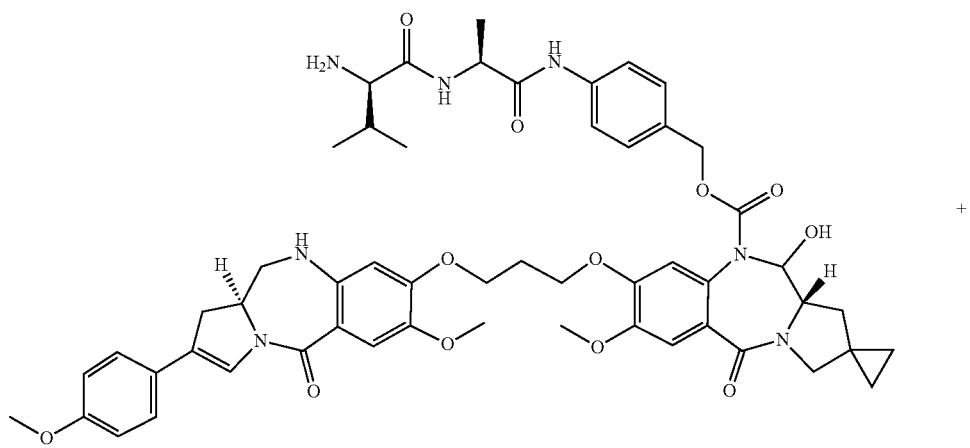

+

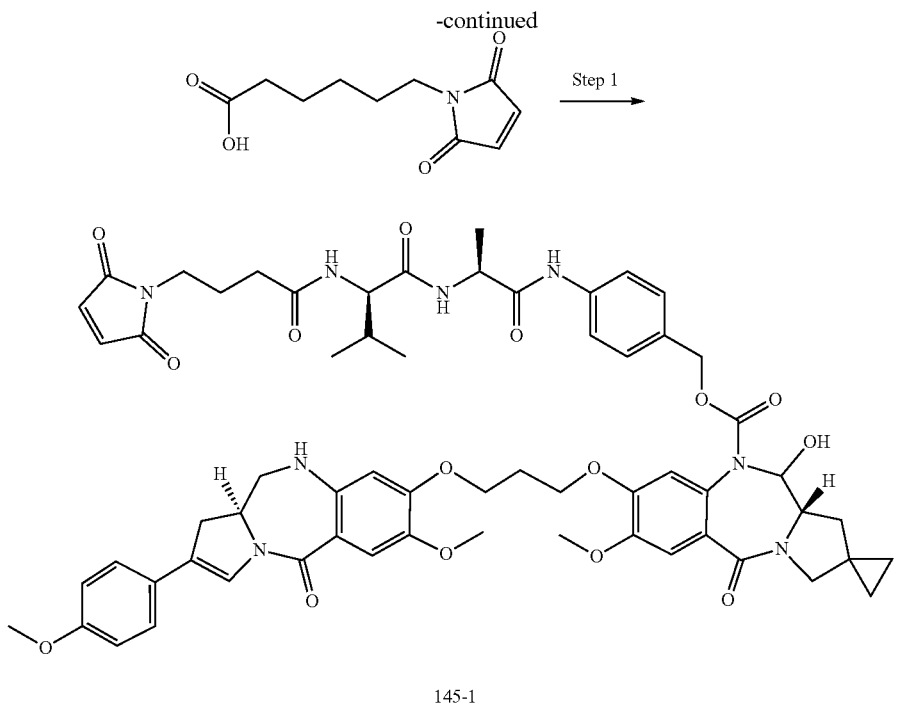

145-1

To a solution of the compound obtained in step 12 of Example 3 (0.051 g, 0.049 mmol) and commercially available maleimidocaproic acid (0.011 g, 0.054 mmol) in dichloromethane (5 mL), 1-(3-dimethylaminopropyl)-3-ethylcarbodiimide hydrochloride (0.010 g, 0.054 mmol) was added at room temperature, and the resultant was stirred at room temperature for 2 hours. After the reaction solution was diluted with chloroform, the organic layer was washed with water and dried over sodium sulfate. After the organic solvent was concentrated, the resulting residue was purified by silica gel chromatography (chloroform:methanol=97.5: 2.5 (v/v) to 90:10 (v/v)) to afford the desired compound (41 mg, 69%).

$^1$H-NMR (DMSO-D$_6$) δ:9.94 (1H, s), 8.20-8.12 (1H, m), 7.86-7.77 (1H, m), 7.65-7.52 (2H, m), 7.45 (1H, s), 7.38 (2H, d, J=7.9 Hz), 7.30 (1H, s), 7.24-7.16 (2H, m), 7.11-7.01 (1H, m), 7.00 (2H, s), 6.91 (2H, d, J=8.5 Hz), 6.83-6.67 (1H, m), 6.63-6.45 (2H, m), 6.31 (1H, s), 5.81-5.71 (1H, m), 5.23-5.14 (1H, m), 4.86-4.74 (1H, m), 4.43-4.32 (1H, m), 4.24-4.11 (2H, m), 4.03-3.88 (3H, m), 3.88-3.69 (4H, m), 3.76 (3H, s), 3.66 (3H, s), 3.60-3.49 (2H, m), 3.47-3.08 (5H, m), 2.82-2.64 (1H, m), 2.40-2.29 (1H, m), 2.25-2.04 (2H, m), 2.04-1.89 (1H, m), 1.88-1.67 (4H, m), 1.63-1.38 (7H, m), 1.35-1.09 (6H, m), 0.90-0.76 (6H, m), 0.76-0.50 (4H, m).

MS(APCI, ESI)m/z:1224(M+H)$^+$

An anti-CLDN6 antibody (Example 136 (H1L1))-PBD ADC (cysteine conjugation, m #=2) of drug-linker 43 and drug-linker 44 (Example 146) was produced by using a known method (WO 2014/057687). The ADC exhibited a strong antitumor effect.

Example 146: Drug-Linker 44

[Formula 250]

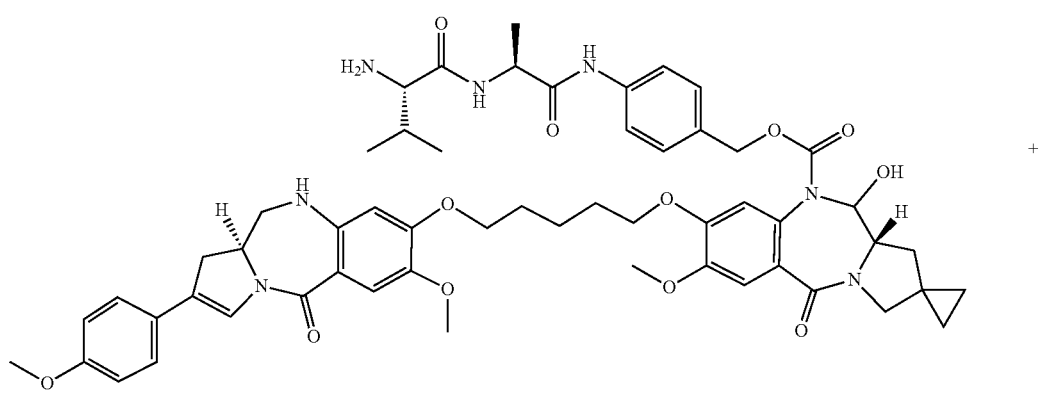

3-13

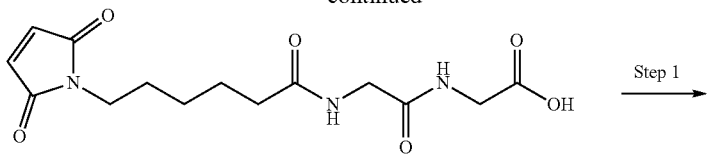

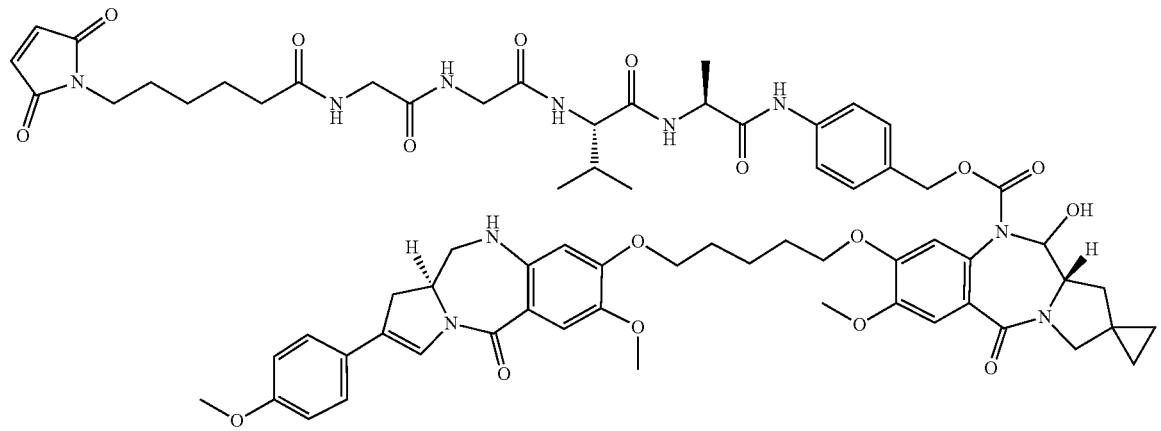

146-1

The compound obtained in step 12 of Example 3 (0.047 g, 0.046 mmol) and commercially available N-[6-(2,5-dioxo-2,5-dihydro-1H-pyrrol-1-yl)hexanoyl]glycylglycine (0.016 g, 0.050 mmol) were reacted in the same manner as in Example 145 to afford the desired compound (30 mg, 50%).

$^1$H-NMR (DMSO-D$_6$) δ:9.92 (1H, s), 8.23 (1H, d, J=6.7 Hz), 8.12-8.02 (2H, m), 7.84 (1H, d, J=9.1 Hz), 7.65-7.50 (2H, m), 7.45 (1H, s), 7.38 (2H, d, J=9.1 Hz), 7.30 (1H, s), 7.26-7.16 (2H, m), 7.10-7.02 (1H, m), 7.00 (2H, s), 6.91 (2H, d, J=9.1 Hz), 6.82-6.67 (1H, m), 6.62-6.48 (2H, m), 6.31 (1H, s), 5.80-5.72 (1H, m), 5.25-5.15 (1H, m), 4.85- 4.77 (1H, m), 4.43-4.30 (1H, m), 4.25-4.14 (2H, m), 4.06-3.87 (3H, m), 3.86-3.71 (6H, m), 3.76 (3H, s), 3.71-3.62 (2H, m), 3.66 (3H, s), 3.61-3.45 (2H, m), 3.45-3.08 (1H, m), 2.81-2.64 (2H, m), 2.39-2.29 (1H, m), 2.14-2.04 (2H, m), 2.05-1.90 (1H, m), 1.90-1.68 (1H, m), 1.62-1.39 (7H, m), 1.35-1.26 (6H, m), 1.26-1.13 (6H, m), 0.91-0.77 (6H, m), 0.75-0.52 (4H, m).

MS(APCI, ESI)m/z:1338(M+H)$^+$

Example 147: Drug-Linker 45

[Formula 251]

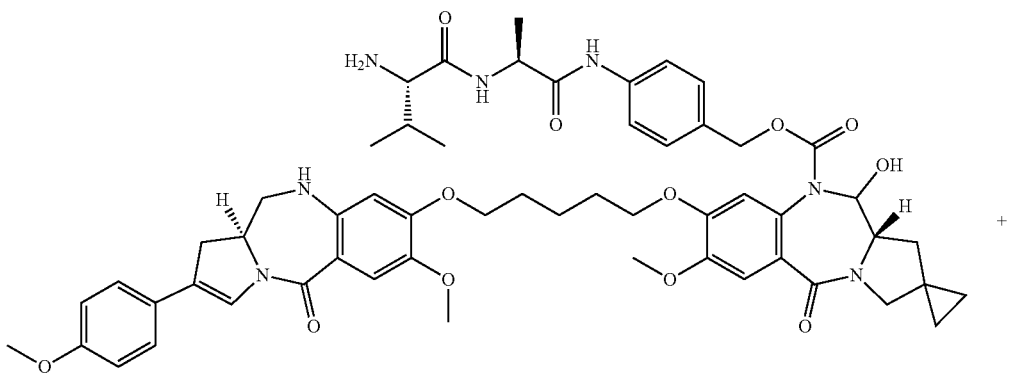

3-13

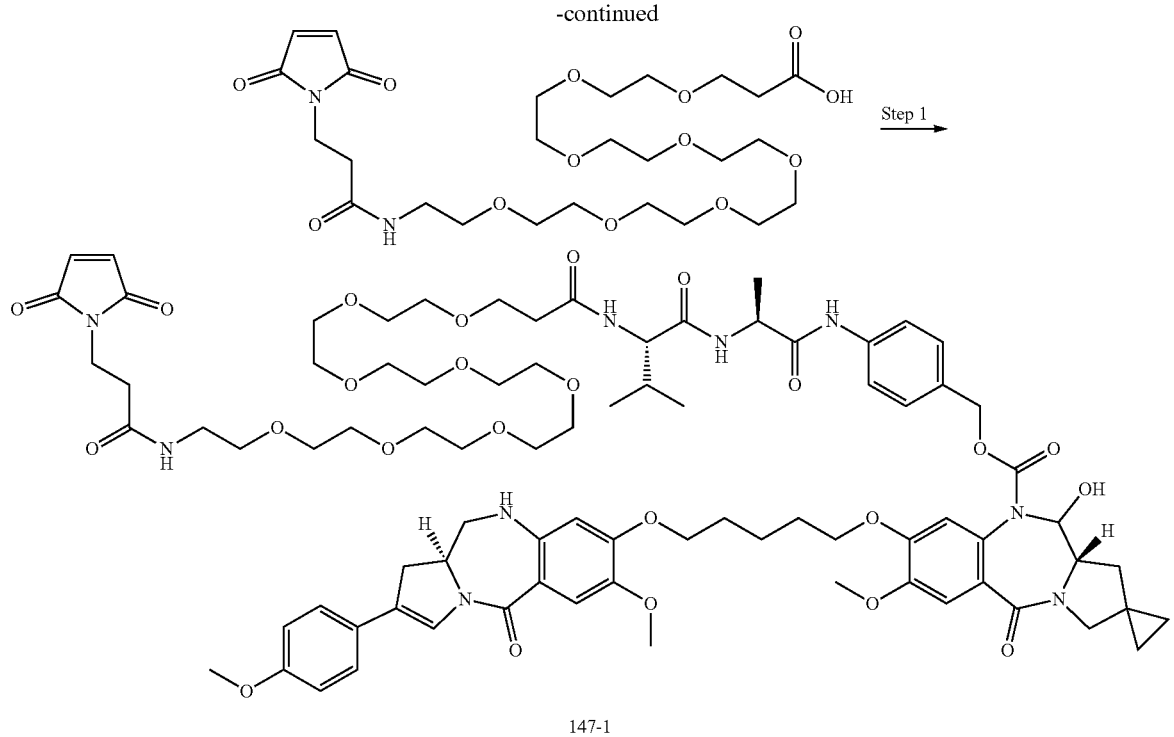
147-1
The compound obtained in step 12 of Example 3 (0.050 g, 0.049 mmol) and commercially available 31-(2,5-dioxo-2,5-dihydro-1H-pyrrol-1-yl)-29-oxo-4,7,10,13,16,19,22,25-octaoxa-28-azahentriacontan-1-oic acid (0.029 g, 0.049 mmol) were reacted in the same manner as in Example 145 to afford the desired compound (45 mg, 57%).
MS (APCI, ESI)m/z:1604 (M+H)⁺
Example 148: Drug-Linker 46
[Formula 252]
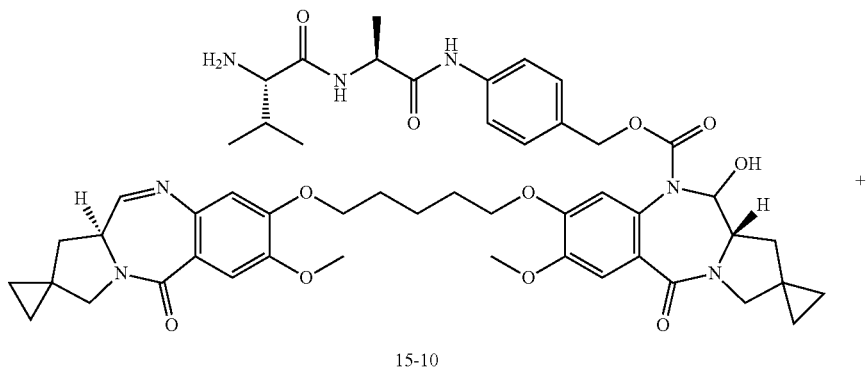
15-10
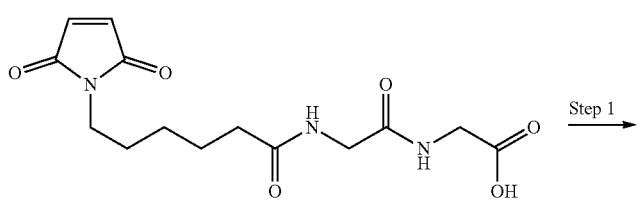

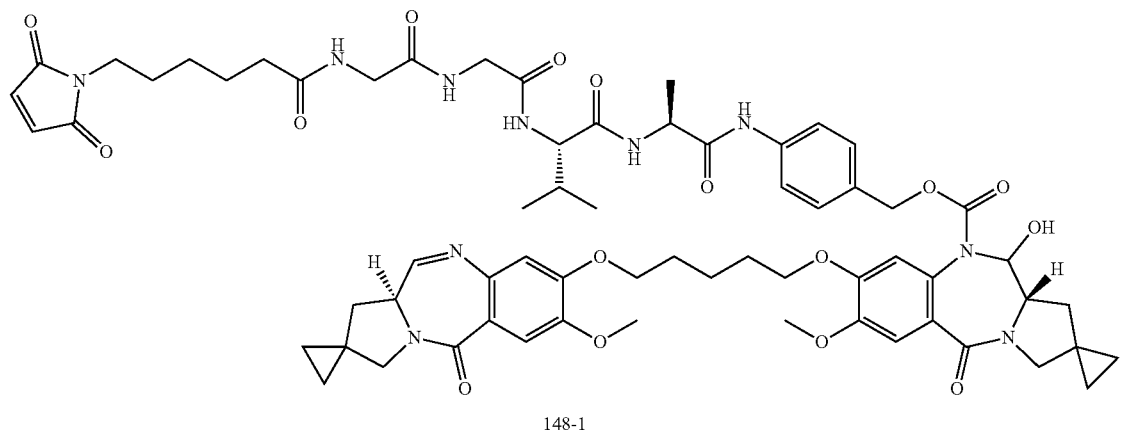
148-1
The compound obtained in step 9 of Example 15 (0.081 g, 0.085 mmol) and commercially available N-[6-(2,5-dioxo-2,5-dihydro-1H-pyrrol-1-yl)hexanoyl]glycylglycine (0.042 g, 0.13 mmol) were reacted in the same manner as in step 1 of Example 16 to afford the desired compound (0.089 g, 82%).
MS (APCI, ESI)m/z:1257 (M+H)$^+$
Example 149: Drug-Linker 47
[Formula 253]
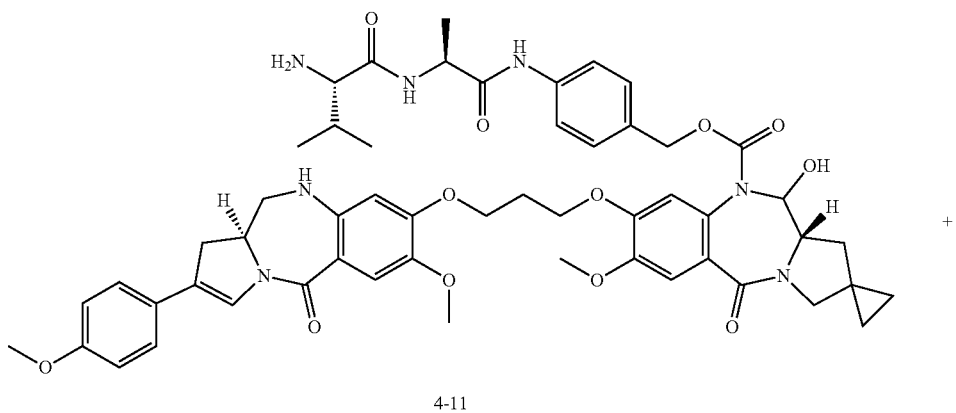
4-11
+
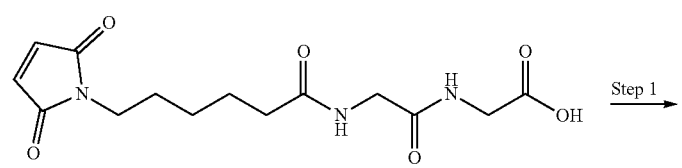
Step 1

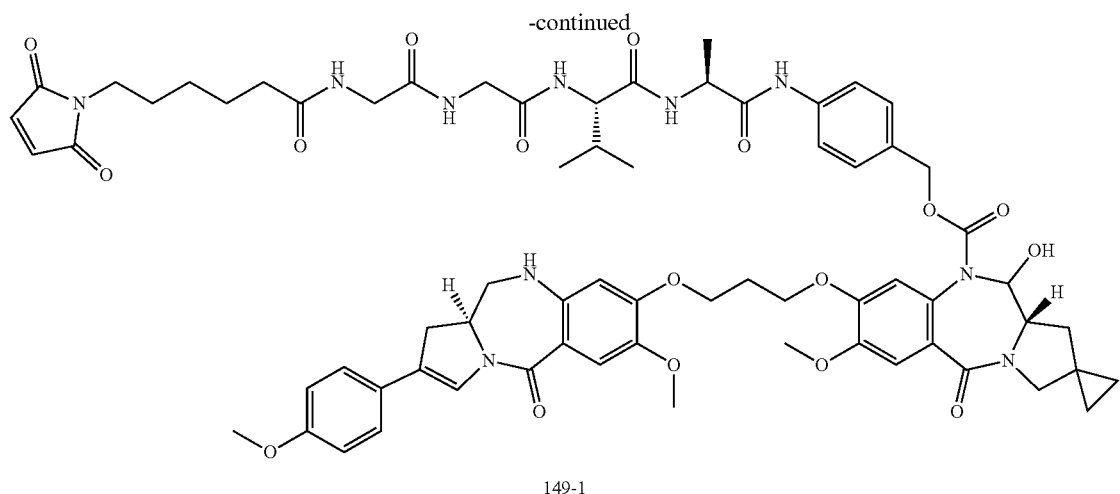

149-1

To a solution of commercially available N-[6-(2,5-dioxo-2,5-dihydro-1H-pyrrol-1-yl)hexanoyl]glycylglycine (0.036 g, 0.11 mmol) in dichloromethane (10 mL), N-ethoxycarbonyl-2-ethoxy-1,2-dihydroquinoline (0.035 g, 0.14 mmol) was added at room temperature, and the resultant was stirred at room temperature for 1 hour. To the reaction solution, the compound obtained in step 11 of Example 4 (0.10 g, 0.10 mmol) and methanol (1 mL) were added, and the resultant was stirred at room temperature for 18 hours. After the reaction solution was concentrated, the resulting residue was purified by silica gel chromatography (chloroform-chloroform: methanol=80:20 (v/v)) to afford the desired compound (0.078 g, 60%).

MS (APCI, ESI)m/z:1309 (M+H)$^+$

Example 150: Drug 11

[Formula 254]

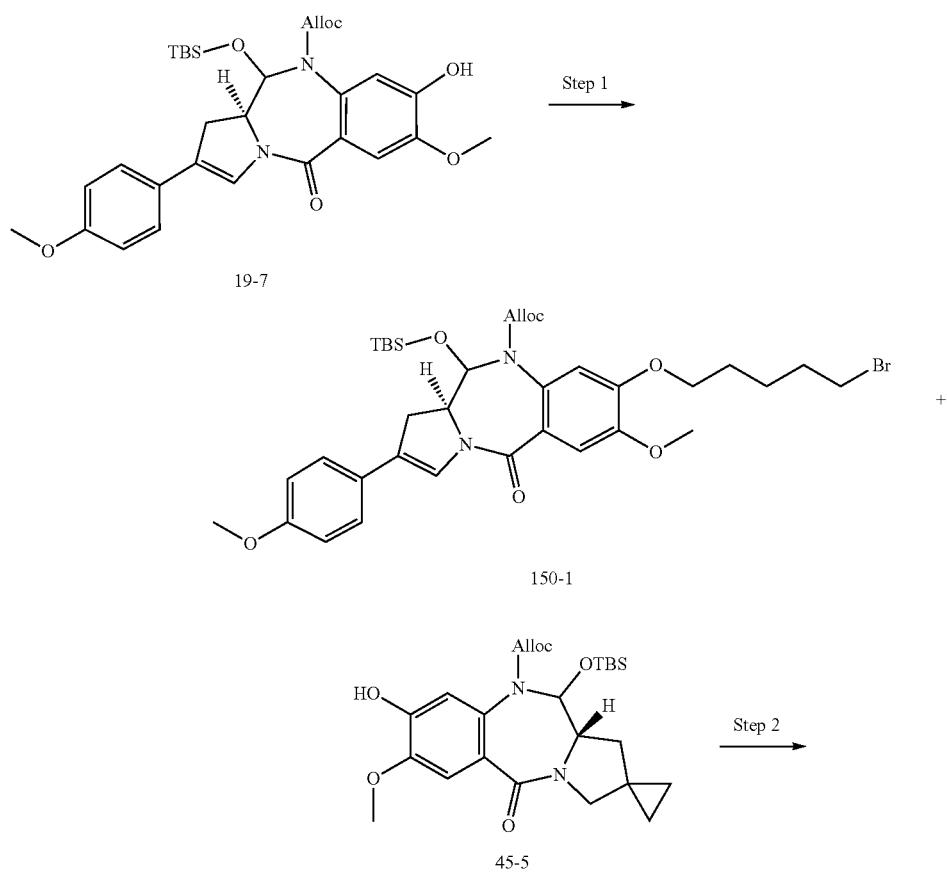

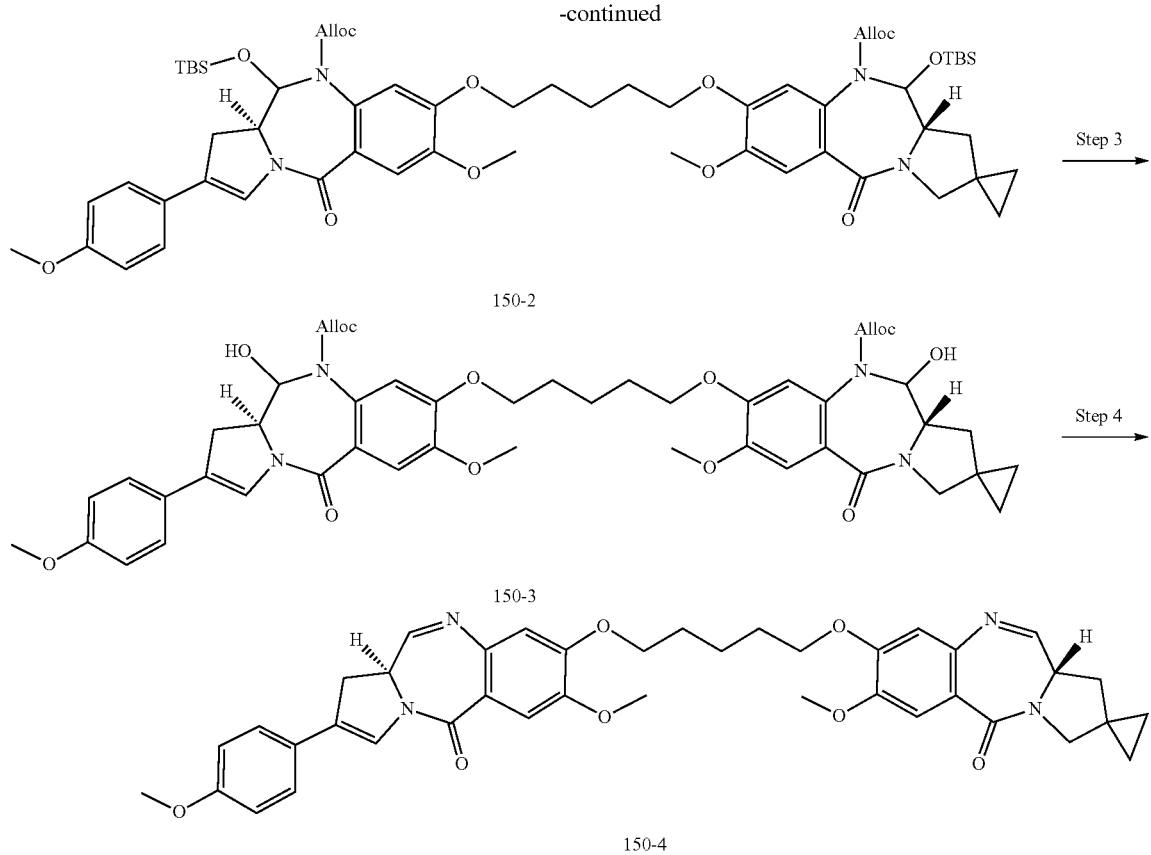
150-2
150-3
150-4
[Steps 1 to 4]
The compound obtained in step 7 of Example 19 was reacted in the same manner as in step 2 of Example 3, step 10 of Example 3, step 11 of Example 3, and step 12 of Example 3 to afford drug 11.
$^1$H-NMR (CDCl$_3$) δ:7.89-7.80 (1H, m), 7.60-7.51 (2H, m), 7.43-7.40 (1H, m), 7.34-7.30 (2H, m), 6.91-6.88 (2H, m), 6.81 (1H, d, J=3.0 Hz), 4.39-4.32 (1H, m), 4.11-4.06 (4H, m), 3.95 (4H, d, J=3.0 Hz), 3.87-3.84 (5H, m), 3.68-3.61 (2H, m), 3.51-3.49 (3H, m), 3.44-3.34 (2H, m), 2.53 (1H, dd, J=13.0, 8.2 Hz), 2.01-1.96 (4H, m), 1.69-1.68 (2H, m), 1.30-1.25 (1H, m), 0.93-0.77 (4H, m).
MS(APCI, ESI)m/z:691(M+H)$^+$.
Example 151: Drug 12
[Formula 255]
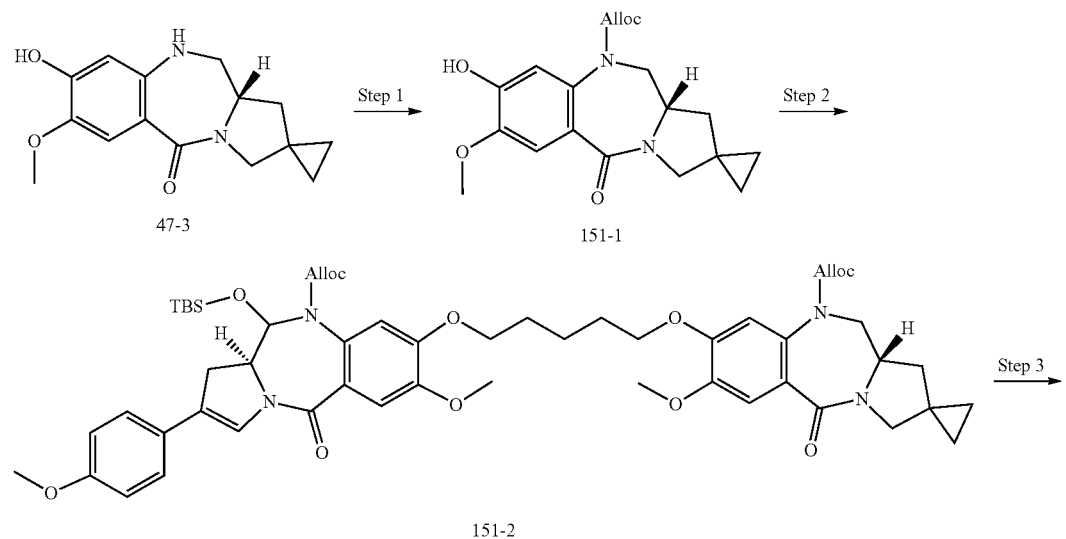
47-3
151-1
151-2

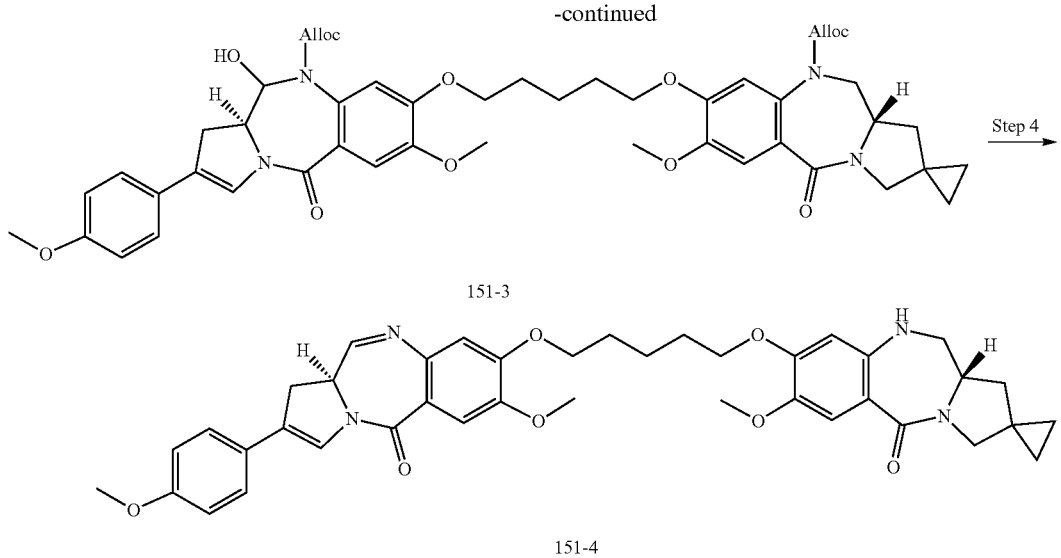

151-3

151-4

[Step 1]

The compound obtained in step 3 of Example 47 (0.77 g, 2.8 mmol) was dissolved in dichloromethane (20 mL), and pyridine (0.338 mL, 4.20 mmol) and allyl chloroformate (0.355 mL, 3.36 mmol) were added thereto at 0° C., and the resultant was stirred at room temperature for 2 hours. After the reaction solution was concentrated, the resulting residue was dissolved in methanol (20 mL), and potassium carbonate (1.93 g, 14.0 mmol) was added thereto at room temperature, and the resultant was continually stirred for 3 hours. Water was added to the reaction solution, and methanol was distilled off under reduced pressure, and 1 N hydrochloric acid was added to the resulting residue, which was extracted with chloroform. The organic layer was dried over sodium sulfate, and filtered, and the solvent was then distilled off under reduced pressure. The resulting residue was purified by silica gel column chromatography [hexane:ethyl acetate=100:0 (v/v) to 0:100 (v/v)] to afford the desired compound (0.921 g, 92%) as a pale yellow solid.

MS (APCI, ESI)m/z:359 (M+H)$^+$.

[Steps 2 to 4]

The compound obtained in step 1 was reacted in the same manner as in steps 10 to 12 of Example 3 to afford drug 12.

$^1$HNMR(CDCl$_3$) δ:7.89 (1H, d, J=4.2 Hz), 7.59 (1H, s), 7.53 (1H, s), 7.40 (1H, s), 7.34 (2H, d, J=8.5 Hz), 6.91 (2H, d, J=8.5 Hz), 6.82 (1H, s), 6.05 (1H, s), 4.44-4.39 (1H, m), 4.16-4.11 (2H, m), 4.09-4.04 (2H, m), 3.99 (2H, t, J=6.7 Hz), 3.95 (3H, s), 3.84 (6H, s), 3.72 (1H, d, J=12.1 Hz), 3.59-3.49 (3H, m), 3.45-3.34 (2H, m), 2.00-1.92 (4H, m), 1.79 (1H, dd, J=12.4, 7.0 Hz), 1.70-1.64 (2H, m), 1.25 (1H, t, J=7.0 Hz), 0.73-0.55 (4H, m).

MS(APCI, ESI)m/z:693(M+H)$^+$.

Example 152: Drugs 13 to 16

[Formula 256]

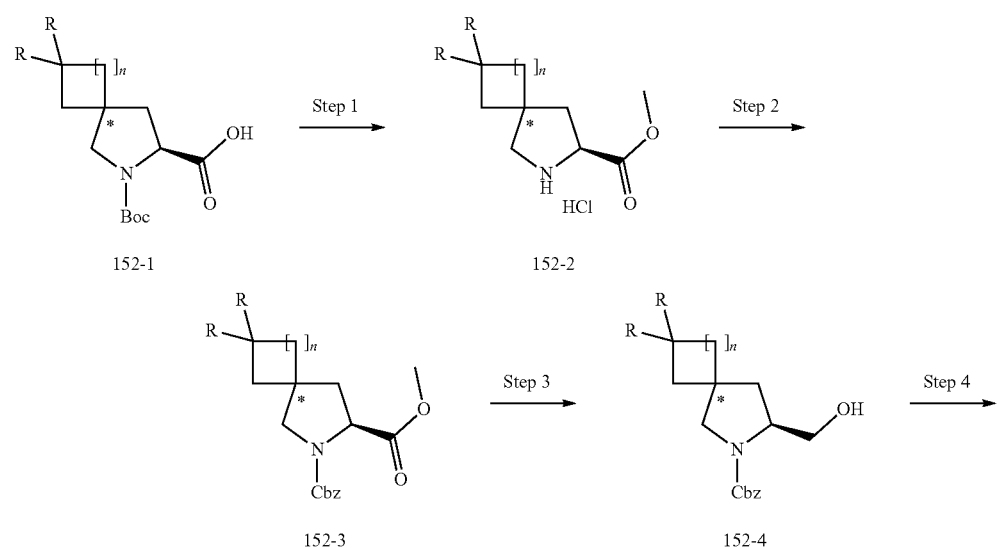

152-1   152-2

152-3   152-4

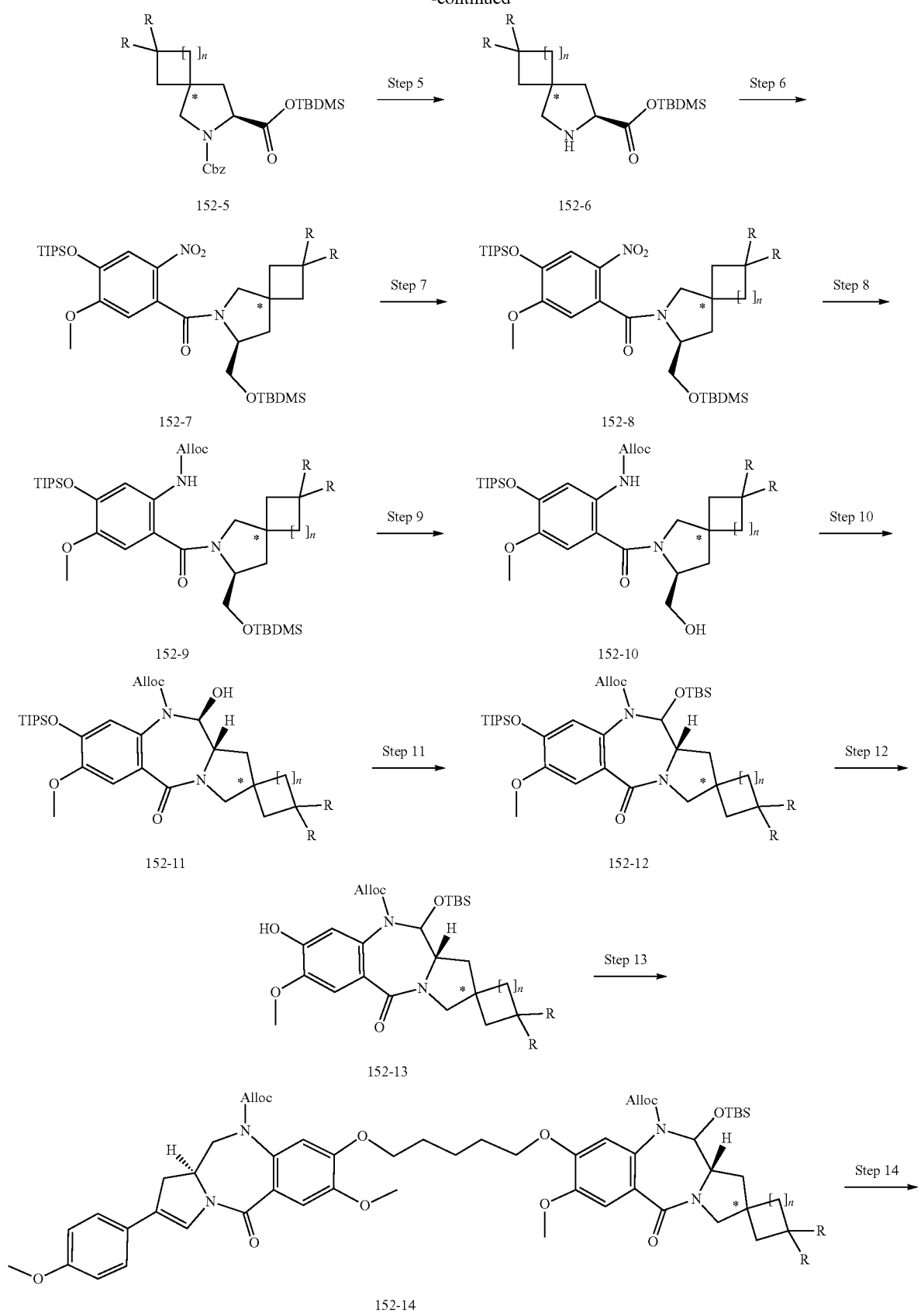

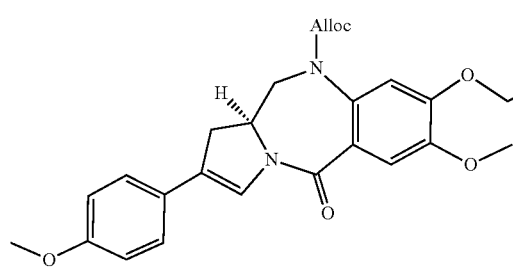
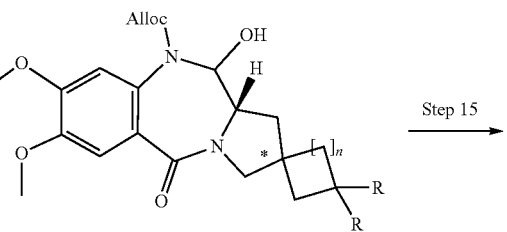
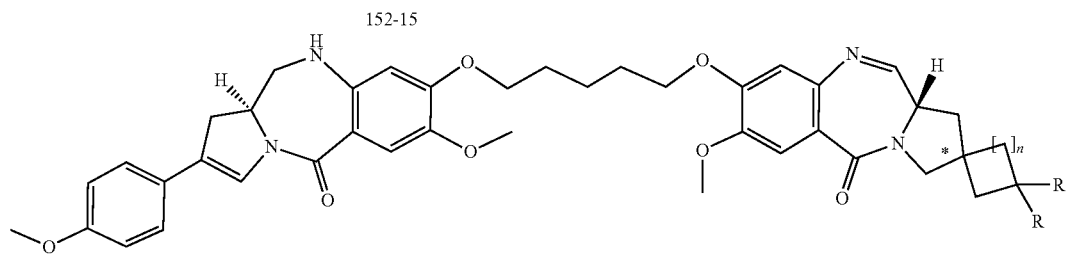

n = 0 R = F, *: (R) or (S)
n = 1 R = F or H

[Cyclobutyl Derivative: Drug 13]n=1, R=F
[Step 1]

To a solution of commercially available N-T-BOC-4-(3,3-difluorocyclobutyl)-L-proline (OmegaChem Inc., OC-0707) (12 g, 41 mmol) in methanol (200 mL), thionyl chloride (10 mL, 138 mmol) was slowly added dropwise at −78° C. (dry ice-acetone bath). After the dropwise addition, the refrigerant bath was removed, and the reaction mixture was stirred at room temperature overnight. The reaction mixture was concentrated under reduced pressure, and the residue was washed with diethyl ether to afford the desired compound (10 g, quant.).

[Step 2]

To a suspension solution of the compound obtained in step 1 (10 g, 41.4 mmol) and sodium carbonate (8.77 g, 82.7 mmol) in 1,4-dioxane (200 mL) and water (50 mL), benzyl chloroformate (8.82 mL, 62.0 mmol) was slowly added under ice-cooling. After the completion of the reaction, water was added thereto, and the reaction mixture was extracted with ethyl acetate. The organic layer was washed with water and brine, and dried over anhydrous sodium sulfate. After filtration, the solvent was distilled off under reduced pressure to afford the desired compound.

[Steps 3 to 15]

The compound obtained in the previous step was reacted in the same manner as in steps 1 to 5 of Example 1 and steps 1 to 8 of Example 45 to afford drug 13.

$^1$HNMR(CDCl$_3$) δ:7.72-7.71 (1H, m), 7.53-7.49 (3H, m), 7.34-7.28 (2H, m), 6.91-6.78 (3H, m), 6.06-6.03 (1H, m), 4.35-4.28 (1H, m), 4.16-4.04 (2H, m), 4.02-3.96 (1H, m), 3.94 (3H, s), 3.90-3.76 (2H, m), 3.84 (2H, s), 3.82 (3H, s), 3.59-3.31 (2H, m), 2.76-2.44 (8H, m), 1.99-1.88 (4H, m), 1.71-1.59 (4H, m).

MS(APCI, ESI)m/z:743(M+H)$^+$.

[Cyclobutyl Derivative: Drug 14]n=1, R=H
[Steps 2 to 15]

Commercially available 4-cyclobutyl-L-proline methyl ester hydrochloride (OmegaChem Inc., OC-0728) was reacted in the same manner as in step 2, steps 1 to 5 of Example 1, and steps 1 to 8 of Example 45 to afford drug-linker 14.

$^1$HNMR(CDCl$_3$) δ:7.73-7.45 (3H, m), 7.34-7.14 (2H, m), 6.94-6.42 (3H, m), 6.05-5.99 (1H, m), 5.30-5.06 (2H, m), 4.49-4.28 (2H, m), 4.17-3.96 (2H, m), 3.95-3.79 (9H, m), 3.77-3.30 (6H, m), 2.77-2.70 (1H, m), 2.37-2.30 (1H, m), 2.19-1.85 (8H, m), 1.73-1.55 (4H, m), 1.30-1.16 (2H, m).

MS(APCI, ESI)m/z:707(M+H)$^+$.

[Cyclopropyl Derivative: Drug 15]n=0, R=F, *: (S)

Commercially available N-t-BOC-4S-(2,2-difluorocyclopropyl)-L-proline (OmegaChem Inc., OC-0732) was reacted in the same manner as in steps 1 to 15 to afford drug-linker 15.

$^1$HNMR(CDCl$_3$) δ:7.76-7.75 (1H, m), 7.54-7.47 (3H, m), 7.33-7.27 (2H, m), 6.93-6.85 (2H, m), 6.83-6.79 (1H, m), 6.08-5.96 (1H, m), 4.32-4.30 (1H, m), 4.16-3.96 (3H, m), 3.94 (3H, s), 3.84 (3H, s), 3.82 (3H, s), 3.74-3.67 (3H, m), 3.59-3.51 (2H, m), 3.39-3.34 (1H, m), 2.76-2.69 (2H, m), 2.38-2.33 (1H, m), 1.98-1.89 (4H, m), 1.69-1.54 (4H, m), 1.30-1.22 (2H, m).

MS(APCI, ESI)m/z:729(M+H)$^+$.

[Cyclopropyl Derivative: Drug 16]n=0, R=F, *: (R)

Commercially available N-t-BOC-4R-(2,2-difluorocyclopropyl)-L-proline (OmegaChem Inc., OC-0722) was reacted in the same manner as in steps 1 to 15 to afford drug-linker 16.

$^1$HNMR(CDCl$_3$) δ:7.76-7.69 (1H, m), 7.55-7.44 (3H, m), 7.33-7.28 (2H, m), 6.94-6.80 (2H, m), 6.59-6.42 (1H, m), 6.08-5.97 (1H, m), 4.36-4.24 (1H, m), 4.20-3.95 (3H, m), 3.95-3.76 (12H, m), 3.75-3.50 (2H, m), 3.42-3.31 (1H, m), 2.79-2.52 (2H, m), 2.48-2.32 (1H, m), 2.06-1.83 (4H, m), 1.72-1.41 (4H, m), 1.28-1.15 (2H, m).

MS(APCI, ESI)m/z:729(M+H)$^+$.

Example 153: [N$_3$-PEG (3)]$_2$-SG (10)

Step 1: Fmoc-(SG-)Asn Free Form

Fmoc-(SG-)Asn (1S2S-11NC-Asn-Fmoc, produced by GlyTech, Inc., 2 g) was dissolved in an appropriate amount of a 0.1% aqueous solution of trifluoroacetic acid, and subjected to separation/purification by reversed-phase HPLC in multiple separate operations. The eluent was a 0.1% aqueous solution of trifluoroacetic acid and a 0.1% acetonitrile solution of trifluoroacetic acid, the apparatus used was a Purif-Rp2 (produced by Shoko Scientific Co., Ltd.), and the column used was an Inertsil ODS-3 (produced by GL Sciences, Inc.). Fractions containing the desired product UV-detected (220 nm) during the elution were collected together, and freeze-dried. A colorless solid (1.8 g) was obtained.

Step 2: Synthesis of ([N$_3$-PEG (3)]$_2$-SG)-Asn-PEG (3)-N$_3$

The reaction solution was halved and transferred into two jumbo conical tubes (175 mL) to each of which diethyl ether (100 mL) had been added in advance. The solid matter was precipitated by using a small centrifuge (Hitachi Koki Co., Ltd., CF16RX) and the supernatant was removed. The gum-like solid matter was transferred into a centrifuge tube (50 mL), and diethyl ether (30 mL) and acetonitrile (10 mL) were added thereto, and the resultant was decanted. This operation was repeated twice. In the same manner, an appropriate amount of acetonitrile or an appropriate amount of diethyl ether was added and the resultant was decanted, and then dried under reduced pressure to afford a crude

[Formula 257]

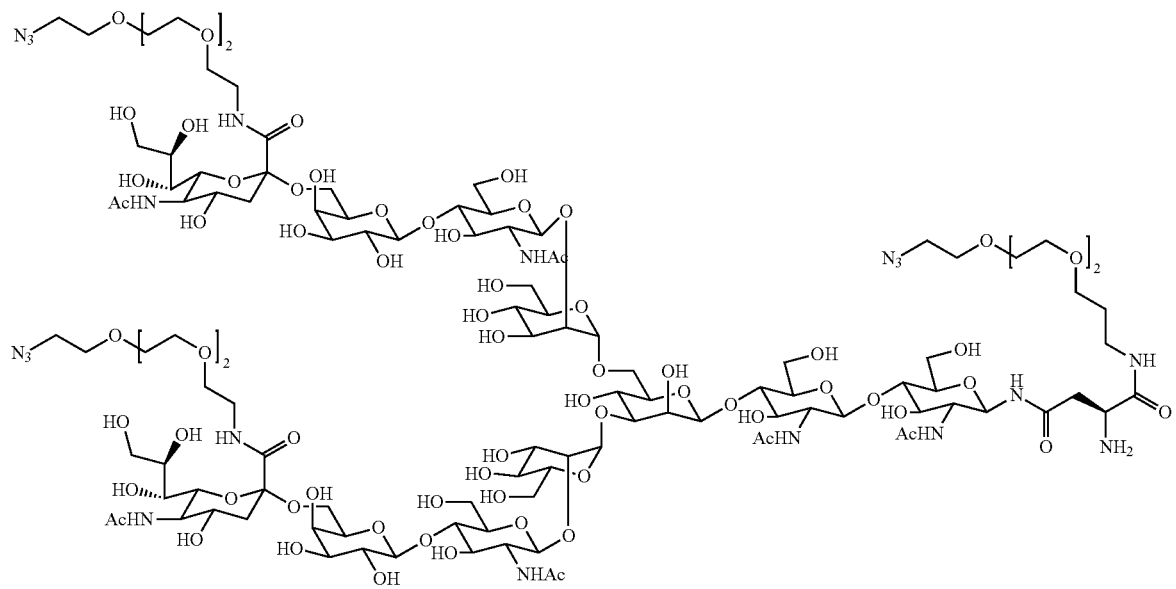

To an N,N-dimethylformamide solution (10 mL) of the Fmoc-(SG-)Asn free form prepared in step 1 (1000 mg), an N,N-dimethylformamide solution (3 mL) of HATU (891 mg, 2.34 mmol) and an N,N-dimethylformamide solution (3 mL) of 11-azide-3,6,9-trioxaundecane-1-amine (Tokyo Chemical Industry Co., Ltd., 511 mg, 2.34 mmol) and diisopropylethylamine (816 µL, 4.69 mmol) were added, and the resultant was stirred at 37° C. for 3 hours. Further, an N,N-dimethylformamide solution (500 µL) of HATU (148 mg, 0.39 mmol) was added thereto, and the resultant was stirred at 37° C. for 1 hour. Thereafter, piperidine (386 µL, 3.91 mmol) was added thereto, and the resultant was stirred at 37° C. for 1 hour. After the completion of the reaction, acetic acid (469 µL) was added thereto.

product. The solid matter obtained was dissolved in an appropriate amount of a 0.2% trifluoroacetic acid aqueous solution, and subjected to separation/purification by reversed-phase HPLC. The eluent was a 0.1% trifluoroacetic acid aqueous solution and a 0.1% trifluoroacetic acid acetonitrile solution, the apparatus used was a Purif-Rp2 (produced by Shoko Scientific Co., Ltd.), and the column used was an Inertsil ODS-3 (produced by GL Sciences, Inc.). Fractions containing the desired product UV-detected (220 nm) during the elution were collected together, and freeze-dried to afford the titled desired compound (637 mg) as a colorless solid.

ESI-MS: Calcd for $C_{112}H_{192}N_{20}O_{70}$: $[M+3H]^{3+}$ 980.6 (ave.), Found 980.4

Step 3: Synthesis of [N₃-PEG (3)]₂-SG (10)

[Formula 258]

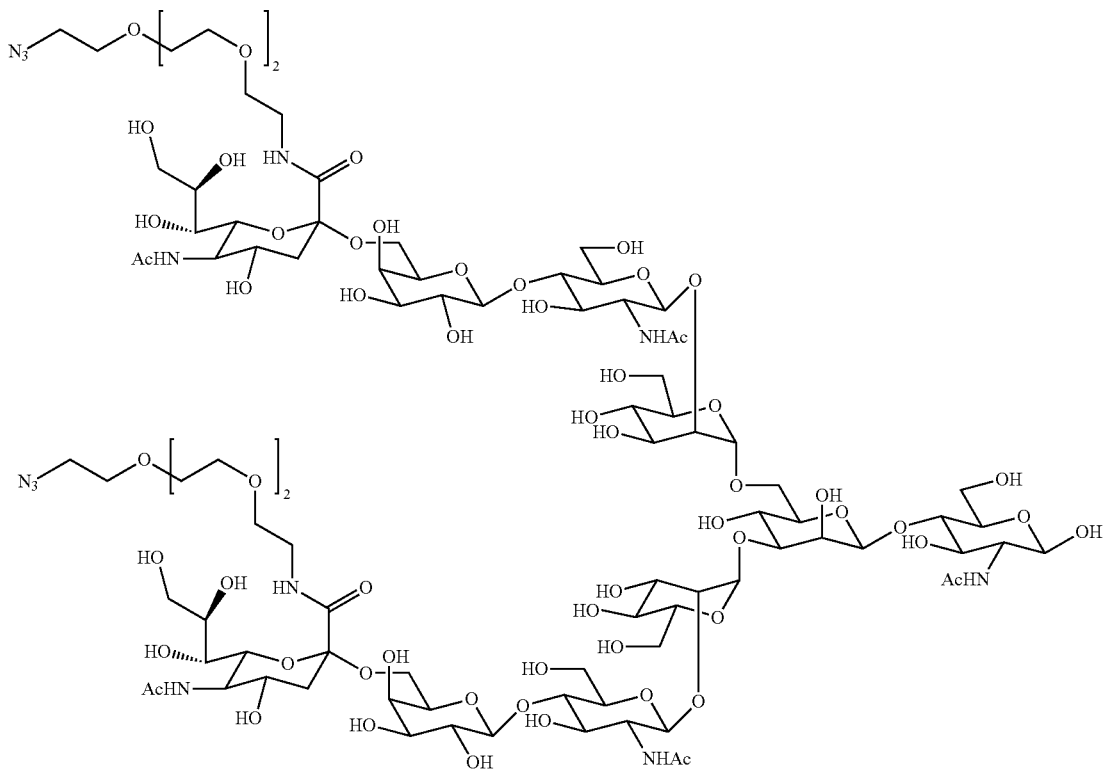

In a 2 mL tube, ([N₃-PEG (3)]₂-SG)-Asn-PEG (3)-N₃ synthesized in step-2 (78.6 mg) was dissolved in 100 mM phosphate buffer (NACALAI TESQUE, INC., 465 μL) at pH 6.0. Thereto, 1 U/mL EndoM (Tokyo Chemical Industry Co., Ltd., 70 μL) was added, and the resultant was shaken at 28° C. for 5 hours, and then left to stand at room temperature for 4 days. After the completion of the reaction, an appropriate amount of a 0.2% trifluoroacetic acid aqueous solution was added thereto, and the resultant was subjected to separation/purification by reversed-phase HPLC. The eluent was a 0.1% trifluoroacetic acid aqueous solution and a 0.1% trifluoroacetic acid acetonitrile solution, the apparatus used was a Purif-Rp2 (produced by Shoko Scientific Co., Ltd.), and the column used was an Inertsil ODS-3 (produced by GL Sciences, Inc.). Fractions containing the desired product UV-detected (220 nm) during the elution were collected together, and freeze-dried to afford the titled desired compound (40 mg) as a colorless solid.

ESI-MS: Calcd for $C_{92}H_{157}N_{13}O_{61}$: $[M+2H]^{2+}$ 1211.7 (ave.), Found 1211.5

Example 154: [N₃-PEG (3)]-MSG2 (9), [N₃-PEG (3)]-MSG1 (9)

Step 1: (MSG1-)Asn and (MSG2-)Asn

The commercially available product monosialo-Asn free (1S2G/1G2S-10NC-Asn, produced by GlyTech, Inc.) (referred to as "(MSG-)Asn") (500 mg) was subjected to separation/purification by reversed-phase HPLC under conditions below to separate into (MSG1-)Asn eluted as the 1st main peak (retention time: around 15 to 19 min) and (MSG2-)Asn eluted as the 2nd main peak (retention time: around 21 to 26 min). The eluent used was a 0.1% aqueous solution of formic acid, the apparatus used was an ELS-PDA trigger preparative system (produced by JASCO Corporation), the column used was an Inertsil ODS-3 (10 um, 30φ×250 mm, produced by GL Sciences, Inc.), and the flow rate was 30 mL/min. Fractions belonging to the first peak UV-detected (210 nm) during the elution were collected together, and freeze-dried to afford (MSG1-)Asn (238 mg) as a colorless solid. Fractions belonging to the second peak UV-detected were collected together, and freeze-dried to afford (MSG2-)Asn (193 mg) as a colorless solid.

Step-2: Fmoc-(MSG2-)Asn Free Form

[Formula 259]

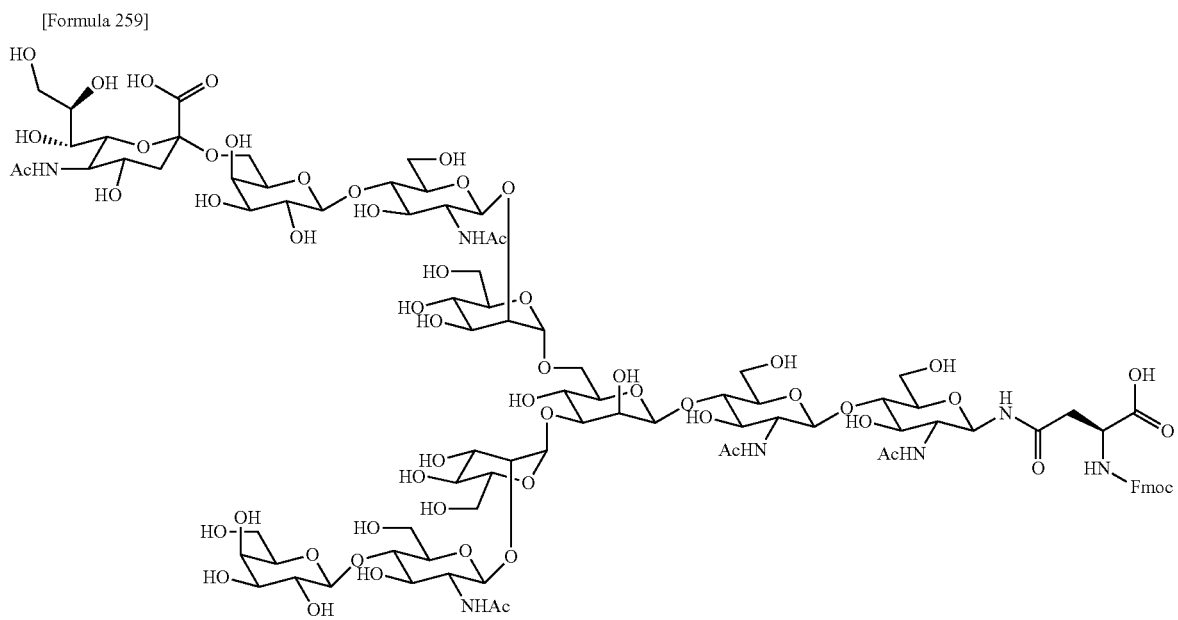

(MSG2-)Asn synthesized in step 1 (900 mg) was dissolved in an N,N-dimethylformamide solution (6 mL)/distilled water (2 mL), and diisopropylethylamine (0.23 mL) and 9-fluorenylmethyl N-succinimidyl carbonate (223 mg) were added thereto, and the resultant was stirred at room temperature for 30 minutes. Further, diisopropylethylamine (0.16 mL), 9-fluorenylmethyl N-succinimidyl carbonate (74 mg), and N,N-dimethylformamide solution (1 mL) were added thereto, and the resultant was stirred at room temperature for 30 minutes.

The reaction solution was halved and transferred into two jumbo conical tubes (175 mL) to each of which diethyl ether (80 mL)/acetonitrile (4 mL) had been added in advance. The solid matter was precipitated by using a small centrifuge (Hitachi Koki Co., Ltd., CF16RX) and the supernatant was removed. The gum-like solid matter was transferred into a centrifuge tube (50 mL), and diethyl ether (30 mL) and acetonitrile (10 mL) were added thereto, and the resultant was decanted. This operation was repeated twice. In the same manner, an appropriate amount of acetonitrile or an appropriate amount of diethyl ether was added and the resultant was decanted, and then dried under reduced pressure to afford a crude product. The solid matter obtained was dissolved in an appropriate amount of a 0.2% trifluoroacetic acid aqueous solution, and subjected to separation/purification by reversed-phase HPLC. The eluent was a 0.1% trifluoroacetic acid aqueous solution and a 0.1% trifluoroacetic acid acetonitrile solution, the apparatus used was a Purif-Rp2 (produced by Shoko Scientific Co., Ltd.), and the column used was an Inertsil ODS-3 (produced by GL Sciences, Inc.). During eluting, fractions containing the UV-detected (220 nm) desired product were collected together, and freeze-dried to afford the titled desired compound (830 mg) as a colorless solid.

Step 3: ([N₃-PEG (3)]-MSG2)-Asn-PEG (3)-N₃
[Formula 260]
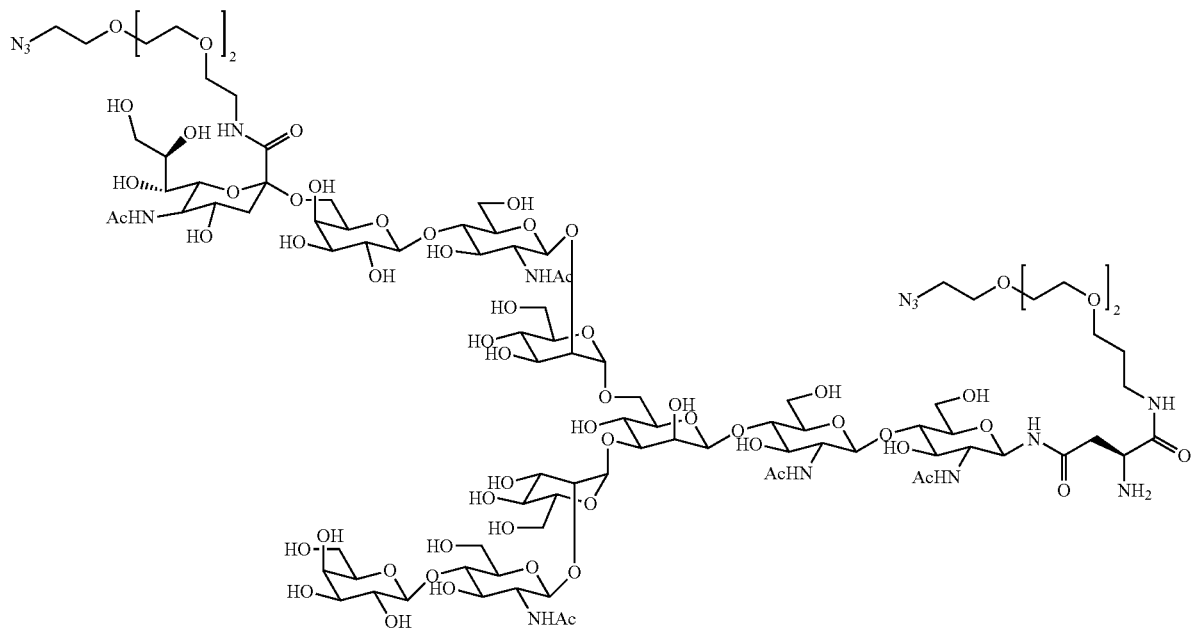
With use of Fmoc-(MSG2-)Asn) synthesized in step 2 (830 mg, a crude product of the titled desired product (1.06 g) was obtained in the same manner as in step 2 of Example 153. This was used for the subsequent reaction without additional purification.
Similarly, the following ([N₃-PEG (3)]-MSG1)-Asn-PEG (3)-N₃ can be synthesized from Fmoc-(MSG1-)Asn.
[Formula 261]
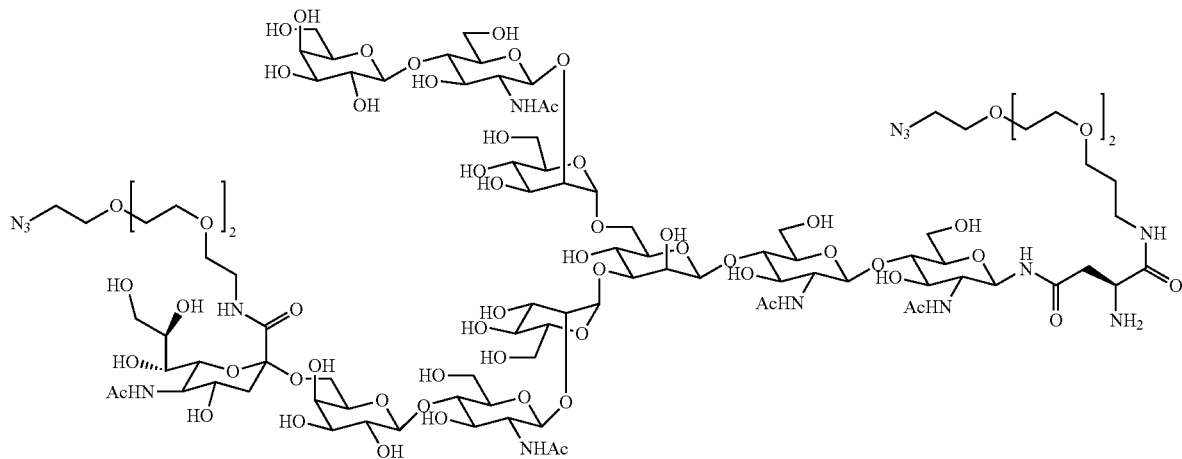

Step 4: [N₃-PEG (3)]-MSG2 (9)

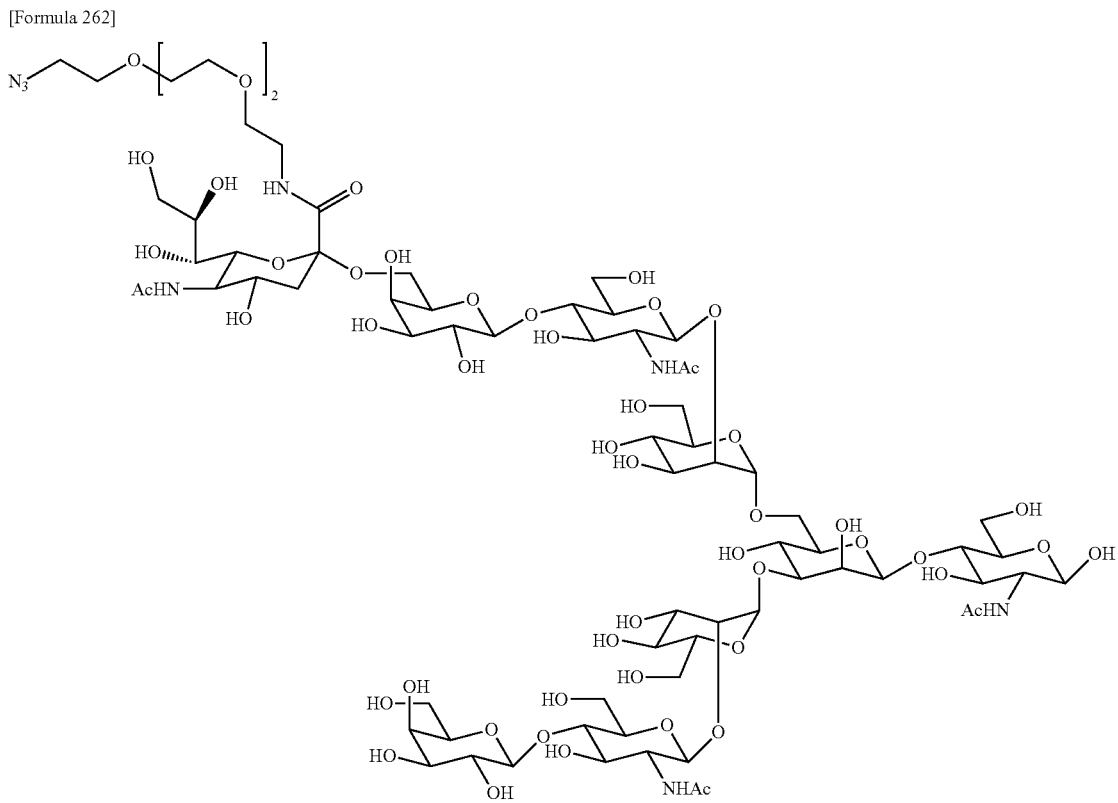

[Formula 262]

In a 2 mL collection vial, the crude product of ([N₃-PEG (3)]-MSG2)-Asn-PEG (3)-N₃ synthesized in step 3 (150 mg) was dissolved in 200 mM potassium phosphate buffer (750 μL) at pH 6.25 prepared with 200 mM KH₂PO₄ and 200 mM KH₂PO₄. Endo-Rp (3 ug) was added thereto, and the resultant was left to stand at 50° C. for 16 hours. After the completion of the reaction, a 5% aqueous solution of trifluoroacetic acid (150 μL) was added thereto, and the resultant was subjected to separation/purification by reversed-phase HPLC. The eluent was a 0.1% aqueous solution of trifluoroacetic acid aqueous solution and a 0.1% trifluoroacetic acid acetonitrile solution, the apparatus used was an ELS-PDA trigger preparative system (produced by JASCO Corporation), and the column used was an Inertsil ODS-3 (produced by GL Sciences, Inc.). Fractions containing the desired product UV-detected (210 nm) during the elution were collected together, and freeze-dried to afford the titled desired compound (62 mg) as a colorless solid.

ESI-MS: Calcd for $C_{73}H_{124}N_8O_{51}$. $[M+2H]^{2+}$ 965.3 (ave.), Found 965.4

Similarly, the following [N₃-PEG (3)]-MSG1 (9) can be synthesized from ([N₃-PEG (3)]-MSG1)-Asn-PEG (3)-N₃.

[Formula 263]

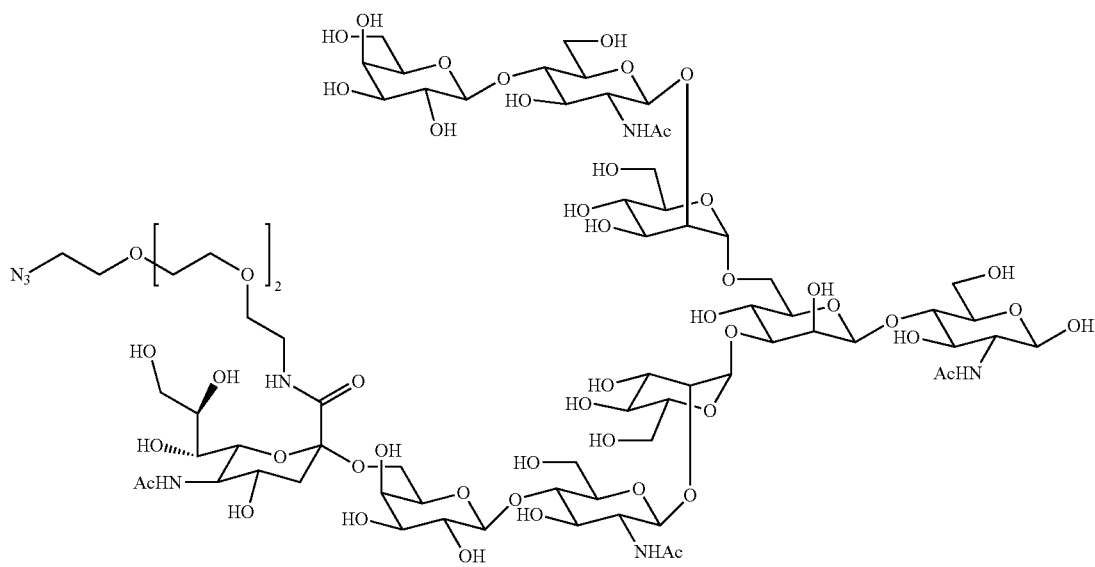

INDUSTRIAL APPLICABILITY

Use of the antibody-drug conjugate, antibody and/or PBD derivative, and so on of the present invention enables treatment or prevention of various cancers.

Free Text of Sequence Listing

SEQ ID NO: 1—Amino acid sequence of human CLDN6
SEQ ID NO: 2—Nucleotide sequence of cDNA encoding amino acid sequence of human CLDN6
SEQ ID NO: 3—Amino acid sequence of human CLDN9
SEQ ID NO: 4—Nucleotide sequence of cDNA encoding amino acid sequence of human CLDN9
SEQ ID NO: 5—Amino acid sequence of CDRL1 of B1 antibody light chain
SEQ ID NO: 6—Amino acid sequence of CDRL2 of B1 antibody light chain
SEQ ID NO: 7—Amino acid sequence of CDRL3 of B1 antibody light chain
SEQ ID NO: 8—Amino acid sequence of CDRL3 of humanized B1 antibody light chain L4
SEQ ID NO: 9—Amino acid sequence of CDRH1 of B1 antibody heavy chain
SEQ ID NO: 10—Amino acid sequence of CDRH2 of B1 antibody heavy chain
SEQ ID NO: 11—Amino acid sequence of CDRH3 of B1 antibody heavy chain
SEQ ID NO: 12—Amino acid sequence of CDRL1 of C7 antibody light chain
SEQ ID NO: 13—Amino acid sequence of CDRL2 of C7 antibody light chain
SEQ ID NO: 14—Amino acid sequence of CDRL3 of C7 antibody light chain
SEQ ID NO: 15—Amino acid sequence of CDRH1 of C7 antibody heavy chain
SEQ ID NO: 16—Amino acid sequence of CDRH2 of C7 antibody heavy chain
SEQ ID NO: 17—Amino acid sequence of CDRH3 of C7 antibody heavy chain
SEQ ID NO: 18—Nucleotide sequence of cDNA encoding variable region of B1 antibody light chain
SEQ ID NO: 19—Amino acid sequence of variable region of B1 antibody light chain
SEQ ID NO: 20—Nucleotide sequence of cDNA encoding variable region of B1 antibody heavy chain
SEQ ID NO: 21—Amino acid sequence of variable region of B1 antibody heavy chain
SEQ ID NO: 22—Nucleotide sequence of cDNA encoding variable region of C7 antibody light chain
SEQ ID NO: 23—Amino acid sequence of variable region of C7 antibody light chain
SEQ ID NO: 24—Nucleotide sequence of cDNA encoding variable region of C7 antibody heavy chain
SEQ ID NO: 25—Amino acid sequence of variable region of C7 antibody heavy chain
SEQ ID NO: 26—DNA fragment including DNA sequence encoding human light chain signal sequence and human κ chain constant region
SEQ ID NO: 27—DNA fragment including DNA sequence encoding human heavy chain signal sequence and human IgG1 LALA constant region
SEQ ID NO: 28—Amino acid sequence of chB1 light chain
SEQ ID NO: 29—DNA fragment including DNA sequence encoding amino acid sequence of chB1 light chain
SEQ ID NO: 30—Amino acid sequence of variable region of chB1 light chain
SEQ ID NO: 31—Nucleotide sequence encoding chB1 light chain variable region
SEQ ID NO: 32—Amino acid sequence of chB1 heavy chain
SEQ ID NO: 33—Nucleotide sequence encoding chB1 heavy chain
SEQ ID NO: 34—Amino acid sequence of variable region of chB1 heavy chain
SEQ ID NO: 35—Nucleotide sequence encoding variable region of chB1 heavy chain
SEQ ID NO: 36—Amino acid sequence of humanized antibody light chain hL1
SEQ ID NO: 37—Nucleotide sequence encoding humanized antibody light chain hL1

SEQ ID NO: 38—Amino acid sequence of variable region of humanized antibody light chain hL1
SEQ ID NO: 39—Nucleotide sequence encoding variable region of humanized antibody light chain hL1
SEQ ID NO: 40—Amino acid sequence of humanized antibody light chain hL2
SEQ ID NO: 41—Nucleotide sequence encoding humanized antibody light chain hL2
SEQ ID NO: 42—Amino acid sequence of variable region of humanized antibody light chain hL2
SEQ ID NO: 43—Nucleotide sequence encoding variable region of humanized antibody light chain hL2
SEQ ID NO: 44—Amino acid sequence of humanized antibody light chain hL3
SEQ ID NO: 45—Nucleotide sequence encoding humanized antibody light chain hL3
SEQ ID NO: 46—Amino acid sequence of variable region of humanized antibody light chain hL3
SEQ ID NO: 47—Nucleotide sequence encoding variable region of humanized antibody light chain hL3
SEQ ID NO: 48—Amino acid sequence of humanized antibody light chain hL4
SEQ ID NO: 49—Nucleotide sequence encoding humanized antibody light chain hL4
SEQ ID NO: 50—Amino acid sequence of variable region of humanized antibody light chain hL4
SEQ ID NO: 51—Nucleotide sequence encoding variable region of humanized antibody light chain hL4
SEQ ID NO: 52—Amino acid sequence of humanized antibody heavy chain hH1
SEQ ID NO: 53—Nucleotide sequence encoding humanized antibody heavy chain hH1
SEQ ID NO: 54—Amino acid sequence of variable region of humanized antibody heavy chain hH1
SEQ ID NO: 55—Nucleotide sequence encoding variable region of humanized antibody heavy chain hH1
SEQ ID NO: 56—Amino acid sequence of humanized antibody heavy chain hH2
SEQ ID NO: 57—Nucleotide sequence encoding humanized antibody heavy chain hH2
SEQ ID NO: 58—Amino acid sequence of variable region of humanized antibody heavy chain hH2
SEQ ID NO: 59—Nucleotide sequence encoding variable region of humanized antibody heavy chain hH2
SEQ ID NO: 60—Amino acid sequence of humanized antibody heavy chain hH3
SEQ ID NO: 61—Nucleotide sequence encoding humanized antibody heavy chain hH3
SEQ ID NO: 62—Amino acid sequence of variable region of humanized antibody heavy chain hH3
SEQ ID NO: 63—Nucleotide sequence encoding variable region of humanized antibody heavy chain hH3
SEQ ID NO: 64—Amino acid sequence of Trastuzumab light chain
SEQ ID NO: 65—Amino acid sequence of Trastuzumab heavy chain
SEQ ID NO: 66—Amino acid sequence of anti-LPS antibody (h #1G5-H1L1) light chain
SEQ ID NO: 67—Amino acid sequence of anti-LPS antibody (h #1G5-H1L1) heavy chain
SEQ ID NO: 68—Amino acid sequence of anti-TROP2 antibody (hRS7) light chain
SEQ ID NO: 69—Amino acid sequence of anti-TROP2 antibody (hRS7) heavy chain
SEQ ID NO: 70—Amino acid sequence of anti-CD98 antibody (hM23-H1L1) light chain
SEQ ID NO: 71—Amino acid sequence of anti-CD98 antibody (hM23-H1L1) heavy chain
SEQ ID NO: 72—Nucleotide sequence encoding Trastuzumab variant light chain
SEQ ID NO: 73—Amino acid sequence of Trastuzumab variant light chain
SEQ ID NO: 74—Nucleotide sequence encoding Trastuzumab variant heavy chain
SEQ ID NO: 75—Amino acid sequence of Trastuzumab variant heavy chain

The invention claimed is:

1. A method for treating a tumor, comprising administering to a patient in need thereof an antibody-drug conjugate selected from the following group:

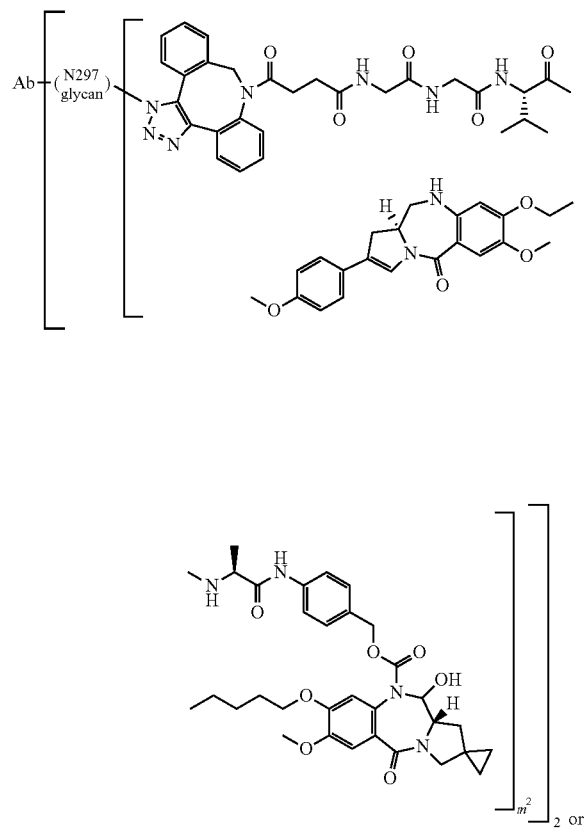

or

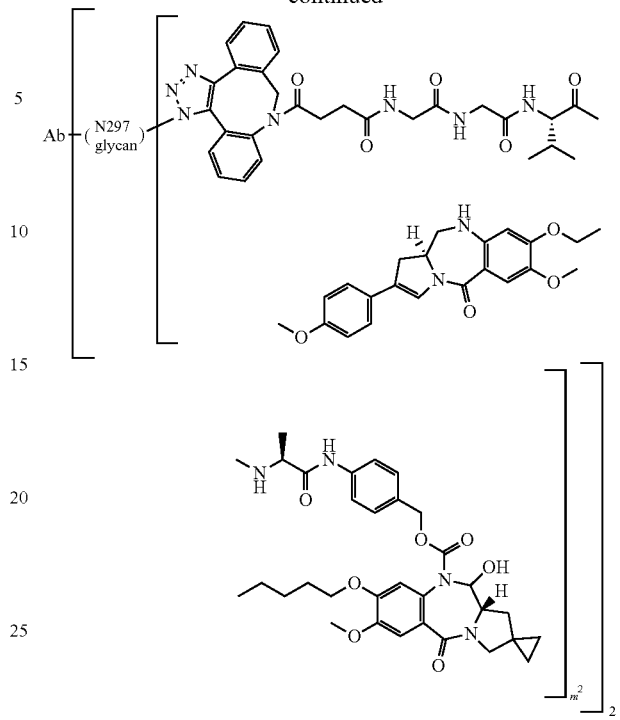

wherein, in each structural formula shown above,
$m^2$ represents an integer of 1 or 2;
Ab represents an antibody or a functional fragment of the antibody, wherein the antibody is an antibody which binds to CLDN6 and/or CLDN9;
the N297 glycan of Ab represents any one of N297-(Fuc)MSG1, N297-(Fuc)MSG2, and a mixture thereof, and N297-(Fuc)SG, with N297-(Fuc)MSG1, N297-(Fuc)MSG2, and N297-(Fuc)SG having structures represented by the following formulas:

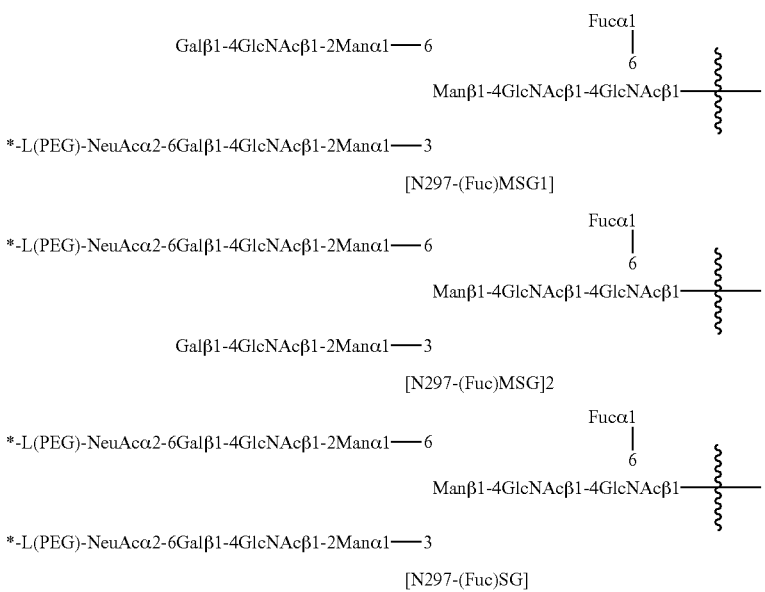

wherein
- each wavy line represents bonding to Asn297 of the antibody,
- L(PEG) represents —NH—CH$_2$CH$_2$—(O—CH$_2$CH$_2$)$_3$—*, wherein the amino group at the left end is bound via an amide bond to carboxylic acid at the 2-position of a sialic acid at the non-reducing terminal in each or either one of the 1-3 and 1-6 branched chains of β-Man in the N297 glycan, and each asterisk represents bonding to a nitrogen atom at the 1- or 3-position of the triazole ring in the corresponding structural formula.

2. The method according to claim 1, wherein the tumor expresses CLDN6, CLDN9, or a combination thereof.

3. The method according to claim 1, wherein the tumor is ovarian cancer, lung cancer, gastric cancer, endometrial cancer, testicular cancer, uterine cervix cancer, placental choriocarcinoma, kidney cancer, urothelial cancer, colorectal cancer, prostate cancer, glioblastoma multiforme, brain tumor, pancreatic cancer, breast cancer, melanoma, liver cancer, bladder cancer, or esophageal cancer.

4. The method according to claim 1, wherein the antibody comprises a heavy chain comprising CDRH1, CDRH2, and CDRH3 and a light chain comprising CDRL1, CDRL2, and CDRL3 as described in any one of the following:
   (a) CDRH1 consisting of an amino acid sequence represented by SEQ ID NO: 9, CDRH2 consisting of an amino acid sequence represented by SEQ ID NO: 10, and CDRH3 consisting of an amino acid sequence represented by SEQ ID NO: 11, and CDRL1 consisting of an amino acid sequence represented by SEQ ID NO: 5, CDRL2 consisting of an amino acid sequence represented by SEQ ID NO: 6, and CDRL3 consisting of an amino acid sequence represented by SEQ ID NO: 7 or an amino acid sequence having one or two amino acid substitutions in the amino acid sequence represented by SEQ ID NO: 7;
   (b) CDRH1 consisting of an amino acid sequence represented by SEQ ID NO: 15, CDRH2 consisting of an amino acid sequence represented by SEQ ID NO: 16, and CDRH3 consisting of an amino acid sequence represented by SEQ ID NO: 17, and CDRL1 consisting of an amino acid sequence represented by SEQ ID NO: 12, CDRL2 consisting of an amino acid sequence represented by SEQ ID NO: 13, and CDRL3 consisting of an amino acid sequence represented by SEQ ID NO: 14;
   (c) CDRH1 consisting of an amino acid sequence represented by SEQ ID NO: 9, CDRH2 consisting of an amino acid sequence represented by SEQ ID NO: 10, and CDRH3 consisting of an amino acid sequence represented by SEQ ID NO: 11, and CDRL1 consisting of an amino acid sequence represented by SEQ ID NO: 5, CDRL2 consisting of an amino acid sequence represented by SEQ ID NO: 6, and CDRL3 consisting of an amino acid sequence represented by SEQ ID NO: 7 or an amino acid sequence represented by SEQ ID NO: 8.

5. The method according to claim 1, wherein the antibody comprises a heavy chain variable region and a light chain variable region as described in any one of the following (a) and (b):
   (a) a heavy chain variable region consisting of an amino acid sequence represented by SEQ ID NO: 21 and a light chain variable region consisting of an amino acid sequence represented by SEQ ID NO: 19; and
   (b) a heavy chain variable region consisting of an amino acid sequence represented by SEQ ID NO: 25 and a light chain variable region consisting of an amino acid sequence represented by SEQ ID NO: 23.

6. The method according to claim 1, wherein the antibody comprises a heavy chain variable region consisting of an amino acid sequence selected from the group consisting of the following (a) to (e) and a light chain variable region consisting of an amino acid sequence selected from the group consisting of the following (f) to (k):
   (a) an amino acid sequence represented by SEQ ID NO: 54;
   (b) an amino acid sequence represented by SEQ ID NO: 58;
   (c) an amino acid sequence represented by SEQ ID NO: 62;
   (d) an amino acid sequence with a homology of at least 95% or higher to a sequence of a framework region excluding CDR sequences in any of the sequences (a) to (c);
   (e) an amino acid sequence having one to several amino acid deletions, substitutions, or additions in a sequence of a framework region excluding CDR sequences in any of the sequences (a) to (c);
   (f) an amino acid sequence represented by SEQ ID NO: 38;
   (g) an amino acid sequence represented by SEQ ID NO: 42;
   (h) an amino acid sequence represented by SEQ ID NO: 46;
   (i) an amino acid sequence represented by SEQ ID NO: 50;
   (j) an amino acid sequence with a homology of at least 95% or higher to a sequence of a framework region excluding CDR sequences in any of the sequences (f) to (i); and
   (k) an amino acid sequence having one to several amino acid deletions, substitutions, or additions in a sequence of a framework region excluding CDR sequences in any of the sequences (f) to (i).

7. The method according to claim 6, the antibody comprising a heavy chain variable region and a light chain variable region selected from the group consisting of the following (a) to (e):
   (a) a heavy chain variable region consisting of an amino acid sequence represented by SEQ ID NO: 54 and a light chain variable region consisting of an amino acid sequence represented by SEQ ID NO: 38;
   (b) a heavy chain variable region consisting of an amino acid sequence represented by SEQ ID NO: 58 and a light chain variable region consisting of an amino acid sequence represented by SEQ ID NO: 42;
(c) a heavy chain variable region consisting of an amino acid sequence represented by SEQ ID NO: 54 and a light chain variable region consisting of an amino acid sequence represented by SEQ ID NO: 46;
(d) a heavy chain variable region consisting of an amino acid sequence represented by SEQ ID NO: 58 and a light chain variable region consisting of an amino acid sequence represented by SEQ ID NO: 50; and
(e) a heavy chain variable region consisting of an amino acid sequence represented by SEQ ID NO: 62 and a light chain variable region consisting of an amino acid sequence represented by SEQ ID NO: 46.

8. The method according to claim 1, the antibody comprising a heavy chain and a light chain selected from the group consisting of the following (a) to (e):
(a) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 36 (H1L1);
(b) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 40 (H2L2);
(c) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 44 (H1L3);
(d) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 48 (H2L4); and
(e) a heavy chain consisting of an amino acid sequence consisting of amino acid residues 20 to 471 of SEQ ID NO: 60 and a light chain consisting of an amino acid sequence consisting of amino acid residues 21 to 234 of SEQ ID NO: 44 (H3L3).

9. The method according to claim 1, the antibody comprising a heavy chain and a light chain selected from the group consisting of the following (a) to (e):
(a) a heavy chain comprising an amino acid sequence comprising amino acid residues 20 to 471, 20 to 470, or 20 to 469 of SEQ ID NO: 52, and a light chain comprising an amino acid sequence comprising amino acid residues 21 to 234 of SEQ ID NO: 36 (H1L1);
(b) a heavy chain comprising an amino acid sequence comprising amino acid residues 20 to 471, 20 to 470, or 20 to 469 of SEQ ID NO: 56, and a light chain comprising an amino acid sequence comprising amino acid residues 21 to 234 of SEQ ID NO: 40 (H2L2);
(c) a heavy chain comprising an amino acid sequence comprising amino acid residues 20 to 471, 20 to 470, or 20 to 469 of SEQ ID NO: 52, and a light chain comprising an amino acid sequence comprising amino acid residues 21 to 234 of SEQ ID NO: 44 (H1L3);
(d) a heavy chain comprising an amino acid sequence comprising amino acid residues 20 to 471, 20 to 470, or 20 to 469 of SEQ ID NO: 56, and a light chain comprising an amino acid sequence comprising amino acid residues 21 to 234 of SEQ ID NO: 48 (H2L4); and
(e) a heavy chain comprising an amino acid sequence comprising amino acid residues 20 to 471, 20 to 470, or 20 to 469 of SEQ ID NO: 60, and a light chain comprising an amino acid sequence comprising amino acid residues 21 to 234 of SEQ ID NO: 44 (H3L3),
wherein the antibody comprises one or more modifications selected from the group consisting of N-linked glycosylation, O-linked glycosylation, N-terminal processing, C-terminal processing, deamidation, isomerization of aspartic acid, oxidation of methionine, addition of a methionine residue at an N terminus, and amidation of a proline residue.

10. A method for treating a tumor, comprising administering to a patient in need thereof an antibody-drug conjugate selected from the following group:

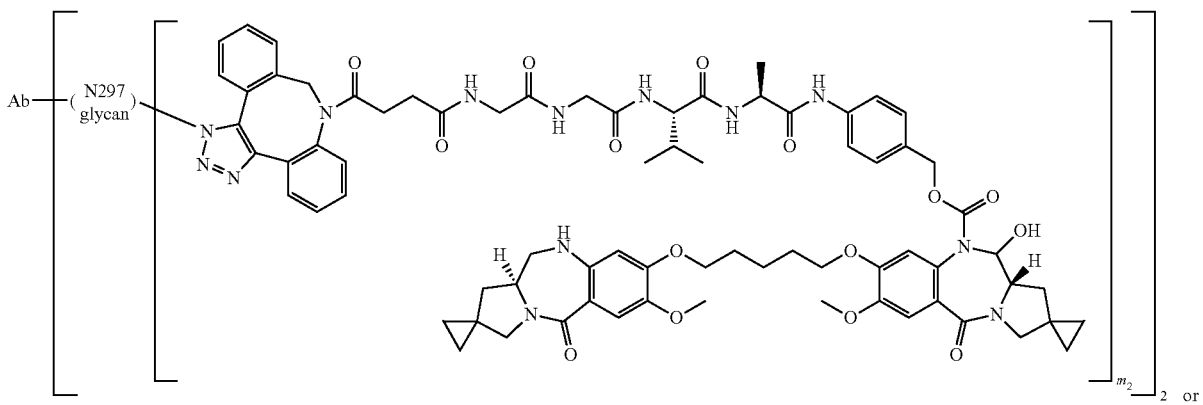

-continued

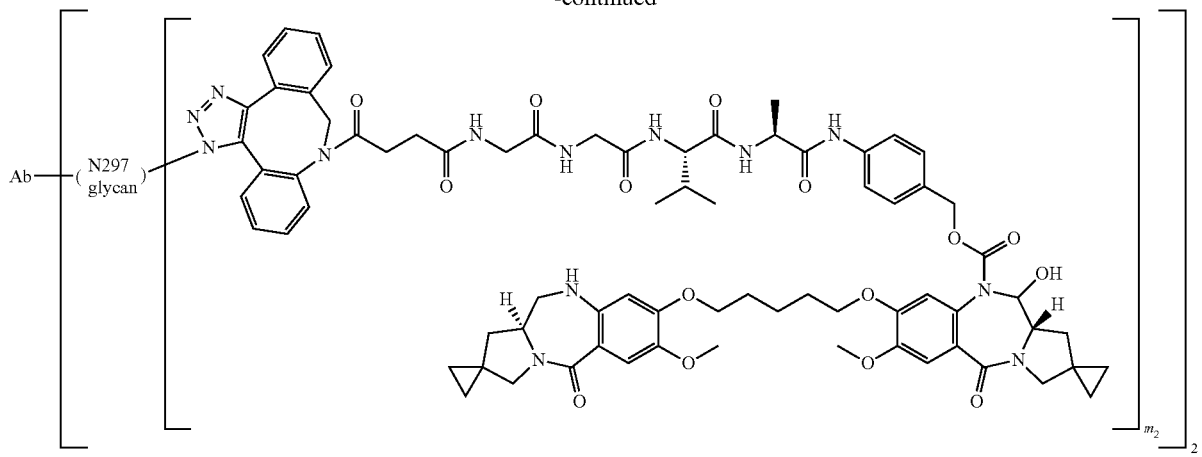

wherein, in each structural formula shown above,
$m^2$ represents an integer of 1 or 2;
Ab represents an antibody or a functional fragment of the antibody, wherein the antibody is an antibody which binds to CLDN6 and/or CLDN9;
the N297 glycan of Ab represents any one of N297-(Fuc) MSG1, N297-(Fuc) MSG2, and a mixture thereof, and N297-(Fuc)SG, with N297-(Fuc)MSG1, N297-(Fuc) MSG2, and N297-(Fuc)SG having structures represented by the following formulas:

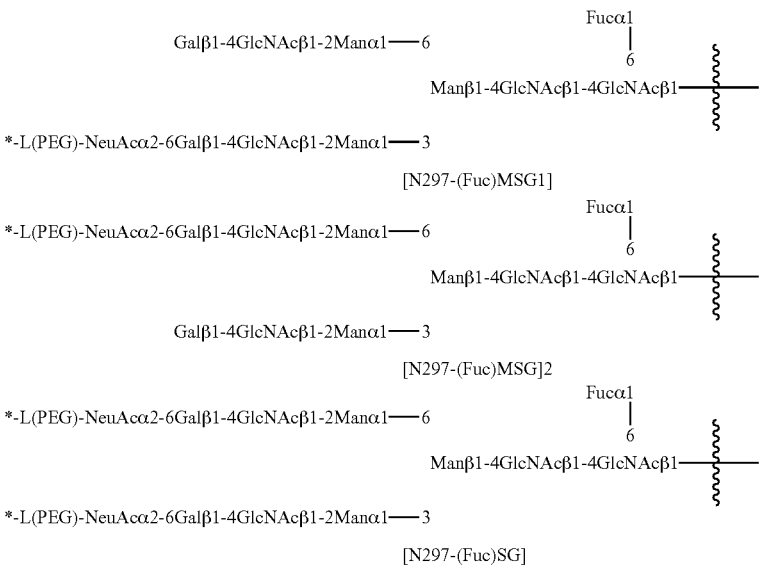

wherein
each wavy line represents bonding to Asn297 of the antibody,
L(PEG) represents —NH—CH$_2$CH$_2$—(O—CH$_2$CH$_2$)$_3$—*, wherein the amino group at the left end is bound via an amide bond to carboxylic acid at the 2-position of a sialic acid at the non-reducing terminal in each or either one of the 1-3 and 1-6 branched chains of β-Man in the N297 glycan, and each asterisk represents bonding to a nitrogen atom at the 1- or 3-position of the triazole ring in the corresponding structural formula.

11. The method according to claim 10, wherein the tumor expresses CLDN6, CLDN9, or a combination thereof.

12. The method according to claim 10, wherein the tumor is ovarian cancer, lung cancer, gastric cancer, endometrial cancer, testicular cancer, uterine cervix cancer, placental choriocarcinoma, kidney cancer, urothelial cancer, colorectal cancer, prostate cancer, glioblastoma multiforme, brain tumor, pancreatic cancer, breast cancer, melanoma, liver cancer, bladder cancer, or esophageal cancer.

13. The method according to claim 10, wherein the antibody comprises a heavy chain comprising CDRH1, CDRH2, and CDRH3 and a light chain comprising CDRL1, CDRL2, and CDRL3 as described in any one of the following:
(a) CDRH1 consisting of an amino acid sequence represented by SEQ ID NO: 9, CDRH2 consisting of an amino acid sequence represented by SEQ ID NO: 10, and CDRH3 consisting of an amino acid sequence represented by SEQ ID NO: 11, and CDRL1 consisting of an amino acid sequence represented by SEQ ID NO: 5, CDRL2 consisting of an amino acid sequence represented by SEQ ID NO: 6, and CDRL3 consisting of an amino acid sequence represented by SEQ ID NO: 7 or an amino acid sequence having one or two amino acid substitutions in the amino acid sequence represented by SEQ ID NO: 7;
(b) CDRH1 consisting of an amino acid sequence represented by SEQ ID NO: 15, CDRH2 consisting of an amino acid sequence represented by SEQ ID NO: 16, and CDRH3 consisting of an amino acid sequence represented by SEQ ID NO: 17, and CDRL1 consisting of an amino acid sequence represented by SEQ ID NO: 12, CDRL2 consisting of an amino acid sequence represented by SEQ ID NO: 13, and CDRL3 consisting of an amino acid sequence represented by SEQ ID NO: 14;
(c) CDRH1 consisting of an amino acid sequence represented by SEQ ID NO: 9, CDRH2 consisting of an amino acid sequence represented by SEQ ID NO: 10, and CDRH3 consisting of an amino acid sequence represented by SEQ ID NO: 11, and CDRL1 consisting of an amino acid sequence represented by SEQ ID NO: 5, CDRL2 consisting of an amino acid sequence represented by SEQ ID NO: 6, and CDRL3 consisting of an amino acid sequence represented by SEQ ID NO: 7 or an amino acid sequence represented by SEQ ID NO: 8.

14. The method according to claim 10, wherein the antibody comprises a heavy chain variable region and a light chain variable region as described in any one of the following (a) and (b):
    (a) a heavy chain variable region consisting of an amino acid sequence represented by SEQ ID NO: 21 and a light chain variable region consisting of an amino acid sequence represented by SEQ ID NO: 19; and
    (b) a heavy chain variable region consisting of an amino acid sequence represented by SEQ ID NO: 25 and a light chain variable region consisting of an amino acid sequence represented by SEQ ID NO: 23.

15. The method according to claim 10, wherein the antibody comprises a heavy chain variable region consisting of an amino acid sequence selected from the group consisting of the following (a) to (e) and a light chain variable region consisting of an amino acid sequence selected from the group consisting of the following (f) to (k):
    (a) an amino acid sequence represented by SEQ ID NO: 54;
    (b) an amino acid sequence represented by SEQ ID NO: 58;
    (c) an amino acid sequence represented by SEQ ID NO: 62;
    (d) an amino acid sequence with a homology of at least 95% or higher to a sequence of a framework region excluding CDR sequences in any of the sequences (a) to (c);
    (e) an amino acid sequence having one to several amino acid deletions, substitutions, or additions in a sequence of a framework region excluding CDR sequences in any of the sequences (a) to (c);
    (f) an amino acid sequence represented by SEQ ID NO: 38;
    (g) an amino acid sequence represented by SEQ ID NO: 42;
    (h) an amino acid sequence represented by SEQ ID NO: 46;
    (i) an amino acid sequence represented by SEQ ID NO: 50;
    (j) an amino acid sequence with a homology of at least 95% or higher to a sequence of a framework region excluding CDR sequences in any of the sequences (f) to (i); and
    (k) an amino acid sequence having one to several amino acid deletions, substitutions, or additions in a sequence of a framework region excluding CDR sequences in any of the sequences (f) to (i).

16. The method according to claim 15, the antibody comprising a heavy chain variable region and a light chain variable region selected from the group consisting of the following (a) to (e):
    (a) a heavy chain variable region consisting of an amino acid sequence represented by SEQ ID NO: 54 and a light chain variable region consisting of an amino acid sequence represented by SEQ ID NO: 38;
    (b) a heavy chain variable region consisting of an amino acid sequence represented by SEQ ID NO: 58 and a light chain variable region consisting of an amino acid sequence represented by SEQ ID NO: 42;
    (c) a heavy chain variable region consisting of an amino acid sequence represented by SEQ ID NO: 54 and a light chain variable region consisting of an amino acid sequence represented by SEQ ID NO: 46;
    (d) a heavy chain variable region consisting of an amino acid sequence represented by SEQ ID NO: 58 and a light chain variable region consisting of an amino acid sequence represented by SEQ ID NO: 50; and
    (e) a heavy chain variable region consisting of an amino acid sequence represented by SEQ ID NO: 62 and a light chain variable region consisting of an amino acid sequence represented by SEQ ID NO: 46.

17. The method according to claim 10, the antibody comprising a heavy chain and a light chain selected from the group consisting of the following (a) to (e):
    (a) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 36 (H1L1);
    (b) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 40 (H2L2);
    (c) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 44 (H1L3);
    (d) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 48 (H2L4); and
    (e) a heavy chain consisting of an amino acid sequence consisting of amino acid residues 20 to 471 of SEQ ID NO: 60 and a light chain consisting of an amino acid sequence consisting of amino acid residues 21 to 234 of SEQ ID NO: 44 (H3L3).

18. The method according to claim 10, the antibody comprising a heavy chain and a light chain selected from the group consisting of the following (a) to (e):
    (a) a heavy chain comprising an amino acid sequence comprising amino acid residues 20 to 471, 20 to 470, or 20 to 469 of SEQ ID NO: 52, and a light chain comprising an amino acid sequence comprising amino acid residues 21 to 234 of SEQ ID NO: 36 (H1L1);

(b) a heavy chain comprising an amino acid sequence comprising amino acid residues 20 to 471, 20 to 470, or 20 to 469 of SEQ ID NO: 56, and a light chain comprising an amino acid sequence comprising amino acid residues 21 to 234 of SEQ ID NO: 40 (H2L2);

(c) a heavy chain comprising an amino acid sequence comprising amino acid residues 20 to 471, 20 to 470, or 20 to 469 of SEQ ID NO: 52, and a light chain comprising an amino acid sequence comprising amino acid residues 21 to 234 of SEQ ID NO: 44 (H1L3);

(d) a heavy chain comprising an amino acid sequence comprising amino acid residues 20 to 471, 20 to 470, or 20 to 469 of SEQ ID NO: 56, and a light chain comprising an amino acid sequence comprising amino acid residues 21 to 234 of SEQ ID NO: 48 (H2L4); and (e) a heavy chain comprising an amino acid sequence comprising amino acid residues 20 to 471, 20 to 470, or 20 to 469 of SEQ ID NO: 60, and a light chain comprising an amino acid sequence comprising amino acid residues 21 to 234 of SEQ ID NO: 44 (H3L3), wherein the antibody comprises one or more modifications selected from the group consisting of N-linked glycosylation, O-linked glycosylation, N-terminal processing, C-terminal processing, deamidation, isomerization of aspartic acid, oxidation of methionine, addition of a methionine residue at an N terminus, and amidation of a proline residue.

19. A method for treating a tumor, comprising administering to a patient in need thereof an antibody-drug conjugate selected from the following group:

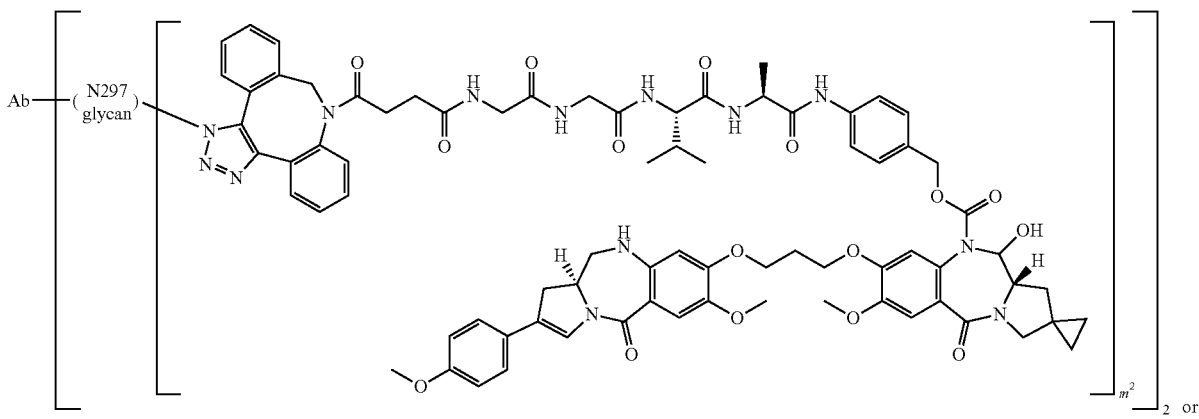

or

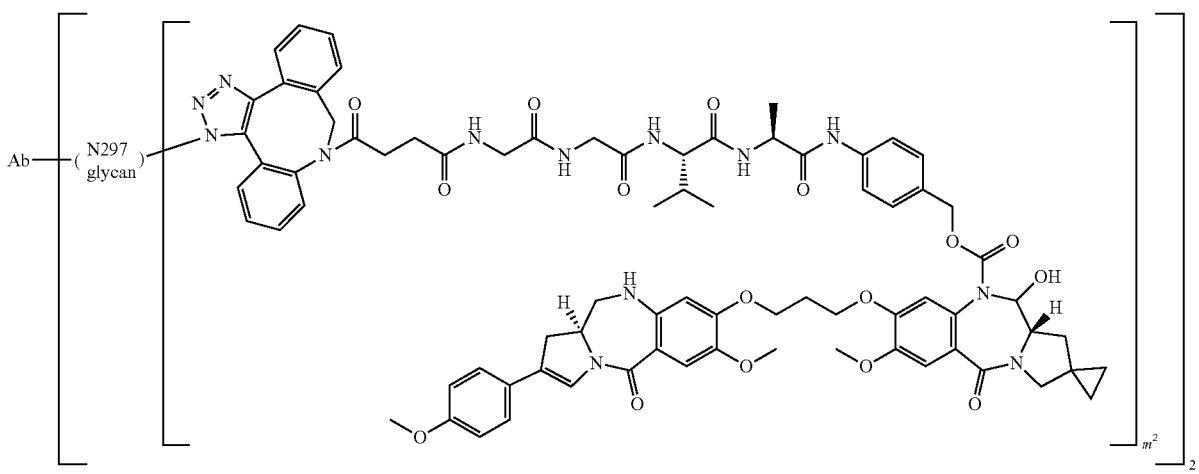

wherein, in each structural formula shown above, $m^2$ represents an integer of 1 or 2;

Ab represents an antibody or a functional fragment of the antibody, wherein the antibody is an antibody which binds to CLDN6 and/or CLDN9;

the N297 glycan of Ab represents any one of N297-(Fuc)MSG1, N297-(Fuc)MSG2, and a mixture thereof, and N297-(Fuc)SG, with N297-(Fuc)MSG1, N297-(Fuc)MSG2, and N297-(Fuc)SG having structures represented by the following formulas:

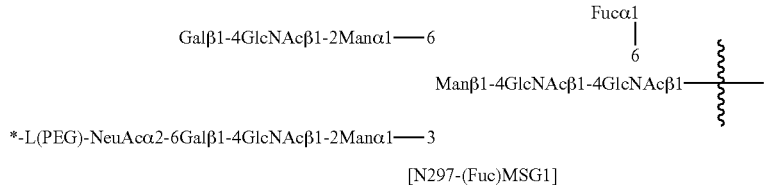

[N297-(Fuc)MSG1]

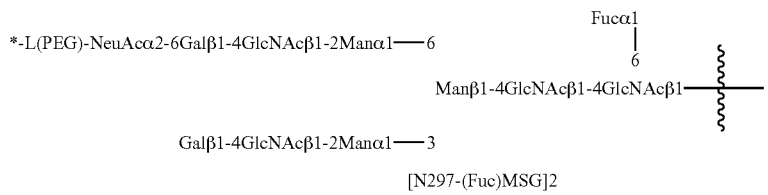

[N297-(Fuc)MSG]2

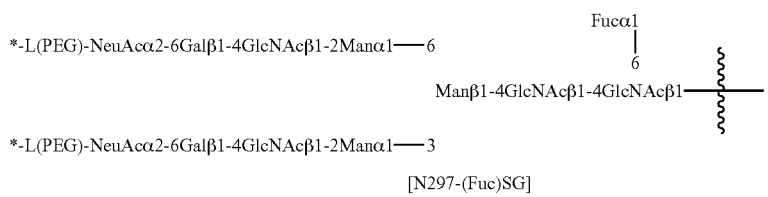

[N297-(Fuc)SG]

wherein
each wavy line represents bonding to Asn297 of the antibody,
L(PEG) represents —NH—CH$_2$CH$_2$—(O—CH$_2$CH$_2$)$_3$—*, wherein the amino group at the left end is bound via an amide bond to carboxylic acid at the 2-position of a sialic acid at the non-reducing terminal in each or either one of the 1-3 and 1-6 branched chains of β-Man in the N297 glycan, and each asterisk represents bonding to a nitrogen atom at the 1- or 3-position of the triazole ring in the corresponding structural formula.

20. The method according to claim 19, wherein the tumor expresses CLDN6, CLDN9, or a combination thereof.

21. The method according to claim 19, wherein the tumor is ovarian cancer, lung cancer, gastric cancer, endometrial cancer, testicular cancer, uterine cervix cancer, placental choriocarcinoma, kidney cancer, urothelial cancer, colorectal cancer, prostate cancer, glioblastoma multiforme, brain tumor, pancreatic cancer, breast cancer, melanoma, liver cancer, bladder cancer, or esophageal cancer.

22. The method to claim 19, wherein the antibody comprises a heavy chain comprising CDRH1, CDRH2, and CDRH3 and a light chain comprising CDRL1, CDRL2, and CDRL3 as described in any one of the following:

(a) CDRH1 consisting of an amino acid sequence represented by SEQ ID NO: 9, CDRH2 consisting of an amino acid sequence represented by SEQ ID NO: 10, and CDRH3 consisting of an amino acid sequence represented by SEQ ID NO: 11, and CDRL1 consisting of an amino acid sequence represented by SEQ ID NO: 5, CDRL2 consisting of an amino acid sequence represented by SEQ ID NO: 6, and CDRL3 consisting of an amino acid sequence represented by SEQ ID NO: 7 or an amino acid sequence having one or two amino acid substitutions in the amino acid sequence represented by SEQ ID NO: 7;

(b) CDRH1 consisting of an amino acid sequence represented by SEQ ID NO: 15, CDRH2 consisting of an amino acid sequence represented by SEQ ID NO: 16, and CDRH3 consisting of an amino acid sequence represented by SEQ ID NO: 17, and CDRL1 consisting of an amino acid sequence represented by SEQ ID NO: 12, CDRL2 consisting of an amino acid sequence represented by SEQ ID NO: 13, and CDRL3 consisting of an amino acid sequence represented by SEQ ID NO: 14;

(c) CDRH1 consisting of an amino acid sequence represented by SEQ ID NO: 9, CDRH2 consisting of an amino acid sequence represented by SEQ ID NO: 10, and CDRH3 consisting of an amino acid sequence represented by SEQ ID NO: 11, and CDRL1 consisting of an amino acid sequence represented by SEQ ID NO: 5, CDRL2 consisting of an amino acid sequence represented by SEQ ID NO: 6, and CDRL3 consisting of an amino acid sequence represented by SEQ ID NO: 7 or an amino acid sequence represented by SEQ ID NO: 8.

23. The method according to claim 19, wherein the antibody comprises a heavy chain variable region and a light chain variable region as described in any one of the following (a) and (b):

(a) a heavy chain variable region consisting of an amino acid sequence represented by SEQ ID NO: 21 and a light chain variable region consisting of an amino acid sequence represented by SEQ ID NO: 19; and
(b) a heavy chain variable region consisting of an amino acid sequence represented by SEQ ID NO: 25 and a light chain variable region consisting of an amino acid sequence represented by SEQ ID NO: 23.

24. The method according to claim 19, wherein the antibody comprises a heavy chain variable region consisting of an amino acid sequence selected from the group consisting of the following (a) to (e) and a light chain variable region consisting of an amino acid sequence selected from the group consisting of the following (f) to (k):
(a) an amino acid sequence represented by SEQ ID NO: 54;
(b) an amino acid sequence represented by SEQ ID NO: 58;
(c) an amino acid sequence represented by SEQ ID NO: 62;
(d) an amino acid sequence with a homology of at least 95% or higher to a sequence of a framework region excluding CDR sequences in any of the sequences (a) to (c);
(e) an amino acid sequence having one to several amino acid deletions, substitutions, or additions in a sequence of a framework region excluding CDR sequences in any of the sequences (a) to (c);
(f) an amino acid sequence represented by SEQ ID NO: 38;
(g) an amino acid sequence represented by SEQ ID NO: 42;
(h) an amino acid sequence represented by SEQ ID NO: 46;
(i) an amino acid sequence represented by SEQ ID NO: 50;
(j) an amino acid sequence with a homology of at least 95% or higher to a sequence of a framework region excluding CDR sequences in any of the sequences (f) to (i); and
(k) an amino acid sequence having one to several amino acid deletions, substitutions, or additions in a sequence of a framework region excluding CDR sequences in any of the sequences (f) to (i).

25. The method according to claim 24, the antibody comprising a heavy chain variable region and a light chain variable region selected from the group consisting of the following (a) to (e):
(a) a heavy chain variable region consisting of an amino acid sequence represented by SEQ ID NO: 54 and a light chain variable region consisting of an amino acid sequence represented by SEQ ID NO: 38;
(b) a heavy chain variable region consisting of an amino acid sequence represented by SEQ ID NO: 58 and a light chain variable region consisting of an amino acid sequence represented by SEQ ID NO: 42;
(c) a heavy chain variable region consisting of an amino acid sequence represented by SEQ ID NO: 54 and a light chain variable region consisting of an amino acid sequence represented by SEQ ID NO: 46;
(d) a heavy chain variable region consisting of an amino acid sequence represented by SEQ ID NO: 58 and a light chain variable region consisting of an amino acid sequence represented by SEQ ID NO: 50; and
(e) a heavy chain variable region consisting of an amino acid sequence represented by SEQ ID NO: 62 and a light chain variable region consisting of an amino acid sequence represented by SEQ ID NO: 46.

26. The method according to claim 19, the antibody comprising a heavy chain and a light chain selected from the group consisting of the following (a) to (e):
(a) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 36 (H1L1);
(b) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 40 (H2L2);
(c) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 44 (H1L3);
(d) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 48 (H2L4); and
(e) a heavy chain consisting of an amino acid sequence consisting of amino acid residues 20 to 471 of SEQ ID NO: 60 and a light chain consisting of an amino acid sequence consisting of amino acid residues 21 to 234 of SEQ ID NO: 44 (H3L3).

27. The method according to claim 19, the antibody comprising a heavy chain and a light chain selected from the group consisting of the following (a) to (e):
(a) a heavy chain comprising an amino acid sequence comprising amino acid residues 20 to 471, 20 to 470, or 20 to 469 of SEQ ID NO: 52, and a light chain comprising an amino acid sequence comprising amino acid residues 21 to 234 of SEQ ID NO: 36 (H1L1);
(b) a heavy chain comprising an amino acid sequence comprising amino acid residues 20 to 471, 20 to 470, or 20 to 469 of SEQ ID NO: 56, and a light chain comprising an amino acid sequence comprising amino acid residues 21 to 234 of SEQ ID NO: 40 (H2L2);
(c) a heavy chain comprising an amino acid sequence comprising amino acid residues 20 to 471, 20 to 470, or 20 to 469 of SEQ ID NO: 52, and a light chain comprising an amino acid sequence comprising amino acid residues 21 to 234 of SEQ ID NO: 44 (H1L3);
(d) a heavy chain comprising an amino acid sequence comprising amino acid residues 20 to 471, 20 to 470, or 20 to 469 of SEQ ID NO: 56, and a light chain comprising an amino acid sequence comprising amino acid residues 21 to 234 of SEQ ID NO: 48 (H2L4); and
(e) a heavy chain comprising an amino acid sequence comprising amino acid residues 20 to 471, 20 to 470, or 20 to 469 of SEQ ID NO: 60, and a light chain comprising an amino acid sequence comprising amino acid residues 21 to 234 of SEQ ID NO: 44 (H3L3), wherein the antibody comprises one or more modifications selected from the group consisting of N-linked glycosylation, O-linked glycosylation, N-terminal processing, C-terminal processing, deamidation, isomerization of aspartic acid, oxidation of methionine, addition of a methionine residue at an N terminus, and amidation of a proline residue.

28. A method for treating a tumor, comprising administering to a patient in need thereof an antibody-drug conjugate selected from the following group:

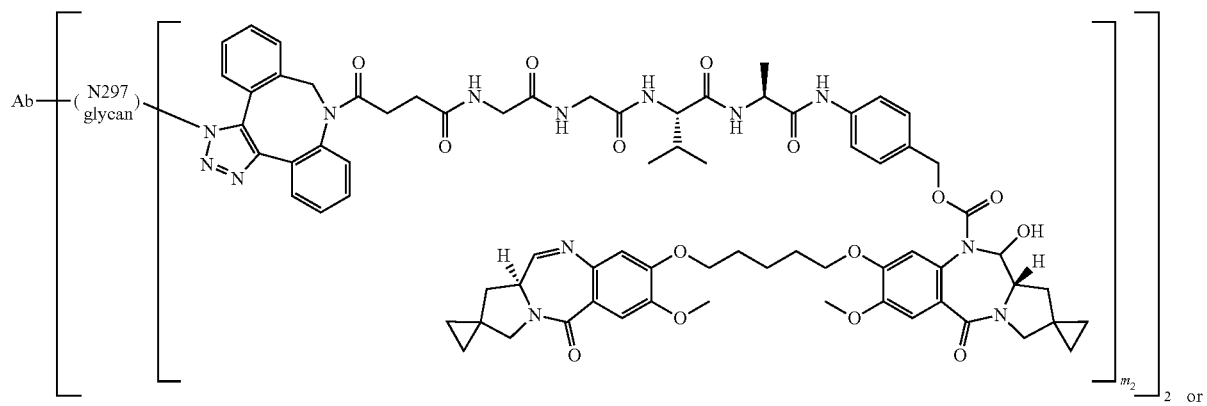

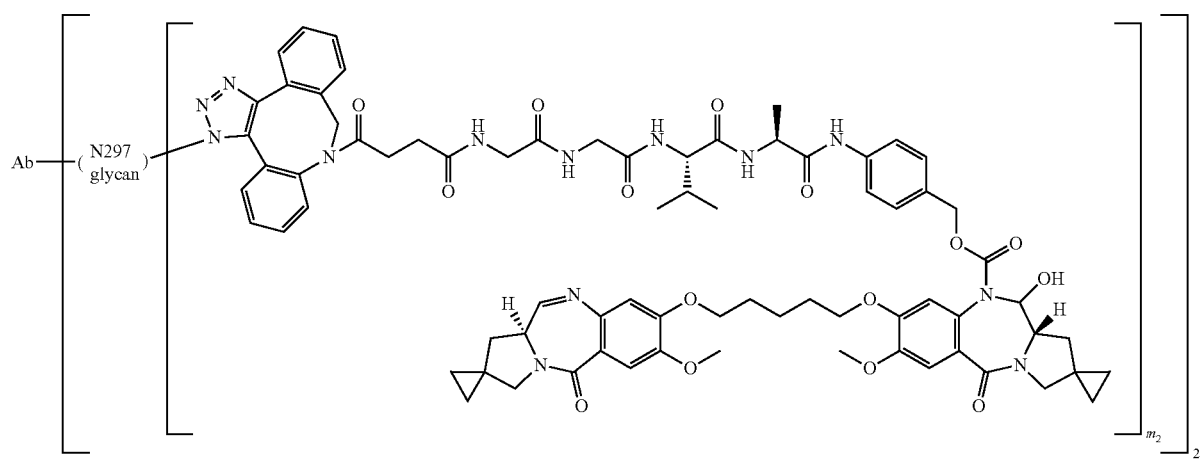

wherein, in each structural formula shown above,
$m^2$ represents an integer of 1 or 2;
Ab represents an antibody or a functional fragment of the antibody, wherein the antibody is an antibody which binds to CLDN6 and/or CLDN9;

the N297 glycan of Ab represents any one of N297-(Fuc)MSG1, N297-(Fuc)MSG2, and a mixture thereof, and N297-(Fuc)SG, with N297-(Fuc)MSG1, N297-(Fuc)MSG2, and N297-(Fuc)SG having structures represented by the following formulas:

-continued

\*-L(PEG)-NeuAcα2-6Galβ1-4GlcNAcβ1-2Manα1——6

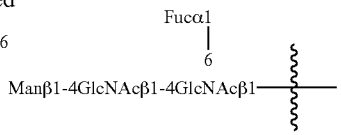

\*-L(PEG)-NeuAcα2-6Galβ1-4GlcNAcβ1-2Manα1——3

[N297-(Fuc)SG]

wherein
each wavy line represents bonding to Asn297 of the antibody,
L(PEG) represents —NH—CH$_2$CH$_2$—(O—CH$_2$CH$_2$)$_3$—\*, wherein the amino group at the left end is bound via an amide bond to carboxylic acid at the 2-position of a sialic acid at the non-reducing terminal in each or either one of the 1-3 and 1-6 branched chains of β-Man in the N297 glycan, and each asterisk represents bonding to a nitrogen atom at the 1- or 3-position of the triazole ring in the corresponding structural formula.

29. The method according to claim 28, wherein the tumor expresses CLDN6, CLDN9, or a combination thereof.

30. The method according to claim 28, wherein the tumor is ovarian cancer, lung cancer, gastric cancer, endometrial cancer, testicular cancer, uterine cervix cancer, placental choriocarcinoma, kidney cancer, urothelial cancer, colorectal cancer, prostate cancer, glioblastoma multiforme, brain tumor, pancreatic cancer, breast cancer, melanoma, liver cancer, bladder cancer, or esophageal cancer.

31. The method according to claim 28, wherein the antibody comprises a heavy chain comprising CDRH1, CDRH2, and CDRH3 and a light chain comprising CDRL1, CDRL2, and CDRL3 as described in any one of the following:
   (a) CDRH1 consisting of an amino acid sequence represented by SEQ ID NO: 9, CDRH2 consisting of an amino acid sequence represented by SEQ ID NO: 10, and CDRH3 consisting of an amino acid sequence represented by SEQ ID NO: 11, and CDRL1 consisting of an amino acid sequence represented by SEQ ID NO: 5, CDRL2 consisting of an amino acid sequence represented by SEQ ID NO: 6, and CDRL3 consisting of an amino acid sequence represented by SEQ ID NO: 7 or an amino acid sequence having one or two amino acid substitutions in the amino acid sequence represented by SEQ ID NO: 7;
   (b) CDRH1 consisting of an amino acid sequence represented by SEQ ID NO: 15, CDRH2 consisting of an amino acid sequence represented by SEQ ID NO: 16, and CDRH3 consisting of an amino acid sequence represented by SEQ ID NO: 17, and CDRL1 consisting of an amino acid sequence represented by SEQ ID NO: 12, CDRL2 consisting of an amino acid sequence represented by SEQ ID NO: 13, and CDRL3 consisting of an amino acid sequence represented by SEQ ID NO: 14;
   (c) CDRH1 consisting of an amino acid sequence represented by SEQ ID NO: 9, CDRH2 consisting of an amino acid sequence represented by SEQ ID NO: 10, and CDRH3 consisting of an amino acid sequence represented by SEQ ID NO: 11, and CDRL1 consisting of an amino acid sequence represented by SEQ ID NO: 5, CDRL2 consisting of an amino acid sequence represented by SEQ ID NO: 6, and CDRL3 consisting of an amino acid sequence represented by SEQ ID NO: 7 or an amino acid sequence represented by SEQ ID NO: 8.

32. The method according to claim 28, wherein the antibody comprises a heavy chain variable region and a light chain variable region as described in any one of the following (a) and (b):
   (a) a heavy chain variable region consisting of an amino acid sequence represented by SEQ ID NO: 21 and a light chain variable region consisting of an amino acid sequence represented by SEQ ID NO: 19; and
   (b) a heavy chain variable region consisting of an amino acid sequence represented by SEQ ID NO: 25 and a light chain variable region consisting of an amino acid sequence represented by SEQ ID NO: 23.

33. The method according to claim 28, wherein the antibody comprises a heavy chain variable region consisting of an amino acid sequence selected from the group consisting of the following (a) to (e) and a light chain variable region consisting of an amino acid sequence selected from the group consisting of the following (f) to (k):
   (a) an amino acid sequence represented by SEQ ID NO: 54;
   (b) an amino acid sequence represented by SEQ ID NO: 58;
   (c) an amino acid sequence represented by SEQ ID NO: 62;
   (d) an amino acid sequence with a homology of at least 95% or higher to a sequence of a framework region excluding CDR sequences in any of the sequences (a) to (c);
   (e) an amino acid sequence having one to several amino acid deletions, substitutions, or additions in a sequence of a framework region excluding CDR sequences in any of the sequences (a) to (c);
   (f) an amino acid sequence represented by SEQ ID NO: 38;
   (g) an amino acid sequence represented by SEQ ID NO: 42;
   (h) an amino acid sequence represented by SEQ ID NO: 46;
   (i) an amino acid sequence represented by SEQ ID NO: 50;
   (j) an amino acid sequence with a homology of at least 95% or higher to a sequence of a framework region excluding CDR sequences in any of the sequences (f) to (i); and
   (k) an amino acid sequence having one to several amino acid deletions, substitutions, or additions in a sequence of a framework region excluding CDR sequences in any of the sequences (f) to (i).

34. The method according to claim 33, the antibody comprising a heavy chain variable region and a light chain variable region selected from the group consisting of the following (a) to (e):

(a) a heavy chain variable region consisting of an amino acid sequence represented by SEQ ID NO: 54 and a light chain variable region consisting of an amino acid sequence represented by SEQ ID NO: 38;
(b) a heavy chain variable region consisting of an amino acid sequence represented by SEQ ID NO: 58 and a light chain variable region consisting of an amino acid sequence represented by SEQ ID NO: 42;
(c) a heavy chain variable region consisting of an amino acid sequence represented by SEQ ID NO: 54 and a light chain variable region consisting of an amino acid sequence represented by SEQ ID NO: 46;
(d) a heavy chain variable region consisting of an amino acid sequence represented by SEQ ID NO: 58 and a light chain variable region consisting of an amino acid sequence represented by SEQ ID NO: 50; and
(e) a heavy chain variable region consisting of an amino acid sequence represented by SEQ ID NO: 62 and a light chain variable region consisting of an amino acid sequence represented by SEQ ID NO: 46.

35. The method according to claim 28, the antibody comprising a heavy chain and a light chain selected from the group consisting of the following (a) to (e):
(a) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 36 (H1L1);
(b) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 40 (H2L2);
(c) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 44 (H1L3);
(d) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 48 (H2L4); and
(e) a heavy chain consisting of an amino acid sequence consisting of amino acid residues 20 to 471 of SEQ ID NO: 60 and a light chain consisting of an amino acid sequence consisting of amino acid residues 21 to 234 of SEQ ID NO: 44 (H3L3).

36. The method according to claim 28, the antibody comprising a heavy chain and a light chain selected from the group consisting of the following (a) to (e):
(a) a heavy chain comprising an amino acid sequence comprising amino acid residues 20 to 471, 20 to 470, or 20 to 469 of SEQ ID NO: 52, and a light chain comprising an amino acid sequence comprising amino acid residues 21 to 234 of SEQ ID NO: 36 (H1L1);
(b) a heavy chain comprising an amino acid sequence comprising amino acid residues 20 to 471, 20 to 470, or 20 to 469 of SEQ ID NO: 56, and a light chain comprising an amino acid sequence comprising amino acid residues 21 to 234 of SEQ ID NO: 40 (H2L2);
(c) a heavy chain comprising an amino acid sequence comprising amino acid residues 20 to 471, 20 to 470, or 20 to 469 of SEQ ID NO: 52, and a light chain comprising an amino acid sequence comprising amino acid residues 21 to 234 of SEQ ID NO: 44 (H1L3);
(d) a heavy chain comprising an amino acid sequence comprising amino acid residues 20 to 471, 20 to 470, or 20 to 469 of SEQ ID NO: 56, and a light chain comprising an amino acid sequence comprising amino acid residues 21 to 234 of SEQ ID NO: 48 (H2L4); and
(e) a heavy chain comprising an amino acid sequence comprising amino acid residues 20 to 471, 20 to 470, or 20 to 469 of SEQ ID NO: 60, and a light chain comprising an amino acid sequence comprising amino acid residues 21 to 234 of SEQ ID NO: 44 (H3L3),
wherein the antibody comprises one or more modifications selected from the group consisting of N-linked glycosylation, O-linked glycosylation, N-terminal processing, C-terminal processing, deamidation, isomerization of aspartic acid, oxidation of methionine, addition of a methionine residue at an N terminus, and amidation of a proline residue.

* * * * *

UNITED STATES PATENT AND TRADEMARK OFFICE
CERTIFICATE OF CORRECTION

| | | |
|---|---|---|
| PATENT NO. | : 12,350,344 B2 | Page 1 of 1 |
| APPLICATION NO. | : 17/714032 | |
| DATED | : July 8, 2025 | |
| INVENTOR(S) | : Narihiro Toda et al. | |

It is certified that error appears in the above-identified patent and that said Letters Patent is hereby corrected as shown below:

In the Claims

In Claim 1, Column 754, Lines 40-65, please delete "[N297-(Fuc)MSG]2"; and replace with -- [N297-(Fuc)MSG2] --

In Claim 10, Column 759, Lines 31-55, please delete "[N297-(Fuc)MSG]2"; and replace with -- [N297-(Fuc)MSG2] --

In Claim 19, Column 765, Lines 1-34, please delete "[N297-(Fuc)MSG]2"; and replace with -- [N297-(Fuc)MSG2] --

In Claim 28, Column 770, Lines 50-65, please delete "[N297-(Fuc)MSG]2"; and replace with -- [N297-(Fuc)MSG2] --

Signed and Sealed this
Thirtieth Day of September, 2025

John A. Squires
*Director of the United States Patent and Trademark Office*